US012583858B2

(12) United States Patent
Lin et al.

(10) Patent No.: US 12,583,858 B2
(45) **Date of Patent: *Mar. 24, 2026**

(54) TDO2 INHIBITORS

(71) Applicants: Genentech, Inc., South San Francisco, CA (US); NewLink Genetics Corporation, Ames, IA (US)

(72) Inventors: Xingyu Lin, Beijing (CN); Po-wai Yuen, Beijing (CN); Rohan Mendonca, South San Francisco, CA (US); Brendan Parr, South San Francisco, CA (US); Richard Pastor, South San Francisco, CA (US); Zhonghua Pei, South San Francisco, CA (US); Lewis Gazzard, South San Francisco, CA (US); Firoz Jaipuri, Ames, IA (US); Sanjeev Kumar, Ames, IA (US); Xiaokai Li, Ames, IA (US); Roheeth Pavana, Ames, IA (US); Hima Potturi, Ames, IA (US); Venkata Velvadapu, Ames, IA (US); Jesse Waldo, Ames, IA (US); Zuhui Zhang, Ames, IA (US); Guosheng Wu, Beijing (CN); Benjamin Douglas Sellers, South San Francisco, CA (US)

(73) Assignees: Genentech, Inc., South San Francisco, CA (US); NewLink Genetics Corporation, Ames, IA (US)

( * ) Notice: Subject to any disclaimer, the term of this patent is extended or adjusted under 35 U.S.C. 154(b) by 1062 days.

This patent is subject to a terminal disclaimer.

(21) Appl. No.: 17/068,574

(22) Filed: Oct. 12, 2020

(65) Prior Publication Data

US 2022/0306635 A1 Sep. 29, 2022

Related U.S. Application Data

(63) Continuation of application No. 16/065,397, filed as application No. PCT/CN2016/111730 on Dec. 23, 2016, now Pat. No. 10,800,780.

(30) Foreign Application Priority Data

| | | |
|---|---|---|
| Dec. 24, 2015 | (WO) | PCT/CN2015/098685 |
| Oct. 26, 2016 | (WO) | PCT/CN2016/103358 |
| Nov. 21, 2016 | (WO) | PCT/CN2016/106624 |

(51) Int. Cl.

| | |
|---|---|
| *C07D 487/04* | (2006.01) |
| *A61K 38/16* | (2006.01) |
| *A61K 45/06* | (2006.01) |
| *A61P 35/00* | (2006.01) |
| *A61P 35/02* | (2006.01) |
| *C07D 519/00* | (2006.01) |

(52) U.S. Cl.

CPC ............ *C07D 487/04* (2013.01); *A61K 38/16* (2013.01); *A61K 45/06* (2013.01); *A61P 35/00* (2018.01); *C07D 519/00* (2013.01); *A61K 2300/00* (2013.01)

(58) Field of Classification Search

CPC .... C07D 487/04; C07D 519/00; A61K 38/16; A61K 45/06; A61K 2300/00; A61P 35/00; A61P 35/02

See application file for complete search history.

(56) References Cited

U.S. PATENT DOCUMENTS

| | | | | |
|---|---|---|---|---|
| 9,260,434 B2 | 2/2016 | Mautino | | |
| 9,388,191 B2 | 7/2016 | Mautino | | |
| 10,233,190 B2 | 3/2019 | Mautino | | |
| 10,800,780 B2 * | 10/2020 | Lin | ......................... | A61P 35/00 |
| 11,603,373 B2 * | 3/2023 | Pei | ......................... | A61P 35/00 |
| 2018/0118750 A1 | 5/2018 | Tu et al. | | |

FOREIGN PATENT DOCUMENTS

| | | | |
|---|---|---|---|
| WO | WO 2012/142237 | 10/2012 | |
| WO | WO-2012142237 A1 * | 10/2012 | ........... C07D 487/04 |
| WO | WO 2015/091862 | 6/2015 | |
| WO | WO 2015/150097 | 10/2015 | |
| WO | WO 2016/059412 | 4/2016 | |
| WO | 2016/165613 | 10/2016 | |
| WO | 2016/169421 | 10/2016 | |

OTHER PUBLICATIONS

International Search Report for International Application No. PCT/CN2016/111730 mailed Mar. 27, 2017, 3 pages.

* cited by examiner

*Primary Examiner* — Joseph K McKane
*Assistant Examiner* — Sagar Patel
(74) *Attorney, Agent, or Firm* — McDonnell Boehnen Hulbert & Berghoff LLP

(57) ABSTRACT

Presently provided are inhibitors of cellularly expressed TD02 and pharmaceutical compositions thereof, useful for modulating an activity of tryptophan 2, 3 dioxygenase; treating immunosuppression; treating a medical conditions that benefit from the inhibition of tryptophan degradation; enhancing the effectiveness of an anti-cancer treatment comprising administering an anti-cancer agent; and treating tumor-specific immunosuppression associated with cancer.

14 Claims, No Drawings

TDO2 INHIBITORS

This application is a continuation of U.S. application Ser. No. 16/065,397, filed Jun. 22, 2018, now U.S. Pat. No. 10,800,780, which is a U.S. national phase application under 35 USC 371 of International Patent Application No. PCT/CN2016/111730, filed Dec. 23, 2016, which claims the benefit of International Application No. PCT/CN2015/098685, filed Dec. 24, 2015; International Application No. PCT/CN2016/103358, filed Oct. 26, 2016; and International Application No. PCT/CN2016/106624, filed Nov. 21, 2016.

BACKGROUND OF THE INVENTION

Field of the Invention

The present disclosure relates to compounds and methods for inhibition of tryptophan 2,3-dioxygenase (TDO2); further the disclosure relates to method of treatment of diseases and disorders mediated by tryptophan deficiency.

Summary of the Related Art

Tryptophan (Trp) is an essential amino acid required for the biosynthesis of proteins, niacin and the neurotransmitter 5-hydroxytryptamine (serotonin). The enzymes indoleamine 2,3-dioxygenase 1 (also known as INDO1 or IDO1), indoleamine-2,3-dioxygenase 2 (INDOL1 or IDO2) and tryptophan-2,3-dioxygenase (TDO2) catalyze the first and rate limiting step in the degradation of L-tryptophan to N-formyl-kynurenine. Although these enzymes catalyze the same reaction, differential expression and compartmentalization of IDO1 and TDO2 in different tissues is thought to mediate their different biological roles. IDO1 is normally expressed in cells of the gastrointestinal and pulmonary epithelia, epididymus, placenta, pDCs in draining lymph nodes and tumor cells. IDO2 is expressed mainly in brain and placenta, but certain splice variants are also detected in liver, small intesting, spleen, placenta, thymus lung, brain, kidney and colon. TDO2 is expressed mainly in liver, and controls the flux of dietary Trp to the serotonin and kynurenine pathways, and is also expressed in tumors and tumor cell lines.

Several lines of evidence suggest that IDO1 and TDO2 are involved in induction of immune tolerance. Studies of mammalian pregnancy, tumor resistance, chronic infections and autoimmune diseases have shown that cells expressing IDO1 can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO1 is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO1 inhibition can enhance the levels of virus-specific T cells and, concomitantly, reduce the number of virally infected macrophages in a mouse model of HIV (Portula et al., 2005, Blood, 106:2382-90).

IDO1 is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO1 is expressed by human syncytiotrophoblast cells and systemic tryptophan concentration falls during normal pregnancy, it was hypothesized that IDO1 expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO1 comes from the observation that most human tumors constitutively express IDO, and that expression of IDO1 by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO1 inhibitor (Uyttenhove et al., 2003, Nature Med., 9: 1269-74). It has also been shown that the IDO1 inhibitor, 1-MT, can synergize with chemotherapeutic agents to reduce tumor growth in mice, suggesting that IDO1 inhibition may also enhance the anti-tumor activity of conventional cytotoxic therapies (Muller et al., 2005, Nature Med., 11:312-9).

A similar situation has been observed with TDO2. It has been shown that a significant proportion of primary human tumors express elevated levels of TDO2 or TDO2 plus IDO1 (Pilotte et al. 2012, P.N.A.S). Moreover, pharmacological inhibition of TDO2 activity with TDO2 inhibitors, leads to immune-mediated rejection of tumors overexpressing TDO2, which means that TDO2, just as seen in IDO1, can mediate tumor-promoting immunosuppressive effects.

Small molecule inhibitors of IDO1 are being developed to treat or prevent IDO1-related diseases such as those described above. For example, PCT Publication WO 99/29310 reports methods for altering T cell-mediated immunity comprising altering local extracellular concentrations of tryptophan and tryptophan metabolites, using an inhibitor of IDO1 such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2009/073620; WO 2009/132238; WO 2011/056652 and WO 2012/142237. In particular, the compounds of WO 2012/142237 encompass a series of tricyclic imidazoisoindoles with potent IDO1 inhibitory activity.

SUMMARY OF THE INVENTION

We recognized that in light of the experimental data indicating a role for IDO1 and/or TDO2 in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO1 and/or TDO2 activity are desirable. Specific or dual inhibitors of IDO1 and TDO2 can be used to activate T cells and therefore enhance T cell activation when the T cells are suppressed by pregnancy, malignancy or a virus such as HIV. Inhibition of IDO1 and/or TDO2 may also be an important treatment strategy for patients with neurological or neuropsychiatric diseases or disorders such as depression. The compounds, compositions and methods herein help meet the current need for IDO1 and TDO2 modulators.

In this disclosure, we describe novel structures related to imidazoisoindoles, with different electronic and heme binding properties, that can specifically inhibit IDO1 or TDO2, or that can exert combined inhibition of tryptophan degradation mediated by any of these enzymes.

In one aspect, the invention comprises compounds according to the formula (I),

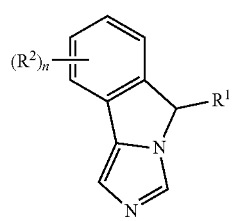

(I)

or a stereoisomer thereof, or a pharmaceutically acceptable salt thereof, wherein $R^1$ is $C_{1-6}$alkyl, $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—;

(b) when $R^1$ is $C_{1-6}$alkyl, $R^1$ is substituted with —$NR_2$ or —OH on the carbon atom bonded to the 5H-imidazo[5,1-a]isoindolyl; and (c) when $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In an embodiment, the invention provides compounds of formula (I), wherein $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—; and (b) when $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In an embodiment, the invention provides compounds of formula (I), wherein $R^1$ is $C_{3-10}$cycloalkyl, 3-7 membered heterocyclyl (e.g., a 4-6 membered heterocyclyl or a 5-6 membered heterocyclyl), wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—; and (b) when $R^1$ is $C_{3-10}$cycloalkyl, 3-7 membered heterocyclyl (e.g., a 4-6 membered heterocyclyl or a 5-6 membered heterocyclyl), $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In one embodiment of the compounds for Formula (I), $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl. In other embodiments, the invention comprises compounds of Formula (I) $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl and n is 0. In other embodiments, the invention comprises compounds of Formula (I) $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl and n is 1.

In an embodiment, the invention comprises compounds of Formula (II), (II)

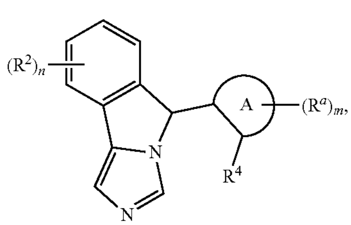

which are compounds of Formula (I) wherein $R^1$ is

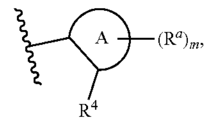

ring A is $C_{3-10}$cycloalkyl or 3-7 membered heterocyclyl;

m is 0, 1, 2, 3 or 4; and $R^4$ is —$NR_2$ or —OR.

In one embodiment, the invention comprises compounds of Formula (II) wherein $R^4$ is —OH. In other embodiments, $R^4$ is —OH and n is 0. In other embodiments, $R^4$ is —OH and n is 1.

In another embodiment, the invention comprises compounds of Formula (III), (III)

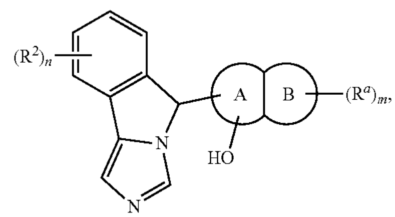

which are compounds of Formula (I) wherein $R^1$ is

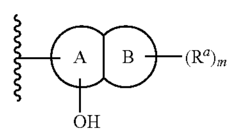

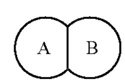

is a fused bicyclic ring system consisting of a ring A and a ring B;

ring A is $C_{3-8}$cycloalkyl or 3-7 membered heterocyclyl;

ring B is aryl, heteroaryl, $C_{3-7}$cycloalkyl or 3-7 membered heterocyclyl;

m is 0, 1, 2, 3 or 4; and the hydroxy moiety is bonded to the A ring and each $R^a$ is independently a substituent of the A ring or the B ring.

In one embodiment, the invention comprises compounds of Formula (III) wherein n is 0. In other embodiments, n is 1.

In another embodiment, the invention comprises compounds of Formula (IV), (IV)

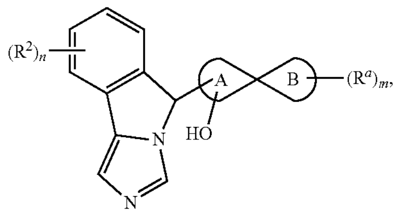

which are compounds of Formula (I) wherein $R^1$ is

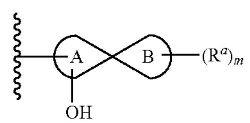

ring A and ring B form a spirocyclic system, ring A is $C_{3-8}$cycloalkyl or 3-7 membered heterocyclyl;

ring Bis $C_{3-7}$cycloalkyl,3-7 membered heterocyclyl, aryl or heteroaryl;

m is 0, 1, 2, 3 or 4; and the hydroxy moiety is bonded to the A ring and each $R^a$ is independently a substituent of the A ring or the B ring.

In one embodiment, the invention comprises compounds of Formula (IV) wherein n is 0. In other embodiments, n is 1.

In an embodiment, the invention comprises compounds of Formula (V), (V)

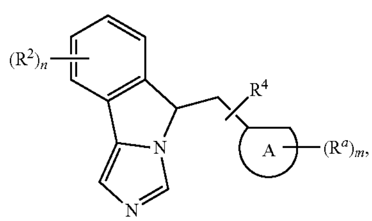

which are compounds of Formula (I) wherein $R^1$ is

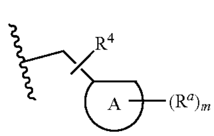

ring A is $C_{3-10}$cycloalkyl, 3-7 membered heterocyclyl or heteroaryl and $R^4$ is a substituent on the A ring or the methylene bonded to the A ring;

m is 0, 1, 2, 3 or 4; and $R^4$ is —$NR_2$ or —OR.

In one embodiment, the invention comprises compounds of Formula (V) wherein $R^4$ is —OH. In other embodiments, $R^4$ is —OH and n is 0. In other embodiments, $R^4$ is —OH and n is 1.

In another aspect, pharmaceutical compositions are provided comprising a pharmaceutically acceptable excipient, diluent, or carrier, and a compound according to formula (I), (II), (III), (IV) or (V).

In another aspect, pharmaceutical compositions are provided comprising a pharmaceutically acceptable excipient, diluent, or carrier, a compound according to formula (I), (II), (III), (IV) or (V), and a second therapeutic agent.

In another aspect, a kit is provided comprising a pharmaceutically acceptable excipient, diluent, or carrier, a compound according to formula (I), (II), (III), (IV) or (V), and a second therapeutic agent.

In another aspect methods are provided for a) modulating an activity of IDO1 or TDO2 in a cell-free system or in a cell (ex vivo or in vivo) comprising contacting an IDO1 or TDO2 with a modulation effective amount of a compound according to formula (I), or a pharmaceutical composition comprising a compound according to formula (I);

b) treating IDO1 or TDO2 mediated immunosuppression in a subject in need thereof, comprising administering an effective inhibiting amount of a compound according to formula (I), or a pharmaceutical composition comprising a compound according to formula (I);

c) treating a medical condition that benefits from the inhibition of tryptophan degradation mediated by IDO1 and/or TDO2 comprising administering an effective amount of a compound of formula (I), or a pharmaceutical composition comprising a compound according to formula (I);

d) enhancing the effectiveness of an anti-cancer treatment comprising administering an anti-cancer agent and a compound according to formula (I), or a pharmaceutical composition comprising a compound according to formula (I); and e) treating immunosuppression associated with cancer comprising administering an effective amount of a compound according to formula (I), or a pharmaceutical composition comprising a compound according to formula (I).

In another aspect, the invention comprises use of any genus of compounds or species defined herein for the manufacture of a medicament for the treatment of medical conditions that benefit from the inhibition of enzymatic activity of IDO1 or TDO2.

In another aspect, the invention comprises any genus of compounds or species defined herein for use in the inhibition of enzymatic activity of IDO1 or TDO2 and the treatment of medical conditions that benefit from the inhibition of enzymatic activity of IDO1 or TDO2.

In another aspect, the invention comprises use of any genus of compounds or species defined herein for the treatment of immunosuppression associated with cancer, infectious diseases, or viral infections.

DETAILED DESCRIPTION OF THE INVENTION

The purpose of the present invention to develop small molecules that inhibit the enzymatic activity of TDO2. Alignment between IDO1 and IDO2 amino acid sequences reveals highly conserved features that mediate heme and substrate binding. Even though the amino acid sequence identity between IDO1 and IDO2 or IDO1 and TDO2 are not particularly high, significant residues determined to be important for catalytic activity by IDO1 and TDO2 mutagenesis and by crystallographic analysis are highly conserved between IDO1, IDO2 and TDO2, suggesting a structural and functional analogy in the mechanism of tryophan dioxygenation. Despite these structural similarities at the active site, IDO1 and TDO2 have different substrate specificity with TDO2 being almost exclusively specific for L-Trp and L-Trp derivatives substituted at the 5- and 6-positions of the indole group, while IDO1 can accept and oxygenate a wider variety of substrates such as D-Trp, tryptamine, serotonin and 1-methyl-L-Trp. These minor structural differences in the active site of IDO1 and TDO2 determine that these two proteins show differential response to the same enzymatic inhibitor molecules, with some inhibitors showing TDO2-specific response, others showing IDO1-specific response and some showing dual IDO1 and TDO2 inhibition. Moreover, the specificity of IDO1 and TDO2 inhibition by a particular class of small molecule inhibitors depends on whether IDO1 and TDO2 activity is measured using bioassays that employ recombinant purified IDO1 or TDO2 protein, or IDO1 or TDO2 protein expressed within a cell. For example, compounds described in patent applications WO2012142237 and WO2014159248 show potent IDO1 inhibition when tested against the purified recombinant protein and against cellularly expressed IDO1, or against recombinant purified TDO2 protein. However, compounds of that class show a remarkable 10-100 fold decreased potency when tested against TDO2 expressed within a cell. Therefore, those compounds are not likely to contribute to significant inhibition of TDO2 in vivo. For this reason, the present invention describes a novel class of molecules that show potent TDO2 inhibition in cellular bioassays and in vivo.

In one aspect, the invention provides compounds of formula (I), (I)

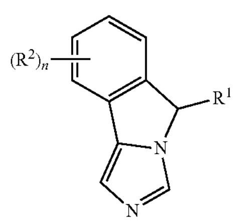

or a stereoisomer thereof, or a pharmaceutically acceptable salt thereof, wherein $R^1$ is $C_{1-6}$alkyl, $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—;

(b) when $R^1$ is $C_{1-6}$alkyl, $R^1$ is substituted with —$NR_2$ or —OH on the carbon atom bonded to the 5H-imidazo[5,1-a]isoindolyl; and (c) when $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In one embodiment, the invention provides compounds of formula (I), wherein $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—;

(b) when $R^1$ is $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or a -$C_1$alkyl-heteroaryl, $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In another embodiment, the invention provides compounds of formula (I), wherein $R^1$ is $C_{3-10}$cycloalkyl or 3-7 membered heterocyclyl (e.g., a 4-6 membered heterocyclyl or a 5-6 membered heterocyclyl), wherein the $C_{3-10}$cycloalkyl or 3-7 membered heterocyclyl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N$(R)_2$, —C(O)R, —S(O)R, —S(O)OR, —S(O)N$(R)_2$, —S$(O)_2$R, —S$(O)_2$OR, —S$(O)_2$N$(R)_2$, —OC(O)R, —OC(O)OR, —OC(O)N$(R)_2$, —N(R)C(O)R, —N(R)C(O)OR, and —N(R)C(O)N$(R)_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is 3-7 membered heterocyclyl (e.g., a 4-6 membered heterocyclyl or a 5-6 membered heterocyclyl), no member of the 3-7 membered heterocyclyl is an —NH—; and (b) when $R^1$ is $C_{3-10}$cycloalkyl, 3-7 membered heterocyclyl (e.g., a 4-6 membered heterocyclyl or a 5-6 membered heterocyclyl), $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In another embodiment, the invention provides compounds of formula (I), (I)

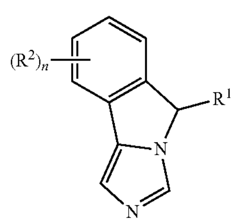

or a stereoisomer thereof, or a pharmaceutically acceptable salt thereof, wherein $R^1$ is —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, wherein the $C_{3-10}$cycloalkyl, 3-7 membered heterocyclyl or heteroaryl is optionally fused to aryl, heteroaryl, $C_{3-8}$cycloalkyl or 3-7 membered heterocyclyl; or wherein the $C_{3-10}$cycloalkyl or 3-7 membered heterocyclyl is optionally substituted by =(spiro-$C_{3-7}$cycloalkyl) or =(spiro-(3-7 membered heterocyclyl));

wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N$(R)_2$, —C(O)R, —S(O)R, —S(O)OR, —S(O)N$(R)_2$, —S$(O)_2$R, —S$(O)_2$OR, —S$(O)_2$N$(R)_2$, —OC(O)R, —OC(O)OR, —OC(O)N$(R)_2$, —N(R)C(O)R, —N(R)C(O)OR, and —N(R)C(O)N$(R)_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is independently hydrogen, $C_{1-6}$alkyl or $C_{1-6}$haloalkyl;

provided that (a) when $R^1$ is —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl, $R^1$ is substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In one embodiment of the compounds for Formula (I), $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl. In other embodiments, the invention comprises compounds of Formula (I) $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl and n is 0. In other embodiments, the invention comprises compounds of Formula (I) $R^1$ is substituted with —OH on the carbon atom bonded to the 5H-imidazo[5,1-a]isoindolyl, or on a carbon atom adjacent to the carbon atom bonded to the 5H-imidazo[5,1-a]isoindolyl and n is 1.

The invention further comprises subgenera and species of formula (I) that are any combination of species and genera of structural formula (I), n, $R^1$, and $R^2$, as defined herein below. So, for example, the invention also comprises the subgenus of compounds of structural formula (I) where n is defined as in (1c) below, $R^1$ is defined in (2h) below, and $R^2$ is defined in (3k) below.

n is selected from one of the following groups (1a)-(1k):

(1a) n is 1, 2, 3, or 4.

(1b) n is 0, 1, 2, or 3.

(1c) n is 0, 1, or 2.

(1d) n is 0 or 1.

(1e) n is 1 or 2.

(1f) n is 2 or 3.

(1g) n is 1.

(1h) n is 2.

(1i) nis 3.

(1j) n is 4.

(1k) n is 0.

$R^2$ is selected from one of the following groups (2a)-(2t):

(2a) $R^2$ is independently halogen, cyano, $C_{1-6}$alkyl, $C_3$cycloalkyl, —$C_{1-6}$haloalkyl, —OR, or —$NR_2$.

(2b) $R^2$ is independently halogen, cyano, $C_{1-6}$alkyl, $C_3$cycloalkyl, —OR, or —$NR_2$.

(2c) $R^2$ is independently halogen, cyano, $C_{1-6}$alkyl, $C_3$cycloalkyl, or —OR.

(2d) $R^2$ is independently halogen, $C_{1-6}$alkyl, $C_3$cycloalkyl, or —OR.

(2e) $R^2$ is independently halogen, cyano, $C_{1-6}$alkyl, or —OR.

(2f) $R^2$ is independently halogen, $C_{1-6}$alkyl or —OR.

(2g) $R^2$ is independently halogen or —OR.

(2h) $R^2$ is independently $C_{1-6}$alkyl or —OR.

(2i) $R^2$ is independently-OR.

(2j) $R^2$ is independently halogen, methyl or —OR.

(2k) $R^2$ is independently halogen, methyl, —OH or —OMe.

(2i) $R^2$ is independently chloro, fluoro, methyl or —OR.

(2m) $R^2$ is independently chloro, fluoro, methyl, —OH or —OMe.

(2n) $R^2$ is independently chloro, fluoro, methyl or —OH.

(2o) $R^2$ is independently fluoro, methyl or —OH.

(2p) $R^2$ is independently fluoro or —OH.

(2q) $R^2$ is independently fluoro or methyl.

(2r) $R^2$ is fluoro.

(2s) $R^2$ is methyl.

(2t) $R^2$ is —OH.

$R^1$ is selected from one of the following groups (3a)-(3cccc):

(3a) $R^1$ is $C_{3-10}$cycloalkyl or 3-7 membered heterocyclyl (e.g., a 4-6 membered heterocyclyl or a 5-6 membered heterocyclyl),
wherein the $C_{3-10}$cycloalkyl or 3-7 membered heterocyclyl is optionally fused to aryl, heteroaryl, $C_{3-7}$cycloalkyl or 3-7 membered heterocyclyl; or
wherein the $C_{3-10}$cycloalkyl or 3-7 membered heterocyclyl is optionally substituted by =(spiro-$C_{3-7}$cycloalkyl) or =(spiro-(3-7 membered heterocyclyl));
wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$.

(3b) Group (3a), wherein $R^1$ is $C_{4-6}$cycloalkyl or 5-6 membered heterocyclyl,
wherein the $C_{4-6}$cycloalkyl or 5-6-membered heterocyclyl is optionally fused to aryl or heteroaryl; or
wherein the $C_{4-6}$cycloalkyl is optionally substituted by =(spiro-$C_4$cycloalkyl) or =(spiro-(4-membered heterocyclyl)).

(3c) Group (3a), wherein $R^1$ is $C_{4-6}$cycloalkyl or 5-6 membered heterocyclyl,
wherein the $C_{4-6}$cycloalkyl or 5-6 membered heterocyclyl is optionally fused to aryl or heteroaryl; or
wherein the $C_{4-6}$cycloalkyl or 5-6 membered heterocyclyl is optionally substituted by =(spiro-$C_4$cycloalkyl) or =(spiro-(4-membered heterocyclyl)).

(3d) Group (3a), wherein $R^1$ is cyclobutyl, cyclopentyl, cyclohexyl, pyrrolidinyl or piperidinyl,
wherein the cyclopentyl is optionally fused to phenyl, the cyclohexyl is optionally fused to pyridinyl or phenyl, and the piperidinyl is optionally fused to pyrrolidinyl or phenyl; or
wherein the cyclobutyl is optionally substituted by =(spiro-cyclobutyl) or =(spiro-azetidinyl).

(3e) Group (3a), wherein $R^1$ is $C_{3-10}$cycloalkyl or 3-7 membered heterocyclyl.

(3f) Group (3a), wherein $R^1$ is $C_{3-10}$cycloalkyl.

(3g) Group (3a), wherein $R^1$ is $C_{5-8}$bridged bicyclic.

(3h) Group (3a), wherein $R^1$ is cyclobutyl or cyclopentyl.

(3i) Group (3a), wherein $R^1$ is cyclobutyl.

(3j) Group (3a), wherein $R^1$ is cyclopentyl.

(3k) Group (3a), wherein $R^1$ is 3-7 membered heterocyclyl.

(3l) Group (3a), wherein $R^1$ is pyrrolidinyl or piperdinyl.

(3m) Group (3a), wherein $R^1$ is pyrrolidinyl.

(3n) Group (3a), wherein $R^1$ is piperdinyl.

(3o) Group (3a), wherein $R^1$ is $C_{3-8}$cycloalkyl or 3-7 membered heterocyclyl (e.g., a 4-6 membered heterocyclyl or a 5-6 membered heterocyclyl), wherein the $C_{3-8}$cycloalkyl or 3-7 membered heterocyclyl is fused to aryl, heteroaryl, $C_{3-7}$cycloalkyl or 3-7 membered heterocyclyl.

(3p) Group (3a), wherein $R^1$ is $C_{3-8}$cycloalkyl,
wherein the $C_{3-8}$cycloalkyl is fused to aryl, heteroaryl, $C_{3-7}$cycloalkyl or 3-7 membered heterocyclyl.

(3q) Group (3a), wherein $R^1$ is $C_{3-8}$cycloalkyl,
wherein the $C_{3-8}$cycloalkyl is fused to heteroaryl, $C_{3-7}$cycloalkyl or 3-7 membered heterocyclyl.

(3r) Group (3a), wherein $R^1$ is $C_{3-8}$cycloalkyl, wherein the $C_{3-8}$cycloalkyl is fused to aryl, $C_{3-7}$cycloalkyl or 3-7 membered heterocyclyl.

(3s) Group (3a), wherein $R^1$ is $C_{3-8}$cycloalkyl, wherein the $C_{3-8}$cycloalkyl is fused to aryl, heteroaryl, or 3-7 membered heterocyclyl.

(3t) Group (3a), wherein $R^1$ is $C_{3-8}$cycloalkyl, wherein the $C_{3-8}$cycloalkyl is fused to aryl, heteroaryl or $C_{3-7}$cycloalkyl.

(3u) Group (3a), wherein $R^1$ is $C_{3-8}$cycloalkyl, wherein the $C_{3-8}$cycloalkyl is fused to aryl.

(3v) Group (3a), wherein $R^1$ is $C_{3-8}$cycloalkyl, wherein the $C_{3-8}$cycloalkyl is fused to heteroaryl.

(3w) Group (3a), wherein $R^1$ is $C_{3-8}$cycloalkyl, wherein the $C_{3-8}$cycloalkyl is fused to $C_{3-7}$cycloalkyl.

(3x) Group (3a), wherein $R^1$ is $C_{3-8}$cycloalkyl, wherein the $C_{3-8}$cycloalkyl is fused to 3-7 membered heterocyclyl.

(3y) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl, $C_{3-7}$cycloalkyl or 3-7 membered heterocyclyl.

(3z) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to heteroaryl, $C_{3-7}$cycloalkyl or 3-7 membered heterocyclyl.

(3aa) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, $C_{3-7}$cycloalkyl or 3-7 membered heterocyclyl.

(3bb) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl, or 3-7 membered heterocyclyl.

(3cc) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl or $C_{3-7}$cycloalkyl.

(3dd) Group (3a), wherein $R^1$ is 3-7 membered heterocyclyl (e.g., a 4-6 membered heterocyclyl or a 5-6 membered heterocyclyl), wherein the 3-7 membered heterocyclyl is fused to aryl.

(3ee) Group (3a), wherein $R^1$ is 3-7 membered heterocyclyl (e.g., a 4-6 membered heterocyclyl or a 5-6 membered heterocyclyl), wherein the 3-7 membered heterocyclyl is fused to heteroaryl.

(3ff) Group (3a), wherein $R^1$ is 3-7 membered heterocyclyl (e.g., a 4-6 membered heterocyclyl or a 5-6 membered heterocyclyl), wherein the 3-7 membered heterocyclyl is fused to $C_{3-7}$cycloalkyl.

(3gg) Group (3a), wherein $R^1$ is 3-7 membered heterocyclyl (e.g., a 4-6 membered heterocyclyl or a 5-6 membered heterocyclyl), wherein the 3-7 membered heterocyclyl is fused to 3-7 membered heterocyclyl.

(3hh) Group (3a), wherein $R^1$ is $C_{3-10}$cycloalkyl or 3-7 membered heterocyclyl (e.g., a 4-6 membered heterocyclyl or a 5-6 membered heterocyclyl), wherein the $C_{3-7}$cycloalkyl or 3-7 membered heterocyclyl is substituted by =(spiro-$C_{3-8}$cycloalkyl) or =(spiro-(3-7 membered heterocyclyl)).

(3ii) Group (3a), wherein $R^1$ is $C_{3-8}$cycloalkyl, wherein the $C_{3-8}$cycloalkyl is substituted by =(spiro-$C_{3-7}$cycloalkyl).

(3jj) Group (3a), wherein $R^1$ is $C_{3-8}$cycloalkyl, wherein the $C_{3-8}$cycloalkyl is substituted by =(spiro-(3-7 membered heterocyclyl)).

(3kk) Group (3a), wherein $R^1$ is 3-7 membered heterocyclyl (e.g., a 4-6 membered heterocyclyl or a 5-6 membered heterocyclyl), wherein the 3-7 membered heterocyclyl is substituted by =(spiro-$C_{3-7}$cycloalkyl).

(3ll) Group (3a), wherein $R^1$ is 3-7 membered heterocyclyl (e.g., a 4-6 membered heterocyclyl or a 5-6 membered heterocyclyl), wherein the 3-7 membered heterocyclyl is substituted by =(spiro-(3-7 membered heterocyclyl)).

(3mm) Any of groups (3b)-(3ll), wherein $R^1$ is substituted by at least one $R^a$ group selected from —OR and —$NR_2$.

(3nn) Any of groups (3b)-(3ll), wherein $R^1$ is substituted by at least one $R^a$ group selected from —OR.

(3oo) Any of groups (3b)-(3ll), wherein $R^1$ is substituted by at least one $R^a$ group selected from —$NR_2$.

(3pp) Any of groups (3b)-(3oo), wherein $R^1$ is substituted by one, two or three $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N$(R)_2$, —C(O)R, —S(O)R, —S(O)OR, —S(O)N$(R)_2$, —$S(O)_2$R, —$S(O)_2$OR, —$S(O)_2$N$(R)_2$, —OC(O)R, —OC(O)OR, —OC(O)N$(R)_2$, —N(R)C(O)R, —N(R)C(O)OR, and —N(R)C(O)N$(R)_2$.

(3qq) Any of groups (3b)-(3oo), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —OR, —$NR_2$, —$S(O)_2$R, —$S(O)_2$OR, —$S(O)_2$N$(R)_2$, —OC(O)R, —OC(O)OR, —OC(O)N$(R)_2$, —N(R)C(O)R, —N(R)C(O)OR, and —N(R)C(O)N$(R)_2$.

(3rr) Any of groups (3b)-(3oo), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —OR, —S(O)R, —S(O)OR, —S(O)N$(R)_2$, —$S(O)_2$R, —$S(O)_2$OR, —$S(O)_2$N$(R)_2$, —OC(O)R, —OC(O)OR and —OC(O)N$(R)_2$.

(3ss) Any of groups (3b)-(3oo), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —OR, —S(O)R, —S(O)OR, —S(O)N$(R)_2$, —$S(O)_2$R, —$S(O)_2$OR, —$S(O)_2$N$(R)_2$, —N(R)C(O)R, —N(R)C(O)OR, and —N(R)C(O)N$(R)_2$.

(3tt) Any of groups (3b)-(3oo), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —OR, —$S(O)_2$R, —$S(O)_2$OR and —$S(O)_2$N$(R)_2$.

(3uu) Any of groups (3b)-(3oo), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —OR, —$S(O)_2$R, —$S(O)_2$OR and —$S(O)_2$N$(R)_2$.

(3vv) Any of groups (3b)-(3oo), wherein $R^1$ is substituted by one, two or three $R^a$ groups independently selected from $C_{1-6}$alkyl, —OR, —$S(O)_2$R, —$S(O)_2$OR and —$S(O)_2$N$(R)_2$.

(3ww) Any of groups (3b)-(3oo), wherein $R^1$ is substituted by one, two or three $R^a$ groups independently selected from oxo, halogen, $C_{1-6}$alkyl, —OR, —$S(O)_2$R, —$S(O)_2$OR and —$S(O)_2$N$(R)_2$.

(3xx) Any of groups (3b)-(3oo), wherein $R^1$ is substituted by one, two or three $R^a$ groups independently selected from oxo, halogen, $C_{1-6}$alkyl, —OR, —$S(O)_2$R and —$S(O)_2$N$(R)_2$.

(3yy) Any of groups (3b)-(3oo), wherein $R^1$ is substituted by one, two or three $R^a$ groups independently selected from $C_{1-6}$alkyl, —OR, —$S(O)_2$R and —$S(O)_2$N$(R)_2$.

(3zz) Any of groups (3b)-(3oo), wherein $R^1$ is substituted by one or two $R^a$ groups independently selected from $C_{1-6}$alkyl, —OR, —$S(O)_2$R and —$S(O)_2$N$(R)_2$.

(3aaa) Any of groups (3b)-(3oo), wherein $R^1$ is substituted by one or two $R^a$ groups independently selected from $C_{1-6}$alkyl, —OR and —$S(O)_2$N$(R)_2$.

(3bbb) Any of groups (3b)-(3oo), wherein $R^1$ is substituted by one or two $R^a$ groups independently selected from $C_{1-6}$alkyl, —OR and —$S(O)_2$R.

(3ccc) Any of groups (3b)-(3oo), wherein $R^1$ is substituted by one or two $R^a$ groups independently selected from $C_{1-6}$alkyl and —OR.

(3ddd) Any of groups (3b)-(3oo), wherein $R^1$ is substituted by one or two $R^a$ groups independently selected from methyl, ethyl, propyl, -iso-propyl, —OMe and —OH.

(3eee) Any of groups (3b)-(3oo), wherein $R^1$ is substituted by one or two $R^a$ groups independently selected from methyl and ethyl.

(3fff) Any of groups (3b)-(3oo), wherein $R^1$ is substituted by one $R^a$ group independently selected from $C_{1-6}$alkyl, —OR, —$S(O)_2$R and —$S(O)_2$N$(R)_2$.

(3ggg) Any of groups (3b)-(3oo), wherein $R^1$ is substituted by one $R^a$ group independently selected from $C_{1-6}$alkyl, —OR and —$S(O)_2$N$(R)_2$.

(3hhh) Any of groups (3b)-(3oo), wherein $R^1$ is substituted by one $R^a$ group independently selected from $C_{1-6}$alkyl, —OR and —$S(O)_2$R.

(3iii) Any of groups (3b)-(3oo), wherein $R^1$ is substituted by one $R^a$ group independently selected from $C_{1-6}$alkyl and —OR.

(3jjj) Any of groups (3b)-(3oo), wherein $R^1$ is substituted by one $R^a$ group independently selected from methyl, ethyl, propyl, -iso-propyl, —OMe and —OH.

(3kkk) Any of groups (3b)-(3oo), wherein $R^1$ is substituted by one $R^a$ group independently selected from methyl and ethyl.

(3lll) Any of groups (3b)-(3oo), wherein $R^1$ is substituted by one methyl group.

(3mmm) Any of groups (3b)-(3oo), wherein $R^1$ is substituted by one ethyl group.

(3nnn) $R^1$ is $C_{1-6}$alkyl, $C_{3-10}$cycloalkyl, 3-7 membered heterocyclyl (e.g., a 4-6 membered heterocyclyl or a 5-6 membered heterocyclyl), —$C_1$alkyl-$C_{3-10}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl
 wherein the $C_{3-10}$cycloalkyl or 3-7 membered heterocyclyl is optionally fused to aryl, heteroaryl, $C_{3-7}$cycloalkyl or 3-7 membered heterocyclyl; or
 wherein the $C_{3-10}$cycloalkyl or 3-7 membered heterocyclyl is optionally substituted by =(spiro-$C_{3-7}$cycloalkyl) or =(spiro-(3-7 membered heterocyclyl));
 wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N$(R)_2$, —C(O)R, —S(O)R, —S(O)OR, —S(O)N$(R)_2$, —$S(O)_2$R, —$S(O)_2$OR, —$S(O)_2$ N$(R)_2$, —OC(O)R, —OC(O)OR, —OC(O)N$(R)_2$, —N(R)C(O)R, —N(R)C(O)OR, and —N(R)C(O)N $(R)_2$.

(3ooo) Group (3nnn), wherein $R^1$ is $C_{1-6}$alkyl, $C_{4-6}$cycloalkyl or 5-6 membered heterocyclyl,
 wherein the $C_{4-6}$cycloalkyl or 5-6-membered heterocyclyl is optionally fused to aryl or heteroaryl; or
 wherein the $C_4$cycloalkyl is optionally substituted by =(spiro-$C_4$cycloalkyl) or =(spiro-(4-membered heterocyclyl)).

(3ppp) Group (3nnn), wherein $R^1$ is $C_{1-6}$alkyl, $C_{4-6}$cycloalkyl or 5-6 membered heterocyclyl,
 wherein the $C_{4-6}$cycloalkyl or 5-6 membered heterocyclyl is optionally fused to aryl or heteroaryl; or
 wherein the $C_{4-6}$cycloalkyl or 5-6 membered heterocyclyl is optionally substituted by =(spiro-$C_4$cycloalkyl) or =(spiro-(4-membered heterocyclyl)).

(3qqq) Group (3nnn), wherein $R^1$ is $C_{1-6}$alkyl.

(3rrr) Group (3nnn), wherein $R^1$ is methyl, ethyl, propyl, butyl, pentyl or hexyl.

(3sss) Group (3nnn), wherein $R^1$ is methyl, ethyl, propyl or butyl.

(3ttt) Group (3nnn), wherein $R^1$ is methyl, ethyl or butyl.

(3uuu) Group (3nnn), wherein $R^1$ is methyl or ethyl.

(3vvv) Group (3nnn), wherein $R^1$ is methyl.

(3www) Group (3nnn), wherein $R^1$ is ethyl.

(3xxx) Group (3nnn), wherein $R^1$ is butyl.

(3yyy) Any of groups (3nnn)-(3xxx), wherein $R^1$ is substituted by one or two $R^a$ groups independently selected from halogen, $C_{1-6}$alkyl, —$C_{1-6}$haloalkyl, $C_3$cycloalkyl or —OR.

(3zzz) Any of groups (3nnn)-(3xxx), wherein $R^1$ is substituted by $C_3$cycloalkyl and —OH.

(3aaaa) Any of groups (3nnn)-(3xxx), wherein $R^1$ is substituted by one or two —OH.

(3bbbb) Any of groups (3nnn)-(3xxx), wherein $R^1$ is substituted by one —OH.

(3cccc) Any of groups (3nnn)-(3xxx), wherein $R^1$ is substituted by two —OH.

The invention further comprises subgenera and species of formula (I) that are any combination of species and genera of structural formula (I) can be any of formula (Ia)-(Ii) wherein n, $R^2$ and $R^1$ are defined above. So, for example, the invention also comprises the subgenus of compounds of structural formula (Ie) where n is defined as in (1g) above, and $R^2$ is defined in (2r) above.

Structural Formula I is One of Formulae (Ia)-(Ii):

(Ia)

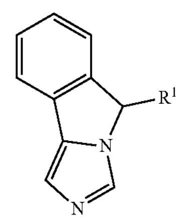

(Ib)

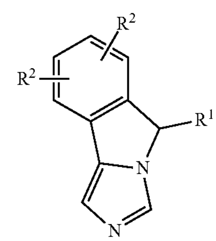

(Ic)

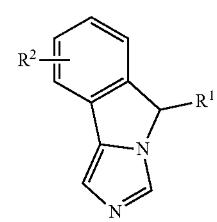

(Id)

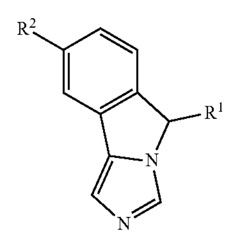

(Ie)

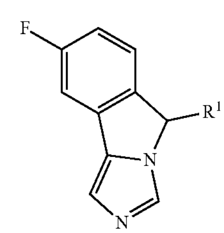

-continued (If)

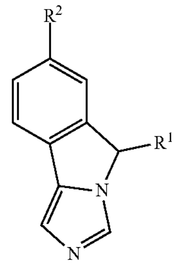

(Ig)

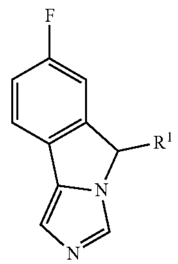

(Ih)

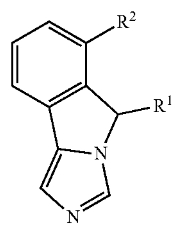

(Ii)

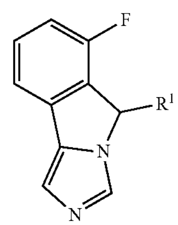

Particular embodiments of this aspect of the invention include compounds of any one of the formulae (I) and (Ia)-(Ii), each as defined in each of the following rows, wherein each entry is a group number as defined above (e.g., (2r) refers to $R^2$ is fluoro), an "X" indicates that the variable is defined by another group in the embodiment (e.g., in embodiment (1)-X below, $R^1$ is defined in Formula (X)) and a dash "-" indicates that the variable is as defined for Formula (I) or (Ia)-(Ii) or defined according to any one of the applicable variable definitions (1a)-(3cccc) [e.g., when the entry for $R^2$ is a dash, it can be either as defined for Formula (I)—(IVi) or any one of definitions (2a)-(2t)]:

| | (I) | n | $R^2$ | $R^1$ |
|---|---|---|---|---|
| (1)-1 | (I) | (1a) | (2a) | (3e) |
| (1)-2 | (I) | (1a) | (2b) | (3f) |
| (1)-3 | (I) | (1a) | (2f) | (3k) |
| (1)-4 | (I) | (1a) | (2h) | (3u) |
| (1)-5 | (I) | (1a) | (2k) | (3v) |
| (1)-6 | (I) | (1a) | (2n) | (3e) |
| (1)-7 | (I) | (1b) | (2a) | (3ee) |
| (1)-8 | (I) | (1b) | (2b) | (3ii) |
| (1)-9 | (I) | (1b) | (2f) | (3jj) |
| (1)-10 | (I) | (1b) | (2h) | (3kk) |
| (1)-11 | (I) | (1b) | (2k) | (3ll) |
| (1)-12 | (I) | (1b) | (2n) | (3mm) |
| (1)-13 | (I) | (1c) | — | (3nn) |
| (1)-14 | (I) | (1c) | (2b) | (3oo) |
| (1)-15 | (I) | — | (2f) | (3e) |
| (1)-16 | (I) | (1c) | (2h) | (3f) |
| (1)-17 | (I) | (1c) | (2k) | (3k) |
| (1)-18 | (I) | (1c) | (2n) | (3u) |
| (1)-19 | (I) | (1e) | (2a) | (3mm) |
| (1)-20 | (I) | (1e) | — | (3nn) |
| (1)-21 | (I) | (1e) | (2f) | (3oo) |
| (1)-22 | (I) | (1e) | (2h) | (3kk) |
| (1)-23 | (I) | (1e) | (2k) | (3e) |
| (1)-24 | (I) | (1e) | (2n) | (3f) |
| (1)-25 | (I) | (1f) | (2a) | (3k) |
| (1)-26 | (I) | (1f) | (2b) | (3u) |
| (1)-27 | (I) | (1f) | (2f) | (3nn) |
| (1)-28 | (I) | — | (2h) | (3oo) |
| (1)-29 | (I) | (1f) | (2k) | (3v) |
| (1)-30 | (I) | (1f) | — | (3e) |
| (1)-31 | (Ia) | X | X | (3ee) |
| (1)-32 | (Ia) | X | X | (3ii) |
| (1)-33 | (Ia) | X | X | (3jj) |
| (1)-34 | (Ia) | X | X | (3kk) |
| (1)-35 | (Ia) | X | X | (3mm) |
| (1)-36 | (Ia) | X | X | (3nn) |
| (1)-37 | (Ia) | X | X | (3f) |
| (1)-38 | (Ia) | X | X | (3k) |
| (1)-39 | (Ia) | X | X | (3u) |
| (1)-40 | (Ia) | X | X | (3k) |
| (1)-41 | (Ia) | X | X | (3u) |
| (1)-42 | (Ia) | X | X | (3v) |
| (1)-43 | (Ia) | X | X | (3e) |
| (1)-44 | (Ia) | X | X | (3ee) |
| (1)-45 | (Ia) | X | X | (3e) |
| (1)-46 | (Ia) | X | X | (3f) |
| (1)-47 | (Ia) | X | X | — |
| (1)-48 | (Ia) | X | X | (3u) |
| (1)-49 | (Ia) | X | X | (3mm) |
| (1)-50 | (Ia) | X | X | (3nn) |
| (1)-51 | (Ia) | X | X | (3oo) |
| (1)-52 | (Ia) | X | X | (3mm) |
| (1)-53 | (Ia) | X | X | (3nn) |
| (1)-54 | (Ia) | X | X | (3u) |
| (1)-55 | (Ia) | X | X | (3v) |
| (1)-56 | (Ia) | X | X | (3e) |
| (1)-57 | (Ia) | X | X | (3ee) |
| (1)-58 | (Ia) | X | X | — |
| (1)-59 | (Ia) | X | X | (3f) |
| (1)-60 | (Ib) | X | (2a) | (3k) |
| (1)-61 | (Ib) | X | (2b) | (3u) |
| (1)-62 | (Ib) | X | (2f) | (3kk) |
| (1)-63 | (Ib) | X | (2h) | (3mm) |
| (1)-64 | (Ib) | X | (2k) | (3nn) |
| (1)-65 | (Ib) | X | (2n) | (3u) |
| (1)-66 | (Ib) | X | (2a) | (3v) |
| (1)-67 | (Ib) | X | (2b) | (3e) |
| (1)-68 | (Ib) | X | — | (3ee) |
| (1)-69 | (Ib) | X | (2h) | (3mm) |
| (1)-70 | (Ib) | X | (2k) | (3nn) |
| (1)-71 | (Ib) | X | (2n) | (3f) |
| (1)-72 | (Ib) | X | (2b) | — |
| (1)-73 | (Ib) | X | (2f) | (3u) |
| (1)-74 | (Ib) | X | (2h) | (3jj) |
| (1)-75 | (Ib) | X | (2b) | (3kk) |
| (1)-76 | (Ib) | X | (2f) | (3u) |
| (1)-77 | (Ib) | X | (2h) | — |
| (1)-78 | (Ib) | X | (2b) | (3e) |
| (1)-79 | (Ib) | X | (2f) | (3ee) |
| (1)-80 | (Ib) | X | (2h) | (3e) |
| (1)-81 | (Ib) | X | (2a) | (3f) |
| (1)-82 | (Ib) | X | (2b) | (3k) |
| (1)-83 | (Ib) | X | (2f) | (3u) |
| (1)-84 | (Ib) | X | (2h) | (3ll) |
| (1)-85 | (Ib) | X | (2k) | (3mm) |
| (1)-86 | (Ib) | X | — | (3nn) |
| (1)-87 | (Ib) | X | (2b) | (3oo) |
| (1)-88 | (Ib) | X | (2f) | (3u) |

-continued

| | (I) | n | $R^2$ | $R^1$ |
|---|---|---|---|---|
| (1)-89 | (Ib) | X | (2h) | (3v) |
| (1)-90 | (Ib) | X | (2b) | (3e) |
| (1)-91 | (Ic) | X | (2f) | (3ee) |
| (1)-92 | (Ic) | X | (2h) | — |
| (1)-93 | (Ic) | X | (2k) | (3nn) |
| (1)-94 | (Ic) | X | (2n) | (3kk) |
| (1)-95 | (Ic) | X | (2b) | (3ll) |
| (1)-96 | (Ic) | X | (2f) | (3mm) |
| (1)-97 | (Ic) | X | (2h) | (3nn) |
| (1)-98 | (Ic) | X | (2b) | (3oo) |
| (1)-99 | (Ic) | X | — | (3kk) |
| (1)-100 | (Ic) | X | (2f) | (3mm) |
| (1)-101 | (Ic) | X | (2h) | (3nn) |
| (1)-102 | (Ic) | X | (2a) | (3f) |
| (1)-103 | (Ic) | X | (2b) | (3k) |
| (1)-104 | (Ic) | X | (2f) | — |
| (1)-105 | (Ic) | X | (2h) | (3k) |
| (1)-106 | (Ic) | X | (2k) | (3u) |
| (1)-107 | (Ic) | X | (2n) | (3v) |
| (1)-108 | (Ic) | X | (2b) | (3e) |
| (1)-109 | (Ic) | X | (2f) | (3ee) |
| (1)-110 | (Ic) | X | (2h) | (3mm) |
| (1)-111 | (Ic) | X | (2b) | (3nn) |
| (1)-112 | (Ic) | X | (2f) | (3lll) |
| (1)-113 | (Ic) | X | (2h) | (3mm) |
| (1)-114 | (Ic) | X | (2k) | (3nn) |
| (1)-115 | (Ic) | X | (2n) | (3oo) |
| (1)-116 | (Ic) | X | (2a) | (3ii) |
| (1)-117 | (Ic) | X | (2b) | (3jj) |
| (1)-118 | (Ic) | X | (2f) | (3kk) |
| (1)-119 | (Ic) | X | (2h) | (3e) |
| (1)-120 | (Ic) | X | — | (3f) |
| (1)-121 | (Id) | X | (2n) | (3k) |
| (1)-122 | (Id) | X | (2f) | (3u) |
| (1)-123 | (Id) | X | (2h) | (3k) |
| (1)-124 | (Id) | X | (2k) | (3u) |
| (1)-125 | (Id) | X | (2n) | (3v) |
| (1)-126 | (Id) | X | (2k) | (3e) |
| (1)-127 | (Id) | X | (2n) | — |
| (1)-128 | (Id) | X | (2f) | (3e) |
| (1)-129 | (Id) | X | (2h) | (3f) |
| (1)-130 | (Id) | X | — | (3k) |
| (1)-131 | (Id) | X | (2n) | (3u) |
| (1)-132 | (Id) | X | (2a) | (3jj) |
| (1)-133 | (Id) | X | — | (3kk) |
| (1)-134 | (Id) | X | (2f) | — |
| (1)-135 | (Id) | X | (2h) | (3nn) |
| (1)-136 | (Id) | X | (2k) | (3jj) |
| (1)-137 | (Id) | X | (2n) | (3kk) |
| (1)-138 | (Id) | X | (2a) | (3k) |
| (1)-139 | (Id) | X | (2b) | (3u) |
| (1)-140 | (Id) | X | (2f) | (3v) |
| (1)-141 | (Id) | X | — | (3e) |
| (1)-142 | (Id) | X | (2k) | (3ee) |
| (1)-143 | (Id) | X | (2n) | (3mm) |
| (1)-144 | (Id) | X | (2a) | (3nn) |
| (1)-145 | (Id) | X | (2b) | (3e) |
| (1)-146 | (Id) | X | — | (3kk) |
| (1)-147 | (Id) | X | (2h) | (3ll) |
| (1)-148 | (Id) | X | (2k) | (3mm) |
| (1)-149 | (Id) | X | (2n) | (3nn) |
| (1)-150 | (Id) | X | (2n) | — |
| (1)-151 | (Ie) | X | X | (3v) |
| (1)-152 | (Ie) | X | X | (3e) |
| (1)-153 | (Ie) | X | X | (3ee) |
| (1)-154 | (Ie) | X | X | (3e) |
| (1)-155 | (Ie) | X | X | (3f) |
| (1)-156 | (Ie) | X | X | (3k) |
| (1)-157 | (Ie) | X | X | (3u) |
| (1)-158 | (Ie) | X | X | (3kk) |
| (1)-159 | (Ie) | X | X | (3ll) |
| (1)-160 | (Ie) | X | X | (3mm) |
| (1)-161 | (Ie) | X | X | (3nn) |
| (1)-162 | (Ie) | X | X | — |
| (1)-163 | (Ie) | X | X | (3ll) |
| (1)-164 | (Ie) | X | X | (3jj) |
| (1)-165 | (Ie) | X | X | (3kk) |

-continued

| | (I) | n | $R^2$ | $R^1$ |
|---|---|---|---|---|
| (1)-166 | (Ie) | X | X | (3mm) |
| (1)-167 | (Ie) | X | X | (3nn) |
| (1)-168 | (Ie) | X | X | (3ii) |
| (1)-169 | (Ie) | X | X | (3jj) |
| (1)-170 | (Ie) | X | X | (3kk) |
| (1)-171 | (Ie) | X | X | (3mm) |
| (1)-172 | (Ie) | X | X | (3nn) |
| (1)-173 | (Ie) | X | X | (3ll) |
| (1)-174 | (Ie) | X | X | — |
| (1)-175 | (Ie) | X | X | (3nn) |
| (1)-176 | (Ie) | X | X | (3oo) |
| (1)-177 | (Ie) | X | X | (3e) |
| (1)-178 | (Ie) | X | X | (3ee) |
| (1)-179 | (Ie) | X | X | (3mm) |
| (1)-180 | (Ie) | X | X | — |
| (1)-181 | (If) | X | (2a) | (3f) |
| (1)-182 | (If) | X | (2b) | (3k) |
| (1)-183 | (If) | X | — | (3u) |
| (1)-184 | (If) | X | (2h) | (3ll) |
| (1)-185 | (If) | X | (2k) | (3mm) |
| (1)-186 | (If) | X | (2n) | — |
| (1)-187 | (If) | X | (2f) | (3oo) |
| (1)-188 | (If) | X | — | (3kk) |
| (1)-189 | (If) | X | (2k) | (3e) |
| (1)-190 | (If) | X | (2n) | (3e) |
| (1)-191 | (If) | X | (2a) | (3f) |
| (1)-192 | (If) | X | (2b) | (3k) |
| (1)-193 | (If) | X | (2f) | (3u) |
| (1)-194 | (If) | X | (2h) | (3v) |
| (1)-195 | (If) | X | (2k) | (3e) |
| (1)-196 | (If) | X | (2n) | (3ee) |
| (1)-197 | (If) | X | (2f) | (3kk) |
| (1)-198 | (If) | X | (2h) | (3ll) |
| (1)-199 | (If) | X | (2k) | (3mm) |
| (1)-200 | (If) | X | (2n) | (3nn) |
| (1)-201 | (If) | X | (2f) | (3oo) |
| (1)-202 | (If) | X | (2h) | (3mm) |
| (1)-203 | (If) | X | (2k) | (3nn) |
| (1)-204 | (If) | X | (2n) | (3ii) |
| (1)-205 | (If) | X | (2a) | (3jj) |
| (1)-206 | (If) | X | (2b) | (3kk) |
| (1)-207 | (If) | X | (2f) | — |
| (1)-208 | (If) | X | (2h) | (3nn) |
| (1)-209 | (If) | X | (2k) | (3e) |
| (1)-210 | (If) | X | — | (3kk) |
| (1)-211 | (Ig) | X | X | (3ll) |
| (1)-212 | (Ig) | X | X | (3mm) |
| (1)-213 | (Ig) | X | X | (3nn) |
| (1)-214 | (Ig) | X | X | (3oo) |
| (1)-215 | (Ig) | X | X | (3mm) |
| (1)-216 | (Ig) | X | X | (3nn) |
| (1)-217 | (Ig) | X | X | (3k) |
| (1)-218 | (Ig) | X | X | — |
| (1)-219 | (Ig) | X | X | (3v) |
| (1)-220 | (Ig) | X | X | (3e) |
| (1)-221 | (Ig) | X | X | (3ee) |
| (1)-222 | (Ig) | X | X | (3kk) |
| (1)-223 | (Ig) | X | X | (3ll) |
| (1)-224 | (Ig) | X | X | (3mm) |
| (1)-225 | (Ig) | X | X | (3nn) |
| (1)-226 | (Ig) | X | X | (3oo) |
| (1)-227 | (Ig) | X | X | (3jj) |
| (1)-228 | (Ig) | X | X | — |
| (1)-229 | (Ig) | X | X | (3e) |
| (1)-230 | (Ig) | X | X | (3e) |
| (1)-231 | (Ig) | X | X | (3kk) |
| (1)-232 | (Ig) | X | X | (3ll) |
| (1)-233 | (Ig) | X | X | (3mm) |
| (1)-234 | (Ig) | X | X | (3nn) |
| (1)-235 | (Ig) | X | X | (3oo) |
| (1)-236 | (Ig) | X | X | (3kk) |
| (1)-237 | (Ig) | X | X | (3e) |
| (1)-238 | (Ig) | X | X | (3f) |
| (1)-239 | (Ig) | X | X | (3k) |
| (1)-240 | (Ig) | X | X | (3u) |
| (1)-241 | (Ih) | X | (2b) | (3u) |
| (1)-242 | (Ih) | X | — | (3v) |

-continued

| | (I) | n | $R^2$ | $R^1$ |
|---|---|---|---|---|
| (1)-243 | (Ih) | X | (2h) | — |
| (1)-244 | (Ih) | X | (2k) | (3ee) |
| (1)-245 | (Ih) | X | (2n) | (3ii) |
| (1)-246 | (Ih) | X | (2f) | (3jj) |
| (1)-247 | (Ih) | X | (2h) | (3kk) |
| (1)-248 | (Ih) | X | (2k) | (3e) |
| (1)-249 | (Ih) | X | — | (3f) |
| (1)-250 | (Ih) | X | (2a) | (3k) |
| (1)-251 | (Ih) | X | (2b) | (3mm) |
| (1)-252 | (Ih) | X | (2f) | (3nn) |
| (1)-253 | (Ih) | X | (2h) | (3oo) |
| (1)-254 | (Ih) | X | (2k) | (3e) |
| (1)-255 | (Ih) | X | (2n) | (3k) |
| (1)-256 | (Ih) | X | (2f) | (3u) |
| (1)-257 | (Ih) | X | (2h) | (3v) |
| (1)-258 | (Ih) | X | (2k) | (3e) |
| (1)-259 | (Ih) | X | (2n) | (3ee) |
| (1)-260 | (Ih) | X | (2f) | (3ii) |
| (1)-261 | (Ih) | X | (2h) | — |
| (1)-262 | (Ih) | X | (2k) | (3kk) |
| (1)-263 | (Ih) | X | (2n) | (3e) |
| (1)-264 | (Ih) | X | — | (3f) |
| (1)-265 | (Ih) | X | (2b) | (3k) |
| (1)-266 | (Ih) | X | (2f) | (3kk) |
| (1)-267 | (Ih) | X | (2h) | (3e) |
| (1)-268 | (Ih) | X | (2k) | (3f) |
| (1)-269 | (Ih) | X | (2n) | (3k) |
| (1)-270 | (Ih) | X | — | (3u) |
| (1)-271 | (Ii) | X | X | (3ll) |
| (1)-272 | (Ii) | X | X | (3mm) |
| (1)-273 | (Ii) | X | X | (3nn) |
| (1)-274 | (Ii) | X | X | (3oo) |
| (1)-275 | (Ii) | X | X | (3v) |
| (1)-276 | (Ii) | X | X | (3e) |
| (1)-277 | (Ii) | X | X | (3ee) |
| (1)-278 | (Ii) | X | X | (3e) |
| (1)-279 | (Ii) | X | X | (3f) |
| (1)-280 | (Ii) | X | X | (3k) |
| (1)-281 | (Ii) | X | X | (3u) |
| (1)-282 | (Ii) | X | X | (3mm) |
| (1)-283 | (Ii) | X | X | (3nn) |
| (1)-284 | (Ii) | X | X | (3k) |
| (1)-285 | (Ii) | X | X | (3u) |
| (1)-286 | (Ii) | X | X | (3v) |
| (1)-287 | (Ii) | X | X | (3e) |
| (1)-288 | (Ii) | X | X | (3ee) |
| (1)-289 | (Ii) | X | X | (3ii) |
| (1)-290 | (Ii) | X | X | (3jj) |
| (1)-291 | (Ii) | X | X | (3kk) |
| (1)-292 | (Ii) | X | X | (3e) |
| (1)-293 | (Ii) | X | X | — |
| (1)-294 | (Ii) | X | X | (3k) |
| (1)-295 | (Ii) | X | X | (3ll) |
| (1)-296 | (Ii) | X | X | (3mm) |
| (1)-297 | (Ii) | X | X | (3nn) |
| (1)-298 | (Ii) | X | X | (3oo) |
| (1)-299 | (Ii) | X | X | (3mm) |
| (1)-300 | (Ii) | X | X | (3nn) |
| (1)-301 | (Ia) | X | X | (3nnn) |
| (1)-302 | (Ia) | X | X | (3ooo) |
| (1)-303 | (Ia) | X | X | (3ppp) |
| (1)-304 | (Ia) | X | X | (3qqq) |
| (1)-305 | (Ia) | X | X | (3rrr) |
| (1)-306 | (Ia) | X | X | (3sss) |
| (1)-307 | (Ia) | X | X | (3ttt) |
| (1)-308 | (Ia) | X | X | (3uuu) |
| (1)-309 | (Ia) | X | X | (3vvv) |
| (1)-310 | (Ia) | X | X | (3www) |
| (1)-311 | (Ia) | X | X | (3xxx) |
| (1)-312 | (Ia) | X | X | (3yyy) |
| (1)-313 | (Ia) | X | X | (3zzz) |
| (1)-314 | (Ia) | X | X | (3aaaa) |
| (1)-315 | (Ia) | X | X | (3bbbb) |
| (1)-316 | (Ia) | X | X | (3cccc) |

In an embodiment, the invention comprises compounds of Formula (II), (II)

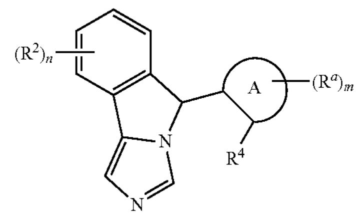

which is a compound of Formula (I) wherein $R^1$ is

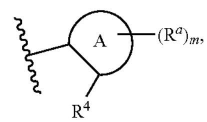

ring A is $C_{3-10}$cycloalkyl or 3-7 membered heterocyclyl;

m is 0, 1, 2, 3 or 4; and $R^4$ is —$NR_2$ or —OR.

In one embodiment, the invention comprises compounds of Formula (II) wherein $R^4$ is —OH. In other embodiments, $R^4$ is —OH and n is 0. In other embodiments, $R^4$ is —OH and n is 1.

The invention further comprises subgenera of formula (II) in which the substituents are selected as any and all combinations of one or more of structural formula (II), $R^2$, $R^a$, m and ring A, as defined herein, including without limitation, the following:

Structural Formula I is One of Formulae (Ia)-(II):

(IIa)

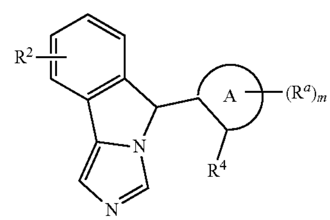

(IIb)

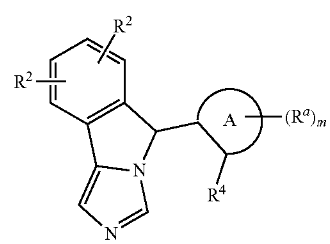

(IIc)

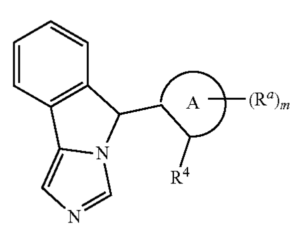

-continued (IId)

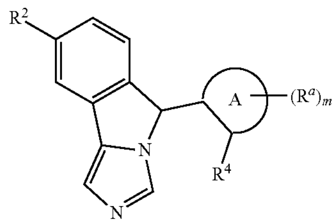

(IIe)

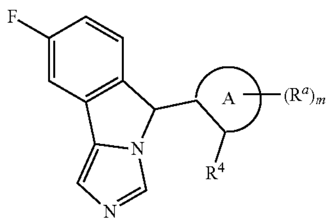

(IIf)

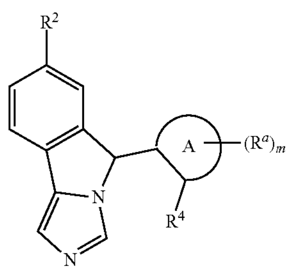

(IIg)

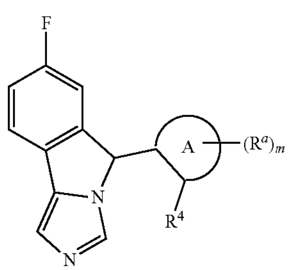

(IIh)

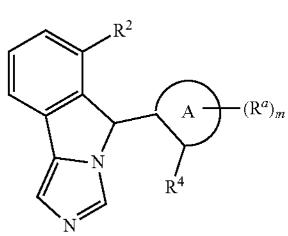

(IIi)

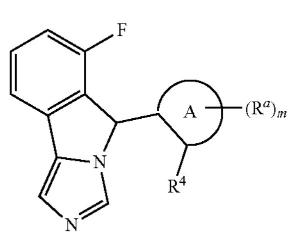

-continued (IIj)

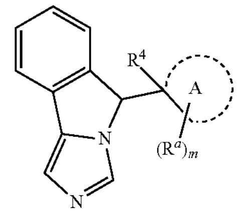

(IIk)

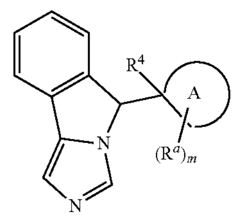

(IIl)

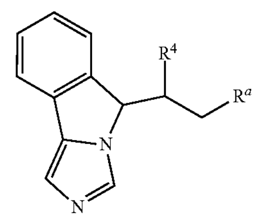

(IIm)

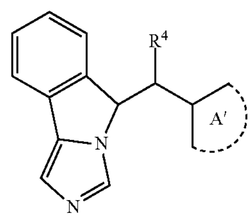

(IIn)

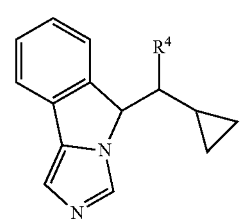

(IIo)

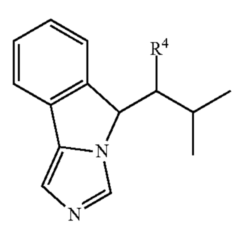

Ring A is selected from one of the following groups (4a)-(4ccc);

(4a) Ring A is $C_{3-10}$cycloalkyl or 3-7 membered heterocyclyl (e.g., a 4-6 membered heterocyclyl or a 5-6 membered heterocyclyl), wherein m is 0, 1, 2 or 3, each $R^a$ is independently selected from halogen, $C_{1-6}$alkyl, —OR, —$S(O)_2R$ and —$S(O)_2N(R)_2$, and each R is independently hydrogen, $C_{1-6}$alkyl or $C_{1-6}$ haloalkyl.

(4b) $R^1$ is:

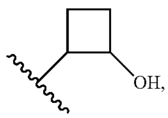 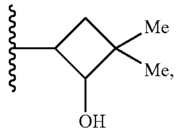 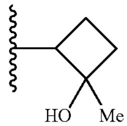,

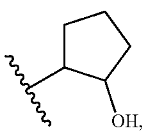 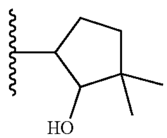, 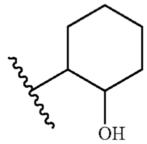,

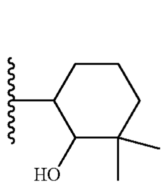, 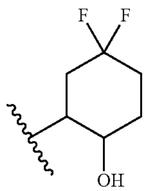, 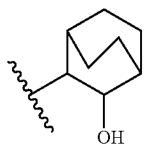,

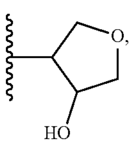 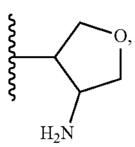 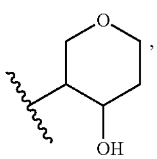

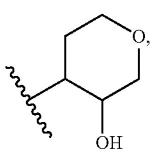 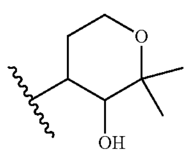,

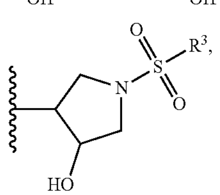

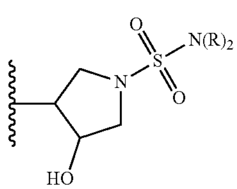, 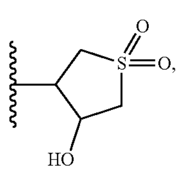

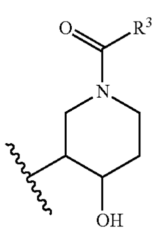, 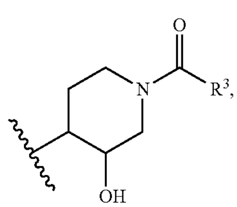

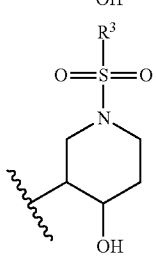, 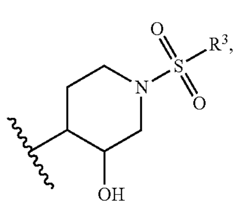

-continued

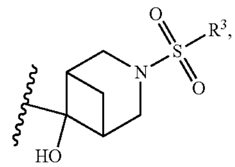 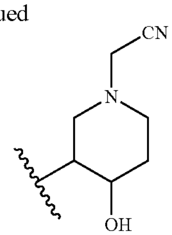,

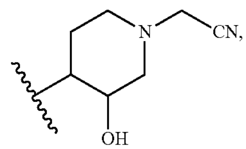 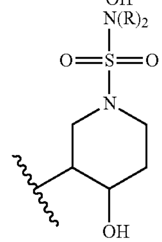 or

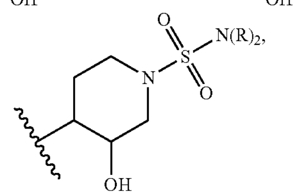

wherein each R is independently hydrogen or $C_{1-6}$alkyl;

$R^3$ is methyl, ethyl or —O-butyl.

(4c) Group (4a), wherein ring A is $C_{4-6}$cycloalkyl or 4-6 membered heterocyclyl.

(4d) Group (4a), wherein ring A is $C_{3-8}$cycloalkyl.

(4e) Group (4b), wherein ring A is cyclopropyl, cyclobutyl, cyclopentyl or cyclohexyl.

(4f) Group (4b), wherein ring A is cyclobutyl, cyclopentyl or cyclohexyl.

(4g) Group (4b), wherein ring A is cyclobutyl or cyclohexyl.

(4h) Group (4b), wherein ring A is cyclobutyl or cyclopentyl.

(4i) Group (4b), wherein ring A is cyclopentyl or cyclohexyl.

(4j) Group (4b), wherein ring A is cyclopropyl.

(4k) Group (4b), wherein ring A is cyclobutyl.

(4l) Group (4b), wherein ring A is cyclopentyl.

(4m) Group (4b), wherein ring A is cyclohexyl.

(4n) $R^1$ is:

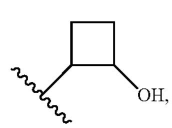 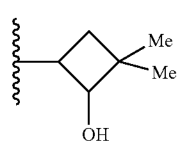, 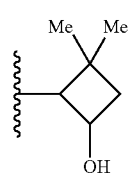,

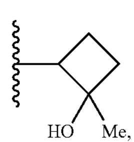 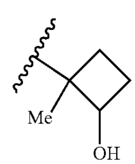, 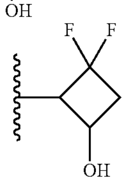, 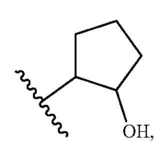

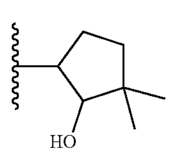, 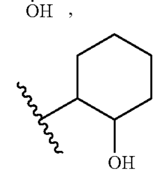, 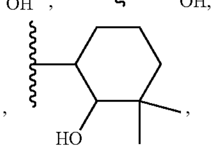,

-continued

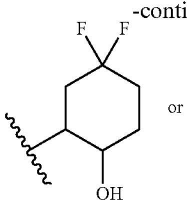

or

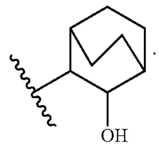

.

(4o) $R^1$ is:

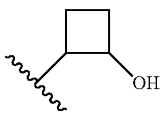

,

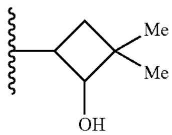

,

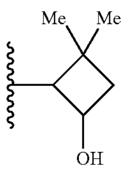

,

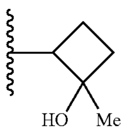

,

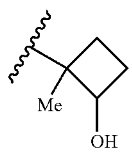

or

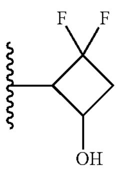

.

(4p) $R^1$ is:

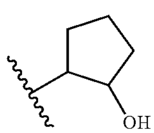

or

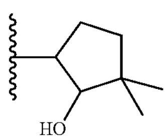

.

(4q) $R^1$ is:

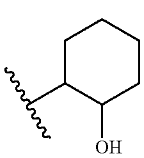

,

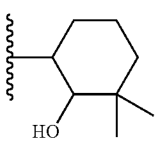

or

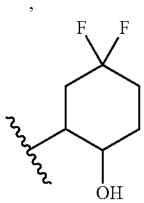

.

(4r) Group (4a), wherein ring A is 3-7 membered heterocyclyl.

(4s) Group (4p), wherein ring A is aziridinyl, azetidinyl, pyrrolidinyl or piperdinyl.

(4t) Group (4p), wherein ring A is azetidinyl, pyrrolidinyl or piperdinyl.

(4u) Group (4p), wherein ring A is azetidinyl or pyrrolidinyl.

(4v) Group (4p), wherein ring A is azetidinyl or piperdinyl.

(4w) Group (4p), wherein ring A is pyrrolidinyl or piperdinyl.

(4x) Group (4p), wherein ring A is pyrrolidinyl.

(4y) Group (4p), wherein ring A is piperdinyl.

(4z) $R^1$ is:

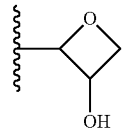

,

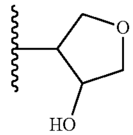

,

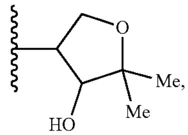

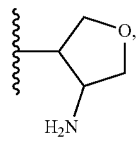

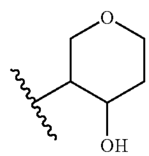

,

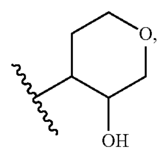

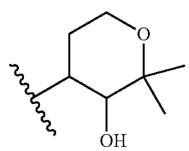

,

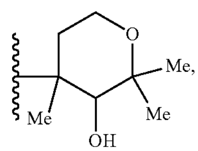

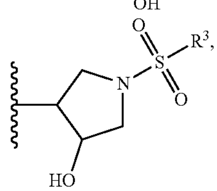

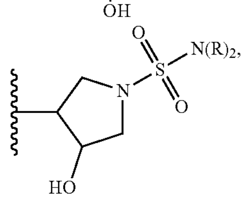

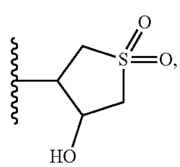

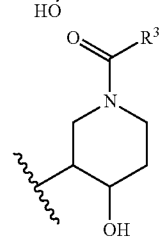

,

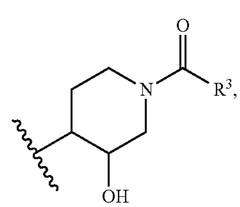

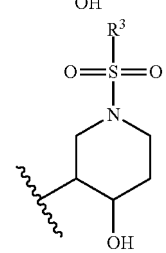

,

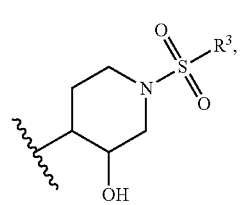

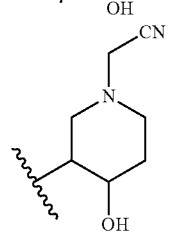

,

-continued
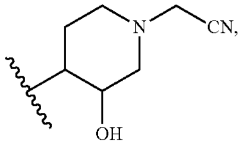, 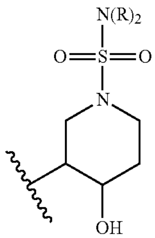 or
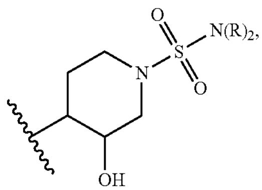
wherein
$R^3$ is methyl, ethyl, propyl, butyl, —O-methyl, —O-ethyl, —O-propyl, or —O-butyl.
(4aa) $R^1$ is:
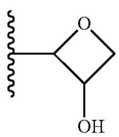, 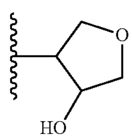, 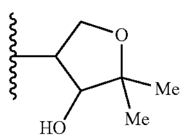,
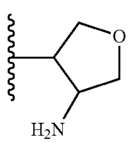, 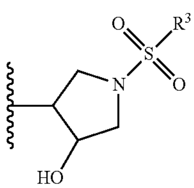 or
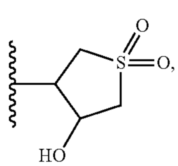
wherein
$R^3$ is methyl, ethyl, propyl, or butyl.
(4bb) $R^1$ is:
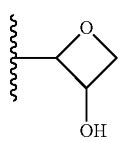, 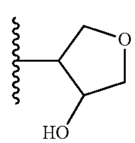, 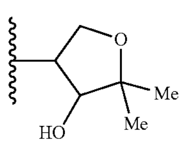
or.
(4cc) $R^1$ is:
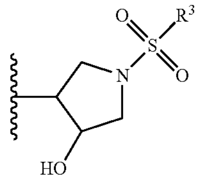 or 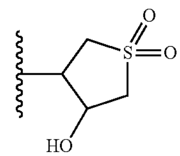,
wherein
$R^3$ is methyl, ethyl, propyl, or butyl.
(4dd) $R^1$ is:
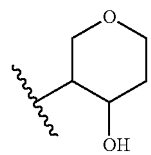, 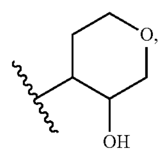, 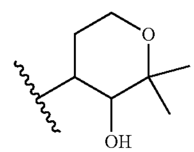,
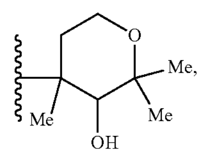, 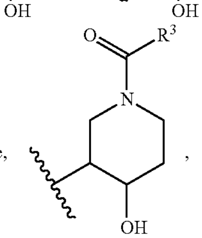,
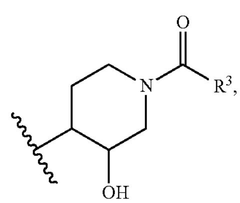, 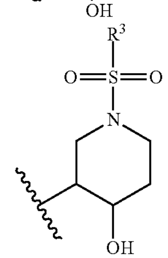,
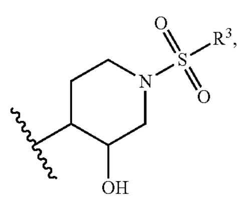, 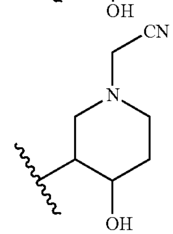,
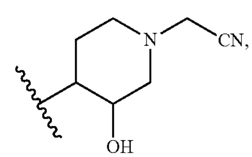, 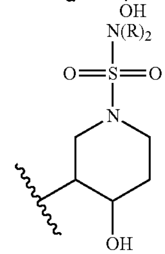 or
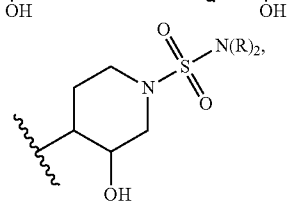
wherein
$R^3$ is methyl, ethyl, propyl, butyl, —O-methyl, —O-ethyl, —O-propyl, or —O-butyl.

(4ee) $R^1$ is:

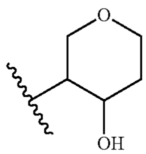,
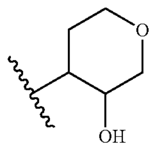,
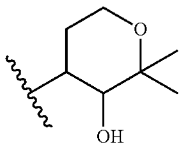
or
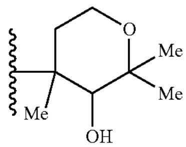, wherein $R^3$ is methyl, ethyl, propyl, butyl, —O-methyl, —O-ethyl, —O-propyl, or —O-butyl.

(4ff) $R^1$ is:

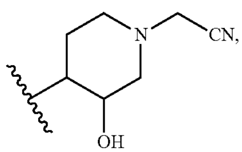
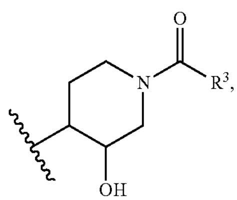
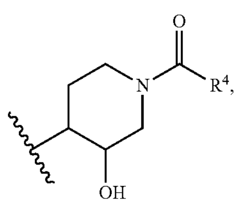
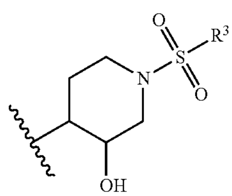,
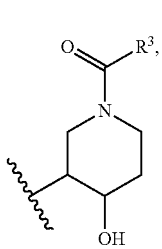
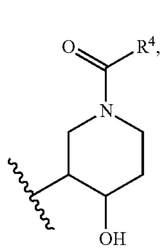
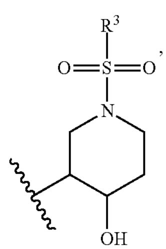
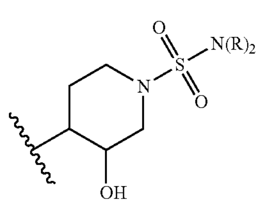
or
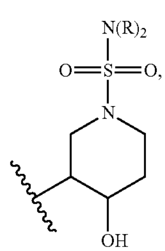

wherein $R^3$ is methyl, ethyl, propyl, butyl, —O-methyl, —O-ethyl, —O-propyl, or —O-butyl.

(4gg) $R^1$ is:

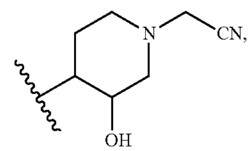
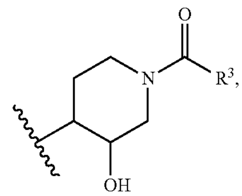
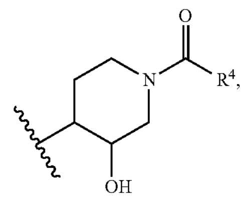
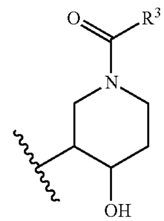
or
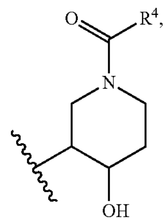

wherein $R^3$ is methyl, ethyl, propyl, butyl, —O-methyl, —O-ethyl, —O-propyl, or —O-butyl.

(4hh) $R^1$ is:

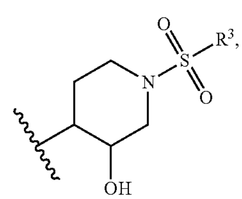
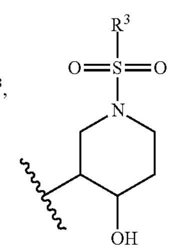,
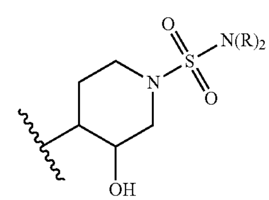
or
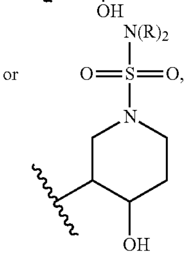

wherein $R^3$ is methyl, ethyl, propyl, butyl, —O-methyl, —O-ethyl, —O-propyl, or —O-butyl.

(4ii) Any of groups (4c)-(4m) or (4r)-(4y), wherein m is 1, 2 or 3, and each $R^a$ is independently selected from halogen, $C_{1-6}$alkyl, —OR, —$S(O)_2R$ and —$S(O)_2N(R)_2$.

(4jj) Any of groups (4c)-(4m) or (4r)-(4y), wherein m is 1, 2 or 3, and each $R^a$ is independently selected from chloro, fluoro, methyl, —OH, —$S(O)_2$ethyl, —$S(O)_2NMe_2$. and —$S(O)_2NH_2$.

(4kk) Any of groups (4c)-(4m) or (4r)-(4y), wherein m is 1 or 2, and each $R^a$ is independently selected from $C_{1-6}$alkyl, —OR, —$S(O)_2R$ and —$S(O)_2N(R)_2$.

(4ll) Any of groups (4c)-(4m) or (4r)-(4y), wherein m is 3, and each $R^a$ is independently selected from halogen, $C_{1-6}$alkyl and —OR.

(4mm) Any of groups (4c)-(4m) or (4r)-(4y), wherein m is 3, and each $R^a$ is independently selected from fluoro, methyl and —OH.

(4nn) Any of groups (4c)-(4m) or (4r)-(4y), wherein m is 2, and each $R^a$ is independently selected from $C_{1-6}$alkyl and —OR.

(4oo) Any of groups (4c)-(4m) or (4r)-(4y), wherein m is 2, and both $R^2$ are methyl.

(4pp) Any of groups (4c)-(4m) or (4r)-(4y), wherein m is 2, and both $R^a$ are fluoro.

(4qq) Any of groups (4c)-(4m) or (4r)-(4y), wherein m is 2, and each $R^a$ is independently selected from methyl and —OH.

(4rr) Any of groups (4c)-(4m) or (4r)-(4y), wherein m is 1, and $R^a$ is selected from $C_{1-6}$alkyl, —OR, —$S(O)_2R$ and —$S(O)_2N(R)_2$.

(4ss) Any of groups (4c)-(4m) or (4r)-(4y), wherein m is 1, and $R^a$ is selected from $C_{1-6}$alkyl, —OR and —$S(O)_2N(R)_2$.

(4tt) Any of groups (4c)-(4m) or (4r)-(4y), wherein m is 1, and $R^a$ is selected from $C_{1-6}$alkyl, —OR and —$S(O)_2R$.

(4uu) Any of groups (4c)-(4m) or (4r)-(4y), wherein m is 1, and $R^a$ is selected from $C_{1-6}$alkyl and —OR.

(4vv) Any of groups (4c)-(4m) or (4r)-(4y), wherein m is 1, and $R^a$ is selected from methyl and —OH.

(4ww) Any of groups (4c)-(4m) or (4r)-(4y), wherein m is 1, and $R^a$ is selected from $C_{1-6}$alkyl, —$S(O)_2R$ and —$S(O)_2N(R)_2$.

(4xx) Any of groups (4c)-(4m) or (4r)-(4y), wherein m is 1, and $R^a$ is $C_{1-6}$alkyl.

(4yy) Any of groups (4c)-(4m) or (4r)-(4y), wherein m is 1, and $R^a$ is methyl or ethyl.

(4zz) Any of groups (4c)-(4m) or (4r)-(4y), wherein m is 1, and $R^a$ is methyl.

(4aaa) Any of groups (4c)-(4m) or (4r)-(4y), wherein m is 1, and $R^a$ is —OMe or —OH.

(4bbb) $R^1$ is:

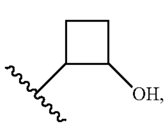
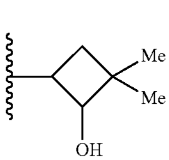
,
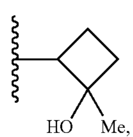
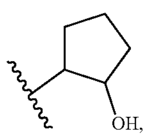
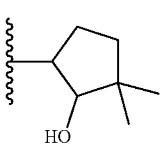
,
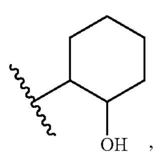
,
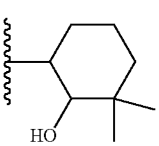
,
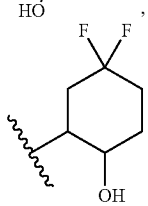
,
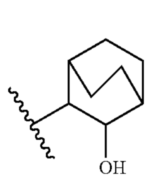
,
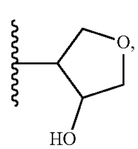
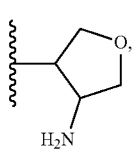
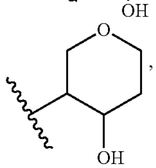
, -continued

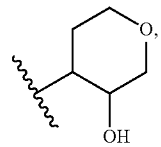
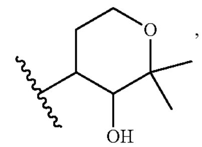
,
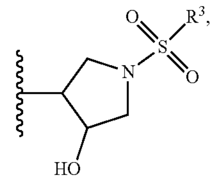
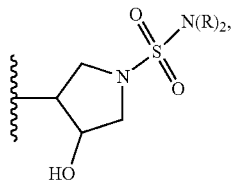
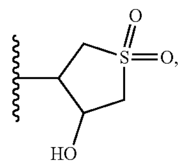
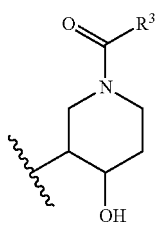
,
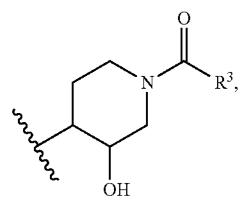
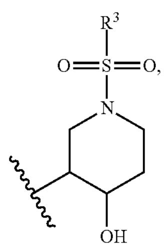
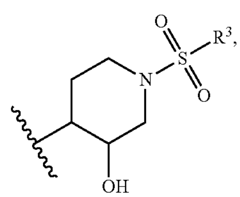
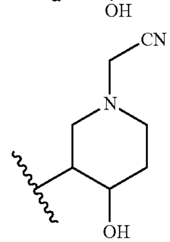
,
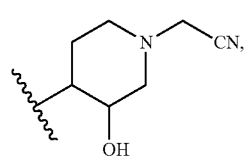
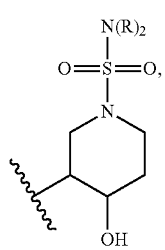
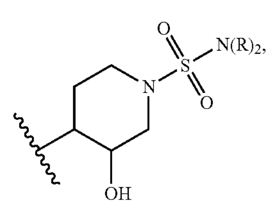
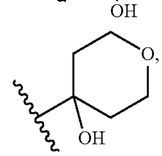
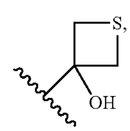
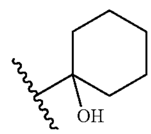
,
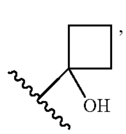
,
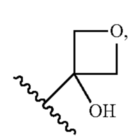
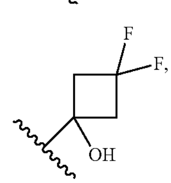

-continued

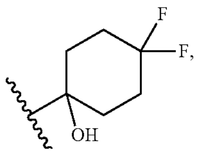

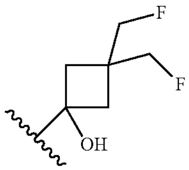

or

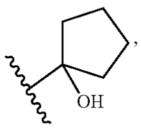

wherein each R is independently hydrogen or $C_{1-6}$alkyl;

$R^3$ is methyl, ethyl or —O-butyl.

(4ccc) $R^1$ is:

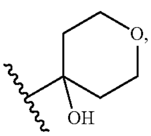

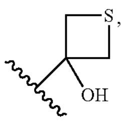

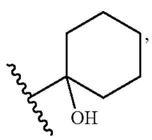

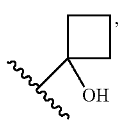

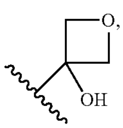

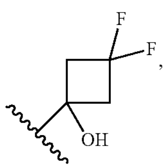

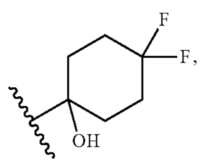

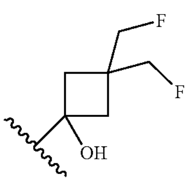

or

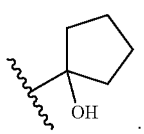

.

In another embodiment, the invention comprises compounds of Formula (III), (III)

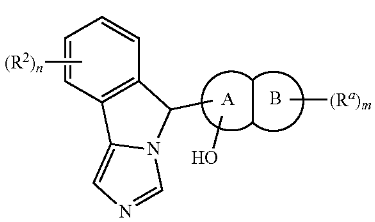

which are compounds for Formula (I) wherein $R^1$ is

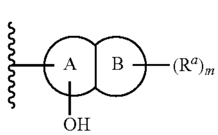

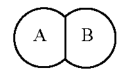

is a fused bicyclic ring system consisting of a ring A and a ring B;

ring A is $C_{3-8}$cycloalkyl or 3-7 membered heterocyclyl;

ring B is aryl, heteroaryl, $C_{3-7}$cycloalkyl or 3-7 membered heterocyclyl;

m is 0, 1, 2, 3 or 4; and the hydroxy moiety is bonded to the A ring and each $R^a$ is independently a substituent of the A ring or the B ring.

In one embodiment, the invention comprises compounds of Formula (III) wherein n is 0. In other embodiments, n is 1.

The invention further comprises subgenera of formula (III) in which the substituents are selected as any and all combinations of one or more of structural formula (III), $R^2$, $R^a$, m, ring A and ring B, as defined herein, including without limitation, the following:

Structural Formula I is One of Formulae (IIIa)-(IIIi):

(IIIa)

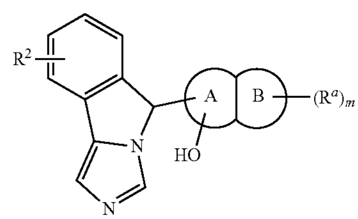

(IIIb)

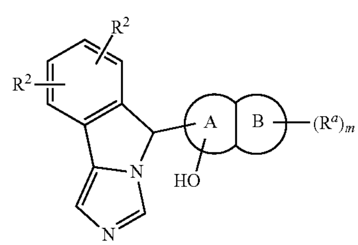

(IIIc)

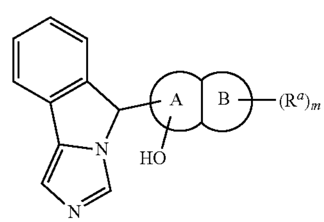

(IIId)

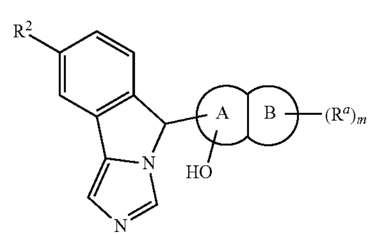

-continued (IIIe)

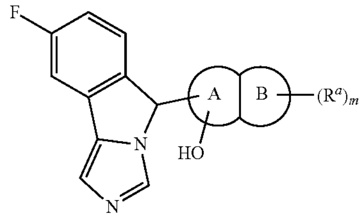

(IIIf)

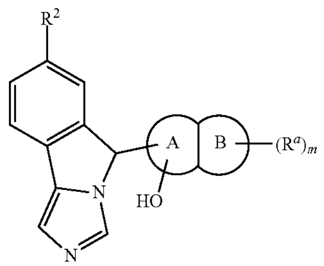

(IIIg)

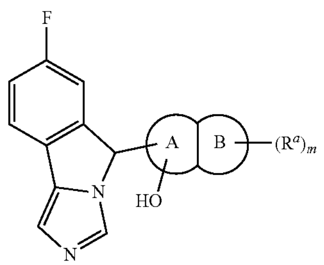

(IIIh)

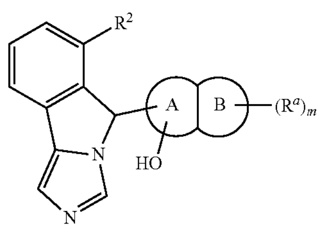

(IIIi)

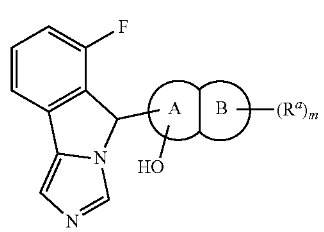

Ring A/B is selected from one of the following groups (5a)-(5yy):

(5a) Ring A is $C_{3-8}$cycloalkyl or 3-7 membered heterocyclyl (e.g., a 4-6 membered heterocyclyl or a 5-6 membered heterocyclyl), and ring B is aryl, heteroaryl, $C_{3-8}$cycloalkyl or 3-7 membered heterocyclyl (e.g., a 4-6 membered heterocyclyl or a 5-6 membered heterocyclyl), wherein m is 0, 1, 2 or 3, and each $R^a$ is independently selected from halogen, $C_{1-6}$alkyl, —OR, —C(O)N(R)$_2$, —S(O)$_2$R and —S(O)$_2$N(R)$_2$.

(5b) Group (5a), wherein ring A is $C_{5-6}$cycloalkyl, and ring B is aryl or heteroaryl.

(5c) Group (5a), wherein ring A is cyclopentyl or cyclohexyl, and ring B is aryl or heteroaryl.

(5d) Group (5a), wherein ring A is $C_{5-6}$cycloalkyl, and ring B is phenyl or pyridinyl.

(5e) Group (5a), wherein ring A is cyclopentyl or cyclohexyl, and ring B is phenyl or pyridinyl.

(5f) Group (5a), wherein ring A is $C_{3-8}$cycloalkyl, and ring B is aryl, heteroaryl, $C_{3-8}$cycloalkyl or 3-7 membered heterocyclyl.

(5g) Group (5a), wherein ring A is cyclopropyl, and ring B is aryl, heteroaryl, $C_{3-7}$cycloalkyl or 3-7 membered heterocyclyl.

(5h) Group (5a), wherein ring A is cyclobutyl, and ring B is aryl, heteroaryl, $C_{3-8}$cycloalkyl or 3-7 membered heterocyclyl.

(5i) Group (5a), wherein ring A is cyclopentyl or cyclohexyl, and ring B is aryl, heteroaryl, $C_{3-8}$cycloalkyl or 3-7 membered heterocyclyl.

(5j) Group (5a), wherein ring A is $C_{3-8}$cycloalkyl, and ring B is pyridinyl, pyrazinyl, pyrimidinyl, pyridazinyl, pyrazolyl, imidazolyl, thiazolyl, triazolyl, oxazolyl or oxadiazolyl.

(5k) Group (5a), wherein ring A is cyclopentyl or cyclohexyl, and ring B is aryl.

(5l) Group (5a), wherein ring A is cyclopentyl or cyclohexyl, and ring B is phenyl.

(5m) Group (5a), wherein ring A is cyclopentyl, and ring B is heteroaryl.

(5n) Group (5a), wherein ring A is cyclopentyl or cyclohexyl, and ring B is pyridinyl, pyrazinyl, pyrimidinyl, pyridazinyl, pyrazolyl, imidazolyl, thiazolyl, triazolyl, oxazolyl or oxadiazolyl.

(5o) Group (5a), wherein ring A is cyclopentyl, and ring B is pyridinyl, pyrazinyl, pyrimidinyl, pyridazinyl, pyrazolyl, imidazolyl, thiazolyl, triazolyl, oxazolyl or oxadiazolyl.

(5p) Group (5a), wherein ring A is cyclohexyl, and ring B is pyridinyl, pyrazinyl, pyrimidinyl, pyridazinyl, pyrazolyl, imidazolyl, thiazolyl, triazolyl, oxazolyl or oxadiazolyl.

(5q) Group (5a), wherein ring A is cyclohexyl, and ring B is pyridinyl, pyrazinyl, pyrimidinyl, or pyridazinyl.

(5r) Group (5a), wherein ring A is 3-7 membered heterocyclyl (e.g., a 4-6 membered heterocyclyl or a 5-6 membered heterocyclyl), and ring B is aryl, heteroaryl, $C_{3-8}$cycloalkyl or 3-7 membered heterocyclyl.

(5s) Group (5a), wherein ring A is 3-7 membered heterocyclyl (e.g., a 4-6 membered heterocyclyl or a 5-6 membered heterocyclyl), and ring B is aryl, or heteroaryl.

(5t) Group (5a), wherein ring A is 3-7 membered heterocyclyl (e.g., a 4-6 membered heterocyclyl or a 5-6 membered heterocyclyl), and ring B is aryl.

(5u) Group (5a), wherein ring A is 3-7 membered heterocyclyl (e.g., a 4-6 membered heterocyclyl or a 5-6 membered heterocyclyl), and ring B is heteroaryl.

(5v) Group (5a), wherein ring A is piperdinyl, and ring B is aryl.

(5w) Group (5a), wherein ring A is piperdinyl, and ring B is heteroaryl.

(5x) Any of groups (5b)-(5w), wherein m is 1, 2 or 3, and each $R^a$ is independently selected from $C_{1-6}$alkyl, —OR, —C(O)N(R)$_2$, —S(O)$_2$R and —S(O)$_2$N(R)$_2$.

(5y) Any of groups (5b)-(5w), wherein m is 1, 2 or 3, and each $R^a$ is independently selected from methyl, —OH, —S(O)$_2$ethyl, —C(O)NH$_2$, —C(O)N(Me)(H), —S(O)$_2$NMe$_2$ and —S(O)$_2$NH$_2$.

(5z) Any of groups (5b)-(5w), wherein m is 1 or 2, and each $R^a$ is independently selected from $C_{1-6}$alkyl, —OR, —S(O)$_2$R and —S(O)$_2$N(R)$_2$.

(5aa) Any of groups (5b)-(5w), wherein m is 3, and each $R^a$ is independently selected from $C_{1-6}$alkyl and —OR.

(5bb) Any of groups (5b)-(5w), wherein m is 3, and each $R^a$ is independently selected from methyl and —OH.

(5cc) Any of groups (5b)-(5w), wherein m is 2, and each $R^a$ is independently selected from $C_{1-6}$alkyl and —OR.

(5dd) Any of groups (5b)-(5w), wherein m is 2, and each $R^a$ is independently selected from methyl and —OH.

(5ee) Any of groups (5b)-(5w), wherein m is 1, and $R^a$ is selected from $C_{1-6}$alkyl, —OR, —$C(O)N(R)_2$, —$S(O)_2R$ and —$S(O)_2N(R)_2$.

(5ff) Any of groups (5b)-(5w), wherein m is 1, and $R^a$ is selected from $C_{1-6}$alkyl, —OR and —$S(O)_2N(R)_2$.

(5gg) Any of groups (5b)-(5w), wherein m is 1, and $R^a$ is selected from $C_{1-6}$alkyl, —OR and —$S(O)_2R$.

(5hh) Any of groups (5b)-(5w), wherein m is 1, and $R^a$ is selected from $C_{1-6}$alkyl and —OR.

(5ii) Any of groups (5b)-(5w), wherein m is 1, and $R^a$ is selected from methyl, —$C(O)NH_2$, —C(O)N(Me)(H), and —OH.

(5jj) Any of groups (5b)-(5w), wherein m is 1, and $R^a$ is selected from $C_{1-6}$alkyl, —$S(O)_2R$ and —$S(O)_2N(R)_2$.

(5kk) Any of groups (5b)-(5w), wherein m is 1, and $R^a$ is $C_{1-6}$alkyl.

(5ll) Any of groups (5b)-(5w), wherein m is 1, and $R^a$ is methyl or ethyl.

(5mm) Any of groups (5b)-(5w), wherein m is 1, and $R^a$ is methyl.

(5nn) Any of groups (5b)-(5w), wherein m is 1, and $R^a$ is —OMe or —OH.

(5oo) Any of groups (5b)-(5w), wherein m is 0.

(5pp) $R^1$ is

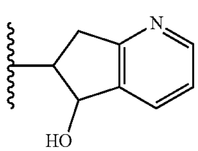,
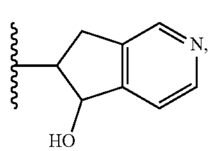
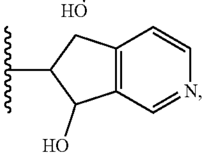
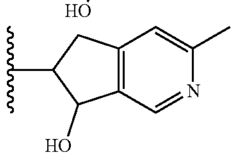,
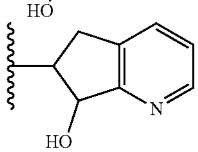,
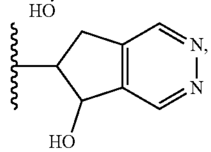
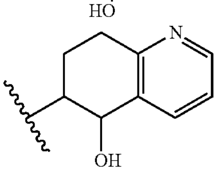,
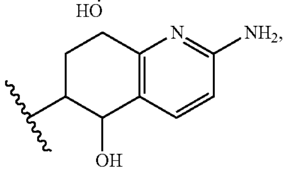
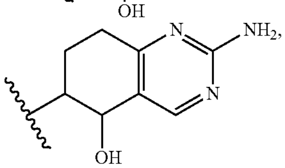
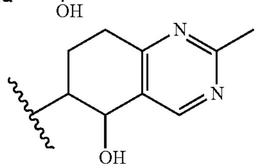,
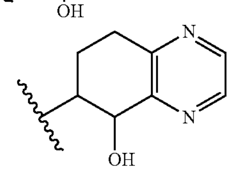,
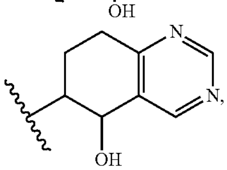

-continued

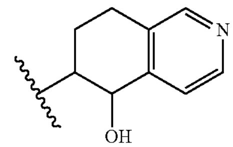,
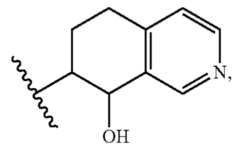
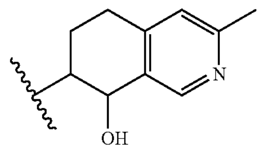,
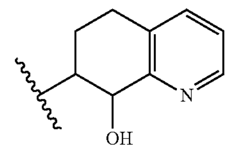,
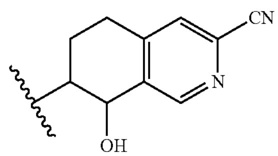,
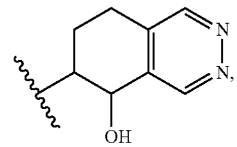
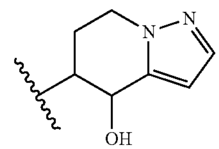,
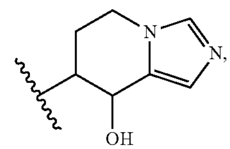
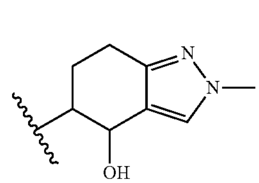,
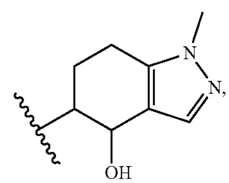
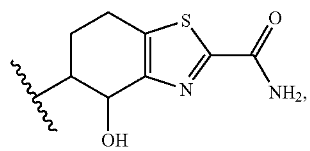
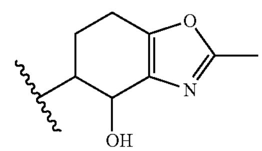,
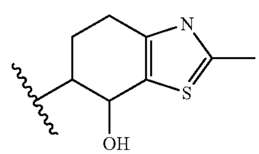,
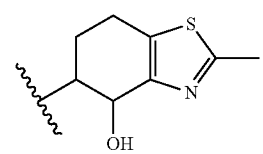,
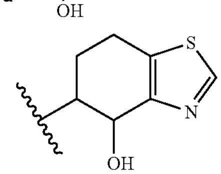,
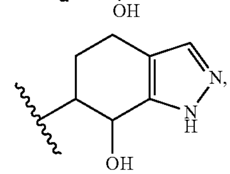
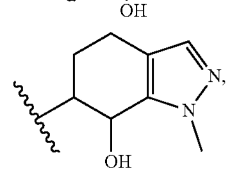
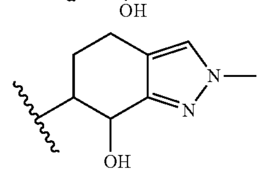
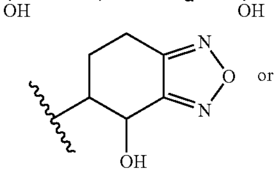 or
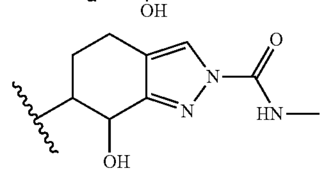.

(5qq) $R^1$ is
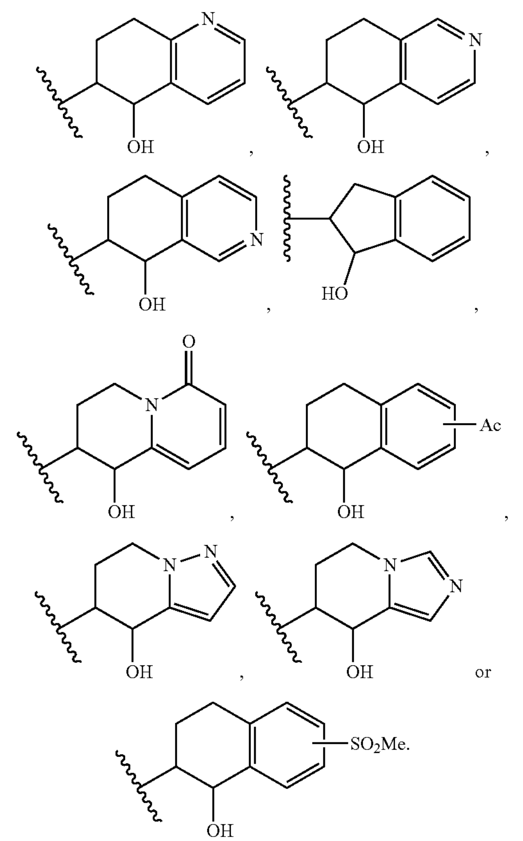
or
-continued
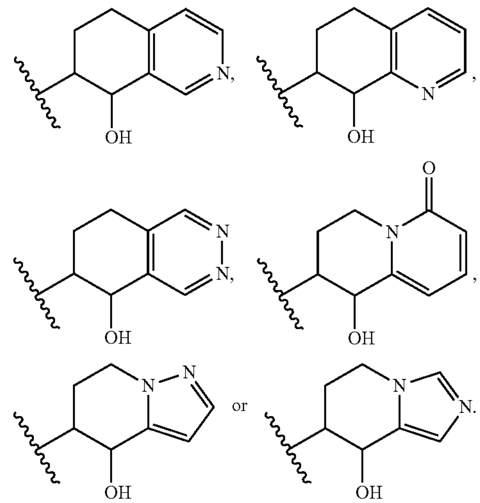
or
(5rr) $R^1$ is
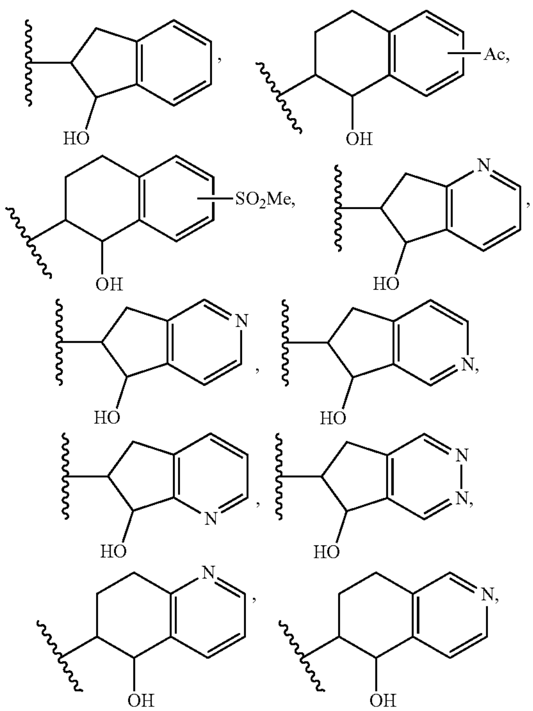
(5ss) $R^1$ is
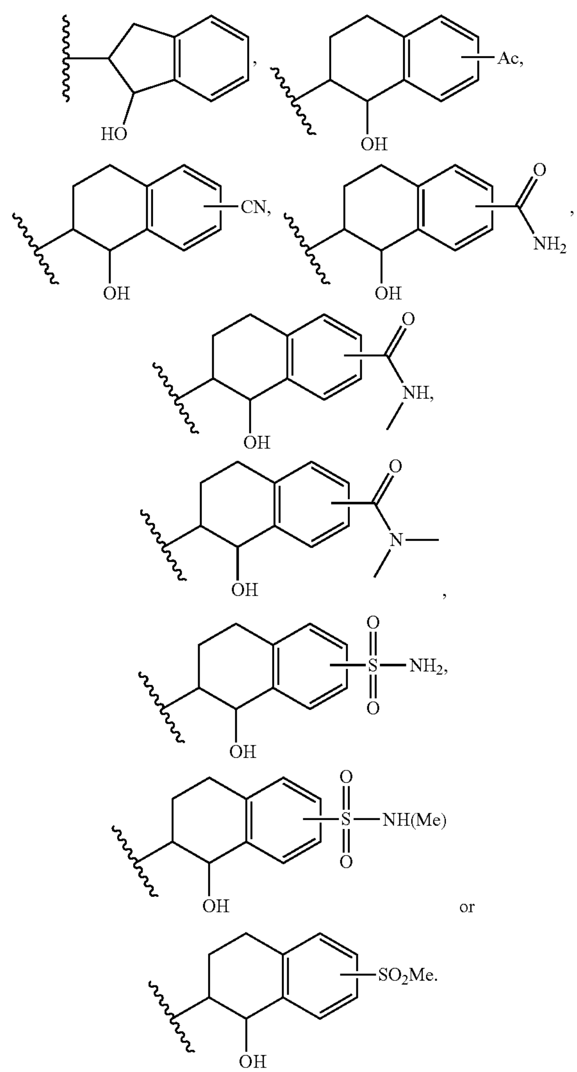
or (5tt) $R^1$ is
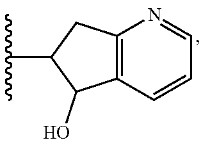
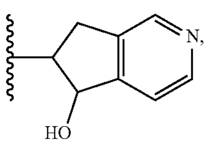
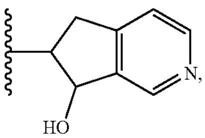
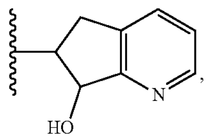
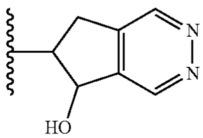
or
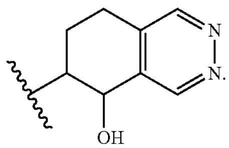
(5uu) $R^1$ is
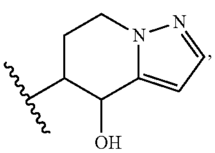
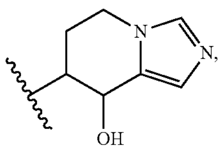
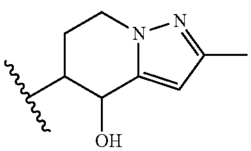
,
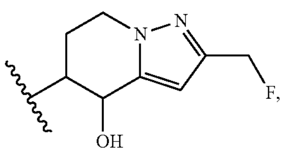
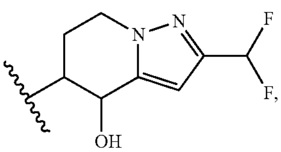
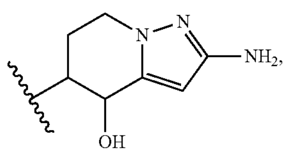
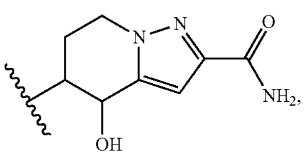
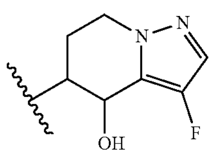
,
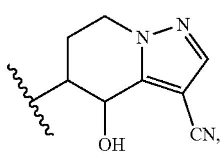
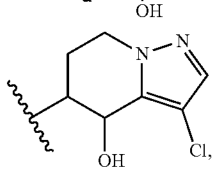
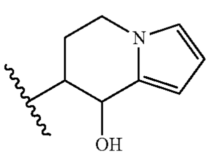
,
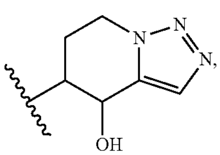
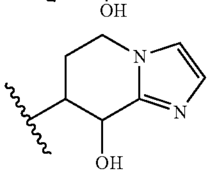
,
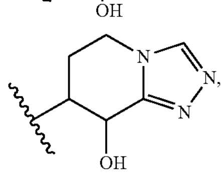
-continued
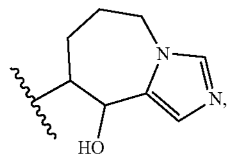
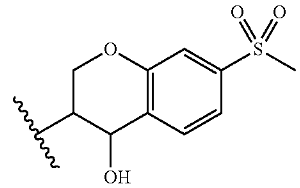
,
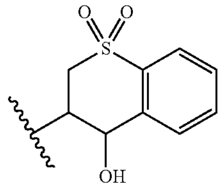
or
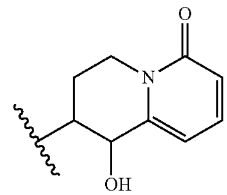
(5vv) $R^1$ is
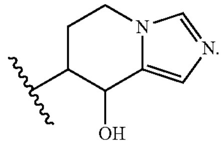 [SMILES: *C1CCn2cncc2C1O]
(5ww) $R^1$ is
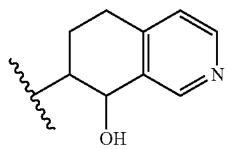
or
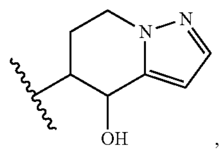
,
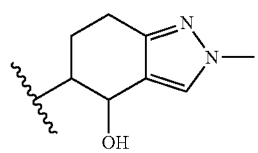
,
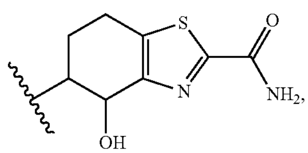
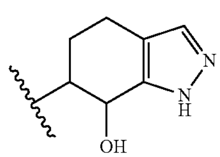
or
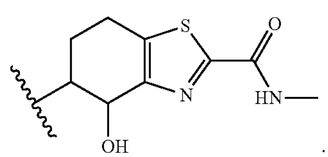
.
(5xx) $R^1$ is
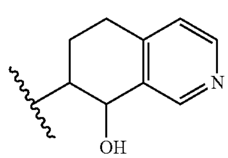
or
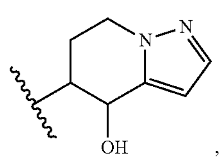
, (5yy) $R^1$ is

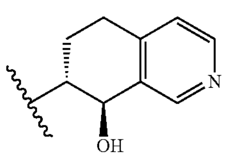
or
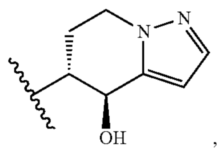
,

In another embodiment, the invention comprises compounds of Formula (IV), (IV)

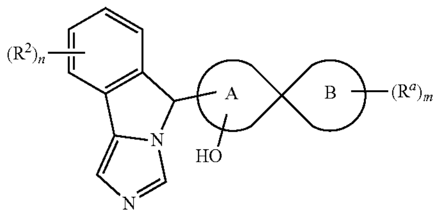

which are compounds of Formula (I) wherein $R^1$ is

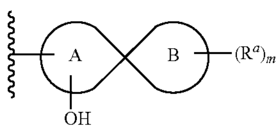

ring A and ring B form a spirocyclic system, ring A is $C_{3-8}$cycloalkyl or 3-7 membered heterocyclyl;

ring B is $C_{3-7}$cycloalkyl, 3-7 membered heterocyclyl, aryl or heteroaryl;

m is 0, 1, 2, 3 or 4; and the hydroxy moiety is bonded to the A ring and each $R^a$ is independently a substituent of the A ring or the Bring.

In one embodiment, the invention comprises compounds of Formula (IV) wherein n is 0. In other embodiments, n is 1.

The invention further comprises subgenera of formula (IV) in which the substituents are selected as any and all combinations of one or more of structural formula (IV), $R^2$, $R^a$, m, ring A and ring B, as defined herein, including without limitation, the following:

Structural Formula I is One of Formulae (IVa)-(IVi):

(IVa)

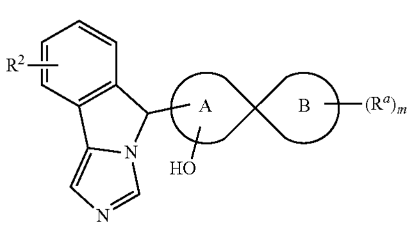

-continued (IVb)

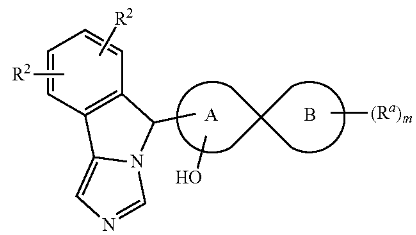

(IVc)

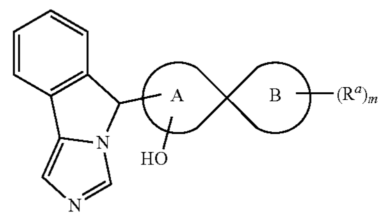

(IVd)

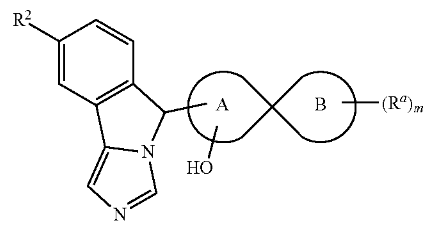

(IVe)

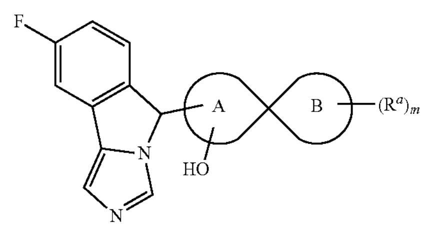

(IVf)

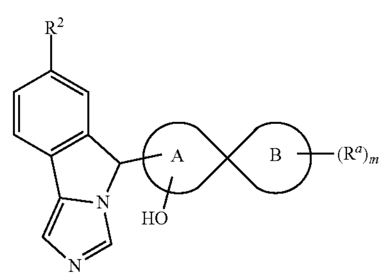

(IVg)

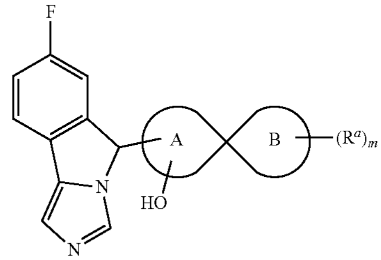

-continued (IVh)

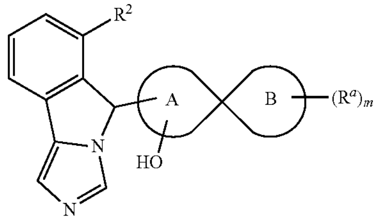

(IVi)

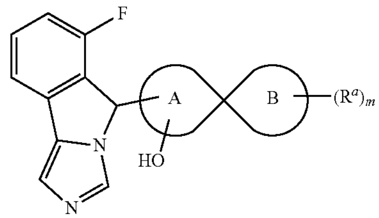

Ring A/B is selected from one of the following groups (6a)-(6zz):

(6a) Ring A is $C_{3-8}$cycloalkyl or 3-7 membered heterocyclyl (e.g., a 4-6 membered heterocyclyl or a 5-6 membered heterocyclyl), and ring B is $C_{3-8}$cycloalkyl or 3-7 membered heterocyclyl (e.g., a 4-6 membered heterocyclyl or a 5-6 membered heterocyclyl), aryl or heteroaryl, wherein m is 0, 1, 2 or 3, and each $R^a$ is independently selected from halogen, $C_{1-6}$alkyl, —OR, —$S(O)_2R$ and —$S(O)_2N(R)_2$.

(6b) Group (6a), wherein ring A is $C_{4-5}$cycloalkyl or 4-6 membered heterocyclyl, and ring B is $C_{4-6}$cycloalkyl or 4-6 membered heterocyclyl.

(6c) Group (6a), wherein ring A is $C_{3-8}$cycloalkyl, and ring B is $C_{3-8}$cycloalkyl or 3-7 membered heterocyclyl.

(6d) Group (6a), wherein ring A is 3-7 membered heterocyclyl (e.g., a 4-6 membered heterocyclyl or a 5-6 membered heterocyclyl), and ring B is $C_{3-7}$cycloalkyl.

(6e) Group (6a), wherein ring A is $C_{3-8}$cycloalkyl or 3-7 membered heterocyclyl (e.g., a 4-6 membered heterocyclyl or a 5-6 membered heterocyclyl), and ring B is $C_{3-7}$cycloalkyl.

(6f) Group (6a), wherein ring A is $C_{3-8}$cycloalkyl or 3-7 membered heterocyclyl (e.g., a 4-6 membered heterocyclyl or a 5-6 membered heterocyclyl), and ring B is 3-7 membered heterocyclyl.

(6g) Group (6a), wherein ring A is $C_{3-8}$cycloalkyl, and ring B is aryl or heteroaryl.

(6h) Group (6a), wherein ring A is $C_{3-8}$cycloalkyl, and ring B is 3-7 membered heterocyclyl.

(6i) Group (6a), wherein ring A is 3-7 membered heterocyclyl (e.g., a 4-6 membered heterocyclyl or a 5-6 membered heterocyclyl), and ring B is aryl.

(6j) Group (6a), wherein ring A is 3-7 membered heterocyclyl (e.g., a 4-6 membered heterocyclyl or a 5-6 membered heterocyclyl), and ring B is heteroaryl.

(6k) Group (6a), wherein ring A is cyclobutyl, and ring B is $C_{3-8}$cycloalkyl or 3-7 membered heterocyclyl.

(6l) Group (6a), wherein ring A is cyclobutyl, and ring B is $C_{3-8}$cycloalkyl.

(6m) Group (6a), wherein ring A is cyclobutyl, and ring B is cyclobutyl.

(6n) Group (6a), wherein ring A is cyclobutyl, and ring B is 3-7 membered heterocyclyl.

(6o) Group (6a), wherein ring A is cyclobutyl, and ring B is 4-6 membered heterocyclyl.

(6p) Group (6a), wherein ring A is cyclobutyl, and ring B is 4-membered heterocyclyl.

(6q) Group (6a), wherein ring A is cyclobutyl, and ring B is 5-membered heterocyclyl.

(6r) Group (6a), wherein ring A is cyclobutyl, and ring B is 6-membered heterocyclyl.

(6s) Group (6a), wherein ring A is cyclobutyl, and ring B is azetidinyl, oxatanyl, tetrahydrofuranyl, pyrrolidinyl, piperidinyl or tetrahydropyranyl.

(6t) Group (6a), wherein ring A is cyclobutyl, and ring B is azetidinyl, oxatanyl, piperidinyl or tetrahydropyranyl.

(6u) Group (6a), wherein ring A is cyclobutyl, and ring B is azetidinyl or oxatanyl.

(6v) Group (6a), wherein ring A is cyclobutyl, and ring B is piperidinyl or tetrahydropyranyl.

(6w) Group (6a), wherein ring A is cyclobutyl, and ring B is azetidinyl or piperidinyl.

(6x) Group (6a), wherein ring A is cyclobutyl, and ring B is oxatanyl or tetrahydropyranyl.

(6y) Any of groups (6b)-(6x), wherein m is 1, 2 or 3, and each $R^a$ is independently selected from halogen, $C_{1-6}$alkyl, —OR, —$S(O)_2R$ and —$S(O)_2N(R)_2$.

(6z) Any of groups (6b)-(6x), wherein m is 1, 2 or 3, and each $R^a$ is independently selected from chloro, fluoro, methyl, —OH, —$S(O)_2$ethyl, —$S(O)_2NMe_2$. and —$S(O)_2NH_2$.

(6aa) Any of groups (6b)-(6x), wherein m is 1 or 2, and each $R^a$ is independently selected from halogen, $C_{1-6}$alkyl, —OR, —$S(O)_2R$ and —$S(O)_2N(R)_2$.

(6bb) Any of groups (6b)-(6x), wherein m is 3, and each $R^a$ is independently selected from halogen, $C_{1-6}$alkyl and —OR.

(6cc) Any of groups (6b)-(6x), wherein m is 3, and each $R^a$ is independently selected from fluoro, methyl and —OH.

(6dd) Any of groups (6b)-(6x), wherein m is 2, and each $R^a$ is independently selected from $C_{1-6}$alkyl and —OR.

(6ee) Any of groups (6b)-(6x), wherein m is 2, and each $R^a$ is independently selected from methyl and —OH.

(6ff) Any of groups (6b)-(6x), wherein m is 2, and both $R^a$ are methyl.

(6gg) Any of groups (6b)-(6x), wherein m is 2, and both $R^a$ are fluoro.

(6hh) Any of groups (6b)-(6x), wherein m is 1, and $R^a$ is selected from $C_{1-6}$alkyl, —OR, —$S(O)_2R$ and —$S(O)_2N(R)_2$.

(6ii) Any of groups (6b)-(6x), wherein m is 1, and $R^a$ is selected from $C_{1-6}$alkyl, —OR and —$S(O)_2N(R)_2$.

(6jj) Any of groups (6b)-(6x), wherein m is 1, and $R^a$ is selected from $C_{1-6}$alkyl, —OR and —$S(O)_2R$.

(6kk) Any of groups (6b)-(6x), wherein m is 1, and $R^a$ is selected from $C_{1-6}$alkyl and —OR.

(6ll) Any of groups (6b)-(6x), wherein m is 1, and $R^a$ is selected from methyl and —OH.

(6mm) Any of groups (6b)-(6x), wherein m is 1, and $R^a$ is selected from $C_{1-6}$alkyl, —$S(O)_2R$ and —$S(O)_2N(R)_2$.

(6nn) Any of groups (6b)-(6x), wherein m is 1, and $R^a$ is $C_{1-6}$alkyl.

(6oo) Any of groups (6b)-(6x), wherein m is 1, and $R^a$ is methyl or ethyl.

(6pp) Any of groups (6b)-(6x), wherein m is 1, and $R^a$ is methyl.

(6qq) Any of groups (6b)-(6x), wherein m is 1, and $R^a$ is —OMe or —OH.
(6rr) Any of groups (6b)-(6x), wherein m is 0.
(6ss) $R^1$ is
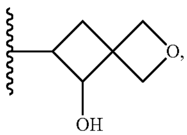
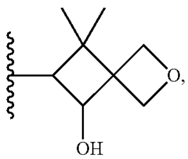
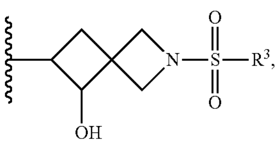
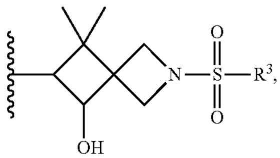
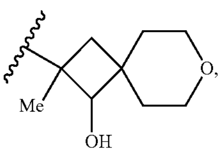
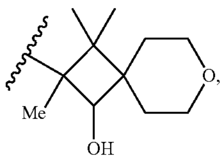
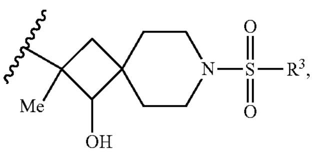
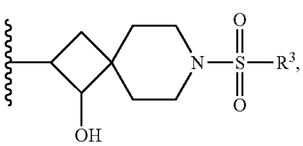
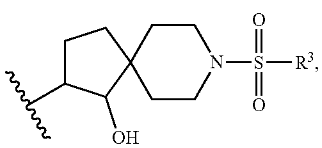
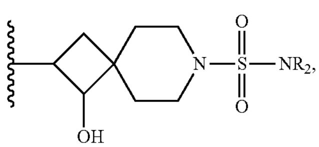
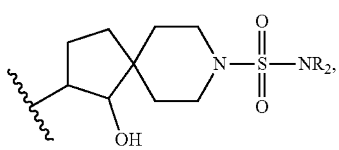
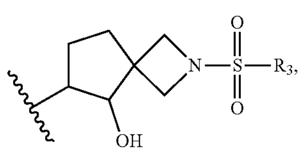
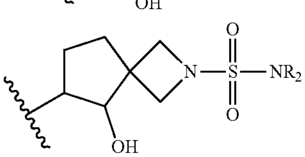
or
-continued
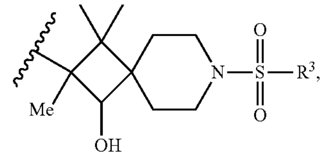
wherein
$R^3$ is methyl, ethyl, propyl, butyl, —O-methyl, —O-ethyl, —O-propyl, or —O-butyl.
(6tt) $R^1$ is
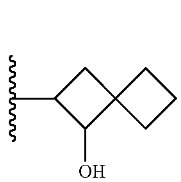
or
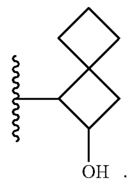
.
(6uu) $R^1$ is
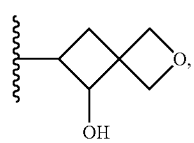
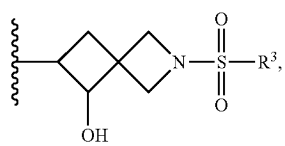
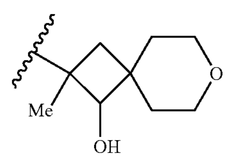
or
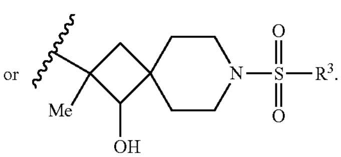
(6vv) $R^1$ is
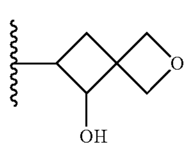
or
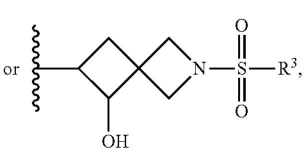
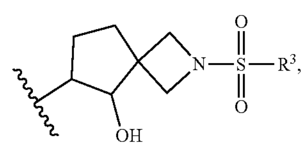
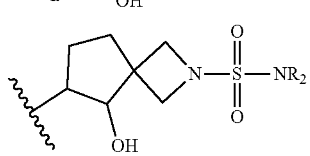

(6ww) $R^1$ is

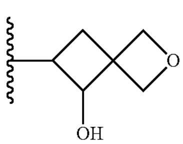
or
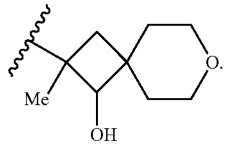

(6xx) $R^1$ is

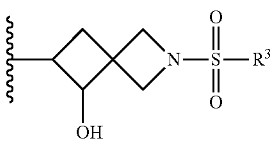
or
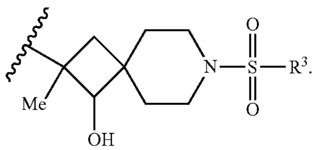

(6yy) $R^1$ is

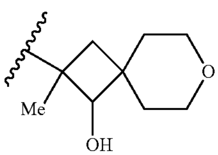
or
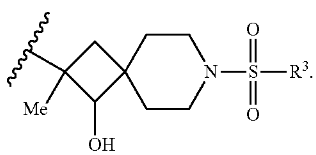

(6zz) $R^1$ is

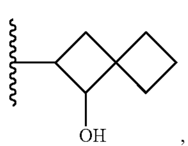
,
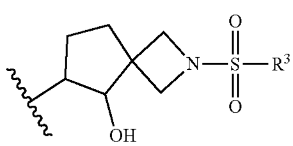
or
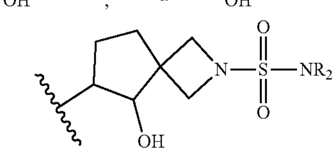

In another embodiment, the invention comprises compounds of Formula (V), (V)

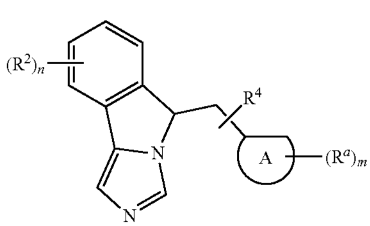

wherein ring A is $C_{3-10}$cycloalkyl, 3-7 membered heterocyclyl or heteroaryl;

m is 0, 1, 2, 3 or 4; and $R^4$ is —$NR_2$ or —OR substituted on the A ring or the methylene bonded to the A ring.

In one embodiment, the invention comprises compounds of Formula (V) wherein $R^4$ is —OH. In other embodiments, $R^4$ is —OH and n is 0. In other embodiments, $R^4$ is —OH and n is 1.

The invention further comprises subgenera of formula (V) in which the substituents are selected as any and all combinations of one or more of structural formula (V), $R^4$, $R^a$, m, and ring A, as defined herein, including without limitation, the following:

Structural Formula I is One of Formulae (Va)-(Vf):

(Va)

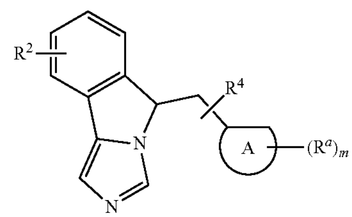

(Vb)

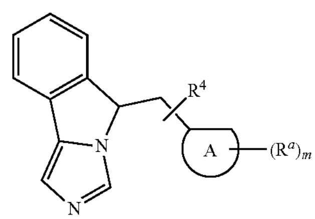

(Vc)

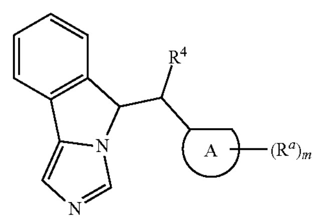

(Vd)

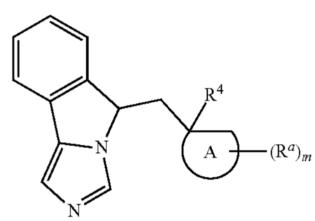

(Ve)

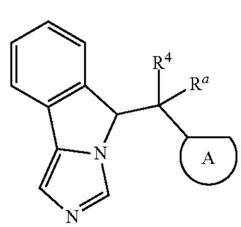

-continued (Vf)

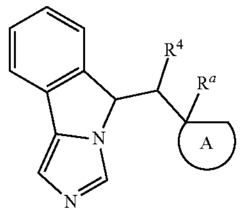

Ring A is selected from one of the following groups (7a)-(7cc):

(7a) Ring A is $C_{3-8}$cycloalkyl, 3-7 membered heterocyclyl or heteroaryl, wherein m is 0, 1, 2 or 3, and each $R^a$ is independently selected from halogen, $C_{1-6}$alkyl, —$S(O)_2R$, —C(O)N(R)$_2$ and $C_{1-6}$alkyl-cyano.

(7b) Group (7a), wherein ring A is $C_{3-6}$cycloalkyl, 4-6 membered heterocyclyl or heteroaryl.

(7c) Group (7a), wherein ring A is (7d)

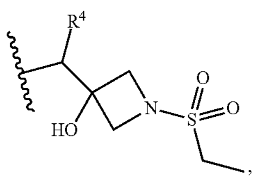
,
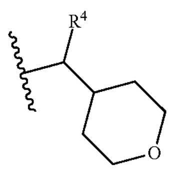
,
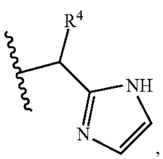
,
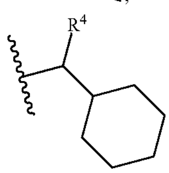
,
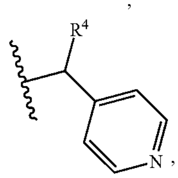
,
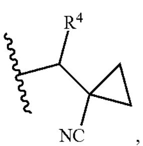
,
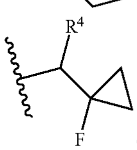
or
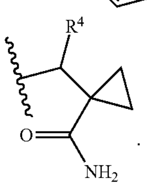
.

(7e) Group (7a), wherein ring A is $C_{3-8}$cycloalkyl.

(7f) Group (7a), wherein ring A is $C_{3-6}$cycloalkyl.

(7g) Group (7a), wherein ring A is cyclopropyl.

(7h) Group (7a), wherein ring A is cyclohexyl.

(7i) Group (7a), wherein ring A is 3-7 membered heterocyclyl.

(7j) Group (7a), wherein ring A is 4-6 membered heterocyclyl.

(7k) Group (7a), wherein ring A is 4-membered heterocyclyl.

(7l) Group (7a), wherein ring A is 5-membered heterocyclyl.

(7m) Group (7a), wherein ring A is 6-membered heterocyclyl.

(7n) Any of groups (7b)-(7l), wherein m is 0, 1, 2 or 3, and each $R^a$ is independently selected from halogen, $C_{1-6}$alkyl, —$S(O)_2R$, —C(O)N(R)$_2$ and $C_{1-6}$alkyl-cyano.

(7o) Group (7m), wherein each $R^a$ is independently selected from halogen, $C_{1-6}$alkyl, —$S(O)_2R$, —C(O)N(R)$_2$ and $C_{1-6}$alkyl-cyano.

(7p) Group (7m), wherein each $R^a$ is independently selected from halogen, $C_{1-6}$alkyl, —$S(O)_2R$ and —C(O)N(R)$_2$.

(7q) Group (7m), wherein each $R^a$ is independently selected from halogen, $C_{1-6}$alkyl and —$S(O)_2R$.

(7r) Group (7m), wherein each $R^a$ is independently selected from halogen, $C_{1-6}$alkyl and $C_{1-6}$alkyl-cyano.

(7s) Group (7m), wherein each $R^a$ is halogen.

(7t) Group (7m), wherein each $R^a$ is $C_{1-6}$alkyl.

(7u) Group (7m), wherein each $R^a$ is —$S(O)_2R$.

(7v) Group (7m), wherein each $R^a$ is —C(O)N(R)$_2$.

(7w) Group (7m), wherein each $R^a$ is $C_{1-6}$alkyl-cyano.

(7x) Any of groups (7b)-(7v), wherein m is 0, 1, 2 or 3.

(7y) Any of groups (7b)-(7v), wherein m is 0, 1 or 2.

(7z) Any of groups (7b)-(7v), wherein m is 0 or 1.

(7aa) Any of groups (7b)-(7v), wherein m is 3.

(7bb) Any of groups (7b)-(7v), wherein m is 2.

(7cc) Any of groups (7b)-(7v), wherein m is 1.

(7dd) Any of groups (7b)-(7v), wherein m is 0.

Particular embodiments of this aspect of the invention include compounds of any one of the formulae (II), (IIa)-(IIi), (III), (IIIa)-(IIIi), (IV) and (IVa)-(IVi), (V) and (Va)-(Vf) each as defined in each of the following rows, wherein each entry is a group number as defined above (e.g., (2r) refers to $R^2$ is fluoro), an "X" indicates that the variable is defined by another group in the embodiment (e.g., in embodiment (2)-X below, ring A is defined in Formula (X)) and a dash "-" indicates that the variable is as defined for Formula (I)—(Vf) or defined according to any one of the applicable variable definitions (1a)-(7xx) [e.g., when the entry for $R^2$ is a dash, it can be either as defined for Formula (II)—(Vf) or any one of definitions (2a)-(2t)]:

| | (I) | $R^2$ | A or A/B |
|---|---|---|---|
| (2)-1 | (IIa) | (2a) | (4a) |
| (2)-2 | (IIa) | (2b) | (4b) |
| (2)-3 | (IIa) | (2f) | (4c) |
| (2)-4 | (IIa) | (2h) | (4d) |
| (2)-5 | (IIa) | (2k) | (4n) |
| (2)-6 | (IIa) | (2n) | (4r) |
| (2)-7 | (IIa) | (2s) | (4z) |
| (2)-8 | (IIa) | (2t) | (4dd) |
| (2)-9 | (IIa) | (2a) | (4ff) |
| (2)-10 | (IIa) | (2b) | (4kk) |
| (2)-11 | (IIa) | (2f) | (4b) |
| (2)-12 | (IIa) | (2h) | (4c) |
| (2)-13 | (IIa) | (2k) | (4d) |
| (2)-14 | (IIa) | (2n) | (4n) |
| (2)-15 | (IIa) | (2s) | (4r) |
| (2)-16 | (IIa) | (2a) | (4a) |
| (2)-17 | (IIa) | (2b) | (4b) |
| (2)-18 | (IIa) | (2b) | (4c) |
| (2)-19 | (IIa) | (2f) | (4d) |
| (2)-20 | (IIa) | (2h) | (4n) |
| (2)-21 | (IIb) | (2k) | (4r) |
| (2)-22 | (IIb) | (2s) | (4z) |
| (2)-23 | (IIb) | (2t) | (4dd) |
| (2)-24 | (IIb) | (2a) | (4ff) |
| (2)-25 | (IIb) | (2a) | (4kk) |
| (2)-26 | (IIb) | (2b) | (4n) |
| (2)-27 | (IIb) | (2f) | (4r) |
| (2)-28 | (IIb) | (2h) | (4n) |
| (2)-29 | (IIb) | (2k) | (4r) |
| (2)-30 | (IIb) | (2a) | (4a) |
| (2)-31 | (IIb) | (2b) | (4b) |
| (2)-32 | (IIb) | (2t) | (4c) |
| (2)-33 | (IIb) | (2a) | (4d) |
| (2)-34 | (IIb) | (2s) | (4n) |
| (2)-35 | (IIb) | (2t) | (4r) |
| (2)-36 | (IIb) | (2a) | (4z) |
| (2)-37 | (IIb) | (2b) | (4dd) |
| (2)-38 | (IIb) | (2f) | (4ff) |
| (2)-39 | (IIb) | (2s) | (4kk) |
| (2)-40 | (IIb) | (2t) | (4c) |
| (2)-41 | (IIc) | X | (4d) |

-continued

| | (I) | $R^2$ | A or A/B |
|---|---|---|---|
| (2)-42 | (IIc) | X | (4n) |
| (2)-43 | (IIc) | X | (4r) |
| (2)-44 | (IIc) | X | (4z) |
| (2)-45 | (IIc) | X | (4dd) |
| (2)-46 | (IIc) | X | (4ff) |
| (2)-47 | (IIc) | X | (4kk) |
| (2)-48 | (IIc) | X | (4b) |
| (2)-49 | (IIc) | X | (4c) |
| (2)-50 | (IIc) | X | (4d) |
| (2)-51 | (IIc) | X | (4r) |
| (2)-52 | (IIc) | X | (4b) |
| (2)-53 | (IIc) | X | (4c) |
| (2)-54 | (IIc) | X | (4d) |
| (2)-55 | (IIc) | X | (4c) |
| (2)-56 | (IIc) | X | (4d) |
| (2)-57 | (IIc) | X | (4n) |
| (2)-58 | (IIc) | X | (4r) |
| (2)-59 | (IIc) | X | (4z) |
| (2)-60 | (IIc) | X | (4dd) |
| (2)-61 | (IId) | (2a) | (4ff) |
| (2)-62 | (IId) | (2b) | (4kk) |
| (2)-63 | (IId) | (2f) | (4n) |
| (2)-64 | (IId) | (2h) | (4r) |
| (2)-65 | (IId) | (2k) | (4b) |
| (2)-66 | (IId) | (2n) | (4c) |
| (2)-67 | (IId) | (2s) | (4d) |
| (2)-68 | (IId) | (2t) | (4n) |
| (2)-69 | (IId) | (2a) | (4r) |
| (2)-70 | (IId) | (2b) | (4b) |
| (2)-71 | (IId) | (2f) | (4c) |
| (2)-72 | (IId) | (2h) | (4d) |
| (2)-73 | (IId) | (2k) | (4c) |
| (2)-74 | (IId) | (2n) | (4d) |
| (2)-75 | (IId) | (2s) | (4n) |
| (2)-76 | (IId) | (2a) | (4r) |
| (2)-77 | (IId) | (2b) | (4z) |
| (2)-78 | (IId) | (2b) | (4dd) |
| (2)-79 | (IId) | (2f) | (4ff) |
| (2)-80 | (IId) | (2h) | (4b) |
| (2)-81 | (IIe) | X | (4c) |
| (2)-82 | (IIe) | X | (4d) |
| (2)-83 | (IIe) | X | (4n) |
| (2)-84 | (IIe) | X | (4r) |
| (2)-85 | (IIe) | X | (4b) |
| (2)-86 | (IIe) | X | (4c) |
| (2)-87 | (IIe) | X | (4d) |
| (2)-88 | (IIe) | X | (4n) |
| (2)-89 | (IIe) | X | (4r) |
| (2)-90 | (IIe) | X | (4z) |
| (2)-91 | (IIe) | X | (4a) |
| (2)-92 | (IIe) | X | (4b) |
| (2)-93 | (IIe) | X | (4c) |
| (2)-94 | (IIe) | X | (4d) |
| (2)-95 | (IIe) | X | (4n) |
| (2)-96 | (IIe) | X | (4r) |
| (2)-97 | (IIe) | X | (4z) |
| (2)-98 | (IIe) | X | (4dd) |
| (2)-99 | (IIe) | X | (4ff) |
| (2)-100 | (IIe) | X | (4kk) |
| (2)-101 | (IIIa) | (2a) | (5a) |
| (2)-102 | (IIIa) | (2b) | (5b) |
| (2)-103 | (IIIa) | (2f) | (5c) |
| (2)-104 | (IIIa) | (2h) | (5i) |
| (2)-105 | (IIIa) | (2k) | (5r) |
| (2)-106 | (IIIa) | (2n) | (5p) |
| (2)-107 | (IIIa) | (2s) | (5x) |
| (2)-108 | (IIIa) | (2t) | (5gg) |
| (2)-109 | (IIIa) | (2a) | (5oo) |
| (2)-110 | (IIIa) | (2b) | (5b) |
| (2)-111 | (IIIa) | (2f) | (5c) |
| (2)-112 | (IIIa) | (2h) | (5i) |
| (2)-113 | (IIIa) | (2k) | (5r) |
| (2)-114 | (IIIa) | (2n) | (5x) |
| (2)-115 | (IIIa) | (2s) | (5gg) |
| (2)-116 | (IIIa) | (2a) | (5oo) |
| (2)-117 | (IIIa) | (2b) | (5c) |
| (2)-118 | (IIIa) | (2b) | (5i) |

-continued

| | (I) | $R^2$ | A or A/B |
|---|---|---|---|
| (2)-119 | (IIIa) | (2f) | (5r) |
| (2)-120 | (IIIa) | (2h) | (5gg) |
| (2)-121 | (IIIb) | (2k) | (5oo) |
| (2)-122 | (IIIb) | (2s) | (5b) |
| (2)-123 | (IIIb) | (2t) | (5c) |
| (2)-124 | (IIIb) | (2a) | (5i) |
| (2)-125 | (IIIb) | (2a) | (5r) |
| (2)-126 | (IIIb) | (2b) | (5p) |
| (2)-127 | (IIIb) | (2f) | (5x) |
| (2)-128 | (IIIb) | (2h) | (5gg) |
| (2)-129 | (IIIb) | (2k) | (5oo) |
| (2)-130 | (IIIb) | (2a) | (5x) |
| (2)-131 | (IIIb) | (2b) | (5gg) |
| (2)-132 | (IIIb) | (2t) | (5oo) |
| (2)-133 | (IIIb) | (2a) | (5vv) |
| (2)-134 | (IIIb) | (2s) | (5x) |
| (2)-135 | (IIIb) | (2t) | (5a) |
| (2)-136 | (IIIb) | (2a) | (5b) |
| (2)-137 | (IIIb) | (2b) | (5c) |
| (2)-138 | (IIIb) | (2f) | (5i) |
| (2)-139 | (IIIb) | (2s) | (5r) |
| (2)-140 | (IIIb) | (2t) | (5ww) |
| (2)-141 | (IIIc) | X | (5x) |
| (2)-142 | (IIIc) | X | (5gg) |
| (2)-143 | (IIIc) | X | (5oo) |
| (2)-144 | (IIIc) | X | (5c) |
| (2)-145 | (IIIc) | X | (5i) |
| (2)-146 | (IIIc) | X | (5r) |
| (2)-147 | (IIIc) | X | (5oo) |
| (2)-148 | (IIIc) | X | (5c) |
| (2)-149 | (IIIc) | X | (5i) |
| (2)-150 | (IIIc) | X | (5r) |
| (2)-151 | (IIIc) | X | (5p) |
| (2)-152 | (IIIc) | X | (5x) |
| (2)-153 | (IIIc) | X | (5gg) |
| (2)-154 | (IIIc) | X | (5oo) |
| (2)-155 | (IIIc) | X | (5b) |
| (2)-156 | (IIIc) | X | (5c) |
| (2)-157 | (IIIc) | X | (5i) |
| (2)-158 | (IIIc) | X | (5r) |
| (2)-159 | (IIIc) | X | (5vv) |
| (2)-160 | (IIIc) | X | (5ww) |
| (2)-161 | (IIId) | (2a) | (5gg) |
| (2)-162 | (IIId) | (2b) | (5oo) |
| (2)-163 | (IIId) | (2f) | (5c) |
| (2)-164 | (IIId) | (2h) | (5i) |
| (2)-165 | (IIId) | (2k) | (5r) |
| (2)-166 | (IIId) | (2n) | (5gg) |
| (2)-167 | (IIId) | (2s) | (5oo) |
| (2)-168 | (IIId) | (2t) | (5c) |
| (2)-169 | (IIId) | (2a) | (5i) |
| (2)-170 | (IIId) | (2b) | (5r) |
| (2)-171 | (IIId) | (2f) | (5p) |
| (2)-172 | (IIId) | (2h) | (5x) |
| (2)-173 | (IIId) | (2k) | (5gg) |
| (2)-174 | (IIId) | (2n) | (5oo) |
| (2)-175 | (IIId) | (2s) | (5c) |
| (2)-176 | (IIId) | (2a) | (5i) |
| (2)-177 | (IIId) | (2b) | (5r) |
| (2)-178 | (IIId) | (2b) | (5a) |
| (2)-179 | (IIId) | (2f) | (5b) |
| (2)-180 | (IIId) | (2h) | (5c) |
| (2)-181 | (IIIe) | X | (5i) |
| (2)-182 | (IIIe) | X | (5r) |
| (2)-183 | (IIIe) | X | (5p) |
| (2)-184 | (IIIe) | X | (5x) |
| (2)-185 | (IIIe) | X | (5gg) |
| (2)-186 | (IIIe) | X | (5oo) |
| (2)-187 | (IIIe) | X | (5c) |
| (2)-188 | (IIIe) | X | (5i) |
| (2)-189 | (IIIe) | X | (5r) |
| (2)-190 | (IIIe) | X | (5c) |
| (2)-191 | (IIIe) | X | (5i) |
| (2)-192 | (IIIe) | X | (5r) |
| (2)-193 | (IIIe) | X | (5b) |
| (2)-194 | (IIIe) | X | (5c) |
| (2)-195 | (IIIe) | X | (5i) |

-continued

| | (I) | $R^2$ | A or A/B |
|---|---|---|---|
| (2)-196 | (IIIe) | X | (5r) |
| (2)-197 | (IIIe) | X | (5vv) |
| (2)-198 | (IIIe) | X | (5ww) |
| (2)-199 | (IIIe) | X | (5gg) |
| (2)-200 | (IIIe) | X | (5oo) |
| (2)-201 | (IVa) | (2a) | (6a) |
| (2)-202 | (IVa) | (2b) | (6b) |
| (2)-203 | (IVa) | (2f) | (6c) |
| (2)-204 | (IVa) | (2h) | (6g) |
| (2)-205 | (IVa) | (2k) | (6k) |
| (2)-206 | (IVa) | (2n) | (6m) |
| (2)-207 | (IVa) | (2s) | (6u) |
| (2)-208 | (IVa) | (2t) | (6ss) |
| (2)-209 | (IVa) | (2a) | (6tt) |
| (2)-210 | (IVa) | (2b) | (6b) |
| (2)-211 | (IVa) | (2f) | (6c) |
| (2)-212 | (IVa) | (2h) | (6g) |
| (2)-213 | (IVa) | (2k) | (6c) |
| (2)-214 | (IVa) | (2n) | (6g) |
| (2)-215 | (IVa) | (2s) | (6ss) |
| (2)-216 | (IVa) | (2a) | (6tt) |
| (2)-217 | (IVa) | (2b) | (6b) |
| (2)-218 | (IVa) | (2b) | (6m) |
| (2)-219 | (IVa) | (2f) | (6u) |
| (2)-220 | (IVa) | (2h) | (6ss) |
| (2)-221 | (IVb) | (2k) | (6tt) |
| (2)-222 | (IVb) | (2s) | (6b) |
| (2)-223 | (IVb) | (2t) | (6g) |
| (2)-224 | (IVb) | (2a) | (6a) |
| (2)-225 | (IVb) | (2a) | (6b) |
| (2)-226 | (IVb) | (2b) | (6c) |
| (2)-227 | (IVb) | (2f) | (6g) |
| (2)-228 | (IVb) | (2h) | (6k) |
| (2)-229 | (IVb) | (2k) | (6m) |
| (2)-230 | (IVb) | (2a) | (6u) |
| (2)-231 | (IVb) | (2b) | (6ss) |
| (2)-232 | (IVb) | (2t) | (6tt) |
| (2)-233 | (IVb) | (2a) | (6b) |
| (2)-234 | (IVb) | (2s) | (6c) |
| (2)-235 | (IVb) | (2t) | (6g) |
| (2)-236 | (IVb) | (2a) | (6k) |
| (2)-237 | (IVb) | (2b) | (6m) |
| (2)-238 | (IVb) | (2f) | (6u) |
| (2)-239 | (IVb) | (2s) | (6ss) |
| (2)-240 | (IVb) | (2t) | (6tt) |
| (2)-241 | (IVc) | X | (6b) |
| (2)-242 | (IVc) | X | (6c) |
| (2)-243 | (IVc) | X | (6g) |
| (2)-244 | (IVc) | X | (6ss) |
| (2)-245 | (IVc) | X | (6tt) |
| (2)-246 | (IVc) | X | (6b) |
| (2)-247 | (IVc) | X | (6m) |
| (2)-248 | (IVc) | X | (6u) |
| (2)-249 | (IVc) | X | (6a) |
| (2)-250 | (IVc) | X | (6b) |
| (2)-251 | (IVc) | X | (6c) |
| (2)-252 | (IVc) | X | (6g) |
| (2)-253 | (IVc) | X | (6k) |
| (2)-254 | (IVc) | X | (6m) |
| (2)-255 | (IVc) | X | (6u) |
| (2)-256 | (IVc) | X | (6ss) |
| (2)-257 | (IVc) | X | (6tt) |
| (2)-258 | (IVc) | X | (6ss) |
| (2)-259 | (IVc) | X | (6tt) |
| (2)-260 | (IVc) | X | (6b) |
| (2)-261 | (IVd) | (2a) | (6u) |
| (2)-262 | (IVd) | (2b) | (6a) |
| (2)-263 | (IVd) | (2f) | (6b) |
| (2)-264 | (IVd) | (2h) | (6c) |
| (2)-265 | (IVd) | (2k) | (6g) |
| (2)-266 | (IVd) | (2n) | (6k) |
| (2)-267 | (IVd) | (2s) | (6m) |
| (2)-268 | (IVd) | (2t) | (6u) |
| (2)-269 | (IVd) | (2a) | (6ss) |
| (2)-270 | (IVd) | (2b) | (6tt) |
| (2)-271 | (IVd) | (2f) | (6ss) |
| (2)-272 | (IVd) | (2h) | (6tt) |

-continued

| | (I) | $R^2$ | A or A/B |
|---|---|---|---|
| (2)-273 | (IVd) | (2k) | (6b) |
| (2)-274 | (IVd) | (2n) | (6k) |
| (2)-275 | (IVd) | (2s) | (6m) |
| (2)-276 | (IVd) | (2a) | (6u) |
| (2)-277 | (IVd) | (2b) | (6ss) |
| (2)-278 | (IVd) | (2b) | (6tt) |
| (2)-279 | (IVd) | (2f) | (6b) |
| (2)-280 | (IVd) | (2h) | (6g) |
| (2)-281 | (IVe) | X | (6ss) |
| (2)-282 | (IVe) | X | (6tt) |
| (2)-283 | (IVe) | X | (6b) |
| (2)-284 | (IVe) | X | (6c) |
| (2)-285 | (IVe) | X | (6g) |
| (2)-286 | (IVe) | X | (6k) |
| (2)-287 | (IVe) | X | (6m) |
| (2)-288 | (IVe) | X | (6u) |
| (2)-289 | (IVe) | X | (6ss) |
| (2)-290 | (IVe) | X | (6tt) |
| (2)-291 | (IVe) | X | (6k) |
| (2)-292 | (IVe) | X | (6m) |
| (2)-293 | (IVe) | X | (6u) |
| (2)-294 | (IVe) | X | (6b) |
| (2)-295 | (IVe) | X | (6c) |
| (2)-296 | (IVe) | X | (6g) |
| (2)-297 | (IVe) | X | (6k) |
| (2)-298 | (IVe) | X | (6m) |
| (2)-299 | (IVe) | X | (6u) |
| (2)-300 | (IVe) | X | (6ss) |
| (2)-301 | (IIj) | X | (4a) |
| (2)-302 | (IIj) | X | (4c) |
| (2)-303 | (IIj) | X | (4f) |
| (2)-304 | (IIj) | X | (4g) |
| (2)-305 | (IIj) | X | (4k) |
| (2)-306 | (IIj) | X | (4l) |
| (2)-307 | (IIj) | X | (4m) |
| (2)-308 | (IIj) | X | (4bbb) |
| (2)-309 | (IIj) | X | (4ccc) |
| (2)-310 | (IIk) | X | (4a) |
| (2)-311 | (IIk) | X | (4c) |
| (2)-312 | (IIk) | X | (4f) |
| (2)-313 | (IIk) | X | (4g) |
| (2)-314 | (IIk) | X | (4k) |
| (2)-315 | (IIk) | X | (4l) |
| (2)-316 | (IIk) | X | (4m) |
| (2)-317 | (IIk) | X | (4bbb) |
| (2)-318 | (IIk) | X | (4ccc) |
| (2)-319 | (IIl) | X | (4a) |
| (2)-320 | (IIl) | X | (4c) |
| (2)-321 | (IIl) | X | (4f) |
| (2)-322 | (IIl) | X | (4g) |
| (2)-323 | (IIl) | X | (4k) |
| (2)-324 | (IIl) | X | (4l) |
| (2)-325 | (IIl) | X | (4m) |
| (2)-326 | (IIl) | X | (4bbb) |
| (2)-327 | (IIl) | X | (4ccc) |
| (2)-328 | (IIm) | X | (4a) |
| (2)-329 | (IIm) | X | (4c) |
| (2)-330 | (IIm) | X | (4f) |
| (2)-331 | (IIm) | X | (4g) |
| (2)-332 | (IIm) | X | (4k) |
| (2)-333 | (IIm) | X | (4l) |
| (2)-334 | (IIm) | X | (4m) |
| (2)-335 | (IIm) | X | (4bbb) |
| (2)-336 | (IIm) | X | (4ccc) |
| (2)-337 | (IIn) | X | (4a) |
| (2)-338 | (IIn) | X | (4c) |
| (2)-339 | (IIn) | X | (4f) |
| (2)-340 | (IIn) | X | (4g) |
| (2)-341 | (IIn) | X | (4k) |
| (2)-342 | (IIn) | X | (4l) |
| (2)-343 | (IIn) | X | (4m) |
| (2)-344 | (IIn) | X | (4bbb) |
| (2)-345 | (IIn) | X | (4ccc) |
| (2)-346 | (IIo) | X | (4a) |
| (2)-347 | (IIo) | X | (4c) |
| (2)-348 | (IIo) | X | (4f) |
| (2)-349 | (IIo) | X | (4g) |

-continued

| | (I) | $R^2$ | A or A/B |
|---|---|---|---|
| (2)-350 | (IIo) | X | (4k) |
| (2)-351 | (IIo) | X | (4l) |
| (2)-352 | (IIo) | X | (4m) |
| (2)-353 | (IIo) | X | (4bbb) |
| (2)-354 | (IIo) | X | (4ccc) |
| (2)-355 | (IIIc) | X | (5ww) |
| (2)-356 | (IIIc) | X | (5xx) |
| (2)-357 | (IIIc) | X | (5yy) |
| (2)-358 | (Vb) | X | (7b) |
| (2)-359 | (Vb) | X | (7c) |
| (2)-360 | (Vb) | X | (7x) |
| (2)-361 | (Vb) | X | (7bb) |
| (2)-362 | (Vb) | X | (7f) |
| (2)-363 | (Vc) | X | (7aa) |
| (2)-364 | (Vc) | X | (7b) |
| (2)-365 | (Vc) | X | (7c) |
| (2)-366 | (Vc) | X | (7x) |
| (2)-367 | (Vc) | X | (7bb) |
| (2)-368 | (Vd) | X | (7f) |
| (2)-369 | (Vd) | X | (7aa) |
| (2)-370 | (Vd) | X | (7b) |
| (2)-371 | (Vd) | X | (7c) |
| (2)-372 | (Vd) | X | (7x) |
| (2)-373 | (Ve) | X | (7b) |
| (2)-374 | (Ve) | X | (7c) |
| (2)-375 | (Ve) | X | (7e) |
| (2)-376 | (Ve) | X | (7i) |
| (2)-377 | (Ve) | X | (7l) |
| (2)-378 | (Vf) | X | (7b) |
| (2)-379 | (Vf) | X | (7c) |
| (2)-380 | (Vf) | X | (7e) |
| (2)-381 | (Vf) | X | (7i) |
| (2)-382 | (Vf) | X | (7l) |
| (2)-383 | (Vf) | X | (7f) |

In another embodiment, each R is independently hydrogen or $C_{1-6}$alkyl. In other embodiments, R is independently hydrogen, methyl, ethyl or trifluoromethyl.

In another embodiment, the compounds of the invention are of Formulae (IIk) or (III), (IIk)

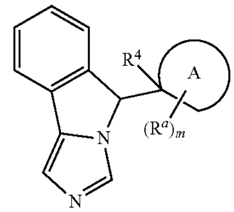

(III)

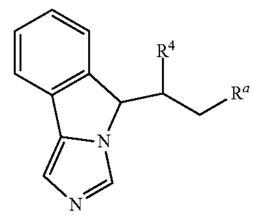

which are compounds of Formula (I) wherein, $R^1$ is

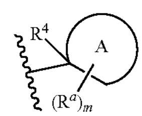 or 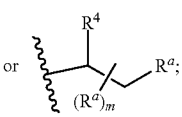

ring A is $C_{3-10}$cycloalkyl or 3-7 membered heterocyclyl (e.g., a 4-6 membered heterocyclyl or a 5-6 membered heterocyclyl), m is 0, 1, 2, 3 or 4; and 1

$R^4$ is —$NR_2$ or —OR.

In another aspect, the present disclosure provides compounds that are:

| No. | Structure | Name |
|---|---|---|
| 1 | 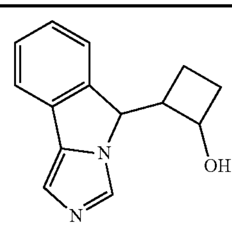 | 2-(5H-imidazo[5,1-a]isoindol-5-yl)cyclobutan-1-ol |
| 2 | 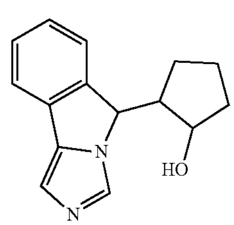 [SMILES: OC1CCCC1C1c2ccccc2-c2cncn21] | 2-(5H-imidazo[5,1-a]isoindol-5-yl)cyclopentan-1-ol |
| 3 | 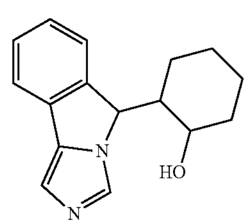 [SMILES: OC1CCCCC1C1c2ccccc2-c2cncn21] | 2-(5H-imidazo[5,1-a]isoindol-5-yl)cyclohexan-1-ol |

-continued

| No. | Structure | Name |
|---|---|---|
| 4 | 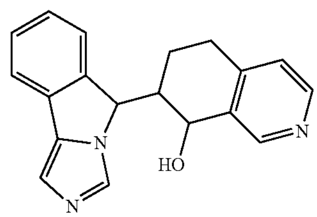 [SMILES: OC1c2cnccc2CCC1C1c2ccccc2-c2cncn21] | 7-(5H-imidazo[5,1-a]isoindol-5-yl)-5,6,7,8-tetrahydroisoquinolin-8-ol |
| 5 | 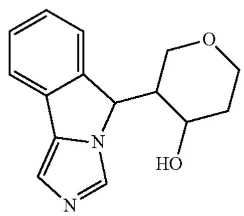 [SMILES: OC1CCOCC1C1c2ccccc2-c2cncn21] | 3-(5H-imidazo[5,1-a]isoindol-5-yl)-tetrahydro-2H-pyran-4-ol |
| 6 | 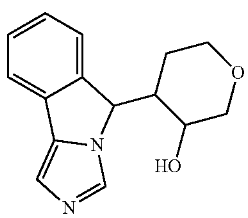 [SMILES: OC1COCCC1C1c2ccccc2-c2cncn21] | 4-(5H-imidazo[5,1-a]isoindol-5-yl)-tetrahydro-2H-pyran-3-ol |
| 7 | 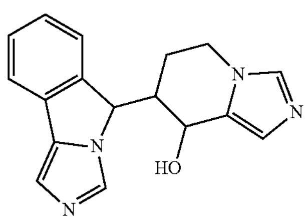 [SMILES: OC1c2cncn2CCC1C1c2ccccc2-c2cncn21] | 7-(5H-imidazo[4,3-a]isoindol-5-yl)-5H,6H,7H,8H-imidazo[1,5-a]pyridin-8-ol |
| 8 | 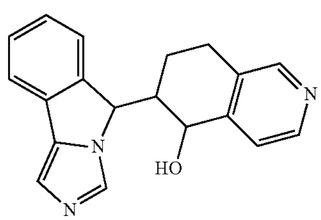 [SMILES: OC1c2ccncc2CCC1C1c2ccccc2-c2cncn21] | 6-(5H-imidazo[4,3-a]isoindol-5-yl)-5,6,7,8-tetrahydroisoquinolin-5-ol |
| 9 | 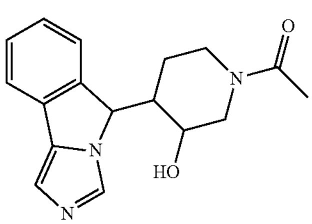 [SMILES: CC(=O)N1CCC(C2c3ccccc3-c3cncn32)C(O)C1] | 1-(3-hydroxy-4-(5H-imidazo[5,1-a]isoindol-5-yl)piperidin-1-yl)ethan-1-one |
| 10 | 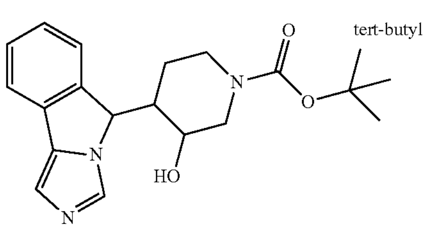 | tert-butyl 3-hydroxy-4-(5H-imidazo[5,1-a]isoindol-5-yl)piperidine-1-carboxylate |

-continued
| No. | Structure | Name |
|---|---|---|
| 11 | 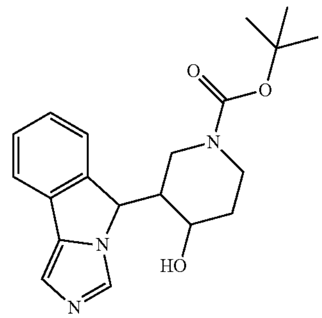 [SMILES: CC(C)(C)OC(=O)N1CCC(O)C(C2c3ccccc3-c3cncn32)C1] | tert-butyl 4-hydroxy-3-(5H-imidazo[5,1-a]isoindol-5-yl)piperidine-1-carboxylate |
| 12 | 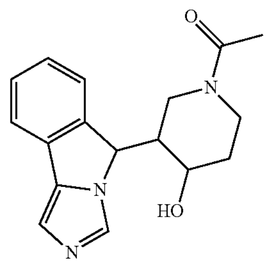 [SMILES: CC(=O)N1CCC(O)C(C2c3ccccc3-c3cncn32)C1] | 1-(4-hydroxy-3-(5H-imidazo[5,1-a]isoindol-5-yl)piperidin-1-yl)ethan-1-one |
| 13 | 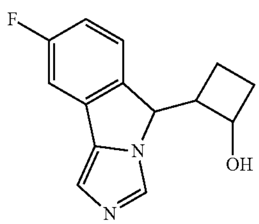 [SMILES: OC1CCC1C1c2ccc(F)cc2-c2cncn21] | 2-(8-fluoro-5H-imidazo[5,1-a]isoindol-5-yl)cyclobutan-1-ol |
| 14 | 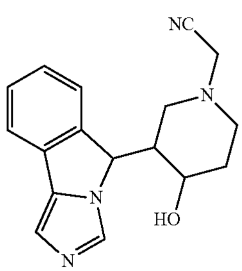 [SMILES: N#CCN1CCC(O)C(C2c3ccccc3-c3cncn32)C1] | 2-(4-hydroxy-3-(5H-imidazo[5,1-a]isoindol-5-yl)piperidin-1-yl)acetonitrile |
| 15 | 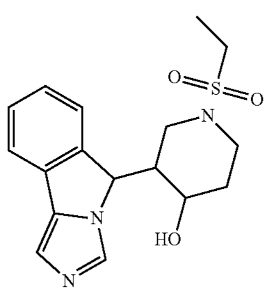 | 1-(ethylsulfonyl)-3-(5H-imidazo[5,1-a]isoindol-5-yl)piperidin-4-ol |
| 16 | 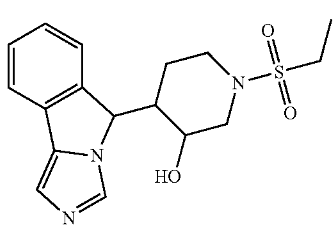 [SMILES: CCS(=O)(=O)N1CCC(C2c3ccccc3-c3cncn32)C(O)C1] | 1-(ethylsulfonyl)-4-(5H-imidazo[5,1-a]isoindol-5-yl)piperidin-3-ol |

-continued
| No. | Structure | Name |
|---|---|---|
| 17 | 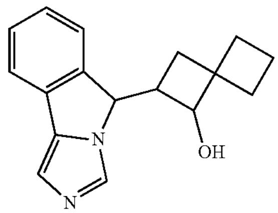 [SMILES: OC1C(C2c3ccccc3-c3cncn32)CC12CCC2] | 2-(5H-imidazo[5,1-a]isoindol-5-yl)spiro[3.3]heptan-1-ol |
| 18 | 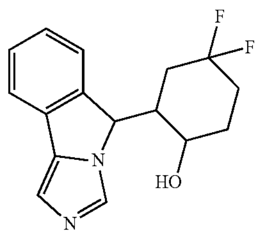 [SMILES: OC1CCC(F)(F)CC1C1c2ccccc2-c2cncn21] | 4,4-difluoro-2-((S)-5H-imidazo[5,1-a]isoindol-5-yl)cyclohexan-1-ol |
| 19 | 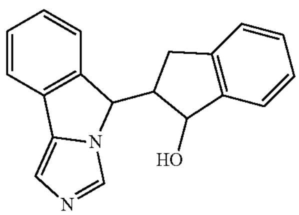 [SMILES: OC1c2ccccc2CC1C1c2ccccc2-c2cncn21] | 2-(5H-imidazo[5,1-a]isoindol-5-yl)-2,3-dihydro-1H-inden-1-ol |
| 20 | 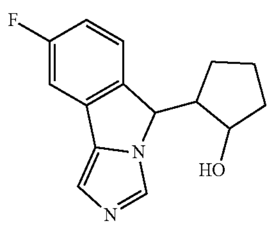 [SMILES: OC1CCCC1C1c2ccc(F)cc2-c2cncn21] | 2-(8-fluoro-5H-imidazo[5,1-a]isoindol-5-yl)cyclopentan-1-ol |
| 21 | 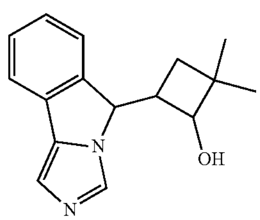 [SMILES: CC1(C)CC(C2c3ccccc3-c3cncn32)C1O] | 4-(5H-imidazo[5,1-a]isoindol-5-yl)-2,2-dimethylcyclobutan-1-ol |
| 22 | 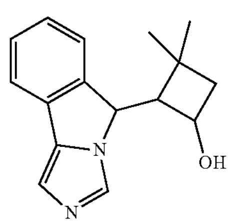 [SMILES: CC1(C)CC(O)C1C1c2ccccc2-c2cncn21] | 2-(5H-imidazo[5,1-a]isoindol-5-yl)-3,3-dimethylcyclobutan-1-ol |
| 23 | 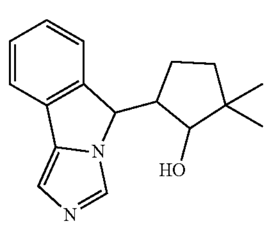 [SMILES: CC1(C)CCC(C2c3ccccc3-c3cncn32)C1O] | 5-(5H-imidazo[5,1-a]isoindol-5-yl)-2,2-dimethylcyclopentan-1-ol |

-continued
| No. | Structure | Name |
| --- | --- | --- |
| 24 | 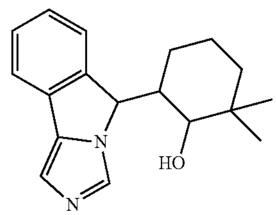 [SMILES: CC1(C)CCCC(C2c3ccccc3-c3cncn32)C1O] | 6-(5H-imidazo[5,1-a]isoindol-5-yl)-2,2-dimethylcyclohexan-1-ol |
| 25 | 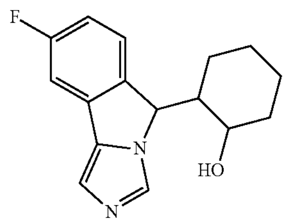 [SMILES: OC1CCCCC1C1c2ccc(F)cc2-c2cncn21] | 2-(8-fluoro-5H-imidazo[5,1-a]isoindol-5-yl)cyclohexan-1-ol |
| 26 | 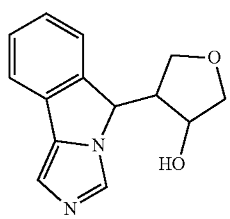 [SMILES: OC1COCC1C1c2ccccc2-c2cncn21] | 4-(5H-imidazo[5,1-a]isoindol-5-yl)tetrahydrofuran-3-ol |
| 27 | 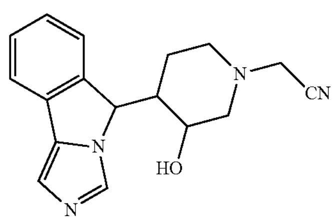 [SMILES: N#CCN1CCC(C2c3ccccc3-c3cncn32)C(O)C1] | 2-(3-hydroxy-4-(-5H-imidazo[5,1-a]isoindol-5-yl)piperidin-1-yl)acetonitrile |
| 28 | 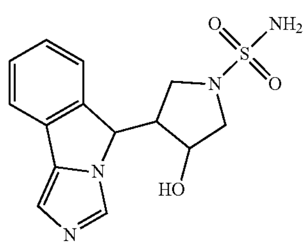 [SMILES: NS(=O)(=O)N1CC(O)C(C2c3ccccc3-c3cncn32)C1] | 3-hydroxy-4-(5H-imidazo[5,1-a]isoindol-5-yl)pyrrolidine-1-sulfonamide |
| 29 | 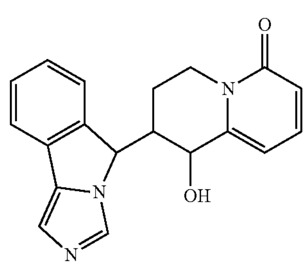 [SMILES: O=c1cccc2n1CCC(C1c3ccccc3-c3cncn31)C2O] | 9-hydroxy-8-(5H-imidazo[5,1-a]isoindol-5-yl)-6,7,8,9-tetrahydro-4H-quinolizin-4-one |

-continued

| No. | Structure | Name |
|---|---|---|
| 30 | 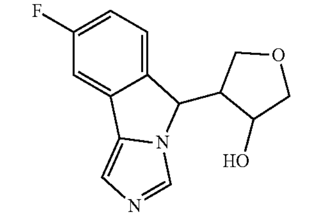 [SMILES: OC1COCC1C1c2ccc(F)cc2-c2cncn21] | 4-(8-fluoro-5H-imidazo[5,1-a]isoindol-5-yl)tetrahydrofuran-3-ol |
| 31 | 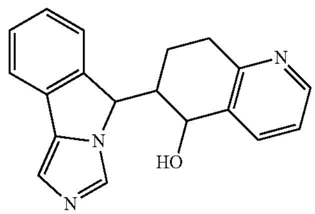 [SMILES: OC1c2cccnc2CCC1C1c2ccccc2-c2cncn21] | 6-(5H-imidazo[5,1-a]isoindol-5-yl)-5,6,7,8-tetrahydroquinolin-5-ol |
| 32 | 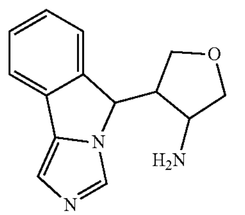 [SMILES: NC1COCC1C1c2ccccc2-c2cncn21] | 4-(5H-imidazo[5,1-a]isoindol-5-yl)tetrahydrofuran-3-amine |
| 33 | 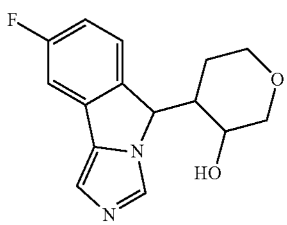 [SMILES: OC1COCCC1C1c2ccc(F)cc2-c2cncn21] | 4-(8-fluoro-5H-imidazo[5,1-a]isoindol-5-yl)-tetrahydro-2H-pyran-3-ol |
| 34 | 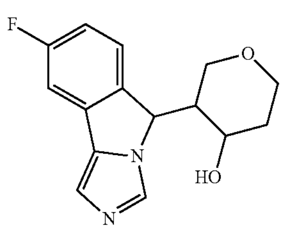 [SMILES: OC1CCOCC1C1c2ccc(F)cc2-c2cncn21] | 3-(8-fluoro-5H-imidazo[5,1-a]isoindol-5-yl)-tetrahydro-2H-pyran-4-ol |
| 35 | 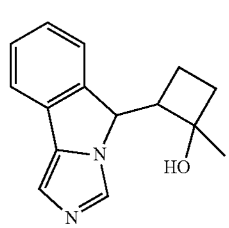 [SMILES: CC1(O)CCC1C1c2ccccc2-c2cncn21] | 2-(5H-imidazo[5,1-a]isoindol-5-yl)-1-methylcyclobutan-1-ol |
| 36 | 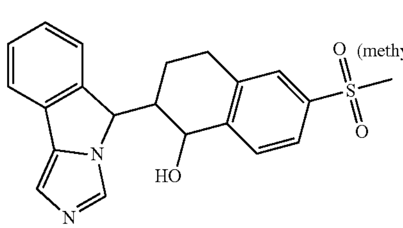 | 2-(5H-imidazo[5,1-a]isoindol-5-yl)-6-(methylsulfonyl)-1,2,3,4-tetrahydronaphthalen-1-ol |

-continued

| No. | Structure | Name |
|---|---|---|
| 37 | 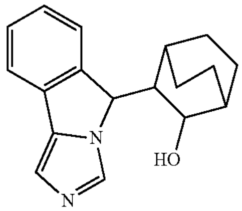 [SMILES: OC1C2CCC(CC2)C1C1c2ccccc2-c2cncn21] | 3-(5H-imidazo[5,1-a]isoindol-5-yl)bicyclo[2.2.2]octan-2-ol |
| 38 | 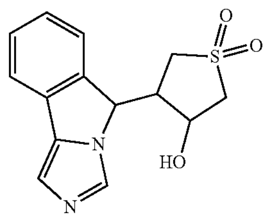 [SMILES: O=S1(=O)CC(O)C(C2c3ccccc3-c3cncn32)C1] | 3-hydroxy-4-(5H-imidazo[5,1-a]isoindol-5-yl)tetrahydrothiophene 1,1-dioxide |
| 39 | 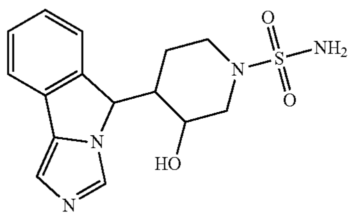 [SMILES: NS(=O)(=O)N1CCC(C2c3ccccc3-c3cncn32)C(O)C1] | 3-hydroxy-4-(5H-imidazo[5,1-a]isoindol-5-yl)piperidine-1-sulfonamide |
| 40 | 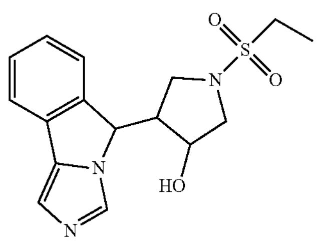 [SMILES: CCS(=O)(=O)N1CC(O)C(C2c3ccccc3-c3cncn32)C1] | 1-(ethylsulfonyl)-4-(5H-imidazo[5,1-a]isoindol-5-yl)pyrrolidin-3-ol |
| 41 | 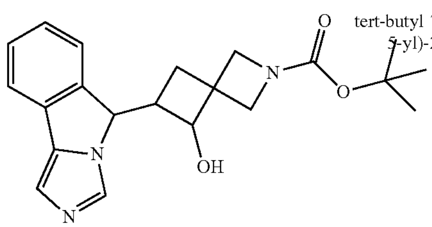 | tert-butyl 7-hydroxy-6-(5H-imidazo[1,5-b]isoindol-5-yl)-2-azaspiro[3.3]heptane-2-carboxylate |
| 42 | 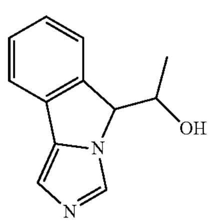 | 1-(5H-imidazo[5,1-a]isoindol-5-yl)ethan-1-ol |
| 43 | 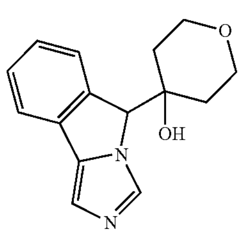 [SMILES: OC1(C2c3ccccc3-c3cncn32)CCOCC1] | 4-(5H-imidazo[5,1-a]isoindol-5-yl)tetrahydro-2H-pyran-4-ol |

-continued
| No. | Structure | Name |
|---|---|---|
| 44 | 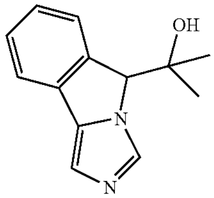 [SMILES: CC(C)(O)C1c2ccccc2-c2cncn21] | 2-(5H-imidazo[5,1-a]isoindol-5-yl)propan-2-ol |
| 45 | 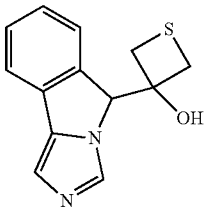 [SMILES: OC1(C2c3ccccc3-c3cncn32)CSC1] | 3-(5H-imidazo[5,1-a]isoindol-5-yl)thietan-3-ol |
| 46 | 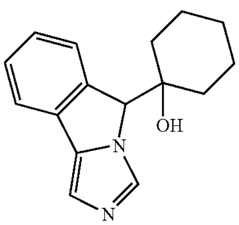 [SMILES: OC1(C2c3ccccc3-c3cncn32)CCCCC1] | 1-(5H-imidazo[5,1-a]isoindol-5-yl)cyclohexan-1-ol |
| 47 | 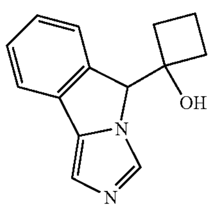 [SMILES: OC1(C2c3ccccc3-c3cncn32)CCC1] | 1-(5H-imidazo[5,1-a]isoindol-5-yl)cyclobutan-1-ol |
| 48 | 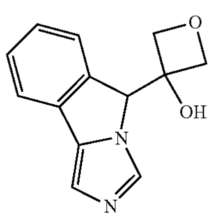 [SMILES: OC1(C2c3ccccc3-c3cncn32)COC1] | 3-(5H-imidazo[5,1-a]isoindol-5-yl)oxetan-3-ol |
| 49 | 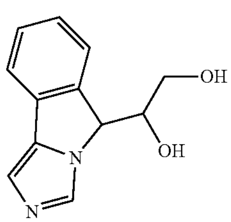 [SMILES: OCC(O)C1c2ccccc2-c2cncn21] | 1-(5H-imidazo[5,1-a]isoindol-5-yl)ethane-1,2-diol |
| 50 | 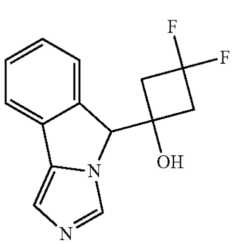 [SMILES: OC1(C2c3ccccc3-c3cncn32)CC(F)(F)C1] | 3,3-difluoro-1-(5H-imidazo[5,1-a]isoindol-5-yl)cyclobutan-1-ol |

-continued
| No. | Structure | Name |
| --- | --- | --- |
| 51 | 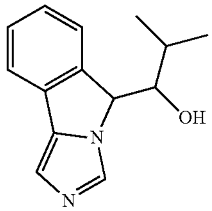 [SMILES: CC(C)C(O)C1c2ccccc2-c2cncn21] | 1-(5H-imidazo[5,1-a]isoindol-5-yl)-2-methylpropan-1-ol |
| 52 | 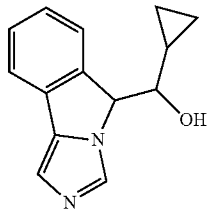 [SMILES: OC(C1CC1)C1c2ccccc2-c2cncn21] | cyclopropyl(5H-imidazo[5,1-a]isoindol-5-yl)methanol |
| 53 | 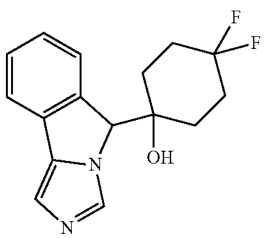 [SMILES: OC1(C2c3ccccc3-c3cncn32)CCC(F)(F)CC1] | 4,4-difluoro-1-(5H-imidazo[5,1-a]isoindol-5-yl)cyclohexan-1-ol |
| 54 | 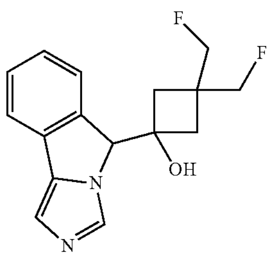 [SMILES: OC1(C2c3ccccc3-c3cncn32)CC(CF)(CF)C1] | 3,3-bis(fluoromethyl)-1-(5H-imidazo[5,1-a]isoindol-5-yl)cyclobutan-1-ol |
| 55 | 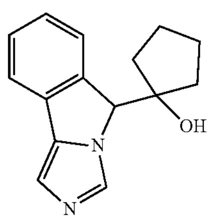 [SMILES: OC1(C2c3ccccc3-c3cncn32)CCCC1] | 1-(5H-imidazo[5,1-a]isoindol-5-yl)cyclopentan-1-ol |
| 56 | 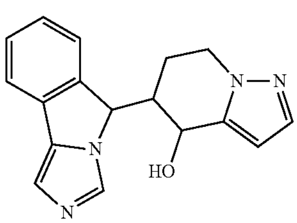 [SMILES: OC1c2ccnn2CCC1C1c2ccccc2-c2cncn21] | 5-(5H-imidazo[5,1-a]isoindol-5-yl)-4,5,6,7-tetrahydropyrazolo[1,5-a]pyridin-4-ol |
| 57 | 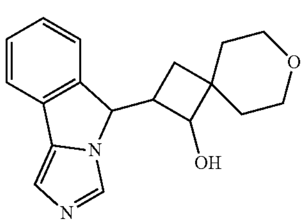 [SMILES: OC1C(C2c3ccccc3-c3cncn32)CC12CCOCC2] | 2-(5H-imidazo[5,1-a]isoindol-5-yl)-7-oxaspiro[3.5]nonan-1-ol |

-continued

| No. | Structure | Name |
| --- | --- | --- |
| 58 | 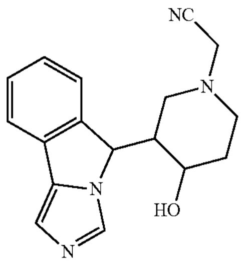 [SMILES: N#CCN1CCC(O)C(C2c3ccccc3-c3cncn32)C1] | 2-(4-hydroxy-3-(5H-imidazo[5,1-a]isoindol-5-yl)piperidin-1-yl)acetonitrile |
| 59 | 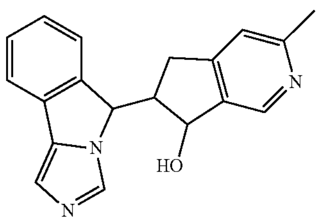 [SMILES: Cc1cc2c(cn1)C(O)C(C1c3ccccc3-c3cncn31)C2] | 6-(5H-imidazo[5,1-a]isoindol-5-yl)-3-methyl-6,7-dihydro-5H-cyclopenta[c]pyridin-7-ol |
| 60 | 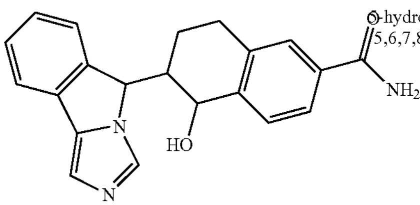 [SMILES: NC(=O)c1ccc2c(c1)CCC(C1c3ccccc3-c3cncn31)C2O] | 5-hydroxy-6-(5H-imidazo[5,1-a]isoindol-5-yl)-5,6,7,8-tetrahydronaphthalene-2-carboxamide |
| 61 | 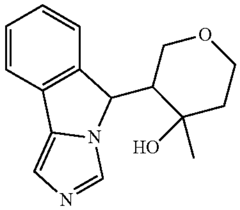 [SMILES: CC1(O)CCOCC1C1c2ccccc2-c2cncn21] | 3-(5H-imidazo[5,1-a]isoindol-5-yl)-4-methyltetrahydro-2H-pyran-4-ol |
| 62 | 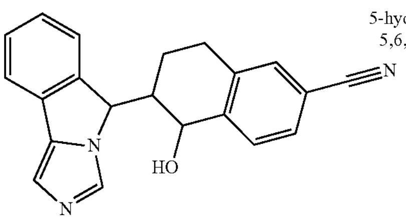 | 5-hydroxy-6-(5H-imidazo[5,1-a]isoindol-5-yl)-5,6,7,8-tetrahydronaphthalene-2-carbonitrile |
| 63 | 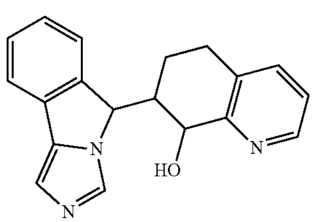 [SMILES: OC1c2ncccc2CCC1C1c2ccccc2-c2cncn21] | 7-(5H-imidazo[5,1-a]isoindol-5-yl)-5,6,7,8-tetrahydroquinolin-8-ol |
| 64 | 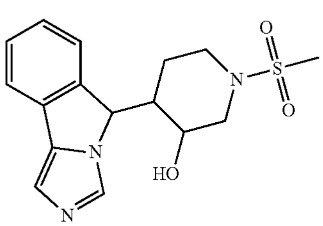 [SMILES: CS(=O)(=O)N1CCC(C2c3ccccc3-c3cncn32)C(O)C1] | 4-(5H-imidazo[5,1-a]isoindol-5-yl)-1-(methylsulfonyl)piperidin-3-ol |

-continued
| No. | Structure | Name |
| --- | --- | --- |
| 66 | 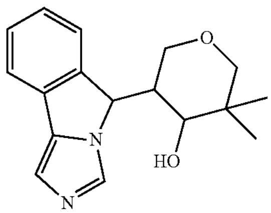 | 5-(5H-imidazo[5,1-a]isoindol-5-yl)-3,3-dimethyltetrahydro-2H-pyran-4-ol |
| 67 | 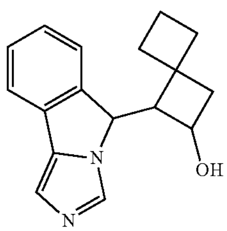 [SMILES: OC1CC2(CCC2)C1C1c2ccccc2-c2cncn21] | 1-(5H-imidazo[5,1-a]isoindol-5-yl)spiro[3.3]heptan-2-ol |
| 68 | 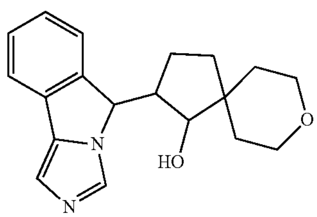 [SMILES: OC1C(C2c3ccccc3-c3cncn32)CCC12CCOCC2] | 2-(5H-imidazo[5,1-a]isoindol-5-yl)-8-oxaspiro[4.5]decan-1-ol |
| 69 | 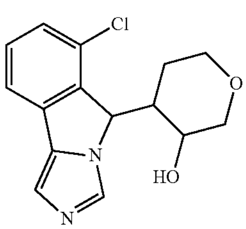 [SMILES: OC1COCCC1C1c2c(Cl)cccc2-c2cncn21] | 4-(6-chloro-5H-imidazo[5,1-a]isoindol-5-yl)tetrahydro-2H-pyran-3-ol |
| 69-1 | 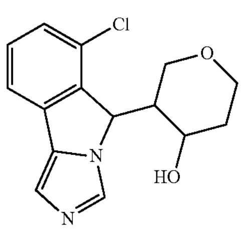 | 3-(6-chloro-5H-imidazo[5,1-a]isoindol-5-yl)tetrahydro-2H-pyran-4-ol |
| 70 | 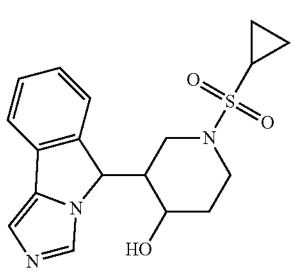 [SMILES: O=S(=O)(C1CC1)N1CCC(O)C(C2c3ccccc3-c3cncn32)C1] | 1-(cyclopropylsulfonyl)-3-(5H-imidazo[5,1-a]isoindol-5-yl)piperidin-4-ol |

-continued
| No. | Structure | Name |
|---|---|---|
| 71 | 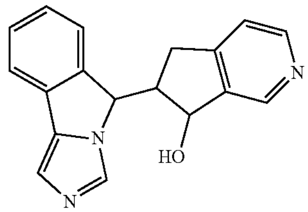 [SMILES: OC1c2cnccc2CC1C1c2ccccc2-c2cncn21] | 6-(5H-imidazo[5,1-a]isoindol-5-yl)-6,7-dihydro-5H-cyclopenta[c]pyridin-7-ol |
| 72 | 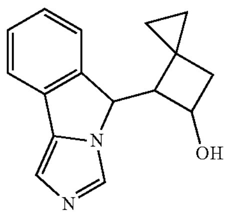 [SMILES: OC1CC2(CC2)C1C1c2ccccc2-c2cncn21] | 4-(5H-imidazo[5,1-a]isoindol-5-yl)spiro[2.3]hexan-5-ol |
| 73 | 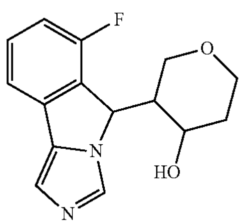 [SMILES: OC1CCOCC1C1c2c(F)cccc2-c2cncn21] | 3-(6-fluoro-5H-imidazo[5,1-a]isoindol-5-yl)tetrahydro-2H-pyran-4-ol |
| 74 | 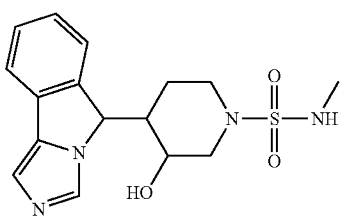 [SMILES: CNS(=O)(=O)N1CCC(C2c3ccccc3-c3cncn32)C(O)C1] | 3-hydroxy-4-(5H-imidazo[5,1-a]isoindol-5-yl)-N-methylpiperidine-1-sulfonamide |
| 75 | 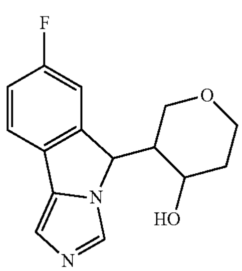 [SMILES: OC1CCOCC1C1c2cc(F)ccc2-c2cncn21] | 3-(7-fluoro-5H-imidazo[5,1-a]isoindol-5-yl)tetrahydro-2H-pyran-4-ol |
| 75-1 | 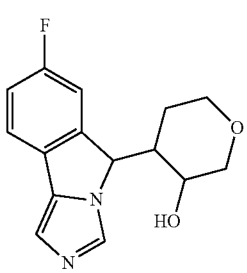 [SMILES: OC1COCCC1C1c2cc(F)ccc2-c2cncn21] | 4-(7-fluoro-5H-imidazo[5,1-a]isoindol-5-yl)tetrahydro-2H-pyran-3-ol |

-continued

| No. | Structure | Name |
| --- | --- | --- |
| 76 | 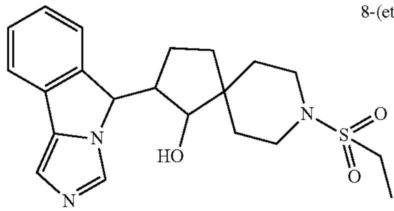 [SMILES: CCS(=O)(=O)N1CCC2(CCC(C3c4ccccc4-c4cncn43)C2O)CC1] | 8-(ethylsulfonyl)-2-(5H-imidazo[5,1-a]isoindol-5-yl)-8-azaspiro[4.5]decan-1-ol |
| 77 | 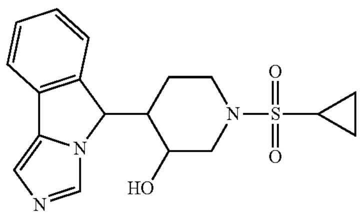 [SMILES: O=S(=O)(C1CC1)N1CCC(C2c3ccccc3-c3cncn32)C(O)C1] | 1-(cyclopropylsulfonyl)-4-(5H-imidazo[5,1-a]isoindol-5-yl)piperidin-3-ol |
| 78 | 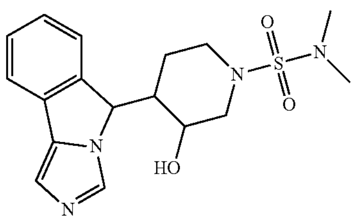 [SMILES: CN(C)S(=O)(=O)N1CCC(C2c3ccccc3-c3cncn32)C(O)C1] | 3-hydroxy-4-(5H-imidazo[5,1-a]isoindol-5-yl)-N,N-dimethylpiperidine-1-sulfonamide |
| 79 | 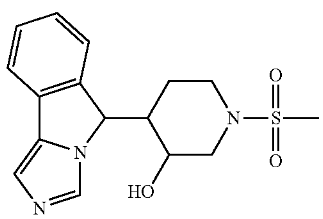 [SMILES: CS(=O)(=O)N1CCC(C2c3ccccc3-c3cncn32)C(O)C1] | 4-(5H-imidazo[5,1-a]isoindol-5-yl)-1-(methylsulfonyl)piperidin-3-ol |
| 80 | 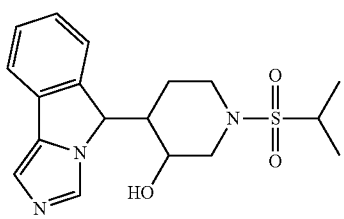 [SMILES: CC(C)S(=O)(=O)N1CCC(C2c3ccccc3-c3cncn32)C(O)C1] | 4-(5H-imidazo[5,1-a]isoindol-5-yl)-1-(isopropylsulfonyl)piperidin-3-ol |
| 81 | 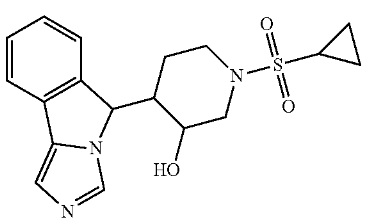 [SMILES: O=S(=O)(C1CC1)N1CCC(C2c3ccccc3-c3cncn32)C(O)C1] | 1-(cyclopropylsulfonyl)-4-(5H-imidazo[5,1-a]isoindol-5-yl)piperidin-3-ol |
| 82 | 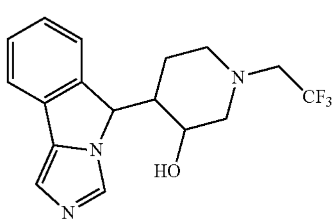 [SMILES: OC1CN(CC(F)(F)F)CCC1C1c2ccccc2-c2cncn21] | 4-(5H-imidazo[5,1-a]isoindol-5-yl)-1-(2,2,2-trifluoroethyl)piperidin-3-ol |

-continued

| No. | Structure | Name |
|---|---|---|
| 83 | 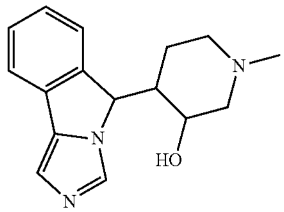 [SMILES: CN1CCC(C2c3ccccc3-c3cncn32)C(O)C1] | 4-(5H-imidazo[5,1-a]isoindol-5-yl)-1-methylpiperidin-3-ol |
| 84 | 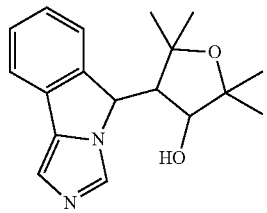 [SMILES: CC1(C)OC(C)(C)C(C2c3ccccc3-c3cncn32)C1O] | 4-(5H-imidazo[5,1-a]isoindol-5-yl)-2,2,5,5-tetramethyltetrahydrofuran-3-ol |
| 85 | 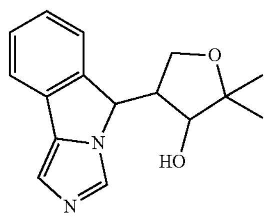 [SMILES: CC1(C)OCC(C2c3ccccc3-c3cncn32)C1O] | 4-(5H-Imidazo[5,1-a]isoindol-5-yl)-2,2-dimethyltetrahydrofuran-3-ol |
| 86 | 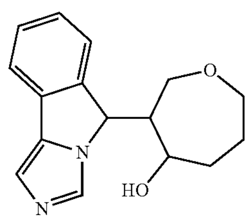 [SMILES: OC1CCCOCC1C1c2ccccc2-c2cncn21] | 3-(5H-imidazo[5,1-a]isoindol-5-yl)oxepan-4-ol |
| 87 | 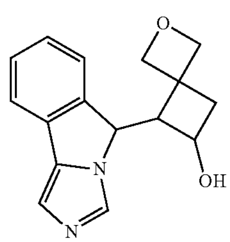 [SMILES: OC1CC2(COC2)C1C1c2ccccc2-c2cncn21] | 5-(5H-imidazo[5,1-a]isoindol-5-yl)-2-oxaspiro[3.3]heptan-6-ol |
| 88 | 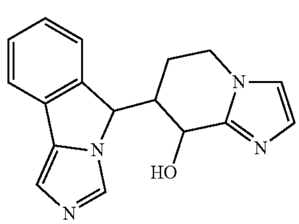 | 7-(5H-imidazo[5,1-a]isoindol-5-yl)-5,6,7,8-tetrahydroimidazo[1,2-a]pyridin-8-ol |
| 89 | 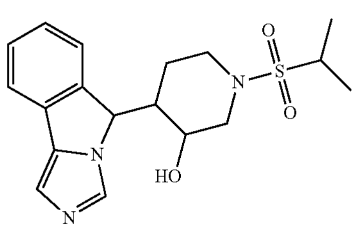 [SMILES: CC(C)S(=O)(=O)N1CCC(C2c3ccccc3-c3cncn32)C(O)C1] | 4-(5H-imidazo[5,1-a]isoindol-5-yl)-1-(isopropylsulfonyl)piperidin-3-ol |

-continued

| No. | Structure | Name |
|---|---|---|
| 90 | 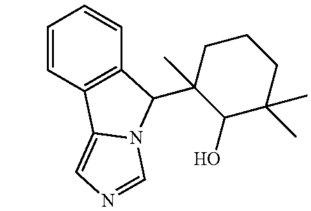 [SMILES: CC1(C)CCCC(C)(C2c3ccccc3-c3cncn32)C1O] | 2-(5H-imidazo[5,1-a]isoindol-5-yl)-2,6,6-trimethyleyclohexan-1-ol |
| 91 | 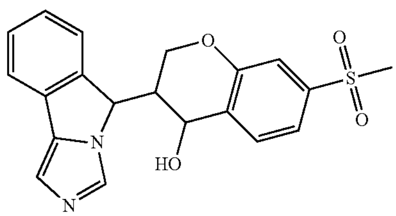 [SMILES: CS(=O)(=O)c1ccc2c(c1)OCC(C1c3ccccc3-c3cncn31)C2O] | 3-(5H-imidazo[5,1-a]isoindol-5-yl)-7-(methylsulfonyl)chroman-4-ol |
| 92 | 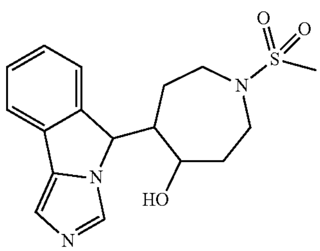 [SMILES: CS(=O)(=O)N1CCC(O)C(C2c3ccccc3-c3cncn32)CC1] | 5-(5H-imidazo[5,1-a]isoindol-5-yl)-1-(methylsulfonyl)azepan-4-ol |
| 93 | 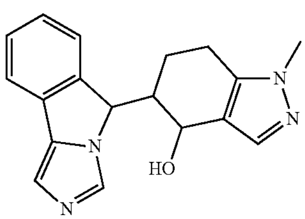 [SMILES: Cn1ncc2c1CCC(C1c3ccccc3-c3cncn31)C2O] | 5-(5H-imidazo[5,1-a]isoindol-5-yl)-1-methyl-4,5,6,7-tetrahydro-1H-indazol-4-ol |
| 94 | 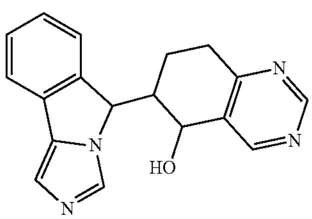 [SMILES: OC1c2cncnc2CCC1C1c2ccccc2-c2cncn21] | 6-(5H-imidazo[5,1-a]isoindol-5-yl)-5,6,7,8-tetrahydroquinazolin-5-ol |
| 95 | 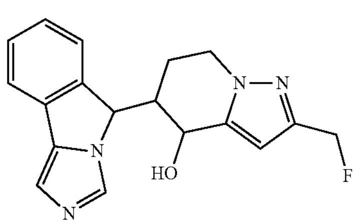 [SMILES: OC1c2cc(CF)nn2CCC1C1c2ccccc2-c2cncn21] | 2-(fluoromethyl)-5-(5H-imidazo[5,1-a]isoindol-5-yl)-4,5,6,7-tetrahydropyrazolo[1,5-a]pyridin-4-ol |
| 96 | 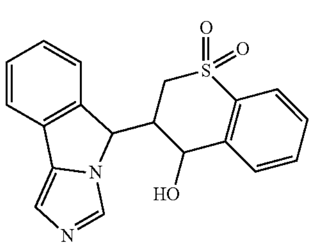 [SMILES: O=S1(=O)CC(C2c3ccccc3-c3cncn32)C(O)c2ccccc21] | 4-hydroxy-3-(5H-imidazo[5,1-a]isoindol-5-yl)thiochromane 1,1-dioxide |

-continued

| No. | Structure | Name |
|---|---|---|
| 97 | 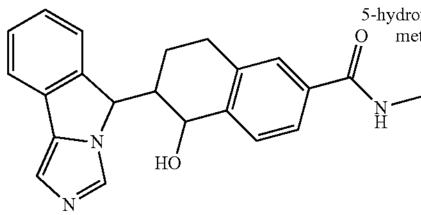 | 5-hydroxy-6-(5H-imidazo[5,1-a]isoindol-5-yl)-N-methyl-5,6,7,8-tetrahydronaphthalene-2-carboxamide |
| 98 | 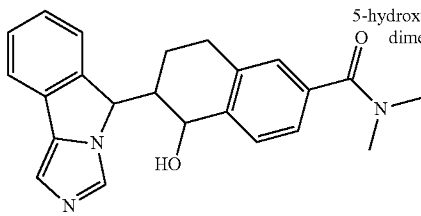 | 5-hydroxy-6-(5H-imidazo[5,1-a]isoindol-5-yl)-N,N-dimethyl-5,6,7,8-tetrahydronaphthalene-2-carboxamide |
| 99 | 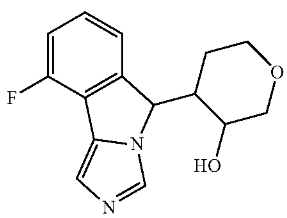 [SMILES: OC1COCCC1C1c2cccc(F)c2-c2cncn21] | 4-(9-fluoro-5H-imidazo[5,1-a]isoindol-5-yl)tetrahydro-2H-pyran-3-ol |
| 100 | 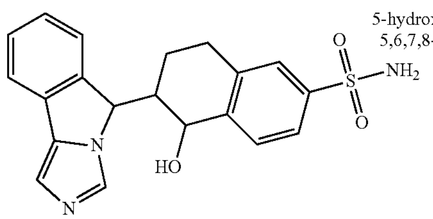 | 5-hydroxy-6-(5H-imidazo[5,1-a]isoindol-5-yl)-5,6,7,8-tetrahydronaphthalene-2-sulfonamide |
| 101 | 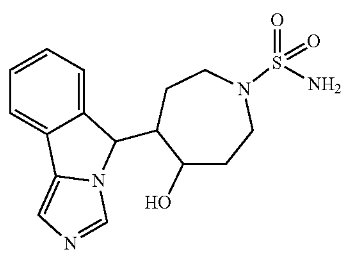 [SMILES: NS(=O)(=O)N1CCC(O)C(C2c3ccccc3-c3cncn32)CC1] | 4-hydroxy-5-(5H-imidazo[5,1-a]isoindol-5-yl)azepane-1-sulfonamide |
| 102 | 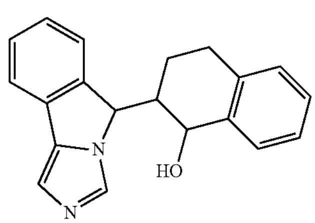 [SMILES: OC1c2ccccc2CCC1C1c2ccccc2-c2cncn21] | 2-(5H-imidazo[5,1-a]isoindol-5-yl)-1,2,3,4-tetrahydronaphthalen-1-ol |
| 103 | 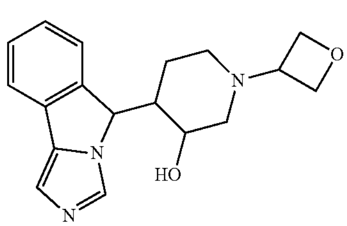 [SMILES: OC1CN(C2COC2)CCC1C1c2ccccc2-c2cncn21] | 4-(5H-imidazo[5,1-a]isoindol-5-yl)-1-(oxetan-3-yl)piperidin-3-ol |

-continued

| No. | Structure | Name |
| --- | --- | --- |
| 104 | 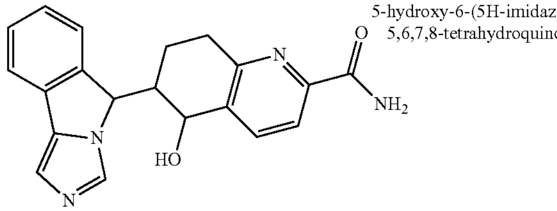 | 5-hydroxy-6-(5H-imidazo[5,1-a]isoindol-5-yl)-5,6,7,8-tetrahydroquinoline-2-carboxamide |
| 105 | 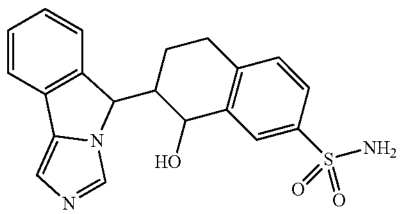 [SMILES: NS(=O)(=O)c1ccc2c(c1)C(O)C(C1c3ccccc3-c3cncn31)CC2] | 8-hydroxy-7-(5H-imidazo[5,1-a]isoindol-5-yl)-5,6,7,8-tetrahydronaphthalene-2-sulfonamide |
| 106 | 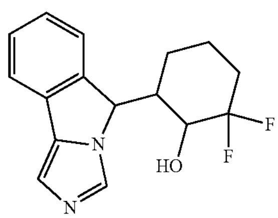 [SMILES: OC1C(C2c3ccccc3-c3cncn32)CCCC1(F)F] | 2,2-difluoro-6-(5H-imidazo[5,1-a]isoindol-5-yl)cyclohexan-1-ol |
| 107 | 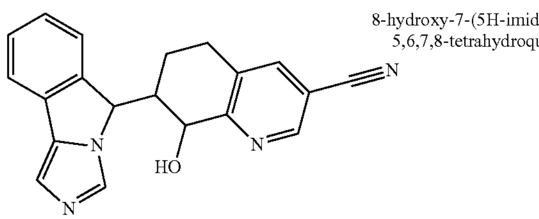 | 8-hydroxy-7-(5H-imidazo[5,1-a]isoindol-5-yl)-5,6,7,8-tetrahydroquinoline-3-carbonitrile |
| 108 | 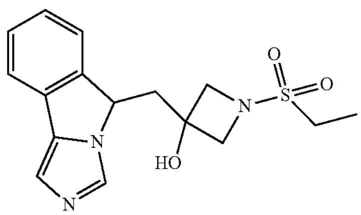 [SMILES: CCS(=O)(=O)N1CC(O)(CC2c3ccccc3-c3cncn32)C1] | 3-((5H-imidazo[5,1-a]isoindol-5-yl)methyl)-1-(ethylsulfonyl)azetidin-3-ol |
| 109 | 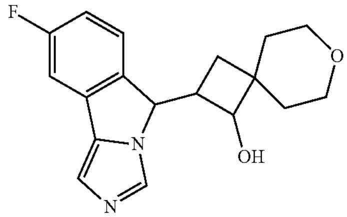 [SMILES: OC1C(C2c3ccc(F)cc3-c3cncn32)CC12CCOCC2] | 2-(8-fluoro5H-imidazo[5,1-a]isoindol-5-yl)-7-oxaspiro[3.5]nonan-1-ol |

-continued
| No. | Structure | Name |
|---|---|---|
| 110 | 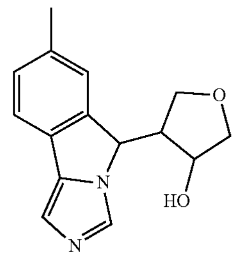 [SMILES: Cc1ccc2c(c1)C(C1COCC1O)n1cncc1-2] | 4-(7-methyl-5H-imidazo[5,1-a]isoindol-5-yl)tetrahydrofuran-3-ol |
| 111 | 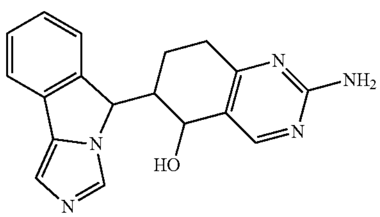 [SMILES: Nc1ncc2c(n1)CCC(C1c3ccccc3-c3cncn31)C2O] | 2-amino-6-(5H-imidazo[5,1-a]isoindol-5-yl)-5,6,7,8-tetrahydroquinazolin-5-ol |
| 112 | 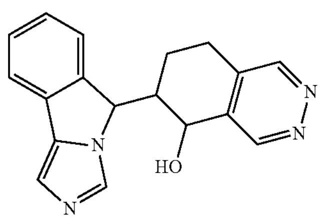 [SMILES: OC1c2cnncc2CCC1C1c2ccccc2-c2cncn21] | 6-(5H-imidazo[5,1-a]isoindol-5-yl)-5,6,7,8-tetrahydrophthalazin-5-ol |
| 113 | 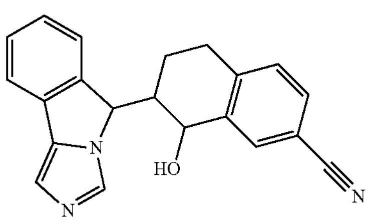 [SMILES: N#Cc1ccc2c(c1)C(O)C(C1c3ccccc3-c3cncn31)CC2] | 8-hydroxy-7-(5H-imidazo[5,1-a]isoindol-5-yl)-5,6,7,8-tetrahydronaphthalene-2-carbonitrile |
| 114 | 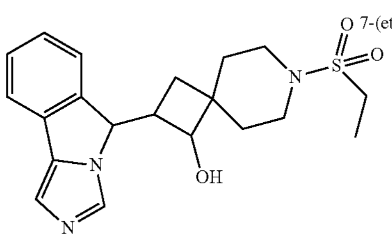 | 7-(ethylsulfonyl)-2-(5H-imidazo[5,1-a]isoindol-5-yl)-7-azaspiro[3.5]nonan-1-ol |
| 115 | 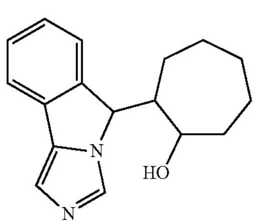 [SMILES: OC1CCCCCC1C1c2ccccc2-c2cncn21] | 2-(5H-imidazo[5,1-a]isoindol-5-yl)cycloheptan-1-ol |

-continued

| No. | Structure | Name |
|---|---|---|
| 116 | 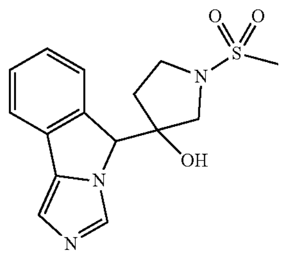 [SMILES: CS(=O)(=O)N1CCC(O)(C2c3ccccc3-c3cncn32)C1] | 3-(5H-imidazo[5,1-a]isoindol-5-yl)-1-(methylsulfonyl)pyrrolidin-3-ol |
| 117 | 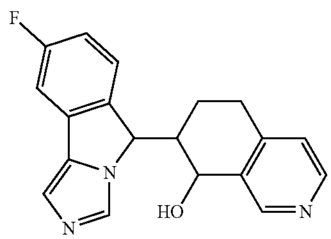 | 7-(8-fluoro-5H-imidazo[5,1-a]isoindol-5-yl)-5,6,7,8-tetrahydroisoquinolin-8-ol |
| 118 | 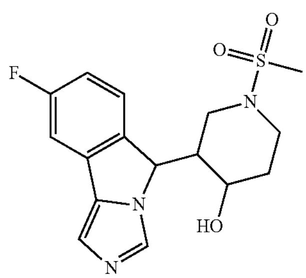 [SMILES: CS(=O)(=O)N1CCC(O)C(C2c3ccc(F)cc3-c3cncn32)C1] | 3-(8-fluoro-5H-imidazo[5,1-a]isoindol-5-yl)-1-(methylsulfonyl)piperidin-4-ol |
| 119 | 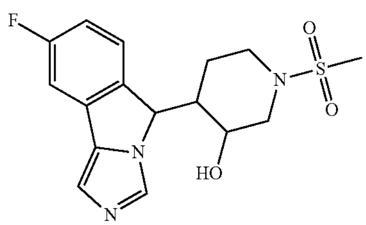 [SMILES: CS(=O)(=O)N1CCC(C2c3ccc(F)cc3-c3cncn32)C(O)C1] | 4-(8-fluoro-5H-imidazo[5,1-a]isoindol-5-yl)-1-(methylsulfonyl)piperidin-3-ol |
| 120 | 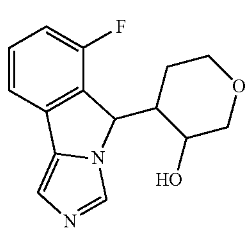 [SMILES: OC1COCCC1C1c2c(F)cccc2-c2cncn21] | 4-(6-fluoro-5H-imidazo[5,1-a]isoindol-5-yl)tetrahydro-2H-pyran-3-ol |
| 121 | 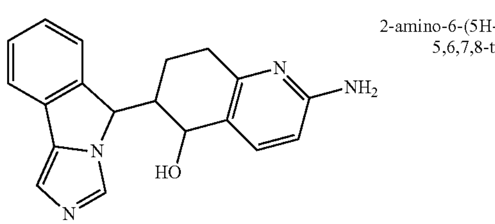 | 2-amino-6-(5H-imidazo[5,1-a]isoindol-5-yl)-5,6,7,8-tetrahydroquinolin-5-ol |

-continued

| No. | Structure | Name |
| --- | --- | --- |
| 122 | 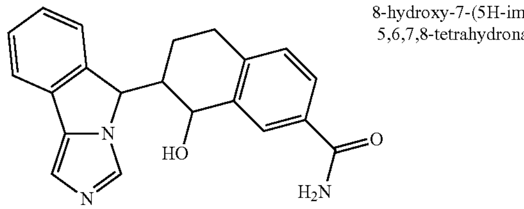 | 8-hydroxy-7-(5H-imidazo[5,1-a]isoindol-5-yl)-5,6,7,8-tetrahydronaphthalene-2-carboxamide |
| 123 | 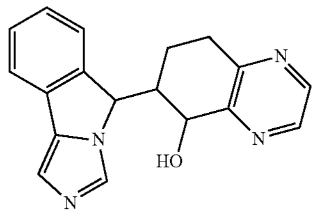 [SMILES: OC1c2nccnc2CCC1C1c2ccccc2-c2cncn21] | 6-(5H-imidazo[5,1-a]isoindol-5-yl)-5,6,7,8-tetrahydroquinoxalin-5-ol |
| 124 | 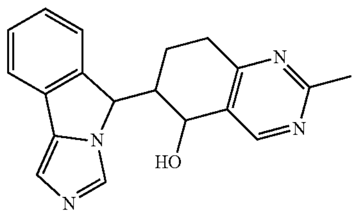 [SMILES: Cc1ncc2c(n1)CCC(C1c3ccccc3-c3cncn31)C2O] | 6-(5H-imidazo[5,1-a]isoindol-5-yl)-2-methyl-5,6,7,8-tetrahydroquinazolin-5-ol |
| 125 | 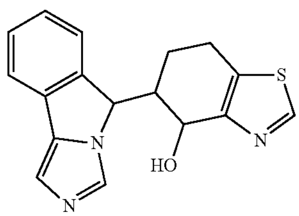 [SMILES: OC1c2ncsc2CCC1C1c2ccccc2-c2cncn21] | 5-(5H-imidazo[5,1-a]isoindol-5-yl)-4,5,6,7-tetrahydrobenzo[d]thiazol-4-ol |
| 126 | 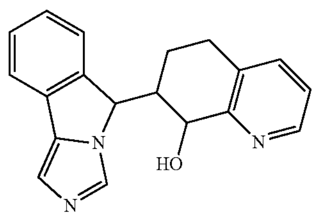 [SMILES: OC1c2ncccc2CCC1C1c2ccccc2-c2cncn21] | 7-(5H-imidazo[5,1-a]isoindol-5-yl)-5,6,7,8-tetrahydroquinolin-8-ol |
| 127 | 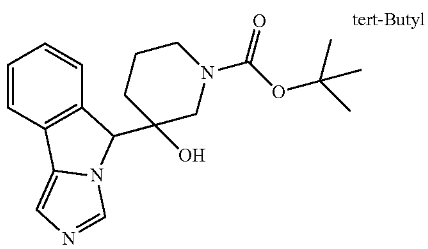 | tert-Butyl 3-hydroxy-3-(5H-imidazo[5,1-a]isoindol-5-yl)piperidine-1-carboxylate |
| 128 | 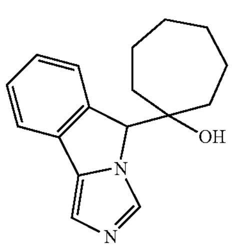 [SMILES: OC1(C2c3ccccc3-c3cncn32)CCCCCC1] | 1-(5H-imidazo[5,1-a]isoindol-5-yl)cycloheptan-1-ol |

-continued

| No. | Structure | Name |
|---|---|---|
| 129 | 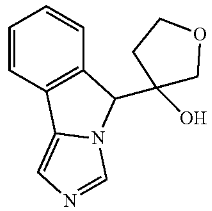 [SMILES: OC1(C2c3ccccc3-c3cncn32)CCOC1] | 3-(5H-imidazo[5,1-a]isoindol-5-yl)tetrahydrofuran-3-ol |
| 130 | 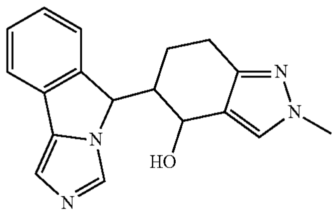 [SMILES: Cn1cc2c(n1)CCC(C1c3ccccc3-c3cncn31)C2O] | 5-(5H-imidazo[5,1-a]isoindol-5-yl)-2-methyl-4,5,6,7-tetrahydro-2H-indazol-4-ol |
| 131 | 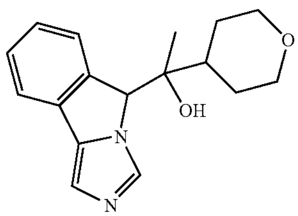 [SMILES: CC(O)(C1CCOCC1)C1c2ccccc2-c2cncn21] | 1-(5H-imidazo[5,1-a]isoindol-5-yl)-1-(tetrahydro-2H-pyran-4-yl)ethan-1-ol |
| 132 | 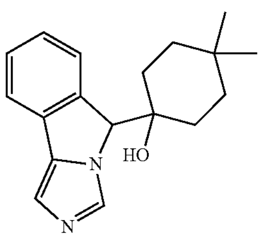 [SMILES: CC1(C)CCC(O)(C2c3ccccc3-c3cncn32)CC1] | 1-(5H-imidazo[5,1-a]isoindol-5-yl)-4,4-dimethylcyclohexan-1-ol |
| 133 | 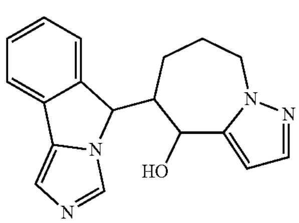 [SMILES: OC1c2ccnn2CCCC1C1c2ccccc2-c2cncn21] | 5-(5H-imidazo[5,1-a]isoindol-5-yl)-5,6,7,8-tetrahydro-4H-pyrazolo[1,5-a]azepin-4-ol |
| 134 | 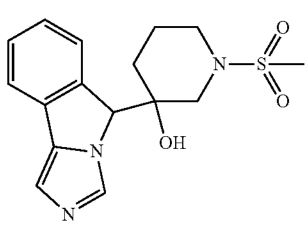 [SMILES: CS(=O)(=O)N1CCCC(O)(C2c3ccccc3-c3cncn32)C1] | 3-(5H-imidazo[5,1-a]isoindol-5-yl)-1-(methylsulfonyl)piperidin-3-ol |
| 135 | 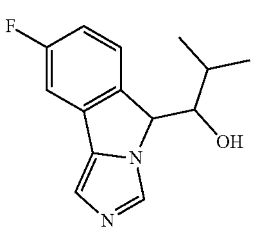 | 1-(8-fluoro-5H-imidazo[5,1-a]isoindol-5-yl)-2-methylpropan-1-ol |

-continued
| No. | Structure | Name |
|---|---|---|
| 136 | 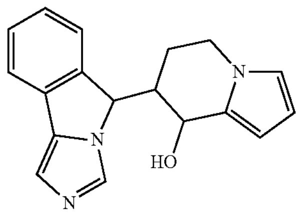 [SMILES: OC1c2cccn2CCC1C1c2ccccc2-c2cncn21] | 7-(5H-imidazo[5,1-a]isoindol-5-yl)-5,6,7,8-tetrahydroindolizin-8-ol |
| 137 | 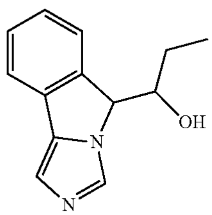 [SMILES: CCC(O)C1c2ccccc2-c2cncn21] | 1-(5H-imidazo[5,1-a]isoindol-5-yl)propan-1-ol |
| 138 | 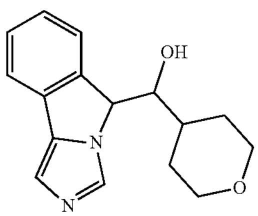 [SMILES: OC(C1CCOCC1)C1c2ccccc2-c2cncn21] | (5H-imidazo[5,1-a]isoindol-5-yl)(tetrahydro-2H-pyran-4-yl)methanol |
| 139 | 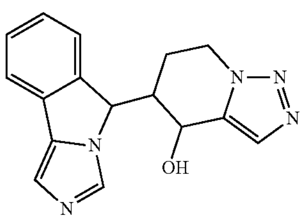 [SMILES: OC1c2cnnn2CCC1C1c2ccccc2-c2cncn21] | 5-(5H-imidazo[5,1-a]isoindol-5-yl)-4,5,6,7-tetrahydro-[1,2,3]triazolo[1,5-a]pyridin-4-ol |
| 139-1 | 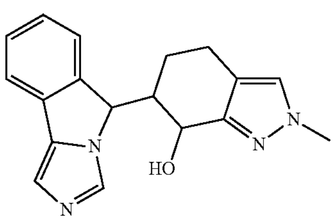 [SMILES: Cn1cc2c(n1)C(O)C(C1c3ccccc3-c3cncn31)CC2] | 6-(5H-imidazo[5,1-a]isoindol-5-yl)-2-methyl-4,5,6,7-tetrahydro-2H-indazol-7-ol |
| 140 | 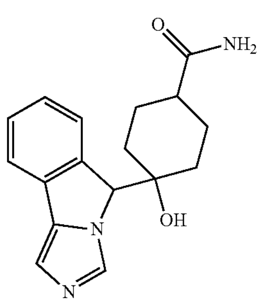 [SMILES: NC(=O)C1CCC(O)(C2c3ccccc3-c3cncn32)CC1] | 4-hydroxy-4-(5H-imidazo[5,1-a]isoindol-5-yl)cyclohexane-1-carboxamide |

-continued
| No. | Structure | Name |
| --- | --- | --- |
| 141 | 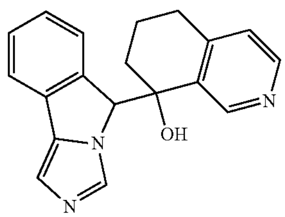 [SMILES: OC1(C2c3ccccc3-c3cncn32)CCCc2ccncc21] | 8-(5H-imidazo[5,1-a]isoindol-5-yl)-5,6,7,8-tetrahydroisoquinolin-8-ol |
| 142 | 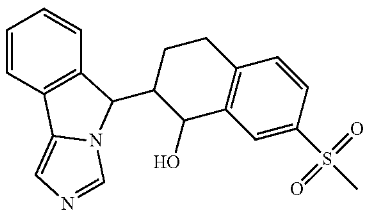 [SMILES: CS(=O)(=O)c1ccc2c(c1)C(O)C(C1c3ccccc3-c3cncn31)CC2] | 2-(5H-imidazo[5,1-a]isoindol-5-yl)-7-(methylsulfonyl)-1,2,3,4-tetrahydronaphthalen-1-ol |
| 143 | 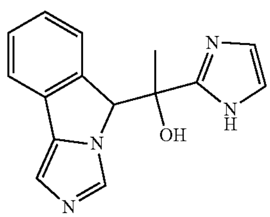 [SMILES: CC(O)(c1ncc[nH]1)C1c2ccccc2-c2cncn21] | 1-(5H-imidazo[5,1-a]isoindol-5-yl)-1-(1H-imidazol-2-yl)ethan-1-ol |
| 144 | 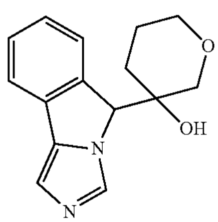 [SMILES: OC1(C2c3ccccc3-c3cncn32)CCCOC1] | 3-(5H-Imidazo[5,1-a]isoindol-5-yl)tetrahydro-2H-pyran-3-ol |
| 145 | 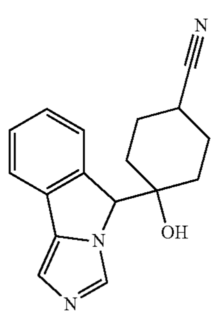 [SMILES: N#CC1CCC(O)(C2c3ccccc3-c3cncn32)CC1] | 4-hydroxy-4-(5H-imidazo[5,1-a]isoindol-5-yl)cyclohexane-1-carbonitrile |
| 146 | 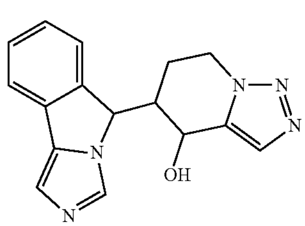 [SMILES: OC1c2cnnn2CCC1C1c2ccccc2-c2cncn21] | 5-(5H-imidazo[5,1-a]isoindol-5-yl)-4,5,6,7-tetrahydro-[1,2,3]triazolo[1,5-a]pyridin-4-ol |

-continued

| No. | Structure | Name |
|---|---|---|
| 146-1 | 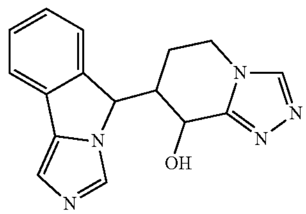 [SMILES: OC1c2nncn2CCC1C1c2ccccc2-c2cncn21] | 7-(5H-imidazo[5,1-a]isoindol-5-yl)-5,6,7,8-tetrahydro-[1,2,4]triazolo[4,3-a]pyridin-8-ol |
| 147 | 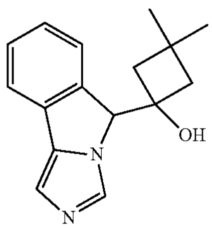 [SMILES: CC1(C)CC(O)(C2c3ccccc3-c3cncn32)C1] | 1-(5H-imidazo[5,1-a]isoindol-5-yl)-3,3-dimethylcyclobutan-1-ol |
| 148 | 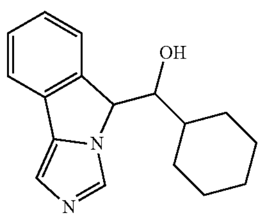 [SMILES: OC(C1CCCCC1)C1c2ccccc2-c2cncn21] | cyclohexyl(5H-imidazo[5,1-a]isoindol-5-yl)methanol |
| 149 | 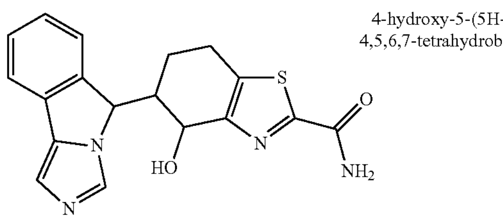 | 4-hydroxy-5-(5H-imidazo[5,1-a]isoindol-5-yl)-4,5,6,7-tetrahydrobenzo[d]thiazole-2-carboxamide |
| 150 | 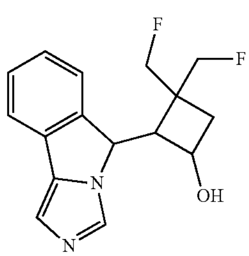 [SMILES: OC1CC(CF)(CF)C1C1c2ccccc2-c2cncn21] | 3,3-bis(fluoromethyl)-2-(5H-imidazo[5,1-a]isoindol-5-yl)cyclobutan-1-ol |
| 151 | 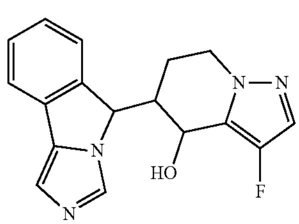 | 3-fluoro-5-(5H-imidazo[5,1-a]isoindol-5-yl)-4,5,6,7-tetrahydropyrazolo[1,5-a]pyridin-4-ol |

-continued

| No. | Structure | Name |
|---|---|---|
| 152 | 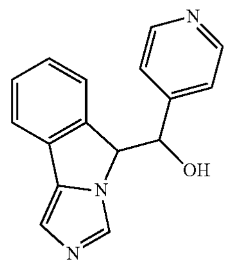 [SMILES: OC(c1ccncc1)C1c2ccccc2-c2cncn21] | (5H-imidazo[5,1-a]isoindol-5-yl)(pyridin-4-yl)methanol |
| 153 | 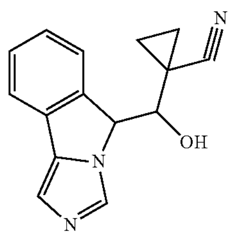 [SMILES: N#CC1(C(O)C2c3ccccc3-c3cncn32)CC1] | 1-(hydroxy(5H-imidazo[5,1-a]isoindol-5-yl)methyl)cyclopropane-1-carbonitrile |
| 154 | 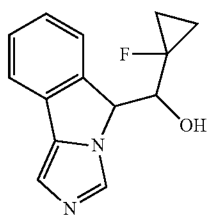 [SMILES: OC(C1c2ccccc2-c2cncn21)C1(F)CC1] | (1-fluorocyclopropyl)(5H-imidazo[5,1-a]isoindol-5-yl)methanol |
| 155 | 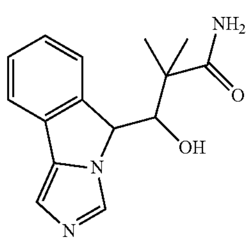 [SMILES: CC(C)(C(N)=O)C(O)C1c2ccccc2-c2cncn21] | 3-hydroxy-3-(5H-imidazo[5,1-a]isoindol-5-yl)-2,2-dimethylpropanamide |
| 156 | 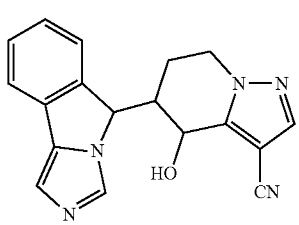 | 4-hydroxy-5-(5H-imidazo[5,1-a]isoindol-5-yl)-4,5,6,7-tetrahydropyrazolo[1,5-a]pyridine-3-carbonitrile |
| 157 | 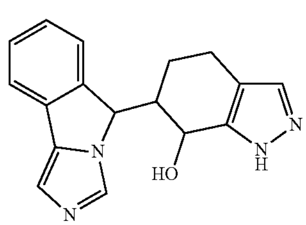 [SMILES: OC1c2[nH]ncc2CCC1C1c2ccccc2-c2cncn21] | 6-(5H-imidazo[5,1-a]isoindol-5-yl)-4,5,6,7-tetrahydro-1H-indazol-7-ol |

-continued

| No. | Structure | Name |
|---|---|---|
| 158 | 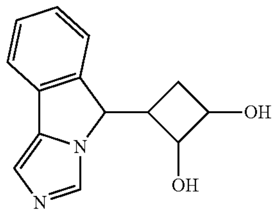 [SMILES: OC1CC(C2c3ccccc3-c3cncn32)C1O] | 3-(5H-imidazo[5,1-a]isoindol-5-yl)cyclobutane-1,2-diol |
| 159 | 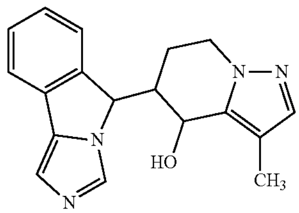 [SMILES: Cc1cnn2c1C(O)C(C1c3ccccc3-c3cncn31)CC2] | 5-(5H-imidazo[5,1-a]isoindol-5-yl)-3-methyl-4,5,6,7-tetrahydropyrazolo[1,5-a]pyridin-4-ol |
| 160 | 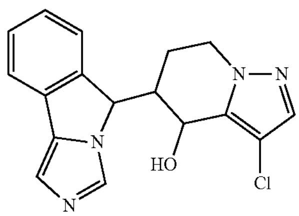 [SMILES: OC1c2c(Cl)cnn2CCC1C1c2ccccc2-c2cncn21] | 3-chloro-5-(5H-imidazo[5,1-a]isoindol-5-yl)-4,5,6,7-tetrahydropyrazolo[1,5-a]pyridin-4-ol |
| 161 | 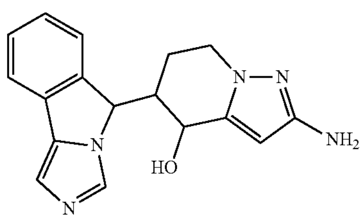 [SMILES: Nc1cc2n(n1)CCC(C1c3ccccc3-c3cncn31)C2O] | 2-amino-5-(5H-imidazo[5,1-a]isoindol-5-yl)-4,5,6,7-tetrahydropyrazolo[1,5-a]pyridin-4-ol |
| 162 | 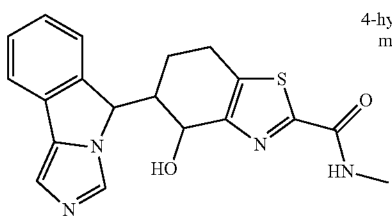 [SMILES: CNC(=O)c1nc2c(s1)CCC(C1c3ccccc3-c3cncn31)C2O] | 4-hydroxy-5-(5H-imidazo[5,1-a]isoindol-5-yl)-N-methyl-4,5,6,7-tetrahydrobenzo[d]thiazole-2-carboxamide |
| 163 | 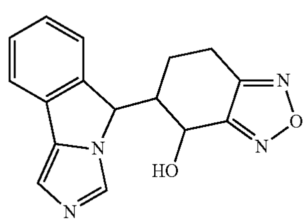 [SMILES: OC1c2nonc2CCC1C1c2ccccc2-c2cncn21] | 5-(5H-imidazo[5,1-a]isoindol-5-yl)-4,5,6,7-tetrahydrobenzo[c][1,2,5]oxadiazol-4-ol |
| 164 | 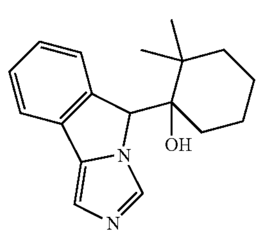 [SMILES: CC1(C)CCCCC1(O)C1c2ccccc2-c2cncn21] | 1-(5H-imidazo[5,1-a]isoindol-5-yl)-2,2-dimethylcyclohexan-1-ol |

-continued

| No. | Structure | Name |
| --- | --- | --- |
| 165 | 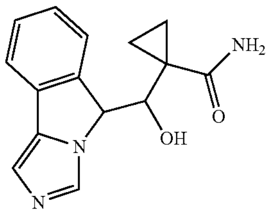 [SMILES: NC(=O)C1(C(O)C2c3ccccc3-c3cncn32)CC1] | 1-(hydroxy(5H-imidazo[5,1-a]isoindol-5-yl)methyl)cyclopropane-1-carboxamide |
| 166 | 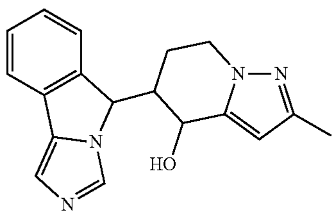 [SMILES: Cc1cc2n(n1)CCC(C1c3ccccc3-c3cncn31)C2O] | 5-(5H-imidazo[5,1-a]isoindol-5-yl)-2-methyl-4,5,6,7-tetrahydropyrazolo[1,5-a]pyridin-4-ol |
| 167 | 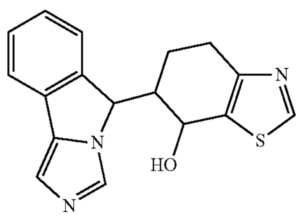 [SMILES: OC1c2scnc2CCC1C1c2ccccc2-c2cncn21] | 6-(5H-imidazo[5,1-a]isoindol-5-yl)-4,5,6,7-tetrahydrobenzo[d]thiazol-7-ol |
| 168 | 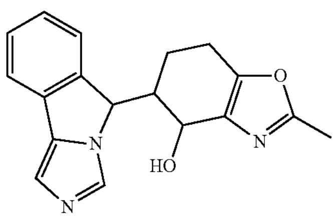 [SMILES: Cc1nc2c(o1)CCC(C1c3ccccc3-c3cncn31)C2O] | 5H-imidazo[5,1-a]isoindol-5-yl)-2-methyl-4,5,6,7-tetrahydrobenzo[d]oxazol-4-ol |
| 169 | 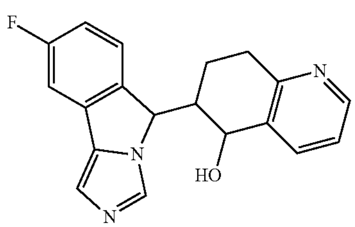 [SMILES: OC1c2cccnc2CCC1C1c2ccc(F)cc2-c2cncn21] | 8-fluoro-5H-imidazo[5,1-a]isoindol-5-yl)-5,6,7,8-tetrahydroquinolin-5-ol |
| 170 | 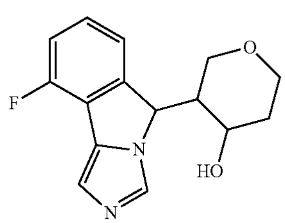 [SMILES: OC1CCOCC1C1c2cccc(F)c2-c2cncn21] | 3-(9-fluoro-5H-imidazo[5,1-a]isoindol-5-yl)tetrahydro-2H-pyran-4-ol |
| 171 | 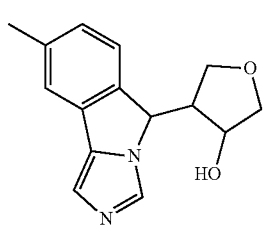 [SMILES: Cc1ccc2c(c1)-c1cncn1C2C1COCC1O] | 4-(8-methyl-5H-imidazo[5,1-a]isoindol-5-yl)tetrahydrofuran-3-ol |

-continued

| No. | Structure | Name |
| --- | --- | --- |
| 172 | 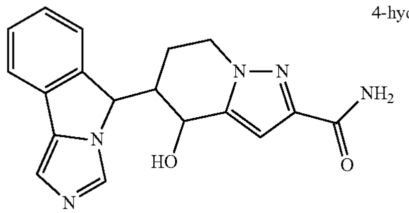 | 4-hydroxy-5-(5H-imidazo[5,1-a]isoindol-5-yl)-4,5,6,7-tetrahydropyrazolo[1,5-a]pyridine-2-carboxamide |
| 173 | 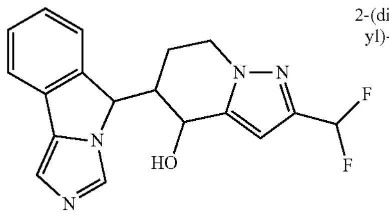 | 2-(difluoromethyl)-5-(5H-imidazo[5,1-a]isoindol-5-yl)-4,5,6,7-tetrahydropyrazolo[1,5-a]pyridin-4-ol |
| 174 | 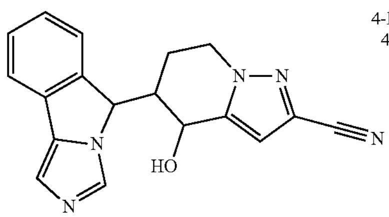 [SMILES: N#Cc1cc2n(n1)CCC(C1c3ccccc3-c3cncn31)C2O] | 4-hydroxy-5-(5H-imidazo[5,1-a]isoindol-5-yl)-4,5,6,7-tetrahydropyrazolo[1,5-a]pyridine-2-carbonitrile |
| 175 | 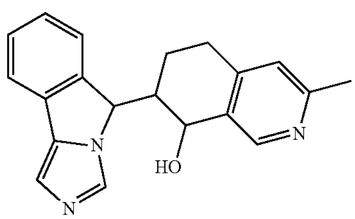 [SMILES: Cc1cc2c(cn1)C(O)C(C1c3ccccc3-c3cncn31)CC2] | 7-(5H-imidazo[5,1-a]isoindol-5-yl)-3-methyl-5,6,7,8-tetrahydroisoquinolin-8-ol |
| 176 | 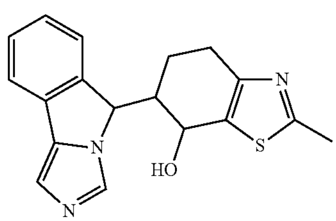 [SMILES: Cc1nc2c(s1)C(O)C(C1c3ccccc3-c3cncn31)CC2] | 6-(5H-imidazo[5,1-a]isoindol-5-yl)-2-methyl-4,5,6,7-tetrahydrobenzo[d]thiazol-7-ol |
| 177 | 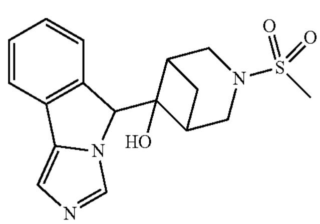 [SMILES: CS(=O)(=O)N1CC2CC(C1)C2(O)C1c2ccccc2-c2cncn21] | 6-(5H-imidazo[5,1-a]isoindol-5-yl)-3-(methylsulfonyl)-3-azabicyclo[3.1.1]heptan-6-ol |
| 178 | 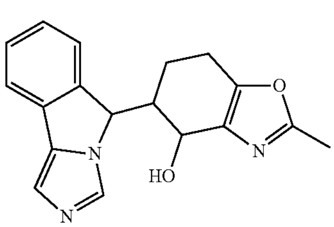 [SMILES: Cc1nc2c(o1)CCC(C1c3ccccc3-c3cncn31)C2O] | 5-(5H-imidazo[5,1-a]isoindol-5-yl)-2-methyl-4,5,6,7-tetrahydrobenzo[d]oxazol-4-ol |

-continued

| No. | Structure | Name |
|---|---|---|
| 179 | 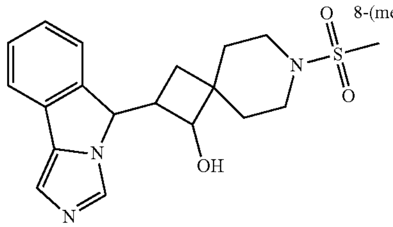 | 8-(methylsulfonyl)-2-(5H-imidazo[5,1-a]isoindol-5-yl)-8-azaspiro[4.5]decan-1-ol |
| 180 | 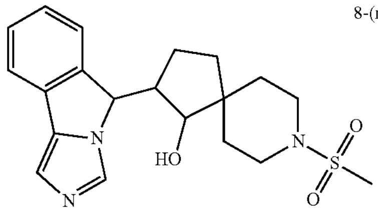 | 8-(methylsulfonyl)-2-(5H-imidazo[5,1-a]isoindol-5-yl)-8-azaspiro[4.5]decan-1-ol |
| 181 | 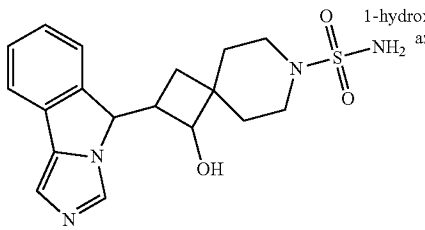 | 1-hydroxy-2-(5H-imidazo[4,3-a]isoindol-5-yl)-7-azaspiro[3.5]nonane-7-sulfonamide |
| 182 | 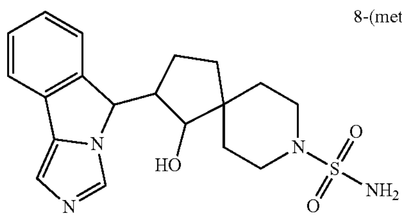 | 8-(methylsulfonyl)-2-(5H-imidazo[5,1-a]isoindol-5-yl)-8-azaspiro[4.5]decan-1-ol |
| 183 | 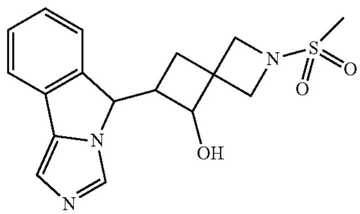 [SMILES: CS(=O)(=O)N1CC2(CC(C3c4ccccc4-c4cncn43)C2O)C1] | 6-(5H-imidazo[5,1-a]isoindol-5-yl)-2-(methylsulfonyl)-2-azaspiro[3.3]heptan-5-ol |

or a pharmaceutically acceptable salt thereof, or an enantio 182mer or diastereoisomer thereof, or a racemic mixture thereof.

In one embodiment, the compounds of the invention are (1R,2S)-2-((S)-5H-imidazo[5,1-a]isoindol-5-yl)cyclobutan-1-ol;

5H-imidazo[5,1-a]isoindol-5-yl)-5,6,7,8-tetrahydroisoquinolin-8-ol;

(3S,4S)-4-((S)-5H-imidazo[5,1-a]isoindol-5-yl)-tetrahydro-2H-pyran-3-ol;

(5R,6R)-6-((R)-5H-imidazo[5,1-a]isoindol-5-yl)-5,6,7,8-tetrahydroquinazolin-5-ol;

(7R,8R)-8-hydroxy-7-((R)-5H-imidazo[5,1-a]isoindol-5-yl)-5,6,7,8-tetrahydronaphthalene-2-carboxamide; and (6S,7R)-6-((R)-5H-imidazo[5,1-a]isoindol-5-yl)-4,5,6,7-tetrahydrobenzo[d]thiazol-7-ol.

In another embodiment, the compounds of the invention are (7S,8S)-7-((S)-5H-imidazo[5,1-a]isoindol-5-yl)-5,6,7,8-tetrahydroimidazo[1,5-a]pyridin-8-ol;

8-fluoro-5H-imidazo[4,3-a]isoindol-5-yl]cyclobutan-1-ol;

3-(-5H-imidazo[5,1-a]isoindol-5-yl) bicyclo[2.2.2]octan-2-ol;

(5S,6S)-5-hydroxy-6-((S)-5H-imidazo[5,1-a]isoindol-5-yl)-N-methyl-5,6,7,8-tetrahydronaphthalene-2-carboxamide;

(1R,2S)-2-((R)-8-fluoro-5H-imidazo[5,1-a]isoindol-5-yl)-7-oxaspiro[3.5]nonan-1-ol; and (4S,5R)-5-((S)-5H-imidazo[5,1-a]isoindol-5-yl)-2-methyl-4,5,6,7-tetrahydro-2H-indazol-4-ol;

In another embodiment, the compounds of the invention are 4-(5H-imidazo[1,5-b]isoindol-5-yl)-2,2-dimethyl-cyclobutanol;

(S)-1-((R)-5H-imidazo[5,1-a]isoindol-5-yl)ethan-1-ol;

(R)-1-(5H-imidazo[5,1-a]isoindol-5-yl)cyclohexan-1-ol;

(4S,5S)-5-((S)-5H-imidazo[5,1-a]isoindol-5-yl)-4,5,6,7-tetrahydropyrazolo[1,5-a]pyridin-4-ol;
((5R,6S)-5-hydroxy-6-((R)-5H-imidazo[5,1-a]isoindol-5-yl)-5,6,7,8-tetrahydronaphthalene-2-sulfonamide; and
(4S,5S)-4-hydroxy-5-((R)-5H-imidazo[5,1-a]isoindol-5-yl)-4,5,6,7-tetrahydrobenzo[d]thiazole-2-carboxamide.

In another embodiment, the compounds of the invention are 2-(5H-imidazo[1,5-b]isoindol-5-yl)spiro[3.3]heptan-3-ol;
(1R,2S)-2-((S)-5H-imidazo[5,1-a]isoindol-5-yl)-3,3-dimethylcyclobutan-1-ol;
(5S,6S)-5-hydroxy-6-((S)-5H-imidazo[5,1-a]isoindol-5-yl)-5,6,7,8-tetrahydronaphthalene-2-carboxamide;
4-hydroxy-5-(5H-imidazo[5,1-a]isoindol-5-yl)azepane-1-sulfonamide;
(5R,6R)-6-((S)-5H-imidazo[5,1-a]isoindol-5-yl)-5,6,7,8-tetrahydrophthalazin-5-ol; and
(6S,7S)-6-((S)-5H-imidazo[5,1-a]isoindol-5-yl)-4,5,6,7-tetrahydro-1H-indazol-7-ol.

In another embodiment, the compounds of the invention are (3S,4S)-1-(ethylsulfonyl)-4-((S)-5H-imidazo[5,1-a]isoindol-5-yl)piperidin-3-ol;
3-(5H-imidazo[5,1-a]isoindol-5-yl)thietan-3-ol;
(4S,5S)-5-((S)-5H-imidazo[5,1-a]isoindol-5-yl)-1-methyl-4,5,6,7-tetrahydro-1H-indazol-4-ol;
(7S,8S)-7-((S)-8-fluoro-5H-imidazo[5,1-a]isoindol-5-yl)-5,6,7,8-tetrahydroisoquinolin-8-ol;
(4S,5S)-4-hydroxy-5-((S)-5H-imidazo[5,1-a]isoindol-5-yl)-N-methyl-4,5,6,7-tetrahydrobenzo[d]thiazole-2-carboxamide; and
6-(5H-imidazo[5,1-a]isoindol-5-yl)-3-(methylsulfonyl)-3-azabicyclo[3.1.1]heptan-6-ol.

The invention further comprises subgenera of formula (I), in which the structure of any of formulae (I), (Ia)-(Ii), (II), (IIa)-(IIi), (III), (IIIa)-(IIIi), (IV), (IVa)-(IVi), (V) or (Va)-(Vf) comprising the structural element

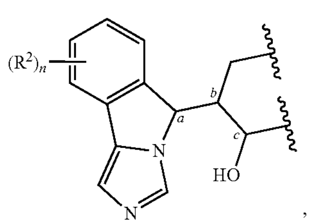

, having the stereoisomeric configuration of any of configurations 1-27 below, wherein the stereochemistry of each stereoisomeric carbon atom (labeled “a,” “b,” and “c” above) is designated as racemic (“-”), “S,” or “R”:

Structural Formula I is One of Stereoisomeric Configurations (1)-(27):

| Configuration | a | b | c |
|---|---|---|---|
| 1 | S | — | — |
| 2 | R | — | — |
| 3 | — | S | — |
| 4 | — | R | — |
| 5 | — | — | S |
| 6 | — | — | R |
| 7 | S | S | — |
| 8 | S | R | — |
| 9 | R | S | — |
| 10 | R | R | — |
| 11 | — | S | S |
| 12 | — | S | R |
| 13 | — | R | S |
| 14 | — | R | R |
| 15 | S | — | S |
| 16 | S | — | R |
| 17 | R | — | S |
| 18 | R | — | R |
| 19 | S | S | S |
| 20 | S | S | R |
| 21 | S | R | S |
| 22 | S | R | R |
| 23 | R | S | S |
| 24 | R | S | R |
| 25 | R | R | S |
| 26 | R | R | R |
| 27 | — | — | — |

-continued

In one embodiment, the compounds of the disclosure are in the S stereoconfiguration at the position labeled “a” above. For example, the compounds have a stereoconfiguration of configuration 1, 7, 8, 15, 16 or 19-22.

In another embodiment, the compounds of the disclosure are in the R stereoconfiguration at the position labeled “a” above. For example, the compounds have a stereoconfiguration of configuration 2, 9, 10, 17, 18 or 23-26.

In one embodiment, the compounds of the disclosure are in the stereoconfiguration of configuration 20.

In another embodiment, the compounds of the disclosure are in the stereoconfiguration of configuration 19.

In another aspect, the present disclosure provides each of compounds 1-41 and 56-115, 117-126, 130, 133, 136, 139, 139-1, 142, 146, 146-1, 149-151, 156-163, 166-176 and 178-183 in each of stereoisomeric configurations 1-27. For example:

| No. | Con. |
|---|---|
| 1 | 1 |
| 1 | 2 |
| 1 | 3 |
| 1 | 4 |
| 1 | 5 |
| 1 | 6 |
| 1 | 7 |
| 1 | 8 |
| 1 | 9 |
| 1 | 10 |
| 1 | 11 |
| 1 | 12 |
| 1 | 13 |
| 1 | 14 |
| 1 | 15 |
| 1 | 16 |
| 1 | 17 |
| 1 | 18 |
| 1 | 19 |
| 1 | 20 |
| 1 | 21 |
| 1 | 22 |
| 1 | 23 |
| 1 | 24 |
| 1 | 25 |
| 1 | 26 |
| 1 | 27 |
| 2 | 1 |
| 2 | 2 |
| 2 | 3 |
| 2 | 4 |
| 2 | 5 |
| 2 | 6 |

-continued

| No. | Con. |
|---|---|
| 2 | 7 |
| 2 | 8 |
| 2 | 9 |
| 2 | 10 |
| 2 | 11 |
| 2 | 12 |
| 2 | 13 |
| 2 | 14 |
| 2 | 15 |
| 2 | 16 |
| 2 | 17 |
| 2 | 18 |
| 2 | 19 |
| 2 | 20 |
| 2 | 21 |
| 2 | 22 |
| 2 | 23 |
| 2 | 24 |
| 2 | 25 |
| 2 | 26 |
| 2 | 27 |
| 3 | 1 |
| 3 | 2 |
| 3 | 3 |
| 3 | 4 |
| 3 | 5 |
| 3 | 6 |
| 3 | 7 |
| 3 | 8 |
| 3 | 9 |
| 3 | 10 |
| 3 | 11 |
| 3 | 12 |
| 3 | 13 |
| 3 | 14 |
| 3 | 15 |
| 3 | 16 |
| 3 | 17 |
| 3 | 18 |
| 3 | 19 |
| 3 | 20 |
| 3 | 21 |
| 3 | 22 |
| 3 | 23 |
| 3 | 24 |
| 3 | 25 |
| 3 | 26 |
| 3 | 27 |
| 4 | 1 |
| 4 | 2 |
| 4 | 3 |
| 4 | 4 |
| 4 | 5 |
| 4 | 6 |
| 4 | 7 |
| 4 | 8 |
| 4 | 9 |
| 4 | 10 |
| 4 | 11 |
| 4 | 12 |
| 4 | 13 |
| 4 | 14 |
| 4 | 15 |
| 4 | 16 |
| 4 | 17 |
| 4 | 18 |
| 4 | 19 |
| 4 | 20 |
| 4 | 21 |
| 4 | 22 |
| 4 | 23 |
| 4 | 24 |
| 4 | 25 |
| 4 | 26 |
| 4 | 27 |
| 5 | 1 |
| 5 | 2 |

-continued

| No. | Con. |
|---|---|
| 5 | 3 |
| 5 | 4 |
| 5 | 5 |
| 5 | 6 |
| 5 | 7 |
| 5 | 8 |
| 5 | 9 |
| 5 | 10 |
| 5 | 11 |
| 5 | 12 |
| 5 | 13 |
| 5 | 14 |
| 5 | 15 |
| 5 | 16 |
| 5 | 17 |
| 5 | 18 |
| 5 | 19 |
| 5 | 20 |
| 5 | 21 |
| 5 | 22 |
| 5 | 23 |
| 5 | 24 |
| 5 | 25 |
| 5 | 26 |
| 5 | 27 |
| 6 | 1 |
| 6 | 2 |
| 6 | 3 |
| 6 | 4 |
| 6 | 5 |
| 6 | 6 |
| 6 | 7 |
| 6 | 8 |
| 6 | 9 |
| 6 | 10 |
| 6 | 11 |
| 6 | 12 |
| 6 | 13 |
| 6 | 14 |
| 6 | 15 |
| 6 | 16 |
| 6 | 17 |
| 6 | 18 |
| 6 | 19 |
| 6 | 20 |
| 6 | 21 |
| 6 | 22 |
| 6 | 23 |
| 6 | 24 |
| 6 | 25 |
| 6 | 26 |
| 6 | 27 |
| 7 | 1 |
| 7 | 2 |
| 7 | 3 |
| 7 | 4 |
| 7 | 5 |
| 7 | 6 |
| 7 | 7 |
| 7 | 8 |
| 7 | 9 |
| 7 | 10 |
| 7 | 11 |
| 7 | 12 |
| 7 | 13 |
| 7 | 14 |
| 7 | 15 |
| 7 | 16 |
| 7 | 17 |
| 7 | 18 |
| 7 | 19 |
| 7 | 20 |
| 7 | 21 |
| 7 | 22 |
| 7 | 23 |
| 7 | 24 |
| 7 | 25 |

-continued

| No. | Con. |
|---|---|
| 7 | 26 |
| 7 | 27 |
| 8 | 1 |
| 8 | 2 |
| 8 | 3 |
| 8 | 4 |
| 8 | 5 |
| 8 | 6 |
| 8 | 7 |
| 8 | 8 |
| 8 | 9 |
| 8 | 10 |
| 8 | 11 |
| 8 | 12 |
| 8 | 13 |
| 8 | 14 |
| 8 | 15 |
| 8 | 16 |
| 8 | 17 |
| 8 | 18 |
| 8 | 19 |
| 8 | 20 |
| 8 | 21 |
| 8 | 22 |
| 8 | 23 |
| 8 | 24 |
| 8 | 25 |
| 8 | 26 |
| 8 | 27 |
| 9 | 1 |
| 9 | 2 |
| 9 | 3 |
| 9 | 4 |
| 9 | 5 |
| 9 | 6 |
| 9 | 7 |
| 9 | 8 |
| 9 | 9 |
| 9 | 10 |
| 9 | 11 |
| 9 | 12 |
| 9 | 13 |
| 9 | 14 |
| 9 | 15 |
| 9 | 16 |
| 9 | 17 |
| 9 | 18 |
| 9 | 19 |
| 9 | 20 |
| 9 | 21 |
| 9 | 22 |
| 9 | 23 |
| 9 | 24 |
| 9 | 25 |
| 9 | 26 |
| 9 | 27 |
| 10 | 1 |
| 10 | 2 |
| 10 | 3 |
| 10 | 4 |
| 10 | 5 |
| 10 | 6 |
| 10 | 7 |
| 10 | 8 |
| 10 | 9 |
| 10 | 10 |
| 10 | 11 |
| 10 | 12 |
| 10 | 13 |
| 10 | 14 |
| 10 | 15 |
| 10 | 16 |
| 10 | 17 |
| 10 | 18 |
| 10 | 19 |
| 10 | 20 |
| 10 | 21 |

-continued

| No. | Con. |
|---|---|
| 10 | 22 |
| 10 | 23 |
| 10 | 24 |
| 10 | 25 |
| 10 | 26 |
| 10 | 27 |
| 11 | 1 |
| 11 | 2 |
| 11 | 3 |
| 11 | 4 |
| 11 | 5 |
| 11 | 6 |
| 11 | 7 |
| 11 | 8 |
| 11 | 9 |
| 11 | 10 |
| 11 | 11 |
| 11 | 12 |
| 11 | 13 |
| 11 | 14 |
| 11 | 15 |
| 11 | 16 |
| 11 | 17 |
| 11 | 18 |
| 11 | 19 |
| 11 | 20 |
| 11 | 21 |
| 11 | 22 |
| 11 | 23 |
| 11 | 24 |
| 11 | 25 |
| 11 | 26 |
| 11 | 27 |
| 12 | 1 |
| 12 | 2 |
| 12 | 3 |
| 12 | 4 |
| 12 | 5 |
| 12 | 6 |
| 12 | 7 |
| 12 | 8 |
| 12 | 9 |
| 12 | 10 |
| 12 | 11 |
| 12 | 12 |
| 12 | 13 |
| 12 | 14 |
| 12 | 15 |
| 12 | 16 |
| 12 | 17 |
| 12 | 18 |
| 12 | 19 |
| 12 | 20 |
| 12 | 21 |
| 12 | 22 |
| 12 | 23 |
| 12 | 24 |
| 12 | 25 |
| 12 | 26 |
| 12 | 27 |
| 13 | 1 |
| 13 | 2 |
| 13 | 3 |
| 13 | 4 |
| 13 | 5 |
| 13 | 6 |
| 13 | 7 |
| 13 | 8 |
| 13 | 9 |
| 13 | 10 |
| 13 | 11 |
| 13 | 12 |
| 13 | 13 |
| 13 | 14 |
| 13 | 15 |
| 13 | 16 |
| 13 | 17 |

-continued

| No. | Con. |
|---|---|
| 13 | 18 |
| 13 | 19 |
| 13 | 20 |
| 13 | 21 |
| 13 | 22 |
| 13 | 23 |
| 13 | 24 |
| 13 | 25 |
| 13 | 26 |
| 13 | 27 |
| 14 | 1 |
| 14 | 2 |
| 14 | 3 |
| 14 | 4 |
| 14 | 5 |
| 14 | 6 |
| 14 | 7 |
| 14 | 8 |
| 14 | 9 |
| 14 | 10 |
| 14 | 11 |
| 14 | 12 |
| 14 | 13 |
| 14 | 14 |
| 14 | 15 |
| 14 | 16 |
| 14 | 17 |
| 14 | 18 |
| 14 | 19 |
| 14 | 20 |
| 14 | 21 |
| 14 | 22 |
| 14 | 23 |
| 14 | 24 |
| 14 | 25 |
| 14 | 26 |
| 14 | 27 |
| 15 | 1 |
| 15 | 2 |
| 15 | 3 |
| 15 | 4 |
| 15 | 5 |
| 15 | 6 |
| 15 | 7 |
| 15 | 8 |
| 15 | 9 |
| 15 | 10 |
| 15 | 11 |
| 15 | 12 |
| 15 | 13 |
| 15 | 14 |
| 15 | 15 |
| 15 | 16 |
| 15 | 17 |
| 15 | 18 |
| 15 | 19 |
| 15 | 20 |
| 15 | 21 |
| 15 | 22 |
| 15 | 23 |
| 15 | 24 |
| 15 | 25 |
| 15 | 26 |
| 15 | 27 |
| 16 | 1 |
| 16 | 2 |
| 16 | 3 |
| 16 | 4 |
| 16 | 5 |
| 16 | 6 |
| 16 | 7 |
| 16 | 8 |
| 16 | 9 |
| 16 | 10 |
| 16 | 11 |
| 16 | 12 |
| 16 | 13 |

-continued

| No. | Con. |
|---|---|
| 16 | 14 |
| 16 | 15 |
| 16 | 16 |
| 16 | 17 |
| 16 | 18 |
| 16 | 19 |
| 16 | 20 |
| 16 | 21 |
| 16 | 22 |
| 16 | 23 |
| 16 | 24 |
| 16 | 25 |
| 16 | 26 |
| 16 | 27 |
| 17 | 1 |
| 17 | 2 |
| 17 | 3 |
| 17 | 4 |
| 17 | 5 |
| 17 | 6 |
| 17 | 7 |
| 17 | 8 |
| 17 | 9 |
| 17 | 10 |
| 17 | 11 |
| 17 | 12 |
| 17 | 13 |
| 17 | 14 |
| 17 | 15 |
| 17 | 16 |
| 17 | 17 |
| 17 | 18 |
| 17 | 19 |
| 17 | 20 |
| 17 | 21 |
| 17 | 22 |
| 17 | 23 |
| 17 | 24 |
| 17 | 25 |
| 17 | 26 |
| 17 | 27 |
| 18 | 1 |
| 18 | 2 |
| 18 | 3 |
| 18 | 4 |
| 18 | 5 |
| 18 | 6 |
| 18 | 7 |
| 18 | 8 |
| 18 | 9 |
| 18 | 10 |
| 18 | 11 |
| 18 | 12 |
| 18 | 13 |
| 18 | 14 |
| 18 | 15 |
| 18 | 16 |
| 18 | 17 |
| 18 | 18 |
| 18 | 19 |
| 18 | 20 |
| 18 | 21 |
| 18 | 22 |
| 18 | 23 |
| 18 | 24 |
| 18 | 25 |
| 18 | 26 |
| 18 | 27 |
| 19 | 1 |
| 19 | 2 |
| 19 | 3 |
| 19 | 4 |
| 19 | 5 |
| 19 | 6 |
| 19 | 7 |
| 19 | 8 |
| 19 | 9 |

-continued

| No. | Con. |
|---|---|
| 19 | 10 |
| 19 | 11 |
| 19 | 12 |
| 19 | 13 |
| 19 | 14 |
| 19 | 15 |
| 19 | 16 |
| 19 | 17 |
| 19 | 18 |
| 19 | 19 |
| 19 | 20 |
| 19 | 21 |
| 19 | 22 |
| 19 | 23 |
| 19 | 24 |
| 19 | 25 |
| 19 | 26 |
| 19 | 27 |
| 20 | 1 |
| 20 | 2 |
| 20 | 3 |
| 20 | 4 |
| 20 | 5 |
| 20 | 6 |
| 20 | 7 |
| 20 | 8 |
| 20 | 9 |
| 20 | 10 |
| 20 | 11 |
| 20 | 12 |
| 20 | 13 |
| 20 | 14 |
| 20 | 15 |
| 20 | 16 |
| 20 | 17 |
| 20 | 18 |
| 20 | 19 |
| 20 | 20 |
| 20 | 21 |
| 20 | 22 |
| 20 | 23 |
| 20 | 24 |
| 20 | 25 |
| 20 | 26 |
| 20 | 27 |
| 21 | 1 |
| 21 | 2 |
| 21 | 3 |
| 21 | 4 |
| 21 | 5 |
| 21 | 6 |
| 21 | 7 |
| 21 | 8 |
| 21 | 9 |
| 21 | 10 |
| 21 | 11 |
| 21 | 12 |
| 21 | 13 |
| 21 | 14 |
| 21 | 15 |
| 21 | 16 |
| 21 | 17 |
| 21 | 18 |
| 21 | 19 |
| 21 | 20 |
| 21 | 21 |
| 21 | 22 |
| 21 | 23 |
| 21 | 24 |
| 21 | 25 |
| 21 | 26 |
| 21 | 27 |
| 22 | 1 |
| 22 | 2 |
| 22 | 3 |
| 22 | 4 |
| 22 | 5 |

-continued

| No. | Con. |
|---|---|
| 22 | 6 |
| 22 | 7 |
| 22 | 8 |
| 22 | 9 |
| 22 | 10 |
| 22 | 11 |
| 22 | 12 |
| 22 | 13 |
| 22 | 14 |
| 22 | 15 |
| 22 | 16 |
| 22 | 17 |
| 22 | 18 |
| 22 | 19 |
| 22 | 20 |
| 22 | 21 |
| 22 | 22 |
| 22 | 23 |
| 22 | 24 |
| 22 | 25 |
| 22 | 26 |
| 22 | 27 |
| 23 | 1 |
| 23 | 2 |
| 23 | 3 |
| 23 | 4 |
| 23 | 5 |
| 23 | 6 |
| 23 | 7 |
| 23 | 8 |
| 23 | 9 |
| 23 | 10 |
| 23 | 11 |
| 23 | 12 |
| 23 | 13 |
| 23 | 14 |
| 23 | 15 |
| 23 | 16 |
| 23 | 17 |
| 23 | 18 |
| 23 | 19 |
| 23 | 20 |
| 23 | 21 |
| 23 | 22 |
| 23 | 23 |
| 23 | 24 |
| 23 | 25 |
| 23 | 26 |
| 23 | 27 |
| 24 | 1 |
| 24 | 2 |
| 24 | 3 |
| 24 | 4 |
| 24 | 5 |
| 24 | 6 |
| 24 | 7 |
| 24 | 8 |
| 24 | 9 |
| 24 | 10 |
| 24 | 11 |
| 24 | 12 |
| 24 | 13 |
| 24 | 14 |
| 24 | 15 |
| 24 | 16 |
| 24 | 17 |
| 24 | 18 |
| 24 | 19 |
| 24 | 20 |
| 24 | 21 |
| 24 | 22 |
| 24 | 23 |
| 24 | 24 |
| 24 | 25 |
| 24 | 26 |
| 24 | 27 |
| 25 | 1 |

-continued

| No. | Con. |
|---|---|
| 25 | 2 |
| 25 | 3 |
| 25 | 4 |
| 25 | 5 |
| 25 | 6 |
| 25 | 7 |
| 25 | 8 |
| 25 | 9 |
| 25 | 10 |
| 25 | 11 |
| 25 | 12 |
| 25 | 13 |
| 25 | 14 |
| 25 | 15 |
| 25 | 16 |
| 25 | 17 |
| 25 | 18 |
| 25 | 19 |
| 25 | 20 |
| 25 | 21 |
| 25 | 22 |
| 25 | 23 |
| 25 | 24 |
| 25 | 25 |
| 25 | 26 |
| 25 | 27 |
| 26 | 1 |
| 26 | 2 |
| 26 | 3 |
| 26 | 4 |
| 26 | 5 |
| 26 | 6 |
| 26 | 7 |
| 26 | 8 |
| 26 | 9 |
| 26 | 10 |
| 26 | 11 |
| 26 | 12 |
| 26 | 13 |
| 26 | 14 |
| 26 | 15 |
| 26 | 16 |
| 26 | 17 |
| 26 | 18 |
| 26 | 19 |
| 26 | 20 |
| 26 | 21 |
| 26 | 22 |
| 26 | 23 |
| 26 | 24 |
| 26 | 25 |
| 26 | 26 |
| 26 | 27 |
| 27 | 1 |
| 27 | 2 |
| 27 | 3 |
| 27 | 4 |
| 27 | 5 |
| 27 | 6 |
| 27 | 7 |
| 27 | 8 |
| 27 | 9 |
| 27 | 10 |
| 27 | 11 |
| 27 | 12 |
| 27 | 13 |
| 27 | 14 |
| 27 | 15 |
| 27 | 16 |
| 27 | 17 |
| 27 | 18 |
| 27 | 19 |
| 27 | 20 |
| 27 | 21 |
| 27 | 22 |
| 27 | 23 |
| 27 | 24 |

-continued

| No. | Con. |
|---|---|
| 27 | 25 |
| 27 | 26 |
| 27 | 27 |
| 28 | 1 |
| 28 | 2 |
| 28 | 3 |
| 28 | 4 |
| 28 | 5 |
| 28 | 6 |
| 28 | 7 |
| 28 | 8 |
| 28 | 9 |
| 28 | 10 |
| 28 | 11 |
| 28 | 12 |
| 28 | 13 |
| 28 | 14 |
| 28 | 15 |
| 28 | 16 |
| 28 | 17 |
| 28 | 18 |
| 28 | 19 |
| 28 | 20 |
| 28 | 21 |
| 28 | 22 |
| 28 | 23 |
| 28 | 24 |
| 28 | 25 |
| 28 | 26 |
| 28 | 27 |
| 29 | 1 |
| 29 | 2 |
| 29 | 3 |
| 29 | 4 |
| 29 | 5 |
| 29 | 6 |
| 29 | 7 |
| 29 | 8 |
| 29 | 9 |
| 29 | 10 |
| 29 | 11 |
| 29 | 12 |
| 29 | 13 |
| 29 | 14 |
| 29 | 15 |
| 29 | 16 |
| 29 | 17 |
| 29 | 18 |
| 29 | 19 |
| 29 | 20 |
| 29 | 21 |
| 29 | 22 |
| 29 | 23 |
| 29 | 24 |
| 29 | 25 |
| 29 | 26 |
| 29 | 27 |
| 30 | 1 |
| 30 | 2 |
| 30 | 3 |
| 30 | 4 |
| 30 | 5 |
| 30 | 6 |
| 30 | 7 |
| 30 | 8 |
| 30 | 9 |
| 30 | 10 |
| 30 | 11 |
| 30 | 12 |
| 30 | 13 |
| 30 | 14 |
| 30 | 15 |
| 30 | 16 |
| 30 | 17 |
| 30 | 18 |
| 30 | 19 |
| 30 | 20 |

-continued

| No. | Con. |
|---|---|
| 30 | 21 |
| 30 | 22 |
| 30 | 23 |
| 30 | 24 |
| 30 | 25 |
| 30 | 26 |
| 30 | 27 |
| 31 | 1 |
| 31 | 2 |
| 31 | 3 |
| 31 | 4 |
| 31 | 5 |
| 31 | 6 |
| 31 | 7 |
| 31 | 8 |
| 31 | 9 |
| 31 | 10 |
| 31 | 11 |
| 31 | 12 |
| 31 | 13 |
| 31 | 14 |
| 31 | 15 |
| 31 | 16 |
| 31 | 17 |
| 31 | 18 |
| 31 | 19 |
| 31 | 20 |
| 31 | 21 |
| 31 | 22 |
| 31 | 23 |
| 31 | 24 |
| 31 | 25 |
| 31 | 26 |
| 31 | 27 |
| 32 | 1 |
| 32 | 2 |
| 32 | 3 |
| 32 | 4 |
| 32 | 5 |
| 32 | 6 |
| 32 | 7 |
| 32 | 8 |
| 32 | 9 |
| 32 | 10 |
| 32 | 11 |
| 32 | 12 |
| 32 | 13 |
| 32 | 14 |
| 32 | 15 |
| 32 | 16 |
| 32 | 17 |
| 32 | 18 |
| 32 | 19 |
| 32 | 20 |
| 32 | 21 |
| 32 | 22 |
| 32 | 23 |
| 32 | 24 |
| 32 | 25 |
| 32 | 26 |
| 32 | 27 |
| 33 | 1 |
| 33 | 2 |
| 33 | 3 |
| 33 | 4 |
| 33 | 5 |
| 33 | 6 |
| 33 | 7 |
| 33 | 8 |
| 33 | 9 |
| 33 | 10 |
| 33 | 11 |
| 33 | 12 |
| 33 | 13 |
| 33 | 14 |
| 33 | 15 |
| 33 | 16 |

-continued

| No. | Con. |
|---|---|
| 33 | 17 |
| 33 | 18 |
| 33 | 19 |
| 33 | 20 |
| 33 | 21 |
| 33 | 22 |
| 33 | 23 |
| 33 | 24 |
| 33 | 25 |
| 33 | 26 |
| 33 | 27 |
| 34 | 1 |
| 34 | 2 |
| 34 | 3 |
| 34 | 4 |
| 34 | 5 |
| 34 | 6 |
| 34 | 7 |
| 34 | 8 |
| 34 | 9 |
| 34 | 10 |
| 34 | 11 |
| 34 | 12 |
| 34 | 13 |
| 34 | 14 |
| 34 | 15 |
| 34 | 16 |
| 34 | 17 |
| 34 | 18 |
| 34 | 19 |
| 34 | 20 |
| 34 | 21 |
| 34 | 22 |
| 34 | 23 |
| 34 | 24 |
| 34 | 25 |
| 34 | 26 |
| 34 | 27 |
| 35 | 1 |
| 35 | 2 |
| 35 | 3 |
| 35 | 4 |
| 35 | 5 |
| 35 | 6 |
| 35 | 7 |
| 35 | 8 |
| 35 | 9 |
| 35 | 10 |
| 35 | 11 |
| 35 | 12 |
| 35 | 13 |
| 35 | 14 |
| 35 | 15 |
| 35 | 16 |
| 35 | 17 |
| 35 | 18 |
| 35 | 19 |
| 35 | 20 |
| 35 | 21 |
| 35 | 22 |
| 35 | 23 |
| 35 | 24 |
| 35 | 25 |
| 35 | 26 |
| 35 | 27 |
| 36 | 1 |
| 36 | 2 |
| 36 | 3 |
| 36 | 4 |
| 36 | 5 |
| 36 | 6 |
| 36 | 7 |
| 36 | 8 |
| 36 | 9 |
| 36 | 10 |
| 36 | 11 |
| 36 | 12 |

-continued

| No. | Con. |
|---|---|
| 36 | 13 |
| 36 | 14 |
| 36 | 15 |
| 36 | 16 |
| 36 | 17 |
| 36 | 18 |
| 36 | 19 |
| 36 | 20 |
| 36 | 21 |
| 36 | 22 |
| 36 | 23 |
| 36 | 24 |
| 36 | 25 |
| 36 | 26 |
| 36 | 27 |
| 37 | 1 |
| 37 | 2 |
| 37 | 3 |
| 37 | 4 |
| 37 | 5 |
| 37 | 6 |
| 37 | 7 |
| 37 | 8 |
| 37 | 9 |
| 37 | 10 |
| 37 | 11 |
| 37 | 12 |
| 37 | 13 |
| 37 | 14 |
| 37 | 15 |
| 37 | 16 |
| 37 | 17 |
| 37 | 18 |
| 37 | 19 |
| 37 | 20 |
| 37 | 21 |
| 37 | 22 |
| 37 | 23 |
| 37 | 24 |
| 37 | 25 |
| 37 | 26 |
| 37 | 27 |
| 38 | 1 |
| 38 | 2 |
| 38 | 3 |
| 38 | 4 |
| 38 | 5 |
| 38 | 6 |
| 38 | 7 |
| 38 | 8 |
| 38 | 9 |
| 38 | 10 |
| 38 | 11 |
| 38 | 12 |
| 38 | 13 |
| 38 | 14 |
| 38 | 15 |
| 38 | 16 |
| 38 | 17 |
| 38 | 18 |
| 38 | 19 |
| 38 | 20 |
| 38 | 21 |
| 38 | 22 |
| 38 | 23 |
| 38 | 24 |
| 38 | 25 |
| 38 | 26 |
| 38 | 27 |
| 39 | 1 |
| 39 | 2 |
| 39 | 3 |
| 39 | 4 |
| 39 | 5 |
| 39 | 6 |
| 39 | 7 |
| 39 | 8 |

-continued

| No. | Con. |
|---|---|
| 39 | 9 |
| 39 | 10 |
| 39 | 11 |
| 39 | 12 |
| 39 | 13 |
| 39 | 14 |
| 39 | 15 |
| 39 | 16 |
| 39 | 17 |
| 39 | 18 |
| 39 | 19 |
| 39 | 20 |
| 39 | 21 |
| 39 | 22 |
| 39 | 23 |
| 39 | 24 |
| 39 | 25 |
| 39 | 26 |
| 39 | 27 |
| 40 | 1 |
| 40 | 2 |
| 40 | 3 |
| 40 | 4 |
| 40 | 5 |
| 40 | 6 |
| 40 | 7 |
| 40 | 8 |
| 40 | 9 |
| 40 | 10 |
| 40 | 11 |
| 40 | 12 |
| 40 | 13 |
| 40 | 14 |
| 40 | 15 |
| 40 | 16 |
| 40 | 17 |
| 40 | 18 |
| 40 | 19 |
| 40 | 20 |
| 40 | 21 |
| 40 | 22 |
| 40 | 23 |
| 40 | 24 |
| 40 | 25 |
| 40 | 26 |
| 40 | 27 |
| 41 | 1 |
| 41 | 2 |
| 41 | 3 |
| 41 | 4 |
| 41 | 5 |
| 41 | 6 |
| 41 | 7 |
| 41 | 8 |
| 41 | 9 |
| 41 | 10 |
| 41 | 11 |
| 41 | 12 |
| 41 | 13 |
| 41 | 14 |
| 41 | 15 |
| 41 | 16 |
| 41 | 17 |
| 41 | 18 |
| 41 | 19 |
| 41 | 20 |
| 41 | 21 |
| 41 | 22 |
| 41 | 23 |
| 41 | 24 |
| 41 | 25 |
| 41 | 26 |
| 41 | 27 |
| 56 | 1 |
| 56 | 2 |
| 56 | 3 |
| 56 | 4 |

-continued

| No. | Con. |
|---|---|
| 56 | 5 |
| 56 | 6 |
| 56 | 7 |
| 56 | 8 |
| 56 | 9 |
| 56 | 10 |
| 56 | 11 |
| 56 | 12 |
| 56 | 13 |
| 56 | 14 |
| 56 | 15 |
| 56 | 16 |
| 56 | 17 |
| 56 | 18 |
| 56 | 19 |
| 56 | 20 |
| 56 | 21 |
| 56 | 22 |
| 56 | 23 |
| 56 | 24 |
| 56 | 25 |
| 56 | 26 |
| 56 | 27 |
| 57 | 1 |
| 57 | 2 |
| 57 | 3 |
| 57 | 4 |
| 57 | 5 |
| 57 | 6 |
| 57 | 7 |
| 57 | 8 |
| 57 | 9 |
| 57 | 10 |
| 57 | 11 |
| 57 | 12 |
| 57 | 13 |
| 57 | 14 |
| 57 | 15 |
| 57 | 16 |
| 57 | 17 |
| 57 | 18 |
| 57 | 19 |
| 57 | 20 |
| 57 | 21 |
| 57 | 22 |
| 57 | 23 |
| 57 | 24 |
| 57 | 25 |
| 57 | 26 |
| 57 | 27 |
| 58 | 1 |
| 58 | 2 |
| 58 | 3 |
| 58 | 4 |
| 58 | 5 |
| 58 | 6 |
| 58 | 7 |
| 58 | 8 |
| 58 | 9 |
| 58 | 10 |
| 58 | 11 |
| 58 | 12 |
| 58 | 13 |
| 58 | 14 |
| 58 | 15 |
| 58 | 16 |
| 58 | 17 |
| 58 | 18 |
| 58 | 19 |
| 58 | 20 |
| 58 | 21 |
| 58 | 22 |
| 58 | 23 |
| 58 | 24 |
| 58 | 25 |
| 58 | 26 |
| 58 | 27 |

-continued

| No. | Con. |
|---|---|
| 59 | 1 |
| 59 | 2 |
| 59 | 3 |
| 59 | 4 |
| 59 | 5 |
| 59 | 6 |
| 59 | 7 |
| 59 | 8 |
| 59 | 9 |
| 59 | 10 |
| 59 | 11 |
| 59 | 12 |
| 59 | 13 |
| 59 | 14 |
| 59 | 15 |
| 59 | 16 |
| 59 | 17 |
| 59 | 18 |
| 59 | 19 |
| 59 | 20 |
| 59 | 21 |
| 59 | 22 |
| 59 | 23 |
| 59 | 24 |
| 59 | 25 |
| 59 | 26 |
| 59 | 27 |
| 60 | 1 |
| 60 | 2 |
| 60 | 3 |
| 60 | 4 |
| 60 | 5 |
| 60 | 6 |
| 60 | 7 |
| 60 | 8 |
| 60 | 9 |
| 60 | 10 |
| 60 | 11 |
| 60 | 12 |
| 60 | 13 |
| 60 | 14 |
| 60 | 15 |
| 60 | 16 |
| 60 | 17 |
| 60 | 18 |
| 60 | 19 |
| 60 | 20 |
| 60 | 21 |
| 60 | 22 |
| 60 | 23 |
| 60 | 24 |
| 60 | 25 |
| 60 | 26 |
| 60 | 27 |
| 61 | 1 |
| 61 | 2 |
| 61 | 3 |
| 61 | 4 |
| 61 | 5 |
| 61 | 6 |
| 61 | 7 |
| 61 | 8 |
| 61 | 9 |
| 61 | 10 |
| 61 | 11 |
| 61 | 12 |
| 61 | 13 |
| 61 | 14 |
| 61 | 15 |
| 61 | 16 |
| 61 | 17 |
| 61 | 18 |
| 61 | 19 |
| 61 | 20 |
| 61 | 21 |
| 61 | 22 |
| 61 | 23 |

-continued

| No. | Con. |
|---|---|
| 61 | 24 |
| 61 | 25 |
| 61 | 26 |
| 61 | 27 |
| 62 | 1 |
| 62 | 2 |
| 62 | 3 |
| 62 | 4 |
| 62 | 5 |
| 62 | 6 |
| 62 | 7 |
| 62 | 8 |
| 62 | 9 |
| 62 | 10 |
| 62 | 11 |
| 62 | 12 |
| 62 | 13 |
| 62 | 14 |
| 62 | 15 |
| 62 | 16 |
| 62 | 17 |
| 62 | 18 |
| 62 | 19 |
| 62 | 20 |
| 62 | 21 |
| 62 | 22 |
| 62 | 23 |
| 62 | 24 |
| 62 | 25 |
| 62 | 26 |
| 62 | 27 |
| 63 | 1 |
| 63 | 2 |
| 63 | 3 |
| 63 | 4 |
| 63 | 5 |
| 63 | 6 |
| 63 | 7 |
| 63 | 8 |
| 63 | 9 |
| 63 | 10 |
| 63 | 11 |
| 63 | 12 |
| 63 | 13 |
| 63 | 14 |
| 63 | 15 |
| 63 | 16 |
| 63 | 17 |
| 63 | 18 |
| 63 | 19 |
| 63 | 20 |
| 63 | 21 |
| 63 | 22 |
| 63 | 23 |
| 63 | 24 |
| 63 | 25 |
| 63 | 26 |
| 63 | 27 |
| 64 | 1 |
| 64 | 2 |
| 64 | 3 |
| 64 | 4 |
| 64 | 5 |
| 64 | 6 |
| 64 | 7 |
| 64 | 8 |
| 64 | 9 |
| 64 | 10 |
| 64 | 11 |
| 64 | 12 |
| 64 | 13 |
| 64 | 14 |
| 64 | 15 |
| 64 | 16 |
| 64 | 17 |
| 64 | 18 |
| 64 | 19 |

-continued

| No. | Con. |
|---|---|
| 64 | 20 |
| 64 | 21 |
| 64 | 22 |
| 64 | 23 |
| 64 | 24 |
| 64 | 25 |
| 64 | 26 |
| 64 | 27 |
| 65 | 1 |
| 65 | 2 |
| 65 | 3 |
| 65 | 4 |
| 65 | 5 |
| 65 | 6 |
| 65 | 7 |
| 65 | 8 |
| 65 | 9 |
| 65 | 10 |
| 65 | 11 |
| 65 | 12 |
| 65 | 13 |
| 65 | 14 |
| 65 | 15 |
| 65 | 16 |
| 65 | 17 |
| 65 | 18 |
| 65 | 19 |
| 65 | 20 |
| 65 | 21 |
| 65 | 22 |
| 65 | 23 |
| 65 | 24 |
| 65 | 25 |
| 65 | 26 |
| 65 | 27 |
| 66 | 1 |
| 66 | 2 |
| 66 | 3 |
| 66 | 4 |
| 66 | 5 |
| 66 | 6 |
| 66 | 7 |
| 66 | 8 |
| 66 | 9 |
| 66 | 10 |
| 66 | 11 |
| 66 | 12 |
| 66 | 13 |
| 66 | 14 |
| 66 | 15 |
| 66 | 16 |
| 66 | 17 |
| 66 | 18 |
| 66 | 19 |
| 66 | 20 |
| 66 | 21 |
| 66 | 22 |
| 66 | 23 |
| 66 | 24 |
| 66 | 25 |
| 66 | 26 |
| 66 | 27 |
| 67 | 1 |
| 67 | 2 |
| 67 | 3 |
| 67 | 4 |
| 67 | 5 |
| 67 | 6 |
| 67 | 7 |
| 67 | 8 |
| 67 | 9 |
| 67 | 10 |
| 67 | 11 |
| 67 | 12 |
| 67 | 13 |
| 67 | 14 |
| 67 | 15 |

-continued

| No. | Con. |
|---|---|
| 67 | 16 |
| 67 | 17 |
| 67 | 18 |
| 67 | 19 |
| 67 | 20 |
| 67 | 21 |
| 67 | 22 |
| 67 | 23 |
| 67 | 24 |
| 67 | 25 |
| 67 | 26 |
| 67 | 27 |
| 68 | 1 |
| 68 | 2 |
| 68 | 3 |
| 68 | 4 |
| 68 | 5 |
| 68 | 6 |
| 68 | 7 |
| 68 | 8 |
| 68 | 9 |
| 68 | 10 |
| 68 | 11 |
| 68 | 12 |
| 68 | 13 |
| 68 | 14 |
| 68 | 15 |
| 68 | 16 |
| 68 | 17 |
| 68 | 18 |
| 68 | 19 |
| 68 | 20 |
| 68 | 21 |
| 68 | 22 |
| 68 | 23 |
| 68 | 24 |
| 68 | 25 |
| 68 | 26 |
| 68 | 27 |
| 69 | 1 |
| 69 | 2 |
| 69 | 3 |
| 69 | 4 |
| 69 | 5 |
| 69 | 6 |
| 69 | 7 |
| 69 | 8 |
| 69 | 9 |
| 69 | 10 |
| 69 | 11 |
| 69 | 12 |
| 69 | 13 |
| 69 | 14 |
| 69 | 15 |
| 69 | 16 |
| 69 | 17 |
| 69 | 18 |
| 69 | 19 |
| 69 | 20 |
| 69 | 21 |
| 69 | 22 |
| 69 | 23 |
| 69 | 24 |
| 69 | 25 |
| 69 | 26 |
| 69 | 27 |
| 69-1 | 1 |
| 69-1 | 2 |
| 69-1 | 3 |
| 69-1 | 4 |
| 69-1 | 5 |
| 69-1 | 6 |
| 69-1 | 7 |
| 69-1 | 8 |
| 69-1 | 9 |
| 69-1 | 10 |
| 69-1 | 11 |

-continued

| No. | Con. |
|---|---|
| 69-1 | 12 |
| 69-1 | 13 |
| 69-1 | 14 |
| 69-1 | 15 |
| 69-1 | 16 |
| 69-1 | 17 |
| 69-1 | 18 |
| 69-1 | 19 |
| 69-1 | 20 |
| 69-1 | 21 |
| 69-1 | 22 |
| 69-1 | 23 |
| 69-1 | 24 |
| 69-1 | 25 |
| 69-1 | 26 |
| 69-1 | 27 |
| 70 | 1 |
| 70 | 2 |
| 70 | 3 |
| 70 | 4 |
| 70 | 5 |
| 70 | 6 |
| 70 | 7 |
| 70 | 8 |
| 70 | 9 |
| 70 | 10 |
| 70 | 11 |
| 70 | 12 |
| 70 | 13 |
| 70 | 14 |
| 70 | 15 |
| 70 | 16 |
| 70 | 17 |
| 70 | 18 |
| 70 | 19 |
| 70 | 20 |
| 70 | 21 |
| 70 | 22 |
| 70 | 23 |
| 70 | 24 |
| 70 | 25 |
| 70 | 26 |
| 70 | 27 |
| 71 | 1 |
| 71 | 2 |
| 71 | 3 |
| 71 | 4 |
| 71 | 5 |
| 71 | 6 |
| 71 | 7 |
| 71 | 8 |
| 71 | 9 |
| 71 | 10 |
| 71 | 11 |
| 71 | 12 |
| 71 | 13 |
| 71 | 14 |
| 71 | 15 |
| 71 | 16 |
| 71 | 17 |
| 71 | 18 |
| 71 | 19 |
| 71 | 20 |
| 71 | 21 |
| 71 | 22 |
| 71 | 23 |
| 71 | 24 |
| 71 | 25 |
| 71 | 26 |
| 71 | 27 |
| 72 | 1 |
| 72 | 2 |
| 72 | 3 |
| 72 | 4 |
| 72 | 5 |
| 72 | 6 |
| 72 | 7 |

-continued

| No. | Con. |
|---|---|
| 72 | 8 |
| 72 | 9 |
| 72 | 10 |
| 72 | 11 |
| 72 | 12 |
| 72 | 13 |
| 72 | 14 |
| 72 | 15 |
| 72 | 16 |
| 72 | 17 |
| 72 | 18 |
| 72 | 19 |
| 72 | 20 |
| 72 | 21 |
| 72 | 22 |
| 72 | 23 |
| 72 | 24 |
| 72 | 25 |
| 72 | 26 |
| 72 | 27 |
| 73 | 1 |
| 73 | 2 |
| 73 | 3 |
| 73 | 4 |
| 73 | 5 |
| 73 | 6 |
| 73 | 7 |
| 73 | 8 |
| 73 | 9 |
| 73 | 10 |
| 73 | 11 |
| 73 | 12 |
| 73 | 13 |
| 73 | 14 |
| 73 | 15 |
| 73 | 16 |
| 73 | 17 |
| 73 | 18 |
| 73 | 19 |
| 73 | 20 |
| 73 | 21 |
| 73 | 22 |
| 73 | 23 |
| 73 | 24 |
| 73 | 25 |
| 73 | 26 |
| 73 | 27 |
| 74 | 1 |
| 74 | 2 |
| 74 | 3 |
| 74 | 4 |
| 74 | 5 |
| 74 | 6 |
| 74 | 7 |
| 74 | 8 |
| 74 | 9 |
| 74 | 10 |
| 74 | 11 |
| 74 | 12 |
| 74 | 13 |
| 74 | 14 |
| 74 | 15 |
| 74 | 16 |
| 74 | 17 |
| 74 | 18 |
| 74 | 19 |
| 74 | 20 |
| 74 | 21 |
| 74 | 22 |
| 74 | 23 |
| 74 | 24 |
| 74 | 25 |
| 74 | 26 |
| 74 | 27 |
| 75 | 1 |
| 75 | 2 |
| 75 | 3 |

-continued

| No. | Con. |
|---|---|
| 75 | 4 |
| 75 | 5 |
| 75 | 6 |
| 75 | 7 |
| 75 | 8 |
| 75 | 9 |
| 75 | 10 |
| 75 | 11 |
| 75 | 12 |
| 75 | 13 |
| 75 | 14 |
| 75 | 15 |
| 75 | 16 |
| 75 | 17 |
| 75 | 18 |
| 75 | 19 |
| 75 | 20 |
| 75 | 21 |
| 75 | 22 |
| 75 | 23 |
| 75 | 24 |
| 75 | 25 |
| 75 | 26 |
| 75 | 27 |
| 75-1 | 1 |
| 75-1 | 2 |
| 75-1 | 3 |
| 75-1 | 4 |
| 75-1 | 5 |
| 75-1 | 6 |
| 75-1 | 7 |
| 75-1 | 8 |
| 75-1 | 9 |
| 75-1 | 10 |
| 75-1 | 11 |
| 75-1 | 12 |
| 75-1 | 13 |
| 75-1 | 14 |
| 75-1 | 15 |
| 75-1 | 16 |
| 75-1 | 17 |
| 75-1 | 18 |
| 75-1 | 19 |
| 75-1 | 20 |
| 75-1 | 21 |
| 75-1 | 22 |
| 75-1 | 23 |
| 75-1 | 24 |
| 75-1 | 25 |
| 75-1 | 26 |
| 75-1 | 27 |
| 76 | 1 |
| 76 | 2 |
| 76 | 3 |
| 76 | 4 |
| 76 | 5 |
| 76 | 6 |
| 76 | 7 |
| 76 | 8 |
| 76 | 9 |
| 76 | 10 |
| 76 | 11 |
| 76 | 12 |
| 76 | 13 |
| 76 | 14 |
| 76 | 15 |
| 76 | 16 |
| 76 | 17 |
| 76 | 18 |
| 76 | 19 |
| 76 | 20 |
| 76 | 21 |
| 76 | 22 |
| 76 | 23 |
| 76 | 24 |
| 76 | 25 |
| 76 | 26 |

-continued

| No. | Con. |
|---|---|
| 76 | 27 |
| 77 | 1 |
| 77 | 2 |
| 77 | 3 |
| 77 | 4 |
| 77 | 5 |
| 77 | 6 |
| 77 | 7 |
| 77 | 8 |
| 77 | 9 |
| 77 | 10 |
| 77 | 11 |
| 77 | 12 |
| 77 | 13 |
| 77 | 14 |
| 77 | 15 |
| 77 | 16 |
| 77 | 17 |
| 77 | 18 |
| 77 | 19 |
| 77 | 20 |
| 77 | 21 |
| 77 | 22 |
| 77 | 23 |
| 77 | 24 |
| 77 | 25 |
| 77 | 26 |
| 77 | 27 |
| 78 | 1 |
| 78 | 2 |
| 78 | 3 |
| 78 | 4 |
| 78 | 5 |
| 78 | 6 |
| 78 | 7 |
| 78 | 8 |
| 78 | 9 |
| 78 | 10 |
| 78 | 11 |
| 78 | 12 |
| 78 | 13 |
| 78 | 14 |
| 78 | 15 |
| 78 | 16 |
| 78 | 17 |
| 78 | 18 |
| 78 | 19 |
| 78 | 20 |
| 78 | 21 |
| 78 | 22 |
| 78 | 23 |
| 78 | 24 |
| 78 | 25 |
| 78 | 26 |
| 78 | 27 |
| 79 | 1 |
| 79 | 2 |
| 79 | 3 |
| 79 | 4 |
| 79 | 5 |
| 79 | 6 |
| 79 | 7 |
| 79 | 8 |
| 79 | 9 |
| 79 | 10 |
| 79 | 11 |
| 79 | 12 |
| 79 | 13 |
| 79 | 14 |
| 79 | 15 |
| 79 | 16 |
| 79 | 17 |
| 79 | 18 |
| 79 | 19 |
| 79 | 20 |
| 79 | 21 |
| 79 | 22 |

-continued

| No. | Con. |
|---|---|
| 79 | 23 |
| 79 | 24 |
| 79 | 25 |
| 79 | 26 |
| 79 | 27 |
| 80 | 1 |
| 80 | 2 |
| 80 | 3 |
| 80 | 4 |
| 80 | 5 |
| 80 | 6 |
| 80 | 7 |
| 80 | 8 |
| 80 | 9 |
| 80 | 10 |
| 80 | 11 |
| 80 | 12 |
| 80 | 13 |
| 80 | 14 |
| 80 | 15 |
| 80 | 16 |
| 80 | 17 |
| 80 | 18 |
| 80 | 19 |
| 80 | 20 |
| 80 | 21 |
| 80 | 22 |
| 80 | 23 |
| 80 | 24 |
| 80 | 25 |
| 80 | 26 |
| 80 | 27 |
| 81 | 1 |
| 81 | 2 |
| 81 | 3 |
| 81 | 4 |
| 81 | 5 |
| 81 | 6 |
| 81 | 7 |
| 81 | 8 |
| 81 | 9 |
| 81 | 10 |
| 81 | 11 |
| 81 | 12 |
| 81 | 13 |
| 81 | 14 |
| 81 | 15 |
| 81 | 16 |
| 81 | 17 |
| 81 | 18 |
| 81 | 19 |
| 81 | 20 |
| 81 | 21 |
| 81 | 22 |
| 81 | 23 |
| 81 | 24 |
| 81 | 25 |
| 81 | 26 |
| 81 | 27 |
| 82 | 1 |
| 82 | 2 |
| 82 | 3 |
| 82 | 4 |
| 82 | 5 |
| 82 | 6 |
| 82 | 7 |
| 82 | 8 |
| 82 | 9 |
| 82 | 10 |
| 82 | 11 |
| 82 | 12 |
| 82 | 13 |
| 82 | 14 |
| 82 | 15 |
| 82 | 16 |
| 82 | 17 |
| 82 | 18 |

-continued

| No. | Con. |
|---|---|
| 82 | 19 |
| 82 | 20 |
| 82 | 21 |
| 82 | 22 |
| 82 | 23 |
| 82 | 24 |
| 82 | 25 |
| 82 | 26 |
| 82 | 27 |
| 83 | 1 |
| 83 | 2 |
| 83 | 3 |
| 83 | 4 |
| 83 | 5 |
| 83 | 6 |
| 83 | 7 |
| 83 | 8 |
| 83 | 9 |
| 83 | 10 |
| 83 | 11 |
| 83 | 12 |
| 83 | 13 |
| 83 | 14 |
| 83 | 15 |
| 83 | 16 |
| 83 | 17 |
| 83 | 18 |
| 83 | 19 |
| 83 | 20 |
| 83 | 21 |
| 83 | 22 |
| 83 | 23 |
| 83 | 24 |
| 83 | 25 |
| 83 | 26 |
| 83 | 27 |
| 84 | 1 |
| 84 | 2 |
| 84 | 3 |
| 84 | 4 |
| 84 | 5 |
| 84 | 6 |
| 84 | 7 |
| 84 | 8 |
| 84 | 9 |
| 84 | 10 |
| 84 | 11 |
| 84 | 12 |
| 84 | 13 |
| 84 | 14 |
| 84 | 15 |
| 84 | 16 |
| 84 | 17 |
| 84 | 18 |
| 84 | 19 |
| 84 | 20 |
| 84 | 21 |
| 84 | 22 |
| 84 | 23 |
| 84 | 24 |
| 84 | 25 |
| 84 | 26 |
| 84 | 27 |
| 85 | 1 |
| 85 | 2 |
| 85 | 3 |
| 85 | 4 |
| 85 | 5 |
| 85 | 6 |
| 85 | 7 |
| 85 | 8 |
| 85 | 9 |
| 85 | 10 |
| 85 | 11 |
| 85 | 12 |
| 85 | 13 |
| 85 | 14 |

-continued

| No. | Con. |
|---|---|
| 85 | 15 |
| 85 | 16 |
| 85 | 17 |
| 85 | 18 |
| 85 | 19 |
| 85 | 20 |
| 85 | 21 |
| 85 | 22 |
| 85 | 23 |
| 85 | 24 |
| 85 | 25 |
| 85 | 26 |
| 85 | 27 |
| 86 | 1 |
| 86 | 2 |
| 86 | 3 |
| 86 | 4 |
| 86 | 5 |
| 86 | 6 |
| 86 | 7 |
| 86 | 8 |
| 86 | 9 |
| 86 | 10 |
| 86 | 11 |
| 86 | 12 |
| 86 | 13 |
| 86 | 14 |
| 86 | 15 |
| 86 | 16 |
| 86 | 17 |
| 86 | 18 |
| 86 | 19 |
| 86 | 20 |
| 86 | 21 |
| 86 | 22 |
| 86 | 23 |
| 86 | 24 |
| 86 | 25 |
| 86 | 26 |
| 86 | 27 |
| 87 | 1 |
| 87 | 2 |
| 87 | 3 |
| 87 | 4 |
| 87 | 5 |
| 87 | 6 |
| 87 | 7 |
| 87 | 8 |
| 87 | 9 |
| 87 | 10 |
| 87 | 11 |
| 87 | 12 |
| 87 | 13 |
| 87 | 14 |
| 87 | 15 |
| 87 | 16 |
| 87 | 17 |
| 87 | 18 |
| 87 | 19 |
| 87 | 20 |
| 87 | 21 |
| 87 | 22 |
| 87 | 23 |
| 87 | 24 |
| 87 | 25 |
| 87 | 26 |
| 87 | 27 |
| 88 | 1 |
| 88 | 2 |
| 88 | 3 |
| 88 | 4 |
| 88 | 5 |
| 88 | 6 |
| 88 | 7 |
| 88 | 8 |
| 88 | 9 |
| 88 | 10 |

-continued

| No. | Con. |
|---|---|
| 88 | 11 |
| 88 | 12 |
| 88 | 13 |
| 88 | 14 |
| 88 | 15 |
| 88 | 16 |
| 88 | 17 |
| 88 | 18 |
| 88 | 19 |
| 88 | 20 |
| 88 | 21 |
| 88 | 22 |
| 88 | 23 |
| 88 | 24 |
| 88 | 25 |
| 88 | 26 |
| 88 | 27 |
| 89 | 1 |
| 89 | 2 |
| 89 | 3 |
| 89 | 4 |
| 89 | 5 |
| 89 | 6 |
| 89 | 7 |
| 89 | 8 |
| 89 | 9 |
| 89 | 10 |
| 89 | 11 |
| 89 | 12 |
| 89 | 13 |
| 89 | 14 |
| 89 | 15 |
| 89 | 16 |
| 89 | 17 |
| 89 | 18 |
| 89 | 19 |
| 89 | 20 |
| 89 | 21 |
| 89 | 22 |
| 89 | 23 |
| 89 | 24 |
| 89 | 25 |
| 89 | 26 |
| 89 | 27 |
| 90 | 1 |
| 90 | 2 |
| 90 | 3 |
| 90 | 4 |
| 90 | 5 |
| 90 | 6 |
| 90 | 7 |
| 90 | 8 |
| 90 | 9 |
| 90 | 10 |
| 90 | 11 |
| 90 | 12 |
| 90 | 13 |
| 90 | 14 |
| 90 | 15 |
| 90 | 16 |
| 90 | 17 |
| 90 | 18 |
| 90 | 19 |
| 90 | 20 |
| 90 | 21 |
| 90 | 22 |
| 90 | 23 |
| 90 | 24 |
| 90 | 25 |
| 90 | 26 |
| 90 | 27 |
| 91 | 1 |
| 91 | 2 |
| 91 | 3 |
| 91 | 4 |
| 91 | 5 |
| 91 | 6 |

-continued

| No. | Con. |
|---|---|
| 91 | 7 |
| 91 | 8 |
| 91 | 9 |
| 91 | 10 |
| 91 | 11 |
| 91 | 12 |
| 91 | 13 |
| 91 | 14 |
| 91 | 15 |
| 91 | 16 |
| 91 | 17 |
| 91 | 18 |
| 91 | 19 |
| 91 | 20 |
| 91 | 21 |
| 91 | 22 |
| 91 | 23 |
| 91 | 24 |
| 91 | 25 |
| 91 | 26 |
| 91 | 27 |
| 92 | 1 |
| 92 | 2 |
| 92 | 3 |
| 92 | 4 |
| 92 | 5 |
| 92 | 6 |
| 92 | 7 |
| 92 | 8 |
| 92 | 9 |
| 92 | 10 |
| 92 | 11 |
| 92 | 12 |
| 92 | 13 |
| 92 | 14 |
| 92 | 15 |
| 92 | 16 |
| 92 | 17 |
| 92 | 18 |
| 92 | 19 |
| 92 | 20 |
| 92 | 21 |
| 92 | 22 |
| 92 | 23 |
| 92 | 24 |
| 92 | 25 |
| 92 | 26 |
| 92 | 27 |
| 93 | 1 |
| 93 | 2 |
| 93 | 3 |
| 93 | 4 |
| 93 | 5 |
| 93 | 6 |
| 93 | 7 |
| 93 | 8 |
| 93 | 9 |
| 93 | 10 |
| 93 | 11 |
| 93 | 12 |
| 93 | 13 |
| 93 | 14 |
| 93 | 15 |
| 93 | 16 |
| 93 | 17 |
| 93 | 18 |
| 93 | 19 |
| 93 | 20 |
| 93 | 21 |
| 93 | 22 |
| 93 | 23 |
| 93 | 24 |
| 93 | 25 |
| 93 | 26 |
| 93 | 27 |
| 94 | 1 |
| 94 | 2 |

-continued

| No. | Con. |
|---|---|
| 94 | 3 |
| 94 | 4 |
| 94 | 5 |
| 94 | 6 |
| 94 | 7 |
| 94 | 8 |
| 94 | 9 |
| 94 | 10 |
| 94 | 11 |
| 94 | 12 |
| 94 | 13 |
| 94 | 14 |
| 94 | 15 |
| 94 | 16 |
| 94 | 17 |
| 94 | 18 |
| 94 | 19 |
| 94 | 20 |
| 94 | 21 |
| 94 | 22 |
| 94 | 23 |
| 94 | 24 |
| 94 | 25 |
| 94 | 26 |
| 94 | 27 |
| 95 | 1 |
| 95 | 2 |
| 95 | 3 |
| 95 | 4 |
| 95 | 5 |
| 95 | 6 |
| 95 | 7 |
| 95 | 8 |
| 95 | 9 |
| 95 | 10 |
| 95 | 11 |
| 95 | 12 |
| 95 | 13 |
| 95 | 14 |
| 95 | 15 |
| 95 | 16 |
| 95 | 17 |
| 95 | 18 |
| 95 | 19 |
| 95 | 20 |
| 95 | 21 |
| 95 | 22 |
| 95 | 23 |
| 95 | 24 |
| 95 | 25 |
| 95 | 26 |
| 95 | 27 |
| 96 | 1 |
| 96 | 2 |
| 96 | 3 |
| 96 | 4 |
| 96 | 5 |
| 96 | 6 |
| 96 | 7 |
| 96 | 8 |
| 96 | 9 |
| 96 | 10 |
| 96 | 11 |
| 96 | 12 |
| 96 | 13 |
| 96 | 14 |
| 96 | 15 |
| 96 | 16 |
| 96 | 17 |
| 96 | 18 |
| 96 | 19 |
| 96 | 20 |
| 96 | 21 |
| 96 | 22 |
| 96 | 23 |
| 96 | 24 |
| 96 | 25 |

-continued

| No. | Con. |
|---|---|
| 96 | 26 |
| 96 | 27 |
| 97 | 1 |
| 97 | 2 |
| 97 | 3 |
| 97 | 4 |
| 97 | 5 |
| 97 | 6 |
| 97 | 7 |
| 97 | 8 |
| 97 | 9 |
| 97 | 10 |
| 97 | 11 |
| 97 | 12 |
| 97 | 13 |
| 97 | 14 |
| 97 | 15 |
| 97 | 16 |
| 97 | 17 |
| 97 | 18 |
| 97 | 19 |
| 97 | 20 |
| 97 | 21 |
| 97 | 22 |
| 97 | 23 |
| 97 | 24 |
| 97 | 25 |
| 97 | 26 |
| 97 | 27 |
| 98 | 1 |
| 98 | 2 |
| 98 | 3 |
| 98 | 4 |
| 98 | 5 |
| 98 | 6 |
| 98 | 7 |
| 98 | 8 |
| 98 | 9 |
| 98 | 10 |
| 98 | 11 |
| 98 | 12 |
| 98 | 13 |
| 98 | 14 |
| 98 | 15 |
| 98 | 16 |
| 98 | 17 |
| 98 | 18 |
| 98 | 19 |
| 98 | 20 |
| 98 | 21 |
| 98 | 22 |
| 98 | 23 |
| 98 | 24 |
| 98 | 25 |
| 98 | 26 |
| 98 | 27 |
| 99 | 1 |
| 99 | 2 |
| 99 | 3 |
| 99 | 4 |
| 99 | 5 |
| 99 | 6 |
| 99 | 7 |
| 99 | 8 |
| 99 | 9 |
| 99 | 10 |
| 99 | 11 |
| 99 | 12 |
| 99 | 13 |
| 99 | 14 |
| 99 | 15 |
| 99 | 16 |
| 99 | 17 |
| 99 | 18 |
| 99 | 19 |
| 99 | 20 |
| 99 | 21 |

-continued

| No. | Con. |
|---|---|
| 99 | 22 |
| 99 | 23 |
| 99 | 24 |
| 99 | 25 |
| 99 | 26 |
| 99 | 27 |
| 100 | 1 |
| 100 | 2 |
| 100 | 3 |
| 100 | 4 |
| 100 | 5 |
| 100 | 6 |
| 100 | 7 |
| 100 | 8 |
| 100 | 9 |
| 100 | 10 |
| 100 | 11 |
| 100 | 12 |
| 100 | 13 |
| 100 | 14 |
| 100 | 15 |
| 100 | 16 |
| 100 | 17 |
| 100 | 18 |
| 100 | 19 |
| 100 | 20 |
| 100 | 21 |
| 100 | 22 |
| 100 | 23 |
| 100 | 24 |
| 100 | 25 |
| 100 | 26 |
| 100 | 27 |
| 101 | 1 |
| 101 | 2 |
| 101 | 3 |
| 101 | 4 |
| 101 | 5 |
| 101 | 6 |
| 101 | 7 |
| 101 | 8 |
| 101 | 9 |
| 101 | 10 |
| 101 | 11 |
| 101 | 12 |
| 101 | 13 |
| 101 | 14 |
| 101 | 15 |
| 101 | 16 |
| 101 | 17 |
| 101 | 18 |
| 101 | 19 |
| 101 | 20 |
| 101 | 21 |
| 101 | 22 |
| 101 | 23 |
| 101 | 24 |
| 101 | 25 |
| 101 | 26 |
| 101 | 27 |
| 102 | 1 |
| 102 | 2 |
| 102 | 3 |
| 102 | 4 |
| 102 | 5 |
| 102 | 6 |
| 102 | 7 |
| 102 | 8 |
| 102 | 9 |
| 102 | 10 |
| 102 | 11 |
| 102 | 12 |
| 102 | 13 |
| 102 | 14 |
| 102 | 15 |
| 102 | 16 |
| 102 | 17 |

-continued

| No. | Con. |
|---|---|
| 102 | 18 |
| 102 | 19 |
| 102 | 20 |
| 102 | 21 |
| 102 | 22 |
| 102 | 23 |
| 102 | 24 |
| 102 | 25 |
| 102 | 26 |
| 102 | 27 |
| 103 | 1 |
| 103 | 2 |
| 103 | 3 |
| 103 | 4 |
| 103 | 5 |
| 103 | 6 |
| 103 | 7 |
| 103 | 8 |
| 103 | 9 |
| 103 | 10 |
| 103 | 11 |
| 103 | 12 |
| 103 | 13 |
| 103 | 14 |
| 103 | 15 |
| 103 | 16 |
| 103 | 17 |
| 103 | 18 |
| 103 | 19 |
| 103 | 20 |
| 103 | 21 |
| 103 | 22 |
| 103 | 23 |
| 103 | 24 |
| 103 | 25 |
| 103 | 26 |
| 103 | 27 |
| 104 | 1 |
| 104 | 2 |
| 104 | 3 |
| 104 | 4 |
| 104 | 5 |
| 104 | 6 |
| 104 | 7 |
| 104 | 8 |
| 104 | 9 |
| 104 | 10 |
| 104 | 11 |
| 104 | 12 |
| 104 | 13 |
| 104 | 14 |
| 104 | 15 |
| 104 | 16 |
| 104 | 17 |
| 104 | 18 |
| 104 | 19 |
| 104 | 20 |
| 104 | 21 |
| 104 | 22 |
| 104 | 23 |
| 104 | 24 |
| 104 | 25 |
| 104 | 26 |
| 104 | 27 |
| 105 | 1 |
| 105 | 2 |
| 105 | 3 |
| 105 | 4 |
| 105 | 5 |
| 105 | 6 |
| 105 | 7 |
| 105 | 8 |
| 105 | 9 |
| 105 | 10 |
| 105 | 11 |
| 105 | 12 |
| 105 | 13 |

-continued

| No. | Con. |
|---|---|
| 105 | 14 |
| 105 | 15 |
| 105 | 16 |
| 105 | 17 |
| 105 | 18 |
| 105 | 19 |
| 105 | 20 |
| 105 | 21 |
| 105 | 22 |
| 105 | 23 |
| 105 | 24 |
| 105 | 25 |
| 105 | 26 |
| 105 | 27 |
| 106 | 1 |
| 106 | 2 |
| 106 | 3 |
| 106 | 4 |
| 106 | 5 |
| 106 | 6 |
| 106 | 7 |
| 106 | 8 |
| 106 | 9 |
| 106 | 10 |
| 106 | 11 |
| 106 | 12 |
| 106 | 13 |
| 106 | 14 |
| 106 | 15 |
| 106 | 16 |
| 106 | 17 |
| 106 | 18 |
| 106 | 19 |
| 106 | 20 |
| 106 | 21 |
| 106 | 22 |
| 106 | 23 |
| 106 | 24 |
| 106 | 25 |
| 106 | 26 |
| 106 | 27 |
| 107 | 1 |
| 107 | 2 |
| 107 | 3 |
| 107 | 4 |
| 107 | 5 |
| 107 | 6 |
| 107 | 7 |
| 107 | 8 |
| 107 | 9 |
| 107 | 10 |
| 107 | 11 |
| 107 | 12 |
| 107 | 13 |
| 107 | 14 |
| 107 | 15 |
| 107 | 16 |
| 107 | 17 |
| 107 | 18 |
| 107 | 19 |
| 107 | 20 |
| 107 | 21 |
| 107 | 22 |
| 107 | 23 |
| 107 | 24 |
| 107 | 25 |
| 107 | 26 |
| 107 | 27 |
| 108 | 1 |
| 108 | 2 |
| 108 | 3 |
| 108 | 4 |
| 108 | 5 |
| 108 | 6 |
| 108 | 7 |
| 108 | 8 |
| 108 | 9 |

-continued

| No. | Con. |
|---|---|
| 108 | 10 |
| 108 | 11 |
| 108 | 12 |
| 108 | 13 |
| 108 | 14 |
| 108 | 15 |
| 108 | 16 |
| 108 | 17 |
| 108 | 18 |
| 108 | 19 |
| 108 | 20 |
| 108 | 21 |
| 108 | 22 |
| 108 | 23 |
| 108 | 24 |
| 108 | 25 |
| 108 | 26 |
| 108 | 27 |
| 109 | 1 |
| 109 | 2 |
| 109 | 3 |
| 109 | 4 |
| 109 | 5 |
| 109 | 6 |
| 109 | 7 |
| 109 | 8 |
| 109 | 9 |
| 109 | 10 |
| 109 | 11 |
| 109 | 12 |
| 109 | 13 |
| 109 | 14 |
| 109 | 15 |
| 109 | 16 |
| 109 | 17 |
| 109 | 18 |
| 109 | 19 |
| 109 | 20 |
| 109 | 21 |
| 109 | 22 |
| 109 | 23 |
| 109 | 24 |
| 109 | 25 |
| 109 | 26 |
| 109 | 27 |
| 110 | 1 |
| 110 | 2 |
| 110 | 3 |
| 110 | 4 |
| 110 | 5 |
| 110 | 6 |
| 110 | 7 |
| 110 | 8 |
| 110 | 9 |
| 110 | 10 |
| 110 | 11 |
| 110 | 12 |
| 110 | 13 |
| 110 | 14 |
| 110 | 15 |
| 110 | 16 |
| 110 | 17 |
| 110 | 18 |
| 110 | 19 |
| 110 | 20 |
| 110 | 21 |
| 110 | 22 |
| 110 | 23 |
| 110 | 24 |
| 110 | 25 |
| 110 | 26 |
| 110 | 27 |
| 111 | 1 |
| 111 | 2 |
| 111 | 3 |
| 111 | 4 |
| 111 | 5 |

-continued

| No. | Con. |
|---|---|
| 111 | 6 |
| 111 | 7 |
| 111 | 8 |
| 111 | 9 |
| 111 | 10 |
| 111 | 11 |
| 111 | 12 |
| 111 | 13 |
| 111 | 14 |
| 111 | 15 |
| 111 | 16 |
| 111 | 17 |
| 111 | 18 |
| 111 | 19 |
| 111 | 20 |
| 111 | 21 |
| 111 | 22 |
| 111 | 23 |
| 111 | 24 |
| 111 | 25 |
| 111 | 26 |
| 111 | 27 |
| 112 | 1 |
| 112 | 2 |
| 112 | 3 |
| 112 | 4 |
| 112 | 5 |
| 112 | 6 |
| 112 | 7 |
| 112 | 8 |
| 112 | 9 |
| 112 | 10 |
| 112 | 11 |
| 112 | 12 |
| 112 | 13 |
| 112 | 14 |
| 112 | 15 |
| 112 | 16 |
| 112 | 17 |
| 112 | 18 |
| 112 | 19 |
| 112 | 20 |
| 112 | 21 |
| 112 | 22 |
| 112 | 23 |
| 112 | 24 |
| 112 | 25 |
| 112 | 26 |
| 112 | 27 |
| 113 | 1 |
| 113 | 2 |
| 113 | 3 |
| 113 | 4 |
| 113 | 5 |
| 113 | 6 |
| 113 | 7 |
| 113 | 8 |
| 113 | 9 |
| 113 | 10 |
| 113 | 11 |
| 113 | 12 |
| 113 | 13 |
| 113 | 14 |
| 113 | 15 |
| 113 | 16 |
| 113 | 17 |
| 113 | 18 |
| 113 | 19 |
| 113 | 20 |
| 113 | 21 |
| 113 | 22 |
| 113 | 23 |
| 113 | 24 |
| 113 | 25 |
| 113 | 26 |
| 113 | 27 |
| 114 | 1 |

-continued

| No. | Con. |
|---|---|
| 114 | 2 |
| 114 | 3 |
| 114 | 4 |
| 114 | 5 |
| 114 | 6 |
| 114 | 7 |
| 114 | 8 |
| 114 | 9 |
| 114 | 10 |
| 114 | 11 |
| 114 | 12 |
| 114 | 13 |
| 114 | 14 |
| 114 | 15 |
| 114 | 16 |
| 114 | 17 |
| 114 | 18 |
| 114 | 19 |
| 114 | 20 |
| 114 | 21 |
| 114 | 22 |
| 114 | 23 |
| 114 | 24 |
| 114 | 25 |
| 114 | 26 |
| 114 | 27 |
| 115 | 1 |
| 115 | 2 |
| 115 | 3 |
| 115 | 4 |
| 115 | 5 |
| 115 | 6 |
| 115 | 7 |
| 115 | 8 |
| 115 | 9 |
| 115 | 10 |
| 115 | 11 |
| 115 | 12 |
| 115 | 13 |
| 115 | 14 |
| 115 | 15 |
| 115 | 16 |
| 115 | 17 |
| 115 | 18 |
| 115 | 19 |
| 115 | 20 |
| 115 | 21 |
| 115 | 22 |
| 115 | 23 |
| 115 | 24 |
| 115 | 25 |
| 115 | 26 |
| 115 | 27 |
| 117 | 1 |
| 117 | 2 |
| 117 | 3 |
| 117 | 4 |
| 117 | 5 |
| 117 | 6 |
| 117 | 7 |
| 117 | 8 |
| 117 | 9 |
| 117 | 10 |
| 117 | 11 |
| 117 | 12 |
| 117 | 13 |
| 117 | 14 |
| 117 | 15 |
| 117 | 16 |
| 117 | 17 |
| 117 | 18 |
| 117 | 19 |
| 117 | 20 |
| 117 | 21 |
| 117 | 22 |
| 117 | 23 |
| 117 | 24 |

-continued

| No. | Con. |
|---|---|
| 117 | 25 |
| 117 | 26 |
| 117 | 27 |
| 118 | 1 |
| 118 | 2 |
| 118 | 3 |
| 118 | 4 |
| 118 | 5 |
| 118 | 6 |
| 118 | 7 |
| 118 | 8 |
| 118 | 9 |
| 118 | 10 |
| 118 | 11 |
| 118 | 12 |
| 118 | 13 |
| 118 | 14 |
| 118 | 15 |
| 118 | 16 |
| 118 | 17 |
| 118 | 18 |
| 118 | 19 |
| 118 | 20 |
| 118 | 21 |
| 118 | 22 |
| 118 | 23 |
| 118 | 24 |
| 118 | 25 |
| 118 | 26 |
| 118 | 27 |
| 119 | 1 |
| 119 | 2 |
| 119 | 3 |
| 119 | 4 |
| 119 | 5 |
| 119 | 6 |
| 119 | 7 |
| 119 | 8 |
| 119 | 9 |
| 119 | 10 |
| 119 | 11 |
| 119 | 12 |
| 119 | 13 |
| 119 | 14 |
| 119 | 15 |
| 119 | 16 |
| 119 | 17 |
| 119 | 18 |
| 119 | 19 |
| 119 | 20 |
| 119 | 21 |
| 119 | 22 |
| 119 | 23 |
| 119 | 24 |
| 119 | 25 |
| 119 | 26 |
| 119 | 27 |
| 120 | 1 |
| 120 | 2 |
| 120 | 3 |
| 120 | 4 |
| 120 | 5 |
| 120 | 6 |
| 120 | 7 |
| 120 | 8 |
| 120 | 9 |
| 120 | 10 |
| 120 | 11 |
| 120 | 12 |
| 120 | 13 |
| 120 | 14 |
| 120 | 15 |
| 120 | 16 |
| 120 | 17 |
| 120 | 18 |
| 120 | 19 |
| 120 | 20 |

-continued

| No. | Con. |
|---|---|
| 120 | 21 |
| 120 | 22 |
| 120 | 23 |
| 120 | 24 |
| 120 | 25 |
| 120 | 26 |
| 120 | 27 |
| 121 | 1 |
| 121 | 2 |
| 121 | 3 |
| 121 | 4 |
| 121 | 5 |
| 121 | 6 |
| 121 | 7 |
| 121 | 8 |
| 121 | 9 |
| 121 | 10 |
| 121 | 11 |
| 121 | 12 |
| 121 | 13 |
| 121 | 14 |
| 121 | 15 |
| 121 | 16 |
| 121 | 17 |
| 121 | 18 |
| 121 | 19 |
| 121 | 20 |
| 121 | 21 |
| 121 | 22 |
| 121 | 23 |
| 121 | 24 |
| 121 | 25 |
| 121 | 26 |
| 121 | 27 |
| 122 | 1 |
| 122 | 2 |
| 122 | 3 |
| 122 | 4 |
| 122 | 5 |
| 122 | 6 |
| 122 | 7 |
| 122 | 8 |
| 122 | 9 |
| 122 | 10 |
| 122 | 11 |
| 122 | 12 |
| 122 | 13 |
| 122 | 14 |
| 122 | 15 |
| 122 | 16 |
| 122 | 17 |
| 122 | 18 |
| 122 | 19 |
| 122 | 20 |
| 122 | 21 |
| 122 | 22 |
| 122 | 23 |
| 122 | 24 |
| 122 | 25 |
| 122 | 26 |
| 122 | 27 |
| 123 | 1 |
| 123 | 2 |
| 123 | 3 |
| 123 | 4 |
| 123 | 5 |
| 123 | 6 |
| 123 | 7 |
| 123 | 8 |
| 123 | 9 |
| 123 | 10 |
| 123 | 11 |
| 123 | 12 |
| 123 | 13 |
| 123 | 14 |
| 123 | 15 |
| 123 | 16 |

-continued

| No. | Con. |
|---|---|
| 123 | 17 |
| 123 | 18 |
| 123 | 19 |
| 123 | 20 |
| 123 | 21 |
| 123 | 22 |
| 123 | 23 |
| 123 | 24 |
| 123 | 25 |
| 123 | 26 |
| 123 | 27 |
| 124 | 1 |
| 124 | 2 |
| 124 | 3 |
| 124 | 4 |
| 124 | 5 |
| 124 | 6 |
| 124 | 7 |
| 124 | 8 |
| 124 | 9 |
| 124 | 10 |
| 124 | 11 |
| 124 | 12 |
| 124 | 13 |
| 124 | 14 |
| 124 | 15 |
| 124 | 16 |
| 124 | 17 |
| 124 | 18 |
| 124 | 19 |
| 124 | 20 |
| 124 | 21 |
| 124 | 22 |
| 124 | 23 |
| 124 | 24 |
| 124 | 25 |
| 124 | 26 |
| 124 | 27 |
| 125 | 1 |
| 125 | 2 |
| 125 | 3 |
| 125 | 4 |
| 125 | 5 |
| 125 | 6 |
| 125 | 7 |
| 125 | 8 |
| 125 | 9 |
| 125 | 10 |
| 125 | 11 |
| 125 | 12 |
| 125 | 13 |
| 125 | 14 |
| 125 | 15 |
| 125 | 16 |
| 125 | 17 |
| 125 | 18 |
| 125 | 19 |
| 125 | 20 |
| 125 | 21 |
| 125 | 22 |
| 125 | 23 |
| 125 | 24 |
| 125 | 25 |
| 125 | 26 |
| 125 | 27 |
| 126 | 1 |
| 126 | 2 |
| 126 | 3 |
| 126 | 4 |
| 126 | 5 |
| 126 | 6 |
| 126 | 7 |
| 126 | 8 |
| 126 | 9 |
| 126 | 10 |
| 126 | 11 |
| 126 | 12 |

-continued

| No. | Con. |
|---|---|
| 126 | 13 |
| 126 | 14 |
| 126 | 15 |
| 126 | 16 |
| 126 | 17 |
| 126 | 18 |
| 126 | 19 |
| 126 | 20 |
| 126 | 21 |
| 126 | 22 |
| 126 | 23 |
| 126 | 24 |
| 126 | 25 |
| 126 | 26 |
| 126 | 27 |
| 130 | 1 |
| 130 | 2 |
| 130 | 3 |
| 130 | 4 |
| 130 | 5 |
| 130 | 6 |
| 130 | 7 |
| 130 | 8 |
| 130 | 9 |
| 130 | 10 |
| 130 | 11 |
| 130 | 12 |
| 130 | 13 |
| 130 | 14 |
| 130 | 15 |
| 130 | 16 |
| 130 | 17 |
| 130 | 18 |
| 130 | 19 |
| 130 | 20 |
| 130 | 21 |
| 130 | 22 |
| 130 | 23 |
| 130 | 24 |
| 130 | 25 |
| 130 | 26 |
| 130 | 27 |
| 133 | 1 |
| 133 | 2 |
| 133 | 3 |
| 133 | 4 |
| 133 | 5 |
| 133 | 6 |
| 133 | 7 |
| 133 | 8 |
| 133 | 9 |
| 133 | 10 |
| 133 | 11 |
| 133 | 12 |
| 133 | 13 |
| 133 | 14 |
| 133 | 15 |
| 133 | 16 |
| 133 | 17 |
| 133 | 18 |
| 133 | 19 |
| 133 | 20 |
| 133 | 21 |
| 133 | 22 |
| 133 | 23 |
| 133 | 24 |
| 133 | 25 |
| 133 | 26 |
| 133 | 27 |
| 136 | 1 |
| 136 | 2 |
| 136 | 3 |
| 136 | 4 |
| 136 | 5 |
| 136 | 6 |
| 136 | 7 |
| 136 | 8 |

-continued

| No. | Con. |
|---|---|
| 136 | 9 |
| 136 | 10 |
| 136 | 11 |
| 136 | 12 |
| 136 | 13 |
| 136 | 14 |
| 136 | 15 |
| 136 | 16 |
| 136 | 17 |
| 136 | 18 |
| 136 | 19 |
| 136 | 20 |
| 136 | 21 |
| 136 | 22 |
| 136 | 23 |
| 136 | 24 |
| 136 | 25 |
| 136 | 26 |
| 136 | 27 |
| 139 | 1 |
| 139 | 2 |
| 139 | 3 |
| 139 | 4 |
| 139 | 5 |
| 139 | 6 |
| 139 | 7 |
| 139 | 8 |
| 139 | 9 |
| 139 | 10 |
| 139 | 11 |
| 139 | 12 |
| 139 | 13 |
| 139 | 14 |
| 139 | 15 |
| 139 | 16 |
| 139 | 17 |
| 139 | 18 |
| 139 | 19 |
| 139 | 20 |
| 139 | 21 |
| 139 | 22 |
| 139 | 23 |
| 139 | 24 |
| 139 | 25 |
| 139 | 26 |
| 139 | 27 |
| 139-1 | 1 |
| 139-1 | 2 |
| 139-1 | 3 |
| 139-1 | 4 |
| 139-1 | 5 |
| 139-1 | 6 |
| 139-1 | 7 |
| 139-1 | 8 |
| 139-1 | 9 |
| 139-1 | 10 |
| 139-1 | 11 |
| 139-1 | 12 |
| 139-1 | 13 |
| 139-1 | 14 |
| 139-1 | 15 |
| 139-1 | 16 |
| 139-1 | 17 |
| 139-1 | 18 |
| 139-1 | 19 |
| 139-1 | 20 |
| 139-1 | 21 |
| 139-1 | 22 |
| 139-1 | 23 |
| 139-1 | 24 |
| 139-1 | 25 |
| 139-1 | 26 |
| 139-1 | 27 |
| 142 | 1 |
| 142 | 2 |
| 142 | 3 |
| 142 | 4 |

-continued

| No. | Con. |
|---|---|
| 142 | 5 |
| 142 | 6 |
| 142 | 7 |
| 142 | 8 |
| 142 | 9 |
| 142 | 10 |
| 142 | 11 |
| 142 | 12 |
| 142 | 13 |
| 142 | 14 |
| 142 | 15 |
| 142 | 16 |
| 142 | 17 |
| 142 | 18 |
| 142 | 19 |
| 142 | 20 |
| 142 | 21 |
| 142 | 22 |
| 142 | 23 |
| 142 | 24 |
| 142 | 25 |
| 142 | 26 |
| 142 | 27 |
| 146 | 1 |
| 146 | 2 |
| 146 | 3 |
| 146 | 4 |
| 146 | 5 |
| 146 | 6 |
| 146 | 7 |
| 146 | 8 |
| 146 | 9 |
| 146 | 10 |
| 146 | 11 |
| 146 | 12 |
| 146 | 13 |
| 146 | 14 |
| 146 | 15 |
| 146 | 16 |
| 146 | 17 |
| 146 | 18 |
| 146 | 19 |
| 146 | 20 |
| 146 | 21 |
| 146 | 22 |
| 146 | 23 |
| 146 | 24 |
| 146 | 25 |
| 146 | 26 |
| 146 | 27 |
| 146-1 | 1 |
| 146-1 | 2 |
| 146-1 | 3 |
| 146-1 | 4 |
| 146-1 | 5 |
| 146-1 | 6 |
| 146-1 | 7 |
| 146-1 | 8 |
| 146-1 | 9 |
| 146-1 | 10 |
| 146-1 | 11 |
| 146-1 | 12 |
| 146-1 | 13 |
| 146-1 | 14 |
| 146-1 | 15 |
| 146-1 | 16 |
| 146-1 | 17 |
| 146-1 | 18 |
| 146-1 | 19 |
| 146-1 | 20 |
| 146-1 | 21 |
| 146-1 | 22 |
| 146-1 | 23 |
| 146-1 | 24 |
| 146-1 | 25 |
| 146-1 | 26 |
| 146-1 | 27 |

-continued

| No. | Con. |
|---|---|
| 149 | 1 |
| 149 | 2 |
| 149 | 3 |
| 149 | 4 |
| 149 | 5 |
| 149 | 6 |
| 149 | 7 |
| 149 | 8 |
| 149 | 9 |
| 149 | 10 |
| 149 | 11 |
| 149 | 12 |
| 149 | 13 |
| 149 | 14 |
| 149 | 15 |
| 149 | 16 |
| 149 | 17 |
| 149 | 18 |
| 149 | 19 |
| 149 | 20 |
| 149 | 21 |
| 149 | 22 |
| 149 | 23 |
| 149 | 24 |
| 149 | 25 |
| 149 | 26 |
| 149 | 27 |
| 150 | 1 |
| 150 | 2 |
| 150 | 3 |
| 150 | 4 |
| 150 | 5 |
| 150 | 6 |
| 150 | 7 |
| 150 | 8 |
| 150 | 9 |
| 150 | 10 |
| 150 | 11 |
| 150 | 12 |
| 150 | 13 |
| 150 | 14 |
| 150 | 15 |
| 150 | 16 |
| 150 | 17 |
| 150 | 18 |
| 150 | 19 |
| 150 | 20 |
| 150 | 21 |
| 150 | 22 |
| 150 | 23 |
| 150 | 24 |
| 150 | 25 |
| 150 | 26 |
| 150 | 27 |
| 151 | 1 |
| 151 | 2 |
| 151 | 3 |
| 151 | 4 |
| 151 | 5 |
| 151 | 6 |
| 151 | 7 |
| 151 | 8 |
| 151 | 9 |
| 151 | 10 |
| 151 | 11 |
| 151 | 12 |
| 151 | 13 |
| 151 | 14 |
| 151 | 15 |
| 151 | 16 |
| 151 | 17 |
| 151 | 18 |
| 151 | 19 |
| 151 | 20 |
| 151 | 21 |
| 151 | 22 |
| 151 | 23 |

-continued

| No. | Con. |
|---|---|
| 151 | 24 |
| 151 | 25 |
| 151 | 26 |
| 151 | 27 |
| 156 | 1 |
| 156 | 2 |
| 156 | 3 |
| 156 | 4 |
| 156 | 5 |
| 156 | 6 |
| 156 | 7 |
| 156 | 8 |
| 156 | 9 |
| 156 | 10 |
| 156 | 11 |
| 156 | 12 |
| 156 | 13 |
| 156 | 14 |
| 156 | 15 |
| 156 | 16 |
| 156 | 17 |
| 156 | 18 |
| 156 | 19 |
| 156 | 20 |
| 156 | 21 |
| 156 | 22 |
| 156 | 23 |
| 156 | 24 |
| 156 | 25 |
| 156 | 26 |
| 156 | 27 |
| 157 | 1 |
| 157 | 2 |
| 157 | 3 |
| 157 | 4 |
| 157 | 5 |
| 157 | 6 |
| 157 | 7 |
| 157 | 8 |
| 157 | 9 |
| 157 | 10 |
| 157 | 11 |
| 157 | 12 |
| 157 | 13 |
| 157 | 14 |
| 157 | 15 |
| 157 | 16 |
| 157 | 17 |
| 157 | 18 |
| 157 | 19 |
| 157 | 20 |
| 157 | 21 |
| 157 | 22 |
| 157 | 23 |
| 157 | 24 |
| 157 | 25 |
| 157 | 26 |
| 157 | 27 |
| 158 | 1 |
| 158 | 2 |
| 158 | 3 |
| 158 | 4 |
| 158 | 5 |
| 158 | 6 |
| 158 | 7 |
| 158 | 8 |
| 158 | 9 |
| 158 | 10 |
| 158 | 11 |
| 158 | 12 |
| 158 | 13 |
| 158 | 14 |
| 158 | 15 |
| 158 | 16 |
| 158 | 17 |
| 158 | 18 |
| 158 | 19 |

-continued

| No. | Con. |
|---|---|
| 158 | 20 |
| 158 | 21 |
| 158 | 22 |
| 158 | 23 |
| 158 | 24 |
| 158 | 25 |
| 158 | 26 |
| 158 | 27 |
| 159 | 1 |
| 159 | 2 |
| 159 | 3 |
| 159 | 4 |
| 159 | 5 |
| 159 | 6 |
| 159 | 7 |
| 159 | 8 |
| 159 | 9 |
| 159 | 10 |
| 159 | 11 |
| 159 | 12 |
| 159 | 13 |
| 159 | 14 |
| 159 | 15 |
| 159 | 16 |
| 159 | 17 |
| 159 | 18 |
| 159 | 19 |
| 159 | 20 |
| 159 | 21 |
| 159 | 22 |
| 159 | 23 |
| 159 | 24 |
| 159 | 25 |
| 159 | 26 |
| 159 | 27 |
| 160 | 1 |
| 160 | 2 |
| 160 | 3 |
| 160 | 4 |
| 160 | 5 |
| 160 | 6 |
| 160 | 7 |
| 160 | 8 |
| 160 | 9 |
| 160 | 10 |
| 160 | 11 |
| 160 | 12 |
| 160 | 13 |
| 160 | 14 |
| 160 | 15 |
| 160 | 16 |
| 160 | 17 |
| 160 | 18 |
| 160 | 19 |
| 160 | 20 |
| 160 | 21 |
| 160 | 22 |
| 160 | 23 |
| 160 | 24 |
| 160 | 25 |
| 160 | 26 |
| 160 | 27 |
| 161 | 1 |
| 161 | 2 |
| 161 | 3 |
| 161 | 4 |
| 161 | 5 |
| 161 | 6 |
| 161 | 7 |
| 161 | 8 |
| 161 | 9 |
| 161 | 10 |
| 161 | 11 |
| 161 | 12 |
| 161 | 13 |
| 161 | 14 |
| 161 | 15 |

-continued

| No. | Con. |
|---|---|
| 161 | 16 |
| 161 | 17 |
| 161 | 18 |
| 161 | 19 |
| 161 | 20 |
| 161 | 21 |
| 161 | 22 |
| 161 | 23 |
| 161 | 24 |
| 161 | 25 |
| 161 | 26 |
| 161 | 27 |
| 162 | 1 |
| 162 | 2 |
| 162 | 3 |
| 162 | 4 |
| 162 | 5 |
| 162 | 6 |
| 162 | 7 |
| 162 | 8 |
| 162 | 9 |
| 162 | 10 |
| 162 | 11 |
| 162 | 12 |
| 162 | 13 |
| 162 | 14 |
| 162 | 15 |
| 162 | 16 |
| 162 | 17 |
| 162 | 18 |
| 162 | 19 |
| 162 | 20 |
| 162 | 21 |
| 162 | 22 |
| 162 | 23 |
| 162 | 24 |
| 162 | 25 |
| 162 | 26 |
| 162 | 27 |
| 163 | 1 |
| 163 | 2 |
| 163 | 3 |
| 163 | 4 |
| 163 | 5 |
| 163 | 6 |
| 163 | 7 |
| 163 | 8 |
| 163 | 9 |
| 163 | 10 |
| 163 | 11 |
| 163 | 12 |
| 163 | 13 |
| 163 | 14 |
| 163 | 15 |
| 163 | 16 |
| 163 | 17 |
| 163 | 18 |
| 163 | 19 |
| 163 | 20 |
| 163 | 21 |
| 163 | 22 |
| 163 | 23 |
| 163 | 24 |
| 163 | 25 |
| 163 | 26 |
| 163 | 27 |
| 166 | 1 |
| 166 | 2 |
| 166 | 3 |
| 166 | 4 |
| 166 | 5 |
| 166 | 6 |
| 166 | 7 |
| 166 | 8 |
| 166 | 9 |
| 166 | 10 |
| 166 | 11 |

-continued

| No. | Con. |
|---|---|
| 166 | 12 |
| 166 | 13 |
| 166 | 14 |
| 166 | 15 |
| 166 | 16 |
| 166 | 17 |
| 166 | 18 |
| 166 | 19 |
| 166 | 20 |
| 166 | 21 |
| 166 | 22 |
| 166 | 23 |
| 166 | 24 |
| 166 | 25 |
| 166 | 26 |
| 166 | 27 |
| 167 | 1 |
| 167 | 2 |
| 167 | 3 |
| 167 | 4 |
| 167 | 5 |
| 167 | 6 |
| 167 | 7 |
| 167 | 8 |
| 167 | 9 |
| 167 | 10 |
| 167 | 11 |
| 167 | 12 |
| 167 | 13 |
| 167 | 14 |
| 167 | 15 |
| 167 | 16 |
| 167 | 17 |
| 167 | 18 |
| 167 | 19 |
| 167 | 20 |
| 167 | 21 |
| 167 | 22 |
| 167 | 23 |
| 167 | 24 |
| 167 | 25 |
| 167 | 26 |
| 167 | 27 |
| 168 | 1 |
| 168 | 2 |
| 168 | 3 |
| 168 | 4 |
| 168 | 5 |
| 168 | 6 |
| 168 | 7 |
| 168 | 8 |
| 168 | 9 |
| 168 | 10 |
| 168 | 11 |
| 168 | 12 |
| 168 | 13 |
| 168 | 14 |
| 168 | 15 |
| 168 | 16 |
| 168 | 17 |
| 168 | 18 |
| 168 | 19 |
| 168 | 20 |
| 168 | 21 |
| 168 | 22 |
| 168 | 23 |
| 168 | 24 |
| 168 | 25 |
| 168 | 26 |
| 168 | 27 |
| 169 | 1 |
| 169 | 2 |
| 169 | 3 |
| 169 | 4 |
| 169 | 5 |
| 169 | 6 |
| 169 | 7 |

-continued

| No. | Con. |
|---|---|
| 169 | 8 |
| 169 | 9 |
| 169 | 10 |
| 169 | 11 |
| 169 | 12 |
| 169 | 13 |
| 169 | 14 |
| 169 | 15 |
| 169 | 16 |
| 169 | 17 |
| 169 | 18 |
| 169 | 19 |
| 169 | 20 |
| 169 | 21 |
| 169 | 22 |
| 169 | 23 |
| 169 | 24 |
| 169 | 25 |
| 169 | 26 |
| 169 | 27 |
| 170 | 1 |
| 170 | 2 |
| 170 | 3 |
| 170 | 4 |
| 170 | 5 |
| 170 | 6 |
| 170 | 7 |
| 170 | 8 |
| 170 | 9 |
| 170 | 10 |
| 170 | 11 |
| 170 | 12 |
| 170 | 13 |
| 170 | 14 |
| 170 | 15 |
| 170 | 16 |
| 170 | 17 |
| 170 | 18 |
| 170 | 19 |
| 170 | 20 |
| 170 | 21 |
| 170 | 22 |
| 170 | 23 |
| 170 | 24 |
| 170 | 25 |
| 170 | 26 |
| 170 | 27 |
| 171 | 1 |
| 171 | 2 |
| 171 | 3 |
| 171 | 4 |
| 171 | 5 |
| 171 | 6 |
| 171 | 7 |
| 171 | 8 |
| 171 | 9 |
| 171 | 10 |
| 171 | 11 |
| 171 | 12 |
| 171 | 13 |
| 171 | 14 |
| 171 | 15 |
| 171 | 16 |
| 171 | 17 |
| 171 | 18 |
| 171 | 19 |
| 171 | 20 |
| 171 | 21 |
| 171 | 22 |
| 171 | 23 |
| 171 | 24 |
| 171 | 25 |
| 171 | 26 |
| 171 | 27 |
| 172 | 1 |
| 172 | 2 |
| 172 | 3 |

-continued

| No. | Con. |
|---|---|
| 172 | 4 |
| 172 | 5 |
| 172 | 6 |
| 172 | 7 |
| 172 | 8 |
| 172 | 9 |
| 172 | 10 |
| 172 | 11 |
| 172 | 12 |
| 172 | 13 |
| 172 | 14 |
| 172 | 15 |
| 172 | 16 |
| 172 | 17 |
| 172 | 18 |
| 172 | 19 |
| 172 | 20 |
| 172 | 21 |
| 172 | 22 |
| 172 | 23 |
| 172 | 24 |
| 172 | 25 |
| 172 | 26 |
| 172 | 27 |
|  | 1 |
| 172 | 2 |
| 172 | 3 |
| 172 | 4 |
| 172 | 5 |
| 172 | 6 |
| 172 | 7 |
| 172 | 8 |
| 172 | 9 |
| 172 | 10 |
| 172 | 11 |
| 172 | 12 |
| 172 | 13 |
| 172 | 14 |
| 172 | 15 |
| 172 | 16 |
| 172 | 17 |
| 172 | 18 |
| 172 | 19 |
| 172 | 20 |
| 172 | 21 |
| 172 | 22 |
| 172 | 23 |
| 172 | 24 |
| 172 | 25 |
| 172 | 26 |
| 172 | 27 |
| 173 | 1 |
| 173 | 2 |
| 173 | 3 |
| 173 | 4 |
| 173 | 5 |
| 173 | 6 |
| 173 | 7 |
| 173 | 8 |
| 173 | 9 |
| 173 | 10 |
| 173 | 11 |
| 173 | 12 |
| 173 | 13 |
| 173 | 14 |
| 173 | 15 |
| 173 | 16 |
| 173 | 17 |
| 173 | 18 |
| 173 | 19 |
| 173 | 20 |
| 173 | 21 |
| 173 | 22 |
| 173 | 23 |
| 173 | 24 |
| 173 | 25 |
| 173 | 26 |

-continued

| No. | Con. |
|---|---|
| 173 | 27 |
| 174 | 1 |
| 174 | 2 |
| 174 | 3 |
| 174 | 4 |
| 174 | 5 |
| 174 | 6 |
| 174 | 7 |
| 174 | 8 |
| 174 | 9 |
| 174 | 10 |
| 174 | 11 |
| 174 | 12 |
| 174 | 13 |
| 174 | 14 |
| 174 | 15 |
| 174 | 16 |
| 174 | 17 |
| 174 | 18 |
| 174 | 19 |
| 174 | 20 |
| 174 | 21 |
| 174 | 22 |
| 174 | 23 |
| 174 | 24 |
| 174 | 25 |
| 174 | 26 |
| 174 | 27 |
| 175 | 1 |
| 175 | 2 |
| 175 | 3 |
| 175 | 4 |
| 175 | 5 |
| 175 | 6 |
| 175 | 7 |
| 175 | 8 |
| 175 | 9 |
| 175 | 10 |
| 175 | 11 |
| 175 | 12 |
| 175 | 13 |
| 175 | 14 |
| 175 | 15 |
| 175 | 16 |
| 175 | 17 |
| 175 | 18 |
| 175 | 19 |
| 175 | 20 |
| 175 | 21 |
| 175 | 22 |
| 175 | 23 |
| 175 | 24 |
| 175 | 25 |
| 175 | 26 |
| 175 | 27 |
| 176 | 1 |
| 176 | 2 |
| 176 | 3 |
| 176 | 4 |
| 176 | 5 |
| 176 | 6 |
| 176 | 7 |
| 176 | 8 |
| 176 | 9 |
| 176 | 10 |
| 176 | 11 |
| 176 | 12 |
| 176 | 13 |
| 176 | 14 |
| 176 | 15 |
| 176 | 16 |
| 176 | 17 |
| 176 | 18 |
| 176 | 19 |
| 176 | 20 |
| 176 | 21 |
| 176 | 22 |

-continued

| No. | Con. |
|---|---|
| 176 | 23 |
| 176 | 24 |
| 176 | 25 |
| 176 | 26 |
| 176 | 27 |
| 178 | 1 |
| 178 | 2 |
| 178 | 3 |
| 178 | 4 |
| 178 | 5 |
| 178 | 6 |
| 178 | 7 |
| 178 | 8 |
| 178 | 9 |
| 178 | 10 |
| 178 | 11 |
| 178 | 12 |
| 178 | 13 |
| 178 | 14 |
| 178 | 15 |
| 178 | 16 |
| 178 | 17 |
| 178 | 18 |
| 178 | 19 |
| 178 | 20 |
| 178 | 21 |
| 178 | 22 |
| 178 | 23 |
| 178 | 24 |
| 178 | 25 |
| 178 | 26 |
| 178 | 27 |
| 179 | 1 |
| 179 | 2 |
| 179 | 3 |
| 179 | 4 |
| 179 | 5 |
| 179 | 6 |
| 179 | 7 |
| 179 | 8 |
| 179 | 9 |
| 179 | 10 |
| 179 | 11 |
| 179 | 12 |
| 179 | 13 |
| 179 | 14 |
| 179 | 15 |
| 179 | 16 |
| 179 | 17 |
| 179 | 18 |
| 179 | 19 |
| 179 | 20 |
| 179 | 21 |
| 179 | 22 |
| 179 | 23 |
| 179 | 24 |
| 179 | 25 |
| 179 | 26 |
| 179 | 27 |
| 180 | 1 |
| 180 | 2 |
| 180 | 3 |
| 180 | 4 |
| 180 | 5 |
| 180 | 6 |
| 180 | 7 |
| 180 | 8 |
| 180 | 9 |
| 180 | 10 |
| 180 | 11 |
| 180 | 12 |
| 180 | 13 |
| 180 | 14 |
| 180 | 15 |
| 180 | 16 |
| 180 | 17 |
| 180 | 18 |

-continued

| No. | Con. |
|---|---|
| 180 | 19 |
| 180 | 20 |
| 180 | 21 |
| 180 | 22 |
| 180 | 23 |
| 180 | 24 |
| 180 | 25 |
| 180 | 26 |
| 180 | 27 |
| 181 | 1 |
| 181 | 2 |
| 181 | 3 |
| 181 | 4 |
| 181 | 5 |
| 181 | 6 |
| 181 | 7 |
| 181 | 8 |
| 181 | 9 |
| 181 | 10 |
| 181 | 11 |
| 181 | 12 |
| 181 | 13 |
| 181 | 14 |
| 181 | 15 |
| 181 | 16 |
| 181 | 17 |
| 181 | 18 |
| 181 | 19 |
| 181 | 20 |
| 181 | 21 |
| 181 | 22 |
| 181 | 23 |
| 181 | 24 |
| 181 | 25 |
| 181 | 26 |
| 181 | 27 |
| 182 | 1 |
| 182 | 2 |
| 182 | 3 |
| 182 | 4 |
| 182 | 5 |
| 182 | 6 |
| 182 | 7 |
| 182 | 8 |
| 182 | 9 |
| 182 | 10 |
| 182 | 11 |
| 182 | 12 |
| 182 | 13 |
| 182 | 14 |
| 182 | 15 |
| 182 | 16 |
| 182 | 17 |
| 182 | 18 |
| 182 | 19 |
| 182 | 20 |
| 182 | 21 |
| 182 | 22 |
| 182 | 23 |
| 182 | 24 |
| 182 | 25 |
| 182 | 26 |
| 182 | 27 |
| 183 | 1 |
| 183 | 2 |
| 183 | 3 |
| 183 | 4 |
| 183 | 5 |
| 183 | 6 |
| 183 | 7 |
| 183 | 8 |
| 183 | 9 |
| 183 | 10 |
| 183 | 11 |
| 183 | 12 |
| 183 | 13 |
| 183 | 14 |

-continued

| No. | Con. |
|---|---|
| 183 | 15 |
| 183 | 16 |
| 183 | 17 |
| 183 | 18 |
| 183 | 19 |
| 183 | 20 |
| 183 | 21 |
| 183 | 22 |
| 183 | 23 |
| 183 | 24 |
| 183 | 25 |
| 183 | 26 |
| 183 | 27 |

The invention further comprises subgenera of formula (I), in which the structure of any of formulae (I), (I) or (IIj)-(IIo) comprising the structural element,

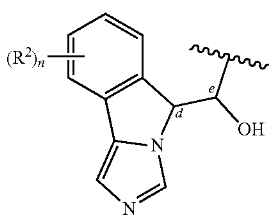

having the stereoisomeric configuration of any of configurations 28-36 below, wherein the stereochemistry of each stereoisomeric carbon atom (labeled "d" and "c" above) is designated as racemic ("-"), "S," or "R": Structural Formula I is One of Stereoisomeric Configurations (28)-(36):

| Configuration | d | e |
|---|---|---|
| 28 | S | — |
| 29 | R | — |
| 30 | — | S |
| 31 | — | R |
| 32 | — | — |
| 33 | S | S |
| 34 | S | R |
| 35 | R | S |
| 36 | R | R |

In another aspect, the present disclosure provides compounds 42-55, 116, 127-129, 131-132, 134-135, 137-138, 140-141, 143-145, 147-148, 152-155, 164-165, and 177 as each of stereoisomeric configurations 28-36. For example:

| No. | Config. |
|---|---|
| 42 | 28 |
| 42 | 29 |
| 42 | 30 |
| 42 | 31 |
| 42 | 32 |
| 42 | 33 |
| 42 | 34 |
| 42 | 35 |
| 42 | 36 |
| 43 | 28 |
| 43 | 29 |
| 43 | 30 |
| 43 | 31 |

-continued

| No. | Config. |
|---|---|
| 43 | 32 |
| 43 | 33 |
| 43 | 34 |
| 43 | 35 |
| 43 | 36 |
| 44 | 28 |
| 44 | 29 |
| 44 | 30 |
| 44 | 31 |
| 44 | 32 |
| 44 | 33 |
| 44 | 34 |
| 44 | 35 |
| 44 | 36 |
| 45 | 28 |
| 45 | 29 |
| 45 | 30 |
| 45 | 31 |
| 45 | 32 |
| 45 | 33 |
| 45 | 34 |
| 45 | 35 |
| 45 | 36 |
| 46 | 28 |
| 46 | 29 |
| 46 | 30 |
| 46 | 31 |
| 46 | 32 |
| 46 | 33 |
| 46 | 34 |
| 46 | 35 |
| 46 | 36 |
| 47 | 28 |
| 47 | 29 |
| 47 | 30 |
| 47 | 31 |
| 47 | 32 |
| 47 | 33 |
| 47 | 34 |
| 47 | 35 |
| 47 | 36 |
| 48 | 28 |
| 48 | 29 |
| 48 | 30 |
| 48 | 31 |
| 48 | 32 |
| 48 | 33 |
| 48 | 34 |
| 48 | 35 |
| 48 | 36 |
| 49 | 28 |
| 49 | 29 |
| 49 | 30 |
| 49 | 31 |
| 49 | 32 |
| 49 | 33 |
| 49 | 34 |
| 49 | 35 |
| 49 | 36 |
| 50 | 28 |
| 50 | 29 |
| 50 | 30 |
| 50 | 31 |
| 50 | 32 |
| 50 | 33 |
| 50 | 34 |
| 50 | 35 |
| 50 | 36 |
| 51 | 28 |
| 51 | 29 |
| 51 | 30 |
| 51 | 31 |
| 51 | 32 |
| 51 | 33 |
| 51 | 34 |
| 51 | 35 |
| 51 | 36 |

-continued

| No. | Config. |
|---|---|
| 52 | 28 |
| 52 | 29 |
| 52 | 30 |
| 52 | 31 |
| 52 | 32 |
| 52 | 33 |
| 52 | 34 |
| 52 | 35 |
| 52 | 36 |
| 53 | 28 |
| 53 | 29 |
| 53 | 30 |
| 53 | 31 |
| 53 | 32 |
| 53 | 33 |
| 53 | 34 |
| 53 | 35 |
| 53 | 36 |
| 54 | 28 |
| 54 | 29 |
| 54 | 30 |
| 54 | 31 |
| 54 | 32 |
| 54 | 33 |
| 54 | 34 |
| 54 | 35 |
| 54 | 36 |
| 55 | 28 |
| 55 | 29 |
| 55 | 30 |
| 55 | 31 |
| 55 | 32 |
| 55 | 33 |
| 55 | 34 |
| 55 | 35 |
| 55 | 36 |
| 116 | 28 |
| 116 | 29 |
| 116 | 30 |
| 116 | 31 |
| 116 | 32 |
| 116 | 33 |
| 116 | 34 |
| 116 | 35 |
| 116 | 36 |
| 127 | 28 |
| 127 | 29 |
| 127 | 30 |
| 127 | 31 |
| 127 | 32 |
| 127 | 33 |
| 127 | 34 |
| 127 | 35 |
| 127 | 36 |
| 128 | 28 |
| 128 | 29 |
| 128 | 30 |
| 128 | 31 |
| 128 | 32 |
| 128 | 33 |
| 128 | 34 |
| 128 | 35 |
| 128 | 36 |
| 129 | 28 |
| 129 | 29 |
| 129 | 30 |
| 129 | 31 |
| 129 | 32 |
| 129 | 33 |
| 129 | 34 |
| 129 | 35 |
| 129 | 36 |
| 131 | 28 |
| 131 | 29 |
| 131 | 30 |
| 131 | 31 |
| 131 | 32 |

-continued

| No. | Config. |
|---|---|
| 131 | 33 |
| 131 | 34 |
| 131 | 35 |
| 131 | 36 |
| 132 | 28 |
| 132 | 29 |
| 132 | 30 |
| 132 | 31 |
| 132 | 32 |
| 132 | 33 |
| 132 | 34 |
| 132 | 35 |
| 132 | 36 |
| 132 | 10 |
| 134 | 28 |
| 134 | 29 |
| 134 | 30 |
| 134 | 31 |
| 134 | 32 |
| 134 | 33 |
| 134 | 34 |
| 134 | 35 |
| 134 | 36 |
| 135 | 28 |
| 135 | 29 |
| 135 | 30 |
| 135 | 31 |
| 135 | 32 |
| 135 | 33 |
| 135 | 34 |
| 135 | 35 |
| 135 | 36 |
| 137 | 28 |
| 137 | 29 |
| 137 | 30 |
| 137 | 31 |
| 137 | 32 |
| 137 | 33 |
| 137 | 34 |
| 137 | 35 |
| 137 | 36 |
| 138 | 28 |
| 138 | 29 |
| 138 | 30 |
| 138 | 31 |
| 138 | 32 |
| 138 | 33 |
| 138 | 34 |
| 138 | 35 |
| 138 | 36 |
| 140 | 28 |
| 140 | 29 |
| 140 | 30 |
| 140 | 31 |
| 140 | 32 |
| 140 | 33 |
| 140 | 34 |
| 140 | 35 |
| 140 | 36 |
| 141 | 28 |
| 141 | 29 |
| 141 | 30 |
| 141 | 31 |
| 141 | 32 |
| 141 | 33 |
| 141 | 34 |
| 141 | 35 |
| 141 | 36 |
| 143 | 28 |
| 143 | 29 |
| 143 | 30 |
| 143 | 31 |
| 143 | 32 |
| 143 | 33 |
| 143 | 34 |
| 143 | 35 |
| 143 | 36 |

-continued

| No. | Config. |
|---|---|
| 144 | 28 |
| 144 | 29 |
| 144 | 30 |
| 144 | 31 |
| 144 | 32 |
| 144 | 33 |
| 144 | 34 |
| 144 | 35 |
| 144 | 36 |
| 145 | 28 |
| 145 | 29 |
| 145 | 30 |
| 145 | 31 |
| 145 | 32 |
| 145 | 33 |
| 145 | 34 |
| 145 | 35 |
| 145 | 36 |
| 147 | 28 |
| 147 | 29 |
| 147 | 30 |
| 147 | 31 |
| 147 | 32 |
| 147 | 33 |
| 147 | 34 |
| 147 | 35 |
| 147 | 36 |
| 148 | 28 |
| 148 | 29 |
| 148 | 30 |
| 148 | 31 |
| 148 | 32 |
| 148 | 33 |
| 148 | 34 |
| 148 | 35 |
| 148 | 36 |
| 152 | 28 |
| 152 | 29 |
| 152 | 30 |
| 152 | 31 |
| 152 | 32 |
| 152 | 33 |
| 152 | 34 |
| 152 | 35 |
| 152 | 36 |
| 153 | 28 |
| 153 | 29 |
| 153 | 30 |
| 153 | 31 |
| 153 | 32 |
| 153 | 33 |
| 153 | 34 |
| 153 | 35 |
| 153 | 36 |
| 154 | 28 |
| 154 | 29 |
| 154 | 30 |
| 154 | 31 |
| 154 | 32 |
| 154 | 33 |
| 154 | 34 |
| 154 | 35 |
| 154 | 36 |
| 155 | 28 |
| 155 | 29 |
| 155 | 30 |
| 155 | 31 |
| 155 | 32 |
| 155 | 33 |
| 155 | 34 |
| 155 | 35 |
| 155 | 36 |
| 164 | 28 |
| 164 | 29 |
| 164 | 30 |
| 164 | 31 |
| 164 | 32 |

-continued

| No. | Config. |
|---|---|
| 164 | 33 |
| 164 | 34 |
| 164 | 35 |
| 164 | 36 |
| 165 | 28 |
| 165 | 29 |
| 165 | 30 |
| 165 | 31 |
| 165 | 32 |
| 165 | 33 |
| 165 | 34 |
| 165 | 35 |
| 165 | 36 |
| 177 | 28 |
| 177 | 29 |
| 177 | 30 |
| 177 | 31 |
| 177 | 32 |
| 177 | 33 |
| 177 | 34 |
| 177 | 35 |
| 177 | 36 |

In another aspect, the present disclosure provides a compound according to any one of the preceding aspects includes one or more stable isotopes. The stable isotope may replace any atom, for example, hydrogen, and may include any stable isotope, for example, deuterium.

In another aspect, the present disclosure provides compounds and pharmaceutical compositions comprising the compounds according to any one of the preceding aspects of the invention or any embodiment thereof, together with a pharmaceutically acceptable excipient, diluent, or carrier.

In another aspect, the invention provides methods for treating tryptophan 2,3-dioxygenase (TDO2) mediated immunosuppression in a subject in need thereof, comprising administering an effective tryptophan 2,3-dioxygenase inhibiting amount of a compound or a pharmaceutical composition according to any of the preceding aspects of the invention or any embodiment thereof.

In one embodiment, the immunosuppression is associated with cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of IDO1 or TDO2. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In another aspect, the invention provides the use of compounds described by any one of the preceding aspects (and any embodiment thereof), as defined above, for the preparation of a medicament for the treatment of immunosuppression associated with cancer or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to $—CH_2—$, $—CH_2CH_2—$, $—CH_2CH_2CHC(CH_3)—$, $—CH_2CH(CH_2CH_3)CH_2—$.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2 (3H)-on-5-yl, benzo[d]oxazin-2 (3H)-on-6-yl, benzo[d]oxazin-2 (3H)-on-7-yl, benzo[d]oxazin-2 (3H)-on-8-yl, quinazolin-4 (3H)-on-5-yl, quinazolin-4 (3H)-on-6-yl, quinazolin-4 (3H)-on-7-yl, quinazolin-4 (3H)-on-8-yl, quinoxalin-2 (1H)-on-5-yl, quinoxalin-2 (1H)-on-6-yl, quinoxalin-2 (1H)-on-7-yl, quinoxalin-2 (1H)-on-8-yl, benzo[d]thiazol-2 (3H)-on-4-yl, benzo[d]thiazol-2 (3H)-on-5-yl, benzo[d]thiazol-2 (3H)-on-6-yl, and, benzo[d]thiazol-2 (3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 10 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $—(CH_2)_w—$, where w is 1, 2, 3 or 4). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane and adamantane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 10 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form $-(CH_2)_w-$, where w is 1, 2, 3 or 4). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl) propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. Bicyclic heterocycles that are fused through a heteroatom can be categorized according to the ring A/B convention of the present disclosure as if the heteroatom was in either of ring A or ring B. For example, 6,7,8,9-tetrahydro-4H-quinolizin-4-on-yl:

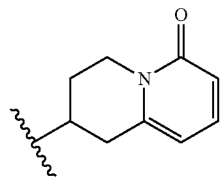 [SMILES: *C1CCn2c(cccc2=O)C1]

can be categorized as a ring A=$C_6$cycloalkyl and ring B=6-membered heterocyclyl substituted with an oxo group, or A=6-membered heterocyclyl and ring B=$C_6$cycloalkenyl substituted with an oxo group. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a $—NO_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "spiro" as used herein refers to a cyclic moiety formed by the substituted atom and two available substitutable positions on that same atom. For example, moiety such as

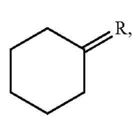

where R is a spiro-cycloalkyl=group includes compounds such as

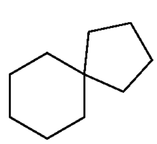

, where the spiro-cyclopentyl group is the R group attached to the parent cyclohexyl ring by two single bonds. Similarly, where R is a spiro-heterocyclyl group, such compounds include

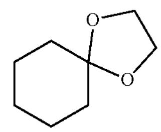

where the spiro-1,3-dioxolanyl ring is the R group attached to the parent cyclohexyl ring by two single bonds.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TDO2 enzyme with a compound includes the administration of a compound described herein to an individual or patient, such as a human, having TDO2, as well as, for example, introducing a compound into a sample containing a cellular or purified preparation containing the TDO2 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., TDO2 modulation or tryptophan degradation inhibition).

Manifestation of amelioration of a disease condition with underlying TDO2-mediated immunosuppression may require the concomitant or sequential administration of additional therapeutic agents, such as antineoplastic agents in the case of cancer, or antiretroviral agents in the case of viral diseases. For example, administration of TDO2 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC—(CH_2)_n—COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme tryptophan 2,3-dioxygenase (TDO2). The term "modulate" is meant to refer to an ability to decrease activity of an enzyme or receptor. Accordingly, compounds described herein can be used in methods of modulating TDO2 by contacting the enzyme with any one or more of the compounds or compositions described herein. In some embodiments, the compounds described herein can act as inhibitors of TDO2. In further embodiments, the compounds described herein can be used to modulate activity of TDO2 in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing TDO2 such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as TDO2-mediated immunosuppression in a patient by administering to the patient an effective amount of a compound or composition recited herein. TDO2-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of TDO2 in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the TDO2 enzyme, such as over expression or abnormal activity. An TDO2-associated disease can also include any disease, disorder or condition that can be prevented, ameliorated, or cured by modulating enzyme activity.

Examples of TDO2-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or indoleamine 2,3-dioxygenase (IDO) inhibitors can be used in combination with the compounds and pharmaceutical compositions described herein for treatment of TDO2-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Therapeutic agents that constitute the standard of care for a particular cancer type or infectious disease are expected to benefit when combined with TDO2 inhibitors of the present invention. For example, for the case of tumors, is it preferable that the tumor is sensitive to the cytotoxic effects of the chemotherapeutic agent in order to stimulate the release of antigens that will eventually mediate an immune response that will be enhanced by addition of TDO2 inhibitors to the combination treatment. A person of skill in the art will know how to select such chemotherapeutic agent based on the clinical characteristics and known sensitivity of each tumor to different antineoplastic agents.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4,4-1BB, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such adoptive T cell transfer.

Anti-cancer vaccines include dendritic cells, synthetic peptides, DNA vaccines and recombinant viruses.

The compounds of the present application can also be used in combination therapy with therapeutic treatments suppressing or inhibiting biologic pathways modulated by PD-1 (programmed cell death protein 1) or its ligand PD-L1. Such therapeutic treatments include those that suppress or inhibit the expression of PD-1 or PD-L1 as well as those that suppress or inhibit the activity of the PD-1 or PD-L1 proteins themselves. Examples of anti-PD-1 compounds include, for example, pembrolizumab, nivolumab, pidilizumab, and BMS 936559. Examples of anti-PD-L1 include, for example, atezolizumab and avelumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

Kits

Also included are pharmaceutical kits useful, for example, in the treatment or prevention of TDO2-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 μm particle sizes. All reactions were performed in flame or oven-dried glassware under a nitrogen atmosphere. All reactions were stirred magnetically at ambient temperature unless otherwise indicated. $^1H$ NMR spectra were obtained with a Bruker DRX400, Varian VXR400 or VXR300. $^1H$ NMR spectra were reported in parts per million (δ) relative to TMS (0.0), DMSO-d6 (2.50) or $CD_3OD$ (4.80) as an internal reference. All $^1H$ NMR spectra were taken in CDCl3 unless otherwise indicated. The phosphonates were prepared according to the literature procedure: (U.S. Pat. No. 5,807,892 A1, 1998; Patent: US2012/033245; Patent: US2008/306084 A1, 2008). 1-(azidomethyl)-2,4-dimethoxybenzene was synthesized according to Chem Med Chem, 2011, vol. 6, #5, 840-847.

Synthetic Route LA

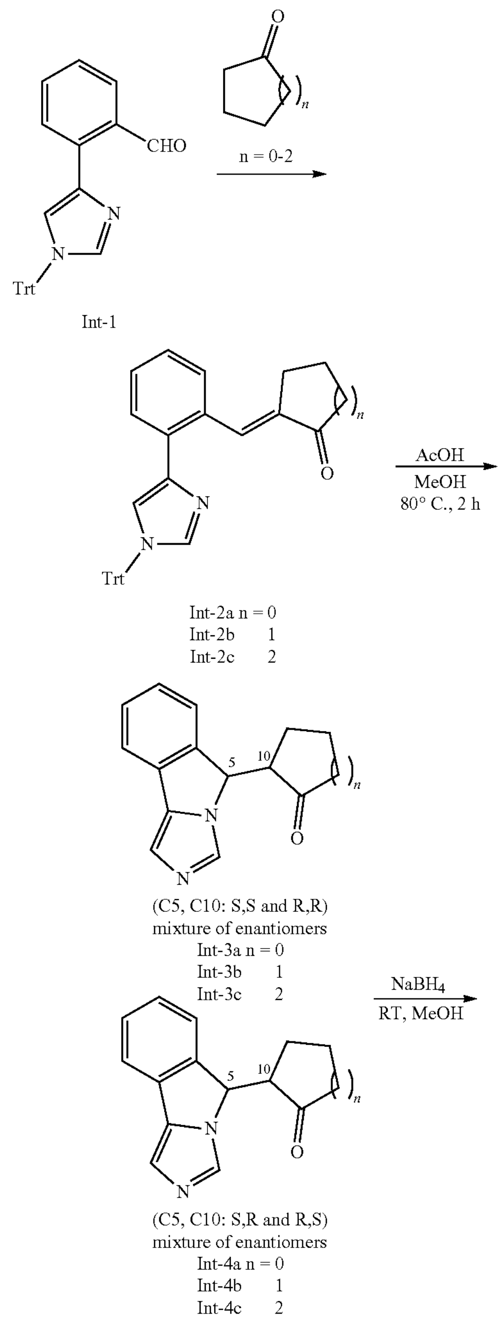

Int-1

Int-2a n = 0
Int-2b 1
Int-2c 2

(C5, C10: S,S and R,R)
mixture of enantiomers
Int-3a n = 0
Int-3b 1
Int-3c 2

(C5, C10: S,R and R,S)
mixture of enantiomers
Int-4a n = 0
Int-4b 1
Int-4c 2

-continued

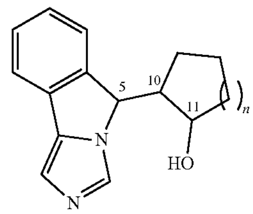

mixture of diastereomers
Int-5a n = 0
Int-5b 1
Int-5c 2

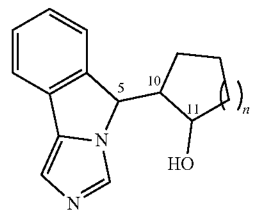

mixture of diastereomers
Int-6a n = 0
Int-6b 1
Int-6c 2

(General Procedure for the Synthesis of Int-2:

Base (1 equiv) was added to a stirred mixture of ketone (1 equiv) and 2-(1-trityl-1H-imidazol-4-yl)benzaldehyde (1 equiv), in MeOH (15 mL). The reaction mixture was heated at 50° C. for 2 hours until TLC showed disappearance of SM. After cooling to rt, the reaction mixture was diluted with DCM (50 mL) and washed with water, dried over $Na_2SO_4$, filtered and concentrated. The crude product was purified by combi-flash using EtOAc/hexanes as eluent.

TABLE 1

| Compound ID | Structure | Conditions | MS (M + H)$^+$ |
|---|---|---|---|
| Int-2a | 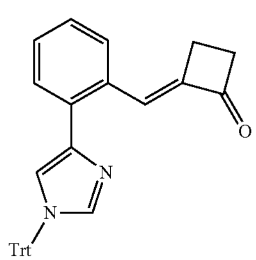 | NaOH, MeOH, 40° C., 6 h | 467.2 |
| Int-2b | 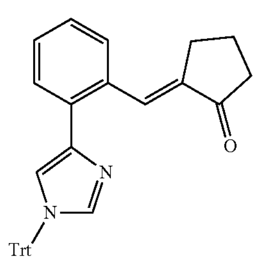 | Pyrrolidine, MeOH, 40° C., 2 h | 481.4 |

TABLE 1-continued

| Compound ID | Structure | Conditions | MS (M + H)$^+$ |
|---|---|---|---|
| Int-2c | 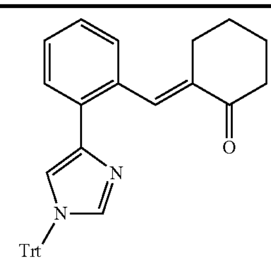 | Pyrrolidine, MeOH, 70° C., 12 h | 495.4 |

General Procedure for the Synthesis of Int-3 and Int-4:

Int-2 (1 equiv) was stirred in MeOH and AcOH (5:1) at 80° C. for 2 h. After cooling to rt, the solvent was removed under reduced pressure and sat'd $NaHCO_3$ was added to the residue until it was neutral. The aqueous layer was extracted with DCM. The combined organic layers were dried over $Na_2SO_4$, filtered and concentrated. The crude was purified by combi-flash using EtOAc/DCM as eluent to separate mixture of four diastereomers into two mixture of enantiomers represented by Int-3 and Int-4.

General Procedure for the Synthesis of 5 and 6:

Int-3 or Int-4 (1 equiv) was dissolved in MeOH (6 mL) and $NaBH_4$ (3 equiv) was added the reaction mixture was stirred for 2 h. $NH_4Cl$ (5 mL) was added to the reaction mixture and stirred for 5 min. The solution was poured into a separatory funnel containing water (10 mL). The aqueous layer was extracted with DCM (2×20 mL). The combined organic layers were dried over $Na_2SO_4$ and the solvent evaporated under reduced pressure to afford the crude product which was purified Combi-Flash using methanol/dcm gradient.

Synthetic Route for C10-OH Analogues

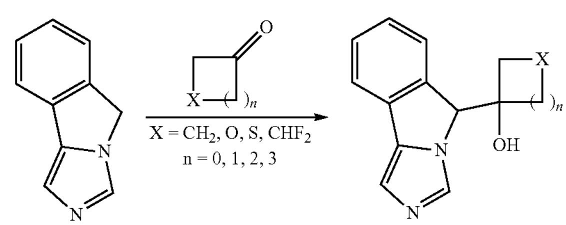

43-45, 46a-b, 47a-b, 48, 50

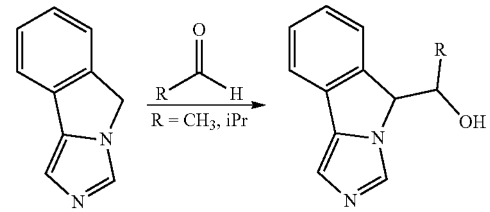

42a-d, 51a-d, 52a-d

General Procedure for Aldehyde or Ketone Addition

To a solution of 5H-imidazo[5,1-a]isoindole (650 mg, 4.16 mmol) in anhydrous THF (10 mL) at −40° C. was added n-BuLi (1.66 mL, 4.16 mmol) and the solution was stirred at −40° C. for 1 h. Aldehyde or ketone (6.24 mmol) was added and the reaction was allowed to warm to rt and stirred overnight. The reaction was quenched by adding saturated ammonium chloride (10 mL) solution and water (15 mL), the product was extracted with $CH_2Cl_2$ (3×30 mL). The solvent was distilled under reduced pressure to afford the crude product. The crude product was purified by Combi-Flash to afford the desired product.

General Procedure of Chiral Separation of Stereoisomers and Analysis

Stereoisomers of final products were separated by chromatography. Unless otherwise specified, the following general conditions are used:

A. Method development/sequential Screening of 14 chiral columns

Fourteen chiral columns are routinely screened on a Waters UPC2 HPLC system under the following conditions: Mobile Phase A: carbon dioxide, mobile phase B: methanol w/0.1% $NH_4OH$, or Ethanol, IPA, or mixtures, 5-60% B in 1.8 minutes, flow rate of 4 ml/min, run time: 2.5 min, pressure: 120 bar, temperature: 40° C. The 14 columns screened (4.6×50 mm, 3 um) on a regular basis are: Chiralpak AD, Chiralpak AS, Chiralpak IA, Chiralpak IB, Chiralpak IC, Chiralpak ID, Chiralpak IE, Chiralpak OJ, ChiralpakOX from Chiral Technologies, Lux Cellulose-1, Lux Cellulose-2, Lux Cellulose-3, Lux Cellulose-4 from Phenomenex and Whelk O-1 (s,s) from Regis.

B. Purification on Preparative SFC

The column that provided resolution value Rs>0.5 is picked to perform the preparative separation. The preparative runs are performed on PIC 100 SFC instrument, the corresponding column displaying best resolution of enantiomers from step A is used (150×20 mm, 5 um) with Isocratic mobile phase B identified in step A, mobile phase A: Carbon Dioxide, mobile phase B: Methanol w/0.1% NH4OH, flow rate: 70 ml/min, Pressure: 100 bar, temperature: 40° C.

C. Typical conditions to separate compounds with 2 chiral centers are:
Column: Chiralpak AD (250×20 mm, 5 um)
Method: Isocratic at 25% B
MP A: Carbon Dioxide
MP B: Ethanol w/0.1% $NH_4OH$
Flow: 70 ml/min
Pressure: 100 bar
Temperature: 40 40° C.

D. Typical conditions to separate compounds with 3 chiral centers:
Stage: 1
Column: Chiralpak OX (250×20 mm, 5 um)
Method: Isocratic at 20% B
MP A: Carbon Dioxide
MP B: Ethanol w/0.1% $NH_4OH$
Flow: 70 ml/min
Pressure: 100 bar
Temperature: 40 40° C.
Stage 2:
Column: Cellulose-1(250×20 mm, 5 um)
Method: Isocratic at 15% B
MP A: Carbon Dioxide
MP B: Methanol w/0.1% $NH_4OH$
Flow: 70 ml/min
Pressure: 100 bar
Temperature: 40 degC.
Stage 3:
Column: Chiralcel OX (250×20 mm, 5 um)
Method: Isocratic at 15% B
MP A: Carbon Dioxide
MP B: Methanol w/0.1% $NH_4OH$
Flow: 70 ml/min
Pressure: 100 bar
Temperature: 40° C.

E. QC of final products to obtain % ee

The purity of each isomer separated in Step B above is analyzed with chiral analytical SFC as the following: Instrument: Waters UPC2; Column: Column used for purification (50×4.6 mm, 3 um); Method: Mobile Phase A: Carbon Dioxide, isocratic mobile Phase B with same percentage of mobile phase B used in step B, Flow Rate: 4 ml/min, Run time: 2.5 min, Pressure: 120 bar, Temperature: 40° C.

TABLE 2

| Ex. # | Structure | $^1H$ NMR | MS $(M + H)^+$ |
|---|---|---|---|
| 1a | 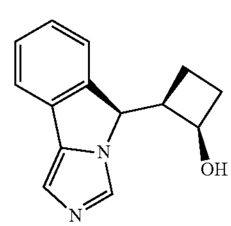 [SMILES: O[C@@H]1CC[C@@H]1[C@@H]1c2ccccc2-c2cncn21] | (400 MHz, DMSO-$d_6$) δ 8.03 (s, 1H), 7.57 (dd, J = 13.5, 7.7 Hz, 2H), 7.36 (t, J = 7.5 Hz, 1H), 7.25 (td, J = 7.4, 1.1 Hz, 1H), 7.14 (s, 1H), 5.74 (d, J = 4.5 Hz, 1H), 5.49 (d, J = 6.2 Hz, 1H), 4.59-4.48 (m, 1H), 2.88-2.75 (m, 1H), 2.24-2.10 (m, 1H), 1.85-1.52 (m, 3H). | 227.3 |
| 1b | 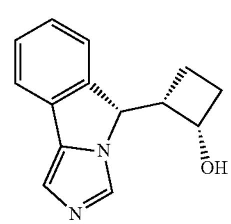 [SMILES: O[C@H]1CC[C@H]1[C@H]1c2ccccc2-c2cncn21] | (400 MHz, DMSO-$d_6$) δ 8.03 (s, 1H), 7.57 (dd, J = 13.3, 7.6 Hz, 2H), 7.36 (t, J = 7.5 Hz, 1H), 7.29-7.20 (m, 1H), 7.14 (s ,1H), 5.74 (d, J = 4.0 Hz, 1H), 5.49 (d, J = 6.3 Hz, 1H), 4.52 (d, J = 11.3 Hz, 1H), 2.82 (p, J = 6.3 Hz, 1H), 2.24-2.09 (m, 1H), 1.85-1.52 (m, 3H). | 227.3 |

TABLE 2-continued

| Ex. # | Structure | $^1$H NMR | MS (M + H)$^+$ |
|---|---|---|---|
| 1c | 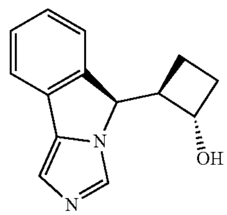 [SMILES: O[C@H]1CC[C@@H]1[C@@H]1c2ccccc2-c2cncn21] | (400 MHz, DMSO-$d_6$) δ 7.84 (s, 1H), 7.61-7.54 (m, 2H), 7.36 (t, J = 7.6 Hz, 1H), 7.31-7.21 (m, 1H), 7.13 (s, 1H), 5.34 (dd, J = 15.4, 6.8 Hz, 2H), 4.25 (p, J = 7.5 Hz, 1H), 2.41 (dq, J = 9.6, 7.7 Hz, 1H), 2.15-2.03 (m, 1H), 1.73-1.50 (m, 2H), 1.12 (qd, J = 10.2, 8.1 Hz, 1H). | 227.3 |
| 1d | 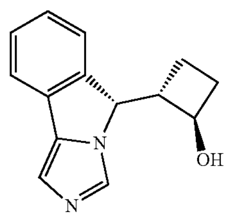 [SMILES: O[C@@H]1CC[C@H]1[C@H]1c2ccccc2-c2cncn21] | (400 MHz, DMSO-$d_6$) δ 7.84 (s, 1H), 7.61-7.54 (m, 2H), 7.36 (t, J = 7.6 Hz, 1H), 7.31-7.21 (m, 1H), 7.13 (s, 1H), 5.34 (dd, J = 15.4, 6.8 Hz, 2H), 4.25 (p, J = 7.5 Hz, 1H), 2.41 (dq, J = 9.6, 7.7 Hz, 1H), 2.15-2.03 (m, 1H), 1.73-1.50 (m, 2H), 1.12 (qd, J = 10.2, 8.1 Hz, 1H). | 227.3 |
| 1e | 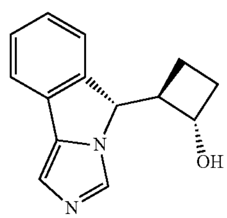 [SMILES: O[C@H]1CC[C@@H]1[C@H]1c2ccccc2-c2cncn21] | (400 MHz, DMSO-$d_6$) δ 7.84 (s, 1H), 7.60 (d, J = 7.5 Hz, 1H), 7.49 (d, J = 7.5 Hz, 1H), 7.38 (t, J = 7.6 Hz, 1H), 7.28-7.19 (m, 1H), 7.10 (s, 1H), 5.72 (d, J = 3.7 Hz, 1H), 5.45 (d, J = 9.6 Hz, 1H), 4.42 (s, 1H), 2.39 (tt, J = 10.2, 7.7 Hz, 2H), 2.24 (ddt, J = 14.9, 12.1, 7.4 Hz, 1H), 2.01-1.81 (m, 2H). | 227.3 |
| 1f | 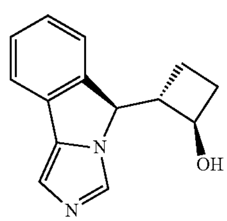 [SMILES: O[C@@H]1CC[C@H]1[C@@H]1c2ccccc2-c2cncn21] | (400 MHz, DMSO-$d_6$) δ 7.89 (s, 1H), 7.58 (d, J = 7.5 Hz, 1H), 7.42-7.31 (m, 2H), 7.29-7.20 (m, 1H), 7.10 (s, 1H), 5.30 (dd, J = 25.5, 8.2 Hz, 2H), 4.14 (p, J = 7.6 Hz, 1H), 2.33-2.05 (m, 2H), 1.84-1.50 (m, 3H). | 227.3 |
| 1g | 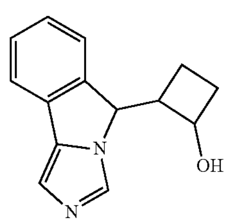 [SMILES: OC1CCC1C1c2ccccc2-c2cncn21] | (400 MHz, DMSO-$d_6$) δ 7.84 (s, 1H), 7.63-7.45 (m, 2H), 7.37 (q, J = 7.4 Hz, 1H), 7.24 (q, J = 7.1 Hz, 1H), 7.12 (d, J = 13.9 Hz, 1H), 5.73 (dd, J = 9.0, 5.1 Hz, 1H), 5.47 (dd, J = 14.1, 7.9 Hz, 1H), 4.42 (tp, J = 5.6, 2.5 Hz, 1H), 2.48-2.12 (m, 3H), 2.01-1.81 (m, 2H). | 227.3 |
| 1h | 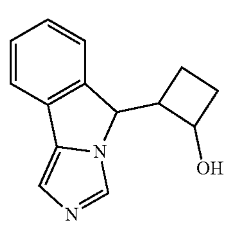 [SMILES: OC1CCC1C1c2ccccc2-c2cncn21] | (400 MHz, DMSO-$d_6$) δ 7.84 (s, 1H), 7.60 (d, J = 7.5 Hz, 1H), 7.49 (d, J = 7.5 Hz, 1H), 7.38 (t, J = 7.6 Hz, 1H), 7.28-7.19 (m, 1H), 7.10 (s, 1H), 5.72 (d, J = 3.7 Hz, 1H), 5.45 (d, J = 9.6 Hz, 1H), 4.42 (s, 1H), 2.39 (tt, J = 10.2, 7.7 Hz, 2H), 2.24 (ddt, J = 14.9, 12.1, 7.4 Hz, 1H), 2.01-1.81 (m, 2H). | 227.3 |
| 2a | 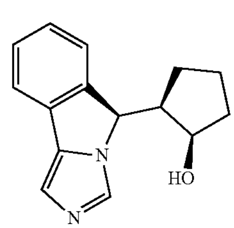 [SMILES: O[C@@H]1CCC[C@@H]1[C@@H]1c2ccccc2-c2cncn21] | (400 MHz, DMSO-$d_6$) δ 7.90 (s, 1H), 7.61 (dd, J = 22.5, 7.6 Hz, 2H), 7.37 (t, J = 7.5 Hz, 1H), 7.31-7.23 (m, 1H), 5.39 (d, J = 6.8 Hz, 1H), 5.16 (d, J = 3.8 Hz, 1H), 4.37 (q, J = 4.7 Hz, 1H), 2.14-2.01 (m, 1H), 1.84-1.39 (m, 7H). | 241.3 |

TABLE 2-continued
| Ex. # | Structure | $^1$H NMR | MS $(M + H)^+$ |
|---|---|---|---|
| 2b | 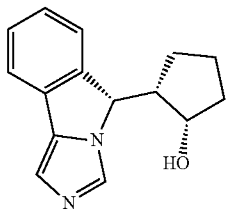 [SMILES: O[C@H]1CCC[C@H]1[C@H]1c2ccccc2-c2cncn21] | (400 MHz, DMSO-$d_6$) δ 7.90 (s, 1H), 7.67-7.54 (m, 2H), 7.37 (t, J = 7.5 Hz, 1H), 7.31-7.22 (m, 1H), 5.39 (d, J = 6.9 Hz, 1H), 5.16 (d, J = 3.9 Hz, 1H), 4.38 (qd, J = 4.6, 2.6 Hz, 1H), 2.08 (p, J = 8.4 Hz, 1H), 1.84-1.37 (m, 7H). | 241.3 |
| 2c | 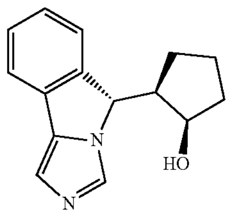 [SMILES: O[C@@H]1CCC[C@@H]1[C@H]1c2ccccc2-c2cncn21] | (400 MHz, DMSO-$d_6$) δ 7.90 (s, 1H), 7.60 (d, J = 7.5 Hz, 1H), 7.50 (d, J = 7.9 Hz, 1H), 7.37 (t, J = 7.5 Hz, 1H), 7.24 (td, J = 7.7, 1.3 Hz, 1H), 7.12 (s, 1H), 5.26 (d, J = 10.2 Hz, 1H), 5.07 (d, J = 4.1 Hz, 1H), 4.30 (p, J = 3.7 Hz, 1H), 2.03-1.82 (m, 3H), 1.76-1.55 (m, 4H). | 241.3 |
| 2d | 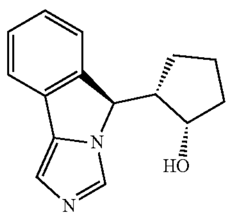 [SMILES: O[C@H]1CCC[C@H]1[C@@H]1c2ccccc2-c2cncn21] | (400 MHz, DMSO-$d_6$) δ 7.90 (s, 1H), 7.60 (d, J = 7.5 Hz, 1H), 7.50 (d, J = 7.7 Hz, 1H), 7.37 (t, J = 7.5 Hz, 1H), 7.24 (td, J = 7.4, 1.2 Hz, 1H), 7.12 (s, 1H), 5.26 (d, J = 10.2 Hz, 1H), 5.06 (d, J = 4.2 Hz, 1H), 4.30 (q, J = 3.5 Hz, 1H), 2.02-1.82 (m, 3H), 1.76-1.58 (m, 4H). | 241.3 |
| 2e | 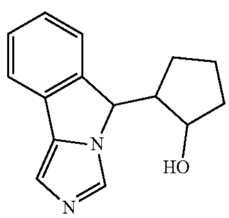 [SMILES: OC1CCCC1C1c2ccccc2-c2cncn21] | NA | 241.3 |
| 2f | 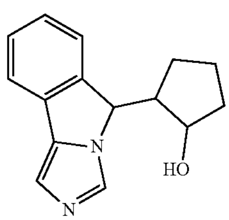 [SMILES: OC1CCCC1C1c2ccccc2-c2cncn21] | NA | 241.3 |
| 2g | 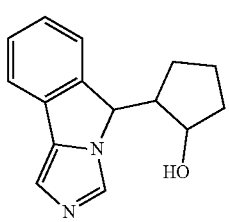 [SMILES: OC1CCCC1C1c2ccccc2-c2cncn21] | NA | 241.3 |
| 2h | 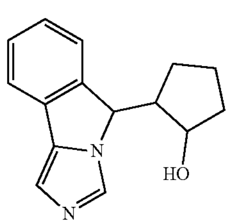 [SMILES: OC1CCCC1C1c2ccccc2-c2cncn21] | NA | 241.3 |

TABLE 2-continued

| Ex. # | Structure | $^1$H NMR | MS (M + H)$^+$ |
|---|---|---|---|
| 3a | 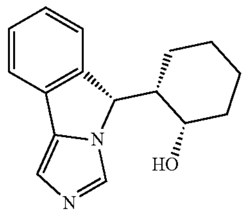 [SMILES: O[C@H]1CCCC[C@H]1[C@H]1c2ccccc2-c2cncn21] | $^1$H NMR (400 MHz, DMSO-$d_6$) δ 8.01 (s, 1H), 7.57-7.51 (m, 2H), 7.40-7.31 (m, 1H), 7.30-7.21 (m, 1H), 7.08 (s, 1H), 5.23 (d, J = 2.7 Hz, 1H), 4.94-4.89 (m, 1H), 4.27-4.22 (m, 1H), 2.03-1.93 (m, 1H), 1.83-1.75 (m, 1H), 1.65-1.43 (m, 3H), 1.39-1.30 (m, 1H), 1.22-0.98 (m, 2H), 0.79-0.71 (m, 1H). | 255.3 |
| 3b | 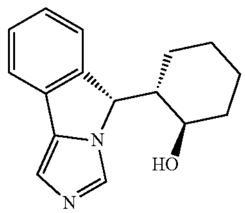 [SMILES: O[C@@H]1CCCC[C@H]1[C@H]1c2ccccc2-c2cncn21] | $^1$H NMR (400 MHz, DMSO-$d_6$) δ 7.88 (s, 1H), 7.66 (d, J = 7.5 Hz, 1H), 7.58 (d, J = 7.5 Hz, 1H), 7.40-7.32 (m, 1H), 7.27-7.18 (m, 1H), 7.10 (s, 1H), 5.16 (d, J = 5.4 Hz, 1H), 4.69 (d, J = 4.0 Hz, 1H), 4.09-4.04 (m, 1H), 1.82-1.30 (m, 7H), 1.18-1.10 (m, 1H). | 255.3 |
| 3c | 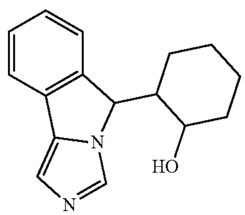 [SMILES: OC1CCCCC1C1c2ccccc2-c2cncn21] | $^1$H NMR (400 MHz, DMSO-$d_6$) δ 7.87 (s, 1H), 7.60 (d, J = 7.5 Hz, 1H), 7.51 (d, 1H), 7.41-7.34 (m, 1H), 7.30-7.23 (m, 1H), 7.11 (s, 1H), 5.73 (d, J = 3.9 Hz, 1H), 5.20 (d, J = 5.2 Hz, 1H), 3.69-3.57 (m, 1H), 2.20-1.92 (m, 2H), 1.65-1.54 (m, 1H), 1.42-1.20 (m, 2H), 1.12-0.89 (m, 1H), 0.62-0.51 (m, 1H), 0.26-0.12 (m, 1H). | 255.3 |
| 3d | 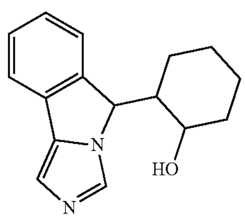 [SMILES: OC1CCCCC1C1c2ccccc2-c2cncn21] | $^1$H NMR (400 MHz, DMSO-$d_6$) δ 7.80 (s, 1H), 7.61-7.55 (m, 1H), 7.50-7.41 (m, 1H), 7.41-7.33 (m, 1H), 7.33-7.25 (m, 1H), 7.14 (s, 1H), 5.73 (d, J = 2.2 Hz, 1H), 5.24 (d, J = 5.7 Hz, 1H), 3.70-3.58 (m, 1H), 2.05-1.90 (m, 2H), 1.66-1.56 (m, 1H), 1.41-1.21 (m, 2H), 1.20-0.89 (m, 2H), 0.75-0.64 (m, 1H), 0.26-0.10 (m, 1H). | 255.3 |
| 3e | 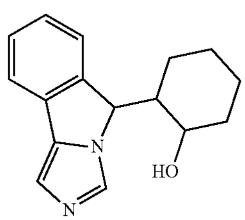 [SMILES: OC1CCCCC1C1c2ccccc2-c2cncn21] | $^1$H NMR (400 MHz, DMSO-$d_6$) δ 7.80 (s, 1H), 7.61-7.56 (m, 1H), 7.47-7.41 (m, 1H), 7.41-7.33 (m, 1H), 7.33-7.25 (m, 1H), 7.14 (s, 1H), 5.73 (d, J = 2.3 Hz, 1H), 5.25 (d, J = 5.7 Hz, 1H), 3.69-3.59 (m, 1H), 2.05-1.90 (m, 2H), 1.66-1.55 (m, 1H), 1.41-1.26 (m, 2H), 1.20-0.89 (m, 2H), 0.74-0.66 (m, 1H), 0.26-0.10 (m, 1H). | 255.3 |
| 3f | 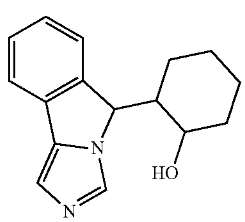 [SMILES: OC1CCCCC1C1c2ccccc2-c2cncn21] | $^1$H NMR (400 MHz, DMSO-$d_6$) δ 7.87 (s, 1H), 7.60 (d, J = 7.5 Hz, 1H), 7.50 (d, J = 7.7, 1.1 Hz, 1H), 7.42-7.33 (m, 1H), 7.31-7.22 (m, 1H), 7.11 (s, 1H), 5.73 (d, J = 3.7 Hz, 1H), 5.20 (d, J = 5.2 Hz, 1H), 3.68-3.56 (m, 1H), 2.18-2.08 (m, 1H), 2.00-1.91 (m, 1H), 1.63-1.55 (m, 1H), 1.42-1.21 (m, 2H), 1.12-0.89 (m, 1H), 0.60-0.52 (m, 1H), 0.27-0.12 (m, 1H). | 255.3 |
| 3g | 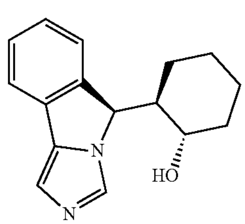 [SMILES: O[C@H]1CCCC[C@@H]1[C@@H]1c2ccccc2-c2cncn21] | $^1$H NMR (400 MHz, DMSO-$d_6$) δ 7.87 (s, 1H), 7.66 (d, J = 7.7, 0.9 Hz, 1H), 7.57 (d, 1H), 7.40-7.31 (m, 1H), 7.27-7.18 (m, 1H), 7.10 (s, 1H), 5.16 (d, J = 5.4 Hz, 1H), 4.69 (d, J = 3.9 Hz, 1H), 4.09-4.04 (m, 1H), 1.79-1.31 (m, 7H), 1.21-1.08 (m, 1H) | 255.3 |

TABLE 2-continued
| Ex. # | Structure | $^1$H NMR | MS $(M + H)^+$ |
|---|---|---|---|
| 3h | 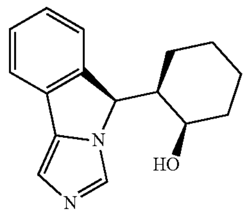 [SMILES: O[C@@H]1CCCC[C@@H]1[C@@H]1c2ccccc2-c2cncn21] | $^1$H NMR (400 MHz, DMSO-$d_6$) δ 8.01 (s, 1H), 7.58-7.51 (m, 2H), 7.40-7.31 (m, 1H), 7.30-7.21 (m, 1H), 7.08 (s, 1H), 5.23 (d, J = 2.7 Hz, 1H), 4.94-4.89 (m, 1H), 4.27-4.22 (m, 1H), 2.03-1.93 (m, 1H), 1.83-1.74 (m, 1H), 1.61-1.46 (m, 2H), 1.39-1.30 (m, 1H), 1.21-1.02 (m, 2H), 0.79-0.71 (m, 1H). | 255.3 |
| 4a | 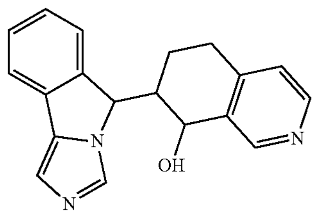 [SMILES: OC1c2cnccc2CCC1C1c2ccccc2-c2cncn21] | $^1$HNMR (300 MHz, $CD_3OD$) δ 8.74 (s, 1H), 8.25 (d, J = 5.4 Hz, 1H), 7.91 (s, 1H), 7.68-7.62 (m, 2H), 7.46-7.41 (m, 1H), 7.34-7.29 (m, 1H), 7.11 (s, 1H), 7.10 (d, J = 5.4 Hz, 1H), 5.89 (d, J = 3.0 Hz, 1H), 5.09 (d, J = 10.5 Hz, 1H), 2.71-2.62 (m, 3H), 1.09-1.04 (m, 2H) | 304 |
| 4b | 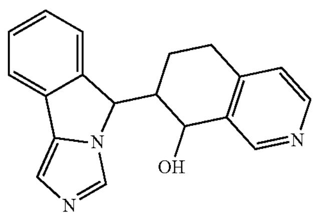 [SMILES: OC1c2cnccc2CCC1C1c2ccccc2-c2cncn21] | Same as 4a | 304 |
| 4c | 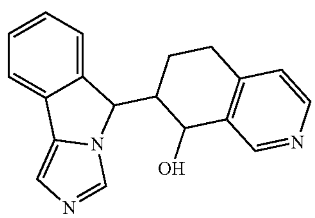 [SMILES: OC1c2cnccc2CCC1C1c2ccccc2-c2cncn21] | $^1$HNMR (300 MHz, $CD_3OD$) δ 8.42 (s, 1H), 8.27 (d, J = 5.1 Hz, 1H), 8.04 (s, 1H), 7.73-7.70 (m, 1H), 7.64-7.61 (m, 1H), 7.43-7.38 (m, 1H), 7.31-7.26 (m, 1H), 7.18 (d, J = 5.1 Hz, 1H), 7.15 (s, 1H), 5.50 (d, J = 3.0 Hz, 1H), 4.88 (d, J = 10.5 Hz, 1H), 3.06-2.93 (m, 1H), 2.82-2.70 (m, 1H), 2.26-1.97 (m, 3H) | 304 |
| 4d | 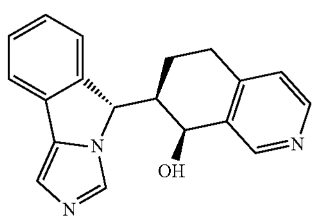 [SMILES: O[C@@H]1c2cnccc2CC[C@@H]1[C@H]1c2ccccc2-c2cncn21] | Same as 4c | 304 |
| 4e | 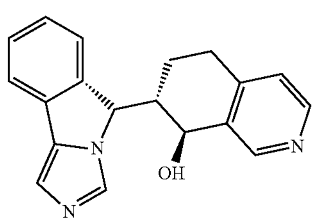 | $^1$HNMR (300 MHz, $CD_3OD$) δ 8.79 (s, 1H), 8.27 (d, J = 5.1 Hz, 1H), 7.99 (s, 1H), 7.66-7.64 (m, 1H), 7.50-7.32 (m, 3H), 7.20 (s, 1H), 7.18 (d, J = 5.1 Hz, 1H), 5.89 (d, J = 3.0 Hz, 1H), 5.10 (d, J = 10.5 Hz, 1H), 2.70-2.68 (m, 2H), 2.50-2.42 (m, 1H), 1.14-0.98 (m, 2H) | 304 |
| 4f | 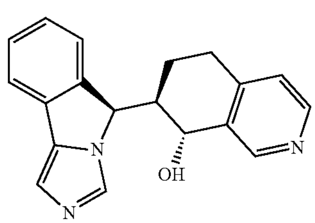 [SMILES: O[C@H]1c2cnccc2CC[C@@H]1[C@@H]1c2ccccc2-c2cncn21] | Same as 4e | 304 |

TABLE 2-continued

| Ex. # | Structure | $^1$H NMR | MS $(M + H)^+$ |
|---|---|---|---|
| 4g | 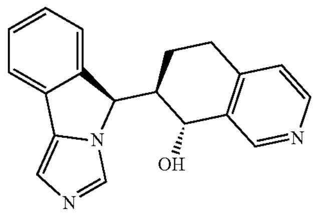 [SMILES: O[C@H]1c2cnccc2CC[C@@H]1[C@@H]1c2ccccc2-c2cncn21] | $^1$HNMR (300 MHz, $CD_3OD$) δ 8.56 (s, 1H), 8.30 (d, J = 5.2 Hz, 1H), 8.11 (s, 1H), 7.62-7.56 (m, 2H), 7.43-7.39 (m, 1H), 7.34-7.30 (m, 1H), 7.16 (d, J = 5.4 Hz, 1H), 7.14 (s, 1H), 5.92 (d, J = 3.0 Hz, 1H), 5.12 (d, J = 10.5 Hz, 1H), 2.84-2.78 (m, 1H), 2.66-2.54 (m, 2H), 1.61-1.57 (m, 1H), 1.10-1.05 (m, 1H) | 304 |
| 4h | 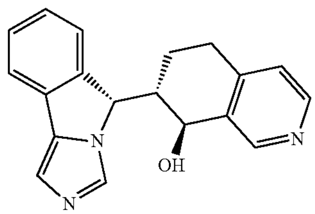 [SMILES: O[C@@H]1c2cnccc2CC[C@H]1[C@H]1c2ccccc2-c2cncn21] | Same as 4g | 304 |
| 5a | 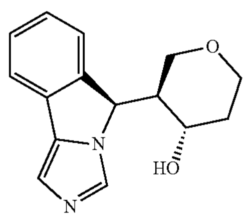 [SMILES: O[C@H]1CCOC[C@@H]1[C@@H]1c2ccccc2-c2cncn21] | $^1$HNMR (300 MHz, $CDCl_3$) δ 7.80 (s, 1H), 7.53-7.50 (m, 1H), 7.39-7.24 (m, 3H), 7.17 (s, 1H), 5.82 (d, J = 2.1 Hz, 1H), 4.14-4.06 (m, 1H), 3.94-3.89 (m, 1H), 3.31-3.21 (m, 2H), 2.57-2.49 (m, 1H), 2.42-2.33 (m, 1H), 2.11-2.05 (m, 1H), 1.90-1.77 (m, 1H) | 257 |
| 5b | 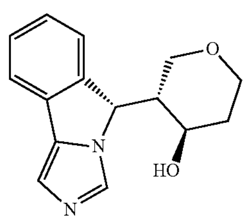 [SMILES: O[C@@H]1CCOC[C@H]1[C@H]1c2ccccc2-c2cncn21] | $^1$HNMR (300 MHz, $CDCl_3$) δ 7.80 (s, 1H), 7.53-7.50 (m, 1H), 7.39-7.24 (m, 3H), 7.17 (s, 1H), 5.82 (d, J = 2.1 Hz, 1H), 4.14-4.06 (m, 1H), 3.94-3.89 (m, 1H), 3.31-3.21 (m, 2H), 2.57-2.49 (m, 1H), 2.42-2.33 (m, 1H), 2.11-2.05 (m, 1H), 1.90-1.77 (m, 1H) | 257 |
| 5c | 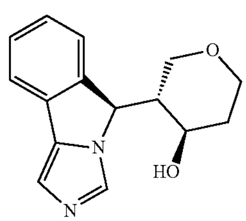 [SMILES: O[C@@H]1CCOC[C@H]1[C@@H]1c2ccccc2-c2cncn21] | $^1$HNMR (300 MHz, $CDCl_3$) δ 7.82 (s, 1H), 7.57-7.48 (m, 2H), 7.42-7.37 (m, 1H), 7.29-7.24 (m, 1H), 7.20 (s, 1H), 5.70 (d, J = 3.3 Hz, 1H), 4.07-3.90 (m, 2H), 3.32-3.23 (m, 2H), 2.81-2.73 (m, 1H), 2.50-2.43 (m, 1H), 2.00-1.96 (m, 1H), 1.77-1.72 (m, 1H) | 257 |
| 5d | 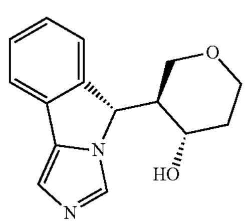 [SMILES: O[C@H]1CCOC[C@@H]1[C@H]1c2ccccc2-c2cncn21] | $^1$HNMR (300 MHz, $CDCl_3$) δ 7.82 (s, 1H), 7.57-7.48 (m, 2H), 7.42-7.37 (m, 1H), 7.29-7.24 (m, 1H), 7.20 (s, 1H), 5.70 (d, J = 3.3 Hz, 1H), 4.07-3.90 (m, 2H), 3.32-3.23 (m, 2H), 2.81-2.73 (m, 1H), 2.50-2.43 (m, 1H), 2.00-1.96 (m, 1H), 1.77-1.72 (m, 1H) | 257 |
| 6a | 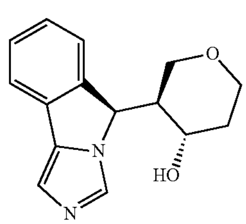 [SMILES: O[C@H]1CCOC[C@@H]1[C@@H]1c2ccccc2-c2cncn21] | Same as 6b | 257 |

TABLE 2-continued

| Ex. # | Structure | $^1$H NMR | MS (M + H)$^+$ |
|---|---|---|---|
| 6b | 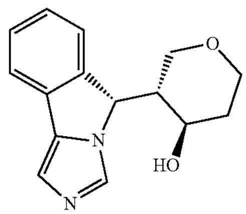 [SMILES: O[C@@H]1CCOC[C@H]1[C@H]1c2ccccc2-c2cncn21] | $^1$HNMR (300 MHz, $CDCl_3$) δ 8.02 (s, 1H), 7.55-7.53 (m, 1H), 7.40-7.28 (m, 3H), 7.20 (s, 1H), 5.85 (d, J = 2.1 Hz, 1H), 4.16-4.11 (m, 1H), 4.07-3.97 (m, 1H), 3.75-3.69 (m, 1H), 3.27-3.12 (m, 2H), 2.40-2.30 (m, 1H), 0.92-0.72 (m, 2H) | 257 |
| 6c | 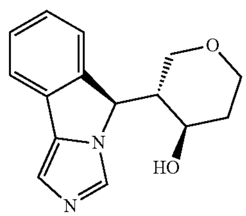 [SMILES: O[C@@H]1CCOC[C@H]1[C@@H]1c2ccccc2-c2cncn21] | Same as 6d | 257 |
| 6d | 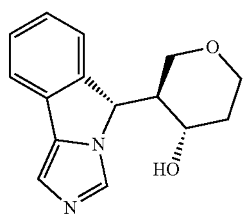 [SMILES: O[C@H]1CCOC[C@@H]1[C@H]1c2ccccc2-c2cncn21] | $^1$HNMR (300 MHz, $CDCl_3$) δ 7.72 (s, 1H), 7.58-7.55 (m, 1H), 7.49-7.46 (m, 1H), 7.42-7.37 (m, 1H), 7.27-7.19 (m, 2H), 5.79 (d, J = 3.3 Hz, 1H), 4.13-3.96 (m, 2H), 3.78-3.73 (m, 1H), 3.28-3.15 (m, 2H), 2.39-2.29 (m, 1H), 0.94-0.85 (m, 2H) | 257 |
| 6e | 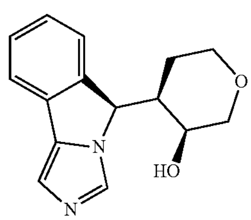 [SMILES: O[C@@H]1COCC[C@@H]1[C@@H]1c2ccccc2-c2cncn21] | 1H NMR (300 MHz, CDCl3) δ 8.09 (s, 1H), 7.58-7.15 (m, 5H), 5.27 (d, J = 4.3 Hz, 1H), 4.16 (s, 1H), 4.10-3.90 (m, 2H), 3.58 (dd, J = 12.2, 1.2 Hz, 1H), 3.42-3.26 (m, 2H), 2.16-1.98 (m, 1H), 1.79-1.60 (m, 1H), 1.19 (d, J = 12.6 Hz, 1H). | 257.3 |
| 6f | 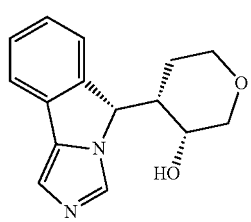 [SMILES: O[C@H]1COCC[C@H]1[C@H]1c2ccccc2-c2cncn21] | 1H NMR (300 MHz, CDCl3) δ 8.42 (s, 1H), 7.58 (d, J = 7.5 Hz, 1H), 7.53-7.23 (m, 4H), 5.42 (d, J = 3.6 Hz, 1H), 4.23 (s, 1H), 4.07 (d, J = 12.1 Hz, 1H), 3.94 (dd, J = 11.5, 4.8 Hz, 1H), 3.64-3.53 (m, 1H), 3.32 (td, J = 12.1, 2.3 Hz, 1H), 2.19 (dd, J = 12.2, 3.1 Hz, 1H), 1.66 (td, J = 12.9, 4.9 Hz, 1H), 1.26 (s, 1H), 1.09 (d, J = 13.1 Hz, 1H). | 257.2 |
| 6g | 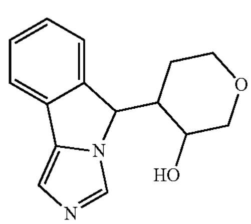 [SMILES: OC1COCCC1C1c2ccccc2-c2cncn21] | 1H NMR (400 MHz, DMSO-d6) δ 8.53 (s, 1H), 7.61 (d, J = 7.6 Hz, 1H), 7.50-7.40 (m, 2H), 7.31-7.29 (m, 2H), 5.30 (d, J = 9.0 Hz, 1H), 4.14-4.03 (m, 3H), 3.49-3.31 (m, 2H), 2.19 (qd, J = 12.6, 4.7 Hz, 1H), 1.90 (d, J = 13.3 Hz, 1H), 1.80-1.71 (m, 1H). | 257.3 |
| 6h | 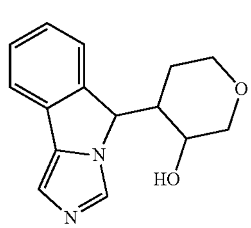 [SMILES: OC1COCCC1C1c2ccccc2-c2cncn21] | 8.11 (s, 1H), 7.60 (d, J = 7.6 Hz, 1H), 7.56-7.37 (m, 2H), 7.26-7.24 (m, 2H), 5.20 (d, J = 8.9 Hz, 1H), 4.12-4.01 (m, 3H), 3.47-3.31 (m, 2H), 2.15 (qd, J = 12.7, 4.9 Hz, 1H), 1.89 (d, d, J = 13.3 Hz, 1H), 1.78-1.69 (m, 1H). | 257.3 |

TABLE 2-continued

| Ex. # | Structure | $^1$H NMR | MS $(M + H)^+$ |
| --- | --- | --- | --- |
| 7a | 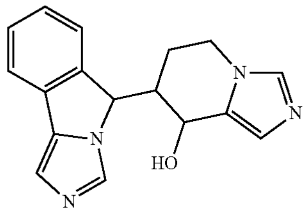 [SMILES: OC1c2cncn2CCC1C1c2ccccc2-c2cncn21] | $^1$HNMR (300 MHz, DMSO-$d_6$) δ 7.92 (s, 1H), 7.62 (m, 2H), 7.45-7.35 (m, 2H), 7.28-7.23 (m, 1H), 7.17 (s, 1H), 6.90 (s, 1H), 6.06 (d, J = 6.6 Hz, 1H), 5.76 (d, J = 3.0 Hz, 1H), 4.98-4.93 (m, 1H), 3.96-3.90 (m, 1H), 3.70-3.61 (m, 1H), 2.67-2.57 (m, 1H), 1.16-0.92 (m, 2H) | 293.1 |
| 7b | 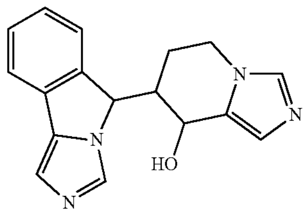 [SMILES: OC1c2cncn2CCC1C1c2ccccc2-c2cncn21] | $^1$HNMR (300 MHz, DMSO-$d_6$) δ 7.92 (s, 1H), 7.62 (m, 2H), 7.45-7.35 (m, 2H), 7.28-7.23 (m, 1H), 7.17 (s, 1H), 6.90 (s, 1H), 6.06 (d, J = 6.6 Hz, 1H), 5.76 (d, J = 3.0 Hz, 1H), 4.98-4.93 (m, 1H), 3.96-3.90 (m, 1H), 3.70-3.61 (m, 1H), 2.67-2.57 (m, 1H), 1.16-0.92 (m, 2H) | 293.1 |
| 7c | 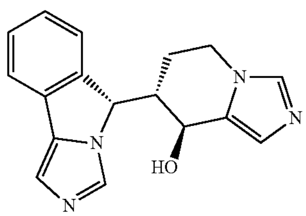 [SMILES: O[C@@H]1c2cncn2CC[C@H]1[C@H]1c2ccccc2-c2cncn21] | $^1$HNMR (300 MHz, DMSO-$d_6$) δ 7.97 (s, 1H), 7.65-7.62 (m, 1H), 7.51-7.39 (m, 3H), 7.35-7.29 (m, 1H), 7.18 (s, 1H), 6.93 (s, 1H), 7.78-7.75 (m, 1H), 5.05-4.99 (m, 1H), 3.95-3.89 (m, 1H), 3.58-3.68 (m, 1H), 2.49-2.40 (m, 1H), 1.04-0.95 (m, 2H) | 293.1 |
| 7d | 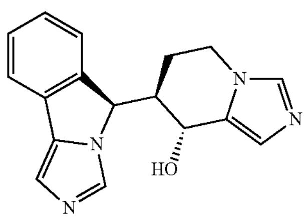 [SMILES: O[C@H]1c2cncn2CC[C@@H]1[C@@H]1c2ccccc2-c2cncn21] | $^1$HNMR (300 MHz, DMSO-$d_6$) δ 7.97 (s, 1H), 7.65-7.62 (m, 1H), 7.51-7.39 (m, 3H), 7.35-7.29 (m, 1H), 7.18 (s, 1H), 6.93 (s, 1H), 7.78-7.75 (m, 1H), 5.05-4.99 (m, 1H), 3.95-3.89 (m, 1H), 3.58-3.68 (m, 1H), 2.49-2.40 (m, 1H), 1.04-0.95 (m, 2H) | 293.1 |
| 7e | 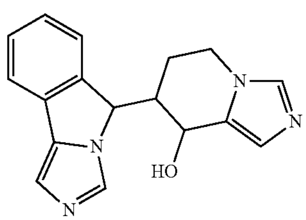 [SMILES: OC1c2cncn2CCC1C1c2ccccc2-c2cncn21] | $^1$HNMR (300 MHz, DMSO-$d_6$) δ 7.97 (s, 1H), 7.74-7.72 (m, 1H), 7.63-7.60 (m, 1H), 7.50 (s, 1H), 7.42-7.37 (t, 1H), 7.27-7.21 (m, 1H), 7.14 (s, 1H), 6.87 (s, 1H), 5.62-5.60 (m, 1H), 5.45-5.44 (m, 1H), 5.02-4.96 (m, 1H), 4.21-4.16 (m, 1H), 3.77-3.68 (m, 1H), 2.23-2.17 (m, 2H), 1.82-1.78 (m, 1H) | 293.1 |
| 7f | 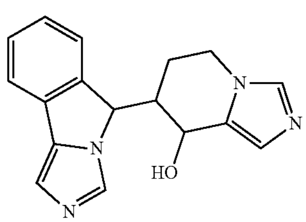 [SMILES: OC1c2cncn2CCC1C1c2ccccc2-c2cncn21] | $^1$HNMR (300 MHz, DMSO-$d_6$) δ 7.97 (s, 1H), 7.74-7.72 (m, 1H), 7.63-7.60 (m, 1H), 7.50 (s, 1H), 7.42-7.37 (t, 1H), 7.27-7.21 (m, 1H), 7.14 (s, 1H), 6.87 (s, 1H), 5.62-5.60 (m, 1H), 5.45-5.44 (m, 1H), 5.02-4.96 (m, 1H), 4.21-4.16 (m, 1H), 3.77-3.68 (m, 1H), 2.23-2.17 (m, 2H), 1.82-1.78 (m, 1H) | 293.1 |
| 7g | 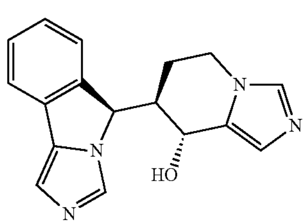 [SMILES: O[C@H]1c2cncn2CC[C@@H]1[C@@H]1c2ccccc2-c2cncn21] | same as 7h | 293.1 |

TABLE 2-continued
| Ex. # | Structure | $^1$H NMR | MS $(M + H)^+$ |
| --- | --- | --- | --- |
| 7h | 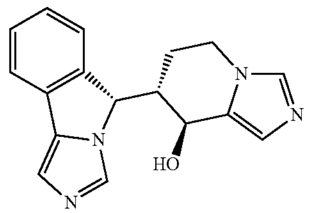 [SMILES: O[C@@H]1c2cncn2CC[C@H]1[C@H]1c2ccccc2-c2cncn21] | $^1$HNMR (300 MHz, DMSO-$d_6$) δ 7.95 (s, 1H), 7.65-7.57 (m, 2H), 7.49 (s, 1H), 7.42-7.36 (m, 1H), 7.31-7.26 (m, 1H), 7.12 (s, 1H), 6.92 (s, 1H), 5.90-5.86 (m, 1H), 5.53-5.50 (m, 1H), 5.21-5.18 (m, 1H), 4.09-4.03 (m, 1H), 3.67-3.57 (m, 1H), 2.56-2.51 (m, 1H), 1.86-1.71 (m, 1H), 1.15-1.07 (m, 1H) | 293.1 |
| 8a | 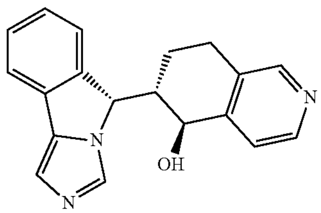 [SMILES: O[C@@H]1c2ccncc2CC[C@H]1[C@H]1c2ccccc2-c2cncn21] | $^1$HNMR (300 MHz, $CD_3OD$) δ 8.39-8.37 (m, 1H), 8.23 (s, 1H), 8.04 (s, 1H), 7.72-7.66 (m, 2H), 7.51-7.35 (m, 3H), 7.24 (s, 1H), 5.91 (s, 1H), 5.04 (d, J = 5.4 Hz, 1H), 2.71-2.68 (m, 2H), 2.53-2.46 (m, 1H), 1.20-1.17 (m, 1H), 1.08-0.94 (m, 1H). | 304.0 |
| 8b | 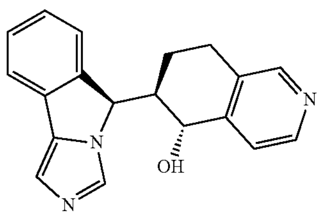 [SMILES: O[C@H]1c2ccncc2CC[C@@H]1[C@@H]1c2ccccc2-c2cncn21] | Same as 8a | 304.0 |
| 8c | 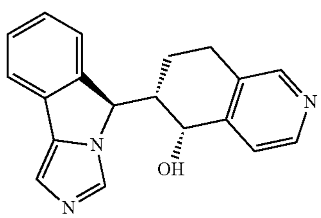 [SMILES: O[C@H]1c2ccncc2CC[C@H]1[C@@H]1c2ccccc2-c2cncn21] | $^1$HNMR (300 MHz, $CD_3OD$) δ 8.31 (s, 2H), 8.06 (s, 1H), 8.04 (s, 1H), 7.70-7.62 (m, 2H), 7.43-7.24 (m, 3H), 7.17 (s, 1H), 5.54-5.52 (m, 1H), 4.79-4.78 (m, 1H), 3.00-2.92 (m, 1H), 2.78-2.68 (m, 1H), 2.32-2.25 (m, 1H), 2.10-1.99 (m, 2H) | 304.0 |
| 8d | 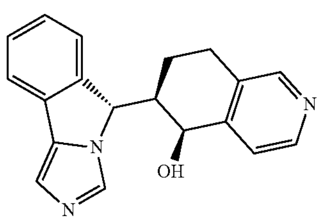 [SMILES: O[C@@H]1c2ccncc2CC[C@@H]1[C@H]1c2ccccc2-c2cncn21] | Same as 8c | 304.0 |
| 8e | 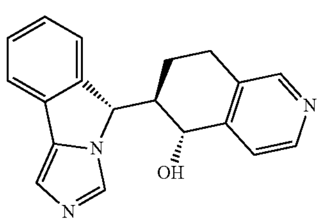 [SMILES: O[C@H]1c2ccncc2CC[C@@H]1[C@H]1c2ccccc2-c2cncn21] | 1HNMR (300 MHz, CD3OD) δ 8.38-8.36 (m, 1H), 8.23 (s, 1H), 7.92 (s, 1H), 7.69-7.61 (M, 3h), 7.46-7.42 (m, 1H), 7.35-7.29 (m, 1H), 7.20 (s, 1H), 5.90-5.89 (m, 1H), 4.98 (d, J = 5.1 Hz, 1H), 2.71-2.68 (m, 2H), 2.72-2.58 (m, 3H), 1.14-0.97 (m, 2H). | 304.0 |
| 8f | 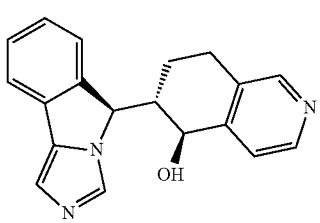 [SMILES: O[C@@H]1c2ccncc2CC[C@H]1[C@@H]1c2ccccc2-c2cncn21] | Same as 8e | 304.0 |

TABLE 2-continued
| Ex. # | Structure | $^1$H NMR | MS $(M + H)^+$ |
|---|---|---|---|
| 8g | 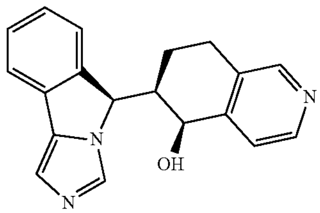 [SMILES: O[C@@H]1c2ccncc2CC[C@@H]1[C@@H]1c2ccccc2-c2cncn21] | Same as 8h | 304.0 |
| 8h | 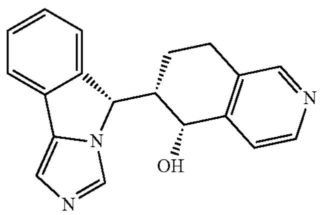 [SMILES: O[C@H]1c2ccncc2CC[C@H]1[C@H]1c2ccccc2-c2cncn21] | $^1$HNMR (300 MHz, $CD_3OD$) δ 8.39-8.38 (m, 1H), 8.30 (s, 1H), 8.07 (s, 1H), 7.63-7.57 (m, 2H), 7.54-7.49 (m, 1H), 7.45-7.41 (m, 1H), 7.36-7.32 (m, 1H), 7.14 (s, 1H), 5.63-5.61 (m, 1H), 5.12-5.11 (m, 1H), 2.82-2.77 (m, 1H), 2.64-2.53 (m, 2H), 1.58-1.48 (m, 1H), 1.15-1.13 (m, 1H). | 304.0 |
| 9a | 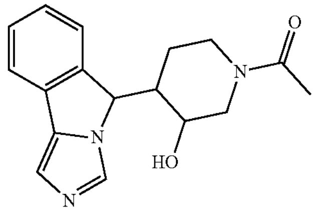 [SMILES: CC(=O)N1CCC(C2c3ccccc3-c3cncn32)C(O)C1] | $^1$HNMR (300 MHz, $CD_3OD$) δ 7.95-7.90 (m, 1H), 7.64-7.62 (m, 1H), 7.52-7.36 (m, 3H), 7.20 (s, 1H), 5.84-5.83 (m, 1H), 4.88-3.67 (m, 3H), 3.06-2.85 (m, 1H), 2.55-2.28 (m, 2H), 2.14-1.98 (m, 3H), 1.00-0.85 (m, 1H), 0.59-0.58 (m, 1H) | 298.2 |
| 9b | 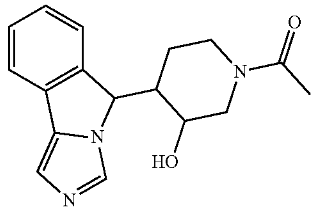 [SMILES: CC(=O)N1CCC(C2c3ccccc3-c3cncn32)C(O)C1] | same as 9a | 298.2 |
| 9c | 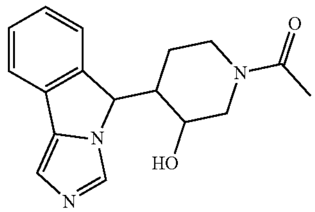 [SMILES: CC(=O)N1CCC(C2c3ccccc3-c3cncn32)C(O)C1] | $^1$HNMR (400 MHz, $CD_3OD$) δ 7.91 (s, 1H), 7.63-7.62 (m, 1H), 7.53-7.50 (m, 1H), 7.43-7.39 (m, 1H), 7.32-7.28 (m, 1H), 7.15 (s, 1H), 5.82-5.80 (m, 1H), 4.86-3.65 (m, 3H), 3.00-2.93 (m, 1H), 2.49-2.35 (m, 2H), 2.09-1.94 (m, 3H), 0.84-0.71 (m, 1H), 0.63-0.42 (m, 1H); | 298.2 |
| 9d | 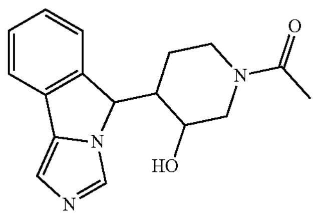 [SMILES: CC(=O)N1CCC(C2c3ccccc3-c3cncn32)C(O)C1] | same as 9c | 298.2 |
| 10a | 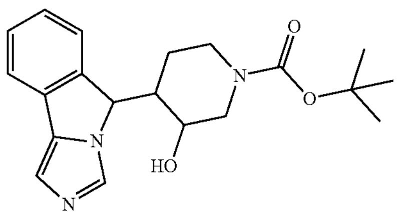 [SMILES: CC(C)(C)OC(=O)N1CCC(C2c3ccccc3-c3cncn32)C(O)C1] | $^1$HNMR (400 MHz, $CD_3OD$) δ 7.89 (s, 1H), 7.64 (d, J = 7.6 Hz, 1H), 7.49 (d, J = 7.6 Hz, 1H), 7.45-7.34 (m, 2H), 7.20 (s, 1H), 5.82 (d, J = 4.0 Hz, 1H), 4.37-4.33 (m, 1H), 3.86-3.71 (m, 2H), 2.62-2.50 (m, 2H), 2.27-2.20 (m, 1H), 1.43 (s, 9H), 0.87-0.83 (m, 1H), 0.47-0.42 (m, 1H) | 356.2 |

TABLE 2-continued
| Ex. # | Structure | $^1$H NMR | MS (M + H)$^+$ |
|---|---|---|---|
| 10b | 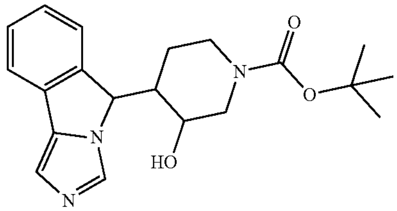 [SMILES: CC(C)(C)OC(=O)N1CCC(C2c3ccccc3-c3cncn32)C(O)C1] | $^1$HNMR (400 MHz, $CD_3OD$) δ 7.89 (s, 1H), 7.64 (d, J = 7.6 Hz, 1H), 7.49 (d, J = 7.6 Hz, 1H), 7.45-7.34 (m, 2H), 7.20 (s, 1H), 5.82 (d, J = 4.0 Hz, 1H), 4.37-4.33 (m, 1H), 3.86-3.71 (m, 2H), 2.62-2.50 (m, 2H), 2.27-2.20 (m, 1H), 1.43 (s, 9H), 0.87-0.83 (m, 1H), 0.47-0.42 (m, 1H). | 356.2 |
| 10c | 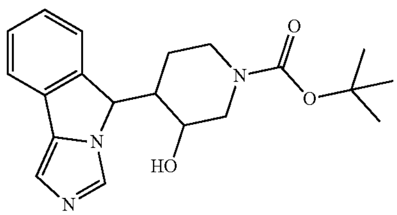 [SMILES: CC(C)(C)OC(=O)N1CCC(C2c3ccccc3-c3cncn32)C(O)C1] | $^1$HNMR (400 MHz, $CD_3OD$) δ 7.93 (s, 1H), 7.65 (d, J = 7.6 Hz, 1H), 7.53 (d, J = 7.6 Hz, 1H), 7.46-7.42 (m, 1H), 7.35-7.31 (m, 1H), 7.17 (s, 1H), 5.82 (d, J = 4.0 Hz, 1H), 4.31-4.28 (m, 1H), 3.87-3.74 (m, 2H), 2.61-2.50 (m, 2H), 2.40-2.34 (m, 1H), 1.41 (s, 9H), 0.73-0.70 (m, 1H), 0.56-0.46 (m, 1H). | 356.2 |
| 10d | 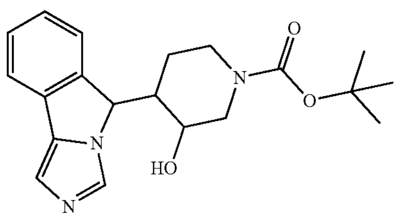 [SMILES: CC(C)(C)OC(=O)N1CCC(C2c3ccccc3-c3cncn32)C(O)C1] | $^1$HNMR (400 MHz, $CD_3OD$) δ 7.93 (s, 1H), 7.65 (d, J = 7.6 Hz, 1H), 7.53 (d, J = 7.6 Hz, 1H), 7.46-7.42 (m, 1H), 7.35-7.31 (m, 1H), 7.17 (s, 1H), 5.82 (d, J = 4.0 Hz, 1H), 4.31-4.28 (m, 1H), 3.87-3.74 (m, 2H), 2.61-2.50 (m, 2H), 2.40-2.34 (m, 1H), 1.41 (s, 9H), 0.73-0.70 (m, 1H), 0.56-0.46 (m, 1H) | 356.2 |
| 11a | 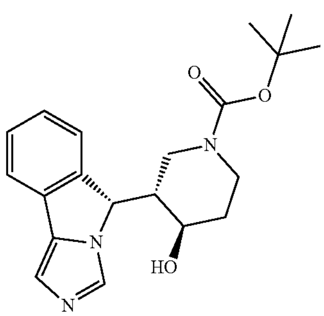 [SMILES: CC(C)(C)OC(=O)N1CC[C@@H](O)[C@H]([C@H]2c3ccccc3-c3cncn32)C1] | $^1$HNMR (400 MHz, $CD_3OD$) δ 7.96 (s, 1H), 7.66 (d, J = 7.2 Hz, 1H), 7.54 (d, J = 7.2 Hz, 1H), 7.46-7.38 (m, 2H), 7.21 (s, 1H), 5.83 (d, J = 4.0 Hz, 1H), 4.07-4.00 (m, 2H), 3.34-3.32 (m, 1H), 2.79-2.65 (m, 1H), 2.21-2.07 (m, 2H), 1.84-1.77 (m, 1H), 1.60-1.49 (m, 1H), 1.27 (s, 9H) | 356.2 |
| 11b | 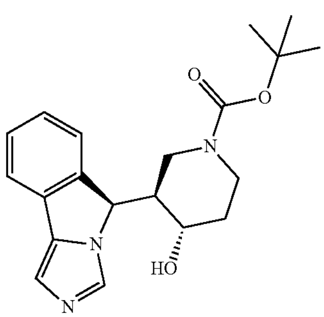 [SMILES: CC(C)(C)OC(=O)N1CC[C@H](O)[C@@H]([C@@H]2c3ccccc3-c3cncn32)C1] | Same as 11a | 356.2 |

TABLE 2-continued
| Ex. # | Structure | $^1$H NMR | MS (M + H)$^+$ |
|---|---|---|---|
| 11c | 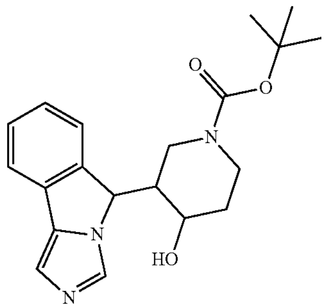 [SMILES: CC(C)(C)OC(=O)N1CCC(O)C(C2c3ccccc3-c3cncn32)C1] | $^1$HNMR (400 MHz, $CD_3OD$) δ 7.98 (s, 1H), 7.67 (d, J = 7.6 Hz, 1H), 7.61 (d, J = 7.6 Hz, 1H), 7.47-7.33 (m, 2H), 7.21 (s, 1H), 5.84 (d, J = 4.0 Hz, 1H), 4.06-4.00 (m, 2H), 3.18-3.11 (m, 1H), 2.71-2.55 (m, 1H), 2.35-2.21 (m, 1H), 2.11-2.04 (m, 1H), 1.95-1.85 (s, 1H), 1.61-1.49 (m, 1H), 1.37 (s, 9H) | 356.2 |
| 11d | 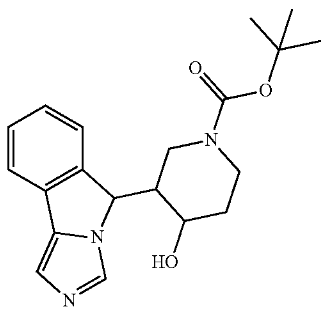 [SMILES: CC(C)(C)OC(=O)N1CCC(O)C(C2c3ccccc3-c3cncn32)C1] | $^1$HNMR (400 MHz, $CD_3OD$) δ 7.98 (s, 1H), 7.67 (d, J = 7.6 Hz, 1H), 7.61 (d, J = 7.6 Hz, 1H), 7.47-7.33 (m, 2H), 7.21 (s, 1H), 5.84 (d, J = 4.0 Hz, 1H), 4.06-4.00 (m, 2H), 3.18-3.11 (m, 1H), 2.71-2.55 (m, 1H), 2.35-2.21 (m, 1H), 2.11-2.04 (m, 1H), 1.95-1.85 (s, 1H), 1.61-1.49 (m, 1H), 1.37 (s, 9H) | 356.2 |
| 12a | 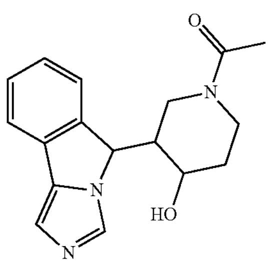 [SMILES: CC(=O)N1CCC(O)C(C2c3ccccc3-c3cncn32)C1] | δ 8.05-7.92 (m, 1H), 7.70-7.62 (m, 2H), 7.49-7.35 (m, 2H), 7.24-7.20 (m, 1H), 5.87-5.82 (m, 1H), 4.55-4.45 (m, 0.5H), 4.12-4.05 (m, 1H), 3.94-3.71 (m, 1H), 3.55-3.53 (m, 0.5H), 3.01-2.75 (m, 1H), 2.51-2.04 (m, 4H), 1.82-1.75 (m, 3H) | 298.2 |
| 12b | 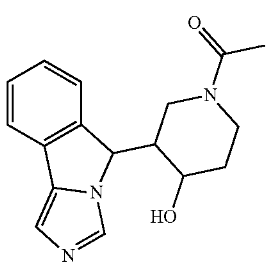 [SMILES: CC(=O)N1CCC(O)C(C2c3ccccc3-c3cncn32)C1] | same as 12a | 298.2 |
| 12c | 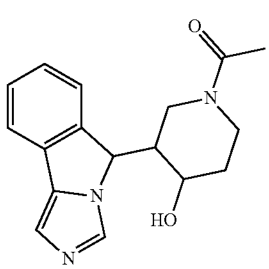 [SMILES: CC(=O)N1CCC(O)C(C2c3ccccc3-c3cncn32)C1] | $^1$HNMR (400 MHz, $CD_3OD$) δ 7.95-7.90 (m, 1H), 7.69-7.60 (m, 1H), 7.50-7.37 (m, 3H), 7.21 (s, 1H), 5.84-5.82 (m, 1H), 4.55-4.45 (m, 0.5H), 4.08-4.07 (m, 1H), 3.88-3.84 (m, 1H), 3.05-2.98 (m, 1H), 2.55-2.53 (m, 0.5H), 2.27-2.03 (m, 4H), 1.72-1.48 (m, 3H) | 298.2 |

TABLE 2-continued
| Ex. # | Structure | $^1$H NMR | MS $(M+H)^+$ |
|---|---|---|---|
| 12d | 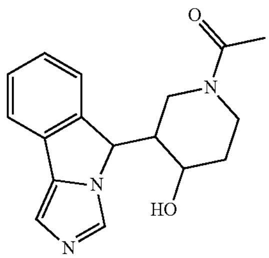 [SMILES: CC(=O)N1CCC(O)C(C2c3ccccc3-c3cncn32)C1] | same as 12c | 298.2 |
| 13a | 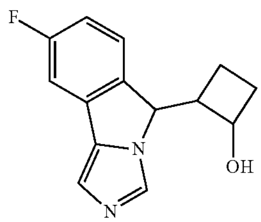 [SMILES: OC1CCC1C1c2ccc(F)cc2-c2cncn21] | $^1$HNMR (300 MHz, $CD_3OD$) δ 7.93 (s, 1H), 7.63-7.59 (m, 1H), 7.40-7.37 (m, 1H), 7.23 (s, 1H), 7.08-7.02 (m, 1H), 5.37 (d, J = 9 Hz, 1H), 4.34-4.30 (m, 1H), 2.62-2.46 (m, 1H), 2.32-2.14 (m, 1H), 1.88-1.67 (m, 2H), 1.38-1.20 (m, 2H). | 245.2 |
| 13b | 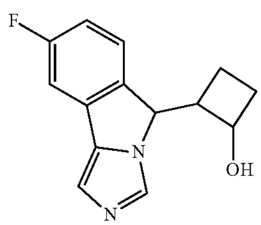 [SMILES: OC1CCC1C1c2ccc(F)cc2-c2cncn21] | $^1$HNMR (300 MHz, $CD_3OD$) δ 7.93 (s, 1H), 7.63-7.59 (m, 1H), 7.40-7.37 (m, 1H), 7.23 (s, 1H), 7.08-7.02 (m, 1H), 5.37 (d, J = 9 Hz, 1H), 4.34-4.30 (m, 1H), 2.62-2.46 (m, 1H), 2.32-2.14 (m, 1H), 1.88-1.67 (m, 2H), 1.38-1.20 (m, 2H). | 245.2 |
| 13c | 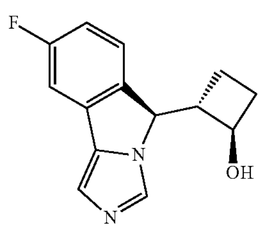 [SMILES: O[C@@H]1CC[C@H]1[C@@H]1c2ccc(F)cc2-c2cncn21] | $^1$HNMR (300 MHz, $CD_3OD$) δ 8.01 (s, 1H), 7.46-7.37 (m, 2H), 7.19 (s, 1H), 7.10-6.95 (m, 1H), 5.33 (d, J = 6 Hz, 1H), 4.22-4.18 (m, 1H), 2.52-2.34 (m, 1H), 2.36-2.23 (m, 1H), 2.01-1.79 (m, 2H), 1.78-1.59 (m, 1H) | 245.2 |
| 13d | 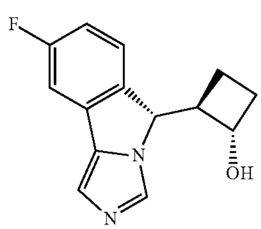 [SMILES: O[C@H]1CC[C@@H]1[C@H]1c2ccc(F)cc2-c2cncn21] | $^1$HNMR (300 MHz, $CD_3OD$) δ 8.01 (s, 1H), 7.46-7.37 (m, 2H), 7.19 (s, 1H), 7.10-6.95 (m, 1H), 5.33 (d, J = 21 Hz, 1H), 4.22-4.18 (m, 1H), 2.52-2.34 (m, 1H), 2.36-2.23 (m, 1H), 2.01-1.79 (m, 2H), 1.78-1.59 (m, 1H) | 245.2 |
| 13e | 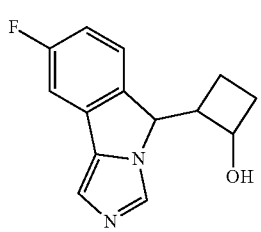 [SMILES: OC1CCC1C1c2ccc(F)cc2-c2cncn21] | $^1$HNMR (300 MHz, $CD_3OD$) δ 8.19 (s, 1H), 7.58-7.53 (m, 1H), 7.39-7.36 (m, 1H), 7.23 (s, 1H), 7.09-6.96 (m, 1H), 5.55 (d, J = 5.9 Hz, 1H), 4.68-4.64 (m, 1H), 3.05-2.87 (m, 1H), 2.41-2.20 (m, 1H), 1.97-1.76 (m, 2H), 1.59-1.50 (m, 1H) | 245.2 |

TABLE 2-continued
| Ex. # | Structure | $^1$H NMR | MS (M + H)$^+$ |
|---|---|---|---|
| 13f | 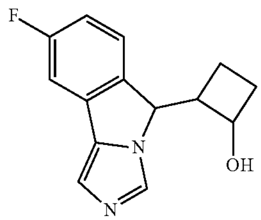 [SMILES: OC1CCC1C1c2ccc(F)cc2-c2cncn21] | $^1$HNMR (300 MHz, $CD_3OD$) δ 8.19 (s, 1H), 7.58-7.53 (m, 1H), 7.39-7.36 (m, 1H), 7.23 (s, 1H), 7.09-6.96 (m, 1H), 5.55 (d, J = 5.9 Hz, 1H), 4.68-4.64 (m, 1H), 3.05-2.87 (m, 1H), 2.41-2.20 (m, 1H), 1.97-1.76 (m, 2H), 1.59-1.50 (m, 1H) | 245.2 |
| 13g | 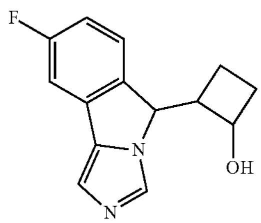 [SMILES: OC1CCC1C1c2ccc(F)cc2-c2cncn21] | $^1$HNMR (300 MHz, $CD_3OD$) δ 7.98 (s, 1H), 7.53-7.48 (m, 1H), 7.40-7.36 (m, 1H), 7.19 (s, 1H), 7.01-6.93 (m, 1H), 5.51 (d, J = 9.0 Hz, 1H), 4.56-4.51 (m, 1H), 2.60-2.31 (m, 3H), 2.21-1.90 (m, 2H) | 245.2 |
| 13h | 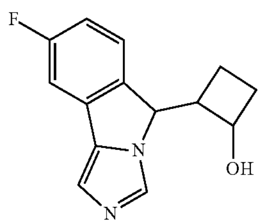 [SMILES: OC1CCC1C1c2ccc(F)cc2-c2cncn21] | $^1$HNMR (300 MHz, $CD_3OD$) δ 7.98 (s, 1H), 7.53-7.48 (m, 1H), 7.40-7.36 (m, 1H), 7.19 (s, 1H), 7.01-6.93 (m, 1H), 5.51 (d, J = 9.0 Hz, 1H), 4.56-4.51 (m, 1H), 2.60-2.31 (m, 3H), 2.21-1.90 (m, 2H) | 245.2 |
| 14a | 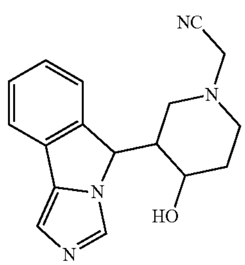 [SMILES: N#CCN1CCC(O)C(C2c3ccccc3-c3cncn32)C1] | $^1$HNMR (300 MHz, $CD_3OD$) δ 7.93 (s, 1H), 7.66 (d, J = 7.6 Hz, 1H), 7.52 (d, J = 7.5 Hz, 1H), 7.48-7.34 (m, 2H), 7.22 (s, 1H), 5.82 (d, J = 3.0 Hz, 1H), 3.95-3.83 (m, 1H), 3.52-3.33 (m, 2H), 2.92-2.83 (m, 1H), 2.47-2.05 (m, 4H), 1.85-1.73 (m, 1H), 1.48-1.41 (m, 1H) | 295.1 |
| 14b | 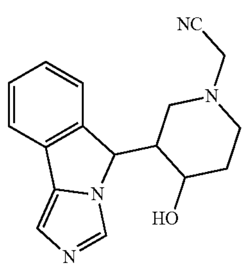 [SMILES: N#CCN1CCC(O)C(C2c3ccccc3-c3cncn32)C1] | Same as 14a | 295.1 |
| 14c | 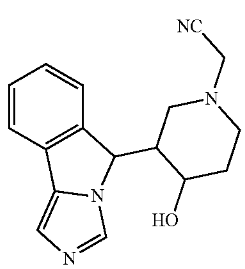 [SMILES: N#CCN1CCC(O)C(C2c3ccccc3-c3cncn32)C1] | $^1$HNMR (400 MHz, $CD_3OD$) δ 7.89 (s, 1H), 7.64 (d, J = 7.6 Hz, 1H), 7.49 (d, J = 7.6 Hz, 1H), 7.45-7.34 (m, 2H), 7.20 (s, 1H), 5.82 (d, J = 4.0 Hz, 1H), 4.37-4.33 (m, 1H), 3.86-3.71 (m, 2H), 2.62-2.50 (m, 2H), 2.27-2.20 (m, 1H), 1.43 (s, 9H), 0.87-0.83 (m, 1H), 0.47-0.42 (m, 1H) | 295.1 |

TABLE 2-continued
| Ex. # | Structure | $^1$H NMR | MS (M + H)$^+$ |
|---|---|---|---|
| 14d | 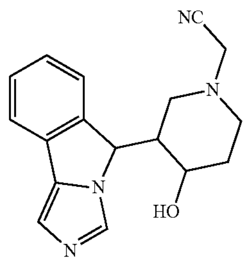 [SMILES: N#CCN1CCC(O)C(C2c3ccccc3-c3cncn32)C1] | Same as 14c | 295.1 |
| 15a | 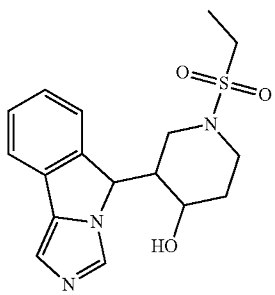 [SMILES: CCS(=O)(=O)N1CCC(O)C(C2c3ccccc3-c3cncn32)C1] | $^1$HNMR (400 MHz, $CD_3OD$) δ 7.98 (s, 1H), 7.66 (d, J = 7.6 Hz, 1H), 7.2 (d, J = 7.6 Hz, 1H), 7.48-7.34 (m, 2H), 7.21 (s, 1H), 5.85 (d, J = 4.0 Hz, 1H), 4.01-3.98 (m, 1H), 3.74-3.70 (m, 1H), 2.90-2.76 (m, 4H), 2.55-2.45 (m, 1H), 2.13-2.05 (m, 2H), 1.80-1.68 (m, 1H), 1.16 (t, J = 7.2 Hz, 3H) | 348.2 |
| 15b | 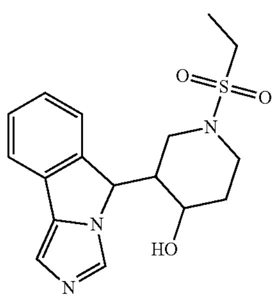 [SMILES: CCS(=O)(=O)N1CCC(O)C(C2c3ccccc3-c3cncn32)C1] | Same as 15a | 348.2 |
| 15c | 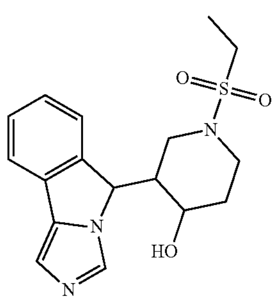 [SMILES: CCS(=O)(=O)N1CCC(O)C(C2c3ccccc3-c3cncn32)C1] | $^1$HNMR (400 MHz, $CD_3OD$) δ 7.93 (s, 1H), 7.64 (d, J = 7.6 Hz, 1H), 7.51 (d, J = 7.6 Hz, 1H), 7.45-7.37 (m, 2H), 7.19 (s, 1H), 5.83 (d, J = 3.6 Hz, 1H), 4.03-3.92 (m, 1H), 3.75-3.65 (m, 1H), 3.02-2.98 (m, 1H), 2.85-2.70 (m, 3H), 2.40-2.30 (m, 1H), 2.20-2.15 (m, 1H), 2.00-1.90 (m, 1H), 1.79-1.65 (m, 1H), 1.12 (t, J = 7.2 Hz, 3H) | 348.2 |
| 15d | 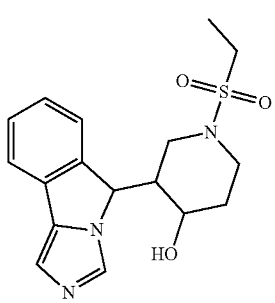 [SMILES: CCS(=O)(=O)N1CCC(O)C(C2c3ccccc3-c3cncn32)C1] | Same as 15c | 348.2 |

TABLE 2-continued

| Ex. # | Structure | $^1$H NMR | MS (M + H)$^+$ |
|---|---|---|---|
| 16a | 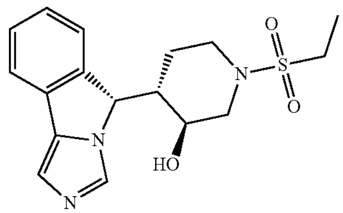 [SMILES: CCS(=O)(=O)N1CC[C@@H]([C@H]2c3ccccc3-c3cncn32)[C@H](O)C1] | $^1$HNMR (400 MHz, $CD_3OD$) δ 7.95 (s, 1H), 7.65 (d, J = 7.6 Hz, 1H), 7.55 (d, J = 7.6 Hz, 1H), 7.46-7.32 (m, 2H), 7.17 (s, 1H), 5.83 (d, J = 3.6 Hz, 1H), 4.01-3.90 (m, 2H), 3.53-4.90 (m, 1H), 3.00 (q, J = 7.2 Hz, 2H), 2.74-2.65 (m, 2H), 2.42-2.30 (m, 1H), 1.30 (t, J = 7.2 Hz, 3H), 0.85-0.79 (m, 1H), 0.75-0.60 (m, 1H) | 348.2 |
| 16b | 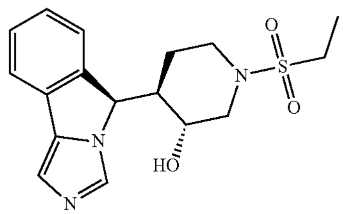 [SMILES: CCS(=O)(=O)N1CC[C@H]([C@@H]2c3ccccc3-c3cncn32)[C@@H](O)C1] | Same as 16a | 348.2 |
| 16c | 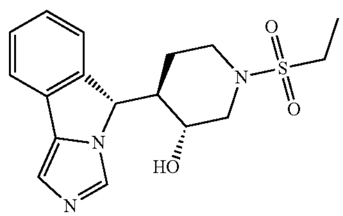 [SMILES: CCS(=O)(=O)N1CC[C@H]([C@H]2c3ccccc3-c3cncn32)[C@@H](O)C1] | $^1$HNMR (400 MHz, $CD_3OD$) δ 7.93 (s, 1H), 7.64 (d, J = 7.6 Hz, 1H), 7.50 (d, J = 7.6 Hz, 1H), 7.46-7.35 (m, 2H), 7.21 (s, 1H), 5.84 (d, J = 3.6 Hz, 1H), 4.03-3.83 (m, 2H), 3.54-3.51 (m, 1H), 3.03 (q, J = 7.2 Hz, 2H), 2.78-2.67 (m, 2H), 2.25-2.19 (m, 1H), 1.30 (t, J = 7.2 Hz, 3H), 0.98-0.94 (m, 1H), 0.69-0.55 (m, 1H) | 348.2 |
| 16d | 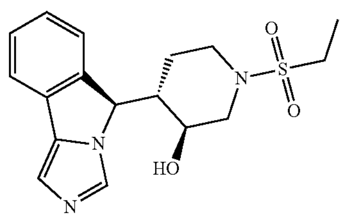 [SMILES: CCS(=O)(=O)N1CC[C@@H]([C@@H]2c3ccccc3-c3cncn32)[C@H](O)C1] | Same as 16c | 348.2 |
| 17a | 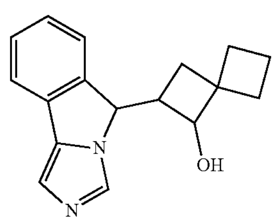 [SMILES: OC1C(C2c3ccccc3-c3cncn32)CC12CCC2] | NA | 267 |
| 17b | 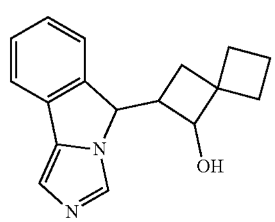 [SMILES: OC1C(C2c3ccccc3-c3cncn32)CC12CCC2] | $^1$H NMR (400 MHz, DMSO-$d_6$) δ 7.90 (s, 1H), 7.65-7.46 (m, 1H), 7.44-7.29 (m, 2H), 7.23 (td, J = 7.5, 1.1 Hz, 1H), 7.09 (s, 1H), 5.30 (d, J = 7.6 Hz, 2H), 3.86 (t, J = 7.5 Hz, 1H), 2.42-2.23 (m, 1H), 2.09-1.69 (m, 5H), 1.69-1.45 (m, 2H) | 267 |
| 17c | 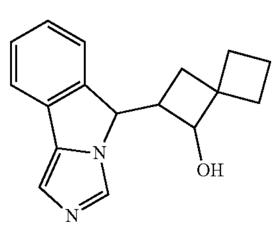 [SMILES: OC1C(C2c3ccccc3-c3cncn32)CC12CCC2] | $^1$H NMR (400 MHz, DMSO-$d_6$) δ 7.90 (s, 1H), δ 7.59 (t, J = 8.0 Hz, 2H), 7.36 (dd, J = 7.9, 6.8 Hz, 1H), 7.25 (td, J = 7.5, 1.0 Hz, 1H), 7.09 (s, 1H), 5.75 (d, J = 4.9 Hz, 1H), 5.35 (d, J = 8.3 Hz, 1H), 4.18 (s, 1H), 2.42 (d, J = 8.3 Hz, 1H), 2.35-2.18 (m, 1H), 2.04 (t, J = 9.9 Hz, 1H), 1.90 (q, J = 6.6 Hz, 3H), 1.76 (q, J = 7.3 Hz, 2H), 1.56 (d, J = 10.0 Hz, 1H) | 267 |

TABLE 2-continued
| Ex. # | Structure | $^1$H NMR | MS (M + H)$^+$ |
|---|---|---|---|
| 17d | 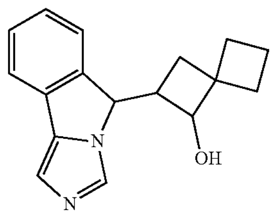 [SMILES: OC1C(C2c3ccccc3-c3cncn32)CC12CCC2] | NA | 267 |
| 17e | 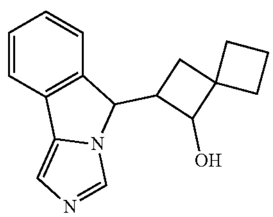 [SMILES: OC1C(C2c3ccccc3-c3cncn32)CC12CCC2] | Same as 17b | 267 |
| 18a | 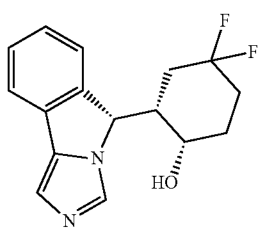 [SMILES: O[C@H]1CCC(F)(F)C[C@H]1[C@H]1c2ccccc2-c2cncn21] | $^1$H NMR (400 MHz, DMSO-d$_6$) δ 8.02 (s, 1H), 7.61-7.55 (m, 2H), 7.39 (d, J = 1.1 Hz, 1H), 7.32-7.32 (m, 1H), 5.45 (s, 1H), 7.11 (s, 1H), 5.32 (d, J = 3.1 Hz, 1H), 4.29 (s, 1H), 2.38-2.31 (m, 1H), 2.15-1.95 (m, 1H), 1.94-1.78 (m, 2H), 1.77-1.67 (m, 1H), 1.65-1.46 (m, 1H), 1.15-1.03 (m, 1H) | 291.26 |
| 18b | 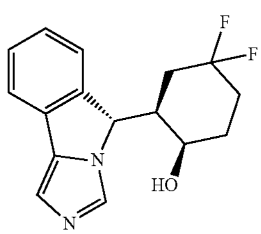 [SMILES: O[C@@H]1CCC(F)(F)C[C@@H]1[C@H]1c2ccccc2-c2cncn21] | $^1$H NMR (400 MHz, DMSO-d$_6$) δ 7.91 (s, 1H), 7.69 (d, J = 7.6 Hz, 1H), 7.60 (d, J = 7.4 Hz, 1H), 7.39 (t, J = 7.6 Hz, 1H), 7.27 (dd, J = 7.5, 1.4 Hz, 1H), 7.12 (s, 1H), 5.33 (d, J = 6.2 Hz, 1H), 5.09-5.05 (s, 1H), 4.07 (s, 1H), 2.22-1.96 (m, 3H), 1.91-1.79 (m, 3H), 1.65-1.54 (m, 1H) | 291.3 |
| 18c | 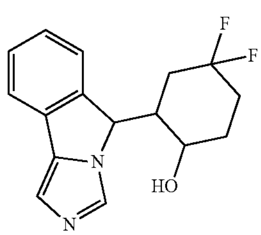 [SMILES: OC1CCC(F)(F)CC1C1c2ccccc2-c2cncn21] | $^1$H NMR (400 MHz, DMSO-d$_6$) δ 7.95 (s, 1H), 7.63 (d, J = 7.8 Hz, 1H), 7.54 (d, J = 7.6 Hz, 1H), 7.42 (t, J = 1.0 Hz, 1H), 7.31 (dd, J = 7.6, 1.4 Hz, 1H), 7.15 (s, 1H), 5.72 (t, J = 3.2 Hz, 1H) 5.52 (s, 1H), 3.87-3.76 (m, 1H), 2.04-1.70 (m, 3H), 1.58-1.45 (m, 1H), 0.90-0.73 (m, 2H) | 291.3 |
| 18d | 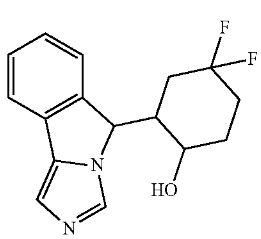 [SMILES: OC1CCC(F)(F)CC1C1c2ccccc2-c2cncn21] | Same as 18c | 291.3 |

TABLE 2-continued

| Ex. # | Structure | $^1$H NMR | MS (M + H)$^+$ |
|---|---|---|---|
| 18e | 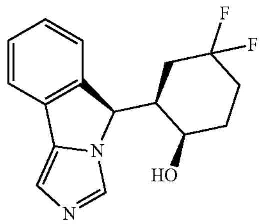 [SMILES: O[C@@H]1CCC(F)(F)C[C@@H]1[C@@H]1c2ccccc2-c2cncn21] | Same as 18a | 291.3 |
| 18f | 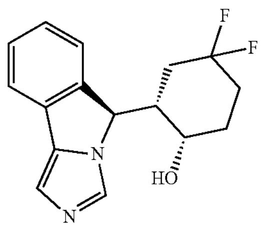 [SMILES: O[C@H]1CCC(F)(F)C[C@H]1[C@@H]1c2ccccc2-c2cncn21] | Same as 18b | 291.3 |
| 18g | 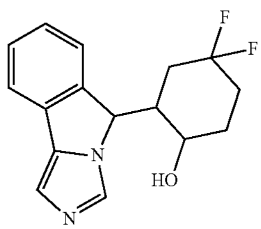 [SMILES: OC1CCC(F)(F)CC1C1c2ccccc2-c2cncn21] | $^1$H NMR (400 MHz, DMSO-d$_6$) δ 7.85 (s, 1H), 7.62 (d, J = 7.4 Hz, 1H), 7.48 (d, J = 7.4 Hz, 1H), 7.41 (t, J = 7.5 Hz, 1H), 7.35-7.29 (m, 1H), 7.18 (s, 1H), 5.74 (s, 1H), 5.55 (d, J = 5.8 Hz, 1H), 3.86 (dt, J = 10.8, 5.8 Hz, 1H), 2.34-2.22 (m, 1H), 2.08-1.77 (m, 2H), 1.48-1.61 (m, 1H), 0.99 (d, J = 5.4 Hz, 1H), 0.90-0.70 (m, 1H). | 291.3 |
| 18h | 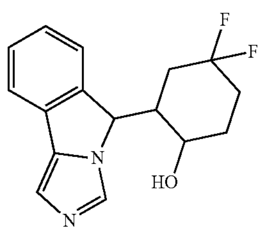 [SMILES: OC1CCC(F)(F)CC1C1c2ccccc2-c2cncn21] | Same as 18g | 291.3 |
| 19a | 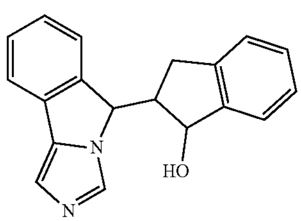 [SMILES: OC1c2ccccc2CC1C1c2ccccc2-c2cncn21] | (400 MHz, DMSO-d$_6$) δ 7.88 (s, 1H), 7.62 (d, J = 7.4 Hz, 1H), 7.53 (d, J = 7.7 Hz, 1H), 7.37 (d, J = 7.5 Hz, 1H), 7.27 (d, J = 5.5 Hz, 1H), 7.25-7.21 (m, 1H), 7.20-7.14 (m, 2H), 7.12 (s, 2H), 5.70 (d, J = 4.9 Hz, 1H), 5.57 (d, J = 6.5 Hz, 1H), 5.09 (s, 1H), 2.95 (dd, J = 7.3, 4.9 Hz, 1H), 2.78 (dd, J = 15.9, 8.6 Hz, 1H). | 289.3 |
| 19b | 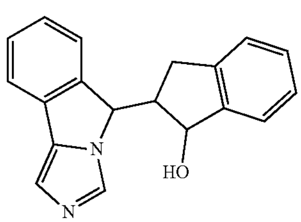 [SMILES: OC1c2ccccc2CC1C1c2ccccc2-c2cncn21] | (400 MHz, DMSO-d$_6$) δ 7.88 (s, 1H), 7.62 (d, J = 7.6 Hz, 1H), 7.53 (d, J = 7.5 Hz, 1H), 7.38 (t, J = 7.6 Hz, 1H), 7.29-7.25 (m, 1H), 7.25-7.20 (m, 1H), 7.19-7.15 (m, 2H), 7.11 (d, J = 6.1 Hz, 2H), 5.70 (d, J = 4.9 Hz, 1H), 5.57 (d, J = 6.5 Hz, 1H), 5.09 (t, J = 6.7 Hz, 1H), 2.95 (tdd, J = 8.6, 7.0, 5.0 Hz, 1H), 2.78 (dd, J = 15.9, 8.6 Hz, 1H), 2.48-2.39 (m, 1H). | 289.3 |
| 19c | 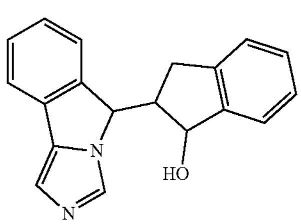 [SMILES: OC1c2ccccc2CC1C1c2ccccc2-c2cncn21] | (400 MHz, DMSO-d$_6$) δ 8.05 (s, 1H), 7.62 (d, J = 7.8 Hz, 1H), 7.55 (d, J = 7.7 Hz, 1H), 7.49-7.42 (m, 1H), 7.38 (t, J = 7.4 Hz, 1H), 7.26-7.18 (m, 4H), 7.16 (s, 1H), 5.77 (d, J = 6.2 Hz, 1H), 5.53 (d, J = 9.8 Hz, 1H), 5.17 (t, J = 6.0 Hz, 1H), 3.28-3.20 (m, 1H), 2.97 (dd, J = 15.5, 7.8 Hz, 1H), 2.40 (tdd, J = 9.5, 7.7, 5.9 Hz, 1H). | 289.3 |

TABLE 2-continued

| Ex. # | Structure | $^1$H NMR | MS (M + H)$^+$ |
|---|---|---|---|
| 19d | 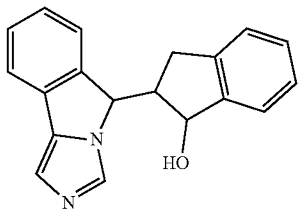 [SMILES: OC1c2ccccc2CC1C1c2ccccc2-c2cncn21] | (400 MHz, DMSO-$d_6$) δ 7.72 (d, J = 7.5 Hz, 1H), 7.60 (d, J = 7.2 Hz, 1H), 7.51 (s, 1H), 7.46-7.37 (m, 2H), 7.32 (dd, J = 7.5, 1.4 Hz, 1H), 7.26-7.19 (m, 1H), 7.17 (dd, J = 7.4, 1.4 Hz, 1H), 7.07-7.01 (m, 2H), 6.04 (d, J = 5.1 Hz, 1H), 5.63 (d, J = 5.4 Hz, 1H), 5.39 (dd, J = 7.1, 5.2 Hz, 1H), 2.99 (dtd, J = 8.3, 6.6, 5.1 Hz, 1H), 2.73 (dd, J = 16.1, 8.4 Hz, 1H), 2.45 (dd, J = 16.0, 6.4 Hz, 1H). | 289.3 |
| 19e | 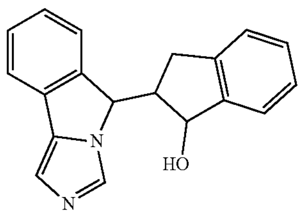 [SMILES: OC1c2ccccc2CC1C1c2ccccc2-c2cncn21] | (400 MHz, DMSO-$d_6$) δ 7.72 (d, J = 7.4 Hz, 1H), 7.60 (d, J = 7.4 Hz, 1H), 7.51 (s, 1H), 7.41 (q, J = 7.2 Hz, 2H), 7.35-7.28 (m, 1H), 7.25-7.19 (m, 1H), 7.16 (td, J = 7.3, 1.4 Hz, 1H), 7.06-7.00 (m, 2H), 6.04 (d, J = 5.1 Hz, 1H), 5.63 (d, J = 5.4 Hz, 1H), 5.39 (dd, J = 7.0, 5.2 Hz, 1H), 3.04-2.92 (m, 1H), 2.73 (dd, J = 16.1, 8.3 Hz, 1H), 2.45 (dd, J = 16.1, 6.5 Hz, 1H). | 289.3 |
| 19f | 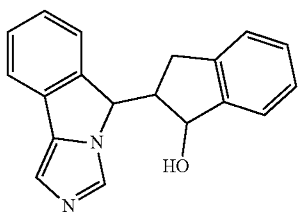 [SMILES: OC1c2ccccc2CC1C1c2ccccc2-c2cncn21] | (400 MHz, DMSO-$d_6$) δ 8.05 (s, 1H), 7.62 (d, J = 7.4 Hz, 1H), 7.55 (d, J = 7.7 Hz, 1H), 7.47-7.41 (m, 1H), 7.38 (t, J = 7.5 Hz, 1H), 7.27-7.19 (m, 4H), 7.16 (s, 1H), 5.77 (d, J = 6.1 Hz, 1H), 5.53 (d, J = 10.0 Hz, 1H), 5.17 (t, J = 6.1 Hz, 1H), 3.29-3.22 (m, 1H), 2.97 (dd, J = 15.5, 7.7 Hz, 1H), 2.40 (tdd, J = 9.5, 7.9, 6.0 Hz, 1H). | 289.3 |
| 20a | 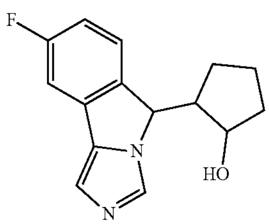 [SMILES: OC1CCCC1C1c2ccc(F)cc2-c2cncn21] | $^1$H NMR (300 MHz, $CD_3OD$) δ 8.11 (s, 1H), 7.45 (dd, J = 8.5, 4.8 Hz, 1H), 7.34 (dd, J = 8.6, 2.5 Hz, 1H), 7.21 (s, 1H), 7.01-6.95 (m, 1H), 5.46 (d, J = 4.4 Hz, 1H), 3.97-3.94 (m, 1H), 2.48-2.38 (m, 1H), 1.67-1.56 (m, 3H), 1.54-1.42 (m, 2H), 1.16-1.10 (m, 1H) | 259.2 |
| 20b | 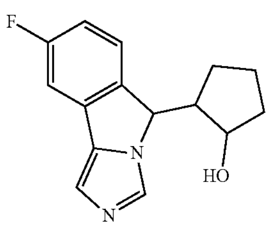 [SMILES: OC1CCCC1C1c2ccc(F)cc2-c2cncn21] | $^1$H NMR (300 MHz, $CD_3OD$) δ 8.11 (s, 1H), 7.45 (dd, J = 8.5, 4.8 Hz, 1H), 7.34 (dd, J = 8.6, 2.5 Hz, 1H), 7.21 (s, 1H), 7.01-6.95 (m, 1H), 5.46 (d, J = 4.4 Hz, 1H), 3.97-3.94 (m, 1H), 2.48-2.38 (m, 1H), 1.67-1.56 (m, 3H), 1.54-1.42 (m, 2H), 1.16-1.10 (m, 1H) | 259.2 |
| 20c | 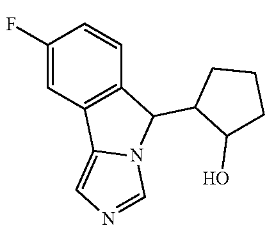 [SMILES: OC1CCCC1C1c2ccc(F)cc2-c2cncn21] | $^1$H NMR (300 MHz, $CD_3OD$) δ 7.83 (s, 1H), 7.37 (dd, J = 8.4, 4.8 Hz, 1H), 7.26 (dd, J = 8.7, 2.5 Hz, 1H), 7.12 (s, 1H), 6.98-6.91 (m, 1H), 5.45-5.44 (m, 1H), 4.16 (q, J = 7.0 Hz, 1H), 2.43-2.39 (m, 1H), 1.80-1.75 (m, 1H), 1.55-1.48 (m, 2H), 1.34-1.18 (m, 2H), 0.62-0.55 (m, 1H) | 259.2 |
| 20d | 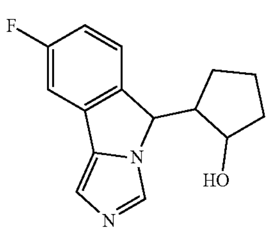 [SMILES: OC1CCCC1C1c2ccc(F)cc2-c2cncn21] | $^1$H NMR (300 MHz, $CD_3OD$) δ 7.83 (s, 1H), 7.37 (dd, J = 8.4, 4.8 Hz, 1H), 7.26 (dd, J = 8.7, 2.5 Hz, 1H), 7.12 (s, 1H), 6.98-6.91 (m, 1H), 5.45-5.44 (m, 1H), 4.16 (q, J = 7.0 Hz, 1H), 2.43-2.39 (m, 1H), 1.80-1.75 (m, 1H), 1.55-1.48 (m, 2H), 1.34-1.18 (m, 2H), 0.62-0.55 (m, 1H) | 259.2 |

TABLE 2-continued

| Ex. # | Structure | $^1$H NMR | MS (M + H)$^+$ |
|---|---|---|---|
| 21a | 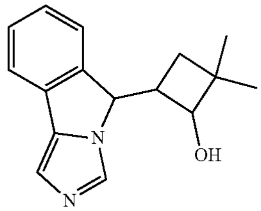 [SMILES: CC1(C)CC(C2c3ccccc3-c3cncn32)C1O] | $^1$H NMR (400 MHz, DMSO-$d_6$) δ 7.81 (s, 1H), 7.68-7.52 (m, 2H), 7.36 (tdd, J = 7.5, 1.2, 0.6 Hz, 1H), 7.25 (td, J = 7.5, 1.2 Hz, 1H), 7.12 (s, 1H), 5.62 (d, J = 5.0 Hz, 1H), 5.42 (d, J = 9.2 Hz, 1H), 3.94 (ddd, J = 8.9, 4.8, 2.1 Hz, 1H), 2.06-1.92 (m, 1H), 1.70 (ddd, J = 10.7, 8.3, 3.4 Hz, 1H), 1.04 (d, J = 7.6 Hz, 6H) | 255 |
| 21b | 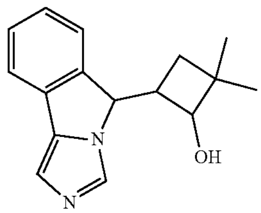 [SMILES: CC1(C)CC(C2c3ccccc3-c3cncn32)C1O] | $^1$H NMR (400 MHz, DMSO-$d_6$) δ 7.81 (s, 1H), 7.58 (ddt, J = 9.6, 7.5, 0.9 Hz, 2H), 7.36 (tdd, J = 7.5, 1.2, 0.6 Hz, 1H), 7.25 (td, J = 7.5, 1.2 Hz, 1H), 7.13 (s, 1H), 5.36 (d, J = 7.6 Hz, 1H), 5.14 (d, J = 6.9 Hz, 1H), 4.03-3.81 (m, 1H), 2.45-2.21 (m, 1H), 1.46 (dd, J = 10.7, 9.0 Hz, 1H), 1.19-1.05 (m, 1H), 1.01 (s, 3H), 0.95 (s, 3H) | 255 |
| 21c | 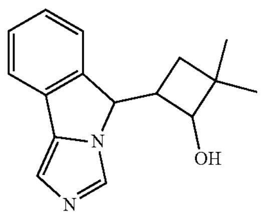 [SMILES: CC1(C)CC(C2c3ccccc3-c3cncn32)C1O] | $^1$H NMR (400 MHz, DMSO-$d_6$) δ 7.90 (s, 1H), 7.58 (dd, J = 7.6, 1.2 Hz, 1H), 7.36 (t, J = 7.9 Hz, 2H), 7.23 (td, J = 7.5, 1.1 Hz, 1H), 7.09 (s, 1H), 5.34 (d, J = 8.9 Hz, 1H), 5.09 (d, J = 7.1 Hz, 1H), 3.85 (t, J = 7.6 Hz, 1H), 2.31-2.07 (m, 1H), 1.65 (td, J = 9.7, 9.3, 1.0 Hz, 1H), 1.52 (t, J = 10.3 Hz, 1H), 1.05 (s, 3H), 0.95 (s, 3H) | 255 |
| 21d | 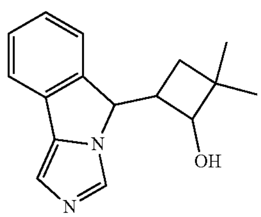 [SMILES: CC1(C)CC(C2c3ccccc3-c3cncn32)C1O] | Same as 21b | 255 |
| 21e | 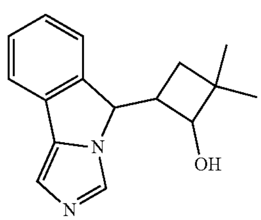 [SMILES: CC1(C)CC(C2c3ccccc3-c3cncn32)C1O] | Same as 21a | 255 |
| 21f | 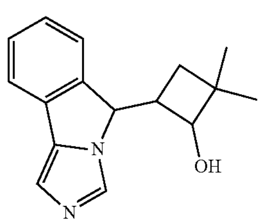 [SMILES: CC1(C)CC(C2c3ccccc3-c3cncn32)C1O] | Same as 21c | 255 |
| 22a | 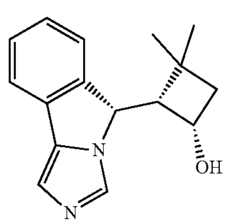 [SMILES: CC1(C)C[C@H](O)[C@@H]1[C@H]1c2ccccc2-c2cncn21] | (400 MHz, DMSO-$d_6$) δ 7.96 (d, J = 0.7 Hz, 1H), 7.70 (dt, J = 7.6, 0.9 Hz, 1H), 7.59 (dt, J = 7.6, 0.9 Hz, 1H), 7.40-7.33 (m, 1H), 7.29-7.22 (m, 1H), 7.14 (s, 1H), 5.58 (d, J = 3.2 Hz, 1H), 5.48 (d, J = 8.7 Hz, 1H), 4.45 (dq, J = 6.5, 3.1 Hz, 1H), 2.28-2.17 (m, 1H), 1.99-1.89 (m, 1H), 1.71-1.64 (m, 1H), 1.18 (s, 3H), 1.04 (s, 3H). | 255.3 |

TABLE 2-continued

| Ex. # | Structure | $^1$H NMR | MS (M + H)$^+$ |
|---|---|---|---|
| 22b | 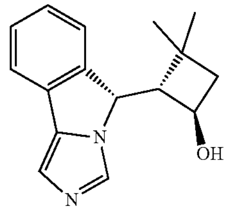 [SMILES: CC1(C)C[C@@H](O)[C@@H]1[C@H]1c2ccccc2-c2cncn21] | (400 MHz, DMSO-d$_6$) δ 7.87 (d, J = 0.8 Hz, 1H), 7.62-7.55 (m, 2H), 7.40-7.33 (m, 1H), 7.25 (dd, J = 7.6, 1.1 Hz, 1H), 7.14 (s, 1H), 5.47-5.39 (m, 1H), 5.11 (d, J = 7.5 Hz, 1H), 4.45-4.32 (m, 1H), 2.11 G (t, J = 8.1 Hz, 1H), 1.99 (dd, J = 10.4, 7.8 Hz, 1H), 1.53 (dd, J = 10.5, 8.1 Hz, 1H), 0.95 (s, 3H), 0.84 (s, 3H). | 255.3 |
| 22c | 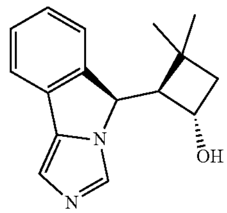 [SMILES: CC1(C)C[C@H](O)[C@H]1[C@@H]1c2ccccc2-c2cncn21] | (400 MHz, DMSO-d$_6$) δ 7.87 (t, J = 0.6 Hz, 1H), 7.61-7.54 (m, 2H), 7.40-7.32 (m, 1H), 7.23 (td, J = 7.6, 1.1 Hz, 1H), 7.14 (s, 1H), 5.42 (d, J = 8.0 Hz, 1H), 5.11 (d, J = 7.4 Hz, 1H), 4.39 (p, J = 7.9 Hz, 1H), 2.11 (t, J = 8.1 Hz, 1H), 2.03-1.94 (m, 1H), 1.53 (dd, J = 10.4, 8.1 Hz, 1H), 0.94 (s, 3H), 0.84 (s, 3H). | 255.3 |
| 22d | 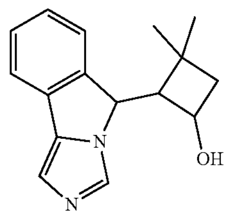 [SMILES: CC1(C)CC(O)C1C1c2ccccc2-c2cncn21] | (400 MHz, DMSO-d$_6$) δ 7.87 (s, 1H), 7.59 (d, J = 7.4 Hz, 1H), 7.46 (d, J = 7.6 Hz, 1H), 7.38 (t, J = 7.5 Hz, 1H), 7.26 (td, J = 7.6, 1.2 Hz, 1H), 7.09 (s, 1H), 5.43 (d, J = 9.9 Hz, 1H), 5.08 (d, J = 7.9 Hz, 1H), 4.44 (p, J = 7.9 Hz, 1H), 2.07 (dd, J = 10.5, 7.7 Hz, 1H), 1.91 (dd, J = 9.9, 7.9 Hz, 1H), 1.53 (dd, J = 10.5, 8.2 Hz, 1H), 1.19 (s, 3H), 1.10 (s, 3H). | 255.3 |
| 22e | 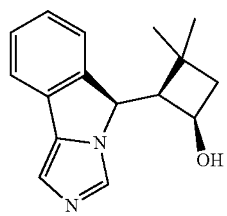 [SMILES: CC1(C)C[C@@H](O)[C@H]1[C@@H]1c2ccccc2-c2cncn21] | (400 MHz, DMSO-d$_6$) δ 7.96 (t, J = 0.6 Hz, 1H), 7.73-7.66 (m, 1H), 7.59 (dt, J = 7.5, 0.9 Hz, 1H), 7.40-7.31 (m, 1H), 7.25 (td, J = 7.6, 1.2 Hz, 1H), 7.14 (s, 1H), 5.59 (d, J = 3.2 Hz, 1H), 5.48 (d, J = 8.7 Hz, 1H), 4.44 (tt, J = 6.3, 2.9 Hz, 1H), 2.26-2.15 (m, 1H), 1.94 (ddd, J = 11.6, 5.9, 1.0 Hz, 1H), 1.67 (ddd, J = 11.9, 2.7, 0.8 Hz, 1H), 1.18 (s, 3H), 1.04 (s, 3H). | 255.3 |
| 22f | 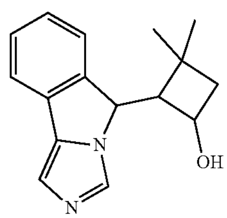 [SMILES: CC1(C)CC(O)C1C1c2ccccc2-c2cncn21] | (400 MHz, DMSO-d$_6$) δ 7.89 (d, J = 0.7 Hz, 1H), 7.61 (dt, J = 7.6, 1.0 Hz, 1H), 7.53-7.47 (m, 1H), 7.42-7.36 (m, 1H), 7.27 (td, J = 7.6, 1.2 Hz, 1H), 7.12 (s, 1H), 5.62 (d, J = 3.2 Hz, 1H), 5.47 (d, J = 11.2 Hz, 1H), 4.33 (td, J = 5.8, 2.8 Hz, 1H), 1.99-1.89 (m, 2H), 1.68 (dt, J = 12.0, 0.9 Hz, 1H), 1.61 (s, 3H), 1.08 (s, 3H). | 255.3 |
| 22g | 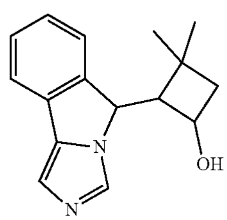 [SMILES: CC1(C)CC(O)C1C1c2ccccc2-c2cncn21] | (400 MHz, DMSO-d$_6$) δ 7.89 (t, J = 0.7 Hz, 1H), 7.61 (dt, J = 7.6, 0.9 Hz, 1H), 7.52-7.46 (m, 1H), 7.42-7.35 (m, 1H), 7.28 (td, J = 7.6, 1.2 Hz, 1H), 7.12 (s, 1H), 5.62 (d, J = 3.0 Hz, 1H), 5.47 (d, J = 11.2 Hz, 1H), 4.36-4.30 (m, 1H), 2.00-1.87 (m, 2H), 1.74-1.64 (m, 1H), 1.61 (s, 3H), 1.08 (s, 3H). | 255.3 |
| 22h | 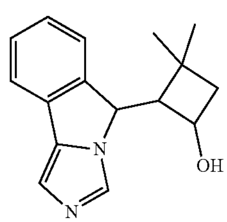 [SMILES: CC1(C)CC(O)C1C1c2ccccc2-c2cncn21] | (400 MHz, DMSO-d$_6$) δ 7.87 (s, 1H), 7.63-7.56 (m, 1H), 7.45 (dd, J = 7.6, 0.9 Hz, 1H), 7.37 (dd, J = 7.9, 7.1 Hz, 1H), 7.27 (dd, J = 7.6, 1.2 Hz, 1H), 7.09 (s, 1H), 5.43 (d, J = 10.0 Hz, 1H), 5.08 (d, J = 7.9 Hz, 1H), 4.44 (p, J = 7.9 Hz, 1H), 2.11-2.02 (m, 1H), 1.91 (dd, J = 9.9, 8.0 Hz, 1H), 1.53 (dd, J = 10.5, 8.2 Hz, 1H), 1.19 (s, 3H), 1.09 (s, 3H). | 255.3 |

TABLE 2-continued
| Ex. # | Structure | $^1$H NMR | MS (M + H)$^+$ |
|---|---|---|---|
| 23a | 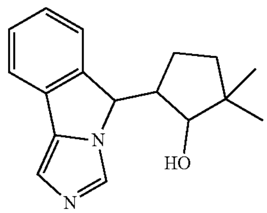 [SMILES: CC1(C)CCC(C2c3ccccc3-c3cncn32)C1O] | (400 MHz, DMSO-$d_6$) δ 7.91 (s, 1H), 7.59 (d, J = 7.5 Hz, 1H), 7.53 (d, J = 7.6 Hz, 1H), 7.38 (t, J = 7.2 Hz, 1H), 7.26 (td, J = 7.6, 1.2 Hz, 1H), 7.10 (s, 1H), 5.43 (d, J = 4.4 Hz, 1H), 4.89-4.83 (m, 1H), 3.56 (d, J = 9.6 Hz, 1H), 2.64 (m, 1H), 1.39-1.20 (m, 3H), 1.14-1.00 (m, 1H), 0.90 (s, 3H), 0.84 (s, 3H). | 269.2 |
| 23b | 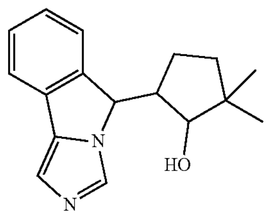 [SMILES: CC1(C)CCC(C2c3ccccc3-c3cncn32)C1O] | (400 MHz, DMSO-$d_6$) δ 7.92 (s, 1H), 7.60 (d, J = 7.5 Hz, 1H), 7.48 (d, J = 8.5 Hz, 1H), 7.40-7.32 (m, 1H), 7.27-7.19 (m, 1H), 7.11 (s, 1H), 5.25 (dd, J = 15.3, 7.6 Hz, 2H), 3.61 (dd, J = 8.5, 1.1 Hz, 1H), 2.07 (dd, J = 13.3, 4.4 Hz, 2H), 2.00-1.87 (m, 1H), 1.83-1.70 (m, 1H), 1.45-1.34 (m, 1H), 1.06 (s, 3H), 0.79 (s, 3H). | 269.2 |
| 23c | 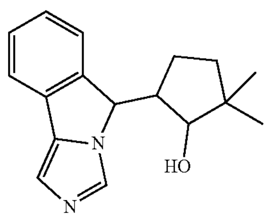 [SMILES: CC1(C)CCC(C2c3ccccc3-c3cncn32)C1O] | (400 MHz, DMSO-$d_6$) δ 7.88 (s, 1H), 7.67 (dd, J = 7.6, 0.8 Hz, 1H), 7.58 (d, J = 7.5 Hz, 1H), 7.37 (t, J = 7.7 Hz, 1H), 7.26 (td, J = 7.6, 1.2 Hz, 1H), 7.11 (s, 1H), 5.37 (d, J = 7.6 Hz, 1H), 5.28 (d, J = 5.2 Hz, 1H), 3.72 (t, J = 5.1 Hz, 1H), 2.41-2.28 (m, 1H), 1.80-1.55 (m, 3H), 1.35-1.26 (m, 1H), 1.02 (s, 3H), 0.82 (s, 3H). | 269.2 |
| 23d | 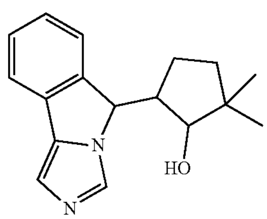 [SMILES: CC1(C)CCC(C2c3ccccc3-c3cncn32)C1O] | Same as 23a | 269.2 |
| 23e | 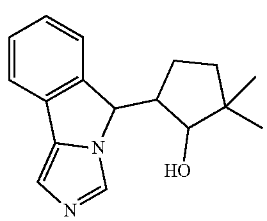 [SMILES: CC1(C)CCC(C2c3ccccc3-c3cncn32)C1O] | Same as 23c | 269.2 |
| 23f | 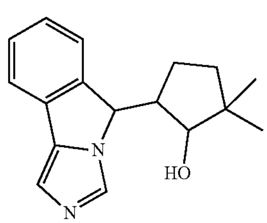 [SMILES: CC1(C)CCC(C2c3ccccc3-c3cncn32)C1O] | Same as 23b | 269.2 |
| 24a | 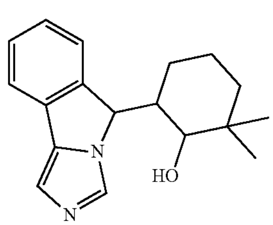 [SMILES: CC1(C)CCCC(C2c3ccccc3-c3cncn32)C1O] | Same as 24h | 283.1 |

TABLE 2-continued

| Ex. # | Structure | $^1$H NMR | MS (M + H)$^+$ |
|---|---|---|---|
| 24b | 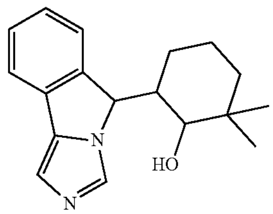 [SMILES: CC1(C)CCCC(C2c3ccccc3-c3cncn32)C1O] | $^1$H NMR (400 MHz, DMSO-d$_6$) δ 7.93 (t, J = 0.6 Hz, 1H), 7.64-7.55 (m, 2H), 7.41-7.32 (m, 1H), 7.23 (td, J = 7.6, 1.2 Hz, 1H), 7.10 (d, J = 0.5 Hz, 1H), 5.15 (d, J = 7.3 Hz, 1H), 4.83 (d, J = 5.8 Hz, 1H), 3.42-3.38 (m, 1H), 1.84-1.72 (m, 1H), 1.66-1.46 (m, 4H), 1.37 (dtd, J = 13.7, 10.0, 8.8, 3.5 Hz, 1H), 1.08-1.00 (m, 1H), 0.91 (s, 3H), 0.76 (s, 3H). | 283.1 |
| 24c | 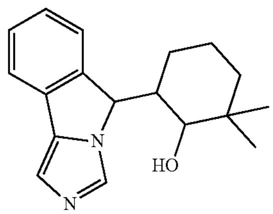 [SMILES: CC1(C)CCCC(C2c3ccccc3-c3cncn32)C1O] | $^1$H NMR (400 MHz, DMSO-d$_6$) δ 7.85 (s, 1H), 7.58 (dt, J = 7.5, 1.0 Hz, 1H), 7.47 (dq, J = 7.5, 0.9 Hz, 1H), 7.36 (tdd, J = 7.5, 1.2, 0.6 Hz, 1H), 7.28 (td, J = 7.5, 1.2 Hz, 1H), 7.13 (s, 1H), 5.68 (d, J = 2.4 Hz, 1H), 5.18 (d, J = 6.5 Hz, 1H), 2.23-2.11 (m, 1H), 1.33 (dd, J = 13.0, 2.6 Hz, 1H), 1.26-1.12 (m, 2H), 1.09-1.03 (m, 1H), 1.02 (s, 3H), 0.92 (s, 3H), 0.68 (d, J = 13.2 Hz, 1H), 0.21-0.05 (m, 1H). | 283.1 |
| 24d | 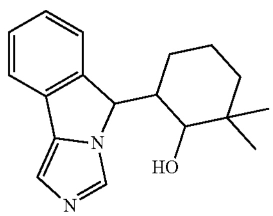 [SMILES: CC1(C)CCCC(C2c3ccccc3-c3cncn32)C1O] | Same as 24e | 283.1 |
| 24e | 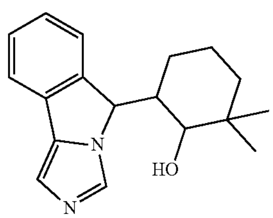 [SMILES: CC1(C)CCCC(C2c3ccccc3-c3cncn32)C1O] | $^1$H NMR (400 MHz, DMSO-d$_6$) δ 7.90 (s, 1H), 7.58 (ddt, J = 12.8, 8.3, 0.8 Hz, 2H), 7.42-7.32 (m, 1H), 7.27 (td, J = 7.5, 1.2 Hz, 1H), 7.10 (s, 1H), 5.69 (d, J = 3.9 Hz, 1H), 5.12 (d, J = 6.3 Hz, 1H), 2.40-2.27 (m, 1H), 1.31 (dd, J = 18.0, 2.4 Hz, 1H), 1.20-1.13 (m, 2H), 0.98 (s, 3H), 0.92 (s, 3H), 0.52 (d, J = 13.1 Hz, 1H), 0.23-0.04 (m, 1H). | 283.1 |
| 24f | 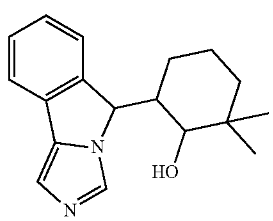 [SMILES: CC1(C)CCCC(C2c3ccccc3-c3cncn32)C1O] | Same as 24c | 283.1 |
| 24g | 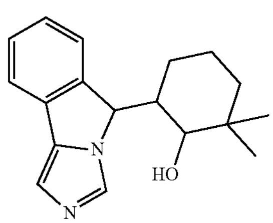 [SMILES: CC1(C)CCCC(C2c3ccccc3-c3cncn32)C1O] | Same as 24b | 283.1 |
| 24h | 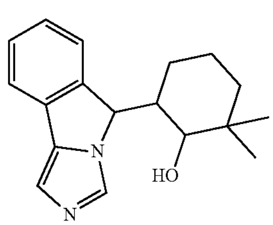 [SMILES: CC1(C)CCCC(C2c3ccccc3-c3cncn32)C1O] | $^1$H NMR (400 MHz, DMSO-d$_6$) δ 7.97 (t, J = 0.7 Hz, 1H), 7.56 (dt, J = 3.0, 0.8 Hz, 1H), 7.55-7.52 (m, 1H), 7.41-7.31 (m, 1H), 7.26 (td, J = 7.6, 1.2 Hz, 1H), 7.08 (s, 1H), 5.19 (d, J = 3.1 Hz, 1H), 5.06 (dd, J = 6.0, 0.7 Hz, 1H), 3.63-3.55 (m, 1H), 2.23-2.14 (m, 1H), 1.48 (td, J = 13.2, 4.3 Hz, 1H), 1.40-1.19 (m, 2H), 1.18-0.99 (m, 2H), 0.94 (s, 3H), 0.91 (s, 3H), 0.77 (dd, J = 12.3, 3.4 Hz, 1H). | 283.1 |

TABLE 2-continued
| Ex. # | Structure | $^1$H NMR | MS (M + H)$^+$ |
|---|---|---|---|
| 25a | 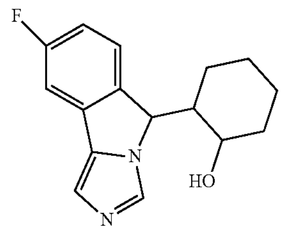 [SMILES: OC1CCCCC1C1c2ccc(F)cc2-c2cncn21] | $^1$HNMR (300 MHz, $CD_3OD$) $^1$HNMR (300 MHz, $CD_3OD$) δ 7.90 (s, 1H), 7.58-7.52 (m, 1H), 7.43-7.38 (m, 1H), 7.20 (s, 1H), 7.09-7.02 (m, 1H), 5.80 (d, J = 3.0 Hz, 1H), 3.78-3.72 (m, 1H), 2.26-2.03 (m, 2H), 1.81-1.67 (m, 1H), 1.39-1.31 (m, 2H), 1.14-1.00 (m, 2H), 0.75-0.60 (m, 1H), 0.39-0.24 (m, 1H) | 273.2 |
| 25b | 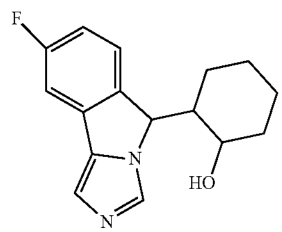 [SMILES: OC1CCCCC1C1c2ccc(F)cc2-c2cncn21] | Same as 25a | 273.2 |
| 25c | 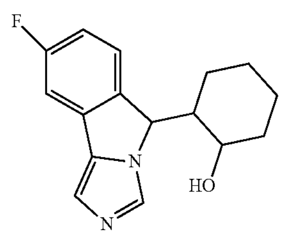 [SMILES: OC1CCCCC1C1c2ccc(F)cc2-c2cncn21] | $^1$HNMR (300 MHz, $CD_3OD$) δ 7.90 (s, 1H), 7.50-7.34 (m, 2H), 7.22 (s, 1H), 7.07-7.04 (m, 1H), 5.80 (d, J = 3.0 Hz, 1H), 3.75-3.72 (m, 1H), 2.22-1.96 (m, 2H), 1.84-1.67 (m, 1H), 1.45-1.39 (m 2H), 1.34-1.02 (m, 2H), 0.96-0.83 (m, 1H), 0.45-0.23 (m, 1H). | 273.2 |
| 25d | 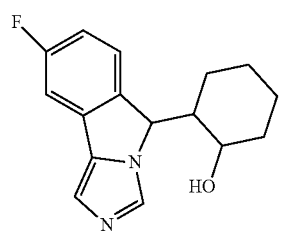 [SMILES: OC1CCCCC1C1c2ccc(F)cc2-c2cncn21] | Same as 25c | 273.2 |
| 26a | 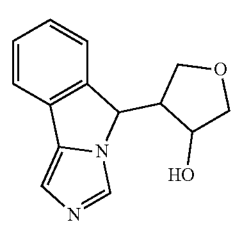 [SMILES: OC1COCC1C1c2ccccc2-c2cncn21] | (400 MHz, DMSO-$d_6$) δ 7.94 (s, 1H), 7.59 (d, J = 7.6 Hz, 1H), 7.54 (dd, J = 7.6, 0.9 Hz, 1H), 7.38 (t, J = 7.5 Hz, 1H), 7.27 (td, J = 7.6, 1.2 Hz, 1H), 7.14 (s, 1H), 5.58 (d, J = 4.1 Hz, 1H), 5.26 (d, J = 4.6 Hz, 1H), 4.31 (dt, J = 8.5, 4.2 Hz, 1H), 3.73-3.67 (m, 1H), 3.58 (dd, J = 9.2, 5.7 Hz, 1H), 3.43 (dd, J = 9.6, 3.6 Hz, 1H), 3.14 (dd, J = 9.1, 6.5 Hz, 1H), 2.86-2.79 (m, 1H). | 243.2 |
| 26b | 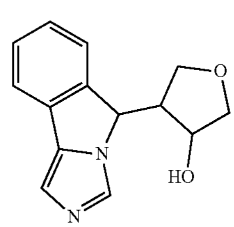 [SMILES: OC1COCC1C1c2ccccc2-c2cncn21] | Same as 26a | 243.2 |

TABLE 2-continued

| Ex. # | Structure | $^{1}$H NMR | MS (M + H)$^{+}$ |
|---|---|---|---|
| 26c | 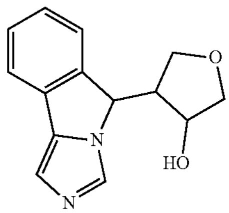 [SMILES: OC1COCC1C1c2ccccc2-c2cncn21] | (400 MHz, DMSO-$d_6$) δ 7.88 (s, 1H), 7.60 (d, J = 7.5 Hz, 1H), 7.52 (dd, J = 7.6, 0.8 Hz, 1H), 7.40 (t, J = 7.5 Hz, 1H), 7.28 (td, J = 7.6, 1.2 Hz, 1H), 7.12 (s, 1H), 5.50 (d, J = 4.6 Hz, 1H), 5.00 (d, J = 4.7 Hz, 1H), 4.02 (dd, J = 9.2, 7.8 Hz, 1H), 3.85-3.78 (m, 2H), 3.38 (d, J = 4.4 Hz, 2H), 2.81-2.72 (m, 1H). | |
| 26d | 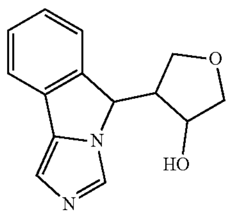 [SMILES: OC1COCC1C1c2ccccc2-c2cncn21] | Same as 26c | 243.2 |
| 27a | 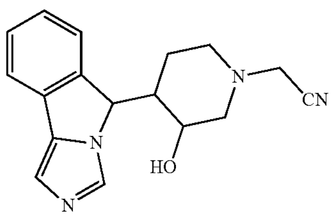 [SMILES: N#CCN1CCC(C2c3ccccc3-c3cncn32)C(O)C1] | $^{1}$HNMR (300 MHz, $CD_3OD$) δ 7.92 (s, 1H), 7.65 (d, J = 7.5 Hz, 1H), 7.56 (d, J = 7.5 Hz, 1H), 7.47-7.42 (m, 1H), 7.36-7.31 (m, 1H), 7.18 (s, 1H), 5.81 (d, J = 3.0 Hz, 1H), 4.03-3.95 (m, 1H), 3.64 (s, 2H), 3.13-3.08 (m, 1H), 2.65-2.61 (m, 1H), 2.31-2.12 (m, 3H), 0.82-0.70 (m, 2H). | 295.1 |
| 27b | 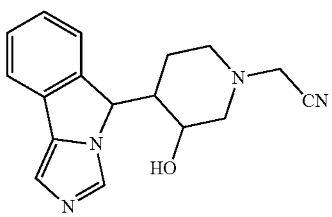 [SMILES: N#CCN1CCC(C2c3ccccc3-c3cncn32)C(O)C1] | Same as 27a | 295.1 |
| 27c | 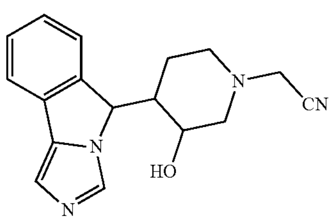 [SMILES: N#CCN1CCC(C2c3ccccc3-c3cncn32)C(O)C1] | $^{1}$HNMR (300 MHz, $CD_3OD$) δ 7.90 (s, 1H), 7.64 (d, J = 7.8 Hz, 1H), 7.52 (d, J = 7.8 Hz, 1H), 7.48-7.34 (m, 2H), 7.20 (s, 1H), 5.81 (d, J = 3.6 Hz, 1H), 4.00-3.91 (m, 1H), 3.65 (s, 2H), 3.19-3.14 (m, 1H), 2.63-2.60 (m, 1H), 2.31-2.03 (m, 3H), 0.94-0.89 (m, 1H), 0.72-0.58 (m, 1H). | 295.1 |
| 27d | 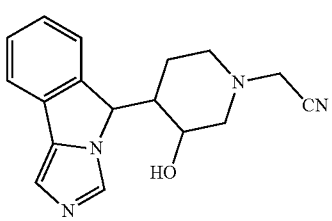 [SMILES: N#CCN1CCC(C2c3ccccc3-c3cncn32)C(O)C1] | Same as 27c | 295.1 |
| 28a | 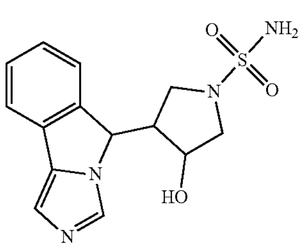 [SMILES: NS(=O)(=O)N1CC(O)C(C2c3ccccc3-c3cncn32)C1] | $^{1}$HNMR (300 MHz, DMSO) δ 7.98 (s, 1H), 7.62 (d, J = 3.7 Hz, 1H), 7.57 (d, J = 3.7 Hz, 1H), 7.41 (t, J = 3.6 Hz, 1H), 7.33-7.28 (m, 1H), 7.19 (s, 1H), 6.72 (s, 2H), 5.68 (d, J = 2.5 Hz, 1H), 5.60 (d, J = 0.6 Hz, 1H), 4.48-4.35 (m, 1H), 3.32-3.27 (m, 1H), 2.95-2.80 (m, 3H), 2.18-2.08 (m, 1H) | 321 |

TABLE 2-continued
| Ex. # | Structure | $^{1}H$ NMR | MS $(M + H)^+$ |
|---|---|---|---|
| 28b | 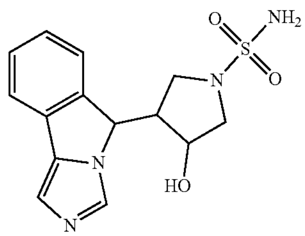 [SMILES: NS(=O)(=O)N1CC(O)C(C2c3ccccc3-c3cncn32)C1] | Same as 28a | 321 |
| 28c | 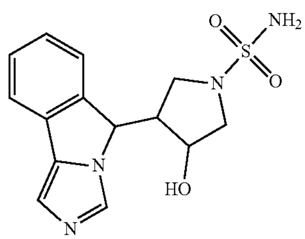 [SMILES: NS(=O)(=O)N1CC(O)C(C2c3ccccc3-c3cncn32)C1] | $^{1}$HNMR (300 MHz, $CD_3OD$) δ 8.01 (s, 1H), 7.64 (d, J = 3.7 Hz, 1H), 7.57 (d, J = 3.9 Hz, 1H), 7.45 (t, J = 3.6 Hz, 1H), 7.37-7.32 (m, 1H), 7.17 (s, 1H), 5.57 (d, J = 2.1 Hz, 1H), 4.05 (d, J = 2.7 Hz, 1H), 3.52 (m, 1H), 3.25-3.16 (m, 2H), 3.06-2.95 (m, 2H) | 321 |
| 28d | 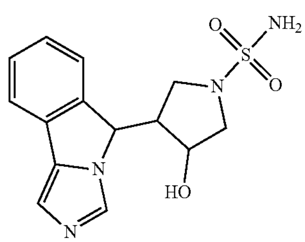 [SMILES: NS(=O)(=O)N1CC(O)C(C2c3ccccc3-c3cncn32)C1] | Same as 28c | 321 |
| 29a | 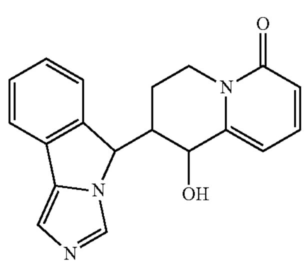 [SMILES: O=c1cccc2n1CCC(C1c3ccccc3-c3cncn31)C2O] | (400 MHz, DMSO-$d_6$) δ 8.00 (s, 1H), 7.63 (d, J = 7.6 Hz, 1H), 7.50-7.46 (m, 1H), 7.45 (dd, J = 8.3, 6.2 Hz, 1H), 7.40 (t, J = 7.4 Hz, 1H), 7.28 (td, J = 7.6, 1.2 Hz, 1H), 7.20 (s, 1H), 6.57-6.50 (m, 2H), 6.27 (dt, J = 9.0, 1.0 Hz, 1H), 5.74 (d, J = 2.2 Hz, 1H), 4.90 (d, J = 10.9 Hz, 1H), 4.40 (dt, J = 14.1, 6.2 Hz, 1H), 3.43-3.29 (m, 1H), 2.62-2.48 (m, 1H), 1.29-1.18 (m, 1H), 0.88-0.76 (m, 1H). | |
| 29b | 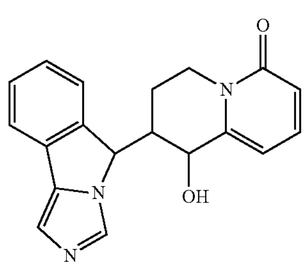 [SMILES: O=c1cccc2n1CCC(C1c3ccccc3-c3cncn31)C2O] | Same as 29a | |
| 29c | 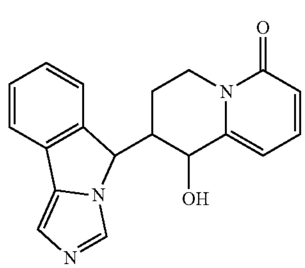 [SMILES: O=c1cccc2n1CCC(C1c3ccccc3-c3cncn31)C2O] | (400 MHz, DMSO-$d_6$) δ 7.97 (s, 1H), 7.66-7.58 (m, 2H), 7.43-7.35 (m, 2H), 7.22 (td, J = 7.6, 1.1 Hz, 1H), 7.15 (s, 1H), 6.35-6.27 (m, 2H), 6.21 (d, J = 4.9 Hz, 1H), 5.49 (d, J = 6.4 Hz, 1H), 4.79 (t, J = 4.4 Hz, 1H), 4.09 (dt, J = 14.5, 5.2 Hz, 1H), 3.61 (ddd, J = 15.2, 9.0, 6.8 Hz, 1H), 2.39 (dtd, J = 10.3, 6.7, 3.8 Hz, 1H), 2.03-1.89 (m, 2H). | |

TABLE 2-continued
| Ex. # | Structure | $^1$H NMR | MS (M + H)$^+$ |
|---|---|---|---|
| 29d | 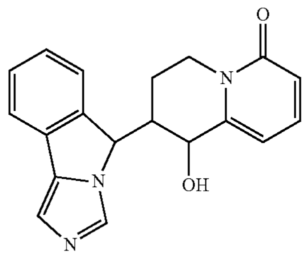 [SMILES: O=c1cccc2n1CCC(C1c3ccccc3-c3cncn31)C2O] | Same as 29c | |
| 29e | 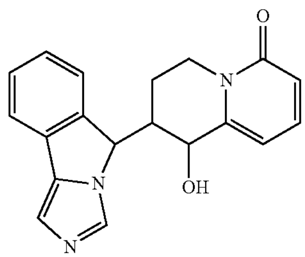 [SMILES: O=c1cccc2n1CCC(C1c3ccccc3-c3cncn31)C2O] | (400 MHz, DMSO-d$_6$) δ 7.72 (s, 1H), 7.60 (s, 1H), 7.58 (s, 1H), 7.45 (dd, J = 9.1, 6.8 Hz, 1H), 7.39 (dd, J = 8.1, 7.0 Hz, 1H), 7.30 (td, J = 7.5, 1.2 Hz, 1H), 7.10 (s, 1H), 6.51 (s, 1H), 6.42 (dd, J = 7.5, 1.3 Hz, 1H), 6.31 (dd, J = 9.1, 1.3 Hz, 1H), 5.62 (d, J = 2.8 Hz, 1H), 5.01 (d, J = 5.2 Hz, 1H), 4.11 (ddd, J = 14.3, 5.7, 3.6 Hz, 1H), 3.48-3.38 (m, 1H), 2.85-2.74 (m, 1H), 1.46-1.34 (m, 1H), 1.23 (dtd, J = 13.6, 10.7, 5.7 Hz, 1H). | |
| 29f | 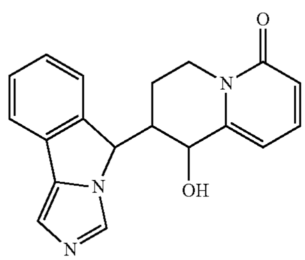 [SMILES: O=c1cccc2n1CCC(C1c3ccccc3-c3cncn31)C2O] | Same as 29e | |
| 30a | 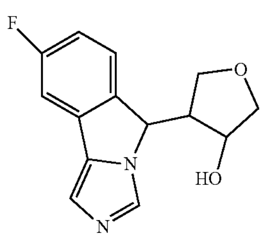 [SMILES: OC1COCC1C1c2ccc(F)cc2-c2cncn21] | $^1$HNMR (300 MHz, CD$_3$OD) δ 8.01 (s, 1H), 7.60-7.56 (m, 1H), 7.43-7.39 (m, 1H), 7.25 (s, 1H), 7.07-7.05 (m, 1H), 5.59 (d, J = 6 Hz, 1H), 4.29-4.24 (m, 1H), 3.94-3.90 (m, 1H), 3.68-3.62 (m, 1H), 3.57-3.50 (m, 1H), 3.47-3.43 (m, 1H), 3.00-2.89 (m, 1H). | 261.2 |
| 30b | 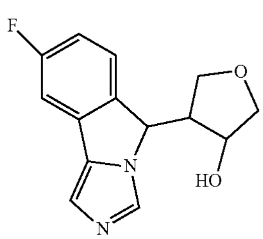 [SMILES: OC1COCC1C1c2ccc(F)cc2-c2cncn21] | Same as 30a | 261.2 |
| 30c | 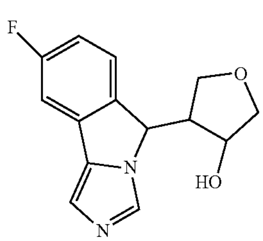 [SMILES: OC1COCC1C1c2ccc(F)cc2-c2cncn21] | $^1$HNMR (300 MHz, CD$_3$OD) δ 7.97 (s, 1H), 7.58-7.54 (m, 1H), 7.47-7.41 (m, 1H), 7.22 (s, 1H), 7.10-7.03 (m, 1H), 5.52 (d, J = 3.0 Hz, 1H), 4.26-4.20 (m, 1H), 4.09-4.05 (m, 1H), 3.84-3.81 (m, 1H), 3.53-3.51 (m, 2H), 2.90-2.84 (m, 1H) | 261.2 |

TABLE 2-continued

| Ex. # | Structure | $^1$H NMR | MS $(M + H)^+$ |
|---|---|---|---|
| 30d | 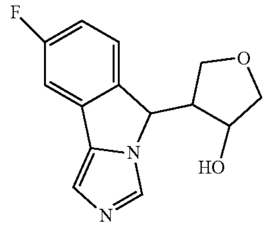 [SMILES: OC1COCC1C1c2ccc(F)cc2-c2cncn21] | Same as 30c | 261.2 |
| 31a | 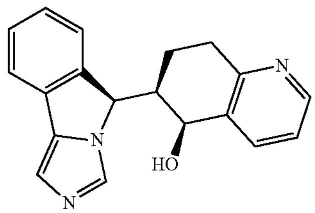 [SMILES: O[C@@H]1c2cccnc2CC[C@@H]1[C@@H]1c2ccccc2-c2cncn21] | $^1$H NMR (500 MHz, Chloroform-d) δ 8.56 (dd, J = 4.8, 1.7 Hz, 1H), 8.16 (s, 1H), 7.84 (dd, J = 7.8, 1.8 Hz, 1H), 7.49 (dt, J = 7.6, 1.0 Hz, 1H), 7.41-7.32 (m, 2H), 7.25 (ddd, J = 7.6, 6.2, 1.2 Hz, 2H), 6.51 (s, 1H), 5.50 (s, 1H), 5.15-5.10 (m, 1H), 4.94 (s, 1H), 2.86 (dd, J = 17.7, 5.1 Hz, 1H), 2.68 (ddd, J = 18.2, 12.6, 6.2 Hz, 1H), 2.41 (dd, J = 12.8, 2.6 Hz, 1H), 1.34 (qd, J = 12.9, 5.6 Hz, 1H), 1.11-1.03 (m, 1H). | 304.2 |
| 31b | 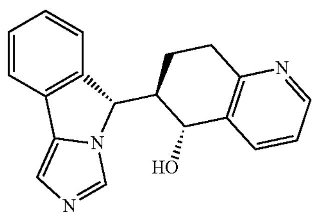 [SMILES: O[C@H]1c2cccnc2CC[C@@H]1[C@H]1c2ccccc2-c2cncn21] | $^1$H NMR (500 MHz, Chloroform-d) δ 8.42 (ddd, J = 4.8, 1.8, 0.7 Hz, 1H), 7.91 (ddd, J = 7.8, 1.7, 1.0 Hz, 1H), 7.67 (s, 1H), 7.63-7.52 (m, 1H), 7.50 (dd, J = 7.7, 1.0 Hz, 1H), 7.46-7.36 (m, 1H), 7.31-7.21 (m, 1H), 7.23 (s, 1H), 7.18 (dd, J = 7.9, 4.8 Hz, 1H), 5.77 (d, J = 2.9 Hz, 1H), 4.96 (d, J = 10.4 Hz, 1H), 2.89 (dd, J = 8.9, 4.0 Hz, 2H), 2.59-2.49 (m, 1H), 1.48-1.28 (m, 2H). | 304.2 |
| 31c | 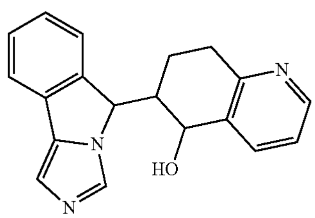 [SMILES: OC1c2cccnc2CCC1C1c2ccccc2-c2cncn21] | $^1$H NMR (500 MHz, Chloroform-d) δ 8.48-8.43 (m, 1H), 7.99 (d, J = 8.1 Hz, 1H), 7.75 (s, 1H), 7.58 (d, J = 7.6 Hz, 1H), 7.45-7.38 (m, 1H), 7.35 (d, J = 7.4 Hz, 1H), 7.30 (td, J = 7.5, 1.1 Hz, 1H), 7.21 (dd, J = 7.9, 4.7 Hz, 2H), 5.84 (s, 1H), 5.03 (d, J = 10.5 Hz, 1H), 2.84 (dd, J = 10.1, 6.2 Hz, 1H), 2.40 (dd, J = 13.8, 9.3 Hz, 1H), 1.36-1.09 (m, 3H). | 304.2 |
| 31d | 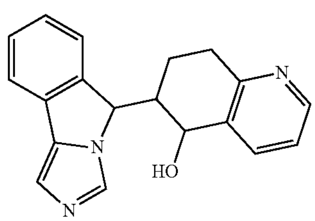 [SMILES: OC1c2cccnc2CCC1C1c2ccccc2-c2cncn21] | $^1$H NMR (500 MHz, Chloroform-d) δ 8.49 (dd, J = 4.8, 1.7 Hz, 1H), 7.98 (s, 1H), 7.64-7.54 (m, 3H), 7.41 (tt, J = 7.6, 0.8 Hz, 1H), 7.27 (td, J = 7.6, 1.2 Hz, 1H), 7.18 (s, 1H), 7.16 (dd, J = 7.7, 4.7 Hz, 1H), 5.37 (d, J = 7.6 Hz, 1H), 4.89 (s, 1H), 3.18 (ddd, J = 18.0, 5.3, 2.1 Hz, 1H), 2.91 (ddd, J = 18.4, 12.0, 6.9 Hz, 1H), 2.41-2.27 (m, 1H), 2.13-2.04 (m, 1H). | 304.2 |
| 31e | 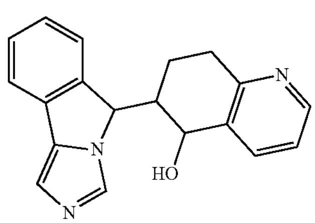 [SMILES: OC1c2cccnc2CCC1C1c2ccccc2-c2cncn21] | $^1$H NMR (500 MHz, Chloroform-d) δ 8.48 (dd, J = 4.8, 1.7 Hz, 1H), 7.98 (s, 1H), 7.65-7.52 (m, 3H), 7.45-7.34 (m, 1H), 7.27 (td, J = 7.6, 1.2 Hz, 1H), 7.19-7.12 (m, 2H), 5.37 (d, J = 7.6 Hz, 1H), 4.89 (d, J = 3.0 Hz, 1H), 3.18 (ddd, J = 17.9, 5.4, 2.1 Hz, 1H), 2.91 (ddd, J = 18.3, 12.0, 6.8 Hz, 2H), 2.42-2.28 (m, 1H), 2.31 (s, 1H), 2.08 (ddt, J = 9.1, 7.7, 3.7 Hz, 1H). | 304.2 |
| 31f | 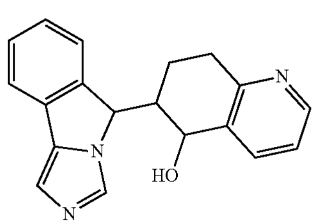 [SMILES: OC1c2cccnc2CCC1C1c2ccccc2-c2cncn21] | $^1$H NMR (500 MHz, Chloroform-d) δ 8.43 (dd, J = 4.9, 1.6 Hz, 1H), 8.03-7.97 (m, 1H), 7.74 (s, 1H), 7.57 (d, J = 7.5 Hz, 1H), 7.41 (td, J = 7.4, 1.1 Hz, 1H), 7.34 (d, J = 7.5 Hz, 1H), 7.30 (dd, J = 7.4, 1.1 Hz, 1H), 7.20 (dd, J = 7.9, 4.7 Hz, 2H), 5.85 (s, 1H), 5.02 (d, J = 10.6 Hz, 1H), 2.84 (dt, J = 9.7, 4.4 Hz, 1H), 2.41 (t, J = 11.5 Hz, 1H), 1.34-1.24 (m, 2H), 1.23-1.07 (m, 1H). | 304.2 |

TABLE 2-continued

| Ex. # | Structure | $^1$H NMR | MS (M + H)$^+$ |
|---|---|---|---|
| 31g | 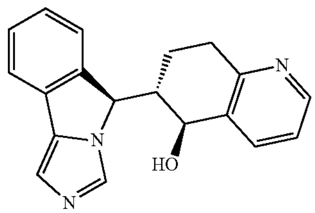 [SMILES: O[C@@H]1c2cccnc2CC[C@H]1[C@@H]1c2ccccc2-c2cncn21] | 1H NMR (500 MHz, Chloroform-d) δ 8.56 (dd, J = 4.8, 1.7 Hz, 1H), 8.16 (s, 1H), 7.84 (dd, J = 7.8, 1.8 Hz, 1H), 7.49 (dt, J = 7.6, 1.0 Hz, 1H), 7.41-7.32 (m, 2H), 7.25 (ddd, J = 7.6, 6.2, 1.2 Hz, 2H), 6.51 (s, 1H), 5.50 (s, 1H), 5.15-5.10 (m, 1H), 4.94 (s, 1H), 2.86 (dd, J = 17.7, 5.1 Hz, 1H), 2.68 (ddd, J = 18.2, 12.6, 6.2 Hz, 1H), 2.41 (dd, J = 12.8, 2.6 Hz, 1H), 1.34 (qd, J = 12.9, 5.6 Hz, 1H), 1.11-1.03 (m, 1H). | 304.2 |
| 31h | 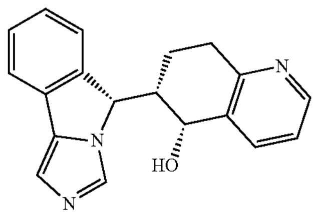 [SMILES: O[C@H]1c2cccnc2CC[C@H]1[C@H]1c2ccccc2-c2cncn21] | $^1$H NMR (500 MHz, Chloroform-d) δ 8.55 (dd, J = 4.8, 1.8 Hz, 1H), 8.17 (s, 1H), 7.84 (dd, J = 7.8, 1.8 Hz, 1H), 7.49 (dt, J = 7.6, 1.0 Hz, 1H), 7.40-7.32 (m, 2H), 7.30-7.18 (m, 2H), 6.52 (s, 1H), 5.50 (d, J = 1.7 Hz, 1H), 5.12 (dt, J = 4.0, 2.0 Hz, 1H), 2.86 (dd, J = 17.7, 5.3 Hz, 1H), 2.68 (ddd, J = 18.2, 12.6, 6.2 Hz, 1H), 2.42 (dd, J = 12.7, 2.6 Hz, 1H), 1.41-1.24 (m, 1H), 1.06 (dd, J = 13.4, 6.0 Hz, 1H). | 304.2 |
| 32a | 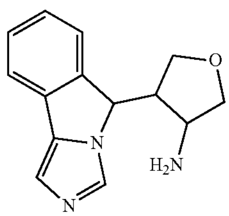 [SMILES: NC1COCC1C1c2ccccc2-c2cncn21] | 1H NMR (300 MHz, Chloroform-d) δ 7.70 (s, 1H), 7.66 (d, J = 7.6 Hz, 1H), 7.56 (d, J = 7.5 Hz, 1H), 7.40 (t, J = 7.5 Hz, 1H), 7.32-7.24 (m, 2H), 7.19 (s, 1H), 5.50 (d, J = 9.0 Hz, 1H), 4.14 (t, J = 8.3 Hz, 1H), 4.02 (dd, J = 9.6, 8.2 Hz, 1H), 3.93 (dd, J = 8.9, 4.0 Hz, 1H), 3.84-3.72 (m, 2H), 2.49 (qd, J = 9.1, 5.7 Hz, 1H); | 242 |
| 32b | 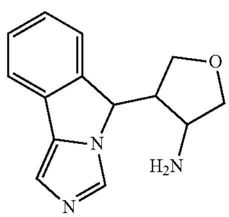 [SMILES: NC1COCC1C1c2ccccc2-c2cncn21] | Same as 32a | 242 |
| 32c | 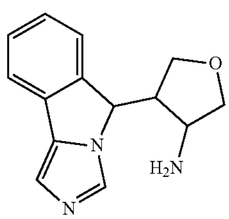 [SMILES: NC1COCC1C1c2ccccc2-c2cncn21] | $^1$H NMR (300 MHz, Chloroform-d) δ 8.10 (s, 1H), 7.57 (d, J = 7.6 Hz, 1H), 7.39 (t, J = 7.4 Hz, 1H), 7.28-7.14 (m, 3H), 5.43 (d, J = 10.8 Hz, 1H), 4.20 (dd, J = 9.5, 4.7 Hz, 2H), 3.93-3.76 (m, 2H), 3.71 (dd, J = 5.4, 3.2 Hz, 1H), 2.47-2.28 (m, 1H); | 242 |
| 32d | 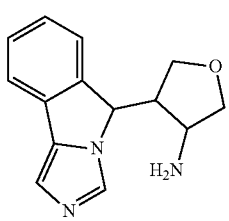 [SMILES: NC1COCC1C1c2ccccc2-c2cncn21] | Same as 32c | 242 |
| 33a | 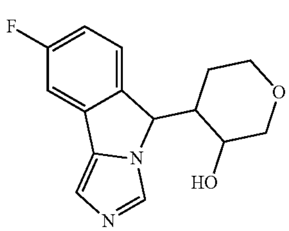 [SMILES: OC1COCCC1C1c2ccc(F)cc2-c2cncn21] | $^1$HNMR (300 MHz, $CD_3OD$) δ 7.95 (s, 1H), 7.49 (dd, J = 8.4 Hz, 4.8 Hz, 1H), 7.41 (dd, J = 8.8 Hz, 2.4 Hz, 1H), 7.25 (s, 1H), 7.12-7.07 (m, 1H), 5.80 (s, 1H), 4.05 (dd, J = 10.8 Hz, 4.8 Hz, 1H), 3.88-3.82 (m, 1H), 3.70 (dd, J = 11.2 Hz, 4.8 Hz, 1H), 3.28-3.16 (m, 2H), 2.27 (t, J = 2.0 Hz, 1H), 0.86 (d, J = 7.6 Hz, 1H), 0.71-0.60 (m, 1H). | 274.0 |

TABLE 2-continued

| Ex. # | Structure | $^1$H NMR | MS (M + H)$^+$ |
|---|---|---|---|
| 33b | 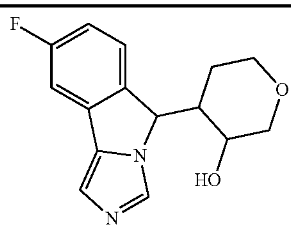 | Same as 33a | 274.0 |
| 33c | 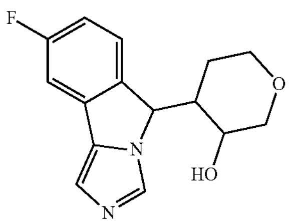 [SMILES: OC1COCCC1C1c2ccc(F)cc2-c2cncn21] | $^1$HNMR (300 MHz, $CD_3OD$) δ 7.95 (s, 1H), 7.56 (dd, J = 8.4 Hz, 4.8 Hz, 1H), 7.42 (dd, J = 8.4 Hz, 2.4 Hz, 1H), 7.22 (s, 1H), 7.11-7.06 (m, 1H), 5.79 (s, 1H), 3.99 (dd, J = 10.4 Hz, 4.8 Hz, 1H), 3.87-3.80 (m, 1H), 3.72 (d, J = 6.8 Hz, 1H), 3.29-3.22 (m, 1H), 3.15 (t, J = 10.4 Hz, 1H), 2.43-2.40 (m, 1H), 0.77-0.73 (m, 2H). | 274.0 |
| 33d | 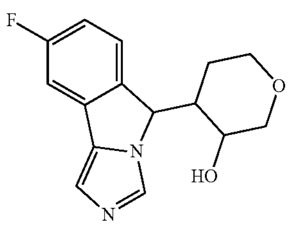 [SMILES: OC1COCCC1C1c2ccc(F)cc2-c2cncn21] | Same as 33c | 274.0 |
| 34a | 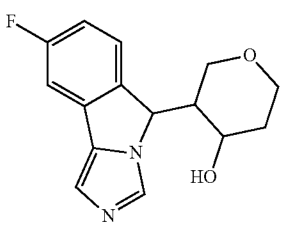 [SMILES: OC1CCOCC1C1c2ccc(F)cc2-c2cncn21] | $^1$HNMR (300 MHz, $CD_3OD$) δ 8.0 (s, 1H), 7.59 (dd, J = 8.4 Hz, 4.8 Hz, 1H), 7.42 (dd, J = 8.8 Hz, 2.4 Hz, 1H), 7.23 (s, 1H), 7.11-7.06 (m, 1H), 5.76 (s, 1H), 3.98-3.91 (m, 1H), 3.88 (dd, J = 11.6 Hz, 4.8 Hz, 1H), 3.34-3.26 (m 1H), 3.08 (dd, J = 11.6 Hz, 4.0 Hz, 1H), 2.71 (t, J = 11.2 Hz, 1H), 2.47-2.43 (m, 1H), 1.97 (dd, J = 12.8 Hz, 2.4 Hz, 1H), 1.71-1.67 (m, 1H). | 274.0 |
| 34b | 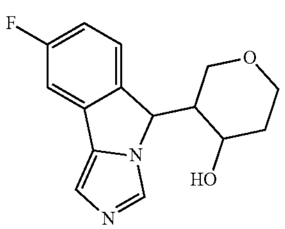 [SMILES: OC1CCOCC1C1c2ccc(F)cc2-c2cncn21] | Same as 34a | 274.0 |
| 34c | 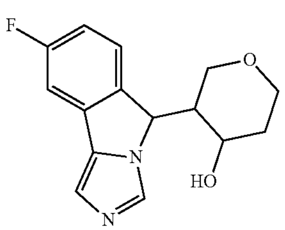 [SMILES: OC1CCOCC1C1c2ccc(F)cc2-c2cncn21] | $^1$HNMR (300 MHz, $CD_3OD$) δ 7.9 (s, 1H), 7.53 (dd, J = 8.4 Hz, 4.8 Hz, 1H), 7.41 (dd, J = 8.4 Hz, 2.4 Hz, 1H), 7.25 (s, 1H), 7.14-7.09 (m, 1H), 5.80 (s, 1H), 4.07-4.03 (m, 1H), 3.90 (dd, J = 12.0 Hz, 4.8 Hz, 1H), 3.33-3.29 (m 1H), 3.16 (dd, J = 12.0 Hz, 4.4 Hz, 1H), 2.51 (t, J = 11.2 Hz, 1H), 2.34-2.31 (m, 1H), 2.06 (dd, J = 10.4 Hz, 2.4 Hz, 1H), 1.75-1.71 (m, 1H). | 274.0 |
| 34d | 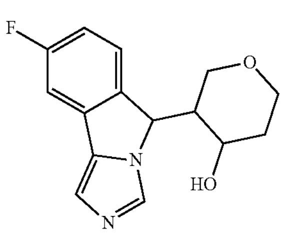 [SMILES: OC1CCOCC1C1c2ccc(F)cc2-c2cncn21] | Same as 34c | 274.0 |

TABLE 2-continued

| Ex. # | Structure | $^1$H NMR | MS (M + H)$^+$ |
|---|---|---|---|
| 35a | 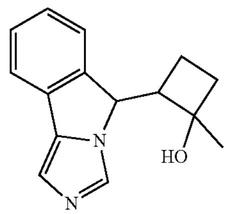 [SMILES: CC1(O)CCC1C1c2ccccc2-c2cncn21] | (500 MHz, Chloroform-d) δ 8.02 (t, J = 0.7 Hz, 1H), 7.52 (dt, J = 7.6, 1.1 Hz, 1H), 7.48 (dq, J = 7.6, 0.9 Hz, 1H), 7.34 (tdd, J = 7.6, 1.1, 0.6 Hz, 1H), 7.22 (td, J = 7.6, 1.2 Hz, 1H), 7.19 (s, 1H), 5.46 (d, J = 5.9 Hz, 1H), 2.65-2.56 (m, 1H), 2.10-1.96 (m, 2H), 1.82 (dtd, J = 11.9, 8.8, 6.2 Hz, 1H), 1.70-1.63 (m, 1H), 1.51 (d, J = 0.5 Hz, 3H). | 241.3 |
| 35b | 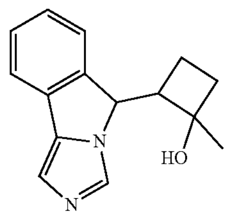 [SMILES: CC1(O)CCC1C1c2ccccc2-c2cncn21] | (500 MHz, Chloroform-d) δ 8.02 (t, J = 0.7 Hz, 1H), 7.52 (dt, J = 7.6, 1.1 Hz, 1H), 7.48 (dq, J = 7.6, 0.9 Hz, 1H), 7.34 (tdd, J = 7.6, 1.1, 0.6 Hz, 1H), 7.22 (td, J = 7.6, 1.2 Hz, 1H), 7.19 (s, 1H), 5.46 (d, J = 5.9 Hz, 1H), 2.65-2.56 (m, 1H), 2.11-1.97 (m, 2H), 1.82 (dtd, J = 11.9, 8.8, 6.2 Hz, 1H), 1.66 (ddt, J = 11.9, 10.4, 6.7 Hz, 1H), 1.51 (d, J = 0.5 Hz, 3H). | 241.3 |
| 35c | 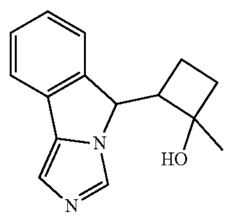 [SMILES: CC1(O)CCC1C1c2ccccc2-c2cncn21] | (500 MHz, Chloroform-d) δ 8.00 (s, 1H), 7.52 (dt, J = 7.4, 1.0 Hz, 1H), 7.37-7.32 (m, 2H), 7.18 (td, J = 7.6, 1.2 Hz, 1H), 7.15 (s, 1H), 5.43 (d, J = 10.2 Hz, 1H), 2.46-2.26 (m, 2H), 2.19-2.03 (m, 3H), 1.40 (s, 3H). | 241.3 |
| 35d | 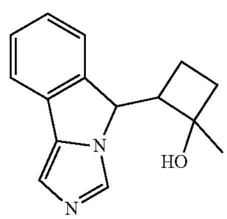 [SMILES: CC1(O)CCC1C1c2ccccc2-c2cncn21] | (500 MHz, Chloroform-d) δ 8.00 (s, 1H), 7.52 (dt, J = 7.5, 1.1 Hz, 1H), 7.39-7.31 (m, 2H), 7.18 (td, J = 7.6, 1.2 Hz, 1H), 7.15 (s, 1H), 5.43 (d, J = 10.2 Hz, 1H), 2.46-2.26 (m, 2H), 2.21-2.02 (m, 3H), 1.40 (s, 3H). | 241.3 |
| 36a | 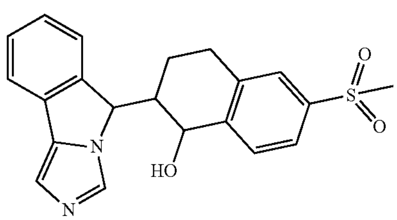 [SMILES: CS(=O)(=O)c1ccc2c(c1)CCC(C1c3ccccc3-c3cncn31)C2O] | $^1$H NMR (500 MHz, Chloroform-d) δ 7.82 (d, J = 8.3 Hz, 1H), 7.77 (dd, J = 8.2, 1.9 Hz, 1H), 7.66-7.58 (m, 3H), 7.50 (dd, J = 7.7, 1.0 Hz, 1H), 7.45-7.37 (m, 1H), 7.29-7.21 (m, 2H), 5.78 (d, J = 2.9 Hz, 1H), 4.96 (d, J = 10.5 Hz, 1H), 3.02 (s, 3H), 2.80 (dd, J = 11.5, 5.5 Hz, 2H), 2.55 (s, 1H), 1.27-1.40 (m, 1H), 1.26 (s, 1H) | 381.2 |
| 36b | 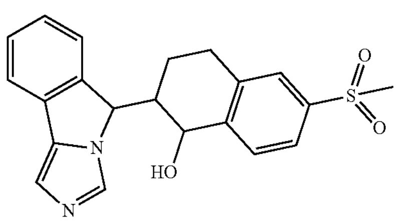 [SMILES: CS(=O)(=O)c1ccc2c(c1)CCC(C1c3ccccc3-c3cncn31)C2O] | $^1$H NMR (500 MHz, Chloroform-d) δ 7.92 (d, J = 8.2 Hz, 1H), 7.68 (s, 1H), 7.79 (d, J = 8.3 Hz, 1H), 7.62-7.54 (m, 2H), 7.40 (t, J = 7.5 Hz, 1H), 7.31 (dd, J = 20.3, 7.6 Hz, 2H), 7.19 (s, 1H), 5.86 (s, 1H), 4.98 (d, J = 10.7 Hz, 1H), 3.04 (s, 3H), 2.80-2.69 (m, 2H), 2.42 (t, J = 11.6 Hz, 1H), 1.25 (d, J = 14.1 Hz, 1H), 1.04 (dd, J = 12.4, 6.9 Hz, 1H) | 381.2 |
| 36c | 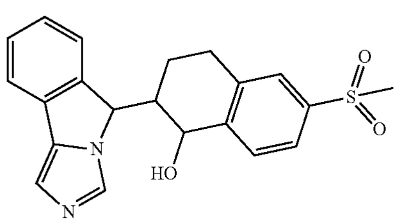 [SMILES: CS(=O)(=O)c1ccc2c(c1)CCC(C1c3ccccc3-c3cncn31)C2O] | $^1$H NMR (500 MHz, Chloroform-d) δ 7.98 (s, 1H), 7.78-7.72 (m, 2H), 7.62-7.53 (m, 2H), 7.57-7.47 (m, 1H), 7.42 (tt, J = 7.6, 7.6, 0.8 Hz, 1H), 7.30-7.21 (m, 1H), 7.19 (s, 1H), 5.39 (d, J = 7.4 Hz, 1H), 4.91 (d, J = 3.0 Hz, 1H), 3.15-3.02 (m, 1H), 3.03 (s, 3H), 2.85 (ddd, J = 17.8, 11.6, 6.8 Hz, 1H), 2.69 (s, 1H), 2.34-2.21 (m, 1H), 2.25 (s, 1H), 2.08 (ddt, J = 11.5, 7.3, 3.4 Hz, 1H) | 381.2 |

TABLE 2-continued
| Ex. # | Structure | $^1$H NMR | MS (M + H)$^+$ |
|---|---|---|---|
| 36d | 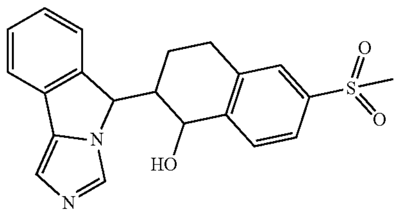 [SMILES: CS(=O)(=O)c1ccc2c(c1)CCC(C1c3ccccc3-c3cncn31)C2O] | same as 36b | 381.2 |
| 36e | 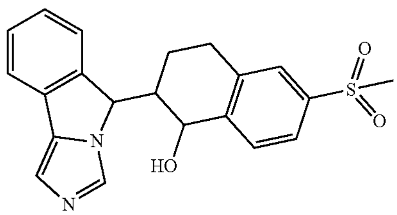 [SMILES: CS(=O)(=O)c1ccc2c(c1)CCC(C1c3ccccc3-c3cncn31)C2O] | $^1$H NMR (500 MHz, Chloroform-d) δ 7.91 (s, 1H), 7.81 (dd, J = 7.8, 1.8 Hz, 1H), 7.71-7.63 (m, 2H), 7.55-7.49 (m, 1H), 7.42-7.35 (m, 2H), 7.36-7.21 (m, 1H), 6.91 (s, 1H), 5.47 (d, J = 1.9 Hz, 1H), 5.15 (d, J = 3.4 Hz, 1H), 3.06 (s, 3H), 2.81 (dd, J = 17.1, 5.2 Hz, 1H), 2.64 (ddd, J = 17.8, 12.4, 6.0 Hz, 1H), 2.45-2.38 (m, 1H), 1.66-1.47 (m, 1H), 1.16 (dd, J = 11.3, 3.6 Hz, 1H) | 381.2 |
| 36f | 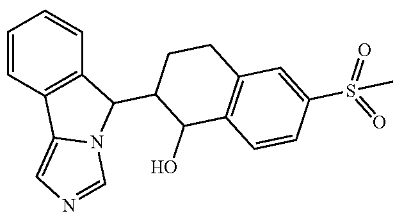 [SMILES: CS(=O)(=O)c1ccc2c(c1)CCC(C1c3ccccc3-c3cncn31)C2O] | Same as 36e | 381.2 |
| 36g | 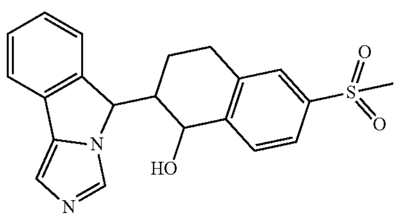 [SMILES: CS(=O)(=O)c1ccc2c(c1)CCC(C1c3ccccc3-c3cncn31)C2O] | Same as 36a | 381.2 |
| 36h | 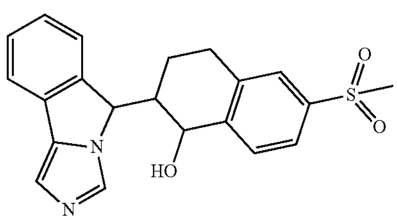 [SMILES: CS(=O)(=O)c1ccc2c(c1)CCC(C1c3ccccc3-c3cncn31)C2O] | Same as 36c | 381.2 |
| 37a | 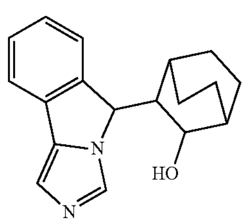 [SMILES: OC1C2CCC(CC2)C1C1c2ccccc2-c2cncn21] | No NMR data due to small sample quantity | 281.4 |
| 37b | 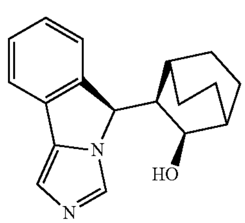 [SMILES: O[C@@H]1C2CCC(CC2)[C@@H]1[C@@H]1c2ccccc2-c2cncn21] | $^1$H NMR (500 MHz, Chloroform-d) δ 7.94 (s, 1H), 7.59 (dq, J = 7.7, 0.9 Hz, 1H), 7.53 (dt, J = 7.5, 0.9 Hz, 1H), 7.34 (tt, J = 7.4, 0.9 Hz, 1H), 7.23 (td, J = 7.6, 1.2 Hz, 1H), 7.18 (s, 1H), 5.64 (d, J = 6.6 Hz, 1H), 4.35 (dd, J = 8.8, 4.4 Hz, 1H), 2.06 (dd, J = 8.7, 6.8 Hz, 1H), 1.98-1.92 (m, 1H), 1.84-1.78 (m, 1H), 1.71-1.60 (m, 1H), 1.49-1.34 (m, 4H), 1.33-1.24 (m, 2H). | 281.4 |

TABLE 2-continued

| Ex. # | Structure | $^1$H NMR | MS (M + H)$^+$ |
|---|---|---|---|
| 37c | 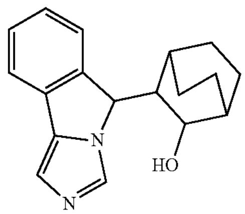 [SMILES: OC1C2CCC(CC2)C1C1c2ccccc2-c2cncn21] | $^1$H NMR (500 MHz, Chloroform-d) δ 8.11 (s, 1H), 7.54 (dt, J = 7.6, 0.9 Hz, 1H), 7.35 (tt, J = 7.6, 0.8 Hz, 1H), 7.29 (dq, J = 7.7, 0.9 Hz, 1H), 7.19 (td, J = 7.6, 1.1 Hz, 1H), 7.17 (s, 1H), 5.64 (d, J = 10.5 Hz, 1H), 4.24 (dd, J = 8.3, 4.5 Hz, 1H), 2.11-1.92 (m, 2H), 1.89 (dd, J = 5.9, 3.3 Hz, 1H), 1.70-1.56 (m, 5H), 1.56-1.46 (m, 1H), 1.45-1.24 (m, 2H). | 281.4 |
| 37d | 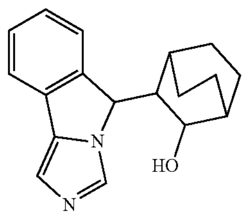 [SMILES: OC1C2CCC(CC2)C1C1c2ccccc2-c2cncn21] | $^1$H NMR (500 MHz, Chloroform-d) δ 8.11 (s, 1H), 7.54 (dt, J = 7.8, 1.0 Hz, 1H), 7.35 (tt, J = 7.6, 0.8 Hz, 1H), 7.29 (dd, J = 7.7, 1.0 Hz, 1H), 7.19 (td, J = 7.6, 1.2 Hz, 1H), 7.17 (s, 1H), 5.64 (d, J = 10.5 Hz, 1H), 4.25 (dd, J = 8.3, 4.5 Hz, 1H), 2.11-1.92 (m, 2H), 1.92-1.87 (m, 1H), 1.69-1.56 (m, 5H), 1.56-1.47 (m, 1H), 1.39-1.24 (m, 2H) | 281.4 |
| 37e | 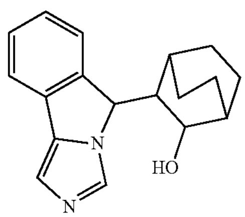 [SMILES: OC1C2CCC(CC2)C1C1c2ccccc2-c2cncn21] | $^1$H NMR (500 MHz, Chloroform-d) δ 7.95 (s, 1H), 7.59 (dq, J = 7.6, 0.9 Hz, 1H), 7.53 (dt, J = 7.6, 0.9 Hz, 1H), 7.38-7.31 (m, 1H), 7.23 (td, J = 7.6, 1.2 Hz, 1H), 7.18 (s, 1H), 5.64 (d, J = 6.6 Hz, 1H), 4.35 (dd, J = 8.8, 4.4 Hz, 1H), 2.07 (t, J = 7.7 Hz, 1H), 1.98-1.92 (m, 1H), 1.85-1.78 (m, 1H), 1.71-1.60 (m, 1H), 1.51 (s, 1H), 1.49-1.33 (m, 3H), 1.31-1.24 (m, 2H). | 281.4 |
| 37f | 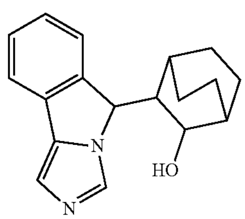 [SMILES: OC1C2CCC(CC2)C1C1c2ccccc2-c2cncn21] | No NMR data due to small sample quantity | 281.4 |
| 37g | 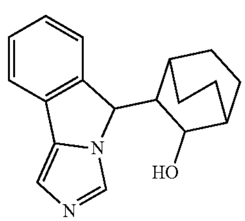 [SMILES: OC1C2CCC(CC2)C1C1c2ccccc2-c2cncn21] | No NMR data due to small sample quantity | 281.4 |
| 38a | 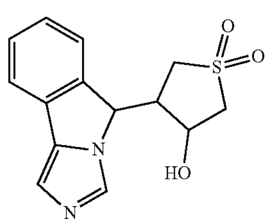 [SMILES: O=S1(=O)CC(O)C(C2c3ccccc3-c3cncn32)C1] | (500 MHz, Chloroform-d) δ 8.01 (s, 1H), 7.58 (d, J = 7.6 Hz, 1H), 7.43 (dd, J = 15.8, 7.8 Hz, 2H), 7.35 (t, J = 7.5 Hz, 1H), 7.24 (s, 1H), 5.78 (d, J = 2.8 Hz, 1H), 4.76 (q, J = 8.9 Hz, 1H), 3.62 (dd, J = 13.1, 7.5 Hz, 1H), 3.28-3.21 (m, 1H), 2.74 (dd, J = 13.3, 7.5 Hz, 1H), 2.22 (t, J = 13.1 Hz, 1H). | 291.3 |
| 38b | 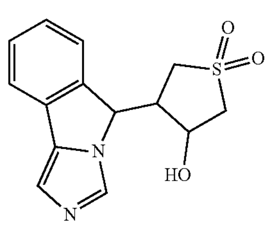 [SMILES: O=S1(=O)CC(O)C(C2c3ccccc3-c3cncn32)C1] | (500 MHz, Chloroform-d) δ 8.17 (s, 1H), 7.58 (d, J = 7.6 Hz, 1H), 7.48-7.40 (m, 2H), 7.36 (t, J = 7.8 Hz, 1H), 7.25-7.24 (m, 1H), 5.80 (s, 1H), 4.78 (q, J = 8.9 Hz, 1H), 3.63 (dd, J = 13.0, 7.5 Hz, 1H), 3.25 (dd, J = 12.9, 9.0 Hz, 1H), 2.74 (dd, J = 13.4, 7.4 Hz, 1H), 2.21 (t, J = 13.1 Hz, 2H). | 291.3 |

TABLE 2-continued

| Ex. # | Structure | $^1$H NMR | MS $(M + H)^+$ |
|---|---|---|---|
| 38c | 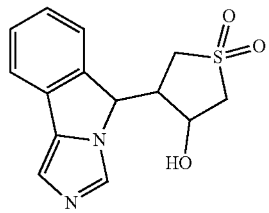 [SMILES: O=S1(=O)CC(O)C(C2c3ccccc3-c3cncn32)C1] | (500 MHz, Chloroform-d) δ 7.76 (s, 1H), 7.60 (d, J = 7.6 Hz, 1H), 7.49-7.45 (m, 1H), 7.43 (d, J = 7.7 Hz, 1H), 7.35-7.29 (m, 1H), 7.22 (s, 1H), 5.64 (d, J = 3.7 Hz, 1H), 4.62 (q, J = 7.7 Hz, 1H), 3.46 (dd, J = 13.3, 7.4 Hz, 1H), 3.27 (ddd, J = 12.0, 8.1, 3.6 Hz, 1H), 3.22-3.14 (m, 1H), 2.96 (dd, J = 13.3, 7.5 Hz, 1H), 2.58-2.50 (m, 1H). | 291.3 |
| 38d | 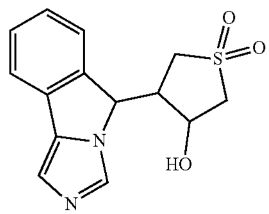 [SMILES: O=S1(=O)CC(O)C(C2c3ccccc3-c3cncn32)C1] | (500 MHz, Chloroform-d) δ 7.75 (s, 1H), 7.60 (d, J = 7.7 Hz, 1H), 7.49-7.45 (m, 1H), 7.43 (d, J = 7.7 Hz, 1H), 7.32 (td, J = 7.6, 1.1 Hz, 1H), 7.23 (s, 1H), 5.63 (d, J = 3.7 Hz, 1H), 4.62 (q, J = 7.7 Hz, 1H), 3.45 (dd, J = 13.4, 7.4 Hz, 1H), 3.27 (dp, J = 11.9, 4.1 Hz, 1H), 3.18 (ddd, J = 13.3, 7.4, 1.5 Hz, 1H), 2.97 (dd, J = 12.5, 7.9 Hz, 1H), 2.59-2.51 (m, 1H). | 291.3 |
| 39a | 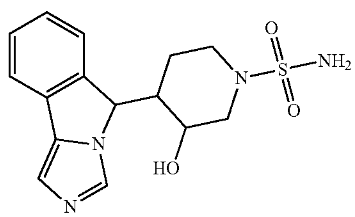 [SMILES: NS(=O)(=O)N1CCC(C2c3ccccc3-c3cncn32)C(O)C1] | $^1$HNMR (300 MHz, DMSO-$d_6$) δ 7.94 (s, 1H), 7.63 (d, J = 7.5 Hz, 1H), 7.52 (d, J = 7.5 Hz, 1H), 7.42-7.38 (m, 1H), 7.31-7.28 (m, 1H), 7.15 (s, 1H), 6.78 (s, 2H), 5.73-5.71 (m, 2H), 3.78-3.65 (m, 2H), 3.25-3.20 (m, 1H), 2.32-2.20 (m, 3H), 0.71-0.65 (m, 1H), 0.58-0.40 (m, 1H) | 298.2 |
| 39b | 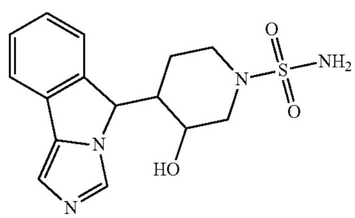 [SMILES: NS(=O)(=O)N1CCC(C2c3ccccc3-c3cncn32)C(O)C1] | Same as 39a | 298.2 |
| 39c | 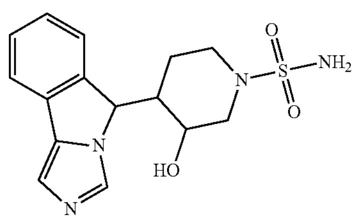 [SMILES: NS(=O)(=O)N1CCC(C2c3ccccc3-c3cncn32)C(O)C1] | $^1$HNMR (300 MHz, $CD_3OD$) δ 7.93 (s, 1H), 7.64 (d, J = 7.5 Hz, 1H), 7.49 (d, J = 7.5 Hz, 1H), 7.46-7.34 (m, 2H), 7.20 (s, 1H), 5.82 (d, J = 1.5 Hz, 1H), 4.01-3.92 (m, 2H), 3.46-3.45 (m, 1H), 2.58-2.41 (m, 2H), 2.20-2.10 (m, 1H), 0.99-0.93 (m, 1H), 0.71-0.65 (m, 1H) | 298.2 |
| 39d | 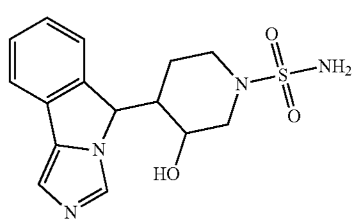 [SMILES: NS(=O)(=O)N1CCC(C2c3ccccc3-c3cncn32)C(O)C1] | Same as 39c | 298.2 |
| 40a | 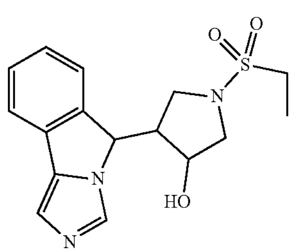 [SMILES: CCS(=O)(=O)N1CC(O)C(C2c3ccccc3-c3cncn32)C1] | (400 MHz, DMSO-$d_6$) δ 7.98 (s, 1H), 7.62 (d, J = 7.6 Hz, 1H), 7.57 (dd, J = 7.6, 1.0 Hz, 1H), 7.40 (d, J = 7.5 Hz, 1H), 7.31 (dd, J = 7.5, 1.1 Hz, 1H), 7.18 (s, 1H), 5.71 (d, J = 4.9 Hz, 1H), 5.60 (d, J = 3.3 Hz, 1H), 4.37 (dd, J = 7.0, 5.1 Hz, 1H), 3.40 (dd, J = 9.7, 6.6 Hz, 1H), 3.08-3.00 (m, 2H), 2.96 (p, J = 7.1 Hz, 3H), 2.36 (dd, J = 9.3, 8.1 Hz, 1H), 1.08 (t, J = 7.3 Hz, 3H). | 334.1 |

TABLE 2-continued

| Ex. # | Structure | $^1H$ NMR | MS $(M + H)^+$ |
|---|---|---|---|
| 40b | 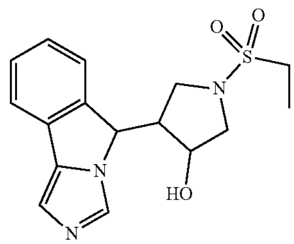 [SMILES: CCS(=O)(=O)N1CC(O)C(C2c3ccccc3-c3cncn32)C1] | (400 MHz, DMSO-$d_6$) δ 7.98 (s, 1H), 7.62 (d, J = 7.5 Hz, 1H), 7.59-7.54 (m, 1H), 7.41 (t, J = 7.7 Hz, 1H), 7.33-7.26 (m, 1H), 7.18 (s, 1H), 5.71 (d, J = 4.9 Hz, 1H), 5.60 (d, J = 3.3 Hz, 1H), 4.42-4.33 (m, 1H), 3.40 (dd, J = 9.7, 6.6 Hz, 1H), 3.08-3.00 (m, 2H), 2.96 (p, J = 7.2 Hz, 3H), 2.40-2.33 (m, 1H), 1.08 (t, J = 7.4 Hz, 3H). | 334.1 |
| 40c | 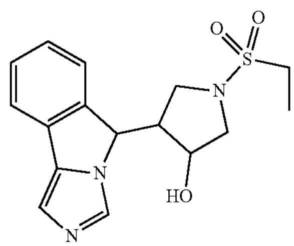 [SMILES: CCS(=O)(=O)N1CC(O)C(C2c3ccccc3-c3cncn32)C1] | (400 MHz, DMSO-$d_6$) δ 7.93 (s, 1H), 7.62 (d, J = 7.5 Hz, 1H), 7.56 (dd, J = 7.8, 1.0 Hz, 1H), 7.42 (t, J = 7.5 Hz, 1H), 7.32-7.27 (m, 1H), 7.14 (s, 1H), 5.55 (d, J = 4.5 Hz, 1H), 5.38 (d, J = 4.6 Hz, 1H), 4.00 (t, J = 5.3 Hz, 1H), 3.45 (dd, J = 10.1, 8.4 Hz, 1H), 3.11 (dd, J = 10.2, 6.4 Hz, 2H), 3.08-2.99 (m, 3H), 2.98-2.89 (m, 1H), 1.15 (t, J = 7.4 Hz, 3H). | 334.1 |
| 40d | 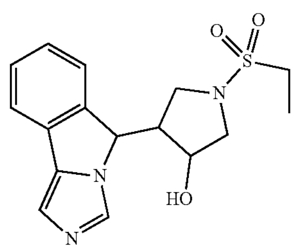 [SMILES: CCS(=O)(=O)N1CC(O)C(C2c3ccccc3-c3cncn32)C1] | (400 MHz, DMSO-$d_6$) δ 7.93 (s, 1H), 7.62 (d, J = 7.5 Hz, 1H), 7.56 (dd, J = 7.6, 1.0 Hz, 1H), 7.45-7.38 (m, 1H), 7.31 (dd, J = 7.6, 1.1 Hz, 1H), 7.14 (s, 1H), 5.55 (d, J = 4.5 Hz, 1H), 5.38 (d, J = 4.7 Hz, 1H), 4.00 (p, J = 5.3 Hz, 1H), 3.45 (dd, J = 10.1, 8.4 Hz, 1H), 3.11 (dd, J = 10.1, 6.4 Hz, 2H), 3.08-2.99 (m, 3H), 2.94 (td, J = 7.5, 3.6 Hz, 1H), 1.15 (t, J = 7.3 Hz, 3H). | 334.1 |
| 41a | 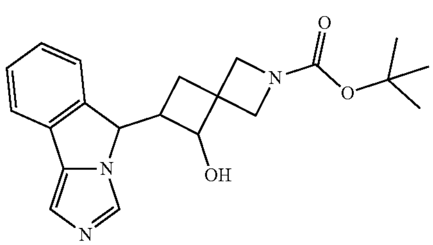 [SMILES: CC(C)(C)OC(=O)N1CC2(CC(C3c4ccccc4-c4cncn43)C2O)C1] | $^1H$ NMR (400 MHz, DMSO-$d_6$) δ 7.89 (t, J = 0.6 Hz, 1H), 7.65-7.51 (m, 1H), 7.47-7.30 (m, 2H), 7.24 (td, J = 7.7, 1.1 Hz, 1H), 7.10 (s, 1H), 5.63 (d, J = 7.1 Hz, 1H), 5.33 (d, J = 8.0 Hz, 1H), 4.22-3.97 (m, 2H), 3.73 (s, 2H), 3.57 (s, 1H), 2.05 (dq, J = 17.0, 8.7 Hz, 1H), 1.86 (t, J = 9.5 Hz, 1H), 1.36 (s, 9H) | |
| 41b | 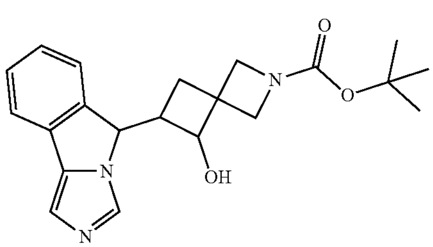 [SMILES: CC(C)(C)OC(=O)N1CC2(CC(C3c4ccccc4-c4cncn43)C2O)C1] | same as 41a | |
| 41c | 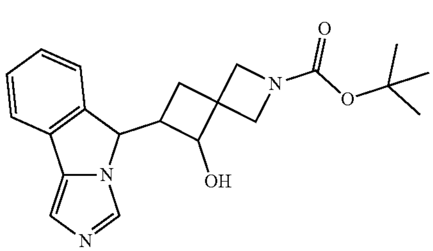 [SMILES: CC(C)(C)OC(=O)N1CC2(CC(C3c4ccccc4-c4cncn43)C2O)C1] | $^1H$ NMR (400 MHz, DMSO-$d_6$) δ 7.94-7.82 (m, 1H), 7.64-7.51 (m, 2H), 7.36 (tdd, J = 7.4, 1.5, 0.7 Hz, 1H), 7.25 (td, J = 7.6, 1.1 Hz, 1H), 7.13 (s, 1H), 6.12 (d, J = 4.7 Hz, 1H), 5.38 (d, J = 7.6 Hz, 1H), 4.39 (t, J = 5.8 Hz, 1H), 4.13 (d, J = 8.9 Hz, 1H), 3.89-3.56 (m, 2H), 2.60 (p, J = 7.9 Hz, 1H), 2.03 (d, J = 8.5 Hz, 2H), 1.36 (s, 9H) | |

TABLE 2-continued
| Ex. # | Structure | $^1$H NMR | MS (M + H)$^+$ |
|---|---|---|---|
| 41d | 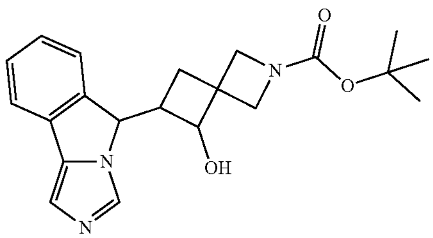 [SMILES: CC(C)(C)OC(=O)N1CC2(CC(C3c4ccccc4-c4cncn43)C2O)C1] | $^1$H NMR (400 MHz, DMSO-$d_6$) δ 7.83 (s, 1H), 7.59 (J = 7.6, 1.1 Hz, 1H), 7.51-7.30 (m, 2H), 7.23 (td, J = 7.6, 1.2 Hz, 1H), 7.11 (s, 1H), 6.11 (d ,J = 5.2 Hz, 1H), 5.31 (d, J = 10.1 Hz, 1H), 4.33 (q, J = 5.0 Hz, 1H), 4.14 (d, J = 9.0 Hz, 1H), 3.81 (d, J = 11.4 Hz, 1H), 3.63 (s, 1H), 2.71-2.54 (m, 1H), 2.23 (dqd, J = 11.5, 8.3, 4.6 Hz, 2H), 1.38 (s, 9H). | |
| 41e | 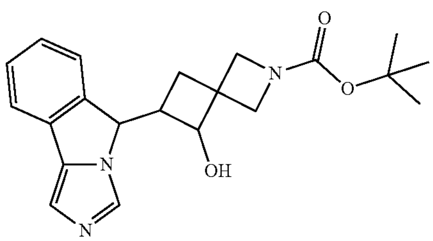 [SMILES: CC(C)(C)OC(=O)N1CC2(CC(C3c4ccccc4-c4cncn43)C2O)C1] | Same as 41c | |
| 41f | 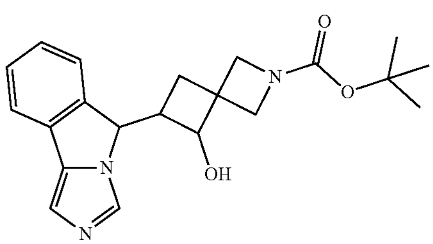 [SMILES: CC(C)(C)OC(=O)N1CC2(CC(C3c4ccccc4-c4cncn43)C2O)C1] | Same as 41d | |
| 41g | 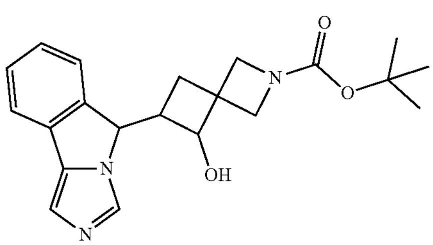 [SMILES: CC(C)(C)OC(=O)N1CC2(CC(C3c4ccccc4-c4cncn43)C2O)C1] | $^1$H NMR (400 MHz, DMSO-$d_6$) δ 7.81 (s, 1H), 7.66-7.48 (m, 2H), 7.46-7.32 (m, 1H), 7.26 (td, J = 7.5, 1.2 Hz, 1H), 7.13 (s, 1H), 5.69 (d, J = 6.8 Hz, 1H), 5.36 (d, J = 7.4 Hz, 1H), 4.16 (t, J = 7.3 Hz, 2H), 3.75 (d, J = 9.0 Hz, 1H), 3.66 (s, 1H), 3.55 (s, 1H), 2.14 (p, J = 8.6 Hz, 1H), 1.89 (dd, J = 11.2, 8.6 Hz, 1H), 1.44 (t, J = 10.7 Hz, 1H), 1.36 (s, 9H) | |
| 41h | 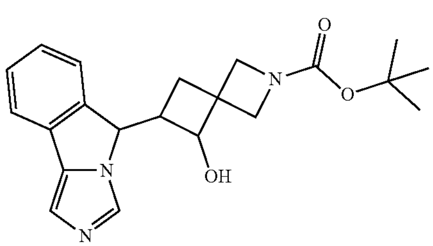 [SMILES: CC(C)(C)OC(=O)N1CC2(CC(C3c4ccccc4-c4cncn43)C2O)C1] | Same as 41g | |
| 42a | 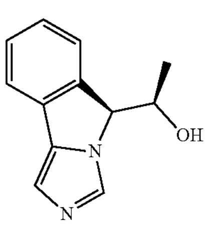 | 1H NMR (DMSO-d6, 500 MHz): δ (ppm) 7.79 (s, 1H), 7.59 (d, J = 7.6 Hz, 1H), 7.48-7.52 (m, 1H), 7.8 (t, J = 7.1 Hz, 1H), 7.26 (td, J = 7.5, 1.1 Hz, 1H), 7.14 (s, 1H), 5.48 (d, J = 3.7 Hz, 1H), 5.36 (d, J = 3.3 Hz, 1H), 4.38 (tdd, J = 6.3, 3.6, 2.6 Hz, 1H), 0.48 (d, J = 6.3 Hz, 3H) | 201.1 |

TABLE 2-continued

| Ex. # | Structure | $^1$H NMR | MS $(M + H)^+$ |
|---|---|---|---|
| 42b | 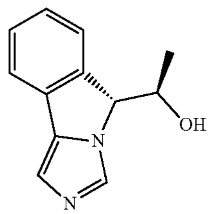 | 1H NMR (DMSO-d6, 500 MHz): δ (ppm) 0.93 (d, J = 6.3 Hz, 3H), 4.00-4.16 (m, 1H), 5.20 (d, J = 5.2 Hz, 1H), 5.35 (d, J = 4.8 Hz, 1H), 7.11 (s, 1H), 7.26 (td, J = 7.6, 1.1 Hz, 1H), 7.35-7.43 (m, 1H), 7.55-7.67 (m, 2H), 7.87 (s, 1H) | 201.1 |
| 42c | 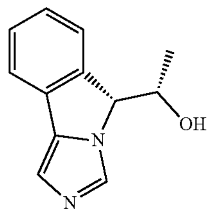 | Same as 42a | 201.1 |
| 42d | 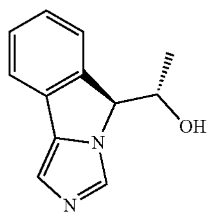 | Same as 42b | 201.2 |
| 43 | 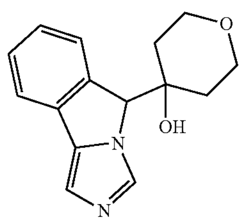 | 1H NMR (Chloroform-d, 400 MHz): δ (ppm) 7.98 (s, 1H), 7.50 (dd, J = 12.4, 7.6 Hz, 2H), 7.38 (t, J = 7.5 Hz, 1H), 7.25 (t, J = 7.6 Hz, 1H), 7.11 (s, 1H), 5.08 (s, 1H), 3.76-3.95 (m, 2H), 3.51-3.72 (m, 2H), 3.31 (d, J = 36.2 Hz, 2H), 2.15 (ddd, J = 13.0, 10.3, 7.0 Hz, 1H), 1.68 (d, J = 12.7 Hz, 1H), 1.05-1.28 (m, 1H), 0.78 (d, J = 12.9 Hz, 1H) | 257.3 |
| 44 | 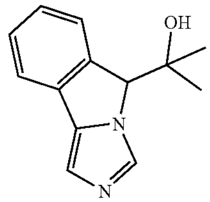 [SMILES: CC(C)(O)C1c2ccccc2-c2cncn21] | 1H NMR (400 MHz, Chloroform-d) δ 7.89 (s, 1H), 7.54 (d, J = 7.6 Hz, 1H), 7.49 (d, J = 7.7 Hz, 1H), 7.38 (t, J = 7.5 Hz, 1H), 7.23 (dd, J = 7.5, 1.1 Hz, 1H), 7.18 (s, 1H), 5.09 (s, 1H), 1.49 (s, 3H), 0.83 (s, 3H) | |
| 45 | 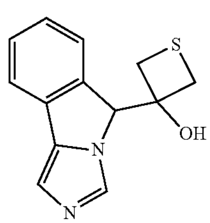 [SMILES: OC1(C2c3ccccc3-c3cncn32)CSC1] | 1H NMR (400 MHz, DMSO-d6) δ 7.92 (s, 1H), 7.71 (d, J = 7.7 Hz, 1H), 7.61 (d, J = 7.6 Hz, 1H), 7.41 (t, J = 7.5 Hz, 1H), 7.20-7.29 (m, 1H), 7.14 (s, 1H), 6.61 (s, 1H), 5.40 (s, 1H), 3.45 (d, J = 10.4 Hz, 1H), 3.27 (d, J = 10.5 Hz, 1H), 3.14 (s, 2H). | 245 |
| 46a | 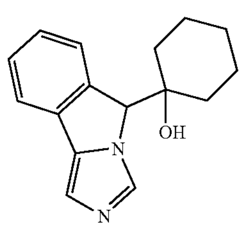 [SMILES: OC1(C2c3ccccc3-c3cncn32)CCCCC1] | 1H NMR (Chloroform-d, 400 MHz): δ (ppm) 8.00 (s, 1H), 7.52 (t, J = 7.9 Hz, 2H), 7.38 (t, J = 7.5 Hz, 1H), 7.25 (t, J = 7.4 Hz, 1H), 7.13 (s, 1H), 5.05 (s, 1H), 2.94 (br s, 1H), 1.68 (dt, J = 39.3, 11.9 Hz, 5H), 1.34-1.53 (m, 2H), 0.89-1.06 (m, 2H), 0.81 (dt, J = 13.3, 6.6 Hz, 1H) | 255.3 |

TABLE 2-continued
| Ex. # | Structure | $^1$H NMR | MS $(M + H)^+$ |
|---|---|---|---|
| 46b | 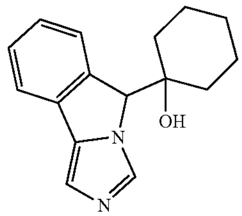 [SMILES: OC1(C2c3ccccc3-c3cncn32)CCCCC1] | Same as 46a | 255.3 |
| 47a | 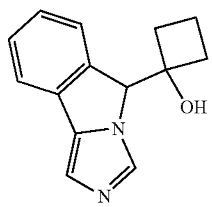 [SMILES: OC1(C2c3ccccc3-c3cncn32)CCC1] | 1H NMR (Chloroform-d, 400 MHz): δ (ppm) 7.95 (s, 1H), 7.57 (t, J = 6.7 Hz, 2H), 7.41 (t, J = 7.7 Hz, 1H), 7.15 (s, 1H), 7.22-7.36 (m, 1H), 2.87 (br s, H), 5.22 (s, 1H), 2.57 (dd, J = 8.5, 4.4 Hz, 1H), 2.28 (p, J = 8.7, 8.2 Hz, 1H), 1.78-2.04 (m, 3H), 1.27-1.44 (m, 1H) | 227.5 |
| 47b | 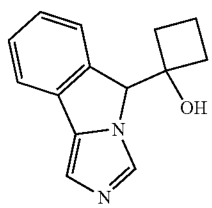 [SMILES: OC1(C2c3ccccc3-c3cncn32)CCC1] | Same as 47a | 227.5 |
| 48 | 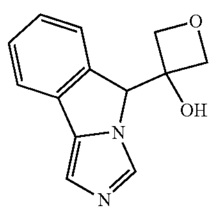 [SMILES: OC1(C2c3ccccc3-c3cncn32)COC1] | 1H NMR (DMSO-d6, 400 MHz): δ (ppm) 7.92 (s, 1H), 7.62 (d, J = 7.7 Hz, 2H), 7.42 (t, J = 7.5 Hz, 1H), 7.26 (t, J = 8.1 Hz, 1H), 7.16 (s, 1H), 6.51 (s, 1H), 5.61 (s, 1H), 4.71 (d, J = 7.1 Hz, 1H), 4.60 (d, J = 7.0 Hz, 1H), 4.52 (d, J = 7.1 Hz, 1H), 4.47 (d, J = 7.1 Hz, 1H). | 229.1 |
| 49a | 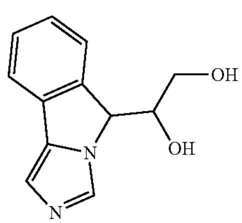 [SMILES: OCC(O)C1c2ccccc2-c2cncn21] | NA | 217 |
| 49b | 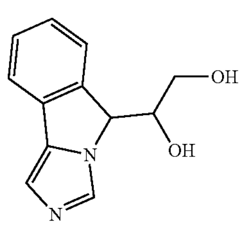 [SMILES: OCC(O)C1c2ccccc2-c2cncn21] | NA | 217 |
| 49c | 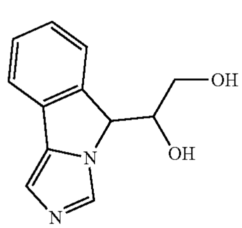 [SMILES: OCC(O)C1c2ccccc2-c2cncn21] | 1H NMR (400 MHz, DMSO-d6) δ 8.40 (s, 1H), 7.68 (dt, J = 7.6, 1.0 Hz, 1H), 7.59 (dq, J = 7.6, 1.0 Hz, 1H), 7.51-7.39 (m, 2H), 7.35 (td, J = 7.5, 1.2 Hz, 1H), 5.56 (d, J = 4.0 Hz, 1H), 5.46 (d, J = 4.9 Hz, 1H), 4.84 (t, J = 5.2 Hz, 1H), 4.20 (p, J = 5.2 Hz, 1H) | 217 |

TABLE 2-continued

| Ex. # | Structure | $^1$H NMR | MS (M + H)$^+$ |
|---|---|---|---|
| 49d | 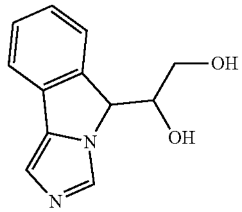 [SMILES: OCC(O)C1c2ccccc2-c2cncn21] | 1H NMR (400 MHz, DMSO-d6) δ 7.81 (d, J = 0.7 Hz, 1H), 7.56 (ddt, J = 13.4, 7.6, 0.9 Hz, 2H), 7.38 (tdd, J = 7.6, 1.2, 0.7 Hz, 1H), 7.25 (td, J = 7.6, 1.2 Hz, 1H), 7.11 (s, 1H), 5.42 (d, J = 4.9 Hz, 1H), 5.38 (d, J = 4.3 Hz, 1H), 4.75 (t, J = 5.4 Hz, 1H), 4.15-3.98 (m, 1H), 3.22-3.06 (m, 2H). | 217 |
| 50 | 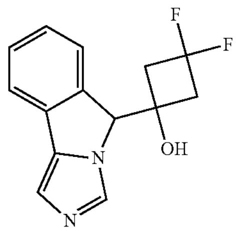 [SMILES: OC1(C2c3ccccc3-c3cncn32)CC(F)(F)C1] | 1H NMR (400 MHz, DMSO-d6) δ 7.91 (s, 1H), 7.57 (ddt, J = 12.0, 7.6, 0.9 Hz, 2H), 7.41-7.37 (m, 1H), 7.24 (td, J = 7.5, 1.1 Hz, 1H), 7.12 (s, 1H), 5.85 (s, 1H), 5.46 (s, 1H), 3.17 (m, 2H), 2.68-2.54 (m, 2H). | |
| 51a | 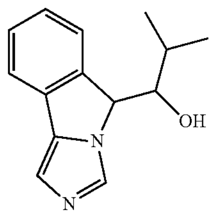 [SMILES: CC(C)C(O)C1c2ccccc2-c2cncn21] | 1H NMR (DMSO-d6, 400 MHz): δ (ppm) 7.82 (t, J = 0.7 Hz, 1H), 7.58 (dt, J = 7.5, 1.0 Hz, 1H), 7.49 (dq, J = 7.6, 0.9 Hz, 1H), 7.37 (tdd, J = 7.5, 1.1, 0.6 Hz, 1H), 7.26 (td, J = 7.6, 1.2 Hz, 1H), 7.12 (s, 1H), 5.32 (d, J = 5.2 Hz, 1H), 5.13 (d, J = 6.5 Hz, 1H), 3.47 (td, J = 6.3, 5.2 Hz, 1H), 1.93 (dt, J = 13.3, 6.6 Hz, 1H), 0.99 (d, J = 6.6 Hz, 3H), 0.93 (d, J = 6.8 Hz, 3H) | 229.4 |
| 51b | 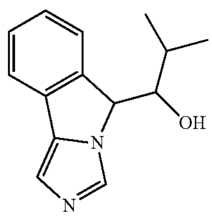 [SMILES: CC(C)C(O)C1c2ccccc2-c2cncn21] | 1H NMR (DMSO-d6, 400 MHz): δ (ppm) 7.81 (t, J = 0.7 Hz, 1H), 7.59 (dt, J = 7.5, 1.0 Hz, 1H), 7.51 (dq, J = 7.6, 0.9 Hz, 1H), 7.37 (tdd, J = 7.5, 1.1, 0.6 Hz, 1H), 7.25 (td, J = 7.5, 1.2 Hz, 1H), 7.11 (s, 1H), 5.39 (d, J = 4.5 Hz, 1H), 5.27 (d, J = 5.6 Hz, 1H), 3.80 (td, J = 5.5, 4.5 Hz, 1H), 1.52-1.67 (m, 1H), 0.81 (d, J = 6.8 Hz, 3H), 0.66 (d, J = 6.7 Hz, 3H) | 229.4 |
| 51c | 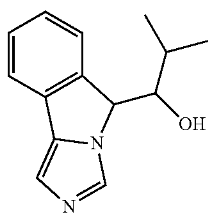 [SMILES: CC(C)C(O)C1c2ccccc2-c2cncn21] | Same as 51b | 229.4 |
| 51d | 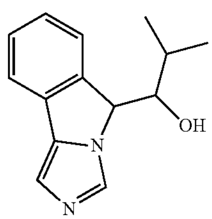 [SMILES: CC(C)C(O)C1c2ccccc2-c2cncn21] | Same as 51a | 229.4 |
| 52a | 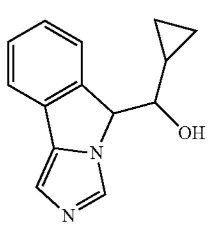 [SMILES: OC(C1CC1)C1c2ccccc2-c2cncn21] | 1H NMR (DMSO-d6, 400 MHz): δ (ppm)-0.16--0.06 (m, 1H), −0.04-0.07 (m, 1H), 0.16 (dddd, J = 9.2, 7.9, 5.6, 1.7 Hz, 2H), 0.26-0.39 (m, 1H), 3.63 (dt, J = 7.4, 4.1 Hz, 1H), 5.39 (d, J = 3.8 Hz, 1H), 5.43 (d, J = 4.3 Hz, 1H), 7.12 (s, 1H), 7.24 (td, J = 7.6, 1.1 Hz, 1H), 7.37 (tt, J = 7.6, 0.9 Hz, 1H), 7.56 (ddt, J = 15.1, 7.6, 0.9 Hz, 2H), 7.82 (t, J = 0.6 Hz, 1H) | 227.4 |

TABLE 2-continued

| Ex. # | Structure | $^1$H NMR | MS (M + H)$^+$ |
|---|---|---|---|
| 52b | 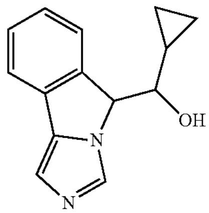 [SMILES: OC(C1CC1)C1c2ccccc2-c2cncn21] | Same as 52a | 227.4 |
| 52c | 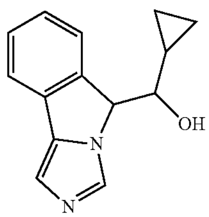 [SMILES: OC(C1CC1)C1c2ccccc2-c2cncn21] | 1H NMR (DMSO-d6, 400 MHz): δ (ppm) 0.06-0.13 (m, 1H), 0.26-0.41 (m, 3H), 0.84 (qt, J = 7.8, 5.0 Hz, 1H), 3.32-3.38 (m, 1H), 5.29 (d, J = 5.2 Hz, 1H), 5.32 (d, J = 5.0 Hz, 1H), 7.10 (s, 1H), 7.24 (td, J = 7.5, 1.2 Hz, 1H), 7.37 (tdd, J = 7.5, 1.1, 0.6 Hz, 1H), 7.58 (dt, J = 7.6, 1.0 Hz, 1H), 7.60-7.64 (m, 1H), 7.87 (t, J = 0.6 Hz, 1H) | 227.4 |
| 52d | 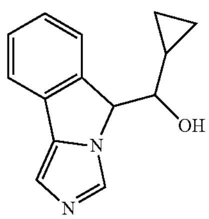 [SMILES: OC(C1CC1)C1c2ccccc2-c2cncn21] | Same as 52d | 227.4 |
| 53 | 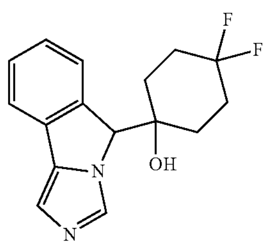 [SMILES: OC1(C2c3ccccc3-c3cncn32)CCC(F)(F)CC1] | 1H NMR (400 MHz, DMSO-d6) δ 7.88 (s, 1H), 7.60 (tt, J = 7.6, 0.9 Hz, 2H), 7.41 (ddd, J = 7.6, 7.0, 1.0 Hz, 1H), 7.27 (td, J = 7.6, 1.2 Hz, 1H), 7.15 (s, 1H), 5.57 (s, 1H), 5.25 (s, 1H), 2.20-1.84 (m, 3H), 1.81-1.65 (m, 3H), 1.11-0.99 (m, 2H). | 291 |
| 54 | 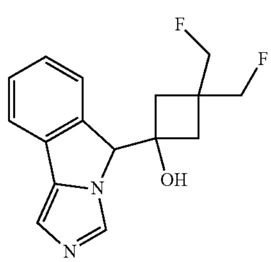 [SMILES: OC1(C2c3ccccc3-c3cncn32)CC(CF)(CF)C1] | 1H NMR (400 MHz, DMSO-d6) δ 7.88 (s, 1H), 7.58 (dt, J = 7.5, 0.9 Hz, 1H), 7.53 (dq, J = 7.7, 0.9 Hz, 1H), 7.38 (tt, J = 7.6, 0.9 Hz, 1H), 7.24 (td, J = 7.5, 1.1 Hz, 1H), 7.12 (s, 1H), 5.51 (s, 1H), 5.40 (s, 1H), 4.57 (d, J = 47.7 Hz, 2H), 4.30 (d, J = 47.5 Hz, 2H), 2.47-2.37 (m, 2H), 1.87 (dd, J = 20.4, 13.5 Hz, 2H). | 291 |
| 55 | 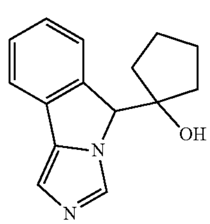 | 1H NMR (400 MHz, DMSO-d6) δ 7.86 (d, J = 0.7 Hz, 1H), 7.59 (d, J = 1.0 Hz, 1H), 7.57 (d, J = 1.1 Hz, 1H), 7.37 (ddd, J = 8.0, 6.9, 0.8 Hz, 1H), 7.23 (td, J = 7.5, 1.2 Hz, 1H), 7.10-7.13 (m, 1H), 5.30-5.34 (m, 1H), 4.97 (s, 1H), 1.60-1.80 (m, 4H), 1.35-1.51 (m, 4H). | 241 |

TABLE 2-continued

| Ex. # | Structure | $^1$H NMR | MS (M + H)$^+$ |
|---|---|---|---|
| 56a | 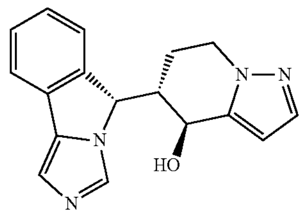 [SMILES: O[C@@H]1c2ccnn2CC[C@H]1[C@H]1c2ccccc2-c2cncn21] | $^1$H NMR (500 MHz, DMSO-d6) δ 1.01-1.16 (m, 2H), 2.51-2.59 (m, 1H), 3.73-3.84 (m, 1H), 3.93-4.01 (m, 1H), 5.03 (dd, J = 10.5, 7.2 Hz, 1H), 5.76 (d, J = 1.9 Hz, 1H), 6.18 (d, J = 7.2 Hz, 1H), 6.31 (dd, J = 1.9, 0.8 Hz, 1H), 7.19 (s, 1H), 7.34 (dd, J = 7.5, 1.1 Hz, 1H), 7.38-7.46 (m, 2H), 7.51 (dd, J = 7.6, 1.0 Hz, 1H), 7.64 (dt, J = 7.6, 0.9 Hz, 1H), 7.98 (s, 1H). | 293.2 |
| 56b | 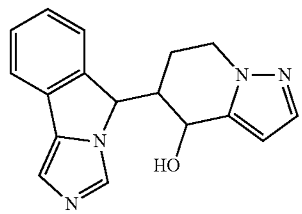 [SMILES: OC1c2ccnn2CCC1C1c2ccccc2-c2cncn21] | $^1$H NMR (500 MHz, DMSO-d6) δ 1.88 (d, J = 12.3 Hz, 1H), 2.28 (qd, J = 12.2, 5.5 Hz, 1H), 2.32-2.38 (m, 1H), 3.80-3.91 (m, 1H), 4.16 (ddd, J = 12.7, 5.5, 1.9 Hz, 1H), 4.99 (s, 1H), 5.48 (d, J = 5.7 Hz, 1H), 5.83 (d, J = 5.4 Hz, 1H), 6.22 (d, J = 1.8 Hz, 1H), 7.14 (s, 1H), 7.25 (td, J = 7.6, 1.2 Hz, 1H), 7.39 (dd, J = 6.3, 1.4 Hz, 2H), 7.62 (dt, J = 7.6, 0.9 Hz, 1H), 7.71 (dd, J = 7.8, 0.9 Hz, 1H), 7.97 (s, 1H). | 293.2 |
| 56c | 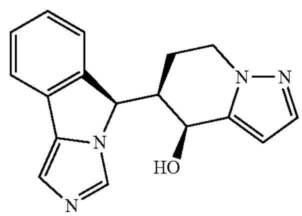 [SMILES: O[C@@H]1c2ccnn2CC[C@@H]1[C@@H]1c2ccccc2-c2cncn21] | $^1$H NMR (500 MHz, DMSO-d6) δ 1.19 (d, J = 13.6 Hz, 1H), 1.86 (qd, J = 12.6, 5.8 Hz, 1H), 2.55-2.66 (m, 1H), 3.77 (td, J = 12.5, 4.9 Hz, 1H), 4.05 (ddd, J = 12.8, 5.8, 2.0 Hz, 1H), 5.19 (t, J = 4.6 Hz, 1H), 5.54 (d, J = 2.5 Hz, 1H), 6.09 (d, J = 5.5 Hz, 1H), 6.27 (d, J = 1.9 Hz, 1H), 7.13 (s, 1H), 7.30 (td, J = 7.6, 1.2 Hz, 1H), 7.36-7.44 (m, 2H), 7.60 (dt, J = 7.6, 0.9 Hz, 1H), 7.64 (dq, J = 7.7, 1.0 Hz, 1H), 7.92 (s, 1H). | 293.2 |
| 56d | 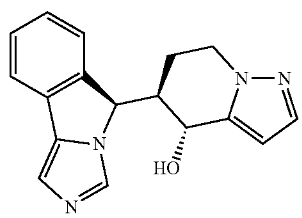 [SMILES: O[C@H]1c2ccnn2CC[C@@H]1[C@@H]1c2ccccc2-c2cncn21] | $^1$H NMR (500 MHz, DMSO-d6) δ 1.01-1.16 (m, 2H), 2.52 (d, J = 2.3 Hz, 1H), 3.78 (td, J = 12.2, 5.1 Hz, 1H), 3.90-4.00 (m, 1H), 5.03 (dd, J = 10.6, 7.2 Hz, 1H), 5.76 (d, J = 1.8 Hz, 1H), 6.18 (d, J = 7.2 Hz, 1H), 6.27-6.34 (m, 1H), 7.19 (s, 1H), 7.33 (td, J = 7.6, 1.1 Hz, 1H), 7.37-7.46 (m, 2H), 7.51 (dd, J = 7.6, 1.0 Hz, 1H), 7.64 (d, J = 7.5 Hz, 1H), 7.98 (s, 1H). | 293.2 |
| 56e | 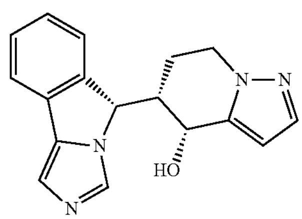 [SMILES: O[C@H]1c2ccnn2CC[C@H]1[C@H]1c2ccccc2-c2cncn21] | $^1$H NMR (500 MHz, DMSO-d6) δ 1.19 (d, J = 13.5 Hz, 1H), 1.77-1.95 (m, 1H), 2.57-2.70 (m, 1H), 3.76 (td, J = 12.2, 4.7 Hz, 1H), 3.99-4.12 (m, 1H), 5.15-5.26 (m, 1H), 5.54 (d, J = 2.6 Hz, 1H), 6.09 (d, J = 5.6 Hz, 1H), 6.27 (d, J = 2.2 Hz, 1H), 7.13 (s, 1H), 7.29 (ddd, J = 8.8, 7.0, 1.3 Hz, 1H), 7.35-7.46 (m, 2H), 7.62 (dd, J = 19.0, 7.6 Hz, 2H), 7.92 (s, 1H). | 293.2 |
| 56f | 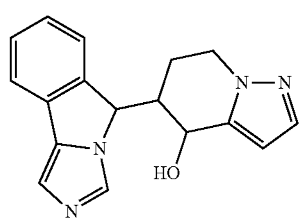 [SMILES: OC1c2ccnn2CCC1C1c2ccccc2-c2cncn21] | $^1$H NMR (500 MHz, DMSO-d6) δ 1.03 (s, 1H), 1.11-1.30 (m, 1H), 2.71 (s, 1H), 3.82 (s, 1H), 3.97 (s, 1H), 4.97 (s, 1H), 5.77 (s, 1H), 6.10-6.24 (m, 1H), 6.28 (s, 1H), 7.18 (d, J = 8.9 Hz, 1H), 7.23-7.35 (m, 1H), 7.40 (d, J = 16.2 Hz, 2H), 7.63 (m, 2H), 7.94 (t, J = 10.8 Hz, 1H). | 293.2 |
| 56g | 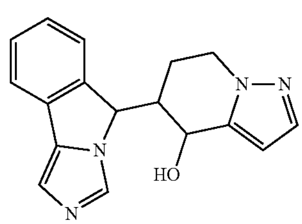 [SMILES: OC1c2ccnn2CCC1C1c2ccccc2-c2cncn21] | $^1$H NMR (500 MHz, DMSO-d6) δ 1.88 (d, J = 10.6 Hz, 1H), 2.28 (tt, J = 12.5, 6.0 Hz, 1H), 2.32-2.39 (m, 1H), 3.86 (td, J = 12.3, 4.8 Hz, 1H), 4.16 (ddd, J = 12.7, 5.5, 1.8 Hz, 1H), 4.99 (dd, J = 5.9, 3.3 Hz, 1H), 5.48 (d, J = 5.7 Hz, 1H), 5.83 (d, J = 5.6 Hz, 1H), 7.14 (s, 1H), 7.25 (dd, J = 7.6, 1.2 Hz, 1H), 7.36-7.42 (m, 2H), 7.62 (dt, J = 7.6, 0.9 Hz, 1H), 7.71 (dd, J = 7.7, 0.9 Hz, 1H), 7.97 (s, 1H). | 293.2 |

TABLE 2-continued

| Ex. # | Structure | $^1$H NMR | MS (M + H)$^+$ |
|---|---|---|---|
| 57a | 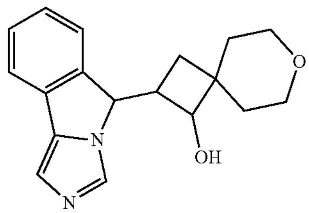 [SMILES: OC1C(C2c3ccccc3-c3cncn32)CC12CCOCC2] | $^1$H NMR (500 MHz, Chloroform-d) δ 7.85 (s, 1H), 7.56-7.51 (m, 1H), 7.37 (d, J = 3.2 Hz, 1H), 7.35-7.32 (m, 1H), 7.25-7.21 (m, 1H), 7.13 (s, 1H), 5.17 (d, J = 7.9 Hz, 1H), 3.88 (dt, J = 11.5, 4.2 Hz, 1H), 3.84 (d, J = 8.0 Hz, 1H), 3.77 (dd, J = 7.9, 3.6 Hz, 1H), 3.61-3.54 (m, 1H), 3.51-3.41 (m, 1H), 2.55 (ddd, J = 17.5, 9.6, 8.0 Hz, 1H), 2.15-2.07 (m, 1H), 1.93-1.84 (m, 1H), 1.79 (ddd, J = 13.7, 10.1, 4.1 Hz, 1H), 1.54-1.49 (m, 2H), 1.42 (d, J = 13.3 Hz, 1H). | 297.2 |
| 57b | 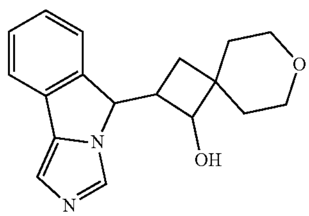 [SMILES: OC1C(C2c3ccccc3-c3cncn32)CC12CCOCC2] | $^1$H NMR (500 MHz, Chloroform-d) δ 7.78 (s, 1H), 7.54 (dd, J = 11.9, 7.6 Hz, 2H), 7.36 (d, J = 7.8 Hz, 1H), 7.23 (dd, J = 7.6, 1.0 Hz, 1H), 7.18 (s, 1H), 5.46 (d, J = 8.8 Hz, 1H), 4.30 (dd, J = 6.5, 2.8 Hz, 1H), 3.70 (dq, J = 9.3, 5.1, 4.1 Hz, 2H), 3.59-3.51 (m, 2H), 2.67-2.57 (m, 1H), 2.07-2.02 (m, 2H), 1.78-1.73 (m, 1H), 1.67 (s, 1H), 1.59 (d, J = 3.8 Hz, 1H), 1.55 (s, 1H). | 297.2 |
| 57c | 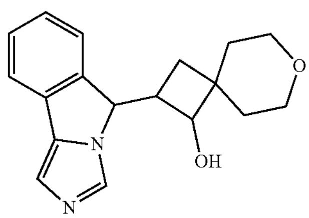 [SMILES: OC1C(C2c3ccccc3-c3cncn32)CC12CCOCC2] | $^1$H NMR (500 MHz, Chloroform-d) δ 7.95 (s, 1H), 7.55 (d, J = 7.6 Hz, 1H), 7.36 (d, J = 5.5 Hz, 1H), 7.33-7.30 (m, 1H), 7.22-7.19 (m, 1H), 7.16 (s, 1H), 5.44 (d, J = 11.0 Hz, 1H), 4.25 (dd, J = 6.1, 3.3 Hz, 1H), 3.79-3.76 (m, 1H), 3.74-3.67 (m, 1H), 3.60 (dddd, J = 19.9, 11.6, 8.2, 3.4 Hz, 2H), 2.49-2.40 (m, 1H), 2.30 (t, J = 10.4 Hz, 1H), 2.15 (ddd, J = 11.3, 8.5, 3.4 Hz, 1H), 1.89-1.82 (m, 1H), 1.76-1.67 (m, 2H), 1.53 (s, 1H). | 297.2 |
| 57d | 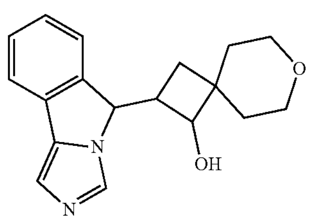 [SMILES: OC1C(C2c3ccccc3-c3cncn32)CC12CCOCC2] | $^1$H NMR (500 MHz, Chloroform-d) δ 7.97 (s, 1H), 7.55 (d, J = 7.6 Hz, 1H), 7.37 (d, J = 7.4 Hz, 1H), 7.31 (d, J = 7.6 Hz, 1H), 7.20 (t, J = 7.6 Hz, 1H), 7.16 (s, 1H), 5.44 (d, J = 11.0 Hz, 1H), 4.25 (dd, J = 5.9, 3.2 Hz, 1H), 3.80-3.76 (m, 1H), 3.70 (dd, J = 10.6, 6.1 Hz, 1H), 3.66-3.56 (m, 2H), 2.49-2.39 (m, 1H), 2.30 (t, J = 10.4 Hz, 1H), 2.18-2.11 (m, 1H), 1.84 (td, J = 8.7, 8.2, 4.1 Hz, 1H), 1.72 (s, 1H), 1.61-1.55 (m, 2H). | 297.2 |
| 57e | 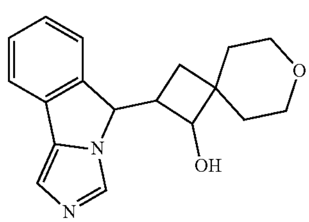 [SMILES: OC1C(C2c3ccccc3-c3cncn32)CC12CCOCC2] | $^1$H NMR (500 MHz, Chloroform-d) δ 7.78 (s, 1H), 7.54 (dd, J = 11.1, 7.6 Hz, 2H), 7.36 (t, J = 7.4 Hz, 1H), 7.24 (td, J = 7.6, 1.1 Hz, 1H), 7.19 (s, 1H), 5.46 (d, J = 8.8 Hz, 1H), 4.30 (dd, J = 6.5, 2.8 Hz, 1H), 3.75-3.68 (m, 2H), 3.58-3.51 (m, 2H), 2.62 (qd, J = 8.7, 6.5 Hz, 1H), 2.10-1.99 (m, 2H), 1.76 (ddd, J = 12.8, 8.7, 3.8 Hz, 1H), 1.63 (ddd, J = 18.6, 10.4, 4.4 Hz, 3H). | 297.2 |
| 57f | 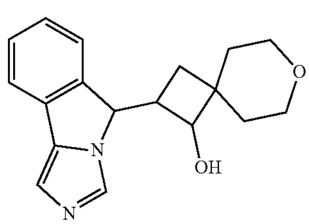 [SMILES: OC1C(C2c3ccccc3-c3cncn32)CC12CCOCC2] | $^1$H NMR (500 MHz, Chloroform-d) δ 7.86 (s, 1H), 7.52 (d, J = 7.6 Hz, 1H), 7.37 (t, J = 7.5 Hz, 1H), 7.35-7.32 (m, 1H), 7.23 (td, J = 7.6, 1.1 Hz, 1H), 7.11 (s, 1H), 5.17 (d, J = 7.9 Hz, 1H), 3.89 (dt, J = 11.4, 4.3 Hz, 1H), 3.76 (dt, J = 11.4, 4.2 Hz, 1H), 3.62-3.55 (m, 1H), 3.50-3.42 (m, 1H), 2.55 (ddd, J = 17.5, 9.5, 8.0 Hz, 1H), 2.14-2.05 (m, 1H), 1.90 (ddd, J = 13.6, 10.3, 3.9 Hz, 1H), 1.79 (ddd, J = 13.9, 10.2, 4.2 Hz, 1H), 1.54-1.49 (m, 2H), 1.42 (d, J = 13.2 Hz, 1H). | 297.2 |
| 57g | 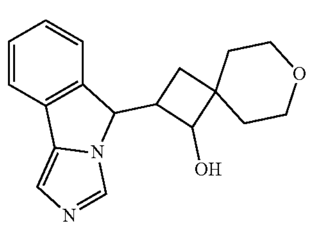 [SMILES: OC1C(C2c3ccccc3-c3cncn32)CC12CCOCC2] | $^1$H NMR (500 MHz, Chloroform-d) δ 7.69 (s, 1H), 7.54 (d, J = 7.6 Hz, 1H), 7.51-7.44 (m, 1H), 7.38 (t, J = 7.4 Hz, 1H), 7.28-7.26 (m, 1H), 7.19 (s, 1H), 5.25 (d, J = 6.8 Hz, 1H), 4.07 (d, J = 8.1 Hz, 1H), 3.87 (dt, J = 11.5, 4.1 Hz, 1H), 3.74 (dt, J = 11.8, 4.1 Hz, 1H), 3.54-3.47 (m, 1H), 3.36 (td, J = 11.4, 2.7 Hz, 1H), 2.65-2.54 (m, 1H), 1.90-1.76 (m, 3H), 1.45 (d, J = 13.5 Hz, 1H), 1.35 (d, J = 13.2 Hz, 1H), 1.07 (t, J = 10.1 Hz, 1H). | 297.2 |

TABLE 2-continued

| Ex. # | Structure | $^1$H NMR | MS (M + H)$^+$ |
|---|---|---|---|
| 57h | 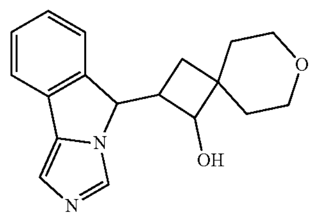 [SMILES: OC1C(C2c3ccccc3-c3cncn32)CC12CCOCC2] | $^1$H NMR (500 MHz, Chloroform-d) δ 7.69 (s, 1H), 7.54 (d, J = 7.6 Hz, 1H), 7.50-7.45 (m, 1H), 7.37 (t, J = 7.5 Hz, 1H), 7.24 (d, J = 1.0 Hz, 1H), 7.19 (s, 1H), 5.25 (d, J = 6.8 Hz, 1H), 4.08 (d, J = 8.1 Hz, 1H), 3.87 (dt, J = 11.4, 4.1 Hz, 1H), 3.74 (dt, J = 11.5, 4.0 Hz, 1H), 3.51 (td, J = 10.9, 10.5, 2.3 Hz, 1H), 3.36 (td, J = 11.4, 2.7 Hz, 1H), 2.69-2.54 (m, 1H), 1.97-1.75 (m, 3H), 1.46 (d, J = 13.4 Hz, 1H), 1.36 (d, J = 13.2 Hz, 1H), 1.07 (t, J = 10.5 Hz, 1H). | 297.2 |
| 58a | 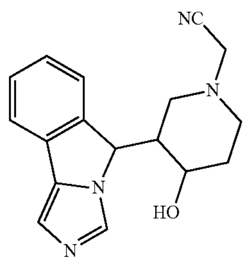 [SMILES: N#CCN1CCC(O)C(C2c3ccccc3-c3cncn32)C1] | $^1$H NMR (300 MHz, $CD_3OD$) δ 7.98 (s, 1H), 7.66 (d, J = 7.5 Hz, 1H), 7.52 (d, J = 7.5 Hz, 1H), 7.48-7.34 (m, 2H), 7.22 (s, 1H), 5.82 (d, J = 3.0 Hz, 1H), 3.95-3.83 (m, 1H), 3.52-3.39 (m, 2H), 2.87-2.83 (m, 1H), 2.46-2.05 (m, 4H), 1.83-1.65 (m, 1H), 1.48-1.41 (m, 1H). | 295.2 |
| 58b | 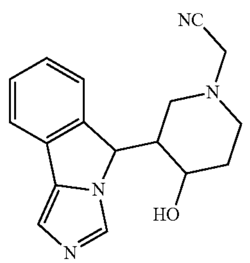 [SMILES: N#CCN1CCC(O)C(C2c3ccccc3-c3cncn32)C1] | The same as 058b. | 295.2 |
| 58c | 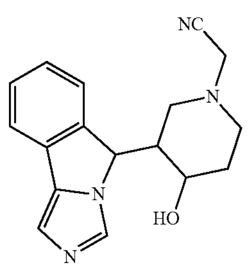 [SMILES: N#CCN1CCC(O)C(C2c3ccccc3-c3cncn32)C1] | $^1$H NMR (300 MHz, $CD_3OD$) δ 7.94 (s, 1H), 7.62 (d, J = 7.5 Hz, 1H), 7.55 (d, J = 7.5 Hz, 1H), 7.44-7.29 (m, 2H), 7.16 (s, 1H), 5.78 (d, J = 3.6 Hz, 1H), 3.88-3.79 (m, 1H), 3.49-3.32 (m, 2H), 2.80-2.76 (m, 1H), 2.53-2.46 (m, 1H), 2.22-1.87 (m, 3H), 1.76-1.67 (m, 1H), 1.55-1.48 (m, 1H). | 295.1 |
| 58d | 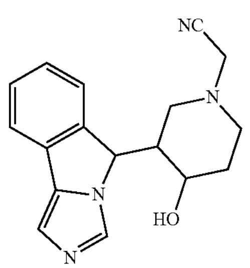 [SMILES: N#CCN1CCC(O)C(C2c3ccccc3-c3cncn32)C1] | The same as 058c. | 295.1 |
| 59a | 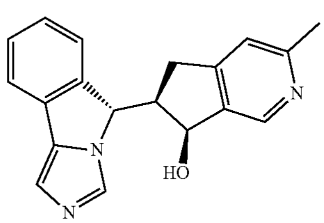 [SMILES: Cc1cc2c(cn1)[C@@H](O)[C@@H]([C@H]1c3ccccc3-c3cncn31)C2] | (500 MHz, Chloroform-d) δ 8.60 (s, 1H), 8.19 (s, 1H), 7.58 (dt, J = 7.5, 0.9 Hz, 1H), 7.48-7.44 (m, 1H), 7.42-7.36 (m, 1H), 7.25 (d, J = 1.1 Hz, 1H), 7.20 (s, 1H), 7.11 (s, 1H), 5.61 (d, J = 10.5 Hz, 1H), 5.42 (d, J = 5.4 Hz, 1H), 3.43-3.33 (m, 1H), 3.12 (dd, J = 16.0, 7.7 Hz, 1H), 2.56 (s, 3H), 2.48-2.37 (m, 1H). | 304.2 |

TABLE 2-continued

| Ex. # | Structure | $^1$H NMR | MS (M + H)$^+$ |
|---|---|---|---|
| 59b | 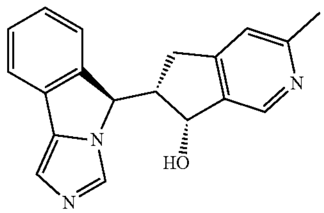 [SMILES: Cc1cc2c(cn1)[C@H](O)[C@H]([C@@H]1c3ccccc3-c3cncn31)C2] | (500 MHz, Chloroform-d) δ 8.58-8.52 (m, 1H), 8.30 (s, 1H), 7.55 (dd, J = 7.5, 1.0 Hz, 1H), 7.47-7.41 (m, 1H), 7.38 (td, J = 7.6, 1.0 Hz, 1H), 7.24 (dd, J = 7.6, 1.1 Hz, 1H), 7.15 (s, 1H), 7.07 (s, 1H), 5.63 (d, J = 10.4 Hz, 1H), 5.41 (d, J = 5.6 Hz, 1H), 3.42-3.32 (m, 1H), 3.08 (dd, J = 16.0, 7.7 Hz, 1H), 2.51 (s, 3H), 2.45-2.34 (m, 1H). | 304.2 |
| 59c | 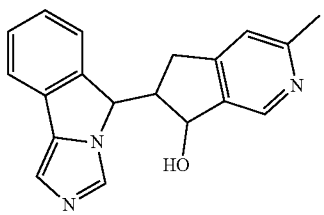 [SMILES: Cc1cc2c(cn1)C(O)C(C1c3ccccc3-c3cncn31)C2] | (500 MHz, Chloroform-d) δ 8.49 (s, 1H), 7.79 (s, 1H), 7.56 (dd, J = 7.7, 1.0 Hz, 1H), 7.52 (dt, J = 7.5, 0.9 Hz, 1H), 7.42-7.33 (m, 1H), 7.28 (dd, J = 7.6, 1.2 Hz, 1H), 7.08 (s, 1H), 6.85 (s, 1H), 5.70 (d, J = 4.8 Hz, 1H), 5.58 (d, J = 6.7 Hz, 1H), 3.02-2.95 (m, 1H), 2.69 (dd, J = 16.9, 8.2 Hz, 1H), 2.56-2.48 (m, 1H), 2.44 (s, 3H). | 304.2 |
| 59d | 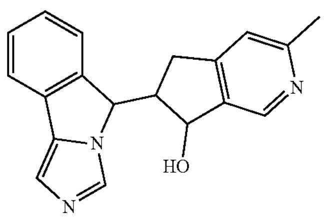 [SMILES: Cc1cc2c(cn1)C(O)C(C1c3ccccc3-c3cncn31)C2] | (500 MHz, Chloroform-d) δ 8.54 (s, 1H), 7.75 (s, 1H), 7.61 (dd, J = 7.7, 0.9 Hz, 1H), 7.55 (dt, J = 7.5, 0.9 Hz, 1H), 7.42-7.37 (m, 1H), 7.29 (td, J = 7.6, 1.2 Hz, 1H), 7.12 (s, 1H), 6.93 (s, 1H), 5.69 (d, J = 5.5 Hz, 1H), 5.57 (d, J = 6.3 Hz, 1H), 2.94-2.87 (m, 1H), 2.79 (dd, J = 16.7, 7.9 Hz, 1H), 2.74-2.66 (m, 1H), 2.50 (s, 3H). | 304.2 |
| 60a | 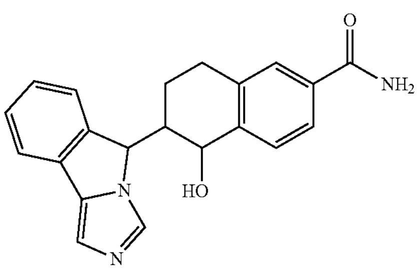 [SMILES: NC(=O)c1ccc2c(c1)CCC(C1c3ccccc3-c3cncn31)C2O] | $^1$H NMR (500 MHz, DMSO-$d_6$) δ 8.01 (s, 1H), 7.88 (s, 1H), 7.75 (d, J = 7.7 Hz, 1H), 7.68-7.59 (m, 4H), 7.39 (dt, J = 7.4, 3.5 Hz, 2H), 7.28-7.22 (m, 2H), 7.14 (s, 1H), 5.61 (d, J = 6.1 Hz, 1H), 5.45 (d, J = 6.0 Hz, 1H), 4.85-4.78 (m, 1H), 2.90-2.81 (m, 1H), 2.73-2.62 (m, 1H), 2.20-2.08 (m, 1H), 2.08-1.91 (m, 1H), 1.76-1.68 (m, 1H). | |
| 60b | 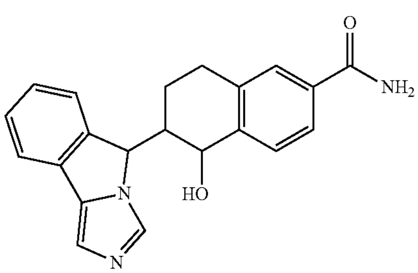 [SMILES: NC(=O)c1ccc2c(c1)CCC(C1c3ccccc3-c3cncn31)C2O] | $^1$H NMR (500 MHz, DMSO-d6) δ 7.95 (d, J = 0.7 Hz, 1H), 7.90 (s, 1H), 7.71 (dd, J = 8.0, 1.8 Hz, 1H), 7.64-7.58 (m, 3H), 7.46 (d, J = 8.0 Hz, 1H), 7.39 (tt, J = 7.6, 0.8 Hz, 1H), 7.29 (td, J = 8.0, 1.4 Hz, 2H), 7.11 (s, 1H), 5.54 (d, J = 2.3 Hz, 1H), 5.02 (d, J = 3.7 Hz, 1H), 2.76-2.69 (m, 1H), 2.59-2.54 (s, 1H), 2.50-2.46 (m, 1H), 1.54-1.43 (m, 1H), 1.03-0.95 (m, 1H). | 346.2 |
| 60c | 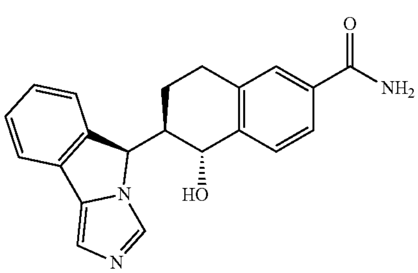 [SMILES: NC(=O)c1ccc2c(c1)CC[C@H]([C@@H]1c3ccccc3-c3cncn31)[C@H]2O] | $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J = 1.6 Hz, 1H), 7.49 (dq, J = 7.6, 0.8 Hz, 1H), 7.43-7.39 (m, 1H), 7.31 (td, J = 7.5, 1.1 Hz, 1H), 7.24 (s, 1H), 7.18 (s, 1H), 6.12 (d, J = 7.6 Hz, 1H), 5.81 (d, J = 1.9 Hz, 1H), 4.94 (dd, J = 10.7, 7.6 Hz, 1H), 2.66-2.57 (m, 2H), 2.44-2.34 (m, 1H), 0.99-0.86 (m, 1H), 0.89-0.76 (m, 1H). | 346.3 |

TABLE 2-continued

| Ex. # | Structure | $^1$H NMR | MS (M + H)$^+$ |
|---|---|---|---|
| 60d | 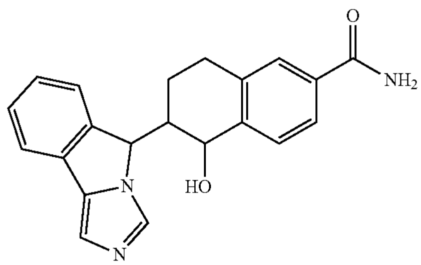 | $^1$H NMR (500 MHz, DMSO-$d_6$) δ 8.01 (s, 1H), 7.88 (s, 1H), 7.75 (d, J = 7.7 Hz, 1H), 7.68-7.59 (m, 4H), 7.39 (dt, J = 7.4, 3.5 Hz, 2H), 7.28-7.22 (m, 2H), 7.14 (s, 1H), 5.61 (d, J = 6.1 Hz, 1H), 5.45 (d, J = 6.0 Hz, 1H), 4.85-4.78 (m, 1H), 2.90-2.81 (m, 1H), 2.73-2.62 (m, 1H), 2.20-2.08 (m, 1H), 2.08-1.91 (m, 1H), 1.76-1.68 (m, 1H). | 346.3 |
| 60e | 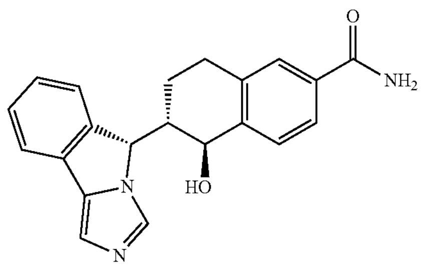 [SMILES: NC(=O)c1ccc2c(c1)CC[C@@H]([C@H]1c3ccccc3-c3cncn31)[C@@H]2O] | $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J = 1.6 Hz, 1H), 7.49 (dq, J = 7.6, 0.8 Hz, 1H), 7.43-7.39 (m, 1H), 7.31 (td, J = 7.5, 1.1 Hz, 1H), 7.24 (s, 1H), 7.18 (s, 1H), 6.12 (d, J = 7.6 Hz, 1H), 5.81 (d, J = 1.9 Hz, 1H), 4.94 (dd, J = 10.7, 7.6 Hz, 1H), 2.66-2.57 (m, 2H), 2.44-2.34 (m, 1H), 0.99-0.86 (m, 1H), 0.89-0.76 (m, 1H). | 346.2 |
| 60f | 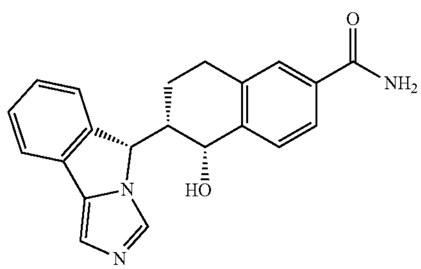 [SMILES: NC(=O)c1ccc2c(c1)CC[C@@H]([C@H]1c3ccccc3-c3cncn31)[C@H]2O] | $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J = 1.6 Hz, 1H), 7.49 (dq, J = 7.6, 0.8 Hz, 1H), 7.43-7.39 (m, 1H), 7.31 (td, J = 7.5, 1.1 Hz, 1H), 7.24 (s, 1H), 7.18 (s, 1H), 6.12 (d, J = 7.6 Hz, 1H), 5.81 (d, J = 1.9 Hz, 1H), 4.94 (dd, J = 10.7, 7.6 Hz, 1H), 2.66-2.57 (m, 2H), 2.44-2.34 (m, 1H), 0.99-0.86 (m, 1H), 0.89-0.76 (m, 1H). | 346.2 |
| 61a | 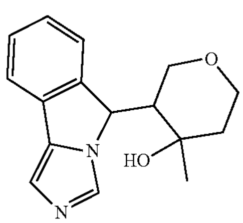 [SMILES: CC1(O)CCOCC1C1c2ccccc2-c2cncn21] | $^1$H NMR (500 MHz, Chloroform-d) δ 8.15 (s, 1H), 7.50 (dt, J = 7.6, 1.0 Hz, 1H), 7.36 (tt, J = 7.5, 0.9 Hz, 1H), 7.33 (dq, J = 7.7, 1.0 Hz, 1H), 7.28-7.24 (m, 1H), 7.14 (s, 1H), 5.49 (s, 1H), 3.80-3.69 (m, 2H), 3.25 (t, J = 11.4 Hz, 1H), 3.02 (dd, J = 11.6, 4.5 Hz, 1H), 2.29 (ddd, J = 11.1, 4.5, 1.1 Hz, 1H), 1.99 (ddd, J = 14.3, 11.7, 6.3 Hz, 2H), 1.61 (s, 3H). | 271 |
| 61b | 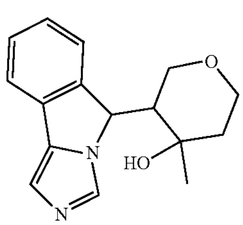 [SMILES: CC1(O)CCOCC1C1c2ccccc2-c2cncn21] | $^1$H NMR (500 MHz, Chloroform-d) δ 7.81 (dt, J = 7.8, 1.0 Hz, 1H), 7.71 (s, 1H), 7.52 (d, J = 7.6 Hz, 1H), 7.37-7.33 (m, 1H), 7.22 (td, J = 7.6, 1.2 Hz, 1H), 7.17 (s, 1H), 5.44 (s, 1H), 3.78-3.73 (m, 2H), 3.55 (t, J = 11.2 Hz, 1H), 3.17 (dd, J = 11.5, 4.4 Hz, 1H), 2.29 (ddd, J = 10.8, 4.4, 1.7 Hz, 1H), 1.93 (ddd, J = 14.2, 10.5, 6.6 Hz, 1H), 1.58 (m, 1H), 1.50 (s, 3H). | 271 |
| 61c | 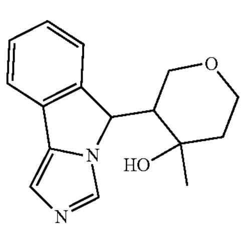 [SMILES: CC1(O)CCOCC1C1c2ccccc2-c2cncn21] | $^1$H NMR (500 MHz, Chloroform-d) δ 7.81 (dq, J = 7.7, 0.9 Hz, 1H), 7.71 (s, 1H), 7.52 (dt, J = 7.8, 1.0 Hz, 1H), 7.35 (tt, J = 7.6, 1.0 Hz, 1H), 7.22 (td, J = 7.6, 1.2 Hz, 1H), 7.17 (s, 1H), 5.44 (d, J = 1.6 Hz, 1H), 3.81-3.72 (m, 2H), 3.55 (dd, J = 11.6, 10.8 Hz, 1H), 3.17 (dd, J = 11.5, 4.4 Hz, 1H), 2.29 (ddd, J = 10.8, 4.4, 1.8 Hz, 1H), 1.93 (ddd, J = 14.2, 10.5, 6.6 Hz, 1H), 1.58 (m, 1H), 1.50 (s, 3H). | 271 |

TABLE 2-continued

| Ex. # | Structure | $^1$H NMR | MS $(M + H)^+$ |
|---|---|---|---|
| 61d | 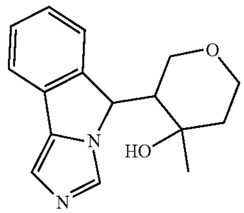 [SMILES: CC1(O)CCOCC1C1c2ccccc2-c2cncn21] | $^1$H NMR (500 MHz, Chloroform-d) δ 8.15 (s, 1H), 7.50 (dt, J = 7.6, 0.9 Hz, 1H), 7.36 (tt, J = 7.5, 0.9 Hz, 1H), 7.33 (dq, J = 7.7, 1.0 Hz, 1H), 7.26 (td, J = 7.5, 1.1 Hz, 1H), 7.14 (s, 1H), 5.49 (s, 1H), 3.79-3.70 (m, 2H), 3.25 (t, J = 11.4 Hz, 1H), 3.02 (dd, J = 11.6, 4.5 Hz, 1H), 2.29 (ddd, J = 11.1, 4.5, 1.1 Hz, 1H), 1.99 (ddd, J = 14.3, 11.8, 6.3 Hz, 1H), 1.61-1.58 (m, 4H). | 271 |
| 62a | 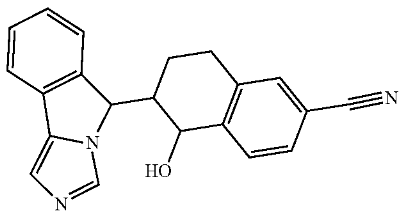 [SMILES: N#Cc1ccc2c(c1)CCC(C1c3ccccc3-c3cncn31)C2O] | $^1$H NMR (500 MHz, Chloroform-d) δ 7.99 (s, 1H), 7.62-7.57 (m, 1H), 7.55 (dd, J = 7.8, 0.9 Hz, 1H), 7.49 (d, J = 7.6 Hz, 1H), 7.45 (d, J = 1.3 Hz, 1H), 7.44-7.37 (m, 2H), 7.24-7.28 (s, 1H), 7.17 (s, 1H), 5.38 (d, J = 7.3 Hz, 1H), 4.88 (s, J = 3.1 Hz, 1H), 3.02 (dd, J = 5.3, 2.3 Hz, 1H), 2.80 (s, 1H), 2.22 (dd, J = 11.2, 5.4 Hz, 2H), 2.08 (dd, J = 7.6, 3.7 Hz, 1H). | 328.1 |
| 62b | 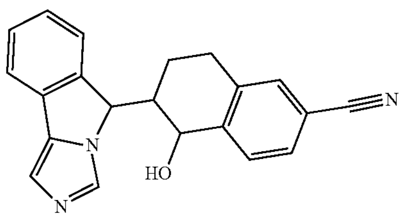 [SMILES: N#Cc1ccc2c(c1)CCC(C1c3ccccc3-c3cncn31)C2O] | $^1$H NMR (500 MHz, Chloroform-d) δ 7.71 (d, J = 8.2 Hz, 1H), 7.68-7.65 (m, 1H), 7.60 (d, J = 7.7 Hz, 1H), 7.48 (d, J = 1.0 Hz, 2H), 7.41 (d, J = 0.9 Hz, 1H), 7.35 (s, 1H), 7.21-7.25 (m, 2H), 5.76 (d, J = 3.0 Hz, 1H), 4.93 (d, J = 10.5 Hz, 1H), 2.82-2.66 (m, 2H), 2.52 (d, J = 11.1 Hz, 1H), 1.41-1.33 (m, 1H), 1.27 (dd, J = 12.6, 5.5 Hz, 2H). | 328.1 |
| 62c | 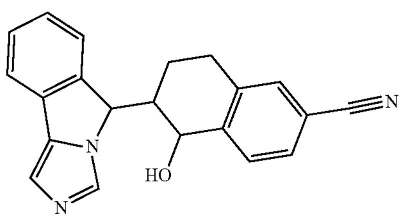 [SMILES: N#Cc1ccc2c(c1)CCC(C1c3ccccc3-c3cncn31)C2O] | $^1$H NMR (500 MHz, Chloroform-d) δ 8.09 (s, 1H), 7.61 (d, J = 8.0 Hz, 1H), 7.59-7.54 (m, 1H), 7.53-7.49 (m, 1H), 7.43 (d, J = 1.5 Hz, 1H), 7.41-7.36 (m, 2H), 7.24-7.29 (s, 1H), 6.67 (s, 1H), 5.48 (s, 1H), 5.14-5.08 (m, 1H), 2.73 (dd, J = 17.2, 5.3 Hz, 1H), 2.61 (dd, J = 12.3, 5.8 Hz, 1H), 2.42-2.35 (m, 1H), 1.39 (dd, J = 12.9, 5.5 Hz, 1H), 1.09 (dd, J = 10.5, 3.0 Hz, 1H). | 328.1 |
| 62d | 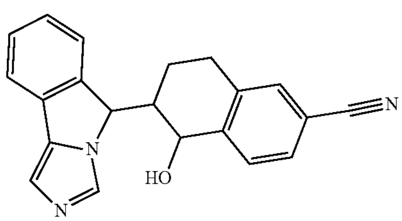 [SMILES: N#Cc1ccc2c(c1)CCC(C1c3ccccc3-c3cncn31)C2O] | $^1$H NMR (500 MHz, Chloroform-d) δ 8.09 (s, 1H), 7.61 (d, J = 8.0 Hz, 1H), 7.59-7.54 (m, 1H), 7.53-7.49 (m, 1H), 7.43 (d, J = 1.5 Hz, 1H), 7.41-7.36 (m, 2H), 7.24-7.29 (s, 1H), 6.67 (s, 1H), 5.48 (s, 1H), 5.14-5.08 (m, 1H), 2.73 (dd, J = 17.2, 5.3 Hz, 1H), 2.61 (dd, J = 12.3, 5.8 Hz, 1H), 2.42-2.35 (m, 1H), 1.39 (dd, J = 12.9, 5.5 Hz, 1H), 1.09 (dd, J = 10.5, 3.0 Hz, 1H). | 328.1 |
| 62e | 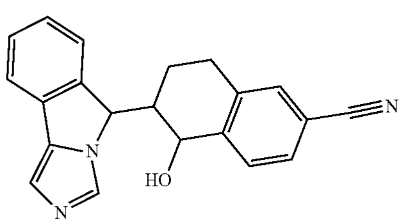 [SMILES: N#Cc1ccc2c(c1)CCC(C1c3ccccc3-c3cncn31)C2O] | na | 328.1 |
| 62f | 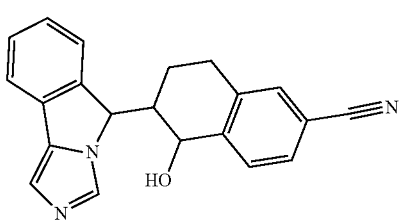 [SMILES: N#Cc1ccc2c(c1)CCC(C1c3ccccc3-c3cncn31)C2O] | na | 328.1 |

TABLE 2-continued

| Ex. # | Structure | $^1$H NMR | MS (M + H)$^+$ |
|---|---|---|---|
| 62g | 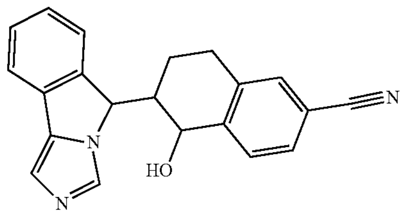 [SMILES: N#Cc1ccc2c(c1)CCC(C1c3ccccc3-c3cncn31)C2O] | $^1$H NMR (500 MHz, Chloroform-d) δ 7.71 (d, J = 8.2 Hz, 1H), 7.68-7.65 (m, 1H), 7.60 (d, J = 7.7 Hz, 1H), 7.48 (d, J = 1.0 Hz, 2H), 7.41 (d, J = 0.9 Hz, 1H), 7.35 (s, 1H), 7.21-7.25 (m, 2H), 5.76 (d, J = 3.0 Hz, 1H), 4.93 (d, J = 10.5 Hz, 1H), 2.82-2.66 (m, 2H), 2.52 (d, J = 11.1 Hz, 1H), 1.41-1.33 (m, 1H), 1.27 (dd, J = 12.6, 5.5 Hz, 2H). | 328.1 |
| 63a | 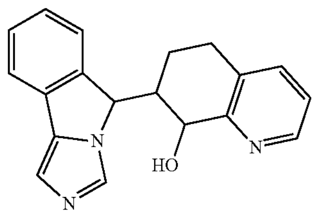 [SMILES: OC1c2ncccc2CCC1C1c2ccccc2-c2cncn21] | (500 MHz, Chloroform-d) δ 8.47 (ddt, J = 4.7, 1.6, 0.8 Hz, 1H), 7.74 (d, J = 0.7 Hz, 1H), 7.54 (dt, J = 7.8, 1.0 Hz, 1H), 7.47 (dq, J = 7.7, 1.0 Hz, 1H), 7.43-7.35 (m, 2H), 7.28 (dd, J = 7.5, 1.1 Hz, 1H), 7.18 (dd, J = 7.7, 4.8 Hz, 1H), 7.15 (s, 1H), 5.63 (d, J = 2.8 Hz, 1H), 5.17 (d, J = 5.0 Hz, 1H), 2.72-2.63 (m, 1H), 2.58 (dd, J = 10.4, 4.9 Hz, 2H), 1.64-1.56 (m, 2H), 1.43-1.34 (m, 1H). | 304.2 |
| 63b | 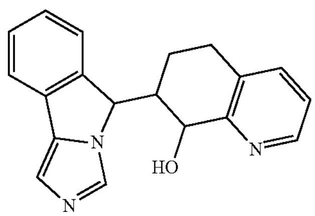 | (500 MHz, Chloroform-d) δ 8.52-8.47 (m, 1H), 7.80 (t, J = 0.7 Hz, 1H), 7.58 (dt, J = 7.6, 0.9 Hz, 1H), 7.51 (dd, J = 7.6, 1.0 Hz, 1H), 7.46-7.39 (m, 2H), 7.31 (dd, J = 7.5, 1.1 Hz, 1H), 7.21 (dd, J = 7.7, 4.8 Hz, 1H), 7.18 (s, 1H), 5.67 (d, J = 2.8 Hz, 1H), 5.21 (d, J = 5.0 Hz, 1H), 2.73-2.68 (m, 1H), 2.66-2.57 (m, 2H), 1.77-1.56 (m, 2H), 1.46-1.38 (m, 1H). | 304.2 |
| 63c | 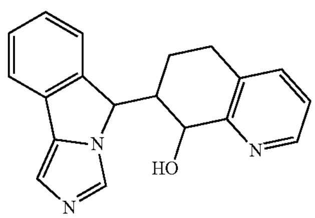 [SMILES: OC1c2ncccc2CCC1C1c2ccccc2-c2cncn21] | (500 MHz, Chloroform-d) δ 8.47-8.42 (m, 1H), 7.96 (s, 1H), 7.53 (dt, J = 7.7, 0.9 Hz, 1H), 7.47 (dq, J = 7.7, 0.9 Hz, 1H), 7.43-7.38 (m, 1H), 7.33 (tt, J = 7.5, 0.9 Hz, 1H), 7.20 (s, 1H), 7.16 (dd, J = 7.7, 4.7 Hz, 1H), 7.12 (td, J = 7.6, 1.1 Hz, 1H), 5.55 (d, J = 6.7 Hz, 1H), 5.03 (d, J = 4.3 Hz, 1H), 2.78-2.60 (m, 2H), 2.44-2.30 (m, 1H), 2.03-1.92 (m, 2H), 1.61 (s, 1H). | 304.2 |
| 63d | 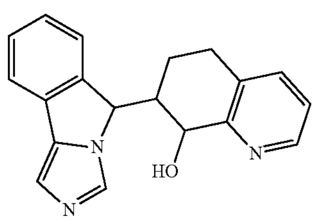 [SMILES: OC1c2ncccc2CCC1C1c2ccccc2-c2cncn21] | (500 MHz, Chloroform-d) δ 8.44 (dd, J = 4.8, 1.6 Hz, 1H), 7.96 (s, 1H), 7.52 (dt, J = 7.8, 1.0 Hz, 1H), 7.48 (dq, J = 7.7, 0.9 Hz, 1H), 7.43-7.39 (m, 1H), 7.33 (tt, J = 7.6, 0.8 Hz, 1H), 7.20 (s, 1H), 7.16 (dd, J = 7.7, 4.7 Hz, 1H), 7.12 (td, J = 7.7, 1.2 Hz, 1H), 5.54 (d, J = 6.7 Hz, 1H), 5.03 (d, J = 4.3 Hz, 1H), 2.78-2.60 (m, 2H), 2.36 (dd, J = 7.9, 4.4 Hz, 1H), 2.04-1.94 (m, 2H), 1.65 (s, 1H). | 304.2 |
| 64a | 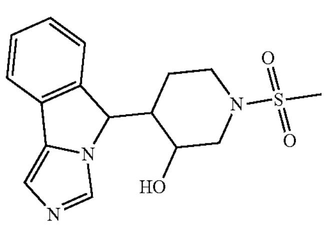 [SMILES: CS(=O)(=O)N1CCC(C2c3ccccc3-c3cncn32)C(O)C1] | $^1$H NMR (300 MHz, $CD_3OD$) 7.91 (s, 1H), 7.65 (d, J = 3.6 Hz, 1H), 7.50 (d, J = 3.6 Hz, 1H), 7.44 (t, J = 7.2 Hz, 1H), 7.36 (t, J = 7.2 Hz, 1H), 7.21 (s, 1H), 5.84 (s, 1H), 4.02-3.91 (m, 2H), 3.51 (dd, J = 9.6 Hz, 2.4 Hz, 1H), 2.84 (s, 3H), 2.68-2.57 (m, 2H), 2.23 (t, J = 5.6 Hz, 1H), 0.98 (dd, J = 13.6 Hz, 3.2 Hz, 1H). 0.68-0.64 (m, 1H). | 334.0 |
| 64b | 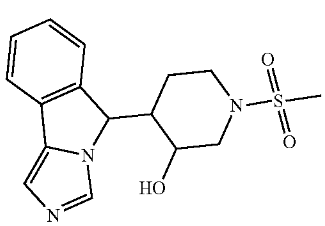 [SMILES: CS(=O)(=O)N1CCC(C2c3ccccc3-c3cncn32)C(O)C1] | The same as 064a. | 334.0 |

TABLE 2-continued

| Ex. # | Structure | $^1$H NMR | MS (M + H)$^+$ |
|---|---|---|---|
| 64c | 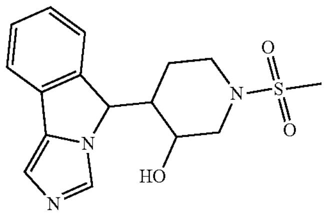 [SMILES: CS(=O)(=O)N1CCC(C2c3ccccc3-c3cncn32)C(O)C1] | $^1$H NMR (300 MHz, $CD_3OD$) 7.95 (s, 1H), 7.66 (d, J = 3.6 Hz, 1H), 7.54 (d, J = 3.6 Hz, 1H), 7.47 (t, J = 7.2 Hz, 1H), 7.40 (t, J = 7.2 Hz, 1H), 7.22 (s, 1H), 5.86 (s, 1H), 4.02-3.91 (m, 2H), 3.73 (dd, J = 9.6 Hz, 2.4 Hz, 1H), 3.01 (dd, J = 4.8 Hz, 2.4 Hz, 1H), 2.80-2.73 (m, 1H), 2.63 (s, 3H), 2.41-2.39 (m, 1H). 2.20 (dd, J = 10.4 Hz, 2.0 Hz, 1H), 1.91 (t, J = 11.6 Hz, 1H), 1.88-1.74 (m, 1H). | 334.0 |
| 64d | 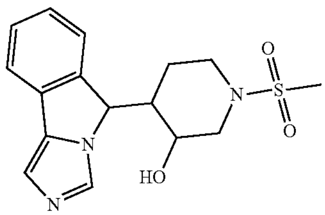 [SMILES: CS(=O)(=O)N1CCC(C2c3ccccc3-c3cncn32)C(O)C1] | The same as 064c. | 334.0 |
| 66a | 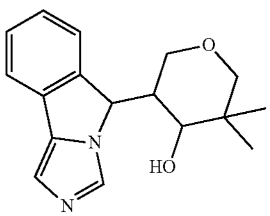 [SMILES: CC1(C)COCC(C2c3ccccc3-c3cncn32)C1O] | $^1$H NMR (500 MHz, DMSO-$d_6$) δ 7.93 (s, 1H), 7.59 (d, J = 7.5 Hz, 1H), 7.57 (d, J = 7.6 Hz, 1H), 7.39 (t, J = 7.5 Hz, 1H), 7.31 (td, J = 7.5, 1.0 Hz, 1H), 7.15 (s, 1H), 5.65 (d, J = 2.3 Hz, 1H), 5.43 (d, J = 6.3 Hz, 1H), 3.60 (dd, J = 10.9, 6.3 Hz, 1H), 2.93 (dd, J = 11.2, 3.9 Hz, 1H), 2.89 (d, J = 11.4 Hz, 1H), 2.44 (ddt, J = 15.1, 7.0, 4.1 Hz, 1H), 2.29 (t, J = 11.3 Hz, 1H), 0.99 (s, 3H), 0.90 (s, 3H). | 285.5 |
| 66b | 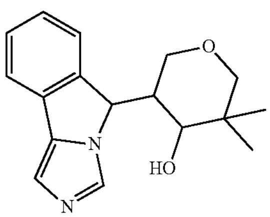 [SMILES: CC1(C)COCC(C2c3ccccc3-c3cncn32)C1O] | $^1$H NMR (500 MHz, DMSO-$d_6$) δ 7.93 (s, 1H), 7.60 (d, J = 7.5 Hz, 1H), 7.58-7.54 (m, 1H), 7.40 (t, J = 7.4 Hz, 1H), 7.31 (td, J = 7.5, 1.1 Hz, 1H), 7.16 (s, 1H), 5.66 (d, J = 2.4 Hz, 1H), 5.43 (d, J = 6.3 Hz, 1H), 3.60 (dd, J = 10.9, 6.3 Hz, 1H), 2.94 (dd, J = 11.1, 3.7 Hz, 1H), 2.89 (d, J = 11.5 Hz, 1H), 2.48-2.39 (m, 1H), 2.29 (t, J = 11.3 Hz, 1H), 0.99 (s, 3H), 0.91 (s, 3H). | 285.5 |
| 66c | 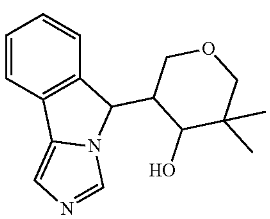 [SMILES: CC1(C)COCC(C2c3ccccc3-c3cncn32)C1O] | $^1$H NMR (500 MHz, DMSO-$d_6$) δ 8.01 (s, 1H), 7.61 (d, J = 8.5 Hz, 2H), 7.40 (t, J = 7.5 Hz, 1H), 7.30 (td, J = 7.5, 1.0 Hz, 1H), 7.13 (s, 1H), 5.64 (d, J = 3.7 Hz, 1H), 5.33 (d, J = 6.1 Hz, 1H), 3.56 (dd, J = 11.0, 6.1 Hz, 1H), 2.90-2.74 (m, 2H), 2.61 (dq, J = 11.2, 3.7 Hz, 1H), 2.41 (t, J = 11.4 Hz, 1H), 0.98 (s, 3H), 0.85 (s, 3H). | 285.5 |
| 66d | 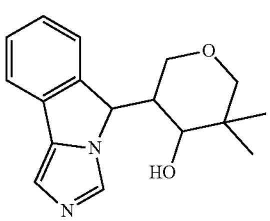 [SMILES: CC1(C)COCC(C2c3ccccc3-c3cncn32)C1O] | $^1$H NMR (500 MHz, DMSO-$d_6$) δ 8.06 (dd, J = 7.9, 1.2 Hz, 1H), 7.74 (s, 1H), 7.30-7.27 (m, 1H), 7.19 (td, J = 7.4, 1.3 Hz, 1H), 6.96 (d, J = 7.5 Hz, 1H), 6.72 (s, 1H), 5.25 (d, J = 4.8 Hz, 1H), 4.36 (d, J = 12.5 Hz, 1H), 4.02-3.85 (m, 2H), 3.46 (d, J = 11.0 Hz, 1H), 3.29-3.23 (m, 2H), 0.95 (s, 3H), 0.91 (s, 3H). | 285.5 |
| 66e | 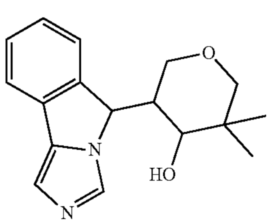 [SMILES: CC1(C)COCC(C2c3ccccc3-c3cncn32)C1O] | $^1$H NMR (500 MHz, DMSO-$d_6$) δ 7.95 (s, 1H), 7.66-7.61 (m, 1H), 7.58 (d, J = 7.5 Hz, 1H), 7.39 (t, J = 7.4 Hz, 1H), 7.29 (td, J = 7.6, 1.1 Hz, 1H), 7.10 (s, 1H), 5.53-5.44 (m, 1H), 5.23 (d, J = 4.9 Hz, 1H), 3.80-3.61 (m, 1H), 3.38 (d, J = 10.8 Hz, 1H), 3.34 (d, J = 11.2 Hz, 1H), 3.10 (d, J = 10.8 Hz, 1H), 2.28 (dq, J = 8.2, 3.7, 2.4 Hz, 1H), 0.94 (s, 3H), 0.83 (s, 3H). | 285.5 |

TABLE 2-continued

| Ex. # | Structure | $^1$H NMR | MS (M + H)$^+$ |
|---|---|---|---|
| 66f | 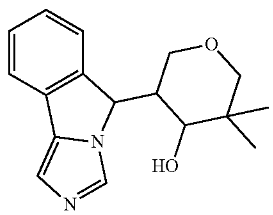 [SMILES: CC1(C)COCC(C2c3ccccc3-c3cncn32)C1O] | $^1$H NMR (500 MHz, DMSO-$d_6$) δ 8.01 (s, 1H), 7.61 (d, J = 8.6 Hz, 2H), 7.40 (t, J = 7.5 Hz, 1H), 7.30 (td, J = 7.5, 1.1 Hz, 1H), 7.13 (s, 1H), 5.64 (d, J = 3.7 Hz, 1H), 5.34 (d, J = 6.1 Hz, 1H), 3.56 (dd, J = 11.0, 6.0 Hz, 1H), 2.88-2.78 (m, 2H), 2.61 (ddt, J = 11.2, 8.0, 4.0 Hz, 1H), 2.41 (t, J = 11.4 Hz, 1H), 0.98 (s, 3H), 0.85 (s, 3H). | 285.5 |
| 66g | 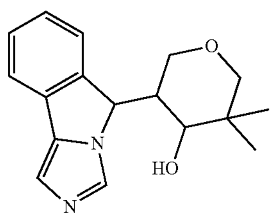 [SMILES: CC1(C)COCC(C2c3ccccc3-c3cncn32)C1O] | $^1$H NMR (500 MHz, DMSO-$d_6$) δ 7.95 (s, 1H), 7.73-7.60 (m, 1H), 7.58 (d, J = 7.5 Hz, 1H), 7.39 (t, J = 7.4 Hz, 1H), 7.28 (td, J = 7.6, 1.1 Hz, 1H), 7.10 (s, 1H), 5.48 (d, J = 4.9 Hz, 1H), 5.23 (d, J = 4.9 Hz, 1H), 3.70 (d, J = 3.2 Hz, 1H), 3.38 (d, J = 10.8 Hz, 1H), 3.34 (d, J = 11.2 Hz, 1H), 3.10 (d, J = 10.8 Hz, 1H), 2.30-2.23 (m, 1H), 0.94 (s, 3H), 0.82 (s, 3H). | 285.5 |
| 67a | 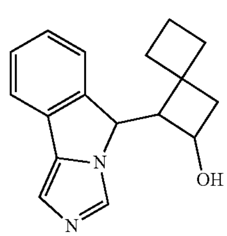 [SMILES: OC1CC2(CCC2)C1C1c2ccccc2-c2cncn21] | (500 MHz, DMSO-$d_6$) δ 7.92 (s, 1H), 7.63-7.61 (m, 1H), 7.60-7.57 (m, 1H), 7.42-7.36 (m, 1H), 7.28 (dd, J = 7.6, 1.2 Hz, 1H), 7.18 (s, 1H), 5.47 (d, J = 5.8 Hz, 1H), 5.25 (d, J = 6.8 Hz, 1H), 4.27-4.16 (m, 1H), 2.32 (s, 2H), 1.71 (dd, J = 10.4, 8.2 Hz, 1H), 1.64-1.55 (m, 3H), 1.42 (d, J = 8.0 Hz, 1H), 1.38-1.30 (m, 1H), 1.23 (d, J = 7.4 Hz, 1H). | 267.2 |
| 67b | 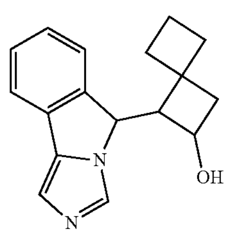 [SMILES: OC1CC2(CCC2)C1C1c2ccccc2-c2cncn21] | (500 MHz, DMSO-$d_6$) δ 8.13 (s, 1H), 7.62-7.56 (m, 2H), 7.38 (t, J = 0.9 Hz, 1H), 7.30 (dd, J = 7.5, 1.1 Hz, 1H), 7.14 (s, 1H), 5.68 (d, J = 3.9 Hz, 1H), 5.40 (d, J = 3.9 Hz, 1H), 4.52 (dd, J = 6.3, 3.9 Hz, 1H), 2.92-2.86 (m, 1H), 2.32 (ddd, J = 11.7, 7.3, 2.4 Hz, 1H), 1.97 (ddd, J = 11.8, 6.2, 1.1 Hz, 1H), 1.80-1.71 (m, 2H), 1.63-1.52 (m, 1H), 1.38-1.28 (m, 2H), 0.96-0.88 (m, 1H). | 267.2 |
| 67c | 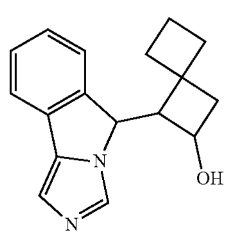 [SMILES: OC1CC2(CCC2)C1C1c2ccccc2-c2cncn21] | (500 MHz, DMSO-$d_6$) δ 7.88 (s, 1H), 7.83 (dd, J = 7.7, 1.0 Hz, 1H), 7.61 (dt, J = 7.6, 0.9 Hz, 1H), 7.43-7.36 (m, 1H), 7.32 (dd, J = 7.6, 1.2 Hz, 1H), 7.14 (s, 1H), 5.55 (d, J = 3.8 Hz, 1H), 5.47 (d, J = 8.4 Hz, 1H), 4.38 (tt, J = 6.5, 3.4 Hz, 1H), 2.33 (t, J = 7.5 Hz, 1H), 2.21-2.14 (m, 2H), 2.07 (dd, J = 11.6, 3.3 Hz, 1H), 2.02 (d, J = 9.8 Hz, 1H), 1.89 (dt, J = 11.2, 8.8 Hz, 1H), 1.75 (tt, J = 9.2, 4.6 Hz, 2H), 1.65 (dd, J = 7.7, 3.8 Hz, 1H). | 267.2 |
| 67d | 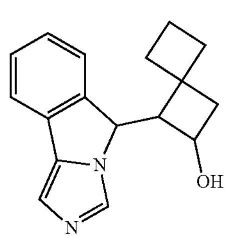 [SMILES: OC1CC2(CCC2)C1C1c2ccccc2-c2cncn21] | (500 MHz, DMSO-$d_6$) δ 7.87 (s, 1H), 7.65-7.56 (m, 2H), 7.40 (tt, J = 7.5, 0.8 Hz, 1H), 7.31 (td, J = 7.6, 1.2 Hz, 1H), 7.12 (s, 1H), 5.46 (d, J = 7.9 Hz, 1H), 5.14 (d, J = 7.3 Hz, 1H), 4.13 (p, J = 7.8 Hz, 1H), 2.44 (dd, J = 10.5, 7.5 Hz, 1H), 2.15 (t, J = 7.5 Hz, 2H), 2.06-1.95 (m, 1H), 1.87 (dt, J = 11.0, 8.6 Hz, 1H), 1.77-1.59 (m, 4H). | 267.2 |

TABLE 2-continued

| Ex. # | Structure | $^1$H NMR | MS $(M + H)^+$ |
|---|---|---|---|
| 67e | 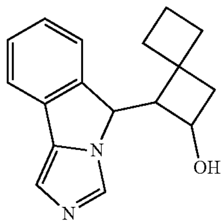 [SMILES: OC1CC2(CCC2)C1C1c2ccccc2-c2cncn21] | (500 MHz, DMSO-$d_6$) δ 8.13 (s, 1H), 7.62-7.54 (m, 2H), 7.38 (tt, J = 7.5, 0.9 Hz, 1H), 7.30 (td, J = 7.5, 1.1 Hz, 1H), 7.14 (s, 1H), 5.68 (d, J = 3.8 Hz, 1H), 5.40 (d, J = 4.0 Hz, 1H), 4.52 (tdd, J = 7.5, 6.2, 3.8 Hz, 1H), 2.91-2.85 (m, 1H), 2.35-2.26 (m, 1H), 1.97 (ddd, J = 11.8, 6.2, 1.1 Hz, 1H), 1.81-1.71 (m, 2H), 1.63-1.52 (m, 1H), 1.37-1.27 (m, 2H), 0.96-0.87 (m, 1H). | 267.2 |
| 67f | 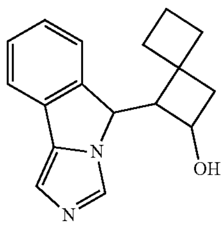 [SMILES: OC1CC2(CCC2)C1C1c2ccccc2-c2cncn21] | (500 MHz, DMSO-$d_6$) δ 7.92 (s, 1H), 7.65-7.55 (m, 2H), 7.39 (tt, J = 7.5, 0.9 Hz, 1H), 7.28 (td, J = 7.6, 1.1 Hz, 1H), 7.18 (s, 1H), 5.47 (d, J = 5.8 Hz, 1H), 5.24 (d, J = 6.8 Hz, 1H), 4.21 (p, J = 7.9 Hz, 1H), 2.38-2.25 (m, 2H), 1.71 (dd, J = 10.4, 8.2 Hz, 1H), 1.61 (dt, J = 4.4, 2.3 Hz, 3H), 1.49-1.38 (m, 1H), 1.35 (s, 1H), 1.23 (d, J = 7.5 Hz, 1H). | 267.2 |
| 67g | 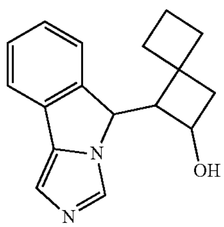 [SMILES: OC1CC2(CCC2)C1C1c2ccccc2-c2cncn21] | (500 MHz, DMSO-$d_6$) δ 7.88 (s, 1H), 7.82 (dq, J = 7.7, 0.9 Hz, 1H), 7.60 (dt, J = 7.6, 0.9 Hz, 1H), 7.39 (tt, J = 7.6, 0.8 Hz, 1H), 7.31 (td, J = 7.6, 1.2 Hz, 1H), 7.14 (s, 1H), 5.55 (d, J = 3.8 Hz, 1H), 5.47 (d, J = 8.5 Hz, 1H), 4.38 (tt, J = 6.5, 3.4 Hz, 1H), 2.33 (t, J = 7.5 Hz, 1H), 2.19 (ddt, J = 9.5, 5.1, 2.8 Hz, 2H), 2.07 (dd, J = 11.6, 3.2 Hz, 1H), 2.02 (d, J = 10.2 Hz, 1H), 1.89 (dt, J = 11.4, 8.8 Hz, 1H), 1.75 (ddd, J = 9.8, 6.0, 3.4 Hz, 2H), 1.65 (dd, J = 7.7, 3.8 Hz, 1H). | 267.2 |
| 67h | 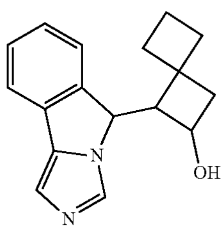 [SMILES: OC1CC2(CCC2)C1C1c2ccccc2-c2cncn21] | (500 MHz, DMSO-$d_6$) δ 7.86 (s, 1H), 7.64-7.54 (m, 2H), 7.40 (tt, J = 7.5, 0.8 Hz, 1H), 7.31 (td, J = 7.6, 1.2 Hz, 1H), 7.12 (s, 1H), 5.46 (d, J = 7.9 Hz, 1H), 5.14 (d, J = 7.4 Hz, 1H), 4.13 (p, J = 7.8 Hz, 1H), 2.44 (dd, J = 10.4, 7.5 Hz, 1H), 2.15 (t, J = 7.6 Hz, 2H), 2.02 (d, J = 9.9 Hz, 1H), 1.87 (dd, J = 9.0, 2.3 Hz, 1H), 1.76-1.60 (m, 4H). | 267.2 |
| 68a | 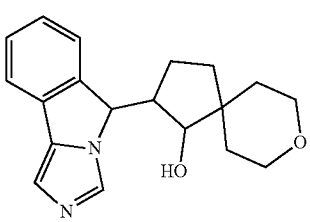 [SMILES: OC1C(C2c3ccccc3-c3cncn32)CCC12CCOCC2] | $^1$H NMR (500 MHz, DMSO-$d_6$) δ 7.94 (dd, J = 7.8, 1.4 Hz, 1H), 7.71 (s, 1H), 7.31 (d, J = 7.6 Hz, 1H), 7.28 (dd, J = 1.9, 1.2 Hz, 1H), 7.22 (td, J = 7.5, 1.4 Hz, 1H), 7.17 (td, J = 7.4, 1.4 Hz, 1H), 6.66 (d, J = 2.0 Hz, 1H), 5.22 (d, J = 5.4 Hz, 1H), 4.04 (d, J = 5.3 Hz, 1H), 3.70 (ddt, J = 19.2, 11.1, 3.9 Hz, 3H), 3.42 (dtd, J = 16.8, 11.3, 2.5 Hz, 3H), 2.48-2.43 (m, 1H), 2.30 (dt, J = 17.4, 9.4 Hz, 1H), 1.94 (ddd, J = 13.1, 9.5, 3.8 Hz, 1H), 1.82-1.73 (m, 1H), 1.72-1.63 (m, 1H), 1.43-1.34 (m, 1H), 1.19 (d, J = 11.4 Hz, 1H), 0.97 (d, J = 13.5 Hz, 1H). | |
| 68b | 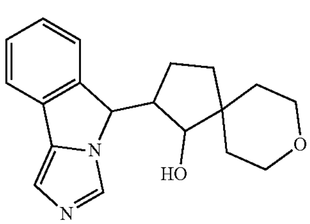 [SMILES: OC1C(C2c3ccccc3-c3cncn32)CCC12CCOCC2] | $^1$H NMR (500 MHz, DMSO-$d_6$) δ 7.99-7.92 (m, 1H), 7.72 (s, 1H), 7.31 (d, J = 7.5 Hz, 1H), 7.28 (s, 1H), 7.23 (t, J = 6.9 Hz, 1H), 7.17 (t, J = 6.8 Hz, 1H), 6.69-6.64 (m, 1H), 5.22 (d, J = 5.4 Hz, 1H), 4.04 (d, J = 5.1 Hz, 1H), 3.78-3.65 (m, 3H), 3.49-3.37 (m, 3H), 2.46 (d, J = 9.5 Hz, 1H), 2.30 (dt, J = 17.3, 8.3 Hz, 1H), 1.95 (ddd, J = 12.9, 9.5, 3.7 Hz, 1H), 1.82-1.73 (m, 1H), 1.72-1.63 (m, 1H), 1.44-1.34 (m, 1H), 1.19 (d, J = 13.4 Hz, 1H), 0.97 (d, J = 13.7 Hz, 1H). | |

TABLE 2-continued

| Ex. # | Structure | $^1$H NMR | MS (M + H)$^+$ |
|---|---|---|---|
| 68c | 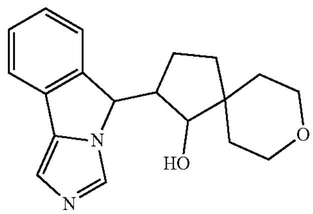 [SMILES: OC1C(C2c3ccccc3-c3cncn32)CCC12CCOCC2] | $^1$H NMR (500 MHz, DMSO-$d_6$) δ 7.95 (dd, J = 7.8, 1.4 Hz, 1H), 7.72 (s, 1H), 7.31 (d, J = 7.6 Hz, 1H), 7.28 (s, 1H), 7.23 (td, J = 7.5, 1.4 Hz, 1H), 7.17 (td, J = 7.4, 1.4 Hz, 1H), 6.67 (d, J = 2.0 Hz, 1H), 5.22 (d, J = 5.4 Hz, 1H), 4.04 (d, J = 5.3 Hz, 1H), 3.70 (dtd, J = 15.2, 7.7, 3.8 Hz, 3H), 3.43 (dtd, J = 16.8, 11.4, 2.5 Hz, 3H), 2.48-2.44 (m, 1H), 2.30 (dt, J = 17.3, 8.4 Hz, 1H), 1.95 (ddd, J = 13.0, 9.5, 3.8 Hz, 1H), 1.82-1.73 (m, 1H), 1.72-1.64 (m, 1H), 1.44-1.35 (m, 1H), 1.22 (d, J = 16.6 Hz, 1H), 0.97 (d, J = 13.7 Hz, 1H). | |
| 68d | 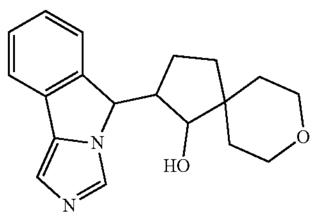 [SMILES: OC1C(C2c3ccccc3-c3cncn32)CCC12CCOCC2] | $^1$H NMR (500 MHz, DMSO-$d_6$) δ 7.91 (s, 1H), 7.60 (d, J = 7.5 Hz, 1H), 7.52 (d, J = 7.7 Hz, 1H), 7.38 (t, J = 7.5 Hz, 1H), 7.26 (td, J = 7.6, 1.1 Hz, 1H), 7.10 (s, 1H), 5.44 (d, J = 4.4 Hz, 1H), 5.02 (d, J = 5.8 Hz, 1H), 3.73 (dt, J = 11.3, 4.3 Hz, 1H), 3.70-3.63 (m, 1H), 3.51 (dd, J = 9.6, 5.7 Hz, 1H), 3.38 (td, J = 11.7, 2.4 Hz, 1H), 3.27 (td, J = 11.9, 2.6 Hz, 1H), 2.63 (qd, J = 9.4, 4.5 Hz, 1H), 1.76-1.62 (m, 3H), 1.36-1.20 (m, 1H), 1.13-1.06 (m, 2H), 0.98 (dd, J = 13.2, 2.1 Hz, 1H), 0.89-0.78 (m, 1H). | |
| 68e | 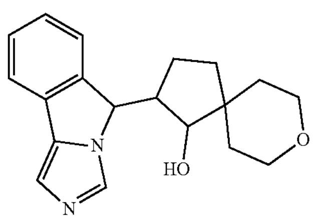 [SMILES: OC1C(C2c3ccccc3-c3cncn32)CCC12CCOCC2] | $^1$H NMR (500 MHz, DMSO-$d_6$) δ 7.91 (s, 1H), 7.59 (d, J = 7.5 Hz, 1H), 7.56-7.50 (m, 1H), 7.38 (t, J = 7.4 Hz, 1H), 7.26 (td, J = 7.6, 1.1 Hz, 1H), 7.10 (s, 1H), 5.44 (d, J = 4.4 Hz, 1H), 5.01 (d, J = 5.8 Hz, 1H), 3.73 (dt, J = 11.3, 4.2 Hz, 1H), 3.69-3.62 (m, 1H), 3.51 (dd, J = 9.6, 5.8 Hz, 1H), 3.38 (td, J = 11.7, 2.4 Hz, 1H), 3.26 (td, J = 11.7, 2.4 Hz, 1H), 2.63 (qd, J = 9.4, 4.5 Hz, 1H), 1.77-1.62 (m, 3H), 1.27 (tdd, J = 13.9, 10.0, 5.5 Hz, 1H), 1.09 (dd, J = 13.2, 2.7 Hz, 2H), 0.98 (dd, J = 13.2, 2.1 Hz, 1H), 0.84 (dtd, J = 13.2, 9.6, 5.9 Hz, 1H). | |
| 68f | 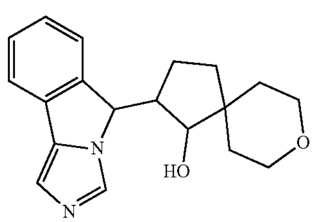 [SMILES: OC1C(C2c3ccccc3-c3cncn32)CCC12CCOCC2] | $^1$H NMR (500 MHz, DMSO-$d_6$) δ 7.87 (s, 1H), 7.70-7.65 (m, 1H), 7.59 (d, J = 7.5 Hz, 1H), 7.38 (t, J = 7.4 Hz, 1H), 7.27 (td, J = 7.6, 1.1 Hz, 1H), 7.12 (s, 1H), 5.40 (d, J = 7.8 Hz, 1H), 5.29 (d, J = 5.3 Hz, 1H), 3.90 (t, J = 5.1 Hz, 1H), 3.71 (dt, J = 11.3, 4.4 Hz, 1H), 3.57 (dt, J = 11.5, 4.3 Hz, 1H), 3.47-3.37 (m, 2H), 2.24 (qd, J = 8.9, 4.6 Hz, 1H), 1.73 (dddt, J = 23.1, 13.7, 9.9, 4.5 Hz, 3H), 1.64-1.55 (m, 2H), 1.45 (d, J = 13.5 Hz, 1H), 1.29 (ddd, J = 13.5, 9.5, 4.2 Hz, 1H), 1.17 (d, J = 13.4 Hz, 1H). | |
| 68g | 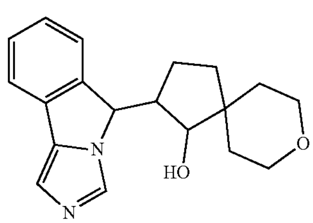 [SMILES: OC1C(C2c3ccccc3-c3cncn32)CCC12CCOCC2] | $^1$H NMR (500 MHz, DMSO-$d_6$) δ 7.93 (s, 1H), 7.59 (d, J = 7.5 Hz, 1H), 7.48 (d, J = 7.6 Hz, 1H), 7.37 (t, J = 7.5 Hz, 1H), 7.23 (t, J = 7.6 Hz, 1H), 7.11 (s, 1H), 5.29 (d, J = 9.7 Hz, 1H), 5.22 (d, J = 5.8 Hz, 1H), 3.84-3.78 (m, 1H), 3.73 (dt, J = 11.3, 4.2 Hz, 1H), 3.54 (dt, J = 11.5, 4.3 Hz, 1H), 3.44-3.34 (m, 2H), 2.16-2.05 (m, 1H), 2.03-1.89 (m, 2H), 1.70 (ddd, J = 13.8, 9.9, 3.8 Hz, 3H), 1.49 (d, J = 13.5 Hz, 1H), 1.25 (ddd, J = 13.6, 9.7, 4.2 Hz, 1H), 1.12 (d, J = 13.4 Hz, 1H). | |

TABLE 2-continued

| Ex. # | Structure | $^1$H NMR | MS (M + H)$^+$ |
|---|---|---|---|
| 68h | 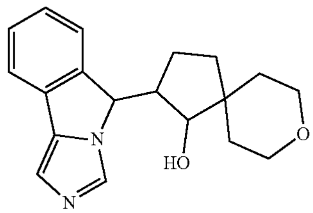 [SMILES: OC1C(C2c3ccccc3-c3cncn32)CCC12CCOCC2] | $^1$H NMR (500 MHz, DMSO-d$_6$) δ 7.87 (s, 1H), 7.68 (d, J = 7.6 Hz, 1H), 7.59 (d, J = 7.5 Hz, 1H), 7.38 (t, J = 7.4 Hz, 1H), 7.27 (td, J = 7.6, 1.1 Hz, 1H), 7.12 (s, 1H), 5.39 (d, J = 7.7 Hz, 1H), 5.29 (d, J = 5.4 Hz, 1H), 3.90 (t, J = 5.1 Hz, 1H), 3.71 (dt, J = 11.4, 4.4 Hz, 1H), 3.57 (dt, J = 11.6, 4.5 Hz, 1H), 3.46-3.35 (m, 2H), 2.29-2.20 (m, 1H), 1.81-1.66 (m, 3H), 1.65-1.54 (m, 2H), 1.45 (d, J = 13.5 Hz, 1H), 1.29 (ddd, J = 13.5, 9.4, 4.1 Hz, 1H), 1.17 (d, J = 13.4 Hz, 1H). | 311.4 |
| 69a | 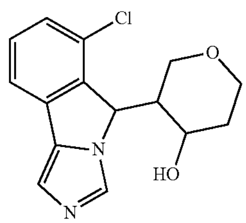 [SMILES: OC1CCOCC1C1c2c(Cl)cccc2-c2cncn21] | $^1$H NMR (500 MHz, DMSO-d$_6$) δ 7.93 (s, 1H), 7.60 (dd, J = 7.5, 0.9 Hz, 1H), 7.45 (td, J = 7.8, 0.6 Hz, 1H), 7.35 (dd, J = 8.0, 0.9 Hz, 1H), 7.23 (s, 1H), 5.88 (d, J = 2.9 Hz, 1H), 5.56 (d, J = 5.6 Hz, 1H), 3.91 (tt, J = 10.4, 5.1 Hz, 1H), 3.75 (dd, J = 11.7, 4.9 Hz, 1H), 3.20-3.07 (m, 1H), 2.92 (dd, J = 11.4, 3.9 Hz, 1H), 2.63 (tt, J = 10.9, 3.5 Hz, 1H), 2.22 (t, J = 11.3 Hz, 1H), 1.92 (ddt, J = 12.7, 4.2, 1.9 Hz, 1H), 1.58 (tdd, J = 12.7, 10.5, 4.8 Hz, 1H). | 291.1 |
| 69b | 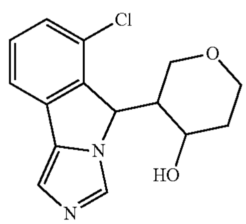 [SMILES: OC1CCOCC1C1c2c(Cl)cccc2-c2cncn21] | $^1$H NMR (500 MHz, DMSO-d$_6$) δ 7.99 (s, 1H), 7.53 (dd, J = 7.5, 0.9 Hz, 1H), 7.36 (ddd, J = 8.1, 7.5, 0.6 Hz, 1H), 7.26 (dd, J = 8.0, 0.9 Hz, 1H), 7.19 (s, 1H), 5.54 (s, 1H), 4.45 (d, J = 5.5 Hz, 1H), 3.79 (dd, J = 11.3, 4.4 Hz, 1H), 3.61 (dd, J = 10.8, 5.1 Hz, 1H), 3.23 (td, J = 11.6, 2.2 Hz, 1H), 3.17 (dq, J = 10.3, 5.1 Hz, 1H), 2.83 (t, J = 10.3 Hz, 1H), 2.60-2.52 (m, 1H), 1.62 (qd, J = 12.8, 4.7 Hz, 1H), 1.52 (d, J = 12.7 Hz, 1H). | 291.1 |
| 69c | 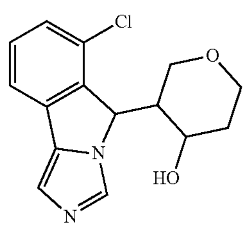 [SMILES: OC1CCOCC1C1c2c(Cl)cccc2-c2cncn21] | $^1$H NMR (500 MHz, DMSO-d$_6$) δ 7.93 (s, 1H), 7.60 (dd, J = 7.6, 0.9 Hz, 1H), 7.45 (td, J = 7.8, 0.6 Hz, 1H), 7.35 (dd, J = 8.0, 0.9 Hz, 1H), 7.23 (s, 1H), 5.88 (d, J = 2.9 Hz, 1H), 5.56 (d, J = 5.6 Hz, 1H), 3.91 (tt, J = 10.4, 5.1 Hz, 1H), 3.75 (dd, J = 11.7, 4.7 Hz, 1H), 3.18-3.09 (m, 1H), 2.92 (dd, J = 11.4, 3.8 Hz, 1H), 2.68-2.58 (m, 1H), 2.22 (t, J = 11.3 Hz, 1H), 1.96-1.88 (m, 1H), 1.64-1.51 (m, 1H). | 291.1 |
| 69d | 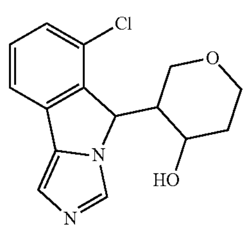 [SMILES: OC1CCOCC1C1c2c(Cl)cccc2-c2cncn21] | $^1$H NMR (500 MHz, DMSO-d$_6$) δ 7.99 (s, 1H), 7.53 (dd, J = 7.6, 0.9 Hz, 1H), 7.36 (t, J = 7.8 Hz, 1H), 7.26 (dd, J = 8.0, 0.9 Hz, 1H), 7.19 (s, 1H), 5.54 (d, J = 1.4 Hz, 1H), 4.45 (d, J = 5.5 Hz, 1H), 3.79 (dd, J = 11.3, 4.3 Hz, 1H), 3.61 (dd, J = 10.7, 5.0 Hz, 1H), 3.23 (td, J = 11.6, 2.2 Hz, 1H), 3.16 (p, J = 5.1 Hz, 1H), 2.83 (t, J = 10.3 Hz, 1H), 2.56 (s, 1H), 1.62 (qd, J = 12.7, 4.7 Hz, 1H), 1.56-1.49 (m, 1H). | 291.1 |
| 69-1a | 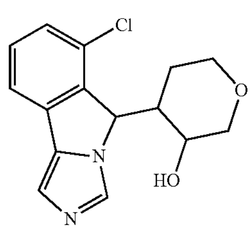 [SMILES: OC1COCCC1C1c2c(Cl)cccc2-c2cncn21] | $^1$H NMR (500 MHz, DMSO-d$_6$) δ 7.91 (s, 1H), 7.60 (dd, J = 7.6, 0.9 Hz, 1H), 7.44 (td, J = 7.8, 0.6 Hz, 1H), 7.33 (dd, J = 8.0, 0.9 Hz, 1H), 7.23 (s, 1H), 5.87 (d, J = 2.6 Hz, 1H), 5.58 (d, J = 5.7 Hz, 1H), 3.90 (dd, J = 10.6, 4.9 Hz, 1H), 3.71 (tt, J = 10.3, 5.3 Hz, 1H), 3.58 (dd, J = 11.3, 4.5 Hz, 1H), 3.15-2.99 (m, 2H), 2.68-2.56 (m, 1H), 0.64 (ddd, J = 11.6, 3.9, 2.0 Hz, 1H), 0.35 (qd, J = 12.6, 4.9 Hz, 1H). | 291.1 |

TABLE 2-continued

| Ex. # | Structure | $^1$H NMR | MS (M + H)$^+$ |
|---|---|---|---|
| 69-1b | 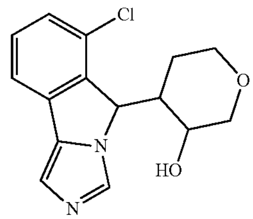 [SMILES: OC1COCCC1C1c2c(Cl)cccc2-c2cncn21] | $^1$H NMR (500 MHz, DMSO-$d_6$) δ 7.97 (s, 1H), 7.51 (dd, J = 7.5, 0.9 Hz, 1H), 7.39-7.32 (m, 1H), 7.25 (dd, J = 8.0, 1.0 Hz, 1H), 7.18 (s, 1H), 5.38 (s, 1H), 4.25 (d, J = 5.3 Hz, 1H), 3.92 (dd, J = 11.3, 4.4 Hz, 1H), 3.76 (d, J = 10.9 Hz, 1H), 3.56 (t, J = 11.4 Hz, 1H), 3.27 (td, J = 11.7, 2.3 Hz, 1H), 3.22-3.14 (m, 1H), 2.69-2.56 (m, 1H), 1.59-1.51 (m, 1H), 1.40-1.28 (m, 1H). | 291.1 |
| 69-1c | 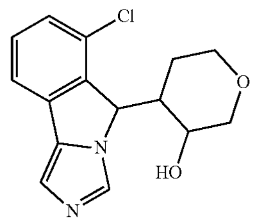 [SMILES: OC1COCCC1C1c2c(Cl)cccc2-c2cncn21] | $^1$H NMR (500 MHz, DMSO-$d_6$) δ 7.97 (s, 1H), 7.51 (dd, J = 7.5, 0.9 Hz, 1H), 7.39-7.32 (m, 1H), 7.25 (dd, J = 8.1, 1.0 Hz, 1H), 7.18 (s, 1H), 5.38 (s, 1H), 4.25 (d, J = 5.4 Hz, 1H), 3.92 (dd, J = 11.5, 4.5 Hz, 1H), 3.76 (d, J = 10.5 Hz, 1H), 3.56 (t, J = 11.4 Hz, 1H), 3.29-3.22 (m, 1H), 3.23-3.13 (m, 1H), 2.64 (s, 1H), 1.59-1.51 (m, 1H), 1.40-1.28 (m, 1H). | 291.1 |
| 69-1d | 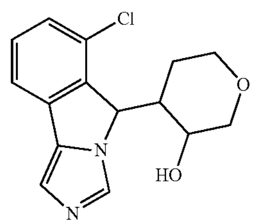 [SMILES: OC1COCCC1C1c2c(Cl)cccc2-c2cncn21] | $^1$H NMR (500 MHz, DMSO-$d_6$) δ 7.91 (s, 1H), 7.60 (dd, J = 7.6, 0.9 Hz, 1H), 7.44 (td, J = 7.8, 0.6 Hz, 1H), 7.33 (dd, J = 8.0, 0.9 Hz, 1H), 7.23 (s, 1H), 5.87 (d, J = 2.6 Hz, 1H), 5.58 (d, J = 5.7 Hz, 1H), 3.90 (dd, J = 10.6, 4.9 Hz, 1H), 3.71 (tt, J = 10.3, 5.2 Hz, 1H), 3.58 (dd, J = 11.3, 4.6 Hz, 1H), 3.14-3.01 (m, 2H), 2.65-2.55 (m, 1H), 0.68-0.60 (m, 1H), 0.35 (qd, J = 12.7, 4.9 Hz, 1H). | 291.1 |
| 70a | 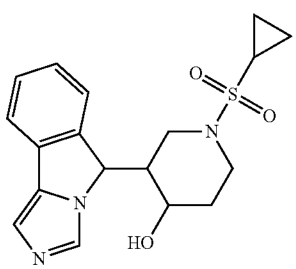 [SMILES: O=S(=O)(C1CC1)N1CCC(O)C(C2c3ccccc3-c3cncn32)C1] | $^1$H NMR (300 MHz, $CD_3OD$) 7.98 (s, 1H), 7.67 (d, J = 3.6 Hz, 1H), 7.54 (d, J = 3.6 Hz, 1H), 7.47 (t, J = 7.2 Hz, 1H), 7.40 (t, J = 7.6 Hz, 1H), 7.22 (s, 1H), 5.87 (s, 1H), 3.99-3.98 (m, 1H), 3.77-3.73 (m, 1H), 3.01 (dd, J = 5.6 Hz, 2.8 Hz, 1H), 2.88 (t, J = 12.8 Hz, 1H), 2.40-2.39 (m, 1H), 2.26-2.17 (m, 1H). 1.99 (t, J = 12 Hz, 1H), 1.77-1.76 (m, 1H), 0.91-0.84 (m, 2H), 0.77-0.74 (m, 1H). | 360.3 |
| 70b | 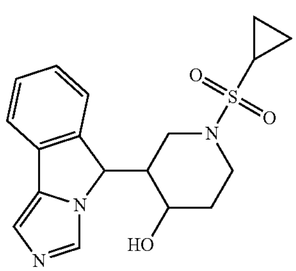 [SMILES: O=S(=O)(C1CC1)N1CCC(O)C(C2c3ccccc3-c3cncn32)C1] | The same as 070a. | 360.0 |
| 70c | 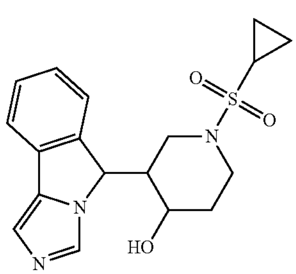 [SMILES: O=S(=O)(C1CC1)N1CCC(O)C(C2c3ccccc3-c3cncn32)C1] | $^1$H NMR (300 MHz, $CD_3OD$) 8.00 (s, 1H), 7.67 (d, J = 3.6 Hz, 1H), 7.62 (d, J = 3.6 Hz, 1H), 7.46 (t, J = 7.2 Hz, 1H), 7.36 (t, J = 7.6 Hz, 1H), 7.22 (s, 1H), 5.86 (s, 1H), 3.98-3.97 (m, 1H), 3.77-3.73 (m, 1H), 2.88-2.79 (m, 2H), 2.62-2.49 (m, 1H), 2.27-2.23 (m, 1H), 2.13-2.07 (m, 2H). 1.75-1.68 (m, 1H), 1.77-1.76 (m, 1H), 0.93-0.79 (m, 3H). | 360.2 |

TABLE 2-continued
| Ex. # | Structure | $^1$H NMR | MS (M + H)$^+$ |
|---|---|---|---|
| 70d | 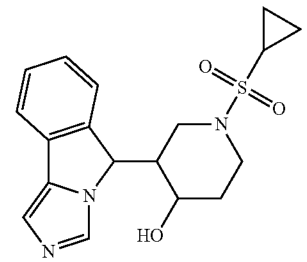 [SMILES: O=S(=O)(C1CC1)N1CCC(O)C(C2c3ccccc3-c3cncn32)C1] | The same as 070d. | 360.1 |
| 71a | 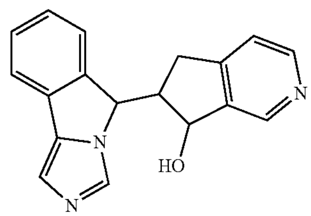 [SMILES: OC1c2cnccc2CC1C1c2ccccc2-c2cncn21] | $^1$H NMR (300 MHz, $CD_3OD$) 8.63 (s, 1H), 8.32 (d, J = 5.1 Hz, 1H), 7.73-7.59 (m, 3H), 7.53-7.32 (m, 2H), 7.17-7.03 (m, 2H), 5.79 (d, J = 4.1 Hz, 1H), 5.70 (d, J = 7.3 Hz, 1H), 3.29 (t, J = 6.4 Hz, 1H), 2.83 (dd, J = 17.3, 8.4 Hz, 1H), 2.43 (dd, J = 17.2, 5.4 Hz, 1H), 1.40-1.28 (m, 1H). | 290.0 |
| 71aa | 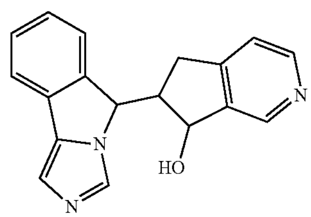 [SMILES: OC1c2cnccc2CC1C1c2ccccc2-c2cncn21] | $^1$H NMR (400 MHz, DMSO-$d_6$) δ 8.53 (s, 1H), 8.34 (d, J = 5.2 Hz, 1H), 7.88 (s, 1H), 7.63 (d, J = 7.6 Hz, 1H), 7.53 (d, J = 7.6 Hz, 1H), 7.43-7.41 (m, 1H), 7.40-7.27 (m, 1H), 7.27 (s, 1H), 7.09 (d, J = 5.2 Hz, 1H), 6.00 (d, J = 4.0 Hz, 1H), 5.78 (d, J = 2.8 Hz, 1H), 5.49 (d, J = 4.8 Hz, 1H), 3.05-3.02 (m, 1H), 2.49-2.47 (m, 1H), 1.91-1.84 (m, 1H). | 290.0 |
| 71b | 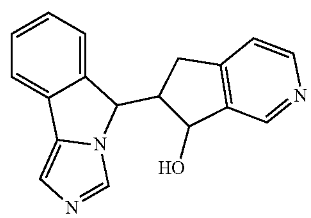 [SMILES: OC1c2cnccc2CC1C1c2ccccc2-c2cncn21] | The same as 071a. | 290.0 |
| 71bb | 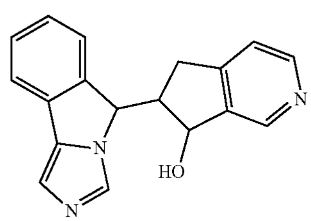 [SMILES: OC1c2cnccc2CC1C1c2ccccc2-c2cncn21] | The same as 071aa. | 290.2 |
| 71c | 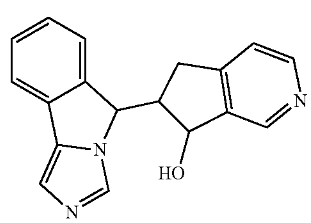 [SMILES: OC1c2cnccc2CC1C1c2ccccc2-c2cncn21] | $^1$H NMR (300 MHz, $CD_3OD$) 8.66 (d, J = 1.3 Hz, 1H), 8.42 (d, J = 5.1 Hz, 1H), 8.20 (s, 1H), 7.63 (dd, J = 18.3, 7.7 Hz, 2H), 7.48-7.18 (m, 4H), 5.74-5.64 (m, 1H), 5.44 (d, J = 6.1 Hz, 1H), 4.83 (s, 2H), 3.18 (dd, J = 16.6, 7.9 Hz, 1H), 2.62 (s, 1H), 1.32 (s, 1H). | 290.0 |
| 71d | 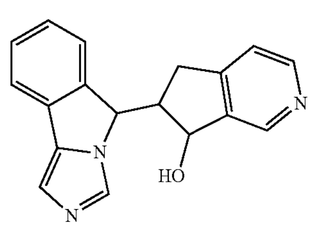 [SMILES: OC1c2cnccc2CC1C1c2ccccc2-c2cncn21] | The same as 071c. | 290.0 |

TABLE 2-continued

| Ex. # | Structure | $^1$H NMR | MS (M + H)$^+$ |
|---|---|---|---|
| 71e | 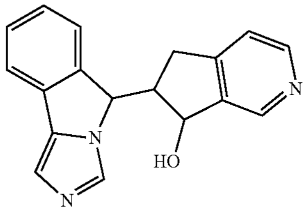 [SMILES: OC1c2cnccc2CC1C1c2ccccc2-c2cncn21] | $^1$H NMR (300 MHz, $CD_3OD$) 8.47 (s, 1H), 8.37 (d, J = 4.9 Hz, 1H), 8.01 (s, 1H), 7.74-7.65 (m, 1H), 7.61-7.40 (m, 2H), 7.38-7.21 (m, 3H), 5.80 (d, J = 4.0 Hz, 1H), 5.25 (d, J = 5.5 Hz, 1H), 3.44 (s, 4H), 3.33 (s, 4H), 3.17 (dd, J = 12.6, 7.3 Hz, 2H), 2.83-2.67 (m, 1H), 1.40-1.29 (m, 1H). | 290.1 |
| 71f | 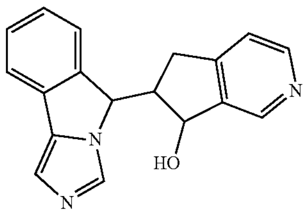 [SMILES: OC1c2cnccc2CC1C1c2ccccc2-c2cncn21] | The same as 071e. | 290.0 |
| 72a | 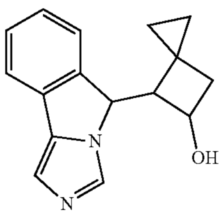 [SMILES: OC1CC2(CC2)C1C1c2ccccc2-c2cncn21] | $^1$H NMR (500 MHz, DMSO-$d_6$) δ 7.86 (s, 1H), 7.77 (dq, J = 7.6, 0.9 Hz, 1H), 7.58 (d, J = 7.5 Hz, 1H), 7.38-7.33 (m, 1H), 7.26 (td, J = 7.5, 1.2 Hz, 1H), 7.10 (s, 1H), 5.56 (d, J = 4.4 Hz, 1H), 5.43 (d, J = 5.3 Hz, 1H), 4.70-4.63 (m, 1H), 3.00 (t, J = 6.4 Hz, 1H), 2.14-2.02 (m, 2H), 0.30 (dddd, J = 24.2, 10.3, 6.1, 4.3 Hz, 2H), 0.13 (dt, J = 9.9, 5.6 Hz, 1H). | 253 |
| 72b | 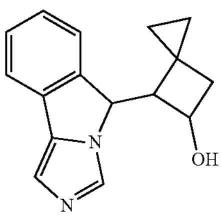 [SMILES: OC1CC2(CC2)C1C1c2ccccc2-c2cncn21] | $^1$H NMR (500 MHz, DMSO-$d_6$) δ 7.93 (s, 1H), 7.59 (d, J = 7.5 Hz, 1H), 7.39-7.33 (m, 2H), 7.26 (td, J = 7.5, 1.1 Hz, 1H), 7.16 (s, 1H), 5.21 (d, J = 3.8 Hz, 1H), 5.01 (d, J = 6.7 Hz, 1H), 3.67 (p, J = 6.3 Hz, 1H), 2.98 (s, 1H), 2.11-2.03 (m, 1H), 1.97 (dd, J = 11.6, 5.9 Hz, 1H), 0.87-0.79 (m, 1H), 0.60-0.47 (m, 3H). | 253 |
| 72c | 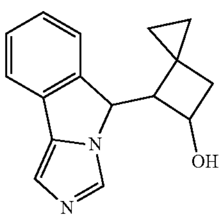 [SMILES: OC1CC2(CC2)C1C1c2ccccc2-c2cncn21] | $^1$H NMR (500 MHz, DMSO-$d_6$) δ 7.81 (s, 1H), 7.71 (d, J = 1.1 Hz, 1H), 7.60 (s, 1H), 7.17 (s, 3H), 6.26 (s, 1H), 5.51 (s, 1H), 5.06 (s, 1H), 2.45 (dd, J = 11.2, 7.6 Hz, 1H), 2.22 (dd, J = 11.2, 5.1 Hz, 1H), 0.87-0.71 (m, 4H). | 253 |
| 72d | 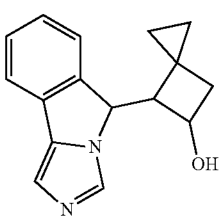 [SMILES: OC1CC2(CC2)C1C1c2ccccc2-c2cncn21] | $^1$H NMR (500 MHz, DMSO-$d_6$) δ 8.23 (s, 1H), 7.56 (dt, J = 7.6, 0.9 Hz, 1H), 7.42-7.30 (m, 2H), 7.24-7.19 (m, 1H), 7.18 (d, J = 9.3 Hz, 1H), 5.89 (d, J = 4.0 Hz, 1H), 5.43-5.38 (m, 1H), 4.87-4.78 (m, 1H), 3.26-3.20 (m, 1H), 2.15-2.02 (m, 2H), 0.20 (ddd, J = 10.0, 6.1, 4.2 Hz, 1H), −0.03-−0.10 (m, 1H), −0.40 (ddd, J = 9.6, 6.4, 5.0 Hz, 1H), −0.50 (ddd, J = 9.7, 6.1, 5.0 Hz, 1H). | 253 |
| 72e | 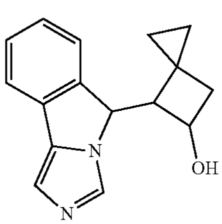 [SMILES: OC1CC2(CC2)C1C1c2ccccc2-c2cncn21] | $^1$H NMR (500 MHz, DMSO-$d_6$) δ 8.24 (s, 1H), 7.57 (dt, J = 7.6, 0.9 Hz, 1H), 7.39 (dd, J = 7.7, 1.0 Hz, 1H), 7.37-7.31 (m, 1H), 7.26-7.15 (m, 2H), 5.90 (d, J = 4.1 Hz, 1H), 5.41 (d, J = 2.3 Hz, 1H), 4.83 (qd, J = 7.8, 4.0 Hz, 1H), 3.25-3.20 (m, 1H), 2.15-2.02 (m, 2H), 0.20 (ddd, J = 10.0, 6.1, 4.2 Hz, 1H), −0.07 (dd, J = 6.3, 4.0 Hz, 1H), −0.40 (ddd, J = 9.7, 6.5, 5.0 Hz, 1H), −0.47-−0.54 (m, 1H). | 253 |

TABLE 2-continued

| Ex. # | Structure | $^1$H NMR | MS (M + H)$^+$ |
|---|---|---|---|
| 72f | 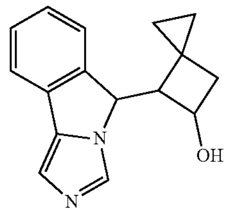 [SMILES: OC1CC2(CC2)C1C1c2ccccc2-c2cncn21] | $^1$H NMR (500 MHz, DMSO-$d_6$) δ 7.80 (s, 1H), 7.71 (d, J = 1.1 Hz, 1H), 7.58 (s, 1H), 7.18 (s, 3H), 6.23 (s, 1H), 5.52 (d, J = 8.1 Hz, 1H), 5.05 (tdd, J = 7.7, 5.1, 2.1 Hz, 1H), 2.45 (dd, J = 11.2, 7.7 Hz, 1H), 2.22 (dd, J = 11.2, 5.1 Hz, 1H), 0.87-0.71 (m, 4H). | 253 |
| 72g | 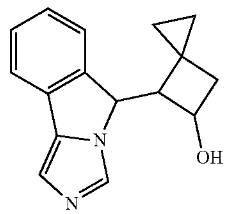 [SMILES: OC1CC2(CC2)C1C1c2ccccc2-c2cncn21] | $^1$H NMR (500 MHz, DMSO-$d_6$) δ 7.93 (s, 1H), 7.59 (dt, J = 7.4, 1.0 Hz, 1H), 7.39-7.33 (m, 2H), 7.26 (td, J = 7.6, 1.2 Hz, 1H), 7.16 (s, 1H), 5.21 (d, J = 3.9 Hz, 1H), 5.02 (d, J = 6.7 Hz, 1H), 3.72-3.63 (m, 1H), 3.00-2.95 (m, 1H), 2.12-1.92 (m, 2H), 0.86-0.78 (m, 1H), 0.60-0.48 (m, 3H). | 253 |
| 72h | 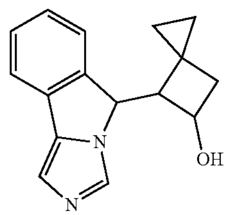 [SMILES: OC1CC2(CC2)C1C1c2ccccc2-c2cncn21] | $^1$H NMR (500 MHz, DMSO-$d_6$) δ 7.87 (s, 1H), 7.77 (dt, J = 7.7, 1.0 Hz, 1H), 7.58 (dt, J = 7.5, 0.9 Hz, 1H), 7.36 (tt, J = 7.6, 0.9 Hz, 1H), 7.26 (td, J = 7.6, 1.2 Hz, 1H), 7.11 (s, 1H), 5.56 (d, J = 4.5 Hz, 1H), 5.43 (d, J = 5.3 Hz, 1H), 4.66 (tdd, J = 7.4, 6.0, 4.6 Hz, 1H), 3.03-2.97 (m, 1H), 2.12 (ddd, J = 11.4, 7.3, 1.8 Hz, 1H), 2.06 (dd, J = 11.2, 6.2 Hz, 1H), 0.30 (dddd, J = 24.2, 10.4, 6.2, 4.3 Hz, 2H), 0.13 (dt, J = 9.7, 5.6 Hz, 1H). | 253 |
| 73a | 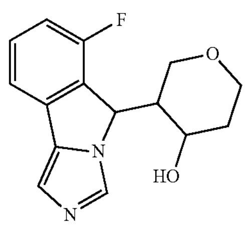 [SMILES: OC1CCOCC1C1c2c(F)cccc2-c2cncn21] | $^1$H NMR (500 MHz, DMSO-$d_6$) δ 7.99 (t, J = 0.6 Hz, 1H), 7.51-7.36 (m, 2H), 7.19 (s, 1H), 7.14-7.05 (m, 1H), 5.77 (d, J = 2.0 Hz, 1H), 4.90 (d, J = 5.3 Hz, 1H), 3.77 (dd, J = 11.7, 4.4 Hz, 1H), 3.66-3.55 (m, 1H), 3.30-3.26 (m, 1H), 3.22 (td, J = 12.0, 2.3 Hz, 1H), 2.96 (t, J = 11.3 Hz, 1H), 2.34 (s, 1H), 1.84-1.71 (m, 1H), 1.44 (qd, J = 12.2, 4.7 Hz, 1H). | 275 |
| 73b | 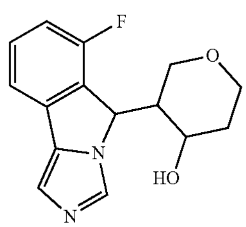 [SMILES: OC1CCOCC1C1c2c(F)cccc2-c2cncn21] | $^1$H NMR (500 MHz, DMSO-$d_6$) δ 7.92 (s, 1H), 7.53-7.43 (m, 2H), 7.21 (s, 1H), 7.17-7.10 (m, 1H), 5.95 (d, J = 2.5 Hz, 1H), 5.52 (d, J = 5.8 Hz, 1H), 3.91 (tt, J = 10.4, 5.2 Hz, 1H), 3.77 (dd, J = 11.7, 4.7 Hz, 1H), 3.17 (td, J = 12.1, 11.7, 2.1 Hz, 1H), 3.07-2.99 (m, 1H), 2.35 (t, J = 10.9 Hz, 1H), 2.32-2.23 (m, 1H), 1.92 (ddd, J = 10.9, 4.7, 2.4 Hz, 1H), 1.63-1.49 (m, 1H). | 275 |
| 73c | 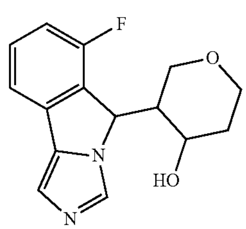 [SMILES: OC1CCOCC1C1c2c(F)cccc2-c2cncn21] | $^1$H NMR (500 MHz, DMSO-$d_6$) δ 7.99 (s, 1H), 7.48-7.37 (m, 2H), 7.19 (s, 1H), 7.10 (ddd, J = 10.4, 6.3, 2.8 Hz, 1H), 5.76 (d, J = 2.1 Hz, 1H), 4.90 (d, J = 5.3 Hz, 1H), 3.77 (dd, J = 11.8, 4.4 Hz, 1H), 3.60 (tt, J = 10.1, 5.0 Hz, 1H), 3.28 (dd, J = 11.6, 4.1 Hz, 1H), 3.22 (td, J = 12.0, 2.3 Hz, 1H), 2.96 (t, J = 11.3 Hz, 1H), 2.34 (s, 1H), 1.76 (ddd, J = 12.8, 4.7, 2.3 Hz, 1H), 1.44 (qd, J = 12.2, 4.8 Hz, 1H). | 275 |
| 73d | 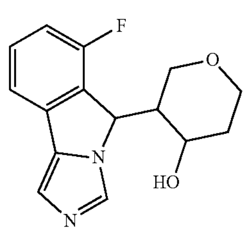 [SMILES: OC1CCOCC1C1c2c(F)cccc2-c2cncn21] | $^1$H NMR (500 MHz, DMSO-$d_6$) δ 7.92 (s, 1H), 7.53-7.43 (m, 2H), 7.21 (s, 1H), 7.18-7.10 (m, 1H), 5.95 (d, J = 2.4 Hz, 1H), 5.52 (d, J = 5.8 Hz, 1H), 3.91 (tt, J = 10.3, 5.2 Hz, 1H), 3.77 (dd, J = 11.7, 4.7 Hz, 1H), 3.22-3.12 (m, 1H), 3.09-2.99 (m, 1H), 2.35 (t, J = 10.9 Hz, 1H), 2.32-2.25 (m, 1H), 1.97-1.85 (m, 1H), 1.56 (tdd, J = 12.6, 10.5, 4.8 Hz, 1H). | 275 |

TABLE 2-continued

| Ex. # | Structure | $^1$H NMR | MS (M + H)$^+$ |
|---|---|---|---|
| 74a | 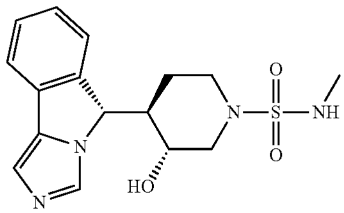 [SMILES: CNS(=O)(=O)N1CC[C@H]([C@H]2c3ccccc3-c3cncn32)[C@@H](O)C1] | $^1$H NMR (400 MHz, DMSO-$d_6$) δ 7.91 (s, 1H), 7.63 (d, J = 7.6, 1H), 7.51 (d, J = 7.6, 1H), 7.43-7.39 (m, 1H), 7.34-7.28 (m, 1H), 7.15 (s, 1H), 7.06 (q, J = 7.6, 1H), 5.72 (d, J = 3.3, 2H), 3.81-3.68 (m, 2H), 3.30-3.27 (m, 1H), 2.51-2.46 (m, 2H), 2.43 (s, 3H), 2.33-2.26 (m, 1H), 0.70-0.64 (m, 1H), 0.54-0.40 (m, 1H). | 349.2 |
| 74b | 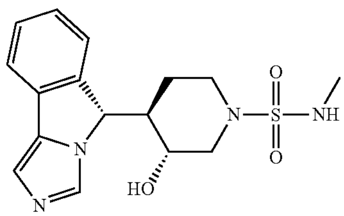 [SMILES: CNS(=O)(=O)N1CC[C@H]([C@H]2c3ccccc3-c3cncn32)[C@@H](O)C1] | $^1$H NMR (300 MHz, $CD_3OD$) δ 7.92 (s, 1H), 7.64 (d, J = 7.5, 1H), 7.49 (d, J = 7.5, 1H), 7.46-7.36 (m, 2H), 7.20 (s, 1H), 5.82 (d, J = 3.3, 1H), 3.97-3.91 (m, 2H), 3.50-3.34 (m, 1H), 2.72-2.58 (m, 2H), 2.56 (s, 3H), 2.27-2.12 (m, 1H), 0.96-0.91 (m, 1H), 0.67-0.63 (m, 1H). | 349.2 |
| 75a | 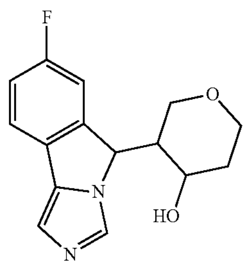 [SMILES: OC1CCOCC1C1c2cc(F)ccc2-c2cncn21] | $^1$H NMR (500 MHz, DMSO-$d_6$) δ 7.98 (s, 1H), 7.63 (dd, J = 8.4, 5.2 Hz, 1H), 7.43-7.37 (m, 1H), 7.24 (ddd, J = 9.0, 8.1, 2.4 Hz, 1H), 7.10 (s, 1H), 5.64 (d, J = 3.6 Hz, 1H), 5.27 (d, J = 5.4 Hz, 1H), 3.83-3.72 (m, 2H), 3.20 (td, J = 12.1, 2.3 Hz, 1H), 2.97 (dd, J = 11.3, 3.9 Hz, 1H), 2.63 (t, J = 11.2 Hz, 1H), 2.39 (ddt, J = 10.6, 6.8, 3.8 Hz, 1H), 1.81 (ddt, J = 12.7, 4.4, 2.1 Hz, 1H), 1.50 (tdd, J = 12.4, 10.3, 4.8 Hz, 1H). | 275.1 |
| 75b | 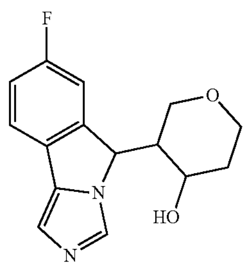 [SMILES: OC1CCOCC1C1c2cc(F)ccc2-c2cncn21] | $^1$H NMR (500 MHz, DMSO-$d_6$) δ 7.97 (d, J = 0.6 Hz, 1H), 7.62 (dd, J = 8.4, 5.2 Hz, 1H), 7.40 (ddd, J = 9.2, 2.5, 0.8 Hz, 1H), 7.24 (dddd, J = 9.2, 8.4, 2.5, 0.6 Hz, 1H), 7.10 (s, 1H), 5.64 (d, J = 3.6 Hz, 1H), 5.27 (d, J = 5.4 Hz, 1H), 3.77 (ddd, J = 14.0, 10.1, 4.7 Hz, 2H), 3.20 (td, J = 12.1, 2.3 Hz, 1H), 3.00-2.94 (m, 1H), 2.63 (t, J = 11.2 Hz, 1H), 2.39 (tt, J = 10.2, 3.6 Hz, 1H), 1.81 (ddd, J = 10.6, 4.7, 2.4 Hz, 1H), 1.55-1.44 (m, 1H). | 275.4 |
| 75c | 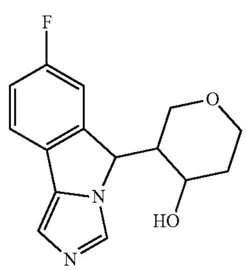 [SMILES: OC1CCOCC1C1c2cc(F)ccc2-c2cncn21] | $^1$H NMR (500 MHz, DMSO-$d_6$) δ 7.88 (s, 1H), 7.63 (dd, J = 8.4, 5.1 Hz, 1H), 7.49 (ddd, J = 9.0, 2.5, 1.0 Hz, 1H), 7.24 (dddd, J = 9.3, 8.5, 2.5, 0.7 Hz, 1H), 7.12 (s, 1H), 5.72 (d, J = 2.6 Hz, 1H), 5.49 (d, J = 5.5 Hz, 1H), 3.93 (tt, J = 10.3, 5.0 Hz, 1H), 3.77 (dd, J = 11.7, 4.7 Hz, 1H), 3.24-3.14 (m, 1H), 3.02-2.95 (m, 1H), 2.36 (t, J = 11.2 Hz, 1H), 2.30-2.21 (m, 1H), 1.96-1.88 (m, 1H), 1.56 (tdd, J = 12.7, 10.6, 4.8 Hz, 1H). | 275.2 |
| 75d | 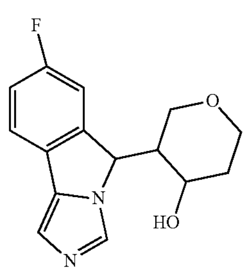 [SMILES: OC1CCOCC1C1c2cc(F)ccc2-c2cncn21] | $^1$H NMR (500 MHz, DMSO-$d_6$) δ 7.88 (s, 1H), 7.63 (dd, J = 8.4, 5.1 Hz, 1H), 7.49 (ddd, J = 9.1, 2.4, 1.0 Hz, 1H), 7.24 (dddd, J = 9.3, 8.4, 2.4, 0.6 Hz, 1H), 7.12 (s, 1H), 5.72 (d, J = 2.5 Hz, 1H), 5.49 (d, J = 5.4 Hz, 1H), 3.94 (tt, J = 10.3, 5.0 Hz, 1H), 3.77 (dd, J = 11.7, 4.7 Hz, 1H), 3.25-3.14 (m, 1H), 3.02-2.95 (m, 1H), 2.36 (t, J = 11.2 Hz, 1H), 2.26 (ddt, J = 14.0, 10.8, 3.1 Hz, 1H), 1.96-1.88 (m, 1H), 1.62-1.50 (m, 1H). | 275.2 |

TABLE 2-continued

| Ex. # | Structure | $^1$H NMR | MS (M + H)$^+$ |
|---|---|---|---|
| 75-1a | 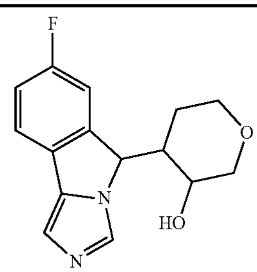 | $^1$H NMR (500 MHz, DMSO-d$_6$) δ 7.91 (t, J = 0.6 Hz, 1H), 7.65 (dd, J = 8.4, 5.1 Hz, 1H), 7.41-7.35 (m, 1H), 7.26 (ddt, J = 10.4, 8.1, 1.4 Hz, 1H), 7.10 (s, 1H), 5.69 (d, J = 3.8 Hz, 1H), 5.44 (d, J = 5.6 Hz, 1H), 3.84 (dd, J = 10.5, 4.8 Hz, 1H), 3.71-3.57 (m, 2H), 3.11 (td, J = 11.3, 3.2 Hz, 1H), 2.98 (dd, J = 10.6, 9.8 Hz, 1H), 2.43-2.34 (m, 1H), 0.64-0.52 (m, 2H). | 275.2 |
| 75-1b | 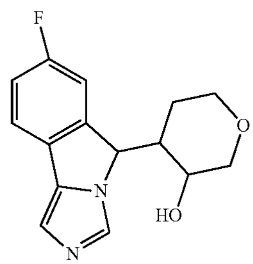 [SMILES: OC1COCCC1C1c2cc(F)ccc2-c2cncn21] | $^1$H NMR (500 MHz, DMSO-d$_6$) δ 7.91 (s, 1H), 7.65 (dd, J = 8.4, 5.2 Hz, 1H), 7.41-7.35 (m, 1H), 7.31-7.22 (m, 1H), 7.10 (s, 1H), 5.69 (d, J = 3.8 Hz, 1H), 5.44 (d, J = 5.6 Hz, 1H), 3.84 (dd, J = 10.6, 4.9 Hz, 1H), 3.71-3.57 (m, 2H), 3.11 (td, J = 11.3, 3.2 Hz, 1H), 2.98 (t, J = 10.2 Hz, 1H), 2.38 (ddd, J = 15.2, 11.0, 4.3 Hz, 1H), 0.65-0.51 (m, 2H). | 275.1 |
| 75-1c | 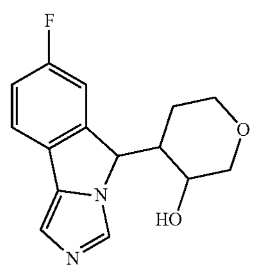 [SMILES: OC1COCCC1C1c2cc(F)ccc2-c2cncn21] | $^1$H NMR (500 MHz, DMSO-d$_6$) δ 7.87 (s, 1H), 7.63 (dd, J = 8.4, 5.1 Hz, 1H), 7.41 (ddd, J = 9.1, 2.4, 1.0 Hz, 1H), 7.27-7.18 (m, 1H), 7.13 (s, 1H), 5.74-5.69 (m, 1H), 5.52 (d, J = 5.7 Hz, 1H), 3.91 (dd, J = 10.6, 4.8 Hz, 1H), 3.73 (tt, J = 10.4, 5.3 Hz, 1H), 3.58 (dd, J = 11.1, 4.7 Hz, 1H), 3.17-3.08 (m, 1H), 3.04 (dd, J = 10.6, 9.9 Hz, 1H), 2.29-2.19 (m, 1H), 0.72-0.65 (m, 1H), 0.45 (qd, J = 12.6, 4.8 Hz, 1H). | 275.2 |
| 75-1d | 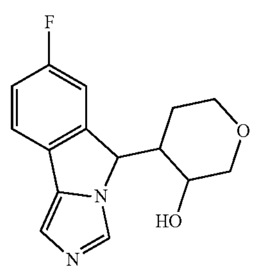 [SMILES: OC1COCCC1C1c2cc(F)ccc2-c2cncn21] | $^1$H NMR (500 MHz, DMSO-d$_6$) δ 7.87 (s, 1H), 7.63 (dd, J = 8.4, 5.1 Hz, 1H), 7.41 (ddd, J = 9.0, 2.6, 1.0 Hz, 1H), 7.26-7.20 (m, 1H), 7.13 (s, 1H), 5.73-5.70 (m, 1H), 5.52 (d, J = 5.8 Hz, 1H), 3.91 (dd, J = 10.6, 4.9 Hz, 1H), 3.73 (tt, J = 10.4, 5.3 Hz, 1H), 3.58 (dd, J = 11.2, 4.7 Hz, 1H), 3.13 (td, J = 11.7, 2.3 Hz, 1H), 3.04 (dd, J = 10.6, 9.9 Hz, 1H), 2.28-2.19 (m, 1H), 0.72-0.64 (m, 1H), 0.45 (qd, J = 12.6, 4.9 Hz, 1H). | 275.5 |
| 76a | 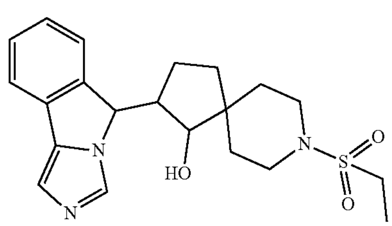 [SMILES: CCS(=O)(=O)N1CCC2(CCC(C3c4ccccc4-c4cncn43)C2O)CC1] | $^1$H NMR (500 MHz, DMSO-d$_6$) δ 7.92 (s, 1H), 7.60 (d, J = 7.5 Hz, 1H), 7.53 (d, J = 7.6 Hz, 1H), 7.39 (t, J = 7.5 Hz, 1H), 7.26 (td, J = 7.6, 1.1 Hz, 1H), 7.10 (s, 1H), 5.45 (d, J = 4.4 Hz, 1H), 5.07 (d, J = 5.7 Hz, 1H), 3.57 (dd, J = 9.6, 5.7 Hz, 1H), 3.47 (d, J = 12.2 Hz, 1H), 3.41 (d, J = 12.4 Hz, 1H), 2.99 (q, J = 7.3 Hz, 2H), 2.87 (td, J = 12.0, 2.7 Hz, 1H), 2.75 (td, J = 12.0, 2.7 Hz, 1H), 2.70-2.60 (m, 1H), 1.75-1.56 (m, 3H), 1.30 (td, J = 9.7, 4.5 Hz, 2H), 1.19 (t, J = 7.4 Hz, 3H), 1.10-1.00 (m, 1H), 0.85 (ddt, J = 13.2, 9.5, 4.8 Hz, 1H). | |
| 76b | 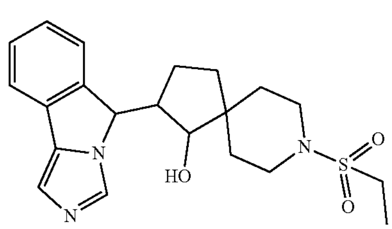 [SMILES: CCS(=O)(=O)N1CCC2(CCC(C3c4ccccc4-c4cncn43)C2O)CC1] | $^1$H NMR (500 MHz, DMSO-d$_6$) δ 7.95 (s, 1H), 7.60 (d, J = 7.5 Hz, 1H), 7.49 (d, J = 7.3 Hz, 1H), 7.38 (t, J = 7.5 Hz, 1H), 7.24 (td, J = 7.6, 1.1 Hz, 1H), 7.12 (s, 1H), 5.32-5.27 (m, 2H), 3.90-3.80 (m, 1H), 3.46-3.36 (m, 1H), 3.25-3.18 (m, 1H), 3.05-2.99 (m, 2H), 2.99-2.91 (m, 2H), 2.12 (dd, J = 18.9, 8.8 Hz, 1H), 2.06-1.91 (m, 2H), 1.77-1.69 (m, 1H), 1.65 (dt, J = 13.2, 6.1 Hz, 3H), 1.32-1.24 (m, 2H), 1.20 (t, J = 7.4 Hz, 3H). | |

TABLE 2-continued

| Ex. # | Structure | $^1$H NMR | MS (M + H)$^+$ |
|---|---|---|---|
| 76c | 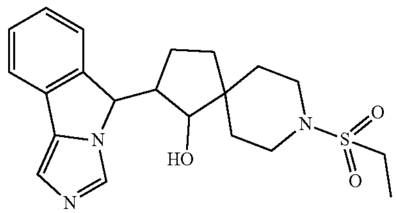 [SMILES: CCS(=O)(=O)N1CCC2(CCC(C3c4ccccc4-c4cncn43)C2O)CC1] | $^1$H NMR (500 MHz, DMSO-$d_6$) δ 7.88 (s, 1H), 7.67 (d, J = 7.6 Hz, 1H), 7.59 (d, J = 7.5 Hz, 1H), 7.38 (t, J = 7.4 Hz, 1H), 7.27 (td, J = 7.6, 1.1 Hz, 1H), 7.12 (s, 1H), 5.39 (dd, J = 11.3, 6.6 Hz, 2H), 3.91 (t, J = 5.2 Hz, 1H), 3.39 (dt, J = 10.0, 4.5 Hz, 1H), 3.28-3.20 (m, 1H), 3.02 (q, J = 7.4 Hz, 2H), 2.99-2.88 (m, 2H), 2.34-2.25 (m, 1H), 1.72 (ddq, J = 14.7, 8.6, 4.8 Hz, 3H), 1.62-1.52 (m, 3H), 1.35-1.30 (m, 2H), 1.20 (t, J = 7.4 Hz, 3H). | |
| 76d | 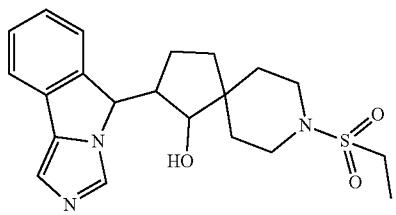 [SMILES: CCS(=O)(=O)N1CCC2(CCC(C3c4ccccc4-c4cncn43)C2O)CC1] | $^1$H NMR (500 MHz, DMSO-$d_6$) δ 7.88 (s, 1H), 7.67 (d, J = 7.6 Hz, 1H), 7.58 (d, J = 7.5 Hz, 1H), 7.37 (t, J = 7.4 Hz, 1H), 7.27 (td, J = 7.6, 1.1 Hz, 1H), 7.12 (s, 1H), 5.38 (dd, J = 11.4, 6.5 Hz, 2H), 3.91 (t, J = 5.2 Hz, 1H), 3.44-3.35 (m, 1H), 3.27-3.19 (m, 1H), 3.04-2.99 (m, 2H), 2.98-2.89 (m, 2H), 2.33-2.25 (m, 1H), 1.71 (dtt, J = 13.1, 9.2, 5.4 Hz, 3H), 1.62-1.51 (m, 3H), 1.34-1.30 (m, 2H), 1.20 (t, J = 7.4 Hz, 3H). | |
| 76e | 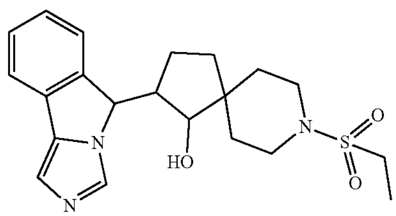 [SMILES: CCS(=O)(=O)N1CCC2(CCC(C3c4ccccc4-c4cncn43)C2O)CC1] | $^1$H NMR (500 MHz, DMSO-$d_6$) δ 7.92 (s, 1H), 7.60 (d, J = 7.5 Hz, 1H), 7.53 (d, J = 7.1 Hz, 1H), 7.39 (t, J = 7.5 Hz, 1H), 7.26 (td, J = 7.6, 1.1 Hz, 1H), 7.11 (s, 1H), 5.45 (d, J = 4.4 Hz, 1H), 5.08 (d, J = 5.7 Hz, 1H), 3.57 (dd, J = 9.6, 5.7 Hz, 1H), 3.47 (d, J = 12.3 Hz, 1H), 3.41 (d, J = 12.4 Hz, 1H), 3.00 (q, J = 7.3 Hz, 2H), 2.87 (td, J = 12.1, 2.8 Hz, 1H), 2.75 (td, J = 11.9, 2.6 Hz, 1H), 2.70-2.59 (m, 1H), 1.73-1.56 (m, 3H), 1.30 (td, J = 9.7, 4.5 Hz, 2H), 1.19 (d, J = 7.4 Hz, 3H), 1.10-1.00 (m, 1H), 0.85 (ddt, J = 19.1, 9.6, 5.4 Hz, 1H). | |
| 77a | 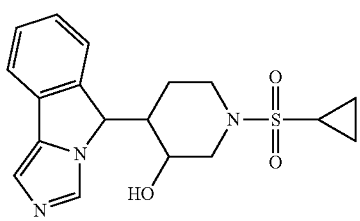 [SMILES: O=S(=O)(C1CC1)N1CCC(C2c3ccccc3-c3cncn32)C(O)C1] | $^1$H NMR (400 MHz, $CD_3OD$) δ 7.92 (s, 1H), 7.65 (d, J = 7.5 Hz, 1H), 7.50 (d, J = 7.9 Hz, 1H), 7.44 (t, J = 7.4 Hz, 1H), 7.41-7.35 (m, 1H), 7.21 (s, 1H), 5.92 (s, 1H), 4.08-3.86 (m, 2H), 3.55-3.48 (m, 1H), 2.85-2.68 (m, 2H), 2.47 (tt, J = 7.6, 5.1 Hz, 1H), 2.31-2.14 (m, 1H), 1.32 (d, J = 6.5 Hz, 1H), 1.09-0.88 (m, 5H), 0.65 (qd, J = 12.7, 4.6 Hz, 1H). | 360.1 |
| 77b | 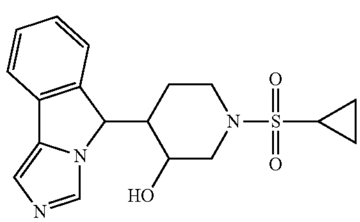 [SMILES: O=S(=O)(C1CC1)N1CCC(C2c3ccccc3-c3cncn32)C(O)C1] | The same as 077b. | 360.2 |
| 78a | 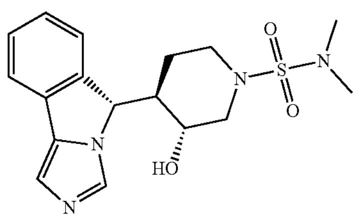 [SMILES: CN(C)S(=O)(=O)N1CC[C@H]([C@H]2c3ccccc3-c3cncn32)[C@@H](O)C1] | $^1$H NMR (300 MHz, $CD_3OD$) δ 7.92 (s, 1H), 7.65 (d, J = 7.5, 1H), 7.56 (d, J = 7.5, 1H), 7.48-7.33 (m, 2H), 7.18 (s, 1H), 5.83 (d, J = 3.3, 1H), 3.95-3.82 (m, 2H), 3.48-3.44 (m, 1H), 2.76 (s, 6H), 2.77-2.63 (m, 2H), 2.41-2.25 (m, 1H), 0.82-0.61 (m, 2H). | 363.2 |
| 78b | 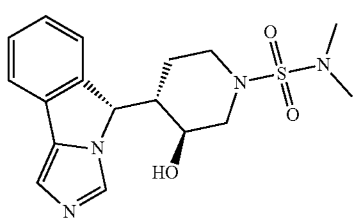 [SMILES: CN(C)S(=O)(=O)N1CC[C@@H]([C@H]2c3ccccc3-c3cncn32)[C@H](O)C1] | $^1$H NMR (300 MHz, $CD_3OD$) δ 7.92 (s, 1H), 7.64 (d, J = 7.5, 1H), 7.49 (d, J = 7.5, 1H), 7.46-7.36 (m, 2H), 7.20 (s, 1H), 5.82 (d, J = 3.3, 1H), 3.95-3.90 (m, 2H), 3.50-3.42 (m, 1H), 2.79 (s, 6H), 2.77-2.65 (m, 2H), 2.21-2.12 (m, 1H), 0.95-0.90 (m, 1H), 0.67-0.63 (m, 1H). | 363.2 |

TABLE 2-continued

| Ex. # | Structure | $^1$H NMR | MS $(M + H)^+$ |
|---|---|---|---|
| 79a | 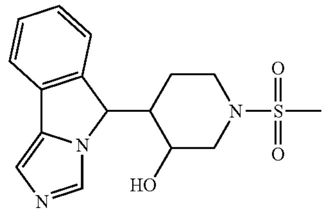 [SMILES: CS(=O)(=O)N1CCC(C2c3ccccc3-c3cncn32)C(O)C1] | $^1$H NMR (300 MHz, DMSO-$d_6$) δ 7.92 (s, 1H), 7.63 (d, J = 7.8 Hz, 1H), 7.52 (d, J = 7.8 Hz, 1H), 7.44-7.27 (m, 2H), 7.15 (s, 1H), 5.81 (d, J = 3.6 Hz, 1H), 5.79 (d, J = 3.6 Hz, 1H), 3.84-3.71 (m, 2H), 3.34-3.29 (m, 1H), 2.84 (s, 3H), 2.55-2.51 (m, 1H), 2.49-2.48 (m, 1H), 2.34-2.21 (m, 1H), 0.71-0.66 (m, 1H), 0.55-0.54 (m, 1H). | 334.1 |
| 79b | 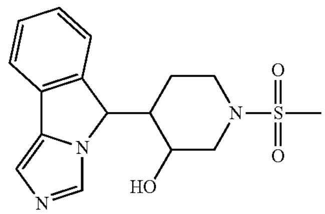 [SMILES: CS(=O)(=O)N1CCC(C2c3ccccc3-c3cncn32)C(O)C1] | The same as 079a. | 334.1 |
| 80a | 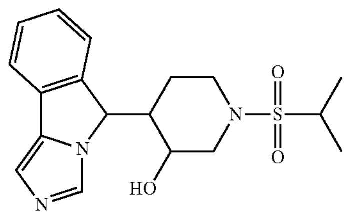 [SMILES: CC(C)S(=O)(=O)N1CCC(C2c3ccccc3-c3cncn32)C(O)C1] | $^1$H NMR (300 MHz, $CD_3OD$) δ 7.88 (s, 1H), 7.62 (d, J = 7.8 Hz, 1H), 7.47 (d, J = 7.8 Hz, 1H), 7.44-7.32 (m, 2H), 7.18 (s, 1H), 5.81 (d, J = 3.6 Hz, 1H), 4.03-3.95 (m, 1H), 3.85-3.82 (m, 1H), 3.55-3.50 (m, 1H), 3.27-3.21 (m, 1H), 2.84-2.70 (m, 2H), 2.28-2.13 (m, 1H), 1.26 (d, J = 2.1 Hz, 6H), 0.94-0.88 (m, 1H), 0.62-0.58 (m, 1H). | 362.2 |
| 80b | 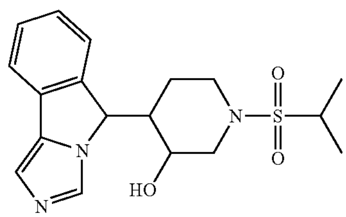 [SMILES: CC(C)S(=O)(=O)N1CCC(C2c3ccccc3-c3cncn32)C(O)C1] | The same as 080a. | 362.3 |
| 81a | 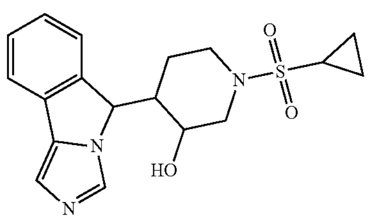 [SMILES: O=S(=O)(C1CC1)N1CCC(C2c3ccccc3-c3cncn32)C(O)C1] | $^1$H NMR (300 MHz, $CD_3OD$) δ 7.91 (s, 1H), 7.66 (d, J = 7.8 Hz, 1H), 7.56 (d, J = 7.8 Hz, 1H), 7.48-7.32 (m, 2H), 7.19 (s, 1H), 5.84 (d, J = 3.6 Hz, 1H), 4.03-3.95 (m, 1H), 3.85-3.82 (m, 1H), 3.55-3.50 (m, 1H), 2.78-2.70 (m, 2H), 2.47-2.28 (m, 2H), 1.04-0.96 (m, 4H), 0.82-0.72 (m, 2H). | 360.1 |
| 81b | 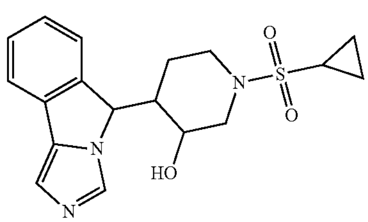 [SMILES: O=S(=O)(C1CC1)N1CCC(C2c3ccccc3-c3cncn32)C(O)C1] | The same as 081a. | 360.2 |
| 82a | 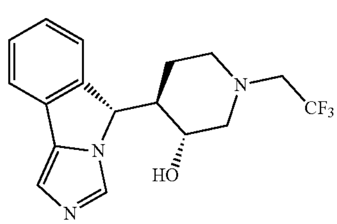 [SMILES: O[C@H]1CN(CC(F)(F)F)CC[C@@H]1[C@H]1c2ccccc2-c2cncn21] | $^1$H NMR (300 MHz, $CD_3OD$) δ 7.91 (s, 1H), 7.63 (d, J = 7.5, 1H), 7.55 (d, J = 7.5, 1H), 7.45-7.31 (m, 2H), 7.16 (s, 1H), 5.78 (d, J = 3.3, 1H), 3.93-3.81 (m, 1H), 3.22-3.15 (m, 1H), 3.09-2.98 (m, 2H), 2.75-2.65 (m, 1H), 2.16-2.05 (m, 3H), 0.72-0.60 (m, 2H). | 338.2 |

TABLE 2-continued

| Ex. # | Structure | $^1$H NMR | MS (M + H)$^+$ |
|---|---|---|---|
| 82b | 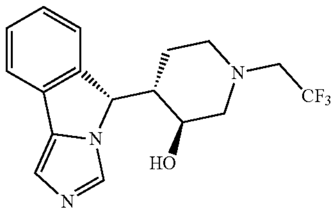 [SMILES: O[C@@H]1CN(CC(F)(F)F)CC[C@H]1[C@H]1c2ccccc2-c2cncn21] | $^1$H NMR (300 MHz, $CD_3OD$) δ 7.92 (s, 1H), 7.63 (d, J = 7.5, 1H), 7.46 (d, J = 7.5, 1H), 7.42-7.33 (m, 2H), 7.19 (s, 1H), 5.78 (d, J = 3.3, 1H), 3.93-3.86 (m, 1H), 3.30-3.26 (m, 1H), 3.13-3.03 (m, 2H), 2.75-2.70 (m, 1H), 2.40-2.15 (m, 2H), 2.04-2.02 (m, 1H), 0.84-0.80 (m, 1H), 0.65-0.59 (m, 1H). | 338.2 |
| 83a | 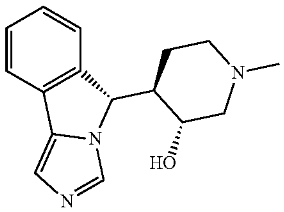 [SMILES: CN1CC[C@H]([C@H]2c3ccccc3-c3cncn32)[C@@H](O)C1] | $^1$H NMR (400 MHz, DMSO-$d_6$) δ 7.92 (s, 1H), 7.61 (d, J = 7.5, 1H), 7.51 (d, J = 7.5, 1H), 7.40-7.26 (m, 2H), 7.13 (s, 1H), 5.30 (d, J = 3.2, 1H), 5.37 (d, J = 3.2, 1H), 3.82-3.73 (m, 1H), 2.95-2.92 (m, 1H), 2.46-2.45 (m, 1H), 2.08 (s, 3H), 2.07-2.03 (m, 1H), 1.76-1.58 (m, 2H), 0.52-0.41 (m, 2H). | 270.2 |
| 83b | 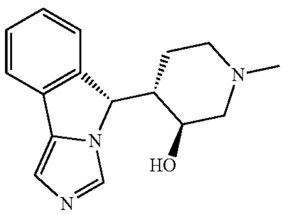 [SMILES: CN1CC[C@@H]([C@H]2c3ccccc3-c3cncn32)[C@H](O)C1] | $^1$H NMR (300 MHz, $CD_3OD$) δ 7.92 (s, 1H), 7.63 (d, J = 7.5, 1H), 7.47 (d, J = 7.5, 1H), 7.42-7.33 (m, 2H), 7.19 (s, 1H), 5.80 (d, J = 3.3, 1H), 3.97-3.90 (m, 1H), 3.18-3.13 (m, 1H), 2.70-2.62 (m, 1H), 2.63 (s, 3H), 2.06-1.83 (m, 3H), 0.91-0.86 (m, 1H), 0.72-0.64 (m, 1H). | 270.2 |
| 84a | 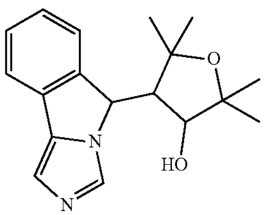 [SMILES: CC1(C)OC(C)(C)C(C2c3ccccc3-c3cncn32)C1O] | $^1$H NMR (500 MHz, DMSO-$d_6$) δ 8.16 (d, J = 7.9 Hz, 1H), 7.71 (s, 1H), 7.51 (s, 1H), 7.33-7.25 (m, 1H), 7.21-7.14 (m, 2H), 6.60 (d, J = 2.2 Hz, 1H), 5.74 (d, J = 5.0 Hz, 1H), 4.37 (dd, J = 4.9, 2.3 Hz, 1H), 1.26 (s, 3H), 1.24 (s, 3H), 1.00 (s, 3H), 0.83 (s, 3H). | 299.2 |
| 84b | 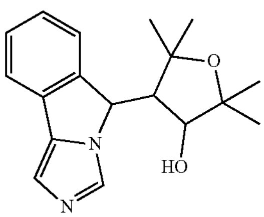 [SMILES: CC1(C)OC(C)(C)C(C2c3ccccc3-c3cncn32)C1O] | $^1$H NMR (500 MHz, DMSO-$d_6$) δ 8.01 (s, 1H), 7.75 (d, J = 7.7 Hz, 1H), 7.60 (d, J = 7.5 Hz, 1H), 7.39 (t, J = 7.4 Hz, 1H), 7.26 (t, J = 7.6 Hz, 1H), 7.12 (s, 1H), 5.78-5.59 (m, 2H), 4.09 (tt, J = 5.2, 3.1 Hz, 1H), 3.17 (d, J = 5.3 Hz, 1H), 1.20 (s, 3H), 1.08 (s, 3H), 1.06 (s, 3H), 0.82 (s, 3H). | 299.2 |
| 84c | 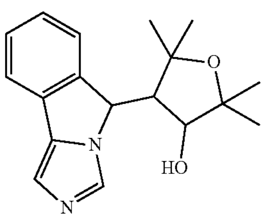 [SMILES: CC1(C)OC(C)(C)C(C2c3ccccc3-c3cncn32)C1O] | $^1$H NMR (500 MHz, DMSO-$d_6$) δ 8.00 (s, 1H), 7.74 (d, J = 7.7 Hz, 1H), 7.60 (d, J = 7.5 Hz, 1H), 7.39 (t, J = 7.5 Hz, 1H), 7.26 (t, J = 7.6 Hz, 1H), 7.11 (s, 1H), 5.75-5.52 (m, 2H), 4.08 (dq, J = 5.2, 3.2, 2.8 Hz, 1H), 1.20 (s, 3H), 1.07 (s, 3H), 1.05 (s, 3H), 0.81 (s, 3H). | 299.2 |
| 84d | 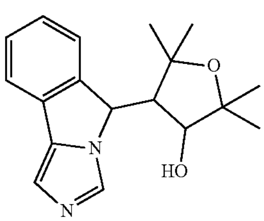 [SMILES: CC1(C)OC(C)(C)C(C2c3ccccc3-c3cncn32)C1O] | $^1$H NMR (500 MHz, DMSO-$d_6$) δ 7.88-7.79 (m, 1H), 7.74 (s, 1H), 7.71 (d, J = 7.4 Hz, 1H), 7.29 (t, J = 6.9 Hz, 1H), 7.25-7.19 (m, 1H), 7.16 (s, 1H), 6.62 (s, 1H), 5.23 (d, J = 5.0 Hz, 1H), 4.08 (d, J = 4.7 Hz, 1H), 1.39 (d, J = 12.3 Hz, 3H), 1.35 (d, J = 7.2 Hz, 3H), 1.18 (s, 3H), 0.99 (d, J = 5.9 Hz, 3H). | 299.2 |

TABLE 2-continued

| Ex. # | Structure | $^1$H NMR | MS (M + H)$^+$ |
|---|---|---|---|
| 84e | 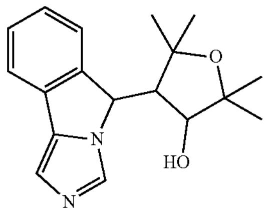 [SMILES: CC1(C)OC(C)(C)C(C2c3ccccc3-c3cncn32)C1O] | $^1$H NMR (500 MHz, DMSO-d$_6$) δ 7.82 (dd, J = 7.8, 1.2 Hz, 1H), 7.74 (s, 1H), 7.72 (d, J = 7.4 Hz, 1H), 7.30 (td, J = 7.5, 1.2 Hz, 1H), 7.23 (td, J = 7.5, 1.3 Hz, 1H), 7.17 (s, 1H), 6.63 (s, 1H), 5.24 (d, J = 5.0 Hz, 1H), 4.10 (dd, J = 9.8, 4.8 Hz, 1H), 1.40 (d, J = 12.6 Hz, 3H), 1.36 (d, J = 7.4 Hz, 3H), 1.19 (s, 3H), 1.00 (d, J = 6.0 Hz, 3H). | 299.2 |
| 84f | 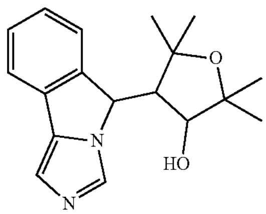 [SMILES: CC1(C)OC(C)(C)C(C2c3ccccc3-c3cncn32)C1O] | $^1$H NMR (500 MHz, DMSO-d$_6$) δ 8.16 (d, J = 7.7 Hz, 1H), 7.71 (s, 1H), 7.51 (dd, J = 2.1, 1.1 Hz, 1H), 7.32-7.26 (m, 1H), 7.21-7.13 (m, 2H), 6.59 (d, J = 2.3 Hz, 1H), 5.74 (d, J = 5.0 Hz, 1H), 4.37 (dd, J = 5.0, 2.4 Hz, 1H), 1.26 (s, 3H), 1.24 (s, 3H), 1.00 (s, 3H), 0.83 (s, 3H). | 299.2 |
| 85a | 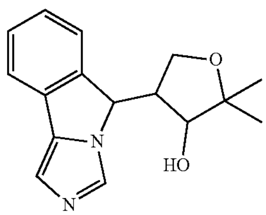 [SMILES: CC1(C)OCC(C2c3ccccc3-c3cncn32)C1O] | (500 MHz, DMSO-d$_6$) δ 7.92 (s, 1H), 7.60 (d, J = 7.6 Hz, 1H), 7.49 (d, J = 7.6 Hz, 1H), 7.39 (t, J = 7.5 Hz, 1H), 7.27 (t, J = 7.6 Hz, 1H), 7.12 (s, 1H), 5.52 (d, J = 4.5 Hz, 1H), 5.06 (d, J = 5.5 Hz, 1H), 3.77 (t, J = 9.0 Hz, 1H), 3.59 (t, J = 6.5 Hz, 1H), 3.52 (t, J = 8.4 Hz, 1H), 2.82 (dq, J = 12.6, 7.6, 6.3 Hz, 1H), 1.01 (d, J = 7.7 Hz, 6H). | 271.2 |
| 85b | 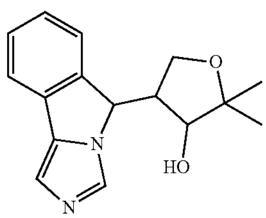 [SMILES: CC1(C)OCC(C2c3ccccc3-c3cncn32)C1O] | (500 MHz, DMSO-d$_6$) δ 7.79 (s, 1H), 7.70 (d, J = 8.2 Hz, 1H), 7.60 (d, J = 7.5 Hz, 1H), 7.40 (t, J = 7.5 Hz, 1H), 7.28 (t, J = 7.6 Hz, 1H), 7.12 (s, 1H), 5.67 (d, J = 5.6 Hz, 1H), 5.47 (d, J = 8.3 Hz, 1H), 3.99 (t, J = 5.6 Hz, 1H), 3.85 (d, J = 9.5 Hz, 2H), 2.73-2.61 (m, 1H), 1.22 (s, 3H), 1.03 (s, 3H). | 271.2 |
| 85c | 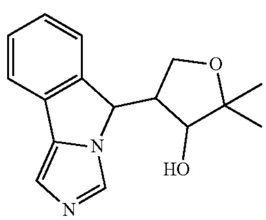 [SMILES: CC1(C)OCC(C2c3ccccc3-c3cncn32)C1O] | (500 MHz, DMSO-d$_6$) δ 7.79 (s, 1H), 7.70 (d, J = 8.2 Hz, 1H), 7.60 (d, J = 7.5 Hz, 1H), 7.40 (t, J = 7.5 Hz, 1H), 7.28 (t, J = 7.6 Hz, 1H), 7.12 (s, 1H), 5.67 (d, J = 5.6 Hz, 1H), 5.47 (d, J = 8.3 Hz, 1H), 3.99 (t, J = 5.6 Hz, 1H), 3.85 (d, J = 9.5 Hz, 2H), 2.73-2.61 (m, 1H), 1.22 (s, 3H), 1.03 (s, 3H). | 271.2 |
| 85d | 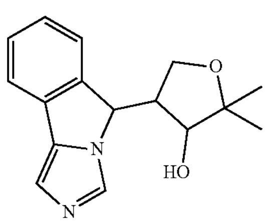 [SMILES: CC1(C)OCC(C2c3ccccc3-c3cncn32)C1O] | (500 MHz, DMSO-d$_6$) δ 7.92 (s, 1H), 7.60 (d, J = 7.6 Hz, 1H), 7.49 (d, J = 7.6 Hz, 1H), 7.39 (t, J = 7.5 Hz, 1H), 7.27 (t, J = 7.6 Hz, 1H), 7.12 (s, 1H), 5.52 (d, J = 4.5 Hz, 1H), 5.06 (d, J = 5.5 Hz, 1H), 3.77 (t, J = 9.0 Hz, 1H), 3.59 (t, J = 6.5 Hz, 1H), 3.52 (t, J = 8.4 Hz, 1H), 2.82 (dq, J = 12.6, 7.6, 6.3 Hz, 1H), 1.01 (d, J = 7.7 Hz, 6H). | 271.2 |
| 85e | 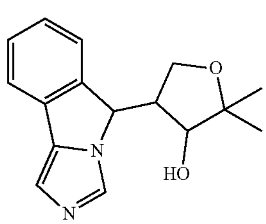 [SMILES: CC1(C)OCC(C2c3ccccc3-c3cncn32)C1O] | (500 MHz, DMSO-d$_6$) δ 7.94 (s, 1H), 7.59 (d, J = 7.5 Hz, 1H), 7.55 (d, J = 7.6 Hz, 1H), 7.38 (t, J = 7.5 Hz, 1H), 7.27 (t, J = 8.1 Hz, 1H), 7.17 (s, 1H), 5.55 (d, J = 3.5 Hz, 1H), 5.45 (d, J = 5.3 Hz, 1H), 3.92 (dd, J = 8.7, 5.3 Hz, 1H), 3.38 (t, J = 9.0 Hz, 1H), 2.94 (qd, J = 8.6, 3.7 Hz, 1H), 2.81-2.70 (m, 1H), 1.12 (s, 3H), 1.04 (s, 3H). | 271.2 |

TABLE 2-continued

| Ex. # | Structure | $^1$H NMR | MS $(M + H)^+$ |
|---|---|---|---|
| 85f | 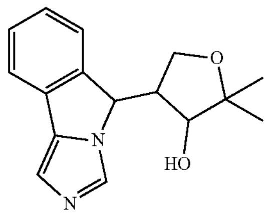 [SMILES: CC1(C)OCC(C2c3ccccc3-c3cncn32)C1O] | (500 MHz, DMSO-$d_6$) δ 7.92 (s, 1H), 7.62 (d, J = 7.6 Hz, 1H), 7.39 (t, J = 7.5 Hz, 1H), 7.29 (d, J = 7.4 Hz, 1H), 7.26-7.20 (m, 1H), 7.15 (s, 1H), 5.66 (d, J = 5.8 Hz, 1H), 5.40 (d, J = 10.6 Hz, 1H), 4.18 (dd, J = 10.1, 8.0 Hz, 1H), 3.96 (t, J = 8.2 Hz, 1H), 3.94-3.90 (m, 1H), 1.25 (s, 3H), 1.01 (s, 3H). | 271.2 |
| 85g | 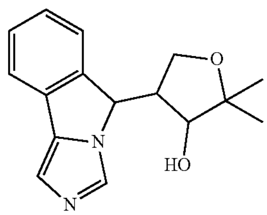 [SMILES: CC1(C)OCC(C2c3ccccc3-c3cncn32)C1O] | (500 MHz, DMSO-$d_6$) δ 7.94 (s, 1H), 7.59 (d, J = 7.5 Hz, 1H), 7.55 (d, J = 7.6 Hz, 1H), 7.38 (t, J = 7.5 Hz, 1H), 7.27 (t, J = 8.1 Hz, 1H), 7.17 (s, 1H), 5.55 (d, J = 3.5 Hz, 1H), 5.45 (d, J = 5.3 Hz, 1H), 3.92 (dd, J = 8.7, 5.3 Hz, 1H), 3.38 (t, J = 9.0 Hz, 1H), 2.94 (qd, J = 8.6, 3.7 Hz, 1H), 2.81-2.70 (m, 1H), 1.12 (s, 3H), 1.04 (s, 3H). | 271.2 |
| 85h | 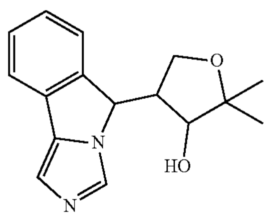 [SMILES: CC1(C)OCC(C2c3ccccc3-c3cncn32)C1O] | (500 MHz, DMSO-$d_6$) δ 7.92 (s, 1H), 7.62 (d, J = 7.6 Hz, 1H), 7.39 (t, J = 7.5 Hz, 1H), 7.29 (d, J = 7.4 Hz, 1H), 7.26-7.20 (m, 1H), 7.15 (s, 1H), 5.66 (d, J = 5.8 Hz, 1H), 5.40 (d, J = 10.6 Hz, 1H), 4.18 (dd, J = 10.1, 8.0 Hz, 1H), 3.96 (t, J = 8.2 Hz, 1H), 3.94-3.90 (m, 1H), 1.25 (s, 3H), 1.01 (s, 3H). | 271.2 |
| 86a | 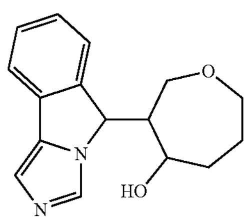 [SMILES: OC1CCCOCC1C1c2ccccc2-c2cncn21] | $^1$H NMR (300 MHz, $CD_3OD$) δ 7.95 (s, 1H), 7.74 (d, J = 7.7 Hz, 1H), 7.69-7.57 (m, 1H), 7.48-7.25 (m, 2H), 7.14 (s, 1H), 5.42 (s, 1H), 4.88 (d, J = 2.1 Hz, 17H), 4.04 (s, 1H), 3.88-3.65 (m, 4H), 3.42 (s, 1H), 2.57 (d, J = 11.5 Hz, 1H), 2.42-2.22 (m, 1H), 1.86-1.66 (m, 2H), 0.70-0.66 (m, 1H). | 271.2 |
| 86b | 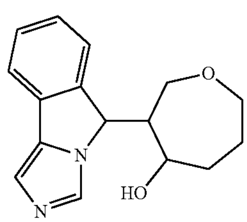 [SMILES: OC1CCCOCC1C1c2ccccc2-c2cncn21] | The same as 086a. | 271.2 |
| 86c | 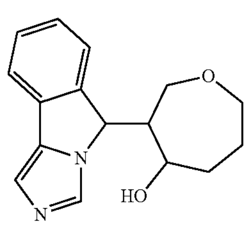 [SMILES: OC1CCCOCC1C1c2ccccc2-c2cncn21] | $^1$H NMR (300 MHz, $CD_3OD$) δ 8.22 (s, 2H), 7.57-7.49 (m, 4H), 7.47-7.27 (m, 4H), 7.12 (s, 2H), 5.46 (s, 2H), 4.55 (q, J = 3.6, 2.7 Hz, 2H), 3.88-3.85 (m, 2H), 3.77-3.57 (m, 4H), 3.35-3.31 (m, 1H), 2.65-2.61 (m, 2H), 2.20-2.00 (m, 2H), 1.99-1.67 (m, 4H), 0.70-0.66 (m, 2H). | 271.2 |
| 86d | 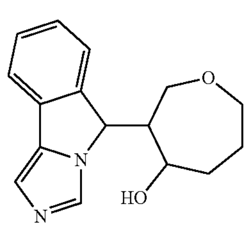 [SMILES: OC1CCCOCC1C1c2ccccc2-c2cncn21] | $^1$H NMR (300 MHz, $CD_3OD$) δ 8.23 (d, J = 2.1 Hz, 1H), 7.58 (dd, J = 11.1, 7.6 Hz, 2H), 7.49-7.29 (m, 2H), 7.17-7.09 (m, 1H), 5.47 (s, 1H), 4.57-4.47 (m, 1H), 3.75-3.56 (m, 2H), 3.36-3.23 (m, 1H), 2.81 (dt, J = 12.6, 2.6 Hz, 1H), 2.66-2.53 (m, 1H), 2.28-2.25 (m, 1H), 2.03-2.01 (m, 2H), 1.64-1.62 (m, 1H). | 271.2 |

TABLE 2-continued

| Ex. # | Structure | $^1$H NMR | MS (M + H)$^+$ |
|---|---|---|---|
| 86e | 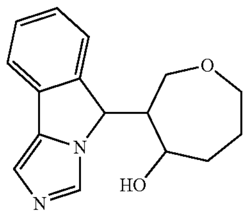 [SMILES: OC1CCCOCC1C1c2ccccc2-c2cncn21] | $^1$H NMR (300 MHz, $CD_3OD$) δ 8.01 (s, 1H), 7.85 (d, J = 7.7 Hz, 1H), 7.62 (d, J = 7.4 Hz, 1H), 7.47-7.25 (m, 2H), 7.17 (s, 1H), 5.45 (d, J = 3.4 Hz, 1H), 4.23 (dd, J = 5.5, 2.9 Hz, 1H), 3.85-3.68 (m, 3H), 3.42 (dt, J = 14.6, 4.8 Hz, 2H), 2.54-2.52 (m, 1H), 2.21-2.19 (m, 1H), 2.03-1.72 (m, 2H), 1.71-1.53 (m, 1H). | 271.2 |
| 86f | 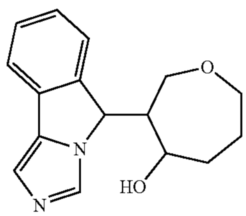 [SMILES: OC1CCCOCC1C1c2ccccc2-c2cncn21] | The same as 086c. | 271.2 |
| 86g | 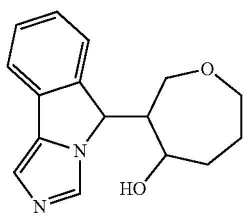 [SMILES: OC1CCCOCC1C1c2ccccc2-c2cncn21] | The same as 086e. | 271.2 |
| 87a | 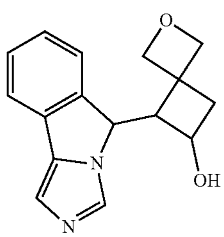 [SMILES: OC1CC2(COC2)C1C1c2ccccc2-c2cncn21] | N/A due to low amount | 269.2 |
| 87b | 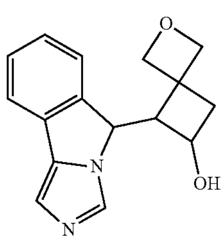 [SMILES: OC1CC2(COC2)C1C1c2ccccc2-c2cncn21] | $^1$H NMR (500 MHz, DMSO-$d_6$) δ 8.18 (s, 1H), 7.65-7.61 (m, 2H), 7.43-7.38 (m, 1H), 7.32-7.26 (m, 1H), 7.19 (s, 1H), 5.67 (d, J = 3.4 Hz, 1H), 5.61 (d, J = 8.3 Hz, 1H), 4.78 (d, J = 7.2 Hz, 1H), 4.50 (d, J = 6.7 Hz, 1H), 4.40 (d, J = 7.2 Hz, 1H), 4.38-4.33 (m, 1H), 4.32 (d, J = 6.8 Hz, 1H), 2.65-2.58 (m, 1H), 2.38 (ddd, J = 12.2, 5.9, 1.4 Hz, 1H), 2.06 (dd, J = 12.4, 2.5 Hz, 1H). | 269.2 |
| 87c | 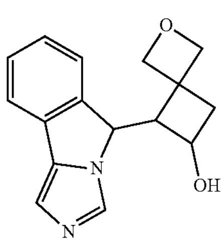 [SMILES: OC1CC2(COC2)C1C1c2ccccc2-c2cncn21] | (500 MHz, DMSO-$d_6$) δ 7.89 (dd, J = 7.7, 1.1 Hz, 1H), 7.84 (s, 1H), 7.67-7.61 (m, 1H), 7.42 (t, J = 7.6 Hz, 1H), 7.32 (td, J = 7.6, 1.2 Hz, 1H), 7.13 (s, 1H), 5.67 (d, J = 9.6 Hz, 1H), 5.29 (d, J = 7.7 Hz, 1H), 5.03 (d, J = 6.9 Hz, 1H), 4.63 (d, J = 7.0 Hz, 1H), 4.52 (d, J = 6.8 Hz, 1H), 4.43 (d, J = 6.7 Hz, 1H), 4.18 (p, J = 7.8 Hz, 1H), 2.60 (dd, J = 11.3, 7.5 Hz, 1H), 2.17 (dd, J = 9.7, 7.7 Hz, 1H), 1.91 (dd, J = 11.3, 8.3 Hz, 1H). | 269.2 |

TABLE 2-continued

| Ex. # | Structure | $^1$H NMR | MS (M + H)$^+$ |
|---|---|---|---|
| 87d | 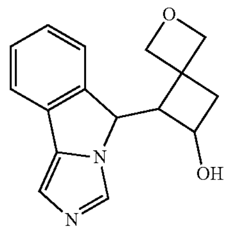 [SMILES: OC1CC2(COC2)C1C1c2ccccc2-c2cncn21] | (500 MHz, DMSO-$d_6$) δ 7.89 (dd, J = 7.7, 0.9 Hz, 1H), 7.84 (s, 1H), 7.64 (dt, J = 7.6, 0.9 Hz, 1H), 7.45-7.39 (m, 1H), 7.32 (td, J = 7.6, 1.2 Hz, 1H), 7.13 (s, 1H), 5.67 (d, J = 9.7 Hz, 1H), 5.29 (d, J = 7.7 Hz, 1H), 5.03 (d, J = 7.0 Hz, 1H), 4.64 (d, J = 7.0 Hz, 1H), 4.52 (d, J = 6.8 Hz, 1H), 4.43 (d, J = 6.8 Hz, 1H), 4.23-4.13 (m, 1H), 2.60 (dd, J = 11.2, 7.5 Hz, 1H), 2.17 (dd, J = 9.7, 7.7 Hz, 1H), 1.91 (dd, J = 11.3, 8.3 Hz, 1H). | 269.2 |
| 87e | 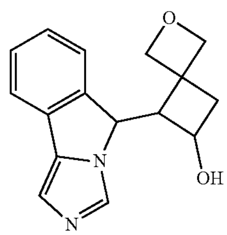 [SMILES: OC1CC2(COC2)C1C1c2ccccc2-c2cncn21] | (500 MHz, DMSO-$d_6$) δ 8.18 (d, J = 2.0 Hz, 1H), 7.67-7.60 (m, 2H), 7.44-7.37 (m, 1H), 7.33-7.27 (m, 1H), 7.19 (d, J = 2.0 Hz, 1H), 5.67 (t, J = 2.8 Hz, 1H), 5.61 (d, J = 8.1 Hz, 1H), 4.78 (dd, J = 7.3, 2.0 Hz, 1H), 4.51 (dd, J = 6.8, 2.0 Hz, 1H), 4.40 (dd, J = 7.1, 2.0 Hz, 1H), 4.35 (dd, J = 6.0, 3.0 Hz, 1H), 4.32 (dd, J = 6.9, 2.0 Hz, 1H), 2.62 (t, J = 7.6 Hz, 1H), 2.38 (dd, J = 12.4, 5.8 Hz, 1H), 2.06 (dt, J = 12.3, 2.4 Hz, 1H). | 269.2 |
| 87f | 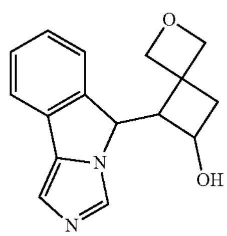 [SMILES: OC1CC2(COC2)C1C1c2ccccc2-c2cncn21] | (500 MHz, DMSO-$d_6$) δ 7.99 (s, 1H), 7.82 (d, J = 13.3 Hz, 1H), 7.65 (s, 1H), 7.51-7.26 (m, 3H), 7.16 (s, 2H), 5.67 (s, 2H), 5.19 (s, 1H), 5.02 (s, 1H), 4.72 (s, 1H), 4.53 (s, 1H), 4.40 (s, 2H), 4.27 (s, 1H), 2.32 (s, 4H), 2.07 (s, 2H), 1.25 (s, 7H), 0.86 (s, 3H). | 269.2 |
| 87g | 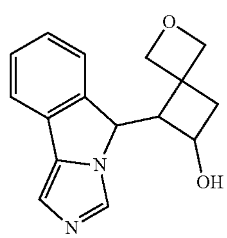 [SMILES: OC1CC2(COC2)C1C1c2ccccc2-c2cncn21] | (500 MHz, DMSO-$d_6$) δ 8.11 (s, 1H), 7.66-7.61 (m, 2H), 7.40 (s, 1H), 7.26 (d, J = 1.2 Hz, 1H), 7.20 (s, 1H), 5.62 (d, J = 8.8 Hz, 1H), 5.30 (d, J = 7.5 Hz, 1H), 4.66 (d, J = 7.1 Hz, 1H), 4.48 (dd, J = 12.2, 6.9 Hz, 2H), 4.21 (dd, J = 15.3, 7.3 Hz, 2H), 2.56 (dd, J = 11.3, 7.7 Hz, 1H), 2.30 (t, J = 8.3 Hz, 1H), 1.91 (dd, J = 11.3, 8.4 Hz, 1H). | 269.2 |
| 87h | 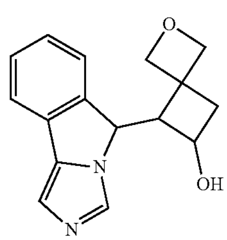 [SMILES: OC1CC2(COC2)C1C1c2ccccc2-c2cncn21] | (500 MHz, DMSO-$d_6$) δ 8.12 (s, 1H), 7.67-7.60 (m, 2H), 7.40 (tt, J = 7.7, 0.8 Hz, 1H), 7.26 (td, J = 7.6, 1.1 Hz, 1H), 7.20 (s, 1H), 5.62 (d, J = 8.7 Hz, 1H), 5.30 (d, J = 7.6 Hz, 1H), 4.66 (d, J = 7.0 Hz, 1H), 4.48 (dd, J = 12.4, 6.9 Hz, 2H), 4.26-4.17 (m, 2H), 2.56 (dd, J = 11.3, 7.6 Hz, 1H), 2.30 (t, J = 8.4 Hz, 1H), 1.91 (dd, J = 11.3, 8.4 Hz, 1H). | 269.2 |
| 88a | 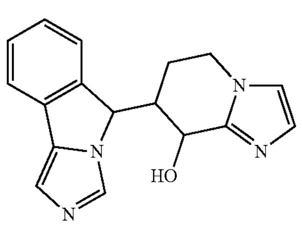 [SMILES: OC1c2nccn2CCC1C1c2ccccc2-c2cncn21] | $^1$H NMR (500 MHz, DMSO-$d_6$) δ 7.93 (s, 1H), 7.64 (d, J = 7.6 Hz, 1H), 7.52 (d, J = 7.7 Hz, 1H), 7.40 (t, J = 7.5 Hz, 1H), 7.25 (ttd, J = 7.6, 1.1 Hz, 1H), 7.17 (s, 1H), 6.96 (d, J = 1.0 Hz, 1H), 6.90 (d, J = 1.0 Hz, 1H), 6.11 (d, J = 6.1 Hz, 1H), 5.75 (d, J = 3.3 Hz, 1H), 4.90 (dd, J = 10.1, 6.1 Hz, 1H), 3.85-3.62 (m, 2H), 2.83-2.68 (m, 1H), 1.11-1.07 (m, 1H), 1.04-0.99 (m, 1H). | 293.2 |

TABLE 2-continued

| Ex. # | Structure | $^1$H NMR | MS (M + H)$^+$ |
|---|---|---|---|
| 88b | 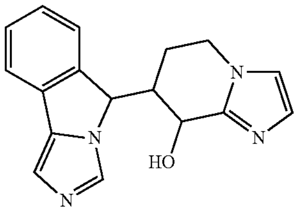 [SMILES: OC1c2nccn2CCC1C1c2ccccc2-c2cncn21] | $^1$H NMR (500 MHz, DMSO-$d_6$) δ 7.96 (s, 1H), 7.67-7.63 (m, 1H), 7.60 (d, J = 7.5 Hz, 1H), 7.40 (t, J = 7.5 Hz, 1H), 7.29 (td, J = 7.6, 1.1 Hz, 1H), 7.13 (s, 1H), 7.01 (d, J = 1.1 Hz, 1H), 6.93 (d, J = 1.1 Hz, 1H), 6.22 (d, J = 4.9 Hz, 1H), 5.51 (d, J = 2.2 Hz, 1H), 5.18-4.84 (m, 1H), 4.08-3.87 (m, 1H), 3.64 (td, J = 12.5, 4.8 Hz, 1H), 2.62 (dd, J = 12.6, 2.6 Hz, 1H), 1.81 (qd, J = 12.8, 5.9 Hz, 1H), 1.16-1.00 (m, 1H). | 293.2 |
| 88c | 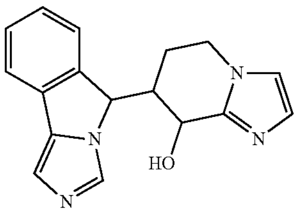 [SMILES: OC1c2nccn2CCC1C1c2ccccc2-c2cncn21] | $^1$H NMR (500 MHz, DMSO-$d_6$) δ 7.90 (s, 1H), 7.64 (d, J = 7.6 Hz, 1H), 7.51 (d, J = 7.6 Hz, 1H), 7.42 (t, J = 7.4 Hz, 1H), 7.33 (td, J = 7.5, 1.0 Hz, 1H), 7.18 (s, 1H), 6.97 (d, J = 0.9 Hz, 1H), 6.92 (d, J = 0.9 Hz, 1H), 6.07 (d, J = 6.6 Hz, 1H), 5.75 (s, 1H), 4.97 (dd, J = 10.1, 6.6 Hz, 1H), 3.89-3.64 (m, 2H), 2.59 (dd, J = 12.4, 4.4 Hz, 1H), 1.08-1.05 (m, 2H). | |
| 88d | 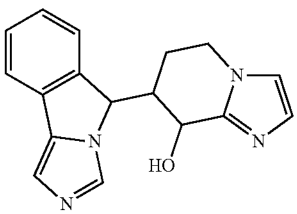 [SMILES: OC1c2nccn2CCC1C1c2ccccc2-c2cncn21] | $^1$H NMR (500 MHz, DMSO-$d_6$) δ 7.93 (s, 1H), 7.65 (d, J = 7.6 Hz, 1H), 7.53 (d, J = 7.7 Hz, 1H), 7.41 (t, J = 7.5 Hz, 1H), 7.25 (t, J = 7.6 Hz, 1H), 7.18 (s, 1H), 6.96 (s, 1H), 6.90 (s, 1H), 6.13 (d, J = 6.1 Hz, 1H), 5.75 (d, J = 3.2 Hz, 1H), 4.90 (dd, J = 10.1, 6.1 Hz, 1H), 3.87-3.64 (m, 2H), 2.85-2.71 (m, 1H), 1.11-1.07 (m, 1H), 1.05-0.99 (m, 1H). | |
| 88e | 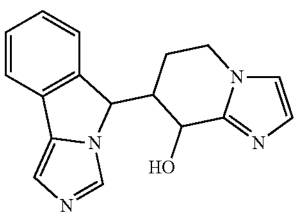 [SMILES: OC1c2nccn2CCC1C1c2ccccc2-c2cncn21] | $^1$H NMR (500 MHz, DMSO-$d_6$) δ 7.90 (s, 1H), 7.64 (d, J = 7.5 Hz, 1H), 7.51 (d, J = 7.5 Hz, 1H), 7.43 (t, J = 7.5 Hz, 1H), 7.33 (t, J = 7.5 Hz, 1H), 7.18 (s, 1H), 6.98 (s, 1H), 6.92 (s, 1H), 6.08 (d, J = 6.6 Hz, 1H), 5.76 (s, 1H), 4.97 (dd, J = 10.0, 6.6 Hz, 1H), 3.82-3.65 (m, 2H), 2.63 (s, 1H), 1.11-1.05 (m, 2H). | |
| 88f | 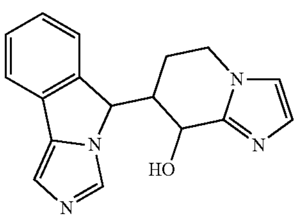 [SMILES: OC1c2nccn2CCC1C1c2ccccc2-c2cncn21] | $^1$H NMR (500 MHz, DMSO-$d_6$) δ 8.00 (s, 1H), 7.76 (d, J = 7.7 Hz, 1H), 7.63 (d, J = 7.5 Hz, 1H), 7.40 (t, J = 7.5 Hz, 1H), 7.26 (td, J = 7.6, 1.1 Hz, 1H), 7.15 (s, 1H), 7.03 (d, J = 1.0 Hz, 1H), 6.92 (d, J = 1.1 Hz, 1H), 6.01 (d, J = 5.1 Hz, 1H), 5.47 (d, J = 6.0 Hz, 1H), 4.95-4.85 (m, 1H), 4.08 (dd, J = 12.8, 4.6 Hz, 1H), 3.74 (td, J = 12.4, 4.8 Hz, 1H), 2.34 (dd, J = 6.1, 3.1 Hz, 1H), 2.21 (qd, J = 12.8, 5.9 Hz, 1H), 1.81 (d, J = 12.6 Hz, 1H). | |
| 88g | 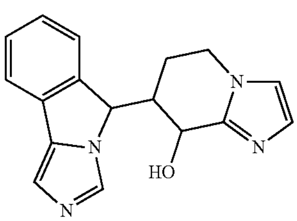 [SMILES: OC1c2nccn2CCC1C1c2ccccc2-c2cncn21] | $^1$H NMR (500 MHz, DMSO-$d_6$) δ 7.96 (s, 1H), 7.73-7.63 (m, 1H), 7.60 (d, J = 7.5 Hz, 1H), 7.40 (t, J = 7.5 Hz, 1H), 7.29 (td, J = 7.6, 1.1 Hz, 1H), 7.13 (s, 1H), 7.01 (d, J = 1.1 Hz, 1H), 6.93 (d, J = 1.1 Hz, 1H), 6.22 (d, J = 4.9 Hz, 1H), 5.51 (d, J = 2.2 Hz, 1H), 5.25-4.88 (m, 1H), 4.05-3.87 (m, 1H), 3.64 (td, J = 12.5, 4.8 Hz, 1H), 2.62 (dd, J = 12.6, 2.6 Hz, 1H), 1.81 (qd, J = 12.7, 5.9 Hz, 1H), 1.12 (dd, J = 16.3, 2.1 Hz, 1H). | |
| 88h | 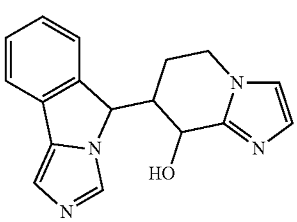 [SMILES: OC1c2nccn2CCC1C1c2ccccc2-c2cncn21] | $^1$H NMR (500 MHz, DMSO-$d_6$) δ 7.99 (s, 1H), 7.75 (d, J = 7.8 Hz, 1H), 7.62 (d, J = 7.5 Hz, 1H), 7.40 (t, J = 7.5 Hz, 1H), 7.25 (td, J = 7.6, 1.1 Hz, 1H), 7.14 (s, 1H), 7.02 (d, J = 1.1 Hz, 1H), 6.91 (d, J = 1.1 Hz, 1H), 6.01 (d, J = 5.1 Hz, 1H), 5.46 (d, J = 6.0 Hz, 1H), 5.08-4.70 (m, 1H), 4.07 (dd, J = 12.8, 4.4 Hz, 1H), 3.73 (ttd, J = 12.5, 4.8 Hz, 1H), 2.33 (dd, J = 6.1, 3.1 Hz, 1H), 2.20 (qd, J = 12.8, 5.9 Hz, 1H), 1.80 (d, J = 13.2 Hz, 1H). | |

TABLE 2-continued

| Ex. # | Structure | $^1$H NMR | MS (M + H)$^+$ |
|---|---|---|---|
| 89a | 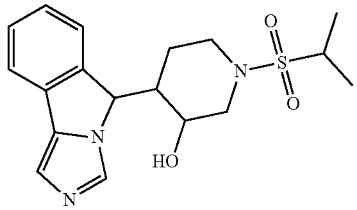 [SMILES: CC(C)S(=O)(=O)N1CCC(C2c3ccccc3-c3cncn32)C(O)C1] | $^1$H NMR (300 MHz, $CD_3OD$) δ 7.91 (s, 1H), 7.65 (d, J = 7.8 Hz, 1H), 7.55 (d, J = 7.8 Hz, 1H), 7.45-7.32 (m, 2H), 7.17 (s, 1H), 5.83 (d, J = 3.6 Hz, 1H), 4.01-3.85 (m, 2H), 3.58-3.52 (m, 1H), 3.27-3.22 (m, 1H), 2.82-2.70 (m, 2H), 2.42-2.28 (m, 1H), 1.27 (d, J = 2.1 Hz, 6H), 0.82-0.58 (m, 2H). | 362.2 |
| 89b | 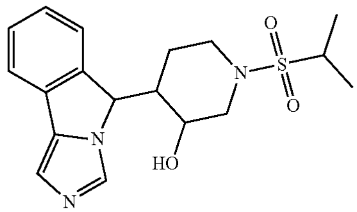 [SMILES: CC(C)S(=O)(=O)N1CCC(C2c3ccccc3-c3cncn32)C(O)C1] | same as 089a. | 362.2 |
| 90a | 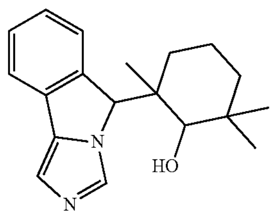 [SMILES: CC1(C)CCCC(C)(C2c3ccccc3-c3cncn32)C1O] | Same as 90b | 297.5 |
| 90b | 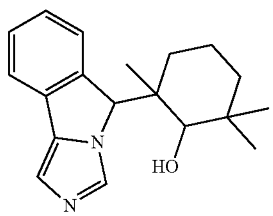 [SMILES: CC1(C)CCCC(C)(C2c3ccccc3-c3cncn32)C1O] | 1H NMR (500 MHz, DMSO-d6) δ 7.92 (s, 1H), 7.63-7.52 (m, 2H), 7.36 (ddd, J = 7.6, 7.0, 0.9 Hz, 1H), 7.21 (td, J = 7.6, 1.3 Hz, 1H), 7.12 (s, 1H), 5.30 (s, 1H), 5.03 (d, J = 6.2 Hz, 1H), 3.36 (d, J = 6.1 Hz, 1H), 1.31 (s, 5H), 1.08 (dt, J = 13.8, 3.5 Hz, 1H), 0.97 (d, J = 7.2 Hz, 6H), 0.82 (td, J = 13.8, 3.7 Hz, 1H), 0.59 (dd, J = 13.2, 2.7 Hz, 1H), 0.24 (td, J = 13.3, 4.0 Hz, 1H). | 297.5 |
| 90c | 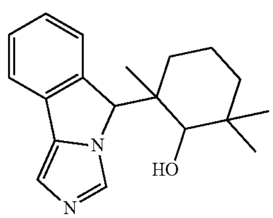 [SMILES: CC1(C)CCCC(C)(C2c3ccccc3-c3cncn32)C1O] | 1H NMR (500 MHz, DMSO-d6) δ 7.94 (s, 1H), 7.66 (d, J = 7.8 Hz, 1H), 7.57 (d, J = 7.4 Hz, 1H), 7.38 (t, J = 7.6 Hz, 1H), 7.25 (td, J = 7.6, 1.2 Hz, 1H), 7.12 (s, 1H), 5.31 (s, 1H), 4.90 (d, J = 6.1 Hz, 1H), 3.41 (d, J = 6.0 Hz, 1H), 1.28 (s, 6H), 1.14-1.07 (m, 1H), 0.93 (d, J = 18.0 Hz, 6H), 0.78 (td, J = 13.5, 3.8 Hz, 1H), 0.53 (dd, J = 13.0, 2.7 Hz, 1H), 0.39 (td, J = 13.3, 4.0 Hz, 1H). | 297.5 |
| 90d | 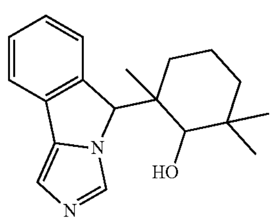 [SMILES: CC1(C)CCCC(C)(C2c3ccccc3-c3cncn32)C1O] | Same as 90c | 297.5 |
| 90e | 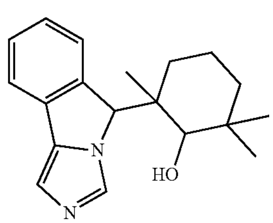 [SMILES: CC1(C)CCCC(C)(C2c3ccccc3-c3cncn32)C1O] | na | 297.5 |

TABLE 2-continued
| Ex. # | Structure | $^{1}H$ NMR | MS $(M + H)^+$ |
|---|---|---|---|
| 90f | 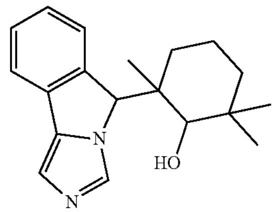 [SMILES: CC1(C)CCCC(C)(C2c3ccccc3-c3cncn32)C1O] | na | 297.5 |
| 91a | 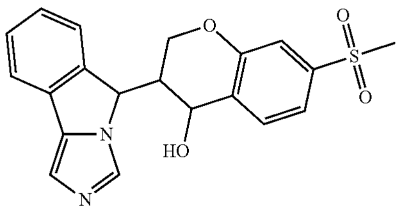 [SMILES: CS(=O)(=O)c1ccc2c(c1)OCC(C1c3ccccc3-c3cncn31)C2O] | $^{1}H$ NMR (400 MHz, $CDCl_3$) δ 7.97 (s, 1H), 7.70 (d, J = 8.1 Hz, 1H), 7.62 (d, J = 7.6 Hz, 1H), 7.59-7.42 (m, 3H), 7.36-7.27 (m, 2H), 7.18 (s, 1H), 5.60 (d, J = 4.2 Hz, 1H), 5.03 (d, J = 8.0 Hz, 1H), 4.01-3.89 (m, 2H), 3.02 (s, 3H), 2.83-2.75 (m, 1H). | 383.0 |
| 91b | 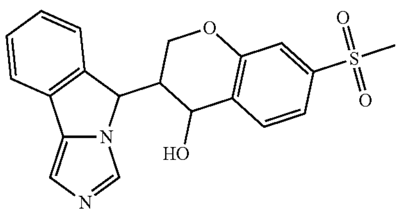 [SMILES: CS(=O)(=O)c1ccc2c(c1)OCC(C1c3ccccc3-c3cncn31)C2O] | The same as 091a. | 383.0 |
| 91c | 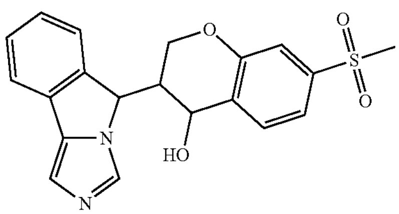 [SMILES: CS(=O)(=O)c1ccc2c(c1)OCC(C1c3ccccc3-c3cncn31)C2O] | $^{1}H$ NMR (400 MHz, $CDCl_3$) δ 8.31 (s, 1H), 7.82 (d, J = 8.1 Hz, 1H), 7.61 (d, J = 7.4 Hz, 1H), 7.59-7.43 (m, 3H), 7.37-7.24 (m, 3H), 5.87 (d, J = 3.0 Hz, 1H), 5.19 (d, J = 9.9 Hz, 1H), 3.82-3.77 (m, 1H), 3.55 (t, J = 11.0 Hz, 1H), 3.02 (s, 3H), 2.85-2.76 (m, 1H). | 383.0 |
| 91d | 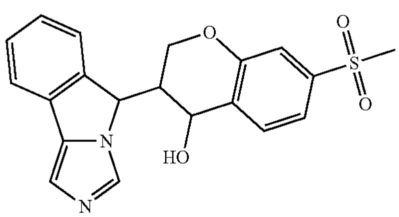 [SMILES: CS(=O)(=O)c1ccc2c(c1)OCC(C1c3ccccc3-c3cncn31)C2O] | The same as 091c. | 383.0 |
| 91e | 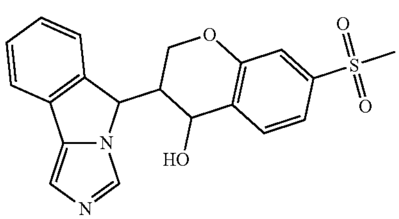 [SMILES: CS(=O)(=O)c1ccc2c(c1)OCC(C1c3ccccc3-c3cncn31)C2O] | $^{1}H$ NMR (400 MHz, $CDCl_3$) δ 8.02 (s, 1H), 7.68-7.57 (m, 3H), 7.46-7.38 (m, 2H), 7.28-7.21 (m, 2H), 7.16 (s, 1H), 6.13 (d, J = 5.5 Hz, 1H), 5.53 (d, J = 6.4 Hz, 1H), 4.84 (dd, J = 5.4, 3.6 Hz, 1H), 4.38-4.26 (m, 2H), 3.19 (s, 3H), 2.54 (dd, J = 7.0, 3.5 Hz, 1H). | 383.0 |
| 91f | 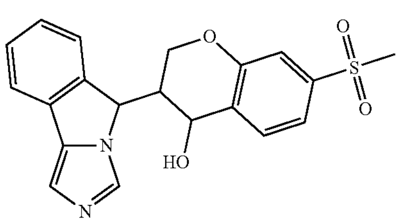 [SMILES: CS(=O)(=O)c1ccc2c(c1)OCC(C1c3ccccc3-c3cncn31)C2O] | The same as 091e. | 383.0 |

TABLE 2-continued

| Ex. # | Structure | $^{1}$H NMR | MS $(M + H)^+$ |
|---|---|---|---|
| 91g | 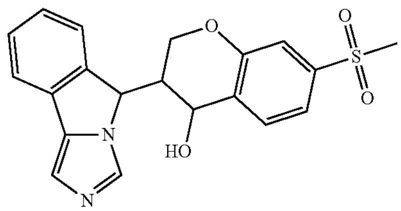 [SMILES: CS(=O)(=O)c1ccc2c(c1)OCC(C1c3ccccc3-c3cncn31)C2O] | $^{1}$H NMR (400 MHz, $CDCl_3$) δ 7.92 (s, 1H), 7.67 (d, J = 8.0 Hz, 1H), 7.55-7.50 (m, 2H), 7.44-7.37 (m, 3H), 7.33-7.28 (m, 1H), 6.91 (s, 1H), 5.58 (s, 1H), 5.17 (d, J = 3.0 Hz, 1H), 3.76 (t, J = 11.2 Hz, 1H), 3.60 (dd, J = 10.9, 3.4 Hz, 1H), 3.04 (s, 3H), 2.73-2.68 (m, 1H). | 383.0 |
| 91h | 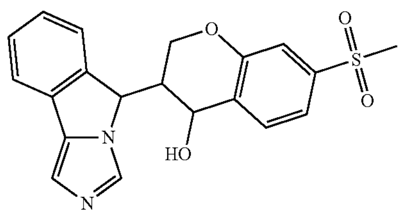 [SMILES: CS(=O)(=O)c1ccc2c(c1)OCC(C1c3ccccc3-c3cncn31)C2O] | The same as 091g. | 383.0 |
| 92a | 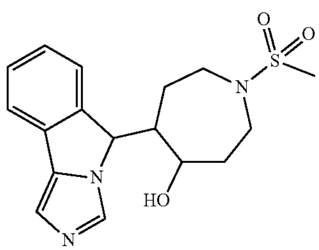 [SMILES: CS(=O)(=O)N1CCC(O)C(C2c3ccccc3-c3cncn32)CC1] | $^{1}$H NMR (400 MHz, DMSO-d6) δ 7.81 (s, 1H), 7.61 (d, J = 7.4 Hz, 1H), 7.46 (d, J = 7.5 Hz, 1H), 7.40 (t, J = 7.5 Hz, 1H), 7.31 (td, J = 7.5, 1.2 Hz, 1H), 7.16 (s, 1H), 5.77-5.74 (m, 1H), 5.45 (d, J = 5.8 Hz, 1H), 3.86 (tdd, J = 9.9, 5.8, 3.9 Hz, 1H), 3.42-3.36 (m, 1H), 3.12-3.02 (m, 2H), 2.87 (ddd, J = 12.9, 10.5, 4.6 Hz, 1H), 2.77 (s, 3H), 2.34-2.28 (m, 1H), 2.21-2.13 (m, 1H), 1.85-1.75 (m, 1H), 0.78-0.65 (m, 2H). | 190 |
| 92b | 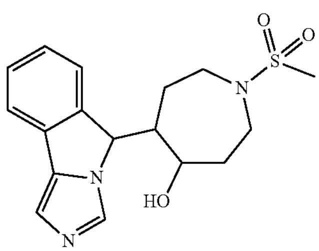 [SMILES: CS(=O)(=O)N1CCC(O)C(C2c3ccccc3-c3cncn32)CC1] | $^{1}$H NMR (400 MHz, DMSO-d6) δ 7.81 (s, 1H), 7.61 (d, J = 7.5 Hz, 1H), 7.46 (dd, J = 7.6, 1.1 Hz, 1H), 7.40 (t, J = 7.4 Hz, 1H), 7.33-7.29 (m, 1H), 7.16 (s, 1H), 5.76-5.74 (m, 1H), 5.45 (d, J = 5.8 Hz, 1H), 3.86 (dt, J = 9.9, 5.9 Hz, 1H), 3.41-3.36 (m, 1H), 3.10-3.02 (m, 2H), 2.91-2.84 (m, 1H), 2.78 (s, 3H), 2.36-2.29 (m, 1H), 2.18 (ddd, J = 11.1, 5.7, 3.2 Hz, 1H), 1.85-1.76 (m, 1H), 0.77-0.67 (m, 2H). | 191 |
| 92c | 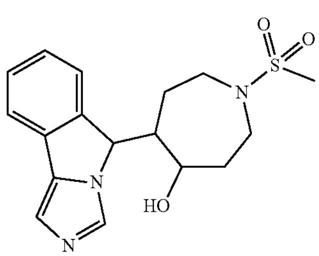 [SMILES: CS(=O)(=O)N1CCC(O)C(C2c3ccccc3-c3cncn32)CC1] | $^{1}$H NMR (400 MHz, DMSO-d6) δ 7.91 (s, 1H), 7.62 (d, J = 7.6 Hz, 1H), 7.55 (d, J = 7.5 Hz, 1H), 7.40 (t, J = 7.5 Hz, 1H), 7.28 (td, J = 7.6, 1.2 Hz, 1H), 7.15 (s, 1H), 5.76 (d, J = 3.6 Hz, 1H), 5.40 (d, J = 5.2 Hz, 1H), 3.83 (dt, J = 9.9, 4.9 Hz, 1H), 3.40-3.34 (m, 1H), 3.11-3.02 (m, 2H), 2.92-2.84 (m, 1H), 2.77 (s, 3H), 2.17-2.11 (m, 1H), 1.82-1.73 (m, 1H), 0.77-0.68 (m, 1H), 0.62-0.56 (m, 1H). | 192 |
| 92d | 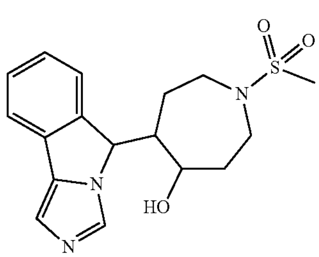 [SMILES: CS(=O)(=O)N1CCC(O)C(C2c3ccccc3-c3cncn32)CC1] | $^{1}$H NMR (400 MHz, DMSO-d6) δ 7.91 (s, 1H), 7.62 (d, J = 7.5 Hz, 1H), 7.56-7.53 (m, 1H), 7.40 (t, J = 7.5 Hz, 1H), 7.28 (td, J = 7.6, 1.2 Hz, 1H), 7.15 (s, 1H), 5.76 (d, J = 3.8 Hz, 1H), 5.40 (d, J = 5.3 Hz, 1H), 3.83 (dt, J = 9.9, 5.1 Hz, 1H), 3.39-3.34 (m, 1H), 3.11-3.02 (m, 2H), 2.92-2.85 (m, 1H), 2.77 (s, 3H), 2.14 (ddt, J = 12.1, 6.3, 3.3 Hz, 1H), 1.82-1.74 (m, 1H), 0.76-0.67 (m, 1H), 0.62-0.55 (m, 1H). | 193 |

TABLE 2-continued

| Ex. # | Structure | $^1H$ NMR | MS $(M + H)^+$ |
|---|---|---|---|
| 93a | 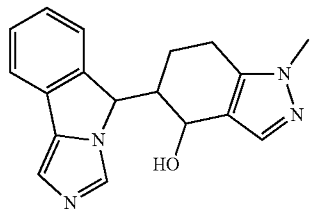 [SMILES: Cn1ncc2c1CCC(C1c3ccccc3-c3cncn31)C2O] | $^1H$ NMR (500 MHz, DMSO-$d_6$) δ 7.92 (s, 1H), 7.63 (d, J = 7.5 Hz, 1H), 7.45 (d, J = 7.6 Hz, 1H), 7.43-7.29 (m, 3H), 7.17 (s, 1H), 5.76 (s, 1H), 5.62 (d, J = 7.1 Hz, 1H), 4.92 (d, J = 8.0 Hz, 1H), 3.58 (s, 3H), 2.44 (dd, J = 16.2, 5.4 Hz, 1H), 2.36-2.25 (m, 1H), 2.20 (td, J = 11.9, 2.5 Hz, 1H), 0.96-0.79 (m, 2H). | 307 |
| 93b | 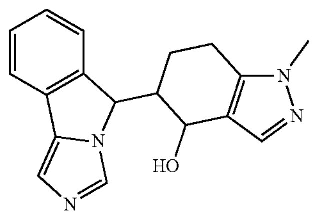 [SMILES: Cn1ncc2c1CCC(C1c3ccccc3-c3cncn31)C2O] | $^1H$ NMR (500 MHz, DMSO-$d_6$) δ 7.95 (s, 1H), 7.77 (dt, J = 7.8, 1.0 Hz, 1H), 7.60 (dt, J = 7.5, 0.9 Hz, 1H), 7.38 (tt, J = 7.6, 0.9 Hz, 1H), 7.32 (s, 1H), 7.23 (td, J = 7.6, 1.2 Hz, 1H), 7.12 (s, 1H), 5.42 (d, J = 5.5 Hz, 1H), 5.19 (d, J = 5.8 Hz, 1H), 4.82 (s, 1H), 3.62 (s, 3H), 2.69 (ddd, J = 16.3, 5.7, 1.7 Hz, 1H), 2.43-2.32 (m, 1H), 2.08-2.02 (m, 1H), 1.90 (qd, J = 12.5, 5.6 Hz, 1H), 1.65 (dd, J = 12.4, 5.8 Hz, 1H). | 307 |
| 93c | 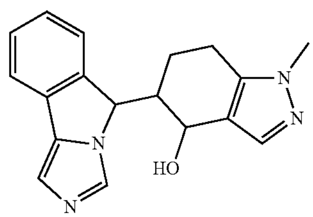 | $^1H$ NMR (500 MHz, DMSO-$d_6$) δ 7.97 (s, 1H), 7.62-7.56 (m, 2H), 7.38 (d, J = 4.9 Hz, 2H), 7.28 (td, J = 7.5, 1.2 Hz, 1H), 7.11 (s, 1H), 5.50-5.42 (m, 2H), 4.99 (dd, J = 5.9, 3.6 Hz, 1H), 3.60 (s, 3H), 2.58 (dd, J = 16.7, 5.0 Hz, 1H), 2.33 (dd, J = 12.6, 3.1 Hz, 1H), 2.26 (ddd, J = 16.8, 12.0, 6.0 Hz, 1H), 1.49 (qd, J = 12.6, 5.7 Hz, 1H), 0.94 (m 1H). | 307 |
| 93d | 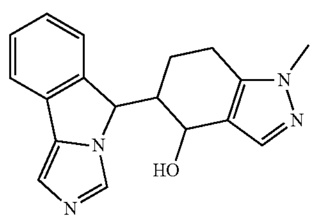 [SMILES: Cn1ncc2c1CCC(C1c3ccccc3-c3cncn31)C2O] | $^1H$ NMR (500 MHz, DMSO-$d_6$) δ 7.95 (s, 1H), 7.77 (dd, J = 7.8, 0.9 Hz, 1H), 7.60 (d, J = 7.5 Hz, 1H), 7.38 (dd, J = 7.9, 7.0 Hz, 1H), 7.32 (s, 1H), 7.23 (td, J = 7.6, 1.2 Hz, 1H), 7.12 (s, 1H), 5.42 (d, J = 5.6 Hz, 1H), 5.18 (d, J = 5.8 Hz, 1H), 4.82 (dd, J = 5.9, 3.3 Hz, 1H), 3.62 (s, 3H), 2.73-2.65 (m, 1H), 2.43-2.32 (m, 1H), 2.09-2.01 (m, 1H), 1.90 (qd, J = 12.5, 5.7 Hz, 1H), 1.65 (dd, J = 12.6, 5.8 Hz, 1H). | 307 |
| 93e | 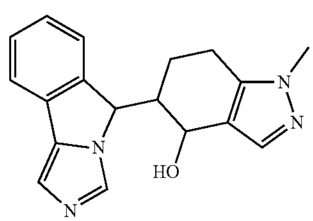 [SMILES: Cn1ncc2c1CCC(C1c3ccccc3-c3cncn31)C2O] | $^1H$ NMR (500 MHz, DMSO-$d_6$) δ 7.92 (s, 1H), 7.63 (dd, J = 7.6, 1.0 Hz, 1H), 7.48-7.34 (m, 3H), 7.32 (td, J = 7.5, 1.1 Hz, 1H), 7.17 (s, 1H), 5.76 (d, J = 1.2 Hz, 1H), 5.61 (d, J = 6.9 Hz, 1H), 4.96-4.89 (m, 1H), 3.58 (s, 3H), 2.44 (dd, J = 16.2, 5.3 Hz, 1H), 2.31 (ddd, J = 16.5, 11.4, 5.8 Hz, 1H), 2.24-2.16 (m, 1H), 0.96-0.76 (m, 2H). | 307 |
| 93f | 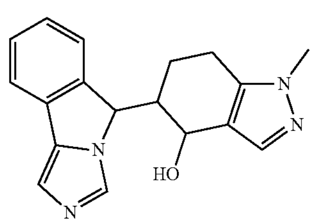 [SMILES: Cn1ncc2c1CCC(C1c3ccccc3-c3cncn31)C2O] | $^1H$ NMR (500 MHz, DMSO-$d_6$) δ 7.97 (d, J = 3.9 Hz, 1H), 7.62-7.56 (m, 2H), 7.42-7.34 (m, 2H), 7.28 (td, J = 7.7, 7.3, 4.8 Hz, 1H), 7.11 (d, J = 3.9 Hz, 1H), 5.50-5.42 (m, 2H), 4.98 (dd, J = 5.9, 3.5 Hz, 1H), 3.60 (d, J = 3.1 Hz, 3H), 2.58 (dd, J = 16.2, 5.3 Hz, 1H), 2.36-2.20 (m, 2H), 1.48 (tt, J = 12.0, 6.0 Hz, 1H), 0.94 (d, J = 13.7 Hz, 1H). | 307 |
| 93g | 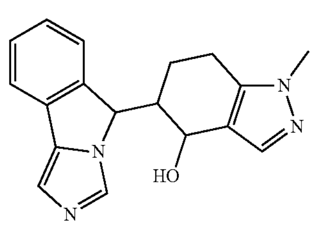 [SMILES: Cn1ncc2c1CCC(C1c3ccccc3-c3cncn31)C2O] | $^1H$ NMR (500 MHz, DMSO-$d_6$) δ 7.88 (s, 1H), 7.64 (dt, J = 7.6, 0.8 Hz, 1H), 7.56 (dd, J = 7.7, 1.0 Hz, 1H), 7.39 (tt, J = 7.6, 0.8 Hz, 1H), 7.36 (s, 1H), 7.25 (td, J = 7.6, 1.2 Hz, 1H), 7.16 (s, 1H), 5.76 (d, J = 3.1 Hz, 1H), 5.64 (d, J = 6.4 Hz, 1H), 4.91 (dd, J = 9.7, 6.4 Hz, 1H), 3.57 (s, 3H), 2.48-2.28 (m, 3H), 0.88 (dq, J = 9.1, 4.9 Hz, 2H). | 307 |

TABLE 2-continued

| Ex. # | Structure | $^1$H NMR | MS $(M + H)^+$ |
|---|---|---|---|
| 94a | 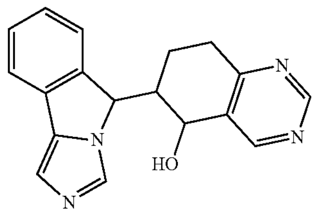 | 1H NMR (500 MHz, DMSO-d6) δ 8.96 (s, 1H), 8.67 (s, 1H), 7.99 (s, 1H), 7.75-7.70 (m, 1H), 7.64-7.60 (m, 1H), 7.43-7.37 (m, 1H), 7.25 (td, J = 7.6, 1.2 Hz, 1H), 7.14 (s, 1H), 5.79 (d, J = 5.9 Hz, 1H), 5.47 (d, J = 6.0 Hz, 1H), 4.93-4.87 (m, 1H), 2.86 (ddd, J = 18.6, 5.7, 1.9 Hz, 1H), 2.75 (ddd, J = 18.5, 12.0, 6.4 Hz, 1H), 2.24 (ddt, J = 12.3, 6.0, 3.0 Hz, 1H), 2.07 (qd, J = 12.7, 5.8 Hz, 1H), 1.86-1.78 (m, 1H). | 305.2 |
| 94b | 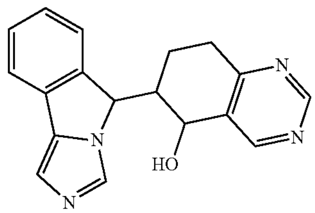 | Same as 094a | 305.2 |
| 94c | 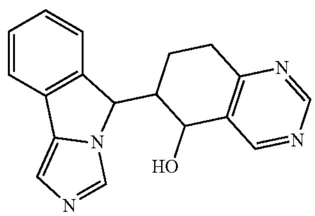 [SMILES: OC1c2cncnc2CCC1C1c2ccccc2-c2cncn21] | 1H NMR (500 MHz, DMSO-d6) δ 8.93 (s, 1H), 8.91 (d, J = 0.8 Hz, 1H), 7.97 (s, 1H), 7.64 (d, J = 7.5 Hz, 1H), 7.50 (dq, J = 7.6, 0.9 Hz, 1H), 7.42 (tt, J = 7.6, 0.9 Hz, 1H), 7.32 (td, J = 7.6, 1.1 Hz, 1H), 7.19 (s, 1H), 6.39 (d, J = 7.4 Hz, 1H), 5.80 (s, 1H), 5.08 (dd, J = 10.6, 7.4 Hz, 1H), 2.70-2.60 (m, 2H), 2.48-2.40 (m, 1H), 1.00-0.84 (m, 2H). | 305.2 |
| 94d | 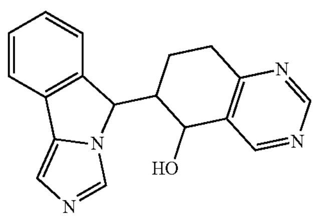 [SMILES: OC1c2cncnc2CCC1C1c2ccccc2-c2cncn21] | 1H NMR (500 MHz, DMSO-d6) δ 8.97 (d, J = 1.2 Hz, 1H), 8.74 (d, J = 1.3 Hz, 1H), 7.97 (s, 1H), 7.61 (dd, J = 8.2, 6.9 Hz, 2H), 7.40 (t, J = 7.5 Hz, 1H), 7.29 (tt, J = 7.4, 1.3 Hz, 1H), 7.13 (s, 1H), 6.11 (dd, J = 5.8, 1.2 Hz, 1H), 5.57 (s, 1H), 5.11 (t, J = 4.7 Hz, 1H), 2.76 (dd, J = 18.6, 5.4 Hz, 1H), 2.63 (ddd, J = 18.7, 12.3, 6.3 Hz, 1H), 2.5-2.50 (m, 1H, merged with DMSO), 1.62 (qd, J = 12.6, 5.7 Hz, 1H), 1.07 (d, J = 9.9 Hz, 1H). | 305.2 |
| 94e | 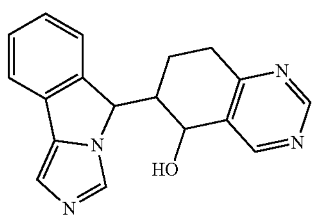 [SMILES: OC1c2cncnc2CCC1C1c2ccccc2-c2cncn21] | 1H NMR (500 MHz, DMSO-d6) δ 8.92 (d, J = 0.7 Hz, 1H), 8.86 (d, J = 0.9 Hz, 1H), 7.91 (s, 1H), 7.64 (ddd, J = 9.1, 7.7, 1.0 Hz, 2H), 7.41 (tt, J = 7.5, 0.8 Hz, 1H), 7.27 (td, J = 7.6, 1.2 Hz, 1H), 7.17 (s, 1H), 6.36 (d, J = 7.2 Hz, 1H), 5.80 (d, J = 3.3 Hz, 1H), 5.01 (dd, J = 10.7, 7.2 Hz, 1H), 2.78-2.57 (m, 3H), 1.01-0.89 (m, 2H). | 305.2 |
| 94f | 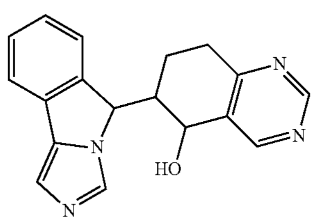 | Same as 094c | 305.2 |
| 94g | 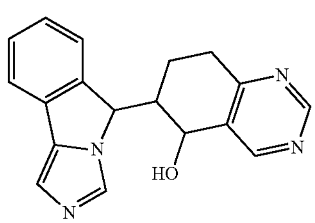 [SMILES: OC1c2cncnc2CCC1C1c2ccccc2-c2cncn21] | Same as 094e | 305.2 |

TABLE 2-continued

| Ex. # | Structure | $^1$H NMR | MS (M + H)$^+$ |
|---|---|---|---|
| 94h | 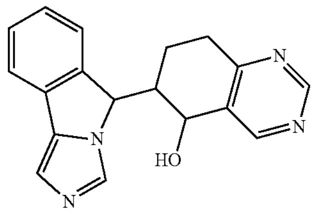 [SMILES: OC1c2cncnc2CCC1C1c2ccccc2-c2cncn21] | Same as 094d | 305.2 |
| 95a | 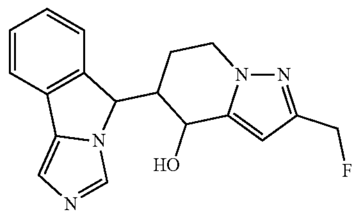 [SMILES: OC1c2cc(CF)nn2CCC1C1c2ccccc2-c2cncn21] | 1H NMR (400 MHz, DMSO-d6) δ 8.01 (s, 1H), 7.65 (dt, J = 7.6, 0.9 Hz, 1H), 7.51 (dq, J = 7.6, 1.0 Hz, 1H), 7.43 (tdd, J = 7.5, 1.1, 0.6 Hz, 1H), 7.33 (td, J = 7.5, 1.2 Hz, 1H), 7.20 (s, 1H), 6.46 (dd, J = 2.0, 0.8 Hz, 1H), 6.32 (d, J = 7.2 Hz, 1H), 5.79-5.76 (m, 1H), 5.28 (d, J = 48.7 Hz, 2H), 5.05 (dd, J = 10.5, 6.9 Hz, 1H), 3.97 (dd, J = 12.8, 5.5 Hz, 1H), 3.86-3.75 (m, 1H), 2.56 (ddd, J = 10.5, 3.2, 1.9 Hz, 1H), 1.16-0.98 (m, 2H). | 325.2 |
| 95b | 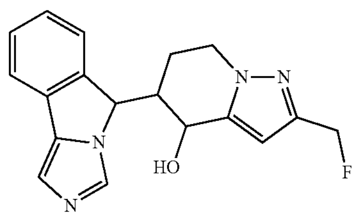 [SMILES: OC1c2cc(CF)nn2CCC1C1c2ccccc2-c2cncn21] | Same as 95a | 325.2 |
| 96a | 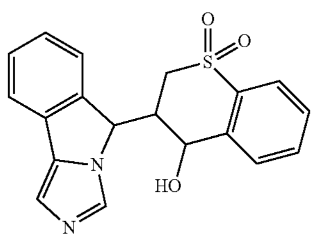 [SMILES: O=S1(=O)CC(C2c3ccccc3-c3cncn32)C(O)c2ccccc21] | $^1$H NMR (400 MHz, DMSO-$d_6$) δ 7.99 (s, 1H), 7.92 (d, J = 7.9 Hz, 1H), 7.80-7.71 (m, 2H), 7.69 (d, J = 7.6 Hz, 1H), 7.58 (t, J = 7.6 Hz, 1H), 7.53 (d, J = 7.7 Hz, 1H), 7.47 (t, J = 7.6 Hz, 1H), 7.40-7.33 (m, 1H), 7.23 (d, J = 2.0 Hz, 1H), 6.82-6.70 (m, 1H), 5.97 (s, 1H), 5.25 (t, J = 9.8 Hz, 1H), 3.26 (t, J = 11.6 Hz, 1H), 2.89 (t, J = 12.9 Hz, 1H), 2.35 (d, J = 13.6 Hz, 1H). | 353.2 |
| 97a | 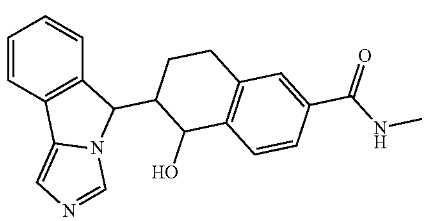 [SMILES: CNC(=O)c1ccc2c(c1)CCC(C1c3ccccc3-c3cncn31)C2O] | (500 MHz, DMSO-$d_6$) δ 8.34 (q, J = 4.5 Hz, 1H), 8.01 (s, 1H), 7.75 (dq, J = 7.7, 0.9 Hz, 1H), 7.65-7.59 (m, 2H), 7.56 (d, J = 1.7 Hz, 1H), 7.42-7.36 (m, 2H), 7.24 (td, J = 7.6, 1.2 Hz, 1H), 7.13 (s, 1H), 5.61 (d, J = 6.0 Hz, 1H), 5.45 (d, J = 6.0 Hz, 1H), 4.82 (dd, J = 6.0, 3.4 Hz, 1H), 2.85 (dd, J = 17.4, 4.7 Hz, 1H), 2.75 (d, J = 4.5 Hz, 3H), 2.71-2.63 (m, 1H), 2.15 (ddd, J = 12.4, 6.1, 3.0 Hz, 1H), 1.95 (qd, J = 12.6, 5.4 hz, 1H), 1.71 (d, J = 13.3 Hz, 1H). | 360.3 |
| 97b | 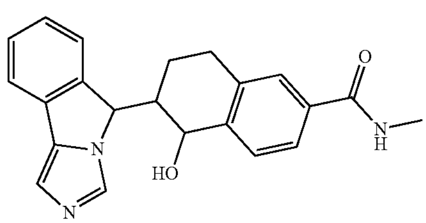 [SMILES: CNC(=O)c1ccc2c(c1)CCC(C1c3ccccc3-c3cncn31)C2O] | (500 MHz, DMSO-$d_6$) δ 8.33 (q, J = 4.3 Hz, 1H), 7.97 (s, 1H), 7.76-7.66 (m, 2H), 7.64 (d, J = 7.6 Hz, 1H), 7.52-7.46 (m, 2H), 7.41 (t, J = 7.4 Hz, 1H), 7.35-7.27 (m, 1H), 7.18 (s, 1H), 6.09 (d, J = 7.7 Hz, 1H), 5.81 (s, 1H), 4.98-4.90 (m, 1H), 2.75 (d, J = 4.5 Hz, 3H), 2.68-2.55 (m, 2H), 2.45-2.35 (m, 1H), 0.92 (d, J = 3.4 Hz, 1H), 0.84 (dt, J = 17.4, 8.3 Hz, 1H). | 360.3 |
| 97c | 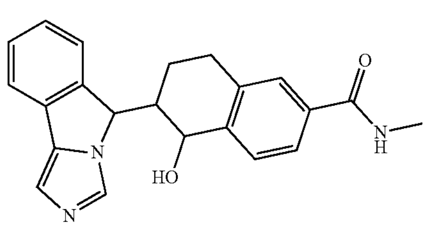 [SMILES: CNC(=O)c1ccc2c(c1)CCC(C1c3ccccc3-c3cncn31)C2O] | (500 MHz, DMSO-$d_6$) δ 8.35 (q, J = 4.5 Hz, 1H), 7.94 (s, 1H), 7.66 (dd, J = 8.0, 1.8 Hz, 1H), 7.63 (dt, J = 7.7, 1.0 Hz, 1H), 7.59 (dt, J = 7.5, 0.9 Hz, 1H), 7.54 (d, J = 1.8 Hz, 1H), 7.46 (d, J = 8.0 Hz, 1H), 7.39 (tt, J = 7.6, 0.9 Hz, 1H), 7.28 (td, J = 7.6, 1.2 Hz, 1H), 7.11 (s, 1H), 5.90 (d, J = 6.1 Hz, 1H), 5.53 (d, J = 2.3 Hz, 1H), 5.01 (dd, J = 6.1, 3.8 Hz, 1H), 2.76 (d, J = 4.5 Hz, 3H), 2.74-2.69 (m, 1H), 2.56 (dt, J = 10.4, 5.2 Hz, 1H), 2.47 (dt, J = 9.7, 3.0 Hz, 1H), 1.49 (qd, J = 12.7, 5.4 Hz, 1H), 0.99 | 360.3 |

TABLE 2-continued

| Ex. # | Structure | $^1$H NMR | MS $(M + H)^+$ |
|---|---|---|---|
| | | (dd, J = 10.1, 3.0 Hz, 1H). | |
| 97d | 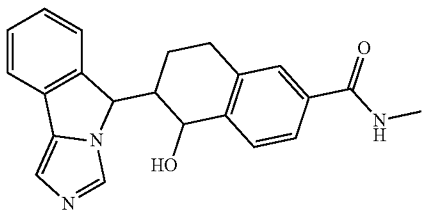 [SMILES: CNC(=O)c1ccc2c(c1)CCC(C1c3ccccc3-c3cncn31)C2O] | (500 MHz, DMSO-$d_6$) δ 8.32 (q, J = 4.3 Hz, 1H), 7.91 (s, 1H), 7.68-7.59 (m, 4H), 7.48 (d, J = 1.6 Hz, 1H), 7.42-7.38 (m, 1H), 7.26 (td, J = 7.6, 1.2 Hz, 1H), 7.17 (s, 1H), 6.10 (d, J = 7.4 Hz, 1H), 5.81 (d, J = 3.3 Hz, 1H), 4.90 (dd, J = 10.7, 7.5 Hz, 1H), 2.75 (d, J = 4.5 Hz, 3H), 2.70-2.53 (m, 3H), 0.87 (h, J = 4.9 Hz, 2H). | 360.3 |
| 97e | 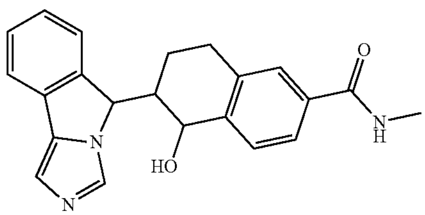 [SMILES: CNC(=O)c1ccc2c(c1)CCC(C1c3ccccc3-c3cncn31)C2O] | (500 MHz, DMSO-$d_6$) δ 8.33 (q, J = 4.5 Hz, 1H), 7.97 (s, 1H), 7.74-7.66 (m, 2H), 7.64 (d, J = 7.5 Hz, 1H), 7.51-7.46 (m, 2H), 7.44-7.39 (m, 1H), 7.31 (td, J = 7.5, 1.1 Hz, 1H), 7.18 (s, 1H), 6.10 (d, J = 7.7 Hz, 1H), 5.81 (d, J = 1.9 Hz, 1H), 4.98-4.91 (m, 1H), 2.75 (d, J = 4.5 Hz, 3H), 2.65-2.55 (m, 2H), 2.40 (t, J = 11.1 Hz, 1H), 0.97-0.89 (m, 1H), 0.83 (dq, J = 17.1, 6.5 Hz, 1H). | 360.3 |
| 97f | 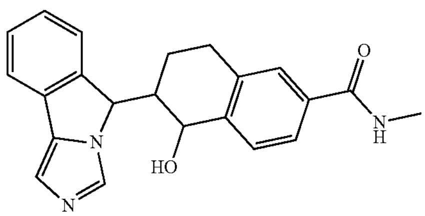 [SMILES: CNC(=O)c1ccc2c(c1)CCC(C1c3ccccc3-c3cncn31)C2O] | (500 MHz, DMSO-$d_6$) δ 8.35 (q, J = 4.5 Hz, 1H), 7.94 (s, 1H), 7.66 (dd, J = 8.0, 1.8 Hz, 1H), 7.63 (dq, J = 7.6, 0.9 Hz, 1H), 7.59 (dt, J = 7.6, 0.9 Hz, 1H), 7.54 (d, J = 1.7 Hz, 1H), 7.46 (d, J = 8.0 Hz, 1H), 7.39 (tt, J = 7.5, 0.9 Hz, 1H), 7.28 (td, J = 7.6, 1.2 Hz, 1H), 7.11 (s, 1H), 5.90 (d, J = 6.1 Hz, 1H), 5.56-5.50 (m, 1H), 5.04-4.98 (m, 1H), 2.76 (d, J = 4.6 Hz, 3H), 2.72 (dd, J = 16.7, 4.2 Hz, 1H), 2.56 (dt, J = 10.5, 5.4 Hz, 1H), 2.47 (dd, J = 12.5, 3.1 Hz, 1H), 1.49 (qd, J = 12.7, 5.4 Hz, 1H), 1.04-0.95 (m, 1H). | 360.3 |
| 97g | 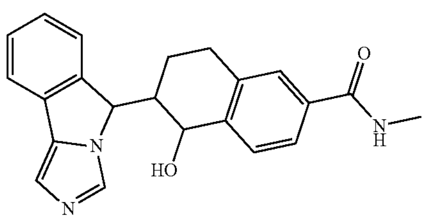 | na | 360.3 |
| 97h | 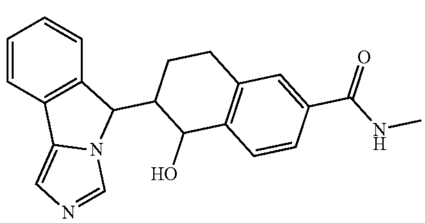 [SMILES: CNC(=O)c1ccc2c(c1)CCC(C1c3ccccc3-c3cncn31)C2O] | (500 MHz, DMSO-$d_6$) δ 8.34 (q, J = 4.4 Hz, 1H), 8.01 (s, 1H), 7.75 (dd, J = 7.7, 1.0 Hz, 1H), 7.65-7.59 (m, 2H), 7.56 (d, J = 1.7 Hz, 1H), 7.42-7.35 (m, 2H), 7.24 (td, J = 7.6, 1.2 Hz, 1H), 7.13 (s, 1H), 5.61 (d, J = 6.0 Hz, 1H), 5.45 (d, J = 5.9 Hz, 1H), 4.82 (dd, J = 6.1, 3.4 Hz, 1H), 2.85 (dd, J = 17.3, 4.7 Hz, 1H), 2.75 (d, J = 4.6 Hz, 3H), 2.72-2.61 (m, 1H), 2.15 (dq, J = 9.4, 3.1 Hz, 1H), 1.95 (qd, J = 12.6, 5.4 Hz, 1H), 1.71 (d, J = 11.3 Hz, 1H). | 360.3 |
| 98a | 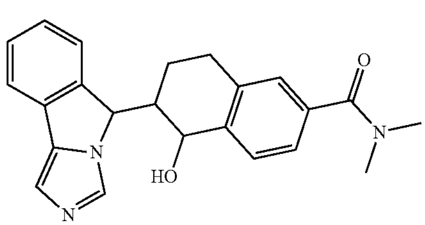 [SMILES: CN(C)C(=O)c1ccc2c(c1)CCC(C1c3ccccc3-c3cncn31)C2O] | (500 MHz, DMSO-$d_6$) δ 7.97 (s, 1H), 7.70 (d, J = 8.0 Hz, 1H), 7.63 (d, J = 7.6 Hz, 1H), 7.48 (dd, J = 7.6, 1.0 Hz, 1H), 7.41 (s, 1H), 7.31 (d, J = 1.2 Hz, 1H), 7.28-7.24 (m, 1H), 7.18 (s, 1H), 7.03 (d, J = 1.7 Hz, 1H), 6.08 (d, J = 7.7 Hz, 1H), 5.81 (s, 1H), 4.98-4.91 (m, 1H), 2.95 (s, 3H), 2.90 (s, 3H), 2.60 (dd, J = 9.4, 5.5 Hz, 2H), 2.40 (t, J = 11.3 Hz, 1H), 0.92 (dd, J = 12.9, 3.8 Hz, 1H), 0.88-0.76 (m, 1H). | 374.3 |

TABLE 2-continued

| Ex. # | Structure | $^1$H NMR | MS $(M + H)^+$ |
|---|---|---|---|
| 98b | 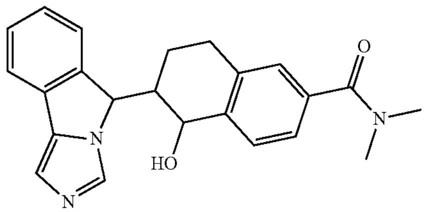 [SMILES: CN(C)C(=O)c1ccc2c(c1)CCC(C1c3ccccc3-c3cncn31)C2O] | (500 MHz, DMSO-$d_6$) δ 7.91 (s, 1H), 7.64 (t, J = 8.6 Hz, 3H), 7.40 (t, J = 7.5 Hz, 1H), 7.25 (ddd, J = 17.9, 7.8, 1.5 Hz, 2H), 7.17 (s, 1H), 7.02 (d, J = 1.7 Hz, 1H), 6.09 (d, J = 7.4 Hz, 1H), 5.80 (d, J = 3.3 Hz, 1H), 4.89 (dd, J = 10.7, 7.4 Hz, 1H), 2.95 (s, 3H), 2.89 (s, 3H), 2.60 (ddt, J = 19.8, 15.9, 2.9 Hz, 3H), 0.91-0.84 (m, 2H). | 374.3 |
| 98c | 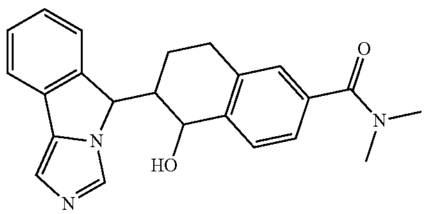 [SMILES: CN(C)C(=O)c1ccc2c(c1)CCC(C1c3ccccc3-c3cncn31)C2O] | (500 MHz, DMSO-$d_6$) δ 7.95 (s, 1H), 7.62 (dt, J = 7.7, 1.0 Hz, 1H), 7.59 (dt, J = 7.5, 0.9 Hz, 1H), 7.45 (d, J = 7.9 Hz, 1H), 7.39 (tt, J = 7.5, 0.9 Hz, 1H), 7.28 (td, J = 7.6, 1.2 Hz, 1H), 7.24 (dd, J = 7.8, 1.7 Hz, 1H), 7.11 (s, 1H), 7.08 (d, J = 1.6 Hz, 1H), 5.90 (d, J = 6.0 Hz, 1H), 5.56-5.50 (m, 1H), 5.01 (dd, J = 6.1, 3.7 Hz, 1H), 2.96 (s, 3H), 2.91 (s, 3H), 2.71 (dd, J = 17.3, 4.4 Hz, 1H), 2.57-2.51 (m, 1H), 2.47 (dd, J = 5.7, 2.7 Hz, 1H), 1.49 (qd, J = 12.7, 5.4 Hz, 1H), 0.97 (dd, J = 10.0, 3.0 Hz, 1H). | 374.3 |
| 98d | 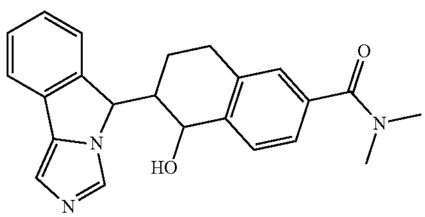 [SMILES: CN(C)C(=O)c1ccc2c(c1)CCC(C1c3ccccc3-c3cncn31)C2O] | (500 MHz, DMSO-$d_6$) δ 7.95 (s, 1H), 7.62 (dt, J = 7.7, 0.9 Hz, 1H), 7.61-7.57 (m, 1H), 7.45 (d, J = 7.9 Hz, 1H), 7.39 (tt, J = 7.5, 0.8 Hz, 1H), 7.28 (td, J = 7.5, 1.2 Hz, 1H), 7.24 (dd, J = 7.9, 1.7 Hz, 1H), 7.11 (s, 1H), 7.08 (d, J = 1.6 Hz, 1H), 5.90 (d, J = 6.0 Hz, 1H), 5.56-5.50 (m, 1H), 5.01 (dd, J = 6.0, 3.7 Hz, 1H), 2.96 (s, 3H), 2.91 (s, 3H), 2.71 (dd, J = 17.3, 4.6 Hz, 1H), 2.58-2.52 (m, 1H), 2.47 (dd, J = 6.4, 3.3 Hz, 1H), 1.49 (qd, J = 12.7, 5.4 Hz, 1H), 0.97 (dd, J = 10.1, 3.0 Hz, 1H). | 374.3 |
| 98e | 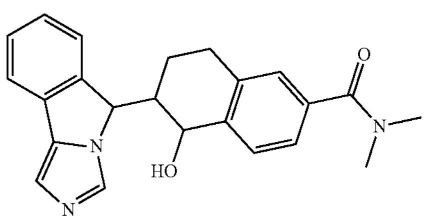 [SMILES: CN(C)C(=O)c1ccc2c(c1)CCC(C1c3ccccc3-c3cncn31)C2O] | (500 MHz, DMSO-$d_6$) δ 8.01 (s, 1H), 7.75 (dq, J = 7.7, 0.9 Hz, 1H), 7.61 (d, J = 7.5 Hz, 1H), 7.38 (dd, J = 7.8, 6.4 Hz, 2H), 7.24 (td, J = 7.6, 1.2 Hz, 1H), 7.20 (dd, J = 7.9, 1.7 Hz, 1H), 7.13 (s, 1H), 7.11 (d, J = 1.6 Hz, 1H), 5.60 (d, J = 6.0 Hz, 1H), 5.46 (d, J = 5.8 Hz, 1H), 4.82 (dd, J = 6.0, 3.4 Hz, 1H), 2.95 (s, 3H), 2.90 (s, 3H), 2.83 (dd, J = 17.4, 4.6 Hz, 1H), 2.64 (ddd, J = 16.2, 12.3, 6.0 Hz, 1H), 2.17 (ddd, J = 12.3, 6.0, 3.1 Hz, 1H), 1.94 (qd, J = 12.6, 5.4 Hz, 1H), 1.72-1.64 (m, 1H). | 374.3 |
| 98f | 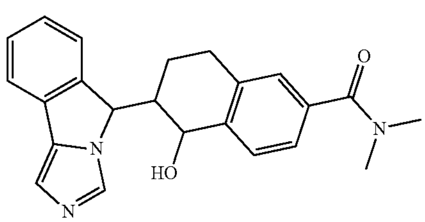 [SMILES: CN(C)C(=O)c1ccc2c(c1)CCC(C1c3ccccc3-c3cncn31)C2O] | (500 MHz, DMSO-$d_6$) δ 8.01 (s, 1H), 7.75 (dd, J = 7.7, 1.0 Hz, 1H), 7.61 (d, J = 7.5 Hz, 1H), 7.38 (dd, J = 7.9, 6.5 Hz, 2H), 7.24 (td, J = 7.6, 1.2 Hz, 1H), 7.20 (dd, J = 7.8, 1.7 Hz, 1H), 7.13 (s, 1H), 7.11 (d, J = 1.7 Hz, 1H), 5.60 (d, J = 5.9 Hz, 1H), 5.46 (d, J = 5.8 Hz, 1H), 4.82 (dd, J = 6.2, 3.4 Hz, 1H), 2.95 (s, 3H), 2.90 (s, 3H), 2.83 (dd, J = 17.4, 4.5 Hz, 1H), 2.69-2.59 (m, 1H), 2.18 (dq, J = 9.3, 3.0 Hz, 1H), 1.94 (qd, J = 12.6, 5.4 Hz, 1H), 1.71-1.65 (m, 1H). | 374.3 |
| 98g | 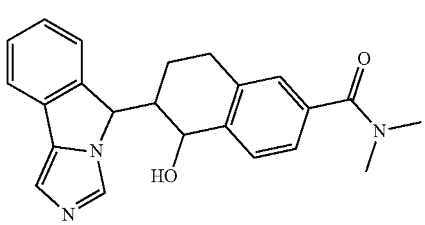 [SMILES: CN(C)C(=O)c1ccc2c(c1)CCC(C1c3ccccc3-c3cncn31)C2O] | (500 MHz, DMSO-$d_6$) δ 7.91 (s, 1H), 7.64 (t, J = 8.6 Hz, 3H), 7.40 (t, J = 7.5 Hz, 1H), 7.29-7.21 (m, 2H), 7.17 (s, 1H), 7.02 (d, J = 1.7 Hz, 1H), 6.08 (d, J = 7.4 Hz, 1H), 5.80 (d, J = 3.2 Hz, 1H), 4.92-4.85 (m, 1H), 2.95 (s, 3H), 2.89 (s, 3H), 2.69-2.53 (m, 3H), 0.92-0.84 (m, 2H). | 374.3 |

TABLE 2-continued

| Ex. # | Structure | $^1$H NMR | MS $(M + H)^+$ |
|---|---|---|---|
| 98h | 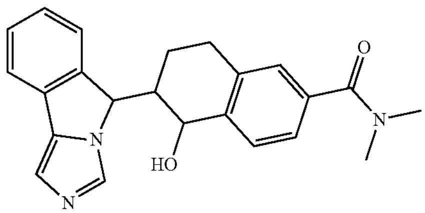 [SMILES: CN(C)C(=O)c1ccc2c(c1)CCC(C1c3ccccc3-c3cncn31)C2O] | (500 MHz, DMSO-$d_6$) δ 7.97 (s, 1H), 7.70 (d, J = 8.0 Hz, 1H), 7.64 (d, J = 7.6 Hz, 1H), 7.49 (d, J = 7.6 Hz, 1H), 7.41 (t, J = 7.5 Hz, 1H), 7.32 (t, J = 7.5 Hz, 1H), 7.25 (dd, J = 8.0, 1.7 Hz, 1H), 7.18 (s, 1H), 7.03 (d, J = 1.7 Hz, 1H), 6.08 (d, J = 7.6 Hz, 1H), 5.81 (s, 1H), 4.98-4.89 (m, 1H), 2.95 (s, 3H), 2.90 (s, 3H), 2.60 (q, J = 6.3 Hz, 2H), 2.46-2.37 (m, 1H), 0.92 (d, J = 13.2 Hz, 1H), 0.88-0.77 (m, 1H). | 374.3 |
| 99a | 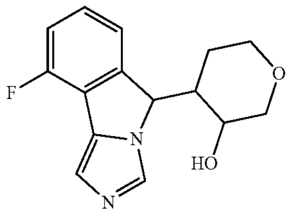 [SMILES: OC1COCCC1C1c2cccc(F)c2-c2cncn21] | $^1$H NMR (500 MHz, DMSO-$d_6$) δ 8.00 (s, 1H), 7.42-7.32 (m, 2H), 7.32-7.26 (m, 1H), 7.11 (s, 1H), 5.78 (d, J = 3.7 Hz, 1H), 5.47 (d, J = 5.5 Hz, 1H), 3.84 (dd, J = 10.5, 4.8 Hz, 1H), 3.73-3.57 (m, 2H), 3.19-3.07 (m, 1H), 2.99 (t, J = 10.2 Hz, 1H), 2.40 (tt, J = 10.9, 4.1 Hz, 1H), 0.65-0.50 (m, 2H). | 275 |
| 99b | 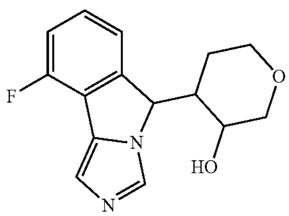 [SMILES: OC1COCCC1C1c2cccc(F)c2-c2cncn21] | $^1$H NMR (500 MHz, DMSO-$d_6$) δ 8.00 (s, 1H), 7.42-7.26 (m, 3H), 7.11 (s, 1H), 5.78 (d, J = 3.7 Hz, 1H), 5.47 (d, J = 5.4 Hz, 1H), 3.84 (dd, J = 10.6, 4.9 Hz, 1H), 3.68 (tt, J = 10.2, 5.1 Hz, 1H), 3.63-3.58 (m, 1H), 3.19-3.07 (m, 1H), 2.99 (t, J = 10.2 Hz, 1H), 2.40 (ddd, J = 14.6, 7.3, 4.0 Hz, 1H), 0.65-0.50 (m, 2H). | 275 |
| 99c | 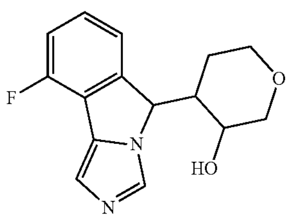 [SMILES: OC1COCCC1C1c2cccc(F)c2-c2cncn21] | $^1$H NMR (500 MHz, DMSO-$d_6$) δ 7.96 (s, 1H), 7.41-7.32 (m, 2H), 7.27 (dq, J = 11.7, 4.8 Hz, 1H), 7.15 (s, 1H), 5.82-5.77 (m, 1H), 5.53 (d, J = 5.9 Hz, 1H), 3.91 (dd, J = 10.6, 4.8 Hz, 1H), 3.74 (tt, J = 10.4, 5.5 Hz, 1H), 3.59 (dd, J = 11.3, 4.5 Hz, 1H), 3.19-3.08 (m, 1H), 3.04 (t, J = 10.2 Hz, 1H), 2.23 (t, J = 11.4 Hz, 1H), 0.72-0.65 (m, 1H), 0.47 (qd, J = 12.5, 4.8 Hz, 1H). | 275 |
| 99d | 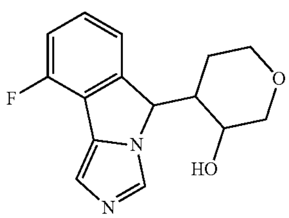 [SMILES: OC1COCCC1C1c2cccc(F)c2-c2cncn21] | $^1$H NMR (500 MHz, DMSO-d6) δ 7.96 (s, 1H), 7.36 (td, J = 3.9, 2.1 Hz, 2H), 7.29-7.24 (m, 1H), 7.14 (s, 1H), 5.80 (d, J = 2.3 Hz, 1H), 5.53 (d, J = 5.9 Hz, 1H), 3.91 (dd, J = 10.6, 4.8 Hz, 1H), 3.74 (tt, J = 10.5, 5.4 Hz, 1H), 3.58 (dd, J = 11.3, 4.6 Hz, 1H), 3.11 (td, J = 11.7, 2.3 Hz, 1H), 3.04 (t, J = 10.3 Hz, 1H), 2.23 (ddd, J = 14.3, 9.3, 3.3 Hz, 1H), 0.69 (d, J = 13.3 Hz, 1H), 0.47 (qd, J = 12.6, 4.8 Hz, 1H). | 275 |
| 100a | 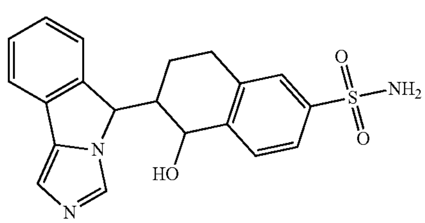 [SMILES: NS(=O)(=O)c1ccc2c(c1)CCC(C1c3ccccc3-c3cncn31)C2O] | $^1$H NMR (500 MHz, DMSO-d6) δ 7.95 (s, 1H), 7.65 (dd, J = 8.1, 1.9 Hz, 1H), 7.62 (dd, J = 7.7, 1.0 Hz, 1H), 7.60 (d, J = 7.6 Hz, 1H), 7.57 (d, J = 8.1 Hz, 1H), 7.52 (d, J = 1.8 Hz, 1H), 7.41-7.37 (m, 1H), 7.30 (dd, J = 7.6, 1.2 Hz, 1H), 7.27 (m, 2H), 7.12 (s, 1H), 6.00 (d, J = 6.1 Hz, 1H), 5.54 (d, J = 2.2 Hz, 1H), 5.03 (dd, J = 6.1, 3.8 Hz, 1H), 2.76 (dd, J = 17.2, 4.6 Hz, 1H), 2.58 (ddd, J = 17.5, 12.5, 5.9 Hz, 1H), 2.47 (dd, J = 6.5, 3.3 Hz, 1H), 1.50 (qd, J = 12.6, 5.4 Hz, 1H), 1.25-0.98 (m, 1H). | 382.2 |
| 100b | 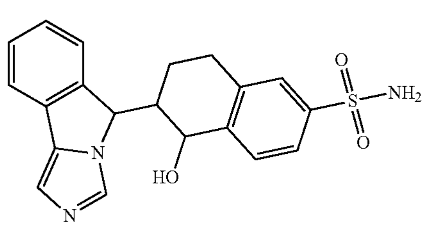 [SMILES: NS(=O)(=O)c1ccc2c(c1)CCC(C1c3ccccc3-c3cncn31)C2O] | $^1$H NMR (500 MHz, DMSO-d6) δ 7.91 (s, 1H), 7.77 (d, J = 8.2 Hz, 1H), 7.68-7.60 (m, 3H), 7.46 (d, J = 1.9 Hz, 1H), 7.41 (t, J = 7.5, 7.5 Hz, 1H), 7.27 (dd, J = 7.6, 1.2 Hz, 1H), 7.25 (s, 2H), 7.17 (s, 1H), 6.21 (d, J = 7.5 Hz, 1H), 5.81 (d, J = 3.3 Hz, 1H), 4.90 (dd, J = 10.7, 7.5 Hz, 1H), 2.70-2.54 (m, 3H), 0.89 (d, J = 4.7 Hz, 2H). | 382.2 |

TABLE 2-continued

| Ex. # | Structure | $^1$H NMR | MS (M + H)$^+$ |
|---|---|---|---|
| 100c | 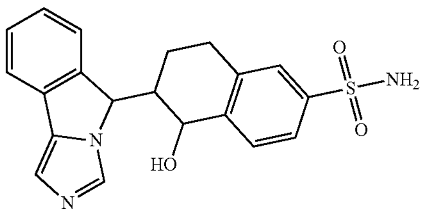 [SMILES: NS(=O)(=O)c1ccc2c(c1)CCC(C1c3ccccc3-c3cncn31)C2O] | $^1$H NMR (500 MHz, DMSO-d6) δ 7.97 (s, 1H), 7.82 (d, J = 8.2 Hz, 1H), 7.70-7.61 (m, 2H), 7.51-7.45 (m, 2H), 7.42 (t, J = 7.5 Hz, 1H), 7.32 (dd, J = 7.6, 1.1 Hz, 1H), 7.25 (s, 2H), 7.18 (s, 1H), 6.21 (d, J = 7.6 Hz, 1H), 5.81 (s, 1H), 4.99-4.88 (m, 1H), 2.69-2.57 (m, 2H), 2.41 (t, J = 11.2 Hz, 1H), 1.00-0.72 (m, 2H). | 382.2 |
| 100d | 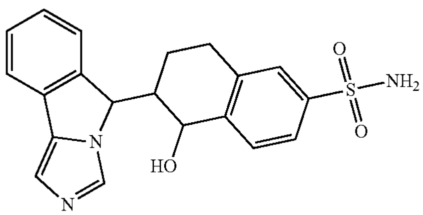 [SMILES: NS(=O)(=O)c1ccc2c(c1)CCC(C1c3ccccc3-c3cncn31)C2O] | $^1$H NMR (500 MHz, DMSO-d6) δ 8.10 (s, 1H), 7.77 (dd, J = 8.3, 3.0 Hz, 1H), 7.71-7.61 (m, 3H), 7.47 (d, J = 3.0 Hz, 1H), 7.43 (td, J = 7.6, 2.8 Hz, 1H), 7.30 (td, J = 7.6, 2.9 Hz, 2H), 7.25 (d, J = 3.0 Hz, 2H), 6.24 (dd, J = 7.5, 3.0 Hz, 1H), 5.85 (d, J = 3.7 Hz, 1H), 4.90 (t, J = 9.0 Hz, 1H), 2.74-2.54 (m, 3H), 0.96-0.85 (m, 2H). | 382.2 |
| 100e | 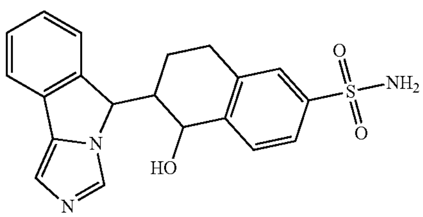 [SMILES: NS(=O)(=O)c1ccc2c(c1)CCC(C1c3ccccc3-c3cncn31)C2O] | $^1$H NMR (500 MHz, DMSO-d6) δ 8.01 (s, 1H), 7.74 (d, J = 7.8 Hz, 1H), 7.64-7.59 (m, 2H), 7.55 (d, J = 1.9 Hz, 1H), 7.50 (d, J = 8.1 Hz, 1H), 7.39 (s, 1H), 7.26 (d, J = 11.2 Hz, 3H), 7.14 (s, 1H), 5.70 (d, J = 6.0 Hz, 1H), 5.46 (d, J = 6.1 Hz, 1H), 4.84 (dd, J = 6.1, 3.3 Hz, 1H), 2.94-2.85 (m, 1H), 2.72 (dd, J = 12.1, 5.9 Hz, 1H), 2.19-2.12 (m, 1H), 1.96 (dd, J = 12.5, 5.4 Hz, 1H), 1.74 (d, J = 12.6 Hz, 1H). | 382.2 |
| 100f | 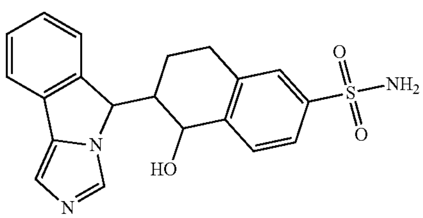 [SMILES: NS(=O)(=O)c1ccc2c(c1)CCC(C1c3ccccc3-c3cncn31)C2O] | $^1$H NMR (500 MHz, DMSO-d6) δ 8.01 (s, 1H), 7.74 (d, J = 7.8 Hz, 1H), 7.64-7.59 (m, 2H), 7.55 (d, J = 1.9 Hz, 1H), 7.50 (d, J = 8.1 Hz, 1H), 7.39 (s, 1H), 7.26 (d, J = 11.2 Hz, 3H), 7.14 (s, 1H), 5.70 (d, J = 6.0 Hz, 1H), 5.46 (d, J = 6.1 Hz, 1H), 4.84 (dd, J = 6.1, 3.3 Hz, 1H), 2.94-2.85 (m, 1H), 2.72 (dd, J = 12.1, 5.9 Hz, 1H), 2.19-2.12 (m, 1H), 1.96 (dd, J = 12.5, 5.4 Hz, 1H), 1.74 (d, J = 12.6 Hz, 1H). | 382.2 |
| 100g | 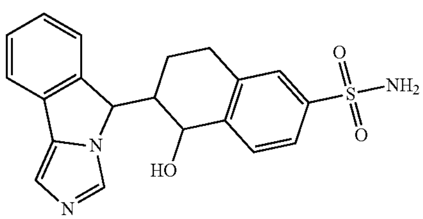 [SMILES: NS(=O)(=O)c1ccc2c(c1)CCC(C1c3ccccc3-c3cncn31)C2O] | $^1$H NMR (500 MHz, DMSO-d6) δ 7.97 (s, 1H), 7.82 (d, J = 8.2 Hz, 1H), 7.70-7.61 (m, 2H), 7.51-7.45 (m, 2H), 7.42 (t, J = 7.5 Hz, 1H), 7.32 (dd, J = 7.6, 1.1 Hz, 1H), 7.25 (s, 2H), 7.18 (s, 1H), 6.21 (d, J = 7.6 Hz, 1H), 5.81 (s, 1H), 4.99-4.88 (m, 1H), 2.69-2.57 (m, 2H), 2.41 (t, J = 11.2 Hz, 1H), 1.00-0.72 (m, 2H). | 382.2 |
| 100h | 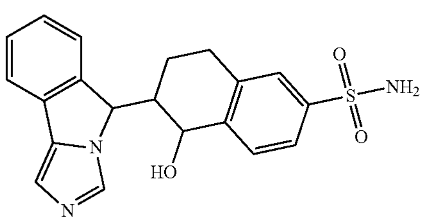 [SMILES: NS(=O)(=O)c1ccc2c(c1)CCC(C1c3ccccc3-c3cncn31)C2O] | $^1$H NMR (500 MHz, DMSO-d6) δ 7.95 (s, 1H), 7.65 (dd, J = 8.1, 1.9 Hz, 1H), 7.62 (dd, J = 7.7, 1.0 Hz, 1H), 7.60 (d, J = 7.6 Hz, 1H), 7.57 (d, J = 8.1 Hz, 1H), 7.52 (d, J = 1.8 Hz, 1H), 7.41-7.37 (m, 1H), 7.30 (dd, J = 7.6, 1.2 Hz, 1H), 7.27 (m, 2H), 7.12 (s, 1H), 6.00 (d, J = 6.1 Hz, 1H), 5.54 (d, J = 2.2 Hz, 1H), 5.03 (dd, J = 6.1, 3.8 Hz, 1H), 2.76 (dd, J = 17.2, 4.6 Hz, 1H), 2.58 (ddd, J = 17.5, 12.5, 5.9 Hz, 1H), 2.47 (dd, J = 6.5, 3.3 Hz, 1H), 1.50 (qd, J = 12.7, 12.6, 5.4 Hz, 1H), 1.25-0.98 (m, 1H). | 382.2 |

TABLE 2-continued

| Ex. # | Structure | $^1$H NMR | MS $(M + H)^+$ |
|---|---|---|---|
| 101b | 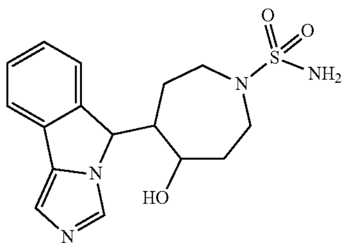 [SMILES: NS(=O)(=O)N1CCC(O)C(C2c3ccccc3-c3cncn32)CC1] | 1H NMR (400 MHz, DMSO-d6) δ 7.89 (s, 1H), 7.62 (d, J = 7.6 Hz, 1H), 7.54 (dd, J = 7.7, 1.1 Hz, 1H), 7.39 (dd, J = 8.0, 6.9 Hz, 1H), 7.30-7.26 (m, 1H), 7.15 (s, 1H), 6.58 (s, 2H), 5.74 (d, J = 3.6 Hz, 1H), 5.35 (d, J = 5.2 Hz, 1H), 3.82 (dt, J = 9.9, 4.9 Hz, 1H), 3.06-3.00 (m, 1H), 2.97-2.90 (m, 1H), 2.84-2.77 (m, 1H), 2.47 (dd, J = 4.0, 2.4 Hz, 1H), 2.12-2.07 (m, 1H), 1.84-1.75 (m, 1H), 0.77-0.69 (m, 1H), 0.60-0.54 (m, 1H). | 249 |
| 101c | 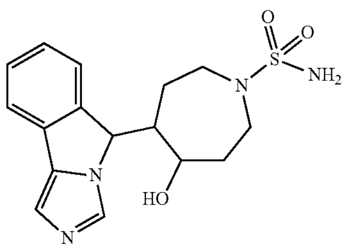 [SMILES: NS(=O)(=O)N1CCC(O)C(C2c3ccccc3-c3cncn32)CC1] | 1H NMR (400 MHz, DMSO-d6) δ 7.89 (s, 1H), 7.62 (d, J = 7.5 Hz, 1H), 7.54 (d, J = 7.6 Hz, 1H), 7.39 (t, J = 7.3 Hz, 1H), 7.28 (td, J = 7.6, 1.2 Hz, 1H), 7.15 (s, 1H), 6.58 (s, 2H), 5.74 (d, J = 3.6 Hz, 1H), 5.35 (d, J = 5.2 Hz, 1H), 3.82 (dt, J = 10.0, 5.1 Hz, 1H), 3.03 (dt, J = 12.9, 4.3 Hz, 1H), 2.97-2.90 (m, 1H), 2.84-2.77 (m, 1H), 2.47-2.43 (m, 1H), 2.13-2.07 (m, 1H), 1.84-1.75 (m, 1H), 0.78-0.68 (m, 1H), 0.61-0.54 (m, 1H). | 250 |
| 101d | 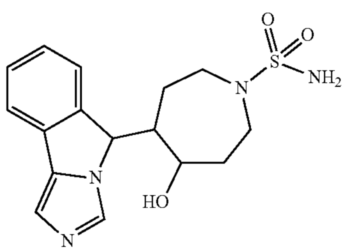 [SMILES: NS(=O)(=O)N1CCC(O)C(C2c3ccccc3-c3cncn32)CC1] | 1H NMR (400 MHz, DMSO-d6) δ 7.81 (s, 1H), 7.61 (d, J = 7.5 Hz, 1H), 7.45 (dd, J = 7.6, 1.1 Hz, 1H), 7.41-7.37 (m, 1H), 7.33-7.29 (m, 1H), 7.15 (s, 1H), 6.58 (s, 2H), 5.74 (d, J = 2.3 Hz, 1H), 5.40 (d, J = 5.7 Hz, 1H), 3.88-3.82 (m, 1H), 3.38-3.34 (m, 1H), 3.00-2.94 (m, 2H), 2.83-2.76 (m, 1H), 2.33-2.29 (m, 1H), 2.17-2.11 (m, 1H), 1.86-1.78 (m, 1H), 0.72 (dt, J = 8.7, 4.6 Hz, 2H). | 251 |
| 102a | 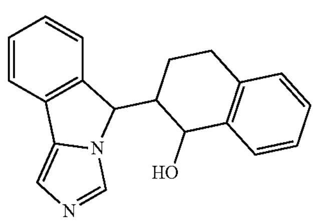 [SMILES: OC1c2ccccc2CCC1C1c2ccccc2-c2cncn21] | 1H NMR (400 MHz, DMSO-d6) δ 7.96 (s, 1H), 7.62 (d, J = 7.6 Hz, 1H), 7.59 (d, J = 7.4 Hz, 1H), 7.42-7.35 (m, 2H), 7.28 (td, J = 7.5, 1.2 Hz, 1H), 7.22-7.18 (m, 2H), 7.11 (s, 1H), 7.06 (dd, J = 6.8, 2.1 Hz, 1H), 5.78 (d, J = 6.1 Hz, 1H), 5.52 (d, J = 2.1 Hz, 1H), 4.98 (dd, J = 6.1, 3.8 Hz, 1H), 2.74-2.65 (m, 1H), 2.47-2.44 (m, 1H), 2.43 (q, J = 2.9 Hz, 1H), 1.50 (qd, J = 12.8, 5.6 Hz, 1H). | 303.3 |
| 102b | 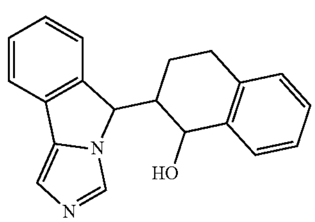 [SMILES: OC1c2ccccc2CCC1C1c2ccccc2-c2cncn21] | Same as 102a | 303.3 |
| 102c | 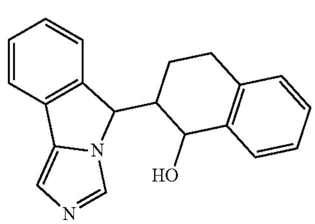 [SMILES: OC1c2ccccc2CCC1C1c2ccccc2-c2cncn21] | 1H NMR (400 MHz, DMSO-d6) δ 8.01 (s, 1H), 7.76 (d, J = 7.7 Hz, 1H), 7.61 (d, J = 7.5 Hz, 1H), 7.38 (t, J = 7.4 Hz, 1H), 7.35-7.30 (m, 1H), 7.24 (td, J = 7.6, 1.2 Hz, 1H), 7.20-7.16 (m, 2H), 7.13 (s, 1H), 7.10-7.06 (m, 1H), 5.49 (d, J = 5.9 Hz, 1H), 5.44 (d, J = 6.0 Hz, 1H), 4.79 (dd, J = 6.2, 3.3 Hz, 1H), 2.81 (ddd, J = 17.3, 5.6, 2.1 Hz, 1H), 2.63 (ddd, J = 17.4, 12.3, 5.9 Hz, 1H), 2.12 (ddt, J = 12.3, 6.1, 3.0 Hz, 1H), 1.95 (qd, J = 12.5, 5.4 Hz, 1H), 1.74-1.63 (m, 1H). | 303.3 |

TABLE 2-continued

| Ex. # | Structure | $^1$H NMR | MS $(M + H)^+$ |
|---|---|---|---|
| 102d | 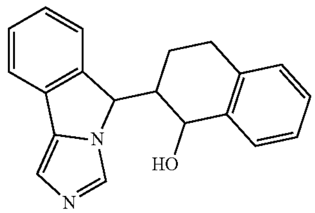 [SMILES: OC1c2ccccc2CCC1C1c2ccccc2-c2cncn21] | Same as 102d | 303.3 |
| 102e | 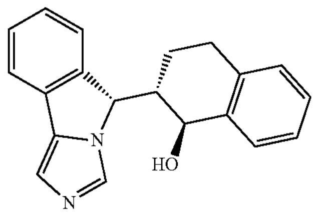 [SMILES: O[C@@H]1c2ccccc2CC[C@H]1[C@H]1c2ccccc2-c2cncn21] | 1H NMR (400 MHz, DMSO-d6) δ 7.96 (s, 1H), 7.66 (d, J = 7.7 Hz, 1H), 7.63 (d, J = 7.4 Hz, 1H), 7.50-7.46 (m, 1H), 7.41 (t, J = 7.4 Hz, 1H), 7.31 (td, J = 7.5, 1.2 Hz, 1H), 7.23 (td, J = 7.5, 1.4 Hz, 1H), 7.18 (s, 1H), 7.14 (td, J = 7.4, 1.4 Hz, 1H), 7.00 (dd, J = 7.5, 1.3 Hz, 1H), 5.97 (d, J = 7.7 Hz, 1H), 5.84-5.78 (m, 1H), 4.93 (dd, J = 10.6, 7.8 Hz, 1H), 2.56 (s, 3H), 2.38 (tt, J = 11.2, 2.9 Hz, 1H), 0.95-0.73 (m, 2H). | 303.3 |
| 102f | 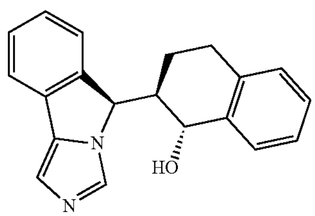 [SMILES: O[C@H]1c2ccccc2CC[C@@H]1[C@@H]1c2ccccc2-c2cncn21] | Same as 102e | 303.3 |
| 102g | 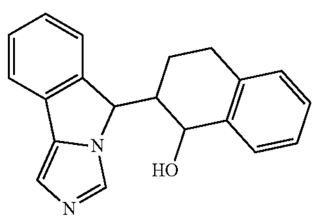 [SMILES: OC1c2ccccc2CCC1C1c2ccccc2-c2cncn21] | 1H NMR (400 MHz, DMSO-d6) δ 7.90 (s, 1H), 7.63 (t, J = 6.8 Hz, 2H), 7.60 (d, J = 4.5 Hz, 1H), 7.40 (t, J = 7.4 Hz, 1H), 7.26 (td, J = 7.5, 1.2 Hz, 1H), 7.21 (td, J = 7.6, 1.4 Hz, 1H), 7.17 (s, 1H), 7.13 (td, J = 7.4, 1.5 Hz, 1H), 6.99 (d, J = 7.6 Hz, 1H), 5.98 (d, J = 7.4 Hz, 1H), 5.80 (d, J = 3.3 Hz, 1H), 4.89 (dd, J = 10.6, 7.5 Hz, 1H), 2.68-2.53 (m, 3H), 0.85 (h, J = 5.3, 4.8 Hz, 2H). | 303.3 |
| 102h | 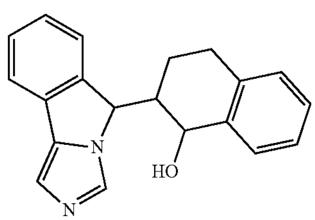 [SMILES: OC1c2ccccc2CCC1C1c2ccccc2-c2cncn21] | Same as 102g | 303.3 |
| 103 | 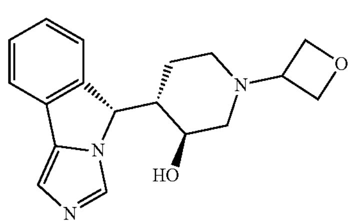 [SMILES: O[C@@H]1CN(C2COC2)CC[C@H]1[C@H]1c2ccccc2-c2cncn21] | $^1$H NMR (300 MHz, $CD_3OD$) δ 7.92 (s, 1H), 7.63 (d, J = 7.5, 1H), 7.48-7.33 (m, 3H), 7.20 (s, 1H), 5.79 (d, J = 3.3, 1H), 4.71-4.47 (m, 4H), 3.97-3.96 (m, 1H), 3.54-3.50 (m, 1H), 3.09-3.04 (m, 1H), 2.61-2.49 (m, 1H), 2.12-2.02 (m, 1H), 1.89-1.65 (m, 2H), 0.92-0.87 (m, 1H), 0.71-0.55 (m, 1H). | 312.3 |
| 104a | 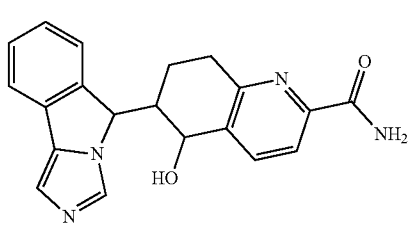 [SMILES: NC(=O)c1ccc2c(n1)CCC(C1c3ccccc3-c3cncn31)C2O] | $^1$H NMR (500 MHz, DMSO-$d_6$) δ 8.11 (d, J = 8.0 Hz, 1H), 7.97 (s, 1H), 7.90 (d, J = 8.0 Hz, 1H), 7.88 (s, 1H), 7.65 (t, J = 8.4 Hz, 2H), 7.52 (s, 1H), 7.41 (t, J = 7.4 Hz, 1H), 7.28 (td, J = 7.6, 1.1 Hz, 1H), 7.20 (s, 1H), 6.34 (d, J = 7.3 Hz, 1H), 5.82 (d, J = 3.1 Hz, 1H), 4.96 (dd, J = 10.7, 7.4 Hz, 1H), 2.76 (dd, J = 8.1, 4.7 Hz, 2H), 2.68-2.60 (m, 1H), 1.05-0.90 (m, 2H). | 347.2 |

TABLE 2-continued

| Ex. # | Structure | $^1$H NMR | MS $(M + H)^+$ |
|---|---|---|---|
| 104b | 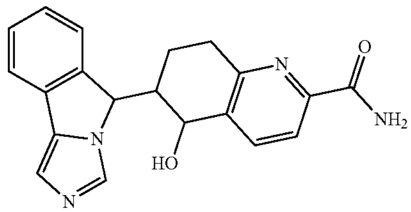 [SMILES: NC(=O)c1ccc2c(n1)CCC(C1c3ccccc3-c3cncn31)C2O] | $^1$H NMR (500 MHz, DMSO-$d_6$) δ 8.16 (d, J = 8.0 Hz, 1H), 7.99 (s, 1H), 7.91 (d, J = 8.0 Hz, 1H), 7.87 (s, 1H), 7.64 (d, J = 7.6 Hz, 1H), 7.53 (s, 1H), 7.50 (d, J = 7.6 Hz, 1H), 7.42 (t, J = 7.5 Hz, 1H), 7.32 (td, J = 7.5, 1.0 Hz, 1H), 7.19 (s, 1H), 6.33 (d, J = 7.5 Hz, 1H), 5.81 (s, 1H), 5.02 (dd, J = 10.6, 7.7 Hz, 1H), 2.82-2.64 (m, 2H), 2.48-2.43 (m, 1H), 1.08-0.84 (m, 2H). | 347.2 |
| 104c | 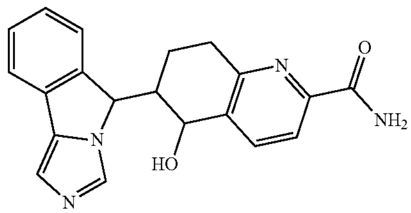 [SMILES: NC(=O)c1ccc2c(n1)CCC(C1c3ccccc3-c3cncn31)C2O] | $^1$H NMR (500 MHz, DMSO-$d_6$) δ 7.97-7.93 (m, 2H), 7.90 (t, J = 6.9 Hz, 2H), 7.62 (dd, J = 14.9, 7.6 Hz, 2H), 7.56 (s, 1H), 7.40 (t, J = 7.5 Hz, 1H), 7.30 (t, J = 7.5 Hz, 1H), 7.12 (s, 1H), 6.09 (d, J = 6.1 Hz, 1H), 5.57 (s, 1H), 5.15-5.06 (m, 1H), 2.85 (dd, J = 17.8, 3.9 Hz, 1H), 2.68 (td, J = 12.2, 6.3 Hz, 1H), 2.56 (d, J = 2.7 Hz, 1H), 1.62 (qd, J = 12.8, 5.5 Hz, 1H), 1.04 (d, J = 6.1 Hz, 1H). | 347.2 |
| 104d | 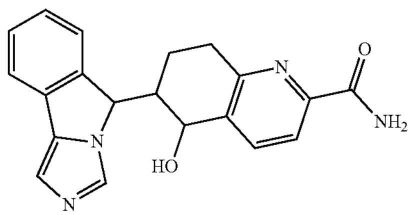 [SMILES: NC(=O)c1ccc2c(n1)CCC(C1c3ccccc3-c3cncn31)C2O] | $^1$H NMR (500 MHz, DMSO-$d_6$) δ 8.01 (s, 1H), 7.92 (s, 1H), 7.87 (q, J = 7.9 Hz, 2H), 7.74 (d, J = 7.7 Hz, 1H), 7.62 (d, J = 7.5 Hz, 1H), 7.56 (s, 1H), 7.39 (t, J = 7.4 Hz, 1H), 7.25 (td, J = 7.6, 1.1 Hz, 1H), 7.15 (s, 1H), 5.79 (d, J = 6.1 Hz, 1H), 5.49 (d, J = 6.0 Hz, 1H), 4.91 (dd, J = 5.8, 3.2 Hz, 1H), 2.96 (dd, J = 17.9, 3.7 Hz, 1H), 2.79 (ddd, J = 18.1, 12.3, 6.4 Hz, 1H), 2.27 (dq, J = 9.2, 3.1 Hz, 1H), 2.07 (qd, J = 12.7, 5.5 Hz, 1H), 1.81 (d, J = 10.0 Hz, 1H). | 347.2 |
| 104e | 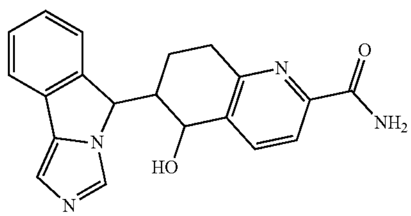 [SMILES: NC(=O)c1ccc2c(n1)CCC(C1c3ccccc3-c3cncn31)C2O] | $^1$H NMR (500 MHz, DMSO-$d_6$) δ 8.01 (s, 1H), 7.93 (s, 1H), 7.87 (q, J = 7.9 Hz, 2H), 7.74 (d, J = 7.7 Hz, 1H), 7.63 (d, J = 7.5 Hz, 1H), 7.56 (s, 1H), 7.40 (t, J = 7.5 Hz, 1H), 7.25 (td, J = 7.6, 1.1 Hz, 1H), 7.15 (s, 1H), 5.79 (d, J = 6.1 Hz, 1H), 5.49 (d, J = 5.9 Hz, 1H), 4.92 (dd, J = 5.7, 3.2 Hz, 1H), 3.04-2.91 (m, 1H), 2.79 (ddd, J = 18.0, 12.4, 6.3 Hz, 1H), 2.27 (dq, J = 9.3, 3.0 Hz, 1H), 2.07 (qd, J = 12.7, 5.5 Hz, 1H), 1.81 (d, J = 7.1 Hz, 1H). | 347.2 |
| 104f | 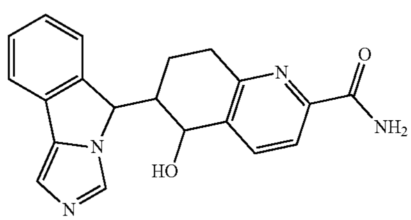 [SMILES: NC(=O)c1ccc2c(n1)CCC(C1c3ccccc3-c3cncn31)C2O] | $^1$H NMR (500 MHz, DMSO-$d_6$) δ 8.16 (d, J = 8.0 Hz, 1H), 7.98 (s, 1H), 7.91 (d, J = 8.0 Hz, 1H), 7.87 (s, 1H), 7.64 (d, J = 7.6 Hz, 1H), 7.53 (s, 1H), 7.50 (d, J = 7.2 Hz, 1H), 7.42 (t, J = 7.5 Hz, 1H), 7.32 (td, J = 7.5, 1.0 Hz, 1H), 7.19 (s, 1H), 6.33 (d, J = 7.5 Hz, 1H), 5.81 (s, 1H), 5.02 (dd, J = 10.6, 7.7 Hz, 1H), 2.82-2.63 (m, 2H), 2.45 (d, J = 11.0 Hz, 1H), 1.07-0.87 (m, 2H). | 347.2 |
| 104g | 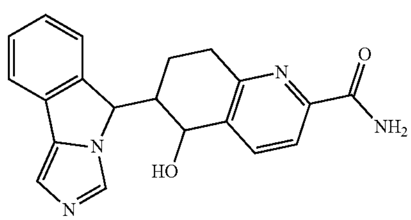 [SMILES: NC(=O)c1ccc2c(n1)CCC(C1c3ccccc3-c3cncn31)C2O] | $^1$H NMR (500 MHz, DMSO-$d_6$) δ 7.97-7.93 (m, 2H), 7.91 (s, 1H), 7.89 (d, J = 7.9 Hz, 1H), 7.63 (d, J = 7.6 Hz, 1H), 7.60 (d, J = 7.5 Hz, 1H), 7.56 (s, 1H), 7.40 (t, J = 7.5 Hz, 1H), 7.30 (t, J = 7.5 Hz, 1H), 7.12 (s, 1H), 6.09 (d, J = 3.8 Hz, 1H), 5.57 (s, 1H), 5.10 (s, 1H), 2.85 (dd, J = 17.7, 3.9 Hz, 1H), 2.67 (td, J = 12.3, 6.3 Hz, 1H), 2.55 (dd, J = 12.6, 2.9 Hz, 1H), 1.62 (qd, J = 12.9, 5.7 Hz, 1H), 1.09 (d, J = 10.0 Hz, 1H). | 347.2 |
| 104h | 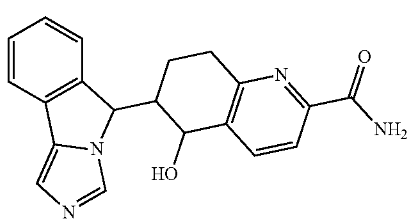 [SMILES: NC(=O)c1ccc2c(n1)CCC(C1c3ccccc3-c3cncn31)C2O] | $^1$H NMR (500 MHz, DMSO-$d_6$) δ 8.11 (d, J = 8.0 Hz, 1H), 7.92 (s, 1H), 7.90 (d, J = 8.1 Hz, 1H), 7.88 (s, 1H), 7.65 (t, J = 7.5 Hz, 2H), 7.52 (s, 1H), 7.41 (t, J = 7.6 Hz, 1H), 7.27 (t, J = 7.7 Hz, 1H), 7.18 (s, 1H), 6.33 (d, J = 7.3 Hz, 1H), 5.81 (d, J = 2.7 Hz, 1H), 4.96 (dd, J = 10.5, 7.6 Hz, 1H), 2.76 (dd, J = 8.1, 4.6 Hz, 2H), 2.64 (t, J = 11.2 Hz, 1H), 0.97 (dd, J = 20.0, 6.5 Hz, 2H). | 347.2 |

TABLE 2-continued

| Ex. # | Structure | ¹H NMR | MS (M + H)+ |
|---|---|---|---|
| 105a | 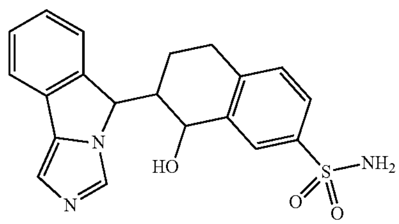 [SMILES: NS(=O)(=O)c1ccc2c(c1)C(O)C(C1c3ccccc3-c3cncn31)CC2] | (500 MHz, DMSO-$d_6$) δ 7.94 (s, 1H), 7.88 (d, J = 2.0 Hz, 1H), 7.63 (dd, J = 8.0, 2.0 Hz, 2H), 7.60 (d, J = 7.5 Hz, 1H), 7.42-7.36 (m, 1H), 7.33-7.27 (m, 3H), 7.25 (d, J = 8.1 Hz, 1H), 7.12 (s, 1H), 6.10 (d, J = 6.5 Hz, 1H), 5.54 (d, J = 2.4 Hz, 1H), 5.03 (dd, J = 6.5, 3.7 Hz, 1H), 2.80-2.71 (m, 1H), 2.55 (ddd, J = 18.5, 12.6, 6.3 Hz, 1H), 2.48-2.43 (m, 1H), 1.49 (qd, J = 12.6, 5.4 Hz, 1H), 1.06-0.96 (m, 1H). | 382.2 |
| 105b | 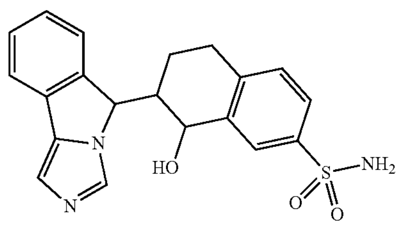 [SMILES: NS(=O)(=O)c1ccc2c(c1)C(O)C(C1c3ccccc3-c3cncn31)CC2] | (500 MHz, DMSO-$d_6$) δ 8.11 (dd, J = 2.1, 0.9 Hz, 1H), 7.91 (s, 1H), 7.64 (ddd, J = 7.3, 5.7, 1.0 Hz, 2H), 7.58 (dd, J = 7.9, 2.0 Hz, 1H), 7.41 (ddd, J = 8.1, 7.2, 1.1 Hz, 1H), 7.32-7.23 (m, 3H), 7.21-7.13 (m, 2H), 6.29 (d, J = 7.6 Hz, 1H), 5.81 (d, J = 3.3 Hz, 1H), 4.95-4.87 (m, 1H), 2.70-2.53 (m, 3H), 0.86 (t, J = 7.1 Hz, 2H). | 382.2 |
| 105c | 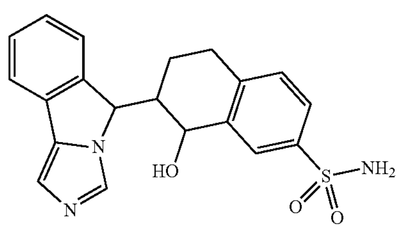 [SMILES: NS(=O)(=O)c1ccc2c(c1)C(O)C(C1c3ccccc3-c3cncn31)CC2] | (500 MHz, DMSO-$d_6$) δ 7.93 (s, 1H), 7.88 (d, J = 2.0 Hz, 1H), 7.63 (dd, J = 8.0, 2.2 Hz, 2H), 7.60 (d, J = 7.5 Hz, 1H), 7.39 (t, J = 7.5 Hz, 1H), 7.33-7.27 (m, 3H), 7.25 (d, J = 8.1 Hz, 1H), 7.12 (s, 1H), 6.10 (d, J = 6.5 Hz, 1H), 5.57-5.50 (m, 1H), 5.03 (dd, J = 6.5, 3.7 Hz, 1H), 2.80-2.72 (m, 1H), 2.56 (ddd, J = 18.3, 12.5, 6.2 Hz, 1H), 2.46 (dd, J = 12.3, 3.2 Hz, 1H), 1.49 (qd, J = 12.7, 5.3 Hz, 1H), 1.05-0.98 (m, 1H). | 382.2 |
| 105d | 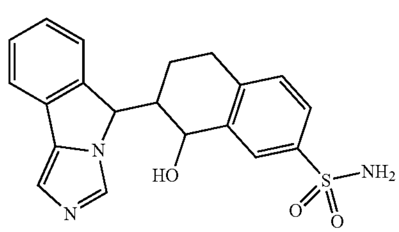 [SMILES: NS(=O)(=O)c1ccc2c(c1)C(O)C(C1c3ccccc3-c3cncn31)CC2] | (500 MHz, DMSO-$d_6$) δ 8.16 (d, J = 2.1 Hz, 1H), 7.98 (s, 1H), 7.64 (d, J = 7.6 Hz, 1H), 7.60 (dd, J = 8.0, 2.0 Hz, 1H), 7.48 (dd, J = 7.6, 1.0 Hz, 1H), 7.42 (t, J = 7.6 Hz, 1H), 7.35-7.27 (m, 3H), 7.19 (d, J = 7.9 Hz, 2H), 6.26 (d, J = 7.8 Hz, 1H), 5.82 (s, 1H), 4.99-4.91 (m, 1H), 2.66-2.59 (m, 2H), 2.41 (t, J = 11.3 Hz, 1H), 0.96-0.88 (m, 1H), 0.88-0.77 (m, 1H). | 382.2 |
| 105e | 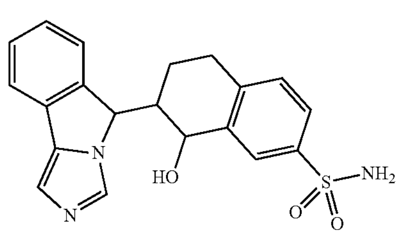 [SMILES: NS(=O)(=O)c1ccc2c(c1)C(O)C(C1c3ccccc3-c3cncn31)CC2] | (500 MHz, DMSO-$d_6$) δ 8.11 (d, J = 2.0 Hz, 1H), 7.90 (s, 1H), 7.64 (dd, J = 7.6, 5.9 Hz, 2H), 7.58 (dd, J = 8.0, 2.0 Hz, 1H), 7.41 (t, J = 7.6 Hz, 1H), 7.32-7.23 (m, 3H), 7.21-7.13 (m, 2H), 6.29 (d, J = 7.6 Hz, 1H), 5.81 (d, J = 3.3 Hz, 1H), 4.95-4.87 (m, 1H), 2.67-2.54 (m, 3H), 0.85 (t, J = 7.3 Hz, 2H). | 382.2 |
| 105f | 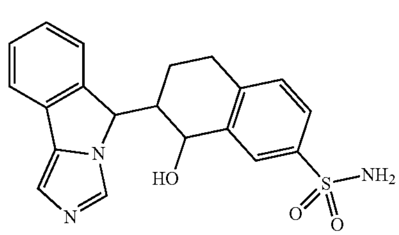 [SMILES: NS(=O)(=O)c1ccc2c(c1)C(O)C(C1c3ccccc3-c3cncn31)CC2] | (500 MHz, DMSO-$d_6$) δ 8.02 (s, 1H), 7.83 (d, J = 2.0 Hz, 1H), 7.73 (dq, J = 7.7, 0.9 Hz, 1H), 7.65-7.59 (m, 2H), 7.42-7.35 (m, 1H), 7.31-7.20 (m, 4H), 7.14 (s, 1H), 5.82 (d, J = 6.5 Hz, 1H), 5.46 (d, J = 6.2 Hz, 1H), 4.85 (dd, J = 6.5, 3.4 Hz, 1H), 2.88 (dd, J = 17.5, 5.1 Hz, 1H), 2.72-2.62 (m, 1H), 2.14 (ddt, J = 12.5, 6.3, 3.1 Hz, 1H), 1.94 (qd, J = 12.7, 5.5 Hz, 1H), 1.73 (d, J = 12.9 Hz, 1H). | 382.2 |

TABLE 2-continued

| Ex. # | Structure | $^1$H NMR | MS $(M + H)^+$ |
|---|---|---|---|
| 105g | 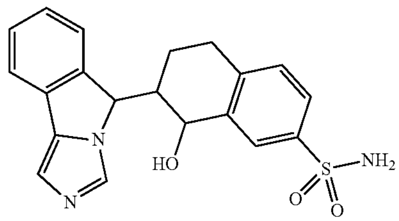 [SMILES: NS(=O)(=O)c1ccc2c(c1)C(O)C(C1c3ccccc3-c3cncn31)CC2] | (500 MHz, DMSO-$d_6$) δ 8.16 (dd, J = 2.1, 0.9 Hz, 1H), 7.98 (s, 1H), 7.64 (d, J = 7.6 Hz, 1H), 7.60 (dd, J = 8.0, 2.0 Hz, 1H), 7.51-7.45 (m, 1H), 7.44-7.39 (m, 1H), 7.32 (td, J = 7.5, 3.2 Hz, 3H), 7.19 (d, J = 7.7 Hz, 2H), 6.26 (d, J = 7.8 Hz, 1H), 5.82 (d, J = 1.9 Hz, 1H), 4.99-4.91 (m, 1H), 2.66-2.59 (m, 2H), 2.41 (t, J = 11.1 Hz, 1H), 0.92 (dq, J = 12.6, 4.3 Hz, 1H), 0.89-0.77 (m, 1H). | 382.2 |
| 105h | 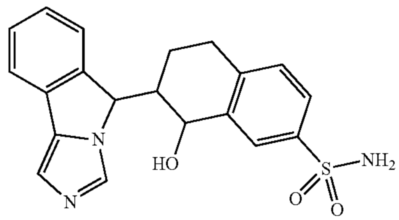 [SMILES: NS(=O)(=O)c1ccc2c(c1)C(O)C(C1c3ccccc3-c3cncn31)CC2] | (500 MHz, DMSO-$d_6$) δ 8.02 (s, 1H), 7.83 (d, J = 1.9 Hz, 1H), 7.73 (d, J = 7.7 Hz, 1H), 7.65-7.59 (m, 2H), 7.39 (t, J = 7.5 Hz, 1H), 7.30-7.21 (m, 4H), 7.14 (s, 1H), 5.82 (d, J = 6.4 Hz, 1H), 5.46 (d, J = 6.1 Hz, 1H), 4.85 (dd, J = 6.6, 3.3 Hz, 1H), 2.89 (dt, J = 17.8, 3.3 Hz, 1H), 2.67 (ddd, J = 17.7, 12.0, 6.1 Hz, 1H), 2.14 (ddd, J = 12.6, 6.3, 3.2 Hz, 1H), 1.95 (qd, J = 12.6, 5.4 Hz, 1H), 1.73 (d, J = 10.3 Hz, 1H). | 382.2 |
| 106a | 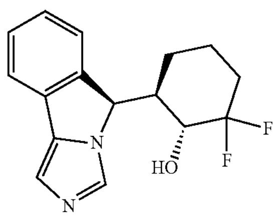 [SMILES: O[C@@H]1[C@@H]([C@@H]2c3ccccc3-c3cncn32)CCCC1(F)F] | (500 MHz, DMSO-$d_6$) δ 7.87 (s, 1H), 7.60 (dt, J = 7.6, 0.9 Hz, 1H), 7.51-7.47 (m, 1H), 7.42-7.36 (m, 1H), 7.29 (td, J = 7.5, 1.1 Hz, 1H), 7.17 (s, 1H), 6.04 (d, J = 7.0 Hz, 1H), 5.65 (d, J = 2.3 Hz, 1H), 3.99-3.86 (m, 1H), 2.30 (t, J = 12.0 Hz, 1H), 1.98 (s, 1H), 1.71 (dt, J = 32.1, 13.8 Hz, 1H), 1.46 (d, J = 13.8 Hz, 1H), 1.27-1.12 (m, 1H), 0.71 (d, J = 13.5 Hz, 1H), 0.36 (qd, J = 13.1, 3.9 Hz, 1H). | 291.2 |
| 106b | 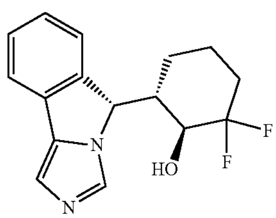 [SMILES: O[C@H]1[C@H]([C@H]2c3ccccc3-c3cncn32)CCCC1(F)F] | (500 MHz, DMSO-$d_6$) δ 7.87 (s, 1H), 7.60 (dt, J = 7.6, 0.9 Hz, 1H), 7.49 (dt, J = 7.6, 0.9 Hz, 1H), 7.41-7.36 (m, 1H), 7.29 (td, J = 7.6, 1.2 Hz, 1H), 7.16 (s, 1H), 6.04 (d, J = 7.0 Hz, 1H), 5.65 (d, J = 2.4 Hz, 1H), 3.99-3.86 (m, 1H), 2.30 (t, J = 12.0 Hz, 1H), 1.98 (s, 1H), 1.81-1.63 (m, 1H), 1.46 (d, J = 13.8 Hz, 1H), 1.20 (q, J = 14.3, 13.1 Hz, 1H), 0.71 (d, J = 13.5 Hz, 1H), 0.36 (qd, J = 13.1, 4.0 Hz, 1H). | 291.2 |
| 106c | 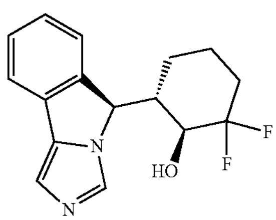 [SMILES: O[C@H]1[C@H]([C@@H]2c3ccccc3-c3cncn32)CCCC1(F)F] | (500 MHz, DMSO-d6) δ 7.93 (s, 1H), 7.62 (d, J = 7.6 Hz, 1H), 7.52 (d, J = 7.6 Hz, 1H), 7.41 (t, J = 7.5 Hz, 1H), 7.29 (td, J = 7.6, 1.1 Hz, 1H), 7.13 (s, 1H), 6.07 (d, J = 6.2 Hz, 1H), 5.65 (d, J = 3.8 Hz, 1H), 3.93-3.80 (m, 1H), 1.97 (s, 1H), 1.64 (dt, J = 32.3, 14.0 Hz, 1H), 1.46 (d, J = 13.8 Hz, 1H), 1.21 (q, J = 13.7 Hz, 1H), 0.57 (d, J = 13.5 Hz, 1H), 0.38 (td, J = 13.1, 3.8 Hz, 1H). | 291.2 |
| 106d | 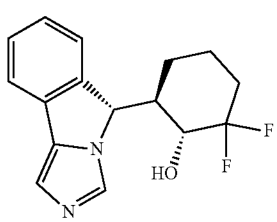 [SMILES: O[C@@H]1[C@@H]([C@H]2c3ccccc3-c3cncn32)CCCC1(F)F] | (500 MHz, DMSO-$d_6$) δ 7.93 (s, 1H), 7.62 (dt, J = 7.6, 0.8 Hz, 1H), 7.52 (dd, J = 7.6, 0.9 Hz, 1H), 7.41 (tt, J = 7.6, 0.8 Hz, 1H), 7.30 (dd, J = 7.6, 1.2 Hz, 1H), 7.13 (s, 1H), 6.07 (d, J = 6.5 Hz, 1H), 5.65 (d, J = 3.8 Hz, 1H), 3.86 (dddd, J = 21.6, 10.9, 6.5, 3.9 Hz, 1H), 1.97 (s, 1H), 1.74-1.55 (m, 1H), 1.46 (d, J = 13.7 Hz, 1H), 1.28-1.14 (m, 1H), 0.57 (d, J = 13.3 Hz, 1H), 0.38 (td, J = 13.1, 3.8 Hz, 1H). | 291.2 |
| 107a | 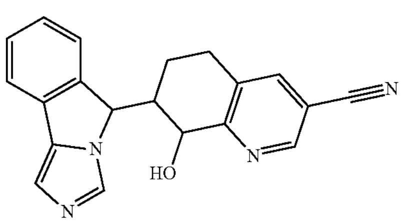 [SMILES: N#Cc1cnc2c(c1)CCC(C1c3ccccc3-c3cncn31)C2O] | (500 MHz, DMSO-$d_6$) δ 8.91 (d, J = 2.0 Hz, 1H), 8.51 (s, 1H), 8.05-8.02 (m, 1H), 7.76 (d, J = 7.6 Hz, 1H), 7.65 (d, J = 7.7 Hz, 1H), 7.49 (s, 1H), 7.47 (d, J = 7.6 Hz, 1H), 7.37 (td, J = 7.5, 1.1 Hz, 1H), 6.19 (d, J = 4.6 Hz, 1H), 5.94 (d, J = 3.5 Hz, 1H), 4.89 (dd, J = 10.7, 3.6 Hz, 1H), 2.85-2.76 (m, 1H), 2.73-2.62 (m, 2H), 0.99 (dd, J = 8.6, 4.6 Hz, 2H). | 329.3 |

TABLE 2-continued

| Ex. # | Structure | $^1$H NMR | MS $(M + H)^+$ |
|---|---|---|---|
| 107b | 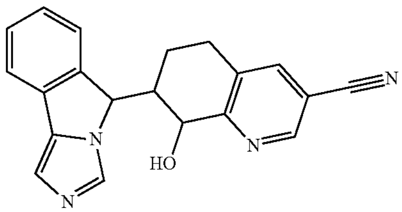 [SMILES: N#Cc1cnc2c(c1)CCC(C1c3ccccc3-c3cncn31)C2O] | (500 MHz, DMSO-$d_6$) δ 8.90 (d, J = 2.0 Hz, 1H), 8.09 (d, J = 2.0 Hz, 1H), 8.05 (s, 1H), 7.65 (dq, J = 7.6, 0.9 Hz, 1H), 7.63-7.60 (m, 1H), 7.41 (tt, J = 7.6, 0.8 Hz, 1H), 7.31 (td, J = 7.5, 1.2 Hz, 1H), 7.18 (s, 1H), 6.34 (d, J = 5.5 Hz, 1H), 5.58 (s, 1H), 5.04 (dd, J = 5.3, 3.8 Hz, 1H), 2.78 (dd, J = 17.5, 5.3 Hz, 1H), 2.58 (dd, J = 12.2, 5.7 Hz, 2H), 1.50 (qd, J = 12.8, 5.5 Hz, 1H), 1.07-0.99 (m, 1H). | 329.3 |
| 107c | 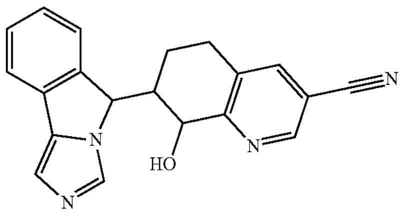 [SMILES: N#Cc1cnc2c(c1)CCC(C1c3ccccc3-c3cncn31)C2O] | (500 MHz, DMSO-$d_6$) δ 8.86 (d, J = 2.0 Hz, 1H), 8.11 (d, J = 2.0 Hz, 1H), 8.01 (s, 1H), 7.75 (dd, J = 7.7, 1.0 Hz, 1H), 7.62 (d, J = 7.5 Hz, 1H), 7.39 (t, J = 7.5 Hz, 1H), 7.26 (dd, J = 7.7, 1.2 Hz, 1H), 7.14 (s, 1H), 6.09 (d, J = 5.3 Hz, 1H), 5.48 (d, J = 6.0 Hz, 1H), 4.86-4.79 (m, 1H), 2.89 (dd, J = 17.5, 5.3 Hz, 1H), 2.69 (ddd, J = 17.8, 12.2, 6.1 Hz, 1H), 2.28 (dq, J = 9.4, 3.0 Hz, 1H), 1.93 (qd, J = 12.7, 5.5 Hz, 1H), 1.76-1.69 (m, 1H). | 329.3 |
| 107d | 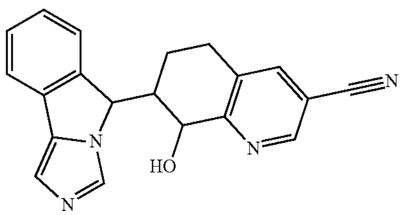 [SMILES: N#Cc1cnc2c(c1)CCC(C1c3ccccc3-c3cncn31)C2O] | (500 MHz, DMSO-$d_6$) δ 8.86 (d, J = 2.0 Hz, 1H), 8.11 (d, J = 2.0 Hz, 1H), 8.01 (s, 1H), 7.78-7.73 (m, 1H), 7.62 (d, J = 7.5 Hz, 1H), 7.39 (td, J = 7.5, 0.9 Hz, 1H), 7.25 (td, J = 7.6, 1.2 Hz, 1H), 7.14 (s, 1H), 6.09 (dd, J = 5.5, 0.7 Hz, 1H), 5.48 (d, J = 6.0 Hz, 1H), 4.82 (dd, J = 5.2, 3.4 Hz, 1H), 2.89 (dd, J = 17.5, 4.9 Hz, 1H), 2.69 (ddd, J = 17.8, 12.3, 6.1 Hz, 1H), 2.33-2.25 (m, 1H), 1.93 (qd, J = 12.8, 5.5 Hz, 1H), 1.75-1.68 (m, 1H). | 329.3 |
| 107e | 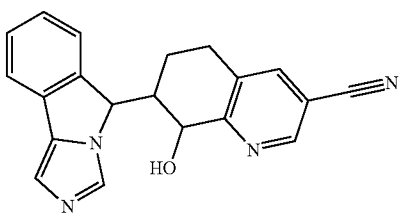 [SMILES: N#Cc1cnc2c(c1)CCC(C1c3ccccc3-c3cncn31)C2O] | (500 MHz, DMSO-$d_6$) δ 8.92 (d, J = 2.0 Hz, 1H), 8.02 (dd, J = 2.0, 1.0 Hz, 1H), 7.93 (s, 1H), 7.64 (d, J = 7.5 Hz, 1H), 7.51 (dd, J = 7.5, 1.0 Hz, 1H), 7.42 (t, J = 7.5 Hz, 1H), 7.32 (td, J = 7.5, 1.1 Hz, 1H), 7.18 (s, 1H), 6.10 (d, J = 5.2 Hz, 1H), 5.80 (d, J = 2.2 Hz, 1H), 4.95 (dd, J = 10.7, 5.2 Hz, 1H), 2.66 (ddd, J = 13.3, 10.0, 3.7 Hz, 2H), 2.57 (t, J = 11.3 Hz, 1H), 1.01-0.95 (m, 1H), 0.89 (ddt, J = 18.2, 12.3, 6.2 Hz, 1H). | 329.3 |
| 107f | 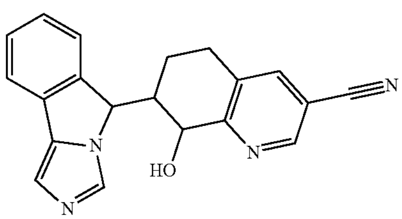 [SMILES: N#Cc1cnc2c(c1)CCC(C1c3ccccc3-c3cncn31)C2O] | (500 MHz, DMSO-$d_6$) δ 8.92 (d, J = 2.0 Hz, 1H), 8.02 (dd, J = 2.0, 1.0 Hz, 1H), 7.93 (s, 1H), 7.64 (dt, J = 7.5, 0.9 Hz, 1H), 7.51 (dq, J = 7.6, 0.9 Hz, 1H), 7.42 (tt, J = 7.6, 0.8 Hz, 1H), 7.32 (td, J = 7.5, 1.1 Hz, 1H), 7.18 (s, 1H), 6.10 (d, J = 5.1 Hz, 1H), 5.80 (d, J = 2.2 Hz, 1H), 4.95 (dd, J = 10.8, 5.2 Hz, 1H), 2.71-2.61 (m, 2H), 2.60-2.53 (m, 1H), 1.01-0.94 (m, 1H), 0.94-0.84 (m, 1H). | 329.3 |
| 107g | 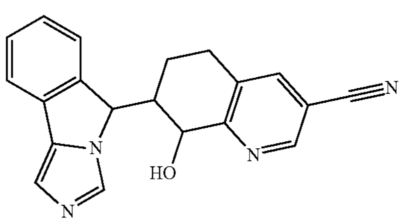 [SMILES: N#Cc1cnc2c(c1)CCC(C1c3ccccc3-c3cncn31)C2O] | (500 MHz, DMSO-$d_6$) δ 8.90 (d, J = 2.0 Hz, 1H), 8.02 (dd, J = 2.1, 1.0 Hz, 1H), 7.93 (s, 1H), 7.65 (d, J = 7.6 Hz, 1H), 7.62-7.57 (m, 1H), 7.41 (t, J = 7.5 Hz, 1H), 7.26 (td, J = 7.6, 1.2 Hz, 1H), 7.17 (s, 1H), 6.13 (d, J = 4.7 Hz, 1H), 5.78 (d, J = 3.6 Hz, 1H), 4.87 (dd, J = 10.7, 4.7 Hz, 1H), 2.77-2.64 (m, 3H), 0.92 (h, J = 4.8 Hz, 2H). | 329.3 |
| 107h | 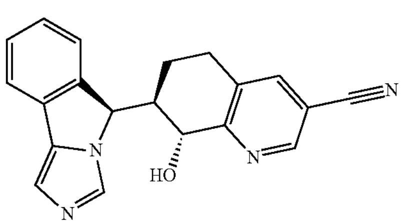 [SMILES: N#Cc1cnc2c(c1)CC[C@H]([C@@H]1c3ccccc3-c3cncn31)[C@H]2O] | (500 MHz, DMSO-$d_6$) δ 8.90 (d, J = 2.0 Hz, 1H), 8.09 (d, J = 2.0 Hz, 1H), 7.97 (s, 1H), 7.64 (dq, J = 7.6, 0.9 Hz, 1H), 7.60 (dt, J = 7.6, 0.9 Hz, 1H), 7.39 (tt, J = 7.6, 0.8 Hz, 1H), 7.29 (td, J = 7.6, 1.2 Hz, 1H), 7.12 (s, 1H), 6.32 (dd, J = 5.6, 0.7 Hz, 1H), 5.55 (d, J = 2.5 Hz, 1H), 5.04 (dd, J = 5.5, 3.8 Hz, 1H), 2.82-2.75 (m, 1H), 2.60-2.53 (m, 2H), 1.51 (qd, J = 12.8, 5.5 Hz, 1H), 1.03 (d, J = 13.1 Hz, 1H). | 329.3 |

TABLE 2-continued

| Ex. # | Structure | $^1$H NMR | MS $(M + H)^+$ |
|---|---|---|---|
| 108a | 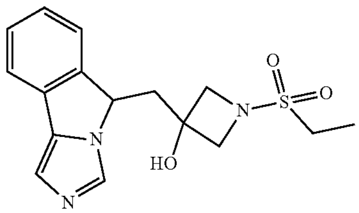 [SMILES: CCS(=O)(=O)N1CC(O)(CC2c3ccccc3-c3cncn32)C1] | $^1$H NMR (400 MHz, $CD_3OD$) δ 8.01 (s, 1H), 7.66-7.50 (m, 2H), 7.48-7.28 (m, 2H), 7.15 (s, 1H), 5.44 (dd, J = 8.5, 3.6 Hz, 1H), 4.12-3.94 (m, 3H), 3.78-3.68 (m, 1H), 3.09 (q, J = 7.4 Hz, 2H), 2.67 (dd, J = 14.9, 3.7 Hz, 1H), 2.27 (ddd, J = 14.9, 8.6, 1.1 Hz, 1H), 1.33 (t, J = 7.4 Hz, 3H). | 334.0 |
| 108b | 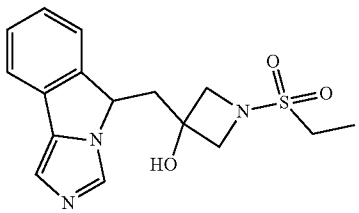 [SMILES: CCS(=O)(=O)N1CC(O)(CC2c3ccccc3-c3cncn32)C1] | The same as 108a. | 334.0 |
| 109a | 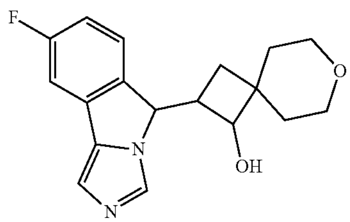 [SMILES: OC1C(C2c3ccc(F)cc3-c3cncn32)CC12CCOCC2] | $^1$H NMR (500 MHz, DMSO-$d_6$) δ 7.86 (s, 1H), 7.48 (dd, J = 9.0, 2.5 Hz, 1H), 7.40 (dd, J = 8.4, 5.0 Hz, 1H), 7.16 (s, 1H), 7.04 (td, J = 9.5, 2.5 Hz, 1H), 5.72 (d, J = 5.9 Hz, 1H), 5.38 (d, J = 10.9 Hz, 1H), 4.06 (td, J = 5.9, 3.2 Hz, 1H), 3.61 (ddd, J = 10.6, 6.7, 3.5 Hz, 1H), 3.54 (dt, J = 10.3, 5.0 Hz, 1H), 3.50-3.43 (m, 2H), 2.31 (dd, J = 16.4, 9.2 Hz, 1H), 2.20 (t, J = 10.4 Hz, 1H), 1.91 (ddd, J = 11.2, 8.4, 3.2 Hz, 1H), 1.73 (ddd, J = 11.2, 7.5, 3.4 Hz, 1H), 1.50 (q, J = 5.9, 4.9 Hz, 3H). | 315.2 |
| 109b | 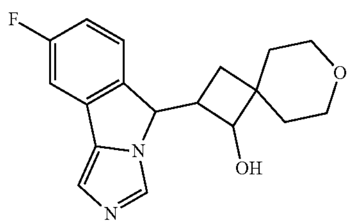 [SMILES: OC1C(C2c3ccc(F)cc3-c3cncn32)CC12CCOCC2] | $^1$H NMR (500 MHz, DMSO-$d_6$) δ 7.92 (s, 1H), 7.46 (dd, J = 9.0, 2.5 Hz, 1H), 7.40 (dd, J = 8.4, 5.0 Hz, 1H), 7.14 (s, 1H), 7.05 (ddd, J = 9.5, 8.5, 2.5 Hz, 1H), 5.36 (d, J = 8.5 Hz, 1H), 5.16 (d, J = 7.0 Hz, 1H), 3.84 (t, J = 7.4 Hz, 1H), 3.71 (dt, J = 11.2, 4.1 Hz, 1H), 3.63 (dt, J = 11.2, 4.1 Hz, 1H), 3.47-3.39 (m, 1H), 3.36-3.31 (m, 1H), 2.38-2.25 (m, 1H), 1.88 (t, J = 10.2 Hz, 1H), 1.71-1.56 (m, 2H), 1.50 (t, J = 10.3 Hz, 1H), 1.36 (d, J = 13.7 Hz, 2H), 1.06-0.99 (m, 1H). | 315.2 |
| 109c | 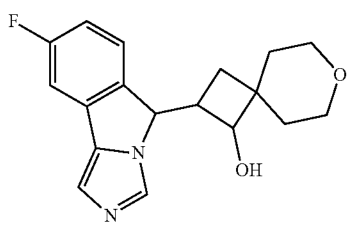 [SMILES: OC1C(C2c3ccc(F)cc3-c3cncn32)CC12CCOCC2] | $^1$H NMR (500 MHz, DMSO-$d_6$) δ 7.86 (s, 1H), 7.58 (dd, J = 8.4, 5.1 Hz, 1H), 7.46 (dd, J = 9.0, 2.5 Hz, 1H), 7.17 (s, 1H), 7.07 (ddd, J = 9.6, 8.5, 2.5 Hz, 1H), 5.39 (d, J = 7.5 Hz, 1H), 5.24 (d, J = 6.7 Hz, 1H), 3.99 (t, J = 7.3 Hz, 1H), 3.71 (dt, J = 11.1, 4.1 Hz, 1H), 3.62 (dt, J = 11.2, 4.2 Hz, 1H), 3.40 (td, J = 11.1, 2.7 Hz, 1H), 3.27 (td, J = 11.1, 2.7 Hz, 1H), 2.40 (ddd, J = 17.2, 9.4, 7.9 Hz, 1H), 1.77-1.58 (m, 3H), 1.32 (dd, J = 36.9, 13.3 Hz, 2H), 1.06 (t, J = 10.3 Hz, 1H). | 315.2 |
| 109d | 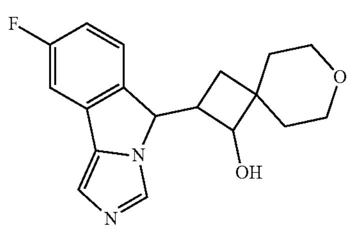 [SMILES: OC1C(C2c3ccc(F)cc3-c3cncn32)CC12CCOCC2] | $^1$H NMR (500 MHz, DMSO-$d_6$) δ 7.88 (s, 1H), 7.63 (dd, J = 8.4, 5.1 Hz, 1H), 7.46 (dd, J = 9.0, 2.5 Hz, 1H), 7.17 (s, 1H), 7.08 (ddd, J = 9.5, 8.5, 2.5 Hz, 1H), 5.70 (d, J = 5.5 Hz, 1H), 5.43 (d, J = 9.0 Hz, 1H), 4.08 (td, J = 6.4, 3.1 Hz, 1H), 3.59 (ddd, J = 10.5, 6.7, 3.6 Hz, 1H), 3.53 (dt, J = 10.2, 4.8 Hz, 1H), 3.44 (ddt, J = 16.1, 8.0, 4.4 Hz, 2H), 1.95-1.88 (m, 1H), 1.82 (ddd, J = 11.2, 8.4, 3.0 Hz, 1H), 1.70 (ddd, J = 11.3, 7.7, 3.5 Hz, 1H), 1.48 (d, J = 4.3 Hz, 2H), 1.43 (ddd, J = 13.1, 6.6, 3.3 Hz, 1H). | 315.2 |

TABLE 2-continued

| Ex. # | Structure | $^1H$ NMR | MS $(M + H)^+$ |
|---|---|---|---|
| 109e | 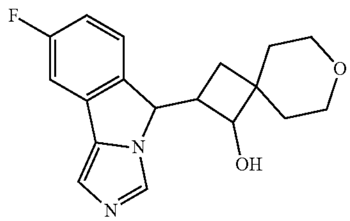 [SMILES: OC1C(C2c3ccc(F)cc3-c3cncn32)CC12CCOCC2] | $^1H$ NMR (500 MHz, DMSO-$d_6$) δ 7.85 (s, 1H), 7.48 (dd, J = 9.0, 2.5 Hz, 1H), 7.40 (dd, J = 8.4, 5.0 Hz, 1H), 7.15 (s, 1H), 7.03 (ddd, J = 9.5, 8.5, 2.5 Hz, 1H), 5.72 (d, J = 4.4 Hz, 1H), 5.38 (d, J = 10.9 Hz, 1H), 4.06 (s, 2H), 3.60 (ddd, J = 10.5, 6.6, 3.5 Hz, 1H), 3.54 (dt, J = 10.2, 4.9 Hz, 1H), 3.46 (dq, J = 11.1, 4.2, 3.0 Hz, 2H), 2.37-2.27 (m, 1H), 2.23-2.14 (m, 1H), 1.90 (ddd, J = 11.2, 8.4, 3.2 Hz, 1H), 1.73 (ddd, J = 11.2, 7.6, 3.5 Hz, 1H), 1.50 (q, J = 5.9, 4.9 Hz, 3H). | 315.2 |
| 109f | 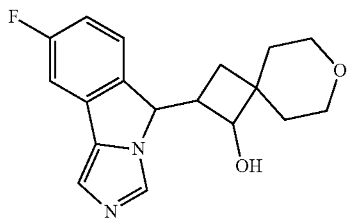 [SMILES: OC1C(C2c3ccc(F)cc3-c3cncn32)CC12CCOCC2] | $^1H$ NMR (500 MHz, DMSO-$d_6$) δ 7.92 (s, 1H), 7.47 (dd, J = 9.0, 2.5 Hz, 1H), 7.40 (dd, J = 8.4, 5.0 Hz, 1H), 7.14 (s, 1H), 7.05 (ddd, J = 9.5, 8.5, 2.5 Hz, 1H), 5.36 (d, J = 8.5 Hz, 1H), 5.17 (d, J = 7.0 Hz, 1H), 3.84 (t, J = 7.3 Hz, 1H), 3.71 (dt, J = 11.2, 4.1 Hz, 1H), 3.64 (dt, J = 11.2, 4.1 Hz, 1H), 3.43 (td, J = 11.2, 2.7 Hz, 1H), 3.36-3.31 (m, 1H), 2.36-2.26 (m, 1H), 1.88 (t, J = 10.2 Hz, 1H), 1.72-1.58 (m, 2H), 1.50 (t, J = 10.3 Hz, 1H), 1.37 (d, J = 13.6 Hz, 2H). | 315.2 |
| 109g | 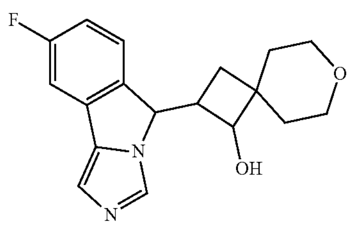 [SMILES: OC1C(C2c3ccc(F)cc3-c3cncn32)CC12CCOCC2] | $^1H$ NMR (500 MHz, DMSO-$d_6$) δ 7.89 (s, 1H), 7.63 (dd, J = 8.4, 5.1 Hz, 1H), 7.46 (dd, J = 9.0, 2.5 Hz, 1H), 7.17 (s, 1H), 7.08 (ddd, J = 9.6, 8.5, 2.5 Hz, 1H), 5.70 (d, J = 5.5 Hz, 1H), 5.43 (d, J = 9.0 Hz, 1H), 4.08 (td, J = 6.4, 3.1 Hz, 1H), 3.58 (ddd, J = 10.5, 6.7, 3.5 Hz, 1H), 3.53 (dt, J = 10.2, 4.8 Hz, 1H), 3.43 (ddt, J = 16.1, 7.9, 4.4 Hz, 2H), 1.96-1.88 (m, 1H), 1.81 (ddd, J = 11.2, 8.4, 3.0 Hz, 1H), 1.70 (ddd, J = 11.4, 7.7, 3.5 Hz, 1H), 1.48 (d, J = 4.4 Hz, 2H), 1.43 (ddd, J = 13.2, 6.7, 3.4 Hz, 1H). | 315.2 |
| 109h | 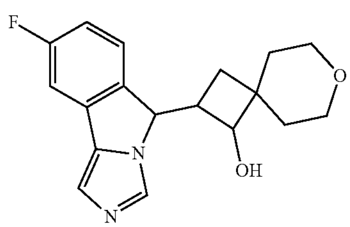 [SMILES: OC1C(C2c3ccc(F)cc3-c3cncn32)CC12CCOCC2] | $^1H$ NMR (500 MHz, DMSO-$d_6$) δ 8.06 (s, 1H), 7.60 (dd, J = 8.4, 5.0 Hz, 1H), 7.49 (dd, J = 9.0, 2.5 Hz, 1H), 7.27 (s, 1H), 7.11 (ddd, J = 9.5, 8.5, 2.5 Hz, 1H), 5.44 (d, J = 7.6 Hz, 1H), 5.24 (d, J = 6.7 Hz, 1H), 3.98 (t, J = 7.2 Hz, 1H), 3.70 (dt, J = 11.2, 4.2 Hz, 1H), 3.62 (dt, J = 11.2, 4.1 Hz, 1H), 3.39 (td, J = 11.2, 2.7 Hz, 1H), 3.29-3.24 (m, 2H), 2.44-2.36 (m, 1H), 1.76-1.70 (m, 1H), 1.69-1.58 (m, 2H), 1.36 (d, J = 13.6 Hz, 1H), 1.29 (d, J = 13.2 Hz, 1H), 1.13-0.98 (m, 2H). | 315.2 |
| 110a | 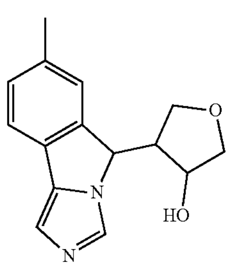 [SMILES: Cc1ccc2c(c1)C(C1COCC1O)n1cncc1-2] | $^1H$ NMR (500 MHz, DMSO-$d_6$) δ 7.96 (s, 1H), 7.48 (d, J = 7.7 Hz, 1H), 7.36 (dd, J = 1.7, 0.8 Hz, 1H), 7.20 (ddt, J = 7.7, 1.5, 0.7 Hz, 1H), 7.11 (s, 1H), 5.54 (d, J = 4.0 Hz, 1H), 5.26 (d, J = 4.6 Hz, 1H), 4.33 (dq, J = 5.7, 4.2 Hz, 1H), 3.69 (dd, J = 9.2, 8.1 Hz, 1H), 3.61 (dd, J = 9.2, 5.7 Hz, 1H), 3.46-3.36 (m, 1H), 3.10 (dd, J = 9.2, 6.5 Hz, 1H), 2.80 (ddt, J = 8.0, 6.4, 4.0 Hz, 1H), 2.35 (s, 3H). | 257 |
| 110b | 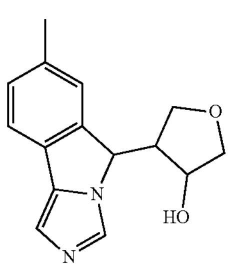 [SMILES: Cc1ccc2c(c1)C(C1COCC1O)n1cncc1-2] | $^1H$ NMR (500 MHz, DMSO-$d_6$) δ 7.94 (s, 1H), 7.48 (d, J = 7.7 Hz, 1H), 7.38-7.33 (m, 1H), 7.20 (ddt, J = 7.8, 1.6, 0.7 Hz, 1H), 7.10 (s, 1H), 5.54 (d, J = 4.0 Hz, 1H), 5.26 (d, J = 4.5 Hz, 1H), 4.33 (dq, J = 5.7, 4.2 Hz, 1H), 3.69 (dd, J = 9.2, 8.1 Hz, 1H), 3.61 (dd, J = 9.2, 5.7 Hz, 1H), 3.43 (dd, J = 9.2, 4.1 Hz, 1H), 3.10 (dd, J = 9.2, 6.5 Hz, 1H), 2.80 (ddt, J = 8.1, 6.5, 4.0 Hz, 1H), 2.35 (s, 3H). | 257 |

TABLE 2-continued

| Ex. # | Structure | $^1$H NMR | MS $(M + H)^+$ |
|---|---|---|---|
| 110c | 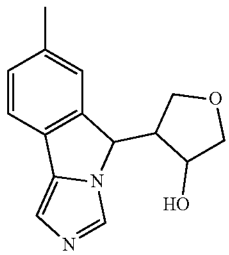 [SMILES: Cc1ccc2c(c1)C(C1COCC1O)n1cncc1-2] | $^1$H NMR (500 MHz, DMSO-$d_6$) δ 7.97 (s, 1H), 7.51 (d, J = 7.7 Hz, 1H), 7.35 (dd, J = 1.6, 0.8 Hz, 1H), 7.22 (ddt, J = 7.7, 1.4, 0.7 Hz, 1H), 7.12 (s, 1H), 5.48 (d, J = 4.6 Hz, 1H), 5.01 (d, J = 4.7 Hz, 1H), 4.03 (dd, J = 9.2, 7.7 Hz, 1H), 3.87-3.79 (m, 2H), 3.42-3.34 (m, 2H), 2.76 (dtt, J = 7.8, 5.3, 2.9 Hz, 1H), 2.37 (s, 3H). | 257 |
| 110d | 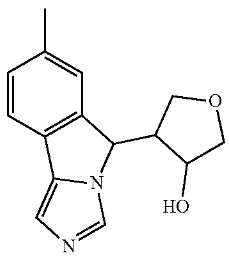 [SMILES: Cc1ccc2c(c1)C(C1COCC1O)n1cncc1-2] | $^1$H NMR (500 MHz, DMSO-$d_6$) δ 7.83 (s, 1H), 7.48 (d, J = 7.7 Hz, 1H), 7.33 (dq, J = 1.5, 0.8 Hz, 1H), 7.21 (ddt, J = 7.7, 1.5, 0.7 Hz, 1H), 7.05 (s, 1H), 5.44 (d, J = 4.5 Hz, 1H), 5.00 (d, J = 4.7 Hz, 1H), 4.03 (dd, J = 9.2, 7.8 Hz, 1H), 3.82 (ddd, J = 8.1, 5.1, 3.4 Hz, 2H), 3.42-3.32 (m, 2H), 2.79-2.71 (m, 1H), 2.36 (s, 3H). | 257 |
| 111a | 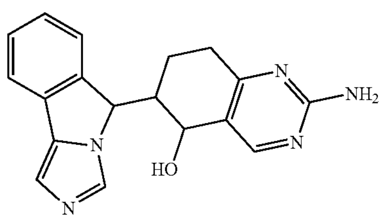 [SMILES: Nc1ncc2c(n1)CCC(C1c3ccccc3-c3cncn31)C2O] | (500 MHz, DMSO-$d_6$) δ 8.21 (s, 1H), 8.19 (s, 1H), 7.65 (d, J = 1.6 Hz, 1H), 7.63 (s, 1H), 7.42 (t, J = 7.5 Hz, 1H), 7.33 (td, J = 7.6, 1.1 Hz, 1H), 7.27 (s, 1H), 6.47 (s, 2H), 5.69 (d, J = 5.6 Hz, 1H), 5.58 (d, J = 2.3 Hz, 1H), 4.92 (dd, J = 5.5, 3.4 Hz, 1H), 2.49-2.44 (m, 1H), 2.43-2.34 (m, 2H), 1.55 (qd, J = 12.7, 5.7 Hz, 1H), 0.96 (d, J = 12.4 Hz, 1H). | 320.2 |
| 111b | 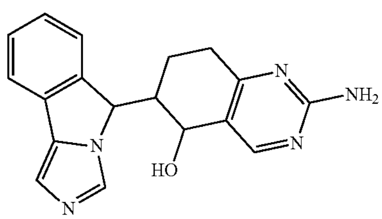 | (500 MHz, DMSO-$d_6$) δ 8.73 (s, 1H), 8.35 (s, 1H), 7.77 (d, J = 7.5 Hz, 1H), 7.61 (s, 1H), 7.57 (d, J = 7.6 Hz, 1H), 7.51 (t, J = 7.5 Hz, 1H), 7.48-7.40 (m, 1H), 6.41 (s, 2H), 5.94 (s, 1H), 5.81 (d, J = 7.5 Hz, 1H), 4.84-4.74 (m, 1H), 2.49-2.34 (m, 3H), 1.07-0.95 (m, 2H). | 320.2 |
| 111c | 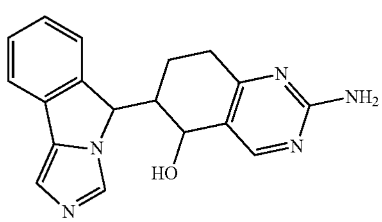 | (500 MHz, DMSO-$d_6$) δ 8.34 (s, 1H), 7.99 (s, 1H), 7.65 (d, J = 7.6 Hz, 1H), 7.61 (d, J = 7.6 Hz, 1H), 7.41 (t, J = 7.5 Hz, 1H), 7.28 (td, J = 7.6, 1.2 Hz, 1H), 7.21 (s, 1H), 6.37 (s, 2H), 5.94 (d, J = 7.1 Hz, 1H), 5.77 (d, J = 3.2 Hz, 1H), 4.85 (dd, J = 10.3, 7.1 Hz, 1H), 2.49-2.41 (m, 2H), 2.40-2.31 (m, 1H), 0.91-0.79 (m, 2H). | 320.2 |
| 111d | 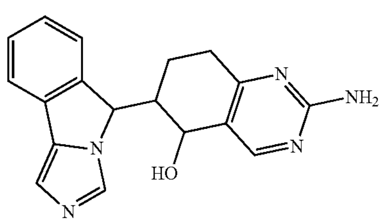 | (500 MHz, DMSO-$d_6$) δ 8.19 (s, 1H), 7.99 (s, 1H), 7.61 (dt, J = 7.7, 0.9 Hz, 1H), 7.60-7.57 (m, 1H), 7.42-7.36 (m, 1H), 7.28 (td, J = 7.5, 1.2 Hz, 1H), 7.11 (s, 1H), 6.46 (s, 2H), 5.63 (d, J = 5.7 Hz, 1H), 5.51-5.46 (m, 1H), 4.90 (dd, J = 5.5, 3.2 Hz, 1H), 2.48-2.44 (m, 1H), 2.43-2.31 (m, 2H), 1.58 (tt, J = 12.7, 6.3 Hz, 1H), 0.98 (d, J = 9.2 Hz, 1H). | 320.2 |

TABLE 2-continued

| Ex. # | Structure | $^{1}$H NMR | MS $(M + H)^+$ |
|---|---|---|---|
| 111e | 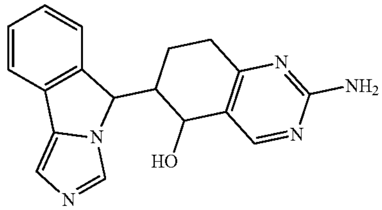 [SMILES: Nc1ncc2c(n1)CCC(C1c3ccccc3-c3cncn31)C2O] | (500 MHz, DMSO-$d_6$) δ 8.13 (s, 1H), 7.97 (s, 1H), 7.73 (dd, J = 7.7, 1.0 Hz, 1H), 7.61 (d, J = 7.5 Hz, 1H), 7.41-7.36 (m, 1H), 7.25 (td, J = 7.6, 1.2 Hz, 1H), 7.13 (s, 1H), 6.44 (s, 2H), 5.39 (d, J = 5.2 Hz, 1H), 5.37 (d, J = 5.7 Hz, 1H), 4.71 (d, J = 5.9 Hz, 1H), 2.65-2.56 (m, 1H), 2.06-1.98 (m, 2H), 1.77-1.70 (m, 1H). | 320.2 |
| 111f | 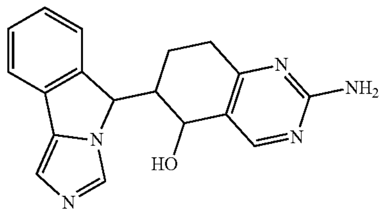 | (500 MHz, DMSO-$d_6$) δ 8.38 (s, 1H), 7.94 (s, 1H), 7.64-7.60 (m, 1H), 7.48 (dd, J = 7.6, 1.0 Hz, 1H), 7.41 (t, J = 7.5 Hz, 1H), 7.31 (td, J = 7.5, 1.1 Hz, 1H), 7.17 (s, 1H), 6.38 (s, 2H), 5.94 (d, J = 7.3 Hz, 1H), 5.76 (d, J = 1.8 Hz, 1H), 4.89 (dd, J = 10.3, 7.4 Hz, 1H), 2.42 (dd, J = 11.8, 6.1 Hz, 1H), 2.39-2.26 (m, 2H), 0.86 (ddt, J = 12.2, 9.2, 4.4 Hz, 1H), 0.79 (dt, J = 12.7, 6.1 Hz, 1H). | 320.2 |
| 111g | 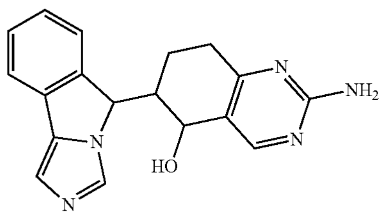 [SMILES: Nc1ncc2c(n1)CCC(C1c3ccccc3-c3cncn31)C2O] | (500 MHz, DMSO-$d_6$) δ 8.34 (s, 1H), 7.90 (s, 1H), 7.63 (d, J = 7.6 Hz, 1H), 7.60 (d, J = 7.7 Hz, 1H), 7.40 (t, J = 7.5 Hz, 1H), 7.26 (td, J = 7.6, 1.1 Hz, 1H), 7.16 (s, 1H), 6.37 (s, 2H), 5.93 (d, J = 7.1 Hz, 1H), 5.75 (d, J = 3.2 Hz, 1H), 4.84 (dd, J = 10.3, 7.1 Hz, 1H), 2.45 (q, J = 9.6, 9.2 Hz, 1H), 2.36 (dt, J = 17.9, 4.0 Hz, 1H), 0.83 (dd, J = 9.5, 4.4 Hz, 2H). | 320.2 |
| 112a | 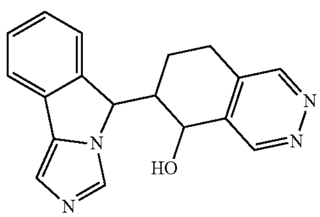 [SMILES: OC1c2cnncc2CCC1C1c2ccccc2-c2cncn21] | $^{1}$H NMR (400 MHz, $CD_3OD$) δ 9.30 (s, 1H), 8.88 (d, J = 1.0 Hz, 1H), 8.30 (s, 1H), 7.78-7.69 (m, 1H), 7.60-7.34 (m, 4H), 5.97 (d, J = 1.5 Hz, 1H), 5.04 (d, J = 10.8 Hz, 1H), 2.75 (dd, J = 8.7, 3.9 Hz, 2H), 2.66-2.50 (m, 1H), 1.36-1.08 (m, 2H). | 305.3 |
| 112b | 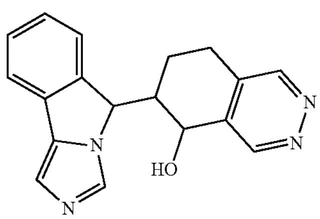 [SMILES: OC1c2cnncc2CCC1C1c2ccccc2-c2cncn21] | The same as 112a. | 305.3 |
| 112c | 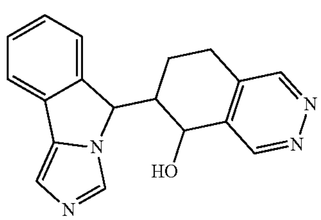 [SMILES: OC1c2cnncc2CCC1C1c2ccccc2-c2cncn21] | 1H NMR (400 MHz, $CD_3OD$) δ 9.29 (s, 1H), 8.86 (d, J = 1.1 Hz, 1H), 7.93 (s, 1H), 7.66 (dd, J = 13.1, 7.7 Hz, 2H), 7.51-7.39 (m, 1H), 7.33 (td, J = 7.6, 1.2 Hz, 1H), 7.21 (s, 1H), 5.91 (d, J = 3.2 Hz, 1H), 5.09 (d, J = 11.0 Hz, 1H), 2.79-2.57 (m, 3H), 1.19-1.04 (m, 2H). | 305.3 |
| 112d | 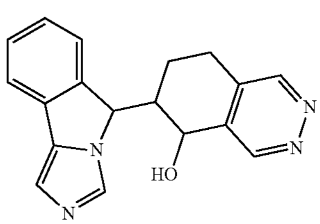 [SMILES: OC1c2cnncc2CCC1C1c2ccccc2-c2cncn21] | The same as 112c. | 305.4 |

TABLE 2-continued

| Ex. # | Structure | $^1$H NMR | MS $(M + H)^+$ |
|---|---|---|---|
| 112e | 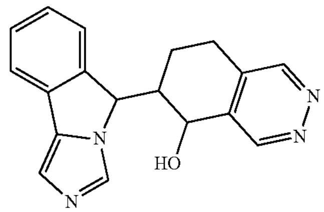 [SMILES: OC1c2cnncc2CCC1C1c2ccccc2-c2cncn21] | $^1$H NMR (400 MHz, $CD_3OD$) δ 9.06-8.92 (m, 2H), 8.04 (s, 1H), 7.76-7.60 (m, 2H), 7.43 (t, J = 7.6 Hz, 1H), 7.29 (td, J = 7.6, 1.2 Hz, 1H), 7.17 (s, 1H), 5.57 (d, J = 5.8 Hz, 1H), 4.88 (d, J = 3.6 Hz, 1H), 2.94 (dd, J = 18.4, 4.9, 2.6 Hz, 1H), 2.78-2.74 (m, 1H), 2.44-2.29 (m, 1H), 2.19-1.96 (m, 2H). | 305.3 |
| 112f | 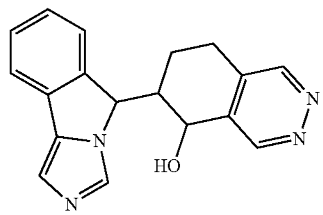 [SMILES: OC1c2cnncc2CCC1C1c2ccccc2-c2cncn21] | The same as 112e. | 305.3 |
| 112g | 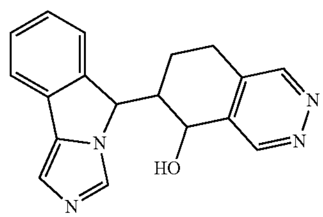 [SMILES: OC1c2cnncc2CCC1C1c2ccccc2-c2cncn21] | $^1$H NMR (400 MHz, $CD_3OD$) δ 9.14 (d, J = 1.1 Hz, 1H), 8.94 (d, J = 1.1 Hz, 1H), 8.08 (s, 1H), 7.67-7.53 (m, 2H), 7.49-7.28 (m, 2H), 7.15 (s, 1H), 5.65 (s, 1H), 5.17 (d, J = 3.7 Hz, 1H), 2.80 (dd, J = 18.2, 4.8 Hz, 1H), 2.57-2.55 (m, 2H), 1.56-1.54 (m, 1H), 1.23-1.10 (m, 1H). | 305.3 |
| 112h | 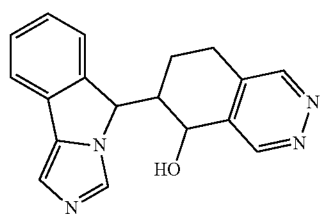 [SMILES: OC1c2cnncc2CCC1C1c2ccccc2-c2cncn21] | The same as 112g. | 305.2 |
| 113a | 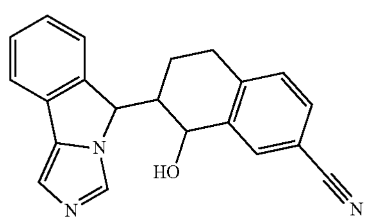 [SMILES: N#Cc1ccc2c(c1)C(O)C(C1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |
| 113b | 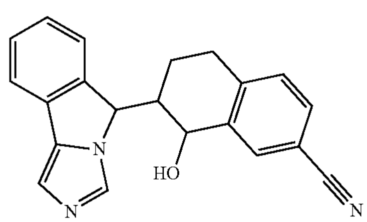 [SMILES: N#Cc1ccc2c(c1)C(O)C(C1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H, 1.47 (qd, J = 15.6, 5.4 Hz, 1H), 0.99 (d, J = 12.8 Hz, 1H). | 328.2 |
| 113c | 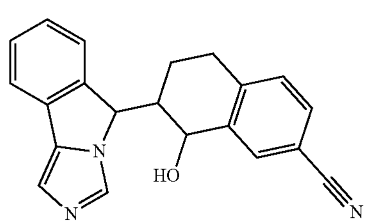 [SMILES: N#Cc1ccc2c(c1)C(O)C(C1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |

TABLE 2-continued

| Ex. # | Structure | $^1$H NMR | MS $(M + H)^+$ |
|---|---|---|---|
| 113d | 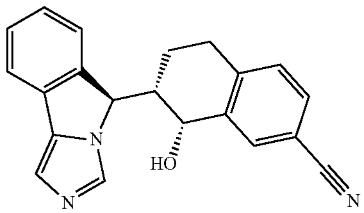 [SMILES: N#Cc1ccc2c(c1)[C@H](O)[C@H]([C@@H]1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |
| 113e | 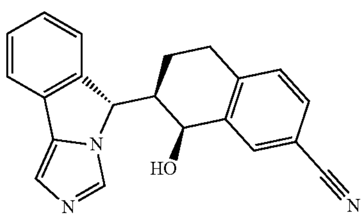 [SMILES: N#Cc1ccc2c(c1)[C@@H](O)[C@@H]([C@H]1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |
| 113f | 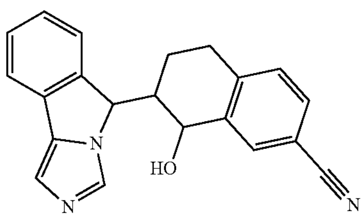 [SMILES: N#Cc1ccc2c(c1)C(O)C(C1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |
| 113g | 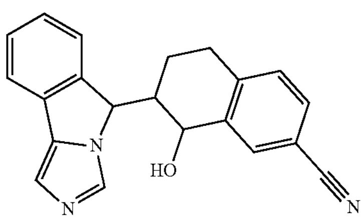 [SMILES: N#Cc1ccc2c(c1)C(O)C(C1c3ccccc3-c3cncn31)CC2] | $^1$H NMR (400 MHz, DMSO-d6) δ 7.94 (s, 1H), 7.84 (d, J = 1.8 Hz, 1H), 7.68-7.56 (m, 3H), 7.44-7.35 (m, 1H), 7.32-7.23 (m, 2H), 7.11 (s, 1H), 6.03 (d, J = 5.6 Hz, 1H), 5.54 (d, J = 2.3 Hz, 1H), 5.08-5.00 (m, 1H), 2.78 (dd, J = 17.9, 5.1 Hz, 1H), 2.68-2.52 (m, 1H), 1.47 (qd, J = 12.6, 5.4 Hz, 1H), 0.99 (d, J = 12.8 Hz, 1H). | 328.2 |
| 114a | 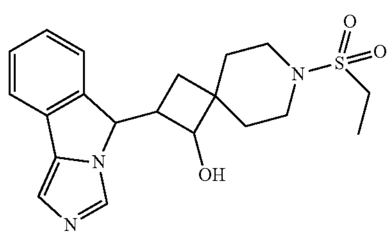 [SMILES: CCS(=O)(=O)N1CCC2(CC1)CC(C1c3ccccc3-c3cncn31)C2O] | $^1$H NMR (500 MHz, DMSO-$d_6$) δ 7.84 (s, 1H), 7.57 (d, J = 7.7 Hz, 2H), 7.36 (t, J = 7.6 Hz, 1H), 7.26 (td, J = 7.6, 1.0 Hz, 1H), 7.14 (s, 1H), 5.42 (d, J = 7.1 Hz, 1H), 5.31 (d, J = 6.4 Hz, 1H), 4.11-4.02 (m, 1H), 3.45-3.35 (m, 1H), 2.98 (q, J = 7.4 Hz, 3H), 2.87-2.77 (m, 1H), 2.47 (d, J = 7.6 Hz, 1H), 1.65 (dtd, J = 27.0, 11.9, 10.1, 5.1 Hz, 3H), 1.53 (d, J = 14.2 Hz, 1H), 1.46-1.34 (m, 1H), 1.17 (t, J = 7.4 Hz, 3H), 0.97 (t, J = 10.4 Hz, 1H). | 388.2 |
| 114b | 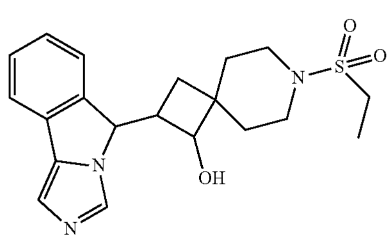 [SMILES: CCS(=O)(=O)N1CCC2(CC1)CC(C1c3ccccc3-c3cncn31)C2O] | $^1$H NMR (500 MHz, DMSO-$d_6$) δ 7.89 (s, 1H), 7.59 (d, J = 7.5 Hz, 1H), 7.45-7.33 (m, 2H), 7.24 (td, J = 7.6, 1.1 Hz, 1H), 7.10 (s, 1H), 5.38 (d, J = 8.6 Hz, 1H), 5.24 (d, J = 6.7 Hz, 1H), 3.95 (t, J = 7.2 Hz, 1H), 3.43-3.37 (m, 1H), 3.37-3.33 (m, 1H), 3.00 (q, J = 7.4 Hz, 3H), 2.93-2.86 (m, 1H), 2.32 (p, J = 9.4 Hz, 1H), 1.86 (t, J = 10.2 Hz, 1H), 1.71-1.59 (m, 2H), 1.58-1.44 (m, 3H), 1.19 (t, J = 7.4 Hz, 3H). | 388.2 |

TABLE 2-continued

| Ex. # | Structure | $^1$H NMR | MS $(M + H)^+$ |
|---|---|---|---|
| 114c | 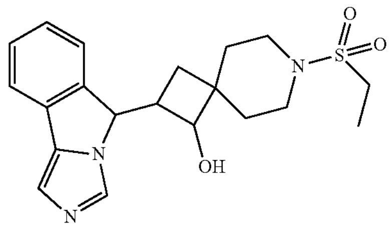 [SMILES: CCS(=O)(=O)N1CCC2(CC1)CC(C1c3ccccc3-c3cncn31)C2O] | $^1$H NMR (500 MHz, DMSO-$d_6$) δ 7.83 (s, 1H), 7.60 (d, J = 7.5 Hz, 1H), 7.48-7.31 (m, 2H), 7.22 (t, J = 7.2 Hz, 1H), 7.11 (s, 1H), 5.77 (d, J = 6.0 Hz, 1H), 5.40 (d, J = 10.9 Hz, 1H), 4.32-3.96 (m, 1H), 3.24 (td, J = 7.6, 7.0, 3.4 Hz, 1H), 3.20-3.13 (m, 1H), 3.09 (dt, J = 10.5, 4.7 Hz, 2H), 3.03 (q, J = 7.4 Hz, 2H), 2.34 (dt, J = 17.2, 9.2 Hz, 1H), 2.21 (t, J = 10.4 Hz, 1H), 1.91 (td, J = 9.9, 8.4, 3.1 Hz, 1H), 1.78 (ddd, J = 11.9, 8.0, 3.4 Hz, 1H), 1.68-1.60 (m, 1H), 1.58 (s, 2H), 1.21 (t, J = 7.4 Hz, 3H). | 388.2 |
| 114d | 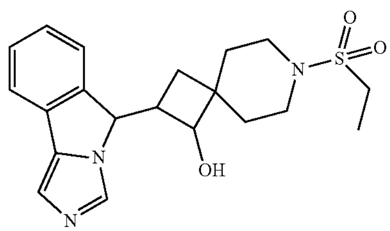 [SMILES: CCS(=O)(=O)N1CCC2(CC1)CC(C1c3ccccc3-c3cncn31)C2O] | $^1$H NMR (500 MHz, DMSO-$d_6$) δ 7.85 (s, 1H), 7.62 (d, J = 7.6 Hz, 1H), 7.58 (d, J = 7.5 Hz, 1H), 7.37 (dd, J = 9.3, 5.8 Hz, 1H), 7.26 (td, J = 7.6, 1.1 Hz, 1H), 7.13 (s, 1H), 5.81-5.69 (m, 1H), 5.45 (d, J = 8.8 Hz, 1H), 4.11 (td, J = 6.5, 3.1 Hz, 1H), 3.23 (ddd, J = 11.4, 7.3, 3.4 Hz, 1H), 3.20-3.13 (m, 1H), 3.07 (dt, J = 13.2, 6.0 Hz, 1H), 3.04-2.98 (m, 3H), 2.60-2.53 (m, 1H), 1.89 (q, J = 10.9 Hz, 1H), 1.81-1.68 (m, 2H), 1.58-1.51 (m, 3H), 1.19 (td, J = 7.4, 3.1 Hz, 3H). | 388.2 |
| 114e | 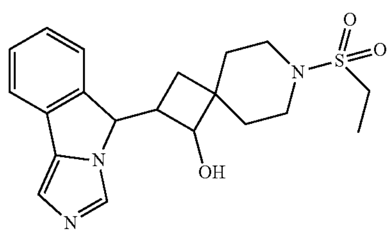 [SMILES: CCS(=O)(=O)N1CCC2(CC1)CC(C1c3ccccc3-c3cncn31)C2O] | $^1$H NMR (500 MHz, DMSO-$d_6$) δ 7.84 (s, 1H), 7.60 (d, J = 7.5 Hz, 1H), 7.46-7.32 (m, 2H), 7.22 (td, J = 7.6, 1.0 Hz, 1H), 7.12 (s, 1H), 5.77 (d, J = 5.9 Hz, 1H), 5.40 (d, J = 10.9 Hz, 1H), 4.08 (td, J = 6.1, 3.2 Hz, 1H), 3.25 (ddd, J = 11.0, 6.9, 3.2 Hz, 1H), 3.17 (dt, J = 11.0, 4.8 Hz, 1H), 3.09 (dt, J = 10.1, 4.8 Hz, 2H), 3.03 (q, J = 7.3 Hz, 2H), 2.34 (dt, J = 17.4, 9.6 Hz, 1H), 2.21 (t, J = 10.4 Hz, 1H), 1.91 (ddd, J = 11.3, 8.4, 3.1 Hz, 1H), 1.78 (ddd, J = 11.7, 8.0, 3.5 Hz, 1H), 1.66-1.60 (m, 1H), 1.58 (s, 2H), 1.21 (t, J = 7.4 Hz, 3H). | 388.2 |
| 114f | 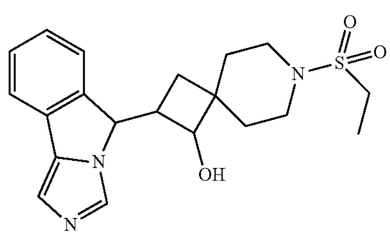 [SMILES: CCS(=O)(=O)N1CCC2(CC1)CC(C1c3ccccc3-c3cncn31)C2O] | $^1$H NMR (500 MHz, DMSO-$d_6$) δ 7.89 (s, 1H), 7.58 (d, J = 7.5 Hz, 1H), 7.45-7.33 (m, 2H), 7.23 (td, J = 7.6, 1.0 Hz, 1H), 7.10 (s, 1H), 5.38 (d, J = 8.6 Hz, 1H), 5.24 (d, J = 6.7 Hz, 1H), 3.95 (t, J = 7.2 Hz, 1H), 3.45-3.36 (m, 1H), 3.37-3.31 (m, 1H), 3.00 (q, J = 7.4 Hz, 3H), 2.94-2.84 (m, 1H), 2.36-2.28 (m, 1H), 1.85 (t, J = 10.2 Hz, 1H), 1.69-1.59 (m, 2H), 1.57-1.45 (m, 3H), 1.19 (t, J = 7.4 Hz, 3H). | 388.2 |
| 114g | 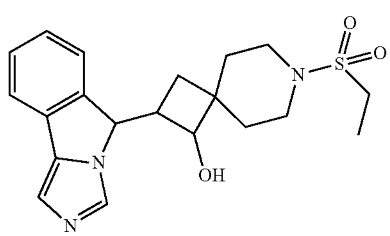 [SMILES: CCS(=O)(=O)N1CCC2(CC1)CC(C1c3ccccc3-c3cncn31)C2O] | $^1$H NMR (500 MHz, DMSO-$d_6$) δ 7.85 (s, 1H), 7.62 (d, J = 7.6 Hz, 1H), 7.58 (d, J = 7.5 Hz, 1H), 7.36 (t, J = 7.5 Hz, 1H), 7.25 (td, J = 7.6, 1.0 Hz, 1H), 7.12 (s, 1H), 5.81-5.68 (m, 1H), 5.45 (d, J = 8.8 Hz, 1H), 4.11 (td, J = 6.4, 3.1 Hz, 1H), 3.22 (ddd, J = 11.2, 7.2, 3.8 Hz, 1H), 3.19-3.12 (m, 1H), 3.07 (q, J = 6.6, 6.1 Hz, 1H), 3.04-2.96 (m, 3H), 2.60-2.52 (m, 1H), 1.93-1.85 (m, 1H), 1.82-1.71 (m, 2H), 1.55 (dt, J = 11.4, 5.7 Hz, 3H), 1.19 (t, J = 7.4 Hz, 3H). | 388.2 |
| 114h | 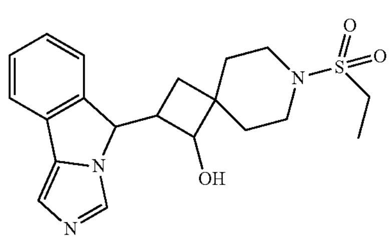 [SMILES: CCS(=O)(=O)N1CCC2(CC1)CC(C1c3ccccc3-c3cncn31)C2O] | $^1$H NMR (500 MHz, DMSO-$d_6$) δ 7.84 (s, 1H), 7.57 (d, J = 7.9 Hz, 2H), 7.36 (t, J = 7.6 Hz, 1H), 7.25 (t, J = 7.9 Hz, 1H), 7.13 (s, 1H), 5.41 (d, J = 7.0 Hz, 1H), 5.31 (d, J = 6.4 Hz, 1H), 4.14-3.96 (m, 1H), 3.42-3.35 (m, 1H), 3.31 (s, 1H), 2.97 (q, J = 7.4 Hz, 3H), 2.88-2.74 (m, 1H), 2.48-2.42 (m, 1H), 1.64 (dtd, J = 27.0, 12.0, 10.1, 5.2 Hz, 3H), 1.52 (d, J = 13.8 Hz, 1H), 1.40 (d, J = 13.4 Hz, 1H), 1.17 (t, J = 7.4 Hz, 3H), 0.96 (t, J = 10.4 Hz, 1H). | 388.2 |

TABLE 2-continued

| Ex. # | Structure | $^1$H NMR | MS (M + H)$^+$ |
|---|---|---|---|
| 115a | 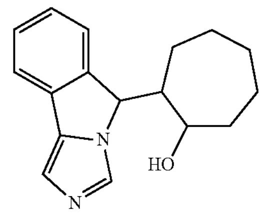 [SMILES: OC1CCCCCC1C1c2ccccc2-c2cncn21] | $^1$H NMR (400 MHz, DMSO-d6) δ 7.84 (s, 1H), 7.59 (dt, J = 7.7, 0.9 Hz, 1H), 7.45 (dt, J = 7.5, 0.9 Hz, 1H), 7.39-7.35 (m, 1H), 7.29 (td, J = 7.5, 1.2 Hz, 1H), 7.13 (s, 1H), 5.66-5.64 (m, 1H), 5.15 (d, J = 5.4 Hz, 1H), 3.92-3.86 (m, 1H), 2.13 (ddd, J = 9.6, 7.1, 2.4 Hz, 1H), 1.98-1.92 (m, 1H), 1.74-1.66 (m, 1H), 1.64-1.56 (m, 1H), 1.46-1.26 (m, 4H), 1.10-1.03 (m, 1H), 0.59-0.45 (m, 2H). | 335 |
| 115b | 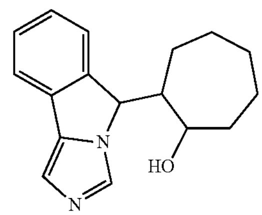 [SMILES: OC1CCCCCC1C1c2ccccc2-c2cncn21] | $^1$H NMR (400 MHz, DMSO-d6) δ 7.89 (s, 1H), 7.60 (dd, J = 7.5, 1.0 Hz, 1H), 7.53 (dd, J = 7.8, 1.0 Hz, 1H), 7.39-7.35 (m, 1H), 7.27-7.23 (m, 1H), 7.12 (s, 1H), 5.65 (d, J = 3.3 Hz, 1H), 5.10 (d, J = 4.7 Hz, 1H), 3.90-3.85 (m, 1H), 2.29 (ddt, J = 9.4, 6.2, 2.8 Hz, 1H), 1.89 (ddq, J = 10.2, 6.4, 1.9 Hz, 1H), 1.68-1.57 (m, 2H), 1.50-1.44 (m, 1H), 1.35 (tdd, J = 8.3, 4.4, 2.6 Hz, 2H), 1.29-1.23 (m, 1H), 1.13-1.06 (m, 1H), 0.51 (q, J = 4.1, 3.0 Hz, 2H). | 336 |
| 115c | 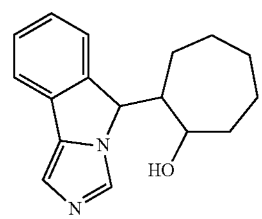 [SMILES: OC1CCCCCC1C1c2ccccc2-c2cncn21] | $^1$H NMR (400 MHz, DMSO-d6) δ 7.84 (s, 1H), 7.59 (d, J = 7.5 Hz, 1H), 7.45 (d, J = 7.4 Hz, 1H), 7.37 (t, J = 7.5 Hz, 1H), 7.31-7.27 (m, 1H), 7.13 (s, 1H), 5.66-5.65 (m, 1H), 5.15 (d, J = 5.4 Hz, 1H), 3.92-3.87 (m, 1H), 2.13 (ddd, J = 9.6, 7.1, 2.4 Hz, 1H), 1.98-1.92 (m, 1H), 1.74-1.67 (m, 1H), 1.61 (ddq, J = 10.9, 5.6, 2.3 Hz, 1H), 1.46-1.28 (m, 4H), 1.06 (dq, J = 13.9, 4.3, 3.7 Hz, 1H), 0.56 (tt, J = 6.5, 3.2 Hz, 1H), 0.52-0.44 (m, 1H). | 337 |
| 115d | 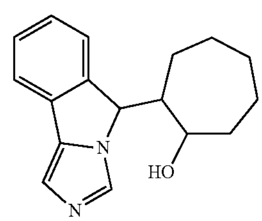 [SMILES: OC1CCCCCC1C1c2ccccc2-c2cncn21] | $^1$H NMR (400 MHz, DMSO-d6) δ 7.89 (s, 1H), 7.60 (dd, J = 7.5, 1.0 Hz, 1H), 7.53 (dd, J = 7.6, 1.1 Hz, 1H), 7.39-7.35 (m, 1H), 7.12 (s, 1H), 5.65 (d, J = 3.2 Hz, 1H), 5.09 (d, J = 4.9 Hz, 1H), 3.87 (dt, J = 6.7, 1.8 Hz, 1H), 2.29 (td, J = 5.9, 5.0, 2.7 Hz, 1H), 1.89 (dtd, J = 8.3, 4.5, 2.3 Hz, 1H), 1.67-1.57 (m, 2H), 1.48 (dt, J = 7.7, 3.0 Hz, 1H), 1.36 (dtd, J = 8.1, 4.4, 2.5 Hz, 2H), 1.26 (ddd, J = 9.1, 5.1, 2.5 Hz, 1H), 1.13-1.07 (m, 1H), 0.52-0.49 (m, 2H). | 338 |
| 116a | 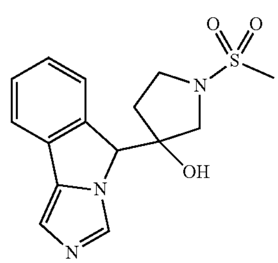 [SMILES: CS(=O)(=O)N1CCC(O)(C2c3ccccc3-c3cncn32)C1] | (400 MHz, DMSO-$d_6$) δ 7.85 (s, 1H), 7.59 (ddd, J = 9.6, 7.6, 0.9 Hz, 2H), 7.44-7.37 (m, 1H), 7.26 (td, J = 7.6, 1.2 Hz, 1H), 7.15 (s, 1H), 5.48 (s, 1H), 5.47 (s, 1H), 3.50 (d, J = 11.1 Hz, 1H), 3.34 (d, J = 4.6 Hz, 4H), 2.84 (s, 3H), 2.07 (dt, J = 12.7, 9.8 Hz, 1H), 1.92-1.81 (m, 1H). | 320.1 |
| 116b | 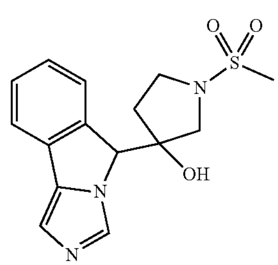 [SMILES: CS(=O)(=O)N1CCC(O)(C2c3ccccc3-c3cncn32)C1] | (400 MHz, DMSO-$d_6$) δ 7.90 (s, 1H), 7.61 (dt, J = 7.7, 1.0 Hz, 1H), 7.51 (dq, J = 7.7, 0.9 Hz, 1H), 7.44-7.38 (m, 1H), 7.28 (td, J = 7.6, 1.2 Hz, 1H), 7.14 (s, 1H), 5.48 (s, 1H), 5.39 (s, 1H), 3.47 (d, J = 10.9 Hz, 1H), 3.41-3.34 (m, 2H), 3.19 (dd, J = 11.0, 1.5 Hz, 1H), 2.83 (s, 3H), 2.20 (ddd, J = 12.7, 10.8, 8.8 Hz, 1H), 2.13-2.03 (m, 1H). | 320.1 |

TABLE 2-continued

| Ex. # | Structure | $^1$H NMR | MS (M + H)$^+$ |
|---|---|---|---|
| 116c | 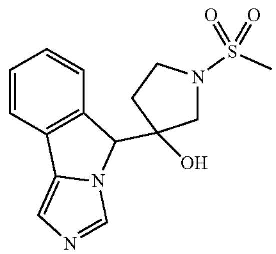 [SMILES: CS(=O)(=O)N1CCC(O)(C2c3ccccc3-c3cncn32)C1] | (400 MHz, DMSO-$d_6$) δ 7.90 (d, J = 0.7 Hz, 1H), 7.61 (dt, J = 7.5, 0.9 Hz, 1H), 7.51 (dq, J = 7.7, 0.9 Hz, 1H), 7.41 (tdd, J = 7.6, 1.1, 0.6 Hz, 1H), 7.28 (td, J = 7.6, 1.2 Hz, 1H), 7.14 (s, 1H), 5.48 (s, 1H), 5.39 (s, 1H), 3.47 (d, J = 10.9 Hz, 1H), 3.42-3.33 (m, 2H), 3.22-3.16 (m, 1H), 2.83 (s, 3H), 2.20 (ddd, J = 12.7, 10.7, 8.7 Hz, 1H), 2.13-2.04 (m, 1H). | 320.1 |
| 116d | 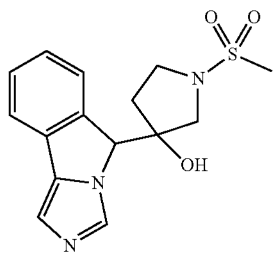 [SMILES: CS(=O)(=O)N1CCC(O)(C2c3ccccc3-c3cncn32)C1] | (400 MHz, DMSO-$d_6$) δ 7.85 (s, 1H), 7.60 (ddt, J = 9.5, 7.7, 0.8 Hz, 2H), 7.41 (tt, J = 7.5, 0.8 Hz, 1H), 7.26 (td, J = 7.6, 1.2 Hz, 1H), 7.15 (s, 1H), 5.49 (s, 1H), 5.48 (s, 1H), 3.50 (d, J = 11.0 Hz, 1H), 3.34 (t, J = 4.8 Hz, 3H), 2.85 (s, 3H), 2.12-2.01 (m, 1H), 1.92-1.82 (m, 1H). | 320.1 |
| 117a | 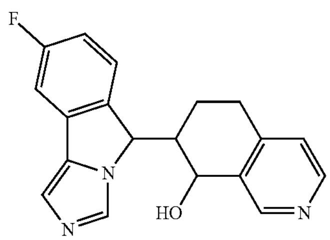 | $^1$H NMR (400 MHz, $CD_3OD$) δ 8.79 (s, 1H), 8.28 (dd, J = 5.2, 0.8 Hz, 1H), 8.05 (s, 1H), 7.55-7.39 (m, 2H), 7.28 (s, 1H), 7.17-7.03 (m, 2H), 5.90 (d, J = 1.8 Hz, 1H), 5.09 (d, J = 10.7 Hz, 1H), 2.78-2.67 (m, 2H), 2.55-2.39 (m, 1H), 1.23-0.91 (m, 2H). | 322.3 |
| 117b | 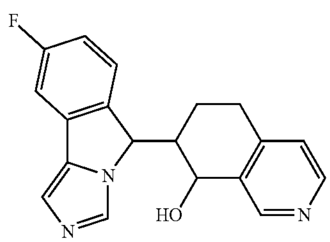 | The same as 117a. | 322.2 |
| 118a | 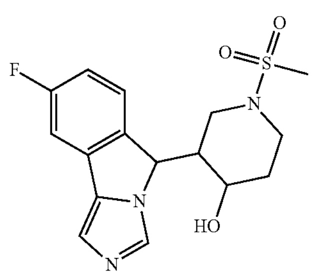 [SMILES: CS(=O)(=O)N1CCC(O)C(C2c3ccc(F)cc3-c3cncn32)C1] | $^1$H NMR (400 MHz, DMSO-$d_6$) δ 8.04 (s, 1H), 7.59-7.47 (m, 2H), 7.19 (s, 1H), 7.11 (ddd, J = 9.5, 8.5, 2.6 Hz, 1H), 5.69 (d, J = 3.5 Hz, 1H), 5.43 (d, J = 5.3 Hz, 1H), 3.72 (tt, J = 10.2, 4.7 Hz, 1H), 3.52-3.44 (m, 1H), 2.77-2.63 (m, 5H), 2.45 (ddt, J = 10.9, 7.6, 3.8 Hz, 1H), 2.03-1.94 (m, 2H), 1.62-1.47 (m, 1H). | 352 |
| 118b | 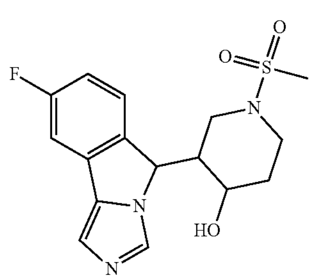 [SMILES: CS(=O)(=O)N1CCC(O)C(C2c3ccc(F)cc3-c3cncn32)C1] | $^1$H NMR (400 MHz, DMSO-$d_6$) δ 7.89 (s, 1H), 7.62-7.56 (m, 1H), 7.51 (dd, J = 9.0, 2.5 Hz, 1H), 7.21 (s, 1H), 7.14 (ddd, J = 9.6, 8.4, 2.5 Hz, 1H), 5.76-5.70 (m, 1H), 5.56 (dd, J = 5.7, 1.2 Hz, 1H), 3.91-3.78 (m, 1H), 3.53-3.47 (m, 1H), 2.83-2.64 (m, 5H), 2.31 (ddt, J = 11.1, 6.5, 3.4 Hz, 1H), 2.10-2.00 (m, 1H), 1.83 (t, J = 11.6 Hz, 1H), 1.66-1.51 (m, 1H). | 352 |

TABLE 2-continued

| Ex. # | Structure | $^1$H NMR | MS (M + H)$^+$ |
|---|---|---|---|
| 118c | 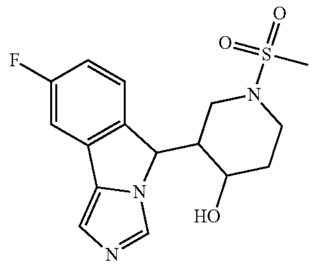 [SMILES: CS(=O)(=O)N1CCC(O)C(C2c3ccc(F)cc3-c3cncn32)C1] | $^1$H NMR (400 MHz, DMSO-$d_6$) δ 7.89 (s, 1H), 7.59 (ddd, J = 8.5, 5.1, 0.9 Hz, 1H), 7.51 (dd, J = 9.0, 2.5 Hz, 1H), 7.21 (s, 1H), 7.14 (ddd, J = 9.5, 8.4, 2.5 Hz, 1H), 5.73 (t, J = 1.7 Hz, 1H), 5.56 (d, J = 5.7 Hz, 1H), 3.85 (dp, J = 10.3, 5.0 Hz, 1H), 3.50 (ddq, J = 12.1, 4.7, 2.5 Hz, 1H), 2.80 (ddd, J = 11.6, 3.7, 2.0 Hz, 1H), 2.72 (td, J = 12.6, 2.8 Hz, 1H), 2.66 (s, 3H), 2.36-2.25 (m, 1H), 2.11-2.00 (m, 1H), 1.83 (t, J = 11.6 Hz, 1H), 1.66-1.51 (m, 1H). | 352 |
| 118d | 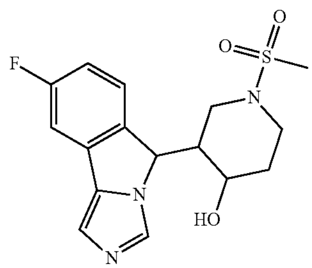 [SMILES: CS(=O)(=O)N1CCC(O)C(C2c3ccc(F)cc3-c3cncn32)C1] | $^1$H NMR (400 MHz, DMSO-$d_6$) δ 8.04 (s, 1H), 7.59-7.47 (m, 2H), 7.19 (s, 1H), 7.11 (ddd, J = 9.5, 8.4, 2.6 Hz, 1H), 5.69 (d, J = 3.7 Hz, 1H), 5.43 (d, J = 5.3 Hz, 1H), 3.72 (tt, J = 10.1, 4.7 Hz, 1H), 3.52-3.44 (m, 1H), 2.79-2.62 (m, 5H), 2.48-2.41 (m, 1H), 2.03-1.94 (m, 2H), 1.62-1.47 (m, 1H). | 352 |
| 119a | 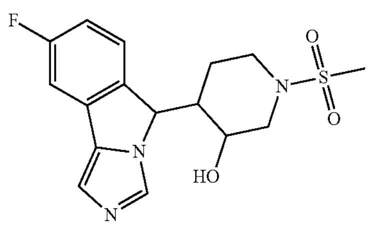 [SMILES: CS(=O)(=O)N1CCC(C2c3ccc(F)cc3-c3cncn32)C(O)C1] | $^1$H NMR (400 MHz, DMSO-$d_6$) δ 7.94 (s, 1H), 7.54-7.49 (m, 2H), 7.19 (s, 1H), 7.11 (ddd, J = 9.4, 8.4, 2.5 Hz, 1H), 5.76 (d, J = 4.8 Hz, 1H), 5.71 (d, J = 3.7 Hz, 1H), 3.73 (ddt, J = 12.1, 6.6, 4.7 Hz, 2H), 3.35 (ddt, J = 4.5, 3.0, 0.7 Hz, 1H), 2.84 (s, 3H), 2.56-2.53 (m, 1H), 2.28 (h, J = 6.5, 5.4 Hz, 1H), 0.70 (dd, J = 13.3, 3.4 Hz, 1H), 0.52 (qd, J = 12.7, 4.6 Hz, 1H). | 352 |
| 119b | 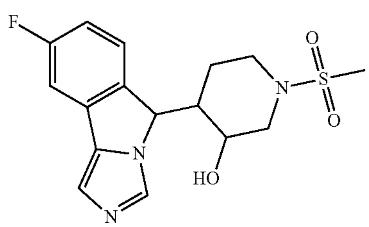 [SMILES: CS(=O)(=O)N1CCC(C2c3ccc(F)cc3-c3cncn32)C(O)C1] | $^1$H NMR (400 MHz, DMSO-$d_6$) δ 7.94 (s, 1H), 7.56-7.47 (m, 2H), 7.19 (s, 1H), 7.14-7.08 (m, 1H), 5.76 (d, J = 4.8 Hz, 1H), 5.71 (d, J = 3.6 Hz, 1H), 3.78-3.67 (m, 2H), 3.35 (dt, J = 4.2, 2.3 Hz, 1H), 2.84 (s, 3H), 2.56-2.51 (m, 1H), 2.28 (tt, J = 10.2, 3.7 Hz, 1H), 0.70 (dd, J = 13.4, 3.3 Hz, 1H), 0.52 (qd, J = 12.7, 4.5 Hz, 1H). | 352 |
| 119c | 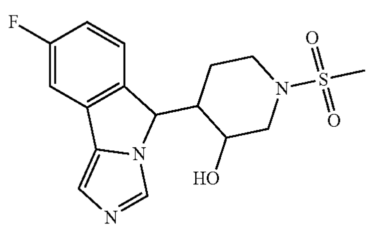 [SMILES: CS(=O)(=O)N1CCC(C2c3ccc(F)cc3-c3cncn32)C(O)C1] | $^1$H NMR (400 MHz, DMSO-$d_6$) δ 7.91 (s, 1H), 7.50 (ddd, J = 8.4, 4.6, 1.4 Hz, 2H), 7.21 (s, 1H), 7.12 (ddd, J = 9.5, 8.4, 2.5 Hz, 1H), 5.79 (d, J = 5.1 Hz, 1H), 5.72 (d, J = 2.0 Hz, 1H), 3.86-3.73 (m, 2H), 3.35 (ddd, J = 4.1, 2.4, 1.3 Hz, 1H), 2.84 (s, 3H), 2.59-2.52 (m, 2H), 2.19-2.08 (m, 1H), 0.87-0.79 (m, 1H), 0.44 (qd, J = 12.7, 4.6 Hz, 1H). | 352 |
| 120a | 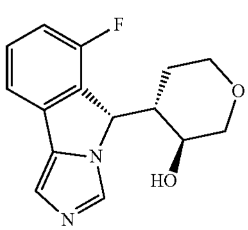 [SMILES: O[C@@H]1COCC[C@H]1[C@H]1c2c(F)cccc2-c2cncn21] | $^1$H NMR (500 MHz, DMSO-$d_6$) δ 7.90 (s, 1H), 7.52-7.41 (m, 2H), 7.22 (s, 1H), 7.17-7.05 (m, 1H), 5.95 (d, J = 2.4 Hz, 1H), 5.57 (d, J = 5.9 Hz, 1H), 3.90 (dd, J = 10.6, 4.9 Hz, 1H), 3.71 (tt, J = 10.4, 5.3 Hz, 1H), 3.60 (dd, J = 11.4, 4.6 Hz, 1H), 3.19-3.09 (m, 1H), 3.05 (dd, J = 10.7, 9.8 Hz, 1H), 2.28 (s, 1H), 0.82-0.68 (m, 1H), 0.45 (qd, J = 12.7, 4.8 Hz, 1H). | 275 |

TABLE 2-continued

| Ex. # | Structure | $^1$H NMR | MS $(M + H)^+$ |
|---|---|---|---|
| 120b | 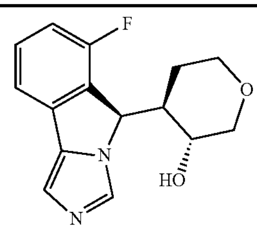 | $^1$H NMR (500 MHz, DMSO-$d_6$) δ 7.90 (s, 1H), 7.54-7.41 (m, 2H), 7.22 (s, 1H), 7.17-7.07 (m, 1H), 5.95 (d, J = 2.3 Hz, 1H), 5.57 (d, J = 5.9 Hz, 1H), 3.90 (dd, J = 10.7, 4.9 Hz, 1H), 3.71 (tt, J = 10.4, 5.4 Hz, 1H), 3.60 (dd, J = 11.4, 4.6 Hz, 1H), 3.20-3.09 (m, 1H), 3.05 (dd, J = 10.7, 9.8 Hz, 1H), 2.28 (s, 1H), 0.82-0.65 (m, 1H), 0.45 (qd, J = 12.7, 4.9 Hz, 1H). | 275 |
| 120c | 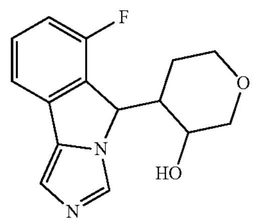 [SMILES: OC1COCCC1C1c2c(F)cccc2-c2cncn21] | $^1$H NMR (500 MHz, DMSO-$d_6$) δ 7.95 (s, 1H), 7.56-7.39 (m, 2H), 7.19 (s, 1H), 7.16-7.06 (m, 1H), 5.87 (d, J = 2.4 Hz, 1H), 5.13 (d, J = 5.4 Hz, 1H), 3.80 (dd, J = 10.6, 5.0 Hz, 1H), 3.65 (dd, J = 11.2, 4.2 Hz, 1H), 3.56 (tt, J = 10.1, 5.0 Hz, 1H), 3.22-3.08 (m, 1H), 2.93 (td, J = 10.3, 1.8 Hz, 1H), 2.37-2.26 (m, 1H), 1.01-0.79 (m, 2H). | 275 |
| 120d | 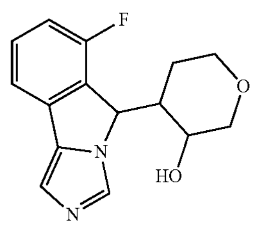 [SMILES: OC1COCCC1C1c2c(F)cccc2-c2cncn21] | $^1$H NMR (500 MHz, DMSO-$d_6$) δ 7.95 (s, 1H), 7.54-7.39 (m, 2H), 7.19 (d, J = 1.2 Hz, 1H), 7.16-7.05 (m, 1H), 5.87 (d, J = 2.3 Hz, 1H), 5.13 (d, J = 5.3 Hz, 1H), 3.80 (dd, J = 10.6, 5.0 Hz, 1H), 3.65 (dd, J = 11.0, 4.0 Hz, 1H), 3.56 (tt, J = 10.3, 5.2 Hz, 1H), 3.13 (td, J = 11.5, 2.7 Hz, 1H), 3.01-2.88 (m, 1H), 1.00-0.76 (m, 2H). | 275 |
| 121a | 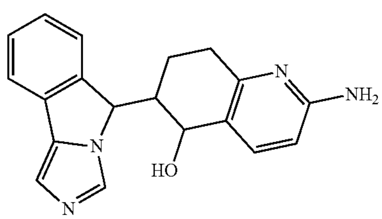 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121b | 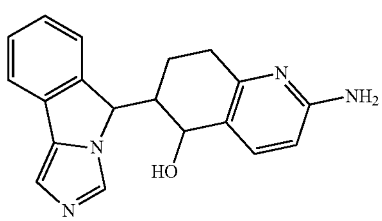 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121c | 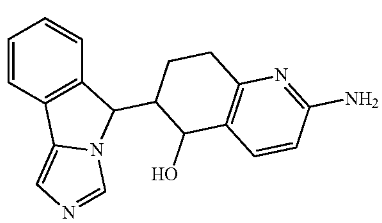 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121d | 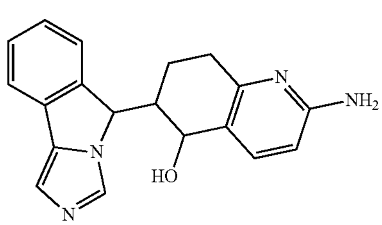 | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |

TABLE 2-continued

| Ex. # | Structure | $^1$H NMR | MS $(M + H)^+$ |
|---|---|---|---|
| 121e | 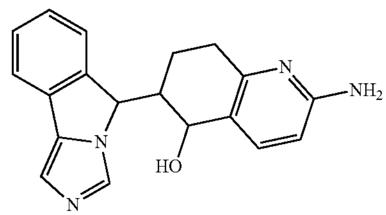 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121f | 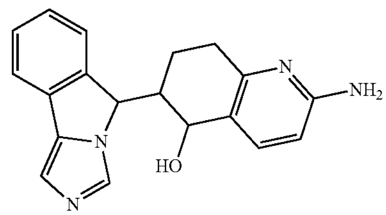 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121g | 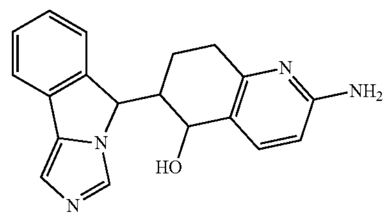 [SMILES: Nc1ccc2c(n1)CCC(C1c3ccccc3-c3cncn31)C2O] | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 121h | 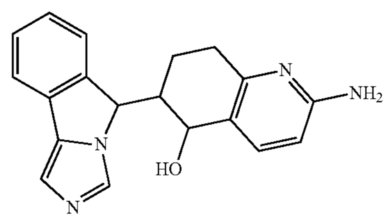 | (400 MHz, DMSO-$d_6$) δ 7.96 (s, 1H), 7.69-7.59 (m, 2H), 7.48 (dq, J = 7.6, 0.9 Hz, 1H), 7.41 (tt, J = 7.6, 0.9 Hz, 1H), 7.32 (td, J = 7.5, 1.1 Hz, 1H), 7.18 (s, 1H), 6.37 (d, J = 8.5 Hz, 1H), 5.84 (s, 2H), 5.78-5.74 (m, 2H), 4.89-4.78 (m, 1H), 2.47-2.23 (m, 3H), 1.28-1.22 (m, 2H). | 319.3 |
| 122a | 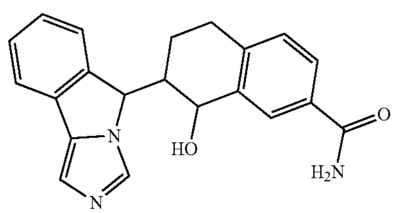 [SMILES: NC(=O)c1ccc2c(c1)C(O)C(C1c3ccccc3-c3cncn31)CC2] | $^1$H NMR (400 MHz, DMSO-$d_6$) δ 8.22 (dd, J = 1.9, 0.9 Hz, 1H), 7.95 (t, J = 0.6 Hz, 1H), 7.90 (s, 1H), 7.69-7.61 (m, 2H), 7.48 (dq, J = 7.6, 0.9 Hz, 1H), 7.46-7.37 (m, 1H), 7.31 (td, J = 7.5, 1.1 Hz, 1H), 7.24 (s, 1H), 7.18 (s, 1H), 7.06 (d, J = 7.9 Hz, 1H), 6.06 (d, J = 7.8 Hz, 1H), 5.83 (d, J = 1.9 Hz, 1H), 5.04-4.85 (m, 1H), 3.51-3.39 (m, 1H), 2.65-2.56 (m, 2H), 2.45-2.32 (m, 1H), 1.30-1.19 (m, 1H). | 346.2 |
| 122b | 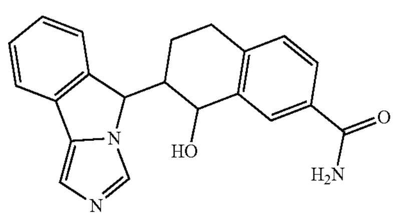 [SMILES: NC(=O)c1ccc2c(c1)C(O)C(C1c3ccccc3-c3cncn31)CC2] | $^1$H NMR (400 MHz, DMSO-$d_6$) δ 8.27-8.19 (m, 1H), 7.95 (s, 1H), 7.90 (s, 1H), 7.69-7.60 (m, 2H), 7.48 (dq, J = 7.5, 0.9 Hz, 1H), 7.41 (tt, J = 7.7, 0.9 Hz, 1H), 7.31 (td, J = 7.5, 1.2 Hz, 1H), 7.26 (d, J = 10.9 Hz, 1H), 7.06 (d, J = 8.0 Hz, 1H), 6.06 (d, J = 7.8 Hz, 1H), 5.83 (d, J = 2.0 Hz, 1H), 4.97-4.90 (m, 1H), 4.33 (t, J = 5.1 Hz, 1H), 3.44 (qd, J = 7.0, 5.1 Hz, 1H), 2.61 (dd, J = 8.9, 4.6 Hz, 2H), 2.06-1.90 (m, 2H). | 346.2 |
| 122c | 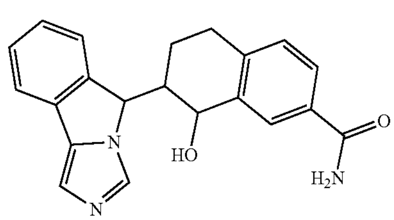 [SMILES: NC(=O)c1ccc2c(c1)C(O)C(C1c3ccccc3-c3cncn31)CC2] | $^1$H NMR (400 MHz, DMSO-$d_6$) δ 7.98-7.94 (m, 2H), 7.91 (s, 1H), 7.70 (dd, J = 8.0, 1.9 Hz, 1H), 7.64 (dq, J = 7.6, 0.9 Hz, 1H), 7.59 (dt, J = 7.6, 0.9 Hz, 1H), 7.42-7.36 (m, 1H), 7.29 (td, J = 7.5, 1.2 Hz, 2H), 7.16-7.08 (m, 2H), 5.85 (d, J = 6.1 Hz, 1H), 5.56-5.50 (m, 1H), 5.01 (dd, J = 6.1, 3.6 Hz, 1H), 2.75 (dd, J = 17.5, 5.1 Hz, 1H), 2.61-2.53 (m, 1H), 2.43 (dq, J = 12.6, 3.1 Hz, 1H), 1.60-1.46 (m, 1H), 1.05-0.98 (m, 1H). | 346.2 |

TABLE 2-continued

| Ex. # | Structure | ¹H NMR | MS (M + H)⁺ |
| --- | --- | --- | --- |
| 122d | 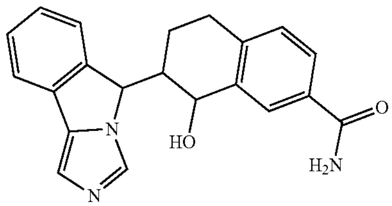 [SMILES: NC(=O)c1ccc2c(c1)C(O)C(C1c3ccccc3-c3cncn31)CC2] | ¹H NMR (400 MHz, DMSO-$d_6$) δ 8.20-8.13 (m, 1H), 7.91 (t, J = 0.6 Hz, 1H), 7.88 (s, 1H), 7.67-7.59 (m, 3H), 7.40 (tt, J = 7.6, 0.8 Hz, 1H), 7.26 (td, J = 7.6, 1.2 Hz, 2H), 7.17 (d, J = 0.5 Hz, 1H), 7.06 (d, J = 8.0 Hz, 1H), 6.08 (d, J = 7.6 Hz, 1H), 5.82 (d, J = 3.3 Hz, 1H), 4.95-4.85 (m, 1H), 2.66-2.54 (m, 3H), 0.91-0.80 (m, 2H). | 346.2 |
| 122e | 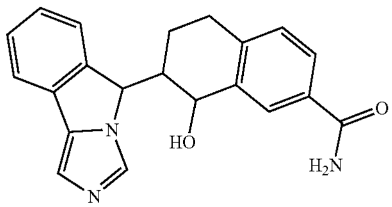 [SMILES: NC(=O)c1ccc2c(c1)C(O)C(C1c3ccccc3-c3cncn31)CC2] | ¹H NMR (400 MHz, DMSO-$d_6$) δ 7.99-7.93 (m, 2H), 7.91 (d, J = 2.5 Hz, 1H), 7.70 (dd, J = 8.0, 1.9 Hz, 1H), 7.61 (ddt, J = 16.2, 7.6, 0.9 Hz, 2H), 7.47-7.35 (m, 1H), 7.29 (td, J = 7.6, 1.2 Hz, 2H), 7.15-7.09 (m, 2H), 5.85 (d, J = 6.1 Hz, 1H), 5.54 (d, J = 2.5 Hz, 1H), 5.01 (dd, J = 6.2, 3.6 Hz, 1H), 3.44 (qd, J = 7.0, 5.1 Hz, 1H), 2.75 (dd, J = 17.3, 5.2 Hz, 1H), 2.56 (dt, J = 11.3, 5.8 Hz, 1H), 2.44 (dt, J = 12.7, 3.1 Hz, 1H), 1.53 (tt, J = 12.7, 6.3 Hz, 1H). | 346.2 |
| 122f | 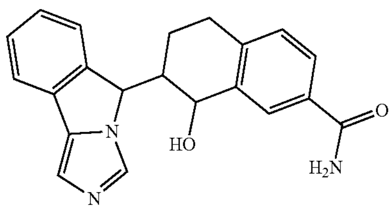 [SMILES: NC(=O)c1ccc2c(c1)C(O)C(C1c3ccccc3-c3cncn31)CC2] | ¹H NMR (400 MHz, DMSO-$d_6$) δ 8.01 (t, J = 0.7 Hz, 1H), 7.89 (d, J = 1.9 Hz, 1H), 7.87 (s, 1H), 7.75 (dq, J = 7.8, 0.9 Hz, 1H), 7.69 (dd, J = 7.9, 1.9 Hz, 1H), 7.62 (dt, J = 7.7, 0.9 Hz, 1H), 7.39 (tt, J = 7.6, 0.8 Hz, 1H), 7.25 (td, J = 7.6, 1.2 Hz, 2H), 7.18-7.10 (m, 2H), 5.58 (d, J = 5.9 Hz, 1H), 5.44 (d, J = 6.1 Hz, 1H), 4.82 (dd, J = 6.0, 3.2 Hz, 1H), 2.88 (dd, J = 17.4, 5.1 Hz, 1H), 2.73-2.60 (m, 1H), 2.11 (ddt, J = 12.2, 6.0, 2.9 Hz, 1H), 1.99 (qd, J = 12.4, 5.4 Hz, 1H), 1.80-1.71 (m, 1H). | 346.2 |
| 123a | 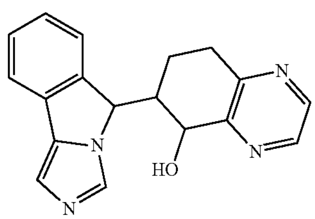 [SMILES: OC1c2nccnc2CCC1C1c2ccccc2-c2cncn21] | (400 MHz, DMSO-$d_6$) δ 8.55 (dd, J = 2.5, 0.9 Hz, 1H), 8.45 (dd, J = 2.5, 0.8 Hz, 1H), 7.94 (t, J = 0.6 Hz, 1H), 7.65 (dt, J = 7.5, 1.0 Hz, 1H), 7.55-7.49 (m, 1H), 7.46-7.39 (m, 1H), 7.32 (td, J = 7.5, 1.1 Hz, 1H), 7.19 (s, 1H), 6.10 (d, J = 5.5 Hz, 1H), 5.82-5.78 (m, 1H), 5.01 (dd, J = 10.7, 5.4 Hz, 1H), 2.85-2.65 (m, 2H), 2.59 (tdd, J = 10.7, 4.1, 2.2 Hz, 1H), 0.98 (ddd, J = 13.5, 8.5, 3.3 Hz, 2H). | 305.2 |
| 123b | 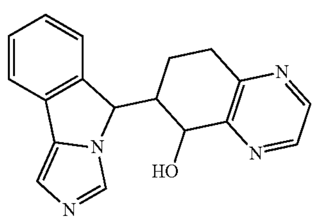 [SMILES: OC1c2nccnc2CCC1C1c2ccccc2-c2cncn21] | (400 MHz, DMSO-$d_6$) δ 8.55 (dd, J = 2.5, 0.9 Hz, 1H), 8.45 (dd, J = 2.5, 0.8 Hz, 1H), 7.94 (d, J = 0.6 Hz, 1H), 7.64 (dt, J = 7.6, 0.9 Hz, 1H), 7.55-7.48 (m, 1H), 7.46-7.39 (m, 1H), 7.32 (td, J = 7.5, 1.2 Hz, 1H), 7.19 (s, 1H), 6.10 (d, J = 5.5 Hz, 1H), 5.82-5.77 (m, 1H), 5.00 (dd, J = 10.8, 5.3 Hz, 1H), 2.85-2.65 (m, 2H), 2.64-2.54 (m, 1H), 1.04-0.94 (m, 2H). | 305.2 |
| 124a | 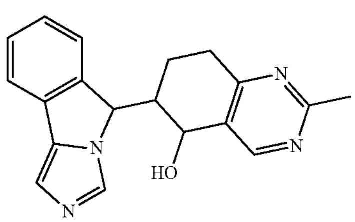 [SMILES: Cc1ncc2c(n1)CCC(C1c3ccccc3-c3cncn31)C2O] | Same as 1H NMR (400 MHz, Chloroform-d) δ 8.90 (d, J = 0.8 Hz, 1H), 7.86 (s, 1H), 7.49 (dt, J = 7.6, 0.9 Hz, 1H), 7.40-7.34 (m, 1H), 7.34-7.27 (m, 2H), 7.15 (s, 1H), 5.90 (d, J = 2.1 Hz, 1H), 5.06 (d, J = 10.8 Hz, 1H), 2.70 (s, 2H), 2.66-2.63 (m, 3H), 2.41 (dd, J = 12.7, 10.5 Hz, 1H), 1.23-1.14 (m, 1H), 0.94 (ddd, J = 22.1, 13.4, 9.3 Hz, 1H). | 319.4 |
| 124b | 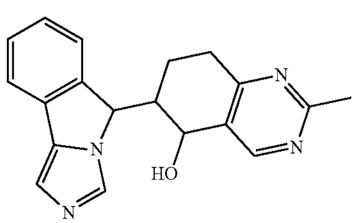 [SMILES: Cc1ncc2c(n1)CCC(C1c3ccccc3-c3cncn31)C2O] | Same as 124a | 319.4 |

TABLE 2-continued

| Ex. # | Structure | $^1$H NMR | MS (M + H)$^+$ |
|---|---|---|---|
| 125a | 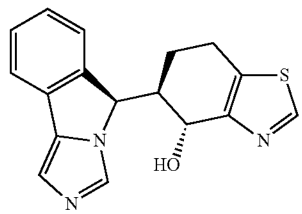 [SMILES: O[C@H]1c2ncsc2CC[C@@H]1[C@@H]1c2ccccc2-c2cncn21] | (400 MHz, DMSO-$d_6$) δ 8.94 (d, J = 0.6 Hz, 1H), 7.94 (s, 1H), 7.63 (dt, J = 7.7, 1.0 Hz, 1H), 7.49 (dq, J = 7.6, 1.0 Hz, 1H), 7.46-7.39 (m, 1H), 7.32 (td, J = 7.5, 1.2 Hz, 1H), 7.17 (s, 1H), 5.91 (d, J = 6.6 Hz, 1H), 5.77 (t, J = 1.4 Hz, 1H), 5.06 (t, J = 8.2 Hz, 1H), 2.69-2.55 (m, 2H), 2.48-2.42 (m, 1H), 1.03-0.86 (m, 2H). | 310.1 |
| 125b | 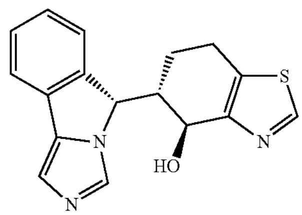 [SMILES: O[C@@H]1c2ncsc2CC[C@H]1[C@H]1c2ccccc2-c2cncn21] | (400 MHz, DMSO-$d_6$) δ 8.94 (d, J = 0.6 Hz, 1H), 7.94 (s, 1H), 7.63 (dt, J = 7.7, 1.0 Hz, 1H), 7.49 (dq, J = 7.6, 1.0 Hz, 1H), 7.46-7.39 (m, 1H), 7.32 (td, J = 7.5, 1.2 Hz, 1H), 7.17 (s, 1H), 5.91 (d, J = 6.6 Hz, 1H), 5.77 (t, J = 1.4 Hz, 1H), 5.06 (t, J = 8.2 Hz, 1H), 2.69-2.55 (m, 2H), 2.48-2.42 (m, 1H), 1.03-0.86 (m, 2H). | 310.1 |
| 126a | 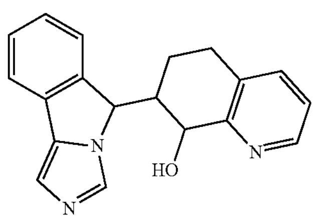 [SMILES: OC1c2ncccc2CCC1C1c2ccccc2-c2cncn21] | (400 MHz, DMSO-$d_6$) δ 8.48 (dd, J = 4.7, 1.6 Hz, 1H), 7.93 (s, 1H), 7.64 (dt, J = 7.5, 0.9 Hz, 1H), 7.52 (dq, J = 7.6, 1.0 Hz, 1H), 7.47 (ddd, J = 7.7, 1.7, 0.9 Hz, 1H), 7.45-7.39 (m, 1H), 7.32 (td, J = 7.5, 1.1 Hz, 1H), 7.23 (ddd, J = 7.7, 4.7, 0.7 Hz, 1H), 7.18 (s, 1H), 5.80 (d, J = 2.1 Hz, 1H), 5.72 (d, J = 4.1 Hz, 1H), 4.91 (dd, J = 10.6, 4.0 Hz, 1H), 2.70-2.58 (m, 2H), 2.58-2.52 (m, 1H), 0.95 (dtd, J = 9.7, 6.8, 6.3, 3.5 Hz, 1H), 0.91-0.80 (m, 1H). | 304.1 |
| 126b | 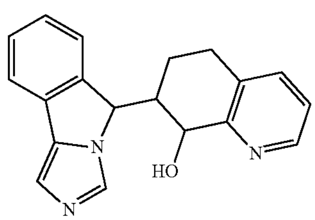 [SMILES: OC1c2ncccc2CCC1C1c2ccccc2-c2cncn21] | (400 MHz, DMSO-$d_6$) δ 8.48 (dd, J = 4.7, 1.7 Hz, 1H), 7.93 (t, J = 0.6 Hz, 1H), 7.64 (dt, J = 7.5, 1.0 Hz, 1H), 7.52 (dq, J = 7.6, 1.0 Hz, 1H), 7.47 (ddd, J = 7.7, 1.8, 0.9 Hz, 1H), 7.45-7.38 (m, 1H), 7.32 (td, J = 7.5, 1.2 Hz, 1H), 7.23 (ddd, J = 7.7, 4.7, 0.7 Hz, 1H), 7.18 (s, 1H), 5.85-5.77 (m, 1H), 5.71 (d, J = 4.1 Hz, 1H), 4.91 (dd, J = 10.5, 4.0 Hz, 1H), 2.71-2.59 (m, 2H), 2.59-2.54 (m, 1H), 1.01-0.79 (m, 2H). | 304.1 |
| 127a | 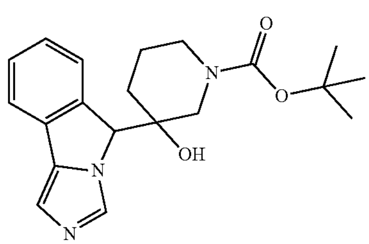 [SMILES: CC(C)(C)OC(=O)N1CCCC(O)(C2c3ccccc3-c3cncn32)C1] | (400 MHz, DMSO-$d_6$) δ 7.87 (s, 1H), 7.60 (d, J = 7.6 Hz, 2H), 7.43-7.36 (m, 1H), 7.29-7.22 (m, 1H), 7.13 (s, 1H), 5.25 (s, 1H), 5.22 (s, 1H), 3.87-3.68 (m, 2H), 3.04-2.85 (m, 1H), 1.72-1.59 (m, 1H), 1.39 (s, 9H), 1.35-1.25 (m, 1H), 1.21-1.08 (m, 2H). | 356.4 |
| 127b | 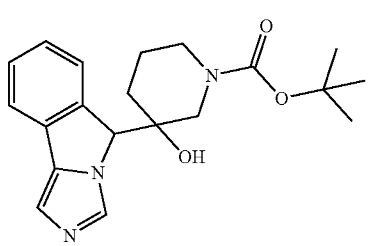 [SMILES: CC(C)(C)OC(=O)N1CCCC(O)(C2c3ccccc3-c3cncn32)C1] | (400 MHz, DMSO-$d_6$) δ 7.89 (s, 1H), 7.61 (dd, J = 12.4, 7.7 Hz, 2H), 7.40 (t, J = 7.6 Hz, 1H), 7.26 (t, J = 7.6 Hz, 1H), 7.14 (s, 1H), 5.22 (s, 2H), 3.85-3.72 (m, 1H), 1.86-1.46 (m, 3H), 1.45-1.38 (m, 1H), 1.34 (s, 9H). | 356.4 |

TABLE 2-continued

| Ex. # | Structure | $^1$H NMR | MS $(M + H)^+$ |
|---|---|---|---|
| 127c | 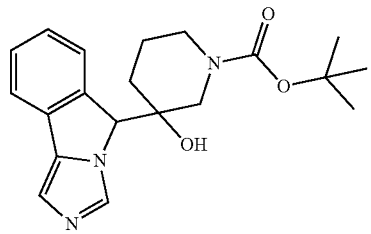 [SMILES: CC(C)(C)OC(=O)N1CCCC(O)(C2c3ccccc3-c3cncn32)C1] | (400 MHz, DMSO-$d_6$) δ 7.87 (s, 1H), 7.60 (d, J = 7.6 Hz, 2H), 7.43-7.36 (m, 1H), 7.29-7.22 (m, 1H), 7.13 (s, 1H), 5.25 (s, 1H), 5.22 (s, 1H), 3.87-3.68 (m, 2H), 3.04-2.85 (m, 1H), 1.72-1.59 (m, 1H), 1.39 (s, 9H), 1.35-1.25 (m, 1H), 1.21-1.08 (m, 2H). | 356.4 |
| 128 | 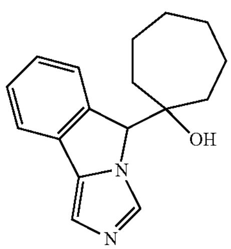 [SMILES: OC1(C2c3ccccc3-c3cncn32)CCCCCC1] | $^1$H NMR (Chloroform-d, 400 MHz): δ (ppm) 7.96 (s, 1H), 7.53 (t, J = 6.8 Hz, 2H), 7.37 (t, J = 7.6 Hz, 1H), 7.22 (td, J = 7.6, 1.0 Hz, 1H), 7.15 (s, 1H), 5.30 (s, 1H), 5.10 (s, 1H), 2.11-1.78 (m, 3H), 1.69-1.40 (m, 5H), 1.38-1.14 (m, 3H), 1.14-1.01 (m, 1H). | 269.2 |
| 129a | 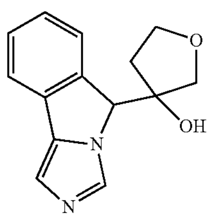 [SMILES: OC1(C2c3ccccc3-c3cncn32)CCOC1] | (400 MHz, DMSO-$d_6$) δ 7.84 (t, J = 0.6 Hz, 1H), 7.61-7.54 (m, 2H), 7.42-7.36 (m, 1H), 7.24 (d, J = 1.2 Hz, 1H), 7.12 (s, 1H), 5.46 (s, 1H), 5.45 (s, 1H), 3.96 (d, J = 9.3 Hz, 1H), 3.79 (ddd, J = 9.1, 8.1, 6.7 Hz, 1H), 3.71-3.62 (m, 2H), 1.91 (dt, J = 12.7, 8.9 Hz, 1H), 1.82-1.72 (m, 1H). | 243.1 |
| 129b | 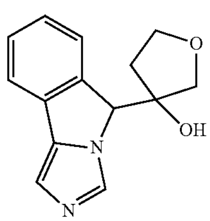 [SMILES: OC1(C2c3ccccc3-c3cncn32)CCOC1] | (400 MHz, DMSO-$d_6$) δ 7.87 (d, J = 0.7 Hz, 1H), 7.58 (s, 1H), 7.50 (d, J = 0.9 Hz, 1H), 7.39 (s, 1H), 7.24 (d, J = 1.2 Hz, 1H), 7.12 (s, 1H), 5.46 (s, 1H), 5.40 (s, 1H), 3.85-3.76 (m, 2H), 3.73 (td, J = 8.4, 3.2 Hz, 1H), 3.56 (dd, J = 9.3, 0.7 Hz, 1H), 2.09 (ddd, J = 12.7, 9.4, 8.6 Hz, 1H), 1.98-1.89 (m, 1H). | 243.1 |
| 129c | 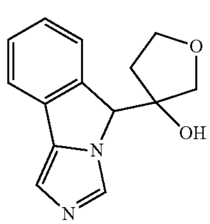 [SMILES: OC1(C2c3ccccc3-c3cncn32)CCOC1] | (400 MHz, DMSO-$d_6$) δ 7.87 (t, J = 0.7 Hz, 1H), 7.59 (dt, J = 7.6, 1.0 Hz, 1H), 7.51 (dq, J = 7.7, 0.9 Hz, 1H), 7.39 (tdd, J = 7.5, 1.1, 0.6 Hz, 1H), 7.24 (td, J = 7.6, 1.2 Hz, 1H), 7.12 (s, 1H), 5.47 (s, 1H), 5.40 (s, 1H), 3.86-3.76 (m, 2H), 3.73 (td, J = 8.4, 3.2 Hz, 1H), 3.56 (dd, J = 9.2, 0.7 Hz, 1H), 2.09 (ddd, J = 12.7, 9.4, 8.6 Hz, 1H), 1.94 (dddd, J = 12.8, 6.5, 3.3, 0.8 Hz, 1H). | 243.1 |
| 129d | 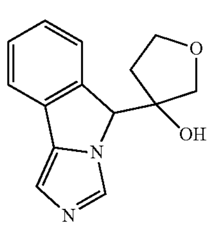 [SMILES: OC1(C2c3ccccc3-c3cncn32)CCOC1] | (400 MHz, DMSO-$d_6$) δ 7.84 (t, J = 0.6 Hz, 1H), 7.62-7.54 (m, 2H), 7.42-7.36 (m, 1H), 7.24 (td, J = 7.6, 1.2 Hz, 1H), 7.12 (s, 1H), 5.46 (s, 1H), 5.45 (s, 1H), 3.96 (d, J = 9.3 Hz, 1H), 3.79 (ddd, J = 9.2, 8.1, 6.7 Hz, 1H), 3.71-3.62 (m, 2H), 1.91 (dt, J = 12.7, 8.9 Hz, 1H), 1.80-1.72 (m, 1H). | 243.1 |

TABLE 2-continued

| Ex. # | Structure | $^1$H NMR | MS (M + H)$^+$ |
|---|---|---|---|
| 130a | 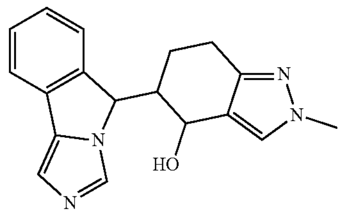 [SMILES: Cn1cc2c(n1)CCC(C1c3ccccc3-c3cncn31)C2O] | $^1$H NMR (400 MHz, DMSO-$d_6$) δ 7.89 (s, 1H), 7.65-7.61 (m, 1H), 7.59-7.53 (m, 2H), 7.41-7.36 (m, 1H), 7.25 (td, J = 7.6, 1.2 Hz, 1H), 7.16 (s, 1H), 5.74 (d, J = 2.9 Hz, 1H), 5.63 (d, J = 6.6 Hz, 1H), 4.90 (dd, J = 10.1, 6.6 Hz, 1H), 3.74 (s, 3H), 2.42-2.18 (m, 3H), 0.83 (m, 2H) | 307 |
| 130b | 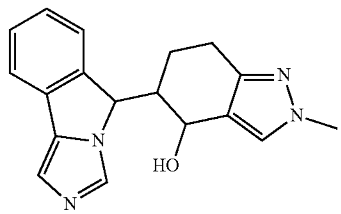 [SMILES: Cn1cc2c(n1)CCC(C1c3ccccc3-c3cncn31)C2O] | $^1$H NMR (400 MHz, DMSO-$d_6$) δ 7.99 (s, 1H), 7.59 (dt, J = 10.7, 2.8 Hz, 3H), 7.38 (t, J = 7.6 Hz, 1H), 7.28 (t, J = 7.7 Hz, 1H), 7.11 (dt, J = 2.3 Hz, 1H), 5.46 (s, 1H), 5.41 (dd, J = 5.9, 2.3 Hz, 1H), 5.02 (d, J = 4.4 Hz, 1H), 3.76 (d, J = 2.5 Hz, 3H), 2.34 (d, J = 12.2 Hz, 1H), 2.21 (t, J = 12.9 Hz, 1H), 1.48 (dd, J = 12.8, 5.0 Hz, 1H), 0.89 (d, J = 13.5 Hz, 1H). | 307 |
| 130c | 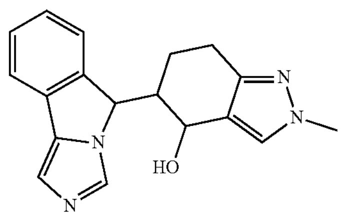 [SMILES: Cn1cc2c(n1)CCC(C1c3ccccc3-c3cncn31)C2O] | $^1$H NMR (400 MHz, DMSO-$d_6$) δ 7.96 (s, 1H), 7.77 (d, J = 7.7 Hz, 1H), 7.61 (d, J = 7.5 Hz, 1H), 7.54 (s, 1H), 7.37 (dd, J = 7.8, 6.8 Hz, 1H), 7.24 (td, J = 7.7, 1.0 Hz, 2H), 5.37 (s, 1H), 5.12 (d, J = 5.4 Hz, 1H), 4.83 (s, 1H), 3.74 (s, 3H), 2.63 (dd, J = 16.0, 4.6 Hz, 1H), 2.39-2.24 (m, 1H), 2.05 (d, J = 16.2 Hz, 1H), 1.91 (dq, J = 13.6, 8.5 Hz, 1H), 1.65 (s, 1H). | 307 |
| 130d | 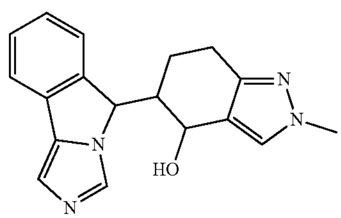 [SMILES: Cn1cc2c(n1)CCC(C1c3ccccc3-c3cncn31)C2O] | $^1$H NMR (400 MHz, DMSO-$d_6$) δ 7.93 (s, 1H), 7.62 (dd, J = 7.6, 0.9 Hz, 1H), 7.58 (s, 1H), 7.46 (dd, J = 7.5, 1.0 Hz, 1H), 7.43-7.38 (m, 1H), 7.31 (td, J = 7.5, 1.1 Hz, 1H), 7.17 (s, 1H), 5.74 (d, J = 1.6 Hz, 1H), 5.62 (d, J = 7.0 Hz, 1H), 4.93 (dd, J = 10.1, 7.1 Hz, 1H), 3.75 (s, 3H), 2.42-2.32 (m, 1H), 2.32-2.15 (m, 2H), 0.92-0.83 (m, 1H), 0.76 (qd, J = 12.5, 5.6 Hz, 1H). | 307 |
| 130e | 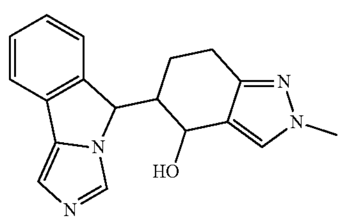 [SMILES: Cn1cc2c(n1)CCC(C1c3ccccc3-c3cncn31)C2O] | $^1$H NMR (400 MHz, DMSO-$d_6$) δ 7.93 (s, 1H), 7.65-7.57 (m, 2H), 7.46 (d, J = 7.6 Hz, 1H), 7.41 (t, J = 7.4 Hz, 1H), 7.31 (td, J = 7.6, 1.1 Hz, 1H), 7.17 (s, 1H), 5.74 (s, 1H), 5.62 (d, J = 7.0 Hz, 1H), 4.93 (dd, J = 10.1, 7.0 Hz, 1H), 3.75 (s, 3H), 3.29-3.23 (m, 1H), 2.37 (dd, J = 16.1, 5.0 Hz, 1H), 2.32-2.15 (m, 2H), 0.92-0.68 (m, 2H). | 307 |
| 130f | 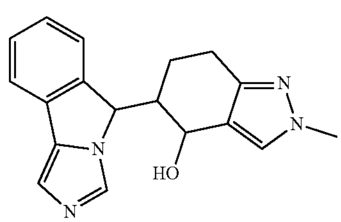 [SMILES: Cn1cc2c(n1)CCC(C1c3ccccc3-c3cncn31)C2O] | $^1$H NMR (400 MHz, DMSO-$d_6$) δ 7.77 (d, J = 7.7 Hz, 1H), 7.60 (d, J = 7.6 Hz, 1H), 7.54 (s, 1H), 7.37 (td, J = 7.5, 1.0 Hz, 1H), 7.24 (td, J = 7.6, 1.0 Hz, 2H), 5.37 (s, 1H), 5.12 (d, J = 5.5 Hz, 1H), 4.83 (s, 1H), 3.74 (s, 3H), 2.63 (dd, J = 16.1, 4.5 Hz, 1H), 2.41-2.26 (m, 1H), 2.03 (s, 1H), 1.92 (tt, J = 12.7, 6.3 Hz, 1H), 1.64 (d, J = 10.9 Hz, 1H). | 307 |
| 130g | 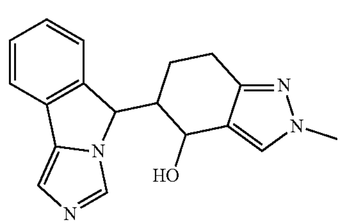 [SMILES: Cn1cc2c(n1)CCC(C1c3ccccc3-c3cncn31)C2O] | $^1$H NMR (400 MHz, DMSO-$d_6$) δ 7.98 (d, J = 0.7 Hz, 1H), 7.62-7.56 (m, 3H), 7.40-7.35 (m, 1H), 7.27 (td, J = 7.5, 1.2 Hz, 1H), 7.10 (s, 1H), 5.46 (d, J = 1.9 Hz, 1H), 5.41 (dd, J = 5.8, 0.5 Hz, 1H), 5.02 (dd, J = 5.7, 3.6 Hz, 1H), 3.76 (s, 3H), 2.37-2.30 (m, 1H), 2.27-2.16 (m, 1H), 1.48 (qd, J = 12.8, 5.5 Hz, 1H), 0.94-0.83 (m, 1H). | 307 |

TABLE 2-continued

| Ex. # | Structure | $^1$H NMR | MS $(M + H)^+$ |
| --- | --- | --- | --- |
| 130h | 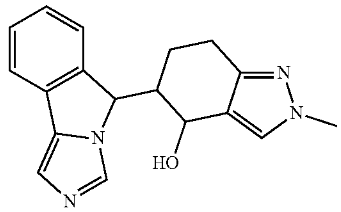 [SMILES: Cn1cc2c(n1)CCC(C1c3ccccc3-c3cncn31)C2O] | $^1$H NMR (400 MHz, DMSO-$d_6$) δ 7.91 (s, 1H), 7.64 (d, J = 7.5 Hz, 1H), 7.56 (d, J = 9.2 Hz, 2H), 7.42-7.36 (m, 1H), 7.25 (td, J = 7.5, 1.0 Hz, 2H), 5.72 (s, 1H), 5.63 (d, J = 6.6 Hz, 1H), 4.90 (dd, J = 9.9, 6.6 Hz, 1H), 3.74 (s, 3H), 2.39-2.24 (m, 3H), 0.82 (m, 2H). | 307 |
| 131a | 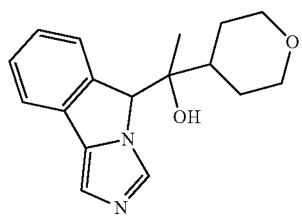 [SMILES: CC(O)(C1CCOCC1)C1c2ccccc2-c2cncn21] | $^1$H NMR (Chloroform-d, 400 MHz): δ (ppm) 7.85 (s, 1H), 7.65-7.54 (m, 2H), 7.41 (t, J = 7.6 Hz, 1H), 7.26 (td, J = 7.8, 1.2 Hz, 1H), 7.20 (s, 1H), 5.31 (s, 1H), 4.02 (d, J = 10.3 Hz, 1H), 3.91 (dd, J = 11.5, 4.4 Hz, 1H), 3.40-3.30 (m, 1H), 3.25 (td, J = 11.9, 2.2 Hz, 1H), 1.79-1.56 (m, 3H), 2.90 (s, 1H), 1.55-1.41 (m, 1H), 1.21 (d, J = 13.2 Hz, 1H), 1.13 (s, 3H). | 285.2 |
| 131b | 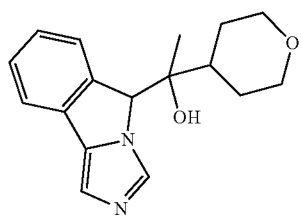 [SMILES: CC(O)(C1CCOCC1)C1c2ccccc2-c2cncn21] | $^1$H NMR (Chloroform-d, 400 MHz): δ (ppm) 8.01 (s, 1H), 7.58 (d, J = 7.5 Hz, 1H), 7.42 (t, J = 7.7 Hz, 1H), 7.35 (d, J = 7.4 Hz, 1H), 7.32-7.24 (m, 1H), 7.20 (s, 1H), 5.42 (s, 1H), 4.25-4.17 (m, 1H), 4.17-4.08 (m, 1H), 3.65-3.44 (m, 3H), 2.17-2.05 (m, 2H), 1.97 (d, J = 11.0 Hz, 1H), 1.87 (dq, J = 19.2, 7.6, 6.1 Hz, 1H), 1.58 (d, J = 13.0 Hz, 1H), 0.58 (s, 3H). | 285.2 |
| 132 | 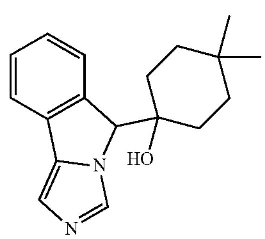 [SMILES: CC1(C)CCC(O)(C2c3ccccc3-c3cncn32)CC1] | 1H NMR (400 MHz, DMSO-d6) δ 7.86 (s, 1H), 7.60 (ddt, J = 9.1, 7.4, 0.9 Hz, 2H), 7.39 (ddd, J = 8.0, 7.4, 0.9 Hz, 1H), 7.26 (td, J = 7.6, 1.2 Hz, 1H), 7.13 (s, 1H), 5.11 (s, 1H), 5.04 (s, 1H), 1.69-1.51 (m, 2H), 1.44 (ddd, J = 13.3, 8.8, 2.7 Hz, 2H), 1.14-0.91 (m, 3H), 0.84 (s, 3H), 0.79 (d, J = 2.9 Hz, 1H), 0.63 (s, 3H). | 283.2 |
| 133a | 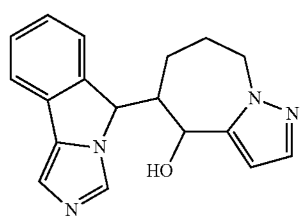 [SMILES: OC1c2ccnn2CCCC1C1c2ccccc2-c2cncn21] | $^1$H NMR (300 MHz, $CD_3OD$) δ 7.92 (s, 1H), 7.68-7.59 (m, 2H), 7.46-7.37 (m, 1H), 7.34-7.26 (m, 1H), 7.20 (d, J = 2.4 Hz, 1H), 7.12 (s, 1H), 5.98 (d, J = 2.1 Hz, 1H), 5.44 (d, J = 1.8 Hz, 1H), 4.75 (d, J = 1.2 Hz, 1H), 4.39-4.00 (m, 2H), 2.50-2.39 (m, 2H), 2.18-2.06 (m, 1H), 1.81-1.60 (m, 2H). | 307.3 |
| 133b | 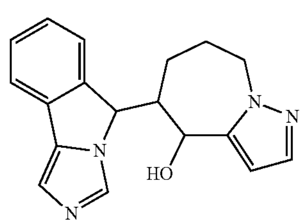 [SMILES: OC1c2ccnn2CCCC1C1c2ccccc2-c2cncn21] | The same as 133a. | 307.3 |
| 133c | 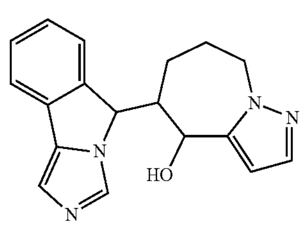 [SMILES: OC1c2ccnn2CCCC1C1c2ccccc2-c2cncn21] | $^1$H NMR (300 MHz, $CD_3OD$) δ 7.90 (s, 1H), 7.69-7.65 (m, 2H), 7.45-7.35 (m, 3H), 7.20 (s, 1H), 6.45 (d, J = 1.5 Hz, 1H), 6.04 (d, J = 3.6 Hz, 1H), 5.04 (d, J = 10.3 Hz, 1H), 4.38-4.26 (m, 1H), 3.93-3.81 (m, 1H), 2.59-2.42 (m, 1H), 1.87-1.71 (m, 1H), 1.49-1.27 (m, 1H), 1.08-0.82 (m, 2H). | 307.1 |

TABLE 2-continued

| Ex. # | Structure | $^1$H NMR | MS (M + H)$^+$ |
|---|---|---|---|
| 133d | 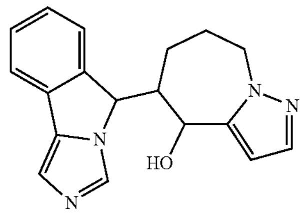 [SMILES: OC1c2ccnn2CCCC1C1c2ccccc2-c2cncn21] | The same as 133d. | 307.2 |
| 133e | 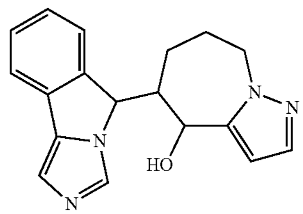 [SMILES: OC1c2ccnn2CCCC1C1c2ccccc2-c2cncn21] | $^1$H NMR (300 MHz, $CD_3OD$) δ 8.18 (s, 1H), 7.61-7.59 (m, 1H), 7.48-7.33 (m, 3H), 7.31 (d, J = 1.5 Hz, 1H), 7.17 (s, 1H), 6.34 (d, J = 1.5 Hz, 1H), 5.58 (d, J = 1.5 Hz, 1H), 5.40 (d, J = 10.2 Hz, 1H), 4.32-4.28 (m, 2H), 2.49-2.41 (m, 1H), 1.92-1.68 (m, 2H), 1.57-1.36 (m, 1H), 1.05-0.92 (m, 1H). | 307.1 |
| 133f | 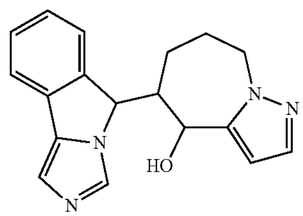 [SMILES: OC1c2ccnn2CCCC1C1c2ccccc2-c2cncn21] | $^1$H NMR (300 MHz, $CD_3OD$) δ 7.92 (s, 1H), 7.64-7.62 (m, 1H), 7.43-7.33 (m, 4H), 7.22 (s, 1H), 6.47 (d, J = 1.5 Hz, 1H), 6.00 (d, J = 1.5 Hz, 1H), 5.05 (d, J = 10.2 Hz, 1H), 4.30-4.28 (m, 1H), 3.98-3.89 (m, 1H), 2.41-2.32 (m, 1H), 1.70-1.66 (m, 1H), 1.42-1.16 (m, 2H), 0.99-0.81 (m, 1H). | 307.4 |
| 133g | 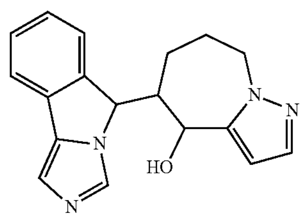 [SMILES: OC1c2ccnn2CCCC1C1c2ccccc2-c2cncn21] | The same as 133f. | 307.1 |
| 133h | 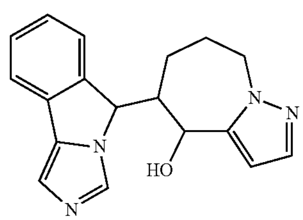 [SMILES: OC1c2ccnn2CCCC1C1c2ccccc2-c2cncn21] | The same as 133h. | 307.4 |
| 134 | 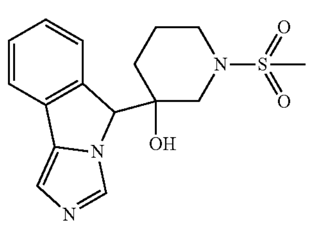 [SMILES: CS(=O)(=O)N1CCCC(O)(C2c3ccccc3-c3cncn32)C1] | $^1$H NMR (400 MHz, DMSO-$d_6$) 7.88 (s, 1H), 7.66 (dd, J = 7.6, 1.0 Hz, 1H), 7.63-7.59 (m, 1H), 7.44 7.38 (m, 1H), 7.30-7.24 (m, 1H), 7.15 (s, 1H), 5.50 5.48 (m, 1H), 5.34-5.31 (m, 1H), 3.53-3.47 (m, 1H), 2.93 (s, 3H), 2.71-2.60 (m, 1H), 1.86-1.75 (m, 1H), 1.53-1.41 (m, 1H), 1.18-1.10 (m, 2H). | 334.1 |
| 135a | 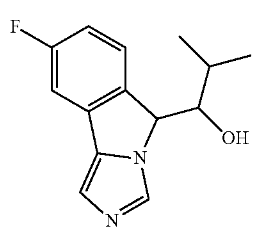 [SMILES: CC(C)C(O)C1c2ccc(F)cc2-c2cncn21] | $^1$H NMR (DMSO-$d_6$, 400 MHz): δ (ppm) 7.85 (d, J = 0.7 Hz, 1H), 7.56-7.43 (m, 2H), 7.16 (s, 1H), 7.06 (ddd, J = 9.6, 8.4, 2.5 Hz, 1H), 5.38 (d, J = 4.6 Hz, 1H), 5.26 (d, J = 5.8 Hz, 1H), 3.80-3.71 (m, 1H), 1.63 (dq, J = 13.4, 6.7 Hz, 1H), 0.84 (d, J = 6.8 Hz, 3H), 0.69 (d, J = 6.6 Hz, 3H). | 247.3 |

TABLE 2-continued

| Ex. # | Structure | $^1$H NMR | MS $(M + H)^+$ |
|---|---|---|---|
| 135b | 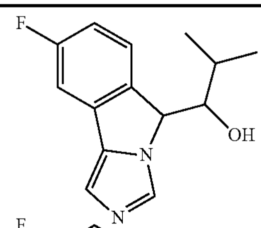 | $^1$H NMR (DMSO-$d_6$, 400 MHz): δ (ppm) 7.84 (s, 1H), 7.54-7.42 (m, 2H), 7.16 (s, 1H), 7.06 (ddd, J = 9.6, 8.4, 2.5 Hz, 1H), 5.33 (d, J = 4.8 Hz, 1H), 5.11 (d, J = 6.4 Hz, 1H), 3.48 (td, J = 6.5, 4.9 Hz, 1H), 1.89 (h, J = 6.6 Hz, 1H), 0.98 (d, J = 6.6 Hz, 3H), 0.94 (d, J = 6.8 Hz, 3H). | 247.3 |
| 135c | 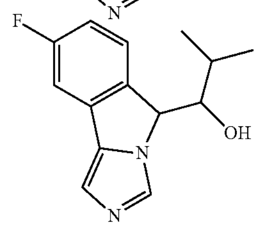 | Same as 135a | 247.3 |
| 135d | 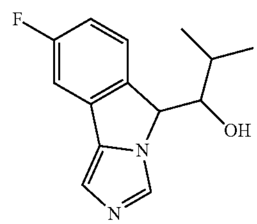 [SMILES: CC(C)C(O)C1c2ccc(F)cc2-c2cncn21] | Same as 135b | 247.3 |
| 136a | 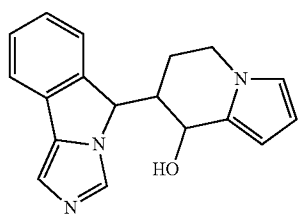 [SMILES: OC1c2cccn2CCC1C1c2ccccc2-c2cncn21] | (400 MHz, DMSO-$d_6$) δ 7.93 (d, J = 0.6 Hz, 1H), 7.63 (dt, J = 7.5, 1.0 Hz, 1H), 7.49 (dd, J = 7.5, 0.9 Hz, 1H), 7.44-7.39 (m, 1H), 7.33 (dd, J = 7.5, 1.2 Hz, 1H), 7.18 (s, 1H), 6.54-6.50 (m, 1H), 6.09 (ddd, J = 3.5, 1.8, 1.0 Hz, 1H), 6.02 (dd, J = 3.5, 2.6 Hz, 1H), 5.79 (d, J = 7.5 Hz, 1H), 5.76 (s, 1H), 4.96 (dd, J = 10.3, 7.4 Hz, 1H), 3.81-3.74 (m, 1H), 3.65-3.55 (m, 1H), 2.47-2.38 (m, 1H), 0.99 (dq, J = 9.0, 4.9 Hz, 2H). | 292.2 |
| 136b | 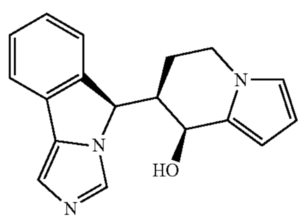 [SMILES: O[C@@H]1c2cccn2CC[C@@H]1[C@@H]1c2ccccc2-c2cncn21] | (400 MHz, DMSO-$d_6$) δ 7.94 (d, J = 0.7 Hz, 1H), 7.64 (dt, J = 7.6, 1.0 Hz, 1H), 7.59 (dt, J = 7.6, 1.0 Hz, 1H), 7.43-7.36 (m, 1H), 7.29 (td, J = 7.5, 1.2 Hz, 1H), 7.12 (s, 1H), 6.58 (dd, J = 2.6, 1.7 Hz, 1H), 6.04 (dd, J = 3.6, 1.7 Hz, 1H), 6.02 (dd, J = 3.5, 2.6 Hz, 1H), 5.63 (dd, J = 5.2, 0.7 Hz, 1H), 5.49 (d, J = 2.6 Hz, 1H), 5.10 (t, J = 4.4 Hz, 1H), 3.91 (ddd, J = 12.4, 5.6, 2.1 Hz, 1H), 3.59 (td, J = 12.3, 4.6 Hz, 1H), 1.82 (qd, J = 12.5, 5.7 Hz, 1H), 1.17-1.07 (m, 1H). | 292.2 |
| 136c | 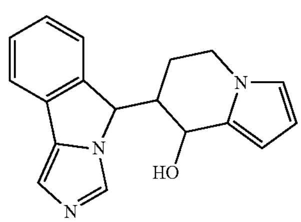 [SMILES: OC1c2cccn2CCC1C1c2ccccc2-c2cncn21] | (400 MHz, DMSO-$d_6$) δ 7.98 (d, J = 0.7 Hz, 1H), 7.74 (dq, J = 7.8, 0.9 Hz, 1H), 7.62 (dt, J = 7.6, 1.0 Hz, 1H), 7.41-7.36 (m, 1H), 7.25 (td, J = 7.6, 1.2 Hz, 1H), 7.14 (s, 1H), 6.59 (dd, J = 2.5, 1.9 Hz, 1H), 6.01-5.96 (m, 2H), 5.42 (d, J = 6.1 Hz, 1H), 5.39 (dd, J = 5.1, 0.7 Hz, 1H), 4.91 (ddd, J = 4.8, 3.3, 0.9 Hz, 1H), 4.05 (ddd, J = 12.4, 5.4, 1.8 Hz, 1H), 3.68 (td, J = 12.1, 4.6 Hz, 1H), 2.30-2.12 (m, 2H), 1.79 (d, J = 3.4 Hz, 1H). | 292.2 |
| 136d | 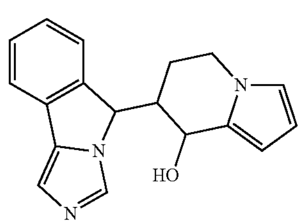 [SMILES: OC1c2cccn2CCC1C1c2ccccc2-c2cncn21] | (400 MHz, DMSO-$d_6$) δ 7.94 (s, 1H), 7.67-7.62 (m, 1H), 7.58 (dd, J = 7.6, 1.0 Hz, 1H), 7.44-7.38 (m, 1H), 7.26 (td, J = 7.6, 1.2 Hz, 1H), 7.19 (s, 1H), 6.51 (dd, J = 2.6, 1.8 Hz, 1H), 6.06 (ddd, J = 3.5, 1.8, 1.0 Hz, 1H), 6.00 (dd, J = 3.5, 2.6 Hz, 1H), 5.80 (d, J = 7.0 Hz, 1H), 5.76 (d, J = 3.2 Hz, 1H), 4.91 (dd, J = 10.4, 7.0 Hz, 1H), 3.79 (ddt, J = 11.3, 5.8, 2.9 Hz, 1H), 3.63 (td, J = 12.2, 4.7 Hz, 1H), 2.63-2.54 (m, 1H), 1.05 (ddt, J = 17.6, 12.2, 6.1 Hz, 1H), 0.99-0.89 (m, 1H). | 292.2 |

TABLE 2-continued

| Ex. # | Structure | $^1$H NMR | MS (M + H)$^+$ |
|---|---|---|---|
| 136e | 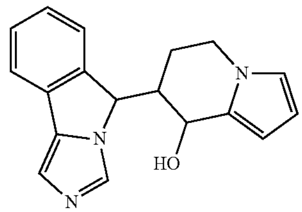 [SMILES: OC1c2cccn2CCC1C1c2ccccc2-c2cncn21] | (400 MHz, DMSO-$d_6$) δ 7.98 (s, 1H), 7.76-7.70 (m, 1H), 7.61 (dt, J = 7.6, 1.0 Hz, 1H), 7.42-7.35 (m, 1H), 7.24 (td, J = 7.6, 1.2 Hz, 1H), 7.13 (s, 1H), 6.59 (dd, J = 2.5, 1.9 Hz, 1H), 6.01-5.96 (m, 2H), 5.42 (d, J = 6.1 Hz, 1H), 5.39 (dd, J = 5.1, 0.7 Hz, 1H), 4.94-4.87 (m, 1H), 4.08-4.00 (m, 1H), 3.68 (td, J = 12.1, 4.6 Hz, 1H), 2.30-2.11 (m, 2H), 1.81 (d, J = 12.5 Hz, 1H). | 292.2 |
| 136f | 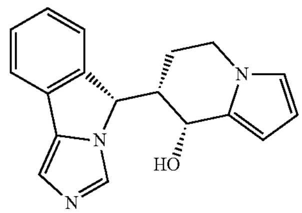 [SMILES: O[C@H]1c2cccn2CC[C@H]1[C@H]1c2ccccc2-c2cncn21] | (400 MHz, DMSO-$d_6$) δ 7.94 (d, J = 0.7 Hz, 1H), 7.64 (dd, J = 7.6, 0.9 Hz, 1H), 7.61-7.57 (m, 1H), 7.42-7.36 (m, 1H), 7.29 (td, J = 7.6, 1.2 Hz, 1H), 7.12 (s, 1H), 6.58 (dd, J = 2.6, 1.7 Hz, 1H), 6.03 (d, J = 1.7 Hz, 1H), 6.02 (dd, J = 3.5, 2.6 Hz, 1H), 5.63 (dd, J = 5.1, 0.7 Hz, 1H), 5.49 (d, J = 2.6 Hz, 1H), 5.10 (t, J = 4.2 Hz, 1H), 3.91 (ddd, J = 12.4, 5.6, 2.1 Hz, 1H), 3.59 (td, J = 12.3, 4.7 Hz, 1H), 1.83 (qd, J = 12.5, 5.7 Hz, 1H), 1.15-1.07 (m, 1H). | 292.2 |
| 136g | 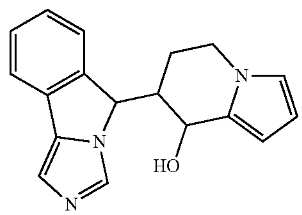 [SMILES: OC1c2cccn2CCC1C1c2ccccc2-c2cncn21] | (400 MHz, DMSO-$d_6$) δ 7.93 (d, J = 0.6 Hz, 1H), 7.63 (dt, J = 7.7, 1.0 Hz, 1H), 7.49 (dd, J = 7.5, 1.0 Hz, 1H), 7.45-7.39 (m, 1H), 7.33 (dd, J = 7.5, 1.2 Hz, 1H), 7.18 (s, 1H), 6.52 (dd, J = 2.6, 1.8 Hz, 1H), 6.09 (dq, J = 2.8, 0.9 Hz, 1H), 6.02 (dd, J = 3.5, 2.6 Hz, 1H), 5.79 (d, J = 7.4 Hz, 1H), 5.76 (d, J = 1.8 Hz, 1H), 5.00-4.91 (m, 1H), 3.78 (dt, J = 12.3, 3.9 Hz, 1H), 3.66-3.55 (m, 1H), 2.46-2.38 (m, 1H), 0.99 (dq, J = 9.2, 5.0 Hz, 2H). | 292.2 |
| 137a | 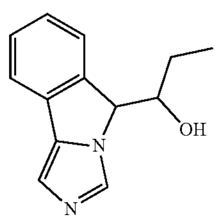 [SMILES: CCC(O)C1c2ccccc2-c2cncn21] | $^1$H NMR (DMSO-$d_6$, 400 MHz): δ (ppm) 7.85 (s, 1H), 7.61-7.50 (m, 2H), 7.37 (tdd, J = 7.5, 1.2, 0.6 Hz, 1H), 7.25 (td, J = 7.5, 1.2 Hz, 1H), 7.11 (s, 1H), 5.27 (s, 1H), 5.24 (s, 1H), 3.90-3.79 (m, 1H), 1.27 (qd, J = 7.8, 6.0 Hz, 2H), 0.88 (t, J = 7.4 Hz, 3H). | 215.2 |
| 137b | 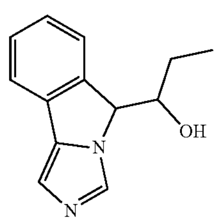 [SMILES: CCC(O)C1c2ccccc2-c2cncn21] | Same as 137a | 215.2 |
| 137c | 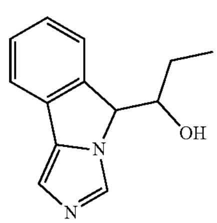 [SMILES: CCC(O)C1c2ccccc2-c2cncn21] | $^1$H NMR (DMSO-$d_6$, 400 MHz): δ (ppm) 7.79 (s, 1H), 7.59 (dt, J = 7.7, 1.1 Hz, 1H), 7.50 (dq, J = 7.6, 0.9 Hz, 1H), 7.38 (tdd, J = 7.5, 1.1, 0.6 Hz, 1H), 7.26 (td, J = 7.5, 1.1 Hz, 1H), 7.13 (s, 1H), 5.46 (d, J = 4.7 Hz, 1H), 5.37 (d, J = 3.7 Hz, 1H), 4.06 (ddt, J = 9.5, 4.6, 3.4 Hz, 1H), 0.90-0.67 (m, 5H) | 215.2 |
| 137d | 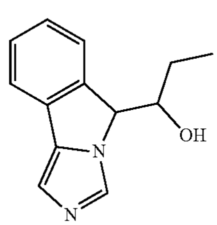 [SMILES: CCC(O)C1c2ccccc2-c2cncn21] | Same as 137c | 215.2 |

TABLE 2-continued

| Ex. # | Structure | $^1$H NMR | MS $(M + H)^+$ |
|---|---|---|---|
| 138a | 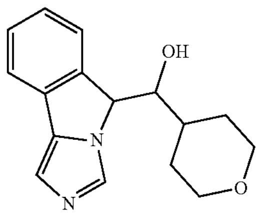 [SMILES: OC(C1CCOCC1)C1c2ccccc2-c2cncn21] | $^1$H NMR (400 MHz, DMSO-d6) δ 7.83 (s, 1H), 7.59 (dd, J = 7.6, 1.0 Hz, 1H), 7.51 (dd, J = 7.5, 1.0 Hz, 1H), 7.38 (ddd, J = 8.2, 7.5, 1.1 Hz, 1H), 7.26 (td, J = 7.5, 1.2 Hz, 1H), 7.12 (s, 1H), 5.42 (d, J = 4.0 Hz, 1H), 5.33 (d, J = 5.7 Hz, 1H), 3.87 (td, J = 5.8, 4.1 Hz, 1H), 3.74 (dd, J = 10.9, 3.8 Hz, 2H), 3.20-3.05 (m, 2H), 1.56 (tt, J = 10.2, 5.3 Hz, 1H), 1.45-1.31 (m, 1H), 1.31-1.19 (m, 3H). | 304 |
| 138b | 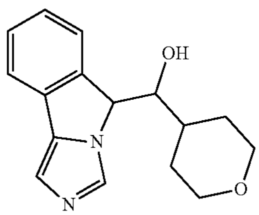 [SMILES: OC(C1CCOCC1)C1c2ccccc2-c2cncn21] | Same as 138a | 304 |
| 138c | 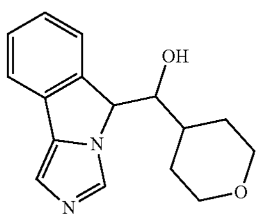 [SMILES: OC(C1CCOCC1)C1c2ccccc2-c2cncn21] | $^1$H NMR (400 MHz, DMSO-d6) δ 7.84 (s, 1H), 7.61-7.54 (m, 1H), 7.51 (dd, J = 7.5, 1.0 Hz, 1H), 7.37 (tt, J = 7.7, 0.8 Hz, 1H), 7.26 (td, J = 7.5, 1.2 Hz, 1H), 7.12 (s, 1H), 5.36 (d, J = 4.2 Hz, 1H), 5.10 (d, J = 6.5 Hz, 1H), 3.92-3.78 (m, 2H), 3.64 (td, J = 6.8, 4.2 Hz, 1H), 1.93-1.79 (m, 1H), 1.78-1.69 (m, 1H), 1.51-1.30 (m, 3H). | 304 |
| 138d | 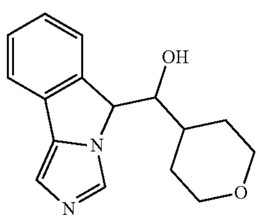 [SMILES: OC(C1CCOCC1)C1c2ccccc2-c2cncn21] | Same as 138c | 304 |
| 139a | 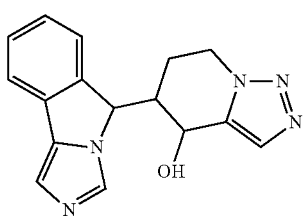 [SMILES: OC1c2cnnn2CCC1C1c2ccccc2-c2cncn21] | $^1$H NMR (300 MHz, DMSO-$d_6$) δ 7.93 (s, 1H), 7.76 (s, 1H), 7.63 (d, J = 7.8 Hz, 1H), 7.61 (d, J = 7.8 Hz, 1H), 7.43-7.39 (m, 1H), 7.33-7.28 (m, 1H), 7.15 (s, 1H), 6.33 (d, J = 5.4 Hz, 1H), 5.58 (d, J = 4.8 Hz, 1H), 5.31-5.29 (m, 1H), 4.44-4.38 (m, 1H), 4.05-3.95 (m, 1H), 2.71-2.66 (m, 1H), 1.92-1.76 (m, 1H), 1.30-1.17 (m, 1H). | 294.3 |
| 139b | 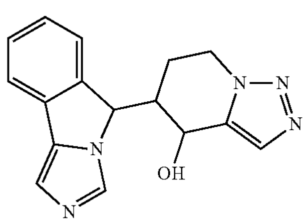 [SMILES: OC1c2cnnn2CCC1C1c2ccccc2-c2cncn21] | The same as 139a. | 294.2 |
| 139-1a | 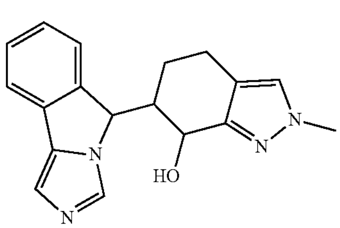 [SMILES: Cn1cc2c(n1)C(O)C(C1c3ccccc3-c3cncn31)CC2] | $^1$H NMR (300 MHz, $CD_3OD$) δ 7.92 (s, 1H), 7.64 (dd, J = 23.2, 7.6 Hz, 2H), 7.44 (dd, J = 8.1, 7.2 Hz, 1H), 7.32 (td, J = 7.6, 1.1 Hz, 1H), 7.22 (d, J = 15.5 Hz, 2H), 5.86 (d, J = 3.0 Hz, 1H), 5.08 (d, J = 10.2 Hz, 1H), 3.86 (s, 3H), 2.56 (ddd, J = 14.1, 10.4, 3.5 Hz, 1H), 2.46-2.28 (m, 2H), 1.04-0.88 (m, 2H). | 307.3 |

TABLE 2-continued
| Ex. # | Structure | $^1$H NMR | MS $(M + H)^+$ |
|---|---|---|---|
| 139-1b | 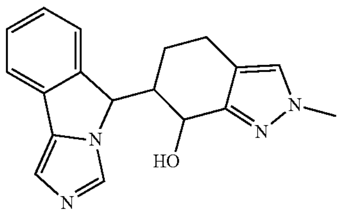 [SMILES: Cn1cc2c(n1)C(O)C(C1c3ccccc3-c3cncn31)CC2] | The same as 139-1a. | 307.2 |
| 139-1c | 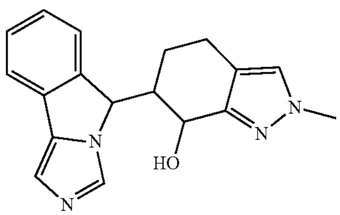 [SMILES: Cn1cc2c(n1)C(O)C(C1c3ccccc3-c3cncn31)CC2] | $^1$H NMR (300 MHz, $CD_3OD$) δ 8.16 (s, 1H), 7.66-7.54 (m, 2H), 7.47-7.25 (m, 3H), 7.16 (s, 1H), 5.60 (s, 1H), 5.16 (d, J = 3.5 Hz, 1H), 3.88 (s, 3H), 2.56 (ddd, J = 16.1, 5.5, 2.3 Hz, 2H), 2.31-2.18 (m, 1H), 1.51 (qd, J = 12.7, 5.5 Hz, 1H), 1.01-0.91 (m, 1H). | 307.3 |
| 136-1d | 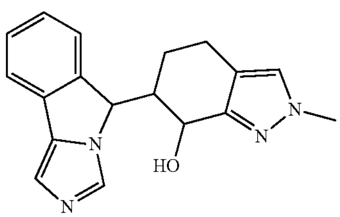 [SMILES: Cn1cc2c(n1)C(O)C(C1c3ccccc3-c3cncn31)CC2] | The same as 139-1c. | 307.2 |
| 139-1e | 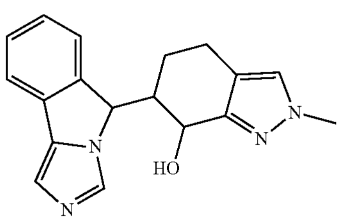 [SMILES: Cn1cc2c(n1)C(O)C(C1c3ccccc3-c3cncn31)CC2] | $^1$H NMR (300 MHz, $CD_3OD$) δ 7.97 (s, 1H), 7.66 (d, J = 7.5 Hz, 1H), 7.50 (d, J = 7.6 Hz, 1H), 7.46 (t, J = 7.4 Hz, 1H), 7.37 (td, J = 7.5, 0.9 Hz, 2H), 7.25 (s, 1H), 7.21 (s, 1H), 5.86 (s, 1H), 5.06 (d, J = 10.2 Hz, 1H), 2.48-2.24 (m, 3H), 1.11-1.00 (m, 1H), 0.95-0.84 (m, 1H). | 307.3 |
| 136-1f | 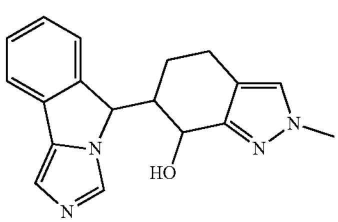 [SMILES: Cn1cc2c(n1)C(O)C(C1c3ccccc3-c3cncn31)CC2] | The same as 139-1e. | 307.2 |
| 140a | 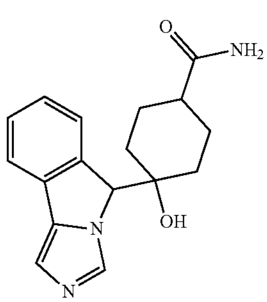 [SMILES: NC(=O)C1CCC(O)(C2c3ccccc3-c3cncn32)CC1] | 1H NMR (DMSO-d6) δ : 7.79 (s, 1H), 7.56 (dt, J = 7.6, 0.9 Hz, 1H), 7.51 (dd, J = 7.8, 1.0 Hz, 1H), 7.42-7.32 (m, 1H), 7.22 (td, J = 7.6, 1.2 Hz, 1H), 7.10 (s, 1H), 7.08-7.00 (m, 1H), 6.60 (s, 1H), 5.10 (s, 1H), 4.99 (s, 1H), 2.36-2.26 (m, 1H), 1.89-1.55 (m, 5H), 1.42 (d, J = 7.0 Hz, 1H), 1.23 (td, J = 12.9, 4.3 Hz, 1H), 0.82 (d, J = 13.3 Hz, 1H) | 298.1 |

TABLE 2-continued
| Ex. # | Structure | $^1$H NMR | MS (M + H)$^+$ |
|---|---|---|---|
| 140b | 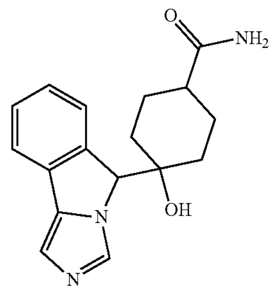 [SMILES: NC(=O)C1CCC(O)(C2c3ccccc3-c3cncn32)CC1] | Same as 140a | 298.1 |
| 140c | 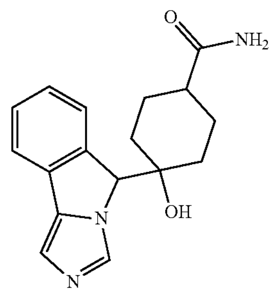 [SMILES: NC(=O)C1CCC(O)(C2c3ccccc3-c3cncn32)CC1] | 1H NMR (400 MHz, DMSO-d6) δ 7.61-7.56 (m, 2H), 7.39 (ddt, J = 8.0, 7.5, 0.6 Hz, 1H), 7.25 (td, J = 7.6, 1.2 Hz, 1H), 7.12 (d, J = 0.5 Hz, 1H), 7.04 (s, 1H), 6.59 (s, 1H), 5.14 (s, 1H), 5.11 (s, 1H), 1.88-1.54 (m, 4H), 1.43 (ddd, J = 29.0, 26.2, 13.7 Hz, 3H), 1.04-0.95 (m, 1H), 0.86 (td, J = 13.3, 4.2 Hz, 1H). | 298.1 |
| 140d | 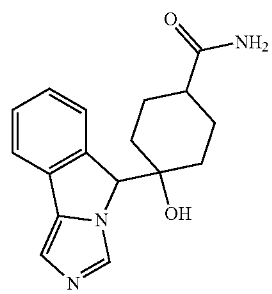 [SMILES: NC(=O)C1CCC(O)(C2c3ccccc3-c3cncn32)CC1] | Same as 140c | 298.1 |
| 141a | 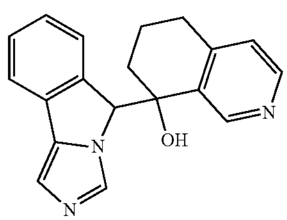 [SMILES: OC1(C2c3ccccc3-c3cncn32)CCCc2ccncc21] | Sam as G03090330.1-1SMDI#81834881 | 304.2 |
| 141b | 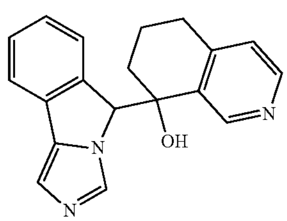 [SMILES: OC1(C2c3ccccc3-c3cncn32)CCCc2ccncc21] | 1H NMR (400 MHz, DMSO-d6) δ 9.16 (s, 1H), 8.48 (d, J = 5.0 Hz, 1H), 7.94 (s, 1H), 7.59 (dt, J = 7.7, 1.0 Hz, 1H), 7.30 (tt, J = 7.6, 1.0 Hz, 1H), 7.23-7.16 (m, 2H), 6.92 (td, J = 7.6, 1.1 Hz, 1H), 6.31 (s, 1H), 6.04 (s, 1H), 5.74 (dq, J = 7.8, 0.9 Hz, 1H), 2.60 (dt, J = 17.4, 4.7 Hz, 1H), 2.23-2.10 (m, 1H), 1.59-1.43 (m, 1H), 1.28-1.10 (m, 2H), 0.85 (ddd, J = 13.6, 11.2, 2.9 Hz, 1H). | 304.2 |
| 141c | 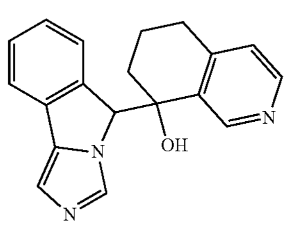 [SMILES: OC1(C2c3ccccc3-c3cncn32)CCCc2ccncc21] | Same as 141b | 304.2 |

TABLE 2-continued

| Ex. # | Structure | $^1$H NMR | MS (M + H)$^+$ |
|---|---|---|---|
| 141d | 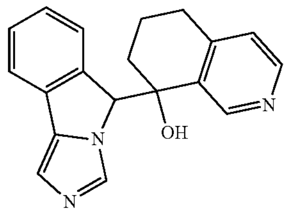 [SMILES: OC1(C2c3ccccc3-c3cncn32)CCCc2ccncc21] | $^1$H NMR (400 MHz, DMSO-d6) δ 9.11 (s, 1H), 8.46 (d, J = 5.0 Hz, 1H), 7.81 (dq, J = 7.7, 1.0 Hz, 1H), 7.61 (dt, J = 7.5, 1.0 Hz, 1H), 7.42 (tdd, J = 7.5, 1.2, 0.6 Hz, 1H), 7.31 (td, J = 7.6, 1.2 Hz, 1H), 7.18 (dd, J = 5.0, 0.8 Hz, 1H), 7.08 (s, 1H), 6.31 (s, 1H), 5.99 (s, 1H), 5.90 (s, 1H), 2.68-2.56 (m, 1H), 2.24 (ddd, J = 16.6, 10.2, 5.2 Hz, 1H), 1.64-1.49 (m, 1H), 1.35 (dd, J = 12.8, 6.1 Hz, 1H), 1.16 (t, J = 7.0 Hz, 1H), 0.92 (ddd, J = 14.3, 11.4, 3.1 Hz, 1H). | 304.2 |
| 142a | 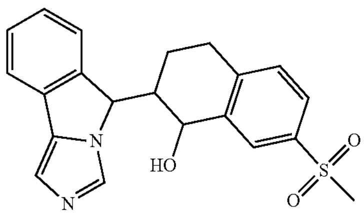 [SMILES: CS(=O)(=O)c1ccc2c(c1)C(O)C(C1c3ccccc3-c3cncn31)CC2] | $^1$H NMR (400 MHz, DMSO-$d_6$) δ 8.22-8.18 (m, 1H), 7.98 (s, 1H), 7.71 (dd, J = 8.0, 2.1 Hz, 1H), 7.64 (d, J = 7.5 Hz, 1H), 7.52-7.47 (m, 1H), 7.42 (t, J = 7.4, 7.4 Hz, 1H), 7.34-7.28 (m, 2H), 7.19 (s, 1H), 6.36 (d, J = 7.6 Hz, 1H), 5.82 (s, 1H), 5.06-4.94 (m, 1H), 3.20 (s, 3H), 2.68 (dd, J = 8.5, 4.5 Hz, 2H), 2.43 (s, 1H), 0.97-0.78 (m, 2H). | 381.2 |
| 142b | 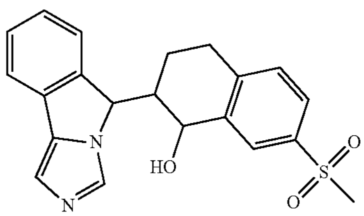 [SMILES: CS(=O)(=O)c1ccc2c(c1)C(O)C(C1c3ccccc3-c3cncn31)CC2] | $^1$H NMR (400 MHz, DMSO-$d_6$) δ 8.22-8.18 (m, 1H), 7.98 (s, 1H), 7.71 (dd, J = 8.0, 2.1 Hz, 1H), 7.64 (d, J = 7.5 Hz, 1H), 7.52-7.47 (m, 1H), 7.42 (t, J = 7.4 Hz, 1H), 7.34-7.28 (m, 2H), 7.19 (s, 1H), 6.36 (d, J = 7.6 Hz, 1H), 5.82 (s, 1H), 5.06-4.94 (m, 1H), 3.20 (s, 3H), 2.68 (dd, J = 8.5, 4.5 Hz, 2H), 2.43 (s, 1H), 0.97-0.78 (m, 2H). | 381.2 |
| 143a | 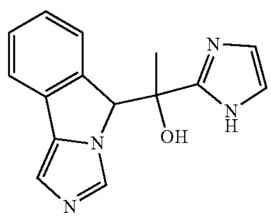 [SMILES: CC(O)(c1ncc[nH]1)C1c2ccccc2-c2cncn21] | $^1$H NMR (500 MHz, DMSO-d6) δ 12.24 (s, 1H), 7.64 (s, 1H), 7.57 (d, J = 7.6 Hz, 1H), 7.32 (dd, J = 8.0, 7.1 Hz, 1H), 7.24-7.22 (m, 1H), 7.15 (s, 1H), 7.05-6.99 (m, 2H), 6.20 (s, 1H), 6.03-5.98 (m, 1H), 5.79 (s, 1H), 0.92 (s, 3H). | 267.2 |
| 143b | 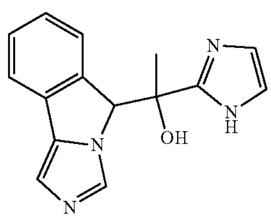 [SMILES: CC(O)(c1ncc[nH]1)C1c2ccccc2-c2cncn21] | $^1$H NMR (500 MHz, DMSO-d6) δ 12.13 (s, 1H), 7.59-7.55 (m, 1H), 7.38 (ddd, J = 7.6, 6.8, 1.0 Hz, 1H), 7.29 (d, J = 7.6 Hz, 1H), 7.21 (td, J = 7.6, 7.5, 1.1 Hz, 1H), 7.18 (dd, J = 2.1, 1.2 Hz, 1H), 7.06 (s, 1H), 6.98 (t, J = 1.3 Hz, 1H), 6.54 (s, 1H), 6.17 (s, 1H), 5.74 (s, 1H), 1.10 (s, 3H). | 267.2 |
| 143c | 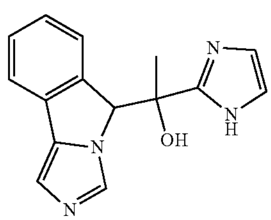 [SMILES: CC(O)(c1ncc[nH]1)C1c2ccccc2-c2cncn21] | $^1$H NMR (500 MHz, DMSO-d6) δ 12.24 (s, 1H), 7.64 (s, 1H), 7.57 (dd, J = 7.6, 0.9 Hz, 1H), 7.32 (t, J = 0.9 Hz, 1H), 7.23 (dd, J = 2.1, 1.2 Hz, 1H), 7.15 (s, 1H), 7.06-6.98 (m, 2H), 6.20 (s, 1H), 6.01 (dd, J = 7.7, 1.0 Hz, 1H), 5.79 (s, 1H), 0.92 (s, 3H). | 267.2 |
| 143d | 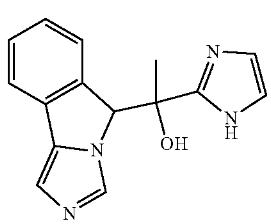 [SMILES: CC(O)(c1ncc[nH]1)C1c2ccccc2-c2cncn21] | $^1$H NMR (500 MHz, DMSO-d6) δ 12.13 (s, 1H), 7.57 (dt, J = 7.5, 0.9 Hz, 1H), 7.38 (tt, J = 7.5, 0.8 Hz, 1H), 7.29 (d, J = 7.6 Hz, 1H), 7.25-7.13 (m, 2H), 7.07 (s, 1H), 6.98 (s, 1H), 6.54 (s, 1H), 6.17 (s, 1H), 5.74 (s, 1H), 1.11 (s, 3H). | 267.2 |

TABLE 2-continued

| Ex. # | Structure | $^1$H NMR | MS (M + H)$^+$ |
|---|---|---|---|
| 144a | 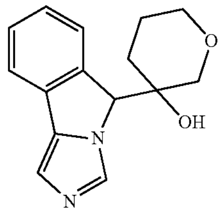 [SMILES: OC1(C2c3ccccc3-c3cncn32)CCCOC1] | (500 MHz, DMSO-$d_6$) δ 7.87 (s, 1H), 7.61 (dq, J = 7.6, 0.9 Hz, 1H), 7.58 (dt, J = 7.6, 0.9 Hz, 1H), 7.39 (tt, J = 7.6, 0.8 Hz, 1H), 7.25 (td, J = 7.6, 1.2 Hz, 1H), 7.12 (s, 1H), 5.36 (s, 1H), 5.19 (s, 1H), 3.69 (d, J = 11.2 Hz, 1H), 3.28-3.21 (m, 2H), 3.16 (td, J = 11.2, 2.6 Hz, 1H), 1.86 (ddt, J = 21.4, 10.6, 5.1 Hz, 1H), 1.58-1.47 (m, 2H). | 257.2 |
| 144b | 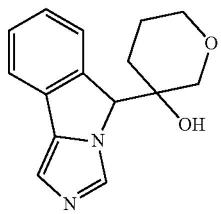 [SMILES: OC1(C2c3ccccc3-c3cncn32)CCCOC1] | (500 MHz, DMSO-$d_6$) δ 7.84 (s, 1H), 7.59 (dt, J = 7.6, 0.9 Hz, 1H), 7.55 (dq, J = 7.9, 1.0 Hz, 1H), 7.39 (tt, J = 7.5, 0.8 Hz, 1H), 7.25 (td, J = 7.6, 1.2 Hz, 1H), 7.13 (s, 1H), 5.37 (s, 1H), 5.20 (s, 1H), 3.70 (dd, J = 11.5, 2.2 Hz, 2H), 3.58 (d, J = 11.5 Hz, 1H), 3.14 (td, J = 11.3, 2.6 Hz, 1H), 1.16-1.02 (m, 2H). | 257.2 |
| 144c | 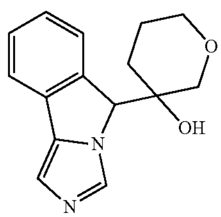 [SMILES: OC1(C2c3ccccc3-c3cncn32)CCCOC1] | (500 MHz, DMSO-$d_6$) δ 7.84 (s, 1H), 7.59 (dt, J = 7.6, 0.9 Hz, 1H), 7.55 (dq, J = 7.9, 1.0 Hz, 1H), 7.39 (tt, J = 7.5, 0.8 Hz, 1H), 7.25 (td, J = 7.6, 1.2 Hz, 1H), 7.13 (s, 1H), 5.37 (s, 1H), 5.20 (s, 1H), 3.70 (dd, J = 11.5, 2.2 Hz, 2H), 3.58 (d, J = 11.5 Hz, 1H), 3.14 (td, J = 11.3, 2.6 Hz, 1H), 1.16-1.02 (m, 2H). | 257.2 |
| 144d | 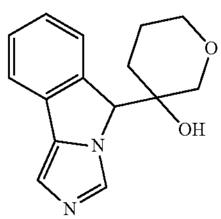 [SMILES: OC1(C2c3ccccc3-c3cncn32)CCCOC1] | (500 MHz, DMSO-$d_6$) δ 7.87 (s, 1H), 7.61 (dq, J = 7.6, 0.9 Hz, 1H), 7.58 (dt, J = 7.6, 0.9 Hz, 1H), 7.39 (tt, J = 7.6, 0.8 Hz, 1H), 7.25 (td, J = 7.6, 1.2 Hz, 1H), 7.12 (s, 1H), 5.36 (s, 1H), 5.19 (s, 1H), 3.69 (d, J = 11.2 Hz, 1H), 3.28-3.21 (m, 2H), 3.16 (td, J = 11.2, 2.6 Hz, 1H), 1.86 (ddt, J = 21.4, 10.6, 5.1 Hz, 1H), 1.58-1.47 (m, 2H). | 257.2 |
| 145a | 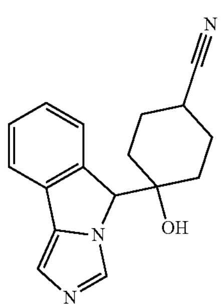 [SMILES: N#CC1CCC(O)(C2c3ccccc3-c3cncn32)CC1] | $^1$H NMR (500 MHz, DMSO-d6) δ 7.83 (s, 1H), 7.59 (dt, J = 7.6, 0.9 Hz, 1H), 7.56 (dt, J = 7.8, 1.0 Hz, 1H), 7.39 (tt, J = 7.5, 0.8 Hz, 1H), 7.25 (td, J = 7.6, 1.2 Hz, 1H), 7.13 (s, 1H), 5.35 (s, 1H), 5.14 (s, 1H), 1.90-1.78 (m, 2H), 1.78-1.66 (m, 2H), 1.62 (dd, J = 13.4, 3.0 Hz, 1H), 1.47 (td, J = 13.1, 6.1 Hz, 1H), 1.00 (dd, J = 13.1, 3.1 Hz, 1H), 0.93 (td, J = 12.8, 4.8 Hz, 1H). | 280.2 |
| 145b | 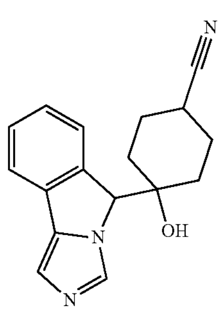 [SMILES: N#CC1CCC(O)(C2c3ccccc3-c3cncn32)CC1] | 1H NMR (500 MHz, DMSO-d6) δ 7.85 (d, J = 0.6 Hz, 1H), 7.62 (dt, J = 1.7, 0.9 Hz, 1H), 7.60 (dq, J = 2.0, 0.9 Hz, 1H), 7.40 (tt, J = 7.6, 0.8 Hz, 1H), 7.27 (td, J = 7.6, 1.2 Hz, 1H), 7.14 (s, 1H), 5.33 (s, 1H), 5.16 (s, 1H), 3.07 (s, 1H), 1.92 (ddt, J = 12.8, 8.7, 4.0 Hz, 1H), 1.85-1.60 (m, 4H), 1.53 (d, J = 13.6 Hz, 1H), 1.09 (td, J = 13.6, 4.0 Hz, 1H), 0.96 (d, J = 14.2 Hz, 1H). | 280.2 |

TABLE 2-continued
| Ex. # | Structure | $^1$H NMR | MS $(M + H)^+$ |
|---|---|---|---|
| 145c | 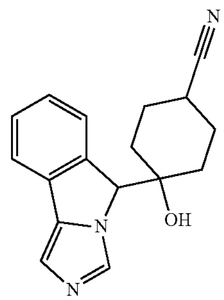 [SMILES: N#CC1CCC(O)(C2c3ccccc3-c3cncn32)CC1] | Same as 145b | 280.2 |
| 145d | 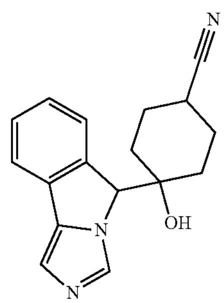 [SMILES: N#CC1CCC(O)(C2c3ccccc3-c3cncn32)CC1] | Same as 145a | 280.2 |
| 146a | 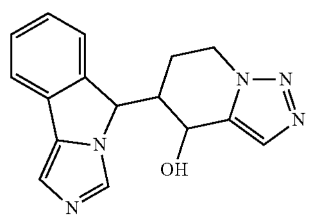 [SMILES: OC1c2cnnn2CCC1C1c2ccccc2-c2cncn21] | $^1$H NMR (300 MHz, $CD_3OD$) δ 8.04 (s, 1H), 7.76 (s, 1H), 7.66 (d, J = 7.5 Hz, 1H), 7.52 (d, J = 7.5 Hz, 1H), 7.46-7.42 (m, 1H), 7.36-7.31 (m, 1H), 7.21 (s, 1H), 6.46 (d, J = 7.2 Hz, 1H), 5.78 (d, J = 2.4 Hz, 1H), 5.18-5.12 (m, 1H), 4.32-4.26 (m, 1H), 4.08-4.00 (m, 1H), 2.64-2.51 (m, 1H), 1.26-1.07 (m, 2H). | 294.3 |
| 146b | 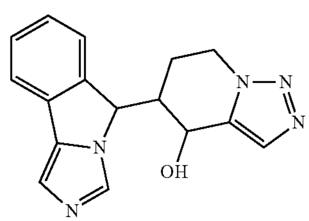 [SMILES: OC1c2cnnn2CCC1C1c2ccccc2-c2cncn21] | The same as 146a. | 294.2 |
| 146-1a | 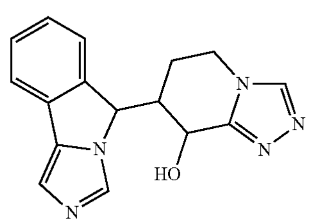 [SMILES: OC1c2nncn2CCC1C1c2ccccc2-c2cncn21] | $^1$H NMR (300 MHz, $CD_3OD$) δ 8.41 (s, 1H), 8.13 (s, 1H), 7.69-7.56 (m, 2H), 7.50-7.29 (m, 2H), 7.17 (s, 1H), 5.68 (s, 1H), 5.47 (d, J = 3.5 Hz, 1H), 4.25-4.12 (m, 1H), 3.79-3.61 (m, 1H), 2.88-2.75 (m, 1H), 1.95-1.89 (m, 1H), 1.24 (d, J = 13.9 Hz, 1H). | 294.2 |
| 146-1b | 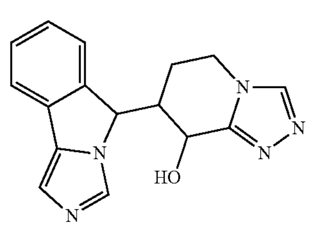 [SMILES: OC1c2nncn2CCC1C1c2ccccc2-c2cncn21] | The same as 146-1a. | 294.3 |

TABLE 2-continued

| Ex. # | Structure | $^1$H NMR | MS $(M + H)^+$ |
|---|---|---|---|
| 146-1c | 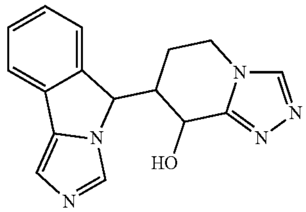 [SMILES: OC1c2nncn2CCC1C1c2ccccc2-c2cncn21] | $^1$H NMR (300 MHz, $CD_3OD$) δ 8.38 (s, 1H), 8.03 (s, 1H), 7.68 (d, J = 7.6 Hz, 1H), 7.59-7.33 (m, 3H), 7.27-7.20 (m, 1H), 5.90 (s, 1H), 5.21 (d, J = 10.7 Hz, 1H), 4.12-4.00 (m, 1H), 3.92-3.75 (m, 1H), 2.73 (s, 1H), 1.35-1.28 (m, 3H). | 294.3 |
| 146-1d | 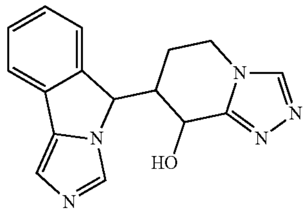 [SMILES: OC1c2nncn2CCC1C1c2ccccc2-c2cncn21] | The same as 146-1c. | 294.2 |
| 147a | 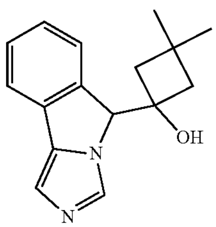 [SMILES: CC1(C)CC(O)(C2c3ccccc3-c3cncn32)C1] | (400 MHz, DMSO-$d_6$) δ 7.84 (s, 1H), 7.57 (d, J = 7.5 Hz, 1H), 7.52 (d, J = 7.6 Hz, 1H), 7.36 (t, J = 7.5 Hz, 1H), 7.23 (d, J = 7.7 Hz, 1H), 7.10 (s, 1H), 5.27 (s, 1H), 5.23 (s, 1H), 2.19 (dd, J = 20.2, 12.4 Hz, 2H), 1.88-1.69 (m, 2H), 1.21 (s, 3H), 0.93 (s, 3H). | 255.2 |
| 148a | 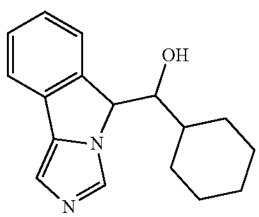 [SMILES: OC(C1CCCCC1)C1c2ccccc2-c2cncn21] | $^1$H NMR (400 MHz, DMSO-d6) δ 7.79 (s, 1H), 7.62-7.55 (m, 1H), 7.48 (dd, J = 7.5, 1.0 Hz, 1H), 7.37 (td, J = 7.5, 1.3 Hz, 1H), 7.25 (td, J = 7.5, 1.2 Hz, 1H), 7.11 (s, 1H), 5.40 (d, J = 4.3 Hz, 1H), 5.17 (d, J = 5.8 Hz, 1H), 3.79 (td, J = 5.9, 4.4 Hz, 1H), 1.63-1.44 (m, 4H), 1.36 (s, 1H), 1.20-0.94 (m, 3H). | 304 |
| 148b | 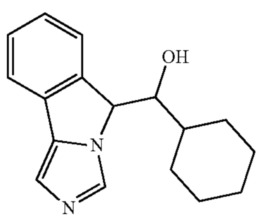 [SMILES: OC(C1CCCCC1)C1c2ccccc2-c2cncn21] | Same as 148a | 304 |
| 148c | 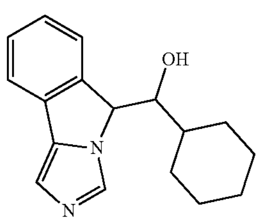 [SMILES: OC(C1CCCCC1)C1c2ccccc2-c2cncn21] | $^1$H NMR (400 MHz, DMSO-d6) δ 7.77 (s, 1H), 7.58 (dt, J = 7.6, 0.9 Hz, 1H), 7.45 (dt, J = 7.5, 1.0 Hz, 1H), 7.46-7.32 (m, 1H), 7.26 (td, J = 7.5, 1.2 Hz, 1H), 7.12 (s, 1H), 5.35 (d, J = 5.1 Hz, 1H), 5.04 (d, J = 6.5 Hz, 1H), 3.50 (td, J = 6.4, 4.9 Hz, 1H), 1.93 (d, J = 12.7 Hz, 1H), 1.84-1.51 (m, 2H), 1.36-1.06 (m, 4H). | 304 |
| 148d | 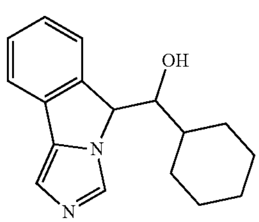 [SMILES: OC(C1CCCCC1)C1c2ccccc2-c2cncn21] | Same as 148c | 304 |

TABLE 2-continued

| Ex. # | Structure | $^1$H NMR | MS $(M + H)^+$ |
|---|---|---|---|
| 149a | 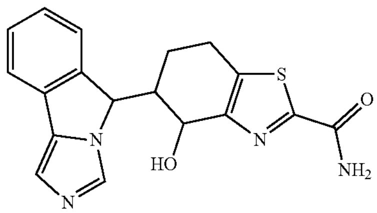 [SMILES: NC(=O)c1nc2c(s1)CCC(C1c3ccccc3-c3cncn31)C2O] | (500 MHz, DMSO-$d_6$) δ 7.90 (s, 1H), 7.84 (s, 1H), 7.81 (s, 1H), 7.64 (d, J = 7.6 Hz, 1H), 7.56 (d, J = 7.7 Hz, 1H), 7.40 (t, J = 7.5 Hz, 1H), 7.25 (td, J = 7.6, 1.1 Hz, 1H), 7.17 (s, 1H), 5.91 (d, J = 7.0 Hz, 1H), 5.77 (d, J = 3.3 Hz, 1H), 5.04-4.97 (m, 1H), 2.70-2.61 (m, 3H), 1.03-0.94 (m, 2H). | 353.2 |
| 149b | 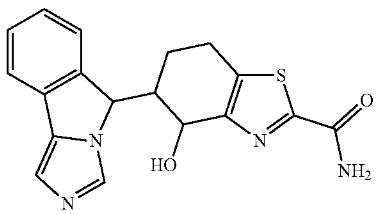 [SMILES: NC(=O)c1nc2c(s1)CCC(C1c3ccccc3-c3cncn31)C2O] | (500 MHz, DMSO-$d_6$) δ 7.94 (s, 1H), 7.87 (s, 1H), 7.81 (s, 1H), 7.64 (d, J = 7.6 Hz, 1H), 7.49 (dd, J = 7.6, 1.0 Hz, 1H), 7.42 (dd, J = 8.0, 7.1 Hz, 1H), 7.33 (td, J = 7.5, 1.1 Hz, 1H), 7.18 (s, 1H), 5.88 (d, J = 7.5 Hz, 1H), 5.78 (s, 1H), 5.05 (t, J = 8.7 Hz, 1H), 2.72-2.56 (m, 3H), 1.03-0.91 (m, 2H). | 353.2 |
| 149c | 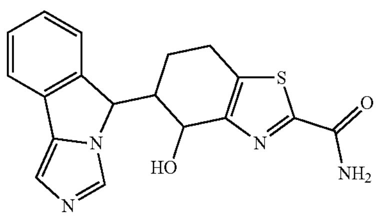 [SMILES: NC(=O)c1nc2c(s1)CCC(C1c3ccccc3-c3cncn31)C2O] | (500 MHz, DMSO-$d_6$) δ 8.04 (s, 1H), 7.99 (s, 1H), 7.78 (s, 1H), 7.65 (dd, J = 7.6, 1.0 Hz, 1H), 7.60 (d, J = 7.5 Hz, 1H), 7.39 (dd, J = 7.9, 7.0 Hz, 1H), 7.29 (td, J = 7.5, 1.1 Hz, 1H), 7.13 (s, 1H), 5.97 (d, J = 6.9 Hz, 1H), 5.52 (s, 1H), 5.11 (dd, J = 7.0, 3.5 Hz, 1H), 2.88 (dd, J = 17.6, 5.2 Hz, 1H), 2.61-2.52 (m, 2H), 1.56 (qd, J = 12.8, 5.6 Hz, 1H), 1.05 (d, J = 13.2 Hz, 1H). | 353.2 |
| 149d | 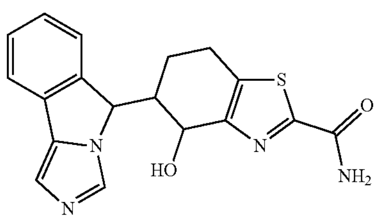 [SMILES: NC(=O)c1nc2c(s1)CCC(C1c3ccccc3-c3cncn31)C2O] | (500 MHz, DMSO-$d_6$) δ 7.99 (s, 1H), 7.97 (s, 1H), 7.78 (s, 1H), 7.77 (s, 1H), 7.62 (d, J = 7.6 Hz, 1H), 7.39 (t, J = 7.5 Hz, 1H), 7.28-7.23 (m, 1H), 7.14 (s, 1H), 5.75 (d, J = 7.0 Hz, 1H), 5.45 (d, J = 5.9 Hz, 1H), 4.91 (dd, J = 7.1, 3.3 Hz, 1H), 2.98 (dd, J = 17.4, 5.3 Hz, 1H), 2.68 (dt, J = 11.4, 5.8 Hz, 1H), 2.23 (d, J = 11.1 Hz, 1H), 1.97 (tt, J = 12.9, 6.5 Hz, 1H), 1.74 (d, J = 12.7 Hz, 1H). | 353.2 |
| 149e | 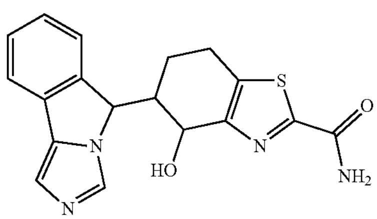 [SMILES: NC(=O)c1nc2c(s1)CCC(C1c3ccccc3-c3cncn31)C2O] | (500 MHz, DMSO-$d_6$) δ 7.94 (s, 1H), 7.87 (s, 1H), 7.81 (s, 1H), 7.64 (d, J = 7.6 Hz, 1H), 7.49 (d, J = 7.6 Hz, 1H), 7.42 (t, J = 7.5 Hz, 1H), 7.33 (td, J = 7.6, 1.2 Hz, 1H), 7.18 (s, 1H), 5.88 (d, J = 7.4 Hz, 1H), 5.78 (s, 1H), 5.05 (t, J = 8.6 Hz, 1H), 2.72-2.56 (m, 2H), 1.04-0.89 (m, 2H). | 353.2 |
| 149f | 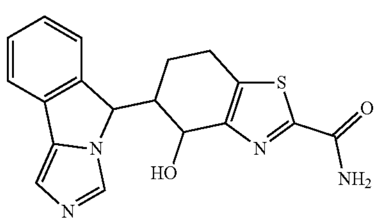 [SMILES: NC(=O)c1nc2c(s1)CCC(C1c3ccccc3-c3cncn31)C2O] | (500 MHz, DMSO-$d_6$) δ 8.04 (s, 1H), 7.99 (s, 1H), 7.82-7.74 (m, 1H), 7.65 (dq, J = 7.7, 1.0 Hz, 1H), 7.62-7.57 (m, 1H), 7.43-7.36 (m, 1H), 7.29 (td, J = 7.6, 1.1 Hz, 1H), 7.13 (s, 1H), 5.97 (d, J = 6.9 Hz, 1H), 5.54-5.49 (m, 1H), 5.11 (dd, J = 7.0, 3.5 Hz, 1H), 2.88 (dd, J = 17.3, 5.3 Hz, 1H), 2.57 (dd, J = 11.9, 5.7 Hz, 1H), 1.56 (qd, J = 12.7, 5.5 Hz, 1H), 1.05 (d, J = 11.7 Hz, 1H). | 353.2 |
| 149g | 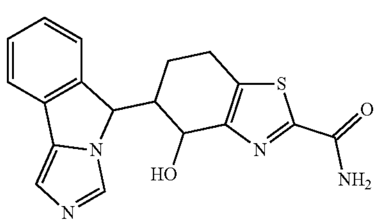 [SMILES: NC(=O)c1nc2c(s1)CCC(C1c3ccccc3-c3cncn31)C2O] | na | 353.2 |

TABLE 2-continued

| Ex. # | Structure | $^1$H NMR | MS (M + H)$^+$ |
|---|---|---|---|
| 149h | 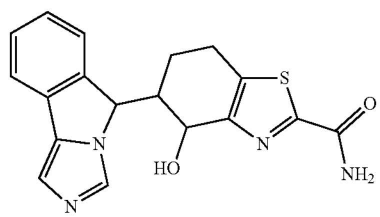 [SMILES: NC(=O)c1nc2c(s1)CCC(C1c3ccccc3-c3cncn31)C2O] | (500 MHz, DMSO-d$_6$) δ 7.90 (s, 1H), 7.84 (s, 1H), 7.81 (s, 1H), 7.64 (d, J = 7.6 Hz, 1H), 7.56 (d, J = 7.7 Hz, 1H), 7.40 (t, J = 7.5 Hz, 1H), 7.25 (td, J = 7.6, 1.1 Hz, 1H), 7.17 (s, 1H), 5.91 (d, J = 7.0 Hz, 1H), 5.77 (d, J = 3.3 Hz, 1H), 5.01 (s, 1H), 2.66 (s, 3H), 1.05-0.90 (m, 2H). | 353.2 |
| 150a | 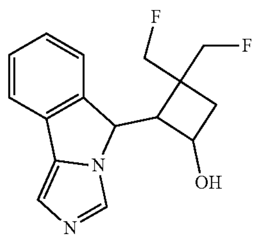 [SMILES: OC1CC(CF)(CF)C1C1c2ccccc2-c2cncn21] | (500 MHz, DMSO-d$_6$) δ 7.94 (s, 1H), 7.73 (dt, J = 7.8, 0.9 Hz, 1H), 7.60 (dd, J = 7.7, 1.0 Hz, 1H), 7.41-7.34 (m, 1H), 7.26 (td, J = 7.6, 1.2 Hz, 1H), 7.15 (s, 1H), 6.01 (d, J = 3.2 Hz, 1H), 5.55 (d, J = 8.8 Hz, 1H), 4.89 (dd, J = 47.7, 9.7 Hz, 1H), 4.65-4.45 (m, 3H), 4.42-4.36 (m, 1H), 4.30 (d, J = 9.5 Hz, 1H), 2.55 (t, J = 7.8 Hz, 1H), 2.12 (dt, J = 12.5, 4.7 Hz, 1H), 1.64 (d, J = 12.5 Hz, 1H). | 291.1 |
| 150b | 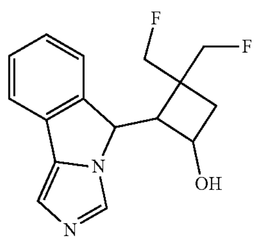 [SMILES: OC1CC(CF)(CF)C1C1c2ccccc2-c2cncn21] | (500 MHz, DMSO-d$_6$) δ 7.86 (s, 1H), 7.62-7.56 (m, 1H), 7.50 (dd, J = 7.7, 0.9 Hz, 1H), 7.38 (dd, J = 7.9, 7.1 Hz, 1H), 7.25 (td, J = 7.6, 1.2 Hz, 1H), 7.09 (s, 1H), 5.52 (d, J = 10.0 Hz, 1H), 5.33 (d, J = 7.8 Hz, 1H), 4.91 (dd, J = 46.8, 10.1 Hz, 1H), 4.75-4.59 (m, 2H), 4.52 (dd, J = 47.5, 9.5 Hz, 1H), 4.38 (dd, J = 47.5, 9.5 Hz, 1H), 2.25-2.19 (m, 1H), 2.10 (dd, J = 11.4, 7.9 Hz, 1H), 1.75 (ddd, J = 12.0, 8.1, 4.8 Hz, 1H). | 291.1 |
| 150c | 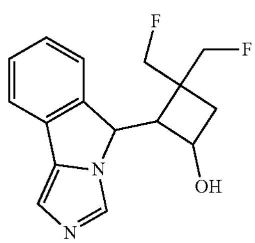 [SMILES: OC1CC(CF)(CF)C1C1c2ccccc2-c2cncn21] | (500 MHz, DMSO-d$_6$) δ 7.94 (s, 1H), 7.73 (dd, J = 7.7, 1.0 Hz, 1H), 7.60 (d, J = 7.5 Hz, 1H), 7.41-7.35 (m, 1H), 7.26 (td, J = 7.6, 1.2 Hz, 1H), 7.15 (s, 1H), 6.01 (d, J = 3.3 Hz, 1H), 5.55 (d, J = 8.8 Hz, 1H), 4.89 (dd, J = 47.8, 9.7 Hz, 1H), 4.56 (dd, J = 47.4, 9.6 Hz, 1H), 4.48 (d, J = 9.4 Hz, 2H), 4.41-4.37 (m, 1H), 4.30 (d, J = 9.5 Hz, 1H), 2.56 (s, 1H), 2.16-2.08 (m, 1H), 1.64 (d, J = 12.7 Hz, 1H). | 291.1 |
| 150d | 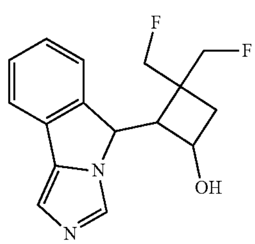 [SMILES: OC1CC(CF)(CF)C1C1c2ccccc2-c2cncn21] | (500 MHz, DMSO-d$_6$) δ 7.83 (s, 1H), 7.59 (ddt, J = 8.3, 7.3, 0.9 Hz, 2H), 7.37 (tt, J = 7.5, 0.8 Hz, 1H), 7.24 (td, J = 7.6, 1.2 Hz, 1H), 7.14 (s, 1H), 5.50 (d, J = 8.7 Hz, 1H), 5.33 (d, J = 7.6 Hz, 1H), 4.74-4.51 (m, 3H), 4.46-4.41 (m, 1H), 4.32 (dd, J = 20.2, 9.5 Hz, 1H), 4.21 (d, J = 9.5 Hz, 1H), 2.36 (t, J = 8.4 Hz, 1H), 2.10 (dd, J = 11.5, 8.0 Hz, 1H), 1.74 (ddd, J = 11.8, 8.1, 4.2 Hz, 1H). | 291.1 |
| 150e | 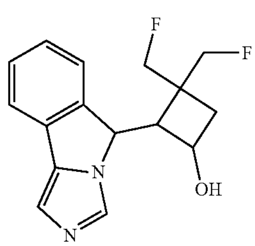 [SMILES: OC1CC(CF)(CF)C1C1c2ccccc2-c2cncn21] | (500 MHz, DMSO-d$_6$) δ 7.83 (s, 1H), 7.58 (tt, J = 7.5, 0.9 Hz, 2H), 7.37 (tt, J = 7.6, 0.8 Hz, 1H), 7.24 (td, J = 7.6, 1.2 Hz, 1H), 7.14 (s, 1H), 5.50 (d, J = 8.7 Hz, 1H), 5.33 (d, J = 7.6 Hz, 1H), 4.74-4.56 (m, 2H), 4.55-4.40 (m, 2H), 4.32 (dd, J = 20.2, 9.5 Hz, 1H), 4.21 (d, J = 9.5 Hz, 1H), 2.36 (t, J = 8.4 Hz, 1H), 2.10 (dd, J = 11.4, 8.0 Hz, 1H), 1.74 (ddd, J = 11.8, 8.1, 4.3 Hz, 1H). | 291.1 |

TABLE 2-continued

| Ex. # | Structure | $^1$H NMR | MS (M + H)$^+$ |
|---|---|---|---|
| 150f | 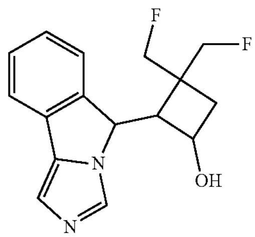 [SMILES: OC1CC(CF)(CF)C1C1c2ccccc2-c2cncn21] | (500 MHz, DMSO-$d_6$) δ 7.86 (s, 1H), 7.59 (dt, J = 7.6, 0.9 Hz, 1H), 7.54-7.48 (m, 1H), 7.38 (tt, J = 7.6, 0.8 Hz, 1H), 7.25 (td, J = 7.6, 1.2 hz, 1H), 7.09 (s, 1H), 5.52 (d, J = 10.0 Hz, 1H), 5.33 (d, J = 7.7 Hz, 1H), 4.91 (ddd, J = 46.9, 10.2, 1.8 Hz, 1H), 4.75-4.59 (m, 2H), 4.52 (dd, J = 47.5, 9.4 Hz, 1H), 4.38 (dd, J = 47.5, 9.4 Hz, 1H), 2.22 (dd, J = 9.9, 7.9 Hz, 1H), 2.10 (dd, J = 11.4, 7.9 Hz, 1H), 1.75 (ddd, J = 11.4, 8.1, 4.8 Hz, 1H). | 291.1 |
| 151b | 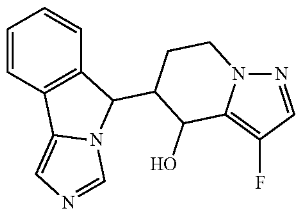 [SMILES: OC1c2c(F)cnn2CCC1C1c2ccccc2-c2cncn21] | The same as 151a. | 311.3 |
| 151c | 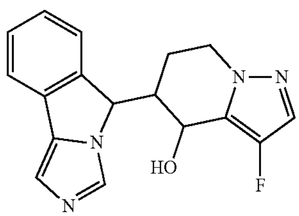 [SMILES: OC1c2c(F)cnn2CCC1C1c2ccccc2-c2cncn21] | $^1$H NMR (300 MHz, $CD_3OD$) δ 7.99 (s, 1H), 7.68 (d, J = 7.5 Hz, 1H), 7.59-7.38 (m, 4H), 7.23 (s, 1H), 5.87 (d, J = 1.9 Hz, 1H), 5.25 (d, J = 10.3 Hz, 1H), 3.98-3.77 (m, 2H), 2.61-2.59 (m, 1H), 1.32-1.28 (m, 2H). | 311.3 |
| 151d | 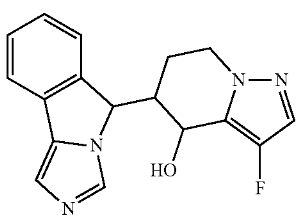 [SMILES: OC1c2c(F)cnn2CCC1C1c2ccccc2-c2cncn21] | The same as 151c. | 311.3 |
| 152a | 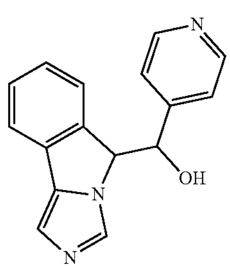 [SMILES: OC(c1ccncc1)C1c2ccccc2-c2cncn21] | (400 MHz, DMSO-$d_6$) δ 8.24-8.22 (m, 2H), 7.83 (t, J = 0.7 Hz, 1H), 7.43 (dt, J = 7.6, 1.0 Hz, 1H), 7.40 (dt, J = 7.6, 1.0 Hz, 1H), 7.30 (tdd, J = 7.5, 1.2, 0.6 Hz, 1H), 7.21 (td, J = 7.5, 1.2 Hz, 1H), 6.96 (s, 1H), 6.91-6.86 (m, 2H), 6.35 (d, J = 3.9 Hz, 1H), 5.71 (d, J = 4.0 Hz, 1H), 5.40 (t, J = 3.9 Hz, 1H). | 264.1 |
| 152b | 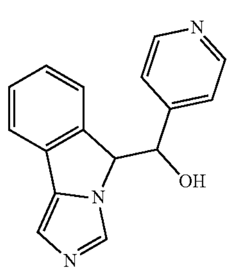 [SMILES: OC(c1ccncc1)C1c2ccccc2-c2cncn21] | (400 MHz, DMSO-$d_6$) δ 8.29-8.22 (m, 2H), 7.83 (d, J = 0.7 Hz, 1H), 7.44 (dd, J = 7.5, 1.0 Hz, 1H), 7.40 (dt, J = 7.5, 1.0 Hz, 1H), 7.32-7.27 (m, 1H), 7.21 (td, J = 7.5, 1.2 Hz, 1H), 6.96 (s, 1H), 6.91-6.86 (m, 2H), 6.35 (d, J = 3.9 Hz, 1H), 5.72 (d, J = 4.0 Hz, 1H), 5.40 (t, J = 3.9 Hz, 1H). | 264.1 |

TABLE 2-continued

| Ex. # | Structure | $^1$H NMR | MS $(M + H)^+$ |
|---|---|---|---|
| 152c | 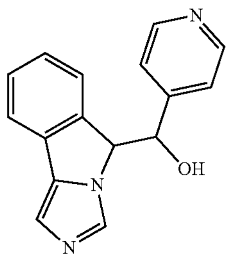 [SMILES: OC(c1ccncc1)C1c2ccccc2-c2cncn21] | (400 MHz, DMSO-$d_6$) δ 8.46-8.41 (m, 2H), 7.59 (d, J = 0.6 Hz, 1H), 7.48 (dt, J = 7.5, 1.0 Hz, 1H), 7.35-7.28 (m, 1H), 7.20-7.12 (m, 4H), 7.04 (s, 1H), 6.30 (d, J = 4.6 Hz, 1H), 5.64 (d, J = 5.5 Hz, 1H), 5.12 (t, J = 5.1 Hz, 1H). | 264.1 |
| 152d | 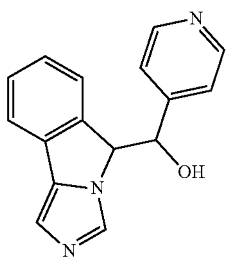 [SMILES: OC(c1ccncc1)C1c2ccccc2-c2cncn21] | $^1$HNMR (400 MHz, DMSO-$d_6$) δ 8.46-8.41 (m, 2H), 7.60 (t, J = 0.6 Hz, 1H), 7.48 (dt, J = 7.7, 1.0 Hz, 1H), 7.35-7.29 (m, 1H), 7.21-7.12 (m, 4H), 7.04 (s, 1H), 6.30 (d, J = 4.6 Hz, 1H), 5.65 (d, J = 5.5 Hz, 1H), 5.12 (t, J = 5.1 Hz, 1H). | 264.1 |
| 153a | 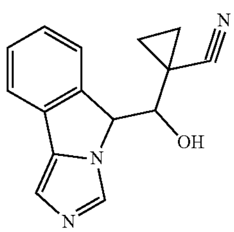 [SMILES: N#CC1(C(O)C2c3ccccc3-c3cncn32)CC1] | $^1$H NMR (400 MHz, DMSO-$d_6$) δ 7.86 (t, J = 0.7 Hz, 1H), 7.67-7.58 (m, 2H), 7.46-7.37 (m, 1H), 7.30-7.22 (m, 1H), 7.14 (s, 1H), 6.46 (s, 1H), 5.48 (d, J = 5.3 Hz, 1H), 3.71 (d, J = 5.3 Hz, 1H), 1.08-0.86 (m, 3H), 0.73 (dd, J = 3.9, 2.7 Hz, 1H). | 252.1 |
| 153b | 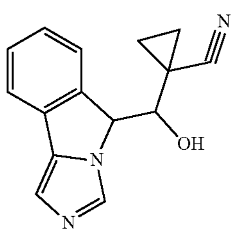 [SMILES: N#CC1(C(O)C2c3ccccc3-c3cncn32)CC1] | $^1$H NMR (400 MHz, DMSO-$d_6$) δ 7.88 (t, J = 0.7 Hz, 1H), 7.67 (dd, J = 7.7, 0.9 Hz, 1H), 7.64-7.59 (m, 1H), 7.45-7.40 (m, 1H), 7.29 (d, J = 1.2 Hz, 1H), 7.14 (s, 1H), 6.52 (s, 1H), 5.42 (d, J = 7.2 Hz, 1H), 3.26 (d, J = 7.3 Hz, 1H), 1.34-1.22 (m, 2H), 1.01 (d, J = 6.8 Hz, 1H), 0.77 (s, 1H). | 252.2 |
| 154a | 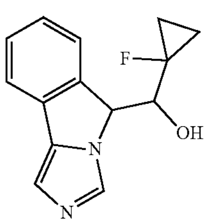 [SMILES: OC(C1c2ccccc2-c2cncn21)C1(F)CC1] | (400 MHz, DMSO-$d_6$) δ 7.83 (d, J = 0.7 Hz, 1H), 7.64 (dq, J = 7.7, 0.9 Hz, 1H), 7.58 (dt, J = 7.5, 1.0 Hz, 1H), 7.38 (tdd, J = 7.6, 1.1, 0.6 Hz, 1H), 7.24 (td, J = 7.6, 1.1 Hz, 1H), 7.11 (s, 1H), 6.01 (d, J = 5.4 Hz, 1H), 5.49 (d, J = 5.9 Hz, 1H), 3.87 (dt, J = 20.5, 5.6 Hz, 1H), 0.98-0.80 (m, 2H), 0.66-0.52 (m, 2H). | 245 |
| 154b | 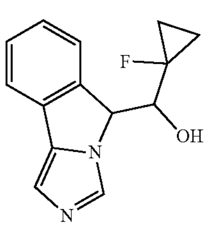 [SMILES: OC(C1c2ccccc2-c2cncn21)C1(F)CC1] | (400 MHz, DMSO-$d_6$) δ 7.83 (q, J = 0.6 Hz, 1H), 7.66-7.61 (m, 1H), 7.58 (dt, J = 7.6, 1.0 Hz, 1H), 7.38 (tdd, J = 7.5, 1.1, 0.6 Hz, 1H), 7.24 (td, J = 7.6, 1.2 Hz, 1H), 7.11 (s, 1H), 6.00 (d, J = 5.5 Hz, 1H), 5.49 (d, J = 5.9 Hz, 1H), 3.87 (dt, J = 20.6, 5.7 Hz, 1H), 0.98-0.80 (m, 2H), 0.66-0.52 (m, 2H). | 245 |

TABLE 2-continued

| Ex. # | Structure | $^{1}$H NMR | MS (M + H)$^{+}$ |
|---|---|---|---|
| 154c | 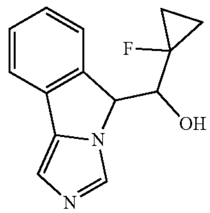 [SMILES: OC(C1c2ccccc2-c2cncn21)C1(F)CC1] | (400 MHz, DMSO-$d_6$) δ 7.82 (s, 1H), 7.63-7.57 (m, 2H), 7.42-7.36 (m, 1H), 7.26 (td, J = 7.6, 1.2 Hz, 1H), 7.12 (s, 1H), 5.92 (d, J = 5.8 Hz, 1H), 5.50 (d, J = 6.3 Hz, 1H), 3.60 (dt, J = 22.0, 6.0 Hz, 1H), 1.17-0.99 (m, 2H), 0.77-0.70 (m, 1H), 0.70-0.60 (m, 1H). | 245 |
| 154d | 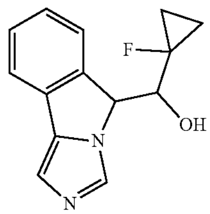 [SMILES: OC(C1c2ccccc2-c2cncn21)C1(F)CC1] | (400 MHz, DMSO-$d_6$) δ 7.83 (d, J = 0.7 Hz, 1H), 7.60 (ddt, J = 6.7, 5.9, 0.8 Hz, 2H), 7.42-7.35 (m, 1H), 7.26 (td, J = 7.6, 1.3 Hz, 1H), 7.12 (s, 1H), 5.92 (d, J = 5.8 Hz, 1H), 5.50 (d, J = 6.3 Hz, 1H), 3.61 (dt, J = 21.9, 6.1 Hz, 1H), 1.18-0.99 (m, 2H), 0.81-0.71 (m, 1H), 0.71-0.61 (m, 1H). | 245 |
| 155b | 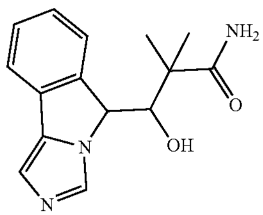 [SMILES: CC(C)(C(N)=O)C(O)C1c2ccccc2-c2cncn21] | $^{1}$H NMR (400 MHz, DMSO-d6) δ 7.83 (s, 1H), 7.55 (d, J = 7.7 Hz, 1H), 7.47 (d, J = 1.0 Hz, 1H), 7.34 (s, 1H), 7.20 (d, J = 1.2 Hz, 1H), 7.09 (s, 2H), 6.93 (s, 1H), 5.67 (d, J = 6.0 Hz, 1H), 5.36 (d, J = 2.9 Hz, 1H), 4.34 (dd, J = 6.0, 3.0 Hz, 1H), 0.98 (s, 3H), 0.97 (s, 3H). | 272.2 |
| 155c | 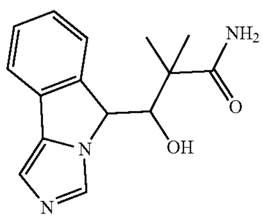 [SMILES: CC(C)(C(N)=O)C(O)C1c2ccccc2-c2cncn21] | $^{1}$H NMR (400 MHz, DMSO-d6) δ 7.67 (d, J = 0.7 Hz, 1H), 7.54 (s, 2H), 7.38-7.32 (m, 1H), 7.26 (d, J = 1.2 Hz, 2H), 7.12 (s, 1H), 7.07 (s, 1H), 5.32-5.18 (m, 1H), 4.17 (d, J = 2.1 Hz, 1H), 1.26 (s, 3H), 1.21 (s, 3H). | 272.2 |
| 155d | 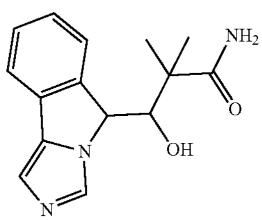 [SMILES: CC(C)(C(N)=O)C(O)C1c2ccccc2-c2cncn21] | $^{1}$H NMR (400 MHz, DMSO-d6) δ 7.67 (s, 1H), 7.54 (ddt, J = 6.5, 5.7, 0.9 Hz, 2H), 7.38-7.32 (m, 1H), 7.29-7.23 (m, 2H), 7.12 (s, 1H), 7.07 (s, 1H), 5.44 (d, J = 6.7 Hz, 1H), 5.29-5.24 (m, 1H), 4.17 (dd, J = 6.7, 2.0 Hz, 1H), 1.26 (s, 3H), 1.21 (s, 3H). | 272.2 |
| 156a | 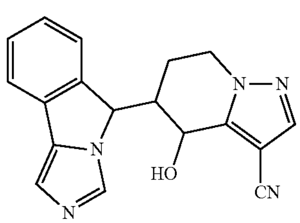 [SMILES: N#Cc1cnn2c1C(O)C(C1c3ccccc3-c3cncn31)CC2] | $^{1}$H NMR (300 MHz, $CD_3OD$) δ 8.09 (s, 1H), 7.92 (s, 1H), 7.66-7.60 (m, 2H), 7.48-7.34 (m, 2H), 7.18 (s, 1H), 5.68 (s, 1H), 5.49 (d, J = 3.6 Hz, 1H), 4.24-4.18 (m, 1H), 3.95-3.84 (m, 1H), 2.84-2.80 (m, 1H), 2.06-1.87 (m, 1H), 1.31-1.29 (m, 1H). | 318.3 |
| 156b | 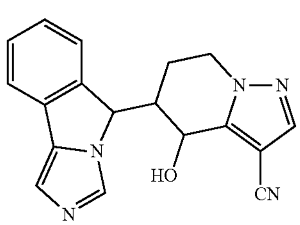 [SMILES: N#Cc1cnn2c1C(O)C(C1c3ccccc3-c3cncn31)CC2] | The same as 156a. | 318.3 |

TABLE 2-continued
| Ex. # | Structure | $^1$H NMR | MS $(M + H)^+$ |
|---|---|---|---|
| 156c | 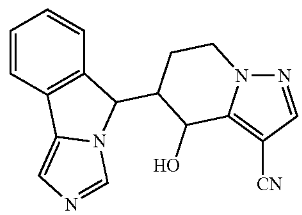 [SMILES: N#Cc1cnn2c1C(O)C(C1c3ccccc3-c3cncn31)CC2] | $^1$H NMR (300 MHz, $CD_3OD$) δ 8.06 (s, 1H), 7.90 (s, 1H), 7.75-7.66 (m, 2H), 7.51-7.39 (m, 1H), 7.32 (td, J = 7.6, 1.2 Hz, 1H), 7.20 (s, 1H), 5.63 (d, J = 5.2 Hz, 1H), 5.21 (d, J = 3.5 Hz, 1H), 4.21-4.15 (m, 1H), 4.03-1.00 (m, 1H), 2.60-2.58 (m, 1H), 2.42-2.39 (m, 1H), 2.08-2.05 (m, 1H). | 318.3 |
| 156d | 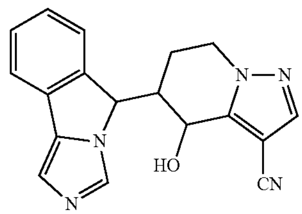 | The same as 156c. | 318.2 |
| 156e | 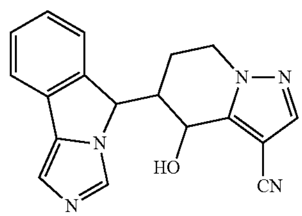 [SMILES: N#Cc1cnn2c1C(O)C(C1c3ccccc3-c3cncn31)CC2] | $^1$H NMR (300 MHz, $CD_3OD$) δ 8.07 (s, 1H), 7.90 (s, 1H), 7.71-7.68 (m, 1H), 7.56-7.37 (m, 3H), 7.25 (s, 1H), 5.87 (d, J = 2.5 Hz, 1H), 5.29 (d, J = 10.7 Hz, 1H), 4.15-4.08 (m, 1H), 4.00-3.90 (m, 1H), 2.71-2.61 (m, 1H), 1.39-1.30 (m, 2H). | 318.3 |
| 156f | 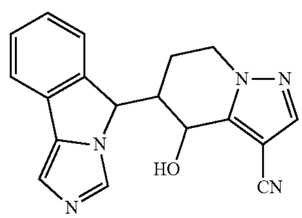 [SMILES: N#Cc1cnn2c1C(O)C(C1c3ccccc3-c3cncn31)CC2] | The same as 156e. | 318.2 |
| 157a | 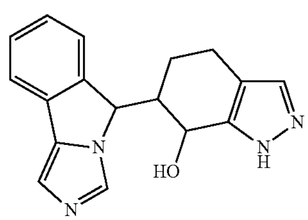 [SMILES: OC1c2[nH]ncc2CCC1C1c2ccccc2-c2cncn21] | $^1$H NMR (300 MHz, $CD_3OD$) δ 8.05 (s, 1H), 7.75-7.59 (m, 2H), 7.53-7.24 (m, 4H), 5.94-5.86 (m, 1H), 5.14 (d, J = 10.2 Hz, 1H), 2.69-2.53 (m, 1H), 2.52-2.30 (m, 2H), 1.04 (m, 2H). | 293.3 |
| 157b | 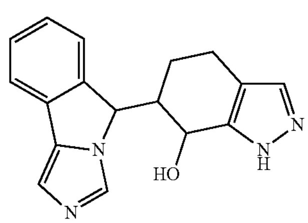 [SMILES: OC1c2[nH]ncc2CCC1C1c2ccccc2-c2cncn21] | The same as 157a. | 293.3 |
| 157c | 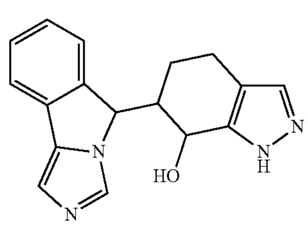 [SMILES: OC1c2[nH]ncc2CCC1C1c2ccccc2-c2cncn21] | $^1$H NMR (300 MHz, $CD_3OD$) δ 8.00 (s, 1H), 7.73-7.63 (m, 1H), 7.56-7.26 (m, 4H), 7.23 (s, 1H), 5.87 (s, 1H), 5.18-5.08 (m, 1H), 2.55-2.31 (m, 3H), 1.15-1.03 (m, 1H), 0.96 (m, 1H). | 293.3 |

TABLE 2-continued
| Ex. # | Structure | $^1$H NMR | MS (M + H)$^+$ |
|---|---|---|---|
| 157d | 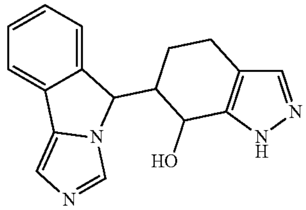 [SMILES: OC1c2[nH]ncc2CCC1C1c2ccccc2-c2cncn21] | $^1$H NMR (300 MHz, $CD_3OD$) δ 8.13 (s, 1H), 7.61 (m, 2H), 7.50-7.28 (m, 3H), 7.21-7.12 (m, 1H), 5.61 (s, 1H), 5.23 (d, J = 3.6 Hz, 1H), 2.59 (m, 2H), 2.36-2.19 (m, 1H), 1.53 (m, 1H), 1.00 (m, 1H). | 293.1 |
| 157e | 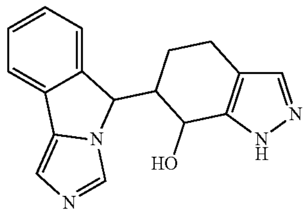 [SMILES: OC1c2[nH]ncc2CCC1C1c2ccccc2-c2cncn21] | The same as 157d. | 293.1 |
| 157f | 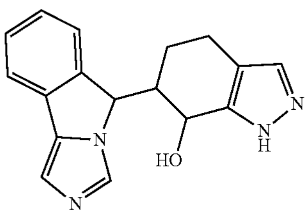 [SMILES: OC1c2[nH]ncc2CCC1C1c2ccccc2-c2cncn21] | $^1$H NMR (300 MHz, $CD_3OD$) δ 8.07 (s, 1H), 7.77 (d, J = 7.7 Hz, 1H), 7.65 (d, J = 7.6 Hz, 1H), 7.49-7.24 (m, 3H), 7.17 (s, 1H), 5.53 (d, J = 5.7 Hz, 1H), 4.91 (s, 1H), 2.77 (d, J = 16.2 Hz, 1H), 2.45 (m, 1H), 2.25 (d, J = 11.0 Hz, 1H), 2.06 (m, 1H), 1.90 (m, 1H). | 293.1 |
| 157g | 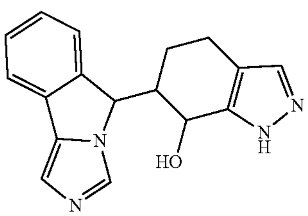 [SMILES: OC1c2[nH]ncc2CCC1C1c2ccccc2-c2cncn21] | The same as 157c. | 293.3 |
| 157h | 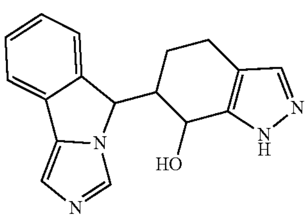 [SMILES: OC1c2[nH]ncc2CCC1C1c2ccccc2-c2cncn21] | The same 157f. | 293.1 |
| 158a | 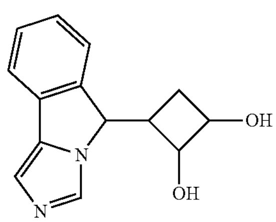 [SMILES: OC1CC(C2c3ccccc3-c3cncn32)C1O] | 1H NMR (400 MHz, DMSO-d6) δ 7.79 (s, 1H), 7.60 (d, J = 7.2 Hz, 1H), 7.39-7.34 (m, 2H), 7.25-7.21 (m, 1H), 7.11 (s, 1H), 5.47 (d, J = 5.2 Hz, 1H), 5.33 (d, J = 8.1 Hz, 1H), 5.04 (d, J = 8.0 Hz, 1H), 4.37-4.32 (m, 1H), 4.00-3.95 (m, 1H), 2.44-2.36 (m, 2H), 1.86-1.77 (m, 1H). | 243.1 |
| 159a | 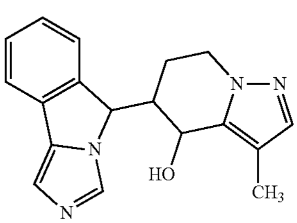 | $^1$H NMR (300 MHz, $CD_3OD$) δ 8.16 (dd, J = 1.5, 0.8 Hz, 1H), 7.66-7.60 (m, 2H), 7.47-7.32 (m, 3H), 7.19 (s, 1H), 5.66 (s, 1H), 5.32 (dd, J = 3.6, 1.2 Hz, 1H), 4.18-4.13 (m, 1H), 3.83-3.73 (m, 1H), 2.73-2.66 (m, 1H), 2.19 (s, 3H), 1.98-1.87 (m, 1H), 1.22 (d, J = 13.7 Hz, 1H). | 307.3 |

TABLE 2-continued
| Ex. # | Structure | $^1H$ NMR | MS $(M + H)^+$ |
|---|---|---|---|
| 159b | 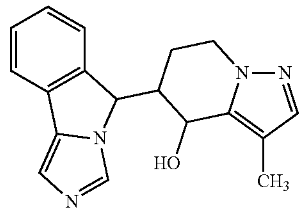 | The same as 159a. | 307.2 |
| 159c | 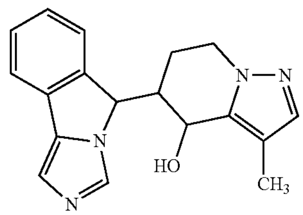 | $^1H$ NMR (300 MHz, $CD_3OD$) δ 8.40 (d, J = 6.3 Hz, 1H), 7.78-7.76 (m, 1H), 7.60-7.44 (m, 4H), 7.27 (s, 1H), 5.97 (d, J = 1.6 Hz, 1H), 5.12 (d, J = 10.1 Hz, 1H), 4.03-3.85 (m, 2H), 2.71-2.64 (m, 1H), 2.22 (s, 3H), 1.44-1.31 (m, 2H). | 307.3 |
| 159d | 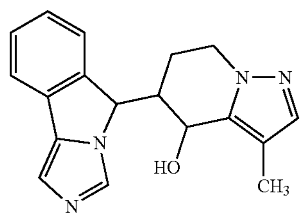 | The same as 159d. | 307.2 |
| 160a | 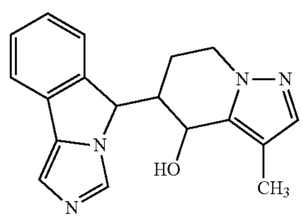 [SMILES: Cc1cnn2c1C(O)C(C1c3ccccc3-c3cncn31)CC2] | $^1H$ NMR (300 MHz, $CD_3OD$) δ 8.15 (d, J = 0.8 Hz, 1H), 7.65-7.60 (m, 2H), 7.50-7.33 (m, 3H), 7.18 (d, J = 0.6 Hz, 1H), 5.65 (d, J = 1.6 Hz, 1H), 5.36 (dd, J = 3.5, 1.2 Hz, 1H), 4.22-4.16 (m, 1H), 3.87-3.77 (m, 1H), 2.75-2.68 (m, 1H), 2.05-1.91 (m, 1H), 1.27-1.22 (m, 1H). | 327.3 |
| 160b | 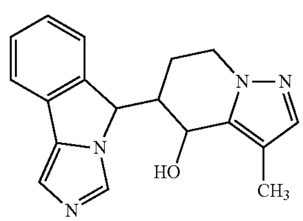 [SMILES: Cc1cnn2c1C(O)C(C1c3ccccc3-c3cncn31)CC2] | The same as 160b. | 327.2 |
| 160c | 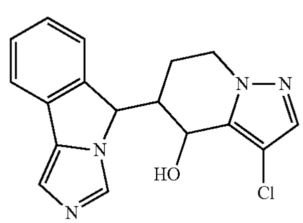 [SMILES: OC1c2c(Cl)cnn2CCC1C1c2ccccc2-c2cncn21] | $^1H$ NMR (300 MHz, $CD_3OD$) δ 8.07 (t, J = 0.7 Hz, 1H), 7.79-7.77 (m, 1H), 7.68-7.66 (m, 1H), 7.47-7.31 (m, 3H), 7.19 (s, 1H), 5.59 (d, J = 5.2 Hz, 1H), 5.07 (dd, J = 3.0, 1.3 Hz, 1H), 4.36-4.30 (m, 1H), 4.00-3.91 (m, 1H), 2.52-2.41 (m, 2H), 2.13-2.07 (m, 1H). | 307.3 |
| 160d | 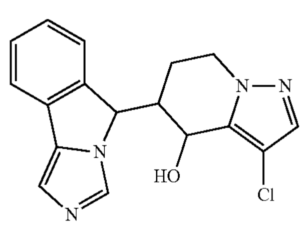 [SMILES: OC1c2c(Cl)cnn2CCC1C1c2ccccc2-c2cncn21] | The same as 160c. | 307.2 |

TABLE 2-continued

| Ex. # | Structure | $^1$H NMR | MS $(M + H)^+$ |
|---|---|---|---|
| 160e | 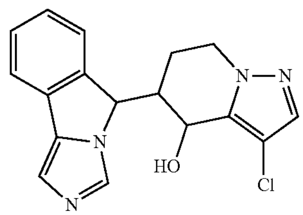 [SMILES: OC1c2c(Cl)cnn2CCC1C1c2ccccc2-c2cncn21] | $^1$H NMR (300 MHz, $CD_3OD$) δ 7.96 (s, 1H), 7.70-7.67 (m, 1H), 7.56-7.37 (m, 4H), 7.23 (s, 1H), 5.86 (d, J = 1.4 Hz, 1H), 5.24 (d, J = 9.8 Hz, 1H), 4.00-3.86 (m, 2H), 2.70-2.61 (m, 1H), 1.38-1.17 (m, 2H). | 327.3 |
| 160f | 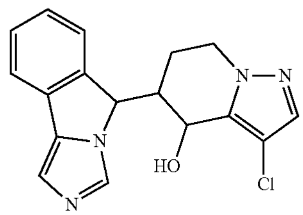 [SMILES: OC1c2c(Cl)cnn2CCC1C1c2ccccc2-c2cncn21] | The same as 160e. | 327.3 |
| 161a | 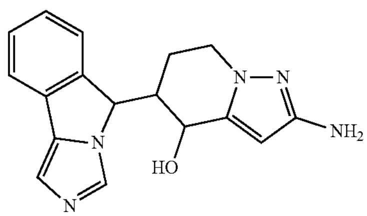 [SMILES: Nc1cc2n(n1)CCC(C1c3ccccc3-c3cncn31)C2O] | $^1$H NMR (500 MHz, DMSO-d6) δ 7.92 (s, 1H), 7.64 (d, J = 7.6 Hz, 1H), 7.57 (d, J = 7.3 Hz, 1H), 7.41 (t, J = 7.5 Hz, 1H), 7.27 (td, J = 7.6, 1.1 Hz, 1H), 7.16 (s, 1H), 5.99 (s, 1H), 5.72 (d, J = 3.2 Hz, 1H), 5.47 (s, 1H), 4.81 (d, J = 10.5 Hz, 1H), 4.49 (s, 2H), 3.65 (dd, J = 12.2, 4.3 Hz, 1H), 3.52 (td, J = 12.2, 4.7 Hz, 1H), 2.64-2.52 (m, 1H), 1.06 (ddt, J = 18.2, 12.4, 5.8 Hz, 1H), 0-95-0.92 (m, 1H). | 308.2 |
| 161b | 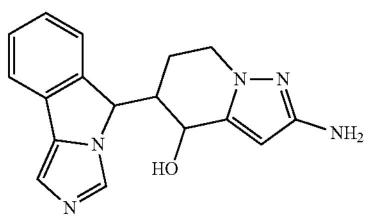 [SMILES: Nc1cc2n(n1)CCC(C1c3ccccc3-c3cncn31)C2O] | $^1$H NMR (500 MHz, DMSO-d6) δ 7.96 (s, 1H), 7.63 (d, J = 7.5 Hz, 1H), 7.50 (d, J = 6.9 Hz, 1H), 7.42 (t, J = 7.4 Hz, 1H), 7.32 (td, J = 7.5, 1.1 Hz, 1H), 7.18 (s, 1H), 5.98 (d, J = 7.3 Hz, 1H), 5.72 (s, 1H), 5.51 (s, 1H), 4.88 (dd, J = 10.4, 7.3 Hz, 1H), 4.50 (s, 2H), 3.64 (dd, J = 10.9, 4.1 Hz, 1H), 3.49 (td, J = 11.6, 5.8 Hz, 1H), 2.48-2.31 (m, 1H), 1.06-0.88 (m, 2H). | 308.2 |
| 161c | 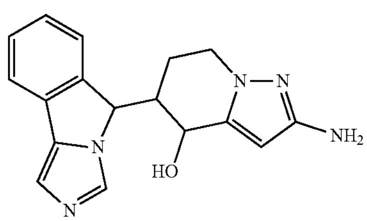 [SMILES: Nc1cc2n(n1)CCC(C1c3ccccc3-c3cncn31)C2O] | $^1$H NMR (500 MHz, DMSO-d6) δ 7.92 (s, 1H), 7.62 (d, J = 7.7 Hz, 1H), 7.59 (d, J = 7.5 Hz, 1H), 7.39 (t, J = 7.5 Hz, 1H), 7.29 (td, J = 7.6, 1.0 Hz, 1H), 7.12 (s, 1H), 5.94 (d, J = 5.4 Hz, 1H), 5.49 (d, J = 2.1 Hz, 1H), 5.44 (s, 1H), 5.07-4.92 (m, 1H), 4.52 (s, 2H), 3.81-3.64 (m, 1H), 3.49 (td, J = 12.1, 4.8 Hz, 1H), 2.49-2.45 (m, 1H), 1.79 (tq, J = 12.3, 5.7 Hz, 1H), 1.12 (d, J = 13.8 Hz, 1H). | 308.2 |
| 161d | 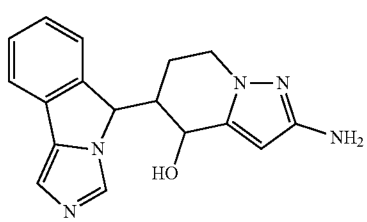 [SMILES: Nc1cc2n(n1)CCC(C1c3ccccc3-c3cncn31)C2O] | $^1$H NMR (500 MHz, DMSO-d6) δ 7.95 (s, 1H), 7.71 (d, J = 7.7 Hz, 1H), 7.61 (d, J = 7.5 Hz, 1H), 7.39 (t, J = 7.5 Hz, 1H), 7.24 (td, J = 7.6, 1.1 Hz, 1H), 7.13 (s, 1H), 5.68 (d, J = 5.4 Hz, 1H), 5.42 (d, J = 5.4 Hz, 1H), 5.38 (s, 1H), 4.81 (d, J = 5.3 Hz, 1H), 4.50 (s, 2H), 3.85 (dd, J = 11.3, 4.3 Hz, 1H), 3.69-3.45 (m, 1H), 2.32-2.09 (m, 2H), 1.81 (d, J = 10.9 Hz, 1H). | 308.2 |
| 161e | 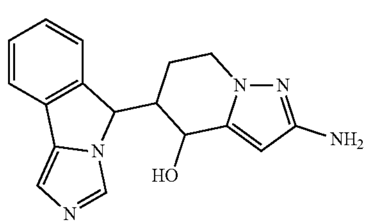 [SMILES: Nc1cc2n(n1)CCC(C1c3ccccc3-c3cncn31)C2O] | $^1$H NMR (500 MHz, DMSO-d6) δ 7.92 (s, 1H), 7.62 (d, J = 7.6 Hz, 1H), 7.59 (d, J = 7.5 Hz, 1H), 7.39 (t, J = 7.5 Hz, 1H), 7.29 (td, J = 7.6, 1.0 Hz, 1H), 7.12 (s, 1H), 5.94 (d, J = 5.4 Hz, 1H), 5.49 (d, J = 2.1 Hz, 1H), 5.44 (s, 1H), 5.05-4.96 (m, 1H), 4.52 (s, 2H), 3.81-3.62 (m, 1H), 3.49 (td, J = 12.1, 4.8 Hz, 1H), 2.47 (d, J = 2.9 Hz, 1H), 1.79 (tq, J = 12.3, 5.8 Hz, 1H), 1.12 (d, J = 13.0 Hz, 1H). | 308.2 |

TABLE 2-continued

| Ex. # | Structure | $^1H$ NMR | MS $(M + H)^+$ |
|---|---|---|---|
| 161f | 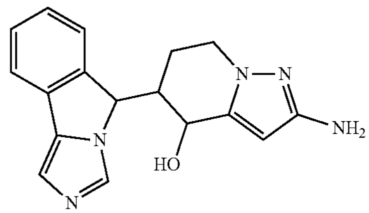 [SMILES: Nc1cc2n(n1)CCC(C1c3ccccc3-c3cncn31)C2O] | $^1H$ NMR (500 MHz, DMSO-d6) δ 7.96 (s, 1H), 7.71 (d, J = 7.7 Hz, 1H), 7.62 (d, J = 7.5 Hz, 1H), 7.39 (t, J = 7.4 Hz, 1H), 7.25 (td, J = 7.6, 1.1 Hz, 1H), 7.13 (s, 1H), 5.68 (d, J = 5.4 Hz, 1H), 5.43 (d, J = 5.4 Hz, 1H), 5.39 (s, 1H), 4.81 (d, J = 5.4 Hz, 1H), 4.50 (s, 2H), 3.85 (dd, J = 11.3, 4.3 Hz, 1H), 3.66-3.50 (m, 1H), 2.33-2.11 (m, 2H), 1.82 (d, J = 10.7 Hz, 1H). | 308.2 |
| 161g | 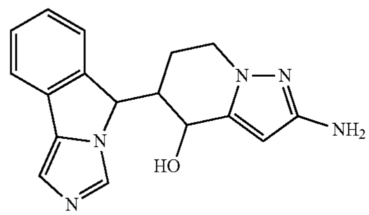 [SMILES: Nc1cc2n(n1)CCC(C1c3ccccc3-c3cncn31)C2O] | $^1H$ NMR (500 MHz, DMSO-d6) δ 7.96 (s, 1H), 7.63 (d, J = 7.6 Hz, 1H), 7.50 (d, J = 7.6 Hz, 1H), 7.42 (t, J = 7.5 Hz, 1H), 7.32 (td, J = 7.5, 1.0 Hz, 1H), 7.18 (s, 1H), 5.98 (d, J = 7.3 Hz, 1H), 5.73 (s, 1H), 5.51 (s, 1H), 4.88 (dd, J = 10.3, 7.4 Hz, 1H), 4.50 (s, 2H), 3.64 (dd, J = 10.7, 4.0 Hz, 1H), 3.49 (td, J = 11.5, 5.8 Hz, 1H), 2.49-2.28 (m, 1H), 1.05-0.85 (m, 2H). | 308.2 |
| 161h | 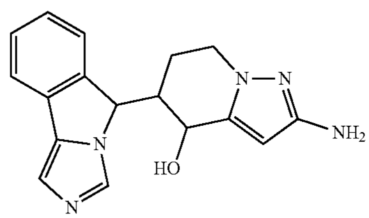 [SMILES: Nc1cc2n(n1)CCC(C1c3ccccc3-c3cncn31)C2O] | $^1H$ NMR (500 MHz, DMSO-d6) δ 7.92 (s, 1H), 7.64 (d, J = 7.6 Hz, 1H), 7.57 (d, J = 7.7 Hz, 1H), 7.41 (t, J = 7.5 Hz, 1H), 7.27 (td, J = 7.6, 1.1 Hz, 1H), 7.17 (s, 1H), 5.98 (d, J = 6.7 Hz, 1H), 5.72 (d, J = 3.1 Hz, 1H), 5.47 (s, 1H), 4.81 (dd, J = 10.5, 6.4 Hz, 1H), 4.49 (s, 2H), 3.65 (dd, J = 12.2, 4.2 Hz, 1H), 3.52 (td, J = 12.0, 4.7 Hz, 1H), 2.65-2.54 (m, 1H), 1.06 (tq, J = 12.5, 5.9 Hz, 1H), 0.93 (d, J = 13.7 Hz, 1H). | 308.2 |
| 162a | 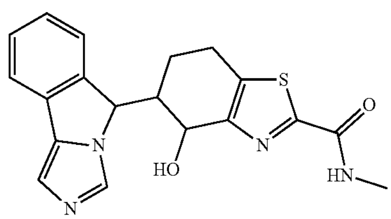 [SMILES: CNC(=O)c1nc2c(s1)CCC(C1c3ccccc3-c3cncn31)C2O] | (500 MHz, DMSO-$d_6$) δ 8.53 (q, J = 4.8 Hz, 1H), 7.90 (s, 1H), 7.64 (dd, J = 7.6, 1.0 Hz, 1H), 7.55 (dd, J = 7.7, 1.0 Hz, 1H), 7.40 (t, J = 7.5 Hz, 1H), 7.25 (td, J = 7.6, 1.1 Hz, 1H), 7.17 (s, 1H), 5.90 (d, J = 7.3 Hz, 1H), 5.77 (d, J = 3.2 Hz, 1H), 5.00 (dd, J = 9.4, 7.4 Hz, 1H), 2.81 (d, J = 4.8 Hz, 3H), 2.70-2.60 (m, 3H), 0.99 (dt, J = 9.8, 6.9 Hz, 2H). | 367.5 |
| 162b | 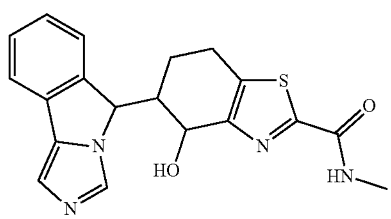 [SMILES: CNC(=O)c1nc2c(s1)CCC(C1c3ccccc3-c3cncn31)C2O] | (500 MHz, DMSO-$d_6$) δ 8.56 (q, J = 4.7 Hz, 1H), 7.93 (s, 1H), 7.64 (dt, J = 7.5, 0.9 Hz, 1H), 7.52-7.46 (m, 1H), 7.46-7.39 (m, 1H), 7.33 (td, J = 7.5, 1.1 Hz, 1H), 7.18 (s, 1H), 5.87 (d, J = 7.7 Hz, 1H), 5.78 (d, J = 1.8 Hz, 1H), 5.04 (t, J = 8.7 Hz, 1H), 2.81 (d, J = 4.7 Hz, 3H), 2.73-2.56 (m, 2H), 1.03-0.88 (m, 2H). | 367.5 |
| 162c | 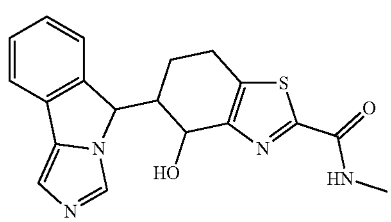 [SMILES: CNC(=O)c1nc2c(s1)CCC(C1c3ccccc3-c3cncn31)C2O] | (500 MHz, DMSO-$d_6$) δ 8.56 (q, J = 4.7 Hz, 1H), 7.93 (s, 1H), 7.64 (dt, J = 7.6, 0.9 Hz, 1H), 7.49 (dq, J = 7.6, 0.9 Hz, 1H), 7.42 (tt, J = 7.5, 0.8 Hz, 1H), 7.33 (td, J = 7.5, 1.1 Hz, 1H), 7.18 (s, 1H), 5.87 (d, J = 7.8 Hz, 1H), 5.78 (d, J = 1.8 Hz, 1H), 5.04 (t, J = 8.6 Hz, 1H), 2.81 (d, J = 4.7 Hz, 3H), 2.73-2.56 (m, 2H), 1.03-0.88 (m, 2H). | 367.5 |
| 162d | 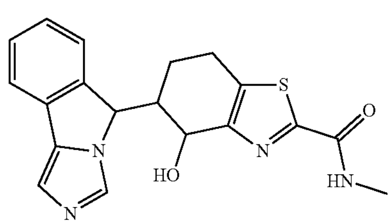 [SMILES: CNC(=O)c1nc2c(s1)CCC(C1c3ccccc3-c3cncn31)C2O] | (500 MHz, DMSO-$d_6$) δ 8.53 (q, J = 4.5 Hz, 1H), 7.90 (s, 1H), 7.64 (d, J = 7.6 Hz, 1H), 7.55 (d, J = 7.7 Hz, 1H), 7.40 (t, J = 7.5 Hz, 1H), 7.25 (td, J = 7.6, 1.1 Hz, 1H), 7.17 (s, 1H), 5.90 (d, J = 7.3 Hz, 1H), 5.77 (d, J = 3.2 Hz, 1H), 5.05-4.96 (m, 1H), 2.80 (d, J = 4.8 Hz, 3H), 2.70-2.61 (m, 3H), 1.03-0.93 (m, 2H). | 367.5 |

TABLE 2-continued

| Ex. # | Structure | $^1$H NMR | MS (M + H)$^+$ |
|---|---|---|---|
| 162e | 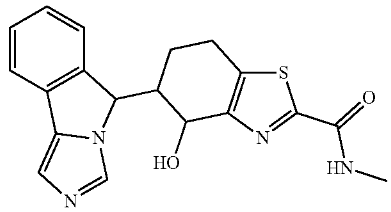 [SMILES: CNC(=O)c1nc2c(s1)CCC(C1c3ccccc3-c3cncn31)C2O] | (500 MHz, DMSO-$d_6$) δ 8.70 (q, J = 4.7 Hz, 1H), 7.99 (s, 1H), 7.65 (dq, J = 7.6, 0.9 Hz, 1H), 7.60 (dt, J = 7.5, 0.9 Hz, 1H), 7.39 (tt, J = 7.6, 0.9 Hz, 1H), 7.29 (td, J = 7.5, 1.2 Hz, 1H), 7.13 (s, 1H), 5.95 (d, J = 7.1 Hz, 1H), 5.52 (d, J = 2.4 Hz, 1H), 5.11 (dd, J = 7.1, 3.5 Hz, 1H), 2.92-2.84 (m, 1H), 2.80 (d, J = 4.8 Hz, 3H), 2.60-2.51 (m, 2H), 1.55 (qd, J = 12.7, 5.5 Hz, 1H), 1.04 (d, J = 6.7 Hz, 1H). | 367.5 |
| 162f | 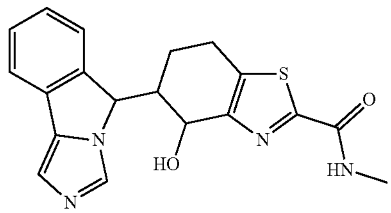 [SMILES: CNC(=O)c1nc2c(s1)CCC(C1c3ccccc3-c3cncn31)C2O] | (500 MHz, DMSO-$d_6$) δ 8.66 (q, J = 4.7 Hz, 1H), 7.97 (s, 1H), 7.78 (dq, J = 7.7, 0.9 Hz, 1H), 7.62 (dt, J = 7.5, 0.9 Hz, 1H), 7.39 (tt, J = 7.6, 0.8 Hz, 1H), 7.25 (td, J = 7.6, 1.2 Hz, 1H), 7.14 (s, 1H), 5.74 (d, J = 7.1 Hz, 1H), 5.46 (d, J = 5.7 Hz, 1H), 4.92 (dd, J = 7.2, 3.3 Hz, 1H), 2.98 (ddd, J = 17.4, 5.5, 1.6 Hz, 1H), 2.66 (ddd, J = 17.5, 11.9, 5.8 Hz, 1H), 2.28-2.19 (m, 1H), 1.96 (qd, J = 12.7, 5.5 Hz, 1H), 1.76-1.66 (m, 1H). | 367.5 |
| 162g | 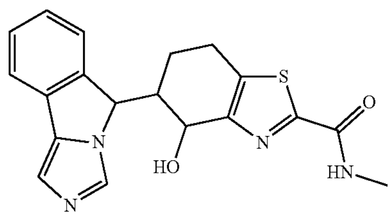 [SMILES: CNC(=O)c1nc2c(s1)CCC(C1c3ccccc3-c3cncn31)C2O] | (500 MHz, DMSO-$d_6$) δ 8.70 (q, J = 4.7 Hz, 1H), 7.99 (s, 1H), 7.65 (dq, J = 7.6, 0.9 Hz, 1H), 7.60 (dt, J = 7.5, 0.9 Hz, 1H), 7.39 (tt, J = 7.6, 0.8 Hz, 1H), 7.29 (td, J = 7.5, 1.1 Hz, 1H), 7.13 (s, 1H), 5.95 (d, J = 7.1 Hz, 1H), 5.55-5.47 (m, 1H), 5.11 (dd, J = 7.1, 3.5 Hz, 1H), 2.92-2.84 (m, 1H), 2.80 (d, J = 4.8 Hz, 3H), 2.60-2.51 (m, 2H), 1.55 (qd, J = 12.7, 5.5 Hz, 1H), 1.04 (d, J = 7.3 Hz, 1H). | 367.5 |
| 162h | 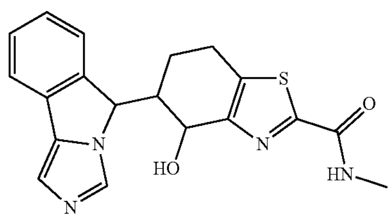 [SMILES: CNC(=O)c1nc2c(s1)CCC(C1c3ccccc3-c3cncn31)C2O] | (500 MHz, DMSO-$d_6$) δ 8.66 (q, J = 4.7 Hz, 1H), 7.97 (s, 1H), 7.78 (dd, J = 7.7, 1.0 Hz, 1H), 7.66-7.58 (m, 1H), 7.39 (dd, J = 8.0, 7.0 Hz, 1H), 7.25 (td, J = 7.6, 1.2 Hz, 1H), 7.14 (s, 1H), 5.74 (d, J = 7.1 Hz, 1H), 5.46 (d, J = 5.7 Hz, 1H), 4.92 (dd, J = 7.2, 3.3 Hz, 1H), 2.98 (ddd, J = 17.4, 5.6, 1.7 Hz, 1H), 2.78 (d, J = 4.8 Hz, 3H), 2.66 (ddd, J = 17.5, 11.9, 5.8 Hz, 1H), 2.24 (ddt, J = 12.0, 5.9, 2.9 Hz, 1H), 1.96 (qd, J = 12.7, 5.5 Hz, 1H), 1.72 (d, J = 7.2 Hz, 1H). | 367.5 |
| 163a | 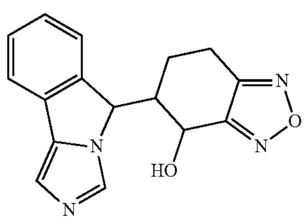 [SMILES: OC1c2nonc2CCC1C1c2ccccc2-c2cncn21] | $^1$H NMR (500 MHz, DMSO-d6) δ 7.93 (s, 1H), 7.73 (dd, J = 7.8, 0.9 Hz, 1H), 7.62 (d, J = 7.6 Hz, 1H), 7.42-7.35 (m, 1H), 7.29-7.22 (m, 1H), 7.14 (s, 1H), 6.36 (d, J = 5.7 Hz, 1H), 5.55 (d, J = 4.9 Hz, 1H), 5.22 (d, J = 2.4 Hz, 1H), 3.06-2.91 (m, 1H), 2.73-2.61 (m, 1H), 1.95 (qd, J = 12.8, 5.6 Hz, 1H), 1.68 (dd, J = 13.4, 6.2 Hz, 1H), 0.90-0.78 (m, 1H). | 295.4 |
| 163b | 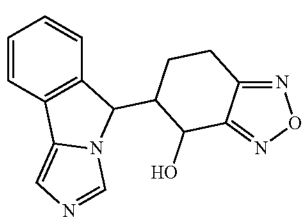 [SMILES: OC1c2nonc2CCC1C1c2ccccc2-c2cncn21] | $^1$H NMR (500 MHz, DMSO-d6) δ 7.92 (s, 1H), 7.60 (ddt, J = 7.7, 6.6, 0.9 Hz, 2H), 7.40 (tt, J = 7.7, 0.8 Hz, 1H), 7.30 (td, J = 7.5, 1.2 Hz, 1H), 7.13 (s, 1H), 6.69 (d, J = 5.7 Hz, 1H), 5.62-5.55 (m, 1H), 5.46 (dd, J = 5.9, 3.5 Hz, 1H), 2.91 (ddd, J = 17.4, 5.6, 1.9 Hz, 1H), 2.68 (dq, J = 12.6, 2.7, Hz, 1H), 2.55 (ddd, J = 17.4, 12.6, 6.3 Hz, 1H), 1.56 (qd, J = 12.9, 5.6 Hz, 1H), 1.06-0.95 (m, 1H). | 295.4 |
| 163c | 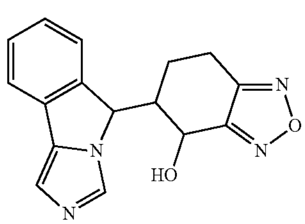 [SMILES: OC1c2nonc2CCC1C1c2ccccc2-c2cncn21] | $^1$H NMR (500 MHz, DMSO-d6) δ 7.92 (s, 1H), 7.60 (tt, J = 7.3, 0.9 Hz, 2H), 7.40 (tt, J = 7.5, 0.8 Hz, 1H), 7.30 (td, J = 7.5, 1.2 Hz, 1H), 7.13 (s, 1H), 6.69 (d, J = 5.5 Hz, 1H), 5.62-5.55 (m, 1H), 5.46 (t, J = 4.5 Hz, 1H), 2.91 (ddd, J = 17.4, 5.6, 1.8 Hz, 1H), 2.68 (dq, J = 12.5, 2.6 Hz, 1H), 2.55 (ddd, J = 17.4, 12.6, 6.2 Hz, 1H), 1.61-1.50 (m, 1H), 1.06-0.98 (m, 1H). | 295.4 |

TABLE 2-continued

| Ex. # | Structure | $^1$H NMR | MS $(M + H)^+$ |
|---|---|---|---|
| 163d | 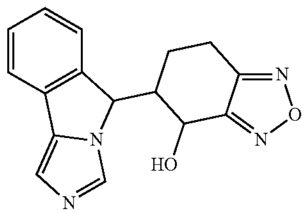 [SMILES: OC1c2nonc2CCC1C1c2ccccc2-c2cncn21] | $^1$H NMR (500 MHz, DMSO-d6) δ 7.99 (s, 1H), 7.64 (dt, J = 7.7, 1.0 Hz, 1H), 7.52-7.46 (m, 1H), 7.43 (tt, J = 7.6, 0.9 Hz, 1H), 7.33 (td, J = 7.6, 1.1 Hz, 1H), 7.19 (s, 1H), 6.69 (d, J = 7.2 Hz, 1H), 5.80-5.71 (m, 1H), 5.26 (dd, J = 11.0, 7.3 Hz, 1H), 2.78 (dt, J = 17.3, 3.8 Hz, 1H), 2.65-2.53 (m, 2H), 0.96 (dtd, J = 11.2, 6.4, 3.9 Hz, 2H). | 295.4 |
| 163e | 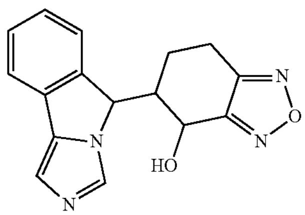 [SMILES: OC1c2nonc2CCC1C1c2ccccc2-c2cncn21] | $^1$H NMR (500 MHz, DMSO-d6) δ 7.90 (s, 1H), 7.65 (d, J = 7.5 Hz, 1H), 7.61 (dd, J = 7.7, 0.9 Hz, 1H), 7.44-7.38 (m, 1H), 7.28 (td, J = 7.6, 1.2 Hz, 1H), 7.18 (s, 1H), 6.71 (d, J = 6.9 Hz, 1H), 5.78 (d, J = 3.2 Hz, 1H), 5.17 (dd, J = 11.1, 6.8 Hz, 1H), 2.80-2.68 (m, 2H), 2.66-2.56 (m, 1H), 0.89-1.04 (m, 2H). | 295.4 |
| 163f | 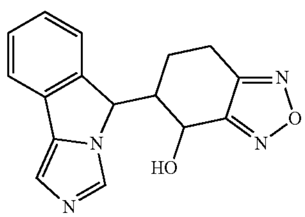 [SMILES: OC1c2nonc2CCC1C1c2ccccc2-c2cncn21] | $^1$H NMR (500 MHz, DMSO-d6) δ 7.99 (s, 1H), 7.64 (dt, J = 7.6, 0.9 Hz, 1H), 7.52-7.47 (m, 1H), 7.46-7.40 (m, 1H), 7.33 (td, J = 7.6, 1.1 Hz, 1H), 7.19 (s, 1H), 6.68 (d, J = 7.3 Hz, 1H), 5.80-5.76 (m, 1H), 5.25 (dd, J = 11.1, 7.3 Hz, 1H), 2.78 (dt, J = 17.3, 3.8 Hz, 1H), 2.65-2.53 (m, 2H), 1.01-0.91 (m, 2H). | 295.4 |
| 163g | 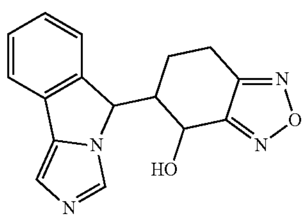 [SMILES: OC1c2nonc2CCC1C1c2ccccc2-c2cncn21] | $^1$H NMR (500 MHz, DMSO-d6) δ 7.90 (s, 1H), 7.65 (d, J = 7.5 Hz, 1H), 7.61 (dd, J = 7.7, 1.0 Hz, 1H), 7.41 (d, J = 0.8 Hz, 1H), 7.28 (dd, J = 7.6, 1.1 Hz, 1H), 7.18 (s, 1H), 6.71 (d, J = 6.7 Hz, 1H), 5.78 (d, J = 3.2 Hz, 1H), 5.17 (dd, J = 11.1, 6.5 Hz, 1H), 2.83-2.69 (m, 2H), 2.66-2.57 (m, 1H), 1.06-0.94 (m, 1H), 0.81-0.93 (m, 1H). | 295.4 |
| 163h | 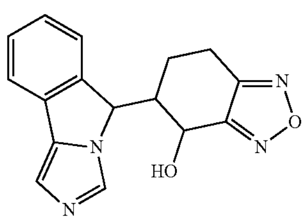 [SMILES: OC1c2nonc2CCC1C1c2ccccc2-c2cncn21] | $^1$H NMR (500 MHz, DMSO-d6) δ 7.93 (s, 1H), 7.73 (dd, J = 7.7, 0.9 Hz, 1H), 7.63 (d, J = 7.6 Hz, 1H), 7.40 (t, J = 0.8 Hz, 1H), 7.25 (d, J = 1.2 Hz, 1H), 7.14 (s, 1H), 6.36 (d, J = 5.8 Hz, 1H), 5.55 (d, J = 4.8 Hz, 1H), 5.22 (dd, J = 5.9, 3.3 Hz, 1H), 3.00 (ddd, J = 17.5, 5.6, 1.9 Hz, 1H), 2.68 (ddd, J = 17.4, 12.3, 6.3 Hz, 1H), 1.95 (qd, J = 12.8, 5.6 Hz, 1H), 1.68 (dd, J = 13.4, 6.2 Hz, 1H), 1.22-1.26 (m, 1H). | 295.4 |
| 164a | 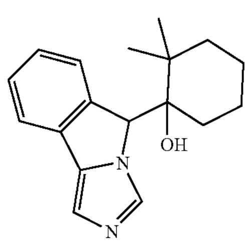 [SMILES: CC1(C)CCCCC1(O)C1c2ccccc2-c2cncn21] | $^1$H NMR (DMSO-$d_6$, 500 MHz): δ (ppm) 7.90 (s, 1H), 7.66-7.53 (m, 2H), 7.37 (tt, J = 7.5, 0.8 Hz, 1H), 7.21 (td, J = 7.6, 1.2 Hz, 1H), 7.11 (s, 1H), 5.12 (s, 1H), 5.11 (s, 1H), 2.40-2.26 (m, 1H), 1.87-1.69 (m, 3H), 1.56 (d, J = 11.9 Hz, 1H), 1.43-1.20 (m, 2H), 0.65 (d, J = 13.1 Hz, 1H), 0.19 (s, 3H), 0.13 (s, 3H). | 283.2 |
| 164b | 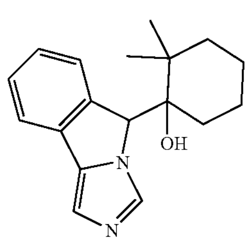 [SMILES: CC1(C)CCCCC1(O)C1c2ccccc2-c2cncn21] | Same as 164a | 283.2 |

TABLE 2-continued

| Ex. # | Structure | $^1$H NMR | MS (M + H)$^+$ |
|---|---|---|---|
| 165a | 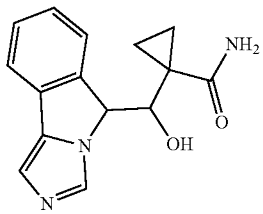 [SMILES: NC(=O)C1(C(O)C2c3ccccc3-c3cncn32)CC1] | $^1$H NMR (500 MHz, DMSO-d6) δ 7.76 (s, 1H), 7.66-7.62 (m, 1H), 7.56 (dt, J = 7.5, 0.9 Hz, 1H), 7.41-7.33 (m, 1H), 7.29-7.17 (m, 3H), 7.09 (s, 1H), 5.94 (d, J = 5.1 Hz, 1H), 5.48 (d, J = 6.9 Hz, 1H), 1.02-0.95 (m, 2H), 0.73-0.65 (m, 1H), 0.52-0.42 (m, 1H). | 270.2 |
| 165b | 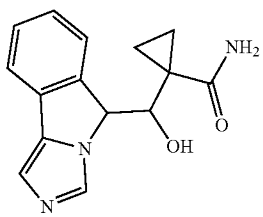 [SMILES: NC(=O)C1(C(O)C2c3ccccc3-c3cncn32)CC1] | $^1$H NMR (500 MHz, DMSO-d6) δ 7.83 (s, 1H), 7.57 (dt, J = 7.5, 0.9 Hz, 1H), 7.51 (dd, J = 7.6, 0.9 Hz, 1H), 7.40-7.35 (m, 1H), 7.32-7.21 (m, 3H), 7.10 (s, 1H), 6.05 (s, 1H), 5.57 (d, J = 7.3 Hz, 1H), 1.10 (ddd, J = 9.4, 6.8, 4.2 Hz, 1H), 0.97 (ddd, J = 9.4, 6.4, 4.1 Hz, 1H), 0.78 (ddd, J = 9.4, 6.8, 4.2 Hz, 1H), 0.40 (ddd, J = 9.4, 6.5, 4.2 Hz, 1H). | 270.2 |
| 165c | 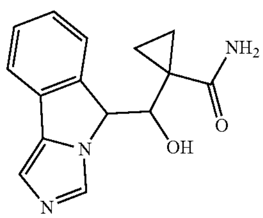 [SMILES: NC(=O)C1(C(O)C2c3ccccc3-c3cncn32)CC1] | $^1$H NMR (500 MHz, DMSO-d6) δ 7.76 (s, 1H), 7.64 (dd, J = 7.7, 1.0 Hz, 1H), 7.59-7.54 (m, 1H), 7.37 (t, J = 7.4 Hz, 1H), 7.23 (td, J = 7.6, 1.2 Hz, 3H), 7.09 (s, 1H), 5.94 (d, J = 5.8 Hz, 1H), 5.48 (d, J = 6.9 Hz, 1H), 1.00-0.97 (m, 2H), 0.72-0.66 (m, 1H), 0.51-0.43 (m, 1H). | 270.2 |
| 165d | 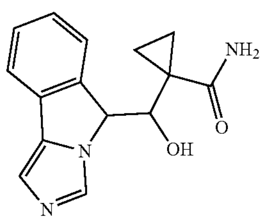 [SMILES: NC(=O)C1(C(O)C2c3ccccc3-c3cncn32)CC1] | $^1$H NMR (500 MHz, DMSO-d6) δ 7.83 (s, 1H), 7.57 (dt, J = 7.5, 0.9 Hz, 1H), 7.51 (dd, J = 7.6, 0.9 Hz, 1H), 7.40-7.35 (m, 1H), 7.32-7.21 (m, 3H), 7.10 (s, 1H), 6.05 (s, 1H), 5.57 (d, J = 7.3 Hz, 1H), 1.10 (ddd, J = 9.4, 6.8, 4.2 Hz, 1H), 0.97 (ddd, J = 9.4, 6.4, 4.1 Hz, 1H), 0.78 (ddd, J = 9.4, 6.8, 4.2 Hz, 1H), 0.40 (ddd, J = 9.4, 6.5, 4.2 Hz, 1H). | 270.2 |
| 166a | 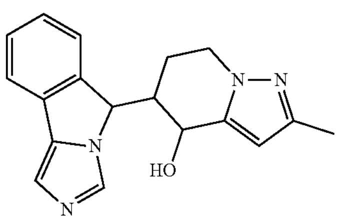 [SMILES: Cc1cc2n(n1)CCC(C1c3ccccc3-c3cncn31)C2O] | $^1$H NMR (500 MHz, DMSO-$d_6$) δ 7.97 (s, 1H), 7.64 (dt, J = 7.6, 0.9 Hz, 1H), 7.50 (dq, J = 7.6, 1.0 Hz, 1H), 7.42 (tt, J = 7.4, 0.9 Hz, 1H), 7.32 (td, J = 7.5, 1.1 Hz, 1H), 7.19 (s, 1H), 6.10 (d, J = 5.6 Hz, 1H), 6.08 (s, 1H), 5.75 (d, J = 1.8 Hz, 1H), 4.97 (dd, J = 10.5, 5.1 Hz, 1H), 3.89-3.82 (m, 1H), 3.69 (td, J = 12.0, 5.4 Hz, 1H), 2.49-2.43 (m, 1H), 2.12 (s, 3H), 1.08-1.00 (m, 2H). | 307 |
| 166b | 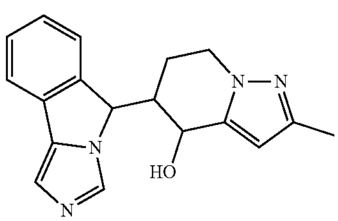 [SMILES: Cc1cc2n(n1)CCC(C1c3ccccc3-c3cncn31)C2O] | $^1$H NMR (500 MHz, DMSO-$d_6$) δ 7.97 (s, 1H), 7.64 (dt, J = 7.6, 0.9 Hz, 1H), 7.50 (dq, J = 7.6, 1.0 Hz, 1H), 7.42 (tt, J = 7.4, 0.9 Hz, 1H), 7.32 (td, J = 7.5, 1.1 Hz, 1H), 7.19 (s, 1H), 6.10 (d, J = 5.6 Hz, 1H), 6.08 (s, 1H), 5.75 (d, J = 1.8 Hz, 1H), 4.97 (dd, J = 10.5, 5.1 Hz, 1H), 3.89-3.82 (m, 1H), 3.69 (td, J = 12.0, 5.4 Hz, 1H), 2.49-2.43 (m, 1H), 2.12 (s, 3H), 1.08-1.00 (m, 2H). | 307 |
| 167a | 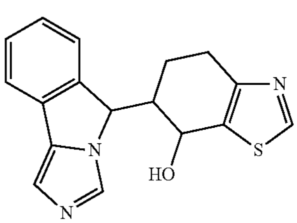 [SMILES: OC1c2scnc2CCC1C1c2ccccc2-c2cncn21] | $^1$H NMR (500 MHz, DMSO-$d_6$) δ 8.97 (s, 1H), 7.97 (s, 1H), 7.75 (dd, J = 7.7, 1.0 Hz, 1H), 7.61 (d, J = 7.5 Hz, 1H), 7.38 (dd, J = 8.0, 7.1 Hz, 1H), 7.24 (td, J = 7.6, 1.1 Hz, 1H), 7.13 (s, 1H), 5.87 (d, J = 6.7 Hz, 1H), 5.47 (d, J = 5.5 Hz, 1H), 5.07 (dd, J = 6.8, 3.6 Hz, 1H), 2.82 (dd, J = 16.8, 3.9 Hz, 1H), 2.57 (ddd, J = 16.9, 11.7, 5.9 Hz, 1H), 2.37-2.28 (m, 1H), 1.94 (qd, J = 12.6, 5.3 Hz, 1H), 1.69 (d, J = 12.6 Hz, 1H). | 310 |

TABLE 2-continued

| Ex. # | Structure | $^1$H NMR | MS (M + H)$^+$ |
|---|---|---|---|
| 167b | 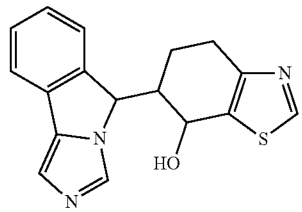 [SMILES: OC1c2scnc2CCC1C1c2ccccc2-c2cncn21] | $^1$H NMR (500 MHz, DMSO-$d_6$) δ 8.94 (d, J = 0.7 Hz, 1H), 7.92 (s, 1H), 7.63 (ddd, J = 14.2, 7.7, 1.0 Hz, 2H), 7.41 (ddd, J = 7.5, 6.9, 0.9 Hz, 1H), 7.26 (td, J = 7.6, 1.2 Hz, 1H), 7.17 (s, 1H), 6.37 (d, J = 6.4 Hz, 1H), 5.76 (d, J = 3.0 Hz, 1H), 5.15 (s, 1H), 2.60-2.52 (m, 2H), 1.06-0.82 (m, 3H). | 310 |
| 167c | 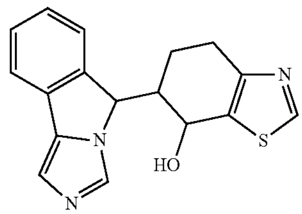 [SMILES: OC1c2scnc2CCC1C1c2ccccc2-c2cncn21] | $^1$H NMR (500 MHz, DMSO-$d_6$) δ 8.96 (d, J = 0.8 Hz, 1H), 8.00 (s, 1H), 7.66-7.62 (m, 1H), 7.49 (dq, J = 7.7, 1.0 Hz, 1H), 7.44-7.41 (m, 1H), 7.33 (td, J = 7.5, 1.1 Hz, 1H), 7.18 (s, 1H), 6.34 (d, J = 7.6 Hz, 1H), 5.76 (s, 1H), 5.20 (t, J = 8.6 Hz, 1H), 2.64-2.57 (m, 1H), 2.46-2.33 (m, 2H), 0.96-0.84 (m, 2H). | 310 |
| 167d | 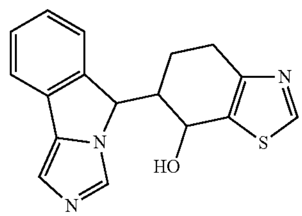 [SMILES: OC1c2scnc2CCC1C1c2ccccc2-c2cncn21] | $^1$H NMR (500 MHz, DMSO-$d_6$) δ 8.96 (d, J = 0.7 Hz, 1H), 8.00 (s, 1H), 7.64 (d, J = 7.5 Hz, 1H), 7.52-7.47 (m, 1H), 7.42 (t, J = 7.5 Hz, 1H), 7.33 (td, J = 7.5, 1.1 Hz, 1H), 7.18 (s, 1H), 6.33 (d, J = 7.6 Hz, 1H), 5.76 (s, 1H), 5.20 (t, J = 8.7 Hz, 1H), 2.59 (s, 1H), 2.43 (t, J = 10.6 Hz, 2H), 0.99-0.84 (m, 2H). | 310 |
| 167e | 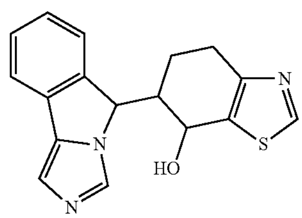 [SMILES: OC1c2scnc2CCC1C1c2ccccc2-c2cncn21] | $^1$H NMR (500 MHz, DMSO-$d_6$) δ 9.00 (s, 1H), 7.94 (s, 1H), 7.61 (ddt, J = 12.0, 7.7, 0.9 Hz, 2H), 7.39 (tt, J = 7.5, 0.9 Hz, 1H), 7.29 (td, J = 7.5, 1.2 Hz, 1H), 7.12 (s, 1H), 6.16 (d, J = 6.6 Hz, 1H), 5.53 (d, J = 1.5 Hz, 1H), 5.25 (dd, J = 6.6, 3.9 Hz, 1H), 2.76-2.68 (m, 1H), 2.62-2.55 (m, 1H), 2.48-2.42 (m, 1H), 1.52 (qd, J = 12.7, 5.6 Hz, 1H), 1.01-0.93 (m, 1H). | 310 |
| 167f | 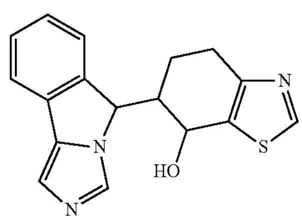 [SMILES: OC1c2scnc2CCC1C1c2ccccc2-c2cncn21] | $^1$H NMR (500 MHz, DMSO-$d_6$) δ 8.97 (s, 1H), 7.97 (s, 1H), 7.75 (dd, J = 7.7, 1.0 Hz, 1H), 7.61 (d, J = 7.5 Hz, 1H), 7.41-7.36 (m, 1H), 7.24 (td, J = 7.6, 1.2 Hz, 1H), 7.13 (s, 1H), 5.87 (d, J = 6.7 Hz, 1H), 5.47 (d, J = 5.6 Hz, 1H), 5.07 (dd, J = 6.7, 3.7 Hz, 1H), 2.85-2.79 (m, 1H), 2.57 (ddd, J = 17.0, 11.7, 5.8 Hz, 1H), 2.33 (ddd, J = 12.9, 5.8, 3.0 Hz, 1H), 1.94 (qd, J = 12.6, 5.5 Hz, 1H), 1.69 (d, J = 11.3 Hz, 1H). | 310 |
| 167g | 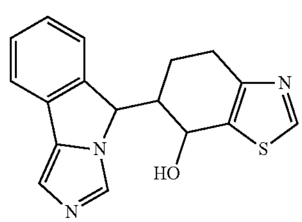 [SMILES: OC1c2scnc2CCC1C1c2ccccc2-c2cncn21] | $^1$H NMR (500 MHz, DMSO-$d_6$) δ 8.94 (d, J = 0.7 Hz, 1H), 7.92 (s, 1H), 7.63 (dd, J = 15.0, 7.6 Hz, 2H), 7.41 (dd, J = 7.9, 7.1 Hz, 1H), 7.26 (td, J = 7.6, 1.2 Hz, 1H), 7.17 (s, 1H), 6.35 (d, J = 7.3 Hz, 1H), 5.76 (d, J = 2.9 Hz, 1H), 5.14 (t, J = 8.6 Hz, 1H), 2.61-2.54 (m, 2H), 1.06-0.79 (m, 3H). | 310 |
| 167h | 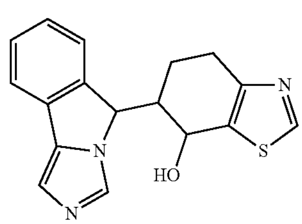 [SMILES: OC1c2scnc2CCC1C1c2ccccc2-c2cncn21] | $^1$H NMR (500 MHz, DMSO-$d_6$) δ 9.00 (s, 1H), 7.94 (s, 1H), 7.61 (ddt, J = 12.1, 7.7, 1.0 Hz, 2H), 7.39 (tt, J = 7.6, 0.9 Hz, 1H), 7.29 (td, J = 7.5, 1.2 Hz, 1H), 7.12 (s, 1H), 6.16 (d, J = 6.6 Hz, 1H), 5.53 (d, J = 1.7 Hz, 1H), 5.25 (dd, J = 6.6, 3.9 Hz, 1H), 2.76-2.69 (m, 1H), 2.62-2.55 (m, 1H), 2.47-2.41 (m, 1H), 1.52 (qd, J = 12.6, 5.5 Hz, 1H), 1.01-0.94 (m, 1H). | 310 |

TABLE 2-continued

| Ex. # | Structure | $^{1}$H NMR | MS $(M + H)^+$ |
|---|---|---|---|
| 168a | 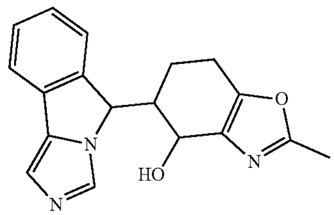 [SMILES: Cc1nc2c(o1)CCC(C1c3ccccc3-c3cncn31)C2O] | $^{1}$H NMR (500 MHz, DMSO-d6) δ 7.91 (s, 1H), 7.63 (dt, J = 7.5, 1.0 Hz, 1H), 7.49-7.37 (m, 2H), 7.32 (td, J = 7.5, 1.2 Hz, 1H), 7.17 (s, 1H), 5.72 (m, J = 6.9 Hz, 2H), 4.89 (m, 1H), 2.43-2.26 (m, 5H), 0.99-0.78 (m, 2H) | 308.1 |
| 168 b | 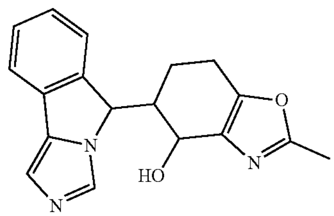 [SMILES: Cc1nc2c(o1)CCC(C1c3ccccc3-c3cncn31)C2O] | Same as 168 a | 308.1 |
| 169a | 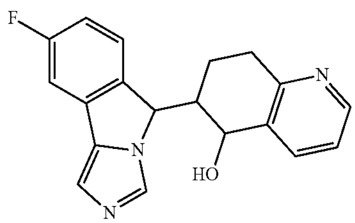 [SMILES: OC1c2cccnc2CCC1C1c2ccc(F)cc2-c2cncn21] | 1H NMR (400 MHz, DMSO-d6) δ 8.35 (ddd, J = 4.7, 1.8, 0.7 Hz, 1H), 8.01 (s, 1H), 8.00-7.97 (m, 1H), 7.53 (ddd, J = 9.6, 6.4, 3.7 Hz, 2H), 7.27 (dd, J = 7.9, 4.7 Hz, 1H), 7.23 (s, 1H), 7.14 (ddd, J = 9.6, 8.4, 2.5 Hz, 1H), 6.21 (d, J = 7.5 Hz, 1H), 5.80 (s, 1H), 4.97 (dd, J = 10.6, 7.6 Hz, 1H), 2.68 (dd, J = 8.8, 4.0 Hz, 2H), 2.47-2.38 (m, 1H), 1.02-0.82 (m, 2H). | |
| 170a | 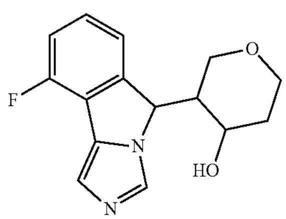 [SMILES: OC1CCOCC1C1c2cccc(F)c2-c2cncn21] | $^{1}$H NMR (500 MHz, DMSO-$d_6$) δ 7.97 (s, 1H), 7.45-7.33 (m, 2H), 7.28 (ddt, J = 9.0, 8.2, 0.8 Hz, 1H), 7.13 (s, 1H), 5.81-5.77 (m, 1H), 5.48 (d, J = 5.7 Hz, 1H), 3.94 (tt, J = 10.4, 5.0 Hz, 1H), 3.77 (dd, J = 11.6, 4.7 Hz, 1H), 3.26-3.15 (m, 1H), 3.03-2.96 (m, 1H), 2.39 (t, J = 11.2 Hz, 1H), 2.25 (tt, J = 10.8, 3.5 Hz, 1H), 1.96-1.88 (m, 1H), 1.62-1.50 (m, 1H). | 275 |
| 170b | 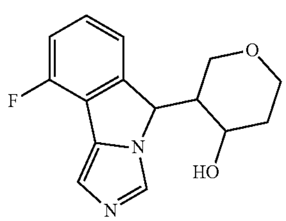 [SMILES: OC1CCOCC1C1c2cccc(F)c2-c2cncn21] | $^{1}$H NMR (500 MHz, DMSO-$d_6$) δ 7.97 (s, 1H), 7.45-7.33 (m, 2H), 7.28 (t, J = 8.8 Hz, 1H), 7.13 (s, 1H), 5.79 (d, J = 2.5 Hz, 1H), 5.48 (d, J = 5.6 Hz, 1H), 3.94 (tt, J = 10.3, 4.9 Hz, 1H), 3.77 (dd, J = 11.7, 4.7 Hz, 1H), 3.20 (td, J = 12.2, 2.1 Hz, 1H), 2.99 (dd, J = 11.5, 4.0 Hz, 1H), 2.39 (t, J = 11.2 Hz, 1H), 2.25 (tt, J = 10.7, 3.5 Hz, 1H), 1.92 (ddt, J = 12.6, 4.2, 2.0 Hz, 1H), 1.56 (tdd, J = 12.5, 10.5, 4.8 Hz, 1H). | 275 |
| 170c | 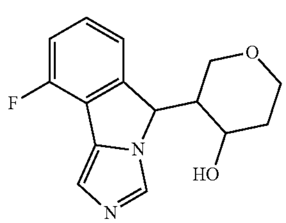 [SMILES: OC1CCOCC1C1c2cccc(F)c2-c2cncn21] | $^{1}$H NMR (500 MHz, DMSO-$d_6$) δ 8.06 (s, 1H), 7.41 (dq, J = 7.6, 0.9 Hz, 1H), 7.38-7.33 (m, 1H), 7.33-7.23 (m, 1H), 7.12 (s, 1H), 5.73 (d, J = 3.5 Hz, 1H), 5.29 (d, J = 5.2 Hz, 1H), 3.79 (qd, J = 13.2, 11.7, 4.7 Hz, 2H), 3.17 (td, J = 12.0, 2.3 Hz, 1H), 3.02-2.95 (m, 1H), 2.61 (t, J = 11.2 Hz, 1H), 2.41 (ddt, J = 10.7, 6.9, 3.8 Hz, 1H), 1.87-1.79 (m, 1H), 1.57-1.45 (m, 1H). | 275 |
| 170d | 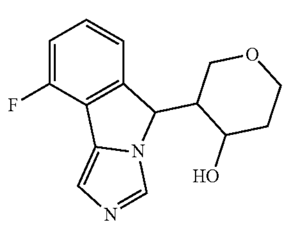 [SMILES: OC1CCOCC1C1c2cccc(F)c2-c2cncn21] | $^{1}$H NMR (500 MHz, DMSO-$d_6$) δ 8.06 (t, J = 0.7 Hz, 1H), 7.41 (dd, J = 7.6, 1.0 Hz, 1H), 7.38-7.33 (m, 1H), 7.33-7.24 (m, 1H), 7.11 (s, 1H), 5.73 (d, J = 3.5 Hz, 1H), 5.29 (s, 1H), 3.78 (ddd, J = 21.3, 10.9, 4.4 Hz, 2H), 3.17 (td, J = 12.0, 2.2 Hz, 1H), 2.99 (dd, J = 11.3, 3.9 Hz, 1H), 2.61 (t, J = 11.2 Hz, 1H), 2.41 (tt, J = 10.8, 3.8 Hz, 1H), 1.87-1.79 (m, 1H), 1.57-1.45 (m, 1H). | 275 |

TABLE 2-continued

| Ex. # | Structure | $^{1}$H NMR | MS $(M + H)^{+}$ |
|---|---|---|---|
| 171a | 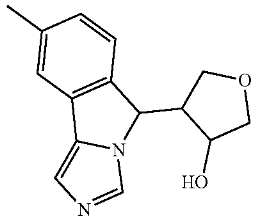 [SMILES: Cc1ccc2c(c1)-c1cncn1C2C1COCC1O] | $^{1}$H NMR (500 MHz, DMSO-$d_6$) δ 8.01 (s, 1H), 7.45-7.39 (m, 2H), 7.16 (s, 1H), 7.12-7.06 (m, 1H), 5.54 (d, J = 4.1 Hz, 1H), 5.22 (d, J = 4.6 Hz, 1H), 4.26 (dq, J = 5.7, 4.1 Hz, 1H), 3.71 (dd, J = 9.2, 8.1 Hz, 1H), 3.57 (dd, J = 9.2, 5.6 Hz, 1H), 3.42 (dd, J = 9.2, 4.0 Hz, 1H), 3.16 (dd, J = 9.2, 6.3 Hz, 1H), 2.81 (ddt, J = 8.1, 6.3, 4.0 Hz, 1H), 2.36 (d, J = 0.8 Hz, 3H). | 257 |
| 171b | 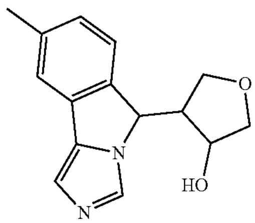 [SMILES: Cc1ccc2c(c1)-c1cncn1C2C1COCC1O] | $^{1}$H NMR (500 MHz, DMSO-$d_6$) δ 8.06 (s, 1H), 7.46-7.40 (m, 2H), 7.19 (s, 1H), 7.10 (ddd, J = 7.8, 1.7, 0.8 Hz, 1H), 5.55 (d, J = 4.1 Hz, 1H), 5.22 (d, J = 4.6 Hz, 1H), 4.25 (dd, J = 5.6, 4.0 Hz, 1H), 3.72 (dd, J = 9.2, 8.1 Hz, 1H), 3.58 (dd, J = 9.2, 5.7 Hz, 1H), 3.41 (dd, J = 9.2, 4.1 Hz, 1H), 3.18 (dd, J = 9.2, 6.3 Hz, 1H), 2.81 (ddt, J = 8.0, 6.2, 4.0 Hz, 1H), 2.38-2.34 (m, 3H). | 257 |
| 171c | 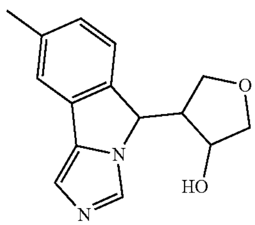 [SMILES: Cc1ccc2c(c1)-c1cncn1C2C1COCC1O] | $^{1}$H NMR (500 MHz, DMSO-$d_6$) δ 8.19 (s, 1H), 7.50-7.46 (m, 1H), 7.43 (d, J = 7.8 Hz, 1H), 7.28 (s, 1H), 7.15 (ddd, J = 7.9, 1.7, 0.8 Hz, 1H), 5.54 (d, J = 4.7 Hz, 1H), 5.03 (d, J = 4.8 Hz, 1H), 4.00 (dd, J = 9.3, 7.7 Hz, 1H), 3.87 (s, 1H), 3.80 (dd, J = 9.3, 5.5 Hz, 1H), 3.44-3.37 (m, 2H), 2.75 (dtd, J = 8.1, 5.3, 3.1 Hz, 1H), 2.38 (s, 3H). | 257 |
| 171d | 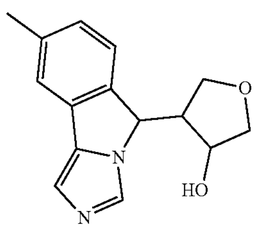 [SMILES: Cc1ccc2c(c1)-c1cncn1C2C1COCC1O] | $^{1}$H NMR (500 MHz, DMSO-$d_6$) δ 8.16 (s, 1H), 7.50-7.45 (m, 1H), 7.42 (d, J = 7.8 Hz, 1H), 7.26 (s, 1H), 7.14 (ddd, J = 7.8, 1.7, 0.8 Hz, 1H), 5.53 (d, J = 4.7 Hz, 1H), 5.03 (d, J = 4.7 Hz, 1H), 4.00 (dd, J = 9.3, 7.7 Hz, 1H), 3.87 (d, J = 4.7 Hz, 1H), 3.79 (dd, J = 9.3, 5.5 Hz, 1H), 3.40 (qd, J = 9.3, 4.5 Hz, 2H), 2.75 (dtd, J = 8.0, 5.3, 3.1 Hz, 1H), 2.37 (s, 3H). | 257 |
| 172a | 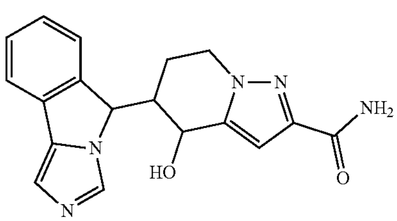 [SMILES: NC(=O)c1cc2n(n1)CCC(C1c3ccccc3-c3cncn31)C2O] | | 336 |
| 172b | 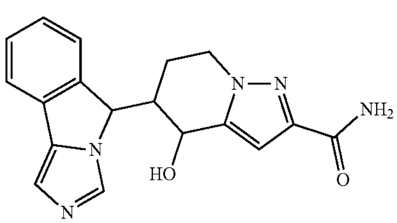 [SMILES: NC(=O)c1cc2n(n1)CCC(C1c3ccccc3-c3cncn31)C2O] | | 336 |
| 173a | 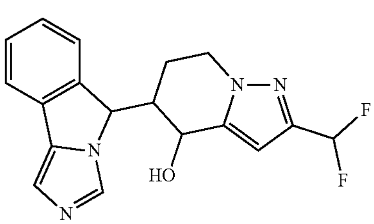 [SMILES: OC1c2cc(C(F)F)nn2CCC1C1c2ccccc2-c2cncn21] | | 343 |

TABLE 2-continued
| Ex. # | Structure | $^1$H NMR | MS $(M + H)^+$ |
|---|---|---|---|
| 173b | 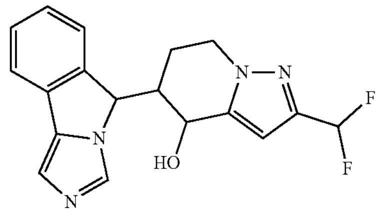 [SMILES: OC1c2cc(C(F)F)nn2CCC1C1c2ccccc2-c2cncn21] | | 343 |
| 174a | 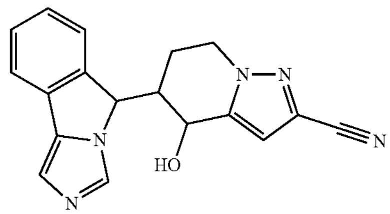 [SMILES: N#Cc1cc2n(n1)CCC(C1c3ccccc3-c3cncn31)C2O] | | 318 |
| 174b | 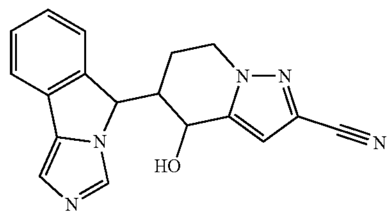 [SMILES: N#Cc1cc2n(n1)CCC(C1c3ccccc3-c3cncn31)C2O] | | 318 |
| 175a | 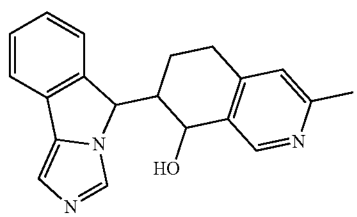 [SMILES: Cc1cc2c(cn1)C(O)C(C1c3ccccc3-c3cncn31)CC2] | | 318 |
| 175b | 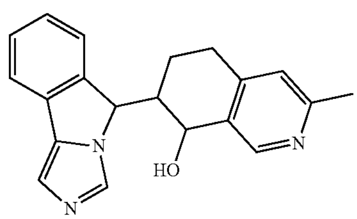 [SMILES: Cc1cc2c(cn1)C(O)C(C1c3ccccc3-c3cncn31)CC2] | | 318 |
| 176a | 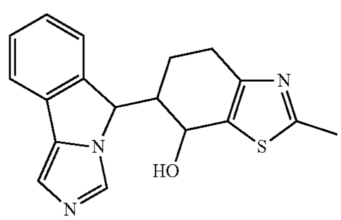 [SMILES: Cc1nc2c(s1)C(O)C(C1c3ccccc3-c3cncn31)CC2] | | 324 |
| 176b | 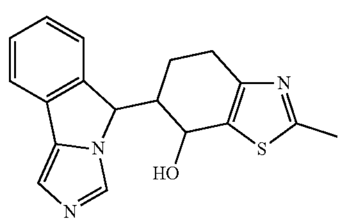 [SMILES: Cc1nc2c(s1)C(O)C(C1c3ccccc3-c3cncn31)CC2] | | 324 |

TABLE 2-continued

| Ex. # | Structure | $^1$H NMR | MS $(M + H)^+$ |
|---|---|---|---|
| 177 | 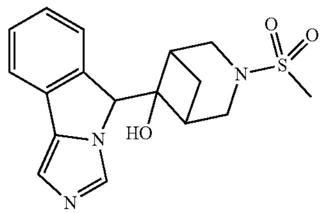 [SMILES: CS(=O)(=O)N1CC2CC(C1)C2(O)C1c2ccccc2-c2cncn21] | | 346 |
| 178a | 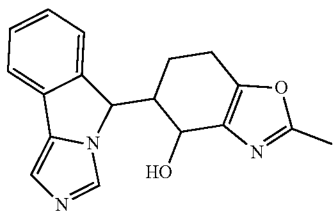 [SMILES: Cc1nc2c(o1)CCC(C1c3ccccc3-c3cncn31)C2O] | | 308 |
| 178b | 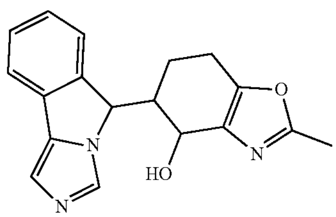 [SMILES: Cc1nc2c(o1)CCC(C1c3ccccc3-c3cncn31)C2O] | | 308 |
| 179a | 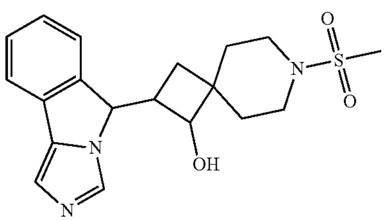 [SMILES: CS(=O)(=O)N1CCC2(CC1)CC(C1c3ccccc3-c3cncn31)C2O] | $^1$H NMR (400 MHz, DMSO-$d_6$) δ 7.86 (s, 1H), 7.63-7.57 (m, 2H), 7.40-7.24 (m, 2H), 7.15 (s, 1H), 5.43 (d, J = 6.9 Hz, 1H), 5.32 (d, J = 6.3 Hz, 1H), 4.08 (dd, J = 7.9, 6.2 Hz, 1H), 3.37-3.31 (m, 1H), 3.28-3.24 (m, 1H), 2.95-2.69 (m, 5H), 2.52-2.47 (m, 1H), 1.74-1.54 (m, 4H), 1.45-1.41 (m, 1H), 0.95 (t, J = 10.4 Hz, 1H). | 374 |
| 179b | 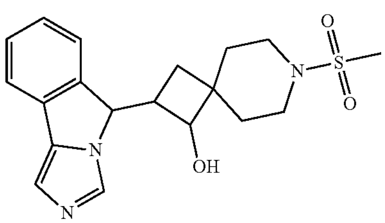 [SMILES: CS(=O)(=O)N1CCC2(CC1)CC(C1c3ccccc3-c3cncn31)C2O] | $^1$H NMR (400 MHz, DMSO-$d_6$) δ 7.86 (s, 1H), 7.63-7.57 (m, 2H), 7.40-7.24 (m, 2H), 7.15 (s, 1H), 5.43 (d, J = 6.9 Hz, 1H), 5.32 (d, J = 6.4 Hz, 1H), 4.08 (dd, J = 7.9, 6.3 Hz, 1H), 3.34-3.32 (m, 1H), 3.32-3.24 (m, 1H), 2.91-2.69 (m, 5H), 1.74-1.54 (m, 4H), 1.43 (d, J = 13.5 Hz, 1H), 0.95 (t, J = 10.5 Hz, 1H) | 374 |
| 179c | 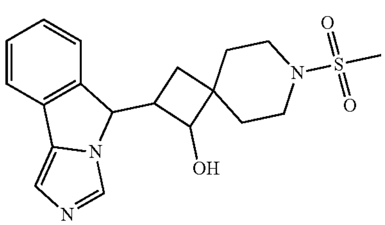 [SMILES: CS(=O)(=O)N1CCC2(CC1)CC(C1c3ccccc3-c3cncn31)C2O] | $^1$H NMR (400 MHz, DMSO-$d_6$) δ 7.95 (s, 1H), 7.61 (dd, J = 7.2, 1.5 Hz, 1H), 7.39 (t, J = 7.5 Hz, 2H), 7.28-7.23 (m, 2H), 7.14 (s, 1H), 5.41 (d, J = 8.6 Hz, 1H), 5.26 (d, J = 6.7 Hz, 1H), 3.98 (t, J = 7.2 Hz, 1H), 3.37-3.27 (m, 2H), 2.94-2.77 (m, 5H), 2.36-2.30 (m, 1H), 1.86 (dd, J = 11.0, 9.5 Hz, 1H), 1.72-1.45 (m, 5H). | 374 |
| 179d | 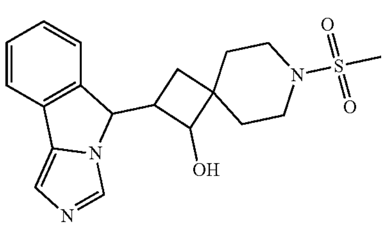 [SMILES: CS(=O)(=O)N1CCC2(CC1)CC(C1c3ccccc3-c3cncn31)C2O] | $^1$H NMR (400 MHz, DMSO-$d_6$) δ 7.90 (s, 1H), 7.67 (d, J = 7.5 Hz, 1H), 7.59 (d, J = 7.5 Hz, 1H), 7.41-7.36 (m, 1H), 7.30-7.25 (m, 1H), 7.13 (s, 1H), 5.40 (d, J = 4.0 Hz, 1H), 5.38 (d, J = 5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H) | 374 |

TABLE 2-continued

| Ex. # | Structure | $^1$H NMR | MS $(M + H)^+$ |
|---|---|---|---|
| 179e | 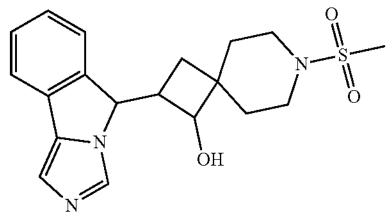 [SMILES: CS(=O)(=O)N1CCC2(CC1)CC(C1c3ccccc3-c3cncn31)C2O] | $^1$H NMR (400 MHz, DMSO-$d_6$) δ 7.86 (s, 1H), 7.70-7.58 (m, 2H), 7.48-7.24 (m, 2H), 7.14 (d, J = 2.9 Hz, 1H), 5.76 (d, J = 5.5 Hz, 1H), 5.47 (d, J = 8.7 Hz, 1H), 4.12 (dd, J = 9.0, 4.8 Hz, 1H), 3.32-2.92 (m, 4H), 2.83 (s, 1H), 2.67-2.52 (m, 1H), 1.94-1.79 (m, 3H), 1.60 (t, J = 5.8 Hz, 3H). | 374 |
| 179f | 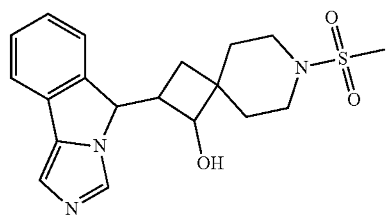 [SMILES: CS(=O)(=O)N1CCC2(CC1)CC(C1c3ccccc3-c3cncn31)C2O] | $^1$H NMR (400 MHz, DMSO-$d_6$) δ 7.86 (s, 1H), 7.65-7.58 (m, 2H), 7.40-7.24 (m 2H), 7.14 (s, 1H), 5.75 (d, J = 5.5 Hz, 1H), 5.47 (d, J = 8.7 Hz, 1H), 4.13 (td, J = 6.3, 3.0 Hz, 1H), 3.19-2.95 (m, 4H), 2.83 (s, 3H), 2.61-2.51 (m, 1H), 1.94-1.75 (m, 3H), 1.60 (t, J = 5.8 Hz, 3H) | 374 |
| 179g | 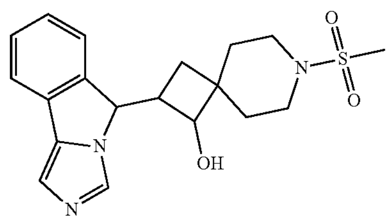 [SMILES: CS(=O)(=O)N1CCC2(CC1)CC(C1c3ccccc3-c3cncn31)C2O] | $^1$H NMR (400 MHz, DMSO-$d_6$) δ 7.85 (s, 1H), 7.63-7.60 (m, 1H), 7.41-7.36 (m, 2H), 7.26-7.20 (m, 1H), 7.13 (s, 1H), 5.79 (d, J = 6.0 Hz, 1H), 5.42 (d, J = 10.6 Hz, 1H), 4.08 (td, J = 5.9, 2.9 Hz, 1H, 3.20-2.98 (m, 4H), 2.85 (s, 3H), 2.35-2.19 (m, 2H), 1.95-1.61 (m, 5H). | 374 |
| 179h | 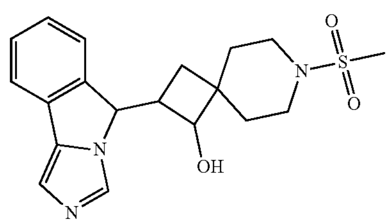 [SMILES: CS(=O)(=O)N1CCC2(CC1)CC(C1c3ccccc3-c3cncn31)C2O] | $^1$H NMR (400 MHz, DMSO-$d_6$) δ 7.86 (s, 1H), 7.63-7.60 (m, 1H), 7.42-7.36 (m, 2H), 7.26-7.20 (m, 1H), 7.14 (s, 1H), 5.79 (d, J = 6.0 Hz, 1H), 5.42 (d, J = 10.7 Hz, 1H), 4.08 (td, J = 6.1, 3.0 Hz, 1H), 3.20-2.98 (m, 4H), 2.85 (s, 3H), 2.35-2.19 (m, 2H), 1.95-1.61 (m, 5H) | 374 |
| 180a | 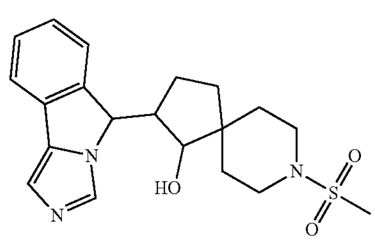 [SMILES: CS(=O)(=O)N1CCC2(CCC(C3c4ccccc4-c4cncn43)C2O)CC1] | $^1$H NMR (400 MHz, DMSO-$d_6$) δ 7.93 (s, 1H), 7.60 (d, J = 7.6 Hz, 1H), 7.54 (d, J = 7.6 Hz, 1H), 7.41-7.37 (m, 1H), 7.29-7.25 (m, 1H), 7.11 (s, 1H), 5.45 (d, J = 4.0 Hz, 1H), 5.08 (d, J = 5.6 Hz, 1H), 3.60-3.57 (m, 1H), 3.44-3.35 (m, 2H), 2.82 (s, 3H), 2.81-2.64 (m, 3H), 1.73-1.58 (m, 3H), 1.35-1.04 (m, 4H), 0.88-0.85 (m, 1H). | 388 |
| 180b | 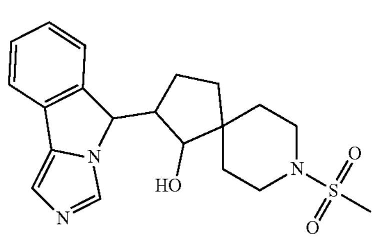 [SMILES: CS(=O)(=O)N1CCC2(CCC(C3c4ccccc4-c4cncn43)C2O)CC1] | $^1$H NMR (400 MHz, DMSO-$d_6$) δ 7.93 (s, 1H), 7.60 (d, J = 7.6 Hz, 1H), 7.54 (d, J = 7.6 Hz, 1H), 7.41-7.37 (m, 1H), 7.29-7.25 (m, 1H), 7.11 (s, 1H), 5.45 (d, J = 4.0 Hz, 1H), 5.08 (d, J = 5.6 Hz, 1H), 3.60-3.57 (m, 1H), 3.44-3.35 (m, 2H), 2.82 (s, 3H), 2.81-2.64 (m, 3H), 1.73-1.58 (m, 3H), 1.35-1.04 (m, 4H), 0.88-0.85 (m, 1H). | 388 |

TABLE 2-continued

| Ex. # | Structure | $^{1}$H NMR | MS (M + H)$^{+}$ |
|---|---|---|---|
| 180c | 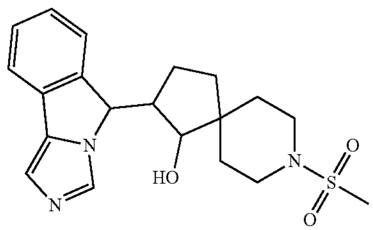 [SMILES: CS(=O)(=O)N1CCC2(CCC(C3c4ccccc4-c4cncn43)C2O)CC1] | $^{1}$H NMR (400 MHz, DMSO-$d_6$) δ 7.90 (s, 1H), 7.67 (d, J = 7.5 Hz, 1H), 7.59 (d, J = 7.5 Hz, 1H), 7.41-7.36 (m, 1H), 7.30-7.25 (m, 1H), 7.13 (s, 1H), 5.40 (d, J = 4.0 Hz, 1H), 5.38 (d, J = 5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H) | 388 |
| 180d | 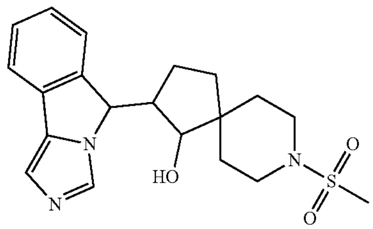 [SMILES: CS(=O)(=O)N1CCC2(CCC(C3c4ccccc4-c4cncn43)C2O)CC1] | $^{1}$H NMR (400 MHz, DMSO-$d_6$) δ 7.90 (s, 1H), 7.67 (d, J = 7.5 Hz, 1H), 7.59 (d, J = 7.5 Hz, 1H), 7.41-7.36 (m, 1H), 7.30-7.25 (m, 1H), 7.13 (s, 1H), 5.40 (d, J = 4.0 Hz, 1H), 5.38 (d, J = 5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H). | 388 |
| 181a | 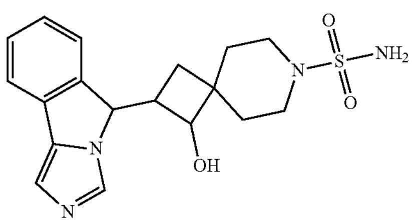 [SMILES: NS(=O)(=O)N1CCC2(CC1)CC(C1c3ccccc3-c3cncn31)C2O] | $^{1}$H NMR (400 MHz, DMSO-$d_6$) δ 7.93 (s, 1H), 7.61-7.58 (m, 2H), 7.41-7.25 (m, 2H), 7.18 (s, 1H), 6.64 (s, 2H), 5.43 (d, J = 7.3 Hz, 1H), 5.29 (d, J = 6.7 Hz, 1H), 4.06 (t, J = 7.2 Hz, 1H), 3.32-3.15 (m, 2H), 2.73-2.51 (m, 4H), 2.50-2.43 (m, 1H), 1.73-1.39 (m, 5H), 1.04 (t, J = 10.4 Hz, 1H). | 375 |
| 181b | 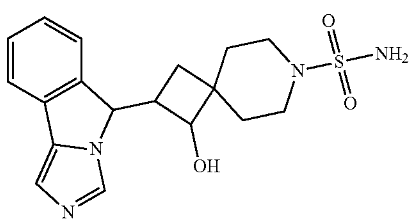 [SMILES: NS(=O)(=O)N1CCC2(CC1)CC(C1c3ccccc3-c3cncn31)C2O] | $^{1}$H NMR (400 MHz, DMSO-$d_6$) δ 7.96 (s, 1H), 7.61 (d, J = 7.5 Hz, 2H), 7.47-7.26 (m, 2H), 7.20 (s, 1H), 6.65 (s, 2H), 5.44 (d, J = 7.4 Hz, 1H), 5.29 (d, J = 6.6 Hz, 1H), 4.06 (t, J = 6.8 Hz, 1H), 3.20-3.16 (m, 2H), 2.73-2.54 (m, 4H), 2.50-2.41 (m, 1H), 1.73-1.43 (m, 5H), 1.05 (t, J = 10.5 Hz, 1H) | 375 |
| 181c | 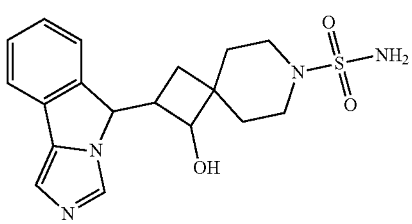 [SMILES: NS(=O)(=O)N1CCC2(CC1)CC(C1c3ccccc3-c3cncn31)C2O] | $^{1}$H NMR (400 MHz, DMSO-$d_6$) δ 8.05 (s, 1H), 7.62 (d, J = 7.5 Hz, 1H), 7.43-7.38 (m, 2H), 7.30-7.24 (m, 1H), 7.20 (s, 1H), 6.67 (s, 2H), 5.43 (d, J = 8.7 Hz, 1H), 5.24 (d, J = 6.9 Hz, 1H), 3.97 (t, J = 7.1 Hz, 1H), 3.26-3.18 (m, 2H), 2.75-2.60 (m, 2H), 2.35-2.29 (m, 1H), 1.86-1.64 (m, 3H), 1.58-1.47 (m, 3H) | 375 |
| 181d | 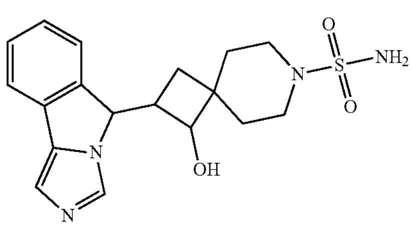 [SMILES: NS(=O)(=O)N1CCC2(CC1)CC(C1c3ccccc3-c3cncn31)C2O] | $^{1}$H NMR (400 MHz, DMSO-$d_6$) δ 7.99 (s, 1H), 7.61 (d, J = 7.5 Hz, 1H), 7.43-7.37 (m, 2H), 7.28-7.23 (m, 1H), 7.16 (s, 1H), 6.67 (s, 2H), 5.41 (d, J = 8.7 Hz, 1H), 5.24 (d, J = 7.0 Hz, 1H), 3.96 (t, J = 7.2 Hz, 1H), 3.26-3.19 (m, 1H), 2.75-2.60 (m, 2H), 2.38-2.26 (m, 1H), 1.86-1.64 (m, 3H), 1.58-1.47 (m, 3H). | 375 |

TABLE 2-continued

| Ex. # | Structure | $^1$H NMR | MS $(M + H)^+$ |
|---|---|---|---|
| 181e | 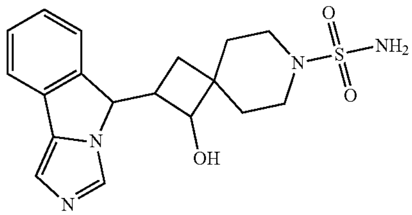 [SMILES: NS(=O)(=O)N1CCC2(CC1)CC(C1c3ccccc3-c3cncn31)C2O] | $^1$H NMR (400 MHz, DMSO-$d_6$) δ 7.86 (s, 1H), 7.65-7.58 (m, 2H), 7.40-7.35 (m, 1H), 7.29-7.24 (m, 1H), 7.14 (s, 1H), 6.69 (s, 2H), 5.76 (d, J = 5.7 Hz, 1H), 5.46 (d, J = 8.9 Hz, 1H), 4.09 (td, J = 6.2, 2.9 Hz, 1H), 3.08-2.98 (m, 2H), 2.88-2.76 (m, 2H), 2.63-2.50 (m, 1H), 1.93 (t, J = 10.4 Hz, 1H), 1.79-1.73 (m, 2H), 1.60 (t, J = 5.5 Hz, 3H). | 375 |
| 181f | 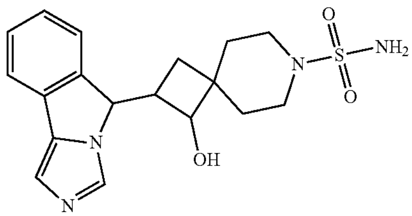 [SMILES: NS(=O)(=O)N1CCC2(CC1)CC(C1c3ccccc3-c3cncn31)C2O] | $^1$H NMR (400 MHz, DMSO-$d_6$) δ 7.86 (s, 1H), 7.65-7.58 (m, 2H), 7.40-7.35 (m, 1H), 7.29-7.24 (m, 1H), 7.14 (s, 1H), 6.69 (s, 2H), 5.77 (d, J = 5.6 Hz, 1H), 5.46 (d, J = 8.9 Hz, 1H), 4.09 (td, J = 6.1, 2.8 Hz, 1H), 3.08-2.98 (m, 2H), 2.88-2.76 (m, 2H), 2.63-2.50 (m, 1H), 1.93 (t, J = 10.4 Hz, 1H), 1.79-1.73 (m, 2H), 1.60 (t, J = 5.5 Hz, 3H). | 375 |
| 181g | 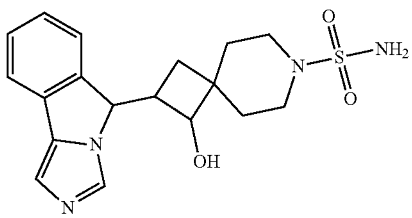 [SMILES: NS(=O)(=O)N1CCC2(CC1)CC(C1c3ccccc3-c3cncn31)C2O] | $^1$H NMR (400 MHz, DMSO-$d_6$) δ 7.89 (s, 1H), 7.62 (d, J = 7.6 Hz, 1H), 7.42-7.36 (m, 2H), 7.26-7.21 (m, 1H), 7.15 (s, 1H), 6.71 (s, 2H), 5.79 (d, J = 6.1 Hz, 1H), 5.42 (d, J = 10.7 Hz, 1H), 4.06 (td, J = 6.4, 3.2 Hz, 1H), 3.20-2.98 (m, 2H), 2.89-2.85 (m, 2H), 2.41-2.28 (m, 1H), 2.22 (t, J = 10.3 Hz, 1H), 1.92-1.76 (m, 2H), 1.68-1.61 (m, 3H). | 375 |
| 181h | 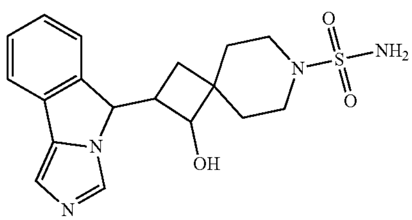 [SMILES: NS(=O)(=O)N1CCC2(CC1)CC(C1c3ccccc3-c3cncn31)C2O] | $^1$H NMR (400 MHz, DMSO-$d_6$) δ 7.89 (s, 1H), 7.62 (d, J = 7.5 Hz, 1H), 7.42-7.36 (m, 2H), 7.26-7.21 (m, 1H), 7.15 (s, 1H), 6.71 (s, 2H), 5.80 (d, J = 6.1 Hz, 1H), 5.42 (d, J = 10.6 Hz, 1H), 4.06 (td, J = 6.0, 2.9 Hz, 1H), 3.20-2.98 (m, 2H), 2.89-2.85 (m, 2H), 2.54 (s, 6H), 2.44-2.29 (m, 1H), 2.22 (t, J = 10.3 Hz, 1H), 1.92-1.76 (m, 2H), 1.68-1.61 (m, 3H). | 375 |
| 182a | 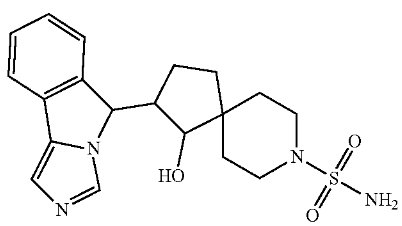 [SMILES: NS(=O)(=O)N1CCC2(CCC(C3c4ccccc4-c4cncn43)C2O)CC1] | $^1$H NMR (400 MHz, DMSO-$d_6$) δ 8.03 (s, 1H), 7.62 (d, J = 7.6 Hz, 1H), 7.54 (d, J = 7.6 Hz, 1H), 7.42-7.30 (m, 1H), 7.29-7.25 (m, 1H), 7.16 (s, 1H), 6.63 (s, 2H), 5.47 (d, J = 4.0 Hz, 1H), 5.07 (d, J = 5.6 Hz, 1H), 3.60-3.55 (m, 1H), 3.28-3.25 (m, 2H), 2.68-2.51 (m, 2H), 2.49-2.45 (m, 1H), 1.74-1.68 (m, 2H), 1.55-1.54 (m, 1H), 1.33-1.01 (m, 4H), 0.86-0.85 (m, 1H). | 389 |
| 182b | 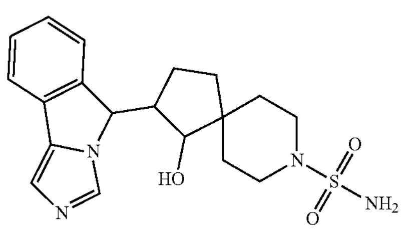 [SMILES: NS(=O)(=O)N1CCC2(CCC(C3c4ccccc4-c4cncn43)C2O)CC1] | $^1$H NMR (400 MHz, DMSO-$d_6$) δ 8.03 (s, 1H), 7.62 (d, J = 7.6 Hz, 1H), 7.54 (d, J = 7.6 Hz, 1H), 7.42-7.30 (m, 1H), 7.29-7.25 (m, 1H), 7.16 (s, 1H), 6.63 (s, 2H), 5.47 (d, J = 4.0 Hz, 1H), 5.07 (d, J = 5.6 Hz, 1H), 3.60-3.55 (m, 1H), 3.28-3.25 (m, 2H), 2.68-2.51 (m, 2H), 2.49-2.45 (m, 1H), 1.74-1.68 (m, 2H), 1.55-1.54 (m, 1H), 1.33-1.01 (m, 4H), 0.86-0.85 (m, 1H). | 389 |
| 182c | 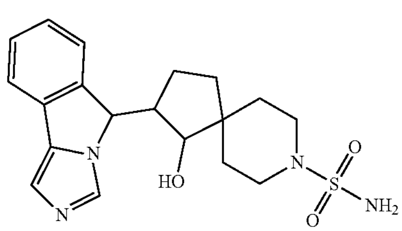 [SMILES: NS(=O)(=O)N1CCC2(CCC(C3c4ccccc4-c4cncn43)C2O)CC1] | $^1$H NMR (400 MHz, DMSO-$d_6$) δ 8.03 (s, 1H), 7.69 (d, J = 7.6 Hz, 1H), 7.61 (d, J = 7.6 Hz, 1H), 7.42-7.38 (m, 1H), 7.31-7.28 (m, 1H), 7.18 (s, 1H), 6.68 (s, 2H), 5.40 (d, J = 4.0 Hz, 1H), 5.38 (d, J = 5.6 Hz, 1H), 3.90-3.88 (m, 1H), 3.23-3.20 (m, 1H), 3.08-3.05 (m, 1H), 2.76-2.67 (m, 2H), 2.32-2.29 (m, 1H), 1.78-1.34 (m, 8H). | 389 |

TABLE 2-continued

| Ex. # | Structure | $^1$H NMR | MS (M + H)$^+$ |
|---|---|---|---|
| 182d | 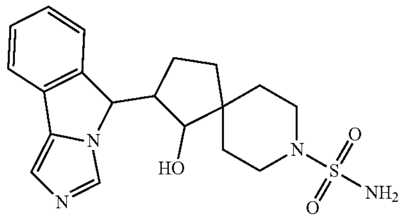 [SMILES: NS(=O)(=O)N1CCC2(CCC(C3c4ccccc4-c4cncn43)C2O)CC1] | $^1$H NMR (400 MHz, DMSO-$d_6$) δ 8.03 (s, 1H), 7.69 (d, J = 7.6 Hz, 1H), 7.61 (d, J = 7.6 Hz, 1H), 7.42-7.38 (m, 1H), 7.31-7.28 (m, 1H), 7.18 (s, 1H), 6.68 (s, 2H), 5.40 (d, J = 4.0 Hz, 1H), 5.38 (d, J = 5.6 Hz, 1H), 3.90-3.88 (m, 1H), 3.23-3.20 (m, 1H), 3.08-3.05 (m, 1H), 2.76-2.67 (m, 2H), 2.32-2.29 (m, 1H), 1.78-1.34 (m, 8H). | 389 |
| 183 | 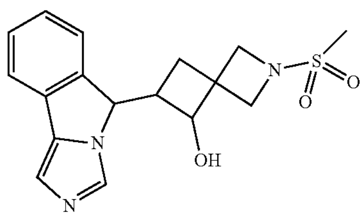 [SMILES: CS(=O)(=O)N1CC2(CC(C3c4ccccc4-c4cncn43)C2O)C1] | | 346 |

Example 1: 2-(5H-imidazo[5,1-a]isoindol-5-yl)cyclobutan-1-ol

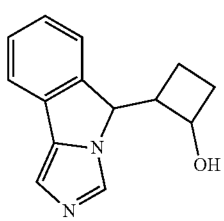 [SMILES: OC1CCC1C1c2ccccc2-c2cncn21]

(1R,2R)-2-((R)-5H-imidazo[5,1-a]isoindol-5-yl)cyclobutan-1-ol (1S,2S)-2-((S)-5H-imidazo[5,1-a]isoindol-5-yl)cyclobutan-1-ol (1S,2R)-2-((R)-5H-imidazo[5,1-a]isoindol-5-yl)cyclobutan-1-ol (1R,2S)-2-((S)-5H-imidazo[5,1-a]isoindol-5-yl)cyclobutan-1-ol (1S,2R)-2-((S)-5H-imidazo[5,1-a]isoindol-5-yl)cyclobutan-1-ol (1R,2S)-2-((R)-5H-imidazo[5,1-a]isoindol-5-yl)cyclobutan-1-ol (1S,2S)-2-((R)-5H-imidazo[5,1-a]isoindol-5-yl)cyclobutan-1-ol (1R,2R)-2-((S)-5H-imidazo[5,1-a]isoindol-5-yl)cyclobutan-1-ol Step 1:

(E)-2-(2-(1-trityl-1H-imidazol-4-yl)benzylidene)cyclobutan-1-one

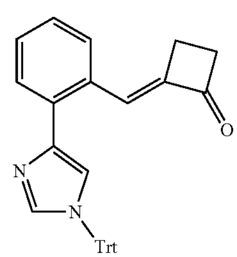

To a solution of 2-[1-(triphenylmethyl)-1H-imidazol-4-yl]benzaldehyde (2.0 g, 4.82 mmol, 1.00 equiv) and cyclobutanone (0.72 mL, 9.65 mmol, 2.00 equiv) in anhydrous ethanol (100 mL) was added NaOH (0.192 g, 4.82 mmol, 1.00 equiv) and the resulting mixture was stirred at 50° C. for 1 hr. The reaction was quenched by 30 mL water and the mixture was extracted by dichloromethane (3×50 mL). The organic layer was combined, washed with brine and water, and dried by anhydrous $Na_2SO_4$. The product was purified by CombiFlash to afford (E)-2-(2-(1-trityl-1H-imidazol-4-yl)benzylidene)cyclobutan-1-one as yellow oil: LCMS (ESI, m/z): 466 [M+H]$^+$ Step 2:

2-(5H-imidazo[5,1-a]isoindol-5-yl)cyclobutan-1-one (cis)

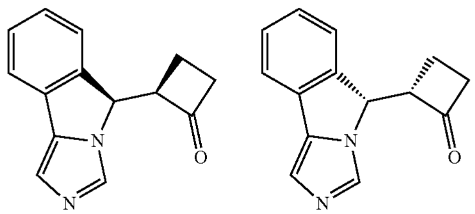

To (E)-2-(2-(1-trityl-1H-imidazol-4-yl)benzylidene)cyclobutan-1-one was added MeOH (16 mL) and AcOH (4 mL). The resulting mixture was stirred at 90° C. for 2 hr. The reaction was quenched by 30 mL saturated $NaHCO_3$ solution and the mixture was extracted by dichloromethane (3×20 mL). The organic layer was combined, washed with brine and water, and dried by anhydrous $Na_2SO_4$. The mixture of diastereomers was separated on CombiFlash to afford 2-(5H-imidazo[5,1-a]isoindol-5-yl)cyclobutan-1-(cis) as a light yellow oil: LCMS (ESI, m/z): 225 $[M+H]^+$.

2-(5H-imidazo[5,1-a]isoindol-5-yl)cyclobutan-1-one (trans)

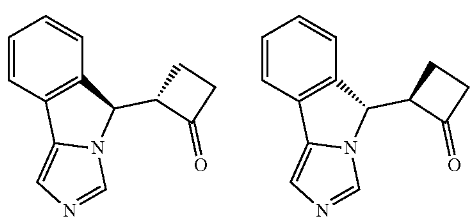

To (E)-2-(2-(1-trityl-1H-imidazol-4-yl)benzylidene)cyclobutan-1-one was added MeOH (16 mL) and AcOH (4 mL). The resulting mixture was stirred at 90° C. for 2 hr. The reaction was quenched by 30 mL saturated $NaHCO_3$ solution and the mixture was extracted by dichloromethane (3×20 mL). The organic layer was combined, washed with brine and water, and dried by anhydrous $Na_2SO_4$. The mixture of diastereomers was separated on CombiFlash to afford 2-(5H-imidazo[5,1-a]isoindol-5-yl)cyclobutan-1-(trans) as a light yellow solid: LCMS (ESI, m/z): 225 $[M+H]^+$.

Step 3:

(1R,2R)-2-((R)-5H-imidazo[5,1-a]isoindol-5-yl)cyclobutan-1-ol (1S,2S)-2-((S)-5H-imidazo[5,1-a]isoindol-5-yl)cyclobutan-1-ol (1S,2R)-2-((R)-5H-imidazo[5,1-a]isoindol-5-yl)cyclobutan-1-ol (1R,2S)-2-((S)-5H-imidazo[5,1-a]isoindol-5-yl)cyclobutan-1-ol 1a

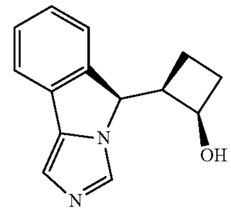

1b

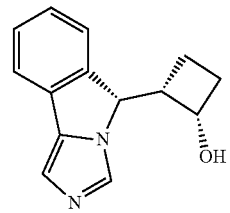

1c

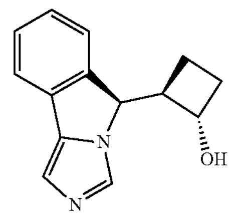

1d

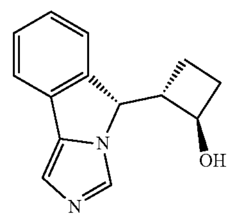

To a solution of 2-(5H-imidazo[5,1-a]isoindol-5-yl)cyclobutan-1-one (cis) (275 mg, 1.23 mmol) in MeOH (10 mL) was added $NaBH_4$ (93 mg, 2.45 mmol) in portions at 0° C. and the solution was stirred at 0° C. for 30 min. The solvent was distilled off and saturated ammonium chloride (10 mL) was added. The aqueous layer was extracted with 5% $CF_3CH_2OH$ in DCM (3×10 mL). The combined organic extract was dried over ($Na_2SO_4$) and concentrated under reduced pressure to afford the crude product. The crude product was purified by Combi-Flash and further isolated by chiral separation to afford 4 isomers as white solid. The absolute configuration of isomers 1a, 1b, 1c, 1d, 1e was determined by X-ray crystallography. The configuration of the rest isomers was assigned arbitrarily.

Example 1a: (1R,2R)-2-((R)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 8.03 (s, 1H), 7.57 (dd, J=13.5, 7.7 Hz, 2H), 7.36 (t, J=7.5 Hz, 1H), 7.25 (td, J=7.4, 1.1 Hz, 1H), 7.14 (s, 1H), 5.74 (d, J=4.5 Hz, 1H), 5.49 (d, J=6.2 Hz, 1H), 4.59-4.48 (m, 1H), 2.88-2.75 (m, 1H), 2.24-2.10 (m, 1H), 1.85-1.52 (m, 3H).

Example 1b: (1S,2S)-2-((S)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 8.03 (s, 1H), 7.57 (dd, J=13.3, 7.6 Hz, 2H), 7.36 (t, J=7.5 Hz, 1H), 7.29-7.20 (m, 1H), 7.14 (s, 1H), 5.74 (d, J=4.0 Hz, 1H), 5.49 (d, J=6.3 Hz, 1H), 4.52 (d, J=11.3 Hz, 1H), 2.82 (p, J=6.3 Hz, 1H), 2.24-2.09 (m, 1H), 1.85-1.52 (m, 3H).

Example 1c: (1S,2R)-2-((R)-5H-imidazo[5,1-a]isoindol-5-yl)cyclobutan-1-ol: LCMS (ESI, m/z): 227.3 $[M+H]^+$.

$^1$HNMR (400 MHz, DMSO-$d_6$) δ 7.84 (s, 1H), 7.61-7.54 (m, 2H), 7.36 (t, J=7.6 Hz, 1H), 7.30-7.21 (m, 1H), 7.13 (s, 1H), 5.34 (dd, J=15.3, 7.4 Hz, 2H), 4.25 (p, J=7.8 Hz, 1H), 3.44-3.21 (m, 2H), 2.41 (dq, J=9.7, 7.8 Hz, 1H), 2.15-2.03 (m, 1H), 1.73-1.50 (m, 2H), 1.12 (qd, J=10.2, 8.1 Hz, 1H).

Example 1d: (1R,2S)-2-((S)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 7.84 (s, 1H), 7.61-7.54 (m, 2H), 7.36 (t, J=7.6 Hz, 1H), 7.31-7.21 (m, 1H), 7.13 (s, 1H), 5.34 (dd, J=15.4, 6.8 Hz, 2H), 4.25 (p, J=7.5 Hz, 1H), 2.41 (dq, J=9.6, 7.7 Hz, 1H), 2.15-2.03 (m, 1H), 1.73-1.50 (m, 2H), 1.12 (qd, J=10.2, 8.1 Hz, 1H).

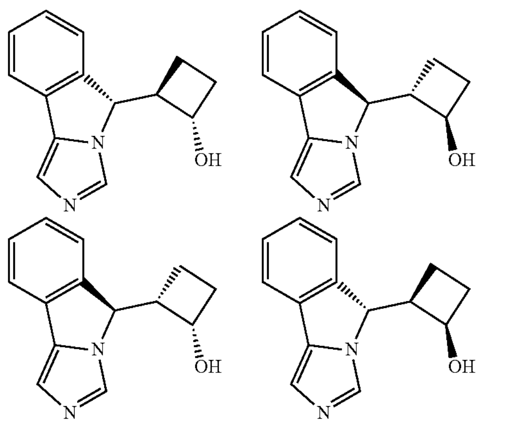

To a solution of 2-(5H-imidazo[5,1-a]isoindol-5-yl)cyclobutan-1-one (trans) (178 mg, 0.79 mmol) in MeOH (10 mL) was added $NaBH_4$ (60 mg, 1.59 mmol) in portions at 0° C. and the solution was stirred at 0° C. for 30 min. The solvent was distilled off and saturated ammonium chloride (10 mL) was added. The aqueous layer was extracted with 5% $CF_3CH_2OH$ in DCM (3×10 mL). The combined organic extract was dried over ($Na_2SO_4$) and concentrated under reduced pressure to afford the crude product. The crude product was purified by Combi-Flash and further isolated by chiral separation to afford 4 isomers as white solid.

Example 1e: (1S,2R)-2-((S)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 7.84 (s, 1H), 7.60 (d, J=7.5 Hz, 1H), 7.49 (d, J=7.5 Hz, 1H), 7.38 (t, J=7.6 Hz, 1H), 7.28-7.19 (m, 1H), 7.10 (s, 1H), 5.72 (d, J=3.7 Hz, 1H), 5.45 (d, J=9.6 Hz, 1H), 4.42 (s, 1H), 2.39 (tt, J=10.2, 7.7 Hz, 2H), 2.24 (ddt, J=14.9, 12.1, 7.4 Hz, 1H), 2.01-1.81 (m, 2H).

Example 1f: (1R,2S)-2-((R)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 7.89 (s, 1H), 7.58 (d, J=7.5 Hz, 1H), 7.42-7.31 (m, 2H), 7.29-7.20 (m, 1H), 7.10 (s, 1H), 5.30 (dd, J=25.5, 8.2 Hz, 2H), 4.14 (p, J=7.6 Hz, 1H), 2.33-2.05 (m, 2H), 1.84-1.50 (m, 3H).

Example 1g: (1S,2S)-2-((R)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 7.84 (s, 1H), 7.63-7.45 (m, 2H), 7.37 (q, J=7.4 Hz, 1H), 7.24 (q, J=7.1 Hz, 1H), 7.12 (d, J=13.9 Hz, 1H), 5.73 (dd, J=9.0, 5.1 Hz, 1H), 5.47 (dd, J=14.1, 7.9 Hz, 1H), 4.42 (tp, J=5.6, 2.5 Hz, 1H), 2.48-2.12 (m, 3H), 2.01-1.81 (m, 2H).

Example 1h: (1R,2R)-2-((S)-5H-imidazo[5,1-a]isoindol-5-yl)cyclobutan-1-ol: LCMS (ESI, m/z): 227.3 $[M+H]^+$. $^1$HNMR (400 MHz, DMSO-$d_6$) δ 7.84 (s, 1H), 7.60 (d, J=7.5 Hz; 1H), 7.49 (d, J=7.5 Hz, 1H), 7.38 (t, J=7.6 Hz, 1H), 7.28-7.19 (m, 1H), 7.10 (s, 1H), 5.72 (d, J=3.7 Hz, 1H), 5.45 (d, J=9.6 Hz, 1H), 4.42 (s, 1H), 2.39 (tt, J=10.2, 7.7 Hz, 2H), 2.24 (ddt, J=14.9, 12.1, 7.4 Hz, 1H), 2.01-1.81 (m, 2H).

Example 2: 2-(5H-imidazo[5,1-a]isoindol-5-yl)cyclopentan-1-ol

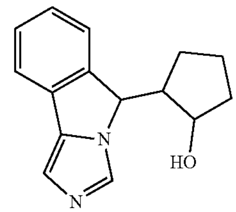

(1R,2R)-2-((R)-5H-imidazo[5,1-a]isoindol-5-yl)cyclopentan-1-ol (1S,2S)-2-((S)-5H-imidazo[5,1-a]isoindol-5-yl)cyclopentan-1-ol (1R,2R)-2-((S)-5H-imidazo[5,1-a]isoindol-5-yl)cyclopentan-1-ol (1S,2S)-2-((R)-5H-imidazo[5,1-a]isoindol-5-yl)cyclopentan-1-ol (1S,2R)-2-((S)-5H-imidazo[5,1-a]isoindol-5-yl)cyclopentan-1-ol (1R,2S)-2-((S)-5H-imidazo[5,1-a]isoindol-5-yl)cyclopentan-1-ol (1R,2S)-2-((R)-5H-imidazo[5,1-a]isoindol-5-yl)cyclopentan-1-ol (1S,2R)-2-((R)-5H-imidazo[5,1-a]isoindol-5-yl)cyclopentan-1-ol Step 1:

(E)-2-(2-(1-trityl-1H-imidazol-4-yl)benzylidene)cyclopentan-1-one

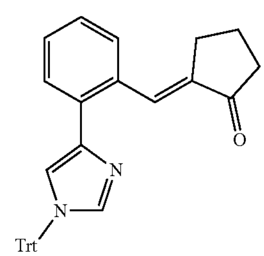

Pyrrolidine (0.22 mL, 2.65 mmol) was added to a stirred mixture of cyclopentanone (0.24 mL, 2.65 mmol) and 2-(1-trityl-1H-imidazol-4-yl)benzaldehyde (1.1 g, 2.65 mmol), in MeOH (15 mL). The reaction mixture was heated at 50° C. for 2 hours until TLC showed-disappearance of SM. After cooling to rt, the reaction mixture was diluted with DCM (50 mL) and washed with water and dried over Na2SO4. The crude product was used directly in the next step: LCMS (ESI, m/z): 481.4 $[M+H]^+$.

Step 2:

2-(5H-imidazo[5,1-a]isoindol-5-yl)cyclopentan-1-one

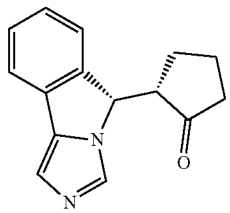
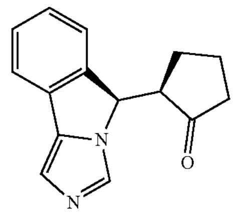
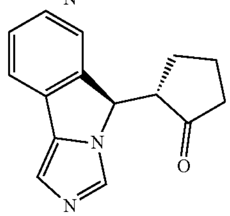
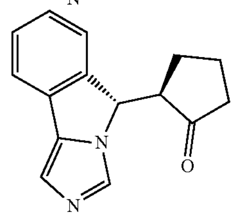

The title compound was synthesized by General Procedure for the Synthesis of Int-3.

The two diastereomeric pairs were separated by combin-flash using EtOAc/DCM as eluent: LCMS (ESI, m/z): +239.2

Step 3a:

(1R,2R)-2-((R)-5H-imidazo[5,1-a]isoindol-5-yl)cyclopentan-1-ol (1S,2S)-2-((S)-5H-imidazo[5,1-a]isoindol-5-yl)cyclopentan-1-ol (1R,2S)-2-((S)-5H-imidazo[5,1-a]isoindol-5-yl)cyclopentan-1-ol (1S,2R)-2-((R)-5H-imidazo[5,1-a]isoindol-5-yl)cyclopentan-1-ol

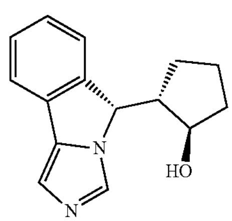
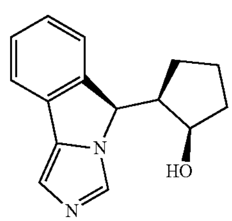
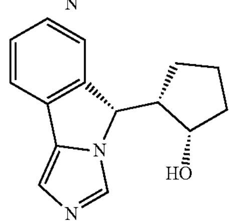
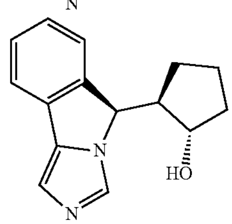

The title compound was synthesized by General Procedure for the Synthesis of Int-5. The product was isolated as a mixture of four diastereomers which were separated by chiral SFC: LCMS (ESI, m/z): 241.3

The absolute configuration of isomers 2a, 2b, 2c, 2d was determined by X-ray crystallography. The configuration of the rest isomers was assigned arbitrarily.

Example 2a: (1R,2R)-2-((R)-5H-imidazo[5,1-a]isoindol-5-yl)cyclopentan-1-ol: LCMS (ESI, m/z): 241.3 $[M+H]^+$; $^1$HNMR (400 MHz, DMSO-$d_6$) δ 7.90 (s, 1H), 7.61 (dd, J=22.5, 7.6 Hz, 2H), 7.37 (t, J=7.5 Hz, 1H), 7.31-7.23 (m, 1H), 5.39 (d, J=6.8 Hz, 1H), 5.16 (d, J=3.8 Hz, 1H), 4.37 (q, J=4.7 Hz, 1H), 2.14-2.01 (m, 1H), 1.84-1.39 (m, 7H).

Example 2b: (1S,2S)-2-((S)-5H-imidazo[5,1-a]isoindol-5-yl)cyclopentan-1-ol. LCMS (ESI, m/z): 241.3 $[M+H]^+$; $^1$HNMR (400 MHz, DMSO-$d_6$) δ 7.90 (s, 1H), 7.67-7.54 (m, 2H), 7.37 (t, J=7.5 Hz, 1H), 7.31-7.22 (m, 1H), 5.39 (d, J=6.9 Hz, 1H), 5.16 (d, J=3.9 Hz, 1H), 4.38 (qd, J=4.6, 2.6 Hz, 1H), 2.08 (p, J=8.4 Hz, 1H), 1.84-1.37 (m, 7H).

Example 2f: 5H-imidazo[5,1-a]isoindol-5-yl)cyclopentan-1-ol: LCMS (ESI, m/z): . . . 241.3 $[M+H]^+$; $^1$HNMR was not obtained due to small sample quantity. Example 2h: -5H. imidazo[5,1-a]isoindol-5-yl)cyclopentan-1-ol: LCMS (ESI, m/z): 241.3 $[M+H]^+$; $^1$HNMR was not obtained due to small sample quantity.

Step 3b:

(1R,2R)-2-((S)-5H-imidazo[5,1-a]isoindol-5-yl)cyclopentan-1-ol (1S,2S)-2-((R)-5H-imidazo[5,1-a]isoindol-5-yl)cyclopentan-1-ol (1S,2R)-2-((S)-5H-imidazo[5,1-a]isoindol-5-yl)cyclopentan-1-ol (1R,2S)-2-((R)-5H-imidazo[5,1-a]isoindol-5-yl)cyclopentan-1-ol

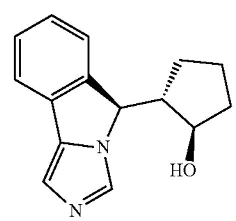
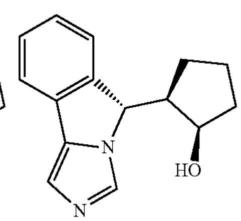
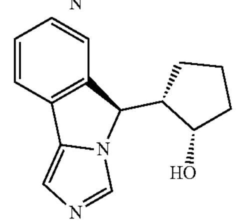
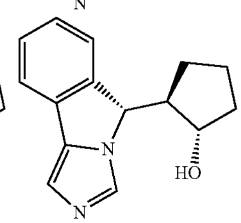

The title compound was synthesized by General Procedure for the Synthesis of Int-5. The product was isolated as a mixture of four diastereomers which were separated by chiral SFC: LCMS (ESI, m/z): 241.3

Example 2c: (1R,2R)-2-((S)-5H-imidazo[5,1-a]isoindol-5-yl)cyclopentan-1-ol: LCMS (ESI, m/z): 241.3 $[M+H]^+$; $^1$HNMR (400 MHz, DMSO-$d_6$) δ 7.90 (s, 1H), 7.60 (d, J=7.5 Hz, 1H), 7.50 (d, J=7.9 Hz, 1H), 7.37 (t, J=7.5 Hz, 1H), 7.24 (td, J=7.7, 1.3 Hz, 1H), 7.12 (s, 1H), 5.26 (d, J=10.2 Hz, 1H), 5.07 (d, J=4.1 Hz, 1H), 4.30 (p, J=3.7 Hz, 1H), 2.03-1.82 (m, 3H), 1.76-1.55 (m, 4H).

Example 2d: (1S,2S)-2-((R)-5H-imidazo[5,1-a]isoindol-5-yl)cyclopentan-1-ol: LCMS (ESI, m/z): 241.3 $[M+H]^+$; $^1$HNMR (400 MHz, DMSO-$d_6$) δ 7.90 (s, 1H), 7.60 (d, J=7.5 Hz, 1H), 7.50 (d, J=7.7 Hz, 1H), 7.37 (t, J=7.5 Hz, 1H), 7.24 (td, J=7.4, 1.2 Hz, 1H), 7.12 (s, 1H), 5.26 (d, J=10.2 Hz, 1H), 5.06 (d, J=4.2 Hz, 1H), 4.30 (q, J=3.5 Hz, 1H), 2.02-1.82 (m, 3H), 1.76-1.58 (m, 4H).

Example 2e: 5H-imidazo[5,1-a]isoindol-5-yl)cyclopentan-1-ol: LCMS (ESI, m/z): 241.3 $[M+H]^+$; $^1$HNMR was not obtained due to small sample quantity.

Example 2g: 5H-imidazo[5,1-a]isoindol-5-yl)cyclopentan-1-ol: LCMS (ESI, m/z): 241.3 $[M+H]^+$; $^1$HNMR was not obtained due to small sample quantity.

Example 3: 2-(5H-imidazo[5,1-a]isoindol-5-yl)cyclohexan-1-ol

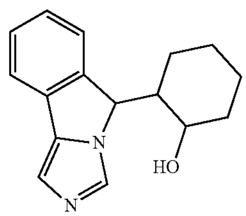 [SMILES: OC1CCCCC1C1c2ccccc2-c2cncn21]

(1S,2S)-2-((S)-5H-imidazo[5,1-a]isoindol-5-yl)cyclohexan-1-ol (1R,2S)-2-((S)-5H-imidazo[5,1-a]isoindol-5-yl)cyclohexan-1-ol (1S,2R)-2-((S)-5H-imidazo[5,1-a]isoindol-5-yl)cyclohexan-1-ol (1R,2R)-2-((S)-5H-imidazo[5,1-a]isoindol-5-yl)cyclohexan-1-ol (1S,2S)-2-((R)-5H-imidazo[5,1-a]isoindol-5-yl)cyclohexan-1-ol (1R,2S)-2-((R)-5H-imidazo[5,1-a]isoindol-5-yl)cyclohexan-1-ol (1S,2R)-2-((R)-5H-imidazo[5,1-a]isoindol-5-yl)cyclohexan-1-ol (1R,2R)-2-((R)-5H-imidazo[5,1-a]isoindol-5-yl)cyclohexan-1-ol Step 1:

(E)-2-(2-(1-trityl-1H-imidazol-4-yl)benzylidene)cyclohexan-1-one

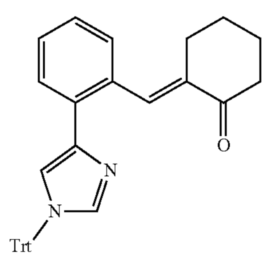

The title compound was synthesized by General Procedure for the Synthesis of Int-2: LCMS (ESI, m/z): 495.4 $[M+H]^+$ Step 2:

2-(5H-imidazo[5,1-a]isoindol-5-yl)cyclohexan-1-one

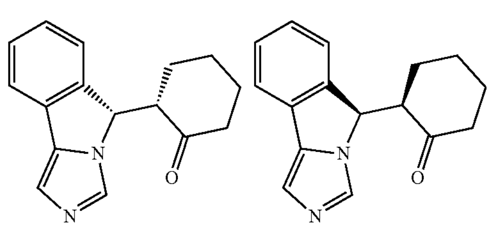

-continued

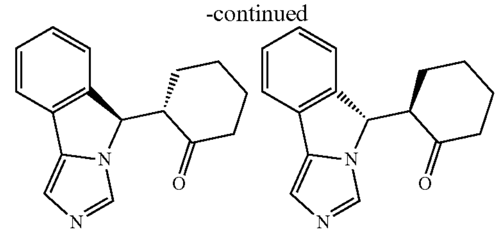

The title compound was synthesized by General Procedure for the Synthesis of Int-3. The two diastereomeric pairs were separated by combin-flash using EtOAc/DCM as eluent: LCMS (ESI, m/z): 253.2

Step 3a:

(1S,2S)-2-((S)-5H-imidazo[5,1-a]isoindol-5-yl)cyclohexan-1-ol (1R,2S)-2-((S)-5H-imidazo[5,1-a]isoindol-5-yl)cyclohexan-1-ol (1S,2R)-2-((S)-5H-imidazo[5,1-a]isoindol-5-yl)cyclohexan-1-ol (1R,2R)-2-((S)-5H-imidazo[5,1-a]isoindol-5-yl)cyclohexan-1-ol

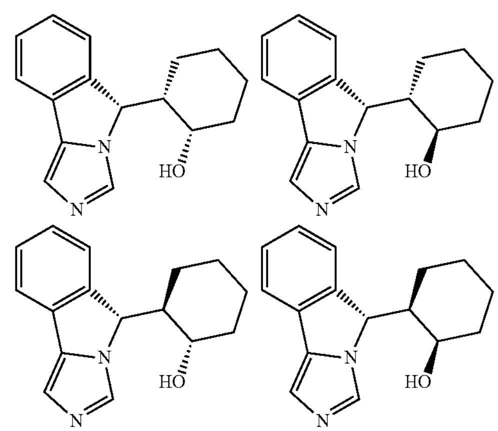

The title compound was synthesized by General Procedure for the Synthesis of Int-5. The product was isolated as a mixture of four enantiomers which were separated by chiral SFC: LCMS (ESI, m/z): 255.3. The absolute configuration of isomers 3a, 3b, 3g and 3h was determined by X-ray crystallography. The configuration of the rest isomers was assigned arbitrarily.

Example 3a: (1S,2S)-2-((S)-5H-imidazo[5,1-a]isoindol-5-yl)cyclohexan-1-ol LCMS (ESI, m/z): 255.3 $[M+H]^+$; $^1H$ NMR (400 MHz, DMSO-$d_6$) δ 8.01 (s, 1H), 7.57-7.51 (m, 2H), 7.40-7.31 (m, 1H), 7.30-7.21 (m, 1H), 7.08 (s, 1H), 5.23 (d, J=2.7 Hz, 1H), 4.94-4.89 (m, 1H), 4.27-4.22 (m, 1H), 2.03-1.93 (m, 1H), 1.83-1.75 (m, 1H), 1.65-1.43 (m, 3H), 1.39-1.30 (m, 1H), 1.22-0.98 (m, 2H), 0.79-0.71 (m, 1H).

Example 3b: (1R,2S)-2-((S)-5H-imidazo[5,1-a]isoindol-5-yl)cyclohexan-1-ol LCMS (ESI, m/z): 255.3 $[M+H]^+$; $^1H$ NMR (400 MHz, DMSO-$d_6$) δ 7.88 (s, 1H), 7.66 (d, J=7.5 Hz, 1H), 7.58 (d, J=7.5 Hz, 1H), 7.40-7.32 (m, 1H), 7.27-7.18 (m, 1H), 7.10 (s, 1H), 5.16 (d, J=5.4 Hz, 1H), 4.69 (d, J=4.0 Hz, 1H), 4.09-4.04 (m, 1H), 1.82-1.30 (m, 7H), 1.18-1.10 (m, 1H).

Example 3c: 5H-imidazo[5,1-a]isoindol-5-yl)cyclohexan-1-ol LCMS (ESI, m/z): 255.3 $[M+H]^+$; $^1H$ NMR (400

MHz, DMSO-$d_6$) δ 7.87 (s, 1H), 7.60 (d, J=7.5 Hz, 1H), 7.51 (d, 1H), 7.41-7.34 (m, 1H), 7.30-7.23 (m, 1H), 7.11 (s, 1H), 5.73 (d, J=3.9 Hz, 1H), 5.20 (d, J=5.2 Hz, 1H), 3.69-3.57 (m, 1H), 2.20-1.92 (m, 2H), 1.65-1.54 (m, 1H), 1.42-1.20 (m, 2H), 1.12-0.89 (m, 1H), 0.62-0.51 (m, 1H), 0.26-0.12 (m, 1H).

Example 3d: 5H-imidazo[5,1-a]isoindol-5-yl)cyclohexan-1-ol LCMS (ESI, m/z): 255.3 $[M+H]^+$; $^1$H NMR (400 MHz, DMSO-$d_6$) δ 7.80 (s, 1H), 7.61-7.55 (m, 1H), 7.50-7.41 (m, 1H), 7.41-7.33 (m, 1H), 7.33-7.25 (m, 1H), 7.14 (s, 1H), 5.73 (d, J=2.2 Hz, 1H), 5.24 (d, J=5.7 Hz, 1H), 3.70-3.58 (m, 1H), 2.05-1.90 (m, 2H), 1.66-1.56 (m, 1H), 1.41-1.21 (m, 2H), 1.20-0.89 (m, 2H), 0.75-0.64 (m, 1H), 0.26-0.10 (m, 1H).

Step 3b:

(1S,2S)-2-((R)-5H-imidazo[5,1-a]isoindol-5-yl)cyclohexan-1-ol (1R,2S)-2-((R)-5H-imidazo[5,1-a]isoindol-5-yl)cyclohexan-1-ol (1S,2R)-2-((R)-5H-imidazo[5,1-a]isoindol-5-yl)cyclohexan-1-ol (1R,2R)-2-((R)-5H-imidazo[5,1-a]isoindol-5-yl)cyclohexan-1-ol

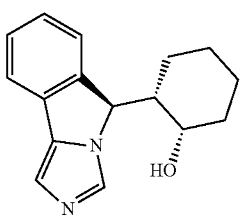
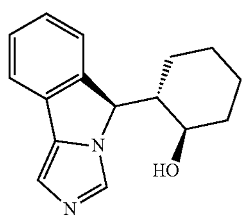
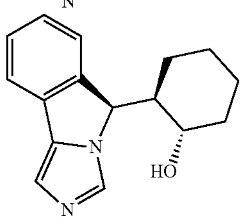
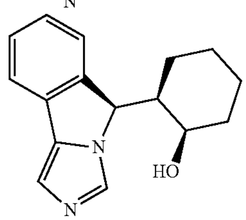

The title compound was synthesized by General Procedure for the Synthesis of Int-5.

The product was isolated as a mixture of four enantiomers which were separated by chiral SFC: LCMS (ESI, m/z): 255.3

Example 3e: 5H-imidazo[5,1-a]isoindol-5-yl)cyclohexan-1-ol LCMS (ESI, m/z): 255.3 $[M+H]^+$; $^1$H NMR (400 MHz, DMSO-$d_6$) δ 7.80 (s, 1H), 7.61-7.56 (m, 1H), 7.47-7.41 (m, 1H), 7.41-7.33 (m, 1H), 7.33-7.25 (m, 1H), 7.14 (s, 1H), 5.73 (d, J=2.3 Hz, 1H), 5.25 (d, J=5.7 Hz, 1H), 3.69-3.59 (m, 1H), 2.05-1.90 (m, 2H), 1.66-1.55 (m, 1H), 1.41-1.26 (m, 2H), 1.20-0.89 (m, 2H), 0.74-0.66 (m, 1H), 0.26-0.10 (m, 1H).

Example 3f: 5H-imidazo[5,1-a]isoindol-5-yl)cyclohexan-1-ol LCMS (ESI, m/z): 255.3 $[M+H]^+$; $^1$H NMR (400 MHz, DMSO-$d_6$) δ 7.87 (s, 1H), 7.60 (d, J=7.5 Hz, 1H), 7.50 (d, J=7.7, 1.1 Hz, 1H), 7.42-7.33 (m, 1H), 7.31-7.22 (m, 1H), 7.11 (s, 1H), 5.73 (d, J=3.7 Hz, 1H), 5.20 (d, J=5.2 Hz, 1H), 3.68-3.56 (m, 1H), 2.18-2.08 (m, 1H), 2.00-1.91 (m, 1H), 1.63-1.55 (m, 1H), 1.42-1.21 (m, 2H), 1.12-0.89 (m, 1H), 0.60-0.52 (m, 1H), 0.27-0.12 (m, 1H).

Example 3g: (1S,2R)-2-((R)-5H-imidazo[5,1-a]isoindol-5-yl)cyclohexan-1-ol LCMS (ESI, m/z): 255.3 $[M+H]^+$; $^1$H NMR (400 MHz, DMSO-$d_6$) δ 7.87 (s, 1H), 7.66 (d, J=7.7, 0.9 Hz, 1H), 7.57 (d, 1H), 7.40-7.31 (m, 1H), 7.27-7.18 (m, 1H), 7.10 (s, 1H), 5.16 (d, J=5.4 Hz, 1H), 4.69 (d, J=3.9 Hz, 1H), 4.09-4.04 (m, 1H), 1.79-1.31 (m, 7H), 1.21-1.08 (m, 1H).

Example 3h: (1R,2R)-2-((R)-5H-imidazo[5,1-a]isoindol-5-yl)cyclohexan-1-ol LCMS (ESI, m/z): 255.3 $[M+H]^+$; $^1$H NMR (400 MHz, DMSO-$d_6$) δ 8.01 (s, 1H), 7.58-7.51 (m, 2H), 7.40-7.31 (m, 1H), 7.30-7.21 (m, 1H), 7.08 (s, 1H), 5.23 (d, J=2.7 Hz, 1H), 4.94-4.89 (m, 1H), 4.27-4.22 (m, 1H), 2.03-1.93 (m, 1H), 1.83-1.74 (m, 1H), 1.61-1.46 (m, 2H), 1.39-1.30 (m, 1H), 1.21-1.02 (m, 2H), 0.79-0.71 (m, 1H).

Example 4: 7-(5H-imidazo[5,1-a]isoindol-5-yl)-5,6,7,8-tetrahydroisoquinolin-8-ol

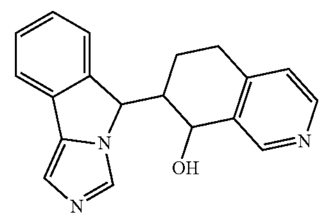 [SMILES: OC1c2cnccc2CCC1C1c2ccccc2-c2cncn21]

(7S,8S)-7-((R)-5H-imidazo[5,1-a]isoindol-5-yl)-5,6,7,8-tetrahydroisoquinolin-8-ol (7S,8R)-7-((R)-5H-imidazo[5,1-a]isoindol-5-yl)-5,6,7,8-tetrahydroisoquinolin-8-ol (7R,8S)-7-((R)-5H-imidazo[5,1-a]isoindol-5-yl)-5,6,7,8-tetrahydroisoquinolin-8-ol (7R,8R)-7-((R)-5H-imidazo[5,1-a]isoindol-5-yl)-5,6,7,8-tetrahydroisoquinolin-8-ol (7R,8R)-7-((S)-5H-imidazo[5,1-a]isoindol-5-yl)-5,6,7,8-tetrahydroisoquinolin-8-ol (7R,8S)-7-((S)-5H-imidazo[5,1-a]isoindol-5-yl)-5,6,7,8-tetrahydroisoquinolin-8-ol (7S,8R)-7-((S)-5H-imidazo[5,1-a]isoindol-5-yl)-5,6,7,8-tetrahydroisoquinolin-8-ol (7S,8S)-7-((S)-5H-imidazo[5,1-a]isoindol-5-yl)-5,6,7,8-tetrahydroisoquinolin-8-ol Synthetic Route IC [Scheme Changed]

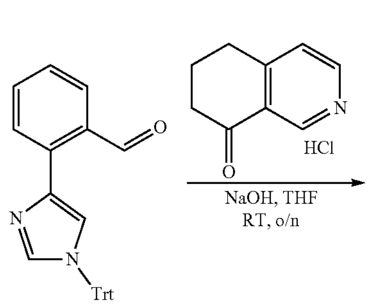

Int-1

-continued

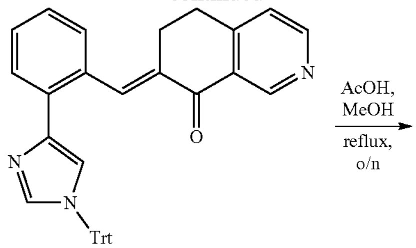

Int-7

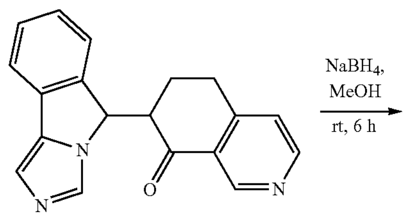

Int-8

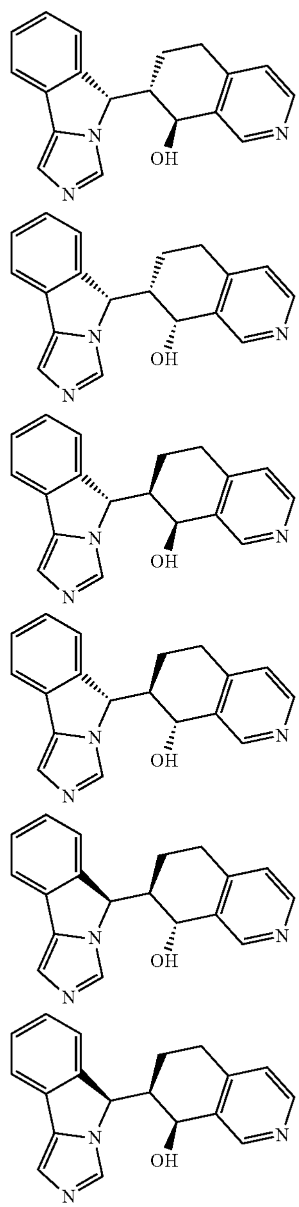

-continued

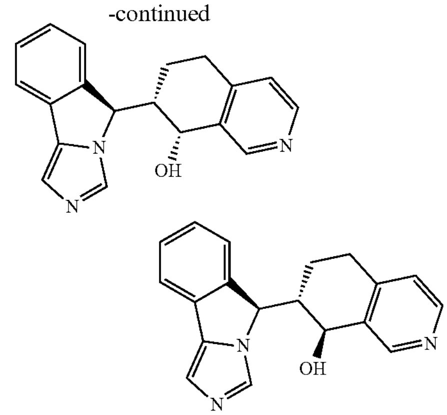

Step 1: 7-([2-[1-(triphenylmethyl)-1H-imidazol-4-yl]phenyl]methylidene)-5,6,7,8-tetrahydroisoquinolin-8-one

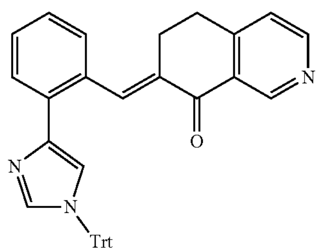

To a solution of 5,6,7,8-tetrahydroisoquinolin-8-one hydrochloride (2.01 g, 10.946 mmol, 1.000 equiv) in tetrahydrofuran (100 mL) was added 2-[1-(triphenylmethyl)-1H-imidazol-4-yl]benzaldehyde (9.07 g, 21.88 mmol) and sodium hydroxide (1.74 g, 43.50 mmol). The reaction was stirred for 6 h at room temperature and the resulting mixture was diluted with water (50 mL). The resulting solution was extracted with dichloromethane (3×200 mL) and the organic phase was combined, dried over anhydrous sodium sulfate and concentrated under vacuum. The residue was diluted with dichloromethane (30 mL) and the solids were collected by filtration to afford 7-([2-[1-(triphenylmethyl)-1H-imidazol-4-yl]phenyl]methylidene)-5,6,7,8-tetrahydroisoquinolin-8-one (2.55 g, 39%) as a light yellow solid: LCMS (ESI, m/z): 544 $[M+H]^+$. $^1$HNMR (300 MHz, $CDCl_3$) δ 9.27 (s, 1H), 8.68 (s, 1H), 8.05 (d, J=9.0 Hz, 1H), 7.88 (s, 1H), 7.57 (s, 1H), 7.56-7.09 (m, 18H), 7.10 (d, J=9.0 Hz, 1H), 6.85 (s, 1H), 2.89 (t, J=3.0 Hz, 2H), 2.73 (t, J=3.0 Hz, 2H).

Step 2: 7-[5H-imidazo[4,3-a]isoindol-5-yl]-5,6,7,8-tetrahydroisoquinolin-8-one

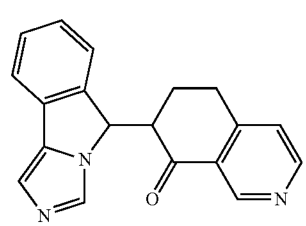 [SMILES: O=C1c2cnccc2CCC1C1c2ccccc2-c2cncn21]

To a solution of (2E)-2-([2-[1-(triphenylmethyl)-1H-imidazol-4-yl]phenyl]methylidene)-1,2,3,4-tetrahydronaphthalen-1-one (2.4 g, 4.42 mmol) in methanol (60 mL) was added acetic acid (2.6 mL, 45.37 mmol). The reaction was stirred for 16 h at 80° C. and then concentrated under vacuum to afford 7-[5H-imidazo[4,3-a]isoindol-5-yl]-5,6,7,8-tetrahydroisoquinolin-8-one (2.0 g, crude) as light yellow oil: LCMS (ESI, m/z): 302 $[M+H]^+$ Step 3:

(7S,8S)-7-[(5R)-5H-imidazo[4,3-a]isoindol-5-yl]-5,6,7,8-tetrahydroisoquinolin-8-ol (7R,8R)-7-[(5S)-5H-imidazo[4,3-a]isoindol-5-yl]-5,6,7,8-tetrahydroisoquinolin-8-ol (7S,8R)-7-[(5R)-5H-imidazo[4,3-a]isoindol-5-yl]-5,6,7,8-tetrahydroisoquinolin-8-ol (7R,8S)-7-[(5S)-5H-imidazo[4,3-a]isoindol-5-yl]-5,6,7,8-tetrahydroisoquinolin-8-ol (7R,8S)-7-((R)-5H-imidazo[5,1-a]isoindol-5-yl)-5,6,7,8-tetrahydroisoquinolin-8-ol (7S,8R)-7-((S)-5H-imidazo[5,1-a]isoindol-5-yl)-5,6,7,8-tetrahydroisoquinolin-8-ol (7R,8R)-7-((R)-5H-imidazo[5,1-a]isoindol-5-yl)-5,6,7,8-tetrahydroisoquinolin-8-ol (7S,8S)-7-((S)-5H-imidazo[5,1-a]isoindol-5-yl)-5,6,7,8-tetrahydroisoquinolin-8-ol To a solution of 7-[5H-imidazo[4,3-a]isoindol-5-yl]-5,6,7,8-tetrahydroisoquinolin-8-one (2.0 g, 6.64 mmol) in methanol (100 mL) was added sodium borohydride (2.5 g, 67.89 mmol). The reaction was stirred for 6 h at room temperature. The resulting mixture was concentrated under vacuum and then diluted with dichloromethane (200 mL). The solids were filtered out and the filtrate was concentrate under vacuum. The crude product was purified by Prep-HPLC and further isolated by chiral separation to afford 8 isomers as white solid. The stereochemistry of each isomer was arbitrarily assigned.

1. Column: Chiralpak IB, 2×25 cm, 5 um; Mobile Phase A:Hex-HPLC, Mobile Phase B: EtOH-HPLC; Flow rate: 20 mL/min; Gradient: 40 B to 40 B in 12 min; 254/220 nm;
2. Column: Chiralpak IC, 2×25 cm, 5 um; Mobile Phase A:Hex-HPLC, Mobile Phase B: EtOH-HPLC; Flow rate: 20 mL/min; Gradient: 40 B to 40 B in 32 min; 254/220 nm;
3. Column: lux-4, 2.12×20 cm, 5 um; Mobile Phase A:Hex-HPLC, Mobile Phase B: EtOH-HPLC; Flow rate: 20 mL/min; Gradient: 50 B to 50 B in 20 min; 254/220 nm;

The absolute configuration of all isomers was assigned arbitrarily.

Example 4a: 5H-imidazo[4,3-a]isoindol-5-yl]-5,6,7,8-tetrahydroisoquinolin-8-ol (47.3 mg, 2%): LCMS (ESI, m/z): 304 $[M+H]^+$; $^1$HNMR (300 MHz, $CD_3OD$) δ 8.74 (s, 1H), 8.25 (d, J=5.4 Hz, 1H), 7.91 (s, 1H), 7.68-7.62 (m, 2H), 7.46-7.41 (m, 1H), 7.34-7.29 (m, 1H), 7.11 (s, 1H), 7.10 (d, J=5.4 Hz, 1H), 5.89 (d, J=3.0 Hz, 1H), 5.09 (d, J=10.5 Hz, 1H), 2.71-2.62 (m, 3H), 1.09-1.04 (m, 2H); tR=1.309 min (Chiralpak IB-3, 0.46×5 cm, 3 um, ethanol:hexane (0.1% DEA)=40:60, 1.0 mL/min). 4b and 4a are enantiomers.

Example 4b: 5H-imidazo[4,3-a]isoindol-5-yl]-5,6,7,8-tetrahydroisoquinolin-8-ol (28.5 mg, 1%): LCMS (ESI, m/z): 304 $[M+H]^+$; $^1$HNMR (300 MHz, $CD_3OD$) δ 8.74 (s, 1H), 8.25 (d, J=5.4 Hz, 1H), 7.91 (s, 1H), 7.68-7.62 (m, 2H), 7.46-7.41 (m, 1H), 7.34-7.29 (m, 1H), 7.11 (s, 1H), 7.10 (d, J=5.4 Hz, 1H), 5.89 (d, J=3.0 Hz, 1H), 5.09 (d, J=10.5 Hz, 1H), 2.71-2.62 (m, 3H), 1.09-1.04 (m, 2H); tR=2.147 min (Chiralpak IB-3, 0.46×5 cm, 3 um, ethanol:hexane (0.1% DEA)=40:60, 1.0 mL/min).

Example 4c: 5H-imidazo[4,3-a]isoindol-5-yl]-5,6,7,8-tetrahydroisoquinolin-8-ol (47.2 mg, 2%): LCMS (ESI, m/z): 304 $[M+H]^+$; $^1$HNMR (300 MHz, $CD_3OD$) δ 8.42 (s, 1H), 8.27 (d, J=5.1 Hz, 1H), 8.04 (s, 1H), 7.73-7.70 (m, 1H), 7.64-7.61 (m, 1H), 7.43-7.38 (m, 1H), 7.31-7.26 (m, 1H), 7.18 (d, J=5.1 Hz, 1H), 7.15 (s, 1H), 5.50 (d, J=3.0 Hz, 1H), 4.88 (d, J=10.5 Hz, 1H), 3.06-2.93 (m, 1H), 2.82-2.70 (m, 1H), 2.26-1.97 (m, 3H); tR=1.505 min, (Chiralpak IB-3, 0.46×5 cm, 3 um, ethanol:hexane (0.1% DEA)=40:60, 1.0 mL/min). 4d and 4c are enantiomers.

Example 4d: 5H-imidazo[4,3-a]isoindol-5-yl]-5,6,7,8-tetrahydroisoquinolin-8-ol (32.1 mg, 2%): LCMS (ESI, m/z): 304 $[M+H]^+$; $^1$HNMR (300 MHz, $CD_3OD$) δ 8.42 (s, 1H), 8.27 (d, J=5.1 Hz, 1H), 8.04 (s, 1H), 7.73-7.70 (m, 1H), 7.64-7.61 (m, 1H), 7.43-7.38 (m, 1H), 7.31-7.26 (m, 1H), 7.18 (d, J=5.1 Hz, 1H), 7.15 (s, 1H), 5.50 (d, J=3.0 Hz, 1H), 4.88 (d, J=10.5 Hz, 1H), 3.06-2.93 (m, 1H), 2.82-2.70 (m, 1H), 2.26-1.97 (m, 3H); tR=2.147 min, (Chiralpak IB-3, 0.46×5 cm, 3 um, ethanol:hexane (0.1% DEA)=40:60, 1.0 mL/min).

Example 4e: 5H-imidazo[5,1-a]isoindol-5-yl)-5,6,7,8-tetrahydroisoquinolin-8-ol (30.3 mg, 2%): LCMS (ESI, m/z): 304 $[M+H]^+$; $^1$HNMR (300 MHz, $CD_3OD$) δ 8.79 (s, 1H), 8.27 (d, J=5.1 Hz, 1H), 7.99 (s, 1H), 7.66-7.64 (m, 1H), 7.50-7.32 (m, 3H), 7.20 (s, 1H), 7.18 (d, J=5.1 Hz, 1H), 5.89 (d, J=3.0 Hz, 1H), 5.10 (d, J=10.5 Hz, 1H), 2.70-2.68 (m, 2H), 2.50-2.42 (m, 1H), 1.14-0.98 (m, 2H); tR=2.893 min, (Chiralpak IC-3, 0.46×5 cm, 3 um, ethanol:hexane (0.1% DEA)=40:60, 1.0 mL/min). 4e and 4f are enantiomers.

Example 4f: 5H-imidazo[5,1-a]isoindol-5-yl)-5,6,7,8-tetrahydroisoquinolin-8-ol (79.2 mg, 5%): LCMS (ESI, m/z): 304 $[M+H]^+$; $^1$HNMR (400 MHz, $CD_3OD$) δ 8.79 (s, 1H), 8.27 (d, J=5.6 Hz, 1H), 7.99 (s, 1H), 7.66-7.64 (m, 1H), 7.50-7.32 (m, 3H), 7.20 (s, 1H), 7.18 (d, J=5.6 Hz, 1H), 5.89 (d, J=3.0 Hz, 1H), 5.10 (d, J=10.4 Hz, 1H), 2.70-2.68 (m, 2H), 2.50-2.42 (m, 1H), 1.14-0.98 (m, 2H); tR=5.240 min, (Chiralpak IC-3, 0.46×5 cm, 3 um, ethanol:hexane (0.1% DEA)=40:60, 1.0 mL/min).

Example 4g: 5H-imidazo[5,1-a]isoindol-5-yl)-5,6,7,8-tetrahydroisoquinolin-8-ol (35.9 mg, 2%): LCMS (ESI, m/z): 304 $[M+H]^+$; $^1$HNMR (400 MHz, $CD_3OD$) δ 8.56 (s, 1H), 8.30 (d, J=5.6 Hz, 1H), 8.11 (s, 1H), 7.62-7.56 (m, 2H), 7.43-7.39 (m, 1H), 7.34-7.30 (m, 1H), 7.16 (d, J=5.6 Hz, 1H), 7.14 (s, 1H), 5.92 (d, J=4.0 Hz, 1H), 5.12 (d, J=10.4 Hz, 1H), 2.84-2.78 (m, 1H), 2.66-2.54 (m, 2H), 1.61-1.57 (m, 1H), 1.10-1.05 (m, 1H); tR=4.569 min, (Chiralpak IC-3, 0.46×5 cm, 3 um, ethanol:hexane (0.1% DEA)=40:60, 1.0 mL/min). 4 h and 4g are enantiomers.

Example 4h: 5H-imidazo[5,1-a]isoindol-5-yl)-5,6,7,8-tetrahydroisoquinolin-8-ol (74.7 mg, 5%): LCMS (ESI, m/z): 304 $[M+H]^+$; $^1$HNMR (300 MHz, $CD_3OD$) δ 8.56 (s, 1H), 8.30 (d, J=5.2 Hz, 1H), 8.11 (s, 1H), 7.62-7.56 (m, 2H), 7.43-7.39 (m, 1H), 7.34-7.30 (m, 1H), 7.16 (d, J=5.4 Hz, 1H), 7.14 (s, 1H), 5.92 (d, J=3.0 Hz, 1H), 5.12 (d, J=10.5 Hz, 1H), 2.84-2.78 (m, 1H), 2.66-2.54 (m, 2H), 1.61-1.57 (m, 1H), 1.10-1.05 (m, 1H); tR=6.44 min, (Chiralpak IC-3, 0.46×5 cm, 3 um, ethanol:hexane (0.1% DEA)=40:60, 1.0 mL/min).

Example 5 and 6: 3-(5H-imidazo[5,1-a]isoindol-5-yl)-tetrahydro-2H-pyran-4-ol and 4-(5H-imidazo[5,1-a]isoindol-5-yl)-tetrahydro-2H-pyran-3-ol

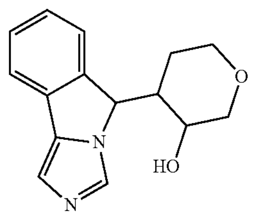 [SMILES: OC1COCCC1C1c2ccccc2-c2cncn21]

(3R,4R)-3-((R)-5H-imidazo[5,1-a]isoindol-5-yl)-tetrahydro-2H-pyran-4-ol (3S,4S)-3-((R)-5H-imidazo[5,1-a]isoindol-5-yl)-tetrahydro-2H-pyran-4-ol (3R,4R)-3-((S)-5H-imidazo[5,1-a]isoindol-5-yl)-tetrahydro-2H-pyran-4-ol (3S,4S)-3-((S)-5H-imidazo[5,1-a]isoindol-5-yl)-tetrahydro-2H-pyran-4-ol (3S,4S)-4-((R)-5H-imidazo[5,1-a]isoindol-5-yl)-tetrahydro-2H-pyran-3-ol (3R,4R)-4-((R)-5H-imidazo[5,1-a]isoindol-5-yl)-tetrahydro-2H-pyran-3-ol (3S,4S)-4-((S)-5H-imidazo[5,1-a]isoindol-5-yl)-tetrahydro-2H-pyran-3-ol (3R,4R)-4-((S)-5H-imidazo[5,1-a]isoindol-5-yl)-tetrahydro-2H-pyran-3-ol Synthetic Route IIA

SCHEME B

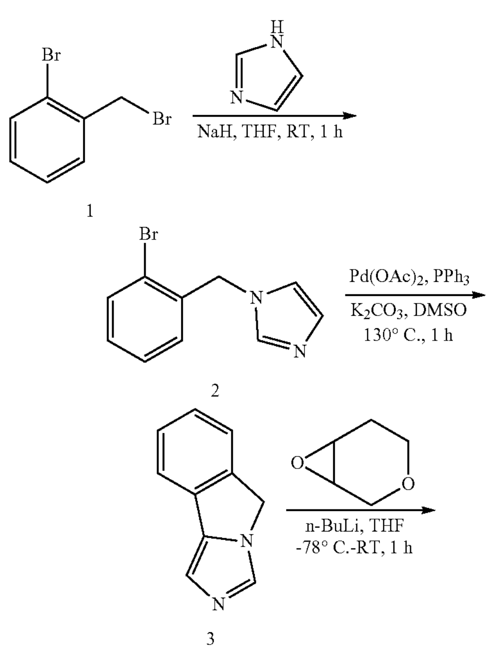

-continued

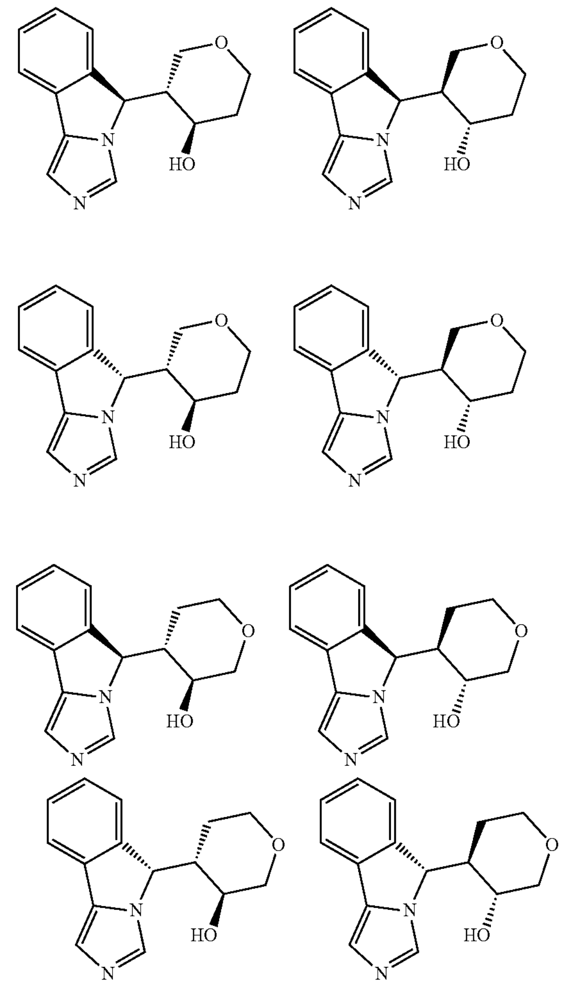

Step 1: 1-(2-bromobenzyl)-1H-imidazole

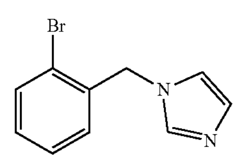 [SMILES: Brc1ccccc1Cn1ccnc1]

To a solution of 1H-imidazole (40 g, 0.587 mol) in tetrahydrofuran (1 L) was added sodium hydride (20 g, 0.833 mol) at 0° C., and the mixture was stirred for 1 hour at room temperature. Then 1-bromo-2-(bromomethyl)benzene (90 g, 0.36 mol) was added and stirred for additional 1 hour at room temperature. The reaction was then quenched by sat ammonium chloride (200 mL) and the resulting solution was extracted with ethyl acetate (3×500 mL). The organic phase was combined, dried over anhydrous sodium sulfate, and concentrated under vacuum. The residue was purified by a silica gel column chromatography and eluted with dichloromethane/ethyl acetate (1:1) to afford 1-[(2-bromophenyl)methyl]-1H-imidazole (90 g, 65%) as yellow oil: LCMS (ESI, m/z): 237, 239 $[M+H]^+$;

Step 2: 5H-imidazo[5,1-a]isoindole

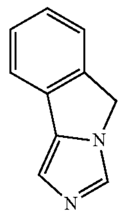 [SMILES: c1ccc2c(c1)Cn1cncc1-2]

A solution of 1-[(2-bromophenyl)methyl]-1H-imidazole (90 g, 0.379 mol), Palladium (II) acetate (3.5 g, 0.015 mol), triphenylphosphane (8.1 g, 0.030 mol) and potassium carbonate (81 g, 0.586 mol) in DMSO (1 L) was stirred for 1 h at 130° C. and then diluted with water (100 mL). The resulting solution was extracted with ethyl acetate (3×200 mL). The organic phase was combined, dried over anhydrous sodium sulfate and concentrated under vacuum. The residue was purified by a silica gel column chromatography and eluted with dichloromethane/ethyl acetate (1:1) to afford 5H-imidazo[4,3-a]isoindole as a yellow solid (20 g, 34%): LCMS (ESI, m/z): 157 [M+H]$^+$.

Step 3:

(3R,4R)-3-((R)-5H-imidazo[5,1-a]isoindol-5-yl)-tetrahydro-2H-pyran-4-ol (3S,4S)-3-((R)-5H-imidazo[5,1-a]isoindol-5-yl)-tetrahydro-2H-pyran-4-ol (3R,4R)-3-((S)-5H-imidazo[5,1-a]isoindol-5-yl)-tetrahydro-2H-pyran-4-ol (3S,4S)-3-((S)-5H-imidazo[5,1-a]isoindol-5-yl)-tetrahydro-2H-pyran-4-ol (3S,4S)-4-((R)-5H-imidazo[5,1-a]isoindol-5-yl)-tetrahydro-2H-pyran-3-ol (3R,4R)-4-((R)-5H-imidazo[5,1-a]isoindol-5-yl)-tetrahydro-2H-pyran-3-ol (3S,4S)-4-((S)-5H-imidazo[5,1-a]isoindol-5-yl)-tetrahydro-2H-pyran-3-ol (3R,4R)-4-((S)-5H-imidazo[5,1-a]isoindol-5-yl)-tetrahydro-2H-pyran-3-ol

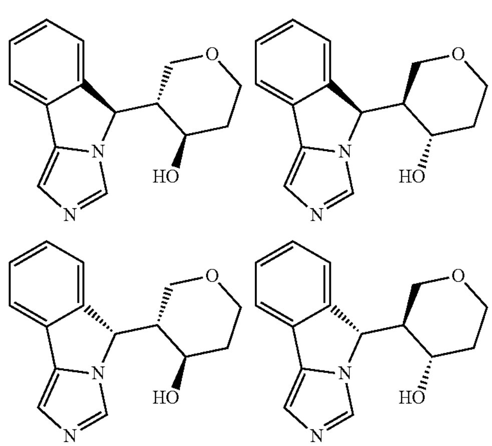

-continued

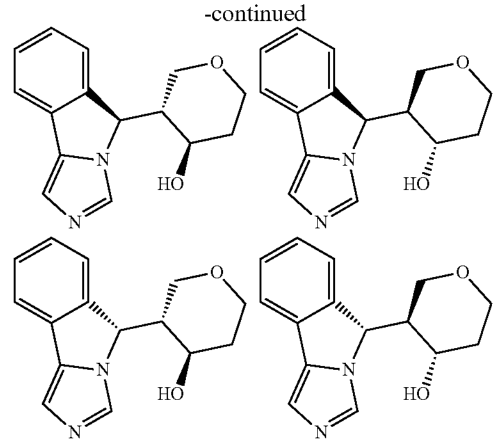

To a solution of 5H-imidazo[4,3-a]isoindole (1.6 g, 10.25 mmol) in tetrahydrofuran (25 mL) was added n-BuLi (6.5 mL, 2.5 M in n-hexane) dropwise at −40° C. After the reaction was stirred for 1 hour at −30° C., 3,7-dioxabicyclo [4.1.0]heptane (1.4 g, 13 mmol) in tetrahydrofuran (3 mL) was added dropwise at −40° C. and then allowed to raise slowly to room temperature and to stir for another 1 hour at room temperature. The reaction was then quenched by sat. ammonium chloride (20 mL) and the resulting solution was extracted with ethyl acetate (3×50 mL). The organic phase was combined, dried over anhydrous sodium sulfate and concentrated under vacuum. The crude product was purified by Prep-HPLC and further isolated by chiral separation to afford 8 isomers as white solid. The absolute configuration of isomers 5a-5d was assigned by X-ray crystallography. The absolute configuration of isomers 6a-6d was assigned by X-ray crystallography.

Example 5a: (3S,4S)-3-((R)-5H-imidazo[5,1-a]isoindol-5-yl)-tetrahydro-2H-pyran-4-ol (65.3 mg, 2%): LCMS (ESI, m/z): 257 [M+H]$^+$; $^1$HNMR (300 MHz, $CDCl_3$) δ 7.80 (s, 1H), 7.53-7.50 (m, 1H), 7.39-7.24 (m, 3H), 7.17 (s, 1H), 5.82 (d, J=2.1 Hz, 1H), 4.14-4.06 (m, 1H), 3.94-3.89 (m, 1H), 3.31-3.21 (m, 2H), 2.57-2.49 (m, 1H), 2.42-2.33 (m, 1H), 2.11-2.05 (m, 1H), 1.90-1.77 (m, 1H); tR=3.537 min (CHIRALCEL OJ-3, 0.46×15 cm; 3 um, Hex(0.1% DEA): EtOH=85:15, 1.0 ml/min).

Example 5b: (3R,4R)-3-((S)-5H-imidazo[5,1-a]isoindol-5-yl)-tetrahydro-2H-pyran-4-ol (70.5 mg, 2%). LCMS (ESI, m/z): 257 [M+H]$^+$; $^1$HNMR (300 MHz, $CDCl_3$) δ 7.98 (s, 1H), 7.55-7.53 (m, 1H), 7.41-7.29 (m, 3H), 7.20 (s, 1H), 5.82 (d, J=2.1 Hz, 1H), 4.16-4.09 (m, 1H), 3.95-3.89 (m, 1H), 3.32-3.21 (m, 2H), 2.57-2.50 (m, 1H), 2.41-2.33 (m, 1H), 2.11-2.05 (m, 1H), 1.88-1.79 (m, 1H); tR=4.966 min (CHIRALCEL OJ-3, 0.46×15 cm; 3 um, Hex(0.1% DEA): EtOH=85:15, 1.0 ml/min).

Example 5c: (3R,4R)-3-((R)-5H-imidazo[5,1-a]isoindol-5-yl)-tetrahydro-2H-pyran-4-ol (62.7 mg, 2%): LCMS (ESI, m/z): 257 [M+H]$^+$; $^1$HNMR (300 MHz, $CDCl_3$) δ 7.82 (s, 1H), 7.57-7.48 (m, 2H), 7.42-7.37 (m, 1H), 7.29-7.24 (m, 1H), 7.20 (s, 1H), 5.70 (d, J=3.3 Hz, 1H), 4.07-3.90 (m, 2H), 3.32-3.23 (m, 2H), 2.81-2.73 (m, 1H), 2.50-2.43 (m, 1H), 2.00-1.96 (m, 1H), 1.77-1.72 (m, 1H); tR=4.866 min (CHIRALCEL OJ-3, 0.46×15 cm; 3 um, Hex(0.1% DEA): EtOH=85:15, 1.0 ml/min).

Example 5d: (3S,4S)-3-((S)-5H-imidazo[5,1-a]isoindol-5-yl)-tetrahydro-2H-pyran-4-ol (63.3 mg, 2%): LCMS (ESI, m/z): 257 [M+H]$^+$; $^1$HNMR (300 MHz, $CDCl_3$) δ 7.98 (m, 1H), 7.58-7.48 (m, 2H), 7.43-7.38 (m, 1H), 7.31-7.24 (m, 1H), 7.20 (s, 1H), 5.73 (d, J=2.7 Hz, 1H), 4.07-3.90 (m, 2H), 3.32-3.23 (m, 2H), 2.78 (t, J=11.1 Hz, 1H), 2.54-2.47 (m, 1H), 2.02-1.96 (m, 1H), 1.82-1.73 (m, 1H); tR=7.967 min (CHIRALCEL OJ-3, 0.46×15 cm; 3 um, Hex(0.1% DEA): EtOH=85:15, 1.0 ml/min).

Example 6a: (3R,4R)-4-((R)-5H-imidazo[5,1-a]isoindol-5-yl)-tetrahydro-2H-pyran-3-ol (53.6 mg, 2%): LCMS (ESI, m/z): 257 $[M+H]^+$; $^1$HNMR (300 MHz, $CDCl_3$) δ 8.02 (s, 1H), 7.55-7.53 (m, 1H), 7.40-7.28 (m, 3H), 7.20 (s, 1H), 5.85 (d, J=2.1 Hz, 1H), 4.16-4.11 (m, 1H), 4.07-3.97 (m, 1H), 3.75-3.69 (m, 1H), 3.27-3.12 (m, 2H), 2.40-2.30 (m, 1H), 0.92-0.72 (m, 2H); tR=2.442 min (CHIRALCEL OJ-3, 0.46×15 cm; 3 um, Hex(0.1% DEA):EtOH=85:15, 1.5 ml/min).

Example 6b: (3S,4S)-4-((S)-5H-imidazo[5,1-a]isoindol-5-yl)-tetrahydro-2H-pyran-3-ol (52.0 mg, 1%): LCMS (ESI, m/z): 257 $[M+H]^+$; $^1$HNMR (300 MHz, $CDCl_3$) δ 7.92 (s, 1H), 7.55-7.52 (m, 1H), 7.39-7.25 (m, 3H), 7.19 (s, 1H), 5.83 (d, J=1.8 Hz, 1H), 4.16-4.11 (m, 1H), 4.06-3.95 (m, 1H), 3.76-3.70 (m, 1H), 3.27-3.18 (m, 2H), 2.29-2.19 (m, 1H), 0.91-0.72 (m, 2H); tR=3.200 min (CHIRALCEL OJ-3, 0.46×15 cm; 3 um, Hex(0.1% DEA):EtOH=85:15, 1.5 ml/min).

Example 6c: (3S,4S)-4-((R)-5H-imidazo[5,1-a]isoindol-5-yl)-tetrahydro-2H-pyran-3-ol (120.7 mg, 2%): LCMS (ESI, m/z): 257 $[M+H]^+$; $^1$HNMR (300 MHz, $CDCl_3$) δ 7.72 (s, 1H), 7.58-7.55 (m, 1H), 7.49-7.46 (m, 1H), 7.42-7.37 (m, 1H), 7.27-7.19 (m, 2H), 5.79 (d, J=3.3 Hz, 1H), 4.13-3.96 (m, 2H), 3.78-3.73 (m, 1H), 3.28-3.15 (m, 2H), 2.39-2.29 (m, 1H), 0.94-0.85 (m, 2H); tR=4.117 min (CHIRALCEL OJ-3, 0.46×15 cm; 3 um, Hex(0.1% DEA):EtOH=85:15, 1.5 ml/min).

Example 6d: (3R,4R)-4-((S)-5H-imidazo[5,1-a]isoindol-5-yl)-tetrahydro-2H-pyran-3-ol (23.9 mg, 2%): LCMS (ESI, m/z): 257 $[M+H]^+$; $^1$HNMR (300 MHz, $CDCl_3$) δ 7.78 (s, 1H), 7.62-7.57 (m, 1H), 7.55-7.49 (m, 1H), 7.41-7.36 (m, 1H), 7.27-7.18 (m, 2H), 5.80 (d, J=3.0 Hz, 1H), 4.11-3.97 (m, 2H), 3.76-3.72 (m, 1H), 3.28-3.15 (m, 2H), 2.40-2.30 (m, 1H), 0.97-0.84 (m, 2H); tR=9.372 min (CHIRALCEL OJ-3, 0.46×15 cm; 3 um, Hex(0.1% DEA):EtOH=85:15, 1.5 ml/min).

Example 6: 4-(5H-imidazo[5,1-a]isoindol-5-yl)tetrahydro-2H-pyran-3-ol

006e

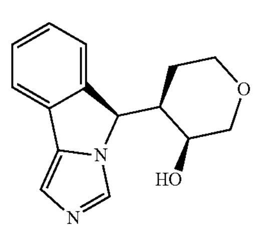

Step 1: (3S,4R)-4-((R)-5H-imidazo[5,1-a]isoindol-5-yl)tetrahydro-2H-pyran-3-yl 4-nitrobenzoate

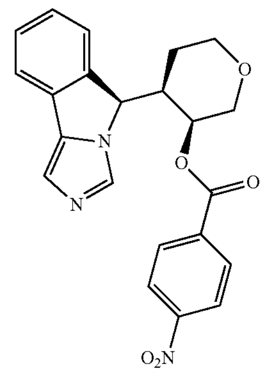 [SMILES: O=C(O[C@@H]1COCC[C@@H]1[C@@H]1c2ccccc2-c2cncn21)c1ccc([N+](=O)[O-])cc1]

Under nitrogen, a solution of (3R,4R)-4-[(5R)-5H-imidazo[4,3-a]isoindol-5-yl]oxan-3-ol (256 mg, 1.00 mmol) and 4-nitrobenzoic acid (200 mg, 1.20 mmol) in THF (50 mL) was added $PPh_3$ (801 mg, 3.05 mmol) and DIAD (606 mg, 3.00 mmol) at 0° C. The resulting solution was stirred for 4 h at room temperature. The reaction was then quenched by the addition of water. The resulting solution was extracted with EtOAc. The organic layers were combined, dried over anhydrous sodium sulfate, and concentrated under vacuum. The crude product was purified by Combi-Flash eluting with DCM/MeOH (20:1) to afford 300 mg (74%) of (3S,4R)-4-[(5R)-5H-imidazo[4,3-a]isoindol-5-yl]oxan-3-yl 4-nitrobenzoate as a yellow solid: LCMS (ESI, m/z): 406 $[M+H]^+$.

Step 2: (3S,4R)-4-((R)-5H-imidazo[5,1-a]isoindol-5-yl)tetrahydro-2H-pyran-3-ol

006e

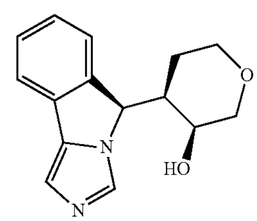

A mixture of (3S,4R)-4-[(5R)-5H-imidazo[4,3-a]isoindol-5-yl]oxan-3-yl 4-nitrobenzoate (300 mg, 0.74 mmol), LiOH (88 mg, 3.68 mmol) in THF (10 mL) and water (10 mL) was stirred for 4 h at room temperature. The reaction was then quenched by the addition of water. The resulting solution was extracted with EtOAc. The organic layers were combined, dried over anhydrous sodium sulfate, and concentrated under vacuum. The crude product was purified by Combi-Flash eluting with DCM/MeOH (10:1).

Example 006e: (3S,4R)-4-((R)-5H-imidazo[5,1-a]isoindol-5-yl)tetrahydro-2H-pyran-3-ol (73.1 mg, 39%) as a white solid: LCMS (ESI, m/z): 257.3 $[M+H]^+$. $^1$H NMR (300 MHz, $CDCl_3$) δ 8.09 (s, 1H), 7.58-7.15 (m, 5H), 5.27 (d, J=4.3 Hz, 1H), 4.16 (s, 1H), 4.10-3.90 (m, 2H), 3.58 (dd, J=12.2, 1.2 Hz, 1H), 3.42-3.26 (m, 2H), 2.16-1.98 (m, 1H), 1.79-1.60 (m, 1H), 1.19 (d, J=12.6 Hz, 1H).

(3R,4S)-4-((S)-5H-imidazo[5,1-a]isoindol-5-yl)tetrahydro-2H-pyran-3-ol

006f

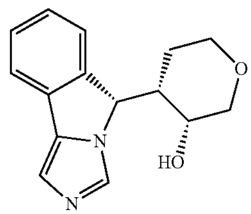

The title compound was synthesized by the same method of example 006e.

Example 006f: (3R,4S)-4-((S)-5H-imidazo[5,1-a]isoindol-5-yl)tetrahydro-2H-pyran-3-ol (77.5 mg, 41%) as a white solid: LCMS (ESI, m/z): 257.2 $[M+H]^+$. $^1H$ NMR (300 MHz, $CDCl_3$) δ 8.42 (s, 1H), 7.58 (d, J=7.5 Hz, 1H), 7.53-7.23 (m, 4H), 5.42 (d, J=3.6 Hz, 1H), 4.23 (s, 1H), 4.07 (d, J=12.1 Hz, 1H), 3.94 (dd, J=11.5, 4.8 Hz, 1H), 3.64-3.53 (m, 1H), 3.32 (td, J=12.1, 2.3 Hz, 1H), 2.19 (dd, J=12.2, 3.1 Hz, 1H), 1.66 (td, J=12.9, 4.9 Hz, 1H), 1.26 (s, 1H), 1.09 (d, J=13.1 Hz, 1H).

4-(5H-imidazo[5,1-a]isoindol-5-yl)tetrahydro-2H-pyran-3-ol

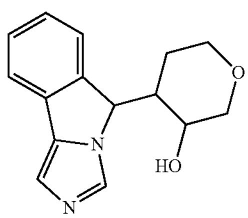 [SMILES: OC1COCCC1C1c2ccccc2-c2cncn21]

The title compounds were synthesized by the same method of example 006e. The absolute configuration of 006g and 006h was assigned arbitrarily.

Example 006g: (3S,4R)-4-((S)-5H-imidazo[5,1-a]isoindol-5-yl)-tetrahydro-2H-pyran-3-ol (25.3 mg, 21%) as a white solid: LCMS (ESI, m/z): 257.3 $[M+H]^+$. $^1H$ NMR (400 MHz, DMSO-$d_6$) δ 8.53 (s, 1H), 7.61 (d, J=7.6 Hz, 1H), 7.50-7.40 (m, 2H), 7.31-7.29 (m, 2H), 5.30 (d, J=9.0 Hz, 1H), 4.14-4.03 (m, 3H), 3.49-3.31 (m, 2H), 2.19 (qd, J=12.6, 4.7 Hz, 1H), 1.90 (d, J=13.3 Hz, 1H), 1.80-1.71 (m, 1H).

Example 006h: (3R,4S)-4-((R)-5H-imidazo[5,1-a]isoindol-5-yl)-tetrahydro-2H-pyran-3-ol (24.0 mg, 21%) as a white solid: LCMS (ESI, m/z): 257.3 $[M+H]^+$. $^1H$ NMR (400 MHz, DMSO-$d_6$) δ 8.11 (s, 1H), 7.60 (d, J=7.6 Hz, 1H), 7.56-7.37 (m, 2H), 7.26-7.24 (m, 2H), 5.20 (d, J=8.9 Hz, 1H), 4.12-4.01 (m, 3H), 3.47-3.31 (m, 2H), 2.15 (qd, J=12.7, 4.9 Hz, 1H), 1.89 (d, d, J=13.3 Hz, 1H), 1.78-1.69 (m, 1H).

Example 7: 7-(5H-imidazo[4,3-a]isoindol-5-yl)-5H,6H,7H,8H-imidazo[1,5-a]pyridin-8-ol

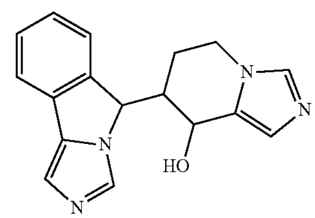 [SMILES: OC1c2cncn2CCC1C1c2ccccc2-c2cncn21]

The title compound was synthesized by the same method of Example 4.

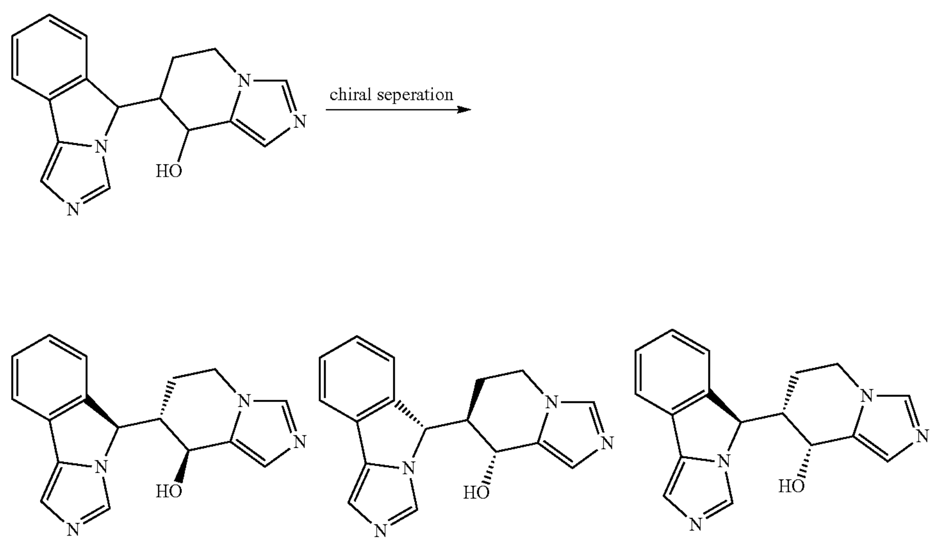

-continued

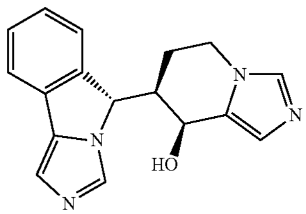

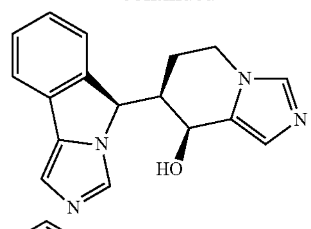

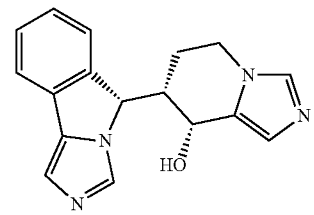

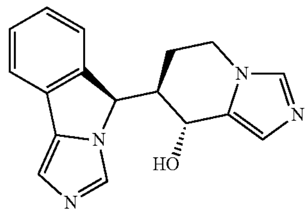

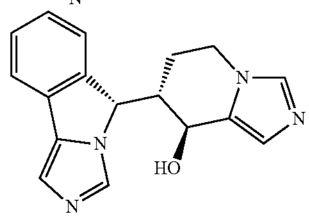

The crude product was purified by Prep-HPLC and further isolated by chiral separation with the following conditions:

1. Column: CHIRALPAK AD-H-TC001 SFC, 20×250 mm, 5 um; Mobile Phase A:Hex (0.1% DEA)-HPLC, Mobile Phase B: IPA-HPLC; Flow rate: 20 mL/min; Gradient: 25 B to 25 B in 34 min; 254/220 nm;
2. Column: CHIRALPAK ID, 2.0 cm I.D×25 cm L; Mobile Phase A:Hex(0.1% DEA)-HPLC, Mobile Phase B: EtOH-HPLC; Flow rate: 20 mL/min; Gradient: 40 B to 40 B in 23 min; 254/220 nm;
3. Column: CHIRALPAK ID, 2.0 cm I.D×25 cm L; Mobile Phase A: CO2:60, Mobile Phase B: IPA (0.2% DEA): 40; Flow rate: 40 mL/min; 220 nm;

The absolute configuration of isomers 7c, 7d, 7g and 7h was assigned by X-ray crystallography. The absolute configuration of the rest isomers was assigned arbitrarily.

Example 7a: 5H-imidazo[5,1-a]isoindol-5-yl)-5,6,7,8-tetrahydroimidazo[1,5-a]pyridin-8-ol as a white solid (38.3 mg, 4%); LCMS (ESI, m/z): 293.1 $[M+H]^+$; $^1$HNMR (300 MHz, DMSO-$d_6$) δ 7.92 (s, 1H), 7.62 (m, 2H), 7.45-7.35 (m, 2H), 7.28-7.23 (m, 1H), 7.17 (s, 1H), 6.90 (s, 1H), 6.06 (d, J=6.6 Hz, 1H), 5.76 (d, J=3.0 Hz, 1H), 4.98-4.93 (m, 1H), 3.96-3.90 (m, 1H), 3.70-3.61 (m, 1H), 2.67-2.57 (m, 1H), 1.16-0.92 (m, 2H); tR=2.538 min, (Chiralpak AD-3, 0.46×5 cm, 3 um; Hex(0.1% DEA):IPA=75:25; 1.0 mL/min). 7a and 7b are enantiomers.

Example 7b: 5H-imidazo[5,1-a]isoindol-5-yl)-5,6,7,8-tetrahydroimidazo[1,5-a]pyridin-8-ol as a white solid (41.0 mg, 4%); LCMS (ESI, m/z): 293.1 $[M+H]^+$; tR=3.257 min, (Chiralpak AD-3, 0.46×5 cm, 3 um; Hex(0.1% DEA): IPA=75:25; 1.0 mL/min). 7a and 7b are enantiomers.

Example 7c: (7S,8R)-7-((S)-5H-imidazo[5,1-a]isoindol-5-yl)-5,6,7,8-tetrahydroimidazo[1,5-a]pyridin-8-ol as a white solid (35.8 mg, 4%); LCMS (ESI, m/z): 293.1 $[M+H]^+$; $^1$HNMR (300 MHz, DMSO-$d_6$) δ 7.97 (s, 1H), 7.65-7.62 (m, 1H), 7.51-7.39 (m, 3H), 7.35-7.29 (m, 1H), 7.18 (s, 1H), 6.93 (s, 1H), 7.78-7.75 (m, 1H), 5.05-4.99 (m, 1H), 3.95-3.89 (m, 1H), 3.58-3.68 (m, 1H), 2.49-2.40 (m, 1H), 1.04-0.95 (m, 2H); tR=4.012 min, (Chiralpak AD-3, 0.46×5 cm, 3 um; Hex(0.1% DEA):IPA=75:25; 1.0 mL/min). 7c and 7d are enantiomers.

Example 7d: (7R,8S)-7-((R)-5H-imidazo[5,1-a]isoindol-5-yl)-5,6,7,8-tetrahydroimidazo[1,5-a]pyridin-8-ol as a white solid (35.6 mg, 4%): LCMS (ESI, m/z): 293.1 $[M+H]^+$; tR=5.054 min, (Chiralpak AD-3, 0.46×5 cm, 3 um; Hex(0.1% DEA):IPA=75:25; 1.0 mL/min). 7c and 7d are enantiomers.

Example 7e: 5H-imidazo[5,1-a]isoindol-5-yl)-5,6,7,8-tetrahydroimidazo[1,5-a]pyridin-8-ol as a white solid (37.7 mg, 4%): LCMS (ESI, m/z): 293.1 $[M+H]^+$; $^1$HNMR (300 MHz, DMSO-$d_6$) δ 7.97 (s, 1H), 7.74-7.72 (m, 1H), 7.63-7.60 (m, 1H), 7.50 (s, 1H), 7.42-7.37 (t, 1H), 7.27-7.21 (m, 1H), 7.14 (s, 1H), 6.87 (s, 1H), 5.62-5.60 (m, 1H), 5.45-5.44 (m, 1H), 5.02-4.96 (m, 1H), 4.21-4.16 (m, 1H), 3.77-3.68 (m, 1H), 2.23-2.17 (m, 2H), 1.82-1.78 (m, 1H); tR=4.468 min, (Chiralpak ID-3, 0.46×10 cm, 3 um; Hex(0.1% DEA): IPA=60:40; 1.0 mL/min). 7e and 7f are enantiomers.

Example 7f: 5H-imidazo[5,1-a]isoindol-5-yl)-5,6,7,8-tetrahydroimidazo[1,5-a]pyridin-8-ol as a white solid (29.3 mg, 3%): LCMS (ESI, m/z): 293.1 $[M+H]^+$; tR=6.020 min, (Chiralpak ID-3, 0.46×10 cm, 3 um; Hex(0.1% DEA): IPA=60:40; 1.0 mL/min). 7e and 7f are enantiomers.

Example 7g: (7R,8R)-7-((R)-5H-imidazo[5,1-a]isoindol-5-yl)-5,6,7,8-tetrahydroimidazo[1,5-a]pyridin-8-ol as a white solid (30.5 mg, 4%): LCMS (ESI, m/z): 293.1 $[M+H]^+$; $^1$HNMR (300 MHz, DMSO-$d_6$) δ 7.95 (s, 1H), 7.65-7.57 (m, 2H), 7.49 (s, 1H), 7.42-7.36 (m, 1H), 7.31-7.26 (m, 1H), 7.12 (s, 1H), 6.92 (s, 1H), 5.90-5.86 (m, 1H), 5.53-5.50 (m, 1H), 5.21-5.18 (m, 1H), 4.09-4.03 (m, 1H), 3.67-3.57 (m, 1H), 2.56-2.51 (m, 1H), 1.86-1.71 (m, 1H), 1.15-1.07 (m, 1H). tR=2.18 min, (Chiralpak ID, 4.6×100 mm, 3 um; IPA (0.1% DEA)=40%; 4 mL/min). 7g and 7h are enantiomers.

Example 7h: (7S,8S)-7-((S)-5H-imidazo[5,1-a]isoindol-5-yl)-5,6,7,8-tetrahydroimidazo[1,5-a]pyridin-8-ol as a white solid (30.6 mg, 4%): LCMS (ESI, m/z): 293.1 $[M+H]^+$; tR=2.92 min, (Chiralpak ID, 4.6×100 mm, 3 um; IPA (0.1% DEA)=40%; 4 mL/min). 7g and 7h are enantiomers.

Example 8: 6-(5H-imidazo[4,3-a]isoindol-5-yl)-5,6,7,8-tetrahydroisoquinolin-5-ol

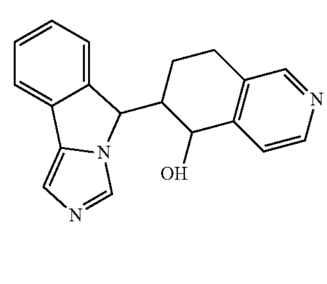 [SMILES: OC1c2ccncc2CCC1C1c2ccccc2-c2cncn21]

The title compound was synthesized by the same method of Example 4:

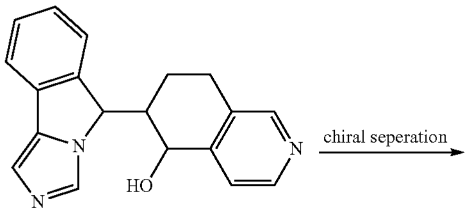

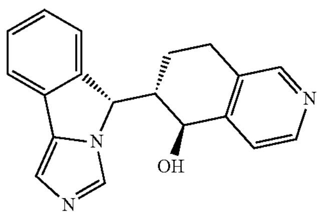

8a

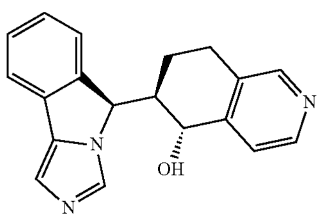

8b

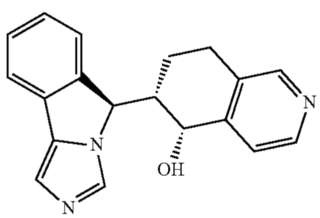

8c

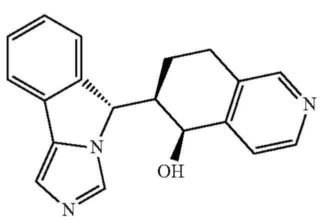

8d

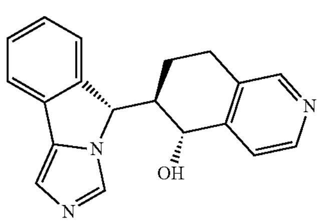

8e

-continued

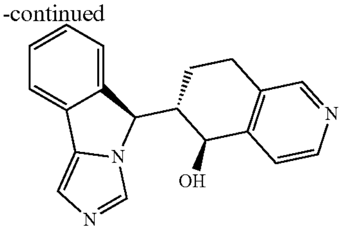

8f

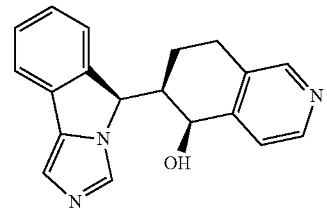

8g

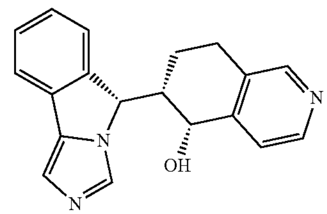

8h

The crude product was purified by Prep-HPLC and further isolated by chiral separation with the following conditions:

1. Column: Chiralpak IC, 2×25 cm, 5 um; Mobile Phase A: CO2:50, Mobile Phase B: MeOH:50; Flow rate: 40 mL/min; 220 nm;
2. Column: CHIRALCEL OD-H, 20×250 mm; Mobile Phase A: CO2:70, Mobile Phase B: MeOH:30; Flow rate: 40 mL/min; 260 nm;
3. Column: CHIRALPAK AD-H, 20×250 mm; Mobile Phase A: CO2:60, Mobile Phase B: MeOH:40; Flow rate: 40 mL/min; 220 nm;

The absolute configuration of all isomers was assigned by X-ray crystallography.

Example 8a: (5S,6S)-6-((S)-5H-imidazo[5,1-a]isoindol-5-yl)-5,6,7,8-tetrahydroisoquinolin-5-ol as a off-white solid (23.9 mg, 1%); LCMS (ESI, m/z): 304 $[M+H]^+$. $^1$HNMR (300 MHz, $CD_3OD$) δ 8.39-8.37 (m, 1H), 8.23 (s, 1H), 8.04 (s, 1H), 7.72-7.66 (m, 2H), 7.51-7.35 (m, 3H), 7.24 (s, 1H), 5.91 (s, 1H), 5.04 (d, J=5.4 Hz, 1H), 2.71-2.68 (m, 2H), 2.53-2.46 (m, 1H), 1.20-1.17 (m, 1H), 1.08-0.94 (m, 1H). tR=1.393 min, (CHIRALPAK AS-3 100×3 mm, 3 um; $CO_2$:MeOH (20 mM $NH_3$), Gradient (B %): 10% to 50% in 4.0 min, hold 2.0 min at 50%; 220 nm; 2 mL/min). 8a and 8b are enantiomers.

Example 8b: (5R,6R)-6-((R)-5H-imidazo[5,1-a]isoindol-5-yl)-5,6,7,8-tetrahydroisoquinolin-5-ol as a off-white solid (22.1 mg, 1%); LCMS (ESI, m/z): 304 $[M+H]^+$. $^1$HNMR (300 MHz, $CD_3OD$) δ 8.39-8.37 (m, 1H), 8.23 (s, 1H), 8.04 (s, 1H), 7.72-7.66 (m, 2H), 7.51-7.35 (m, 3H), 7.24 (s, 1H), 5.91 (s, 1H), 5.04 (d, J=5.4 Hz, 1H), 2.71-2.68 (m, 2H), 2.53-2.46 (m, 1H), 1.20-1.17 (m, 1H), 1.08-0.94 (m, 1H); tR=1.524 min, (CHIRALPAK AS-3 100×3 mm, 3 um; $CO_2$:MeOH (20 mM $NH_3$), Gradient (B %): 10% to 50% in 4.0 min, hold 2.0 min at 50%; 220 nm; 2 mL/min). 8a and 8b are enantiomers.

Example 8c: (5R,6S)-6-((R)-5H-imidazo[5,1-a]isoindol-5-yl)-5,6,7,8-tetrahydroisoquinolin-5-ol as a off-white solid (101.8 mg, 3%); LCMS (ESI, m/z): 304 $[M+H]^+$. $^1$HNMR (300 MHz, $CD_3OD$) δ 8.31 (s, 2H), 8.06 (s, 1H), 8.04 (s, 1H), 7.70-7.62 (m, 2H), 7.43-7.24 (m, 3H), 7.17 (s, 1H), 5.54-5.52 (m, 1H), 4.79-4.78 (m, 1H), 3.00-2.92 (m, 1H), 2.78-2.68 (m, 1H), 2.32-2.25 (m, 1H), 2.10-1.99 (m, 2H); tR=1.632 min, (CHIRALPAK AS-3 100×3 mm, 3 um; $CO_2$:MeOH (20 mM $NH_3$), Gradient (B %): 10% to 50% in 4.0 min, hold 2.0 min at 50%; 220 nm; 2 mL/min). 8c and 8d are enantiomers.

Example 8d: (5S,6R)-6-((S)-5H-imidazo[5,1-a]isoindol-5-yl)-5,6,7,8-tetrahydroisoquinolin-5-ol as a off-white solid (75.7 mg, 3%); LCMS (ESI, m/z): 304 $[M+H]^+$. $^1$HNMR (300 MHz, $CD_3OD$) δ 8.31 (s, 2H), 8.06 (s, 1H), 8.04 (s, 1H), 7.70-7.62 (m, 2H), 7.43-7.24 (m, 3H), 7.17 (s, 1H), 5.54-5.52 (m, 1H), 4.79-4.78 (m, 1H), 3.00-2.92 (m, 1H), 2.78-2.68 (m, 1H), 2.32-2.25 (m, 1H), 2.10-1.99 (m, 2H); tR=1.914 min, (CHIRALPAK AS-3 100×3 mm, 3 um; $CO_2$:MeOH (20 mM $NH_3$), Gradient (B %): 10% to 50% in 4.0 min, hold 2.0 min at 50%; 220 nm; 2 mL/min). 8c and 8d are enantiomers.

Example 8e: (5R,6R)-6-((S)-5H-imidazo[5,1-a]isoindol-5-yl)-5,6,7,8-tetrahydroisoquinolin-5-ol as a off-white solid (18.8 mg, 1%); LCMS (ESI, m/z): 304 $[M+H]^+$; $^1$HNMR (300 MHz, $CD_3OD$) δ 8.38-8.36 (m, 1H), 8.23 (s, 1H), 7.92 (s, 1H), 7.69-7.61 (m, 3H), 7.46-7.42 (m, 1H), 7.35-7.29 (m, 1H), 7.20 (s, 1H), 5.90-5.89 (m, 1H), 4.98 (d, J=5.1 Hz, 1H), 2.71-2.68 (m, 2H), 2.72-2.58 (m, 3H), 1.14-0.97 (m, 2H); tR=1.403 min, (CHIRALPAK AS-3 100×3 mm, 3 um mobile phase: $CO_2$:MeOH (20 mM NH3), Gradient (B %): 10% to 50% in 4.0 min, hold 2.0 min at 50%; 2 ml/min; 220 nm). 8e and 8f are enantiomers.

Example 8f: (5S,6S)-6-((R)-5H-imidazo[5,1-a]isoindol-5-yl)-5,6,7,8-tetrahydroisoquinolin-5-ol as a off-white solid (19.9 mg, 1%); LCMS (ESI, m/z): 304 $[M+H]^+$; $^1$HNMR (300 MHz, $CD_3OD$) δ 8.38-8.36 (m, 1H), 8.23 (s, 1H), 7.92 (s, 1H), 7.69-7.61 (m, 3H), 7.46-7.42 (m, 1H), 7.35-7.29 (m, 1H), 7.20 (s, 1H), 5.90-5.89 (m, 1H), 4.98 (d, J=5.1 Hz, 1H), 2.71-2.68 (m, 2H), 2.72-2.58 (m, 3H), 1.14-0.97 (m, 2H); tR=1.701 min, (CHIRALPAK AS-3 100×3 mm, 3 um mobile phase: $CO_2$:MeOH (20 mM NH3), Gradient (B %): 10% to 50% in 4.0 min, hold 2.0 min at 50%; 2 ml/min; 220 nm). 8e and 8f are enantiomers.

Example 8g: (5S,6R)-6-((R)-5H-imidazo[5,1-a]isoindol-5-yl)-5,6,7,8-tetrahydroisoquinolin-5-ol as a off-white solid (239.8 mg, 6%); LCMS (ESI, m/z): 304 $[M+H]^+$; $^1$HNMR (300 MHz, $CD_3OD$) δ 8.39-8.38 (m, 1H), 8.30 (s, 1H), 8.07 (s, 1H), 7.63-7.57 (m, 2H), 7.54-7.49 (m, 1H), 7.45-7.41 (m, 1H), 7.36-7.32 (m, 1H), 7.14 (s, 1H), 5.63-5.61 (m, 1H), 5.12-5.11 (m, 1H), 2.82-2.77 (m, 1H), 2.64-2.53 (m, 2H), 1.58-1.48 (m, 1H), 1.15-1.13 (m, 1H); tR=2.563 min, (CHIRALPAK AD-3 100×3 mm, 3 um; mobile phase: $CO_2$: MeOH (20 mM $NH_3$), MeOH (20 mM NH3); Gradient (B %): 10% to 50% in 4.0 min, hold 2.0 min at 50%; 220 nm). 8g and 8h are enantiomers.

Example 8h: (5R,6S)-6-((S)-5H-imidazo[5,1-a]isoindol-5-yl)-5,6,7,8-tetrahydroisoquinolin-5-ol as a off-white solid (70.3 mg, 2%); LCMS (ESI, m/z): 304 $[M+H]^+$; $^1$HNMR (300 MHz, $CD_3OD$) δ 8.39-8.38 (m, 1H), 8.30 (s, 1H), 8.07 (s, 1H), 7.63-7.57 (m, 2H), 7.54-7.49 (m, 1H), 7.45-7.41 (m, 1H), 7.36-7.32 (m, 1H), 7.14 (s, 1H), 5.63-5.61 (m, 1H), 5.12-5.11 (m, 1H), 2.82-2.77 (m, 1H), 2.64-2.53 (m, 2H), 1.58-1.48 (m, 1H), 1.15-1.13 (m, 1H); tR=2.776 min, (CHIRALPAK AD-3 100×3 mm, 3 um; mobile phase: $CO_2$: MeOH (20 mM $NH_3$), MeOH (20 mM NH3); Gradient (B %): 10% to 50% in 4.0 min, hold 2.0 min at 50%; 220 nm). 8g and 8h are enantiomers.

The absolute configuration of all isomers was assigned arbitrarily.

Example 9: 1-(3-hydroxy-4-(5H-imidazo[5,1-a]isoindol-5-yl)piperidin-1-yl)ethan-1-one

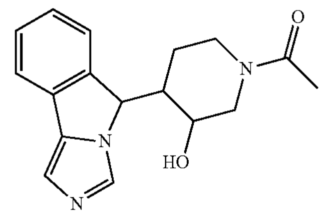 [SMILES: CC(=O)N1CCC(C2c3ccccc3-c3cncn32)C(O)C1]

The title compound was synthesized by the same method of Example 27.

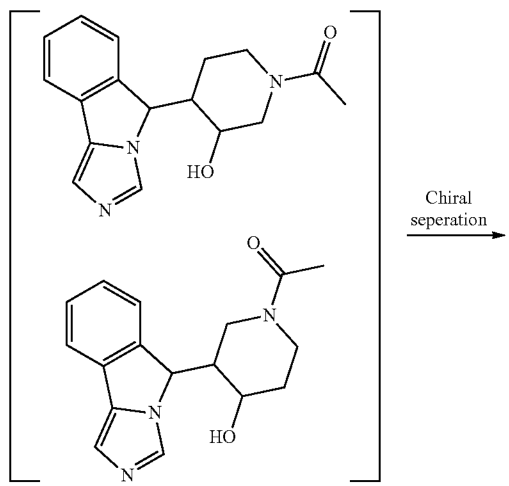

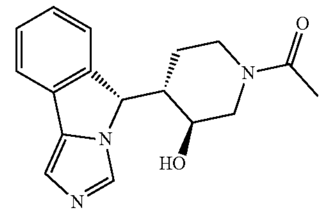

9a-d

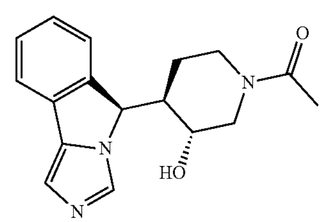

-continued

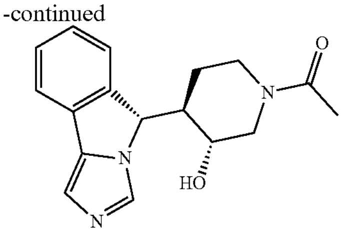

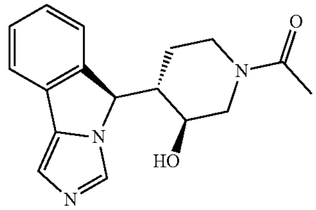

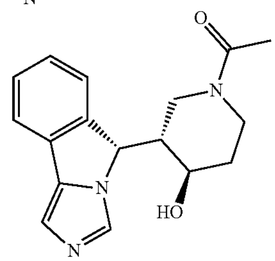

12a-d

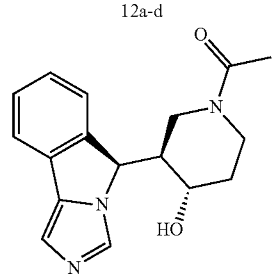

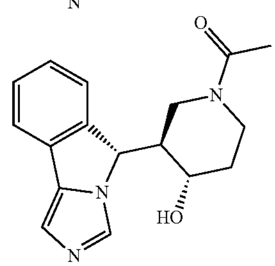

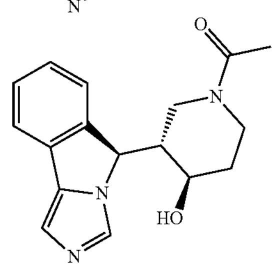

The crude product was purified by Prep-HPLC and further isolated by chiral separation with the following conditions:

1. CHIRALCEL OD-H, 20×250 mm; Mobile Phase A:Hex-HPLC, Mobile Phase B: EtOH-HPLC; Flow rate: 20 mL/min; Gradient: 10 B to 10 B in 24 min; 254/220 nm;
2. CHIRALPAK-AD-H-SL002, 20×250 mm; Mobile Phase A:Hex(0.1% DEA)-HPLC, Mobile Phase B: IPA-HPLC; Flow rate: 20 mL/min; Gradient: 30 B to 30 B in 15 min; 254/220 nm;

Example 9a: 1-(3-hydroxy-4-(5H-imidazo[5,1-a]isoindol-5-yl)piperidin-1-yl)ethan-1-one (10.0 mg, 11%) as a white solid: LCMS (ESI, m/z): 298.2 $[M+H]^+$; $^1$HNMR (300 MHz, $CD_3OD$) δ 7.95-7.90 (m, 1H), 7.64-7.62 (m, 1H), 7.52-7.36 (m, 3H), 7.20 (s, 1H), 5.84-5.83 (m, 1H), 4.88-3.67 (m, 3H), 3.06-2.85 (m, 1H), 2.55-2.28 (m, 2H), 2.14-1.98 (m, 3H), 1.00-0.85 (m, 1H), 0.59-0.58 (m, 1H); tR=9.351 min, (ChiralCELOD-3, 0.46×5 cm, 3 um; ethanol:hexane (0.1% DEA)=7:93; 1.0 mL/min). 9a and 9b are enantiomers.

Example 9b: 1-(3-hydroxy-4-(5H-imidazo[5,1-a]isoindol-5-yl)piperidin-1-yl)ethan-1-one (31.5 mg, 33%) as a white solid: LCMS (ESI, m/z): 298.2 $[M+H]^+$; tR=10.852 min, (ChiralCELOD-3, 0.46×5 cm, 3 um; ethanol:hexane (0.1% DEA)=7:93; 1.0 mL/min). 9a and 9b are enantiomers.

Example 9c: 1-(3-hydroxy-4-(5H-imidazo[5,1-a]isoindol-5-yl)piperidin-1-yl)ethan-1-one (3.2 mg, 3%) as a white solid: LCMS (ESI, m/z): 298.2 $[M+H]^+$; $^1$HNMR (400 MHz, $CD_3OD$) δ 7.91 (s, 1H), 7.63-7.62 (m, 1H), 7.53-7.50 (m, 1H), 7.43-7.39 (m, 1H), 7.32-7.28 (m, 1H), 7.15 (s, 1H), 5.82-5.80 (m, 1H), 4.86-3.65 (m, 3H), 3.00-2.93 (m, 1H), 2.49-2.35 (m, 2H), 2.09-1.94 (m, 3H), 0.84-0.71 (m, 1H), 0.63-0.42 (m, 1H); tR=13.717 min, (ChiralCELOD-3, 0.46×5 cm, 3 um; ethanol:hexane (0.1% DEA)=7:93; 1.0 mL/min). 9c and 9d are enantiomers.

Example 9d: 1-(3-hydroxy-4-(5H-imidazo[5,1-a]isoindol-5-yl)piperidin-1-yl)ethan-1-one (7.0 mg, 7%) as a white solid: LCMS (ESI, m/z): 298.2 $[M+H]^+$; tR=16.140 min, (ChiralCELOD-3, 0.46×5 cm, 3 um; ethanol:hexane (0.1% DEA)=7:93; 1.0 mL/min). 9c and 9d are enantiomers.

Example 10 and 11: tert-butyl 3-hydroxy-4-(5H-imidazo[5,1-a]isoindol-5-yl)piperidine-1-carboxylate and tert-butyl 4-hydroxy-3-(5H-imidazo[5,1-a]isoindol-5-yl)piperidine-1-carboxylate

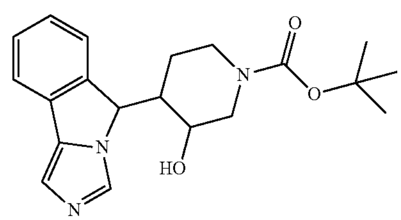

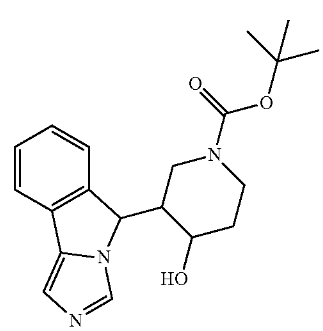

The following isomers were separated with inter-6 by Chiral-HPLC.

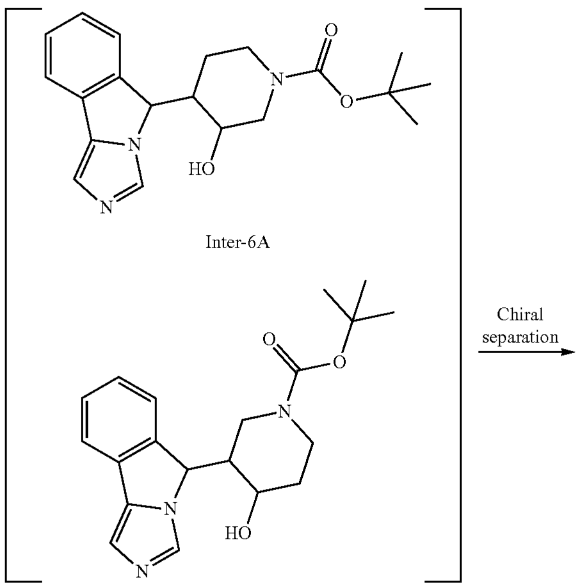

Inter-6A

Inter-6B

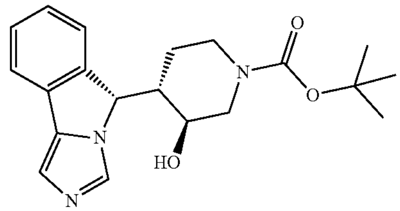

10a-d

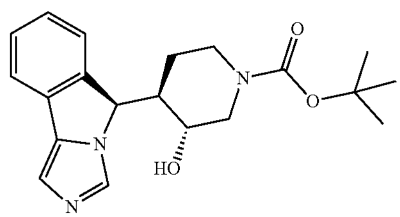

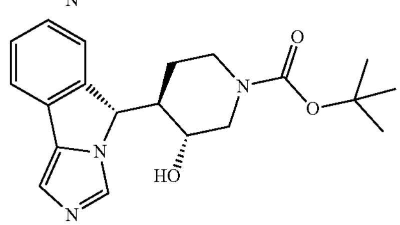

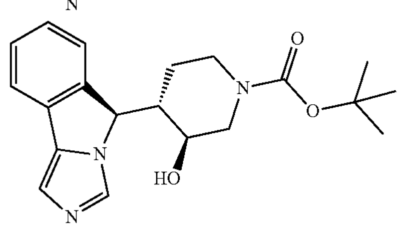

-continued

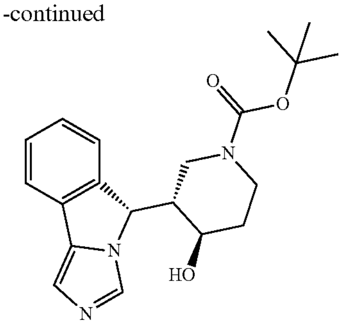

11a-d

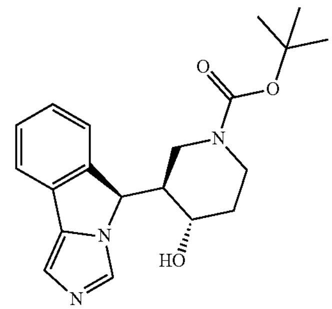

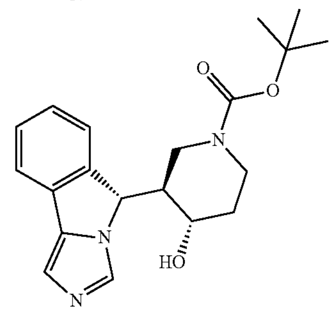

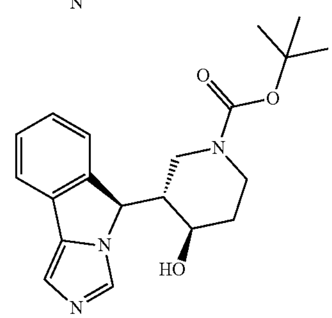

The mixture of inter-6 was purified by Prep-HPLC and further isolated by chiral separation with the following conditions:

1. Chiralpak IA, 2×25 cm, 5 um; Mobile Phase A:Hex-HPLC, Mobile Phase B: EtOH-HPLC; Flow rate: 20 mL/min; Gradient: 30 B to 30 B in 10 min; 254/220 nm;
2. Phenomenex Lux 5 u Cellulose-4,AXIA Packed, 250×21.2 mm, 5 um; Mobile Phase A:Hex-HPLC, Mobile Phase B: EtOH-HPLC; Flow rate: 20 mL/min; Gradient: 30 B to 30 B in 26 min; 254/220 nm;
3. CHIRALPAK ID, 2.0 cm I.D×25 cm L; Mobile Phase A:Hex-HPLC, Mobile Phase B: IPA-HPLC; Flow rate: 20 mL/min; Gradient: 15 B to 15 B in 18 min; 254/220 nm;

4. CHIRALPAK ID, 2.0 cm I.D×25 cm L; Mobile Phase A:Hex-HPLC, Mobile Phase B: IPA-HPLC; Flow rate: 20 mL/min; Gradient: 30 B to 30 B in 13 min; 254/220 nm;
5. The absolute of all isomers was assigned arbitrarily.

Example 10a: tert-butyl 3-hydroxy-4-(5H-imidazo[5,1-a]isoindol-5-yl)piperidine-1-carboxylate (38.7 mg, 1%) as a white solid: LCMS (ESI, m/z): 356.2 $[M+H]^+$; $^1$HNMR (400 MHz, $CD_3OD$) δ 7.89 (s, 1H), 7.64 (d, J=7.6 Hz, 1H), 7.49 (d, J=7.6 Hz, 1H), 7.45-7.34 (m, 2H), 7.20 (s, 1H), 5.82 (d, J=4.0 Hz, 1H), 4.37-4.33 (m, 1H), 3.86-3.71 (m, 2H), 2.62-2.50 (m, 2H), 2.27-2.20 (m, 1H), 1.43 (s, 9H), 0.87-0.83 (m, 1H), 0.47-0.42 (m, 1H); tR=1.323 min, (Chiralpak IA, 0.46×5 cm, 3 um; ethanol:hexane (0.1% DEA)=30:70; 1.0 mL/min). 10a and 10b are enantiomers.

Example 10b: tert-butyl 3-hydroxy-4-(5H-imidazo[5,1-a]isoindol-5-yl)piperidine-1-carboxylate (39.9 mg, 1%) as a white solid: LCMS (ESI, m/z): 356.2 $[M+H]^+$; tR=1.866 min. (Chiralpak IA, 0.46×5 cm, 3 um; ethanol:hexane (0.1% DEA)=30:70; 1.0 mL/min). 10a and 10b are enantiomers.

Example 10c: tert-butyl 3-hydroxy-4-(5H-imidazo[5,1-a]isoindol-5-yl)piperidine-1-carboxylate (16.1 mg, 1%) as a white solid: LCMS (ESI, m/z): 356.2 $[M+H]^+$, $^1$HNMR (400 MHz, $CD_3OD$) δ 7.93 (s, 1H), 7.65 (d, J=7.6 Hz, 1H), 7.53 (d, J=7.6 Hz, 1H), 7.46-7.42 (m, 1H), 7.35-7.31 (m, 1H), 7.17 (s, 1H), 5.82 (d, J=4.0 Hz, 1H), 4.31-4.28 (m, 1H), 3.87-3.74 (m, 2H), 2.61-2.50 (m, 2H), 2.40-2.34 (m, 1H), 1.41 (s, 9H), 0.73-0.70 (m, 1H), 0.56-0.46 (m, 1H). tR=2.348 min (Lux Cellulose-4, 0.46×5 cm, 3 um; ethanol:hexane (0.1% DEA)=30:70; 1.0 mL/min). 10c and 10d are enantiomers.

Example 10d tert-butyl 3-hydroxy-4-(5H-imidazo[5,1-a]isoindol-5-yl)piperidine-1-carboxylate (16.0 mg, 1%) as a white solid: LCMS (ESI, m/z): 356.2 $[M+H]^+$; tR=2.841 min, (Lux Cellulose-4, 0.46×5 cm, 3 um; ethanol:hexane (0.1% DEA)=30:70; 1.0 mL/min). 10c and 10d are enantiomers.

The absolute configuration of isomers 11a & 11b was assigned by X-ray crystallography. The absolute configuration of the rest isomers was assigned arbitrarily.

Example 11a: (3S,4R)-tert-butyl 4-hydroxy-3-((S)-5H-imidazo[5,1-a]isoindol-5-yl)piperidine-1-carboxylate (36.1 mg, 1%) as a white solid: LCMS (ESI, m/z): 356.2 $[M+H]^+$; $^1$HNMR (400 MHz, $CD_3OD$) δ 7.96 (s, 1H), 7.66 (d, J=7.2 Hz, 1H), 7.54 (d, J=7.2 Hz, 1H), 7.46-7.38 (m, 2H), 7.21 (s, 1H), 5.83 (d, J=4.0 Hz, 1H), 4.07-4.00 (m, 2H), 3.34-3.32 (m, 1H), 2.79-2.65 (m, 1H), 2.21-2.07 (m, 2H), 1.84-1.77 (m, 1H), 1.60-1.49 (m, 1H), 1.27 (s, 9H); tR=2.511 min, (Chiralpak ID-3, 0.46×5 cm, 3 um; ethanol:hexane (0.1% DEA)=15:85; 1.0 mL/min). 11a and 11b are enantiomers.

Example 11b: (3R,4S)-tert-butyl 4-hydroxy-3-((R)-5H-imidazo[5,1-a]isoindol-5-yl)piperidine-1-carboxylate (30.1 mg, 1%) as a white solid: LCMS (ESI, m/z): 356.2 $[M+H]^+$. tR=3.240 min. (Chiralpak ID-3, 0.46×5 cm, 3 um; ethanol:hexane (0.1% DEA)=15:85; 1.0 mL/min). 11a and 11b are enantiomers.

Example 11c: tert-butyl 4-hydroxy-3-(5H-imidazo[5,1-a]isoindol-5-yl)piperidine-1-carboxylate (10.6 mg, 1%) as a white solid: LCMS (ESI, m/z): 356.2 $[M+H]^+$. $^1$HNMR (400 MHz, $CD_3OD$) δ 7.98 (s, 1H), 7.67 (d, J=7.6 Hz, 1H), 7.61 (d, J=7.6 Hz, 1H), 7.47-7.33 (m, 2H), 7.21 (s, 1H), 5.84 (d, J=4.0 Hz, 1H), 4.06-4.00 (m, 2H), 3.18-3.11 (m, 1H), 2.71-2.55 (m, 1H), 2.35-2.21 (m, 1H), 2.11-2.04 (m, 1H), 1.95-1.85 (s, 1H), 1.61-1.49 (m, 1H), 1.37 (s, 9H); tR=2.130 min (Chiralpak ID-3, 0.46×5 cm, 3 um; ethanol:hexane (0.1% DEA)=30:70; 1.0 mL/min). 11c and 11d are enantiomers.

Example 11d: tert-butyl 4-hydroxy-3-(5H-imidazo[5,1-a]isoindol-5-yl)piperidine-1-carboxylate (11.4 mg, 1%) as a white solid: LCMS (ESI, m/z): 356.3 $[M+H]^+$; tR=2.788 min, (Chiralpak ID-3, 0.46×5 cm, 3 um; ethanol:hexane (0.1% DEA)=30:70; 1.0 mL/min). 11c and 11d are enantiomers.

Example 12: 1-(4-hydroxy-3-(5H-imidazo[5,1-a]isoindol-5-yl)piperidin-1-yl)ethan-1-one

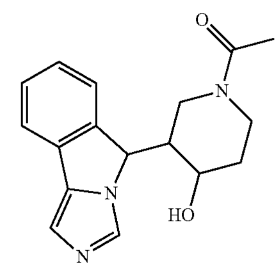 [SMILES: CC(=O)N1CCC(O)C(C2c3ccccc3-c3cncn32)C1]

The absolute configuration of all isomers was assigned arbitrarily.

Example 12a: 1-((3S,4R)-4-hydroxy-3-((S)-5H-imidazo[5,1-a]isoindol-5-yl)piperidin-1-yl)ethanone (16.4 mg, 4%) as a white solid: LCMS (ESI): $M+H^+$=298.2; $^1$HNMR (400 MHz, $CD_3OD$) δ 7.95-7.90 (m, 1H), 7.69-7.60 (m, 1H), 7.50-7.37 (m, 3H), 7.21 (s, 1H), 5.84-5.82 (m, 1H), 4.55-4.45 (m, 0.5H), 4.08-4.07 (m, 1H), 3.88-3.84 (m, 1H), 3.05-2.98 (m, 1H), 2.55-2.53 (m, 0.5H), 2.27-2.03 (m, 4H), 1.72-1.48 (m, 3H); tR=3.477 min, (Column, Lux Cellulose-3, 0.46×5 cm, 3 um; ethanol:hexane (0.1% DEA)=25:75; 1.0 mL/min). 12a and 12b are enantiomers.

Example 12b: 1-((3R,4S)-4-hydroxy-3-((R)-5H-imidazo[5,1-a]isoindol-5-yl)piperidin-1-yl)ethanone (13.8 mg, 4%) as a white solid: LCMS (ESI, m/z): 298.2 $[M+H]^+$; tR=4.190 min (Column, Lux Cellulose-3, 0.46×5 cm, 3 um; ethanol:hexane (0.1% DEA)=25:75; 1.0 mL/min). 12a and 12b are enantiomers.

Example 12c: 1-((3R,4S)-4-hydroxy-3-((S)-5H-imidazo[5,1-a]isoindol-5-yl)piperidin-1-yl)ethanone (8.6 mg, 2%) as a white solid: LCMS (ESI, m/z): 298.2 $[M+H]^+$. $^1$HNMR (400 MHz, $CD_3OD$) δ 8.05-7.92 (m, 1H), 7.70-7.62 (m, 2H), 7.49-7.35 (m, 2H), 7.24-7.20 (m, 1H), 5.87-5.82 (m, 1H), 4.55-4.45 (m, 0.5H), 4.12-4.05 (m, 1H), 3.94-3.71 (m, 1H), 3.55-3.53 (m, 0.5H), 3.01-2.75 (m, 1H), 2.51-2.04 (m, 4H), 1.82-1.75 (m, 3H); tR=5121 min, (Column, Lux Cellulose-3, 0.46×5 cm, 3 um; ethanol:hexane (0.1% DEA)=25:75; 1.0 mL/min). 12c and 12d are enantiomers.

Example 12d: 1-((3S,4R)-4-hydroxy-3-((R)-5H-imidazo[5,1-a]isoindol-5-yl)piperidin-1-yl)ethanone (10.2 mg, 2%) as a white solid: LCMS (ESI, m/z): 298.2 $[M+H]^+$; tR=10.013 min (Column, Lux Cellulose-3, 0.46×5 cm, 3 um; ethanol:hexane (0.1% DEA)=25:75; 1.0 mL/min). 12c and 12d are enantiomers.

Example 13: 2-(8-fluoro-5H-imidazo[5,1-a]isoindol-5-yl)cyclobutan-1-ol

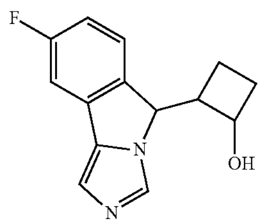 [SMILES: OC1CCC1C1c2ccc(F)cc2-c2cncn21]

The title compound was synthesized by the same method of example 3.

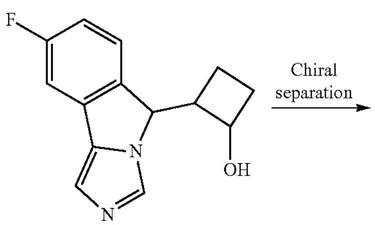

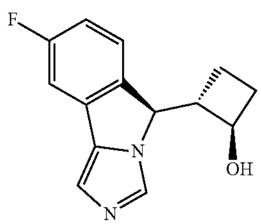

13a-h

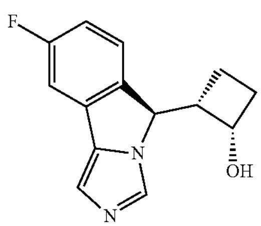

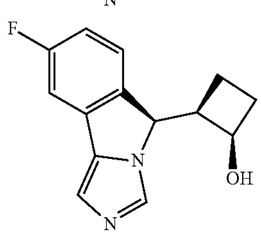

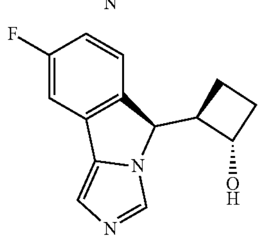

-continued

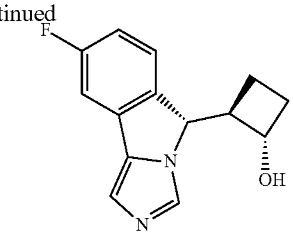

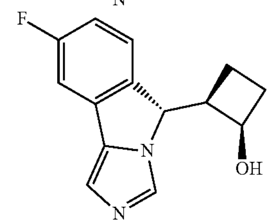

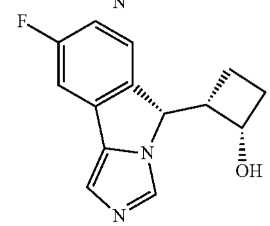

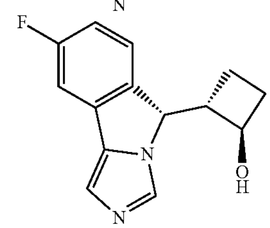

The crude product was purified by Prep-HPLC and further isolated by Chiral separation with the following conditions:

1. Column, ChiralpakOJ-H, 2×25 cm; mobile phase: Hex(0.1% DEA):IPA=12:12; Detector, uv 254 nm; flow rate, 20 mL/min.
2. Column, ChiralpakChiralpak IA, 2×25 cm, 5 um; mobile phase: Hex(0.1% DEA):IPA=30:30; Detector, uv 254 nm; flow rate, 20 mL/min
3. Column, ChiralpakOJ-H, 2×25 cm; mobile phase: Hex(0.1% DEA):IPA=15:15; Detector, uv 254 nm; flow rate, 20 mL/min
4. Column, ChiralpakIA, 2×25 cm, 5 um, 3 um; mobile phase: Hex(0.1% DEA):IPA=10:10; Detector, uv 254 nm; flow rate, 20 mL/min.

The absolute configuration of isomers 13c and 13d was assigned by X-ray crystallography. The absolute configuration of the rest isomers was assigned arbitrarily.

Example 13a: 8-fluoro-5H-imidazo[4,3-a]isoindol-5-yl] cyclobutan-1-ol: LCMS (ESI, m/z): 245.2. $^1$HNMR (300 MHz, $CD_3OD$) δ 7.93 (s, 1H), 7.63-7.59 (m, 1H), 7.40-7.37 (m, 1H), 7.23 (s, 1H), 7.08-7.02 (m, 1H), 5.37 (d, J=9 Hz, 1H), 4.34-4.30 (m, 1H), 2.62-2.46 (m, 1H), 2.32-2.14 (m, 1H), 1.88-1.67 (m, 2H), 1.38-1.20 (m, 2H). tR=6.997 min (Chiralpak OJ=3, 0.46×15 cm, 3 um; Hex(0.1% DEA): IPA=88:12; 1.0 mL/min). 13a and 13b are enantiomers.

Example 13b: 8-fluoro-5H-imidazo[4,3-a]isoindol-5-yl] cyclobutan-1-ol: LCMS (ESI, m/z): 245.2; tR=8.947 min (Chiralpak OJ=3, 0.46×15 cm, 3 um; Hex(0.1% DEA): IPA=88:12; 1.0 mL/min). 13a and 13b are enantiomers.

Example 13c: (1R,2S)-2-[(5R)-8-fluoro-5H-imidazo[4,3-a]isoindol-5-yl]cyclobutan-1-ol: LCMS (ESI, m/z): 245.2. $^1$HNMR (300 MHz, $CD_3OD$) δ 8.01 (s, 1H), 7.46-7.37 (m, 2H), 7.19 (s, 1H), 7.10-6.95 (m, 1H), 5.33 (d, J=6 Hz, 1H), 4.22-4.18 (m, 1H), 2.52-2.34 (m, 1H), 2.36-2.23 (m, 1H), 2.01-1.79 (m, 2H), 1.78-1.59 (m, 1H). tR=1.347 min (Chiralpak IA-3, 0.46×5 cm, 3 um; mobile phase: Hex(0.1% DEA):IPA=70:30; Detector, uv 254 nm; flow rate, 1.0 mL/min). 13c and 13d are enantiomers.

Example 13d: (1S,2R)-2-[(5S)-8-fluoro-5H-imidazo[4,3-a]isoindol-5-yl]cyclobutan-1-ol: LCMS (ESI, m/z): 245.2 $[M+H]^+$; tR=2.379 min (Chiralpak IA-3, 0.46×5 cm, 3 um; mobile phase: Hex(0.1% DEA):IPA=70:30; Detector, uv 254 nm; flow rate, 1.0 mL/min). 13c and 13d are enantiomers.

Example 13e: 8-fluoro-5H-imidazo[4,3-a]isoindol-5-yl] cyclobutan-1-ol: LCMS (ESI, m/z): 245.2 $[M+H]^+$; $^1$HNMR (300 MHz, $CD_3OD$) δ 8.19 (s, 1H), 7.58-7.53 (m, 1H), 7.39-7.36 (m, 1H), 7.23 (s, 1H), 7.09-6.96 (m, 1H), 5.55 (d, J=5.9 Hz, 1H), 4.68-4.64 (m, 1H), 3.05-2.87 (m, 1H), 2.41-2.20 (m, 1H), 1.97-1.76 (m, 2H), 1.59-1.50 (m, 1H). tR=4.185 min (Chiralpak OJ=3, 0.46×15 cm, 3 um; Hex (0.1% DEA):IPA=85:15; 1.0 mL/min).

Example 13f: 8-fluoro-5H-imidazo[4,3-a]isoindol-5-yl] cyclobutan-1-ol: LCMS (ESI, m/z): 245.2 $[M+H]^+$; tR=5.659 min (Chiralpak OJ=3, 0.46×15 cm, 3 um; Hex (0.1% DEA):IPA=85:15; 1.0 mL/min). 13e and 13f are enantiomers.

Example 13g: 8-fluoro-5H-imidazo[4,3-a]isoindol-5-yl] cyclobutan-1-ol: LCMS (ESI, m/z): 245.2 $[M+H]^+$; $^1$HNMR (300 MHz, $CD_3OD$) δ 7.98 (s, 1H), 7.53-7.48 (m, 1H), 7.40-7.36 (m, 1H), 7.19 (s, 1H), 7.01-6.93 (m, 1H), 5.51 (d, J=9.0 Hz, 1H), 4.56-4.51 (m, 1H), 2.60-2.31 (m, 3H), 2.21-1.90 (m, 2H). tR=2.293 min (Chiralpak IA-3, 0.46×5 cm, 3 um; Hex(0.1% DEA):IPA=90:10; 1.0 mL/min). 13g and 13h are enantiomers.

Example 13h: 8-fluoro-5H-imidazo[4,3-a]isoindol-5-yl] cyclobutan-1-ol: LCMS (ESI, m/z): 245.2 $[M+H]^+$; tR=3.120 min (Chiralpak IA-3, 0.46×5 cm, 3 um; Hex(0.1% DEA):IPA=90:10; 1.0 mL/min). 13g and 13h are enantiomers.

Example 15 and 16: 1-(ethylsulfonyl)-3-(5H-imidazo[5,1-a]isoindol-5-yl)piperidin-4-ol and 1-(ethylsulfonyl)-4-(5H-imidazo[5,1-a]isoindol-5-yl)piperidin-3-ol

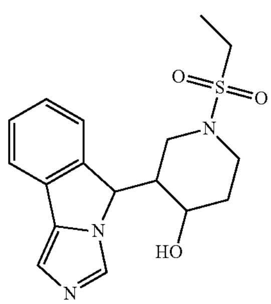

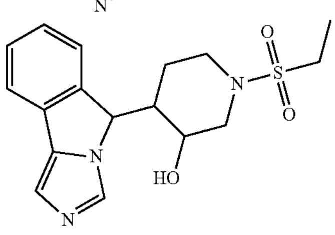

The title compound was synthesized by the same method of Example 27.

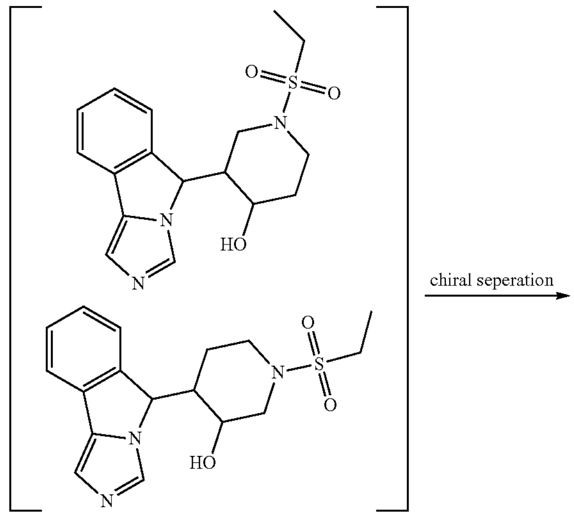

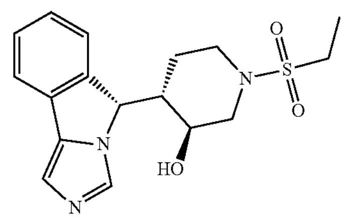

16a-d

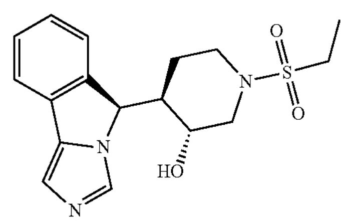

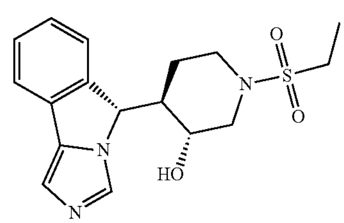

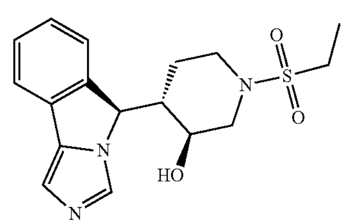

-continued

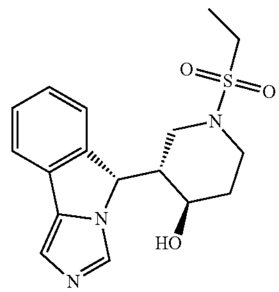

15a-d

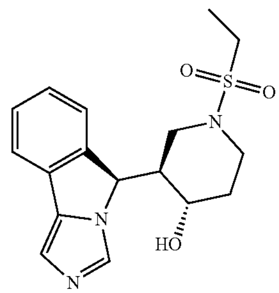

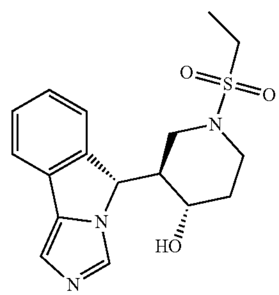

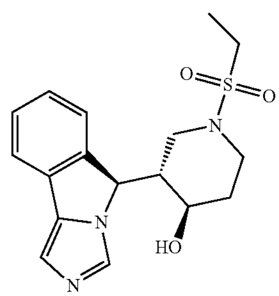

The crude product was purified by Prep-HPLC and further isolated by chiral separation with the following conditions:

1. Chiralpak IC, 2×25 cm, 5 um; Mobile Phase A:Hex-HPLC, Mobile Phase B: EtOH-HPLC; Flow rate: 15 mL/min; Gradient: 50 B to 50 B in 18 min; 254/220 nm;
2. Phenomenex Lux 5 u Cellulose-4,AXIA Packed, 250×21.2 mm, 5 um; Mobile Phase. A:Hex-HPLC, Mobile Phase B: EtOH-HPLC; Flow rate: 20 mL/min; Gradient: 40 B to 40 B in 38 min; 254/220 nm;
3. CHIRALPAK IC, 2×25 cm, 5 um; Mobile Phase A:Hex-HPLC, Mobile Phase B: EtOH-HPLC; Flow rate: 20 mL/min; Gradient: 30 B to 30 B in 20 min; 254/220 nm;

The absolute configuration of isomers 16a-16d was assigned by X-ray crystallography.

Example 16a: (3S,4S)-1-(ethylsulfonyl)-4-((S)-5H-imidazo[5,1-a]isoindol-5-yl)piperidin-3-ol: LCMS (ESI, m/z): 348.2 $[M+H]^+$; $^1$HNMR (400 MHz, $CD_3OD$) δ 7.95 (s, 1H), 7.65 (d, J=7.6 Hz, 1H), 7.55 (d, J=7.6 Hz, 1H), 7.46-7.32 (m, 2H), 7.17 (s, 1H), 5.83 (d, J=3.6 Hz, 1H), 4.01-3.90 (m, 2H), 3.53-4.90 (m, 1H), 3.00 (q, J=7.2 Hz, 2H), 2.74-2.65 (m, 2H), 2.42-2.30 (m, 1H), 1.30 (t, J=7.2 Hz, 3H), 0.85-0.79 (m, 1H), 0.75-0.60 (m, 1H); tR=2.844 min, (Lux Cellulose-4, 0.46×5 cm, 3 um; ethanol:hexane (0.1% DEA)=30:70; 1.5 mL/min). 16a and 16b are enantiomers.

Example 16b: (3R,4R)-1-(ethylsulfonyl)-4-((R)-5H-imidazo[5,1-a]isoindol-5-yl)piperidin-3-ol: LCMS (ESI, m/z): 348.2 $[M+H]^+$; tR=6.072 min, (Lux Cellulose-4, 0.46×5 cm, 3 um; ethanol:hexane (0.1% DEA)=30:70; 1.5 mL/min). 16a and 16b are enantiomers.

Example 16c: (3R,4R)-1-(ethylsulfonyl)-4-((S)-5H-imidazo[5,1-a]isoindol-5-yl)piperidin-3-ol: LCMS (ESI, m/z): 348.2 $[M+H]^+$, $^1$HNMR (400 MHz, $CD_3OD$) δ 7.93 (s, 1H), 7.64 (d, J=7.6 Hz, 1H), 7.50 (d, J=7.6 Hz, 1H), 7.46-7.35 (m, 2H), 7.21 (s, 1H), 5.84 (d, J=3.6 Hz, 1H), 4.03-3.83 (m, 2H), 3.54-3.51 (m, 1H), 3.03 (q, J=7.2 Hz, 2H), 2.78-2.67 (m, 2H), 2.25-2.19 (m, 1H), 1.30 (t, J=7.2 Hz, 3H), 0.98-0.94 (m, 1H), 0.69-0.55 (m, 1H); tR=1.519 min (Chiralpak IC-3, 0.46×5 cm, 3 um; ethanol:hexane (0.1% DEA)=30:70; 1.0 mL/min). 16c and 16d are enantiomers.

Example 16d: (3R,4R)-1-(ethylsulfonyl)-4-((S)-5H-imidazo[5,1-a]isoindol-5-yl)piperidin-3-ol: LCMS (ESI, m/z): 348.2 $[M+H]^+$; tR=2.357 min (Chiralpak IC-3, 0.46×5 cm, 3 um; ethanol:hexane (0.1% DEA)=30:70; 1.0 mL/min). 16c and 16d are enantiomers.

The absolute configuration of all isomers 15a-d was assigned arbitrarily.

Example 15a: (3S,4R)-1-(ethylsulfonyl)-3-((S)-5H-imidazo[5,1-a]isoindol-5-yl)piperidin-4-ol: LCMS (ESI, m/z): 348.2 $[M+H]^+$, $^1$HNMR (400 MHz, $CD_3OD$) δ 7.98 (s, 1H), 7.66 (d, J=7.6 Hz, 1H), 7.20 (d, J=7.6 Hz, 1H), 7.48-7.34 (m, 2H), 7.21 (s, 1H), 5.85 (d, J=4.0 Hz, 1H), 4.01-3.98 (m, 1H), 3.74-3.70 (m, 1H), 2.90-2.76 (m, 4H), 2.55-2.45 (m, 1H), 2.13-2.05 (m, 2H), 1.80-1.68 (m, 1H), 1.16 (t, J=7.2 Hz, 3H); tR=2.495 (Chiralpak IC-3, 0.46×5 cm, 3 um; hexane (0.1% DEA)=30:70; 1.0 mL/min). 15a and 15b are enantiomers.

Example 15b: (3R,4S)-1-(ethylsulfonyl)-3-((R)-5H-imidazo[5,1-a]isoindol-5-yl)piperidin-4-ol: LCMS (ESI, m/z): 348.2 $[M+H]^+$; tR=3.738, (Chiralpak IC-3, 0.46×5 cm, 3 um; hexane (0.1% DEA)=30:70; 1.0 mL/min). 15a and 15b are enantiomers.

Example 15c: (3R,4S)-1-(ethylsulfonyl)-3-((S)-5H-imidazo[5,1-a]isoindol-5-yl)piperidin-4-ol: LCMS (ESI, m/z): 348.2 $[M+H]^+$; $^1$HNMR (400 MHz, $CD_3OD$) δ 7.93 (s, 1H), 7.64 (d, J=7.6 Hz, 1H), 7.51 (d, J=7.6 Hz, 1H), 7.45-7.37 (m, 2H), 7.19 (s, 1H), 5.83 (d, J=3.6 Hz, 1H), 4.03-3.92 (m, 1H), 3.75-3.65 (m, 1H), 3.02-2.98 (m, 1H), 2.85-2.70 (m, 3H), 2.40-2.30 (m, 1H), 2.20-2.15 (m, 1H), 2.00-1.90 (m, 1H), 1.79-1.65 (m, 1H), 1.12 (t, J=7.2 Hz, 3H); R=2.240 min (Lux Cellulose-4, 0.46×5 cm, 3 um; ethanol:hexane (0.1% DEA)=30:70; 1.5 mL/min). 15c and 15d are enantiomers.

Example 15d: (3S,4R)-1-(ethylsulfonyl)-3-((R)-5H-imidazo[5,1-a]isoindol-5-yl)piperidin-4-ol: LCMS (ESI, m/z): 348.2 $[M+H]^+$; tR=3.661 min (Lux Cellulose-4, 0.46×5 cm, 3 um; ethanol:hexane (0.1% DEA)=30:70; 1.5 mL/min). 15c and 15d are enantiomers.

Examples 17: 2-(5H-imidazo[5,1-a]isoindol-5-yl)spiro[3.3]heptan-1-ol

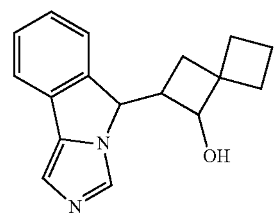 [SMILES: OC1C(C2c3ccccc3-c3cncn32)CC12CCC2]

(1R,2R)-2-((R)-5H-imidazo[5,1-a]isoindol-5-yl)spiro[3.3]heptan-1-ol (1R,2R)-2-((S)-5H-imidazo[5,1-a]isoindol-5-yl)spiro[3.3]heptan-1-ol (1R,2S)-2-((R)-5H-imidazo[5,1-a]isoindol-5-yl)spiro[3.3]heptan-1-ol (1R,2S)-2-((S)-5H-imidazo[5,1-a]isoindol-5-yl)spiro[3.3]heptan-1-ol (1S,2R)-2-((R)-5H-imidazo[5,1-a]isoindol-5-yl)spiro[3.3]heptan-1-ol (1S,2R)-2-((S)-5H-imidazo[5,1-a]isoindol-5-yl)spiro[3.3]heptan-1-ol (1S,2S)-2-((R)-5H-imidazo[5,1-a]isoindol-5-yl)spiro[3.3]heptan-1-ol (1S,2S)-2-((S)-5H-imidazo[5,1-a]isoindol-5-yl)spiro[3.3]heptan-1-ol Examples 17a-e were all synthesized using the reaction conditions for the preparation of examples 1 a-h in which the reagent cyclobutanone was substituted with spiro[3.3]heptan-1-one. Each example is a single diastereomer with undetermined absolute configuration.

The absolute configuration of all isomers 17a-e was assigned arbitrarily.

Example 17a: 2-(5H-imidazo[1,5-b]isoindol-5-yl)spiro[3.3]heptan-3-ol: LCMS (ESI, m/z): 267 $[M+H]^+$; $^1$HNMR: no NMR; tR=0.45 min (Chiralpak AD (250×30 mm, 5 um), Ethanol w/0.1% $NH_4OH$, 1.5 ml/min).

Example 17b: 2-(5H-imidazo[1,5-b]isoindol-5-yl)spiro[3.3]heptan-3-ol: LCMS (ESI, m/z): 267 $[M+H]^+$; $^1$H NMR (400 MHz, DMSO-$d_6$) δ 7.90 (s, 1H), 7.65-7.46 (m, 1H), 7.44-7.29 (m, 2H), 7.23 (td, J=7.5, 1.1 Hz, 1H), 7.09 (s, 1H), 5.30 (d, J=7.6 Hz, 2H), 3.86 (t, J=7.5 Hz, 1H), 2.42-2.23 (m, 1H), 2.09-1.69 (m, 5H), 1.69-1.45 (m, 2H).; tR=0.89 min (Chiralpak AD (250×30 mm, 5 um), Ethanol w/0.1% $NH_4OH$, 1.5 ml/min).

Example 17c: 2-(5H-imidazo[1,5-b]isoindol-5-yl)spiro[3.3]heptan-3-ol: LCMS (ESI, m/z): 267 $[M+H]^+$; $^1$H NMR (400 MHz, DMSO-$d_6$) δ 7.90 (s, 1H), δ 7.59 (t, J=8.0 Hz, 2H), 7.36 (dd, J=7.9, 6.8 Hz, 1H), 7.25 (td, J=7.5, 1.0 Hz, 1H), 7.09 (s, 1H), 5.75 (d, J=4.9 Hz, 1H), 5.35 (d, J=8.3 Hz, 1H), 4.18 (s, 1H), 2.42 (d, J=8.3 Hz, 1H), 2.35-2.18 (m, 1H), 2.04 (t, J=9.9 Hz, 1H), 1.90 (q, J=6.6 Hz, 3H), 1.76 (q, J=7.3 Hz, 2H), 1.56 (d, J=10.0 Hz, 1H).; tR=0.79 min (Chiralpak AD (250×30 mm, 5 um), Ethanol w/0.1% $NH_4OH$, 1.5 ml/min).

Example 17d: 2-(5H-imidazo[1,5-b]isoindol-5-yl)spiro[3.3]heptan-3-ol: LCMS (ESI, m/z): 267 $[M+H]^+$; $^1$HNMR: no NMR; tR=1.15 min (Chiralpak AD (250×30 mm, 5 um), Ethanol w/0.1% $NH_4OH$, 1.5 ml/min).

Example 17e (enantiomer of example 17b): 2-(5H-imidazo[1,5-b]isoindol-5-yl)spiro[3.3]heptan-3-ol: LCMS (ESI, m/z): 267 $[M+H]^+$; no analytical SFC, Chiralpak AD (250×30 mm, 5 um), Ethanol w/0.1% $NH_4OH$, 1.5 ml/min).

Example 18: 4,4-difluoro-2-((S)-5H-imidazo[5,1-a]isoindol-5-yl)cyclohexan-1-ol

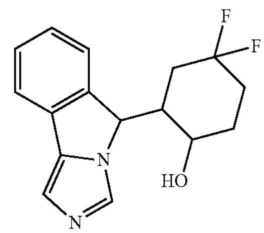 [SMILES: OC1CCC(F)(F)CC1C1c2ccccc2-c2cncn21]

(1S,2S)-4,4-difluoro-2-((S)-5H-imidazo[5,1-a]isoindol-5-yl)cyclohexan-1-ol (18a)

(1S,2S)-4,4-difluoro-2-((R)-5H-imidazo[5,1-a]isoindol-5-yl)cyclohexan-1-ol (18f)

(1S,2R)-4,4-difluoro-2-((S)-5H-imidazo[5,1-a]isoindol-5-yl)cyclohexan-1-ol (1S,2R)-4,4-difluoro-2-((R)-5H-imidazo[5,1-a]isoindol-5-yl)cyclohexan-1-ol (1R,2S)-4,4-difluoro-2-((S)-5H-imidazo[5,1-a]isoindol-5-yl)cyclohexan-1-ol (1R,2S)-4,4-difluoro-2-((R)-5H-imidazo[5,1-a]isoindol-5-yl)cyclohexan-1-ol (1R,2R)-4,4-difluoro-2-((S)-5H-imidazo[5,1-a]isoindol-5-yl)cyclohexan-1-ol (18b)

(1R,2R)-4,4-difluoro-2-((R)-5H-imidazo[5,1-a]isoindol-5-yl)cyclohexan-1-ol (18e)

Step 1:

(E)-4,4-difluoro-2-(2-(1-trityl-1H-imidazol-4-yl)benzylidene)cyclohexan-1-one

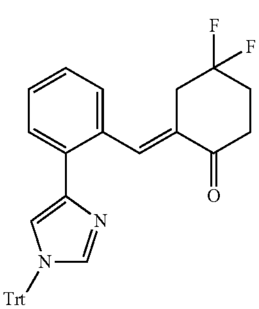

The title compound was synthesized by General Procedure for the Synthesis of Int-2. LCMS (ESI, m/z): 531.3 $[M+H]^+$ Step 2:

4,4-difluoro-2-(5H-imidazo[5,1-a]isoindol-5-yl)cyclohexan-1-one

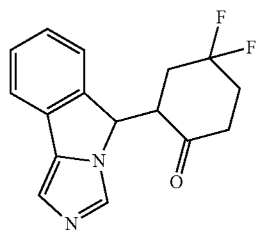 [SMILES: O=C1CCC(F)(F)CC1C1c2ccccc2-c2cncn21]

The title compound was synthesized by General Procedure for the Synthesis of Int-3. LCMS (ESI, m/z): 289.27 $[M+H]^+$ Step 3:

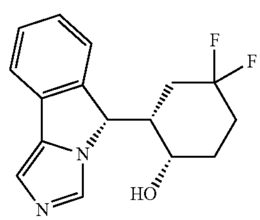

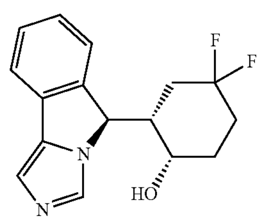

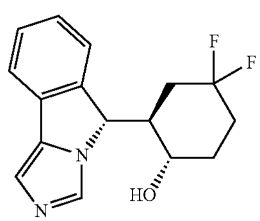

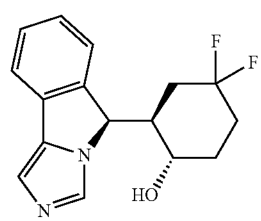

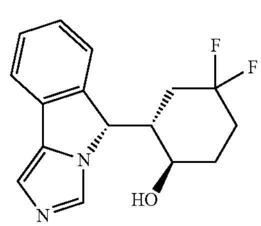

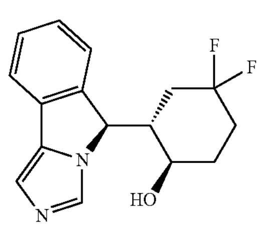

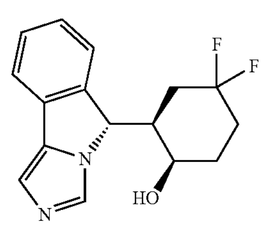

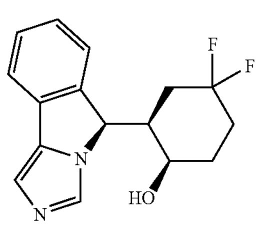

The title compounds were synthesized by General Procedure for the Synthesis of Int-5: LCMS (ESI, m/z): 291.26

The absolute configuration of isomers 18a and 18e was assigned by X-ray crystallography. The absolute configuration of the rest isomers was assigned arbitrarily.

Example 18a: (1S,2S)-4,4-difluoro-2-((S)-5H-imidazo[5,1-a]isoindol-5-yl)cyclohexan-1-ol: LCMS (ESI, m/z): 291.26 $[M+H]^+$; ($^1$H NMR (400 MHz, DMSO-$d_6$) δ 8.02 (s, 1H), 7.61-7.55 (m, 2H), 7.39 (d, J=1.1 Hz, 1H), 7.32-7.32 (m, 1H), 5.45 (s, 1H), 7.11 (s, 1H), 5.32 (d, J=3.1 Hz, 1H), 4.29 (s, 1H), 2.38-2.31 (m, 1H), 2.15-1.95 (m, 1H), 1.94-1.78 (m, 2H), 1.77-1.67 (m, 1H), 1.65-1.46 (m, 1H), 1.15-1.03 (m, 1H)

Example 18b: (1R,2R)-4,4-difluoro-2-((S)-5H-imidazo[5,1-a]isoindol-5-yl)cyclohexan-1-ol: LCMS (ESI, m/z): 291.26 $[M+H]^+$; ($^1$H NMR (400 MHz, DMSO-$d_6$) δ 7.91 (s, 1H), 7.69 (d, J=7.6 Hz, 1H), 7.60 (d, J=7.4 Hz, 1H), 7.39 (t, J=7.5 Hz, 1H), 7.27 (dd, J=7.5, 1.4 Hz, 1H), 7.12 (s, 1H), 5.33 (d, J=6.2 Hz, 1H), 5.09-5.05 (s, 1H), 4.07 (s, 1H), 2.22-1.96 (m, 3H), 1.91-1.79 (m, 3H), 1.65-1.54 (m, 1H)

Example 18c: 4,4-difluoro-2-(5H-imidazo[5,1-a]isoindol-5-yl)cyclohexan-1-ol: LCMS (ESI, m/z): 291.26 $[M+H]^+$; $^1$H NMR (400 MHz, DMSO-$d_6$) δ 7.95 (s, 1H), 7.63 (d, J=7.8 Hz, 1H), 7.54 (d, J=7.6 Hz, 1H), 7.42 (t, J=1.0 Hz, 1H), 7.31 (dd, J=7.6, 1.4 Hz, 1H), 7.15 (s, 1H), 5.72 (t, J=3.2 Hz, 1H) 5.52 (s, 1H), 3.87-3.76 (m, 1H), 2.04-1.70 (m, 3H), 1.58-1.45 (m, 1H), 0.90-0.73 (m, 2H)

Example 18d: 4,4-difluoro-2-(5H-imidazo[5,1-a]isoindol-5-yl)cyclohexan-1-ol: LCMS (ESI, m/z): 291.26 $[M+H]^+$; $^1$H NMR (400 MHz, DMSO-$d_6$) δ 7.95 (s, 1H), 7.63 (d, J=7.8 Hz, 1H), 7.54 (d, J=7.6 Hz, 1H), 7.42 (t, J=1.0 Hz, 1H), 7.31 (dd, J=7.6, 1.4 Hz, 1H), 7.15 (s, 1H), 5.72 (t, J=3.2 Hz, 1H) 5.52 (s, 1H), 3.87-3.76 (m, 1H), 2.04-1.70 (m, 3H), 1.58-1.45 (m, 1H), 0.9-0.73 (m, 2H).

Example 18e: (1R,2R)-4,4-difluoro-2-((R)-5H-imidazo[5,1-a]isoindol-5-yl)cyclohexan-1-ol: LCMS (ESI, m/z): 291.26 $[M+H]^+$; ($^1$H NMR (400 MHz, DMSO-$d_6$) δ 8.02 (s, 1H), 7.61-7.55 (m, 2H), 7.39 (d, J=1.1 Hz, 1H), 7.32-7.25 (m, 1H), 5.45 (s, 1H), 7.11 (s, 1H), 5.32 (d, J=3.1 Hz, 1H), 4.29 (s, 1H), 2.38-2.31 (m, 1H), 2.15-1.95 (m, 1H), 1.94-1.78 (m, 2H), 1.77-1.67 (m, 1H), 1.65-1.46 (m, 1H), 1.15-1.03 (m, 1H)

Example 18f: (1S,2S)-4,4-difluoro-2-((R)-5H-imidazo[5,1-a]isoindol-5-yl)cyclohexan-1-ol: LCMS (ESI, m/z): 291.26 $[M+H]^+$; ($^1$H NMR (400 MHz, DMSO-$d_6$) δ 7.91 (s, 1H), 7.69 (d, J=7.6 Hz, 1H), 7.60 (d, J=7.4 Hz, 1H), 7.39 (t, J=7.5 Hz, 1H), 7.27 (dd, J=7.5, 1.4 Hz, 1H), 7.12 (s, 1H), 5.33 (d, J=6.2 Hz, 1H), 5.09-5.05 (s, 1H), 4.07 (s, 1H), 2.22-1.96 (m, 3H), 1.91-1.79 (m, 3H), 1.65-1.54 (m, 1H)

Example 18g: 4,4-difluoro-2-(5H-imidazo[5,1-a]isoindol-5-yl)cyclohexan-1-ol: LCMS (ESI, m/z): 291.26 $[M+H]^+$; $^1$H NMR (400 MHz, DMSO-$d_6$) δ 7.85 (s, 1H), 7.62 (d, J=7.4 Hz, 1H), 7.48 (d, J=7.4 Hz, 1H), 7.41 (t, J=7.5 Hz, 1H), 7.35-7.29 (m, 1H), 7.18 (s, 1H), 5.74 (s, 1H), 5.55 (d, J=5.8 Hz, 1H), 3.86 (dt, J=10.8, 5.8 Hz, 1H), 2.34-2.22 (m, 1H), 2.08-1.77 (m, 2H), 1.48-1.61 (m, 1H), 0.99 (d, J=5.4 Hz, 1H), 0.90-0.70 (m, 1H).

Example 18h: 4,4-difluoro-2-(5H-imidazo[5,1-a]isoindol-5-yl)cyclohexan-1-ol: LCMS (ESI, m/z): 291.26 $[M+H]^+$; $^1$H NMR (400 MHz, DMSO-$d_6$) δ 7.85 (s, 1H), 7.62 (d, J=7.4 Hz, 1H), 7.48 (d, J=7.4 Hz, 1H), 7.41 (t, J=7.5 Hz, 1H), 7.35-7.29 (m, 1H), 7.18 (s, 1H), 5.74 (s, 1H), 5.55 (d, J=5.8 Hz, 1H), 3.86 (dt, J=10.8, 5.8 Hz, 1H), 2.34-2.22 (m, 1H), 2.08-1.77 (m, 2H), 1.48-1.61 (m, 1H), 0.99 (d, J=5.4 Hz, 1H), 0.90-0.70 (m, 1H).

Example 19: 2-(5H-imidazo[5,1-a]isoindol-5-yl)-2,3-dihydro-1H-inden-1-ol

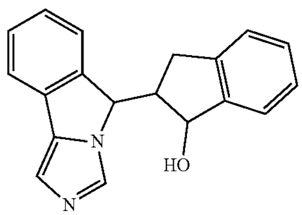 [SMILES: OC1c2ccccc2CC1C1c2ccccc2-c2cncn21]

(1S,2R)-2-((R)-5H-imidazo[5,1-a]isoindol-5-yl)-2,3-dihydro-1H-inden-1-ol (1R,2S)-2-((S)-5H-imidazo[5,1-a]isoindol-5-yl)-2,3-dihydro-1H-inden-1-ol (1S,2S)-2-((S)-5H-imidazo[5,1-a]isoindol-5-yl)-2,3-dihydro-1H-inden-1-ol (1R,2R)-2-((S)-5H-imidazo[5,1-a]isoindol-5-yl)-2,3-dihydro-1H-inden-1-ol (1S,2S)-2-((R)-5H-imidazo[5,1-a]isoindol-5-yl)-2,3-dihydro-1H-inden-1-ol (1R,2R)-2-((R)-5H-imidazo[5,1-a]isoindol-5-yl)-2,3-dihydro-1H-inden-1-ol Step 1:

(E)-2-(2-(1-trityl-1H-imidazol-4-yl)benzylidene)-2,3-dihydro-1H-inden-1-one

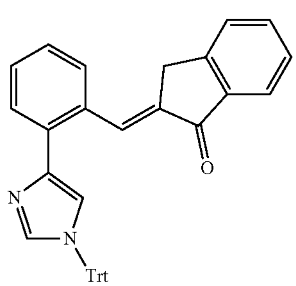

To a solution of 2-[1-(triphenylmethyl)-1H-imidazol-4-yl]benzaldehyde (2.0 g, 4.82 mmol) and 1-indanone (1.28 g, 9.65 mmol) in anhydrous methanol (40 mL) was added piperidine (0.48 mL, 4.82 mmol) and the resulting mixture was stirred at 90° C. for 6 hr. Product precipitated out of the solution. The mixture was cooled on ice bath and the precipitation was filtered and washed with cold methanol (15 mL) to afford crude (E)-2-(2-(1-trityl-1H-imidazol-4-yl)benzylidene)-2,3-dihydro-1H-inden-1-one as light yellow solids. The product was used directly without further purification: LCMS (ESI, m/z): 529.3 $[M+H]^+$.

Step 2:

2-(5H-imidazo[5,1-a]isoindol-5-yl)-2,3-dihydro-1H-inden-1-one

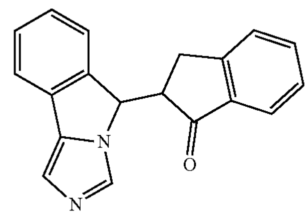 [SMILES: O=C1c2ccccc2CC1C1c2ccccc2-c2cncn21]

To (E)-2-(2-(1-trityl-1H-imidazol-4-yl)benzylidene)-2,3-dihydro-1H-inden-1-one (2.20 g, 4.16 mmol) was added MeOH (56 mL) and AcOH (14 mL). The resulting mixture was stirred at 90° C. for 2 hr. Solvent was removed under reduced pressure. The reaction was quenched by 30 mL saturated $NaHCO_3$ solution (30 mL) and the mixture was extracted with dichloromethane (3×20 mL). The organic layer was combined, washed with brine and water, and dried by anhydrous $Na_2SO_4$. The product was separated by CombiFlash to afford 2-(5H-imidazo[5,1-a]isoindol-5-yl)-2,3-dihydro-1H-inden-1-one as light yellow solids: LCMS (ESI, m/z): 287.3 $[M+H]^+$.

Step 3:

(1S,2R)-2-((R)-5H-imidazo[5,1-a]isoindol-5-yl)-2,3-dihydro-1H-inden-1-ol (1R,2S)-2-((S)-5H-imidazo[5,1-a]isoindol-5-yl)-2,3-dihydro-1H-inden-1-ol (1S,2S)-2-((S)-5H-imidazo[5,1-a]isoindol-5-yl)-2,3-dihydro-1H-inden-1-ol (1R,2R)-2-((S)-5H-imidazo[5,1-a]isoindol-5-yl)-2,3-dihydro-1H-inden-1-ol (1S,2S)-2-((R)-5H-imidazo[5,1-a]isoindol-5-yl)-2,3-dihydro-1H-inden-1-ol (1R,2R)-2-((R)-5H-imidazo[5,1-a]isoindol-5-yl)-2,3-dihydro-1H-inden-1-ol 19a

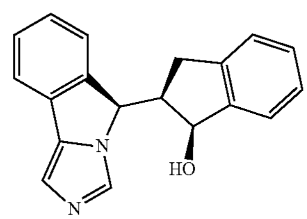

19b

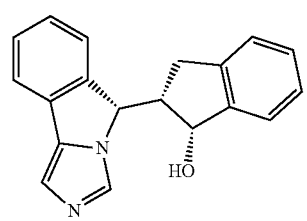

19c

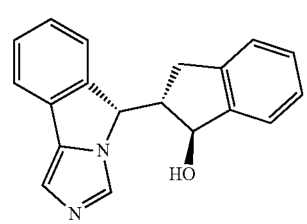

-continued

19d

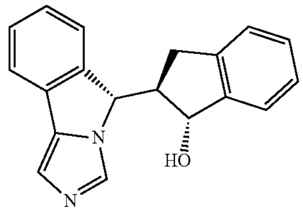

19e

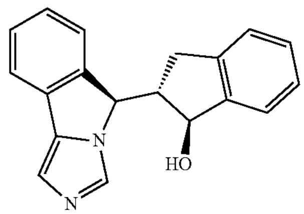

19f

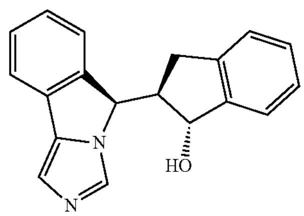

To a solution of the 2-(5H-imidazo[5,1-a]isoindol-5-yl)-2,3-dihydro-1H-inden-1-one (1.06 g, 3.70 mmol) in MeOH (25 mL) was added $NaBH_4$ (280 mg, 7.40 mmol) in portions at 0° C. and the solution was stirred at 0° C. for 2 hrs. The solvent was distilled off and saturated ammonium chloride (20 mL) was added. The aqueous layer was extracted with DCM (3×20 mL). The combined organic extract was dried over ($Na_2SO_4$) and concentrated under reduced pressure to afford the crude product. The crude product was purified by Combi-Flash and further isolated by chiral separation to afford 6 isomers as white solid. The absolute configuration of all isomers was assigned arbitrarily.

Example 19a: (1S,2R)-2-((R)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 7.88 (s, 1H), 7.62 (d, J=7.4 Hz, 1H), 7.53 (d, J=7.7 Hz, 1H), 7.37 (d, J=7.5 Hz, 1H), 7.27 (d, J=5.5 Hz, 1H), 7.25-7.21 (m, 1H), 7.20-7.14 (m, 2H), 7.12 (s, 2H), 5.70 (d, J=4.9 Hz, 1H), 5.57 (d, J=6.5 Hz, 1H), 5.09 (s, 1H), 2.95 (dd, J=7.3, 4.9 Hz, 1H), 2.78 (dd, J=15.9, 8.6 Hz, 1H).

Example 19b: (1R,2S)-2-((S)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 7.88 (s, 1H), 7.62 (d, J=7.6 Hz, 1H), 7.53 (d, J=7.5 Hz, 1H), 7.38 (t, J=7.6 Hz, 1H), 7.29-7.25 (m, 1H), 7.25-7.20 (m, 1H), 7.19-7.15 (m, 2H), 7.11 (d, J=6.1 Hz, 2H), 5.70 (d, J=4.9 Hz, 1H), 5.57 (d, J=6.5 Hz, 1H), 5.09 (t, J=6.7 Hz, 1H), 2.95 (tdd, J=8.6, 7.0, 5.0 Hz, 1H), 2.78 (dd, J=15.9, 8.6 Hz, 1H), 2.48-2.39 (m, 1H).

Example 19c: (1S,2S)-2-((S)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 8.05 (s, 1H), 7.62 (d, J=7.8 Hz, 1H), 7.55 (d, J=7.7 Hz, 1H), 7.49-7.42 (m, 1H), 7.38 (t, J=7.4 Hz, 1H), 7.26-7.18 (m, 4H), 7.16 (s, 1H), 5.77 (d, J=6.2 Hz, 1H), 5.53 (d, J=9.8 Hz, 1H), 5.17 (t, J=6.0 Hz, 1H), 3.28-3.20 (m, 1H), 2.97 (dd, J=15.5, 7.8 Hz, 1H), 2.40 (tdd, J=9.5, 7.7, 5.9 Hz, 1H).

Example 19d: (1R,2R)-2-((S)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 7.72 (d, J=7.5 Hz, 1H), 7.60 (d, J=7.2 Hz, 1H), 7.51 (s, 1H), 7.46-7.37 (m, 2H), 7.32 (dd, J=7.5, 1.4 Hz, 1H), 7.26-7.19 (m, 1H), 7.17 (dd, J=7.4, 1.4 Hz, 1H), 7.07-7.01 (m, 2H), 6.04 (d, J=5.1 Hz, 1H), 5.63 (d, J=5.4 Hz, 1H), 5.39 (dd, J=7.1, 5.2 Hz, 1H), 2.99 (dtd, J=8.3, 6.6, 5.1 Hz, 1H), 2.73 (dd, J=16.1, 8.4 Hz, 1H), 2.45 (dd, J=16.0, 6.4 Hz, 1H).

Example 19e: (1S,2S)-2-((R)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 7.72 (d, J=7.4 Hz, 1H), 7.60 (d, J=7.4 Hz, 1H), 7.51 (s, 1H), 7.41 (q, J=7.2 Hz, 2H), 7.35-7.28 (m, 1H), 7.25-7.19 (m, 1H), 7.16 (td, J=7.3, 1.4 Hz, 1H), 7.06-7.00 (m, 2H), 6.04 (d, J=5.1 Hz, 1H), 5.63 (d, J=5.4 Hz, 1H), 5.39 (dd, J=7.0, 5.2 Hz, 1H), 3.04-2.92 (m, 1H), 2.73 (dd, J=16.1, 8.3 Hz, 1H), 2.45 (dd, J=16.1, 6.5 Hz, 1H).

Example 19f: (1R,2R)-2-((R)-5H-imidazo[5,1-a]isoindol-5-yl)-2,3-dihydro-1H-inden-1-ol: LCMS (ESI, m/z): 289.3 $[M+H]^+$. $^1H$ NMR (400 MHz, DMSO-$d_6$) δ 8.05 (s, 1H), 7.62 (d, J=7.4 Hz, 1H), 7.55 (d, J=7.7 Hz, 1H), 7.47-7.41 (m, 1H), 7.38 (t, J=7.5 Hz, 1H), 7.27-7.19 (m, 4H), 7.16 (s, 1H), 5.77 (d, J=6.1 Hz, 1H), 5.53 (d, J=10.0 Hz, 1H), 5.17 (t, J=6.1 Hz, 1H), 3.29-3.22 (m, 1H), 2.97 (dd, J=15.5, 7.7 Hz, 1H), 2.40 (tdd, J=9.5, 7.9, 6.0 Hz, 1H).

Example 20: 2-(8-fluoro-5H-imidazo[5,1-a]isoindol-5-yl)cyclopentan-1-ol

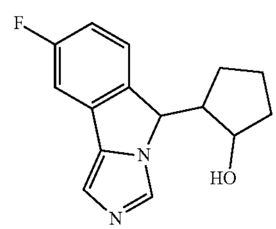 [SMILES: OC1CCCC1C1c2ccc(F)cc2-c2cncn21]

The title compound was synthesized by Example 5 and 6

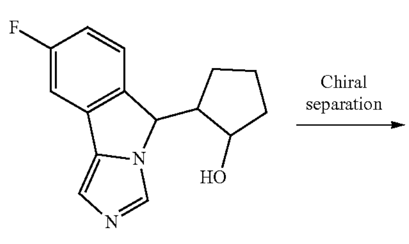

-continued

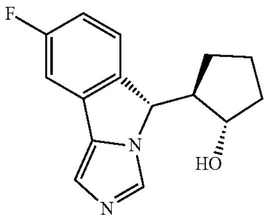

20a

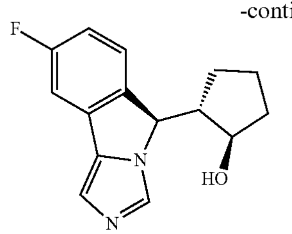

20b

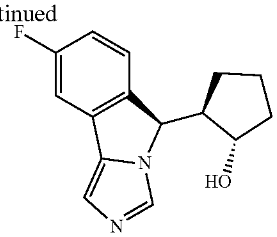

20c

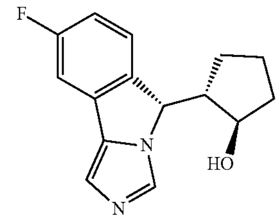

20d

The crude product was purified by Prep-HPLC and further isolated by SFC separation with the following conditions:

Condition 1: Column: CHIRALPAK AD-H-TC001 SFC, 20×250 mm, 5 um; Mobile Phase A: $CO_2$:50, Mobile Phase B: IPA (0.2% DEA): 50; Flow rate: 40 mL/min; 220 nm;

Condition 2: Column: Chiralpak AD-H, 2×25 cm; Mobile Phase A: $CO_2$:60, Mobile Phase B: IPA (0.2% DEA): 40; Flow rate: 40 mL/min; 220 nm;

The absolute configuration of all isomers was assigned arbitrarily.

Example 20a: (1S,2R)-2-[(5R)-8-fluoro-5H-imidazo[4,3-a]isoindol-5-yl]cyclopentan-1-ol: LCMS (ESI, m/z): 259.2 $[M+H]^+$; $^1H$ NMR (300 MHz, $CD_3OD$) δ 8.11 (s, 1H), 7.45 (dd, J=8.5, 4.8 Hz, 1H), 7.34 (dd, J=8.6, 2.5 Hz, 1H), 7.21 (s, 1H), 7.01-6.95 (m, 1H), 5.46 (d, J=4.4 Hz, 1H), 3.97-3.94 (m, 1H), 2.48-2.38 (m, 1H), 1.67-1.56 (m, 3H), 1.54-1.42 (m, 2H), 1.16-1.10 (m, 1H). tR=1.11 min (Chiralpak AD-H, 4.6×100 mm, 5 um; IPA (0.1% DEA)=35%; 4 mL/min). 20a and 20b are enantiomers.

Example 20b: (1S,2R)-2-[(5S)-8-fluoro-5H-imidazo[4,3-a]isoindol-5-yl]cyclopentan-1-ol: LCMS (ESI, m/z): 259.2 $[M+H]^+$; tR=2.17 min (Chiralpak AD-H, 4.6×100 mm, 5 um; IPA (0.1% DEA)=35%; 4 mL/min). 20a and 20b are enantiomers.

Example 20c: (1R,2S)-2-[(5R)-8-fluoro-5H-imidazo[4,3-a]isoindol-5-yl]cyclopentan-1-ol: LCMS (ESI, m/z): 259.2 $[M+H]^+$; $^1H$ NMR (300 MHz, $CD_3OD$) δ 7.83 (s, 1H), 7.37 (dd, J=8.4, 4.8 Hz, 1H), 7.26 (dd, J=8.7, 2.5 Hz, 1H), 7.12 (s, 1H), 6.98-6.91 (m, 1H), 5.45-5.44 (m, 1H), 4.16 (q, J=7.0 Hz, 1H), 2.43-2.39 (m, 1H), 1.80-1.75 (m, 1H), 1.55-1.48 (m, 2H), 1.34-1.18 (m, 2H), 0.62-0.55 (m, 1H). tR=1.002 min (Chiralpak AD-3, 3×100 mm, 3 um; MEOH (0.1% DEA)=15%; 2 mL/min). 20c and 20d are enantiomers.

Example 20d: (1R,2S)-2-[(5S)-8-fluoro-5H-imidazo[4,3-a]isoindol-5-yl]cyclopentan-1-ol. LCMS (ESI, m/z): 259.2 $[M+H]^+$; tR=1.186 min (Chiralpak AD-3, 3×100 mm, 3 um; MEOH (0.1% DEA)=15%; 2 mL/min). 20c and 20d are enantiomers.

Example 21: 4-(5H-imidazo[5,1-a]isoindol-5-yl)-2,2-dimethylcyclobutan-1-ol

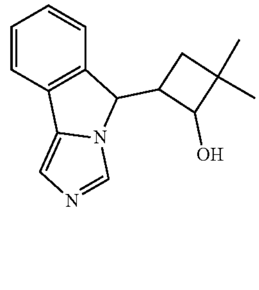 [SMILES: CC1(C)CC(C2c3ccccc3-c3cncn32)C1O]

(1R,4R)-4-((R)-5H-imidazo[5,1-a]isoindol-5-yl)-2,2-dimethylcyclobutan-1-ol (1R,4R)-4-((S)-5H-imidazo[5,1-a]isoindol-5-yl)-2,2-dimethylcyclobutan-1-ol (1R,4S)-4-((R)-5H-imidazo[5,1-a]isoindol-5-yl)-2,2-dimethylcyclobutan-1-ol (1R,4S)-4-((S)-5H-imidazo[5,1-a]isoindol-5-yl)-2,2-dimethylcyclobutan-1-ol (1S,4R)-4-((R)-5H-imidazo[5,1-a]isoindol-5-yl)-2,2-dimethylcyclobutan-1-ol (1S,4R)-4-((S)-5H-imidazo[5,1-a]isoindol-5-yl)-2,2-dimethylcyclobutan-1-ol (1S,4S)-4-((R)-5H-imidazo[5,1-a]isoindol-5-yl)-2,2-dimethylcyclobutan-1-ol (1S,4S)-4-((S)-5H-imidazo[5,1-a]isoindol-5-yl)-2,2-dimethylcyclobutan-1-ol Examples 21a-f were all synthesized using the reaction conditions for the preparation of examples 1 a-h in which the reagent cyclobutanone was substituted with 2,2-dimethylcyclobutan-1-one. Each example is a single diastereomer with undetermined stereochemical configuration Example 21a: 4-(5H-imidazo[1,5-b]isoindol-5-yl)-2,2-dimethyl-cyclobutanol: LCMS (ESI, m/z): 255 $[M+H]^+$; $^1H$ NMR (400 MHz, DMSO-$d_6$) δ 7.81 (s, 1H), 7.68-7.52 (m, 2H), 7.36 (tdd, J=7.5, 1.2, 0.6 Hz, 1H), 7.25 (td, J=7.5, 1.2 Hz, 1H), 7.12 (s, 1H), 5.62 (d, J=5.0 Hz, 1H), 5.42 (d, J=9.2 Hz, 1H), 3.94 (ddd, J=8.9, 4.8, 2.1 Hz, 1H), 2.06-1.92 (m, 1H), 1.70 (ddd, J=10.7, 8.3, 3.4 Hz, 1H), 1.04 (d, J=7.6 Hz, 6H).; tR=1.61 min (Whelk0-1 s,s (250×30 mm, 5 um), Methanol w/0.1% $NH_4OH$, 1.5 ml/min).

Example 21b: 4-(5H-imidazo[1,5-b]isoindol-5-yl)-2,2-dimethyl-cyclobutanol: LCMS (ESI, m/z): 255 $[M+H]^+$; $^1H$ NMR (400 MHz, DMSO-$d_6$) δ 7.81 (s, 1H), 7.58 (ddt, J=9.6, 7.5, 0.9 Hz, 2H), 7.36 (tdd, J=7.5, 1.2, 0.6 Hz, 1H), 7.25 (td, J=7.5, 1.2 Hz, 1H), 7.13 (s, 1H), 5.36 (d, J=7.6 Hz, 1H), 5.14 (d, J=6.9 Hz, 1H), 4.03-3.81 (m, 1H), 2.45-2.21 (m, 1H), 1.46 (dd, J=10.7, 9.0 Hz, 1H), 1.19-1.05. (m, 1H), 1.01 (s, 3H), 0.95 (s, 3H).; tR=0.54 min (Chiralpak AD (250×30 mm, 5 um), Methanol w/0.1% $NH_4OH$, 1.5 ml/min).

Example 21c: 4-(5H-imidazo[1,5-b]isoindol-5-yl)-2,2-dimethyl-cyclobutanol: LCMS (ESI, m/z): 255 $[M+H]^+$; $^1H$ NMR (400 MHz, DMSO-$d_6$) δ 7.90 (s, 1H), 7.58 (dd, J=7.6, 1.2 Hz, 1H), 7.36 (t, J=7.9 Hz, 2H), 7.23 (td, J=7.5, 1.1 Hz, 1H), 7.09 (s, 1H), 5.34 (d, J=8.9 Hz, 1H), 5.09 (d, J=7.1 Hz, 1H), 3.85 (t, J=7.6 Hz, 1H), 2.31-2.07 (m, 1H), 1.65 (td, J=9.7, 9.3, 1.0 Hz, 1H), 1.52 (t, J=10.3 Hz, 1H), 1.05 (s, 3H), 0.95 (s, 3H).; tR=0.67 min (Chiralpak AD (250×30 mm, 5 um), Methanol w/0.1% $NH_4OH$, 1.5 ml/min).

Example 21d (enantiomer of example 21b): 4-(5H-imidazo[1,5-b]isoindol-5-yl)-2,2-dimethyl-cyclobutanol: LCMS (ESI, m/z): 255 $[M+H]^+$; tR=0.74 min (Cellulose-1 (250×30 mm, 5 um), Methanol w/0.1% $NH_4OH$, 1.5 ml/min).

Example 21e (enantiomer of example 21a): 4-(5H-imidazo[1,5-b]isoindol-5-yl)-2,2-dimethyl-cyclobutanol: LCMS (ESI, m/z): 255 $[M+H]^+$; tR=0.99 min (Whelk0-1 s,s (250×30 mm, 5 um), Methanol w/0.1% $NH_4OH$, 1.5 ml/min).

Example 21f (enantiomer of example 21c): 4-(5H-imidazo[1,5-b]isoindol-5-yl)-2,2-dimethyl-cyclobutanol: LCMS (ESI, m/z): 255 $[M+H]^+$; tR=2.19 min (Chiralpak AD (250×30 mm, 5 um), Methanol w/0.1% $NH_4OH$, 1.5 ml/min).

Example 22: 2-(5H-imidazo[5,1-a]isoindol-5-yl)-3,3-dimethylcyclobutan-1-ol

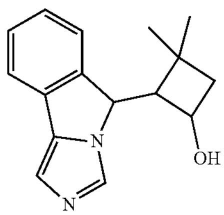 [SMILES: CC1(C)CC(O)C1C1c2ccccc2-c2cncn21]

(1S,2S)-2-((S)-5H-imidazo[5,1-a]isoindol-5-yl)-3,3-dimethylcyclobutan-1-ol
(1R,2S)-2-((S)-5H-imidazo[5,1-a]isoindol-5-yl)-3,3-dimethylcyclobutan-1-ol
(1S,2R)-2-((R)-5H-imidazo[5,1-a]isoindol-5-yl)-3,3-dimethylcyclobutan-1-ol
(1R,2S)-2-((R)-5H-imidazo[5,1-a]isoindol-5-yl)-3,3-dimethylcyclobutan-1-ol
(1R,2R)-2-((R)-5H-imidazo[5,1-a]isoindol-5-yl)-3,3-dimethylcyclobutan-1-ol
(1R,2R)-2-((S)-5H-imidazo[5,1-a]isoindol-5-yl)-3,3-dimethylcyclobutan-1-ol
(1S,2S)-2-((R)-5H-imidazo[5,1-a]isoindol-5-yl)-3,3-dimethylcyclobutan-1-ol
(1S,2R)-2-((S)-5H-imidazo[5,1-a]isoindol-5-yl)-3,3-dimethylcyclobutan-1-ol Step 1:

(E)-3,3-dimethyl-2-(2-(1-trityl-1H-imidazol-4-yl)benzylidene)cyclobutan-1-one

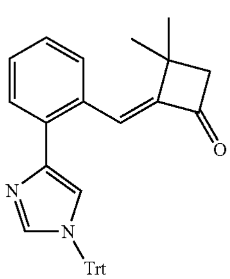

To a solution of the 2-[1-(triphenylmethyl)-1H-imidazol-4-yl]benzaldehyde (2.5 g, 6.03 mmol) and 3,3-dimethylcyclobutan-1-one (888 mg, 9.05 mmol) in MeOH (40 mL) was added piperidine dropwise (0.595 mL, 6.03 mmol). The solution was allowed to reflux overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash to afford (E)-3,3-dimethyl-2-(2-(1-trityl-1H-imidazol-4-yl)benzylidene)cyclobutan-1-one as light yellow solids: LCMS (ESI, m/z): 495.3 $[M+H]^+$.

Step 2:

2-(5H-imidazo[5,1-a]isoindol-5-yl)-3,3-dimethylcyclobutan-1-one

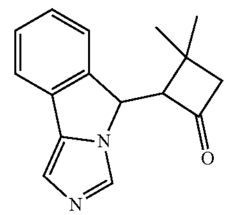 [SMILES: CC1(C)CC(=O)C1C1c2ccccc2-c2cncn21]

(E)-3,3-dimethyl-2-(2-(1-trityl-1H-imidazol-4-yl)benzylidene)cyclobutan-1-one was stirred in 20% AcOH in MeOH (20 mL) at 90° C. for 2 h. After cooling to rt, the solvent was removed under reduced pressure and sat'd $NaHCO_3$ (20 mL) was added to the residue followed by DCM (20 mL). The organic layer was collected and the aqueous layer was extracted with DCM (3×10 mL). The combined organic layers were dried over $Na_2SO_4$ and the solvent evaporated under reduced pressure to afford the crude product. The product was purified by CombiFlash to afford 2-(5H-imidazo[5,1-a]isoindol-5-yl)-3,3-dimethylcyclobutan-1-one as light yellow solids: LCMS (ESI, m/z): 253.3 $[M+H]^+$.

Step 3:

(1S,2S)-2-((S)-5H-imidazo[5,1-a]isoindol-5-yl)-3,3-dimethylcyclobutan-1-ol
(1R,2S)-2-((S)-5H-imidazo[5,1-a]isoindol-5-yl)-3,3-dimethylcyclobutan-1-ol
(1S,2R)-2-((R)-5H-imidazo[5,1-a]isoindol-5-yl)-3,3-dimethylcyclobutan-1-ol
(1R,2S)-2-((R)-5H-imidazo[5,1-a]isoindol-5-yl)-3,3-dimethylcyclobutan-1-ol
(1R,2R)-2-((R)-5H-imidazo[5,1-a]isoindol-5-yl)-3,3-dimethylcyclobutan-1-ol
(1R,2R)-2-((S)-5H-imidazo[5,1-a]isoindol-5-yl)-3,3-dimethylcyclobutan-1-ol
(1S,2S)-2-((R)-5H-imidazo[5,1-a]isoindol-5-yl)-3,3-dimethylcyclobutan-1-ol
(1S,2R)-2-((S)-5H-imidazo[5,1-a]isoindol-5-yl)-3,3-dimethylcyclobutan-1-ol 22a

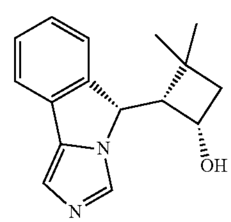

-continued

22b

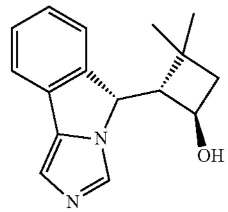

22c

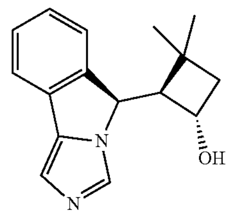

22d

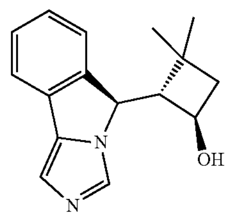

22e

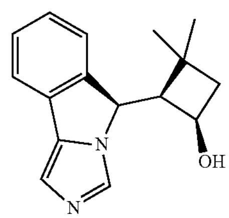

22f

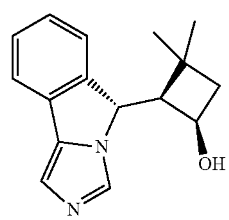

22g

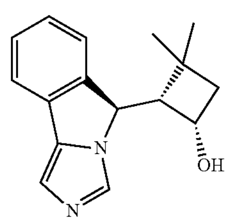

22h

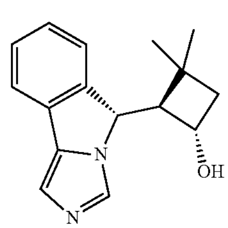

To a solution of 2-(5H-imidazo[5,1-a]isoindol-5-yl)-3,3-dimethylcyclobutan-1-one (1.04 g, 4.12 mmol) in MeOH (10 mL) was added $NaBH_4$ (467 mg, 12.37 mmol) in portions at 0° C. and the solution was stirred at 0° C. for 2 hr. The solvent was distilled off and saturated ammonium chloride solution (10 mL) was added. The aqueous layer was extracted with 5% trifluoroethanol in DCM (3×10 mL). The combined organic extract was dried over ($Na_2SO_4$) and concentrated under reduced pressure to afford the crude product. The crude product was purified by Combi-Flash and further isolated by chiral separation to afford 6 isomers as white solid.

The absolute configuration of isomers 22a, 22b, 22c and 22e was assigned by X-ray crystallography. The absolute configuration of the rest isomers was assigned arbitrarily.

Example 22a: (1S,2S)-2-((S)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.96 (d, J=0.7 Hz, 1H), 7.70 (dt, J=7.6, 0.9 Hz, 1H), 7.59 (dt, J=7.6, 0.9 Hz, 1H), 7.40-7.33 (m, 1H), 7.29-7.22 (m, 1H), 7.14 (s, 1H), 5.58 (d, J=3.2 Hz, 1H), 5.48 (d, J=8.7 Hz, 1H), 4.45 (dq, J=6.5, 3.1 Hz, 1H), 2.28-2.17 (m, 1H), 1.99-1.89 (m, 1H), 1.71-1.64 (m, 1H), 1.18 (s, 3H), 1.04 (s, 3H).

Example 22b: (1R,2S)-2-((S)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.87 (d, J=0.8 Hz, 1H), 7.62-7.55 (m, 2H), 7.40-7.33 (m, 1H), 7.25 (dd, J=7.6, 1.1 Hz, 1H), 7.14 (s, 1H), 5.47-5.39 (m, 1H), 5.11 (d, J=7.5 Hz, 1H), 4.45-4.32 (m, 1H), 2.11 (t, J=8.1 Hz, 1H), 1.99 (dd, J=10.4, 7.8 Hz, 1H), 1.53 (dd, J=10.5, 8.1 Hz, 1H), 0.95 (s, 3H), 0.84 (s, 3H).

Example 22c: (1S,2R)-2-((R)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.87 (t, J=0.6 Hz, 1H), 7.61-7.54 (m, 2H), 7.40-7.32 (m, 1H), 7.23 (td, J=7.6, 1.1 Hz, 1H), 7.14 (s, 1H), 5.42 (d, J=8.0 Hz, 1H), 5.11 (d, J=7.4 Hz, 1H), 4.39 (p, J=7.9 Hz, 1H), 2.11 (t, J=8.1 Hz, 1H), 2.03-1.94 (m, 1H), 1.53 (dd, J=10.4, 8.1 Hz, 1H), 0.94 (s, 3H), 0.84 (s, 3H).

Example 22d: (1R,2S)-2-((R)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.87 (s, 1H), 7.59 (d, J=7.4 Hz, 1H), 7.46 (d, J=7.6 Hz, 1H), 7.38 (t, J=7.5 Hz, 1H), 7.26 (td, J=7.6, 1.2 Hz, 1H), 7.09 (s, 1H), 5.43 (d, J=9.9 Hz, 1H), 5.08 (d, J=7.9 Hz, 1H), 4.44 (p, J=7.9 Hz, 1H), 2.07 (dd, J=10.5, 7.7 Hz, 1H), 1.91 (dd, J=9.9, 7.9 Hz, 1H), 1.53 (dd, J=10.5, 8.2 Hz, 1H), 1.19 (s, 3H), 1.10 (s, 3H).

Example 22e: (1R,2R)-2-((R)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.96 (t, J=0.6 Hz, 1H), 7.73-7.66 (m, 1H), 7.59 (dt, J=7.5, 0.9 Hz, 1H), 7.40-7.31 (m, 1H), 7.25 (td, J=7.6, 1.2 Hz, 1H), 7.14 (s, 1H), 5.59 (d, J=3.2 Hz, 1H), 5.48 (d, J=8.7 Hz, 1H), 4.44 (tt, J=6.3, 2.9 Hz, 1H), 2.26-2.15 (m, 1H), 1.94 (ddd, J=11.6, 5.9, 1.0 Hz, 1H), 1.67 (ddd, J=11.9, 2.7, 0.8 Hz, 1H), 1.18 (s, 3H), 1.04 (s, 3H).

Example 22f: (1R,2R)-2-((S)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.89 (d, J=0.7 Hz, 1H), 7.61 (dt, J=7.6, 1.0 Hz, 1H), 7.53-7.47 (m, 1H), 7.42-7.36 (m, 1H), 7.27 (td, J=7.6, 1.2 Hz, 1H), 7.12 (s, 1H), 5.62 (d, J=3.2 Hz, 1H), 5.47 (d, J=11.2 Hz, 1H), 4.33 (td, J=5.8, 2.8 Hz, 1H), 1.99-1.89 (m, 2H), 1.68 (dt, J=12.0, 0.9 Hz, 1H), 1.61 (s, 3H), 1.08 (s, 3H).

Example 22g: (1S,2S)-2-((R)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.89 (t, J=0.7 Hz, 1H), 7.61 (dt, J=7.6, 0.9 Hz, 1H), 7.52-7.46 (m, 1H), 7.42-7.35 (m, 1H), 7.28 (td, J=7.6, 1.2 Hz, 1H), 7.12 (s, 1H), 5.62 (d, J=3.0 Hz, 1H), 5.47 (d, J=11.2 Hz, 1H), 4.36-4.30 (m, 1H), 2.00-1.87 (m, 2H), 1.74-1.64 (m, 1H), 1.61 (s, 3H), 1.08 (s, 3H). Example 22h: (1S,2R)-2-((S)-5H-imidazo[5,1-a]isoindol-5-yl)-3,3-dimethylcyclobutan-1-ol: LCMS (ESI, m/z): 255.3 $[M+H]^+$. $^1H$ NMR (400 MHz, DMSO-$d_6$) δ 7.87 (s, 1H), 7.63-7.56 (m, 1H), 7.45 (dd, J=7.6, 0.9 Hz, 1H), 7.37 (dd, J=7.9, 7.1 Hz, 1H), 7.27 (dd, J=7.6, 1.2 Hz, 1H), 7.09 (s, 1H), 5.43 (d, J=10.0 Hz, 1H), 5.08 (d, J=7.9 Hz, 1H), 4.44 (p, J=7.9 Hz, 1H), 2.11-2.02 (m, 1H), 1.91 (dd, J=9.9, 8.0 Hz, 1H), 1.53 (dd, J=10.5, 8.2 Hz, 1H), 1.19 (s, 3H), 1.09 (s, 3H).

Example 23: 5-(5H-imidazo[5,1-a]isoindol-5-yl)-2,2-dimethylcyclopentan-1-ol

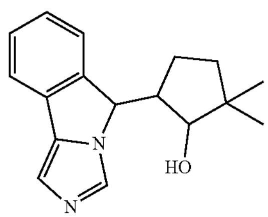 [SMILES: CC1(C)CCC(C2c3ccccc3-c3cncn32)C1O]

(1R,5S)-5-((S)-5H-imidazo[5,1-a]isoindol-5-yl)-2,2-dimethylcyclopentan-1-ol
(1R,5S)-5-((R)-5H-imidazo[5,1-a]isoindol-5-yl)-2,2-dimethylcyclopentan-1-ol
(1R,5R)-5-((R)-5H-imidazo[5,1-a]isoindol-5-yl)-2,2-dimethylcyclopentan-1-ol
(1S,5R)-5-((R)-5H-imidazo[5,1-a]isoindol-5-yl)-2,2-dimethylcyclopentan-1-ol
(1S,5S)-5-((S)-5H-imidazo[5,1-a]isoindol-5-yl)-2,2-dimethylcyclopentan-1-ol
(1S,5R)-5-((S)-5H-imidazo[5,1-a]isoindol-5-yl)-2,2-dimethylcyclopentan-1-ol Step 1:

(E)-2,2-dimethyl-5-(2-(1-trityl-1H-imidazol-4-yl)benzylidene)cyclopentan-1-on

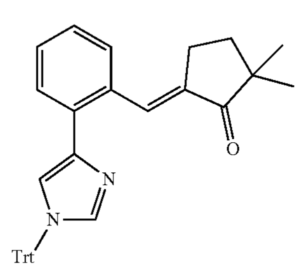

10% aq. Sodium hydroxide (1.93 mL, 4.82 mmol) was added to a stirred mixture of 2,2-dimethylcyclopentan-1-one (281 mg, 2.51 mmol) and 2-(1-trityl-1H-imidazol-4-yl)benzaldehyde (800 mg, 1.93 mmol), in MeOH (15 mL). The reaction mixture was heated at 65° C. for 6 hours until TLC show the disappearance of SM. The reaction mixture was diluted with DCM (30 mL) and the organics were washed with water, dried over $Na_2SO_4$, filtered and concentrated. The crude was taken directly to next step: LCMS (ESI, m/z): 509.4 $[M+H]^+$ Step 2:

5-(5H-imidazo[5,1-a]isoindol-5-yl)-2,2-dimethylcyclopentan-1-one

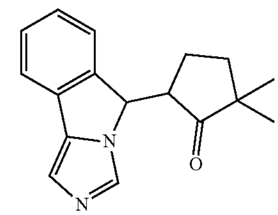 [SMILES: CC1(C)CCC(C2c3ccccc3-c3cncn32)C1=O]

The title compound was synthesized by General Procedure for the Synthesis of Int-3: LCMS (ESI, m/z): 267.4

Step 3:

(1R,5S)-5-((S)-5H-imidazo[5,1-a]isoindol-5-yl)-2,2-dimethylcyclopentan-1-ol
(1R,5S)-5-((R)-5H-imidazo[5,1-a]isoindol-5-yl)-2,2-dimethylcyclopentan-1-ol
(1R,5R)-5-((R)-5H-imidazo[5,1-a]isoindol-5-yl)-2,2-dimethylcyclopentan-1-ol
(1S,5R)-5-((R)-5H-imidazo[5,1-a]isoindol-5-yl)-2,2-dimethylcyclopentan-1-ol
(1S,5S)-5-((S)-5H-imidazo[5,1-a]isoindol-5-yl)-2,2-dimethylcyclopentan-1-ol
(1S,5R)-5-((S)-5H-imidazo[5,1-a]isoindol-5-yl)-2,2-dimethylcyclopentan-1-ol

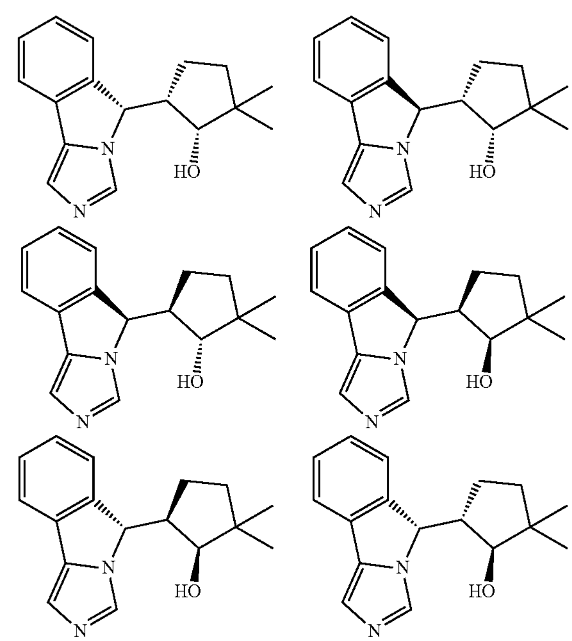

The title compound was synthesized by General Procedure for the Synthesis of Int-5. The product was isolated as a mixture of eight diastereomers which was purified by chiral SFC.

The absolute configuration of all isomers was assigned arbitrarily.

Example 23a: (1R,5S)-5-((S)-5H-imidazo[5,1-a]isoindol-5-yl)-2,2-dimethylcyclopentan-1-ol: LCMS (ESI, m/z):

269.2 $[M+H]^+$; $^1$HNMR (400 MHz, DMSO-$d_6$) δ 7.91 (s, 1H), 7.59 (d, J=7.5 Hz, 1H), 7.53 (d, J=7.6 Hz, 1H), 7.38 (t, J=7.2 Hz, 1H), 7.26 (td, J=7.6, 1.2 Hz, 1H), 7.10 (s, 1H), 5.43 (d, J=4.4 Hz, 1H), 4.89-4.83 (m, 1H), 3.56 (d, J=9.6 Hz, 1H), 2.64 (m, 1H), 1.39-1.20 (m, 3H), 1.14-1.00 (m, 1H), 0.90 (s, 3H), 0.84 (s, 3H).

Example 23b: (1R,5S)-5-((R)-5H-imidazo[5,1-a]isoindol-5-yl)-2,2-dimethylcyclopentan-1-ol: LCMS (ESI, m/z): 269.2 $[M+H]^+$; $^1$HNMR (400 MHz, DMSO-$d_6$) δ 7.92 (s, 1H), 7.60 (d, J=7.5 Hz, 1H), 7.48 (d, J=8.5 Hz, 1H), 7.40-7.32 (m, 1H), 7.27-7.19 (m, 1H), 7.11 (s, 1H), 5.25 (dd, J=15.3, 7.6 Hz, 2H), 3.61 (dd, J=8.5, 1.1 Hz, 1H), 2.07 (dd, J=13.3, 4.4 Hz, 2H), 2.00-1.87 (m, 1H), 1.83-1.70 (m, 1H), 1.45-1.34 (m, 1H), 1.06 (s, 3H), 0.79 (s, 3H).

Example 23c: (1R,5R)-5-((R)-5H-imidazo[5,1-a]isoindol-5-yl)-2,2-dimethylcyclopentan-1-ol: LCMS (ESI, m/z): 269.2 $[M+H]^+$; $^1$HNMR (400 MHz, DMSO-$d_6$) δ 7.88 (s, 1H), 7.67 (dd, J=7.6, 0.8 Hz, 1H), 7.58 (d, J=7.5 Hz, 1H), 7.37 (t, J=7.7 Hz, 1H), 7.26 (td, J=7.6, 1.2 Hz, 1H), 7.11 (s, 1H), 5.37 (d, J=7.6 Hz, 1H), 5.28 (d, J=5.2 Hz, 1H), 3.72 (t, J=5.1 Hz, 1H), 2.41-2.28 (m, 1H), 1.80-1.55 (m, 3H), 1.35-1.26 (m, 1H), 1.02 (s, 3H), 0.82 (s, 3H).

Example 23d: (1S,5R)-5-((R)-5H-imidazo[5,1-a]isoindol-5-yl)-2,2-dimethylcyclopentan-1-ol: LCMS (ESI, m/z): 269.2 $[M+H]^+$; $^1$HNMR Enantiomer to Example 23a.

Example 23e: (1S,5S)-5-((S)-5H-imidazo[5,1-a]isoindol-5-yl)-2,2-dimethylcyclopentan-1-ol: LCMS (ESI, m/z): 269.2 $[M+H]^+$; $^1$HNMR Enantiomer to Example 23c.

Example 23f: (1S,5R)-5-((S)-5H-imidazo[5,1-a]isoindol-5-yl)-2,2-dimethylcyclopentan-1-ol: LCMS (ESI, m/z): 269.2 $[M+H]^+$; $^1$HNMR Enantiomer to Example 23b.

Example 24: 6-(5H-imidazo[5,1-a]isoindol-5-yl)-2,2-dimethylcyclohexan-1-ol

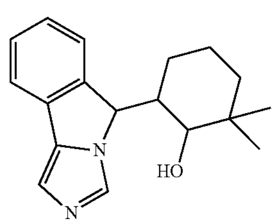 [SMILES: CC1(C)CCCC(C2c3ccccc3-c3cncn32)C1O]

(1R,6S)-6-((S)-5H-imidazo[5,1-a]isoindol-5-yl)-2,2-dimethylcyclohexan-1-ol (1S,6S)-6-((S)-5H-imidazo[5,1-a]isoindol-5-yl)-2,2-dimethylcyclohexan-1-ol (1R,6R)-6-((S)-5H-imidazo[5,1-a]isoindol-5-yl)-2,2-dimethylcyclohexan-1-ol (1S,6R)-6-((S)-5H-imidazo[5,1-a]isoindol-5-yl)-2,2-dimethylcyclohexan-1-ol (1R,6S)-6-((R)-5H-imidazo[5,1-a]isoindol-5-yl)-2,2-dimethylcyclohexan-1-ol (1S,6S)-6-((R)-5H-imidazo[5,1-a]isoindol-5-yl)-2,2-dimethylcyclohexan-1-ol (1R,6R)-6-((R)-5H-imidazo[5,1-a]isoindol-5-yl)-2,2-dimethylcyclohexan-1-ol (1S,6R)-6-((R)-5H-imidazo[5,1-a]isoindol-5-yl)-2,2-dimethylcyclohexan-1-ol Step 1:

(E)-2,2-dimethyl-6-(2-(1-trityl-1H-imidazol-4-yl)benzylidene)cyclohexan-1-one

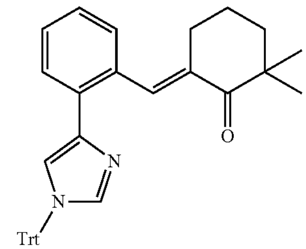

The title compound was synthesized by General Procedure for the Synthesis of Int-2: LCMS (ESI, m/z): 533.2 $[M+H]^+$ Step 2:

6-(5H-imidazo[5,1-a]isoindol-5-yl)-2,2-dimethylcyclohexan-1-one

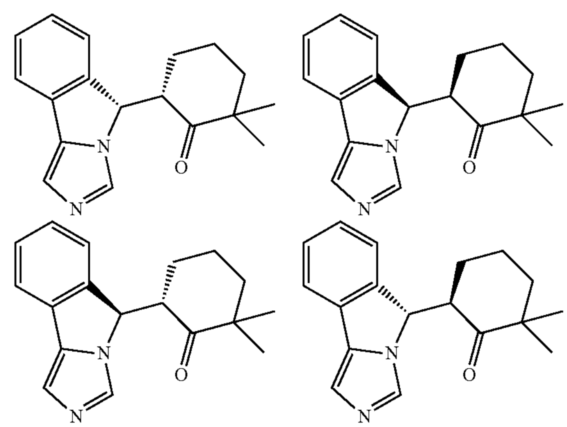

The title compound was synthesized by General Procedure for the Synthesis of Int-3.

The two diastereomeric pairs were not separated and used as a mixture for step 3: LCMS (ESI, m/z): 281.2

Step 3:

(1R,6S)-6-((S)-5H-imidazo[5,1-a]isoindol-5-yl)-2,2-dimethylcyclohexan-1-ol (1S,6S)-6-((S)-5H-imidazo[5,1-a]isoindol-5-yl)-2,2-dimethylcyclohexan-1-ol (1R,6R)-6-((S)-5H-imidazo[5,1-a]isoindol-5-yl)-2,2-dimethylcyclohexan-1-ol (1S,6R)-6-((S)-5H-imidazo[5,1-a]isoindol-5-yl)-2,2-dimethylcyclohexan-1-ol (1R,6S)-6-((R)-5H-imidazo[5,1-a]isoindol-5-yl)-2,2-dimethylcyclohexan-1-ol (1S,6S)-6-((R)-5H-imidazo[5,1-a]isoindol-5-yl)-2,2-dimethylcyclohexan-1-ol (1R,6R)-6-((R)-5H-imidazo[5,1-a]isoindol-5-yl)-2,2-dimethylcyclohexan-1-ol (1S,6R)-6-((R)-5H-imidazo[5,1-a]isoindol-5-yl)-2,2-dimethylcyclohexan-1-ol 24a

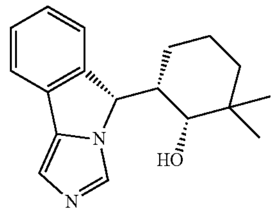

24b

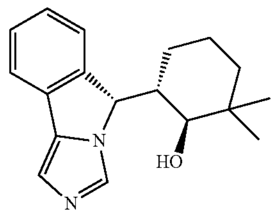

24c

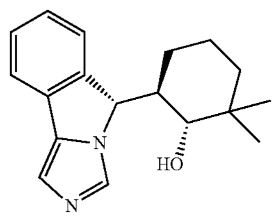

24d

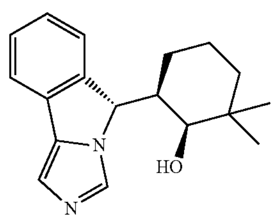

24e

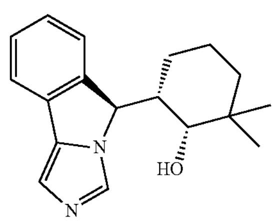

24f

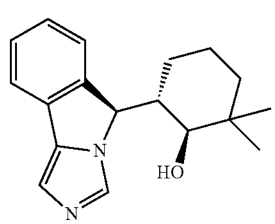

24g

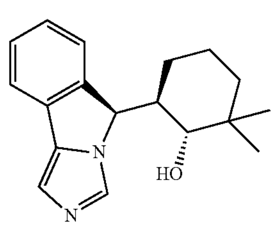

-continued

24h

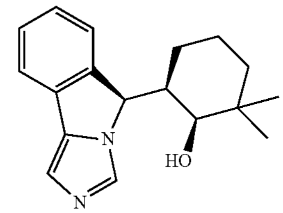

The title compound was synthesized by General Procedure for the Synthesis of Int-5. The product was isolated as a mixture of eight enantiomers which were separated by chiral SFC: LCMS (ESI, m/z): 283.2 for all isomers.

The absolute configuration of all isomers was assigned arbitrarily.

Example 24a: (1R,6S)-6-((S)-5H-imidazo[5,1-a]isoindol-5-yl)-2,2-dimethylcyclohexan-1-ol: LCMS (ESI, m/z): 281.2 $[M+H]^+$; $^1$H NMR same as Example 24h.

Example 24b: (1S,6S)-6-((S)-5H-imidazo[5,1-a]isoindol-5-yl)-2,2-dimethylcyclohexan-1-ol: LCMS (ESI, m/z): 281.2 $[M+H]^+$; $^1$H NMR (400 MHz, DMSO-$d_6$) δ 7.93 (t, J=0.6 Hz, 1H), 7.64-7.55 (m, 2H), 7.41-7.32 (m, 1H), 7.23 (td, J=7.6, 1.2 Hz, 1H), 7.10 (d, J=0.5 Hz, 1H), 5.15 (d, J=7.3 Hz, 1H), 4.83 (d, J=5.8 Hz, 1H), 3.42-3.38 (m, 1H), 1.84-1.72 (m, 1H), 1.66-1.46 (m, 4H), 1.37 (dtd, J=13.7, 10.0, 8.8, 3.5 Hz, 1H), 1.08-1.00 (m, 1H), 0.91 (s, 3H), 0.76 (s, 3H).

Example 24c: (1R,6R)-6-((S)-5H-imidazo[5,1-a]isoindol-5-yl)-2,2-dimethylcyclohexan-1-ol: LCMS (ESI, m/z): 281.2 $[M+H]^+$; $^1$H NMR (400 MHz, DMSO-$d_6$) δ 7.85 (s, 1H), 7.58 (dt, J=7.5, 1.0 Hz, 1H), 7.47 (dq, J=7.5, 0.9 Hz, 1H), 7.36 (tdd, J=7.5, 1.2, 0.6 Hz, 1H), 7.28 (td, J=7.5, 1.2 Hz, 1H), 7.13 (s, 1H), 5.68 (d, J=2.4 Hz, 1H), 5.18 (d, J=6.5 Hz, 1H), 2.23-2.11 (m, 1H), 1.33 (dd, J=13.0, 2.6 Hz, 1H), 1.26-1.12 (m, 2H), 1.09-1.03 (m, 1H), 1.02 (s, 3H), 0.92 (s, 3H), 0.68 (d, J=13.2 Hz, 1H), 0.21-0.05 (m, 1H).

Example 24d: (1S,6R)-6-((S)-5H-imidazo[5,1-a]isoindol-5-yl)-2,2-dimethylcyclohexan-1-ol: LCMS (ESI, m/z): 281.2 $[M+H]^+$; $^1$H NMR same as Example 24e.

Example 24e: (1R,6S)-6-((R)-5H-imidazo[5,1-a]isoindol-5-yl)-2,2-dimethylcyclohexan-1-ol: LCMS (ESI, m/z): 281.2 $[M+H]^+$; $^1$H NMR (400 MHz, DMSO-$d_6$) δ 7.90 (s, 1H), 7.58 (ddt, J=12.8, 8.3, 0.8 Hz, 2H), 7.42-7.32 (m, 1H), 7.27 (td, J=7.5, 1.2 Hz, 1H), 7.10 (s, 1H), 5.69 (d, J=3.9 Hz, 1H), 5.12 (d, J=6.3 Hz, 1H), 2.40-2.27 (m, 1H), 1.31 (dd, J=13.0, 2.5 Hz, 1H), 1.20-1.13 (m, 2H), 0.98 (s, 3H), 0.92 (s, 3H), 0.52 (d, J=13.1 Hz, 1H), 0.23-0.04 (m, 1H).

Example 24f: (1S,6S)-6-((R)-5H-imidazo[5,1-a]isoindol-5-yl)-2,2-dimethylcyclohexan-1-ol: LCMS (ESI, m/z): 281.2 $[M+H]^+$; $^1$H NMR same as Example 24c.

Example 24g: (1R,6R)-6-((R)-5H-imidazo[5,1-a]isoindol-5-yl)-2,2-dimethylcyclohexan-1-ol: LCMS (ESI, m/z): 281.2 $[M+H]^+$; $^1$H NMR same as Example 24b.

Example 24h: (1S,6R)-6-((R)-5H-imidazo[5,1-a]isoindol-5-yl)-2,2-dimethylcyclohexan-1-ol: LCMS (ESI, m/z): 281.2 $[M+H]^+$; $^1$H NMR (400 MHz, DMSO-$d_6$) δ 7.97 (t, J=0.7 Hz, 1H), 7.56 (dt, J=3.0, 0.8 Hz, 1H), 7.55-7.52 (m, 1H), 7.41-7.31 (m, 1H), 7.26 (td, J=7.6, 1.2 Hz, 1H), 7.08 (s, 1H), 5.19 (d, J=3.1 Hz, 1H), 5.06 (dd, J=6.0, 0.7 Hz, 1H), 3.63-3.55 (m, 1H), 2.23-2.14 (m, 1H), 1.48 (td, J=13.2, 4.3 Hz, 1H), 1.40-1.19 (m, 2H), 1.18-0.99 (m, 2H), 0.94 (s, 3H), 0.91 (s, 3H), 0.77 (dd, J=12.3, 3.4 Hz, 1H).

Example 25: 2-(8-fluoro-5H-imidazo[5,1-a]isoindol-5-yl)cyclohexan-1-ol

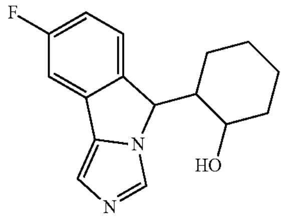 [SMILES: OC1CCCCC1C1c2ccc(F)cc2-c2cncn21]

The title compound was synthesized by the same method of example 5 and 6

Example 25c: (1S,2R)-2-[(5R)-8-fluoro-5H-imidazo[4,3-a]isoindol-5-yl]cyclohexan-1-ol: LCMS (ESI, m/z): 273.2 $[M+H]^+$; $^1$HNMR (300 MHz, $CD_3OD$) δ 7.90 (s, 1H), 7.50-7.34 (m, 2H), 7.22 (s, 1H), 7.07-7.04 (m, 1H), 5.80 (d, J=3.0 Hz, 1H), 3.75-3.72 (m, 1H), 2.22-1.96 (m, 2H), 1.84-1.67 (m, 1H), 1.45-1.39 (m, 2H), 1.34-1.02 (m, 2H), 0.96-0.83 (m, 1H), 0.45-0.23 (m, 1H). tR=3.432 min (Chiralpak ID-3, 0.46×10 cm, 3 um; Hex(0.1% DEA):IPA=90:10; 1 mL/min). 25c and 25d are enantiomers.

Example 25d: (1R,2S)-2-[(5R)-8-fluoro-5H-imidazo[4,3-a]isoindol-5-yl]cyclohexan-1-ol: LCMS (ESI, m/z): 273.2 $[M+H]^+$; tR=4.010 min (Chiralpak ID-3, 0.46×10 cm, 3 um; Hex(0.1% DEA):IPA=90:10; 1 mL/min). 25c and 25d are enantiomers.

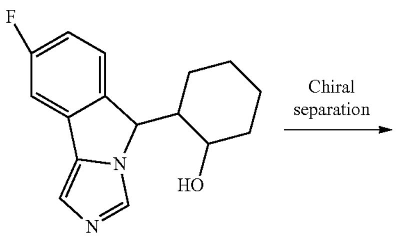

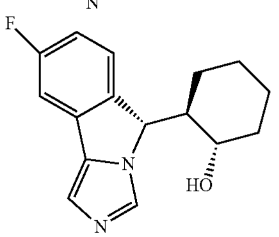

25a

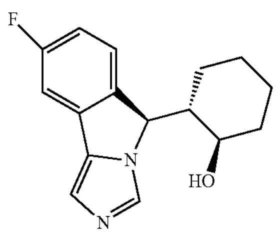

25b

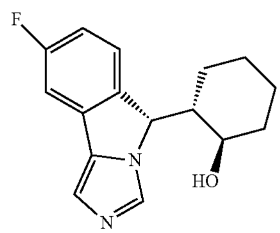

25c

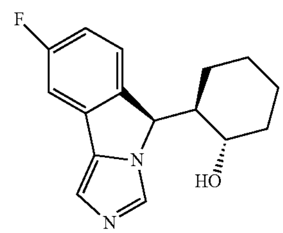

25d

The crude product was purified by Prep-HPLC and further isolated by chiral separation with the following conditions:

1. Column, ChiralpakID, 2.0 cm I.D×25 cm; mobile phase: Hex:IPA=10:10; Detector, uv 254 nm; flow rate, 20 mL/min.
2. Column, ChiralpakIC, 2×25 cm, 5 um; mobile phase: Hex(0.1% DEA):IPA=30:30; Detector, uv 254 nm; flow rate, 20 mL/min.

The absolute configuration of all isomers was assigned arbitrarily.

Example 25a: (1R,2S)-2-[(5S)-8-fluoro-5H-imidazo[4,3-a]isoindol-5-yl]cyclohexan-1-ol: LCMS (ESI, m/z): 273.2 $[M+H]^+$; $^1$HNMR (300 MHz, $CD_3OD$) $^1$HNMR (300 MHz, $CD_3OD$) δ 7.90 (s, 1H), 7.58-7.52 (m, 1H), 7.43-7.38 (m, 1H), 7.20 (s, 1H), 7.09-7.02 (m, 1H), 5.80 (d, J=3.0 Hz, 1H), 3.78-3.72 (m, 1H), 2.26-2.03 (m, 2H), 1.81-1.67 (m, 1H), 1.39-1.31 (m, 2H), 1.14-1.00 (m, 2H), 0.75-0.60 (m, 1H), 0.39-0.24 (m, 1H); tR=1.044 min (Chiralpak IC-3, 0.46×5 cm, 3 um; Hex(0.1% DEA):IPA=70:30; 1.5 ml/min). 25a and 25b are enantiomers.

Example 25b: (1S,2R)-2-[(5S)-8-fluoro-5H-imidazo[4,3-a]isoindol-5-yl]cyclohexan-1-ol: LCMS (ESI, m/z): 273.2 $[M+H]^+$; tR=1.438 min (Chiralpak IC-3, 0.46×5 cm, 3 um; Hex(0.1% DEA):IPA=70:30; 1.5 ml/min). 25a and 25b are enantiomers.

Example 26: 4-(5H-imidazo[5,1-a]isoindol-5-yl)tetrahydrofuran-3-ol

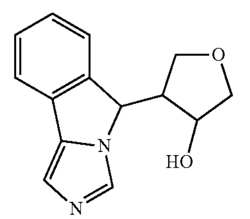 [SMILES: OC1COCC1C1c2ccccc2-c2cncn21]

(3R,4S)-4-((R)-5H-imidazo[5,1-a]isoindol-5-yl)tetrahydrofuran-3-ol
(3S,4R)-4-((S)-5H-imidazo[5,1-a]isoindol-5-yl)tetrahydrofuran-3-ol
(3R,4S)-4-((S)-5H-imidazo[5,1-a]isoindol-5-yl)tetrahydrofuran-3-ol
(3S,4R)-4-((R)-5H-imidazo[5,1-a]isoindol-5-yl)tetrahydrofuran-3-ol
(3R,4S)-4-((R)-5H-imidazo[5,1-a]isoindol-5-yl)tetrahydrofuran-3-ol
(3S,4R)-4-((S)-5H-imidazo[5,1-a]isoindol-5-yl)tetrahydrofuran-3-ol
(3R,4S)-4-((S)-5H-imidazo[5,1-a]isoindol-5-yl)tetrahydrofuran-3-ol (3S,4R)-4-((R)-5H-imidazo[5,1-a]isoindol-5-yl)tetrahydrofuran-3-ol

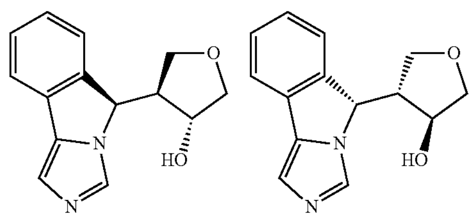

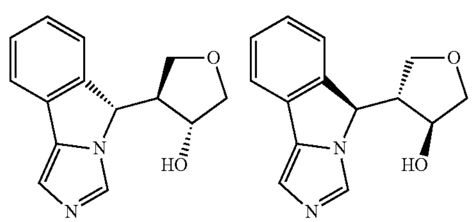

n-Butyllithium (2.5 M in hexane; 1.13 mL, 2.83 mmol) is added dropwise to a solution of 5H-imidazo[5,1-a]isoindole (442 mg, 2.83 mmol) in 6 ml of THF which has been cooled to −78° C. and the mixture is stirred for 45 minutes. A solution of 3,4-Epoxytetrahydrofuran (292 mg, 3.40 mmol) in THF (3 mL) was slowly added followed by boron trifluoride etherate (0.42 mL, 3.40 mmol). The reaction solution is warmed to 0° C. and stirred for a further 5 hours. It is subsequently hydrolyzed with saturated ammonium chloride solution and the aqueous phase is extracted twice with DCM (30 mL). After drying, the solvent is removed under reduced pressure and the crude product is purified by Combi-Flash chromatography. The product is obtained as a mixture of four diastereomers (501 mg, 73%). The pure stereoisomers were obtained after purification by chiral SFC. The absolute configuration of all isomers was assigned arbitrarily.

Example 26a: (3R,4S)-4-((R)-5H-imidazo[5,1-a]isoindol-5-yl)tetrahydrofuran-3-ol: LCMS (ESI, m/z): 243.2 $[M+H]^+$; $^1$HNMR (400 MHz, DMSO-$d_6$) δ 7.94 (s, 1H), 7.59 (d, J=7.6 Hz, 1H), 7.54 (dd, J=7.6, 0.9 Hz, 1H), 7.38 (t, J=7.5 Hz, 1H), 7.27 (td, J=7.6, 1.2 Hz, 1H), 7.14 (s, 1H), 5.58 (d, J=4.1 Hz, 1H), 5.26 (d, J=4.6 Hz, 1H), 4.31 (dt, J=8.5, 4.2 Hz, 1H), 3.73-3.67 (m, 1H), 3.58 (dd, J=9.2, 5.7 Hz, 1H), 3.43 (dd, J=9.6, 3.6 Hz, 1H), 3.14 (dd, J=9.1, 6.5 Hz, 1H), 2.86-2.79 (m, 1H).

Example 26b: (3S,4R)-4-((S)-5H-imidazo[5,1-a]isoindol-5-yl)tetrahydrofuran-3-ol: LCMS (ESI, m/z): 243.2 $[M+H]^+$; $^1$HNMR Enantiomer to Example 26a.

Example 26c: (3R,4S)-4-((S)-5H-imidazo[5,1-a]isoindol-5-yl)tetrahydrofuran-3-ol: LCMS (ESI, m/z): 243.2 $[M+H]^+$; $^1$HNMR (400 MHz, DMSO-$d_6$) δ 7.88 (s, 1H), 7.60 (d, J=7.5 Hz, 1H), 7.52 (dd, J=7.6, 0.8 Hz, 1H), 7.40 (t, J=7.5 Hz, 1H), 7.28 (td, J=7.6, 1.2 Hz, 1H), 7.12 (s, 1H), 5.50 (d, J=4.6 Hz, 1H), 5.00 (d, J=4.7 Hz, 1H), 4.02 (dd, J=9.2, 7.8 Hz, 1H), 3.85-3.78 (m, 2H), 3.38 (d, J=4.4 Hz, 2H), 2.81-2.72 (m, 1H).

Example 26d: (3S,4R)-4-((R)-5H-imidazo[5,1-a]isoindol-5-yl)tetrahydrofuran-3-ol: LCMS (ESI, m/z): 243.2 $[M+H]^+$; $^1$HNMR Enantiomer to Example 26c.

Example 14 and 27: 2-(3-hydroxy-4-(5H-imidazo[5,1-a]isoindol-5-yl)piperidin-1-yl)acetonitrile

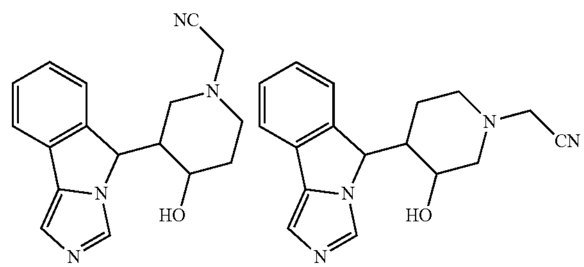

2-((3S,4R)-4-hydroxy-3-((S)-5H-imidazo[5,1-a]isoindol-5-yl)piperidin-1-yl)acetonitrile 2-((3R,4S)-4-hydroxy-3-((R)-5H-imidazo[5,1-a]isoindol-5-yl)piperidin-1-yl)acetonitrile 2-((3R,4S)-4-hydroxy-3-((S)-5H-imidazo[5,1-a]isoindol-5-yl)piperidin-1-yl)acetonitrile 2-((3S,4R)-4-hydroxy-3-((R)-5H-imidazo[5,1-a]isoindol-5-yl)piperidin-1-yl)acetonitrile 2-((3S,4S)-3-hydroxy-4-((S)-5H-imidazo[5,1-a]isoindol-5-yl)piperidin-1-yl)acetonitrile 2-((3R,4R)-3-hydroxy-4-((R)-5H-imidazo[5,1-a]isoindol-5-yl)piperidin-1-yl)acetonitrile 2-((3R,4R)-3-hydroxy-4-((S)-5H-imidazo[5,1-a]isoindol-5-yl)piperidin-1-yl)acetonitrile 2-((3S,4S)-3-hydroxy-4-((R)-5H-imidazo[5,1-a]isoindol-5-yl)piperidin-1-yl)acetonitrile Example 14: 2-(4-hydroxy-3-(5H-imidazo[5,1-a]isoindol-5-yl)piperidin-1-yl)acetonitrile
Synthetic Route IIB
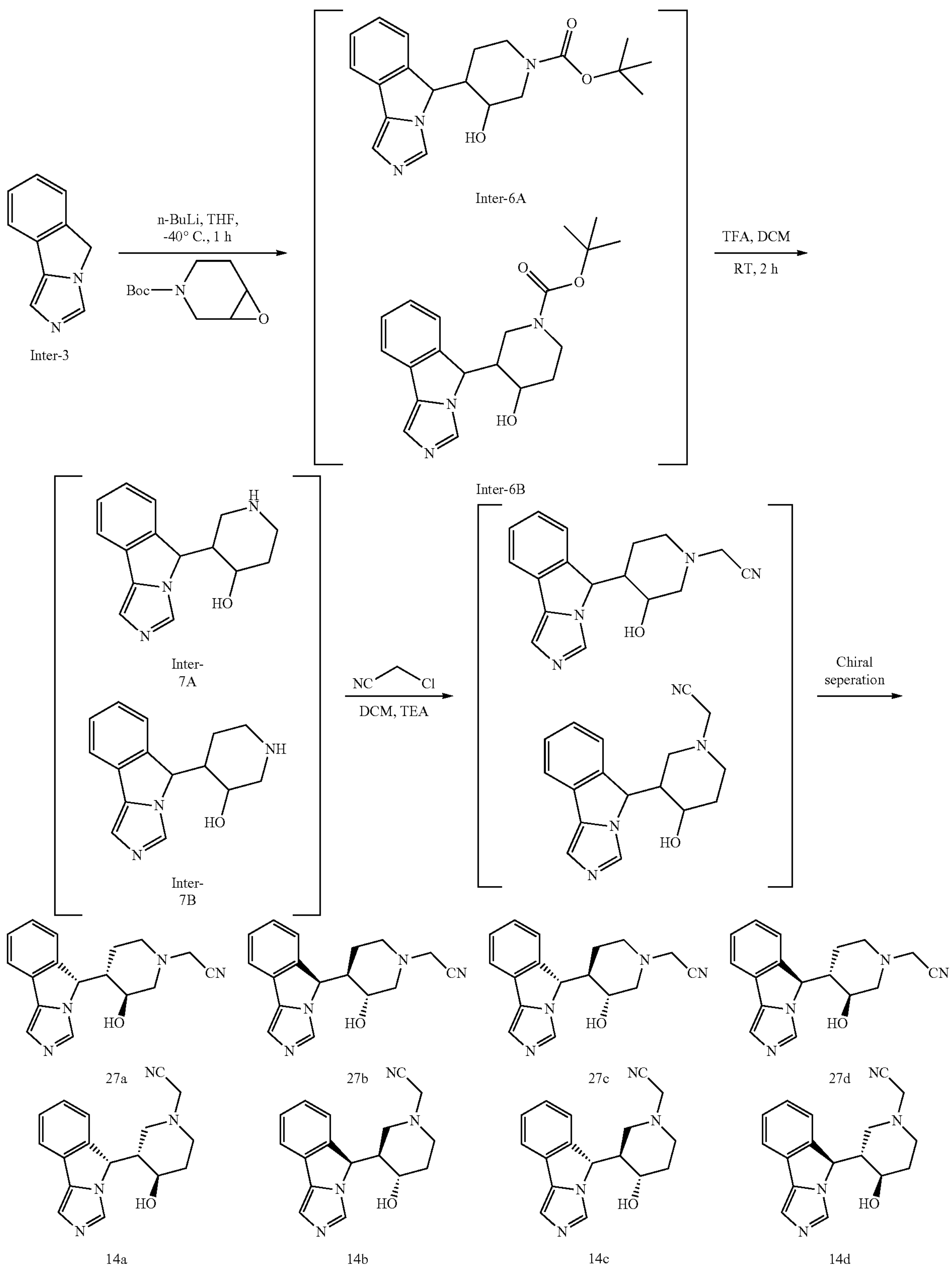
Inter-3
Inter-6A
Inter-6B
Inter-7A
Inter-7B
27a 27b 27c 27d
14a 14b 14c 14d Step 1: Tert-butyl 3-hydroxy-4-(5H-imidazo[5,1-a]isoindol-5-yl)piperidine-1-carboxylate and tert-butyl 4-hydroxy-3-(5H-imidazo[5,1-a]isoindol-5-yl)piperidine-1-carboxylate

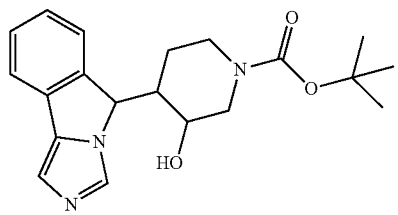

+

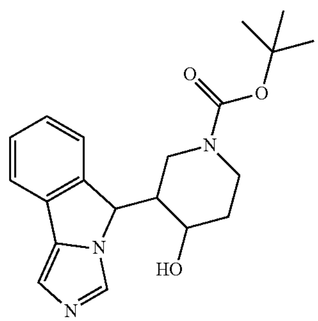

To the solution of 5H-imidazo[4,3-a]isoindole (3.0 g, 19.21 mmol) and tetrahydrofuran (40 mL) was added dropwise n-butyllithium (10 mL in hexane, 2.5 mol/L, 25 mmol) at −60° C. The resulting solution was stirred for 1 hour at −40° C. Tert-butyl 7-oxa-3-azabicyclo[4.1.0]heptane-3-carboxylate (4.8 g, 24.09 mmol) in tetrahydrofuran (10 mL) was added dropwise at −40° C. The reaction was raised slowly to room temperature and then stirred for an additional 1.5 h. The reaction was then quenched by sat.ammoniumchloride (50 mL), extracted with ethyl acetate (3×100 mL) and concentrated invacuo. The residue was purified by a silica gel column chromatography and eluted with dichloromethane/methanol (10/1) to afford the mixture (2.5 g, 37%).

Step 2: 3-[5H-imidazo[4,3-a]isoindol-5-yl]piperidin-4-ol and 4-[5H-imidazo[4,3-a]isoindol-5-yl]piperidin-3-ol

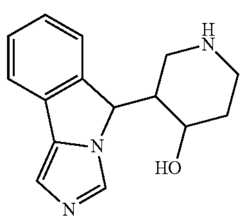

+

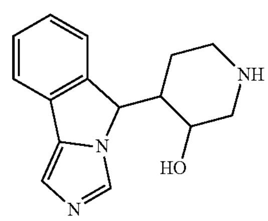

To a solution of the mixture of tert-butyl 3-hydroxy-4-(5H-imidazo[5,1-a]isoindol-5-yl)piperidine-1-carboxylate and tert-butyl 4-hydroxy-3-(5H-imidazo[5,1-a]isoindol-5-yl)piperidine-1-carboxylate (2.5 g, 9.80 mmol) in dichloromethane (30 mL) was added TFA (10 mL). The solution was stirred at room temperature for 2 h. The solution was concentrated under vacuum to afford the mixture of 3-[5H-imidazo[4,3-a]isoindol-5-yl]piperidin-4-ol and 4-[5H-imidazo[4,3-a]isoindol-5-yl]piperidin-3-ol as brown oil (2.8 g, crude): LCMS (ESI, m/z): 256.0 [M+H]$^+$;

Step 3:

2-((3S,4S)-3-hydroxy-4-((S)-5H-imidazo[5,1-a]isoindol-5-yl)piperidin-1-yl)acetonitrile
2-((3R,4R)-3-hydroxy-4-((R)-5H-imidazo[5,1-a]isoindol-5-yl)piperidin-1-yl)acetonitrile
2-((3R,4R)-3-hydroxy-4-((S)-5H-imidazo[5,1-a]isoindol-5-yl)piperidin-1-yl)acetonitrile
2-((3S,4S)-3-hydroxy-4-((R)-5H-imidazo[5,1-a]isoindol-5-yl)piperidin-1-yl)acetonitrile
2-((3S,4R)-4-hydroxy-3-((S)-5H-imidazo[5,1-a]isoindol-5-yl)piperidin-1-yl)acetonitrile
2-((3R,4S)-4-hydroxy-3-((R)-5H-imidazo[5,1-a]isoindol-5-yl)piperidin-1-yl)acetonitrile
2-((3R,4S)-4-hydroxy-3-((S)-5H-imidazo[5,1-a]isoindol-5-yl)piperidin-1-yl)acetonitrile
2-((3S,4R)-4-hydroxy-3-((R)-5H-imidazo[5,1-a]isoindol-5-yl)piperidin-1-yl)acetonitrile 27a

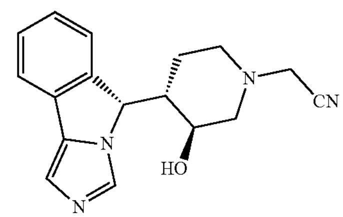

27b

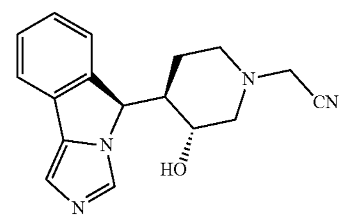

27c

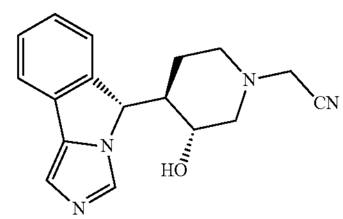

27d

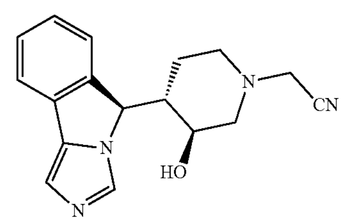

14a

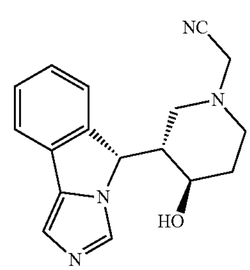

-continued

14b

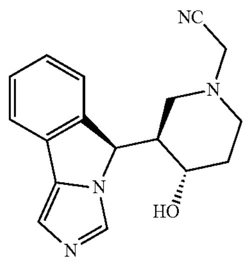

14c

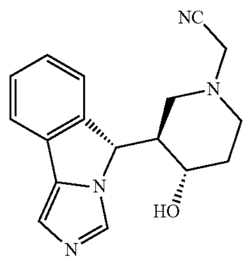

14d

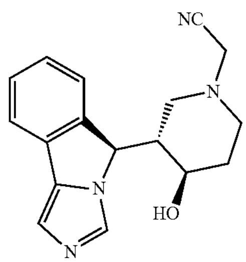

To a solution of the mixture of 3-[5H-imidazo[4,3-a]isoindol-5-yl]piperidin-4-ol and 4-[5H-imidazo[4,3-a]isoindol-5-yl]piperidin-3-ol (2.8 g, crude) in dichloromethane (50 mL) was added triethylamine (50 mL) and 2-chloroacetonitrile (1.4 mL, 22.06 mmol). The resulting solution was stirred for 6 h at room temperature. The resulting solution was diluted with water (50 mL), extracted with dichloromethane (3×100 mL). The combined organic layers was washed with of brine (1×100 mL). The mixture was dried over anhydrous sodium sulfate and concentrated under vacuum to afford the crude product (3.0 g, crude) as a light brown solid. The crude product was purified by Prep-HPLC and further isolated by chiral separation with the following conditions:

1. CHIRALCEL OD-H, 20×250 mm; Mobile Phase A:Hex-HPLC, Mobile Phase B: EtOH-HPLC; Flow rate: 20 mL/min; Gradient: 10 B to 10 B in 24 min;
2. CHIRALPAK-AD-H-SL002, 20×250 mm; Mobile Phase A:Hex(0.1% DEA)-HPLC, Mobile Phase B: IPA-HPLC; Flow rate: 20 mL/min; Gradient: 30 B to 30 B in 15 min; 254/220 nm;

The absolute configuration of all isomers was assigned arbitrarily.

Example 27a: 2-((3S,4S)-3-hydroxy-4-((S)-5H-imidazo[5,1-a]isoindol-5-yl)piperidin-1-yl)acetonitrile (20.8 mg, 1%) as an off-white solid: LCMS (ESI, m/z): 295.1 $[M+H]^+$, $^1$HNMR (300 MHz, $CD_3OD$) δ 7.92 (s, 1H), 7.65 (d, J=7.5 Hz, 1H), 7.56 (d, J=7.5 Hz, 1H), 7.47-7.42 (m, 1H), 7.36-7.31 (m, 1H), 7.18 (s, 1H), 5.81 (d, J=3.0 Hz, 1H), 4.03-3.95 (m, 1H), 3.64 (s, 2H), 3.13-3.08 (m, 1H), 2.65-2.61 (m, 1H), 2.31-2.12 (m, 3H), 0.82-0.70 (m, 2H). tR=3.169 min, (Chiralpak IC-3, 0.46×5 cm, 3 um; ethanol:hexane (0.1% DEA)=30:70; 1.0 mL/min). 27a and 27b are enantiomers.

Example 27b: 2-((3R,4R)-3-hydroxy-4-((R)-5H-imidazo[5,1-a]isoindol-5-yl)piperidin-1-yl)acetonitrile (29.8 mg, 1%) as an off-white solid: LCMS (ESI, m/z): 295.1 $[M+H]^+$; tR=5.009 min, (Chiralpak IC-3, 0.46×5 cm, 3 um; ethanol:hexane (0.1% DEA)=30:70; 1.0 mL/min). 27a and 27b are enantiomers.

Example 27c: 2-((3R,4R)-3-hydroxy-4-((S)-5H-imidazo[5,1-a]isoindol-5-yl)piperidin-1-yl)acetonitrile (75.3 mg, 1%) as a white solid: LCMS (ESI): 348.2 $[M+H]^+$; $^1$HNMR (300 MHz, $CD_3OD$) δ 7.90 (s, 1H), 7.64 (d, J=7.8 Hz, 1H), 7.52 (d, J=7.8 Hz, 1H), 7.48-7.34 (m, 2H), 7.20 (s, 1H), 5.81 (d, J=3.6 Hz, 1H), 4.00-3.91 (m, 1H), 3.65 (s, 2H), 3.19-3.14 (m, 1H), 2.63-2.60 (m, 1H), 2.31-2.03 (m, 3H), 0.94-0.89 (m, 1H), 0.72-0.58 (m, 1H); tR=1.519 min, (Chiralpak AD-3, 0.46×5 cm, 3 um; ethanol:hexane (0.1% DEA)=30:70; 1.0 mL/min). 27c and 27d are enantiomers.

Example 27d: 2-((3S,4S)-3-hydroxy-4-((R)-5H-imidazo[5,1-a]isoindol-5-yl)piperidin-1-yl)acetonitrile (94.8 mg, 1%) as a white solid: LCMS (ESI): 348.2 $[M+H]^+$; tR=2.357 min, (Chiralpak AD-3, 0.46×5 cm, 3 um; ethanol:hexane (0.1% DEA)=30:70; 1.0 mL/min). 27c and 27d are enantiomers.

The absolute configuration of all isomers 14a-d was assigned arbitrarily.

Example 14a: 2-((3S,4R)-4-hydroxy-3-((S)-5H-imidazo[5,1-a]isoindol-5-yl)piperidin-1-yl)acetonitrile (249.8 mg, 1%): LCMS (ESI, m/z): 295.2 $[M+H]^+$; $^1$HNMR (300 MHz, $CD_3OD$) δ 7.93 (s, 1H), 7.66 (d, J=7.5 Hz, 1H), 7.52 (d, J=7.5 Hz, 1H), 7.48-7.34 (m, 2H), 7.22 (s, 1H), 5.82 (d, J=3.0 Hz, 1H), 3.95-3.83 (m, 1H), 3.52-3.33 (m, 2H), 2.92-2.83 (m, 1H), 2.47-2.05 (m, 4H), 1.85-1.73 (m, 1H), 1.48-1.41 (m, 1H); tR=1.156 min, (Chiralpak AD-3, 0.46×5 cm, 3 um; iso-propanol:hexane (0.1% DEA)=30:70; 1.0 mL/min). Example 14a and Example 14b are enantiomers.

Example 14b: 2-((3R,4S)-4-hydroxy-3-((R)-5H-imidazo[5,1-a]isoindol-5-yl)piperidin-1-yl)acetonitrile (241.0 mg, 1%) as an off-white solid: LCMS (ESI, m/z): 295.2 $[M+H]^+$; tR=2.086 min, (Chiralpak AD-3, 0.46×5 cm, 3 um; iso-propanol:hexane (0.1% DEA)=30:70; 1.0 mL/min). Example 14a and Example 14b are enantiomers.

Example 14c: 2-((3R,4S)-4-hydroxy-3-((S)-5H-imidazo[5,1-a]isoindol-5-yl)piperidin-1-yl)acetonitrile (61.9 mg, 1%) as an off-white solid: LCMS (ESI, m/z): 295.1 $[M+H]^+$. $^1$HNMR (400 MHz, $CD_3OD$) δ 7.89 (s, 1H), 7.64 (d, J=7.6 Hz, 1H), 7.49 (d, J=7.6 Hz, 1H), 7.45-7.34 (m, 2H), 7.20 (s, 1H), 5.82 (d, J=4.0 Hz, 1H), 4.37-4.33 (m, 1H), 3.86-3.71 (m, 2H), 2.62-2.50 (m, 2H), 2.27-2.20 (m, 1H), 1.43 (s, 9H), 0.87-0.83 (m, 1H), 0.47-0.42 (m, 1H); tR=4.384 min (Chiralpak AD-3, 0.46×5 cm, 3 um; iso-propanol:hexane (0.1% DEA)=30:70; 1.0 mL/min). Example 14c and Example 14d are enantiomers.

Example 14d: 2-((3S,4R)-4-hydroxy-3-((R)-5H-imidazo[5,1-a]isoindol-5-yl)piperidin-1-yl)acetonitrile (52.4 mg, 1%) as an off-white solid: LCMS (ESI, m/z): 295.1 $[M+H]^+$; tR=6.297 min. (Chiralpak AD-3, 0.46×5 cm, 3 um; iso-propanol:hexane (0.1% DEA)=30:70; 1.0 mL/min). Example 14c and Example 14d are enantiomers.

Example 28: 3-hydroxy-4-(5H-imidazo[5,1-a]isoindol-5-yl)pyrrolidine-1-sulfonamide

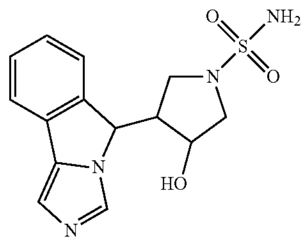 [SMILES: NS(=O)(=O)N1CC(O)C(C2c3ccccc3-c3cncn32)C1]

Step 1: 4-(5H-imidazo[5,1-a]isoindol-5-yl)pyrrolidin-3-ol

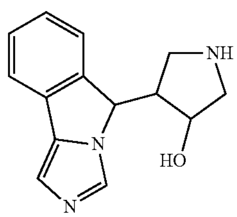 [SMILES: OC1CNCC1C1c2ccccc2-c2cncn21]

To a solution of tert-butyl 3-hydroxy-4-[5H-imidazo[4,3-a]isoindol-5-yl]pyrrolidine-1-carboxylate (2 g, 5.86 mmol) in dichloromethane (25 mL) was added trifluoroacetic acid (5 mL, 67.32 mmol). The resulting solution was stirred for 1 h at 25° C. and then concentrated under vacuum to afford 4-(5H-imidazo[5,1-a]isoindol-5-yl)pyrrolidin-3-ol (3.4 g, crude) as yellow oil: LCMS (ESI, m/z): 242.2 $[M+H]^+$ Step 2: Tert-butyl N-(3-hydroxy-4-[5H-imidazo[4,3-a]isoindol-5-yl]pyrrolidine-1-sulfonyl)carbamate

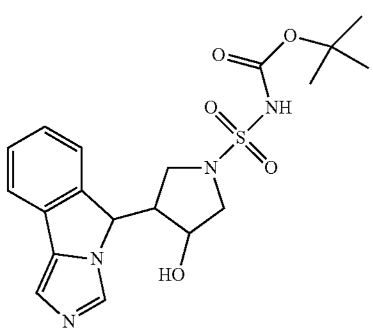 [SMILES: CC(C)(C)OC(=O)NS(=O)(=O)N1CC(O)C(C2c3ccccc3-c3cncn32)C1]

To a solution of 4-[5H-imidazo[4,3-a]isoindol-5-yl]pyrrolidin-3-ol (1.8 g, 7.46 mmol) in dichloromethane (120 mL) was added TEA (2.2 g, 21.74 mmol), 2-methylpropan-2-ol (2.8 g, 37.776 mmol) and [(chlorosulfonyl)imino] methanone (1.6 g, 11.31 mmol). The resulting solution was stirred for 40 min at 25° C. The resulting mixture was concentrated under vacuum. The residue was purified onto a silica gel column with dichloromethane/methanol (15/1) to afford tert-butyl N-(3-hydroxy-4-[5H-imidazo[4,3-a]isoindol-5-yl]pyrrolidine-1-sulfonyl)carbamate (1.45 g, 46%) as yellow oil: LCMS (ESI, m/z): 421.1 $[M+H]^+$ Step 3:
(3R,4R)-3Hydroxy-4-[(5R)-5H-imidazo[4,3-a]isoindol-5-yl]pyrrolidine-1-sulfonamide
(3R,4R)-3-hydroxy-4-[(5S)-5H-imidazo[4,3-a]isoindol-5-yl]pyrrolidine-1-sulfonamide
(3S,4S)-3-hydroxy-4-[(5R)-5H-imidazo[4,3-a]isoindol-5-yl]pyrrolidine-1-sulfonamide
(3S,4S)-3-hydroxy-4-[(5S)-5H-imidazo[4,3-a]isoindol-5-yl]pyrrolidine-1-sulfonamide 28a

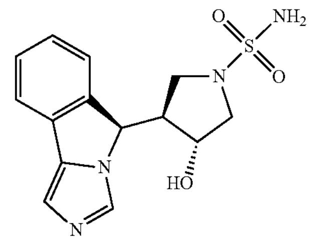

28b

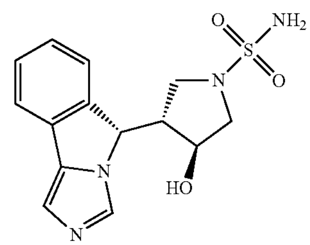

28c

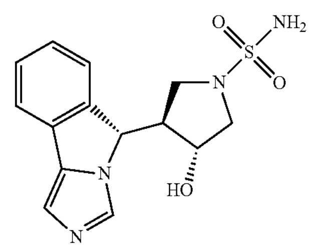

28d

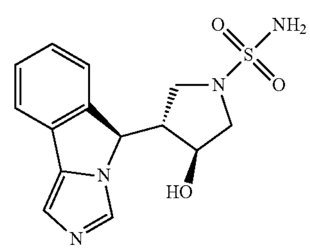

To a solution of tert-butyl N-(3-hydroxy-4-[5H-imidazo [4,3-a]isoindol-5-yl]pyrrolidine-1-sulfonyl)carbamate (400 mg, 0.951 mmol,) in 1,4-dioxane (6 mL) was added hydrogen chloride (2 mL, 65.82 mmol). The resulting solution was stirred for 1.5 h at 25° C. and then concentrated under vacuum. The crude product was purified by Prep-HPLC to afford the two products. These two products were isolated by Chiral separation with the following conditions:

1. Column, Chiralpak IC, 2×25 cm, 5 um; mobile phase: ethanol:hexane=40:40; Detector, uv 254/220 nm; flow rate, 20 mL/min
2. Column, Chiralpak IC, 2×25 cm, 5 um; mobile phase: hexane:ethanol:methanol=50:25:25; Detector, uv 254/220 nm; flow rate, 20 mL/min The absolute configuration of all isomers was assigned arbitrarily.

Example 28a: (3R,4R)-3-hydroxy-4-[(5R)-5H-imidazo[4,3-a]isoindol-5-yl]pyrrolidine-1-sulfonamide (32.1 mg, 11%): LCMS (ESI, m/z): 321 $[M+H]^+$; $^1$HNMR (300 MHz, DMSO) δ 7.98 (s, 1H), 7.62 (d, J=3.7 Hz, 1H), 7.57 (d, J=3.7 Hz, 1H), 7.41 (t, J=3.6 Hz, 1H), 7.33-7.28 (m, 1H), 7.19 (s, 1H), 6.72 (s, 2H), 5.68 (d, J=2.5 Hz, 1H), 5.60 (d, J=0.6 Hz, 1H), 4.48-4.35 (m, 1H), 3.32-3.27 (m, 1H), 2.95-2.80 (m, 3H), 2.18-2.08 (m, 1H); tR=3.129 min, (Chiralpak IB-3, 0.46×5 cm, 3 um, Hex(0.1% DEA):EtOH=70:30, 1.0 mL/min). 28a and 28b are enantiomers Example 28b: (3R,4R)-3-hydroxy-4-[(5S)-5H-imidazo[4,3-a]isoindol-5-yl]pyrrolidine-1-sulfonamide (31.7 mg, 10%): LCMS (ESI, m/z): 321 $[M+H]^+$; tR=4.425 min, (Chiralpak IB-3, 0.46×5 cm, 3 um, Hex(0.1% DEA):EtOH=70:30, 1.0 mL/min). 28a and 28b are enantiomers.

Example 28c: (3S,4S)-3-hydroxy-4-[(5R)-5H-imidazo[4,3-a]isoindol-5-yl]pyrrolidine-1-sulfonamide (15.4 mg, 5%): LCMS (ESI, m/z): 321 $[M+H]^+$; $^1$HNMR (300 MHz, $CD_3OD$) δ 8.01 (s, 1H), 7.64 (d, J=3.7 Hz, 1H), 7.57 (d, J=3.9 Hz, 1H), 7.45 (t, J=3.6 Hz, 1H), 7.37-7.32 (m, 1H), 7.17 (s, 1H), 5.57 (d, J=2.1 Hz, 1H), 4.05 (d, J=2.7 Hz, 1H), 3.52 (dd, J=4.3 Hz, 1H), 3.25-3.16 (m, 2H), 3.06-2.95 (m, 2H); tR=2.173 min, (Chiralpak IB-3, 0.46×5 cm, 3 um, Hex(0.1% DEA):EtOH:MeOH (0.2% IPA)=50:30:20, 1.0 mL/min). 28c and 28d are enantiomers.

Example 28d: (3S,4S)-3-hydroxy-4-[(5S)-5H-imidazo[4,3-a]isoindol-5-yl]pyrrolidine-1-sulfonamide (22.9 mg, 8%): LCMS (ESI, m/z): 321 $[M+H]^+$; tR=4.073 min (Chiralpak IB-3, 0.46×5 cm, 3 um, Hex(0.1% DEA):EtOH:MeOH (0.2% IPA)=50:30:20, 1.0 mL/min). 28c and 28d are enantiomers.

Examples 29: 9-hydroxy-8-(5H-imidazo[5,1-a]isoindol-5-yl)-6,7,8,9-tetrahydro-4H-quinolizin-4-one

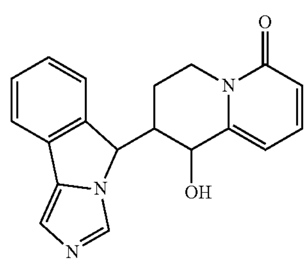 [SMILES: O=c1cccc2n1CCC(C1c3ccccc3-c3cncn31)C2O]

(8R,9R)-9-hydroxy-8-((R)-5H-imidazo[5,1-a]isoindol-5-yl)-6,7,8,9-tetrahydro-4H-quinolizin-4-one
(8R,9R)-9-hydroxy-8-((S)-5H-imidazo[5,1-a]isoindol-5-yl)-6,7,8,9-tetrahydro-4H-quinolizin-4-one
(8R,9S)-9-hydroxy-8-((R)-5H-imidazo[5,1-a]isoindol-5-yl)-6,7,8,9-tetrahydro-4H-quinolizin-4-one
(8R,9S)-9-hydroxy-8-((S)-5H-imidazo[5,1-a]isoindol-5-yl)-6,7,8,9-tetrahydro-4H-quinolizin-4-one
(8S,9R)-9-hydroxy-8-((R)-5H-imidazo[5,1-a]isoindol-5-yl)-6,7,8,9-tetrahydro-4H-quinolizin-4-one (8S,9R)-9-hydroxy-8-((S)-5H-imidazo[5,1-a]isoindol-5-yl)-6,7,8,9-tetrahydro-4H-quinolizin-4-one
(8S,9S)-9-hydroxy-8-((R)-5H-imidazo[5,1-a]isoindol-5-yl)-6,7,8,9-tetrahydro-4H-quinolizin-4-one
(8S,9S)-9-hydroxy-8-((S)-5H-imidazo[5,1-a]isoindol-5-yl)-6,7,8,9-tetrahydro-4H-quinolizin-4-one Examples 29a-f were synthesized from 3,4-dihydro-1H-quinolizine-1,6(2H)-dione using the reaction conditions described for the preparation of example 1. Each example is a single diastereomer. The absolute configuration of all isomers was assigned arbitrarily.

Example 29a: 1-hydroxy-2-(5H-imidazo[5,1-a]isoindol-5-yl)-3,4-dihydro-1H-quinolizin-6(2H)-one: LCMS (ESI) m/z: 320.1 $[M+H]^+$; $^1$H NMR (400 MHz, DMSO-$d_6$) δ 8.00 (s, 1H), 7.63 (d, J=7.6 Hz, 1H), 7.50-7.46 (m, 1H), 7.45 (dd, J=8.3, 6.2 Hz, 1H), 7.40 (t, J=7.4 Hz, 1H), 7.28 (td, J=7.6, 1.2 Hz, 1H), 7.20 (s, 1H), 6.57-6.50 (m, 2H), 6.27 (dt, J=9.0, 1.0 Hz, 1H), 5.74 (d, J=2.2 Hz, 1H), 4.90 (d, J=10.9 Hz, 1H), 4.04 (dt, J=14.1, 6.2 Hz, 1H), 3.43-3.29 (m, 1H), 2.62-2.48 (m, 1H), 1.29-1.18 (m, 1H), 0.88-0.76 (m, 1H); Preparative SFC: Chiralpak AD (250×20 mm, 5 μm), isocratic 70:30-$CO_2$:Methanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 0.999 min.

Example 29b (enantiomer of example 29a): 1-hydroxy-2-(5H-imidazo[5,1-a]isoindol-5-yl)-3,4-dihydro-1H-quinolizin-6(2H)-one: LCMS (ESI) m/z: 320.1 $[M+H]^+$; Preparative SFC: Chiralpak AD (250×20 mm, 5 μm), isocratic 70:30-$CO_2$:Methanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 1.177 min.

Example 29c: 1-hydroxy-2-(5H-imidazo[5,1-a]isoindol-5-yl)-3,4-dihydro-1H-quinolizin-6(2H)-one: LCMS (ESI) m/z: 320.2 $[M+H]^+$; $^1$H NMR (400 MHz, DMSO-$d_6$) δ 7.97 (s, 1H), 7.66-7.58 (m, 2H), 7.43-7.35 (m, 2H), 7.22 (td, J=7.6, 1.1 Hz, 1H), 7.15 (s, 1H), 6.35-6.27 (m, 2H), 6.21 (d, J=4.9 Hz, 1H), 5.49 (d, J=6.4 Hz, 1H), 4.79 (t, J=4.4 Hz, 1H), 4.09 (dt, J=14.5, 5.2 Hz, 1H), 3.61 (ddd, J=15.2, 9.0, 6.8 Hz, 1H), 2.39 (dtd, J=10.3, 6.7, 3.8 Hz, 1H), 2.03-1.89 (m, 2H); Preparative SFC: Chiralpak AD (250×20 mm, 5 μm), isocratic 65:35-$CO_2$:Methanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 1.235 min.

Example 29d (enantiomer of example 29c): 1-hydroxy-2-(5H-imidazo[5,1-a]isoindol-5-yl)-3,4-dihydro-1H-quinolizin-6(2H)-one: LCMS (ESI) m/z: 320.1 $[M+H]^+$; Preparative SFC: Chiralcel OX (150×20 mm, 5 μm), isocratic 60:40-$CO_2$:Methanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 1.458 min.

Example 29e: 1-hydroxy-2-(5H-imidazo[5,1-a]isoindol-5-yl)-3,4-dihydro-1H-quinolizin-6(2H)-one: LCMS (ESI) m/z: 320.1 $[M+H]^+$; $^1$H NMR (400 MHz, DMSO-$d_6$) δ 7.72 (s, 1H), 7.60 (s, 1H), 7.58 (s, 1H), 7.45 (dd, J=9.1, 6.8 Hz, 1H), 7.39 (dd, J=8.1, 7.0 Hz, 1H), 7.30 (td, J=7.5, 1.2 Hz, 1H), 7.10 (s, 1H), 6.51 (s, 1H), 6.42 (dd, J=7.5, 1.3 Hz, 1H), 6.31 (dd, J=9.1, 1.3 Hz, 1H), 5.62 (d, J=2.8 Hz, 1H), 5.01 (d, J=5.2 Hz, 1H), 4.11 (ddd, J=14.3, 5.7, 3.6 Hz, 1H), 3.48-3.38 (m, 1H), 2.85-2.74 (m, 1H), 1.46-1.34 (m, 1H), 1.23 (dtd, J=13.6, 10.7, 5.7 Hz, 1H); Preparative SFC: Chiralcel OX (150×20 mm, 5 μm), isocratic 60:40—$CO_2$:Ethanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 1.595 min.

Example 29f (enantiomer of example 29e): 1-hydroxy-2-(5H-imidazo[5,1-a]isoindol-5-yl)-3,4-dihydro-1H-quinolizin-6(2H)-one: LCMS (ESI) m/z: 320.1 $[M+H]^+$; Preparative SFC: Chiralcel OX (150×20 mm, 5 um), isocratic 60:40-$CO_2$:Ethanol w/0.1% $NH_4OH$, 40° C., 70 ml/min; Analytical SFC: Chiralpak AD (50×4.6 mm, 3 μm), isocratic 25:75-$CO_2$:Ethanol w/0.1% $NH_4OH$, 40° C., 4.0 ml/min, retention time 1.771 min.

Example 30: 4-(8-fluoro-5H-imidazo[5,1-a]isoindol-5-yl)tetrahydrofuran-3-ol

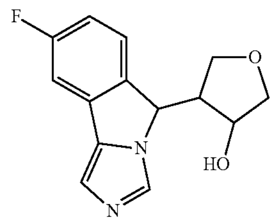 [SMILES: OC1COCC1C1c2ccc(F)cc2-c2cncn21]

The title compound was synthesized by the same method of example 5 and 6

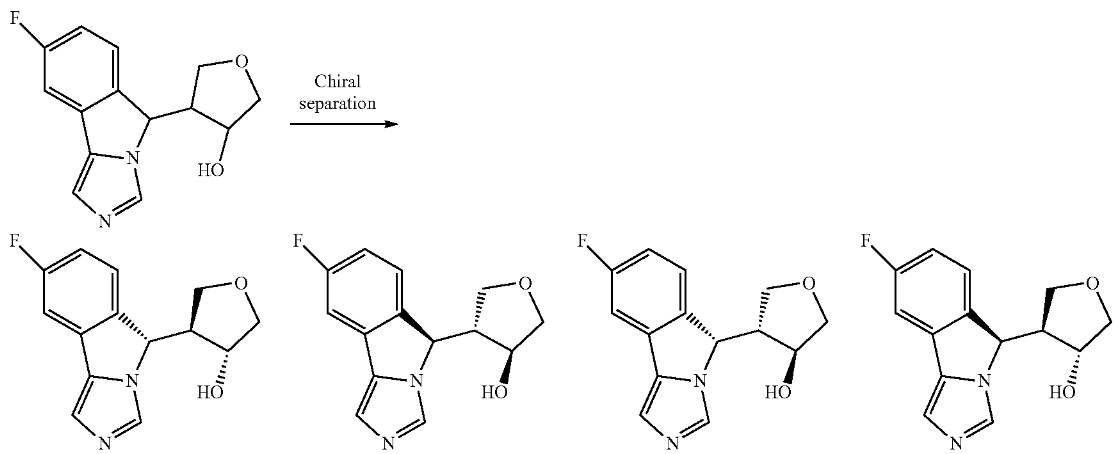

30a 30b 30c 30d

The mixture isolated by Chiral separation with the following condition: Column, ChiralpakAD-H-SL002, 20×250 mm; mobile phase: Hex:IPA=20:20; Detector, uv 254 nm; flow rate, 20 mL/min.

Example 30a: (3R,4S)-4-[(5S)-8-fluoro-5H-imidazo[4,3-a]isoindol-5-yl]oxolan-3-ol: LCMS (ESI, m/z): 261.2 $[M+H]^+$; $^1$HNMR (300 MHz, $CD_3OD$) δ 8.01 (s, 1H), 7.60-7.56 (m, 1H), 7.43-7.39 (m, 1H), 7.25 (s, 1H), 7.07-7.05 (m, 1H), 5.59 (d, J=6 Hz, 1H), 4.29-4.24 (m, 1H), 3.94-3.90 (m, 1H), 3.68-3.62 (m, 1H), 3.57-3.50 (m, 1H), 3.47-3.43 (m, 1H), 3.00-2.89 (m, 1H). tR=5.312 min (Chiralpak AD-3, 0.46×25 cm, 3 um; Hex(0.1% DEA):IPA=80:20; 1 mL/min). 30a and 30b are enantiomers.

Example 30b: (3S,4R)-4-[(5S)-8-fluoro-5H-imidazo[4,3-a]isoindol-5-yl]oxolan-3-ol: LCMS (ESI, m/z): 261.2 $[M+H]^+$; tR=6.457 min (Chiralpak AD-3, 0.46×25 cm, 3 um; Hex(0.1% DEA):IPA=80:20; 1 mL/min). 30a and 30b are enantiomers.

Example 30c: (3S,4R)-4-[(5R)-8-fluoro-5H-imidazo[4,3-a]isoindol-5-yl]oxolan-3-ol: LCMS (ESI, m/z): 261.2 $[M+H]^+$; $^1$HNMR (300 MHz, $CD_3OD$) δ 7.97 (s, 1H), 7.58-7.54 (m, 1H), 7.47-7.41 (m, 1H), 7.22 (s, 1H), 7.10-7.03 (m, 1H), 5.52 (d, J=3.0 Hz, 1H), 4.26-4.20 (m, 1H), 4.09-4.05 (m, 1H), 3.84-3.81 (m, 1H), 3.53-3.51 (m, 2H), 2.90-2.84 (m, 1H). tR=10.558 min (Chiralpak AD-3, 0.46×25 cm, 3 um; Hex(0.1% DEA):IPA=80:20; 1 mL/min). 30c and 30d are enantiomers.

Example 30d: (3R,4S)-4-[(5R)-8-fluoro-5H-imidazo[4,3-a]isoindol-5-yl]oxolan-3-ol: LCMS (ESI, m/z): 261.2 $[M+H]^+$; tR=15.264 min (Chiralpak AD-3, 0.46×25 cm, 3 um; Hex(0.1% DEA):IPA=80:20; 1 mL/min). 30c and 30d are enantiomers.

Example 31: 6-(5H-imidazo[5,1-a]isoindol-5-yl)-5,6,7,8-tetrahydroquinolin-5-ol

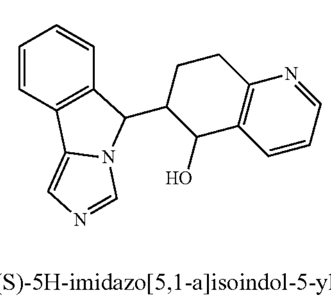

(5R,6S)-6-((S)-5H-imidazo[5,1-a]isoindol-5-yl)-5,6,7,8-tetrahydroquinolin-5-ol (5S,6S)-6-((S)-5H-imidazo[5,1-a]isoindol-5-yl)-5,6,7,8-tetrahydroquinolin-5-ol (5R,6R)-6-((S)-5H-imidazo[5,1-a]isoindol-5-yl)-5,6,7,8-tetrahydroquinolin-5-ol (5S,6R)-6-((S)-5H-imidazo[5,1-a]isoindol-5-yl)-5,6,7,8-tetrahydroquinolin-5-ol (5R,6S)-6-((R)-5H-imidazo[5,1-a]isoindol-5-yl)-5,6,7,8-tetrahydroquinolin-5-ol (5S,6S)-6-((R)-5H-imidazo[5,1-a]isoindol-5-yl)-5,6,7,8-tetrahydroquinolin-5-ol (5R,6R)-6-((R)-5H-imidazo[5,1-a]isoindol-5-yl)-5,6,7,8-tetrahydroquinolin-5-ol (5S,6R)-6-((R)-5H-imidazo[5,1-a]isoindol-5-yl)-5,6,7,8-tetrahydroquinolin-5-ol Step 1:

(E)-6-(2-(1-trityl-1H-imidazol-4-yl)benzylidene)-7,8-dihydroquinolin-5(6H)-one

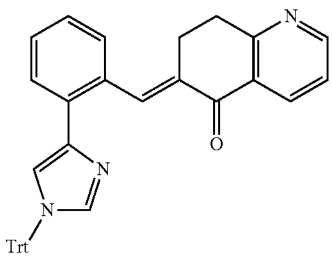

The title compound was synthesized by General Procedure for the Synthesis of Int-2: LCMS (ESI, m/z): 544.2 [M+H]+

Step 2:

(S)-6-((S)-5H-imidazo[5,1-a]isoindol-5-yl)-7,8-dihydroquinolin-5(6H)-one

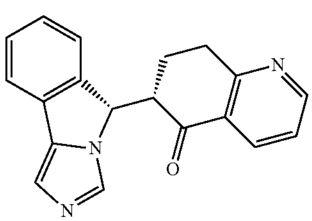

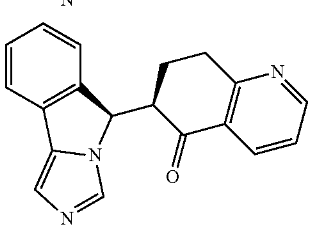

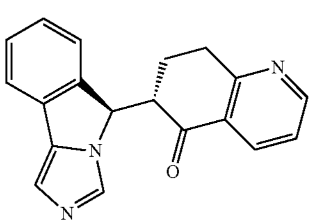

-continued

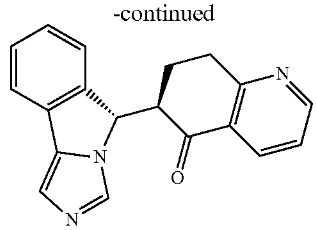

The title compound was synthesized by General Procedure for the Synthesis of Int-3. The two diastereomeric pairs were not separated and used as a mixture for step 3: LCMS (ESI, m/z): 302.1

Step 3:

(5R,6S)-6-((S)-5H-imidazo[5,1-a]isoindol-5-yl)-5,6,7,8-tetrahydroquinolin-5-ol (5S,6S)-6-((S)-5H-imidazo[5,1-a]isoindol-5-yl)-5,6,7,8-tetrahydroquinolin-5-ol (5R,6R)-6-((S)-5H-imidazo[5,1-a]isoindol-5-yl)-5,6,7,8-tetrahydroquinolin-5-ol (5S,6R)-6-((S)-5H-imidazo[5,1-a]isoindol-5-yl)-5,6,7,8-tetrahydroquinolin-5-ol (5R,6S)-6-((R)-5H-imidazo[5,1-a]isoindol-5-yl)-5,6,7,8-tetrahydroquinolin-5-ol (5S,6S)-6-((R)-5H-imidazo[5,1-a]isoindol-5-yl)-5,6,7,8-tetrahydroquinolin-5-ol (5R,6R)-6-((R)-5H-imidazo[5,1-a]isoindol-5-yl)-5,6,7,8-tetrahydroquinolin-5-ol (5S,6R)-6-((R)-5H-imidazo[5,1-a]isoindol-5-yl)-5,6,7,8-tetrahydroquinolin-5-ol 31a-d

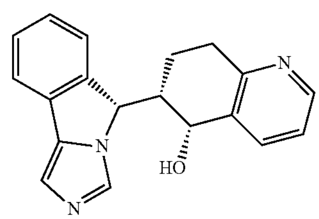 [SMILES: OC1c2cccnc2CCC1C1c2ccccc2-c2cncn21]

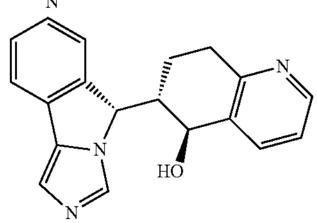

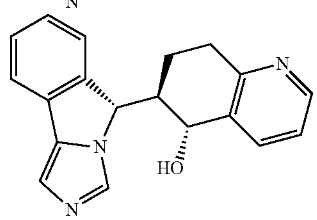

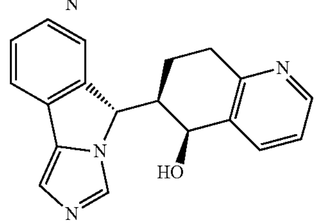

-continued 31e-h

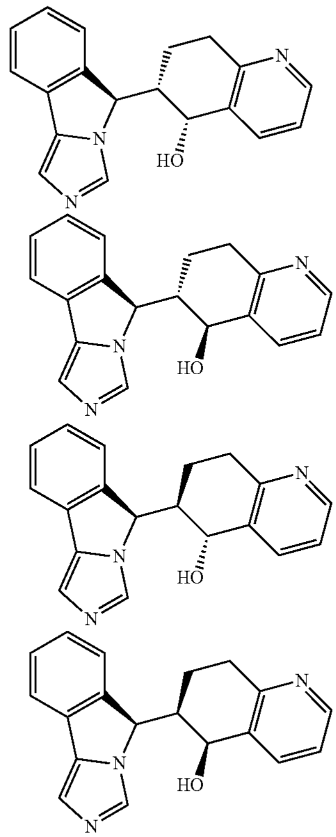

The title compound was synthesized by General Procedure for the Synthesis of Int-5. The product was isolated as a mixture of eight enantiomers which were separated by chiral SFC: LCMS (ESI, m/z): 303.1.

The absolute configuration of isomers 31 a, 31b, 31g and 31h was assigned by X-ray crystallography. The absolute configuration of the rest isomers was assigned arbitrarily.

Example 31a: (5S,6R)-6-((R)-5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.56 (dd, J=4.8, 1.7 Hz, 1H), 8.16 (s, 1H), 7.84 (dd, J=7.8, 1.8 Hz, 1H), 7.49 (dt, J=7.6, 1.0 Hz, 1H), 7.41-7.32 (m, 2H), 7.25 (ddd, J=7.6, 6.2, 1.2 Hz, 2H), 6.51 (s, 1H), 5.50 (s, 1H), 5.15-5.10 (m, 1H), 4.94 (s, 1H), 2.86 (dd, J=17.7, 5.1 Hz, 1H), 2.68 (ddd, J=18.2, 12.6, 6.2 Hz, 1H), 2.41 (dd, J=12.8, 2.6 Hz, 1H), 1.34 (qd, J=12.9, 5.6 Hz, 1H), 1.11-1.03 (m, 1H).

Example 31b: (5R,6R)-6-((S)-5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.42 (ddd, J=4.8, 1.8, 0.7 Hz, 1H), 7.91 (ddd, J=7.8, 1.7, 1.0 Hz, 1H), 7.67 (s, 1H), 7.63-7.52 (m, 1H), 7.50 (dd, J=7.7, 1.0 Hz, 1H), 7.46-7.36 (m, 1H), 7.31-7.21 (m, 1H), 7.23 (s, 1H), 7.18 (dd, J=7.9, 4.8 Hz, 1H), 5.77 (d, J=2.9 Hz, 1H), 4.96 (d, J=10.4 Hz, 1H), 2.89 (dd, J=8.9, 4.0 Hz, 2H), 2.59-2.49 (m, 1H), 1.48-1.28 (m, 2H).

Example 31c: 5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.48-8.43 (m, 1H), 7.99 (d, J=8.1 Hz, 1H), 7.75 (s, 1H), 7.58 (d, J=7.6 Hz, 1H), 7.45-7.38 (m, 1H), 7.35 (d, J=7.4 Hz, 1H), 7.30 (td, J=7.5, 1.1 Hz, 1H), 7.21 (dd, J=7.9, 4.7 Hz, 2H), 5.84 (s, 1H), 5.03 (d, J=10.5 Hz, 1H), 2.84 (dd, J=10.1, 6.2 Hz, 1H), 2.40 (dd, J=13.8, 9.3 Hz, 1H), 1.36-1.09 (m, 3H).

Example 31d: 5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.49 (dd, J=4.8, 1.7 Hz, 1H), 7.98 (s, 1H), 7.64-7.54 (m, 3H), 7.41 (tt, J=7.6, 0.8 Hz, 1H), 7.27 (td, J=7.6, 1.2 Hz, 1H), 7.18 (s, 1H), 7.16 (dd, J=7.7, 4.7 Hz, 1H), 5.37 (d, J=7.6 Hz, 1H), 4.89 (s, 1H), 3.18 (ddd, J=18.0, 5.3, 2.1 Hz, 1H), 2.91 (ddd, J=18.4, 12.0, 6.9 Hz, 1H), 2.41-2.27 (m, 1H), 2.13-2.04 (m, 1H).

Example 31e: 5H-imidazo[5,1-a]isoindol-5-yl)-5,6,7,8-tetrahydroquinolin-5-ol. LCMS (ESI, m/z): 303.1 $[M+H]^+$; $^1$H NMR (500 MHz, Chloroform-d) δ 8.48 (dd, J=4.8, 1.7 Hz, 1H), 7.98 (s, 1H), 7.65-7.52 (m, 3H), 7.45-7.34 (m, 1H), 7.27 (td, J=7.6, 1.2 Hz, 1H), 7.19-7.12 (m, 2H), 5.37 (d, J=7.6 Hz, 1H), 4.89 (d, J=3.0 Hz, 1H), 3.18 (ddd, J=17.9, 5.4, 2.1 Hz, 1H), 2.91 (ddd, J=18.3, 12.0, 6.8 Hz, 2H), 2.42-2.28 (m, 1H), 2.31 (s, 1H), 2.08 (ddt, J=9.1, 7.7, 3.7 Hz, 1H).

Example 31f: 5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.43 (dd, J=4.9, 1.6 Hz, 1H), 8.03-7.97 (m, 1H), 7.74 (s, 1H), 7.57 (d, J=7.5 Hz, 1H), 7.41 (td, J=7.4, 1.1 Hz, 1H), 7.34 (d, J=7.5 Hz, 1H), 7.30 (dd, J=7.4, 1.1 Hz, 1H), 7.20 (dd, J=7.9, 4.7 Hz, 2H), 5.85 (s, 1H), 5.02 (d, J=10.6 Hz, 1H), 2.84 (dt, J=9.7, 4.4 Hz, 1H), 2.41 (t, J=11.5 Hz, 1H), 1.34-1.24 (m, 2H), 1.23-1.07 (m, 1H).

Example 31g: (5S,6S)-6-((R)-5H-imidazo[5,1-a]isoindol-5-yl)-5,6,7,8-tetrahydroquinolin-5-ol. LCMS (ESI, m/z): 303.1 $[M+H]^+$; $^1$H NMR (500 MHz, Chloroform-d) δ 8.56 (dd, J=4.8, 1.7 Hz, 1H), 8.16 (s, 1H), 7.84 (dd, J=7.8, 1.8 Hz, 1H), 7.49 (dt, J=7.6, 1.0 Hz, 1H), 7.41-7.32 (m, 2H), 7.25 (ddd, J=7.6, 6.2, 1.2 Hz, 2H), 6.51 (s, 1H), 5.50 (s, 1H), 5.15-5.10 (m, 1H), 4.94 (s, 1H), 2.86 (dd, J=17.7, 5.1 Hz, 1H), 2.68 (ddd, J=18.2, 12.6, 6.2 Hz, 1H), 2.41 (dd, J=12.8, 2.6 Hz, 1H), 1.34 (qd, J=12.9, 5.6 Hz, 1H), 1.11-1.03 (m, 1H).

Example 31h: (5R,6S)-6-((S)-5H-imidazo[5,1-a]isoindol-5-yl)-5,6,7,8-tetrahydroquinolin-5-ol: LCMS (ESI, m/z): 303.1 $[M+H]^+$; $^1$H NMR (500 MHz, Chloroform-d) δ 8.55 (dd, J=4.8, 1.8 Hz, 1H), 8.17 (s, 1H), 7.84 (dd, J=7.8, 1.8 Hz, 1H), 7.49 (dt, J=7.6, 1.0 Hz, 1H), 7.40-7.32 (m, 2H), 7.30-7.18 (m, 2H), 6.52 (s, 1H), 5.50 (d, J=1.7 Hz, 1H), 5.12 (dt, J=4.0, 2.0 Hz, 1H), 2.86 (dd, J=17.7, 5.3 Hz, 1H), 2.68 (ddd, J=18.2, 12.6, 6.2 Hz, 1H), 2.42 (dd, J=12.7, 2.6 Hz, 1H), 1.41-1.24 (m, 1H), 1.06 (dd, J=13.4, 6.0 Hz, 1H).

Example 32: 4-(5H-imidazo[5,1-a]isoindol-5-yl) tetrahydrofuran-3-amine

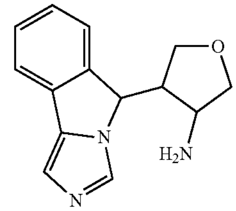 [SMILES: NC1COCC1C1c2ccccc2-c2cncn21]

(3S,4S)-4-((R)-5H-imidazo[5,1-a]isoindol-5-yl)-tetrahydrofuran-3-amine (3R,4R)-4-((S)-5H-imidazo[5,1-a]isoindol-5-yl)-tetrahydrofuran-3-amine (3R,4R)-4-((R)-5H-imidazo[5,1-a]isoindol-5-yl)-tetrahydrofuran-3-amine (3S,4S)-4-((S)-5H-imidazo[5,1-a]isoindol-5-yl)-tetrahydrofuran-3-amine Inter-4 was synthesized by the same method of example 30.

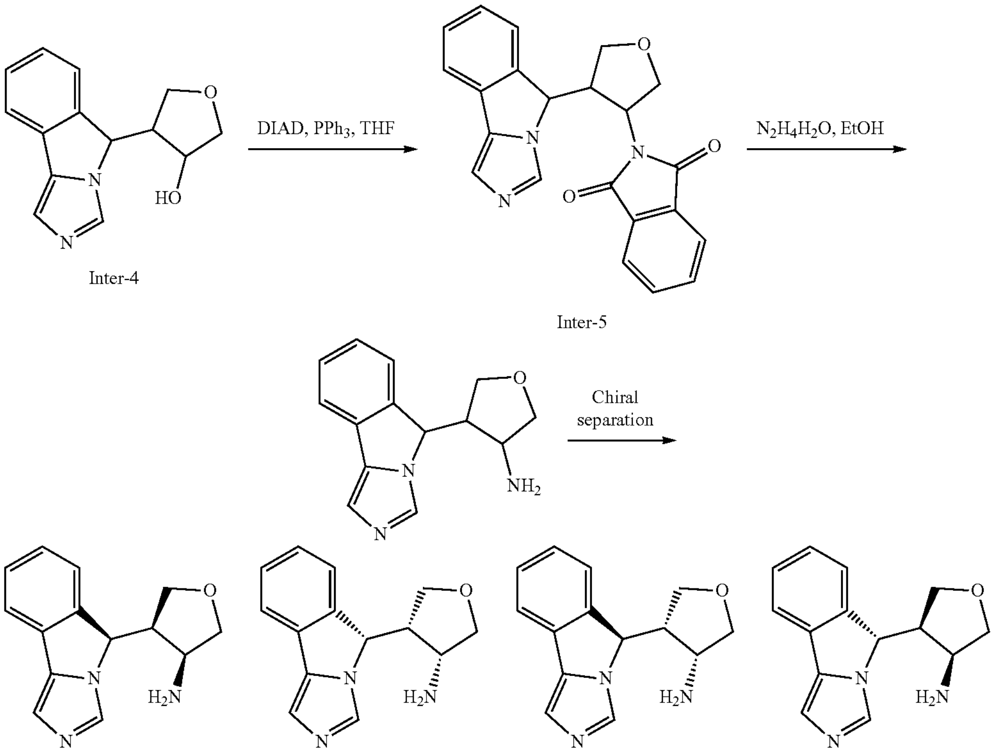

Inter-4

Inter-5

32a 32b 32c 32d

Step 1: 4-[5H-imidazo[4,3-a]isoindol-5-yl]oxolan-3-ol

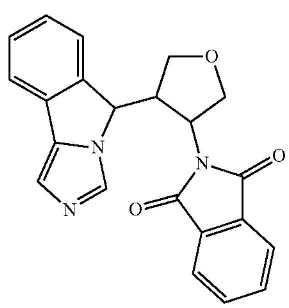 [SMILES: O=C1c2ccccc2C(=O)N1C1COCC1C1c2ccccc2-c2cncn21]

To a solution of 4-[5H-imidazo[4,3-a]isoindol-5-yl]oxolan-3-ol (2 g, 8.255 mmol) in tetrahydrofuran/dichloromethane (100/10 mL) was added diisopropyl azodicarboxylate (1.94 mL, 9.786 mmol), triphenylphosphine (2.5 g, 9.532 mmol) and 2,3-dihydro-1H-isoindole-1,3-dione (1.45 g, 9.855 mmol) under nitrogen, and then stirred for 5 h at room temperature. The resulting mixture was concentrated under vacuum and the residue was purified by a silica gel column with dichloromethane/ethyl acetate (1:1) to afford 2-(4-[5H-imidazo[4,3-a]isoindol-5-yl]oxolan-3-yl)-2,3-dihydro-1H-isoindole-1,3-dione (1.2 g, 39%) as a yellow solid. LCMS (ES, m/z): 372 $[M+H]^+$.

Step 2: (3S,4S)-4-((R)-5H-imidazo[5,1-a]isoindol-5-yl)-tetrahydrofuran-3-amine (3R,4R)-4-((S)-5H-imidazo[5,1-a]isoindol-5-yl)-tetrahydrofuran-3-amine (3R,4R)-4-((R)-5H-imidazo[5,1-a]isoindol-5-yl)-tetrahydrofuran-3-amine (3S,4S)-4-((S)-5H-imidazo[5,1-a]isoindol-5-yl)-tetrahydrofuran-3-amine 32a

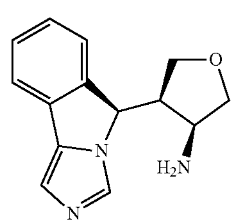

-continued

32b

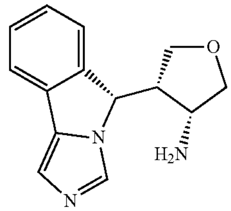

32c

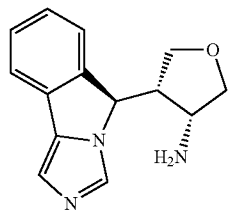

32d

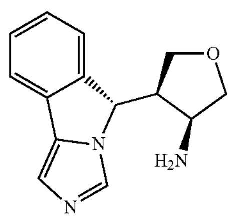

A solution of 2-(4-[5H-imidazo[4,3-a]isoindol-5-yl]oxolan-3-yl)-2,3-dihydro-1H-isoindole-1,3-dione (1.2 g, 3.231 mmol) and hydrazinium hydrate (5 mL, 102.876 mmol, 31.839 equiv) in ethanol (50 mL) was stirred for 5 h at 80° C. The resulting mixture was concentrated under vacuum. The residue was purified onto a silica gel column with dichloromethane/methanol (20:1). The crude product was purified by Prep-HPLC and further isolated by Chiral separation with the following conditions:

1. Column: Lux 5 u Celluloes-3,AXIA Packed, 250×21.2 mm; Mobile Phase A:Hex (0.1% DEA)-HPLC, Mobile Phase B: EtOH-HPLC; Flow rate: 20 mL/min; Gradient: 30 B to 30 B in 22 min; 254/220 nm;
2. Column: Lux 5 u Celluloes-3,AXIA Packed, 250×21.2 mm; Mobile Phase A:Hex (0.1% DEA)-HPLC, Mobile Phase B: EtOH-HPLC; Flow rate: 20 mL/min; Gradient: 30 B to 30 B in 17 min; 254/220 nm.

The absolute configuration of all isomers was assigned arbitrarily.

Example 32a: (3S,4S)-4-[(5R)-5H-imidazo[4,3-a]isoindol-5-yl]oxolan-3-amine (86.7 mg, 11%): LCMS (ESI, m/z): 242 $[M+H]^+$; $^1$H NMR (300 MHz, Chloroform-d) δ 7.70 (s, 1H), 7.66 (d, J=7.6 Hz, 1H), 7.56 (d, J=7.5 Hz, 1H), 7.40 (t, J=7.5 Hz, 1H), 7.32-7.24 (m, 2H), 7.19 (s, 1H), 5.50 (d, J=9.0 Hz, 1H), 4.14 (t, J=8.3 Hz, 1H), 4.02 (dd, J=9.6, 8.2 Hz, 1H), 3.93 (dd, J=8.9, 4.0 Hz, 1H), 3.84-3.72 (m, 2H), 2.49 (qd, J=9.1, 5.7 Hz, 1H); tR=3.249 min (Lux Cellulose-3, 0.46×5 cm, 3 um, Hex(0.1% DEA):EtOH=70:30, 1.0 mL/min). 32a and 32b are enantiomers.

Example 32b: (3R,4R)-4-[(5S)-5H-imidazo[4,3-a]isoindol-5-yl]oxolan-3-amine (78.8 mg, 10%): LCMS (ESI, m/z): 242 $[M+H]^+$; tR=5.074 min (Lux Cellulose-3, 0.46×5 cm, 3 um, Hex(0.1% DEA):EtOH=70:30, 1.0 mL/min). 32a and 32b are enantiomers.

Example 32c: (3R,4R)-4-[(5R)-5H-imidazo[4,3-a]isoindol-5-yl]oxolan-3-amine (61.4 mg, 8%): LCMS (ESI, m/z): 242 $[M+H]^+$; $^1$H NMR (300 MHz, Chloroform-d) δ 8.10 (s, 1H), 7.57 (d, J=7.6 Hz, 1H), 7.39 (t, J=7.4 Hz, 1H), 7.28-7.14 (m, 3H), 5.43 (d, J=10.8 Hz, 1H), 4.20 (dd, J=9.5, 4.7 Hz, 2H), 3.93-3.76 (m, 2H), 3.71 (dd, J=5.4, 3.2 Hz, 1H), 2.47-2.28 (m, 1H); tR=3.584 min (Lux Cellulose-3, 0.46×5 cm, 3 um, Hex(0.1% DEA):EtOH=70:30, 1.0 mL/min). 32c and 32d are enantiomers.

Example 32d: (3S,4S)-4-[(5S)-5H-imidazo[4,3-a]isoindol-5-yl]oxolan-3-amine (70.8 mg, 9%): LCMS (ESI, m/z): 242 $[M+H]^+$; tR=4.409 min (Lux Cellulose-3, 0.46×5 cm, 3 um, Hex(0.1% DEA):EtOH-70:30, 1.0 mL/min). 32c and 32d are enantiomers.

Example 33 and 34: 8-fluoro-5H-imidazo[5,1-a]isoindol-5-yl)-tetrahydro-2H-pyran-3-ol and 8-fluoro-5H-imidazo[5,1-a]isoindol-5-yl)-tetrahydro-2H-pyran-4-ol

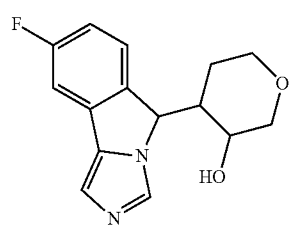

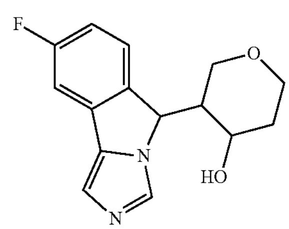

The title compound was synthesized by the same method of example 5 and 6

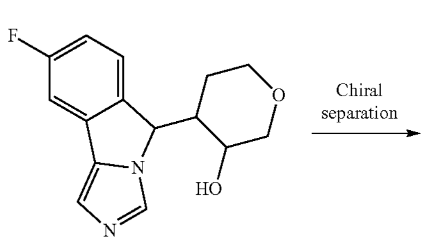

-continued

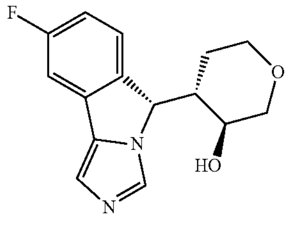
33a

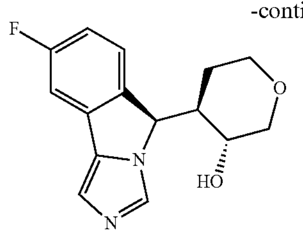
33b

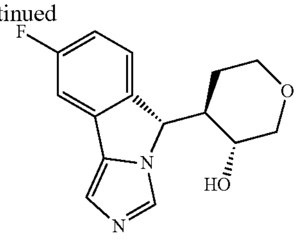
33c

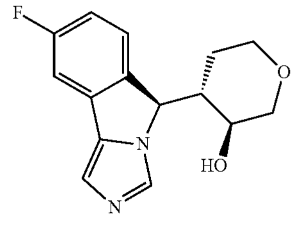
33d

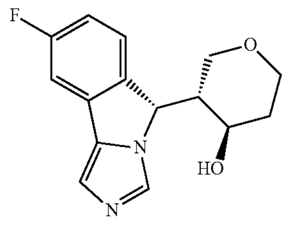
34a

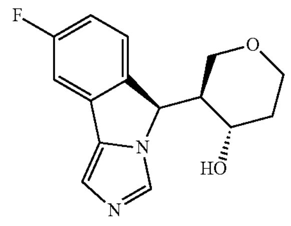
34b

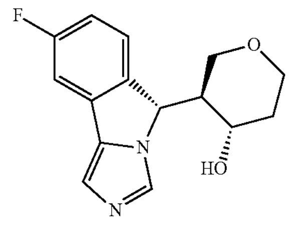
34c

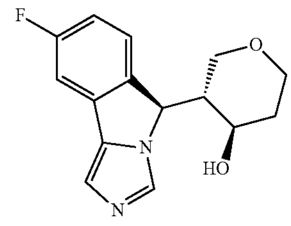
34d

The crude product was purified by Prep-HPLC and further isolated by Chiral separation with the following conditions:

1. Column: CHIRALPAK-AD-H-SL002, 20×250 mm; Mobile Phase A:Hex(0.1% DEA)-HPLC, Mobile Phase B: EtOH-HPLC; Flow rate: 20 mL/min; Gradient: 30 B to 30 B in 13.5 min; 254/220 nm;
2. Column: Lux 5 u Celluloes-3,AXIA Packed, 250×21.2 mm; Mobile Phase A:EtOH (0.1% DEA)-HPLC, Mobile Phase B: EtOH-HPLC; Flow rate: 20 mL/min; Gradient: 30 B to 30 B in 16 min; 254/220 nm;
3. Column: Chiralpak IC, 2×25 cm, 5 um; Mobile Phase A:Hex(0.1% DEA)-HPLC, Mobile Phase B: EtOH-HPLC; Flow rate: 20 mL/min; Gradient: 20 B to 20 B in 16 min; 254/220 nm.

The absolute configuration of all isomers was assigned arbitrarily.

Example 33a: (3R,4R)-4-((S)-8-fluoro-5H-imidazo[5,1-a]isoindol-5-yl)-tetrahydro-2H-pyran-3-ol: LCMS (ESI, m/z): 274.0 $[M+H]^+$; $^1$HNMR (300 MHz, $CD_3OD$) δ 7.95 (s, 1H), 7.49 (dd, J=8.4 Hz, 4.8 Hz, 1H), 7.41 (dd, J=8.8 Hz, 2.4 Hz, 1H), 7.25 (s, 1H), 7.12-7.07 (m, 1H), 5.80 (s, 1H), 4.05 (dd, J=10.8 Hz, 4.8 Hz, 1H), 3.88-3.82 (m, 1H), 3.70 (dd, J=11.2 Hz, 4.8 Hz, 1H), 3.28-3.16 (m, 2H), 2.27 (t, J=2.0 Hz, 1H), 0.86 (d, J=7.6 Hz, 1H), 0.71-0.60 (m, 1H). tR=5.772 min (CHIRALCEL AD-3, 0.46×15 cm, 3 um; Hex(0.1% DEA):EtOH=70:30, 1.0 ml/min). 33a and 33b are enantiomers.

Example 33b: (3S,4S)-3-((S)-8-fluoro-5H-imidazo[5,1-a]isoindol-5-yl)-tetrahydro-2H-pyran-4-ol: LCMS (ESI, m/z): 274.0 $[M+H]^+$; tR=6.618 min (CHIRALCEL AD-3, 0.46×15 cm, 3 um; Hex(0.1% DEA):EtOH=70:30, 1.0 ml/min). 33a and 33b are enantiomers.

Example 33c: (3S,4S)-4-((S)-8-fluoro-5H-imidazo[5,1-a]isoindol-5-yl)-tetrahydro-2H-pyran-3-ol: LCMS (ESI, m/z): 274.0 $[M+H]^+$; $^1$HNMR (300 MHz, $CD_3OD$) δ 7.95 (s, 1H), 7.56 (dd, J=8.4 Hz, 4.8 Hz, 1H), 7.42 (dd, J=8.4 Hz, 2.4 Hz, 1H), 7.22 (s, 1H), 7.11-7.06 (m, 1H), 5.79 (s, 1H), 3.99 (dd, J=10.4 Hz, 4.8 Hz, 1H), 3.87-3.80 (m, 1H), 3.72 (d, J=6.8 Hz, 1H), 3.29-3.22 (m, 1H), 3.15 (t, J=10.4 Hz, 1H), 2.43-2.40 (m, 1H), 0.77-0.73 (m, 2H). tR=2.288 min (CHIRALCEL Lux Cellulose-3, 0.46×10 cm; 3 um, Hex(0.1% DEA):EtOH=70:30, 1.0 ml/min). 33c and 33d are enantiomers.

Example 33d: (3S,4S)-4-((R)-8-fluoro-5H-imidazo[5,1-a]isoindol-5-yl)-tetrahydro-2H-pyran-3-ol: LCMS (ESI, m/z): 274.0 $[M+H]^+$; $^1$HNMR (300 MHz, $CD_3OD$). tR=4.721 min (CHIRALCEL Lux Cellulose-3, 0.46×10 cm; 3 um, Hex (0.1% DEA):EtOH=70:30, 1.0 ml/min). 33c and 33d are enantiomers.

Example 34a: (3R,4R)-3-((S)-8-fluoro-5H-imidazo[5,1-a]isoindol-5-yl)-tetrahydro-2H-pyran-4-ol: LCMS (ESI, m/z): 274.0 $[M+H]^+$; $^1$HNMR (300 MHz, $CD_3OD$) δ 8.0 (s, 1H), 7.59 (dd, J=8.4 Hz, 4.8 Hz, 1H), 7.42 (dd, J=8.8 Hz, 2.4 Hz, 1H), 7.23 (s, 1H), 7.11-7.06 (m, 1H), 5.76 (s, 1H), 3.98-3.91 (m, 1H), 3.88 (dd, J=11.6 Hz, 4.8 Hz, 1H), 3.34-3.26 (m 1H), 3.08 (dd, J=11.6 Hz, 4.0 Hz, 1H), 2.71 (t, J=11.2 Hz, 1H), 2.47-2.43 (m, 1H), 1.97 (dd, J=12.8 Hz, 2.4 Hz, 1H), 1.71-1.67 (m, 1H). tR=2.133 min (CHIRALCEL AD-3, 0.46×5 cm; 3 um, Hex(0.1% DEA):EtOH=70:30, 1.0 ml/min). 34a and 34b are enantiomers.

Example 34b: (3S,4S)-3-((R)-8-fluoro-5H-imidazo[5,1-a]isoindol-5-yl)-tetrahydro-2H-pyran-4-ol: LCMS (ESI, m/z): 274.0 $[M+H]^+$; tR=3.330 min (CHIRALCEL AD-3, 0.46×5 cm; 3 um, Hex(0.1% DEA):EtOH=70:30, 1.0 ml/min). 34a and 34b are enantiomers.

Example 34c: (3R,4R)-4-((R)-8-fluoro-5H-imidazo[5,1-a]isoindol-5-yl)-tetrahydro-2H-pyran-3-ol: LCMS (ESI, m/z): 274.0 $[M+H]^+$; $^1$HNMR (300 MHz, $CD_3OD$) δ 7.9 (s, 1H), 7.53 (dd, J=8.4 Hz, 4.8 Hz, 1H), 7.41 (dd, J=8.4 Hz, 2.4 Hz, 1H), 7.25 (s, 1H), 7.14-7.09 (m, 1H), 5.80 (s, 1H), 4.07-4.03 (m, 1H), 3.90 (dd, J=12.0 Hz, 4.8 Hz, 1H), 3.33-3.29 (m1H), 3.16 (dd, J=12.0 Hz, 4.4 Hz, 1H), 2.51 (t, J=11.2 Hz, 1H), 2.34-2.31 (m, 1H), 2.06 (dd, J=10.4 Hz, 2.4 Hz, 1H), 1.75-1.71 (m, 1H). tR=4.004 min (CHIRALCEL AD-3, 0.46×15 cm; 3 um, Hex(0.1% DEA):EtOH=70:30, 1.0 ml/min). 34c and 34d are enantiomers.

Example 34d: (3R,4R)-3-((R)-8-fluoro-5H-imidazo[5,1-a]isoindol-5-yl)-tetrahydro-2H-pyran-4-ol: LCMS (ESI, m/z): 274.0 $[M+H]^+$; $^1$HNMR (300 MHz, $CD_3OD$). tR=3.340 min tR=4.489 min (CHIRALCEL AD-3, 0.46×15 cm; 3 um, Hex(0.1% DEA):EtOH=70:30, 1.0 ml/min). 34c and 34d are enantiomers.

Example 35: 2-(5H-imidazo[5,1-a]isoindol-5-yl)-1-methylcyclobutan-1-ol (1R,2R)-2-((S)-5H-imidazo[5,1-a]isoindol-5-yl)-1-methylcyclobutan-1-ol
(1S,2S)-2-((R)-5H-imidazo[5,1-a]isoindol-5-yl)-1-methylcyclobutan-1-ol
(1R,2S)-2-((S)-5H-imidazo[5,1-a]isoindol-5-yl)-1-methylcyclobutan-1-ol
(1S,2R)-2-((R)-5H-imidazo[5,1-a]isoindol-5-yl)-1-methylcyclobutan-1-ol Step 1: (E)-2-(2-(1-trityl-1H-imidazol-4-yl)benzylidene)cyclobutan-1-one

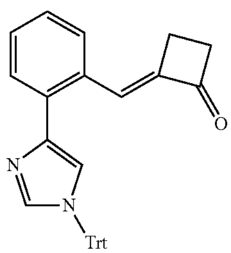

To a solution of 2-[1-(triphenylmethyl)-1H-imidazol-4-yl]benzaldehyde aldehyde (3.0 g, 7.24 mmol) and cyclobutanone (1.01 g, 14.47 mmol) in anhydrous ethanol (30 mL) was added piperidine (0.72 mL, 7.24 mmol) and the resulting mixture was stirred at 90° C. for 6 hr. The mixture was cooled on ice bath and the reaction was quenched by saturated $NH_4Cl$ (30 mL). The aqueous phase was extracted with DCM (3×20 mL) and the organic phases were combined, dried over $Na_2SO_4$, and concentrated. The product was separated by CombiFlash to afford afford (E)-2-(2-(1-trityl-1H-imidazol-4-yl)benzylidene)cyclobutan-1-one as yellow oil: LCMS (ESI, m/z): 466 $[M+H]^+$.

Step 2: 2-(5H-imidazo[5,1-a]isoindol-5-yl)cyclobutan-1-one

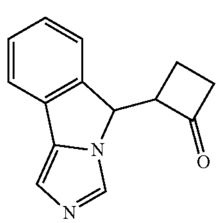 [SMILES: O=C1CCC1C1c2ccccc2-c2cncn21]

To (E)-2-(2-(1-trityl-1H-imidazol-4-yl)benzylidene)cyclobutan-1-one was added MeOH (20 mL) and AcOH (5 mL). The resulting mixture was stirred at 90° C. for 2 hr. Solvent was removed under reduced pressure. The reaction was quenched by 30 mL saturated $NaHCO_3$ solution (30 mL) and the mixture was extracted with dichloromethane (3×20 mL). The organic layer was combined, washed with brine and water, and dried by anhydrous $Na_2SO_4$. The crude product was separated by CombiFlash to afford 2-(5H-imidazo[5,1-a]isoindol-5-yl)cyclobutan-1-one as light yellow oil: LCMS (ESI, m/z): 225.3 $[M+H]^+$.

Step 3:
(1R,2R)-2-((S)-5H-imidazo[5,1-a]isoindol-5-yl)-1-methylcyclobutan-1-ol
(1S,2S)-2-((R)-5H-imidazo[5,1-a]isoindol-5-yl)-1-methylcyclobutan-1-ol
(1R,2S)-2-((S)-5H-imidazo[5,1-a]isoindol-5-yl)-1-methylcyclobutan-1-ol
(1S,2R)-2-((R)-5H-imidazo[5,1-a]isoindol-5-yl)-1-methylcyclobutan-1-ol 35a

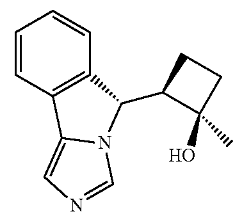

35b

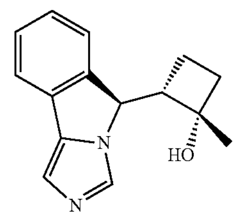

35c

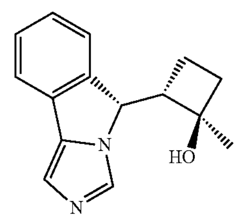

35d

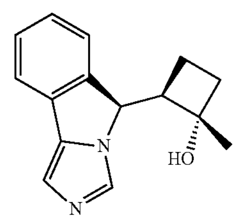

To a solution of 2-(5H-imidazo[5,1-a]isoindol-5-yl)cyclobutan-1-one (0.41 g, 1.83 mmol) in anhydrous THF (10 mL) was added methyl magnesium bromide (0.73 mL, 2.19 mmol) drop-wise at 0° C. and the solution was stirred at 0° C. for additional 1 hrs. The reaction was quenched by 30 mL saturated $NH_4Cl$ solution (10 mL) and the mixture was extracted with dichloromethane (3×10 mL). The organic layer was combined, washed with brine and water, and dried by anhydrous $Na_2SO_4$. The crude product was purified by Combi-Flash and further isolated by chiral separation to afford 4 isomers as white solid. The crude product was purified by Combi-Flash and further isolated by chiral separation to afford 6 isomers as white solid. The absolute configuration of all isomers was assigned arbitrarily.

Example 35a: (1R,2R)-2-((S)-5H-imidazo[5,1-a]isoindol-5-yl)-1-methylcyclobutan-1-ol: LCMS (ESI, m/z): 241.3 $[M+H]^+$. $^1$H NMR (500 MHz, Chloroform-d) δ 8.02 (t, J=0.7 Hz, 1H), 7.52 (dt, J=7.6, 1.1 Hz, 1H), 7.48 (dq, J=7.6, 0.9 Hz, 1H), 7.34 (tdd, J=7.6, 1.1, 0.6 Hz, 1H), 7.22 (td, J=7.6, 1.2 Hz, 1H), 7.19 (s, 1H), 5.46 (d, J=5.9 Hz, 1H), 2.65-2.56 (m, 1H), 2.10-1.96 (m, 2H), 1.82 (dtd, J=11.9, 8.8, 6.2 Hz, 1H), 1.70-1.63 (m, 1H), 1.51 (d, J=0.5 Hz, 3H).

Example 35b: (1S,2S)-2-((R)-5H-imidazo[5,1-a]isoindol-5-yl)-1-methylcyclobutan-1-ol: LCMS (ESI, m/z): 241.3 [M+H]$^+$. $^1$H NMR (500 MHz, Chloroform-d) δ 8.02 (t, J=0.7 Hz, 1H), 7.52 (dt, J=7.6, 1.1 Hz, 1H), 7.48 (dq, J=7.6, 0.9 Hz, 1H), 7.34 (tdd, J=7.6, 1.1, 0.6 Hz, 1H), 7.22 (td, J=7.6, 1.2 Hz, 1H), 7.19 (s, 1H), 5.46 (d, J=5.9 Hz, 1H), 2.65-2.56 (m, 1H), 2.11-1.97 (m, 2H), 1.82 (dtd, J=11.9, 8.8, 6.2 Hz, 1H), 1.66 (ddt, J=11.9, 10.4, 6.7 Hz, 1H), 1.51 (d, J=0.5 Hz, 3H).

Example 35c: (1R,2S)-2-((S)-5H-imidazo[5,1-a]isoindol-5-yl)-1-methylcyclobutan-1-ol: LCMS (ESI, m/z): 241.3 [M+H]$^+$. $^1$H NMR (500 MHz, Chloroform-d) δ 8.00 (s, 1H), 7.52 (dt, J=7.4, 1.0 Hz, 1H), 7.37-7.32 (m, 2H), 7.18 (td, J=7.6, 1.2 Hz, 1H), 7.15 (s, 1H), 5.43 (d, J=10.2 Hz, 1H), 2.46-2.26 (m, 2H), 2.19-2.03 (m, 3H), 1.40 (s, 3H).

Example 35d: (1S,2R)-2-((R)-5H-imidazo[5,1-a]isoindol-5-yl)-1-methylcyclobutan-1-ol: LCMS (ESI, m/z): 241.3 [M+H]$^+$. $^1$H NMR (500 MHz, Chloroform-d) δ 8.00 (s, 1H), 7.52 (dt, J=7.5, 1.1 Hz, 1H), 7.39-7.31 (m, 2H), 7.18 (td, J=7.6, 1.2 Hz, 1H), 7.15 (s, 1H), 5.43 (d, J=10.2 Hz, 1H), 2.46-2.26 (m, 2H), 2.21-2.02 (m, 3H), 1.40 (s, 3H).

Example 36: 2-(5H-imidazo[5,1-a]isoindol-5-yl)-6-(methylsulfonyl)-1,2,3,4-tetrahydronaphthalen-1-ol

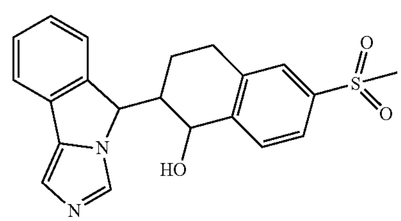 [SMILES: CS(=O)(=O)c1ccc2c(c1)CCC(C1c3ccccc3-c3cncn31)C2O]

(1S,2R)-2-((S)-5H-imidazo[5,1-a]isoindol-5-yl)-6-(methylsulfonyl)-1,2,3,4-tetrahydronaphthalen-1-ol (1S,2S)-2-((S)-5H-imidazo[5,1-a]isoindol-5-yl)-6-(methylsulfonyl)-1,2,3,4-tetrahydronaphthalen-1-ol (1R,2S)-2-((S)-5H-imidazo[5,1-a]isoindol-5-yl)-6-(methylsulfonyl)-1,2,3,4-tetrahydronaphthalen-1-ol (1R,2R)-2-((R)-5H-imidazo[5,1-a]isoindol-5-yl)-6-(methylsulfonyl)-1,2,3,4-tetrahydronaphthalen-1-ol (1R,2R)-2-((S)-5H-imidazo[5,1-a]isoindol-5-yl)-6-(methylsulfonyl)-1,2,3,4-tetrahydronaphthalen-1-ol (1R,2S)-2-((R)-5H-imidazo[5,1-a]isoindol-5-yl)-6-(methylsulfonyl)-1,2,3,4-tetrahydronaphthalen-1-ol (1R,2S)-2-((R)-5H-imidazo[5,1-a]isoindol-5-yl)-6-(methylsulfonyl)-1,2,3,4-tetrahydronaphthalen-1-ol (1S,2R)-2-((R)-5H-imidazo[5,1-a]isoindol-5-yl)-6-(methylsulfonyl)-1,2,3,4-tetrahydronaphthalen-1-ol

Step 1: (E)-6-(methylthio)-2-(2-(1-trityl-1H-imidazol-4-yl)benzylidene)-3,4-dihydronaphthalen-1(2H)-one

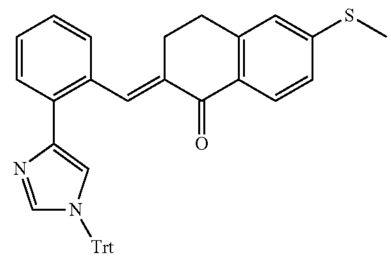

The title compound was synthesized by General Procedure for the Synthesis of Int-2. LCMS (ESI, m/z): 589.3 [M+H]

Step 2: 2-(5H-imidazo[5,1-a]isoindol-5-yl)-6-(methylthio)-3,4-dihydronaphthalen-1(2H)-one

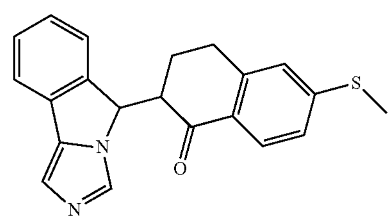 [SMILES: CSc1ccc2c(c1)CCC(C1c3ccccc3-c3cncn31)C2=O]

The title compound was synthesized by General Procedure for the Synthesis of Int-3. LCMS (ESI, m/z): 347.19 [M+H]$^+$

Step 3: 2-(5H-imidazo[5,1-a]isoindol-5-yl)-6-(methylthio)-1,2,3,4-tetrahydronaphthalen-1-ol

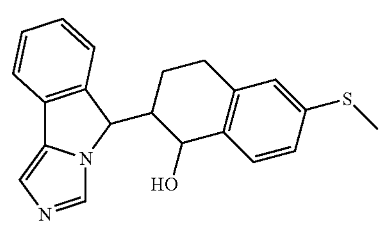 [SMILES: CSc1ccc2c(c1)CCC(C1c3ccccc3-c3cncn31)C2O]

The title compounds were synthesized by General Procedure for the Synthesis of Int-5: LCMS (ESI, m/z): 349.1

Step 4:

(1S,2R)-2-((S)-5H-imidazo[5,1-a]isoindol-5-yl)-6-(methylsulfonyl)-1,2,3,4-tetrahydronaphthalen-1-ol (1S,2S)-2-((S)-5H-imidazo[5,1-a]isoindol-5-yl)-6-(methylsulfonyl)-1,2,3,4-tetrahydronaphthalen-1-ol (1R,2S)-2-((S)-5H-imidazo[5,1-a]isoindol-5-yl)-6-(methylsulfonyl)-1,2,3,4-tetrahydronaphthalen-1-ol (1R,2R)-2-((R)-5H-imidazo[5,1-a]isoindol-5-yl)-6-(methylsulfonyl)-1,2,3,4-tetrahydronaphthalen-1-ol (1R,2R)-2-((S)-5H-imidazo[5,1-a]isoindol-5-yl)-6-(methylsulfonyl)-1,2,3,4-tetrahydronaphthalen-1-ol (1R,2S)-2-((R)-5H-imidazo[5,1-a]isoindol-5-yl)-6-(methylsulfonyl)-1,2,3,4-tetrahydronaphthalen-1-ol (1R,2S)-2-((R)-5H-imidazo[5,1-a]isoindol-5-yl)-6-(methylsulfonyl)-1,2,3,4-tetrahydronaphthalen-1-ol (1S,2R)-2-((R)-5H-imidazo[5,1-a]isoindol-5-yl)-6-(methylsulfonyl)-1,2,3,4-tetrahydronaphthalen-1-ol

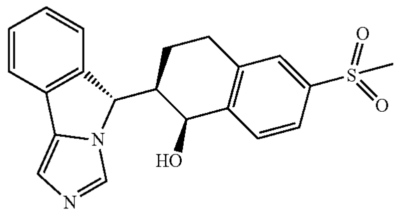

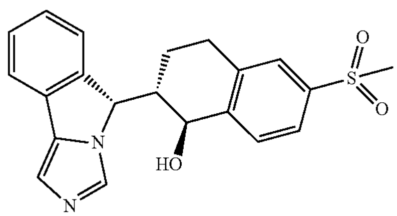

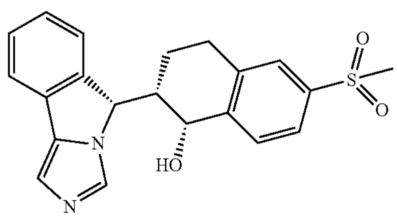

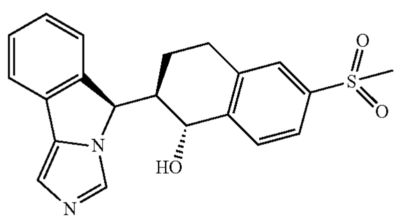

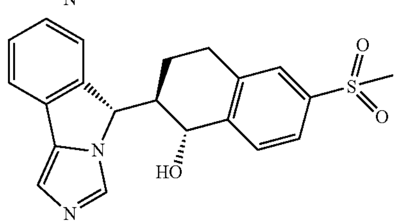

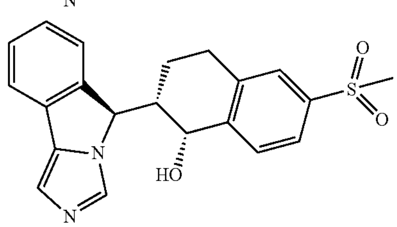

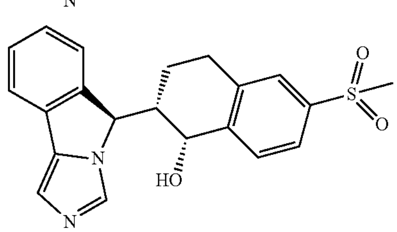

-continued

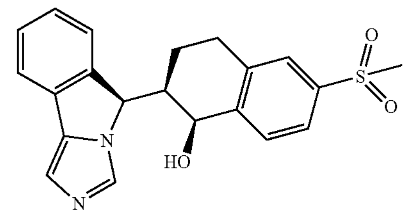

To the solution of 2-(5H-imidazo[5,1-a]isoindol-5-yl)-6-(methylthio)-1,2,3,4-tetrahydronaphthalen-1-ol (1.5 g, 4.3 mmol) in acetic acid (10 mL) was added hydrogen peroxide (30% solution in water, 4.88 g, 4.28 mL, 43.05 mmol) and the reaction was stirred at room temperature for 48 hours. Acetic acid was then removed using a rotovapor, remaining acetic acid was quenched using saturated sodium carbonate solution. The solids were filtered out and the filtrate was concentrate under vacuum. The crude product was purified by Prep-HPLC and further isolated by chiral separation to afford 8 isomers as white solid. The absolute configuration of all isomers was assigned arbitrarily.

Example 36a: (1S,2R)-2-((S)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1$H NMR (500 MHz, Chloroform-d) δ 7.82 (d, J=8.3 Hz, 1H), 7.77 (dd, J=8.2, 1.9 Hz, 1H), 7.66-7.58 (m, 3H), 7.50 (dd, J=7.7, 1.0 Hz, 1H), 7.45-7.37 (m, 1H), 7.29-7.21 (m, 2H), 5.78 (d, J=2.9 Hz, 1H), 4.96 (d, J=10.5 Hz, 1H), 3.02 (s, 3H), 2.80 (dd, J=11.5, 5.5 Hz, 2H), 2.55 (s, 1H), 1.27-1.40 (m, 1H), 1.26 (s, 1H)

Example 36b: (1S,2S)-2-((S)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1$H NMR (500 MHz, Chloroform-d) δ 7.92 (d, J=8.2 Hz, 1H), 7.68 (s, 1H), 7.79 (d, J=8.3 Hz, 1H), 7.62-7.54 (m, 2H), 7.40 (t, J=7.5 Hz, 1H), 7.31 (dd, J=20.3, 7.6 Hz, 2H), 7.19 (s, 1H), 5.86 (s, 1H), 4.98 (d, J=10.7 Hz, 1H), 3.04 (s, 3H), 2.80-2.69 (m, 2H), 2.42 (t, J=11.6 Hz, 1H), 1.25 (d, J=14.1 Hz, 1H), 1.04 (dd, J=12.4, 6.9 Hz, 1H)

Example 36c: (1R,2S)-2-((S)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1$H NMR (500 MHz, Chloroform-d) δ 7.98 (s, 1H), 7.78-7.72 (m, 2H), 7.62-7.53 (m, 2H), 7.57-7.47 (m, 1H), 7.42 (tt, J=7.6, 7.6, 0.8 Hz, 1H), 7.30-7.21 (m, 1H), 7.19 (s, 1H), 5.39 (d, J=7.4 Hz, 1H), 4.91 (d, J=3.0 Hz, 1H), 3.15-3.02 (m, 1H), 3.03 (s, 3H), 2.85 (ddd, J=17.8, 11.6, 6.8 Hz, 1H), 2.69 (s, 1H), 2.34-2.21 (m, 1H), 2.25 (s, 1H), 2.08 (ddt, J=11.5, 7.3, 3.4 Hz, 1H)

Example 36d: (1R,2R)-2-((R)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1$H NMR (500 MHz, Chloroform-d) δ 7.92 (d, J=8.2 Hz, 1H), 7.68 (s, 1H), 7.79 (d, J=8.3 Hz, 1H), 7.62-7.54 (m, 2H), 7.40 (t, J=7.5 Hz, 1H), 7.31 (dd, J=20.3, 7.6 Hz, 2H), 7.19 (s, 1H), 5.86 (s, 1H), 4.98 (d, J=10.7 Hz, 1H), 3.04 (s, 3H), 2.80-2.69 (m, 2H), 2.42 (t, J=11.6 Hz, 1H), 1.25 (d, J=14.1 Hz, 1H), 1.04 (dd, J=12.4, 6.9 Hz, 1H)

Example 36e: (1R,2R)-2-((S)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1$H NMR (500 MHz, Chloroform-d) δ 7.91 (s, 1H), 7.81 (dd, J=7.8, 1.8 Hz, 1H), 7.71-7.63 (m, 2H), 7.55-7.49 (m, 1H), 7.42-7.35 (m, 2H), 7.36-7.21 (m, 1H), 6.91 (s, 1H), 5.47 (d, J=1.9 Hz, 1H), 5.15 (d, J=3.4 Hz, 1H), 3.06 (s, 3H), 2.81 (dd, J=17.1, 5.2 Hz, 1H), 2.64 (ddd, J=17.8, 12.4, 6.0 Hz, 1H), 2.45-2.38 (m, 1H), 1.66-1.47 (m, 1H), 1.16 (dd, J=11.3, 3.6 Hz, 1H)

Example 36f: (1R,2S)-2-((R)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1H$ NMR (500 MHz, Chloroform-d) δ 7.91 (s, 1H), 7.81 (dd, J=7.8, 1.8 Hz, 1H), 7.71-7.63 (m, 2H), 7.55-7.49 (m, 1H), 7.42-7.35 (m, 2H), 7.36-7.21 (m, 1H), 6.91 (s, 1H), 5.47 (d, J=1.9 Hz, 1H), 5.15 (d, J=3.4 Hz, 1H), 3.06 (s, 3H), 2.81 (dd, J=17.1, 5.2 Hz, 1H), 2.64 (ddd, J=17.8, 12.4, 6.0 Hz, 1H), 2.45-2.38 (m, 1H), 1.66-1.47 (m, 1H), 1.16 (dd, J=11.3, 3.6 Hz, 1H)

Example 36g: (1R,2S)-2-((R)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1H$ NMR (500 MHz, Chloroform-d) δ 7.82 (d, J=8.3 Hz, 1H), 7.77 (dd, J=8.2, 1.9 Hz, 1H), 7.66-7.58 (m, 3H), 7.50 (dd, J=7.7, 1.0 Hz, 1H), 7.45-7.37 (m, 1H), 7.29-7.21 (m, 2H), 5.78 (d, J=2.9 Hz, 1H), 4.96 (d, J=10.5 Hz, 1H), 3.02 (s, 3H), 2.80 (dd, J=11.5, 5.5 Hz, 2H), 2.55 (s, 1H), 1.27-1.40 (m, 1H), 1.26 (s, 1H)

Example 36h: (1S,2R)-2-((R)-5H-imidazo[5,1-a]isoindol-5-yl)-6-(methylsulfonyl)-1,2,3,4-tetrahydronaphthalen-1-ol. LCMS (ESI, m/z): 381.2 $[M+H]^+$; $^1H$ NMR (500 MHz, Chloroform-d) δ 7.98 (s, 1H), 7.78-7.72 (m, 2H), 7.62-7.53 (m, 2H), 7.57-7.47 (m, 1H), 7.42 (tt, J=7.6, 7.6, 0.8 Hz, 1H), 7.30-7.21 (m, 1H), 7.19 (s, 1H), 5.39 (d, J=7.4 Hz, 1H), 4.91 (d, J=3.0 Hz, 1H), 3.15-3.02 (m, 1H), 3.03 (s, 3H), 2.85 (ddd, J=17.8, 11.6, 6.8 Hz, 1H), 2.69 (s, 1H), 2.34-2.21 (m, 1H), 2.25 (s, 1H), 2.08 (ddt, J=11.5, 7.3, 3.4 Hz, 1H)

Example 37: 3-(5H-imidazo[5,1-a]isoindol-5-yl) bicyclo[2.2.2]octan-2-ol

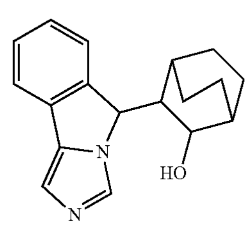 [SMILES: OC1C2CCC(CC2)C1C1c2ccccc2-c2cncn21]

(2S,3S)-3-((S)-5H-imidazo[5,1-a]isoindol-5-yl) bicyclo[2.2.2]octan-2-ol (2S,3R)-3-((S)-5H-imidazo[5,1-a]isoindol-5-yl) bicyclo[2.2.2]octan-2-ol (2R,3R)-3-((S)-5H-imidazo[5,1-a]isoindol-5-yl) bicyclo[2.2.2]octan-2-ol (2S,3S)-3-((R)-5H-imidazo[5,1-a]isoindol-5-yl) bicyclo[2.2.2]octan-2-ol (2R,3S)-3-((R)-5H-imidazo[5,1-a]isoindol-5-yl) bicyclo[2.2.2]octan-2-ol (2R,3R)-3-((R)-5H-imidazo[5,1-a]isoindol-5-yl) bicyclo[2.2.2]octan-2-ol 3-(5H-imidazo[5,1-a]isoindol-5-yl) bicyclo[2.2.2]octan-2-ol Step 1: (E)-3-(2-(1-trityl-1H-imidazol-4-yl)benzylidene) bicyclo[2.2.2]octan-2-one

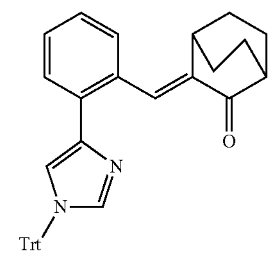

The title compound was synthesized by General Procedure for the Synthesis of Int-2: LCMS (ESI, m/z): 521.2 $[M+H]^+$ Step 2: (S)-6-((S)-5H-imidazo[5,1-a]isoindol-5-yl)-7,8-dihydroquinolin-5(6H)-one

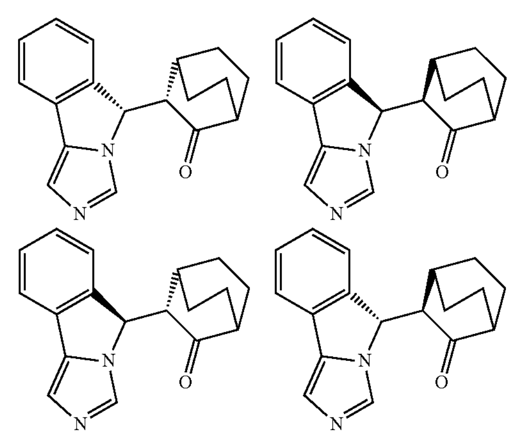

The title compound was synthesized by General Procedure for the Synthesis of Int-3. The two diastereomeric pairs were not separated and used as a mixture for step 3: LCMS (ESI, m/z): 279.1. The absolute configuration of all isomers was assigned arbitrarily.

Step 3:

(2S,3S)-3-((S)-5H-imidazo[5,1-a]isoindol-5-yl) bicyclo[2.2.2]octan-2-ol (2S,3R)-3-((S)-5H-imidazo[5,1-a]isoindol-5-yl) bicyclo[2.2.2]octan-2-ol (2R,3R)-3-((S)-5H-imidazo[5,1-a]isoindol-5-yl) bicyclo[2.2.2]octan-2-ol (2S,3S)-3-((R)-5H-imidazo[5,1-a]isoindol-5-yl) bicyclo[2.2.2]octan-2-ol (2R,3S)-3-((R)-5H-imidazo[5,1-a]isoindol-5-yl) bicyclo[2.2.2]octan-2-ol (2R,3R)-3-((R)-5H-imidazo[5,1-a]isoindol-5-yl) bicyclo[2.2.2]octan-2-ol 3-(5H-imidazo[5,1-a]isoindol-5-yl) bicyclo[2.2.2]octan-2-ol 37a

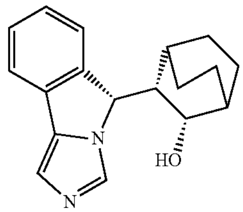

37b

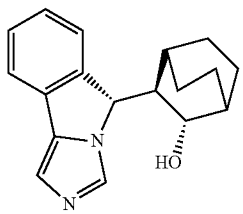

37c

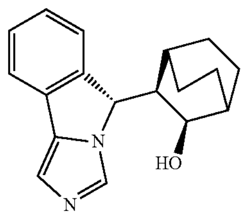

37d

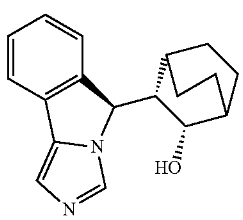

37e

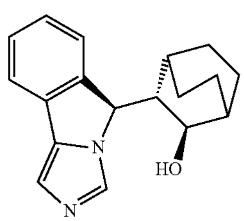

37f

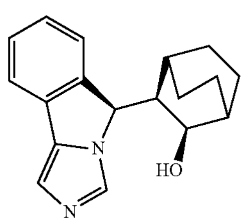

37g

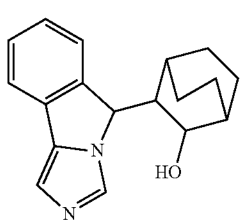

The title compound was synthesized by General Procedure for the Synthesis of Int-5. The product was isolated as a mixture of six enantiomers and one diastereomer which were separated by chiral SFC: LCMS (ESI, m/z): 281.4. The absolute configuration of all isomers was assigned arbitrarily.

Example 37a: (2S,3S)-3-((S)-5H-imidazo[5,1-a]isoindol-5-yl) bicyclo[2.2.2]octan-2-ol: LCMS (ESI, m/z): 281.4 $[M+H]^+$; No $^1H$ NMR data due to small sample quantity Example 37b: (2S,3R)-3-((S)-5H-imidazo[5,1-a]isoindol-5-yl) bicyclo[2.2.2]octan-2-ol: LCMS (ESI, m/z): 281.4 $[M+H]^+$; $^1H$ NMR (500 MHz, Chloroform-d) δ 7.94 (s, 1H), 7.59 (dq, J=7.7, 0.9 Hz, 1H), 7.53 (dt, J=7.5, 0.9 Hz, 1H), 7.34 (tt, J=7.4, 0.9 Hz, 1H), 7.23 (td, J=7.6, 1.2 Hz, 1H), 7.18 (s, 1H), 5.64 (d, J=6.6 Hz, 1H), 4.35 (dd, J=8.8, 4.4 Hz, 1H), 2.06 (dd, J=8.7, 6.8 Hz, 1H), 1.98-1.92 (m, 1H), 1.84-1.78 (m, 1H), 1.71-1.60 (m, 1H), 1.49-1.34 (m, 4H), 1.33-1.24 (m, 2H).

Example 37c: (2R,3R)-3-((S)-5H-imidazo[5,1-a]isoindol-5-yl) bicyclo[2.2.2]octan-2-ol: LCMS (ESI, m/z): 281.4 $[M+H]^+$; $^1H$ NMR (500 MHz, Chloroform-d) δ 8.11 (s, 1H), 7.54 (dt, J=7.6, 0.9 Hz, 1H), 7.35 (tt, J=7.6, 0.8 Hz, 1H), 7.29 (dq, J=7.7, 0.9 Hz, 1H), 7.19 (td, J=7.6, 1.1 Hz, 1H), 7.17 (s, 1H), 5.64 (d, J=10.5 Hz, 1H), 4.24 (dd, J=8.3, 4.5 Hz, 1H), 2.11-1.92 (m, 2H), 1.89 (dd, J=5.9, 3.3 Hz, 1H), 1.70-1.56 (m, 5H), 1.56-1.46 (m, 1H), 1.45-1.24 (m, 2H).

Example 37d: (2S,3S)-3-((R)-5H-imidazo[5,1-a]isoindol-5-yl) bicyclo[2.2.2]octan-2-ol: LCMS (ESI, m/z): 281.4 $[M+H]^+$; $^1H$ NMR (500 MHz, Chloroform-d) δ 8.11 (s, 1H), 7.54 (dt, J=7.8, 1.0 Hz, 1H), 7.35 (tt, J=7.6, 0.8 Hz, 1H), 7.29 (dd, J=7.7, 1.0 Hz, 1H), 7.19 (td, J=7.6, 1.2 Hz, 1H), 7.17 (s, 1H), 5.64 (d, J=10.5 Hz, 1H), 4.25 (dd, J=8.3, 4.5 Hz, 1H), 2.11-1.92 (m, 2H), 1.92-1.87 (m, 1H), 1.69-1.56 (m, 5H), 1.56-1.47 (m, 1H), 1.39-1.24 (m, 2H).

Example 37e: (2R,3S)-3-((R)-5H-imidazo[5,1-a]isoindol-5-yl) bicyclo[2.2.2]octan-2-ol: LCMS (ESI, m/z): 281.4 $[M+H]^+$; $^1H$ NMR (500 MHz, Chloroform-d) δ 7.95 (s, 1H), 7.59 (dq, J=7.6, 0.9 Hz, 1H), 7.53 (dt, J=7.6, 0.9 Hz, 1H), 7.38-7.31 (m, 1H), 7.23 (td, J=7.6, 1.2 Hz, 1H), 7.18 (s, 1H), 5.64 (d, J=6.6 Hz, 1H), 4.35 (dd, J=8.8, 4.4 Hz, 1H), 2.07 (t, J=7.7 Hz, 1H), 1.98-1.92 (m, 1H), 1.85-1.78 (m, 1H), 1.71-1.60 (m, 1H), 1.51 (s, 1H), 1.49-1.33 (m, 3H), 1.31-1.24 (m, 2H).

Example 37f: (2R,3R)-3-((R)-5H-imidazo[5,1-a]isoindol-5-yl) bicyclo[2.2.2]octan-2-ol: LCMS (ESI, m/z): 281.4 $[M+H]^+$; No NMR data due to small sample quantity.

Example 37g: 3-(-5H-imidazo[5,1-a]isoindol-5-yl) bicyclo[2.2.2]octan-2-ol: LCMS (ESI, m/z): 281.4 $[M+H]^+$; No NMR data due to small sample quantity.

Example 38: 3-hydroxy-4-(5H-imidazo[5,1-a]isoindol-5-yl)tetrahydrothiophene 1,1-dioxide

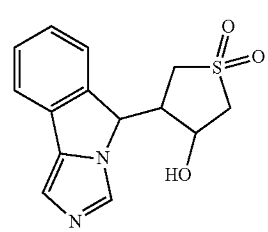 [SMILES: O=S1(=O)CC(O)C(C2c3ccccc3-c3cncn32)C1]

(3R,4R)-3-hydroxy-4-((S)-5H-imidazo[5,1-a]isoindol-5-yl) tetrahydrothiophene 1,1-dioxide (3S,4S)-3-hydroxy-4-((R)-5H-imidazo[5,1-a]isoindol-5-yl) tetrahydrothiophene 1,1-dioxide (3R,4R)-3-hydroxy-4-((R)-5H-imidazo[5,1-a]isoindol-5-yl)tetrahydrothiophene 1,1-dioxide (3S,4S)-3-hydroxy-4-((S)-5H-imidazo[5,1-a]isoindol-5-yl)tetrahydrothiophene 1,1-dioxide Step 1:

(3R,4R)-3-hydroxy-4-((S)-5H-imidazo[5,1-a]isoindol-5-yl)tetrahydrothiophene 1,1-dioxide (3S,4S)-3-hydroxy-4-((R)-5H-imidazo[5,1-a]isoindol-5-yl)tetrahydrothiophene 1,1-dioxide (3R,4R)-3-hydroxy-4-((R)-5H-imidazo[5,1-a]isoindol-5-yl)tetrahydrothiophene 1,1-dioxide (3S,4S)-3-hydroxy-4-((S)-5H-imidazo[5,1-a]isoindol-5-yl)tetrahydrothiophene 1,1-dioxide 38a

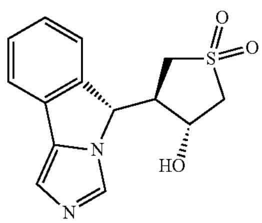

38b

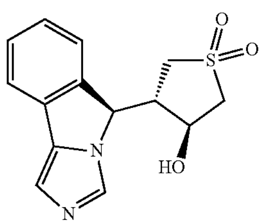

38c

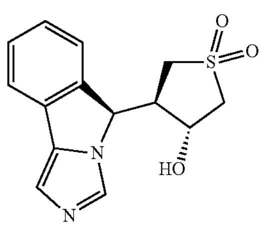

38d

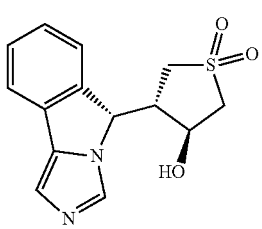

To a solution of 5H-imidazo[5,1-a]isoindole (600 mg, 3.84 mmol) in anhydrous THF (10 mL) was added n-BuLi solution (1.54 mL, 3.84 mmol) at −78° C. and stirred for 1 hr. 6-Oxa-3-thiabicyclo[3.1.0]hexane 3,3-dioxide (618 mg, 4.61 mmol) was dissolved in anhydrous THF (40 mL) and the solution was added into the reaction mixture drop-wise. The reaction was kept at −78° C. for another 30 min and was warmed up to room temperature. The reaction was kept for another 16 hr and was quenched with saturated $NH_4Cl$ solution (10 mL). The mixture was extracted with DCM (3×10 mL) and the organic phase was combined, dried over $Na_2SO_4$, and concentrated. The crude product was purified by Combi-Flash and further isolated by chiral separation to afford 4 isomers as white solid. The absolute configuration of all isomers was assigned arbitrarily.

Example 38a: (3R,4R)-3-hydroxy-4-((S)-5H-imidazo[5,1-a]isoindol-5-yl)tetrahydrothiophene 1,1-dioxide: LCMS (ESI, m/z): 291.3 $[M+H]^+$. $^1$H NMR (500 MHz, Chloroform-d) δ 8.01 (s, 1H), 7.58 (d, J=7.6 Hz, 1H), 7.43 (dd, J=15.8, 7.8 Hz, 2H), 7.35 (t, J=7.5 Hz, 1H), 7.24 (s, 1H), 5.78 (d, J=2.8 Hz, 1H), 4.76 (q, J=8.9 Hz, 1H), 3.62 (dd, J=13.1, 7.5 Hz, 1H), 3.28-3.21 (m, 1H), 2.74 (dd, J=13.3, 7.5 Hz, 1H), 2.22 (t, J=13.1 Hz, 1H).

Example 38b: (3S,4S)-3-hydroxy-4-((R)-5H-imidazo[5,1-a]isoindol-5-yl)tetrahydrothiophene 1,1-dioxide: LCMS (ESI, m/z): 291.3 $[M+H]^+$. $^1$H NMR (500 MHz, Chloroform-d) δ 8.17 (s, 1H), 7.58 (d, J=7.6 Hz, 1H), 7.48-7.40 (m, 2H), 7.36 (t, J=7.8 Hz, 1H), 7.25-7.24 (m, 1H), 5.80 (s, 1H), 4.78 (q, J=8.9 Hz, 1H), 3.63 (dd, J=13.0, 7.5 Hz, 1H), 3.25 (dd, J=12.9, 9.0 Hz, 1H), 2.74 (dd, J=13.4, 7.4 Hz, 1H), 2.21 (t, J=13.1 Hz, 2H).

Example 38c: (3R,4R)-3-hydroxy-4-((R)-5H-imidazo[5,1-a]isoindol-5-yl)tetrahydrothiophene 1,1-dioxide: LCMS (ESI, m/z): 291.3 $[M+H]^+$. $^1$H NMR (500 MHz, Chloroform-d) δ 7.76 (s, 1H), 7.60 (d, J=7.6 Hz, 1H), 7.49-7.45 (m, 1H), 7.43 (d, J=7.7 Hz, 1H), 7.35-7.29 (m, 1H), 7.22 (s, 1H), 5.64 (d, J=3.7 Hz, 1H), 4.62 (q, J=7.7 Hz, 1H), 3.46 (dd, J=13.3, 7.4 Hz, 1H), 3.27 (ddd, J=12.0, 8.1, 3.6 Hz, 1H), 3.22-3.14 (m, 1H), 2.96 (dd, J=13.3, 7.5 Hz, 1H), 2.58-2.50 (m, 1H).

Example 38d: (3S,4S)-3-hydroxy-4-((S)-5H-imidazo[5,1-a]isoindol-5-yl)tetrahydrothiophene 1,1-dioxide: LCMS (ESI, m/z): 291.3 $[M+H]^+$. $^1$H NMR (500 MHz, Chloroform-d) δ 7.75 (s, 1H), 7.60 (d, J=7.7 Hz, 1H), 7.49-7.45 (m, 1H), 7.43 (d, J=7.7 Hz, 1H), 7.32 (td, J=7.6, 1.1 Hz, 1H), 7.23 (s, 1H), 5.63 (d, J=3.7 Hz, 1H), 4.62 (q, J=7.7 Hz, 1H), 3.45 (dd, J=13.4, 7.4 Hz, 1H), 3.27 (dp, J=11.9, 4.1 Hz, 1H), 3.18 (ddd, J=13.3, 7.4, 1.5 Hz, 1H), 2.97 (dd, J=12.5, 7.9 Hz, 1H), 2.59-2.51 (m, 1H).

Example 39: 3-hydroxy-4-(5H-imidazo[5,1-a]isoindol-5-yl)piperidine-1-sulfonamide

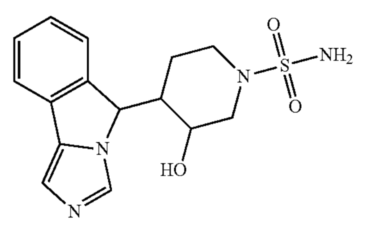 [SMILES: NS(=O)(=O)N1CCC(C2c3ccccc3-c3cncn32)C(O)C1]

The title compound was synthesized by the same method of example 28.

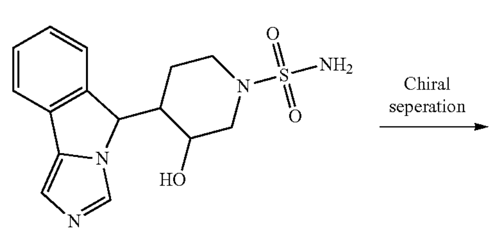

-continued

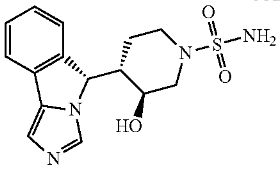

39a

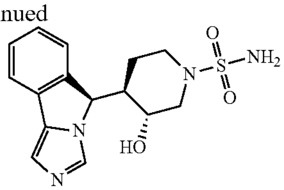

39b

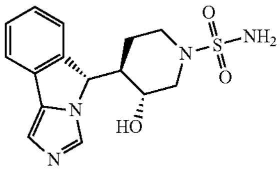

39c

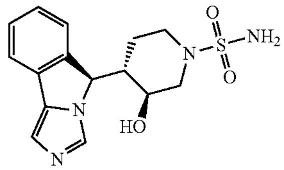

39d

The crude product was purified by Prep-HPLC and further isolated by chiral separation with the following conditions:

1. CHIRALPAK ID, 2.0 cm I.D×25 cm L; Mobile Phase A:Hex-HPLC, Mobile Phase B: IPA-HPLC; Flow rate: 17 mL/min; Gradient: 40 B to 40 B in 33 min; 254/220 nm;
2. Chiralpak IC, 2×25 cm, 5 um; Mobile Phase A:Hex-HPLC, Mobile Phase B: IPA-HPLC; Flow rate: 15 mL/min; Gradient: 50 B to 50 B in 35 min; 254/220 nm.

The absolute configuration of all isomers was assigned arbitrarily.

Example 39a: (3S,4S)-3-hydroxy-4-((S)-5H-imidazo[5,1-a]isoindol-5-yl)piperidine-1-sulfonamide: LCMS (ESI, m/z): 298.2 $[M+H]^+$; $^1$HNMR (400 MHz, DMSO-$d_6$) δ 7.94 (s, 1H), 7.63 (d, J=7.6 Hz, 1H), 7.52 (d, J=7.6 Hz, 1H), 7.42-7.38 (m, 1H), 7.31-7.28 (m, 1H), 7.15 (s, 1H), 6.78 (s, 2H), 5.73-5.71 (m, 2H), 3.78-3.65 (m, 2H), 3.25-3.20 (m, 1H), 2.32-2.20 (m, 3H), 0.71-0.65 (m, 1H), 0.58-0.40 (m, 1H); tR=2.772 min, (CHIRALPAKID-3, 0.46×5 cm, 3 um; iso-propanol:hexane (0.1% DEA)=40:60; 1.0 mL/min). 39a and 39b are enantiomers.

Example 39b: (3R,4R)-3-hydroxy-4-((R)-5H-imidazo[5,1-a]isoindol-5-yl)piperidine-1-sulfonamide: LCMS (ESI, m/z): 298.2 $[M+H]^+$; tR=3.522 min, (CHIRALPAKID-3, 0.46×5 cm, 3 um; iso-propanol:hexane (0.1% DEA)=40:60; 1.0 mL/min). 39a and 39b are enantiomers.

Example 39c: (3R,4R)-3-hydroxy-4-((S)-5H-imidazo[5,1-a]isoindol-5-yl)piperidine-1-sulfonamide: LCMS (ESI, m/z): 298.2 $[M+H]^+$; $^1$HNMR (300 MHz, $CD_3OD$) δ 7.93 (s, 1H), 7.64 (d, J=7.5 Hz, 1H), 7.49 (d, J=7.5 Hz, 1H), 7.46-7.34 (m, 2H), 7.20 (s, 1H), 5.82 (d, J=1.5 Hz, 1H), 4.01-3.92 (m, 2H), 3.46-3.45 (m, 1H), 2.58-2.41 (m, 2H), 2.20-2.10 (m, 1H), 0.99-0.93 (m, 1H), 0.71-0.65 (m, 1H); tR=3.106 min, (CHIRALPAKID-3, 0.46×5 cm, 3 um; iso-propanol:hexane (0.1% DEA)=40:60; 1.0 mL/min). 39c and 39d are enantiomers Example 39d: (3S,4S)-3-hydroxy-4-((R)-5H-imidazo[5,1-a]isoindol-5-yl)piperidine-1-sulfonamide: LCMS (ESI, m/z): 298.2 $[M+H]^+$; tR=7.043 min, (CHIRALPAKID-3, 0.46×5 cm, 3 um; iso-propanol:hexane (0.1% DEA)=40:60; 1.0 mL/min). 39c and 39d are enantiomers

Example 40: 1-(ethylsulfonyl)-4-(5H-imidazo[5,1-a]isoindol-5-yl)pyrrolidin-3-ol

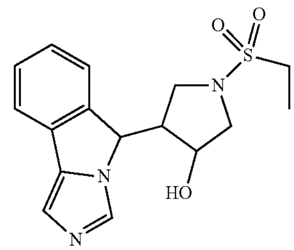 [SMILES: CCS(=O)(=O)N1CC(O)C(C2c3ccccc3-c3cncn32)C1]

(3R,4R)-1-(ethylsulfonyl)-4-((R)-5H-imidazo[5,1-a]isoindol-5-yl)pyrrolidin-3-ol
(3S,4S)-1-(ethylsulfonyl)-4-((S)-5H-imidazo[5,1-a]isoindol-5-yl)pyrrolidin-3-ol
(3R,4R)-1-(ethylsulfonyl)-4-((S)-5H-imidazo[5,1-a]isoindol-5-yl)pyrrolidin-3-ol
(3S,4S)-1-(ethylsulfonyl)-4-((R)-5H-imidazo[5,1-a]isoindol-5-yl)pyrrolidin-3-ol

Step 1: 4-(5H-imidazo[5,1-a]isoindol-5-yl)pyrrolidin-3-ol

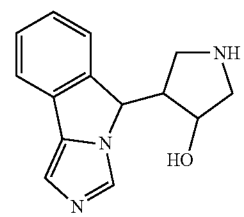 [SMILES: OC1CNCC1C1c2ccccc2-c2cncn21]

To a solution of tert-butyl 3-hydroxy-4-(5H-imidazo[5,1-a]isoindol-5-yl)pyrrolidine-1-carboxylate (500 mg, 1.46 mmol) in anhydrous DCM (10 mL) was added trifluoroacetic acid (5 mL) drop-wise at room temperature and stirred for 30 min. Solvent and extra TFA were removed under reduced pressure and the crude product was left on vacuum pump overnight. The product was directly used without further purification: LCMS (ESI, m/z): 242.2 $[M+H]^+$.

Step 2:
(3R,4R)-1-(ethylsulfonyl)-4-((R)-5H-imidazo[5,1-a]isoindol-5-yl)pyrrolidin-3-ol
(3S,4S)-1-(ethylsulfonyl)-4-((S)-5H-imidazo[5,1-a]isoindol-5-yl)pyrrolidin-3-ol
(3R,4R)-1-(ethylsulfonyl)-4-((S)-5H-imidazo[5,1-a]isoindol-5-yl)pyrrolidin-3-ol
(3S,4S)-1-(ethylsulfonyl)-4-((R)-5H-imidazo[5,1-a]isoindol-5-yl)pyrrolidin-3-ol 40a

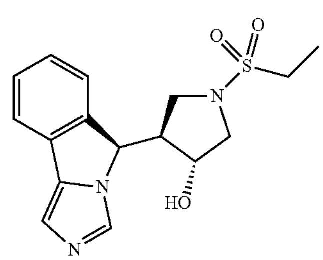

-continued

40b

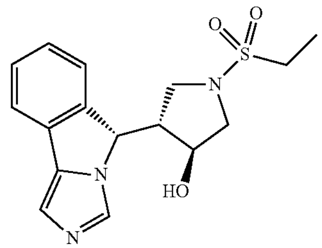

40c

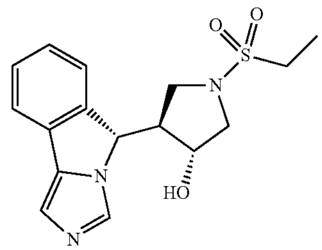

40d

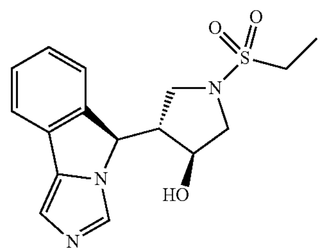

To a solution of 4-(5H-imidazo[5,1-a]isoindol-5-yl)pyrrolidin-3-ol (0.353 g, 1.46 mmol) in anhydrous DCM (10 mL) was added triethylamine (0.41 mL, 2.93 mmol) and ethylsulfonyl chloride (0.153 mL, 1.61 mmol). The reaction mixture was stirred for 1 hour at room temperature. TLC indicated starting material was not consumed and extra triethylamine (0.20 mL, 1.47 mmol) was added. The reaction was kept at room temperature for another 1 hr and quenched with saturated $NaHCO_3$ solution (10 mL). The resulting solution was extracted with DCM (3×10 mL) and the organic phase was combined, dried over anhydrous $Na_2SO_4$ and concentrated. The crude product was purified by Combi-Flash and further isolated by chiral separation to afford 4 isomers as white solid. The absolute configuration of all isomers was assigned arbitrarily.

Example 40a: (3R,4R)-1-(ethylsulfonyl)-4-((R)-5H-imidazo[5,1-a]isoindol-5-yl)pyrrolidin-3-ol: LCMS (ESI, m/z): 334.1 $[M+H]^+$. $^1$H NMR (400 MHz, DMSO-$d_6$) δ 7.98 (s, 1H), 7.62 (d, J=7.6 Hz, 1H), 7.57 (dd, J=7.6, 1.0 Hz, 1H), 7.40 (d, J=7.5 Hz, 1H), 7.31 (dd, J=7.5, 1.1 Hz, 1H), 7.18 (s, 1H), 5.71 (d, J=4.9 Hz, 1H), 5.60 (d, J=3.3 Hz, 1H), 4.37 (dd, J=7.0, 5.1 Hz, 1H), 3.40 (dd, J=9.7, 6.6 Hz, 1H), 3.08-3.00 (m, 2H), 2.96 (p, J=7.1 Hz, 3H), 2.36 (dd, J=9.3, 8.1 Hz, 1H), 1.08 (t, J=7.3 Hz, 3H).

Example 40b: (3S,4S)-1-(ethylsulfonyl)-4-((S)-5H-imidazo[5,1-a]isoindol-5-yl)pyrrolidin-3-ol: LCMS (ESI, m/z): 334.1 $[M+H]^+$. $^1$H NMR (400 MHz, DMSO-$d_6$) δ 7.98 (s, 1H), 7.62 (d, J=7.5 Hz, 1H), 7.59-7.54 (m, 1H), 7.41 (t, J=7.7 Hz, 1H), 7.33-7.26 (m, 1H), 7.18 (s, 1H), 5.71 (d, J=4.9 Hz, 1H), 5.60 (d, J=3.3 Hz, 1H), 4.42-4.33 (m, 1H), 3.40 (dd, J=9.7, 6.6 Hz, 1H), 3.08-3.00 (m, 2H), 2.96 (p, J=7.2 Hz, 3H), 2.40-2.33 (m, 1H), 1.08 (t, J=7.4 Hz, 3H).

Example 40c: (3R,4R)-1-(ethylsulfonyl)-4-((S)-5H-imidazo[5,1-a]isoindol-5-yl)pyrrolidin-3-ol: LCMS (ESI, m/z):

334.1 $[M+H]^+$. $^1$H NMR (400 MHz, DMSO-$d_6$) δ 7.93 (s, 1H), 7.62 (d, J=7.5 Hz, 1H), 7.56 (dd, J=7.8, 1.0 Hz, 1H), 7.42 (t, J=7.5 Hz, 1H), 7.32-7.27 (m, 1H), 7.14 (s, 1H), 5.55 (d, J=4.5 Hz, 1H), 5.38 (d, J=4.6 Hz, 1H), 4.00 (t, J=5.3 Hz, 1H), 3.45 (dd, J=10.1, 8.4 Hz, 1H), 3.11 (dd, J=10.2, 6.4 Hz, 2H), 3.08-2.99 (m, 3H), 2.98-2.89 (m, 1H), 1.15 (t, J=7.4 Hz, 3H).

Example 40d: (3S,4S)-1-(ethylsulfonyl)-4-((R)-5H-imidazo[5,1-a]isoindol-5-yl)pyrrolidin-3-ol: LCMS (ESI, m/z): 334.1 $[M+H]^+$. $^1$H NMR (400 MHz, DMSO-$d_6$) δ 7.93 (s, 1H), 7.62 (d, J=7.5 Hz, 1H), 7.56 (dd, J=7.6, 1.0 Hz, 1H), 7.45-7.38 (m, 1H), 7.31 (dd, J=7.6, 1.1 Hz, 1H), 7.14 (s, 1H), 5.55 (d, J=4.5 Hz, 1H), 5.38 (d, J=4.7 Hz, 1H), 4.00 (p, J=5.3 Hz, 1H), 3.45 (dd, J=10.1, 8.4 Hz, 1H), 3.11 (dd, J=10.1, 6.4 Hz, 2H), 3.08-2.99 (m, 3H), 2.94 (td, J=7.5, 3.6 Hz, 1H), 1.15 (t, J=7.3 Hz, 3H).

Examples 41: tert-butyl 7-hydroxy-6-(5H-imidazo[1,5-b]isoindol-5-yl)-2-azaspiro[3.3]heptane-2-carboxylate

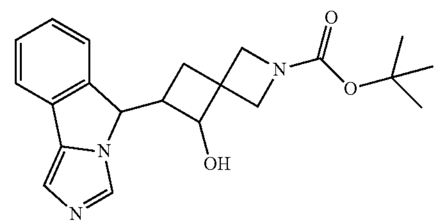 [SMILES: CC(C)(C)OC(=O)N1CC2(CC(C3c4ccccc4-c4cncn43)C2O)C1]

tert-butyl(5R,6R)-5-hydroxy-6-((R)-5H-imidazo[5,1-a]isoindol-5-yl)-2-azaspiro[3.3]heptane-2-carboxylate
tert-butyl(5R,6R)-5-hydroxy-6-((S)-5H-imidazo[5,1-a]isoindol-5-yl)-2-azaspiro[3.3]heptane-2-carboxylate
tert-butyl(5R,6S)-5-hydroxy-6-((R)-5H-imidazo[5,1-a]isoindol-5-yl)-2-azaspiro[3.3]heptane-2-carboxylate
tert-butyl(5R,6S)-5-hydroxy-6-((S)-5H-imidazo[5,1-a]isoindol-5-yl)-2-azaspiro[3.3]heptane-2-carboxylate
tert-butyl(5S,6R)-5-hydroxy-6-((R)-5H-imidazo[5,1-a]isoindol-5-yl)-2-azaspiro[3.3]heptane-2-carboxylate
tert-butyl(5S,6R)-5-hydroxy-6-((S)-5H-imidazo[5,1-a]isoindol-5-yl)-2-azaspiro[3.3]heptane-2-carboxylate
tert-butyl(5S,6S)-5-hydroxy-6-((R)-5H-imidazo[5,1-a]isoindol-5-yl)-2-azaspiro[3.3]heptane-2-carboxylate
tert-butyl(5S,6S)-5-hydroxy-6-((S)-5H-imidazo[5,1-a]isoindol-5-yl)-2-azaspiro[3.3]heptane-2-carboxylate Examples 41a-h were all synthesized using the reaction conditions for the preparation of examples 1 a-h in which the reagent cyclobutanone was substituted with tert-butyl 5-oxo-2-azaspiro[3.3]heptane-2-carboxylate. Each example is a single stereomer with undetermined absolute configuration.

Example 41a: tert-butyl 7-hydroxy-6-(5H-imidazo[1,5-b]isoindol-5-yl)-2-azaspiro[3.3]heptane-2-carboxylate: LCMS (ESI, m/z): 368 $[M+H]^+$; $^1$H NMR (400 MHz, DMSO-$d_6$) δ 7.89 (t, J=0.6 Hz, 1H), 7.65-7.51 (m, 1H), 7.47-7.30 (m, 2H), 7.24 (td, J=7.7, 1.1 Hz, 1H), 7.10 (s, 1H), 5.63 (d, J=7.1 Hz, 1H), 5.33 (d, J=8.0 Hz, 1H), 4.22-3.97 (m, 2H), 3.73 (s, 2H), 3.57 (s, 1H), 2.05 (dq, J=17.0, 8.7 Hz, 1H), 1.86 (t, J=9.5 Hz, 1H), 1.36 (s, 9H).; tR=1.4 min (Chiralcel OX (150×30 mm, 5 uM) Ethanol w/0.1% $NH_4OH$, 1.5 ml/min).

Example 41b (enantiomer of Example 41a): tert-butyl 7-hydroxy-6-(5H-imidazo[1,5-b]isoindol-5-yl)-2-azaspiro

[3.3]heptane-2-carboxylate: LCMS (ESI, m/z): 368 [M+H]$^+$; tR=2.00 min. (Chiralpak AD (250×30 mm, 5 um), Ethanol w/0.1% $NH_4OH$, 1.5 ml/min).

Example 41c: tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; $^1$H NMR (400 MHz, DMSO-$d_6$) δ 7.94-7.82 (m, 1H), 7.64-7.51 (m, 2H), 7.36 (tdd, J=7.4, 1.5, 0.7 Hz, 1H), 7.25 (td, J=7.6, 1.1 Hz, 1H), 7.13 (s, 1H), 6.12 (d, J=4.7 Hz, 1H), 5.38 (d, J=7.6 Hz, 1H), 4.39 (t, J=5.8 Hz, 1H), 4.13 (d, J=8.9 Hz, 1H), 3.89-3.56 (m, 2H), 2.60 (p, J=7.9 Hz, 1H), 2.03 (d, J=8.5 Hz, 2H), 1.36 (s, 9H).; tR=1.56 min. (Chiralpak AD (250×30 mm, 5 um), Ethanol w/0.1% $NH_4OH$, 1.5 ml/min).

Example 41d: tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; $^1$H NMR (400 MHz, DMSO-$d_6$) δ 7.83 (s, 1H), 7.59 (dd, J=7.6, 1.1 Hz, 1H), 7.51-7.30 (m, 2H), 7.23 (td, J=7.6, 1.2 Hz, 1H), 7.11 (s, 1H), 6.11 (d, J=5.2 Hz, 1H), 5.31 (d, J=10.1 Hz, 1H), 4.33 (q, J=5.0 Hz, 1H), 4.14 (d, J=9.0 Hz, 1H), 3.81 (d, J=11.4 Hz, 1H), 3.63 (s, 1H), 2.71-2.54 (m, 1H), 2.23 (dqd, J=11.5, 8.3, 4.6 Hz, 2H), 1.38 (s, 9H).; tR=1.18 min. (Chiralpak AD (250×30 mm, 5 um, Ethanol w/0.1% $NH_4OH$, 1.5 ml/min).

Example 41e (enantiomer of Example 41c): tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; tR=1.15 min. (Chiralcel OX (250×30 mm, 5 um), Ethanol w/0.1% $NH_4OH$, 1.5 ml/min).

Example 41f (enantiomer of Example 41d): tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; tR=0.89 min (Chiralcel OX (250×30 mm, 5 um), Ethanol w/0.1% $NH_4OH$, 1.5 ml/min).

Example 41g: tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; $^1$H NMR (400 MHz, DMSO-$d_6$) δ 7.81 (s, 1H), 7.66-7.48 (m, 2H), 7.46-7.32 (m, 1H), 7.26 (td, J=7.5, 1.2 Hz, 1H), 7.13 (s, 1H), 5.69 (d, J=6.8 Hz, 1H), 5.36 (d, J=7.4 Hz, 1H), 4.16 (t, J=7.3 Hz, 2H), 3.75 (d, J=9.0 Hz, 1H), 3.66 (s, 1H), 3.55 (s, 1H), 2.14 (p, J=8.6 Hz, 1H), 1.89 (dd, J=11.2, 8.6 Hz, 1H), 1.44 (t, J=10.7 Hz, 1H), 1.36 (s, 9H).; tR=0.87 min. Chiralpak IC (150×21.1 mm, 5 um), Ethanol w/0.1% $NH_4OH$, 1.5 ml/min).

Example 41h (enantiomer of Example 41g): tert-butyl 7-hydroxy-6-(5H-imidazo[1,5-b]isoindol-5-yl)-2-azaspiro[3.3]heptane-2-carboxylate: LCMS (ESI, m/z): 368 [M+H]$^+$; tR=1.13 min. Chiralpak AD (150×30 mm, Sum), Ethanol w/0.1% $NH_4OH$, 1.5 ml/min)

Example 42: 1-(5H-imidazo[5,1-a]isoindol-5-yl)ethan-1-ol

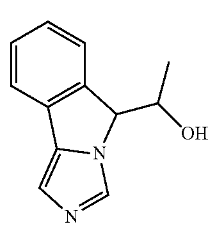

(42%) yield; synthesized according to general procedure: LCMS (ESI, m/z): 201.44 [M+H]$^+$. The stereoisomers were separated by chiral SFC.

42a

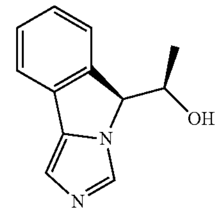

42b

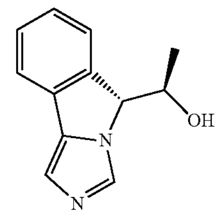

42c

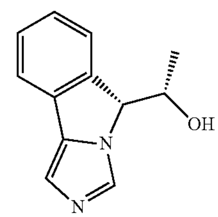

42d

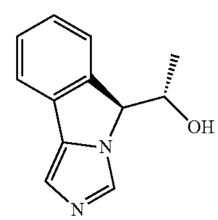

Example 42a: (R)-1-((S)-5H-imidazo[5,1-a]isoindol-5-yl)ethan-1-ol: LCMS (ESI, m/z): 201.1 [M+H]$^+$. $^1$H NMR (DMSO-$d_6$, 500 MHz): δ (ppm) 7.79 (s, 1H), 7.59 (d, J=7.6 Hz, 1H), 7.48-7.52 (m, 1H), 7.8 (t, J=7.1 Hz, 1H), 7.26 (td, J=7.5, 1.1 Hz, 1H), 7.14 (s, 1H), 5.48 (d, J=3.7 Hz, 1H), 5.36 (d, J=3.3 Hz, 1H), 4.38 (tdd, J=6.3, 3.6, 2.6 Hz, 1H), 0.48 (d, J=6.3 Hz, 3H).

Example 42b: (R)-1-((R)-5H-imidazo[5,1-a]isoindol-5-yl)ethan-1-ol: LCMS (ESI, m/z): 201.1 [M+H]$^+$. $^1$H NMR (DMSO-$d_6$, 500 MHz): δ (ppm) 0.93 (d, J=6.3 Hz, 3H), 4.00-4.16 (m, 1H), 5.20 (d, J=5.2 Hz, 1H), 5.35 (d, J=4.8 Hz, 1H), 7.11 (s, 1H), 7.26 (td, J=7.6, 1.1 Hz, 1H), 7.35-7.43 (m, 1H), 7.55-7.67 (m, 2H), 7.87 (s, 1H).

Example 42c: (S)-1-((R)-5H-imidazo[5,1-a]isoindol-5-yl)ethan-1-ol: LCMS (ESI, m/z): 201.1 [M+H]$^+$. $^1$H NMR (DMSO-$d_6$, 500 MHz): Same as 42a Example 42d: (S)-1-((S)-5H-imidazo[5,1-a]isoindol-5-yl)ethan-1-ol: LCMS (ESI, m/z): 201.2 [M+H]$^+$. $^1$H NMR (DMSO-$d_6$, 500 MHz): Same as 42b Example 43: 4-(5H-imidazo[5,1-a]isoindol-5-yl)tetrahydro-2H-pyran-4-ol

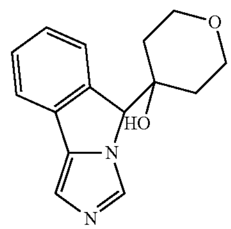 [SMILES: OC1(C2c3ccccc3-c3cncn32)CCOCC1]

Final product (racemate) is a mixture of the following isomers:

(R)-4-(5H-imidazo[5,1-a]isoindol-5-yl)tetrahydro-2H-pyran-4-ol (S)-4-(5H-imidazo[5,1-a]isoindol-5-yl)tetrahydro-2H-pyran-4-ol (57%) yield; synthesized according to general procedure: LCMS (ESI, m/z): 257.3 $[M+H]^+$. $^1$H NMR (Chloroform-d, 400 MHz): δ (ppm) 7.98 (s, 1H), 7.50 (dd, J=12.4, 7.6 Hz, 2H), 7.38 (t, J=7.5 Hz, 1H), 7.25 (t, J=7.6 Hz, 1H), 7.11 (s, 1H), 5.08 (s, 1H), 3.76-3.95 (m, 2H), 3.51-3.72 (m, 2H), 3.31 (d, J=36.2 Hz, 2H), 2.15 (ddd, J=13.0, 10.3, 7.0 Hz, 1H), 1.68 (d, J=12.7 Hz, 1H), 1.05-1.28 (m, 1H), 0.78 (d, J=12.9 Hz, 1H).

Example 44: 2-(5H-imidazo[5,1-a]isoindol-5-yl)propan-2-ol

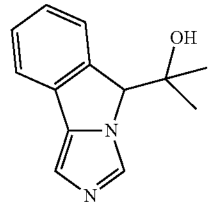 [SMILES: CC(C)(O)C1c2ccccc2-c2cncn21]

Final product (racemate) is a mixture of the following isomers:

(R)-2-(5H-imidazo[5,1-a]isoindol-5-yl)propan-2-ol (S)-2-(5H-imidazo[5,1-a]isoindol-5-yl)propan-2-ol To a solution of 5H-imidazo[5,1-a]isoindole (200 mg, 1.28 mmol) in anhydrous THF (3 mL) was added n-BuLi solution (2.2 M in cyclohexane, 0.58 mL, 1.28 mmol) at −40° C. and stirred for 1 hr. Anhydrous acetone (0.18 mL, 2.56 mmol) was added and the reaction was slowly warmed to room temperature. After 2 hours, reaction was quenched with saturated $NH_4Cl$ solution (5 mL). The mixture was extracted with DCM (3×10 mL) and the organic phases were combined, dried over $Na_2SO_4$, and concentrated to yield crude 2-(5H-imidazo[5,1-a]isoindol-5-yl)propan-2-ol which was further purified by CombiFlash: LCMS (ESI, m/z): 215 $[M+H]^+$. $^1$H NMR (400 MHz, Chloroform-d) δ 7.89 (s, 1H), 7.54 (d, J=7.6 Hz, 1H), 7.49 (d, J=7.7 Hz, 1H), 7.38 (t, J=7.5 Hz, 1H), 7.23 (dd, J=7.5, 1.1 Hz, 1H), 7.18 (s, 1H), 5.09 (s, 1H), 1.49 (s, 3H), 0.83 (s, 3H).

Example 45: 3-(5H-imidazo[5,1-a]isoindol-5-yl)thietan-3-ol

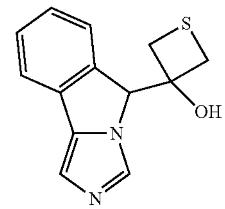 [SMILES: OC1(C2c3ccccc3-c3cncn32)CSC1]

Final product (racemate) is a mixture of the following isomers:

(R)-3-(5H-imidazo[5,1-a]isoindol-5-yl)thietan-3-ol (S)-3-(5H-imidazo[5,1-a]isoindol-5-yl)thietan-3-ol Step 1:

3-(5H-imidazo[5,1-a]isoindol-5-yl)thietan-3-ol

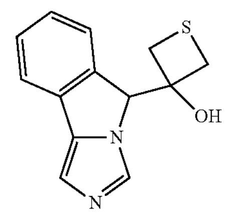 [SMILES: OC1(C2c3ccccc3-c3cncn32)CSC1]

To a solution of 5H-imidazo[5,1-a]isoindole (200 mg, 1.28 mmol, 1.000 equiv.) in anhydrous THF (3 mL) was added n-BuLi solution (0.57 mL, 1.41 mmol, 1.200 equiv.) at −78° C. and stirred for 1 hr. Thietan-3-one (94 mg, 0.70 mmol, 1.5 equiv.) was dissolved in anhydrous THF (3 mL) and the solution was added into the reaction mixture dropwise. The reaction was kept at −78° C. for another 30 min and was warmed up to room temperature. The reaction was kept at room temperature overnight and was quenched with saturated $NH_4Cl$ solution (5 mL). The mixture was extracted with DCM (3×10 mL) and the organic phase was combined, dried over $Na_2SO_4$, and concentrated. The product was separated by CombiFlash and was eluted with DCM:MeOH=96:4. The desired product was isolated as a brown solid.

Example 45: 3-(5H-imidazo[5,1-a]isoindol-5-yl)thietan-3-ol: LCMS (ESI, m/z): 245 $[M+H]^+$. $^1$H NMR (400 MHz, DMSO-$d_6$) δ 7.92 (s, 1H), 7.71 (d, J=7.7 Hz, 1H), 7.61 (d, J=7.6 Hz, 1H), 7.41 (t, J=7.5 Hz, 1H), 7.20-7.29 (m, 1H), 7.14 (s, 1H), 6.61 (s, 1H), 5.40 (s, 1H), 3.45 (d, J=10.4 Hz, 1H), 3.27 (d, J=10.5 Hz, 1H), 3.14 (s, 2H).

Example 46: 1-(5H-imidazo[5,1-a]isoindol-5-yl)cyclohexan-1-ol

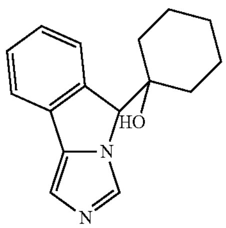 [SMILES: OC1(C2c3ccccc3-c3cncn32)CCCCC1]

(45%) yield; synthesized according to general procedure: LCMS (ESI, m/z): 255.3 $[M+H]^+$. The stereoisomers were separated by chiral SFC.

46a

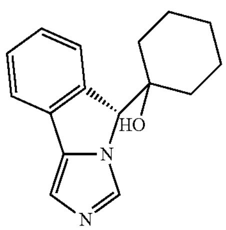

46b

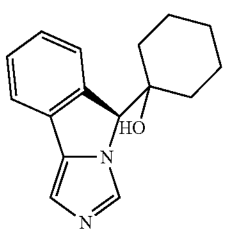

Example 46a: (R)-1-(5H-imidazo[5,1-a]isoindol-5-yl)cyclohexan-1-ol. $^1H$ NMR (Chloroform-d, 400 MHz): δ (ppm) 8.00 (s, 1H), 7.52 (t, J=7.9 Hz, 2H), 7.38 (t, J=7.5 Hz, 1H), 7.25 (t, J=7.4 Hz, 1H), 7.13 (s, 1H), 5.05 (s, 1H), 2.94 (br s, 1H), 1.68 (dt, J=39.3, 11.9 Hz, 5H), 1.34-1.53 (m, 2H), 0.89-1.06 (m, 2H), 0.81 (dt, J=13.3, 6.6 Hz, 1H)

Example 46b: (S)-1-(5H-imidazo[5,1-a]isoindol-5-yl)cyclohexan-1-ol. $^1H$ NMR (DMSO-$d_6$, 400 MHz): Same as 46b Example 47: 1-(5H-imidazo[5,1-a]isoindol-5-yl)cyclobutan-1-ol

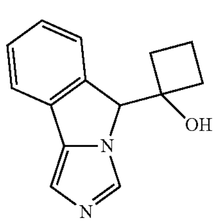 [SMILES: OC1(C2c3ccccc3-c3cncn32)CCC1]

(39%) yield; synthesized according to general procedure: LCMS (ESI, m/z): 227.5 $[M+H]^+$. The stereoisomers were separated by chiral SFC.

47a

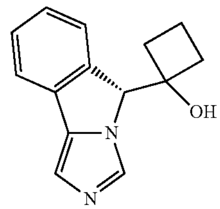

47b

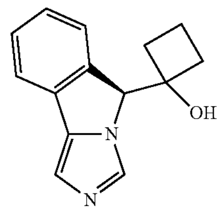

Example 47a: (R)-1-(5H-imidazo[5,1-a]isoindol-5-yl)cyclobutan-1-ol. $^1H$ NMR (Chloroform-d, 400 MHz): δ (ppm) 7.95 (s, 1H), 7.57 (t, J=6.7 Hz, 2H), 7.41 (t, J=7.7 Hz, 1H), 7.15 (s, 1H), 7.22-7.36 (m, 1H), 2.87 (br s, H), 5.22 (s, 1H), 2.57 (dd, J=8.5, 4.4 Hz, 1H), 2.28 (p, J=8.7, 8.2 Hz, 1H), 1.78-2.04 (m, 3H), 1.27-1.44 (m, 1H)

Example 47b: (S)-1-(5H-imidazo[5,1-a]isoindol-5-yl)cyclobutan-1-ol. $^1H$ NMR (DMSO-$d_6$, 400 MHz): Same as 47a.

Example 48: 3-(5H-imidazo[5,1-a]isoindol-5-yl)oxetan-3-ol

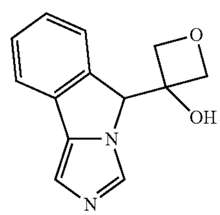 [SMILES: OC1(C2c3ccccc3-c3cncn32)COC1]

Final product (racemate) is a mixture of the following isomers:

(R)-3-(5H-imidazo[5,1-a]isoindol-5-yl) oxetan-3-ol (S)-3-(5H-imidazo[5,1-a]isoindol-5-yl) oxetan-3-ol (61%) yield; synthesized according to general procedure: LCMS (ESI, m/z): 229.1 $[M+H]^+$. $^1H$ NMR (DMSO-$d_6$, 400 MHz): δ (ppm) 7.92 (s, 1H), 7.62 (d, J=7.7 Hz, 2H), 7.42 (t, J=7.5 Hz, 1H), 7.26 (t, J=8.1 Hz, 1H), 7.16 (s, 1H), 6.51 (s, 1H), 5.61 (s, 1H), 4.71 (d, J=7.1 Hz, 1H), 4.60 (d, J=7.0 Hz, 1H), 4.52 (d, J=7.1 Hz, 1H), 4.47 (d, J=7.1 Hz, 1H).

Example 49: 1-(5H-imidazo[5,1-a]isoindol-5-yl)ethane-1,2-diol

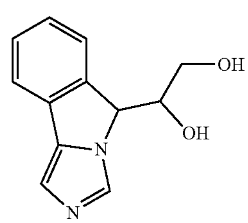

-continued

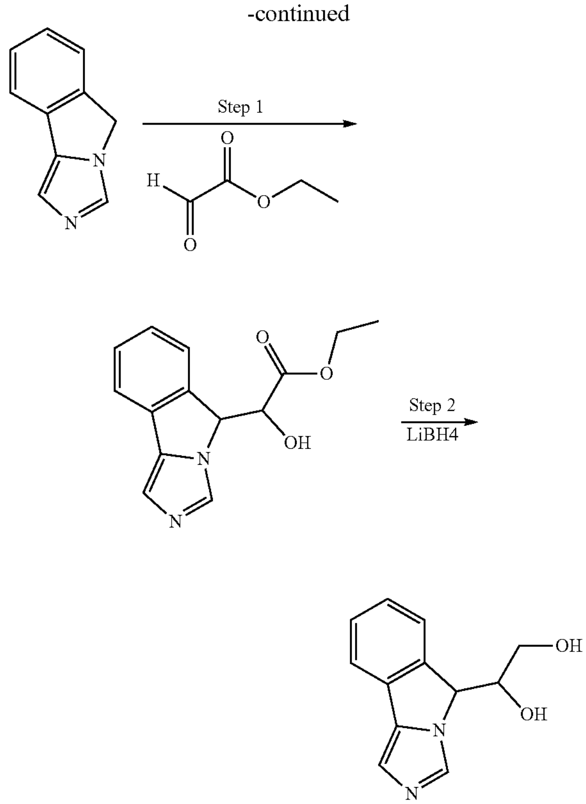

(R)-1-((R)-5H-imidazo[5,1-a]isoindol-5-yl)ethane-1,2-diol
(R)-1-((S)-5H-imidazo[5,1-a]isoindol-5-yl)ethane-1,2-diol
(S)-1-((R)-5H-imidazo[5,1-a]isoindol-5-yl)ethane-1,2-diol
(S)-1-((S)-5H-imidazo[5,1-a]isoindol-5-yl)ethane-1,2-diol Step 1:

A solution of 5H-imidazo[5,1-a]isoindole (1.0 g, 6.4 mmol) in 50 mL of THF was cooled to −78° C. and charged with 2.5 M n-butyl lithium in heptanes (2.6 mL, 6.4 mmol). After stirring at −78° C. for 30 minutes, the solution was charged with 50% ethyl glyoxalate in toluene (3.3 g, 16 mmol) and warmed to −45° C. and stirred at −45° C. for one hour. The solution was then diluted with 300 mL of EtOAc and 100 mL saturated ammonium chloride. The aqueous was discarded and the organic was washed once with water, dried over $Na_2SO_4$, filtered, and concentrated in vacuo to afford ethyl 2-hydroxy-2-(5H-imidazo[1,5-b]isoindol-5-yl)acetate (1.5 g, 5.8 mmol, 90% yield) as a crude residue. LCMS (ESI, m/z): 259.1 (M+H).

Step 2:

The ethyl 2-hydroxy-2-(5H-imidazo[1,5-b]isoindol-5-yl) acetate (500 mg, 1.9 mmol) as crude residue from step 1 was dissolved in 8 mL of ethanol and cooled to 0° C. The mixture then charged with lithium borohydride (1.7 g, 3.9 mmol) pre-dissolved in 10 mL of ethanol and allowed to warm to room temperature. After 2 hours at room temperature, the solution was charged with 4 mL of 1 M ammonium chloride. The mixture was then purified by reverse-phase HPLC to afford 1-(5H-imidazo[5,1-a]isoindol-5-yl)ethane-1,2-diol (100 mg, 23% yield) as a mixture of 4 diastereomers. The mixture was then separated by chiral supercritical fluid chromatography with the described conditions to afford the 4 diastereomers, examples 49 a-d. Each example is a single diastereomer with unknown absolute configuration.

Example 49a: 1-(5H-imidazo[5,1-a]isoindol-5-yl)ethane-1,2-diol. (3 mg, 3% yield). LCMS (ESI, m/z): 217.1 $[M+H]^+$; no NMR; tR=0.82 min (Chiralpak IC (150×21.1 mm, 5 um), Ethanol w/0.1% $NH_4OH$, 1.5 ml/min).

Example 49b. 1-(5H-imidazo[5,1-a]isoindol-5-yl)ethane-1,2-diol. (3 mg, 3% yield). LCMS (ESI, m/z): 217.1 $[M+H]^+$; no NMR; tR=1.03 min (Chiralpak IC (150×21.1 mm, 5 um), Ethanol w/0.1% $NH_4OH$, 1.5 ml/min).

Example 49c: 1-(5H-imidazo[5,1-a]isoindol-5-yl)ethane-1,2-diol. (7 mg, 7% yield). LCMS (ESI, m/z): 217.1 $[M+H]^+$. $^1H$ NMR (400 MHz, DMSO-$d_6$) δ 8.40 (s, 1H), 7.68 (dt, J=7.6, 1.0 Hz, 1H), 7.59 (dq, J=7.6, 1.0 Hz, 1H), 7.51-7.39 (m, 2H), 7.35 (td, J=7.5, 1.2 Hz, 1H), 5.56 (d, J=4.0 Hz, 1H), 5.46 (d, J=4.9 Hz, 1H), 4.84 (t, J=5.2 Hz, 1H), 4.20 (p, J=5.2 Hz, 1H). tR=1.03 min (Chiralpak OX (150×21.1 mm, 5 um), Methanol w/0.1% $NH_4OH$, 1.5 ml/min).

Example 49d: 1-(5H-imidazo[5,1-a]isoindol-5-yl)ethane-1,2-diol. (5 mg, 5% yield). LCMS (ESI, m/z): 217.1 $[M+H]^+$. $^1H$ NMR (400 MHz, DMSO-$d_6$) δ 7.81 (d, J=0.7 Hz, 1H), 7.56 (ddt, J=13.4, 7.6, 0.9 Hz, 2H), 7.38 (tdd, J=7.6, 1.2, 0.7 Hz, 1H), 7.25 (td, J=7.6, 1.2 Hz, 1H), 7.11 (s, 1H), 5.42 (d, J=4.9 Hz, 1H), 5.38 (d, J=4.3 Hz, 1H), 4.75 (t, J=5.4 Hz, 1H), 4.15-3.98 (m, 1H), 3.22-3.06 (m, 2H). tR=1.38 min (Chiralpak IC (150×21.1 mm, 5 um), Ethanol w/0.1% $NH_4OH$, 1.5 ml/min).

Example 50: 3,3-difluoro-1-(5H-imidazo[5,1-a]isoindol-5-yl)cyclobutan-1-ol

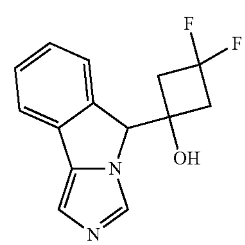 [SMILES: OC1(C2c3ccccc3-c3cncn32)CC(F)(F)C1]

(R)-1-((R)-5H-imidazo[5,1-a]isoindol-5-yl)ethane-1,2-diol
(R)-1-((S)-5H-imidazo[5,1-a]isoindol-5-yl)ethane-1,2-diol
(S)-1-((R)-5H-imidazo[5,1-a]isoindol-5-yl)ethane-1,2-diol
(S)-1-((S)-5H-imidazo[5,1-a]isoindol-5-yl)ethane-1,2-diol To a solution of 5H-imidazo[5,1-a]isoindole (190 mg, 1.22 mmol) in anhydrous THF (10 mL) stirred at −78° C., n-BuLi solution (2.5 M in hexane, 0.535 mL, 1.34 mmol) was added dropwise and stirred for 1 hr. A solution of 3,3-difluorocyclobutan-1-one (193.55 mg, 1.82 mmol) in anhydrous THF (1 mL) was added into the reaction mixture drop-wise and stirred at −78° C. for 90 min. The reaction mixture was warmed to room temperature, stirred for 2 hrs and quenched with saturated $NH_4Cl$ solution (10 mL). The organic layer was extracted first with EtOAc (10 mL), then with DCM (10 mL) and lastly with 5% $CF_3CH_2OH$ in DCM (10 mL). The organic layers were pooled, dried by anhydrous $Na_2SO_4$ and purified by CombiFlash to afford 3,3-difluoro-1-(5H-imidazo[5,1-a]isoindol-5-yl)cyclobutan-1-ol as brown powder: LCMS (ESI, m/z): 263 $[M+H]^+$. $^1H$ NMR (400 MHz, DMSO-$d_6$) δ 7.91 (s, 1H), 7.57 (ddt, J=12.0, 7.6, 0.9 Hz, 2H), 7.41-7.37 (m, 1H), 7.24 (td, J=7.5, 1.1 Hz, 1H), 7.12 (s, 1H), 5.85 (s, 1H), 5.46 (s, 1H), 3.17 (m, 2H), 2.68-2.54 (m, 2H).

Example 51: 1-(5H-imidazo[5,1-a]isoindol-5-yl)-2-methylpropan-1-ol

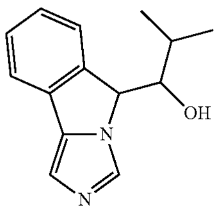 [SMILES: CC(C)C(O)C1c2ccccc2-c2cncn21]

(25%) yield; synthesized according to general procedure: LCMS (ESI, m/z): 229.4 $[M+H]^+$. The stereoisomers were separated by chiral SFC.

51a

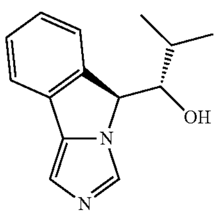

51b

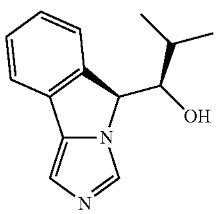

51c

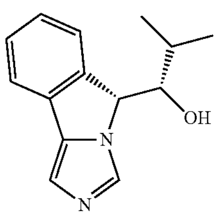

51d

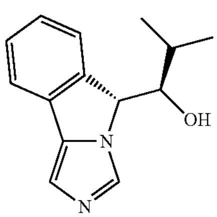

Example 51a: (S)-1-((S)-5H-imidazo[5,1-a]isoindol-5-yl)-2-methylpropan-1-ol. $^1H$ NMR (DMSO-$d_6$, 400 MHz): δ (ppm) 7.82 (t, J=0.7 Hz, 1H), 7.58 (dt, J=7.5, 1.0 Hz, 1H), 7.49 (dq, J=7.6, 0.9 Hz, 1H), 7.37 (tdd, J=7.5, 1.1, 0.6 Hz, 1H), 7.26 (td, J=7.6, 1.2 Hz, 1H), 7.12 (s, 1H), 5.32 (d, J=5.2 Hz, 1H), 5.13 (d, J=6.5 Hz, 1H), 3.47 (td, J=6.3, 5.2 Hz, 1H), 1.93 (dt, J=13.3, 6.6 Hz, 1H), 0.99 (d, J=6.6 Hz, 3H), 0.93 (d, J=6.8 Hz, 3H).

Example 51b: (R)-1-((S)-5H-imidazo[5,1-a]isoindol-5-yl)-2-methylpropan-1-ol. $^1H$ NMR (DMSO-$d_6$, 400 MHz): δ (ppm) 7.81 (t, J=0.7 Hz, 1H), 7.59 (dt, J=7.5, 1.0 Hz, 1H), 7.51 (dq, J=7.6, 0.9 Hz, 1H), 7.37 (tdd, J=7.5, 1.1, 0.6 Hz, 1H), 7.25 (td, J=7.5, 1.2 Hz, 1H), 7.11 (s, 1H), 5.39 (d, J=4.5 Hz, 1H), 5.27 (d, J=5.6 Hz, 1H), 3.80 (td, J=5.5, 4.5 Hz, 1H), 1.52-1.67 (m, 1H), 0.81 (d, J=6.8 Hz, 3H), 0.66 (d, J=6.7 Hz, 3H).

Example 51c: (S)-1-((R)-5H-imidazo[5,1-a]isoindol-5-yl)-2-methylpropan-1-ol. $^1H$ NMR (DMSO-$d_6$, 400 MHz): Same as 51b.

Example 51d: (R)-1-((R)-5H-imidazo[5,1-a]isoindol-5-yl)-2-methylpropan-1-ol. 1H NMR (DMSO-$d_6$, 400 MHz): Same as 51a.

Example 52: cyclopropyl(5H-imidazo[5,1-a]isoindol-5-yl)methanol

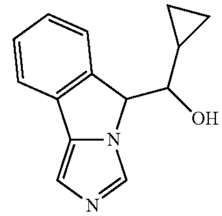 [SMILES: OC(C1CC1)C1c2ccccc2-c2cncn21]

(58%) yield; synthesized according to general procedure: LCMS (ESI, m/z): 227.4 $[M+H]^+$. The stereoisomers were separated by chiral SFC.

52a

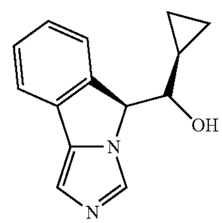

52b

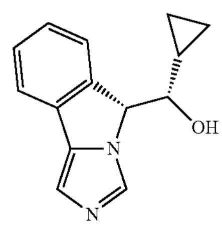

52c

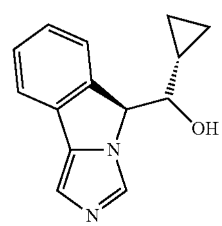

52d

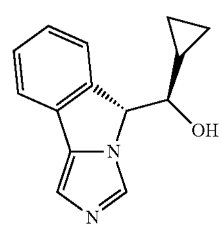

Example 52a: (S)-cyclopropyl((S)-5H-imidazo[5,1-a]isoindol-5-yl)methanol. 1H NMR (DMSO-$d_6$, 400 MHz): δ (ppm) −0.16-−0.06 (m, 1H), −0.04-0.07 (m, 1H), 0.16 (dddd, J=9.2, 7.9, 5.6, 1.7 Hz, 2H), 0.26-0.39 (m, 1H), 3.63 (dt, J=7.4, 4.1 Hz, 1H), 5.39 (d, J=3.8 Hz, 1H), 5.43 (d, J=4.3 Hz, 1H), 7.12 (s, 1H), 7.24 (td, J=7.6, 1.1 Hz, 1H), 7.37 (tt, J=7.6, 0.9 Hz, 1H), 7.56 (ddt, J=15.1, 7.6, 0.9 Hz, 2H), 7.82 (t, J=0.6 Hz, 1H)

Example 52b: (S)-cyclopropyl((R)-5H-imidazo[5,1-a]isoindol-5-yl)methanol. $^1$H NMR (DMSO-$d_6$, 400 MHz): Same as 52a.

Example 52c: (R)-cyclopropyl((S)-5H-imidazo[5,1-a]isoindol-5-yl)methanol. $^1$H NMR (DMSO-$d_6$, 400 MHz): δ (ppm) 0.06-0.13 (m, 1H), 0.26-0.41 (m, 3H), 0.84 (qt, J=7.8, 5.0 Hz, 1H), 3.32-3.38 (m, 1H), 5.29 (d, J=5.2 Hz, 1H), 5.32 (d, J=5.0 Hz, 1H), 7.10 (s, 1H), 7.24 (td, J=7.5, 1.2 Hz, 1H), 7.37 (tdd, J=7.5, 1.1, 0.6 Hz, 1H), 7.58 (dt, J=7.6, 1.0 Hz, 1H), 7.60-7.64 (m, 1H), 7.87 (t, J=0.6 Hz, 1H).

Example 52d: (R)-cyclopropyl((R)-5H-imidazo[5,1-a]isoindol-5-yl)methanol. $^1$H NMR (DMSO-$d_6$, 400 MHz): Same as 52d.

Example 53: 4,4-difluoro-1-(5H-imidazo[5,1-a]isoindol-5-yl)cyclohexan-1-ol

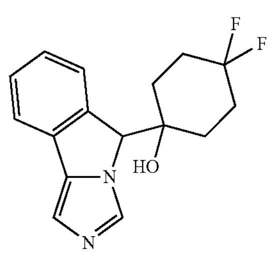 [SMILES: OC1(C2c3ccccc3-c3cncn32)CCC(F)(F)CC1]

Final product (racemate) is a mixture of the following isomers:

(R)-4,4-difluoro-1-(5H-imidazo[5,1-a]isoindol-5-yl)cyclohexan-1-ol (S)-4,4-difluoro-1-(5H-imidazo[5,1-a]isoindol-5-yl)cyclohexan-1-ol To a solution of 5H-imidazo[5,1-a]isoindole (400 mg, 2.56 mmol, 1.0 equiv) in anhydrous THF (20 mL) at −78° C. was added n-BuLi (1.54 mL, 3.84 mmol, 2.5 M solution hexanes, 1.5 equiv). After stirring for 1.5 hr at −78° C., a mixture of 4,4-difluorocyclohexan-1-one (550 mg, 4.1 mmol, 1.6 equiv) was added and the reaction was allowed to warm to rt over a period of 2 hr. The reaction was quenched by adding saturated aqueous solution of $NH_4Cl$ (5 mL) and diluted with water (20 mL), the product was extracted with $CH_2Cl_2$ (3×20 mL). The combined organic extract was dried over $Na_2SO_4$. The product was purified by CombiFlash to afford 4,4-difluoro-1-(5H-imidazo[5,1-a]isoindol-5-yl)cyclohexan-1-ol as beige solid: LCMS (ESI, m/z): 291 [M+H]$^+$ Example 54: 3,3-bis(fluoromethyl)-1-(5H-imidazo[5,1-a]isoindol-5-yl)cyclobutan-1-ol

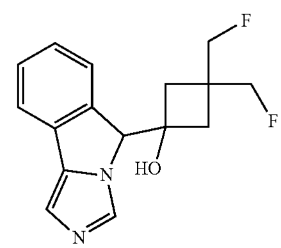 [SMILES: OC1(C2c3ccccc3-c3cncn32)CC(CF)(CF)C1]

Final product (racemate) is a mixture of the following isomers:

(R)-3,3-bis(fluoromethyl)-1-(5H-imidazo[5,1-a]isoindol-5-yl)cyclobutan-1-ol (S)-3,3-bis(fluoromethyl)-1-(5H-imidazo[5,1-a]isoindol-5-yl)cyclobutan-1-ol To a solution of 5H-imidazo[5,1-a]isoindole (100 mg, 0.64 mmol, 1.0 equiv) in anhydrous THF (5 mL) at −78° C. was added n-BuLi (0.38 mL, 0.96 mmol, 2.5 M solution hexanes, 1.5 equiv). After stirring for 1.5 hr at −78° C., a mixture of 3,3-bis(fluoromethyl)cyclobutan-1-one (137 mg, 1.02 mmol, 1.6 equiv) was added and the reaction was allowed to warm to rt over a period of 2 hr. The reaction was quenched by adding saturated aqueous solution of $NH_4Cl$ (2 mL) and diluted with water (10 mL), the product was extracted with $CH_2Cl_2$ (3×10 mL). The combined organic extract was dried over $Na_2SO_4$. The product was purified by CombiFlash to afford 3,3-bis(fluoromethyl)-1-(5H-imidazo[5,1-a]isoindol-5-yl)cyclobutan-1-ol as beige solid: LCMS (ESI, m/z): 291 [M+H]$^+$ Example 55: 1-(5H-imidazo[5,1-a]isoindol-5-yl)cyclopentan-1-ol

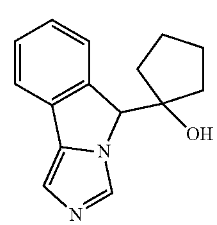 [SMILES: OC1(C2c3ccccc3-c3cncn32)CCCC1]

Final product (racemate) is a mixture of the following isomers:

(R)-1-(5H-imidazo[5,1-a]isoindol-5-yl)cyclopentan-1-ol (S)-1-(5H-imidazo[5,1-a]isoindol-5-yl)cyclopentan-1-ol Step 1:

1-(5H-imidazo[5,1-a]isoindol-5-yl)cyclopentan-1-ol

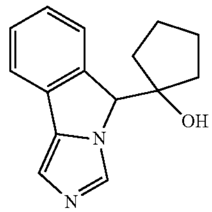

To a solution of 5H-imidazo[5,1-a]isoindole (300 mg, 1.92 mmol, 1.000 equiv.) in anhydrous THF (10 mL) was added n-BuLi solution (0.92 mL, 2.30 mmol, 1.200 equiv.) at −78° C. and stirred for 1 hr. Cyclopentanone (0.26 mL, 2.9 mmol, 1.500 equiv.) was added into the reaction mixture drop-wise. The reaction was kept at −78° C. for another 30 min and was warmed up to room temperature. The reaction was kept at room temperature for another 2 hrs and was quenched with saturated $NH_4Cl$ solution (20 mL). The mixture was extracted with DCM (3×20 mL) and the organic phase was combined, dried over $Na_2SO_4$, and concentrated. The product was separated by CombiFlash and was eluted with DCM:MeOH=95:5. The desired product was separated as light brown solids.

Example 55: 1-(5H-imidazo[5,1-a]isoindol-5-yl)cyclopentan-1-ol: LCMS (ESI, m/z): 241 $[M+H]^+$. $^1$H NMR (400 MHz, DMSO-$d_6$) δ 7.86 (d, J=0.7 Hz, 1H), 7.59 (d, J=1.0 Hz, 1H), 7.57 (d, J=1.1 Hz, 1H), 7.37 (ddd, J=8.0, 6.9, 0.8 Hz, 1H), 7.23 (td, J=7.5, 1.2 Hz, 1H), 7.10-7.13 (m, 1H), 5.30-5.34 (m, 1H), 4.97 (s, 1H), 1.60-1.80 (m, 4H), 1.35-1.51 (m, 4H).

Example 56: 5-(5H-imidazo[5,1-a]isoindol-5-yl)-4,5,6,7-tetrahydropyrazolo[1,5-a]pyridin-4-ol Examples 56a-h were all synthesized using the reaction conditions for the preparation of examples 1 a-h in which the reagent cyclobutanone was substituted with 6,7-dihydropyrazolo[1,5-a]pyridin-4(5H)-one. Each example is a single diastereomer with undetermined absolute configuration. The absolute configuration of 56a, 56c, 56d and 56e were assigned by X-ray crystallography, while the other stereoisomers were assigned arbitrarily.

(4S,5S)-5-((S)-5H-imidazo[5,1-a]isoindol-5-yl)-4,5,6,7-tetrahydropyrazolo[1,5-a]pyridin-4-ol (4S,5R)-5-((S)-5H-imidazo[5,1-a]isoindol-5-yl)-4,5,6,7-tetrahydropyrazolo[1,5-a]pyridin-4-ol (4S,5R)-5-((R)-5H-imidazo[5,1-a]isoindol-5-yl)-4,5,6,7-tetrahydropyrazolo[1,5-a]pyridin-4-ol (4R,5R)-5-((R)-5H-imidazo[5,1-a]isoindol-5-yl)-4,5,6,7-tetrahydropyrazolo[1,5-a]pyridin-4-ol (4R,5S)-5-((S)-5H-imidazo[5,1-a]isoindol-5-yl)-4,5,6,7-tetrahydropyrazolo[1,5-a]pyridin-4-ol (4R,5R)-5-((S)-5H-imidazo[5,1-a]isoindol-5-yl)-4,5,6,7-tetrahydropyrazolo[1,5-a]pyridin-4-ol (4R,5S)-5-((R)-5H-imidazo[5,1-a]isoindol-5-yl)-4,5,6,7-tetrahydropyrazolo[1,5-a]pyridin-4-ol

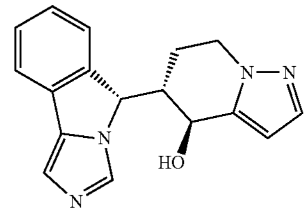

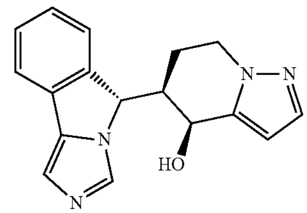

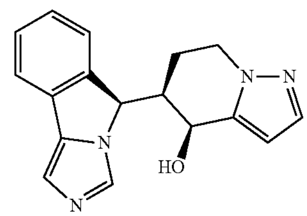

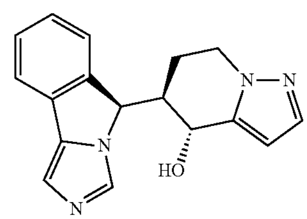

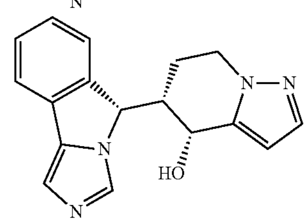

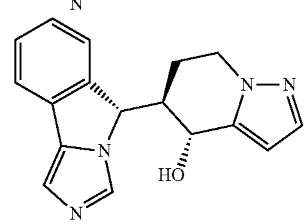

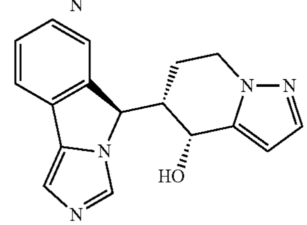

Example 56a: (4S,5S)-5-((S)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.01-1.16 (m, 2H), 2.51-2.59 (m, 1H), 3.73-3.84 (m, 1H), 3.93-4.01 (m, 1H), 5.03 (dd, J=10.5, 7.2 Hz, 1H), 5.76 (d, J=1.9 Hz, 1H), 6.18 (d, J=7.2 Hz, 1H), 6.31 (dd, J=1.9, 0.8 Hz, 1H), 7.19 (s, 1H), 7.34 (dd, J=7.5, 1.1 Hz, 1H), 7.38-7.46 (m, 2H), 7.51 (dd, J=7.6, 1.0 Hz, 1H), 7.64 (dt, J=7.6, 0.9 Hz, 1H), 7.98 (s, 1H).

Example 56b: (4S,5R)-5-((S)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.88 (d, J=12.3 Hz, 1H), 2.28 (qd, J=12.2, 5.5 Hz, 1H), 2.32-2.38 (m, 1H), 3.80-3.91 (m, 1H), 4.16 (ddd, J=12.7, 5.5, 1.9 Hz, 1H), 4.99 (s, 1H), 5.48 (d, J=5.7 Hz, 1H), 5.83 (d, J=5.4 Hz, 1H), 6.22 (d, J=1.8 Hz, 1H), 7.14 (s, 1H), 7.25 (td, J=7.6, 1.2 Hz, 1H), 7.39 (dd, J=6.3, 1.4 Hz, 2H), 7.62 (dt, J=7.6, 0.9 Hz, 1H), 7.71 (dd, J=7.8, 0.9 Hz, 1H), 7.97 (s, 1H).

Example 56c: (4S,5R)-5-((R)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.19 (d, J=13.6 Hz, 1H), 1.86 (qd, J=12.6, 5.8 Hz, 1H), 2.55-2.66 (m, 1H), 3.77 (td, J=12.5, 4.9 Hz, 1H), 4.05 (ddd, J=12.8, 5.8, 2.0 Hz, 1H), 5.19 (t, J=4.6 Hz, 1H), 5.54 (d, J=2.5 Hz, 1H), 6.09 (d, J=5.5 Hz, 1H), 6.27 (d, J=1.9 Hz, 1H), 7.13 (s, 1H), 7.30 (td, J=7.6, 1.2 Hz, 1H), 7.36-7.44 (m, 2H), 7.60 (dt, J=7.6, 0.9 Hz, 1H), 7.64 (dq, J=7.7, 1.0 Hz, 1H), 7.92 (s, 1H).

Example 56d: (4R,5R)-5-((R)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.01-1.16 (m, 2H), 2.52 (d, J=2.3 Hz, 1H), 3.78 (td, J=12.2, 5.1 Hz, 1H), 3.90-4.00 (m, 1H), 5.03 (dd, J=10.6, 7.2 Hz, 1H), 5.76 (d, J=1.8 Hz, 1H), 6.18 (d, J=7.2 Hz, 1H), 6.27-6.34 (m, 1H), 7.19 (s, 1H), 7.33 (td, J=7.6, 1.1 Hz, 1H), 7.37-7.46 (m, 2H), 7.51 (dd, J=7.6, 1.0 Hz, 1H), 7.64 (d, J=7.5 Hz, 1H), 7.98 (s, 1H).

Example 56e: (4R,5S)-5-((S)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.19 (d, J=13.5 Hz, 1H), 1.77-1.95 (m, 1H), 2.57-2.70 (m, 1H), 3.76 (td, J=12.2, 4.7 Hz, 1H), 3.99-4.12 (m, 1H), 5.15-5.26 (m, 1H), 5.54 (d, J=2.6 Hz, 1H), 6.09 (d, J=5.6 Hz, 1H), 6.27 (d, J=2.2 Hz, 1H), 7.13 (s, 1H), 7.29 (ddd, J=8.8, 7.0, 1.3 Hz, 1H), 7.35-7.46 (m, 2H), 7.62 (dd, J=19.0, 7.6 Hz, 2H), 7.92 (s, 1H).

Example 56f: (4R,5R)-5-((S)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.03 (s, 1H), 1.11-1.30 (m, 1H), 2.71 (s, 1H), 3.82 (s, 1H), 3.97 (s, 1H), 4.97 (s, 1H), 5.77 (s, 1H), 6.10-6.24 (m, 1H), 6.28 (s, 1H), 7.18 (d, J=8.9 Hz, 1H), 7.23-7.35 (m, 1H), 7.40 (d, J=16.2 Hz, 2H), 7.63 (m, 2H), 7.94 (t, J=10.8 Hz, 1H).

Example 56g: (4R,5S)-5-((R)-5H-imidazo[5,1-a]isoindol-5-yl)-4,5,6,7-tetrahydropyrazolo[1,5-a]pyridin-4-ol: LCMS (ESI, m/z): 293.2 $[M+H]^+$; $^1H$ NMR (500 MHz, DMSO-d6) δ 1.88 (d, J=10.6 Hz, 1H), 2.28 (tt, J=12.5, 6.0 Hz, 1H), 2.32-2.39 (m, 1H), 3.86 (td, J=12.3, 4.8 Hz, 1H), 4.16 (ddd, J=12.7, 5.5, 1.8 Hz, 1H), 4.99 (dd, J=5.9, 3.3 Hz, 1H), 5.48 (d, J=5.7 Hz, 1H), 5.83 (d, J=5.6 Hz, 1H), 7.14 (s, 1H), 7.25 (dd, J=7.6, 1.2 Hz, 1H), 7.36-7.42 (m, 2H), 7.62 (dt, J=7.6, 0.9 Hz, 1H), 7.71 (dd, J=7.7, 0.9 Hz, 1H), 7.97 (s, 1H).

Example 57: 2-(5H-imidazo[5,1-a]isoindol-5-yl)-7-oxaspiro[3.5]nonan-1-ol

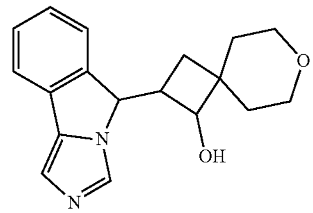 [SMILES: OC1C(C2c3ccccc3-c3cncn32)CC12CCOCC2]

(1R,2R)-2-((S)-5H-imidazo[5,1-a]isoindol-5-yl)-7-oxaspiro[3.5]nonan-1-ol
(1S,2S)-2-((S)-5H-imidazo[5,1-a]isoindol-5-yl)-7-oxaspiro[3.5]nonan-1-ol
(1S,2R)-2-((S)-5H-imidazo[5,1-a]isoindol-5-yl)-7-oxaspiro[3.5]nonan-1-ol
(1R,2S)-2-((R)-5H-imidazo[5,1-a]isoindol-5-yl)-7-oxaspiro[3.5]nonan-1-ol
(1R,2R)-2-((R)-5H-imidazo[5,1-a]isoindol-5-yl)-7-oxaspiro[3.5]nonan-1-ol
(1S,2S)-2-((R)-5H-imidazo[5,1-a]isoindol-5-yl)-7-oxaspiro[3.5]nonan-1-ol
(1R,2S)-2-((S)-5H-imidazo[5,1-a]isoindol-5-yl)-7-oxaspiro[3.5]nonan-1-ol
(1S,2R)-2-((R)-5H-imidazo[5,1-a]isoindol-5-yl)-7-oxaspiro[3.5]nonan-1-ol Step 1: (E)-2-(2-(1-trityl-1H-imidazol-4-yl)benzylidene)-7-oxaspiro[3.5]nonan-1-one

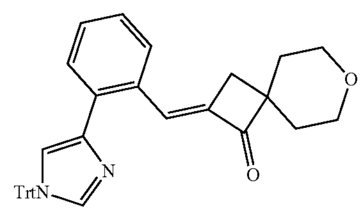

The title compound was synthesized by General Procedure for the Synthesis of Int-2. LCMS (ESI, m/z): 537.3 $[M+H]^+$ Step 2: 2-(5H-imidazo[5,1-a]isoindol-5-yl)-7-oxaspiro[3.5]nonan-1-one

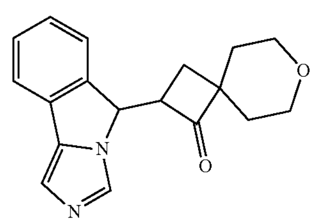 [SMILES: O=C1C(C2c3ccccc3-c3cncn32)CC12CCOCC2]

The title compound was synthesized by General Procedure for the Synthesis of Int-3. LCMS (ESI, m/z): 295.4 $[M+H]^+$ Step 3: 2-(5H-imidazo[5,1-a]isoindol-5-yl)-7-oxaspiro[3.5]nonan-1-ol

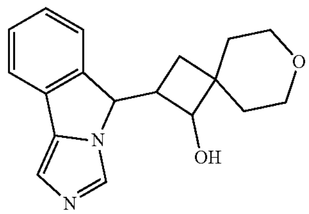 [SMILES: OC1C(C2c3ccccc3-c3cncn32)CC12CCOCC2]

The title compounds were synthesized by General Procedure for the Synthesis of Int-5: LCMS (ESI, m/z): 297.2 $[M+H]^+$. The mixture was isolated by Chiral separation methods and the configuration of the isomers was assigned arbitrarily.

(1R,2R)-2-((S)-5H-imidazo[5,1-a]isoindol-5-yl)-7-oxaspiro[3.5]nonan-1-ol (1S,2S)-2-((S)-5H-imidazo[5,1-a]isoindol-5-yl)-7-oxaspiro[3.5]nonan-1-ol (1S,2R)-2-((S)-5H-imidazo[5,1-a]isoindol-5-yl)-7-oxaspiro[3.5]nonan-1-ol (1R,2S)-2-((R)-5H-imidazo[5,1-a]isoindol-5-yl)-7-oxaspiro[3.5]nonan-1-ol (1R,2R)-2-((R)-5H-imidazo[5,1-a]isoindol-5-yl)-7-oxaspiro[3.5]nonan-1-ol (1S,2S)-2-((R)-5H-imidazo[5,1-a]isoindol-5-yl)-7-oxaspiro[3.5]nonan-1-ol (1R,2S)-2-((S)-5H-imidazo[5,1-a]isoindol-5-yl)-7-oxaspiro[3.5]nonan-1-ol (1S,2R)-2-((R)-5H-imidazo[5,1-a]isoindol-5-yl)-7-oxaspiro[3.5]nonan-1-ol 57a

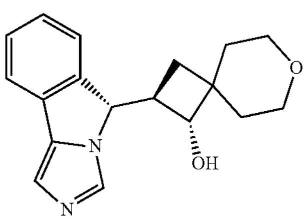

57b

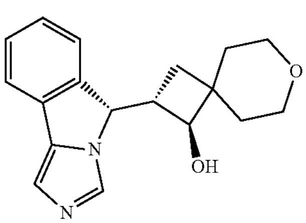

57c

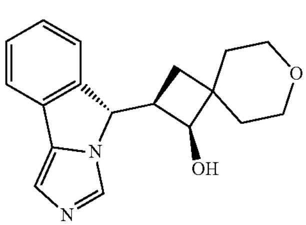

-continued

57d

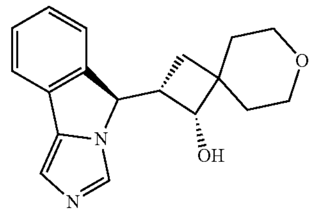

57e

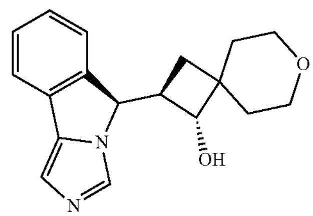

57f

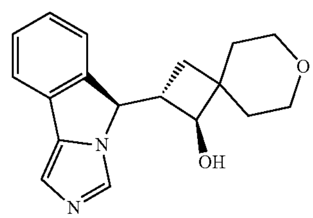

57f

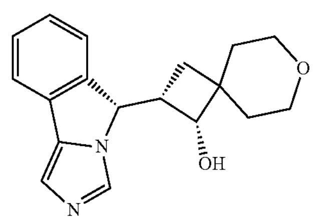

57g

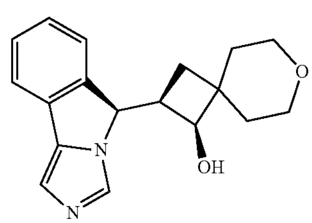

Example 57a: (1R,2R)-2-((S)-5H-imidazo[5,1-a]isoindol-5-yl)-7-oxaspiro[3.5]nonan-1-ol: LCMS (ESI, m/z): 297.2 $[M+H]^+$; $^1H$ NMR (500 MHz, Chloroform-d) δ 7.85 (s, 1H), 7.56-7.51 (m, 1H), 7.37 (d, J=3.2 Hz, 1H), 7.35-7.32 (m, 1H), 7.25-7.21 (m, 1H), 7.13 (s, 1H), 5.17 (d, J=7.9 Hz, 1H), 3.88 (dt, J=11.5, 4.2 Hz, 1H), 3.84 (d, J=8.0 Hz, 1H), 3.77 (dd, J=7.9, 3.6 Hz, 1H), 3.61-3.54 (m, 1H), 3.51-3.41 (m, 1H), 2.55 (ddd, J=17.5, 9.6, 8.0 Hz, 1H), 2.15-2.07 (m, 1H), 1.93-1.84 (m, 1H), 1.79 (ddd, J=13.7, 10.1, 4.1 Hz, 1H), 1.54-1.49 (m, 2H), 1.42 (d, J=13.3 Hz, 1H).

Example 57b: (1S,2S)-2-((S)-5H-imidazo[5,1-a]isoindol-5-yl)-7-oxaspiro[3.5]nonan-1-ol: LCMS (ESI, m/z): 297.2

[M+H]+; $^1$H NMR (500 MHz, Chloroform-d) δ 7.78 (s, 1H), 7.54 (dd, J=11.9, 7.6 Hz, 2H), 7.36 (d, J=7.8 Hz, 1H), 7.23 (dd, J=7.6, 1.0 Hz, 1H), 7.18 (s, 1H), 5.46 (d, J=8.8 Hz, 1H), 4.30 (dd, J=6.5, 2.8 Hz, 1H), 3.70 (dq, J=9.3, 5.1, 4.1 Hz, 2H), 3.59-3.51 (m, 2H), 2.67-2.57 (m, 1H), 2.07-2.02 (m, 2H), 1.78-1.73 (m, 1H), 1.67 (s, 1H), 1.59 (d, J=3.8 Hz, 1H), 1.55 (s, 1H).

Example 57c: (1S,2R)-2-((S)-5H-imidazo[5,1-a]isoindol-5-yl)-7-oxaspiro[3.5]nonan-1-ol: LCMS (ESI, m/z): 297.2 [M+H]+; $^1$H NMR (500 MHz, Chloroform-d) δ 7.95 (s, 1H), 7.55 (d, J=7.6 Hz, 1H), 7.36 (d, J=5.5 Hz, 1H), 7.33-7.30 (m, 1H), 7.22-7.19 (m, 1H), 7.16 (s, 1H), 5.44 (d, J=11.0 Hz, 1H), 4.25 (dd, J=6.1, 3.3 Hz, 1H), 3.79-3.76 (m, 1H), 3.74-3.67 (m, 1H), 3.60 (dddd, J=19.9, 11.6, 8.2, 3.4 Hz, 2H), 2.49-2.40 (m, 1H), 2.30 (t, J=10.4 Hz, 1H), 2.15 (ddd, J=11.3, 8.5, 3.4 Hz, 1H), 1.89-1.82 (m, 1H), 1.76-1.67 (m, 2H), 1.53 (s, 1H).

Example 57d: (1R,2S)-2-((R)-5H-imidazo[5,1-a]isoindol-5-yl)-7-oxaspiro[3.5]nonan-1-ol: LCMS (ESI, m/z): 297.2 [M+H]+; $^1$H NMR (500 MHz, Chloroform-d) δ 7.97 (s, 1H), 7.55 (d, J=7.6 Hz, 1H), 7.37 (d, J=7.4 Hz, 1H), 7.31 (d, J=7.6 Hz, 1H), 7.20 (t, J=7.6 Hz, 1H), 7.16 (s, 1H), 5.44 (d, J=11.0 Hz, 1H), 4.25 (dd, J=5.9, 3.2 Hz, 1H), 3.80-3.76 (m, 1H), 3.70 (dd, J=10.6, 6.1 Hz, 1H), 3.66-3.56 (m, 2H), 2.49-2.39 (m, 1H), 2.30 (t, J=10.4 Hz, 1H), 2.18-2.11 (m, 1H), 1.84 (td, J=8.7, 8.2, 4.1 Hz, 1H), 1.72 (s, 1H), 1.61-1.55 (m, 2H).

Example 57e: (1R,2R)-2-((R)-5H-imidazo[5,1-a]isoindol-5-yl)-7-oxaspiro[3.5]nonan-1-ol: LCMS (ESI, m/z): 297.2 [M+H]+; $^1$H NMR (500 MHz, Chloroform-d) δ 7.78 (s, 1H), 7.54 (dd, J=11.1, 7.6 Hz, 2H), 7.36 (t, J=7.4 Hz, 1H), 7.24 (td, J=7.6, 1.1 Hz, 1H), 7.19 (s, 1H), 5.46 (d, J=8.8 Hz, 1H), 4.30 (dd, J=6.5, 2.8 Hz, 1H), 3.75-3.68 (m, 2H), 3.58-3.51 (m, 2H), 2.62 (qd, J=8.7, 6.5 Hz, 1H), 2.10-1.99 (m, 2H), 1.76 (ddd, J=12.8, 8.7, 3.8 Hz, 1H), 1.63 (ddd, J=18.6, 10.4, 4.4 Hz, 3H).

Example 57f: (1S,2S)-2-((R)-5H-imidazo[5,1-a]isoindol-5-yl)-7-oxaspiro[3.5]nonan-1-ol: LCMS (ESI, m/z): 297.2 [M+H]+; $^1$H NMR (500 MHz, Chloroform-d) δ 7.86 (s, 1H), 7.52 (d, J=7.6 Hz, 1H), 7.37 (t, J=7.5 Hz, 1H), 7.35-7.32 (m, 1H), 7.23 (td, J=7.6, 1.1 Hz, 1H), 7.11 (s, 1H), 5.17 (d, J=7.9 Hz, 1H), 3.89 (dt, J=11.4, 4.3 Hz, 1H), 3.76 (dt, J=11.4, 4.2 Hz, 1H), 3.62-3.55 (m, 1H), 3.50-3.42 (m, 1H), 2.55 (ddd, J=17.5, 9.5, 8.0 Hz, 1H), 2.14-2.05 (m, 1H), 1.90 (ddd, J=13.6, 10.3, 3.9 Hz, 1H), 1.79 (ddd, J=13.9, 10.2, 4.2 Hz, 1H), 1.54-1.49 (m, 2H), 1.42 (d, J=13.2 Hz, 1H).

Example 57g: (1R,2S)-2-((S)-5H-imidazo[5,1-a]isoindol-5-yl)-7-oxaspiro[3.5]nonan-1-ol: LCMS (ESI, m/z): 297.2 [M+H]+; $^1$HNMR (500 MHz, Chloroform-d) δ 7.69 (s, 1H), 7.54 (d, J=7.6 Hz, 1H), 7.51-7.44 (m, 1H), 7.38 (t, J=7.4 Hz, 1H), 7.28-7.26 (m, 1H), 7.19 (s, 1H), 5.25 (d, J=6.8 Hz, 1H), 4.07 (d, J=8.1 Hz, 1H), 3.87 (dt, J=11.5, 4.1 Hz, 1H), 3.74 (dt, J=11.8, 4.1 Hz, 1H), 3.54-3.47 (m, 1H), 3.36 (td, J=11.4, 2.7 Hz, 1H), 2.65-2.54 (m, 1H), 1.90-1.76 (m, 3H), 1.45 (d, J=13.5 Hz, 1H), 1.35 (d, J=13.2 Hz, 1H), 1.07 (t, J=10.1 Hz, 1H).

Example 57h: (1S,2R)-2-((R)-5H-imidazo[5,1-a]isoindol-5-yl)-7-oxaspiro[3.5]nonan-1-ol: LCMS (ESI, m/z): 297.2 [M+H]+; $^1$H NMR (500 MHz, Chloroform-d) δ 7.69 (s, 1H), 7.54 (d, J=7.6 Hz, 1H), 7.50-7.45 (m, 1H), 7.37 (t, J=7.5 Hz, 1H), 7.24 (d, J=1.0 Hz, 1H), 7.19 (s, 1H), 5.25 (d, J=6.8 Hz, 1H), 4.08 (d, J=8.1 Hz, 1H), 3.87 (dt, J=11.4, 4.1, Hz, 1H), 3.74 (dt, J=11.5, 4.0 Hz, 1H), 3.51 (td, J=10.9, 10.5, 2.3 Hz, 1H), 3.36 (td, J=11.4, 2.7 Hz, 1H), 2.69-2.54 (m, 1H), 1.97-1.75 (m, 3H), 1.46 (d, J=13.4 Hz, 1H), 1.36 (d, J=13.2 Hz, 1H), 1.07 (t, J=10.5 Hz, 1H).

Example 58: 2-(4-hydroxy-3-(5H-imidazo[5,1-a]isoindol-5-yl)piperidin-1-yl)acetonitrile

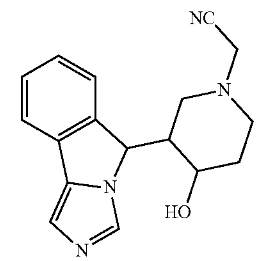 [SMILES: N#CCN1CCC(O)C(C2c3ccccc3-c3cncn32)C1]

Step 1:

2-((3S,4R)-4-hydroxy-3-((S)-5H-imidazo[5,1-a]isoindol-5-yl)piperidin-1-yl)acetonitrile 2-((3R,4S)-4-hydroxy-3-((R)-5H-imidazo[5,1-a]isoindol-5-yl)piperidin-1-yl)acetonitrile 2-((3R,4S)-4-hydroxy-3-((S)-5H-imidazo[5,1-a]isoindol-5-yl)piperidin-1-yl)acetonitrile 2-((3S,4R)-4-hydroxy-3-((R)-5H-imidazo[5,1-a]isoindol-5-yl)piperidin-1-yl)acetonitrile 58a

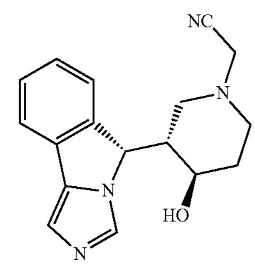

58b

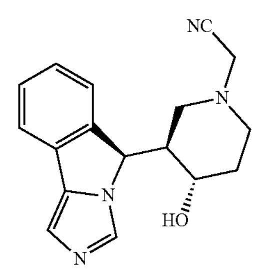

58c

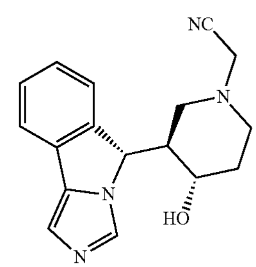

-continued

58d

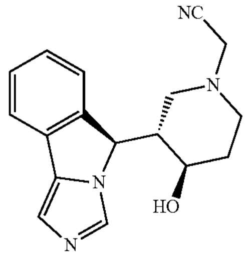

A solution of 3-[5H-imidazo[4,3-a]isoindol-5-yl]piperidin-4-ol and 4-[5H-imidazo[4,3-a]isoindol-5-yl]piperidin-3-ol (2.8 g, 5.48 mmol) and TEA (1.4 mL, 16.46 mmol) in DCM (50 mL) was added 2-chloroacetonitrile (0.42 mL, 6.58 mmol). The resulting solution was stirred for 6 h at room temperature. The resulting solution was diluted with water. The resulting solution was extracted with DCM. The organic layers were combined, dried over anhydrous sodium sulfate, and concentrated under vacuum. The crude product was purified by Combi-Flash and further isolated by chiral separation with the following conditions:

1. Column: CHIRALPAK-AD-H-SL002, 20×250 mm; Mobile Phase A:Hex(0.1% DEA)-HPLC, Mobile Phase B: IPA-HPLC; Flow rate: 20 mL/min; Gradient: 30 B to 30 B in 22 min; Detector, uv 254/220 nm;
2. Column: CHIRALPAK IC, 2×25 cm, 5 um; Mobile Phase A:Hex(0.1% DEA)-HPLC, Mobile Phase B: EtOH-HPLC; Flow rate: 20 mL/min; Gradient: 35 B to 35 B in 20 min; Detector, uv 254/220 nm.

The absolute configuration of all isomers 58a-d was assigned arbitrarily.

Example 58b: 2-((3S,4R)-4-hydroxy-3-((S)-5H-imidazo[5,1-a]isoindol-5-yl)piperidin-1-yl)acetonitrile (249.8 mg, 25%) as a white solid: LCMS (ESI, m/z): 295.2 $[M+H]^+$. $^1H$ NMR (300 MHz, $CD_3OD$) δ 7.98 (s, 1H), 7.66 (d, J=7.5 Hz, 1H), 7.52 (d, J=7.5 Hz, 1H), 7.48-7.34 (m, 2H), 7.22 (s, 1H), 5.82 (d, J=3.0 Hz, 1H), 3.95-3.83 (m, 1H), 3.52-3.39 (m, 2H), 2.87-2.83 (m, 1H), 2.46-2.05 (m, 4H), 1.83-1.65 (m, 1H), 1.48-1.41 (m, 1H). tR=1.156 min (CHIRALPAK AD-3, 0.46×5 cm; 3 um, Hex(0.1% DEA):IPA=70:30, 1.0 ml/min). 58a and 58b are enantiomers.

Example 58b: 2-((3R,4S)-4-hydroxy-3-((R)-5H-imidazo[5,1-a]isoindol-5-yl)piperidin-1-yl)acetonitrile (241 mg, 24%) as a white solid: LCMS (ESI, m/z): 295.2 $[M+H]^+$. tR=2.086 min (CHIRALPAK AD-3, 0.46×5 cm; 3 um, Hex(0.1% DEA):IPA=70:30, 1.0 ml/min). 58a and 58b are enantiomers.

Example 58c: 2-((3R,4S)-4-hydroxy-3-((S)-5H-imidazo[5,1-a]isoindol-5-yl)piperidin-1-yl)acetonitrile (61.9 mg, 6%) as a white solid: LCMS (ESI, m/z): 295.1 $[M+H]^+$. $^1H$ NMR (300 MHz, $CD_3OD$) δ 7.94 (s, 1H), 7.62 (d, J=7.5 Hz, 1H), 7.55 (d, J=7.5 Hz, 1H), 7.44-7.29 (m, 2H), 7.16 (s, 1H), 5.78 (d, J=3.6 Hz, 1H), 3.88-3.79 (m, 1H), 3.49-3.32 (m, 2H), 2.80-2.76 (m, 1H), 2.53-2.46 (m, 1H), 2.22-1.87 (m, 3H), 1.76-1.67 (m, 1H), 1.55-1.48 (m, 1H). tR=4.384 min (CHIRALPAK AD-3, 0.46×5 cm; 3 um, Hex(0.1% DEA):IPA=70:30, 1.0 ml/min). 58c and 58d are enantiomers.

Example 58d: 2-((3R,4S)-4-hydroxy-3-((S)-5H-imidazo[5,1-a]isoindol-5-yl)piperidin-1-yl)acetonitrile (52.4 mg, 5%) as a white solid: LCMS (ESI, m/z): 295.1 $[M+H]^+$. tR=6.297 min (CHIRALPAK AD-3, 0.46×5 cm; 3 um, Hex(0.1% DEA):IPA=70:30, 1.0 ml/min). 58c and 58d are enantiomers.

Example 59: 6-(5H-imidazo[5,1-a]isoindol-5-yl)-3-methyl-6,7-dihydro-5H-cyclopenta[c]pyridin-7-ol

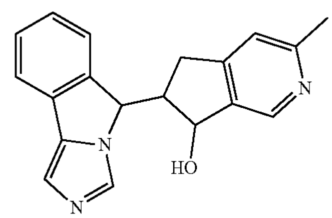 [SMILES: Cc1cc2c(cn1)C(O)C(C1c3ccccc3-c3cncn31)C2]

(6R,7S)-6-((S)-5H-imidazo[5,1-a]isoindol-5-yl)-3-methyl-6,7-dihydro-5H-cyclopenta[c]pyridin-7-ol (6S,7R)-6-((R)-5H-imidazo[5,1-a]isoindol-5-yl)-3-methyl-6,7-dihydro-5H-cyclopenta[c]pyridin-7-ol (6R,7R)-6-((S)-5H-imidazo[5,1-a]isoindol-5-yl)-3-methyl-6,7-dihydro-5H-cyclopenta[c]pyridin-7-ol (6S,7S)-6-((R)-5H-imidazo[5,1-a]isoindol-5-yl)-3-methyl-6,7-dihydro-5H-cyclopenta[c]pyridin-7-ol Step 1: (E)-3-methyl-6-(2-(1-trityl-1H-imidazol-4-yl)benzylidene)-5,6-dihydro-7H-cyclopenta[c]pyridin-7-one

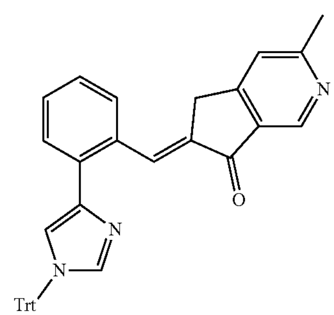

To a solution of the 2-(1-trityl-1H-imidazol-4-yl)benzaldehyde (2.0 g, 4.82 mmol) and 3-methyl-5,6-dihydro-7H-cyclopenta[c]pyridin-7-one (780 mg, 5.31 mmol) in MeOH (25 mL) was added piperidine dropwise (0.52 mL, 5.31 mmol). The mixture was stirred at 80° C. for another 3 hr. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted with EtOAc:Hex=70:30: LCMS (ESI, m/z): 544.3 $[M+H]^+$.

Step 2: 6-(5H-imidazo[5,1-a]isoindol-5-yl)-3-methyl-5,6-dihydro-7H-cyclopenta[c]pyridin-7-one

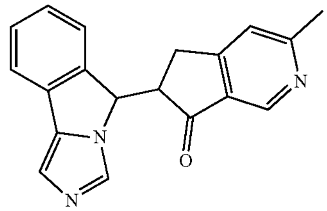 [SMILES: Cc1cc2c(cn1)C(=O)C(C1c3ccccc3-c3cncn31)C2]

(E)-3-methyl-6-(2-(1-trityl-1H-imidazol-4-yl)benzylidene)-5,6-dihydro-7H-cyclopenta[c]pyridin-7-one (1.46 g, 2.69 mmol) was stirred in 20% AcOH in MeOH (20 mL) at 90° C. for 2 h. After cooling to room temperature, the solvent was removed under reduced pressure and saturated $NaHCO_3$ (20 mL) was added to the residue followed by DCM (20 mL). The organic layer was collected and the aqueous layer was extracted with 5% trifluoroethanol in DCM (3×20 mL). The combined organic layers were dried over $Na_2SO_4$ and the solvent evaporated under reduced pressure to afford the crude product which was purified by using CombiFlash. The product was eluted with DCM: MeOH=96:4: LCMS (ESI, m/z): 302.2 $[M+H]^+$.

Step 3:

(6R,7S)-6-((S)-5H-imidazo[5,1-a]isoindol-5-yl)-3-methyl-6,7-dihydro-5H-cyclopenta[c]pyridin-7-ol (6S,7R)-6-((R)-5H-imidazo[5,1-a]isoindol-5-yl)-3-methyl-6,7-dihydro-5H-cyclopenta[c]pyridin-7-ol (6R,7R)-6-((S)-5H-imidazo[5,1-a]isoindol-5-yl)-3-methyl-6,7-dihydro-5H-cyclopenta[c]pyridin-7-ol (6S,7S)-6-((R)-5H-imidazo[5,1-a]isoindol-5-yl)-3-methyl-6,7-dihydro-5H-cyclopenta[c]pyridin-7-ol 59a

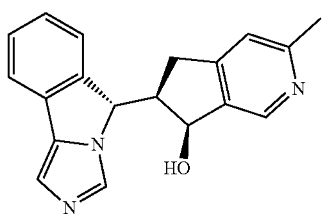

59b

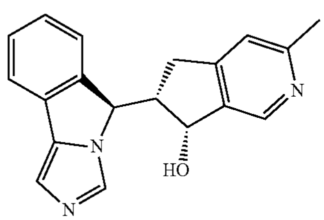

59c

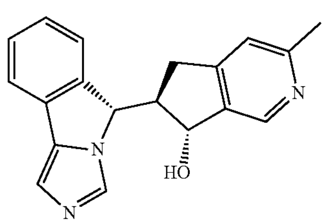

-continued

59d

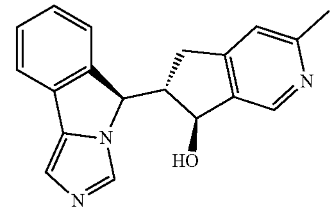

To a solution of 6-(5H-imidazo[5,1-a]isoindol-5-yl)-3-methyl-5,6-dihydro-7H-cyclopenta[c]pyridin-7-one (0.636 g, 2.11 mmol) in MeOH (10 mL) was added $NaBH_4$ (160 mg, 4.22 mmol) in portions at 0° C. and the solution was stirred at 0° C. for additional 2 hr. The solvent was distilled off and saturated ammonium chloride solution (10 mL) was added. The aqueous layer was extracted with 5% trifluoroethanol in DCM (3×10 mL). The combined organic extract was dried over ($Na_2SO_4$) and concentrated under reduced pressure to afford the crude product. The crude was purified by CombiFlash and the product was eluted with DCM: MeOH=90:10. The final products were further isolated by chiral separation to afford 4 isomers and the stereochemistry of each isomer was arbitrarily assigned.

Example 59a: (6R,7S)-6-((S)-5H-imidazo[5,1-a]isoindol-5-yl)-3-methyl-6,7-dihydro-5H-cyclopenta[c]pyridin-7-ol: LCMS (ESI, m/z): 304.2 $[M+H]^+$; $^1$HNMR (500 MHz, Chloroform-d) δ 8.60 (s, 1H), 8.19 (s, 1H), 7.58 (dt, J=7.5, 0.9 Hz, 1H), 7.48-7.44 (m, 1H), 7.42-7.36 (m, 1H), 7.25 (d, J=1.1 Hz, 1H), 7.20 (s, 1H), 7.11 (s, 1H), 5.61 (d, J=10.5 Hz, 1H), 5.42 (d, J=5.4 Hz, 1H), 3.43-3.33 (m, 1H), 3.12 (dd, J=16.0, 7.7 Hz, 1H), 2.56 (s, 3H), 2.48-2.37 (m, 1H).

Example 59b: (6S,7R)-6-((R)-5H-imidazo[5,1-a]isoindol-5-yl)-3-methyl-6,7-dihydro-5H-cyclopenta[c]pyridin-7-ol: LCMS (ESI, m/z): 304.2 $[M+H]^+$; $^1$HNMR (500 MHz, Chloroform-d) δ 8.58-8.52 (m, 1H), 8.30 (s, 1H), 7.55 (dd, J=7.5, 1.0 Hz, 1H), 7.47-7.41 (m, 1H), 7.38 (td, J=7.6, 1.0 Hz, 1H), 7.24 (dd, J=7.6, 1.1 Hz, 1H), 7.15 (s, 1H), 7.07 (s, 1H), 5.63 (d, J=10.4 Hz, 1H), 5.41 (d, J=5.6 Hz, 1H), 3.42-3.32 (m, 1H), 3.08 (dd, J=16.0, 7.7 Hz, 1H), 2.51 (s, 3H), 2.45-2.34 (m, 1H).

Example 59c: (6R,7R)-6-((S)-5H-imidazo[5,1-a]isoindol-5-yl)-3-methyl-6,7-dihydro-5H-cyclopenta[c]pyridin-7-ol: LCMS (ESI, m/z): 304.2 $[M+H]^+$; $^1$HNMR (500 MHz, Chloroform-d) δ 8.49 (s, 1H), 7.79 (s, 1H), 7.56 (dd, J=7.7, 1.0 Hz, 1H), 7.52 (dt, J=7.5, 0.9 Hz, 1H), 7.42-7.33 (m, 1H), 7.28 (dd, J=7.6, 1.2 Hz, 1H), 7.08 (s, 1H), 6.85 (s, 1H), 5.70 (d, J=4.8 Hz, 1H), 5.58 (d, J=6.7 Hz, 1H), 3.02-2.95 (m, 1H), 2.69 (dd, J=16.9, 8.2 Hz, 1H), 2.56-2.48 (m, 1H), 2.44 (s, 3H).

Example 59d: (6S,7S)-6-((R)-5H-imidazo[5,1-a]isoindol-5-yl)-3-methyl-6,7-dihydro-5H-cyclopenta[c]pyridin-7-ol: LCMS (ESI, m/z): 304.2 $[M+H]^+$; $^1$HNMR (500 MHz, Chloroform-d) δ 8.54 (s, 1H), 7.75 (s, 1H), 7.61 (dd, J=7.7, 0.9 Hz, 1H), 7.55 (dt, J=7.5, 0.9 Hz, 1H), 7.42-7.37 (m, 1H), 7.29 (td, J=7.6, 1.2 Hz, 1H), 7.12 (s, 1H), 6.93 (s, 1H), 5.69 (d, J=5.5 Hz, 1H), 5.57 (d, J=6.3 Hz, 1H), 2.94-2.87 (m, 1H), 2.79 (dd, J=16.7, 7.9 Hz, 1H), 2.74-2.66 (m, 1H), 2.50 (s, 3H).

Example 60: 5-hydroxy-6-(5H-imidazo[5,1-a]isoindol-5-yl)-5,6,7,8-tetrahydronaphthalene-2-carboxamide

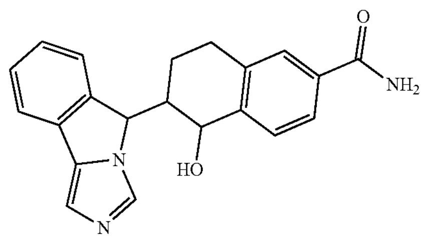 [SMILES: NC(=O)c1ccc2c(c1)CCC(C1c3ccccc3-c3cncn31)C2O]

(5R,6S)-5-hydroxy-6-((S)-5H-imidazo[5,1-a]isoindol-5-yl)-5,6,7,8-tetrahydronaphthalene-2-carboxamide (5R,6R)-5-hydroxy-6-((R)-5H-imidazo[5,1-a]isoindol-5-yl)-5,6,7,8-tetrahydronaphthalene-2-carboxamide (5R,6R)-5-hydroxy-6-((S)-5H-imidazo[5,1-a]isoindol-5-yl)-5,6,7,8-tetrahydronaphthalene-2-carboxamide (5S,6R)-5-hydroxy-6-((R)-5H-imidazo[5,1-a]isoindol-5-yl)-5,6,7,8-tetrahydronaphthalene-2-carboxamide (5S,6S)-5-hydroxy-6-((S)-5H-imidazo[5,1-a]isoindol-5-yl)-5,6,7,8-tetrahydronaphthalene-2-carboxamide (5R,6S)-5-hydroxy-6-((S)-5H-imidazo[5,1-a]isoindol-5-yl)-5,6,7,8-tetrahydronaphthalene-2-carboxamide Step 1:

(5R,6S)-5-hydroxy-6-((S)-5H-imidazo[5,1-a]isoindol-5-yl)-5,6,7,8-tetrahydronaphthalene-2-carboxamide (5R,6R)-5-hydroxy-6-((R)-5H-imidazo[5,1-a]isoindol-5-yl)-5,6,7,8-tetrahydronaphthalene-2-carboxamide (5R,6R)-5-hydroxy-6-((S)-5H-imidazo[5,1-a]isoindol-5-yl)-5,6,7,8-tetrahydronaphthalene-2-carboxamide (5S,6R)-5-hydroxy-6-((R)-5H-imidazo[5,1-a]isoindol-5-yl)-5,6,7,8-tetrahydronaphthalene-2-carboxamide (5S,6S)-5-hydroxy-6-((S)-5H-imidazo[5,1-a]isoindol-5-yl)-5,6,7,8-tetrahydronaphthalene-2-carboxamide (5R,6S)-5-hydroxy-6-((S)-5H-imidazo[5,1-a]isoindol-5-yl)-5,6,7,8-tetrahydronaphthalene-2-carboxamide 60a

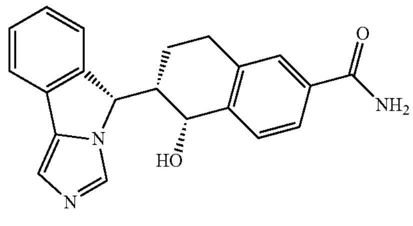

60b

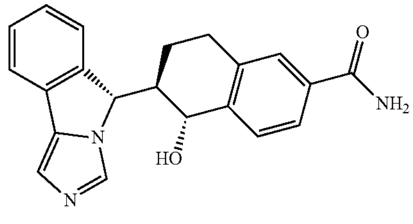

-continued

60c

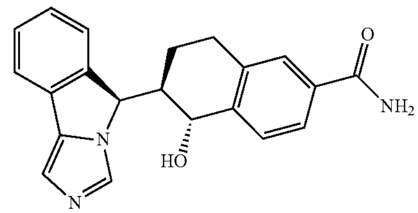

60d

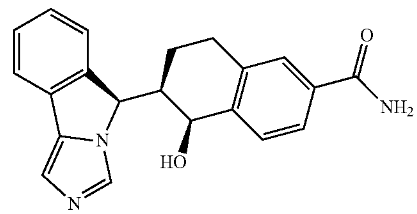

60e

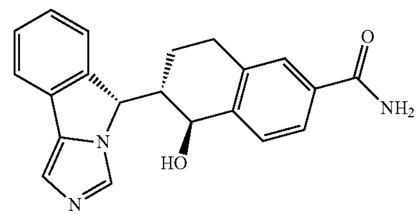

60f

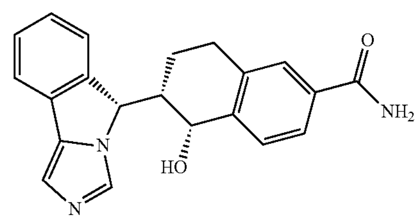

To the solution of 5-hydroxy-6-(5H-imidazo[5,1-a]isoindol-5-yl)-5,6,7,8-tetrahydronaphthalene-2-carbonitrile (400 mg, 1.22 mmol) in methanol (15 mL), sodium hydroxide (488 mg, 12.22 mmol) and hydrogen peroxide (0.367 mL, 12.22 mmol) were added and stirred for 2 hours at room temperature. Solvent was removed and crude product was extracted with 5% 2,2,2-trifluoroetthanol in DCM. Combined organic layers were washed with water, brine, dried over sodium sulfate and evaporated to yield title compound which was further isolated by chiral separation to afford 6 isomers as white solid. The absolute configuration of isomers 60c, 60e, and 60f was determined by X-ray crystallography. The configuration of the rest isomers was assigned arbitrarily.

Example 60a: (5R,6S)-5-hydroxy-6-((S)-5H-imidazo[5,1-a]isoindol-5-yl)-5,6,7,8-tetrahydronaphthalene-2-carboxamide: LCMS (ESI, m/z): 346.3 $[M+H]^+$; $^1H$ NMR (500 MHz, DMSO-$d_6$) δ 8.01 (s, 1H), 7.88 (s, 1H), 7.75 (d, J=7.7 Hz, 1H), 7.68-7.59 (m, 4H), 7.39 (dt, J=7.4, 3.5 Hz, 2H), 7.28-7.22 (m, 2H), 7.14 (s, 1H), 5.61 (d, J=6.1 Hz, 1H), 5.45 (d, J=6.0 Hz, 1H), 4.85-4.78 (m, 1H), 2.90-2.81 (m, 1H), 2.73-2.62 (m, 1H), 2.20-2.08 (m, 1H), 2.08-1.91 (m, 1H), 1.76-1.68 (m, 1H).

Example 60b: (5R,6R)-5-hydroxy-6-((R)-5H-imidazo[5,1-a]isoindol-5-yl)-5,6,7,8-tetrahydronaphthalene-2-carboxamide: LCMS (ESI, m/z): 346.3 $[M+H]^+$; $^1H$ NMR (500 MHz, DMSO-$d_6$) δ 7.95 (d, J=0.7 Hz, 1H), 7.90 (s, 1H), 7.71 (dd, J=8.0, 1.8 Hz, 1H), 7.64-7.58 (m, 3H), 7.46 (d, J=8.0 Hz, 1H), 7.39 (tt, J=7.6, 0.8 Hz, 1H), 7.29 (td, J=8.0, 1.4 Hz, 2H), 7.11 (s, 1H), 5.54 (d, J=2.3 Hz, 1H), 5.02 (d, J=3.7 Hz, 1H), 2.76-2.69 (m, 1H), 2.59-2.54 (s, 1H), 2.50-2.46 (m, 1H), 1.54-1.43 (m, 1H), 1.03-0.95 (m, 1H).

Example 60c: (5R,6R)-5-hydroxy-6-((S)-5H-imidazo[5,1-a]isoindol-5-yl)-5,6,7,8-tetrahydronaphthalene-2-carboxamide: LCMS (ESI, m/z): 346.3 $[M+H]^+$; $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J=1.6 Hz, 1H), 7.49 (dq, J=7.6, 0.8 Hz, 1H), 7.43-7.39 (m, 1H), 7.31 (td, J=7.5, 1.1 Hz, 1H), 7.24 (s, 1H), 7.18 (s, 1H), 6.12 (d, J=7.6 Hz, 1H), 5.81 (d, J=1.9 Hz, 1H), 4.94 (dd, J=10.7, 7.6 Hz, 1H), 2.66-2.57 (m, 2H), 2.44-2.34 (m, 1H), 0.99-0.86 (m, 1H), 0.89-0.76 (m, 1H).

Example 60d: (5S,6R)-5-hydroxy-6-((R)-5H-imidazo[5,1-a]isoindol-5-yl)-5,6,7,8-tetrahydronaphthalenc-2-carboxamide: LCMS (ESI, m/z): 346.3 $[M+H]^+$; $^1$H NMR (500 MHz, DMSO-$d_6$) δ 8.01 (s, 1H), 7.88 (s, 1H), 7.75 (d, J=7.7 Hz, 1H), 7.68-7.59 (m, 4H), 7.39 (dt, J=7.4, 3.5 Hz, 2H), 7.28-7.22 (m, 2H), 7.14 (s, 1H), 5.61 (d, J=6.1 Hz, 1H), 5.45 (d, J=6.0 Hz, 1H), 4.85-4.78 (m, 1H), 2.90-2.81 (m, 1H), 2.73-2.62 (m, 1H), 2.20-2.08 (m, 1H), 2.08-1.91 (m, 1H), 1.76-1.68 (m, 1H).

Example 60e: (5S,6S)-5-hydroxy-6-((S)-5H-imidazo[5,1-a]isoindol-5-yl)-5,6,7,8-tetrahydronaphthalene-2-carboxamide: LCMS (ESI, m/z): 346.3 $[M+H]^+$; $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J=1.6 Hz, 1H), 7.49 (dq, J=7.6, 0.8 Hz, 1H), 7.43-7.39 (m, 1H), 7.31 (td, J=7.5, 1.1 Hz, 1H), 7.24 (s, 1H), 7.18 (s, 1H), 6.12 (d, J=7.6 Hz, 1H), 5.81 (d, J=1.9 Hz, 1H), 4.94 (dd, J=10.7, 7.6 Hz, 1H), 2.66-2.57 (m, 2H), 2.44-2.34 (m, 1H), 0.99-0.86 (m, 1H), 0.89-0.76 (m, 1H).

Example 60f: (5R,6S)-5-hydroxy-6-((S)-5H-imidazo[5,1-a]isoindol-5-yl)-5,6,7,8-tetrahydronaphthalene-2-carboxamide: LCMS (ESI, m/z): 346.3 $[M+H]^+$; $^1$H NMR (500 MHz, DMSO-$d_6$) δ 7.97 (s, 1H), 7.87 (s, 1H), 7.74-7.68 (m, 2H), 7.65-7.61 (m, 1H), 7.53 (d, J=1.6 Hz, 1H), 7.49 (dq, J=7.6, 0.8 Hz, 1H), 7.43-7.39 (m, 1H), 7.31 (td, J=7.5, 1.1 Hz, 1H), 7.24 (s, 1H), 7.18 (s, 1H), 6.12 (d, J=7.6 Hz, 1H), 5.81 (d, J=1.9 Hz, 1H), 4.94 (dd, J=10.7, 7.6 Hz, 1H), 2.66-2.57 (m, 2H), 2.44-2.34 (m, 1H), 0.99-0.86 (m, 1H), 0.89-0.76 (m, 1H).

Example 61: 3-(5H-imidazo[5,1-a]isoindol-5-yl)-4-methyltetrahydro-2H-pyran-4-ol

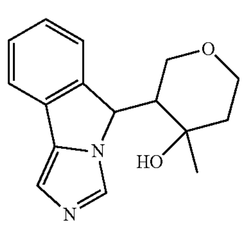 [SMILES: CC1(O)CCOCC1C1c2ccccc2-c2cncn21]

(3S,4R)-3-((R)-5H-imidazo[5,1-a]isoindol-5-yl)-4-methyltetrahydro-2H-pyran-4-ol
(3S,4S)-3-((R)-5H-imidazo[5,1-a]isoindol-5-yl)-4-methyltetrahydro-2H-pyran-4-ol
(3R,4R)-3-((S)-5H-imidazo[5,1-a]isoindol-5-yl)-4-methyltetrahydro-2H-pyran-4-ol
(3R,4S)-3-((S)-5H-imidazo[5,1-a]isoindol-5-yl)-4-methyltetrahydro-2H-pyran-4-ol The title compound was synthesized by the same method of example 35.

61a

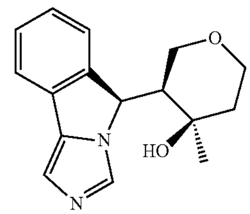

61b

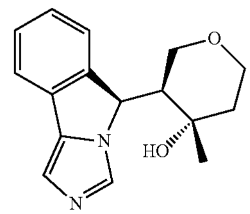

61c

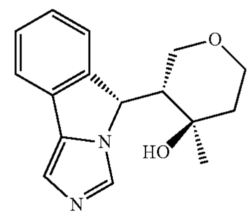

61d

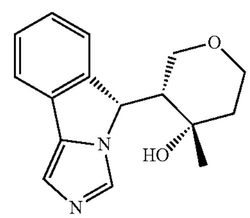

The configurations of the isomers were assigned arbitrarily.

Example 61a: (3S,4R)-3-((R)-5H-imidazo[5,1-a]isoindol-5-yl)-4-methyltetrahydro-2H-pyran-4-ol: LCMS (ESI, m/z): 271.2 $[M+H]^+$; $^1$H NMR (500 MHz, Chloroform-d) δ 8.15 (s, 1H), 7.50 (dt, J=7.6, 1.0 Hz, 1H), 7.36 (tt, J=7.5, 0.9 Hz, 1H), 7.33 (dq, J=7.7, 1.0 Hz, 1H), 7.28-7.24 (m, 1H), 7.14 (s, 1H), 5.49 (s, 1H), 3.80-3.69 (m, 2H), 3.25 (t, J=11.4 Hz, 1H), 3.02 (dd, J=11.6, 4.5 Hz, 1H), 2.29 (ddd, J=11.1, 4.5, 1.1 Hz, 1H), 1.99 (ddd, J=14.3, 11.7, 6.3 Hz, 2H), 1.61 (s, 3H). 61a and 61d are enantiomers.

Example 61b: (3S,4S)-3-((R)-5H-imidazo[5,1-a]isoindol-5-yl)-4-methyltetrahydro-2H-pyran-4-ol: LCMS (ESI, m/z): 271.2 $[M+H]^+$; $^1$H NMR (500 MHz, Chloroform-d) δ 7.81 (dt, J=7.8, 1.0 Hz, 1H), 7.71 (s, 1H), 7.52 (d, J=7.6 Hz, 1H), 7.37-7.33 (m, 1H), 7.22 (td, J=7.6, 1.2 Hz, 1H), 7.17 (s; 1H), 5.44 (s, 1H), 3.78-3.73 (m, 2H), 3.55 (t, J=11.2 Hz, 1H), 3.17 (dd, J=11.5, 4.4 Hz, 1H), 2.29 (ddd, J=10.8, 4.4, 1.7 Hz, 1H), 1.93 (ddd, J=14.2, 10.5, 6.6 Hz, 1H), 1.58 (m, 1H), 1.50 (s, 3H). 61b and 61c are enantiomers.

Example 61c: (3R,4R)-3-((S)-5H-imidazo[5,1-a]isoindol-5-yl)-4-methyltetrahydro-2H-pyran-4-ol: LCMS (ESI, m/z): 271.2 $[M+H]^+$; $^1$H NMR (500 MHz, Chloroform-d) δ 7.81 (dq, J=7.7, 0.9 Hz, 1H), 7.71 (s, 1H), 7.52 (dt, J=7.8, 1.0 Hz, 1H), 7.35 (tt, J=7.6, 1.0 Hz, 1H), 7.22 (td, J=7.6, 1.2 Hz, 1H), 7.17 (s, 1H), 5.44 (d, J=1.6 Hz, 1H), 3.81-3.72 (m, 2H), 3.55 (dd, J=11.6, 10.8 Hz, 1H), 3.17 (dd, J=11.5, 4.4 Hz, 1H), 2.29 (ddd, J=10.8, 4.4, 1.8 Hz, 1H), 1.93 (ddd, J=14.2, 10.5, 6.6 Hz, 1H), 1.58 (m, 1H), 1.50 (s, 3H). 61b and 61c are enantiomers.

Example 61d: (3R,4S)-3-((S)-5H-imidazo[5,1-a]isoindol-5-yl)-4-methyltetrahydro-2H-pyran-4-ol: LCMS (ESI, m/z): 271.2 $[M+H]^+$; $^1$H NMR (500 MHz, Chloroform-d) δ 8.15 (s, 1H), 7.50 (dt, J=7.6, 0.9 Hz, 1H), 7.36 (tt, J=7.5, 0.9 Hz, 1H), 7.33 (dq, J=7.7, 1.0 Hz, 1H), 7.26 (td, J=7.5, 1.1 Hz, 1H), 7.14 (s, 1H), 5.49 (s, 1H), 3.79-3.70 (m, 2H), 3.25 (t, J=11.4 Hz, 1H), 3.02 (dd, J=11.6, 4.5 Hz, 1H), 2.29 (ddd, J=11.1, 4.5, 1.1 Hz, 1H), 1.99 (ddd, J=14.3, 11.8, 6.3 Hz, 1H), 1.61-1.58 (m, 4H). 61a and 61d are enantiomers.

Example 62: 5-hydroxy-6-(5H-imidazo[5,1-a]isoindol-5-yl)-5,6,7,8-tetrahydronaphthalene-2-carbonitrile

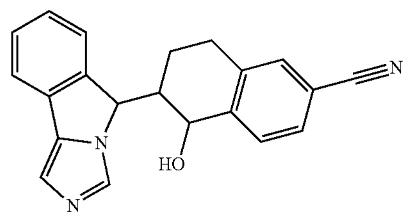 [SMILES: N#Cc1ccc2c(c1)CCC(C1c3ccccc3-c3cncn31)C2O]

(5R,6R)-5-hydroxy-6-((R)-5H-imidazo[5,1-a]isoindol-5-yl)-5,6,7,8-tetrahydronaphthalene-2-carbonitrile
(5R,6S)-5-hydroxy-6-((R)-5H-imidazo[5,1-a]isoindol-5-yl)-5,6,7,8-tetrahydronaphthalene-2-carbonitrile
(5R,6S)-5-hydroxy-6-((S)-5H-imidazo[5,1-a]isoindol-5-yl)-5,6,7,8-tetrahydronaphthalene-2-carbonitrile
(5S,6R)-5-hydroxy-6-((R)-5H-imidazo[5,1-a]isoindol-5-yl)-5,6,7,8-tetrahydronaphthalene-2-carbonitrile
(5S,6R)-5-hydroxy-6-((S)-5H-imidazo[5,1-a]isoindol-5-yl)-5,6,7,8-tetrahydronaphthalene-2-carbonitrile
(5S,6S)-5-hydroxy-6-((R)-5H-imidazo[5,1-a]isoindol-5-yl)-5,6,7,8-tetrahydronaphthalene-2-carbonitrile
(5S,6S)-5-hydroxy-6-((S)-5H-imidazo[5,1-a]isoindol-5-yl)-5,6,7,8-tetrahydronaphthalene-2-carbonitrile Step 1: 6-(5H-imidazo[5,1-a]isoindol-5-yl)-5-oxo-5,6,7,8-tetrahydronaphthalene-2-carbonitrile

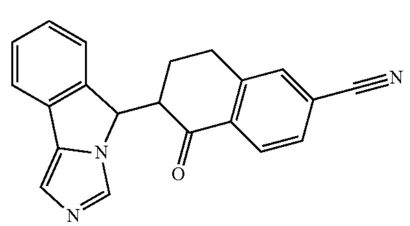 [SMILES: N#Cc1ccc2c(c1)CCC(C1c3ccccc3-c3cncn31)C2=O]

To a solution of the 2-(1-trityl-1H-imidazol-4-yl)benzaldehyde (2 g, 4.83 mmol) and 5-oxo-5,6,7,8-tetrahydronaphthalene-2-carbonitrile (1.24 g, 7.24 mmol) in MeOH (20 mL) was added sodium ethoxide (21% solution in ethanol, 2.7 mL, 7.24 mmol). The solution was allowed to reflux. After 6 h, reaction was complete as indicated by the TLC. Acetic acid (7 mL) was added to the reaction mixture and was refluxed for 2 hours. Methanol and acetic acid were evaporated on a rotary evaporator and crude was dissolved in water, solid sodium carbonate was added portion to neutralize remaining acetic acid. Crude was then extracted using DCM (2×30 mL), which was further purified over Combi-Flash. LCMS (ESI, m/z): 326.2 $[M+H]^+$ Step 2:

(5R,6R)-5-hydroxy-6-((R)-5H-imidazo[5,1-a]isoindol-5-yl)-5,6,7,8-tetrahydronaphthalene-2-carbonitrile
(5R,6S)-5-hydroxy-6-((R)-5H-imidazo[5,1-a]isoindol-5-yl)-5,6,7,8-tetrahydronaphthalene-2-carbonitrile
(5R,6S)-5-hydroxy-6-((S)-5H-imidazo[5,1-a]isoindol-5-yl)-5,6,7,8-tetrahydronaphthalene-2-carbonitrile
(5S,6R)-5-hydroxy-6-((R)-5H-imidazo[5,1-a]isoindol-5-yl)-5,6,7,8-tetrahydronaphthalene-2-carbonitrile
(5S,6R)-5-hydroxy-6-((S)-5H-imidazo[5,1-a]isoindol-5-yl)-5,6,7,8-tetrahydronaphthalene-2-carbonitrile
(5S,6S)-5-hydroxy-6-((R)-5H-imidazo[5,1-a]isoindol-5-yl)-5,6,7,8-tetrahydronaphthalene-2-carbonitrile
(5S,6S)-5-hydroxy-6-((S)-5H-imidazo[5,1-a]isoindol-5-yl)-5,6,7,8-tetrahydronaphthalene-2-carbonitrile 62a

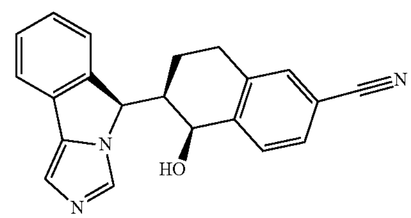

62a

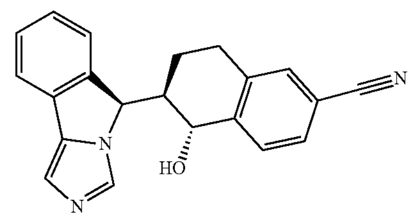

62c

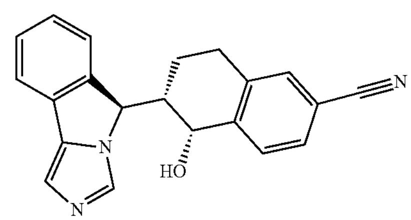

62d

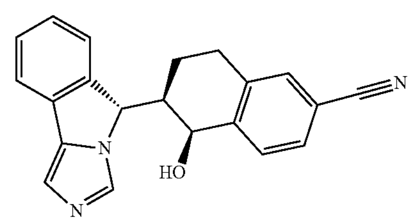

62e

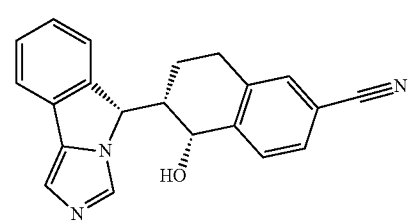

-continued

62f

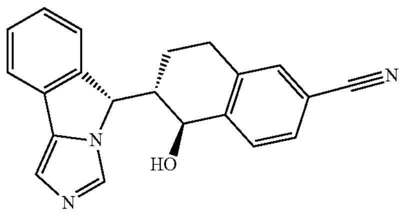

62g

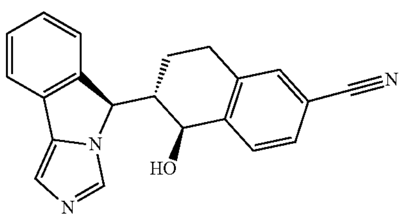

Solution of 6-(5H-imidazo[5,1-a]isoindol-5-yl)-5-oxo-5,6,7,8-tetrahydronaphthalene-2-carbonitrile (1.6 g mL, 4.62 mmol) in methanol (15 mL) was cooled to 0° C. Sodium borohydride (0.524 g, 13.85 mmol) was added and reaction mixture was removed from ice bath. Reaction mixture was allowed to stir at room temperature for 2 hours. Reaction was quenched using sat. $NH_4Cl$ solution (15 mL). Crude was extracted using 5% 2,2,2-trifluoroethanol in DCM, which was on Combi-Flash and further isolated by chiral separation to afford 7 isomers as white solid. The absolute configuration of all isomers was assigned arbitrarily.

Example 62a: (5R,6R)-5-hydroxy-6-((R)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR (500 MHz, Chloroform-d) δ 7.99 (s, 1H), 7.62-7.57 (m, 1H), 7.55 (dd, J=7.8, 0.9 Hz, 1H), 7.49 (d, J=7.6 Hz, 1H), 7.45 (d, J=1.3 Hz, 1H), 7.44-7.37 (m, 2H), 7.24-7.28 (s, 1H), 7.17 (s, 1H), 5.38 (d, J=7.3 Hz, 1H), 4.88 (d, J=3.1 Hz, 1H), 3.02 (dd, J=5.3, 2.3 Hz, 1H), 2.80 (s, 1H), 2.22 (dd, J=11.2, 5.4 Hz, 2H), 2.08 (dd, J=7.6, 3.7 Hz, 1H).

Example 62b: (5R,6S)-5-hydroxy-6-((R)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR (500 MHz, Chloroform-d) δ 7.71 (d, J=8.2 Hz, 1H), 7.68-7.65 (m, 1H), 7.60 (d, J=7.7 Hz, 1H), 7.48 (d, J=1.0 Hz, 2H), 7.41 (d, J=0.9 Hz, 1H), 7.35 (s, 1H), 7.21-7.25 (m, 2H), 5.76 (d, J=3.0 Hz, 1H), 4.93 (d, J=10.5 Hz, 1H), 2.82-2.66 (m, 2H), 2.52 (d, J=11.1 Hz, 1H), 1.41-1.33 (m, 1H), 1.27 (dd, J=12.6, 5.5 Hz, 2H).

Example 62c: (5R,6S)-5-hydroxy-6-((S)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR (500 MHz, Chloroform-d) δ 8.09 (s, 1H), 7.61 (d, J=8.0 Hz, 1H), 7.59-7.54 (m, 1H), 7.53-7.49 (m, 1H), 7.43 (d, J=1.5 Hz, 1H), 7.41-7.36 (m, 2H), 7.24-7.29 (s, 1H), 6.67 (s, 1H), 5.48 (s, 1H), 5.14-5.08 (m, 1H), 2.73 (dd, J=17.2, 5.3 Hz, 1H), 2.61 (dd, J=12.3, 5.8 Hz, 1H), 2.42-2.35 (m, 1H), 1.39 (dd, J=12.9, 5.5 Hz, 1H), 1.09 (dd, J=10.5, 3.0 Hz, 1H).

Example 62d: (5S,6R)-5-hydroxy-6-((R)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR (500 MHz, Chloroform-d) δ 8.09 (s, 1H), 7.61 (d, J=8.0 Hz, 1H), 7.59-7.54 (m, 1H), 7.53-7.49 (m, 1H), 7.43 (d, J=1.5 Hz, 1H), 7.41-7.36 (m, 2H), 7.24-7.29 (s, 1H), 6.67 (s, 1H), 5.48 (s, 1H), 5.14-5.08 (m, 1H), 2.73 (dd, J=17.2, 5.3 Hz, 1H), 2.61 (dd, J=12.3, 5.8 Hz, 1H), 2.42-2.35 (m, 1H), 1.39 (dd, J=12.9, 5.5 Hz, 1H), 1.09 (dd, J=10.5, 3.0 Hz, 1H).

Example 62e: (5S,6R)-5-hydroxy-6-((S)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR not reported.

Example 62f: (5S,6S)-5-hydroxy-6-((R)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR not reported Example 62g: (5S,6S)-5-hydroxy-6-((S)-5H-imidazo[5,1-a]isoindol-5-yl)-5,6,7,8-tetrahydronaphthalene-2-carbonitrile: LCMS (ESI, m/z): 328.1 $[M+H]^+$; $^1$H NMR (500 MHz, Chloroform-d) δ 7.71 (d, J=8.2 Hz, 1H), 7.68-7.65 (m, 1H), 7.60 (d, J=7.7 Hz, 1H), 7.48 (d, J=1.0 Hz, 2H), 7.41 (d, J=0.9 Hz, 1H), 7.35 (s, 1H), 7.21-7.25 (m, 2H), 5.76 (d, J=3.0 Hz, 1H), 4.93 (d, J=10.5 Hz, 1H), 2.82-2.66 (m, 2H), 2.52 (d, J=11.1 Hz, 1H), 1.41-1.33 (m, 1H), 1.27 (dd, J=12.6, 5.5 Hz, 2H).

Example 63: 7-(5H-imidazo[5,1-a]isoindol-5-yl)-5,6,7,8-tetrahydroquinolin-8-ol

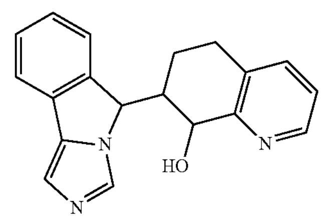 [SMILES: OC1c2ncccc2CCC1C1c2ccccc2-c2cncn21]

Step 1: (E)-7-(2-(1-trityl-1H-imidazol-4-yl)benzylidene)-6,7-dihydroquinolin-8(5H)-one

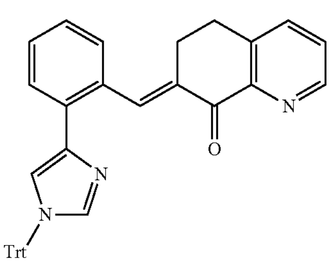

To a solution of 2-(1-trityl-1H-imidazol-4-yl)benzaldehyde (2.5 g, 6.03 mmol) and 6,7-dihydroquinolin-8(5H)-one (888 mg, 9.05 mmol) in EtOH (20 mL) was added sodium ethoxide ethanol solution dropwise (2.25 mL, 6.03 mmol). The mixture was stirred at 90° C. for another 1 hr. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by DCM:MeOH=97:3.

Step 2: 7-(5H-imidazo[5,1-a]isoindol-5-yl)-6,7-dihydroquinolin-8(5H)-one

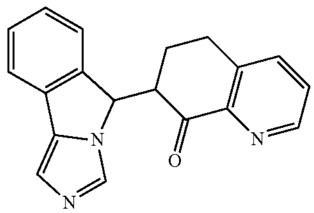 [SMILES: O=C1c2ncccc2CCC1C1c2ccccc2-c2cncn21]

(E)-7-(2-(1-trityl-1H-imidazol-4-yl)benzylidene)-6,7-dihydroquinolin-8(5H)-one (3.28 g, 6.03 mmol) was stirred in 20% AcOH in MeOH (20 mL) at 90° C. for 2 h. After cooling to rt, the solvent was removed under reduced pressure and sat'd $NaHCO_3$ (20 mL) was added to the residue followed by DCM (20 mL). The organic layer was collected and the aqueous layer was extracted with DCM (3×10 mL). The combined organic layers were dried over $Na_2SO_4$ and the solvent evaporated under reduced pressure to afford the crude product which was purified by CombiFlash: LCMS (ESI, m/z): 302.2 $[M+H]^+$.

Step 3:

(7S,8S)-7-((S)-5H-imidazo[5,1-a]isoindol-5-yl)-5,6,7,8-tetrahydroquinolin-8-ol (7R,8R)-7-((R)-5H-imidazo[5,1-a]isoindol-5-yl)-5,6,7,8-tetrahydroquinolin-8-ol (7S,8R)-7-((S)-5H-imidazo[5,1-a]isoindol-5-yl)-5,6,7,8-tetrahydroquinolin-8-ol (7R,8S)-7-((R)-5H-imidazo[5,1-a]isoindol-5-yl)-5,6,7,8-tetrahydroquinolin-8-ol 63a

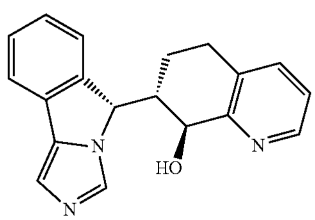

63b

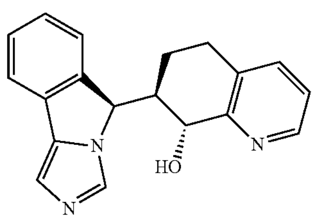

63c

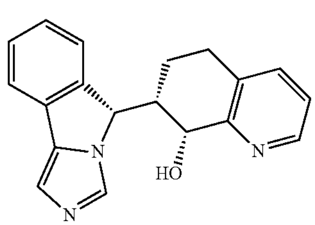

-continued

63d

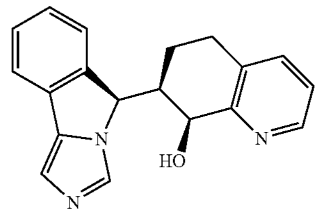

To a solution of (5H-imidazo[5,1-a]isoindol-5-yl)-6,7-dihydroquinolin-8(5H)-one (0.703 g, 2.33 mmol) in MeOH (20 mL) was added $NaBH_4$ (265 mg, 7.0 mmol) in portions at 0° C. and the solution was stirred at 0° C. for 2 hr. The solvent was distilled off and saturated ammonium chloride solution (10 mL) was added. The aqueous layer was extracted with DCM (3×10 mL). The combined organic extract was dried over ($Na_2SO_4$) and concentrated under reduced pressure to afford the crude product. The crude was purified by CombiFlash and the product was eluted with DCM:MeOH=95:5. The final products were further isolated by chiral separation to afford 4 isomers and the stereochemistry of each isomer was arbitrarily assigned.

Example 63a: (7S,8S)-7-((S)-5H-imidazo[5,1-a]isoindol-5-yl)-5,6,7,8-tetrahydroquinolin-8-ol: LCMS (ESI, m/z): 304.2 $[M+H]^+$; $^1$HNMR (500 MHz, Chloroform-d) δ 8.47 (ddt, J=4.7, 1.6, 0.8 Hz, 1H), 7.74 (d, J=0.7 Hz, 1H), 7.54 (dt, J=7.8, 1.0 Hz, 1H), 7.47 (dq, J=7.7, 1.0 Hz, 1H), 7.43-7.35 (m, 2H), 7.28 (dd, J=7.5, 1.1 Hz, 1H), 7.18 (dd, J=7.7, 4.8 Hz, 1H), 7.15 (s, 1H), 5.63 (d, J=2.8 Hz, 1H), 5.17 (d, J=5.0 Hz, 1H), 2.72-2.63 (m, 1H), 2.58 (dd, J=10.4, 4.9 Hz, 2H), 1.64-1.56 (m, 2H), 1.43-1.34 (m, 1H).

Example 63b: (7R,8R)-7-((R)-5H-imidazo[5,1-a]isoindol-5-yl)-5,6,7,8-tetrahydroquinolin-8-ol: LCMS (ESI, m/z): 304.2 $[M+H]^+$; $^1$HNMR (500 MHz, Chloroform-d) δ 8.52-8.47 (m, 1H), 7.80 (t, J=0.7 Hz, 1H), 7.58 (dt, J=7.6, 0.9 Hz, 1H), 7.51 (dd, J=7.6, 1.0 Hz, 1H), 7.46-7.39 (m, 2H), 7.31 (dd, J=7.5, 1.1 Hz, 1H), 7.21 (dd, J=7.7, 4.8 Hz, 1H), 7.18 (s, 1H), 5.67 (d, J=2.8 Hz, 1H), 5.21 (d, J=5.0 Hz, 1H), 2.73-2.68 (m, 1H), 2.66-2.57 (m, 2H), 1.77-1.56 (m, 2H), 1.46-1.38 (m, 1H).

Example 63c: (7S,8R)-7-((S)-5H-imidazo[5,1-a]isoindol-5-yl)-5,6,7,8-tetrahydroquinolin-8-ol: LCMS (ESI, m/z): 304.2 $[M+H]^+$; $^1$HNMR (500 MHz, Chloroform-d) δ 8.47-8.42 (m, 1H), 7.96 (s, 1H), 7.53 (dt, J=7.7, 0.9 Hz, 1H), 7.47 (dq, J=7.7, 0.9 Hz, 1H), 7.43-7.38 (m, 1H), 7.33 (tt, J=7.5, 0.9 Hz, 1H), 7.20 (s, 1H), 7.16 (dd, J=7.7, 4.7 Hz, 1H), 7.12 (td, J=7.6, 1.1 Hz, 1H), 5.55 (d, J=6.7 Hz, 1H), 5.03 (d, J=4.3 Hz, 1H), 2.78-2.60 (m, 2H), 2.44-2.30 (m, 1H), 2.03-1.92 (m, 2H), 1.61 (s, 1H).

Example 63d: (7R,8S)-7-((R)-5H-imidazo[5,1-a]isoindol-5-yl)-5,6,7,8-tetrahydroquinolin-8-ol: LCMS (ESI, m/z): 304.2 $[M+H]^+$; $^1$HNMR (500 MHz, Chloroform-d) δ 8.44 (dd, J=4.8, 1.6 Hz, 1H), 7.96 (s, 1H), 7.52 (dt, J=7.8, 1.0 Hz, 1H), 7.48 (dq, J=7.7, 0.9 Hz, 1H), 7.43-7.39 (m, 1H), 7.33 (tt, J=7.6, 0.8 Hz, 1H), 7.20 (s, 1H), 7.16 (dd, J=7.7, 4.7 Hz, 1H), 7.12 (td, J=7.7, 1.2 Hz, 1H), 5.54 (d, J=6.7 Hz, 1H), 5.03 (d, J=4.3 Hz, 1H), 2.78-2.60 (m, 2H), 2.36 (dd, J=7.9, 4.4 Hz, 1H), 2.04-1.94 (m, 2H), 1.65 (s, 1H).

Example 64: 4-(5H-imidazo[5,1-a]isoindol-5-yl)-1-(methylsulfonyl)piperidin-3-ol

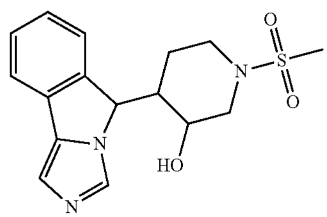 [SMILES: CS(=O)(=O)N1CCC(C2c3ccccc3-c3cncn32)C(O)C1]

Step 1: 4-(5H-imidazo[5,1-a]isoindol-5-yl)piperidin-3-ol

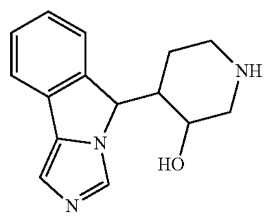 [SMILES: OC1CNCCC1C1c2ccccc2-c2cncn21]

A solution of tert-butyl 3-hydroxy-4-[5H-imidazo[4,3-a]isoindol-5-yl]piperidine-1-carboxylate (100 mg, 0.28 mmol) in 1,4-dioxane (4 mL) was added hydrogen chloride (1 mL). The resulting solution was stirred for 4 h at room temperature. The mixture was concentrated under vacuum. This resulted in 50 mg (70%) of 4-[5H-imidazo[4,3-a]isoindol-5-yl]piperidin-3-ol as yellow oil: LCMS (ESI, m/z): 256.0 $[M+H]^+$.

Step 2:

(3S,4S)-4-((R)-5H-imidazo[5,1-a]isoindol-5-yl)-1-(methylsulfonyl)piperidin-3-ol (3R,4R)-4-((S)-5H-imidazo[5,1-a]isoindol-5-yl)-1-(methylsulfonyl)piperidin-3-ol (3S,4S)-4-((S)-5H-imidazo[5,1-a]isoindol-5-yl)-1-(methylsulfonyl)piperidin-3-ol (3R,4R)-4-((R)-5H-imidazo[5,1-a]isoindol-5-yl)-1-(methylsulfonyl)piperidin-3-ol 64a

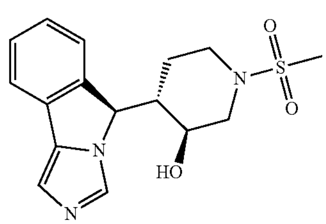

64b

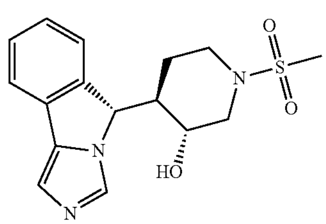

-continued

64c

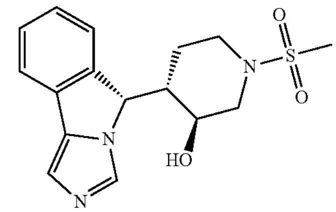

64d

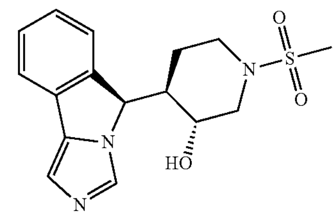

A solution of 4-[5H-imidazo[4,3-a]isoindol-5-yl]piperidin-3-ol (50 mg, 0.20 mmol) and TEA (1 g, 9.88 mmol) in DCM (3 mL) was added methanesulfonyl chloride (100 mg, 0.873 mmol). The resulting solution was stirred for 3 h at room temperature. The resulting mixture was concentrated under vacuum. The crude product was purified by Combi-Flash and further isolated by chiral separation. The absolute configuration of all isomers 064a-d were assigned arbitrarily.

Example 64a: (3S,4S)-4-((R)-5H-imidazo[5,1-a]isoindol-5-yl)-1-(methylsulfonyl)piperidin-3-ol (9.9 mg, 3%) as a white solid: LCMS (ESI, m/z): 334.0 $[M+H]^+$. $^1H$ NMR (300 MHz, $CD_3OD$) 7.91 (s, 1H), 7.65 (d, J=3.6 Hz, 1H), 7.50 (d, J=3.6 Hz, 1H), 7.44 (t, J=7.2 Hz, 1H), 7.36 (t, J=7.2 Hz, 1H), 7.21 (s, 1H), 5.84 (s, 1H), 4.02-3.91 (m, 2H), 3.51 (dd, J=9.6 Hz, 2.4 Hz, 1H), 2.84 (s, 3H), 2.68-2.57 (m, 2H), 2.23 (t, J=5.6 Hz, 1H), 0.98 (dd, J=13.6 Hz, 3.2 Hz, 1H), 0.68-0.64 (m, 1H). tR=1.573 min (CHIRALCEL PAK IC-3, 0.46×5 cm; 3 um, Hex(0.1% DEA):EtOH=50:50, 1.0 ml/min). 64a and 64b are enantiomers.

Example 64b: (3R,4R)-4-((S)-5H-imidazo[5,1-a]isoindol-5-yl)-1-(methylsulfonyl)piperidin-3-ol (16.2 mg, 6%) as a white solid: LCMS (ESI, m/z): 334.0 $[M+H]^+$. tR=2.048 min (CHIRALCEL PAK IC-3, 0.46×5 cm; 3 um, Hex(0.1% DEA):EtOH=50:50, 1.0 ml/min). 64a and 64b are enantiomers.

Example 64c: (3R,4R)-4-((R)-5H-imidazo[5,1-a]isoindol-5-yl)-1-(methylsulfonyl)piperidin-3-ol (4.4 mg, 2%) as a white solid: LCMS (ESI, m/z): 334.0 $[M+H]^+$. $^1H$ NMR (300 MHz, $CD_3OD$) 7.95 (s, 1H), 7.66 (d, J=3.6 Hz, 1H), 7.54 (d, J=3.6 Hz, 1H), 7.47 (t, J=7.2 Hz, 1H), 7.40 (t, J=7.2 Hz, 1H), 7.22 (s, 1H), 5.86 (s, 1H), 4.02-3.91 (m, 2H), 3.73 (dd, J=9.6 Hz, 2.4 Hz, 1H), 3.01 (dd, J=4.8 Hz, 2.4 Hz, 1H), 2.80-2.73 (m, 1H), 2.63 (s, 3H), 2.41-2.39 (m, 1H), 2.20 (dd, J=10.4 Hz, 2.0 Hz, 1H), 1.91 (t, J=11.6 Hz, 1H), 1.88-1.74 (m, 1H). tR=2.268 min (CHIRALCEL PAK IC-3, 0.46×5 cm; 3 um, Hex(0.1% DEA):EtOH=50:50, 1.0 ml/min). 64c and 64d are enantiomers.

Example 64d: (3,4S)-4-((S)-5H-imidazo[5,1-a]isoindol-5-yl)-1-(methylsulfonyl)piperidin-3-ol (6.7 mg, 2%) as a white solid: LCMS (ESI, m/z): 334.0 $[M+H]^+$. tR=3.284 min (CHIRALCEL PAK IC-3, 0.46×5 cm; 3 um, Hex(0.1% DEA):EtOH=50:50, 1.0 ml/min). 64c and 64d are enantiomers.

Example 66: 5-(5H-imidazo[5,1-a]isoindol-5-yl)-3,3-dimethyltetrahydro-2H-pyran-4-ol

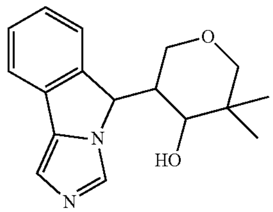 [SMILES: CC1(C)COCC(C2c3ccccc3-c3cncn32)C1O]

(4R,5R)-5-((S)-5H-imidazo[5,1-a]isoindol-5-yl)-3,3-dimethyltetrahydro-2H-pyran-4-ol (4R,5S)-5-((R)-5H-imidazo[5,1-a]isoindol-5-yl)-3,3-dimethyltetrahydro-2H-pyran-4-ol (4S,5R)-5-((S)-5H-imidazo[5,1-a]isoindol-5-yl)-3,3-dimethyltetrahydro-2H-pyran-4-ol (4R,5R)-5-((R)-5H-imidazo[5,1-a]isoindol-5-yl)-3,3-dimethyltetrahydro-2H-pyran-4-ol (4S,5S)-5-((S)-5H-imidazo[5,1-a]isoindol-5-yl)-3,3-dimethyltetrahydro-2H-pyran-4-ol (4S,5R)-5-((R)-5H-imidazo[5,1-a]isoindol-5-yl)-3,3-dimethyltetrahydro-2H-pyran-4-ol (4R,5S)-5-((S)-5H-imidazo[5,1-a]isoindol-5-yl)-3,3-dimethyltetrahydro-2H-pyran-4-ol Step 1: (E)-3,3-dimethyl-5-(2-(1-trityl-1H-imidazol-4-yl)benzylidene)tetrahydro-4H-pyran-4-one 1

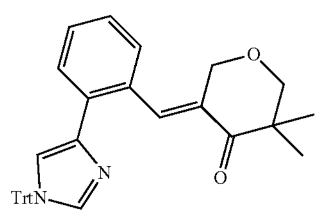

The title compound was synthesized by General Procedure for the Synthesis of Int-2. LCMS (ESI, m/z): 524.4 [M+H]+

Step 2: 5-(5H-imidazo[5,1-a]isoindol-5-yl)-3,3-dimethyltetrahydro-4H-pyran-4-one

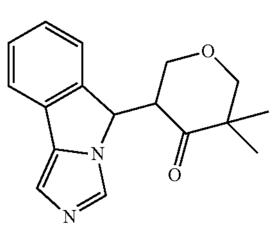 [SMILES: CC1(C)COCC(C2c3ccccc3-c3cncn32)C1=O]

The title compound was synthesized by General Procedure for the Synthesis of Int-3. LCMS (ESI, m/z): 283.2 [M+H]+

Step 3: 5-(5H-imidazo[5,1-a]isoindol-5-yl)-3,3-dimethyltetrahydro-2H-pyran-4-ol

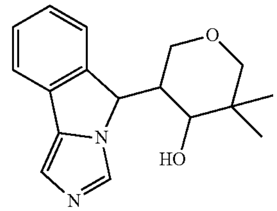 [SMILES: CC1(C)COCC(C2c3ccccc3-c3cncn32)C1O]

The title compounds were synthesized by General Procedure for the Synthesis of Int-5: LCMS (ESI, m/z): 285.5 [M+H]+. The mixture was isolated by Chiral separation methods and the configuration of the isomers was assigned arbitrarily.

(4R,5R)-5-((S)-5H-imidazo[5,1-a]isoindol-5-yl)-3,3-dimethyltetrahydro-2H-pyran-4-ol (4R,5S)-5-((R)-5H-imidazo[5,1-a]isoindol-5-yl)-3,3-dimethyltetrahydro-2H-pyran-4-ol (4S,5R)-5-((S)-5H-imidazo[5,1-a]isoindol-5-yl)-3,3-dimethyltetrahydro-2H-pyran-4-ol (4R,5R)-5-((R)-5H-imidazo[5,1-a]isoindol-5-yl)-3,3-dimethyltetrahydro-2H-pyran-4-ol (4S,5S)-5-((S)-5H-imidazo[5,1-a]isoindol-5-yl)-3,3-dimethyltetrahydro-2H-pyran-4-ol (4S,5R)-5-((R)-5H-imidazo[5,1-a]isoindol-5-yl)-3,3-dimethyltetrahydro-2H-pyran-4-ol (4R,5S)-5-((S)-5H-imidazo[5,1-a]isoindol-5-yl)-3,3-dimethyltetrahydro-2H-pyran-4-ol 66a

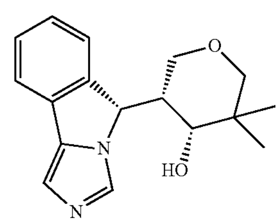

66b

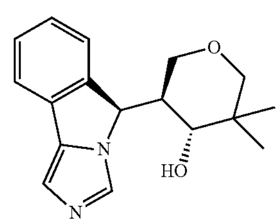

66c

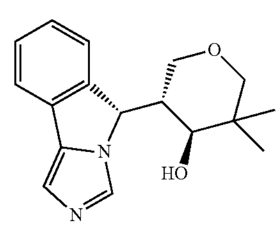

-continued

66d

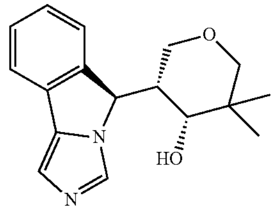

66e

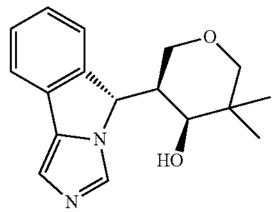

66f

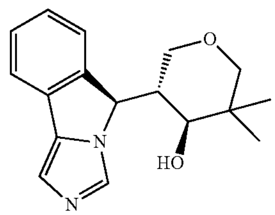

66g

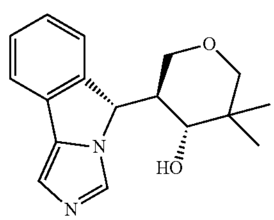

Example 66a: (4R,5R)-5-((S)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 7.93 (s, 1H), 7.59 (d, J=7.5 Hz, 1H), 7.57 (d, J=7.6 Hz, 1H), 7.39 (t, J=7.5 Hz, 1H), 7.31 (td, J=7.5, 1.0 Hz, 1H), 7.15 (s, 1H), 5.65 (d, J=2.3 Hz, 1H), 5.43 (d, J=6.3 Hz, 1H), 3.60 (dd, J=10.9, 6.3 Hz, 1H), 2.93 (dd, J=11.2, 3.9 Hz, 1H), 2.89 (d, J=11.4 Hz, 1H), 2.44 (ddt, J=15.1, 7.0, 4.1 Hz, 1H), 2.29 (t, J=11.3 Hz, 1H), 0.99 (s, 3H), 0.90 (s, 3H).

Example 66b: (4R,5S)-5-((R)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 7.93 (s, 1H), 7.60 (d, J=7.5 Hz, 1H), 7.58-7.54 (m, 1H), 7.40 (t, J=7.4 Hz, 1H), 7.31 (td, J=7.5, 1.1 Hz, 1H), 7.16 (s, 1H), 5.66 (d, J=2.4 Hz, 1H), 5.43 (d, J=6.3 Hz, 1H), 3.60 (dd, J=10.9, 6.3 Hz, 1H), 2.94 (dd, J=11.1, 3.7 Hz, 1H), 2.89 (d, J=11.5 Hz, 1H), 2.48-2.39 (m, 1H), 2.29 (t, J=11.3 Hz, 1H), 0.99 (s, 3H), 0.91 (s, 3H).

Example 66c: (4S,5R)-5-((S)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 8.01 (s, 1H), 7.61 (d, J=8.5 Hz, 2H), 7.40 (t, J=7.5 Hz, 1H), 7.30 (td, J=7.5, 1.0 Hz, 1H), 7.13 (s, 1H), 5.64 (d, J=3.7 Hz, 1H), 5.33 (d, J=6.1 Hz, 1H), 3.56 (dd, J=11.0, 6.1 Hz, 1H), 2.90-2.74 (m, 2H), 2.61 (dq, J=11.2, 3.7 Hz, 1H), 2.41 (t, J=11.4 Hz, 1H), 0.98 (s, 3H), 0.85 (s, 3H).

Example 66d: (4R,5R)-5-((R)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 8.06 (dd, J=7.9, 1.2 Hz, 1H), 7.74 (s, 1H), 7.30-7.27 (m, 1H), 7.19 (td, J=7.4, 1.3 Hz, 1H), 6.96 (d, J=7.5 Hz, 1H), 6.72 (s, 1H), 5.25 (d, J=4.8 Hz, 1H), 4.36 (d, J=12.5 Hz, 1H), 4.02-3.85 (m, 2H), 3.46 (d, J=11.0 Hz, 1H), 3.29-3.23 (m, 2H), 0.95 (s, 3H), 0.91 (s, 3H).

Example 66e: (4S,5S)-5-((S)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 7.95 (s, 1H), 7.66-7.61 (m, 1H), 7.58 (d, J=7.5 Hz, 1H), 7.39 (t, J=7.4 Hz, 1H), 7.29 (td, J=7.6, 1.1 Hz, 1H), 7.10 (s, 1H), 5.53-5.44 (m, 1H), 5.23 (d, J=4.9 Hz, 1H), 3.80-3.61 (m, 1H), 3.38 (d, J=10.8 Hz, 1H), 3.34 (d, J=11.2 Hz, 1H), 3.10 (d, J=10.8 Hz, 1H), 2.28 (dq, J=8.2, 3.7, 2.4 Hz, 1H), 0.94 (s, 3H), 0.83 (s, 3H).

Example 66f: (4S,5R)-5-((R)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 8.01 (s, 1H), 7.61 (d, J=8.6 Hz, 2H), 7.40 (t, J=7.5 Hz, 1H), 7.30 (td, J=7.5, 1.1 Hz, 1H), 7.13 (s, 1H), 5.64 (d, J=3.7 Hz, 1H), 5.34 (d, J=6.1 Hz, 1H), 3.56 (dd, J=11.0, 6.0 Hz, 1H), 2.88-2.78 (m, 2H), 2:61 (ddt, J=11.2, 8.0, 4.0 Hz, 1H), 2.41 (t, J=11.4 Hz, 1H), 0.98 (s, 3H), 0.85 (s, 3H).

Example 66g: (4R,5S)-5-((S)-5H-imidazo[5,1-a]isoindol-5-yl)-3,3-dimethyltetrahydro-2H-pyran-4-ol: LCMS (ESI, m/z): 285.5 $[M+H]^+$; $^1$H NMR (500 MHz, DMSO-$d_6$) δ 7.95 (s, 1H), 7.73-7.60 (m, 1H), 7.58 (d, J=7.5 Hz, 1H), 7.39 (t, J=7.4 Hz, 1H), 7.28 (td, J=7.6, 1.1 Hz, 1H), 7.10 (s, 1H), 5.48 (d, J=4.9 Hz, 1H), 5.23 (d, J=4.9 Hz, 1H), 3.70 (d, J=3.2 Hz, 1H), 3.38 (d, J=10.8 Hz, 1H), 3.34 (d, J=11.2 Hz, 1H), 3.10 (d, J=10.8 Hz, 1H), 2.30-2.23 (m, 1H), 0.94 (s, 3H), 0.82 (s, 3H).

Example 67: 1-(5H-imidazo[5,1-a]isoindol-5-yl) spiro[3.3]heptan-2-ol

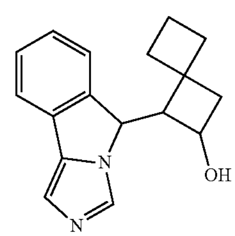 [SMILES: OC1CC2(CCC2)C1C1c2ccccc2-c2cncn21]

(1R,2R)-1-((R)-5H-imidazo[5,1-a]isoindol-5-yl)spiro[3.3]heptan-2-ol (1R,2S)-1-((R)-5H-imidazo[5,1-a]isoindol-5-yl)spiro[3.3]heptan-2-ol (1S,2S)-1-((R)-5H-imidazo[5,1-a]isoindol-5-yl)spiro[3.3]heptan-2-ol (1S,2R)-1-((R)-5H-imidazo[5,1-a]isoindol-5-yl)spiro[3.3]heptan-2-ol (1S,2R)-1-((S)-5H-imidazo[5,1-a]isoindol-5-yl)spiro[3.3]heptan-2-ol (1S,2S)-1-((S)-5H-imidazo[5,1-a]isoindol-5-yl)spiro[3.3]heptan-2-ol (1R,2R)-1-((S)-5H-imidazo[5,1-a]isoindol-5-yl)spiro[3.3]heptan-2-ol (1R,2S)-1-((S)-5H-imidazo[5,1-a]isoindol-5-yl)spiro[3.3]heptan-2-ol Step 1: (E)-1-(2-(1-trityl-1H-imidazol-4-yl)benzylidene)spiro[3.3]heptan-2-one

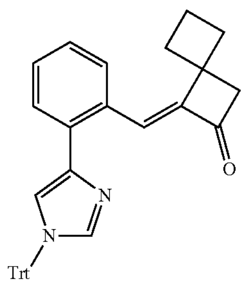

To a solution of 2-(1-trityl-1H-imidazol-4-yl)benzaldehyde (2.5 g, 6.03 mmol) and spiro[3.3]heptan-2-one (863 mg, 7.84 mmol) in MeOH (20 mL) was added piperidine dropwise (0.595 mL, 6.03 mmol). The solution was allowed to reflux for 2 hrs. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by EtOAc: Hexane=25:75: LCMS (ESI, m/z): 507.4 $[M+H]^+$.

Step 2: 1-(5H-imidazo[5,1-a]isoindol-5-yl)spiro[3.3]heptan-2-one

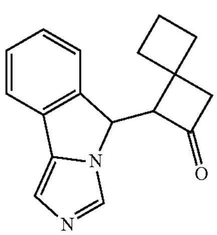 [SMILES: O=C1CC2(CCC2)C1C1c2ccccc2-c2cncn21]

(E)-1-(2-(1-trityl-1H-imidazol-4-yl)benzylidene)spiro[3.3]heptan-2-one (2.38 g, 4.70 mmol) was stirred in 20% AcOH in MeOH (20 mL) at 90° C. for 2 h. After cooling to rt, the solvent was removed under reduced pressure and sat'd $NaHCO_3$ (20 mL) was added to the residue followed by DCM (20 mL). The organic layer was collected and the aqueous layer was extracted with DCM (3×10 mL). The combined organic layers were dried over $Na_2SO_4$ and the solvent evaporated under reduced pressure to afford the crude product which was purified by using CombiFlash. The product was eluted with DCM:MeOH=98:2: LCMS (ESI, m/z): 265.4 $[M+H]^+$.

Step 3:

(1R,2R)-1-((R)-5H-imidazo[5,1-a]isoindol-5-yl)spiro[3.3]heptan-2-ol (1R,2S)-1-((R)-5H-imidazo[5,1-a]isoindol-5-yl)spiro[3.3]heptan-2-ol (1S,2S)-1-((R)-5H-imidazo[5,1-a]isoindol-5-yl)spiro[3.3]heptan-2-ol (1S,2R)-1-((R)-5H-imidazo[5,1-a]isoindol-5-yl)spiro[3.3]heptan-2-ol (1S,2R)-1-((S)-5H-imidazo[5,1-a]isoindol-5-yl)spiro[3.3]heptan-2-ol (1S,2S)-1-((S)-5H-imidazo[5,1-a]isoindol-5-yl)spiro[3.3]heptan-2-ol (1R,2R)-1-((S)-5H-imidazo[5,1-a]isoindol-5-yl)spiro[3.3]heptan-2-ol (1R,2S)-1-((S)-5H-imidazo[5,1-a]isoindol-5-yl)spiro[3.3]heptan-2-ol 67a

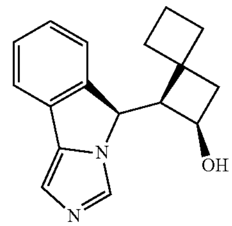

67b

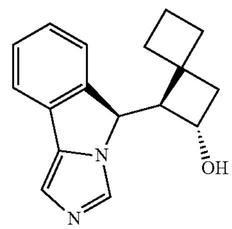

67c

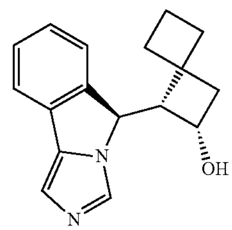

67d

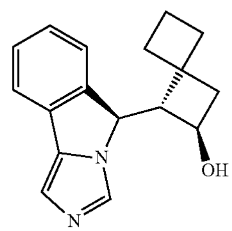

67e

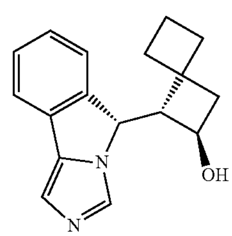

67f

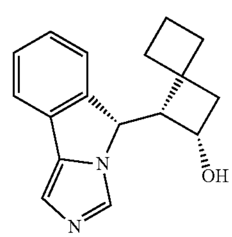

-continued

67g

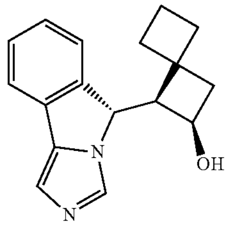

67h

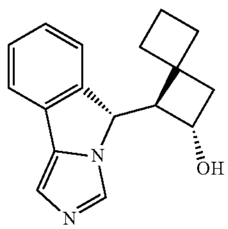

To a solution of 1-(5H-imidazo[5,1-a]isoindol-5-yl)spiro[3.3]heptan-2-one (1.05 g, 3.98 mmol) in MeOH (15 mL) was added $NaBH_4$ (301 mg, 7.97 mmol) in portions at 0° C. and the solution was stirred at 0° C. for additional 2 hr. The solvent was distilled off and saturated ammonium chloride solution (10 mL) was added. The aqueous layer was extracted with 5% trifluoroethanol in DCM (3×10 mL). The combined organic extract was dried over ($Na_2SO_4$) and concentrated under reduced pressure to afford the crude product. The crude was purified by CombiFlash and the product was eluted with DCM:MeOH=95:5. The final products were further isolated by chiral separation to afford 8 isomers and the stereochemistry of each isomer was arbitrarily assigned.

Example 67a: (1R,2R)-1-((R)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.92 (s, 1H), 7.63-7.61 (m, 1H), 7.60-7.57 (m, 1H), 7.42-7.36 (m, 1H), 7.28 (dd, J=7.6, 1.2 Hz, 1H), 7.18 (s, 1H), 5.47 (d, J=5.8 Hz, 1H), 5.25 (d, J=6.8 Hz, 1H), 4.27-4.16 (m, 1H), 2.32 (s, 2H), 1.71 (dd, J=10.4, 8.2 Hz, 1H), 1.64-1.55 (m, 3H), 1.42 (d, J=8.0 Hz, 1H), 1.38-1.30 (m, 1H), 1.23 (d, J=7.4 Hz, 1H).

Example 67b: (1R,2S)-1-((R)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 8.13 (s, 1H), 7.62-7.56 (m, 2H), 7.38 (t, J=0.9 Hz, 1H), 7.30 (dd, J=7.5, 1.1 Hz, 1H), 7.14 (s, 1H), 5.68 (d, J=3.9 Hz, 1H), 5.40 (d, J=3.9 Hz, 1H), 4.52 (dd, J=6.3, 3.9 Hz, 1H), 2.92-2.86 (m, 1H), 2.32 (ddd, J=11.7, 7.3, 2.4 Hz, 1H), 1.97 (ddd, J=11.8, 6.2, 1.1 Hz, 1H), 1.80-1.71 (m, 2H), 1.63-1.52 (m, 1H), 1.38-1.28 (m, 2H), 0.96-0.88 (m, 1H).

Example 67c: (1S,2S)-1-((R)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.88 (s, 1H), 7.83 (dd, J=7.7, 1.0 Hz, 1H), 7.61 (dt, J=7.6, 0.9 Hz, 1H), 7.43-7.36 (m, 1H), 7.32 (dd, J=7.6, 1.2 Hz, 1H), 7.14 (s, 1H), 5.55 (d, J=3.8 Hz, 1H), 5.47 (d, J=8.4 Hz, 1H), 4.38 (tt, J=6.5, 3.4 Hz, 1H), 2.33 (t, J=7.5 Hz, 1H), 2.21-2.14 (m, 2H), 2.07 (dd, J=11.6, 3.3 Hz, 1H), 2.02 (d, J=9.8 Hz, 1H), 1.89 (dt, J=11.2, 8.8 Hz, 1H), 1.75 (tt, J=9.2, 4.6 Hz, 2H), 1.65 (dd, J=7.7, 3.8 Hz, 1H).

Example 67d: (1S,2R)-1-((R)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.87 (s, 1H), 7.65-7.56 (m, 2H), 7.40 (tt, J=7.5, 0.8 Hz, 1H), 7.31 (td, J=7.6, 1.2 Hz, 1H), 7.12 (s, 1H), 5.46 (d, J=7.9 Hz, 1H), 5.14 (d, J=7.3 Hz, 1H), 4.13 (p, J=7.8 Hz, 1H), 2.44 (dd, J=10.5, 7.5 Hz, 1H), 2.15 (t, J=7.5 Hz, 2H), 2.06-1.95 (m, 1H), 1.87 (dt, J=11.0, 8.6 Hz, 1H), 1.77-1.59 (m, 4H).

Example 67e: (1S,2R)-1-((S)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 8.13 (s, 1H), 7.62-7.54 (m, 2H), 7.38 (tt, J=7.5, 0.9 Hz, 1H), 7.30 (td, J=7.5, 1.1 Hz, 1H), 7.14 (s, 1H), 5.68 (d, J=3.8 Hz, 1H), 5.40 (d, J=4.0 Hz, 1H), 4.52 (tdd, J=7.5, 6.2, 3.8 Hz, 1H), 2.91-2.85 (m, 1H), 2.35-2.26 (m, 1H), 1.97 (ddd, J=11.8, 6.2, 1.1 Hz, 1H), 1.81-1.71 (m, 2H), 1.63-1.52 (m, 1H), 1.37-1.27 (m, 2H), 0.96-0.87 (m, 1H).

Example 67f: (1S,2S)-1-((S)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.92 (s, 1H), 7.65-7.55 (m, 2H), 7.39 (tt, J=7.5, 0.9 Hz, 1H), 7.28 (td, J=7.6, 1.1 Hz, 1H), 7.18 (s, 1H), 5.47 (d, J=5.8 Hz, 1H), 5.24 (d, J=6.8 Hz, 1H), 4.21 (p, J=7.9 Hz, 1H), 2.38-2.25 (m, 2H), 1.71 (dd, J=10.4, 8.2 Hz, 1H), 1.61 (dt, J=4.4, 2.3 Hz, 3H), 1.49-1.38 (m, 1H), 1.35 (s, 1H), 1.23 (d, J=. 7.5 Hz, 1H).

Example 67g: (1R,2R)-1-((S)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.88 (s, 1H), 7.82 (dq, J=7.7, 0.9 Hz, 1H), 7.60 (dt, J=7.6, 0.9 Hz, 1H), 7.39 (tt, J=7.6, 0.8 Hz, 1H), 7.31 (td, J=7.6, 1.2 Hz, 1H), 7.14 (s, 1H), 5.55 (d, J=3.8 Hz, 1H), 5.47 (d, J=8.5 Hz, 1H), 4.38 (tt, J=6.5, 3.4 Hz, 1H), 2.33 (t, J=7.5 Hz, 1H), 2.19 (ddt, J=9.5, 5.1, 2.8 Hz, 2H), 2.07 (dd, J=11.6, 3.2 Hz, 1H), 2.02 (d, J=10.2 Hz, 1H), 1.89 (dt, J=11.4, 8.8 Hz, 1H), 1.75 (ddd, J=9.8, 6.0, 3.4 Hz, 2H), 1.65 (dd, J=7.7, 3.8 Hz, 1H).

Example 67h: (1R,2S)-1-((S)-5H-imidazo[5,1-a]isoindol-5-yl)spiro[3.3]heptan-2-ol: LCMS (ESI, m/z): 304.2 $[M+H]^+$; $^1$HNMR (500 MHz, DMSO-$d_6$) δ 7.86 (s, 1H), 7.64-7.54 (m, 2H), 7.40 (tt, J=7.5, 0.8 Hz, 1H), 7.31 (td, J=7.6, 1.2 Hz, 1H), 7.12 (s, 1H), 5.46 (d, J=7.9 Hz, 1H), 5.14 (d, J=7.4 Hz, 1H), 4.13 (p, J=7.8 Hz, 1H), 2.44 (dd, J=10.4, 7.5 Hz, 1H), 2.15 (t, J=7.6 Hz, 2H), 2.02 (d, J=9.9 Hz, 1H), 1.87 (dd, J=9.0, 2.3 Hz, 1H), 1.76-1.60 (m, 4H).

Example 68: 2-(5H-imidazo[5,1-a]isoindol-5-yl)-8-oxaspiro[4.5]decan-1-ol

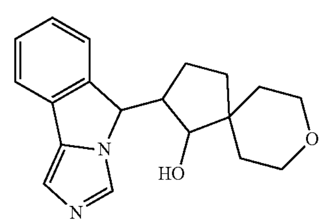 [SMILES: OC1C(C2c3ccccc3-c3cncn32)CCC12CCOCC2]

(1S,2R)-2-((R)-5H-imidazo[5,1-a]isoindol-5-yl)-8-oxaspiro[4.5]decan-1-ol (1R,2S)-2-((S)-5H-imidazo[5,1-a]isoindol-5-yl)-8-oxaspiro[4.5]decan-1-ol (1S,2S)-2-((R)-5H-imidazo[5,1-a]isoindol-5-yl)-8-oxaspiro[4.5]decan-1-ol (1R,2R)-2-((R)-5H-imidazo[5,1-a]isoindol-5-yl)-8-oxaspiro[4.5]decan-1-ol (1S,2S)-2-((S)-5H-imidazo[5,1-a]isoindol-5-yl)-8-oxaspiro[4.5]decan-1-ol (1R,2S)-2-((R)-5H-imidazo[5,1-a]isoindol-5-yl)-8-oxaspiro[4.5]decan-1-ol (1S,2R)-2-((S)-5H-imidazo[5,1-a]isoindol-5-yl)-8-oxaspiro[4.5]decan-1-ol (1R,2R)-2-((S)-5H-imidazo[5,1-a]isoindol-5-yl)-8-oxaspiro[4.5]decan-1-ol Step 1: (E)-2-(2-(1-trityl-1H-imidazol-4-yl)benzylidene)-8-oxaspiro[4.5]decan-1-one

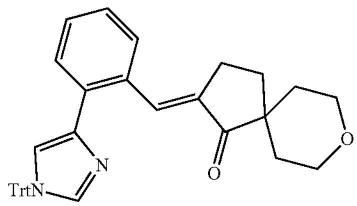

The title compound was synthesized by General Procedure for the Synthesis of Int-2. LCMS (ESI, m/z): 551.6 [M+H]+

Step 2: 2-(5H-imidazo[5,1-a]isoindol-5-yl)-8-oxaspiro[4.5]decan-1-one

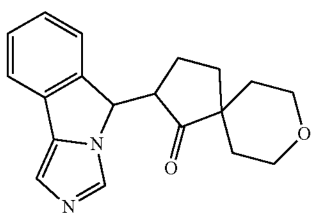 [SMILES: O=C1C(C2c3ccccc3-c3cncn32)CCC12CCOCC2]

The title compound was synthesized by General Procedure for the Synthesis of Int-3. LCMS (ESI, m/z): 309.4 [M+H]+

Step 3: 2-(5H-imidazo[5,1-a]isoindol-5-yl)-8-oxaspiro[4.5]decan-1-ol

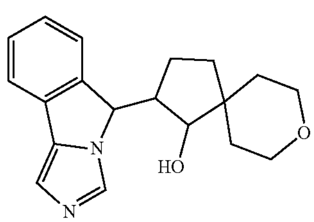 [SMILES: OC1C(C2c3ccccc3-c3cncn32)CCC12CCOCC2]

The title compounds were synthesized by General Procedure for the Synthesis of Int-5: LCMS (ESI, m/z): 311.4 [M+H]+. The mixture was isolated by Chiral separation methods and the configuration of the isomers was assigned arbitrarily.

(1S,2R)-2-((R)-5H-imidazo[5,1-a]isoindol-5-yl)-8-oxaspiro[4.5]decan-1-ol (1R,2S)-2-((S)-5H-imidazo[5,1-a]isoindol-5-yl)-8-oxaspiro[4.5]decan-1-ol (1S,2S)-2-((R)-5H-imidazo[5,1-a]isoindol-5-yl)-8-oxaspiro[4.5]decan-1-ol (1R,2R)-2-((R)-5H-imidazo[5,1-a]isoindol-5-yl)-8-oxaspiro[4.5]decan-1-ol (1S,2S)-2-((S)-5H-imidazo[5,1-a]isoindol-5-yl)-8-oxaspiro[4.5]decan-1-ol (1R,2S)-2-((R)-5H-imidazo[5,1-a]isoindol-5-yl)-8-oxaspiro[4.5]decan-1-ol (1S,2R)-2-((S)-5H-imidazo[5,1-a]isoindol-5-yl)-8-oxaspiro[4.5]decan-1-ol (1R,2R)-2-((S)-5H-imidazo[5,1-a]isoindol-5-yl)-8-oxaspiro[4.5]decan-1-ol 68a

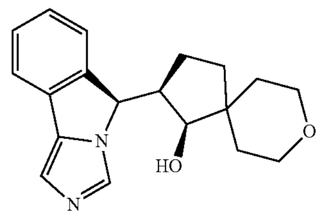

68b

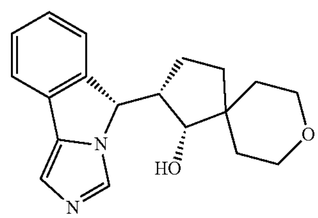

68c

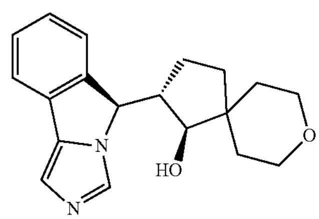

68d

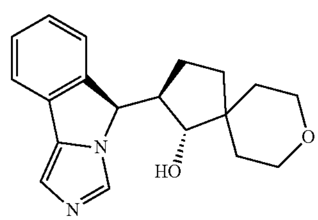

68e

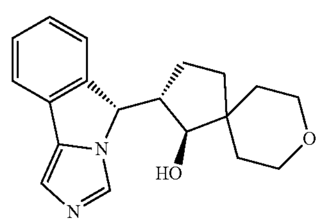

68f

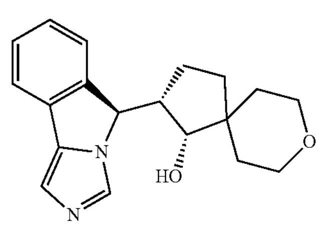

-continued

68g

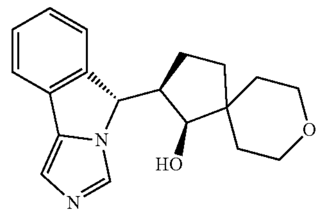

68h

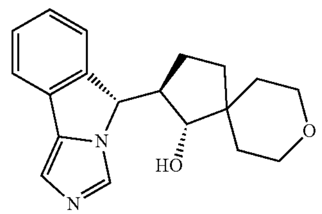

Example 68a: (1S,2R)-2-((R)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.94 (dd, J=7.8, 1.4 Hz, 1H), 7.71 (s, 1H), 7.31 (d, J=7.6 Hz, 1H), 7.28 (dd, J=1.9, 1.2 Hz, 1H), 7.22 (td, J=7.5, 1.4 Hz, 1H), 7.17 (td, J=7.4, 1.4 Hz, 1H), 6.66 (d, J=2.0 Hz, 1H), 5.22 (d, J=5.4 Hz, 1H), 4.04 (d, J=5.3 Hz, 1H), 3.70 (ddt, J=19.2, 11.1, 3.9 Hz, 3H), 3.42 (dtd, J=16.8, 11.3, 2.5 Hz, 3H), 2.48-2.43 (m, 1H), 2.30 (dt, J=17.4, 9.4 Hz, 1H), 1.94 (ddd, J=13.1, 9.5, 3.8 Hz, 1H), 1.82-1.73 (m, 1H), 1.72-1.63 (m, 1H), 1.43-1.34 (m, 1H), 1.19 (d, J=11.4 Hz, 1H), 0.97 (d, J=13.5 Hz, 1H).

Example 68b: (1R,2S)-2-((S)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.99-7.92 (m, 1H), 7.72 (s, 1H), 7.31 (d, J=7.5 Hz, 1H), 7.28 (s, 1H), 7.23 (t, J=6.9 Hz, 1H), 7.17 (t, J=6.8 Hz, 1H), 6.69-6.64 (m, 1H), 5.22 (d, J=5.4 Hz, 1H), 4.04 (d, J=5.1 Hz, 1H), 3.78-3.65 (m, 3H), 3.49-3.37 (m, 3H), 2.46 (d, J=9.5 Hz, 1H), 2.30 (dt, J=17.3, 8.3 Hz, 1H), 1.95 (ddd, J=12.9, 9.5, 3.7 Hz, 1H), 1.82-1.73 (m, 1H), 1.72-1.63 (m, 1H), 1.44-1.34 (m, 1H), 1.19 (d, J=13.4 Hz, 1H), 0.97 (d, J=13.7 Hz, 1H).

Example 68c: (1S,2S)-2-((R)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.95 (dd, J=7.8, 1.4 Hz, 1H), 7.72 (s, 1H), 7.31 (d, J=7.6 Hz, 1H), 7.28 (s, 1H), 7.23 (td, J=7.5, 1.4 Hz, 1H), 7.17 (td, J=7.4, 1.4 Hz, 1H), 6.67 (d, J=2.0 Hz, 1H), 5.22 (d, J=5.4 Hz, 1H), 4.04 (d, J=5.3 Hz, 1H), 3.70 (dtd, J=15.2, 7.7, 3.8 Hz, 3H), 3.43 (dtd, J=16.8, 11.4, 2.5 Hz, 3H), 2.48-2.44 (m, 1H), 2.30 (dt, J=17.3, 8.4 Hz, 1H), 1.95 (ddd, J=13.0, 9.5, 3.8 Hz, 1H), 1.82-1.73 (m, 1H), 1.72-1.64 (m, 1H), 1.44-1.35 (m, 1H), 1.22 (d, J=16.6 Hz, 1H), 0.97 (d, J=13.7 Hz, 1H).

Example 68d: (1R,2R)-2-((R)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.91 (s, 1H), 7.60 (d, J=7.5 Hz, 1H), 7.52 (d, J=7.7 Hz, 1H), 7.38 (t, J=7.5 Hz, 1H), 7.26 (td, J=7.6, 1.1 Hz, 1H), 7.10 (s, 1H), 5.44 (d, J=4.4 Hz, 1H), 5.02 (d, J=5.8 Hz, 1H), 3.73 (dt, J=11.3, 4.3 Hz, 1H), 3.70-3.63 (m, 1H), 3.51 (dd, J=9.6, 5.7 Hz, 1H), 3.38 (td, J=11.7, 2.4 Hz, 1H), 3.27 (td, J=11.9, 2.6 Hz, 1H), 2.63 (qd, J=9.4, 4.5 Hz, 1H), 1.76-1.62 (m, 3H), 1.36-1.20 (m, 1H), 1.13-1.06 (m, 2H), 0.98 (dd, J=13.2, 2.1 Hz, 1H), 0.89-0.78 (m, 1H).

Example 68e: (1S,2S)-2-((S)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.91 (s, 1H), 7.59 (d, J=7.5 Hz, 1H), 7.56-7.50 (m, 1H), 7.38 (t, J=7.4 Hz, 1H), 7.26 (td, J=7.6, 1.1 Hz, 1H), 7.10 (s, 1H), 5.44 (d, J=4.4 Hz, 1H), 5.01 (d, J=5.8 Hz, 1H), 3.73 (dt, J=11.3, 4.2 Hz, 1H), 3.69-3.62 (m, 1H), 3.51 (dd, J=9.6, 5.8 Hz, 1H), 3.38 (td, J=11.7, 2.4 Hz, 1H), 3.26 (td, J=11.7, 2.4 Hz, 1H), 2.63 (qd, J=9.4, 4.5 Hz, 1H), 1.77-1.62 (m, 3H), 1.27 (tdd, J=13.9, 10.0, 5.5 Hz, 1H), 1.09 (dd, J=13.2, 2.7 Hz, 2H), 0.98 (dd, J=13.2, 2.1 Hz, 1H), 0.84 (dtd, J=13.2, 9.6, 5.9 Hz, 1H).

Example 68f: (1R,2S)-2-((R)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.87 (s, 1H), 7.70-7.65 (m, 1H), 7.59 (d, J=7.5 Hz, 1H), 7.38 (t, J=7.4 Hz, 1H), 7.27 (td, J=7.6, 1.1 Hz, 1H), 7.12 (s, 1H), 5.40 (d, J=7.8 Hz, 1H), 5.29 (d, J=5.3 Hz, 1H), 3.90 (t, J=5.1 Hz, 1H), 3.71 (dt, J=11.3, 4.4 Hz, 1H), 3.57 (dt, J=11.5, 4.3 Hz, 1H), 3.47-3.37 (m, 2H), 2.24 (qd, J=8.9, 4.6 Hz, 1H), 1.73 (dddt, J=23.1, 13.7, 9.9, 4.5 Hz, 3H), 1.64-1.55 (m, 2H), 1.45 (d, J=13.5 Hz, 1H), 1.29 (ddd, J=13.5, 9.5, 4.2 Hz, 1H), 1.17 (d, J=13.4 Hz, 1H).

Example 68g: (1S,2R)-2-((S)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.93 (s, 1H), 7.59 (d, J=7.5 Hz, 1H), 7.48 (d, J=7.6 Hz, 1H), 7.37 (t, J=7.5 Hz, 1H), 7.23 (t, J=7.6 Hz, 1H), 7.11 (s, 1H), 5.29 (d, J=9.7 Hz, 1H), 5.22 (d, J=5.8 Hz, 1H), 3.84-3.78 (m, 1H), 3.73 (dt, J=11.3, 4.2 Hz, 1H), 3.54 (dt, J=11.5, 4.3 Hz, 1H), 3.44-3.34 (m, 2H), 2.16-2.05 (m, 1H), 2.03-1.89 (m, 2H), 1.70 (ddd, J=13.8, 9.9, 3.8 Hz, 3H), 1.49 (d, J=13.5 Hz, 1H), 1.25 (ddd, J=13.6, 9.7, 4.2 Hz, 1H), 1.12 (d, J=13.4 Hz, 1H).

Example 68h: (1R,2R)-2-((S)-5H-imidazo[5,1-a]isoindol-5-yl)-8-oxaspiro[4.5]decan-1-ol: LCMS (ESI, m/z): 311.4 $[M+H]^+$; $^1$H NMR (500 MHz, DMSO-$d_6$) δ 7.87 (s, 1H), 7.68 (d, J=7.6 Hz, 1H), 7.59 (d, J=7.5 Hz, 1H), 7.38 (t, J=7.4 Hz, 1H), 7.27 (td, J=7.6, 1.1 Hz, 1H), 7.12 (s, 1H), 5.39 (d, J=7.7 Hz, 1H), 5.29 (d, J=5.4 Hz, 1H), 3.90 (t, J=5.1 Hz, 1H), 3.71 (dt, J=11.4, 4.4 Hz, 1H), 3.57 (dt, J=11.6, 4.5 Hz, 1H), 3.46-3.35 (m, 2H), 2.29-2.20 (m, 1H), 1.81-1.66 (m, 3H), 1.65-1.54 (m, 2H), 1.45 (d, J=13.5 Hz, 1H), 1.29 (ddd, J=13.5, 9.4, 4.1 Hz, 1H), 1.17 (d, J=13.4 Hz, 1H).

Examples 69 and 69-1: 4-(6-chloro-5H-imidazo[5,1-a]isoindol-5-yl)tetrahydro-2H-pyran-3-ol and 3-(6-chloro-5H-imidazo[5,1-a]isoindol-5-yl)tetrahydro-2H-pyran-4-ol

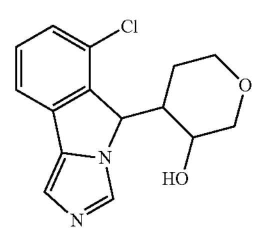

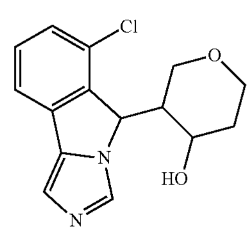

(3R,4R)-3-((S)-6-chloro-5H-imidazo[5,1-a]isoindol-5-yl)tetrahydro-2H-pyran-4-ol (3S,4S)-4-((S)-6-chloro-5H-imidazo[5,1-a]isoindol-5-yl)tetrahydro-2H-pyran-3-ol (3S,4S)-3-((R)-6-chloro-5H-imidazo[5,1-a]isoindol-5-yl)tetrahydro-2H-pyran-4-ol (3R,4R)-4-((R)-6-chloro-5H-imidazo[5,1-a]isoindol-5-yl)tetrahydro-2H-pyran-3-ol (3R,4R)-3-((R)-6-chloro-5H-imidazo[5,1-a]isoindol-5-yl) tetrahydro-2H-pyran-4-ol (3S,4S)-4-((R)-6-chloro-5H-imidazo[5,1-a]isoindol-5-yl) tetrahydro-2H-pyran-3-ol (3R,4R)-4-((S)-6-chloro-5H-imidazo[5,1-a]isoindol-5-yl) tetrahydro-2H-pyran-3-ol (3S,4S)-3-((S)-6-chloro-5H-imidazo[5,1-a]isoindol-5-yl) tetrahydro-2H-pyran-4-ol Synthetic Route

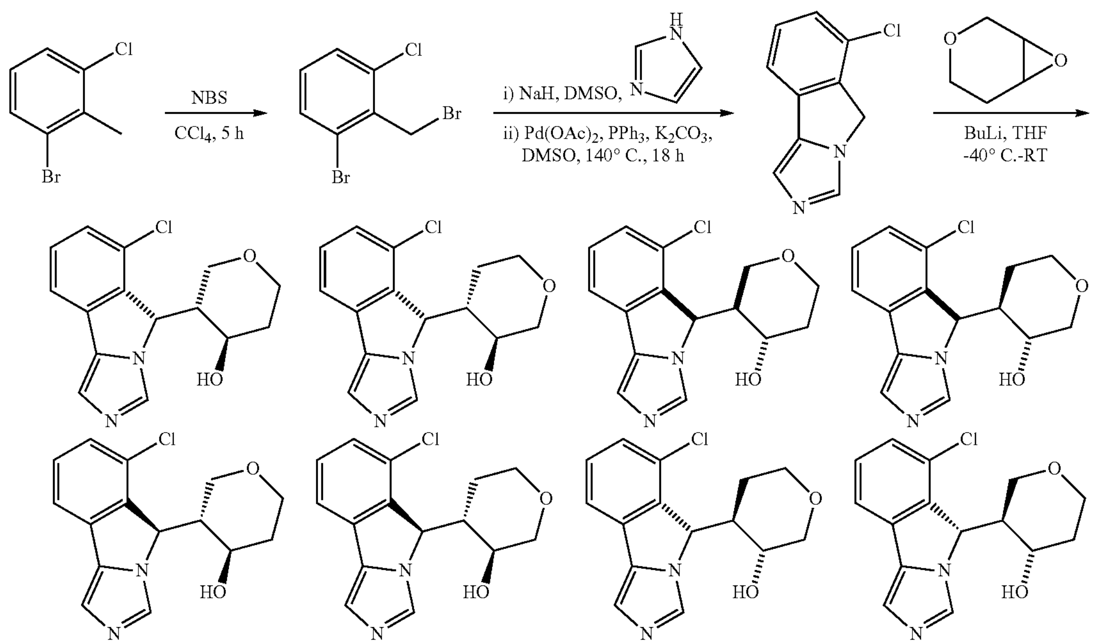

Step 1: 1-bromo-2-(bromomethyl)-3-chlorobenzene

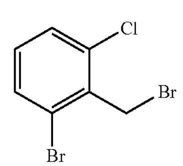

To a solution of 1-bromo-3-chloro-2-methylbenzene (5 g, 24.33 mmol) in tetrachloromethane (60 mL) at 90° C. was added 1-bromopyrrolidine-2,5-dione (2.33 g) followed by benzoyl peroxide (147 mg), the mixture was heated to reflux for 2 hr. Another portion of 1-bromopyrrolidine-2,5-dione (2.0 g) and benzoylperoxide (148 mg) was added and continued the reaction for another 3 hr. After cooling to rt, the reaction was diluted with dichloromethane (60 mL) and the organic layer was washed with ice cold 20% aqueous $NaHCO_3$ (20 mL), and brine (20 mL). The organic phase was dried over $Na_2SO_4$ and concentrated under reduced pressure to afford crude, which was used as such for the next step (6.85 g, 99%). $^1$H NMR (Chloroform-d, 400 MHz): δ (ppm) 7.50 (d, J=8.1 Hz, 1H), 7.36 (d, J=8.0 Hz, 1H), 7.10 (t, J=8.0 Hz, 1H), 4.79 (s, 2H).

Step 2: 6-chloro-5H-imidazo[5,1-a]isoindole

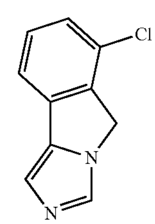 [SMILES: Clc1cccc2c1Cn1cncc1-2]

To a suspension of NaH (23.91 mmol) in anhydrous DSMO (50 mL) at room temperature, was added imidazole (1.63 g, 23.91 mmol) as a solution in DMSO (10 mL). The suspension was stirred for 2 hr at room temperature. 1-Bromo-2-(bromomethyl)-3-chlorobenzene (6.8 g, 23.91 mmol) as a solution in DMSO (10 mL) was added and stirring was continued overnight at rt. Anhydrous $K_2CO_3$ (6.6 g, 47.82 mmol), Pd(OAc) 2 (429.5 mg, 1.91 mmol), and $PPh_3$ (1.0 g, 3.83 mmol) were added to the mixture. The solution was purged with argon for 5 minutes and mixture was stirred at 130° C. for 18 hr. The solution was allowed to cool to rt, diluted with dichloromethane (50 mL) and filtered through celite. The solvent was removed under reduced pressure to afford the crude product which was purified by CombiFlash (2.6 g, 57%): LCMS (ESI, m/z): 191.19 $[M+H]^+$. $^1$H NMR (Chloroform-d, 400 MHz): δ (ppm) 7.76

(s, 1H), 7.43 (d, J=7.3 Hz, 1H), 7.33 (t, J=7.8 Hz, 1H), 7.25-7.17 (m, 2H), 5.02 (s, 2H).

Step 3:

(3R,4R)-3-((S)-6-chloro-5H-imidazo[5,1-a]isoindol-5-yl)tetrahydro-2H-pyran-4-ol (3S,4S)-4-((S)-6-chloro-5H-imidazo[5,1-a]isoindol-5-yl)tetrahydro-2H-pyran-3-ol (3S,4S)-3-((R)-6-chloro-5H-imidazo[5,1-a]isoindol-5-yl)tetrahydro-2H-pyran-4-ol (3R,4R)-4-((R)-6-chloro-5H-imidazo[5,1-a]isoindol-5-yl)tetrahydro-2H-pyran-3-ol (3R,4R)-3-((R)-6-chloro-5H-imidazo[5,1-a]isoindol-5-yl)tetrahydro-2H-pyran-4-ol (3S,4S)-4-((R)-6-chloro-5H-imidazo[5,1-a]isoindol-5-yl)tetrahydro-2H-pyran-3-ol (3R,4R)-4-((S)-6-chloro-5H-imidazo[5,1-a]isoindol-5-yl)tetrahydro-2H-pyran-3-ol (3S,4S)-3-((S)-6-chloro-5H-imidazo[5,1-a]isoindol-5-yl)tetrahydro-2H-pyran-4-ol 69a

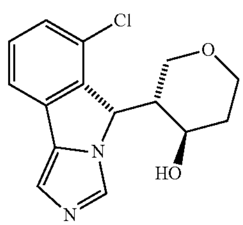

69b

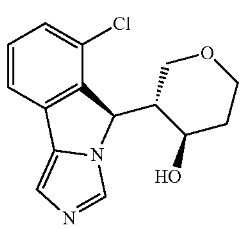

69c

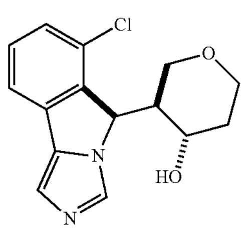

69d

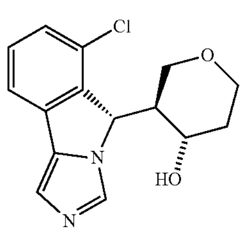

69-1a

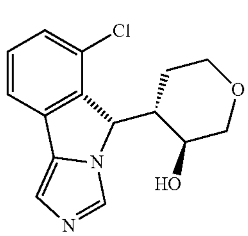

-continued 69-1b

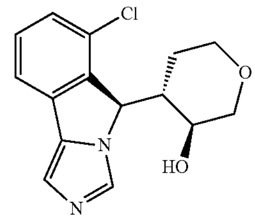

69-1c

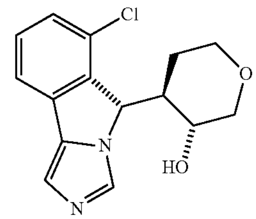

69-1d

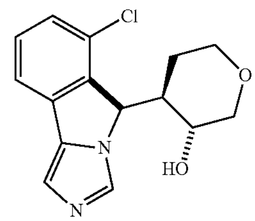

To a solution of 6-chloro-5H-imidazo[5,1-a]isoindole (1.0 g, 5.25 mmol) in anhydrous THF (25 mL) at −40° C. was added n-BuLi (2.3 mL, 5.77 mmol, 2.5 M solution in hexanes). After stirring for 1.5 hr at −40° C., 3,7-dioxabicyclo[4.1.0]heptane (577 mg, 5.77 mmol) was added and the reaction was allowed to warm to rt over a period of 2 hr and continued stirring overnight (18 hr). The reaction was quenched by adding satd. $NH_4Cl$ (5 mL) and the reaction was diluted with water (30 mL), the product was extracted with $CH_2Cl_2$ (3×40 mL). The combined organic extract was dried over ($Na_2SO_4$) and concentrated under reduced pressure to afford the crude product. The crude product was purified by CombiFlash and further isolated by chiral separation to afford 8 isomers as white solid. The configuration of the isomers was assigned arbitrarily.

Example 69a: (3R,4R)-3-((S)-6-chloro-5H-imidazo[5,1-a]isoindol-5-yl)tetrahydro-2H-pyran-4-ol: LCMS (ESI, m/z): 291.1 $[M+H]^+$. $^1$H NMR (500 MHz, DMSO-$d_6$) δ 7.93 (s, 1H), 7.60 (dd, J=7.5, 0.9 Hz, 1H), 7.45 (td, J=7.8, 0.6 Hz, 1H), 7.35 (dd, J=8.0, 0.9 Hz, 1H), 7.23 (s, 1H), 5.88 (d, J=2.9 Hz, 1H), 5.56 (d, J=5.6 Hz, 1H), 3.91 (tt, J=10.4, 5.1 Hz, 1H), 3.75 (dd, J=11.7, 4.9 Hz, 1H), 3.20-3.07 (m, 1H), 2.92 (dd, J=11.4, 3.9 Hz, 1H), 2.63 (tt, J=10.9, 3.5 Hz, 1H), 2.22 (t, J=11.3 Hz, 1H), 1.92 (ddt, J=12.7, 4.2, 1.9 Hz, 1H), 1.58 (tdd, J=12.7, 10.5, 4.8 Hz, 1H).

Example 69b: (3R,4R)-3-((R)-6-chloro-5H-imidazo[5,1-a]isoindol-5-yl)tetrahydro-2H-pyran-4-ol: LCMS (ESI, m/z): 291.1 $[M+H]^+$. $^1$H NMR (500 MHz, DMSO-$d_6$) δ 7.99 (s, 1H), 7.53 (dd, J=7.5, 0.9 Hz, 1H), 7.36 (ddd, J=8.1, 7.5, 0.6 Hz, 1H), 7.26 (dd, J=8.0, 0.9 Hz, 1H), 7.19 (s, 1H), 5.54 (s, 1H), 4.45 (d, J=5.5 Hz, 1H), 3.79 (dd, J=11.3, 4.4 Hz, 1H), 3.61 (dd, J=10.8, 5.1 Hz, 1H), 3.23 (td, J=11.6, 2.2 Hz, 1H), 3.17 (dq, J=10.3, 5.1 Hz, 1H), 2.83 (t, J=10.3 Hz, 1H), 2.60-2.52 (m, 1H), 1.62 (qd, J=12.8, 4.7 Hz, 1H), 1.52 (d, J=12.7 Hz, 1H).

Example 69c: (3S,4S)-3-((R)-6-chloro-5H-imidazo[5,1-a]isoindol-5-yl)tetrahydro-2H-pyran-4-ol: LCMS (ESI, m/z): 291.1 $[M+H]^+$. $^1H$ NMR (500 MHz, DMSO-$d_6$) δ 7.93 (s, 1H), 7.60 (dd, J=7.6, 0.9 Hz, 1H), 7.45 (td, J=7.8, 0.6 Hz, 1H), 7.35 (dd, J=8.0, 0.9 Hz, 1H), 7.23 (s, 1H), 5.88 (d, J=2.9 Hz, 1H), 5.56 (d, J=5.6 Hz, 1H), 3.91 (tt, J=10.4, 5.1 Hz, 1H), 3.75 (dd, J=11.7, 4.7 Hz, 1H), 3.18-3.09 (m, 1H), 2.92 (dd, J=11.4, 3.8 Hz, 1H), 2.68-2.58 (m, 1H), 2.22 (t, J=11.3 Hz, 1H), 1.96-1.88 (m, 1H), 1.64-1.51 (m, 1H).

Example 69d: (3S,4S)-3-((S)-6-chloro-5H-imidazo[5,1-a]isoindol-5-yl)tetrahydro-2H-pyran-4-ol: LCMS (ESI, m/z): 291.1 $[M+H]^+$. $^1H$ NMR (500 MHz, DMSO-$d_6$) δ 7.99 (s, 1H), 7.53 (dd, J=7.6, 0.9 Hz, 1H), 7.36 (t, J=7.8 Hz, 1H), 7.26 (dd, J=8.0, 0.9 Hz, 1H), 7.19 (s, 1H), 5.54 (d, J=1.4 Hz, 1H), 4.45 (d, J=5.5 Hz, 1H), 3.79 (dd, J=11.3, 4.3 Hz, 1H), 3.61 (dd, J=10.7, 5.0 Hz, 1H), 3.23 (td, J=11.6, 2.2 Hz, 1H), 3.16 (p, J=5.1 Hz, 1H), 2.83 (t, J=10.3 Hz, 1H), 2.56 (s, 1H), 1.62 (qd, J=12.7, 4.7 Hz, 1H), 1.56-1.49 (m, 1H).

Example 69-1a: (3S,4S)-4-((S)-6-chloro-5H-imidazo[5,1-a]isoindol-5-yl)tetrahydro-2H-pyran-3-ol: LCMS (ESI, m/z): 291.1 $[M+H]^+$. $^1H$ NMR (500 MHz, DMSO-$d_6$) δ 7.91 (s, 1H), 7.60 (dd, J=7.6, 0.9 Hz, 1H), 7.44 (td, J=7.8, 0.6 Hz, 1H), 7.33 (dd, J=8.0, 0.9 Hz, 1H), 7.23 (s, 1H), 5.87 (d, J=2.6 Hz, 1H), 5.58 (d, J=5.7 Hz, 1H), 3.90 (dd, J=10.6, 4.9 Hz, 1H), 3.71 (tt, J=10.3, 5.3 Hz, 1H), 3.58 (dd, J=11.3, 4.5 Hz, 1H), 3.15-2.99 (m, 2H), 2.68-2.56 (m, 1H), 0.64 (ddd, J=11.6, 3.9, 2.0 Hz, 1H), 0.35 (qd, J=12.6, 4.9 Hz, 1H).

Example 69-1b: (3S,4S)-4-((R)-6-chloro-5H-imidazo[5,1-a]isoindol-5-yl)tetrahydro-2H-pyran-3-ol: LCMS (ESI, m/z): 291.1 $[M+H]^+$. $^1H$ NMR (500 MHz, DMSO-$d_6$) δ 7.97 (s, 1H), 7.51 (dd, J=7.5, 0.9 Hz, 1H), 7.39-7.32 (m, 1H), 7.25 (dd, J=8.0, 1.0 Hz, 1H), 7.18 (s, 1H), 5.38 (s, 1H), 4.25 (d, J=5.3 Hz, 1H), 3.92 (dd, J=11.3, 4.4 Hz, 1H), 3.76 (d, J=10.9 Hz, 1H), 3.56 (t, J=11.4 Hz, 1H), 3.27 (td, J=11.7, 2.3 Hz, 1H), 3.22-3.14 (m, 1H), 2.69-2.56 (m, 1H), 1.59-1.51 (m, 1H), 1.40-1.28 (m, 1H).

Example 69-1c: (3R,4R)-4-((S)-6-chloro-5H-imidazo[5,1-a]isoindol-5-yl)tetrahydro-2H-pyran-3-ol: LCMS (ESI, m/z): 291.1 $[M+H]^+$. $^1H$ NMR (500 MHz, DMSO-$d_6$) δ 7.97 (s, 1H), 7.51 (dd, J=7.5, 0.9 Hz, 1H), 7.39-7.32 (m, 1H), 7.25 (dd, J=8.1, 1.0 Hz, 1H), 7.18 (s, 1H), 5.38 (s, 1H), 4.25 (d, J=5.4 Hz, 1H), 3.92 (dd, J=11.5, 4.5 Hz, 1H), 3.76 (d, J=10.5 Hz, 1H), 3.56 (t, J=11.4 Hz, 1H), 3.29-3.22 (m, 1H), 3.23-3.13 (m, 1H), 2.64 (s, 1H), 1.59-1.51 (m, 1H), 1.40-1.28 (m, 1H).

Example 69-1d: (3R,4R)-4-((R)-6-chloro-5H-imidazo[5,1-a]isoindol-5-yl)tetrahydro-2H-pyran-3-ol: LCMS (ESI, m/z): 291.1 $[M+H]^+$. $^1H$ NMR (500 MHz, DMSO-$d_6$) δ 7.91 (s, 1H), 7.60 (dd, J=7.6, 0.9 Hz, 1H), 7.44 (td, J=7.8, 0.6 Hz, 1H), 7.33 (dd, J=8.0, 0.9 Hz, 1H), 7.23 (s, 1H), 5.87 (d, J=2.6 Hz, 1H), 5.58 (d, J=5.7 Hz, 1H), 3.90 (dd, J=10.6, 4.9 Hz, 1H), 3.71 (tt, J=10.3, 5.2 Hz, 1H), 3.58 (dd, J=11.3, 4.6 Hz, 1H), 3.14-3.01 (m, 2H), 2.65-2.55 (m, 1H), 0.68-0.60 (m, 1H), 0.35 (qd, J=12.7, 4.9 Hz, 1H).

Example 70: 1-(cyclopropylsulfonyl)-3-(5H-imidazo[5,1-a]isoindol-5-yl)piperidin-4-ol

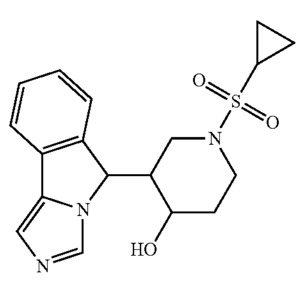 [SMILES: O=S(=O)(C1CC1)N1CCC(O)C(C2c3ccccc3-c3cncn32)C1]

Step 1: 3-(5H-imidazo[5,1-a]isoindol-5-yl)piperidin-4-ol

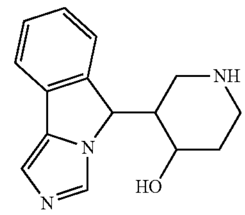 [SMILES: OC1CCNCC1C1c2ccccc2-c2cncn21]

The title compounds were synthesized by the same method of example 064.

Step 2:

(3S,4R)-1-(cyclopropylsulfonyl)-3-((S)-5H-imidazo[5,1-a]isoindol-5-yl)piperidin-4-ol (3R,4S)-1-(cyclopropylsulfonyl)-3-((R)-5H-imidazo[5,1-a]isoindol-5-yl)piperidin-4-ol (3S,4R)-1-(cyclopropylsulfonyl)-3-((R)-5H-imidazo[5,1-a]isoindol-5-yl)piperidin-4-ol (3R,4S)-1-(cyclopropylsulfonyl)-3-((S)-5H-imidazo[5,1-a]isoindol-5-yl)piperidin-4-ol 70a

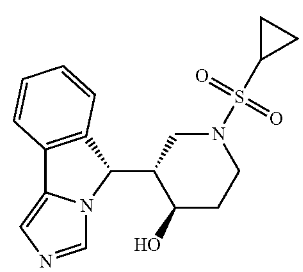

70b

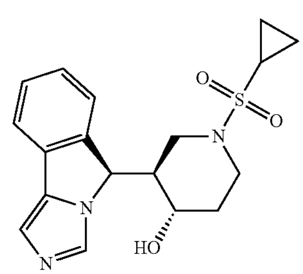

70c

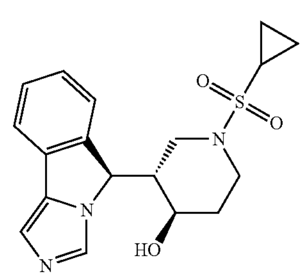

-continued

70d

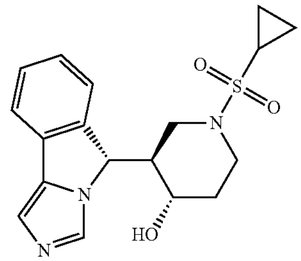

A solution of 3-[5H-imidazo[4,3-a]isoindol-5-yl]piperidin-4-ol (100 mg, 0.39 mmol) and TEA (2 g, 20.00 mmol) in DCM (5 mL) was added cyclopropanesulfonyl chloride (50 mg, 0.37 mmol). The resulting solution was stirred for 2 h at room temperature. The resulting mixture was concentrated under vacuum. The crude product was purified by Combi-Flash and further isolated by chiral separation. The absolute configuration of all isomers 070a-d was assigned arbitrarily.

Example 70a: (3,4R)-1-(cyclopropylsulfonyl)-3-((S)-5H-imidazo[5,1-a]isoindol-5-yl)piperidin-4-ol (10.8 mg, 1%) as a white solid: LCMS (ESI, m/z): 360.3 [M+H]+. $^1$H NMR (300 MHz, $CD_3OD$) 7.98 (s, 1H), 7.67 (d, J=3.6 Hz, 1H), 7.54 (d, J=3.6 Hz, 1H), 7.47 (t, J=7.2 Hz, 1H), 7.40 (t, J=7.6 Hz, 1H), 7.22 (s, 1H), 5.87 (s, 1H), 3.99-3.98 (m, 1H), 3.77-3.73 (m, 1H), 3.01 (dd, J=5.6 Hz, 2.8 Hz, 1H), 2.88 (t, J=12.8 Hz, 1H), 2.40-2.39 (m, 1H), 2.26-2.17 (m, 1H). 1.99 (t, J=12 Hz, 1H), 1.77-1.76 (m, 1H), 0.91-0.84 (m, 2H), 0.77-0.74 (m, 1H). tR=2.056 min (CHIRALPAK IC-3, 0.46×5 cm; 3 um, Hex(0.1% DEA):EtOH=50:50, 1.0 ml/min). 70a and 70b are enantiomers.

Example 70b: (3R,4S)-1-(cyclopropylsulfonyl)-3-((R)-5H-imidazo[5,1-a]isoindol-5-yl)piperidin-4-ol (11.8 mg, 2%) as a white solid: LCMS (ESI, m/z): 360.0 [M+H]+. tR=3.268 min (CHIRALPAK IC-3, 0.46×5 cm; 3 um, Hex (0.1% DEA):EtOH=50:50, 1.0 ml/min). 70a and 70b are enantiomers.

Example 70c: (3S,4R)-1-(cyclopropylsulfonyl)-3-((R)-5H-imidazo[5,1-a]isoindol-5-yl)piperidin-4-ol (12.0 mg, 2%) as a white solid: LCMS (ESI, m/z): 360.2 [M+H]+. $^1$H NMR (300 MHz, $CD_3OD$) 8.00 (s, 1H), 7.67 (d, J=3.6 Hz, 1H), 7.62 (d, J=3.6 Hz, 1H), 7.46 (t, J=7.2 Hz, 1H), 7.36 (t, J=7.6 Hz, 1H), 7.22 (s, 1H), 5.86 (s, 1H), 3.98-3.97 (m, 1H), 3.77-3.73 (m, 1H), 2.88-2.79 (m, 2H), 2.62-2.49 (m, 1H), 2.27-2.23 (m, 1H), 2.13-2.07 (m, 2H). 1.75-1.68 (m, 1H), 1.77-1.76 (m, 1H), 0.93-0.79 (m, 3H). tR=1.740 min (CHIRALPAK IC-3, 0.46×5 cm; 3 um, Hex(0.1% DEA):EtOH=50:50, 1.0 ml/min). 70c and 70d are enantiomers.

Example 70d: (3R,4S)-1-(cyclopropylsulfonyl)-3-((S)-5H-imidazo[5,1-a]isoindol-5-yl)piperidin-4-ol (13.8 mg, 2%) as a white solid: LCMS (ESI, m/z): 360.1 [M+H]+. tR=3.058 min (CHIRALPAK IC-3, 0.46×5 cm; 3 um, Hex (0.1% DEA):EtOH=50:50, 1.0 ml/min). 70c and 70d are enantiomers.

Example 71: 6-(5H-imidazo[5,1-a]isoindol-5-yl)-6,7-dihydro-5H-cyclopenta[c]pyridin-7-ol

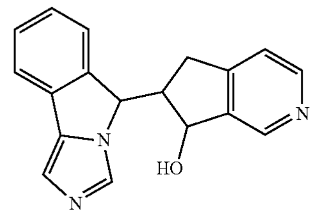 [SMILES: OC1c2cnccc2CC1C1c2ccccc2-c2cncn21]

Step 1: (E)-6-(2-(1-trityl-1H-imidazol-4-yl)benzylidene)-5,6-dihydro-7H-cyclopenta[c]pyridin-7-one

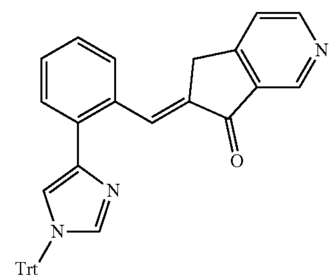

The title compound was synthesized by General Procedure for the Synthesis of Int-2: LCMS (ESI, m/z): 530.6 [M+H]+

Step 2: 6-(5H-imidazo[5,1-a]isoindol-5-yl)-5,6-dihydro-7H-cyclopenta[c]pyridin-7-one

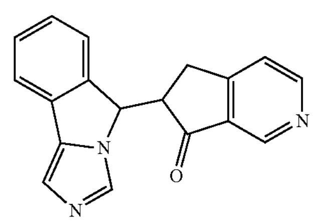 [SMILES: O=C1c2cnccc2CC1C1c2ccccc2-c2cncn21]

The title compound was synthesized by General Procedure for the Synthesis of Int-3: LCMS (ESI, m/z): 288.3 [M+H]+

Step 3:

(6S,7R)-6-((S)-5H-imidazo[5,1-a]isoindol-5-yl)-6,7-dihydro-5H-cyclopenta[c]pyridin-7-ol (6R,7S)-6-((R)-5H-imidazo[5,1-a]isoindol-5-yl)-6,7-dihydro-5H-cyclopenta[c]pyridin-7-ol (6S,7S)-6-((S)-5H-imidazo[5,1-a]isoindol-5-yl)-6,7-dihydro-5H-cyclopenta[c]pyridin-7-ol (6R,7R)-6-((R)-5H-imidazo[5,1-a]isoindol-5-yl)-6,7-dihydro-5H-cyclopenta[c]pyridin-7-ol (6R,7R)-6-((S)-5H-imidazo[5,1-a]isoindol-5-yl)-6,7-dihydro-5H-cyclopenta[c]pyridin-7-ol (6S,7S)-6-((R)-5H-imidazo[5,1-a]isoindol-5-yl)-6,7-dihydro-5H-cyclopenta[c]pyridin-7-ol 71a

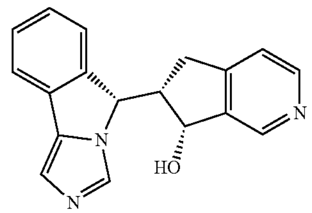

71b

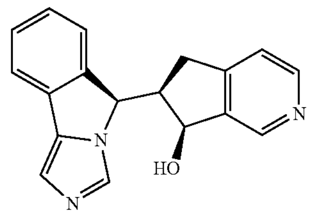

71c

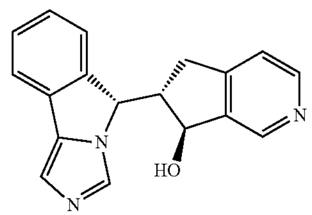

71d

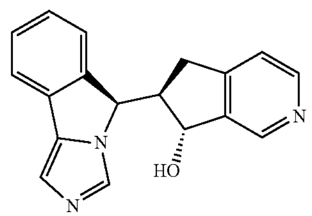

71e

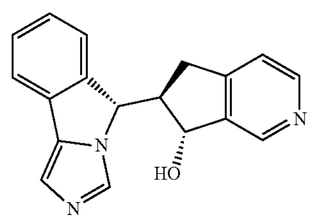

71f

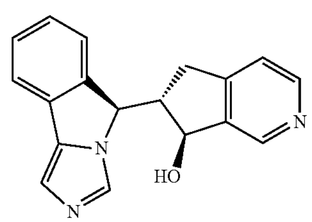

A solution of 6-[5H-imidazo[4,3-a]isoindol-5-yl]-5H,6H,7H-cyclopenta[c]pyridin-7-one (700 mg, 2.44 mmol) in MeOH (20 mL) was added $NaBH_4$ (278 mg, 7.35 mmol). The resulting solution was stirred for 0.5 h at room temperature. The resulting mixture was concentrated under vacuum. The crude product was purified by Combi-Flash and further isolated by chiral separation. The absolute configuration of all isomers 071a-f was assigned arbitrarily.

Example 71a: (6S,7R)-6-((S)-5H-imidazo[5,1-a]isoindol-5-yl)-6,7-dihydro-5H-cyclopenta[c]pyridin-7-ol (3.0 mg, 1%) as a white solid: LCMS (ESI, m/z): 290.0 $[M+H]^+$. $^1H$ NMR (300 MHz, $CD_3OD$) 8.63 (s, 1H), 8.32 (d, J=5.1 Hz, 1H), 7.73-7.59 (m, 3H), 7.53-7.32 (m, 2H), 7.17-7.03 (m, 2H), 5.79 (d, J=4.1 Hz, 1H), 5.70 (d, J=7.3 Hz, 1H), 3.29 (t, J=6.4 Hz, 1H), 2.83 (dd, J=17.3, 8.4 Hz, 1H), 2.43 (dd, J=17.2, 5.4 Hz, 1H), 1.40-1.28 (m, 1H). tR=3.265 min (CHIRALCEL PAK AD-3, 0.46×15 cm; 3 um, 100% MeOH (0.1% DEA), 1.0 ml/min). 71a and 71b are enantiomers.

Example 71b: (6R,7S)-6-((R)-5H-imidazo[5,1-a]isoindol-5-yl)-6,7-dihydro-5H-cyclopenta[c]pyridin-7-ol (4.2 mg, 1%) as a white solid: LCMS (ESI, m/z): 290.0 $[M+H]^+$. tR=3.871 min (CHIRALCEL PAK AD-3, 0.46×15 cm; 3 um, 100% MeOH (0.1% DEA), 1.0 ml/min). 071a and 071b are enantiomers.

Example 71c: (6S,7S)-6-((S)-5H-imidazo[5,1-a]isoindol-5-yl)-6,7-dihydro-5H-cyclopenta[c]pyridin-7-ol (6.3 mg, 2%) as a white solid: LCMS (ESI, m/z): 290.0 $[M+H]^+$. $^1H$ NMR (300 MHz, $CD_3OD$) 8.66 (d, J=1.3 Hz, 1H), 8.42 (d, J=5.1 Hz, 1H), 8.20 (s, 1H), 7.63 (dd, J=18.3, 7.7 Hz, 2H), 7.48-7.18 (m, 4H), 5.74-5.64 (m, 1H), 5.44 (d, J=6.1 Hz, 1H), 4.83 (s, 2H), 3.18 (dd, J=16.6, 7.9 Hz, 1H), 2.62 (s, 1H), 1.32 (s, 1H). tR=3.877 min (CHIRALCEL PAK AD-3, 0.46×15 cm; 3 um, 100% MeOH (0.1% DEA), 1.0 ml/min). 71c and 71d are enantiomers.

Example 71d: (6R,7R)-6-((R)-5H-imidazo[5,1-a]isoindol-5-yl)-6,7-dihydro-5H-cyclopenta[c]pyridin-7-ol (3.1 mg, 1%) as a white solid: LCMS (ESI, m/z): 290.0 $[M+H]^+$. tR=4.877 min (CHIRALCEL PAK AD-3, 0.46×15 cm; 3 um, 100% MeOH (0.1% DEA), 1.0 ml/min). 71c and 71d are enantiomers.

Example 71e: (6R,7R)-6-((S)-5H-imidazo[5,1-a]isoindol-5-yl)-6,7-dihydro-5H-cyclopenta[c]pyridin-7-ol (1.6 mg, 1%) as a white solid: LCMS (ESI, m/z): 290.1 $[M+H]^+$. $^1H$ NMR (300 MHz, $CD_3OD$) 8.47 (s, 1H), 8.37 (d, J=4.9 Hz, 1H), 8.01 (s, 1H), 7.74-7.65 (m, 1H), 7.61-7.40 (m, 2H), 7.38-7.21 (m, 3H), 5.80 (d, J=4.0 Hz, 1H), 5.25 (d, J=5.5 Hz, 1H), 3.44 (s, 4H), 3.33 (s, 4H), 3.17 (dd, J=12.6, 7.3 Hz, 2H), 2.83-2.67 (m, 1H), 1.40-1.29 (m, 1H). tR=3.711 min (CHIRALCEL PAK AD-3, 0.46×15 cm; 3 um, 100% MeOH (0.1% DEA), 1.0 ml/min). 71e and 71f are enantiomers.

Example 71f: (6S,7S)-6-((R)-5H-imidazo[5,1-a]isoindol-5-yl)-6,7-dihydro-5H-cyclopenta[c]pyridin-7-ol (1.2 mg, 1%) as a white solid: LCMS (ESI, m/z): 290.0 $[M+H]^+$. tR=4.911 min (CHIRALCEL PAK AD-3, 0.46×15 cm; 3 um, 100% MeOH (0.1% DEA), 1.0 ml/min). 71e and 71f are enantiomers.

Step 4: 6-(5H-imidazo[5,1-a]isoindol-5-yl)-6,7-dihydro-5H-cyclopenta[c]pyridin-7-ol

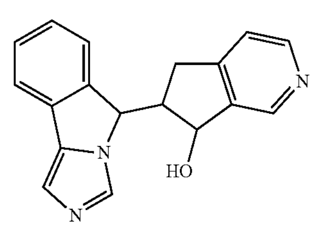 [SMILES: OC1c2cnccc2CC1C1c2ccccc2-c2cncn21]

Under nitrogen, a solution of 6-[5H-imidazo[4,3-a]isoindol-5-yl]-5H,6H,7H-cyclopenta[c]pyridin-7-one (260 mg, 0.91 mmol) in THF (30 mL) was added L-selectride (6 mL, 6.00 mmol, 1 mol/L in THF) at −65° C. in a dry ice bath. The resulting solution was stirred for 1 h at −65° C. The reaction was then quenched by MeOH (10 mL). The resulting solution was diluted with water (20 mL). The solids were filtered out and washed by DCM. The resulting solution was extracted with DCM (3×200 mL) and the organic layers combined. The solution was dried over anhydrous sodium sulfate and concentrated under vacuum. The residue was purified by silica gel column eluting with DCM/MeOH (13:1). This resulted in 60 mg (23%) of 6-[5H-imidazo[4,3-a]isoindol-5-yl]-5H,6H,7H-cyclopenta[c]pyridin-7-ol as a light yellow solid: LCMS (ESI, m/z): 290.0 [M+H]$^+$.

Step 5: 6-(5H-imidazo[5,1-a]isoindol-5-yl)-6,7-dihydro-5H-cyclopenta[c]pyridin-7-yl 4-nitrobenzoate

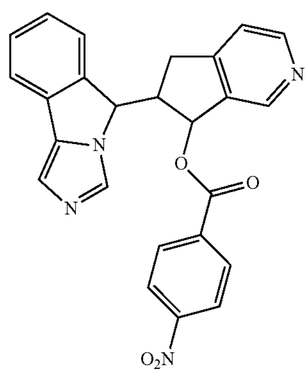 [SMILES: O=C(OC1c2cnccc2CC1C1c2ccccc2-c2cncn21)c1ccc([N+](=O)[O-])cc1]

A solution of 6-(5H-imidazo[5,1-a]isoindol-5-yl)-6,7-dihydro-5H-cyclopenta[c]pyridin-7-ol (200 mg, 0.69 mmol), 4-nitrobenzoic acid (150 mg, 0.90 mmol) and di-tert-butyl azodicarboxylate (800 mg, 3.47 mmol) in THF (30 mL) was added n-tributylphosphane (0.9 mL, 3.60 mmol). The resulting solution was stirred for 16 h at room temperature. The resulting solution was diluted with DCM (300 mL). The resulting mixture was washed with water (2×50 mL). The mixture was dried over anhydrous sodium sulfate and concentrated under vacuum. The residue was purified by silica gel column eluting with DCM/MeOH (20:1). This resulted in 500 mg (crude) of 6-(5H-imidazo[5,1-a]isoindol-5-yl)-6,7-dihydro-5H-cyclopenta[c]pyridin-7-yl 4-nitrobenzoate as a brown solid: LCMS (ESI, m/z): 439.1 [M+H]$^+$.

Step 6:

(6S,7R)-6-((R)-5H-imidazo[5,1-a]isoindol-5-yl)-6,7-dihydro-5H-cyclopenta[c]pyridin-7-ol (6R,7S)-6-((S)-5H-imidazo[5,1-a]isoindol-5-yl)-6,7-dihydro-5H-cyclopenta[c]pyridin-7-ol 71aa

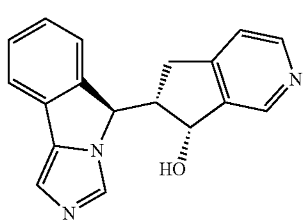

-continued

71bb

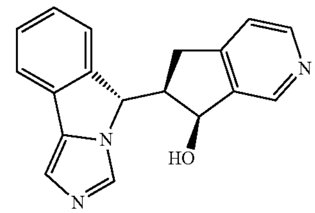

A solution of 6-(5H-imidazo[5,1-a]isoindol-5-yl)-6,7-dihydro-5H-cyclopenta[c]pyridin-7-yl 4-nitrobenzoate (500 mg, 1.14 mmol) in THF (5 mL) and water (1 mL) was added lithium hydroxide (250 mg, 10.44 mmol). The resulting solution was stirred for 30 min at room temperature. The mixture was diluted with DCM (200 mL) and washed with water (1×20 mL). The organic layer was dried over sodium sulfate and concentrated under vacuum. This crude product was purified by Prep-HPLC and Chiral Prep-HPLC with the following conditions:

1. Column, XBridge Prep C18 OBD Column 19×150 mm 5 um; mobile phase, water (0.05% $NH_4OH$): acetonitrile=20%-35%; Detector, uv 254/220 nm; flow rate, 20.0 mL/min to afford 50 mg.
2. Column: CHIRALPAK IC, 2×25 cm, 5 um; Mobile Phase A:Hex-HPLC, Mobile Phase B: EtOH-HPLC; Flow rate: 20 mL/min; Gradient: 50 B to 50 B in 18 min; 220/254 nm Example 71aa: (6S,7R)-6-((R)-5H-imidazo[5,1-a]isoindol-5-yl)-6,7-dihydro-5H-cyclopenta[c]pyridin-7-ol (1.6 mg, 1%) as a white solid: LCMS (ESI, m/z): 290.0 [M+H]$^+$. $^1$H NMR (400 MHz, DMSO-$d_6$) δ 8.53 (s, 1H), 8.34 (d, J=5.2 Hz, 1H), 7.88 (s, 1H), 7.63 (d, J=7.6 Hz, 1H), 7.53 (d, J=7.6 Hz, 1H), 7.43-7.41 (m, 1H), 7.40-7.27 (m, 1H), 7.27 (s, 1H), 7.09 (d, J=5.2 Hz, 1H), 6.00 (d, J=4.0 Hz, 1H), 5.78 (d, J=2.8 Hz, 1H), 5.49 (d, J=4.8 Hz, 1H), 3.05-3.02 (m, 1H), 2.49-2.47 (m, 1H), 1.91-1.84 (m, 1H). tR=2.243 min (CHIRALPAK IC-3, 0.46×15 cm; 3 um, Hex(0.1% DEA):EtOH=50:50, 1.0 ml/min). 71aa and 71bb are enantiomers.

Example 71bb: (6R,7S)-6-((S)-5H-imidazo[5,1-a]isoindol-5-yl)-6,7-dihydro-5H-cyclopenta[c]pyridin-7-ol (13.0 mg, 1%) as a white solid: LCMS (ESI, m/z): 290.2 [M+H]$^+$. tR=3.152 min (CHIRALPAK IC-3, 0.46×15 cm; 3 um, Hex(0.1% DEA):EtOH=50:50, 1.0 ml/min). 71aa and 71bb are enantiomers.

Example 72: 4-(5H-imidazo[5,1-a]isoindol-5-yl)spiro[2.3]hexan-5-ol

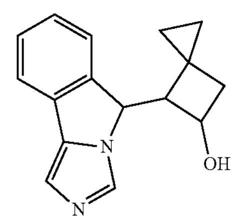 [SMILES: OC1CC2(CC2)C1C1c2ccccc2-c2cncn21]

(4R,5R)-4-((R)-5H-imidazo[5,1-a]isoindol-5-yl)spiro[2.3]hexan-5-ol (4R,5S)-4-((R)-5H-imidazo[5,1-a]isoindol-5-yl)spiro[2.3]hexan-5-ol (4S,5S)-4-((R)-5H-imidazo[5,1-a]isoindol-5-yl)spiro[2.3]hexan-5-ol
(4S,5R)-4-((R)-5H-imidazo[5,1-a]isoindol-5-yl)spiro[2.3]hexan-5-ol
(4R,5S)-4-((S)-5H-imidazo[5,1-a]isoindol-5-yl)spiro[2.3]hexan-5-ol
(4R,5R)-4-((S)-5H-imidazo[5,1-a]isoindol-5-yl)spiro[2.3]hexan-5-ol
(4S,5R)-4-((S)-5H-imidazo[5,1-a]isoindol-5-yl)spiro[2.3]hexan-5-ol
(4S,5S)-4-((S)-5H-imidazo[5,1-a]isoindol-5-yl)spiro[2.3]hexan-5-ol The title compound was synthesized by the same method of example 67.

7.71 (d, J=1.1 Hz, 1H), 7.60 (s, 1H), 7.17 (s, 3H), 6.26 (s, 1H), 5.51 (s, 1H), 5.06 (s, 1H), 2.45 (dd, J=11.2, 7.6 Hz, 1H), 2.22 (dd, J=11.2, 5.1 Hz, 1H), 0.87-0.71 (m, 4H). 72c and 72f are enantiomers.

Example 72d: (4S,5R)-4-((R)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 8.23 (s, 1H), 7.56 (dt, J=7.6, 0.9 Hz, 1H), 7.42-7.30 (m, 2H), 7.24-7.19 (m, 1H), 7.18 (d, J=9.3 Hz, 1H), 5.89 (d, J=4.0 Hz, 1H), 5.43-5.38 (m, 1H), 4.87-4.78 (m, 1H), 3.26-3.20 (m, 1H), 2.15-2.02 (m, 2H), 0.20 (ddd, J=10.0, 6.1, 4.2 Hz, 1H), −0.03-−0.10 (m, 1H), −0.40 (ddd, J=9.6, 6.4, 5.0 Hz, 1H), −0.50 (ddd, J=9.7, 6.1, 5.0 Hz, 1H). 72d and 72e are enantiomers.

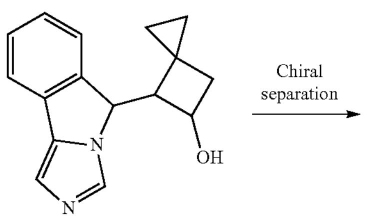

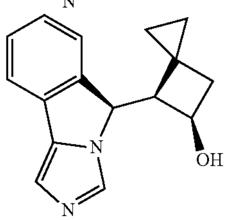
72a

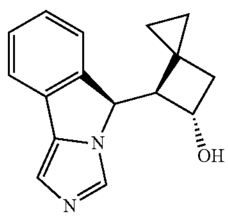
72b

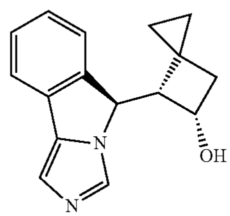
72c

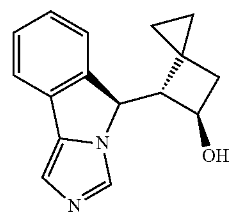
72d

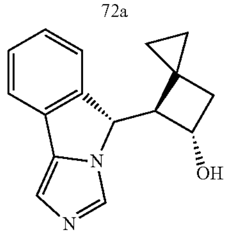
72e

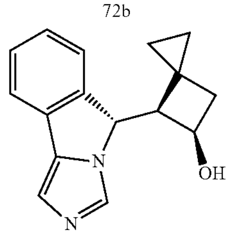
72f

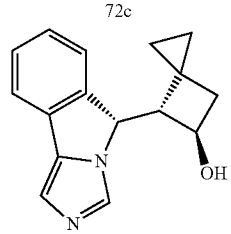
72g

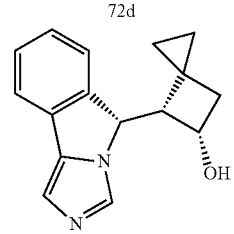
72h

The configurations of the isomers were assigned arbitrarily.

Example 72a: (4R,5R)-4-((R)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 7.86 (s, 1H), 7.77 (dq, J=7.6, 0.9 Hz, 1H), 7.58 (d, J=7.5 Hz, 1H), 7.38-7.33 (m, 1H), 7.26 (td, J=7.5, 1.2 Hz, 1H), 7.10 (s, 1H), 5.56 (d, J=4.4 Hz, 1H), 5.43 (d, J=5.3 Hz, 1H), 4.70-4.63 (m, 1H), 3.00 (t, J=6.4 Hz, 1H), 2.14-2.02 (m, 2H), 0.30 (dddd, J=24.2, 10.3, 6.1, 4.3 Hz, 2H), 0.13 (dt, J=9.9, 5.6 Hz, 1H). 72a and 72h are enantiomers.

Example 72b: (4R,5S)-4-((R)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 7.93 (s, 1H), 7.59 (d, J=7.5 Hz, 1H), 7.39-7.33 (m, 2H), 7.26 (td, J=7.5, 1.1 Hz, 1H), 7.16 (s, 1H), 5.21 (d, J=3.8 Hz, 1H), 5.01 (d, J=6.7 Hz, 1H), 3.67 (p, J=6.3 Hz, 1H), 2.98 (s, 1H), 2.11-2.03 (m, 1H), 1.97 (dd, J=11.6, 5.9 Hz, 1H), 0.87-0.79 (m, 1H), 0.60-0.47 (m, 3H). 72b and 72g are enantiomers.

Example 72c: (4S,5S)-4-((R)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 7.81 (s, 1H), Example 72e: (4R,5S)-4-((S)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 8.24 (s, 1H), 7.57 (dt, J=7.6, 0.9 Hz, 1H), 7.39 (dd, J=7.7, 1.0 Hz, 1H), 7.37-7.31 (m, 1H), 7.26-7.15 (m, 2H), 5.90 (d, J=4.1 Hz, 1H), 5.41 (d, J=2.3 Hz, 1H), 4.83 (qd, J=7.8, 4.0 Hz, 1H), 3.25-3.20 (m, 1H), 2.15-2.02 (m, 2H), 0.20 (ddd, J=10.0, 6.1, 4.2 Hz, 1H), −0.07 (dd, J=6.3, 4.0 Hz, 1H), −0.40 (ddd, J=9.7, 6.5, 5.0 Hz, 1H), −0.47-−0.54 (m, 1H). 72d and 72e are enantiomers.

Example 72f: (4R,5R)-4-((S)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 7.80 (s, 1H), 7.71 (d, J=1.1 Hz, 1H), 7.58 (s, 1H), 7.18 (s, 3H), 6.23 (s, 1H), 5.52 (d, J=8.1 Hz, 1H), 5.05 (tdd, J=7.7, 5.1, 2.1 Hz, 1H), 2.45 (dd, J=11.2, 7.7 Hz, 1H), 2.22 (dd, J=11.2, 5.1 Hz, 1H), 0.87-0.71 (m, 4H). 72c and 72f are enantiomers.

Example 72g: (4S,5R)-4-((S)-5H-imidazo[5,1-a]isoindol-5-yl)spiro[2.3]hexan-5-ol: LCMS (ESI, m/z): 253.1 [M+H]$^+$; $^1$H NMR (500 MHz, DMSO-$d_6$) δ 7.93 (s, 1H), 7.59 (dt, J=7.4, 1.0 Hz, 1H), 7.39-7.33 (m, 2H), 7.26 (td, J=7.6, 1.2 Hz, 1H), 7.16 (s, 1H), 5.21 (d, J=3.9 Hz, 1H), 5.02

(d, J=6:7 Hz, 1H), 3.72-3.63 (m, 1H), 3.00-2.95 (m, 1H), 2.12-1.92 (m, 2H), 0.86-0.78 (m, 1H), 0.60-0.48 (m, 3H). 72b and 72g are enantiomers.

Example 72h: (4S,5S)-4-((S)-5H-imidazo[5,1-a]isoindol-5-yl)spiro[2.3]hexan-5-ol: LCMS (ESI, m/z): 253.1 $[M+H]^+$; $^1$H NMR (500 MHz, DMSO-$d_6$) δ 7.87 (s, 1H), 7.77 (dt, J=7.7, 1.0 Hz, 1H), 7.58 (dt, J=7.5, 0.9 Hz, 1H), 7.36 (tt, J=7.6, 0.9 Hz, 1H), 7.26 (td, J=7.6, 1.2 Hz, 1H), 7.11 (s, 1H), 5.56 (d, J=4.5 Hz, 1H), 5.43 (d, J=5.3 Hz, 1H), 4.66 (tdd, J=7.4, 6.0, 4.6 Hz, 1H), 3.03-2.97 (m, 1H), 2.12 (ddd, J=11.4, 7.3, 1.8 Hz, 1H), 2.06 (dd, J=11.2, 6.2 Hz, 1H), 0.30 (dddd, J=24.2, 10.4, 6.2, 4.3 Hz, 2H), 0.13 (dt, J=9.7, 5.6 Hz, 1H). 72a and 72h are enantiomers.

Example 73: 3-(6-fluoro-5H-imidazo[5,1-a]isoindol-5-yl)tetrahydro-2H-pyran-4-ol

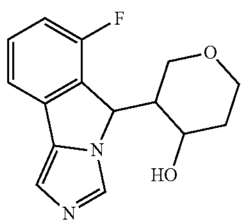 [SMILES: OC1CCOCC1C1c2c(F)cccc2-c2cncn21]

(3R,4R)-3-((S)-6-fluoro-5H-imidazo[5,1-a]isoindol-5-yl) tetrahydro-2H-pyran-4-ol
(3R,4R)-3-((R)-6-fluoro-5H-imidazo[5,1-a]isoindol-5-yl) tetrahydro-2H-pyran-4-ol
(3S,4S)-3-((R)-6-fluoro-5H-imidazo[5,1-a]isoindol-5-yl) tetrahydro-2H-pyran-4-ol
(3S,4S)-3-((S)-6-fluoro-5H-imidazo[5,1-a]isoindol-5-yl)tetrahydro-2H-pyran-4-ol The title compound was synthesized by the same method of example 69.

The configurations of the isomers were assigned arbitrarily.

Example 73a: (3R,4R)-3-((S)-6-fluoro-5H-imidazo[5,1-a]isoindol-5-yl)tetrahydro-2H-pyran-4-ol: LCMS (ESI, m/z): 275.2 $[M+H]^+$; $^1$H NMR (500 MHz, DMSO-$d_6$) δ 7.99 (t, J=0.6 Hz, 1H), 7.51-7.36 (m, 2H), 7.19 (s, 1H), 7.14-7.05 (m, 1H), 5.77 (d, J=2.0 Hz, 1H), 4.90 (d, J=5.3 Hz, 1H), 3.77 (dd, J=11.7, 4.4 Hz, 1H), 3.66-3.55 (m, 1H), 3.30-3.26 (m, 1H), 3.22 (td, J=12.0, 2.3 Hz, 1H), 2.96 (t, J=11.3 Hz, 1H), 2.34 (s, 1H), 1.84-1.71 (m, 1H), 1.44 (qd, J=12.2, 4.7 Hz, 1H). 73a and 73c are enantiomers.

Example 73b: (3R,4R)-3-((R)-6-fluoro-5H-imidazo[5,1-a]isoindol-5-yl)tetrahydro-2H-pyran-4-ol: LCMS (ESI, m/z): 275.2 $[M+H]^+$; $^1$H NMR (500 MHz, DMSO-$d_6$) δ 7.92 (s, 1H), 7.53-7.43 (m, 2H), 7.21 (s, 1H), 7.17-7.10 (m, 1H), 5.95 (d, J=2.5 Hz, 1H), 5.52 (d, J=5.8 Hz, 1H), 3.91 (tt, J=10.4, 5.2 Hz, 1H), 3.77 (dd, J=11.7, 4.7 Hz, 1H), 3.17 (td, J=12.1, 11.7, 2.1 Hz, 1H), 3.07-2.99 (m, 1H), 2.35 (t, J=10.9 Hz, 1H), 2.32-2.23 (m, 1H), 1.92 (ddd, J=10.9, 4.7, 2.4 Hz, 1H), 1.63-1.49 (m, 1H). 73b and 73d are enantiomers.

Example 73c: (3S,4S)-3-((R)-6-fluoro-5H-imidazo[5,1-a]isoindol-5-yl)tetrahydro-2H-pyran-4-ol: LCMS (ESI, m/z): 275.1 $[M+H]^+$; $^1$H NMR (500 MHz, DMSO-$d_6$) δ 7.99 (s, 1H), 7.48-7.37 (m, 2H), 7.19 (s, 1H), 7.10 (ddd, J=10.4, 6.3, 2.8 Hz, 1H), 5.76 (d, J=2.1 Hz, 1H), 4.90 (d, J=5.3 Hz, 1H), 3.77 (dd, J=11.8, 4.4 Hz, 1H), 3.60 (tt, J=10.1, 5.0 Hz, 1H), 3.28 (dd, J=11.6, 4.1 Hz, 1H), 3.22 (td, J=12.0, 2.3 Hz, 1H), 2.96 (t, J=11.3 Hz, 1H), 2.34 (s, 1H), 1.76 (ddd, J=12.8, 4.7, 2.3 Hz, 1H), 1.44 (qd, J=12.2, 4.8 Hz, 1H). 73a and 73c are enantiomers.

Example 73d: (3S,4S)-3-((S)-6-fluoro-5H-imidazo[5,1-a]isoindol-5-yl)tetrahydro-2H-pyran-4-ol: LCMS (ESI, m/z): 275.1 $[M+H]^+$; $^1$H NMR (500 MHz, DMSO-$d_6$) δ 7.92 (s, 1H), 7.53-7.43 (m, 2H), 7.21 (s, 1H), 7.18-7.10 (m, 1H), 5.95 (d, J=2.4 Hz, 1H), 5.52 (d, J=5.8 Hz, 1H), 3.91 (tt, J=10.3, 5.2 Hz, 1H), 3.77 (dd, J=11.7, 4.7 Hz, 1H), 3.22-3.12 (m, 1H), 3.09-2.99 (m, 1H), 2.35 (t, J=10.9 Hz, 1H), 2.32-2.25 (m, 1H), 1.97-1.85 (m, 1H), 1.56 (tdd, J=12.6, 10.5, 4.8 Hz, 1H). 73b and 73d are enantiomers.

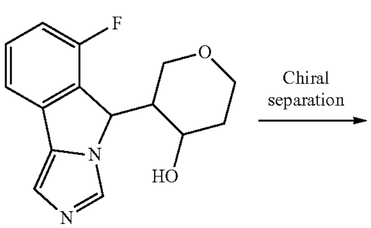

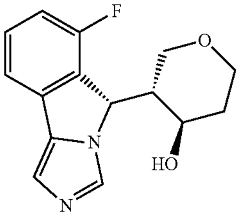

73a

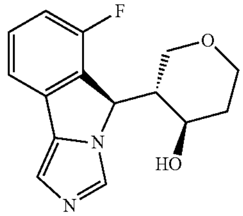

73b

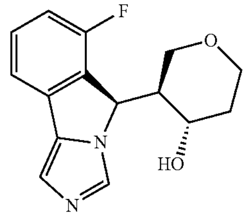

73c

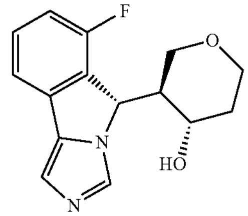

73d

Example 074: (3R,4R)-3-hydroxy-4-((S)-5H-imidazo[5,1-a]isoindol-5-yl)-N-methylpiperidine-1-sulfonamide and (3S,4S)-3-hydroxy-4-((S)-5H-imidazo[5,1-a]isoindol-5-yl)-N-methylpiperidine-1-sulfonamide 74a

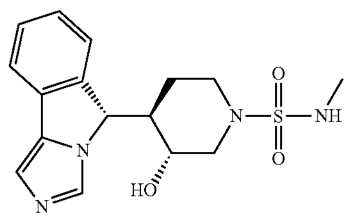

74b

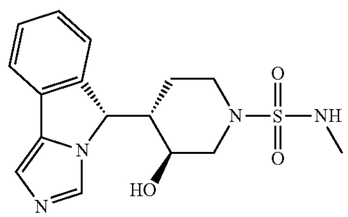

Step 1:

(3R,4R)-4-((S)-5H-imidazo[5,1-a]isoindol-5-yl)piperidin-3-ol

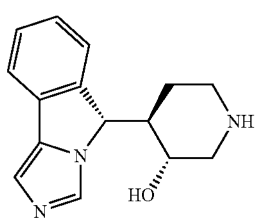 [SMILES: O[C@H]1CNCC[C@@H]1[C@H]1c2ccccc2-c2cncn21]

The title compounds were synthesized by the same method of example 064.

Step 2:

(3R,4R)-3-hydroxy-4-((S)-5H-imidazo[5,1-a]isoindol-5-yl)-N-methylpiperidine-1-sulfonamide 74a

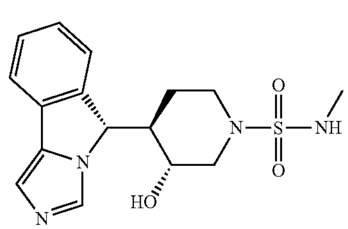

A solution of (3R,4R)-4-[(5S)-5H-imidazo[4,3-a]isoindol-5-yl]piperidin-3-ol (81 mg, 0.32 mmol) in DCM (5.0 mL) was added TEA (0.26 mL, 1.871 mmol) and N-methylsulfamoyl chloride (80 mg, 0.617 mmol) at 0° C. The resulting solution was stirred for 12 h at room temperature. The reaction was then quenched by the addition of water (10 mL). The resulting solution was extracted with of DCM (3×20 mL) and the organic layers combined. The mixture was dried over anhydrous sodium sulfate and concentrated under vacuum. The crude product was purified by Combi-Flash with (DCM/MeOH=10:1).

Example 74a: (3R,4R)-3-hydroxy-4-((S)-5H-imidazo[5,1-a]isoindol-5-yl)-N-methylpiperidine-1-sulfonamide (61.9 mg, 56%) as a white solid: LCMS (ESI, m/z): 349.2 $[M+H]^+$. $^1H$ NMR (400 MHz, DMSO-$d_6$) δ 7.91 (s, 1H), 7.63 (d, J=7.6, 1H), 7.51 (d, J=7.6, 1H), 7.43-7.39 (m, 1H), 7.34-7.28 (m, 1H), 7.15 (s, 1H), 7.06 (q, J=7.6, 1H), 5.72 (d, J=3.3, 2H), 3.81-3.68 (m, 2H), 3.30-3.27 (m, 1H), 2.51-2.46 (m, 2H), 2.43 (s, 3H), 2.33-2.26 (m, 1H), 0.70-0.64 (m, 1H), 0.54-0.40 (m, 1H).

(3S,4S)-3-hydroxy-4-((S)-5H-imidazo[5,1-a]isoindol-5-yl)-N-methylpiperidine-1-sulfonamide 074b

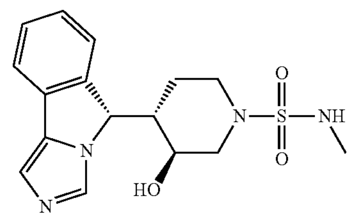

The title compounds were synthesized by the same method of example 074b.

Example 74b: (3S,4S)-3-hydroxy-4-((S)-5H-imidazo[5,1-a]isoindol-5-yl)-N-methylpiperidine-1-sulfonamide (31.7 mg, 32%) as a white solid: LCMS (ESI, m/z): 349.2 $[M+H]^+$. $^1H$ NMR (300 MHz, $CD_3OD$) δ 7.92 (s, 1H), 7.64 (d, J=7.5, 1H), 7.49 (d, J=7.5, 1H), 7.46-7.36 (m, 2H), 7.20 (s, 1H), 5.82 (d, J=3.3, 1H), 3.97-3.91 (m, 2H), 3.50-3.34 (m, 1H), 2.72-2.58 (m, 2H), 2.56 (s, 3H), 2.27-2.12 (m, 1H), 0.96-0.91 (m, 1H), 0.67-0.63 (m, 1H).

Example 75 and 75-1: 3-(7-fluoro-5H-imidazo[5,1-a]isoindol-5-yl)tetrahydro-2H-pyran-4-ol and 4-(7-fluoro-5H-imidazo[5,1-a]isoindol-5-yl)tetrahydro-2H-pyran-3-ol Step 1: 8-fluoro-5H-imidazo[5,1-a]isoindole

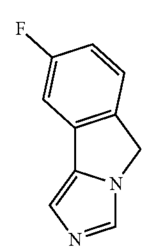 [SMILES: Fc1ccc2c(c1)-c1cncn1C2]

The title compound was synthesized by the same method of example 065.

Step 2:

(3R,4R)-3-((R)-7-fluoro-5H-imidazo[5,1-a]isoindol-5-yl)tetrahydro-2H-pyran-4-ol (3R,4R)-4-((R)-7-fluoro-5H-imidazo[5,1-a]isoindol-5-yl)tetrahydro-2H-pyran-3-ol (3R,4R)-3-((S)-7-fluoro-5H-imidazo[5,1-a]isoindol-5-yl)tetrahydro-2H-pyran-4-ol (3S,4S)-3-((R)-7-fluoro-5H-imidazo[5,1-a]isoindol-5-yl)tetrahydro-2H-pyran-4-ol (3R,4R)-4-((S)-7-fluoro-5H-imidazo[5,1-a]isoindol-5-yl)tetrahydro-2H-pyran-3-ol (3S,4S)-4-((R)-7-fluoro-5H-imidazo[5,1-a]isoindol-5-yl)tetrahydro-2H-pyran-3-ol (3S,4S)-3-((S)-7-fluoro-5H-imidazo[5,1-a]isoindol-5-yl)tetrahydro-2H-pyran-4-ol (3S,4S)-4-((S)-7-fluoro-5H-imidazo[5,1-a]isoindol-5-yl)tetrahydro-2H-pyran-3-ol 75a

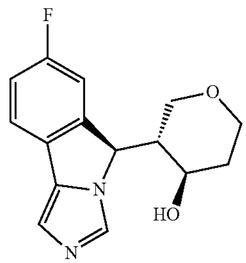

75b

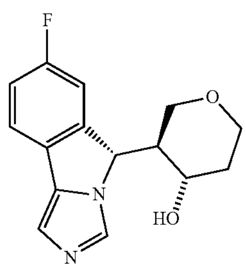

75c

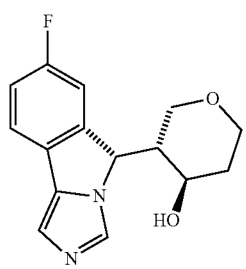

75d

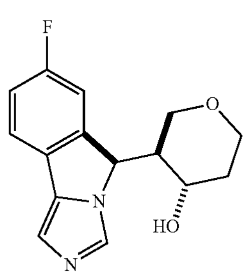

75-1a

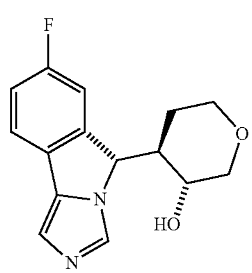

-continued 75-1b

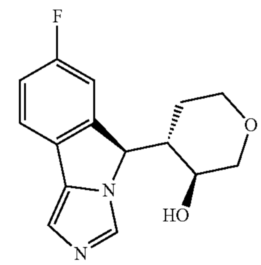

75-1c

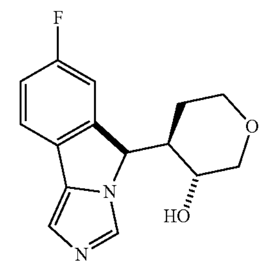

75-1d

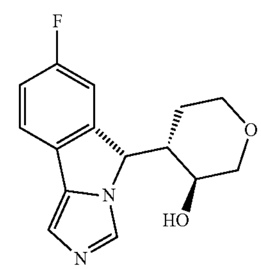

The title compounds were synthesized by the same method of example 065.

Example 75a: (3R,4R)-3-((R)-7-fluoro-5H-imidazo[5,1-a]isoindol-5-yl)tetrahydro-2H-pyran-4-ol: LCMS (ESI, m/z): 275.1 $[M+H]^+$. $^1$H NMR (500 MHz, DMSO-$d_6$) δ 7.98 (s, 1H), 7.63 (dd, J=8.4, 5.2 Hz, 1H), 7.43-7.37 (m, 1H), 7.24 (ddd, J=9.0, 8.1, 2.4 Hz, 1H), 7.10 (s, 1H), 5.64 (d, J=3.6 Hz, 1H), 5.27 (d, J=5.4 Hz, 1H), 3.83-3:72 (m, 2H), 3.20 (td, J=12.1, 2.3 Hz, 1H), 2.97 (dd, J=11.3, 3.9 Hz, 1H), 2.63 (t, J=11.2 Hz, 1H), 2.39 (ddt, J=10.6, 6.8, 3.8 Hz, 1H), 1.81 (ddt, J=12.7, 4.4, 2.1 Hz, 1H), 1.50 (tdd, J=12.4, 10.3, 4.8 Hz, 1H).

Example 75b: (3S,4S)-3-((S)-7-fluoro-5H-imidazo[5,1-a]isoindol-5-yl)tetrahydro-2H-pyran-4-ol: LCMS (ESI, m/z): 275.4 $[M+H]^+$0.1H NMR (500 MHz, DMSO-$d_6$) δ 7.97 (d, J=0.6 Hz, 1H), 7.62 (dd, J=8.4, 5.2 Hz, 1H), 7.40 (ddd, J=9.2, 2.5, 0.8 Hz, 1H), 7.24 (dddd, J=9.2, 8.4, 2.5, 0.6 Hz, 1H), 7.10 (s, 1H), 5.64 (d, J=3.6 Hz, 1H), 5.27 (d, J=5.4 Hz, 1H), 3.77 (ddd, J=14.0, 10.1, 4.7 Hz, 2H), 3.20 (td, J=12.1, 2.3 Hz, 1H), 3.00-2.94 (m, 1H), 2.63 (t, J=11.2 Hz, 1H), 2.39 (tt, J=10.2, 3.6 Hz, 1H), 1.81 (ddd, J=10.6, 4.7, 2.4 Hz, 1H), 1.55-1.44 (m, 1H).

Example 75c: (3R,4R)-3-((S)-7-fluoro-5H-imidazo[5,1-a]isoindol-5-yl)tetrahydro-2H-pyran-4-ol: LCMS (ESI, m/z): 275.2 $[M+H]^+$. $^1$H NMR (500 MHz, DMSO-$d_6$) δ 7.88 (s, 1H), 7.63 (dd, J=8.4, 5.1 Hz, 1H), 7.49 (ddd, J=9.0, 2.5, 1.0 Hz, 1H), 7.24 (dddd, J=9.3, 8.5, 2.5, 0.7 Hz, 1H), 7.12 (s, 1H), 5.72 (d, J=2.6 Hz, 1H), 5.49 (d, J=5.5 Hz, 1H), 3.93 (tt, J=10.3, 5.0 Hz, 1H), 3.77 (dd, J=11.7, 4.7 Hz, 1H), 3.24-3.14 (m, 1H), 3.02-2.95 (m, 1H), 2.36 (t, J=11.2 Hz, 1H), 2.30-2.21 (m, 1H), 1.96-1.88 (m, 1H), 1.56 (tdd, J=12.7, 10.6, 4.8 Hz, 1H).

Example 75d: (3S,4S)-3-((R)-7-fluoro-5H-imidazo[5,1-a]isoindol-5-yl)tetrahydro-2H-pyran-4-ol: LCMS (ESI, m/z): 275.2 [M+H]$^+$. $^1$H NMR (500 MHz, DMSO-$d_6$) δ 7.88 (s, 1H), 7.63 (dd, J=8.4, 5.1 Hz, 1H), 7.49 (ddd, J=9.1, 2.4, 1.0 Hz, 1H), 7.24 (dddd, J=9.3, 8.4, 2.4, 0.6 Hz, 1H), 7.12 (s, 1H), 5.72 (d, J=2.5 Hz, 1H), 5.49 (d, J=5.4 Hz, 1H), 3.94 (tt, J=10.3, 5.0 Hz, 1H), 3.77 (dd, J=11.7, 4.7 Hz, 1H), 3.25-3.14 (m, 1H), 3.02-2.95 (m, 1H), 2.36 (t, J=11.2 Hz, 1H), 2.26 (ddt, J=14.0, 10.8, 3.1 Hz, 1H), 1.96-1.88 (m, 1H), 1.62-1.50 (m, 1H).

Example 75-1a: (3R,4R)-4-((S)-7-fluoro-5H-imidazo[5,1-a]isoindol-5-yl)tetrahydro-2H-pyran-3-ol: LCMS (ESI, m/z): 275.2 [M+H]$^+$. $^1$H NMR (500 MHz, DMSO-$d_6$) δ 7.91 (t, J=0.6 Hz, 1H), 7.65 (dd, J=8.4, 5.1 Hz, 1H), 7.41-7.35 (m, 1H), 7.26 (ddt, J=10.4, 8.1, 1.4 Hz, 1H), 7.10 (s, 1H), 5.69 (d, J=3.8 Hz, 1H), 5.44 (d, J=5.6 Hz, 1H), 3.84 (dd, J=10.5, 4.8 Hz, 1H), 3.71-3.57 (m, 2H), 3.11 (td, J=11.3, 3.2 Hz, 1H), 2.98 (dd, J=10.6, 9.8 Hz, 1H), 2.43-2.34 (m, 1H), 0.64-0.52 (m, 2H).

Example 75-1b: (3S,4S)-4-((R)-7-fluoro-5H-imidazo[5,1-a]isoindol-5-yl)tetrahydro-2H-pyran-3-ol: LCMS (ESI, m/z): 275.1 [M+H]$^+$. $^1$H NMR (500 MHz, DMSO-$d_6$) δ 7.91 (s, 1H), 7.65 (dd, J=8.4, 5.2 Hz, 1H), 7.41-7.35 (m, 1H), 7.31-7.22 (m, 1H), 7.10 (s, 1H), 5.69 (d, J=3.8 Hz, 1H), 5.44 (d, J=5.6 Hz, 1H), 3.84 (dd, J=10.6, 4.9 Hz, 1H), 3.71-3.57 (m, 2H), 3.11 (td, J=11.3, 3.2 Hz, 1H), 2.98 (t, J=10.2 Hz, 1H), 2.38 (ddd, J=15.2, 11.0, 4.3 Hz, 1H), 0.65-0.51 (m, 2H).

Example 75-1c: (3R,4R)-4-((R)-7-fluoro-5H-imidazo[5,1-a]isoindol-5-yl)tetrahydro-2H-pyran-3-ol: LCMS (ESI, m/z): 275.2 [M+H]$^+$0.1H NMR (500 MHz, DMSO-$d_6$) δ 7.87 (s, 1H), 7.63 (dd, J=8.4, 5.1 Hz, 1H), 7.41 (ddd, J=9.1, 2.4, 1.0 Hz, 1H), 7.27-7.18 (m, 1H), 7.13 (s, 1H), 5.74-5.69 (m, 1H), 5.52 (d, J=5.7 Hz, 1H), 3.91 (dd, J=10.6, 4.8 Hz, 1H), 3.73 (tt, J=10.4, 5.3 Hz, 1H), 3.58 (dd, J=11.1, 4.7 Hz, 1H), 3.17-3.08 (m, 1H), 3.04 (dd, J=10.6, 9.9 Hz, 1H), 2.29-2.19 (m, 1H), 0.72-0.65 (m, 1H), 0.45 (qd, J=12.6, 4.8 Hz, 1H).

Example 75-1d: (3S,4S)-4-((S)-7-fluoro-5H-imidazo[5,1-a]isoindol-5-yl)tetrahydro-2H-pyran-3-ol: LCMS (ESI, m/z): 275.5 [M+H]$^+$. $^1$H NMR (500 MHz, DMSO-$d_6$) δ 7.87 (s, 1H), 7.63 (dd, J=8.4, 5.1 Hz, 1H), 7.41 (ddd, J=9.0, 2.6, 1.0 Hz, 1H), 7.26-7.20 (m, 1H), 7.13 (s, 1H), 5.73-5.70 (m, 1H), 5.52 (d, J=5.8 Hz, 1H), 3.91 (dd, J=10.6, 4.9 Hz, 1H), 3.73 (tt, J=10.4, 5.3 Hz, 1H), 3.58 (dd, J=11.2, 4.7 Hz, 1H), 3.13 (td, J=11.7, 2.3 Hz, 1H), 3.04 (dd, J=10.6, 9.9 Hz, 1H), 2.28-2.19 (m, 1H), 0.72-0.64 (m, 1H), 0.45 (qd, J=12.6, 4.9 Hz, 1H).

Example 76: 8-(ethylsulfonyl)-2-(5H-imidazo[5,1-a]isoindol-5-yl)-8-azaspiro[4.5]decan-1-ol

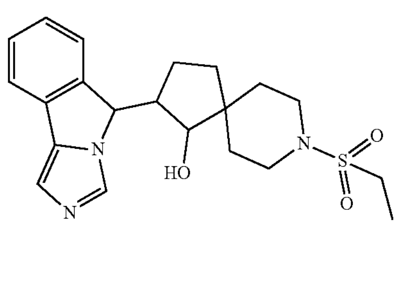 [SMILES: CCS(=O)(=O)N1CCC2(CCC(C3c4ccccc4-c4cncn43)C2O)CC1]

(1S,2R)-8-(ethylsulfonyl)-2-((R)-5H-imidazo[5,1-a]isoindol-5-yl)-8-azaspiro[4.5]decan-1-ol
(1R,2S)-8-(ethylsulfonyl)-2-((S)-5H-imidazo[5,1-a]isoindol-5-yl)-8-azaspiro[4.5]decan-1-ol
(1R,2R)-8-(ethylsulfonyl)-2-((R)-5H-imidazo[5,1-a]isoindol-5-yl)-8-azaspiro[4.5]decan-1-ol
(1S,2S)-8-(ethylsulfonyl)-2-((S)-5H-imidazo[5,1-a]isoindol-5-yl)-8-azaspiro[4.5]decan-1-ol
(1R,2S)-8-(ethylsulfonyl)-2-((R)-5H-imidazo[5,1-a]isoindol-5-yl)-8-azaspiro[4.5]decan-1-ol Step 1: tert-butyl (E)-1-oxo-2-(2-(1-trityl-1H-imidazol-4-yl)benzylidene)-8-azaspiro[4.5]decane-8-carboxylate

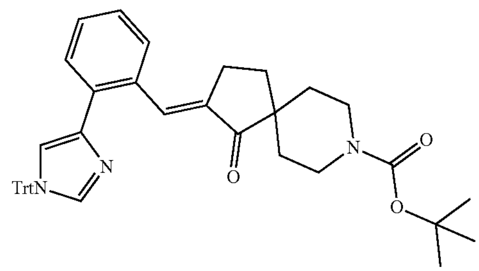

The title compound was synthesized by General Procedure for the Synthesis of Int-2. LCMS (ESI, m/z): 650.4 [M+H]$^+$ Step 2: tert-butyl 2-(5H-imidazo[5,1-a]isoindol-5-yl)-1-oxo-8-azaspiro[4.5]decane-8-carboxylate

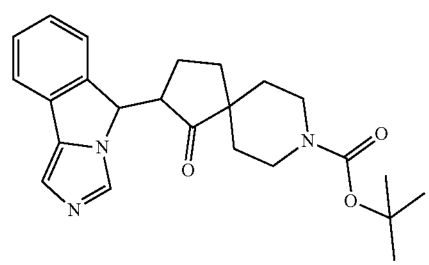 [SMILES: CC(C)(C)OC(=O)N1CCC2(CCC(C3c4ccccc4-c4cncn43)C2=O)CC1]

The title compound was synthesized by General Procedure for the Synthesis of Int-3. LCMS (ESI, m/z): 408.4 [M+H]$^+$ Step 3: 8-(ethylsulfonyl)-2-(5H-imidazo[5,1-a]isoindol-5-yl)-8-azaspiro[4.5]decan-1-ol

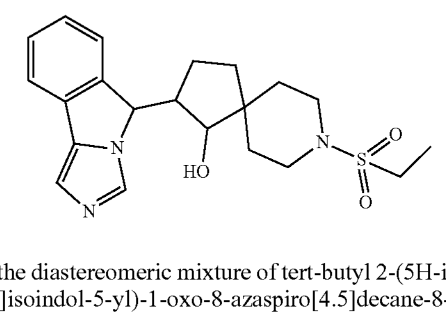

To the diastereomeric mixture of tert-butyl 2-(5H-imidazo[5,1-a]isoindol-5-yl)-1-oxo-8-azaspiro[4.5]decane-8-carboxylate (600 mg, 1.47 mmol) dissolved in dry MeOH (15 mL) at 0° C. was added sodiumborohydride (170 mg, 4.42 mmol) in four portions. The reaction was stirred at room temperature for 2 h. TLC show no SM left. The reaction was quenched by adding $NH_4Cl$ (5 mL) and extracted by DCM (3×25 mL), combined organic phase was washed with brine and dried over $Na_2SO_4$. After removing solvent and the residue was purified by silica gel column chromatograph. To the mixture of alcohol (400 mg, 0.97 mmol) was added 8 mL dry DCM followed by trifluroacetic acid (1.5 mL, 20 mmol) at room temperature and the reaction mixture was stirred for half an hour. TLC indicated no SM and the reaction mixture was concentrated under reduced pressured and the residue was dried under high vacuum pump overnight. This crude mixture was taken to the next step without purification. To the compound (0.25 g, 0.81 mmol) in 8 mL dry DCM was added triethyl amine (0.22 mL, 1.62 mmol) followed by ethyl sulfonyl chloride (0.08 mL, 0.89 mmol) at room temperature and stirred for half hr. After half hr, TLC indicated starting material. So 0.2 mL of triethyl amine was added and the reaction mixture was stirred for another half hr. TLC indicated no SM and the reaction mixture was quenched with water (2 mL) and the reaction was worked up using DCM (3×5 mL). The combined residue was dried over $Na_2SO_4$ and concentrated under reduced pressured and purified using flash silicagel chromatography: LCMS (ESI, m/z): 402.3 $[M+H]^+$. The mixture was isolated by Chiral separation methods and the configuration of the isomers was assigned arbitrarily.

(1S,2R)-8-(ethylsulfonyl)-2-((R)-5H-imidazo[5,1-a]isoindol-5-yl)-8-azaspiro[4.5]decan-1-ol (1R,2S)-8-(ethylsulfonyl)-2-((S)-5H-imidazo[5,1-a]isoindol-5-yl)-8-azaspiro[4.5]decan-1-ol (1R,2R)-8-(ethylsulfonyl)-2-((R)-5H-imidazo[5,1-a]isoindol-5-yl)-8-azaspiro[4.5]decan-1-ol (1S,2S)-8-(ethylsulfonyl)-2-((S)-5H-imidazo[5,1-a]isoindol-5-yl)-8-azaspiro[4.5]decan-1-ol (1R,2S)-8-(ethylsulfonyl)-2-((R)-5H-imidazo[5,1-a]isoindol-5-yl)-8-azaspiro[4.5]decan-1-ol 76a

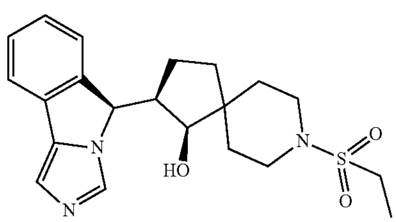

76b

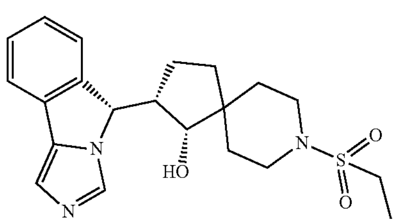

76c

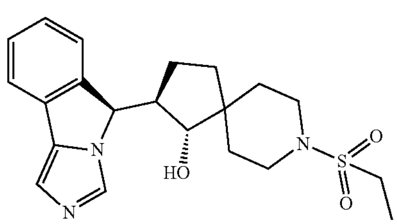

-continued

76d

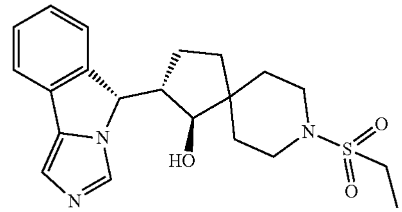

76e

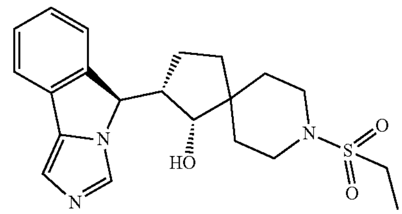

Example 76a: (1S,2R)-8-(ethylsulfonyl)-2-((R)-5H-imidazo[5,1-a]isoindol-5-yl)-8-azaspiro[4.5]decan-1-ol: LCMS (ESI, m/z): 402.3 $[M+H]^+$; $^1$H NMR (500 MHz, DMSO-$d_6$) δ 7.92 (s, 1H), 7.60 (d, J=7.5 Hz, 1H), 7.53 (d, J=7.6 Hz, 1H), 7.39 (t, J=7.5 Hz, 1H), 7.26 (td, J=7.6, 1.1 Hz, 1H), 7.10 (s, 1H), 5.45 (d, J=4.4 Hz, 1H), 5.07 (d, J=5.7 Hz, 1H), 3.57 (dd, J=9.6, 5.7 Hz, 1H), 3.47 (d, J=12.2 Hz, 1H), 3.41 (d, J=12.4 Hz, 1H), 2.99 (q, J=7.3 Hz, 2H), 2.87 (td, J=12.0, 2.7 Hz, 1H), 2.75 (td, J=12.0, 2.7 Hz, 1H), 2.70-2.60 (m, 1H), 1.75-1.56 (m, 3H), 1.30 (td, J=9.7, 4.5 Hz, 2H), 1.19 (t, J=7.4 Hz, 3H), 1.10-1.00 (m, 1H), 0.85 (ddt, J=13.2, 9.5, 4.8 Hz, 1H).

Example 76b: (1R,2S)-8-(ethylsulfonyl)-2-((S)-5H-imidazo[5,1-a]isoindol-5-yl)-8-azaspiro[4.5]decan-1-ol: LCMS (ESI, m/z): 402.3 $[M+H]^+$; $^1$H NMR (500 MHz, DMSO-$d_6$) δ 7.95 (s, 1H), 7.60 (d, J=7.5 Hz, 1H), 7.49 (d, J=7.3 Hz, 1H), 7.38 (t, J=7.5 Hz, 1H), 7.24 (td, J=7.6, 1.1 Hz, 1H), 7.12 (s, 1H), 5.32-5.27 (m, 2H), 3.90-3.80 (m, 1H), 3.46-3.36 (m, 1H), 3.25-3.18 (m, 1H), 3.05-2.99 (m, 2H), 2.99-2.91 (m, 2H), 2.12 (dd, J=18.9, 8.8 Hz, 1H), 2.06-1.91 (m, 2H), 1.77-1.69 (m, 1H), 1.65 (dt, J=13.2, 6.1 Hz, 3H), 1.32-1.24 (m, 2H), 1.20 (t, J=7.4 Hz, 3H).

Example 76c: (1R,2R)-8-(ethylsulfonyl)-2-((R)-5H-imidazo[5,1-a]isoindol-5-yl)-8-azaspiro[4.5]decan-1-ol: LCMS (ESI, m/z): 402.3 $[M+H]^+$; $^1$H NMR (500 MHz, DMSO-$d_6$) δ 7.88 (s, 1H), 7.67 (d, J=7.6 Hz, 1H), 7.59 (d, J=7.5 Hz, 1H), 7.38 (t, J=7.4 Hz, 1H), 7.27 (td, J=7.6, 1.1 Hz, 1H), 7.12 (s, 1H), 5.39 (dd, J=11.3, 6.6 Hz, 2H), 3.91 (t, J=5.2 Hz, 1H), 3.39 (dt, J=10.0, 4.5 Hz, 1H), 3.28-3.20 (m, 1H), 3.02 (q, J=7.4 Hz, 2H), 2.99-2.88 (m, 2H), 2.34-2.25 (m, 1H), 1.72 (ddq, J=14.7, 8.6, 4.8 Hz, 3H), 1.62-1.52 (m, 3H), 1.35-1.30 (m, 2H), 1.20 (t, J=7.4 Hz, 3H).

Example 76d: (1S,2S)-8-(ethylsulfonyl)-2-((S)-5H-imidazo[5,1-a]isoindol-5-yl)-8-azaspiro[4.5]decan-1-ol: LCMS (ESI, m/z): 402.3 $[M+H]^+$; $^1$H NMR (500 MHz, DMSO-$d_6$) δ 7.88 (s, 1H), 7.67 (d, J=7.6 Hz, 1H), 7.58 (d, J=7.5 Hz, 1H), 7.37 (t, J=7.4 Hz, 1H), 7.27 (td, J=7.6, 1.1 Hz, 1H), 7.12 (s, 1H), 5.38 (dd, J=11.4, 6.5 Hz, 2H), 3.91 (t, J=5.2 Hz, 1H), 3.44-3.35 (m, 1H), 3.27-3.19 (m, 1H), 3.04-2.99 (m, 2H), 2.98-2.89 (m, 2H), 2.33-2.25 (m, 1H), 1.71 (dtt, J=13.1, 9.2, 5.4 Hz, 3H), 1.62-1.51 (m, 3H), 1.34-1.30 (m, 2H), 1.20 (t, J=7.4 Hz, 3H).

Example 76e: (1R,2S)-8-(ethylsulfonyl)-2-((R)-5H-imidazo[5,1-a]isoindol-5-yl)-8-azaspiro[4.5]decan-1-ol: LCMS (ESI, m/z): 402.3 $[M+H]^+$; $^1$H NMR (500 MHz, DMSO-$d_6$) δ 7.92 (s, 1H), 7.60 (d, J=7.5 Hz, 1H), 7.53 (d, J=7.1 Hz, 1H), 7.39 (t, J=7.5 Hz, 1H), 7.26 (td, J=7.6, 1.1 Hz, 1H), 7.11

(s, 1H), 5.45 (d, J=4.4 Hz, 1H), 5.08 (d, J=5.7 Hz, 1H), 3.57 (dd, J=9.6, 5.7 Hz, 1H), 3.47 (d, J=12.3 Hz, 1H), 3.41 (d, J=12.4 Hz, 1H), 3.00 (q, J=7.3 Hz, 2H), 2.87 (td, J=12.1, 2.8 Hz, 1H), 2.75 (td, J=11.9, 2.6 Hz, 1H), 2.70-2.59 (m, 1H), 1.73-1.56 (m, 3H), 1.30 (td, J=9.7, 4.5 Hz, 2H), 1.19 (d, J=7.4 Hz, 3H), 1.10-1.00 (m, 1H), 0.85 (ddt, J=19.1, 9.6, 5.4 Hz, 1H).

Example 77: 1-(cyclopropylsulfonyl)-4-(5H-imidazo[5,1-a]isoindol-5-yl)piperidin-3-ol

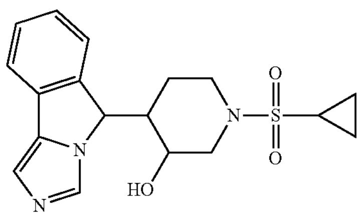 [SMILES: O=S(=O)(C1CC1)N1CCC(C2c3ccccc3-c3cncn32)C(O)C1]

(3R,4R)-1-(cyclopropylsulfonyl)-4-((R)-5H-imidazo[5,1-a]isoindol-5-yl)piperidin-3-ol (3S,4S)-1-(cyclopropylsulfonyl)-4-((S)-5H-imidazo[5,1-a]isoindol-5-yl)piperidin-3-ol 77a

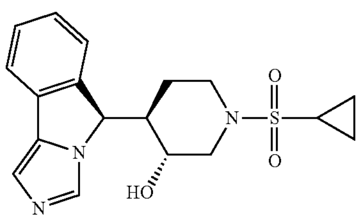

77b

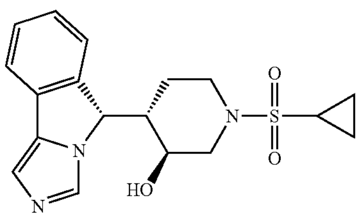

The title compounds were synthesized by the same method of example 070a-d. The configuration two isomers was assigned arbitrarily Example 77a: (3R,4R)-1-(cyclopropylsulfonyl)-4-((R)-5H-imidazo[5,1-a]isoindol-5-yl)piperidin-3-ol (34.6 mg, 18%) as a white solid: LCMS (ESI, m/z): 360.1 $[M+H]^+$. $^1H$ NMR (400 MHz, $CD_3OD$) δ 7.92 (s, 1H), 7.65 (d, J=7.5 Hz, 1H), 7.50 (d, J=7.9 Hz, 1H), 7.44 (t, J=7.4 Hz, 1H), 7.41-7.35 (m, 1H), 7.21 (s, 1H), 5:92 (s, 1H), 4.08-3.86 (m, 2H), 3.55-3.48 (m, 1H), 2.85-2.68 (m, 2H), 2.47 (tt, J=7.6, 5.1 Hz, 1H), 2.31-2.14 (m, 1H), 1.32 (d, J=6.5 Hz, 1H), 1.09-0.88 (m, 5H), 0.65 (qd, J=12.7, 4.6 Hz, 1H). tR=1.478 min (CHIRALPAK IC-3, 0.46×5 cm; 3 um, Hex(0.1% DEA):EtOH=50:50, 1.0 ml/min). 077a and 077b are enantiomers.

Example 77b: (3S,4SR)-1-(cyclopropylsulfonyl)-4-((S)-5H-imidazo[5,1-a]isoindol-5-yl)piperidin-3-ol (23.4 mg, 12%) as a white solid: LCMS (ESI, m/z): 360.2 $[M+H]^+$. tR=2.199 min (CHIRALPAK IC-3, 0.46×5 cm; 3 um, Hex (0.1% DEA):EtOH=50:50, 1.0 ml/min). 077a and 077b are enantiomers.

Example 78: (3R,4R)-3-hydroxy-4-((S)-5H-imidazo[5,1-a]isoindol-5-yl)-N,N-dimethylpiperidine-1-sulfonamide and (3S,4S)-3-hydroxy-4-((S)-5H-imidazo[5,1-a]isoindol-5-yl)-N,N-dimethylpiperidine-1-sulfonamide 78a

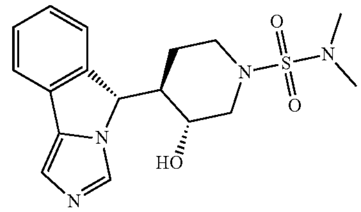

78b

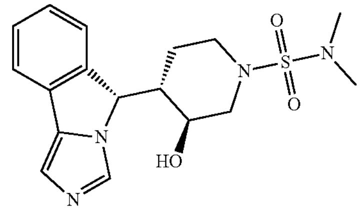

Step 1:

(3R,4R)-3-hydroxy-4-((S)-5H-imidazo[5,1-a]isoindol-5-yl)-N,N-dimethylpiperidine-1-sulfonamide 78a

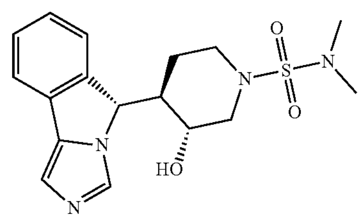

A solution of (3R,4R)-4-[(5S)-5H-imidazo[4,3-a]isoindol-5-yl]piperidin-3-ol (78 mg, 0.31 mmol) in DCM (5.0 mL) was added TEA (0.4 mL, 2.878 mmol) at 0° C. The resulting solution was stirred for 20 min at 0° C. Then N,N-dimethylsulfamoyl chloride (58 mg, 0.41 mmol) was added at 0° C. The resulting solution was allowed to react, with stirring, for an additional 16 h at room temperature. The reaction was then quenched by water (5 mL). The resulting solution was extracted with DCM (3×20 mL) and the organic layers combined. After concentrated under vacuum, the crude product was purified by Prep-HPLC with the following conditions: Column, Xbridge C18; mobile phase, $MeCN/H_2O$=1/30 increasing to $MeCN/H_2O$=1/38 within 40 min; Detector, UV 254 nm.

Example 78a: (3R,4R)-3-hydroxy-4-((S)-5H-imidazo[5,1-a]isoindol-5-yl)-N,N-dimethylpiperidine-1-sulfonamide (27.7 mg, 25%) as a white solid: LCMS (ESI, m/z): 363.2 $[M+H]^+$. $^1H$ NMR (300 MHz, $CD_3OD$) δ 7.92 (s, 1H), 7.65 (d, J=7.5, 1H), 7.56 (d, J=7.5, 1H), 7.48-7.33 (m, 2H), 7.18 (s, 1H), 5.83 (d, J=3.3, 1H), 3.95-3.82 (m, 2H), 3.48-3.44 (m, 1H), 2.76 (s, 6H), 2.77-2.63 (m, 2H), 2.41-2.25 (m, 1H), 0.82-0.61 (m, 2H).

(3S,4S)-3-hydroxy-4-((S)-5H-imidazo[5,1-a]isoindol-5-yl)-N-methylpiperidine-1-sulfonamide 78b

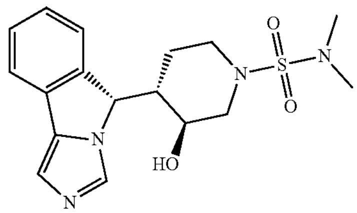

The title compounds were synthesized by the same method of example 078a.

Example 78b: (3S,4S)-3-hydroxy-4-((S)-5H-imidazo[5,1-a]isoindol-5-yl)-N-methylpiperidine-1-sulfonamide (46.2 mg, 38%) as a white solid: LCMS (ESI, m/z): 363.2 $[M+H]^+$. $^1H$ NMR (300 MHz, $CD_3OD$) δ 7.92 (s, 1H), 7.64 (d, J=7.5, 1H), 7.49 (d, J=7.5, 1H), 7.46-7.36 (m, 2H), 7.20 (s, 1H), 5.82 (d, J=3.3, 1H), 3.95-3.90 (m, 2H), 3.50-3.42 (m, 1H), 2.79 (s, 6H), 2.77-2.65 (m, 2H), 2.21-2.12 (m, 1H), 0.95-0.90 (m, 1H), 0.67-0.63 (m, 1H).

Example 79: 4-(5H-imidazo[5,1-a]isoindol-5-yl)-1-(methylsulfonyl)piperidin-3-ol

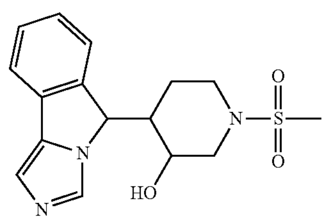 [SMILES: CS(=O)(=O)N1CCC(C2c3ccccc3-c3cncn32)C(O)C1]

(3S,4S)-4-((S)-5H-imidazo[5,1-a]isoindol-5-yl)-1-(methylsulfonyl)piperidin-3-ol (3R,4R)-4-((R)-5H-imidazo[5,1-a]isoindol-5-yl)-1-(methylsulfonyl)piperidin-3-ol 79a

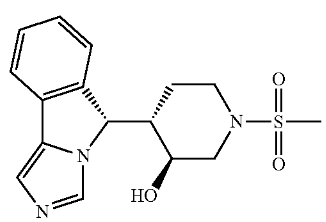

79b

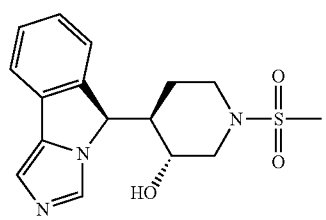

The title compounds were synthesized by the same method of example 064a-b. The configuration two isomers were assigned arbitrarily.

Example 79a: (3S,4S)-4-((S)-5H-imidazo[5,1-a]isoindol-5-yl)-1-(methylsulfonyl)piperidin-3-ol (34.6 mg, 18%) as a white solid: LCMS (ESI, m/z): 334.1 $[M+H]^+$. $^1H$ NMR (300 MHz, DMSO-$d_6$) δ 7.92 (s, 1H), 7.63 (d, J=7.8 Hz, 1H), 7.52 (d, J=7.8 Hz, 1H), 7.44-7.27 (m, 2H), 7.15 (s, 1H), 5.81 (d, J=3.6 Hz, 1H), 5.79 (d, J=3.6 Hz, 1H), 3.84-3.71 (m, 2H), 3.34-3.29 (m, 1H), 2.84 (s, 3H), 2.55-2.51 (m, 1H), 2.49-2.48 (m, 1H), 2.34-2.21 (m, 1H), 0.71-0.66 (m, 1H), 0.55-0.54 (m, 1H). tR=1.717 min (CHIRALPAK IC-3, 0.46×5 cm; 3 um, Hex(0.1% DEA):EtOH=50:50, 1.0 ml/min). 079a and 079b are enantiomers.

Example 79b: (3R,4R)-4-((R)-5H-imidazo[5,1-a]isoindol-5-yl)-1-(methylsulfonyl)piperidin-3-ol (23.4 mg, 12%) as a white solid: LCMS (ESI, m/z): 334.1 $[M+H]^+$. tR=2.291 min (CHIRALPAK IC-3, 0.46×5 cm; 3 um, Hex(0.1% DEA):EtOH=50:50, 1.0 ml/min). 079a and 079b are enantiomers.

Example 80: 4-(5H-imidazo[5,1-a]isoindol-5-yl)-1-(isopropylsulfonyl)piperidin-3-ol

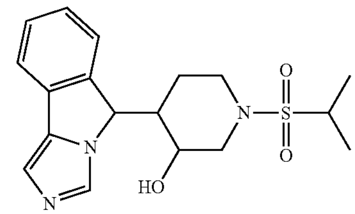 [SMILES: CC(C)S(=O)(=O)N1CCC(C2c3ccccc3-c3cncn32)C(O)C1]

Step 1:

(3S,4S)-4-((S)-5H-imidazo[5,1-a]isoindol-5-yl)-1-(isopropylsulfonyl)piperidin-3-ol (3R,4R)-4-((R)-5H-imidazo[5,1-a]isoindol-5-yl)-1-(isopropylsulfonyl)piperidin-3-ol 80a

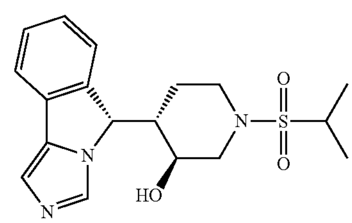

80b

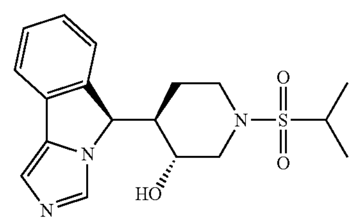

A solution of (3S,4S)-4-[(5S)-5H-imidazo[4,3-a]isoindol-5-yl]piperidin-3-ol and (3R,4R)-4-[(5R)-5H-imidazo[4,3-a]isoindol-5-yl]piperidin-3-ol (99 mg, 0.39 mmol) and TEA (0.45 mL, 3.24 mmol) in DCM (5.0 mL) was added propane-2-sulfonyl chloride (100 mg, 0.70 mmol) at 0° C. The resulting solution was stirred for 20 h at room temperature. The reaction was then quenched by the addition of water (10 mL). The resulting solution was extracted with DCM (3×20 mL). The organic layers were combined, dried over anhydrous sodium sulfate, and concentrated under vacuum. The crude product was purified by Combi-Flash and further isolated by chiral separation with the following conditions:

Column, CHIRALPAK IA, 21.2×250 mm, 5 micron; mobile phase: ethanol:hexane(0.1% DEA)=30:70; Detector, uv 254/220 nm; flow rate, 20 mL/min.

The absolute configuration of all isomers was assigned arbitrarily.

Example 80a: (3S,4S)-4-((S)-5H-imidazo[5,1-a]isoindol-5-yl)-1-(isopropylsulfonyl)piperidin-3-ol (4.8 mg, 1%) as a white solid: LCMS (ESI, m/z): 362.2 $[M+H]^+$. $^1$H NMR (300 MHz, $CD_3OD$) δ 7.88 (s, 1H), 7.62 (d, J=7.8 Hz, 1H), 7.47 (d, J=7.8 Hz, 1H), 7.44-7.32 (m, 2H), 7.18 (s, 1H), 5.81 (d, J=3.6 Hz, 1H), 4.03-3.95 (m, 1H), 3.85-3.82 (m, 1H), 3.55-3.50 (m, 1H), 3.27-3.21 (m, 1H), 2.84-2.70 (m, 2H), 2.28-2.13 (m, 1H), 1.26 (d, J=2.1 Hz, 6H), 0.94-0.88 (m, 1H), 0.62-0.58 (m, 1H). 080a and 080b are enantiomers.

Example 80b: (3R,4R)-4-((R)-5H-imidazo[5,1-a]isoindol-5-yl)-1-(isopropylsulfonyl)piperidin-3-ol (10.8 mg, 2%) as a white solid: LCMS (ESI, m/z): 362.3 $[M+H]^+$. 080a and 080b are enantiomers.

Example 81: 1-(cyclopropylsulfonyl)-4-(5H-imidazo[5,1-a]isoindol-5-yl)piperidin-3-ol

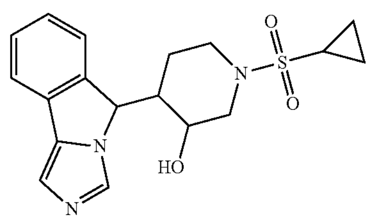 [SMILES: O=S(=O)(C1CC1)N1CCC(C2c3ccccc3-c3cncn32)C(O)C1]

Step 1:
(3R,4R)-1-(cyclopropylsulfonyl)-4-((S)-5H-imidazo[5,1-a]isoindol-5-yl)piperidin-3-ol
(3S,4S)-1-(cyclopropylsulfonyl)-4-((R)-5H-imidazo[5,1-a]isoindol-5-yl)piperidin-3-ol 81a

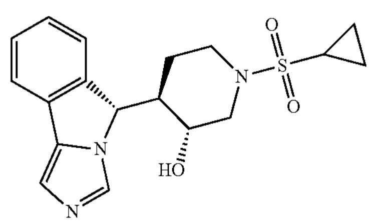

81b

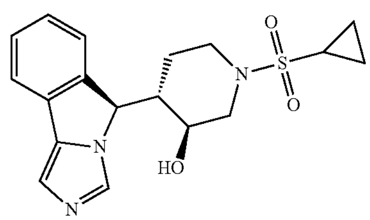

To the mixture of (3R,4R)-4-((S)-5H-imidazo[5,1-a]isoindol-5-yl)piperidin-3-ol and (3S,4S)-4-((R)-5H-imidazo[5,1-a]isoindol-5-yl)piperidin-3-ol (158 mg, 0.62 mmol) and TEA (0.6 mL, 4.32 mmol) in DCM (5.0 mL) was added cyclopropanesulfonyl chloride (260 mg, 1.849 mmol) at 0° C. The resulting solution was stirred for 1 h at room temperature. The reaction was then quenched by the addition of water (10 mL). The resulting solution was extracted with DCM (3×20 mL). The organic layers were combined, dried over anhydrous sodium sulfate, and concentrated under vacuum. The crude product was purified by Combi-Flash and further isolated by chiral separation with the following conditions:

Column, Lux 5 u Cellulose-4,AXIA Packed, 250×21.2 mm; mobile phase: ethanol:hexane(0.1% DEA)=50:50; Detector, uv 254/220 nm; flow rate, 20 mL/min.

The absolute configuration of all isomers 081a-b was assigned arbitrarily.

Example 81a: (3R,4R)-1-(cyclopropylsulfonyl)-4-((S)-5H-imidazo[5,1-a]isoindol-5-yl)piperidin-3-ol (13.3 mg, 1%) as a white solid: LCMS (ESI, m/z): 360.1 $[M+H]^+$. $^1$H NMR (300 MHz, $CD_3OD$) δ 7.91 (s, 1H), 7.66 (d, J=7.8 Hz, 1H), 7.56 (d, J=7.8 Hz, 1H), 7.48-7.32 (m, 2H), 7.19 (s, 1H), 5.84 (d, J=3.6 Hz, 1H), 4.03-3.95 (m, 1H), 3.85-3.82 (m, 1H), 3.55-3.50 (m, 1H), 2.78-2.70 (m, 2H), 2.47-2.28 (m, 2H), 1.04-0.96 (m, 4H), 0.82-0.72 (m, 2H). 081a and 081b are enantiomers.

Example 81b: (3S,4S)-1-(cyclopropylsulfonyl)-4-((R)-5H-imidazo[5,1-a]isoindol-5-yl)piperidin-3-ol (18.8 mg, 1%) as a white solid: LCMS (ESI, m/z): 360.2 $[M+H]^+$. 081a and 81b are enantiomers.

Example 82: (3R,4R)-4-((S)-5H-imidazo[5,1-a]isoindol-5-yl)-1-(2,2,2-trifluoroethyl)piperidin-3-ol and (3S,4S)-4-((S)-5H-imidazo[5,1-a]isoindol-5-yl)-1-(2,2,2-trifluoroethyl)piperidin-3-ol 82a

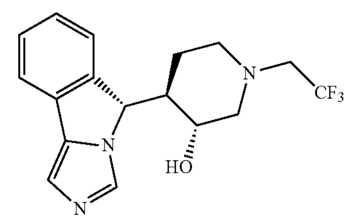

82b

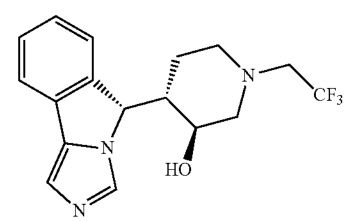

(3R,4R)-4-((S)-5H-imidazo[5,1-a]isoindol-5-yl)-1-(2,2,2-trifluoroethyl)piperidin-3-ol 82a

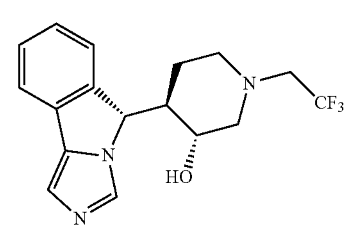

A solution of (3R,4R)-4-[(5S)-5H-imidazo[4,3-a]isoindol-5-yl]piperidin-3-ol (70 mg, 0.27 mmol) and TEA (0.27 mL, 1.94 mmol) in DCM (3.0 mL) was added 2,2,2-trifluoroethyl trifluoromethanesulfonate (100 mg, 0.43 mmol) at 0° C. The resulting solution was stirred for 30 h at room temperature. The reaction was then quenched by the addition of water (10 mL). The resulting solution was extracted with DCM (3×20 mL). The organic layers were combined, dried over anhydrous sodium sulfate, and concentrated under vacuum. The crude product was purified with Combi-flash.

Example 82a: (3R,4R)-4-((S)-5H-imidazo[5,1-a]isoindol-5-yl)-1-(2,2,2-trifluoroethyl)piperidin-3-ol (19.2 mg, 21%) as a white solid: LCMS (ESI, m/z): 338.2 $[M+H]^+$. $^1$H NMR (300 MHz, $CD_3OD$) δ 7.91 (s, 1H), 7.63 (d, J=7.5, 1H), 7.55 (d, J=7.5, 1H), 7.45-7.31 (m, 2H), 7.16 (s, 1H), 5.78 (d, J=3.3, 1H), 3.93-3.81 (m, 1H), 3.22-3.15 (m, 1H), 3.09-2.98 (m, 2H), 2.75-2.65 (m, 1H), 2.16-2.05 (m, 3H), 0.72-0.60 (m, 2H).

(3S,4S)-4-((S)-5H-imidazo[5,1-a]isoindol-5-yl)-1-(2,2,2-trifluoroethyl)piperidin-3-ol 82b

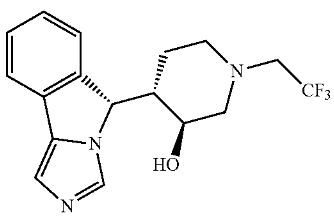

The title compounds were synthesized by the same method of example 82a.

Example 82b: (3S,4S)-4-((S)-5H-imidazo[5,1-a]isoindol-5-yl)-1-(2,2,2-trifluoroethyl)piperidin-3-ol (27.3 mg, 21%) as a white solid: LCMS (ESI, m/z): 338.2 $[M+H]^+$. $^1$H NMR (300 MHz, $CD_3OD$) δ 7.92 (s, 1H), 7.63 (d, J=7.5, 1H), 7.46 (d, J=7.5, 1H), 7.42-7.33 (m, 2H), 7.19 (s, 1H), 5.78 (d, J=3.3, 1H), 3.93-3.86 (m, 1H), 3.30-3.26 (m, 1H), 3.13-3.03 (m, 2H), 2.75-2.70 (m, 1H), 2.40-2.15 (m, 2H), 2.04-2.02 (m, 1H), 0.84-0.80 (m, 1H), 0.65-0.59 (m, 1H).

Example 83: (3R,4R)-4-((S)-5H-imidazo[5,1-a]isoindol-5-yl)-1-methylpiperidin-3-ol and (3S,4S)-4-((S)-5H-imidazo[5,1-a]isoindol-5-yl)-1-methylpiperidin-3-ol 83a

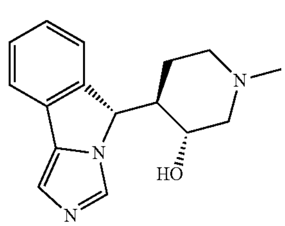

-continued

83b

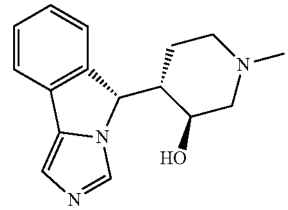

(3R,4R)-4-((S)-5H-imidazo[5,1-a]isoindol-5-yl)-1-methylpiperidin-3-ol

83a

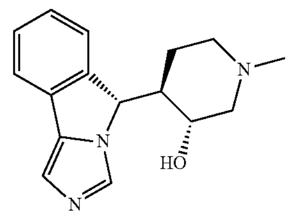

A solution of (3R,4R)-4-[(5S)-5H-imidazo[4,3-a]isoindol-5-yl]piperidin-3-ol (107 mg, 0.42 mmol) in water (4 mL) was added acetic acid (0.5 mL, 17.452 mmol) and formalin (1 mL, 54.62 mmol). The mixture was stirred for 4 h at room temperature.

Sodiumcyanoborohydride (200 mg, 3.18 mmol) was added at 0° C. The resulting solution was stirred for 2 h at room temperature. The reaction was then quenched by the addition of Sat. sodium bisulfate (20 mL). The resulting solution was extracted with DCM (3×30 mL) and the organic layers combined. The mixture was dried over anhydrous sodium sulfate and concentrated under vacuum. The crude product was purified with Combi-flash.

Example 83a: (3R,4R)-4-[(5S)-5H-imidazo[4,3-a]isoindol-5-yl]-1-methylpiperidin-3-ol (1.7 mg, 1%) as a white solid: LCMS (ESI, m/z): 270.2 $[M+H]^+$. $^1$H NMR (400 MHz, DMSO-$d_6$) δ 7.92 (s, 1H), 7.61 (d, J=7.5, 1H), 7.51 (d, J=7.5, 1H), 7.40-7.26 (m, 2H), 7.13 (s, 1H), 5.30 (d, J=3.2, 1H), 5.37 (d, J=3.2, 1H), 3.82-3.73 (m, 1H), 2.95-2.92 (m, 1H), 2.46-2.45 (m, 1H), 2.08 (s, 3H), 2.07-2.03 (m, 1H), 1.76-1.58 (m, 2H), 0.52-0.41 (m, 2H).

(3S,4S)-4-((S)-5H-imidazo[5,1-a]isoindol-5-yl)-1-methylpiperidin-3-ol

83b

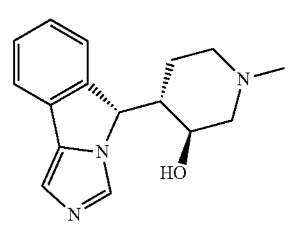

The title compounds were synthesized by the same method of example 83a.

Example 83b: (3S,4S)-4-((S)-5H-imidazo[5,1-a]isoindol-5-yl)-1-methylpiperidin-3-ol (76.8 mg, 25%) as a white solid: LCMS (ESI, m/z): 270.2 [M+H]$^+$. $^1$H NMR (300 MHz, $CD_3OD$) δ 7.92 (s, 1H), 7.63 (d, J=7.5, 1H), 7.47 (d, J=7.5, 1H), 7.42-7.33 (m, 2H), 7.19 (s, 1H), 5.80 (d, J=3.3, 1H), 3.97-3.90 (m, 1H), 3.18-3.13 (m, 1H), 2.70-2.62 (m, 1H), 2.63 (s, 3H), 2.06-1.83 (m, 3H), 0.91-0.86 (m, 1H), 0.72-0.64 (m, 1H).

Example 84: 4-(5H-imidazo[5,1-a]isoindol-5-yl)-2,2,5,5-tetramethyltetrahydrofuran-3-ol

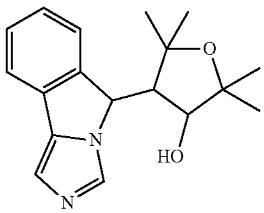 [SMILES: CC1(C)OC(C)(C)C(C2c3ccccc3-c3cncn32)C1O]

(3S,4R)-4-((R)-5H-imidazo[5,1-a]isoindol-5-yl)-2,2,5,5-tetramethyltetrahydrofuran-3-ol
(3R,4R)-4-((R)-5H-imidazo[5,1-a]isoindol-5-yl)-2,2,5,5-tetramethyltetrahydrofuran-3-ol
(3S,4S)-4-((S)-5H-imidazo[5,1-a]isoindol-5-yl)-2,2,5,5-tetramethyltetrahydrofuran-3-ol
(3R,4S)-4-((R)-5H-imidazo[5,1-a]isoindol-5-yl)-2,2,5,5-tetramethyltetrahydrofuran-3-ol
(3S,4R)-4-((S)-5H-imidazo[5,1-a]isoindol-5-yl)-2,2,5,5-tetramethyltetrahydrofuran-3-ol
(3R,4S)-4-((S)-5H-imidazo[5,1-a]isoindol-5-yl)-2,2,5,5-tetramethyltetrahydrofuran-3-ol Step 1: (E)-2,2,5,5-tetramethyl-4-(2-(1-trityl-1H-imidazol-4-yl)benzylidene)dihydrofuran-3(2H)-one

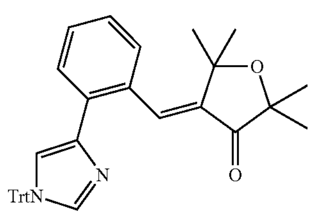

The title compound was synthesized by General Procedure for the Synthesis of Int-2. LCMS (ESI, m/z): 539.4 [M+H]$^+$ Step 2: 4-(5H-imidazo[5,1-a]isoindol-5-yl)-2,2,5,5-tetramethyldihydrofuran-3(2H)-one

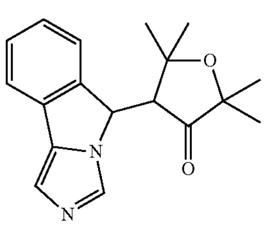 [SMILES: CC1(C)OC(C)(C)C(C2c3ccccc3-c3cncn32)C1=O]

The title compound was synthesized by General Procedure for the Synthesis of Int-3. LCMS (ESI, m/z): 297.4 [M+H]$^+$ Step 3: 4-(5H-imidazo[5,1-a]isoindol-5-yl)-2,2,5,5-tetramethyltetrahydrofuran-3-ol

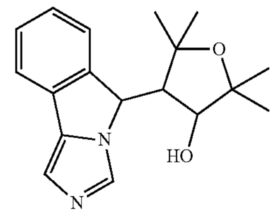 [SMILES: CC1(C)OC(C)(C)C(C2c3ccccc3-c3cncn32)C1O]

The title compounds were synthesized by General Procedure for the Synthesis of Int-5: LCMS (ESI, m/z): 299.2 [M+H]$^+$. The mixture was isolated by Chiral separation methods and the configuration of the isomers was assigned arbitrarily.

(3S,4R)-4-((R)-5H-imidazo[5,1-a]isoindol-5-yl)-2,2,5,5-tetramethyltetrahydrofuran-3-ol
(3R,4R)-4-((R)-5H-imidazo[5,1-a]isoindol-5-yl)-2,2,5,5-tetramethyltetrahydrofuran-3-ol
(3S,4S)-4-((S)-5H-imidazo[5,1-a]isoindol-5-yl)-2,2,5,5-tetramethyltetrahydrofuran-3-ol
(3R,4S)-4-((R)-5H-imidazo[5,1-a]isoindol-5-yl)-2,2,5,5-tetramethyltetrahydrofuran-3-ol
(3S,4R)-4-((S)-5H-imidazo[5,1-a]isoindol-5-yl)-2,2,5,5-tetramethyltetrahydrofuran-3-ol
(3R,4S)-4-((S)-5H-imidazo[5,1-a]isoindol-5-yl)-2,2,5,5-tetramethyltetrahydrofuran-3-ol 84a

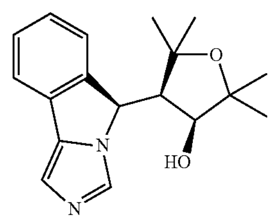

84b

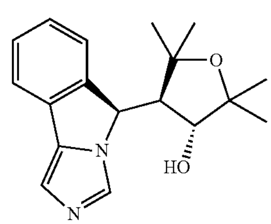

84c

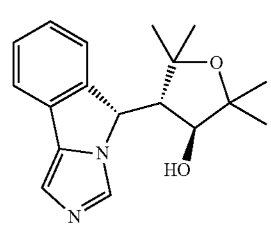

-continued

84d

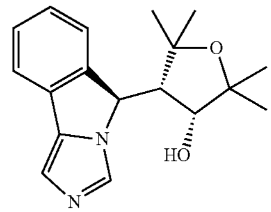

84f

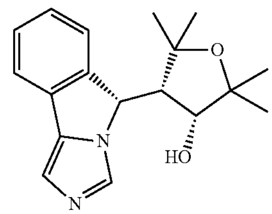

84e

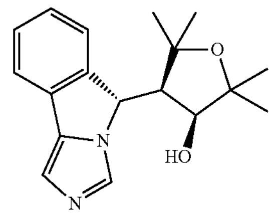

Example 84a: (3S,4R)-4-((R)-5H-imidazo[5,1-a]isoindol-5-yl)-2,2,5,5-tetramethyltetrahydrofuran-3-ol: LCMS (ESI, m/z): 299.2 $[M+H]^+$; $^1H$ NMR (500 MHz, DMSO-$d_6$) δ 8.16 (d, J=7.9 Hz, 1H), 7.71 (s, 1H), 7.51 (s, 1H), 7.33-7.25 (m, 1H), 7.21-7.14 (m, 2H), 6.60 (d, J=2.2 Hz, 1H), 5.74 (d, J=5.0 Hz, 1H), 4.37 (dd, J=4.9, 2.3 Hz, 1H), 1.26 (s, 3H), 1.24 (s, 3H), 1.00 (s, 3H), 0.83 (s, 3H).

Example 84b: (3R,4R)-4-((R)-5H-imidazo[5,1-a]isoindol-5-yl)-2,2,5,5-tetramethyltetrahydrofuran-3-ol: LCMS (ESI, m/z): 299.2 [M+H$^1$H NMR (500 MHz, DMSO-$d_6$) δ 8.01 (s, 1H), 7.75 (d, J=7.7 Hz, 1H), 7.60 (d, J=7.5 Hz, 1H), 7.39 (t, J=7.4 Hz, 1H), 7.26 (t, J=7.6 Hz, 1H), 7.12 (s, 1H), 5.78-5.59 (m, 2H), 4.09 (tt, J=5.2, 3.1 Hz, 1H), 3.17 (d, J=5.3 Hz, 1H), 1.20 (s, 3H), 1.08 (s, 3H), 1.06 (s, 3H), 0.82 (s, 3H).

Example 84c: (3S,4S)-4-((S)-5H-imidazo[5,1-a]isoindol-5-yl)-2,2,5,5-tetramethyltetrahydrofuran-3-ol: LCMS (ESI, m/z): 299.2 $[M+H]^+$; $^1H$ NMR (500 MHz, DMSO-d6) δ 0.81 (s, 3H), 1.05 (s, 3H), 1.07 (s, 3H), 1.20 (s, 3H), 3.17 (d, J=5.3 Hz, 1H), 4.08 (td, J=5.1, 2.7 Hz, 1H), 5.61-5.74 (m, 2H), 7.11 (s, 1H), 7.26 (td, J=7.6, 1.3 Hz, 1H), 7.39 (t, J=7.5 Hz, 1H), 7.60 (d, J=7.6 Hz, 1H), 7.74 (d, J=7.7 Hz, 1H), 8.00 (s, 1H).

Example 84d: (3R,4S)-4-((R)-5H-imidazo[5,1-a]isoindol-5-yl)-2,2,5,5-tetramethyltetrahydrofuran-3-ol: LCMS (ESI, m/z): 299.2 $[M+H]^+$; $^1H$ NMR (500 MHz, DMSO-$d_6$) δ 7.88-7.79 (m, 1H), 7.74 (s, 1H), 7.71 (d, J=7.4 Hz, 1H), 7.29 (t, J=6.9 Hz, 1H), 7.25-7.19 (m, 1H), 7.16 (s, 1H), 6.62 (s, 1H), 5.23 (d, J=5.0 Hz, 1H), 4.08 (d, J=4.7 Hz, 1H), 1.39 (d, J=12.3 Hz, 3H), 1.35 (d, J=7.2 Hz, 3H), 1.18 (s, 3H), 0.99 (d, J=5.9 Hz, 3H).

Example 84e: (3S,4R)-4-((S)-5H-imidazo[5,1-a]isoindol-5-yl)-2,2,5,5-tetramethyltetrahydrofuran-3-ol: LCMS (ESI, m/z): 299.2 $[M+H]^+$; $^1H$ NMR (500 MHz, DMSO-$d_6$) δ 7.82 (dd, J=7.8, 1.2 Hz, 1H), 7.74 (s, 1H), 7.72 (d, J=7.4 Hz, 1H), 7.30 (td, J=7.5, 1.2 Hz, 1H), 7.23 (td, J=7.5, 1.3 Hz, 1H), 7.17 (s, 1H), 6.63 (s, 1H), 5.24 (d, J=5.0 Hz, 1H), 4.10 (dd, J=9.8, 4.8 Hz, 1H), 1.40 (d, J=12.6 Hz, 3H), 1.36 (d, J=7.4 Hz, 3H), 1.19 (s, 3H), 1.00 (d, J=6.0 Hz, 3H).

Example 84f: (3R,4S)-4-((S)-5H-imidazo[5,1-a]isoindol-5-yl)-2,2,5,5-tetramethyltetrahydrofuran-3-ol: LCMS (ESI, m/z): 299.2 $[M+H]^+$; $^1H$ NMR (500 MHz, DMSO-$d_6$) δ 8.16 (d, J=7.7 Hz, 1H), 7.71 (s, 1H), 7.51 (dd, J=2.1, 1.1 Hz, 1H), 7.32-7.26 (m, 1H), 7.21-7.13 (m, 2H), 6.59 (d, J=2.3 Hz, 1H), 5.74 (d, J=5.0 Hz, 1H), 4.37 (dd, J=5.0, 2.4 Hz, 1H), 1.26 (s, 3H), 1.24 (s, 3H), 1.00 (s, 3H), 0.83 (s, 3H).

Example 85: 4-(5H-Imidazo[5,1-a]isoindol-5-yl)-2,2-dimethyltetrahydrofuran-3-ol

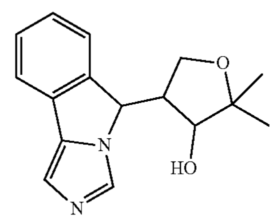 [SMILES: CC1(C)OCC(C2c3ccccc3-c3cncn32)C1O]

(3S,4R)-4-((R)-5H-Imidazo[5,1-a]isoindol-5-yl)-2,2-dimethyltetrahydrofuran-3-ol
(3S,4R)-4-((S)-5H-Imidazo[5,1-a]isoindol-5-yl)-2,2-dimethyltetrahydrofuran-3-ol
(3S,4S)-4-((R)-5H-Imidazo[5,1-a]isoindol-5-yl)-2,2-dimethyltetrahydrofuran-3-ol
(3S,4S)-4-((S)-5H-Imidazo[5,1-a]isoindol-5-yl)-2,2-dimethyltetrahydrofuran-3-ol
(3R,4R)-4-((R)-5H-Imidazo[5,1-a]isoindol-5-yl)-2,2-dimethyltetrahydrofuran-3-ol
(3R,4R)-4-((S)-5H-Imidazo[5,1-a]isoindol-5-yl)-2,2-dimethyltetrahydrofuran-3-ol
(3R,4S)-4-((R)-5H-Imidazo[5,1-a]isoindol-5-yl)-2,2-dimethyltetrahydrofuran-3-ol
(3R,4S)-4-((S)-5H-Imidazo[5,1-a]isoindol-5-yl)-2,2-dimethyltetrahydrofuran-3-ol

Step 1: (E)-2,2-dimethyl-4-(2-(1-trityl-1H-imidazol-4-yl)benzylidene)dihydrofuran-3(2H)-one

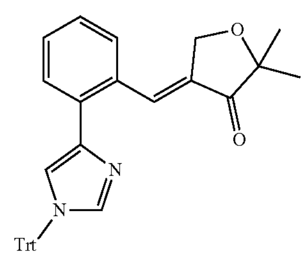

10% aq. Sodium hydroxide (2.41 mL, 6.03 mmol) was added to a stirred mixture of 2,2-dimethyldihydrofuran-3(2H)-one (330 mg, 2.89 mmol) and 2-(1-trityl-1H-imidazol-4-yl)benzaldehyde (1.00 g, 2.41 mmol), in MeOH (20 mL). The reaction mixture was heated at 65° C. for 6 hours until LC-MS showed the disappearance of SM. The reaction mixture was diluted with DCM (60 mL) and the organics were washed with water, dried over $Na_2SO_4$, filtered and concentrated. The crude was taken directly to next step.

Step 2: 4-(5H-imidazo[5,1-a]isoindol-5-yl)-2,2-dimethyldihydrofuran-3(2H)-one

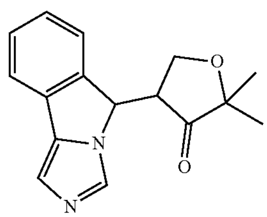 [SMILES: CC1(C)OCC(C2c3ccccc3-c3cncn32)C1=O]

The crude (1.5 g, 2.94 mmol) was dissolved in MeOH (30 mL) and AcOH (3.36 mL, 58.8 mmol) was added and refluxed for 6 h. The reaction mixture was concentrated. The crude was dissolved in DCM (60 mL) and washed with satd. Aq. $NaHCO_3$ (20 mL), dried over sodium sulfate, filtered and concentrated. The crude product was purified by combi-flash using MeOH/DCM as eluent: LCMS (ESI, m/z): 269.2 $[M+H]^+$.

Step 3:

(3S,4R)-4-((R)-5H-Imidazo[5,1-a]isoindol-5-yl)-2,2-dimethyltetrahydrofuran-3-ol (3S,4R)-4-((S)-5H-Imidazo[5,1-a]isoindol-5-yl)-2,2-dimethyltetrahydrofuran-3-ol (3S,4S)-4-((R)-5H-Imidazo[5,1-a]isoindol-5-yl)-2,2-dimethyltetrahydrofuran-3-ol (3S,4S)-4-((S)-5H-Imidazo[5,1-a]isoindol-5-yl)-2,2-dimethyltetrahydrofuran-3-ol (3R,4R)-4-((R)-5H-Imidazo[5,1-a]isoindol-5-yl)-2,2-dimethyltetrahydrofuran-3-ol (3R,4R)-4-((S)-5H-Imidazo[5,1-a]isoindol-5-yl)-2,2-dimethyltetrahydrofuran-3-ol (3R,4S)-4-((R)-5H-Imidazo[5,1-a]isoindol-5-yl)-2,2-dimethyltetrahydrofuran-3-ol (3R,4S)-4-((S)-5H-Imidazo[5,1-a]isoindol-5-yl)-2,2-dimethyltetrahydrofuran-3-ol 85a

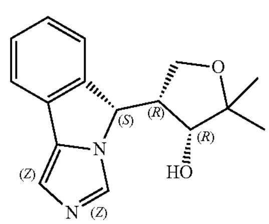

85b

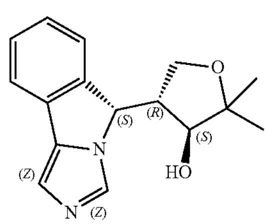

-continued

85c

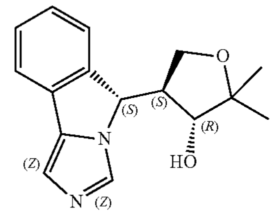

85d

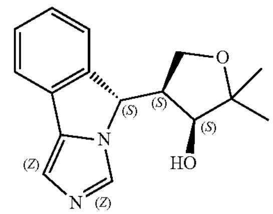

85e

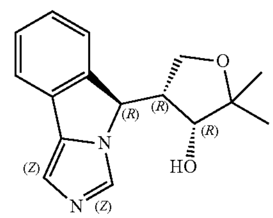

85f

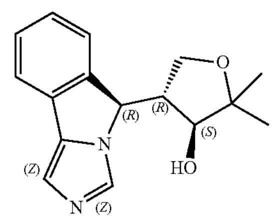

85g

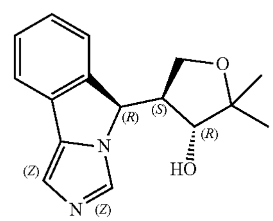

85h

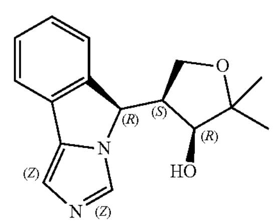

4-(5H-imidazo[5,1-a]isoindol-5-yl)-2,2-dimethyldihydrofuran-3(2H)-one (900 mg mg, 3.35 mmol) was dissolved in MeOH (20 mL) and cooled to 0° C. $NaBH_4$ (381 mg, 10.1 mmol) was added the reaction mixture was stirred for 2 h at RT. $NH_4Cl$ (10 mL) was added to the reaction mixture and stirred for 10 min. The solution was poured into a separatory funnel containing water (20 mL). The aqueous layer was extracted with DCM (2×30 mL). The combined organic layers were dried over $Na_2SO_4$ and the solvent evaporated under reduced pressure to afford the desired product as mixture of diastereomers. The crude was purified by CombiFlash and the product was eluted with DCM:MeOH=95:5.

The final products were further isolated by chiral separation to afford 8 isomers and the stereochemistry of each isomer was arbitrarily assigned.

Example 85a: (3S,4R)-4-((R)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.92 (s, 1H), 7.60 (d, J=7.6 Hz, 1H), 7.49 (d, J=7.6 Hz, 1H), 7.39 (t, J=7.5 Hz, 1H), 7.27 (t, J=7.6 Hz, 1H), 7.12 (s, 1H), 5.52 (d, J=4.5 Hz, 1H), 5.06 (d, J=5.5 Hz, 1H), 3.77 (t, J=9.0 Hz, 1H), 3.59 (t, J=6.5 Hz, 1H), 3.52 (t, J=8.4 Hz, 1H), 2.82 (dq, J=12.6, 7.6, 6.3 Hz, 1H), 1.01 (d, J=7.7 Hz, 6H).

Example 85b: (3S,4R)-4-((S)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.79 (s, 1H), 7.70 (d, J=8.2 Hz, 1H), 7.60 (d, J=7.5 Hz, 1H), 7.40 (t, J=7.5 Hz, 1H), 7.28 (t, J=7.6 Hz, 1H), 7.12 (s, 1H), 5.67 (d, J=5.6 Hz, 1H), 5.47 (d, J=8.3 Hz, 1H), 3.99 (t, J=5.6 Hz, 1H), 3.85 (d, J=9.5 Hz, 2H), 2.73-2.61 (m, 1H), 1.22 (s, 3H), 1.03 (s, 3H).

Example 85c: (3S,4S)-4-((R)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.79 (s, 1H), 7.70 (d, J=8.2 Hz, 1H), 7.60 (d, J=7.5 Hz, 1H), 7.40 (t, J=7.5 Hz, 1H), 7.28 (t, J=7.6 Hz, 1H), 7.12 (s, 1H), 5.67 (d, J=5.6 Hz, 1H), 5.47 (d, J=8.3 Hz, 1H), 3.99 (t, J=5.6 Hz, 1H), 3.85 (d, J=9.5 Hz, 2H), 2.73-2.61 (m, 1H), 1.22 (s, 3H), 1.03 (s, 3H).

Example 85d: (3S,4S)-4-((S)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.92 (s, 1H), 7.60 (d, J=7.6 Hz, 1H), 7.49 (d, J=7.6 Hz, 1H), 7.39 (t, J=7.5 Hz, 1H), 7.27 (t, J=7.6 Hz, 1H), 7.12 (s, 1H), 5.52 (d, J=4.5 Hz, 1H), 5.06 (d, J=5.5 Hz, 1H), 3.77 (t, J=9.0 Hz, 1H), 3.59 (t, J=6.5 Hz, 1H), 3.52 (t, J=8.4 Hz, 1H), 2.82 (dq, J=12.6, 7.6, 6.3 Hz, 1H), 1.01 (d, J=7.7 Hz, 6H).

Example 85e: (3R,4R)-4-((R)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.94 (s, 1H), 7.59 (d, J=7.5 Hz, 1H), 7.55 (d, J=7.6 Hz, 1H), 7.38 (t, J=7.5 Hz, 1H), 7.27 (t, J=8.1 Hz, 1H), 7.17 (s, 1H), 5.55 (d, J=3.5 Hz, 1H), 5.45 (d, J=5.3 Hz, 1H), 3.92 (dd, J=8.7, 5.3 Hz, 1H), 3.38 (t, J=9.0 Hz, 1H), 2.94 (qd, J=8.6, 3.7 Hz, 1H), 2.81-2.70 (m, 1H), 1.12 (s, 3H), 1.04 (s, 3H).

Example 85f: (3R,4R)-4-((S)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.92 (s, 1H), 7.62 (d, J=7.6 Hz, 1H), 7.39 (t, J=7.5 Hz, 1H), 7.29 (d, J=7.4 Hz, 1H), 7.26-7.20 (m, 1H), 7.15 (s, 1H), 5.66 (d, J=5.8 Hz, 1H), 5.40 (d, J=10.6 Hz, 1H), 4.18 (dd, J=10.1, 8.0 Hz, 1H), 3.96 (t, J=8.2 Hz, 1H), 3.94-3.90 (m, 1H), 1.25 (s, 3H), 1.01 (s, 3H).

Example 85g: (3R,4S)-4-((R)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.94 (s, 1H), 7.59 (d, J=7.5 Hz, 1H), 7.55 (d, J=7.6 Hz, 1H), 7.38 (t, J=7.5 Hz, 1H), 7.27 (t, J=8.1 Hz, 1H), 7.17 (s, 1H), 5.55 (d, J=3.5 Hz, 1H), 5.45 (d, J=5.3 Hz, 1H), 3.92 (dd, J=8.7, 5.3 Hz, 1H), 3.38 (t, J=9.0 Hz, 1H), 2.94 (qd, J=8.6, 3.7 Hz, 1H), 2.81-2.70 (m, 1H), 1.12 (s, 3H), 1.04 (s, 3H).

Example 85h: (3R,4S)-4-((S)-5H-Imidazo[5,1-a]isoindol-5-yl)-2,2-dimethyltetrahydrofuran-3-ol: LCMS (ESI, m/z): 271.2 $[M+H]^+$; $^1$HNMR (500 MHz, DMSO-$d_6$) δ 7.92 (s, 1H), 7.62 (d, J=7.6 Hz, 1H), 7.39 (t, J=7.5 Hz, 1H), 7.29 (d, J=7.4 Hz, 1H), 7.26-7.20 (m, 1H), 7.15 (s, 1H), 5.66 (d, J=5.8 Hz, 1H), 5.40 (d, J=10.6 Hz, 1H), 4.18 (dd, J=10.1, 8.0 Hz, 1H), 3.96 (t, J=8.2 Hz, 1H), 3.94-3.90 (m, 1H), 1.25 (s, 3H), 1.01 (s, 3H).

Example 86: 3-(5H-imidazo[5,1-a]isoindol-5-yl)oxepan-4-ol

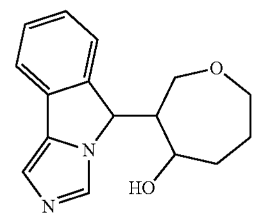 [SMILES: OC1CCCOCC1C1c2ccccc2-c2cncn21]

Step 1: oxepan-4-one

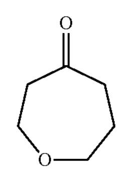

A solution of oxan-4-one (7 mL, 83.90 mmol, 1.000 equiv) and (diazomethyl)trimethylsilane (27.6 mL, 193.31 mmol) in DCM (400 mL) was added boron trifluoride etherate (14 mL, 128.23 mmol) at −25° C. The resulting solution was stirred for 2.5 h at −25° C. The reaction was then quenched with water (400 mL). The resulting solution was extracted with DCM (2×200 mL) and the organic layers combined. The resulting mixture was washed with water (1×200 mL). The resulting mixture was concentrated under vacuum. This resulted in 250 mg (3%) of oxepan-4-one as yellow oil.

Step 2: (E)-3-(2-(1-trityl-1H-imidazol-4-yl)benzylidene)oxepan-4-one

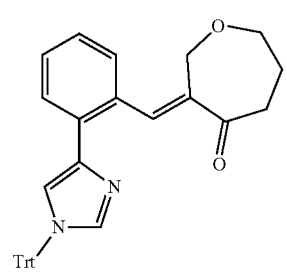

The title compound was synthesized by General Procedure for the Synthesis of Int-2: LCMS (ESI, m/z): 511.6 $[M+H]^+$.

Step 3: 3-(5H-imidazo[5,1-a]isoindol-5-yl)oxepan-4-one

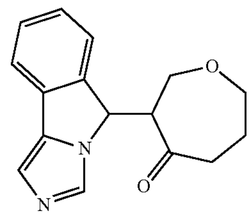 [SMILES: O=C1CCCOCC1C1c2ccccc2-c2cncn21]

The title compound was synthesized by General Procedure for the Synthesis of Int-3: LCMS (ESI, m/z): 269.0 $[M+H]^+$.

Step 4:

(3S,4R)-3-((R)-5H-imidazo[5,1-a]isoindol-5-yl)oxepan-4-ol (3R,4S)-3-((S)-5H-imidazo[5,1-a]isoindol-5-yl)oxepan-4-ol (3S,4S)-3-((R)-5H-imidazo[5,1-a]isoindol-5-yl)oxepan-4-ol (3S,4R)-3-((S)-5H-imidazo[5,1-a]isoindol-5-yl)oxepan-4-ol (3S,4S)-3-((S)-5H-imidazo[5,1-a]isoindol-5-yl)oxepan-4-ol (3R,4R)-3-((S)-5H-imidazo[5,1-a]isoindol-5-yl)oxepan-4-ol (3R,4R)-3-((R)-5H-imidazo[5,1-a]isoindol-5-yl)oxepan-4-ol 86a

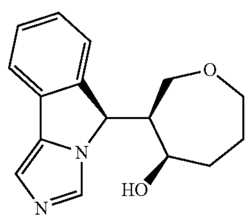

86b

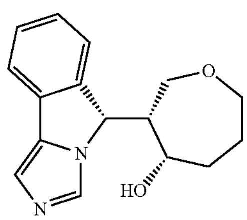

86c

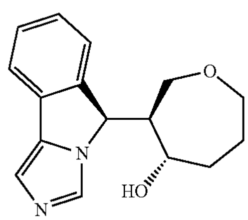

86d

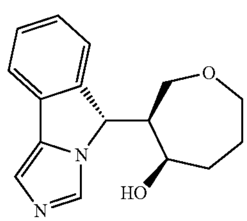

-continued

86e

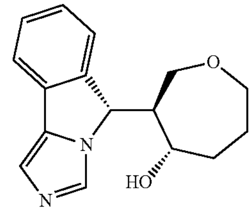

86f

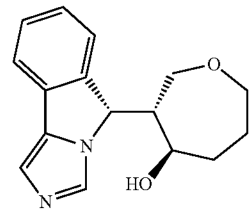

86g

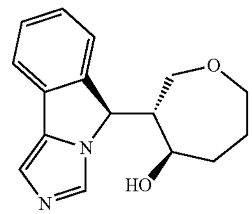

The title compound was synthesized by the same method of example 071.

The title compounds were synthesized by the same method of example 086a-g.

Example 86a: (3S,4R)-3-((R)-5H-imidazo[5,1-a]isoindol-5-yl)oxepan-4-ol (3.8 mg, 1%) as a white solid: LCMS (ESI, m/z): 271.2 $[M+H]^+$. $^1H$ NMR (300 MHz, $CD_3OD$) δ 7.95 (s, 1H), 7.74 (d, J=7.7 Hz, 1H), 7.69-7.57 (m, 1H), 7.48-7.25 (m, 2H), 7.14 (s, 1H), 5.42 (s, 1H), 4.88 (d, J=2.1 Hz, 17H), 4.04 (s, 1H), 3.88-3.65 (m, 4H), 3.42 (s, 1H), 2.57 (d, J=11.5 Hz, 1H), 2.42-2.22 (m, 1H), 1.86-1.66 (m, 2H), 0.70-0.66 (m, 1H). 86a and 86b are enantiomers.

Example 86b: (3R,4S)-3-((S)-5H-imidazo[5,1-a]isoindol-5-yl)oxepan-4-ol (3.3 mg, 1%) as a white solid: LCMS (ESI, m/z): 271.2 $[M+H]^+$. 86a and 86b are enantiomers.

Example 86c: (3S,4S)-3-((R)-5H-imidazo[5,1-a]isoindol-5-yl)oxepan-4-ol (8.4 mg, 2%) as a white solid: LCMS (ESI, m/z): 271.2 $[M+H]^+$. $^1H$ NMR (300 MHz, $CD_3OD$) δ 8.22 (s, 2H), 7.57-7.49 (m, 4H), 7.47-7.27 (m, 4H), 7.12 (s, 2H), 5.46 (s, 2H), 4.55 (q, J=3.6, 2.7 Hz, 2H), 3.88-3.85 (m, 2H), 3.77-3.57 (m, 4H), 3.35-3.31 (m, 1H), 2.65-2.61 (m, 2H), 2.20-2.00 (m, 2H), 1.99-1.67 (m, 4H), 0.70-0.66 (m, 2H). 86c and 86f are enantiomers.

Example 86d: (3S,4R)-3-((S)-5H-imidazo[5,1-a]isoindol-5-yl)oxepan-4-ol (25.2 mg, 5.6%) as a white solid: LCMS (ESI, m/z): 271.2 $[M+H]^+$. $^1H$ NMR (300 MHz, $CD_3OD$) δ 8.23 (d, J=2.1 Hz, 1H), 7.58 (dd, J=11.1, 7.6 Hz, 2H), 7.49-7.29 (m, 2H), 7.17-7.09 (m, 1H), 5.47 (s, 1H), 4.57-4.47 (m, 1H), 3.75-3.56 (m, 2H), 3.36-3.23 (m, 1H), 2.81 (dt, J=12.6, 2.6 Hz, 1H), 2.66-2.53 (m, 1H), 2.28-2.25 (m, 1H), 2.03-2.01 (m, 2H), 1.64-1.62 (m, 1H).

Example 86e: (3S,4S)-3-((S)-5H-imidazo[5,1-a]isoindol-5-yl)oxepan-4-ol (4.5 mg, 1%) as a white solid: LCMS (ESI, m/z): 271.2 $[M+H]^+$. $^1H$ NMR (300 MHz, $CD_3OD$) δ 8.01 (s, 1H), 7.85 (d, J=7.7 Hz, 1H), 7.62 (d, J=7.4 Hz, 1H), 7.47-7.25 (m, 2H), 7.17 (s, 1H), 5.45 (d, J=3.4 Hz, 1H), 4.23 (dd, J=5.5, 2.9 Hz, 1H), 3.85-3.68 (m, 3H), 3.42 (dt, J=14.6, 4.8 Hz, 2H), 2.54-2.52 (m, 1H), 2.21-2.19 (m, 1H), 2.03-1.72 (m, 2H), 1.71-1.53 (m, 1H). 86e and 86g are enantiomers.

Example 86f: (3R,4R)-3-((S)-5H-imidazo[5,1-a]isoindol-5-yl)oxepan-4-ol (10.7 mg, 2%) as a white solid: LCMS (ESI, m/z): 271.2 $[M+H]^+$. 86c and 86f are enantiomers.

Example 86g: (3R,4R)-3-((R)-5H-imidazo[5,1-a]isoindol-5-yl)oxepan-4-ol (5.5 mg, 1%) as a white solid: LCMS (ESI, m/z): 271.2 $[M+H]^+$. 86e and 86g are enantiomers.

Example 87: 5-(5H-imidazo[5,1-a]isoindol-5-yl)-2-oxaspiro[3.3]heptan-6-ol

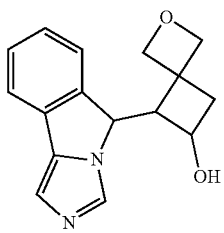 [SMILES: OC1CC2(COC2)C1C1c2ccccc2-c2cncn21]

(5R,6R)-5-((R)-5H-imidazo[5,1-a]isoindol-5-yl)-2-oxaspiro[3.3]heptan-6-ol
(5S,6R)-5-((R)-5H-imidazo[5,1-a]isoindol-5-yl)-2-oxaspiro[3.3]heptan-6-ol
(5S,6S)-5-((R)-5H-imidazo[5,1-a]isoindol-5-yl)-2-oxaspiro[3.3]heptan-6-ol
(5R,6R)-5-((S)-5H-imidazo[5,1-a]isoindol-5-yl)-2-oxaspiro[3.3]heptan-6-ol
(5R,6S)-5-((S)-5H-imidazo[5,1-a]isoindol-5-yl)-2-oxaspiro[3.3]heptan-6-ol
(5S,6S)-5-((S)-5H-imidazo[5,1-a]isoindol-5-yl)-2-oxaspiro[3.3]heptan-6-ol
(5R,6S)-5-((R)-5H-imidazo[5,1-a]isoindol-5-yl)-2-oxaspiro[3.3]heptan-6-ol
(5S,6R)-5-((S)-5H-imidazo[5,1-a]isoindol-5-yl)-2-oxaspiro[3.3]heptan-6-ol

Step 1: (E)-5-(2-(1-trityl-1H-imidazol-4-yl)benzylidene)-2-oxaspiro[3.3]heptan-6-one

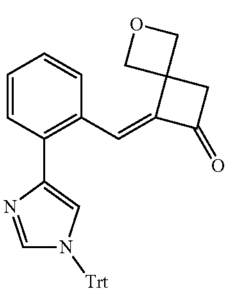

To a solution of 2-(1-trityl-1H-imidazol-4-yl)benzaldehyde (2.5 g, 6.03 mmol) and 2-oxaspiro[3.3]heptan-6-one (879 mg, 7.84 mmol) in MeOH (40 mL) was added piperidine dropwise (0.595 mL, 6.03 mmol). The solution was allowed to reflux overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by EtOAc:Hexane=25:75: LCMS (ESI, m/z): 509.2 $[M+H]^+$.

Step 2: 5-(5H-imidazo[5,1-a]isoindol-5-yl)-2-oxaspiro[3.3]heptan-6-one

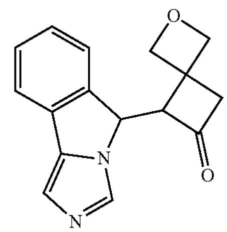 [SMILES: O=C1CC2(COC2)C1C1c2ccccc2-c2cncn21]

(E)-5-(2-(1-trityl-1H-imidazol-4-yl)benzylidene)-2-oxaspiro[3.3]heptan-6-one (0.78 g, 1.53 mmol) was stirred in 20% AcOH in MeOH (10 mL) at 90° C. for 2 h. After cooling to rt, the solvent was removed under reduced pressure and sat'd $NaHCO_3$ (20 mL) was added to the residue followed by DCM (20 mL). The organic layer was collected and the aqueous layer was extracted with DCM (3×10 mL). The combined organic layers were dried over $Na_2SO_4$ and the solvent evaporated under reduced pressure to afford the crude product which was purified by using CombiFlash: LCMS (ESI, m/z): 267.2 $[M+H]^+$.

Step 3:

(5R,6R)-5-((R)-5H-imidazo[5,1-a]isoindol-5-yl)-2-oxaspiro[3.3]heptan-6-ol
(5S,6R)-5-((R)-5H-imidazo[5,1-a]isoindol-5-yl)-2-oxaspiro[3.3]heptan-6-ol
(5S,6S)-5-((R)-5H-imidazo[5,1-a]isoindol-5-yl)-2-oxaspiro[3.3]heptan-6-ol
(5R,6R)-5-((S)-5H-imidazo[5,1-a]isoindol-5-yl)-2-oxaspiro[3.3]heptan-6-ol
(5R,6S)-5-((S)-5H-imidazo[5,1-a]isoindol-5-yl)-2-oxaspiro[3.3]heptan-6-ol
(5S,6S)-5-((S)-5H-imidazo[5,1-a]isoindol-5-yl)-2-oxaspiro[3.3]heptan-6-ol
(5R,6S)-5-((R)-5H-imidazo[5,1-a]isoindol-5-yl)-2-oxaspiro[3.3]heptan-6-ol
(5S,6R)-5-((S)-5H-imidazo[5,1-a]isoindol-5-yl)-2-oxaspiro[3.3]heptan-6-ol 87a

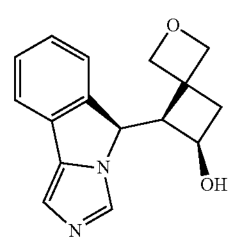

-continued

87b

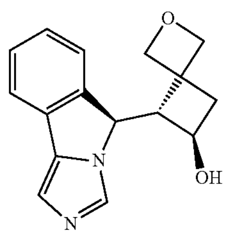

87c

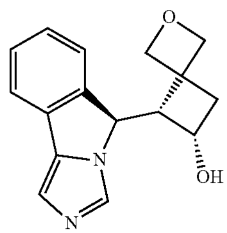

87d

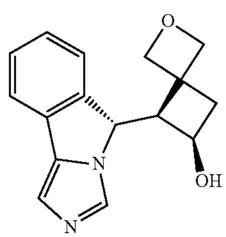

87e

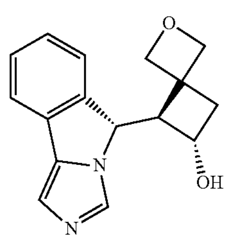

87f

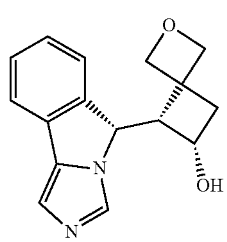

87g

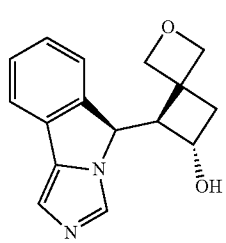

-continued

87h

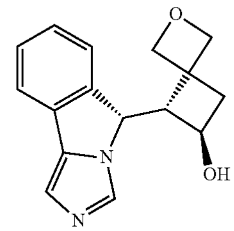

To a solution of 5-(5H-imidazo[5,1-a]isoindol-5-yl)-2-oxaspiro[3.3]heptan-6-one (0.3 g, 1.13 mmol) in MeOH (10 mL) was added $NaBH_4$ (86 mg, 2.25 mmol) in portions at 0° C. and the solution was stirred at 0° C. for 2 hr. The solvent was distilled off and saturated ammonium chloride solution (10 mL) was added. The aqueous layer was extracted with 5% trifluoroethanol in DCM (3×10 mL). The combined organic extract was dried over ($Na_2SO_4$) and concentrated under reduced pressure to afford the crude product. The crude was purified by CombiFlash and the product was eluted with DCM:MeOH=95:5. The final products were further isolated by chiral separation to afford 8 isomers and the stereochemistry of each isomer was arbitrarily assigned.

Example 87a: (5R,6R)-5-((R)-5H-imidazo[5,1-a]isoindol-5-yl)-2-oxaspiro[3.3]heptan-6-ol: LCMS (ESI, m/z): 269.2 $[M+H]^+$.

Example 087b: (5S,6R)-5-((R)-5H-imidazo[5,1-a]isoindol-5-yl)-2-oxaspiro[3.3]heptan-6-ol: LCMS (ESI, m/z): 269.2 $[M+H]^+$; $^1$HNMR $^1$H NMR (500 MHz, DMSO-$d_6$) δ 8.18 (s, 1H), 7.65-7.61 (m, 2H), 7.43-7.38 (m, 1H), 7.32-7.26 (m, 1H), 7.19 (s, 1H), 5.67 (d, J=3.4 Hz, 1H), 5.61 (d, J=8.3 Hz, 1H), 4.78 (d, J=7.2 Hz, 1H), 4.50 (d, J=6.7 Hz, 1H), 4.40 (d, J=7.2 Hz, 1H), 4.38-4.33 (m, 1H), 4.32 (d, J=6.8 Hz, 1H), 2.65-2.58 (m, 1H), 2.38 (ddd, J=12.2, 5.9, 1.4 Hz, 1H), 2.06 (dd, J=12.4, 2.5 Hz, 1H).

Example 87c: (5S,6S)-5-((R)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 7.89 (dd, J=7.7, 1.1 Hz, 1H), 7.84 (s, 1H), 7.67-7.61 (m, 1H), 7.42 (t, J=7.6 Hz, 1H), 7.32 (td, J=7.6, 1.2 Hz, 1H), 7.13 (s, 1H), 5.67 (d, J=9.6 Hz, 1H), 5.29 (d, J=7.7 Hz, 1H), 5.03 (d, J=6.9 Hz, 1H), 4.63 (d, J=7.0 Hz, 1H), 4.52 (d, J=6.8 Hz, 1H), 4.43 (d, J=6.7 Hz, 1H), 4.18 (p, J=7.8 Hz, 1H), 2.60 (dd, J=11.3, 7.5 Hz, 1H), 2.17 (dd, J=9.7, 7.7 Hz, 1H), 1.91 (dd, J=11.3, 8.3 Hz, 1H).

Example 87d: (5R,6R)-5-((S)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 7.89 (dd, J=7.7, 0.9 Hz, 1H), 7.84 (s, 1H), 7.64 (dt, J=7.6, 0.9 Hz, 1H), 7.45-7.39 (m, 1H), 7.32 (td, J=7.6, 1.2 Hz, 1H), 7.13 (s, 1H), 5.67 (d, J=9.7 Hz, 1H), 5.29 (d, J=7.7 Hz, 1H), 5.03 (d, J=7.0 Hz, 1H), 4.64 (d, J=7.0 Hz, 1H), 4.52 (d, J=6.8 Hz, 1H), 4.43 (d, J=6.8 Hz, 1H), 4.23-4.13 (m, 1H), 2.60 (dd, J=11.2, 7.5 Hz, 1H), 2.17 (dd, J=9.7, 7.7 Hz, 1H), 1.91 (dd, J=11.3, 8.3 Hz, 1H).

Example 87e: (5R,6S)-5-((S)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 8.18 (d, J=2.0 Hz, 1H), 7.67-7.60 (m, 2H), 7.44-7.37 (m, 1H), 7.33-7.27 (m, 1H), 7.19 (d, J=2.0 Hz, 1H), 5.67 (t, J=2.8 Hz, 1H), 5.61 (d, J=8.1 Hz, 1H), 4.78 (dd, J=7.3, 2.0 Hz, 1H), 4.51 (dd, J=6.8, 2.0 Hz, 1H), 4.40 (dd, J=7.1, 2.0 Hz, 1H), 4.35 (dd, J=6.0, 3.0 Hz, 1H), 4.32 (dd, J=6.9, 2.0 Hz, 1H), 2.62 (t, J=7.6 Hz, 1H), 2.38 (dd, J=12.4, 5.8 Hz, 1H), 2.06 (dt, J=12.3, 2.4 Hz, 1H).

Example 87f: (5S,6S)-5-((S)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 7.99 (s, 1H), 7.82 (d, J=13.3 Hz, 1H), 7.65 (s, 1H), 7.51-7.26 (m, 3H), 7.16 (s, 2H), 5.67 (s, 2H), 5.19 (s, 1H), 5.02 (s, 1H), 4.72 (s, 1H), 4.53 (s, 1H), 4.40 (s, 2H), 4.27 (s, 1H), 2.32 (s, 4H), 2.07 (s, 2H), 1.25 (s, 7H), 0.86 (s, 3H).

Example 87g: (5R,6S)-5-((R)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 8.11 (s, 1H), 7.66-7.61 (m, 2H), 7.40 (s, 1H), 7.26 (d, J=1.2 Hz, 1H), 7.20 (s, 1H), 5.62 (d, J=8.8 Hz, 1H), 5.30 (d, J=7.5 Hz, 1H), 4.66 (d, J=7.1 Hz, 1H), 4.48 (dd, J=12.2, 6.9 Hz, 2H), 4.21 (dd, J=15.3, 7.3 Hz, 2H), 2.56 (dd, J=11.3, 7.7 Hz, 1H), 2.30 (t, J=8.3 Hz, 1H), 1.91 (dd, J=11.3, 8.4 Hz, 1H).

Example 87h: (5S,6R)-5-((S)-5H-imidazo[5,1-a]isoindol-5-yl)-2-oxaspiro[3.3]heptan-6-ol: LCMS (ESI, m/z): 269.2 $[M+H]^+$; $^1$HNMR (500 MHz, DMSO-$d_6$) δ 8.12 (s, 1H), 7.67-7.60 (m, 2H), 7.40 (tt, J=7.7, 0.8 Hz, 1H), 7.26 (td, J=7.6, 1.1 Hz, 1H), 7.20 (s, 1H), 5.62 (d, J=8.7 Hz, 1H), 5.30 (d, J=7.6 Hz, 1H), 4.66 (d, J=7.0 Hz, 1H), 4.48 (dd, J=12.4, 6.9 Hz, 2H), 4.26-4.17 (m, 2H), 2.56 (dd, J=11.3, 7.6 Hz, 1H), 2.30 (t, J=8.4 Hz, 1H), 1.91 (dd, J=11.3, 8.4 Hz, 1H).

Example 88: 7-(5H-imidazo[5,1-a]isoindol-5-yl)-5,6,7,8-tetrahydroimidazo[1,2-a]pyridin-8-ol

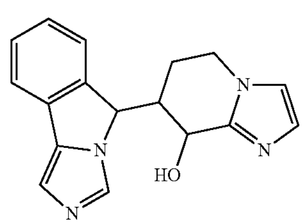 [SMILES: OC1c2nccn2CCC1C1c2ccccc2-c2cncn21]

(7R,8S)-7-((R)-5H-imidazo[5,1-a]isoindol-5-yl)-5,6,7,8-tetrahydroimidazo[1,2-a]pyridin-8-ol (7S,8S)-7-((R)-5H-imidazo[5,1-a]isoindol-5-yl)-5,6,7,8-tetrahydroimidazo[1,2-a]pyridin-8-ol (7S,8R)-7-((R)-5H-imidazo[5,1-a]isoindol-5-yl)-5,6,7,8-tetrahydroimidazo[1,2-a]pyridin-8-ol (7S,8R)-7-((S)-5H-imidazo[5,1-a]isoindol-5-yl)-5,6,7,8-tetrahydroimidazo[1,2-a]pyridin-8-ol (7R,8S)-7-((S)-5H-imidazo[5,1-a]isoindol-5-yl)-5,6,7,8-tetrahydroimidazo[1,2-a]pyridin-8-ol (7R,8R)-7-((R)-5H-imidazo[5,1-a]isoindol-5-yl)-5,6,7,8-tetrahydroimidazo[1,2-a]pyridin-8-ol (7R,8R)-7-((S)-5H-imidazo[5,1-a]isoindol-5-yl)-5,6,7,8-tetrahydroimidazo[1,2-a]pyridin-8-ol (7S,8S)-7-((S)-5H-imidazo[5,1-a]isoindol-5-yl)-5,6,7,8-tetrahydroimidazo[1,2-a]pyridin-8-ol Step 1: (E)-7-(2-(1-trityl-1H-imidazol-4-yl)benzylidene)-6,7-dihydroimidazo[1,2-a]pyridin-8(5H)-one

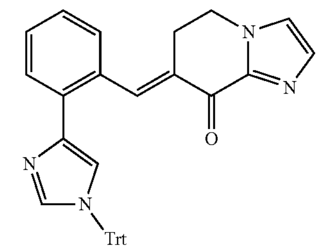

The title compound was synthesized by General Procedure for the Synthesis of Int-2. LCMS (ESI, m/z): 533.3 $[M+H]^+$ Step 2: 7-(5H-imidazo[5,1-a]isoindol-5-yl)-6,7-dihydroimidazo[1,2-a]pyridin-8(5H)-one

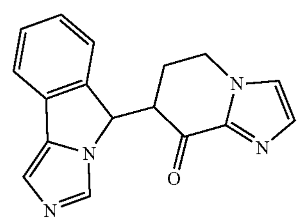 [SMILES: O=C1c2nccn2CCC1C1c2ccccc2-c2cncn21]

The title compound was synthesized by General Procedure for the Synthesis of Int-3. LCMS (ESI, m/z): 291.4 $[M+H]^+$ Step 3: 7-(5H-imidazo[5,1-a]isoindol-5-yl)-5,6,7,8-tetrahydroimidazo[1,2-a]pyridin-8-ol

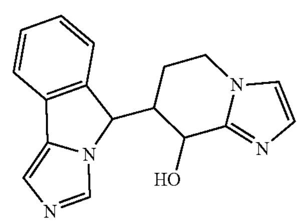 [SMILES: OC1c2nccn2CCC1C1c2ccccc2-c2cncn21]

The title compounds were synthesized by General Procedure for the Synthesis of Int-5: LCMS (ESI, m/z): 293.2 $[M+H]^+$. The mixture was isolated by Chiral separation methods and the configuration of the isomers was assigned arbitrarily.

(7R,8S)-7-((R)-5H-imidazo[5,1-a]isoindol-5-yl)-5,6,7,8-tetrahydroimidazo[1,2-a]pyridin-8-ol (7S,8S)-7-((R)-5H-imidazo[5,1-a]isoindol-5-yl)-5,6,7,8-tetrahydroimidazo[1,2-a]pyridin-8-ol (7S,8R)-7-((R)-5H-imidazo[5,1-a]isoindol-5-yl)-5,6,7,8-tetrahydroimidazo[1,2-a]pyridin-8-ol (7S,8R)-7-((S)-5H-imidazo[5,1-a]isoindol-5-yl)-5,6,7,8-tetrahydroimidazo[1,2-a]pyridin-8-ol (7R,8S)-7-((S)-5H-imidazo[5,1-a]isoindol-5-yl)-5,6,7,8-tetrahydroimidazo[1,2-a]pyridin-8-ol (7R,8R)-7-((R)-5H-imidazo[5,1-a]isoindol-5-yl)-5,6,7,8-tetrahydroimidazo[1,2-a]pyridin-8-ol (7R,8R)-7-((S)-5H-imidazo[5,1-a]isoindol-5-yl)-5,6,7,8-tetrahydroimidazo[1,2-a]pyridin-8-ol (7S,8S)-7-((S)-5H-imidazo[5,1-a]isoindol-5-yl)-5,6,7,8-tetrahydroimidazo[1,2-a]pyridin-8-ol 88a

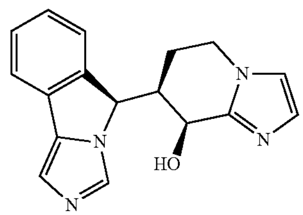

88b

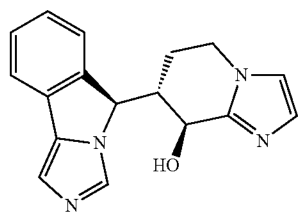

88c

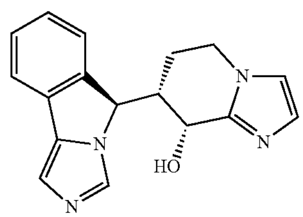

88d

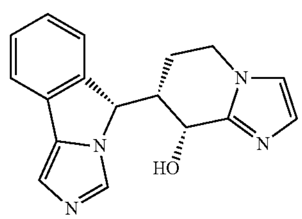

88e

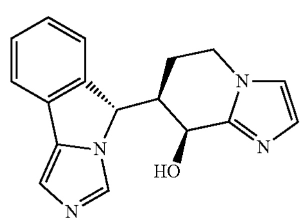

88f

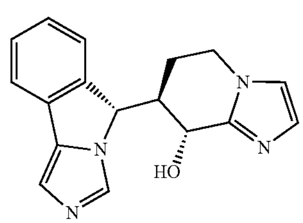

-continued

88g

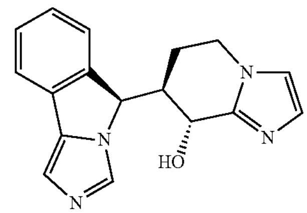

88h

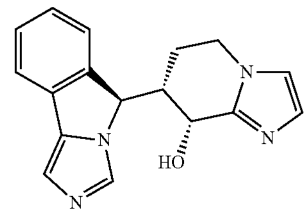

Example 88a: (7R,8S)-7-((R)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1H$ NMR (500 MHz, DMSO-$d_6$) δ 7.93 (s, 1H), 7.64 (d, J=7.6 Hz, 1H), 7.52 (d, J=7.7 Hz, 1H), 7.40 (t, J=7.5 Hz, 1H), 7.25 (td, J=7.6, 1.1 Hz, 1H), 7.17 (s, 1H), 6.96 (d, J=1.0 Hz, 1H), 6.90 (d, J=1.0 Hz, 1H), 6.11 (d, J=6.1 Hz, 1H), 5.75 (d, J=3.3 Hz, 1H), 4.90 (dd, J=10.1, 6.1 Hz, 1H), 3.85-3.62 (m, 2H), 2.83-2.68 (m, 1H), 1.11-1.07 (m, 1H), 1.04-0.99 (m, 1H).

Example 88b: (7S,8S)-7-((R)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1H$ NMR (500 MHz, DMSO-$d_6$) δ 7.96 (s, 1H), 7.67-7.63 (m, 1H), 7.60 (d, J=7.5 Hz, 1H), 7.40 (t, J=7.5 Hz, 1H), 7.29 (td, J=7.6, 1.1 Hz, 1H), 7.13 (s, 1H), 7.01 (d, J=1.1 Hz, 1H), 6.93 (d, J=1.1 Hz, 1H), 6.22 (d, J=4.9 Hz, 1H), 5.51 (d, J=2.2 Hz, 1H), 5.18-4.84 (m, 1H), 4.08-3.87 (m, 1H), 3.64 (td, J=12.5, 4.8 Hz, 1H), 2.62 (dd, J=12.6, 2.6 Hz, 1H), 1.81 (qd, J=12.8, 5.9 Hz, 1H), 1.16-1.00 (m, 1H).

Example 88c: (7S,8R)-7-((R)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1H$ NMR (500 MHz, DMSO-$d_6$) δ 7.90 (s, 1H), 7.64 (d, J=7.6 Hz, 1H), 7.51 (d, J=7.6 Hz, 1H), 7.42 (t, J=7.4 Hz, 1H), 7.33 (td, J=7.5, 1.0 Hz, 1H), 7.18 (s, 1H), 6.97 (d, J=0.9 Hz, 1H), 6.92 (d, J=0.9 Hz, 1H), 6.07 (d, J=6.6 Hz, 1H), 5.75 (s, 1H), 4.97 (dd, J=10.1, 6.6 Hz, 1H), 3.89-3.64 (m, 2H), 2.59 (dd, J=12.4, 4.4 Hz, 1H), 1.08-1.05 (m, 2H).

Example 88d: (7S,8R)-7-((S)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1H$ NMR (500 MHz, DMSO-$d_6$) δ 7.93 (s, 1H), 7.65 (d, J=7.6 Hz, 1H), 7.53 (d, J=7.7 Hz, 1H), 7.41 (t, J=7.5 Hz, 1H), 7.25 (t, J=7.6 Hz, 1H), 7.18 (s, 1H), 6.96 (s, 1H), 6.90 (s, 1H), 6.13 (d, J=6.1 Hz, 1H), 5.75 (d, J=3.2 Hz, 1H), 4.90 (dd, J=10.1, 6.1 Hz, 1H), 3.87-3.64 (m, 2H), 2.85-2.71 (m, 1H), 1.11-1.07 (m, 1H), 1.05-0.99 (m, 1H).

Example 88e: (7R,8S)-7-((S)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1H$ NMR (500 MHz, DMSO-$d_6$) δ 7.90 (s, 1H), 7.64 (d, J=7.5 Hz, 1H), 7.51 (d, J=7.5 Hz, 1H), 7.43 (t, J=7.5 Hz, 1H), 7.33 (t, J=7.5 Hz, 1H), 7.18 (s, 1H), 6.98 (s, 1H), 6.92 (s, 1H), 6.08 (d, J=6.6 Hz, 1H), 5.76 (s, 1H), 4.97 (dd, J=10.0, 6.6 Hz, 1H), 3.82-3.65 (m, 2H), 2.63 (s, 1H), 1.11-1.05 (m, 2H).

Example 88f: (7R,8R)-7-((R)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1$H NMR (500 MHz, DMSO-$d_6$) δ 8.00 (s, 1H), 7.76 (d, J=7.7 Hz, 1H), 7.63 (d, J=7.5 Hz, 1H), 7.40 (t, J=7.5 Hz, 1H), 7.26 (td, J=7.6, 1.1 Hz, 1H), 7.15 (s, 1H), 7.03 (d, J=1.0 Hz, 1H), 6.92 (d, J=1.1 Hz, 1H), 6.01 (d, J=5.1 Hz, 1H), 5.47 (d, J=6.0 Hz, 1H), 4.95-4.85 (m, 1H), 4.08 (dd, J=12.8, 4.6 Hz, 1H), 3.74 (td, J=12.4, 4.8 Hz, 1H), 2.34 (dd, J=6.1, 3.1 Hz, 1H), 2.21 (qd, J=12.8, 5.9 Hz, 1H), 1.81 (d, J=12.6 Hz, 1H).

Example 88g: (7R,8R)-7-((S)-5H-imidazo[5,1-a]isoindol-5-yl)-5,6,7,8-tetrahydroimidazo[1,2-a]pyridin-8-ol: LCMS (ESI, m/z): 293.2 $[M+H]^+$; $^1$H NMR (500 MHz, DMSO-$d_6$) δ 7.96 (s, 1H), 7.73-7.63 (m, 1H), 7.60 (d, J=7.5 Hz, 1H), 7.40 (t, J=7.5 Hz, 1H), 7.29 (td, J=7.6, 1.1 Hz, 1H), 7.13 (s, 1H), 7.01 (d, J=1.1 Hz, 1H), 6.93 (d, J=1.1 Hz, 1H), 6.22 (d, J=4.9 Hz, 1H), 5.51 (d, J=2.2 Hz, 1H), 5.25-4.88 (m, 1H), 4.05-3.87 (m, 1H), 3.64 (td, J=12.5, 4.8 Hz, 1H), 2.62 (dd, J=12.6, 2.6 Hz, 1H), 1.81 (qd, J=12.7, 5.9 Hz, 1H), 1.12 (dd, J=16.3, 2.1 Hz, 1H).

Example 88h: (7S,8S)-7-((S)-5H-imidazo[5,1-a]isoindol-5-yl)-5,6,7,8-tetrahydroimidazo[1,2-a]pyridin-8-ol: LCMS (ESI, m/z): 293.2 [M+H$^1$H NMR (500 MHz, DMSO-$d_6$) δ 7.99 (s, 1H), 7.75 (d, J=7.8 Hz, 1H), 7.62 (d, J=7.5 Hz, 1H), 7.40 (t, J=7.5 Hz, 1H), 7.25 (td, J=7.6, 1.1 Hz, 1H), 7.14 (s, 1H), 7.02 (d, J=1.1 Hz, 1H), 6.91 (d, J=1.1 Hz, 1H), 6.01 (d, J=5.1 Hz, 1H), 5.46 (d, J=6.0 Hz, 1H), 5.08-4.70 (m, 1H), 4.07 (dd, J=12.8, 4.4 Hz, 1H), 3.73 (td, J=12.5, 4.8 Hz, 1H), 2.33 (dd, J=6.1, 3.1 Hz, 1H), 2.20 (qd, J=12.8, 5.9 Hz, 1H), 1.80 (d, J=13.2 Hz, 1H).

Example 89: 4-(5H-imidazo[5,1-a]isoindol-5-yl)-1-(isopropylsulfonyl)piperidin-3-ol

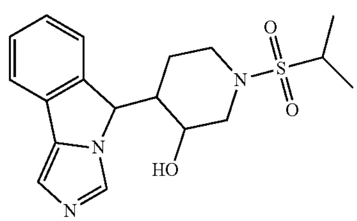 [SMILES: CC(C)S(=O)(=O)N1CCC(C2c3ccccc3-c3cncn32)C(O)C1]

The title compounds were synthesized by the same method of example 089a-b. The configuration two isomers was assigned arbitrarily (3R,4R)-4-((S)-5H-imidazo[5,1-a]isoindol-5-yl)-1-(isopropylsulfonyl)piperidin-3-ol (3S,4S)-4-((R)-5H-imidazo[5,1-a]isoindol-5-yl)-1-(isopropylsulfonyl)piperidin-3-ol 89a

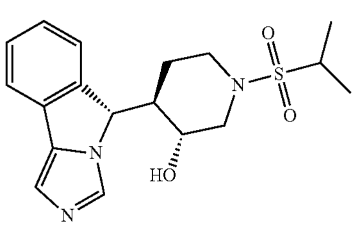

-continued

89b

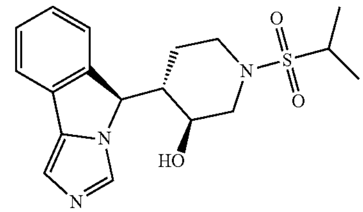

Example 89a: (3R,4R)-4-((S)-5H-imidazo[5,1-a]isoindol-5-yl)-1-(isopropylsulfonyl)piperidin-3-ol (36.0 mg, 15%) as a white solid: LCMS (ESI, m/z): 362.2 $[M+H]^+$. $^1$H NMR (300 MHz, $CD_3OD$) δ 7.91 (s, 1H), 7.65 (d, J=7.8 Hz, 1H), 7.55 (d, J=7.8 Hz, 1H), 7.45-7.32 (m, 2H), 7.17 (s, 1H), 5.83 (d, J=3.6 Hz, 1H), 4.01-3.85 (m, 2H), 3.58-3.52 (m, 1H), 3.27-3.22 (m, 1H), 2.82-2.70 (m, 2H), 2.42-2.28 (m, 1H), 1.27 (d, J=2.1 Hz, 6H), 0.82-0.58 (m, 2H). 89a and 89b are enantiomers.

Example 89b: (3S,4S)-4-((R)-5H-imidazo[5,1-a]isoindol-5-yl)-1-(isopropylsulfonyl)piperidin-3-ol (29.7 mg, 12%) as a white solid: LCMS (ESI, m/z): 362.2 $[M+H]^+$. 89a and 89b are enantiomers.

Example 90: 2-(5H-imidazo[5,1-a]isoindol-5-yl)-2,6,6-trimethylcyclohexan-1-ol

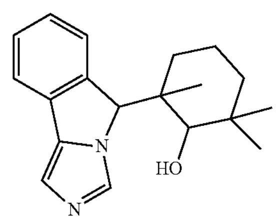

(1R,2R)-2-((S)-5H-imidazo[5,1-a]isoindol-5-yl)-2,6,6-trimethylcyclohexan-1-ol (1S,2S)-2-((R)-5H-imidazo[5,1-a]isoindol-5-yl)-2,6,6-trimethylcyclohexan-1-ol (1R,2S)-2-((S)-5H-imidazo[5,1-a]isoindol-5-yl)-2,6,6-trimethylcyclohexan-1-ol (1S,2R)-2-((R)-5H-imidazo[5,1-a]isoindol-5-yl)-2,6,6-trimethylcyclohexan-1-ol (1S,2R)-2-((S)-5H-imidazo[5,1-a]isoindol-5-yl)-2,6,6-trimethylcyclohexan-1-ol (1R,2S)-2-((R)-5H-imidazo[5,1-a]isoindol-5-yl)-2,6,6-trimethylcyclohexan-1-ol

Step 1: 2-(hydroxy (2-(1-trityl-1H-imidazol-4-yl) phenyl)methyl)-2,6,6-trimethylcyclohexan-1-one

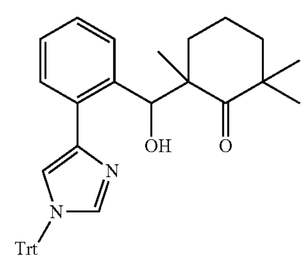

To a solution of Lithium diisopropylamide (2M, 4.8 mL, 9.6 mmol) in THF (50 mL) at −78° C. was added 2,2,6-trimethylcyclohexan-1-one (1.35 g, 9.6 mmol) dropwise. The reaction mixture was then warm up to room temperature and stirred for 40 min. $ZnCl_2$ solution (0.5 M, 19.3 mL) was added and the mixture was stirred for another 10 min before cool down to −78° C. 2-[1-(triphenylmethyl)-1H-imidazol-4-yl]benzaldehyde (2 g, 4.8 mmol) was added at −78° C. as a solution in THF (10 mL). After the reaction mixture had been stirred for 0.5 hr. The reaction was quenched by adding 10 mL of water followed by 30 mL of $NH_4Cl$ solution at −78° C. The reaction was extracted by EtOAc (30 mL×3). Combined organic phase was washed with brine and dried over $Na_2SO_4$. The product was purified over combi-flash using 20%-30% of EtOAc/Hex: LCMS (ESI, m/z): 555.7 $[M+H]^+$.

Step 2: 2-((2-(1H-imidazol-4-yl)phenyl)(hydroxy)methyl)-2,6,6-trimethylcyclohexan-1-one

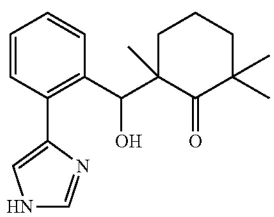 [SMILES: CC1(C)CCCC(C)(C(O)c2ccccc2-c2c[nH]cn2)C1=O]

To the solution of 2-(hydroxy (2-(1-trityl-1H-imidazol-4-yl)phenyl)methyl)-2,6,6-trimethylcyclohexan-1-one in MeOH (15 mL) was added acetic acid (6 mL) and the solution was heated at 90° C. for 3 hr. The solvent was removed under reduced pressure. The product was purified over combiflash using 4%-5% of MeOH/DCM: LCMS (ESI, m/z): 313.3 $[M+H]^+$.

Step 3: 2-(5H-imidazo[5,1-a]isoindol-5-yl)-2,6,6-trimethylcyclohexan-1-one

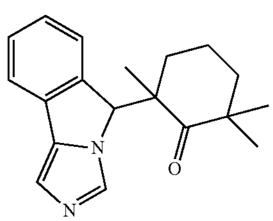 [SMILES: CC1(C)CCCC(C)(C2c3ccccc3-c3cncn32)C1=O]

To a solution of 2-(5H-imidazo[5,1-a]isoindol-5-yl)-2,6,6-trimethylcyclohexan-1-one (1.1 g, 3.52 mmol) in THF (50 mL) at 0° C. was added triphenylphosphine (1.85 g, 7.04 mmol) followed by the addition of diisopropyl (E)-diazene-1,2-dicarboxylate (1.38 mL, 7.04 mmol) and the solution was allowed to warm to 25° C. After stirring at 25° C. for 2 hr the reaction was quenched by adding saturated $NaHCO_3$ solution. The product was extracted with DCM (3×50 mL). The combined organic extract was dried over $Na_2SO_4$ and concentrated under reduced pressure to afford the crude product and further purified on silica gel column chromatography (MeOH/DCM=1%-2%): LCMS (ESI, m/z): 296.3 $[M+H]^+$.

Step 4:

(1R,2R)-2-((S)-5H-imidazo[5,1-a]isoindol-5-yl)-2,6,6-trimethylcyclohexan-1-ol (1S,2S)-2-((R)-5H-imidazo[5,1-a]isoindol-5-yl)-2,6,6-trimethylcyclohexan-1-ol (1R,2S)-2-((S)-5H-imidazo[5,1-a]isoindol-5-yl)-2,6,6-trimethylcyclohexan-1-ol (1S,2R)-2-((R)-5H-imidazo[5,1-a]isoindol-5-yl)-2,6,6-trimethylcyclohexan-1-ol (1S,2R)-2-((S)-5H-imidazo[5,1-a]isoindol-5-yl)-2,6,6-trimethylcyclohexan-1-ol (1R,2S)-2-((R)-5H-imidazo[5,1-a]isoindol-5-yl)-2,6,6-trimethylcyclohexan-1-ol 90a

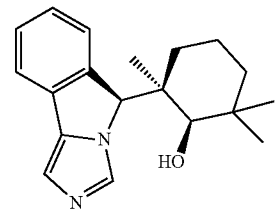

90b

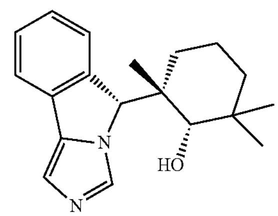

90c

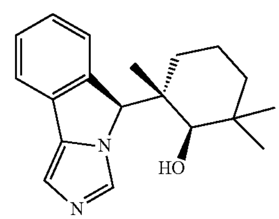

90d

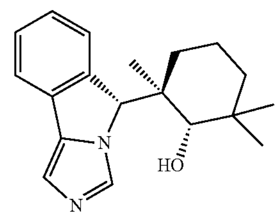

90e

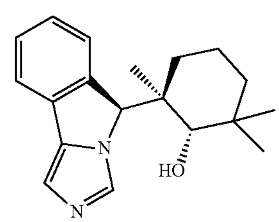

-continued

90f

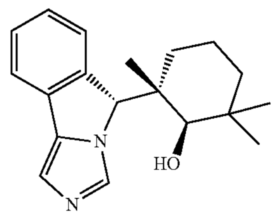

To a solution of 2-(5H-imidazo[5,1-a]isoindol-5-yl)-2,6,6-trimethylcyclohexan-1-one (1.06 g, 3.50 mmol) in MeOH (25 mL) was added $NaBH_4$ (280 mg, 7.40 mmol) in portions at 0° C. and the solution was stirred at 0° C. for 2 hr. The solvent was distilled off and saturated ammonium chloride (20 mL) was added. The aqueous layer was extracted with DCM (3×20 mL). The combined organic extract was dried over ($Na_2SO_4$) and concentrated under reduced pressure to afford the crude product. The crude product was purified by Combi-Flash and further isolated by chiral separation to afford 6 isomers as white solid. The absolute configuration of all isomers was assigned arbitrarily.

Example 90a: (1R,2R)-2-((S)-5H-imidazo[5,1-a]isoindol-5-yl)-2,6,6-trimethylcyclohexan-1-ol: LCMS (ESI, m/z): 297.5 $[M+H]^+$. $^1H$ NMR is the same as Example 90b.

Example 90b: (1S,2S)-2-((R)-5H-imidazo[5,1-a]isoindol-5-yl)-2,6,6-trimethylcyclohexan-1-ol LCMS (ESI, m/z): 297.5 $[M+H]^+$. $^1H$ NMR (500 MHz, DMSO-$d_6$) δ 7.92 (s, 1H), 7.63-7.52 (m, 2H), 7.36 (ddd, J=7.6, 7.0, 0.9 Hz, 1H), 7.21 (td, J=7.6, 1.3 Hz, 1H), 7.12 (s, 1H), 5.30 (s, 1H), 5.03 (d, J=6.2 Hz, 1H), 3.36 (d, J=6.1 Hz, 1H), 1.31 (s, 5H), 1.08 (dt, J=13.8, 3.5 Hz, 1H), 0.97 (d, J=7.2 Hz, 6H), 0.82 (td, J=13.8, 3.7 Hz, 1H), 0.59 (dd, J=13.2, 2.7 Hz, 1H), 0.24 (td, J=13.3, 4.0 Hz, 1H).

Example 90c: (1R,2S)-2-((S)-5H-imidazo[5,1-a]isoindol-5-yl)-2,6,6-trimethylcyclohexan-1-ol: LCMS (ESI, m/z): 297.5 $[M+H]^+$. $^1H$ NMR (500 MHz, DMSO-$d_6$) δ 7.94 (s, 1H), 7.66 (d, J=7.8 Hz, 1H), 7.57 (d, J=7.4 Hz, 1H), 7.38 (t, J=7.6 Hz, 1H), 7.25 (td, J=7.6, 1.2 Hz, 1H), 7.12 (s, 1H), 5.31 (s, 1H), 4.90 (d, J=6.1 Hz, 1H), 3.41 (d, J=6.0 Hz, 1H), 1.28 (s, 6H), 1.14-1.07 (m, 1H), 0.93 (d, J=18.0 Hz, 6H), 0.78 (td, J=13.5, 3.8 Hz, 1H), 0.53 (dd, J=13.0, 2.7 Hz, 1H), 0.39 (td, J=13.3, 4.0 Hz, 1H).

Example 90d: (1S,2R)-2-((R)-5H-imidazo[5,1-a]isoindol-5-yl)-2,6,6-trimethylcyclohexan-1-ol LCMS (ESI, m/z): 297.5 $[M+H]^+$. $^1H$ NMR is the same as Example 90c Example 90e: (1S,2R)-2-((S)-5H-imidazo[5,1-a]isoindol-5-yl)-2,6,6-trimethylcyclohexan-1-ol: LCMS (ESI, m/z): 297.5 $[M+H]^+$. No $^1H$ NMR data Example 90f: (1R,2S)-2-((R)-5H-imidazo[5,1-a]isoindol-5-yl)-2,6,6-trimethylcyclohexan-1-ol: LCMS (ESI, m/z): 297.5 $[M+H]^+$. No $^1H$ NMR data

Example 91: 3-(5H-imidazo[5,1-a]isoindol-5-yl)-7-(methylsulfonyl)chroman-4-ol

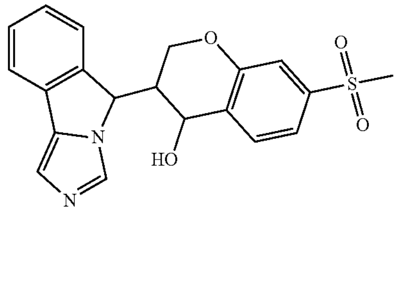 [SMILES: CS(=O)(=O)c1ccc2c(c1)OCC(C1c3ccccc3-c3cncn31)C2O]

Step 1: 7-(methylthio)chroman-4-one

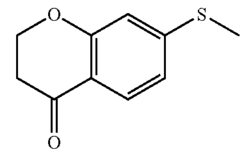

Under nitrogen, a mixture of 7-bromo-3,4-dihydro-2H-1-benzopyran-4-ol (3 g, 13.10 mmol), DIPEA (5.1 g, 39.460 mmol, 3.013 equiv), $Pd_2(dba)_3CHCl_3$ (1.35 g, 1.30 mmol), XantPhos (760 mg, 1.31 mmol) and (methylsulfanyl) sodium (1.39 g, 19.86 mmol) in toluene (100 mL) was stirred for 3 h at 110° C. in an oil bath. The solids were filtered out. The resulting mixture was concentrated under vacuum. The residue was purified by a silica gel column eluting with EtOAc/petroleum ether (1:9). This resulted in 1.8 g (70%) of 7-(methylsulfanyl)-3,4-dihydro-2H-1-benzopyran-4-ol as yellow oil.

Step 2: (E)-7-(methylthio)-3-(2-(1-trityl-1H-imidazol-4-yl)benzylidene)chroman-4-one

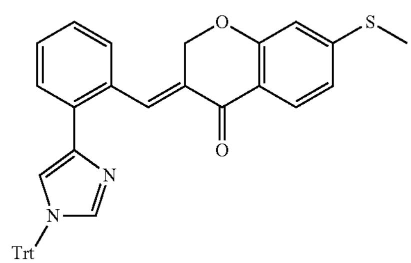

The title compound was synthesized by General Procedure for the Synthesis of Int-2: LCMS (ESI, m/z): 591.0 $[M+H]^+$.

Step 3: 3-(5H-imidazo[5,1-a]isoindol-5-yl)-7-(methylthio)chroman-4-one

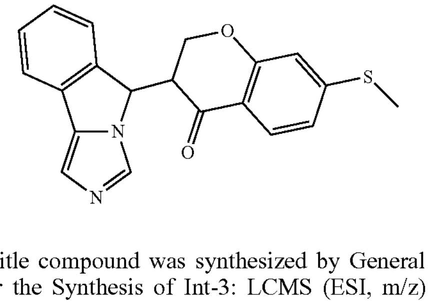

The title compound was synthesized by General Procedure for the Synthesis of Int-3: LCMS (ESI, m/z): 349.3 $[M+H]^+$.

Step 4: 3-(5H-imidazo[5,1-a]isoindol-5-yl)-7-(methylthio)chroman-4-ol

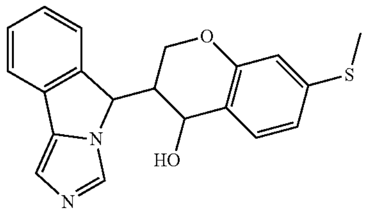 [SMILES: CSc1ccc2c(c1)OCC(C1c3ccccc3-c3cncn31)C2O]

The title compound was synthesized by General Procedure for the Synthesis of Int-6: LCMS (ESI, m/z): 351.3 $[M+H]^+$.

(3S,4S)-3-((R)-5H-imidazo[5,1-a]isoindol-5-yl)-7-(methylsulfonyl)chroman-4-ol (3R,4R)-3-((S)-5H-imidazo[5,1-a]isoindol-5-yl)-7-(methylsulfonyl)chroman-4-ol (3R,4S)-3-((R)-5H-imidazo[5,1-a]isoindol-5-yl)-7-(methylsulfonyl)chroman-4-ol (3S,4R)-3-((S)-5H-imidazo[5,1-a]isoindol-5-yl)-7-(methylsulfonyl)chroman-4-ol (3R,4R)-3-((R)-5H-imidazo[5,1-a]isoindol-5-yl)-7-(methylsulfonyl)chroman-4-ol (3S,4S)-3-((S)-5H-imidazo[5,1-a]isoindol-5-yl)-7-(methylsulfonyl)chroman-4-ol (3S,4R)-3-((R)-5H-imidazo[5,1-a]isoindol-5-yl)-7-(methylsulfonyl)chroman-4-ol (3R,4S)-3-((S)-5H-imidazo[5,1-a]isoindol-5-yl)-7-(methylsulfonyl)chroman-4-ol 91a

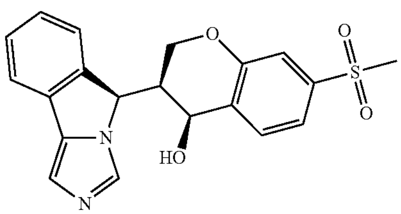

91b

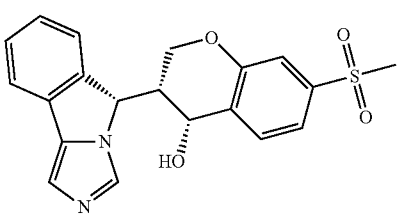

91c

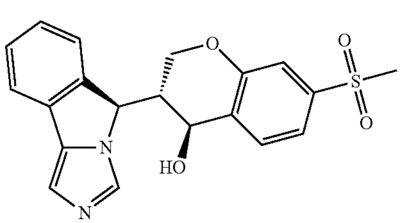

-continued

091d

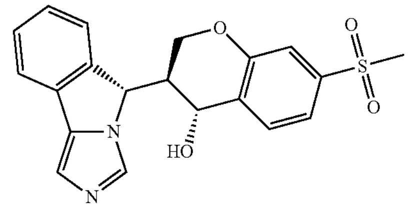

91e

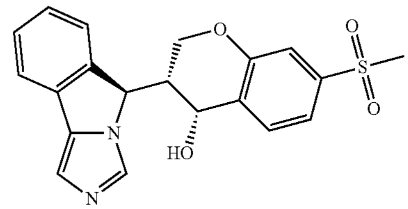

91f

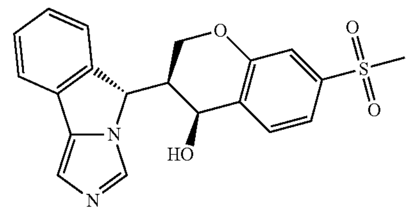

91g

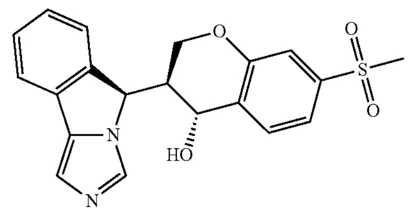

091h

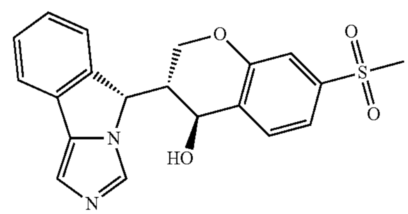

A solution of 3-[5H-imidazo[4,3-a]isoindol-5-yl]-7-(methylsulfanyl)-3,4-dihydro-2H-1-benzopyran-4-ol (1.2 g, 3.42 mmol) in DCM (20 mL) was added MCPBA (1.2 g, 6.95 mmol). The resulting solution was stirred for 3 h at room temperature. The pH value of the solution was adjusted to 7 with Sat. sodium bicarbonate. The resulting solution was extracted with EtOAc. The organic layers were combined, dried over anhydrous sodium sulfate, and concentrated under vacuum. The crude product was purified eluting with DCM/MeOH (90:10). And then further isolated by Prep-HPLC and Chiral-Prep-HPLC with the following conditions:

1. Column, XBridge Shield RP18 OBD Column, 5 um, 19×150 mm; mobile phase, Waters (0.05% $NH_3H_2O$) and ACN (15.0% ACN up to 40.0% in 12 min); Detector, UV 220 nm.
2. Column, CHIRAL ART Cellulose-SB, 250×20 mm I.D.; mobile phase, Hex- and ethanol-(hold 35.0% ethanol-in 21 min); Detector, UV 254/220 nm.

The absolute configuration of all isomers 091a-h was assigned arbitrarily.

Example 91a: (3S,4S)-3-((R)-5H-imidazo[5,1-a]isoindol-5-yl)-7-(methylsulfonyl)chroman-4-ol (14.2 mg, 9%) as a white solid: LCMS (ESI, m/z): 383.0 [M+H]+. $^1$H NMR (400 MHz, $CDCl_3$) δ 7.97 (s, 1H), 7.70 (d, J=8.1 Hz, 1H), 7.62 (d, J=7.6 Hz, 1H), 7.59-7.42 (m, 3H), 7.36-7.27 (m, 2H) 7.18 (s, 1H), 5.60 (d, J=4.2 Hz, 1H), 5.03 (d, J=8.0 Hz, 1H), 4.01-3.89 (m, 2H), 3.02 (s, 3H), 2.83-2.75 (m, 1H). tR=8.606 min (CHIRAL Cellulose-SB, 0.46×15 cm, 3 um; Hex(0.1% DEA):EtOH=70:30, 1.0 ml/min). 91a and 91b are enantiomers.

Example 91b: (3R,4R)-3-((S)-5H-imidazo[5,1-a]isoindol-5-yl)-7-(methylsulfonyl)chroman-4-ol (13.9 mg, 8%) as a white solid: LCMS (ESI, m/z): 383.0 [M+H]+. tR=10.172 min (CHIRAL Cellulose-SB, 0.46×15 cm, 3 um; Hex(0.1% DEA):EtOH=70:30, 1.0 ml/min). 91a and 91b are enantiomers.

Example 91c: (3R,4S)-3-((R)-5H-imidazo[5,1-a]isoindol-5-yl)-7-(methylsulfonyl)chroman-4-ol (5.2 mg, 3%) as a white solid: LCMS (ESI, m/z): 383.0 [M+H]+. $^1$H NMR (400 MHz, $CDCl_3$) δ 8.31 (s, 1H), 7.82 (d, J=8.1 Hz, 1H), 7.61 (d, J=7.4 Hz, 1H), 7.59-7.43 (m, 3H), 7.37-7.24 (m, 3H), 5.87 (d, J=3.0 Hz, 1H), 5.19 (d, J=9.9 Hz, 1H), 3.82-3.77 (m, 1H), 3.55 (t, J=11.0 Hz, 1H), 3.02 (s, 3H), 2.85-2.76 (m, 1H). tR=8.606 min (CHIRALPAK IA-3, 0.46×5 cm; 3 um; Hex(0.1% DEA):EtOH=65:35, 1.0 ml/min). 91a and 91b are enantiomers.

Example 91d: (3S,4R)-3-((S)-5H-imidazo[5,1-a]isoindol-5-yl)-7-(methylsulfonyl)chroman-4-ol (2.9 mg, 2%) as a white solid: LCMS (ESI, m/z): 383.0 [M+H]+. tR=3.482 min (CHIRALPAK IA-3, 0.46×5 cm; 3 um; Hex(0.1% DEA):EtOH=65:35, 1.0 ml/min). 91c and 91d are enantiomers.

Example 91e: (3R,4R)-3-((R)-5H-imidazo[5,1-a]isoindol-5-yl)-7-(methylsulfonyl)chroman-4-ol (26.9 mg, 16%) as a white solid: LCMS (ESI, m/z): 383.0 [M+H]+. $^1$H NMR (400 MHz, $CDCl_3$) δ 8.02 (s, 1H), 7.68-7.57 (m, 3H), 7.46-7.38 (m, 2H), 7.28-7.21 (m, 2H), 7.16 (s, 1H), 6.13 (d, J=5.5 Hz, 1H), 5.53 (d, J=6.4 Hz, 1H), 4.84 (dd, J=5.4, 3.6 Hz, 1H), 4.38-4.26 (m, 2H), 3.19 (s, 3H), 2.54 (dd, J=7.0, 3.5 Hz, 1H). tR=5.875 min (CHIRAL Cellulose-SB, 0.46×15 cm, 3 um; Hex(0.1% DEA):EtOH=50:50, 1.0 ml/min). 91e and 91f are enantiomers.

Example 91f: (3S,4S)-3-((S)-5H-imidazo[5,1-a]isoindol-5-yl)-7-(methylsulfonyl)chroman-4-ol (24.3 mg, 15%) as a white solid: LCMS (ESI, m/z): 383.0 [M+H]+. tR=6.560 min (CHIRAL Cellulose-SB, 0.46×15 cm, 3 um; Hex(0.1% DEA):EtOH=50:50, 1.0 ml/min). 91e and 91f are enantiomers.

Example 91g: (3S,4R)-3-((R)-5H-imidazo[5,1-a]isoindol-5-yl)-7-(methylsulfonyl)chroman-4-ol (45.7 mg, 28%) as a white solid: LCMS (ESI, m/z): 383.0 [M+H]+. $^1$H NMR (400 MHz, $CDCl_3$) δ 7.92 (s, 1H), 7.67 (d, J=8.0 Hz, 1H), 7.55-7.50 (m, 2H), 7.44-7.37 (m, 3H), 7.33-7.28 (m, 1H), 6.91 (s, 1H), 5.58 (s, 1H), 5.17 (d, J=3.0 Hz, 1H), 3.76 (t, J=11.2 Hz, 1H), 3.60 (dd, J=10.9, 3.4 Hz, 1H), 3.04 (s, 3H), 2.73-2.68 (m, 1H). tR=2.241 min (CHIRALPAK IA-3, 0.46×15 cm, 3 um; Hex(0.1% DEA):EtOH=50:50, 1.0 ml/min). 091g and 091h are enantiomers.

Example 91h: (3R,4S)-3-((S)-5H-imidazo[5,1-a]isoindol-5-yl)-7-(methylsulfonyl)chroman-4-ol (51.8 mg, 32%) as a white solid: LCMS (ESI, m/z): 383.0 [M+H]+. tR=2.971 min (CHIRALPAK IA-3, 0.46×15 cm, 3 um; Hex(0.1% DEA):EtOH=50:50, 1.0 ml/min). 91g and 91h are enantiomers.

Example 92: 5-(5H-imidazo[5,1-a]isoindol-5-yl)-1-(methylsulfonyl)azepan-4-ol

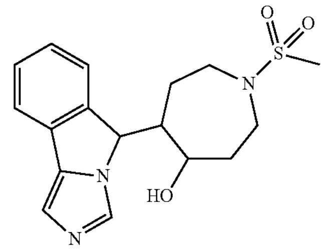 [SMILES: CS(=O)(=O)N1CCC(O)C(C2c3ccccc3-c3cncn32)CC1]

(4R,5S)-5-((S)-5H-imidazo[5,1-a]isoindol-5-yl)-1-(methylsulfonyl)azepan-4-ol
(4S,5R)-5-((R)-5H-imidazo[5,1-a]isoindol-5-yl)-1-(methylsulfonyl)azepan-4-ol
(4R,5S)-5-((R)-5H-imidazo[5,1-a]isoindol-5-yl)-1-(methylsulfonyl)azepan-4-ol
(4S,5R)-5-((S)-5H-imidazo[5,1-a]isoindol-5-yl)-1-(methylsulfonyl)azepan-4-ol Synthetic Route

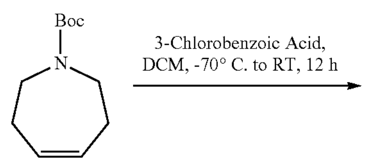

1.

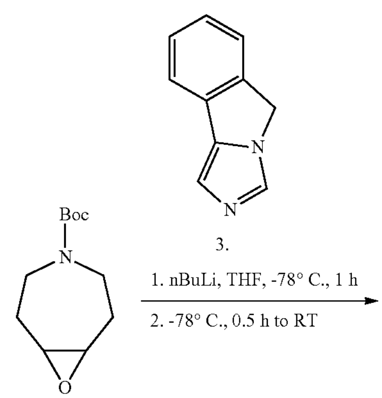

3.

2.

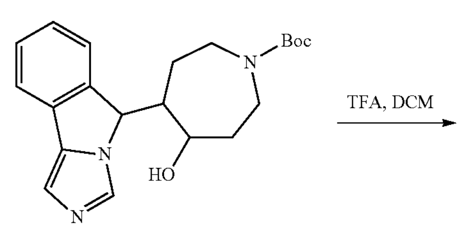

4.

-continued

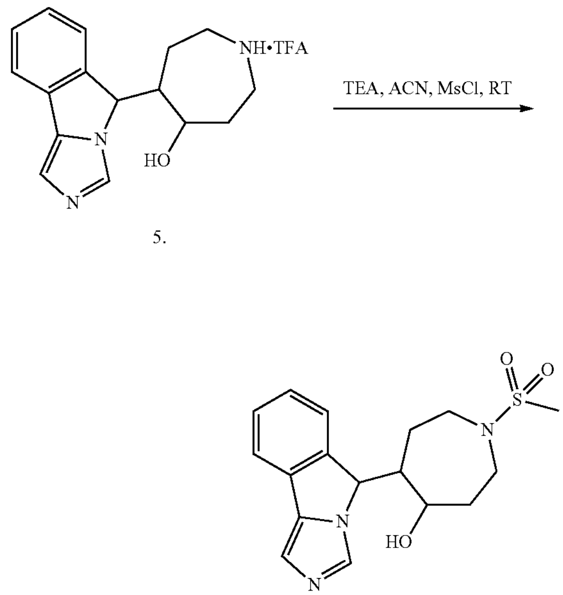

5.

Step 1: tert-butyl 8-oxa-4-azabicyclo[5.1.0]octane-4-carboxylate

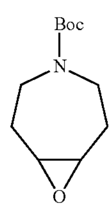 [SMILES: CC(C)(C)OC(=O)N1CCC2OC2CC1]

To a solution of tert-butyl 2,3,6,7-tetrahydroazepine-1-carboxylate (1, 4.23 g, 21.4 mmol, 100 mass %) in dichlormethane (100 mL, 1560 mmol, 100 mass %) at −70° C. under nitrogen was added 3-Chloroperoxybenzoic acid (9.7 g, 43 mmol, 77 mass %) as a solid. This was the stirred overnight under nitrogen, warming to room temperature in the process. Reaction filtered to remove the solids and the filtrate concentrated under reduced pressure to give a waxy white solid. This was then dissolved in 150 mL dichloromethane and washed with 200 mL 1N Sodium Carbonate solution. The organic layer was then dried with sodium sulfate filtered and concentrated to give a pale yellow oil. This was then concentrated dissolved in 35 ml dichloromethane and purified by flash column to afford tert-butyl 8-oxa-4-azabicyclo[5.1.0]octane-4-carboxylate as a clear oil (3.87 g). $^1$H NMR (400 MHz, Chloroform-d) δ 3.78 (dd, J=57.6, 14.2 Hz, 2H), 3.22-3.15 (m, 2H), 2.81-2.65 (m, 2H), 2.23-2.04 (m, 4H), 1.45 (s, 9H).

Step 2: tert-butyl 4-hydroxy-5-(5H-imidazo[5,1-a]isoindol-5-yl)azepane-1-carboxylate

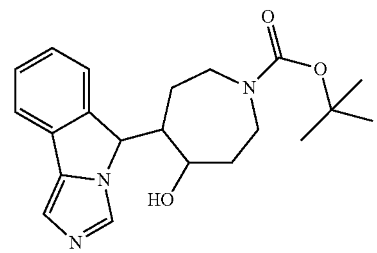 [SMILES: CC(C)(C)OC(=O)N1CCC(O)C(C2c3ccccc3-c3cncn32)CC1]

To a solution of 5H-imidazo[5,1-a]isoindole (3, 1.9 g, 12 mmol, 100 mass %) in tetrahydrofuran (40 mL, 491 mmol, 100 mass %) under nitrogen atmosphere at −78° C. was added dropwise n-BuLi (2.5 mol/L) in hexanes (5.0 mL, 13 mmol, 2.5 mol/L) over 3-4 mins. This was then stirred at −78° C. under nitrogen for 60 minutes. To this at −78° C. under nitrogen was added dropwise over 3 minutes tert-butyl 8-oxa-4-azabicyclo[5.1.0]octane-4-carboxylate (2, 2.495 g, 11.70 mmol, 100 mass %) in tetrahydrofuran (6 mL, 73.7 mmol, 100 mass %). This was then stirred at −78° C. for 30 minutes under nitrogen. The reaction was then warmed to room temperature under nitrogen. After 2 hours the reaction was quenched with saturated ammonium chloride solution (10 mL) and extracted with ethyl acetate (2×50 mL). The combined organic layers were dried with magnesium sulfate, filtered. This was then concentrated under reduced pressure and the residue purified by flash column to afford tert-butyl 4-hydroxy-5-(5H-imidazo[5,1-a]isoindol-5-yl)azepane-1-carboxylate as a off white foamy solid (2.96 g): LCMS (ESI, m/z): 370 [M+H]$^+$.

Step 3: 5-(5H-imidazo[5,1-a]isoindol-5-yl)azepan-4-ol

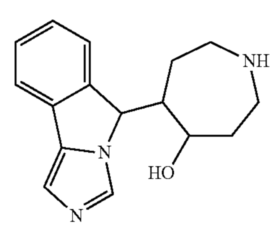 [SMILES: OC1CCNCCC1C1c2ccccc2-c2cncn21]

To a solution of tert-butyl 4-hydroxy-5-(5H-imidazo[1,5-b]isoindol-5-yl)azepane-1-carboxylate (4, 822 mg, 2.225 mmol, 100 mass %) in dichloromethane (20 mL, 312.0 mmol, 100 mass %) was added trifluroroacetic acid (5 mL, 66.13 mmol, 100 mass %) and stirred at room temperature for 45 minutes. The reaction was then concentrated under reduced pressure and used as a TFA salt for the next step: LCMS (ESI, m/z): 270 [M+H]$^+$.

Step 4: 5-(5H-imidazo[5,1-a]isoindol-5-yl)-1-(methylsulfonyl)azepan-4-ol

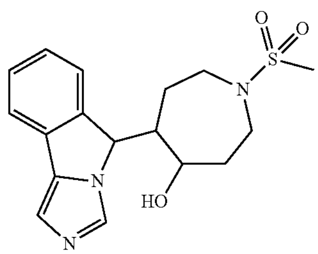

92a-d

To a solution of 5-(5H-imidazo[1,5-b]isoindol-5-yl)azepan-4-ol; 2,2,2-trifluoroperoxyacetic acid (5, 2.22 mmol, 2.22 mmol, 100 mass %) in acetonitrile (30 mL, 572 mmol, 100 mass %) was added triethylamine (5 mL, 35.9 mmol, 100 mass %). This was then stirred for 5 minute. To this was added dropwise with stirring methanesulfonyl chloride (0.26 mL, 3.3 mmol, 100 mass %). This was then stirred at room temperature for 72 h. Reaction concentrated under reduced pressure and purified by flash column to afford 5-(5H-imidazo[5,1-a]isoindol-5-yl)-1-(methylsulfonyl)azepan-4-ol. This was then purified and individual isomers were separated by chiral separation (SFC, Column, Whelko-01, 150×21.2 mm; mobile phase: $CO_2$:methanol=70:30; Isocratic, Detector, uv 270 nm; flow rate 70 mL/min, 40° C.) to afford 4 isomers.

Example 92a: LCMS (ESI, m/z): 348.1 $[M+H]^+$. $^1H$ NMR (400 MHz, DMSO-$d_6$) δ 7.81 (s, 1H), 7.61 (d, J=7.4 Hz, 1H), 7.46 (d, J=7.5 Hz, 1H), 7.40 (t, J=7.5 Hz, 1H), 7.31 (td, J=7.5, 1.2 Hz, 1H), 7.16 (s, 1H), 5.77-5.74 (m, 1H), 5.45 (d, J=5.8 Hz, 1H), 3.86 (tdd, J=9.9, 5.8, 3.9 Hz, 1H), 3.42-3.36 (m, 1H), 3.12-3.02 (m, 2H), 2.87 (ddd, J=12.9, 10.5, 4.6 Hz, 1H), 2.77 (s, 3H), 2.34-2.28 (m, 1H), 2.21-2.13 (m, 1H), 1.85-1.75 (m, 1H), 0.78-0.65 (m, 2H).

Example 92b: LCMS (ESI, m/z): 348.1 $[M+H]^+$. $^1H$ NMR (400 MHz, DMSO-$d_6$) δ 7.81 (s, 1H), 7.61 (d, J=7.5 Hz, 1H), 7.46 (dd, J=7.6, 1.1 Hz, 1H), 7.40 (t, J=7.4 Hz, 1H), 7.33-7.29 (m, 1H), 7.16 (s, 1H), 5.76-5.74 (m, 1H), 5.45 (d, J=5.8 Hz, 1H), 3.86 (dt, J=9.9, 5.9 Hz, 1H), 3.41-3.36 (m, 1H), 3.10-3.02 (m, 2H), 2.91-2.84 (m, 1H), 2.78 (s, 3H), 2.36-2.29 (m, 1H), 2.18 (ddd, J=11.1, 5.7, 3.2 Hz, 1H), 1.85-1.76 (m, 1H), 0.77-0.67 (m, 2H).

Example 92c: LCMS (ESI, m/z): 348.1 $[M+H]^+$. $^1H$ NMR (400 MHz, DMSO-$d_6$) δ 7.91 (s, 1H), 7.62 (d, J=7.5 Hz, 1H), 7.55 (d, J=7.5 Hz, 1H), 7.40 (t, J=7.5 Hz, 1H), 7.28 (td, J=7.6, 1.2 Hz, 1H), 7.15 (s, 1H), 5.76 (d, J=3.6 Hz, 1H), 5.40 (d, J=5.2 Hz, 1H), 3.83 (dt, J=9.9, 4.9 Hz, 1H), 3.40-3.34 (m, 1H), 3.11-3.02 (m, 2H), 2.92-2.84 (m, 1H), 2.77 (s, 3H), 2.17-2.11 (m, 1H), 1.82-1.73 (m, 1H), 0.77-0.68 (m, 1H), 0.62-0.56 (m, 1H).

Example 92d: LCMS (ESI, m/z): 348.1 $[M+H]^+$. $^1H$ NMR (400 MHz, DMSO-$d_6$) δ 7.91 (s, 1H), 7.62 (d, J=7.5 Hz, 1H), 7.56-7.53 (m, 1H), 7.40 (t, J=7.5 Hz, 1H), 7.28 (td, J=7.6, 1.2 Hz, 1H), 7.15 (s, 1H), 5.76 (d, J=3.8 Hz, 1H), 5.40 (d, J=5.3 Hz, 1H), 3.83 (dt, J=9.9, 5.1 Hz, 1H), 3.39-3.34 (m, 1H), 3.11-3.02 (m, 2H), 2.92-2.85 (m, 1H), 2.77 (s, 3H), 2.14 (ddt, J=12.1, 6.3, 3.3 Hz, 1H), 1.82-1.74 (m, 1H), 0.76-0.67 (m, 1H), 0.62-0.55 (m, 1H).

Example 93: 5-(5H-imidazo[5,1-a]isoindol-5-yl)-1-methyl-4,5,6,7-tetrahydro-1H-indazol-4-ol

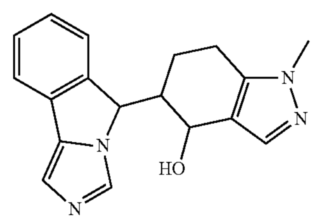 [SMILES: Cn1ncc2c1CCC(C1c3ccccc3-c3cncn31)C2O]

(4S,5S)-5-((S)-5H-imidazo[5,1-a]isoindol-5-yl)-1-methyl-4,5,6,7-tetrahydro-1H-indazol-4-ol (4R,5S)-5-((S)-5H-imidazo[5,1-a]isoindol-5-yl)-1-methyl-4,5,6,7-tetrahydro-1H-indazol-4-ol (4R,5R)-5-((S)-5H-imidazo[5,1-a]isoindol-5-yl)-1-methyl-4,5,6,7-tetrahydro-1H-indazol-4-ol (4S,5R)-5-((R)-5H-imidazo[5,1-a]isoindol-5-yl)-1-methyl-4,5,6,7-tetrahydro-1H-indazol-4-ol (4R,5R)-5-((R)-5H-imidazo[5,1-a]isoindol-5-yl)-1-methyl-4,5,6,7-tetrahydro-1H-indazol-4-ol (4S,5S)-5-((R)-5H-imidazo[5,1-a]isoindol-5-yl)-1-methyl-4,5,6,7-tetrahydro-1H-indazol-4-ol (4S,5R)-5-((S)-5H-imidazo[5,1-a]isoindol-5-yl)-1-methyl-4,5,6,7-tetrahydro-1H-indazol-4-ol The title compound was synthesized by the same method of example 88.

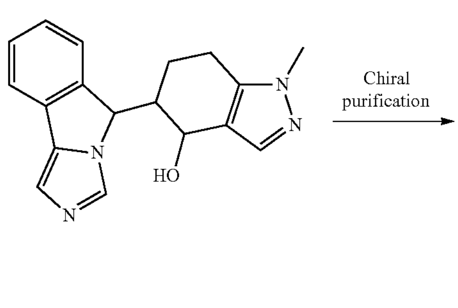

-continued

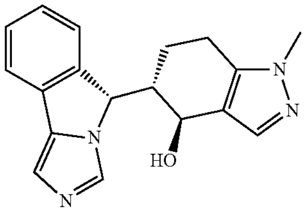

93a

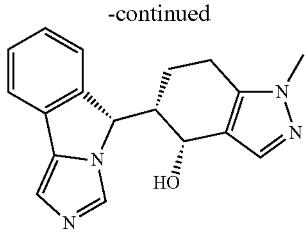

93b

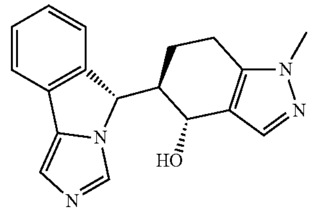

93c

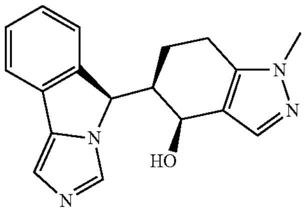

93d

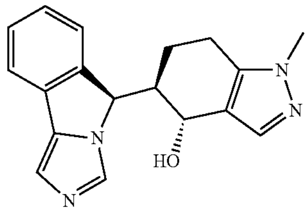

93e

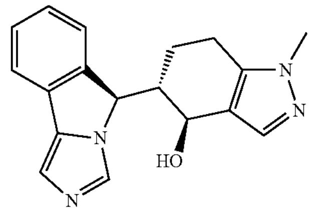

93f

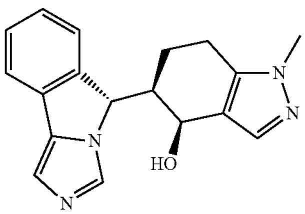

93g

The configurations of the isomers were assigned arbitrarily.

Example 93a: (4S,5S)-5-((S)-5H-imidazo[5,1-a]isoindol-5-yl)-1-methyl-4,5,6,7-tetrahydro-1H-indazol-4-ol: LCMS (ESI, m/z): 307.1 $[M+H]^+$; $^1H$ NMR (500 MHz, DMSO-$d_6$) δ 7.92 (s, 1H), 7.63 (d, J=7.5 Hz, 1H), 7.45 (d, J=7.6 Hz, 1H), 7.43-7.29 (m, 3H), 7.17 (s, 1H), 5.76 (s, 1H), 5.62 (d, J=7.1 Hz, 1H), 4.92 (d, J=8.0 Hz, 1H), 3.58 (s, 3H), 2.44 (dd, J=16.2, 5.4 Hz, 1H), 2.36-2.25 (m, 1H), 2.20 (td, J=11.9, 2.5 Hz, 1H), 0.96-0.79 (m, 2H). 93a and 93e are enantiomers.

Example 93b: (4R,5S)-5-((S)-5H-imidazo[5,1-a]isoindol-5-yl)-1-methyl-4,5,6,7-tetrahydro-1H-indazol-4-ol: LCMS (ESI, m/z): 307.1 $[M+H]^+$; $^1H$ NMR (500 MHz, DMSO-$d_6$) δ 7.95 (s, 1H), 7.77 (dt, J=7.8, 1.0 Hz, 1H), 7.60 (dt, J=7.5, 0.9 Hz, 1H), 7.38 (tt, J=7.6, 0.9 Hz, 1H), 7.32 (s, 1H), 7.23 (td, J=7.6, 1.2 Hz, 1H), 7.12 (s, 1H), 5.42 (d, J=5.5 Hz, 1H), 5.19 (d, J=5.8 Hz, 1H), 4.82 (s, 1H), 3.62 (s, 3H), 2.69 (ddd, J=16.3, 5.7, 1.7 Hz, 1H), 2.43-2.32 (m, 1H), 2.08-2.02 (m, 1H), 1.90 (qd, J=12.5, 5.6 Hz, 1H), 1.65 (dd, J=12.4, 5.8 Hz, 1H). 93b and 93d are enantiomers.

Example 93c: (4R,5R)-5-((S)-5H-imidazo[5,1-a]isoindol-5-yl)-1-methyl-4,5,6,7-tetrahydro-1H-indazol-4-ol: LCMS (ESI, m/z): 307.1 $[M+H]^+$; $^1H$ NMR (500 MHz, DMSO-$d_6$) δ 7.97 (s, 1H), 7.62-7.56 (m, 2H), 7.38 (d, J=4.9 Hz, 2H), 7.28 (td, J=7.5, 1.2 Hz, 1H), 7.11 (s, 1H), 5.50-5.42 (m, 2H), 4.99 (dd, J=5.9, 3.6 Hz, 1H), 3.60 (s, 3H), 2.58 (dd, J=16.7, 5.0 Hz, 1H), 2.33 (dd, J=12.6, 3.1 Hz, 1H), 2.26 (ddd, J=16.8, 12.0, 6.0 Hz, 1H), 1.49 (qd, J=12.6, 5.7 Hz, 1H), 0.94 (m 1H). 93c and 93f are enantiomers.

Example 93d: (4S,5R)-5-((R)-5H-imidazo[5,1-a]isoindol-5-yl)-1-methyl-4,5,6,7-tetrahydro-1H-indazol-4-ol: LCMS (ESI, m/z): 306.9 $[M+H]^+$; $^1H$ NMR (500 MHz, DMSO-$d_6$) δ 7.95 (s, 1H), 7.77 (dd, J=7.8, 0.9 Hz, 1H), 7.60 (d, J=7.5 Hz, 1H), 7.38 (dd, J=7.9, 7.0 Hz, 1H), 7.32 (s, 1H), 7.23 (td, J=7.6, 1.2 Hz, 1H), 7.12 (s, 1H), 5.42 (d, J=5.6 Hz, 1H), 5.18 (d, J=5.8 Hz, 1H), 4.82 (dd, J=5.9, 3.3 Hz, 1H), 3.62 (s, 3H), 2.73-2.65 (m, 1H), 2.43-2.32 (m, 1H), 2.09-2.01 (m, 1H), 1.90 (qd, J=12.5, 5.7 Hz, 1H), 1.65 (dd, J=12.6, 5.8 Hz, 1H). 93b and 93d are enantiomers.

Example 93e: (4R,5R)-5-((R)-5H-imidazo[5,1-a]isoindol-5-yl)-1-methyl-4,5,6,7-tetrahydro-1H-indazol-4-ol: LCMS (ESI, m/z): 306.9 $[M+H]^+$; $^1H$ NMR (500 MHz, DMSO-$d_6$) δ 7.92 (s, 1H), 7.63 (dd, J=7.6, 1.0 Hz, 1H), 7.48-7.34 (m, 3H), 7.32 (td, J=7.5, 1.1 Hz, 1H), 7.17 (s, 1H), 5.76 (d, J=1.2 Hz, 1H), 5.61 (d, J=6.9 Hz, 1H), 4.96-4.89 (m, 1H), 3.58 (s, 3H), 2.44 (dd, J=16.2, 5.3 Hz, 1H), 2.31 (ddd, J=16.5, 11.4, 5.8 Hz, 1H), 2.24-2.16 (m, 1H), 0.96-0.76 (m, 2H). 93a and 93e are enantiomers.

Example 93f: (4S,5S)-5-((R)-5H-imidazo[5,1-a]isoindol-5-yl)-1-methyl-4,5,6,7-tetrahydro-1H-indazol-4-ol: LCMS (ESI, m/z): 307.1 $[M+H]^+$; $^1H$ NMR (500 MHz, DMSO-$d_6$) δ 7.97 (d, J=3.9 Hz, 1H), 7.62-7.56 (m, 2H), 7.42-7.34 (m, 2H), 7.28 (td, J=7.7, 7.3, 4.8 Hz, 1H), 7.11 (d, J=3.9 Hz, 1H), 5.50-5.42 (m, 2H), 4.98 (dd, J=5.9, 3.5 Hz, 1H), 3.60 (d, J=3.1 Hz, 3H), 2.58 (dd, J=16.2, 5.3 Hz, 1H), 2.36-2.20 (m, 2H), 1.48 (tt, J=12.0, 6.0 Hz, 1H), 0.94 (d, J=13.7 Hz, 1H). 93c and 93f are enantiomers.

Example 93g: (4S,5R)-5-((S)-5H-imidazo[5,1-a]isoindol-5-yl)-1-methyl-4,5,6,7-tetrahydro-1H-indazol-4-ol: LCMS (ESI, m/z): 307.4 $[M+H]^+$; $^1H$ NMR (500 MHz, DMSO-$d_6$) δ 7.88 (s, 1H), 7.64 (dt, J=7.6, 0.8 Hz, 1H), 7.56 (dd, J=7.7, 1.0 Hz, 1H), 7.39 (tt, J=7.6, 0.8 Hz, 1H), 7.36 (s, 1H), 7.25 (td, J=7.6, 1.2 Hz, 1H), 7.16 (s, 1H), 5.76 (d, J=3.1 Hz, 1H), 5.64 (d, J=6.5 Hz, 1H), 4.91 (dd, J=9.7, 6.4 Hz, 1H), 3.57 (s, 3H), 2.48-2.28 (m, 3H), 0.88 (dq, J=9.1, 4.9 Hz, 2H).

Example 94: 6-(5H-imidazo[5,1-a]isoindol-5-yl)-5,6,7,8-tetrahydroquinazolin-5-ol

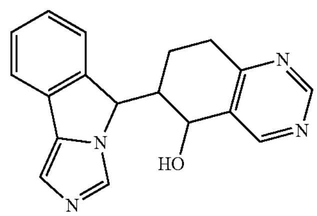 [SMILES: OC1c2cncnc2CCC1C1c2ccccc2-c2cncn21]

(5S,6R)-6-((R)-5H-imidazo[5,1-a]isoindol-5-yl)-5,6,7,8-tetrahydroquinazolin-5-ol (5R,6S)-6-((S)-5H-imidazo[5,1-a]isoindol-5-yl)-5,6,7,8-tetrahydroquinazolin-5-ol (5R,6R)-6-((R)-5H-imidazo[5,1-a]isoindol-5-yl)-5,6,7,8-tetrahydroquinazolin-5-ol (5S,6S)-6-((R)-5H-imidazo[5,1-a]isoindol-5-yl)-5,6,7,8-tetrahydroquinazolin-5-ol (5R,6S)-6-((R)-5H-imidazo[5,1-a]isoindol-5-yl)-5,6,7,8-tetrahydroquinazolin-5-ol (5S,6S)-6-((S)-5H-imidazo[5,1-a]isoindol-5-yl)-5,6,7,8-tetrahydroquinazolin-5-ol (5S,6R)-6-((S)-5H-imidazo[5,1-a]isoindol-5-yl)-5,6,7,8-tetrahydroquinazolin-5-ol (5R,6R)-6-((S)-5H-imidazo[5,1-a]isoindol-5-yl)-5,6,7,8-tetrahydroquinazolin-5-ol Step 1:

(E)-6-(2-(1-trityl-1H-imidazol-4-yl)benzylidene)-7,8-dihydroquinazolin-5(6H)-one

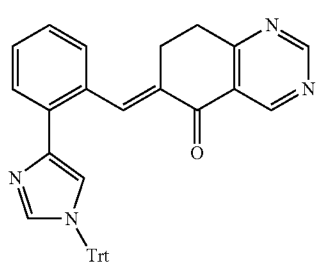

7,8-dihydroquinazolin-5(6H)-one (715 mg., 4.8 mmol) was added to a stirred mixture of 2-(1-trityl-1H-imidazol-4-yl)benzaldehyde (2 g., 4.8 mmol), and piperidine (205 mg, 0.12 mmol) in ethanol solution (30 mL). The reaction mixture was then reflux for 3 hr. After cool down to room temperature, the reaction was quenched with water (100 mL) and extracted by DCM (50 mL×3). Combined organic phase was dried over $Na_2SO_4$ and purified by CombiFlash using 2-4% MeOH/DCM: LCMS (ESI, m/z): 545.6 $[M+H]^+$ Step 2:

6-(5H-imidazo[5,1-a]isoindol-5-yl)-7,8-dihydroquinazolin-5(6H)-one

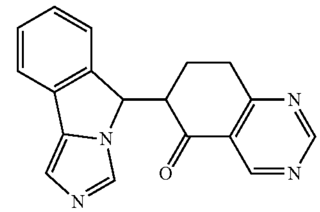 [SMILES: O=C1c2cncnc2CCC1C1c2ccccc2-c2cncn21]

(E)-6-(2-(1-trityl-1H-imidazol-4-yl)benzylidene)-7,8-dihydroquinazolin-5(6H)-one was stirred in MeOH (15 mL) and acetic acid (5 mL) at 80° C. for 2 hr. After cooling to room temperature, the solvent was removed under reduced pressure and saturated $NaHCO_3$ (30 mL) was added to the residue followed by DCM (20 mL). The organic layer was collected and the aqueous layer was extracted with DCM (2×20 mL). The combined organic layers were dried over $Na_2SO_4$ and the solvent evaporated under reduced pressure to afford the crude product which was purified by Combiflash using methanol/DCM 2%-4%: LCMS (ESI, m/z): 303.2 $[M+H]^+$ Step 3:

(5S,6R)-6-((R)-5H-imidazo[5,1-a]isoindol-5-yl)-5,6,7,8-tetrahydroquinazolin-5-ol (5R,6S)-6-((S)-5H-imidazo[5,1-a]isoindol-5-yl)-5,6,7,8-tetrahydroquinazolin-5-ol (5R,6R)-6-((R)-5H-imidazo[5,1-a]isoindol-5-yl)-5,6,7,8-tetrahydroquinazolin-5-ol (5S,6S)-6-((R)-5H-imidazo[5,1-a]isoindol-5-yl)-5,6,7,8-tetrahydroquinazolin-5-ol (5R,6S)-6-((R)-5H-imidazo[5,1-a]isoindol-5-yl)-5,6,7,8-tetrahydroquinazolin-5-ol (5S,6S)-6-((S)-5H-imidazo[5,1-a]isoindol-5-yl)-5,6,7,8-tetrahydroquinazolin-5-ol (5S,6R)-6-((S)-5H-imidazo[5,1-a]isoindol-5-yl)-5,6,7,8-tetrahydroquinazolin-5-ol (5R,6R)-6-((S)-5H-imidazo[5,1-a]isoindol-5-yl)-5,6,7,8-tetrahydroquinazolin-5-ol 94a

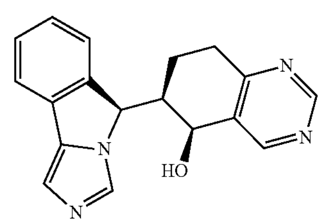

94b

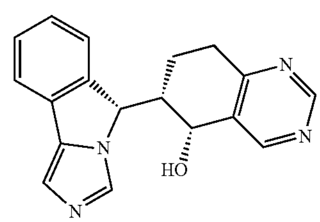

-continued

94c

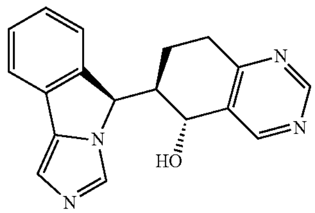

94d

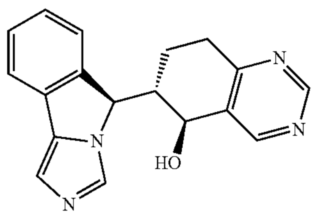

94e

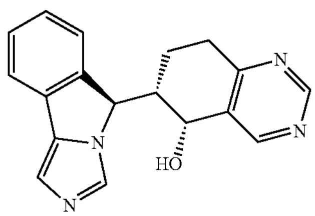

94f

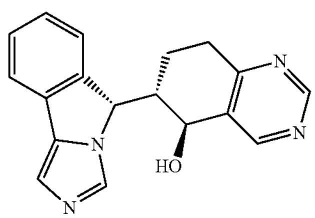

94g

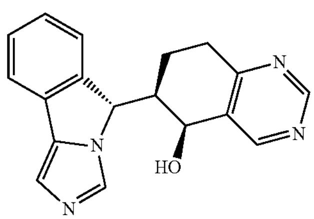

94h

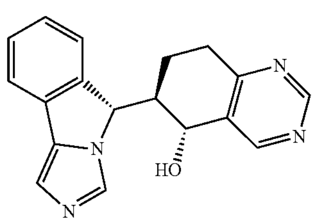

6-(5H-imidazo[5,1-a]isoindol-5-yl)-7,8-dihydroquinazolin-5(6H)-one (750 mg, 2.48 mmol) was dissolved in dry MeOH (15 mL) at 0° C. $NaBH_4$ (375 mg, 9.92 mmol) was added in four portions. The reaction was stirred at room temperature for 0.5 hr. The reaction was quenched by water and extracted by DCM (25 mL×3), combined organic phase was washed with brine and dried over $Na_2SO_4$. The crude product was purified by Combi-Flash and further isolated by chiral separation to afford 8 isomers as white solid. The absolute configuration of all the isomers was assigned arbitrarily.

Example 94a: (5S,6R)-6-((R)-5H-imidazo[5,1-a]isoindol-5-yl)-5,6,7,8-tetrahydroquinazolin-5-ol: LCMS (ESI, m/z): 305.2 $[M+H]^+$; $^1H$ NMR (500 MHz, DMSO-$d_6$) δ 8.96 (s, 1H), 8.67 (s, 1H), 7.99 (s, 1H), 7.75-7.70 (m, 1H), 7.64-7.60 (m, 1H), 7.43-7.37 (m, 1H), 7.25 (td, J=7.6, 1.2 Hz, 1H), 7.14 (s, 1H), 5.79 (d, J=5.9 Hz, 1H), 5.47 (d, J=6.0 Hz, 1H), 4.93-4.87 (m, 1H), 2.86 (ddd, J=18.6, 5.7, 1.9 Hz, 1H), 2.75 (ddd, J=18.5, 12.0, 6.4 Hz, 1H), 2.24 (ddt, J=12.3, 6.0, 3.0 Hz, 1H), 2.07 (qd, J=12.7, 5.8 Hz, 1H), 1.86-1.78 (m, 1H).

Example 94b: (5R,6S)-6-((S)-5H-imidazo[5,1-a]isoindol-5-yl)-5,6,7,8-tetrahydroquinazolin-5-ol: LCMS (ESI, m/z): 305.2 $[M+H]^+$; $^1H$ NMR is the same as Example 94a.

Example 94c: (5R,6R)-6-((R)-5H-imidazo[5,1-a]isoindol-5-yl)-5,6,7,8-tetrahydroquinazolin-5-ol: LCMS (ESI, m/z): 305.2 $[M+H]^+$; $^1H$ NMR (500 MHz, DMSO-$d_6$) δ 8.93 (s, 1H), 8.91 (d, J=0.8 Hz, 1H), 7.97 (s, 1H), 7.64 (d, J=7.5 Hz, 1H), 7.50 (dq, J=7.6, 0.9 Hz, 1H), 7.42 (tt, J=7.6, 0.9 Hz, 1H), 7.32 (td, J=7.6, 1.1 Hz, 1H), 7.19 (s, 1H), 6.39 (d, J=7.4 Hz, 1H), 5.80 (s, 1H), 5.08 (dd, J=10.6, 7.4 Hz, 1H), 2.70-2.60 (m, 2H), 2.48-2.40 (m, 1H), 1.00-0.84 (m, 2H).

Example 94d: (5S,6S)-6-((R)-5H-imidazo[5,1-a]isoindol-5-yl)-5,6,7,8-tetrahydroquinazolin-5-ol: LCMS (ESI, m/z): 305.2 $[M+H]^+$; $^1H$ NMR (500 MHz, DMSO-$d_6$) δ 8.97 (d, J=1.2 Hz, 1H), 8.74 (d, J=1.3 Hz, 1H), 7.97 (s, 1H), 7.61 (dd, J=8.2, 6.9 Hz, 2H), 7.40 (t, J=7.5 Hz, 1H), 7.29 (tt, J=7.4, 1.3 Hz, 1H), 7.13 (s, 1H), 6.11 (dd, J=5.8, 1.2 Hz, 1H), 5.57 (s, 1H), 5.11 (t, J=4.7 Hz, 1H), 2.76 (dd, J=18.6, 5.4 Hz, 1H), 2.63 (ddd, J=18.7, 12.3, 6.3 Hz, 1H), 2.5-2.50 (m, 1H, merged with DMSO), 1.62 (qd, J=12.6, 5.7 Hz, 1H), 1.07 (d, J=9.9 Hz, 1H).

Example 94e: (5R,6S)-6-((R)-5H-imidazo[5,1-a]isoindol-5-yl)-5,6,7,8-tetrahydroquinazolin-5-ol: LCMS (ESI, m/z): 305.2 $[M+H]^+$; $^1H$ NMR (500 MHz, DMSO-$d_6$) δ 8.92 (d, J=0.7 Hz, 1H), 8.86 (d, J=0.9 Hz, 1H), 7.91 (s, 1H), 7.64 (ddd, J=9.1, 7.7, 1.0 Hz, 2H), 7.41 (tt, J=7.5, 0.8 Hz, 1H), 7.27 (td, J=7.6, 1.2 Hz, 1H), 7.17 (s, 1H), 6.36 (d, J=7.2 Hz, 1H), 5.80 (d, J=3.3 Hz, 1H), 5.01 (dd, J=10.7, 7.2 Hz, 1H), 2.78-2.57 (m, 3H), 1.01-0.89 (m, 2H).

Example 94f: (5S,6S)-6-((S)-5H-imidazo[5,1-a]isoindol-5-yl)-5,6,7,8-tetrahydroquinazolin-5-ol: LCMS (ESI, m/z): 305.2 $[M+H]^+$; $^1H$ NMR is the same as Example 94c.

Example 94g: (5S,6R)-6-((S)-5H-imidazo[5,1-a]isoindol-5-yl)-5,6,7,8-tetrahydroquinazolin-5-ol: LCMS (ESI, m/z): 305.2 $[M+H]^+$; $^1H$ NMR is the same as Example 094e.

Example 94h: (5R,6R)-6-((S)-5H-imidazo[5,1-a]isoindol-5-yl)-5,6,7,8-tetrahydroquinazolin-5-ol: LCMS (ESI, m/z): 305.2 $[M+H]^+$; $^1H$ NMR is the same as Example 94d.

Example 95: 2-(fluoromethyl)-5-(5H-imidazo[5,1-a]isoindol-5-vl)-4,5,6,7-tetrahydropyrazolo[1,5-a]pyridin-4-ol

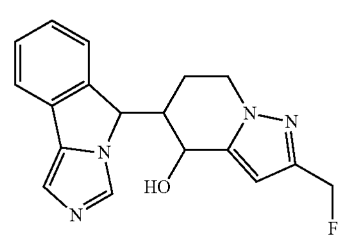 [SMILES: OC1c2cc(CF)nn2CCC1C1c2ccccc2-c2cncn21]

(4S,5S)-2-(fluoromethyl)-5-((S)-5H-imidazo[5,1-a]isoindol-5-yl)-4,5,6,7-tetrahydropyrazolo[1,5-a]pyridin-4-ol (4R,5R)-2-(fluoromethyl)-5-((R)-5H-imidazo[5,1-a]isoindol-5-yl)-4,5,6,7-tetrahydropyrazolo[1,5-a]pyridin-4-ol Synthetic Route

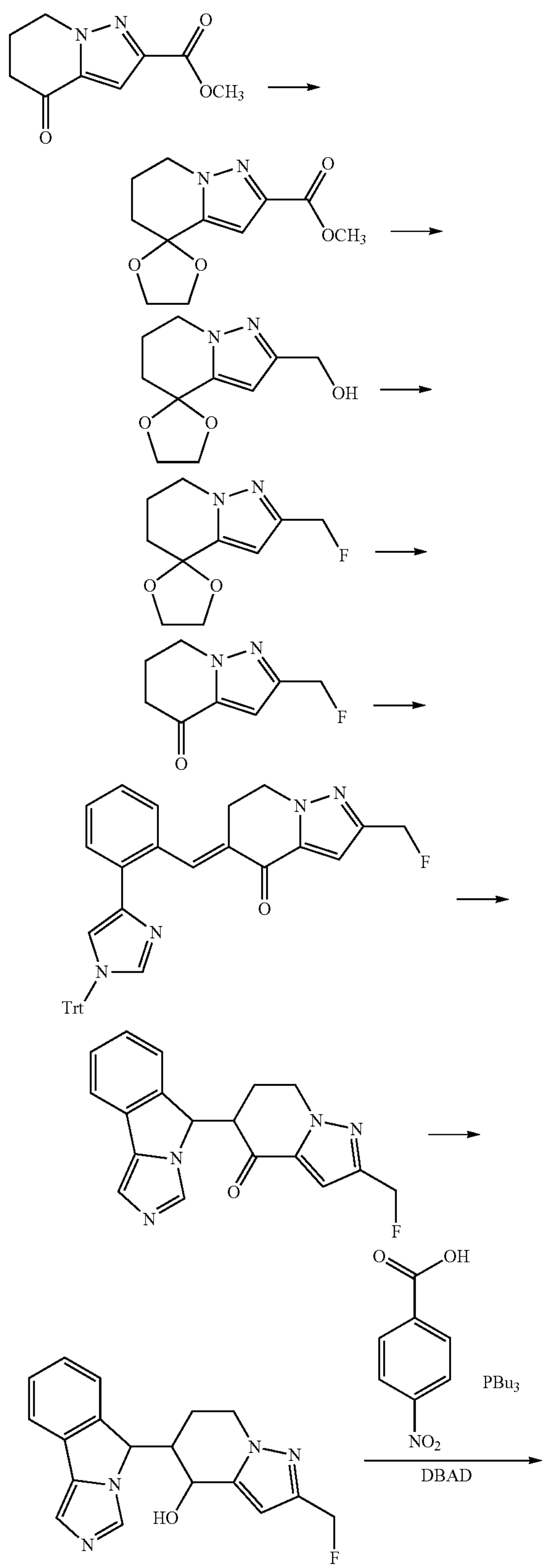

-continued

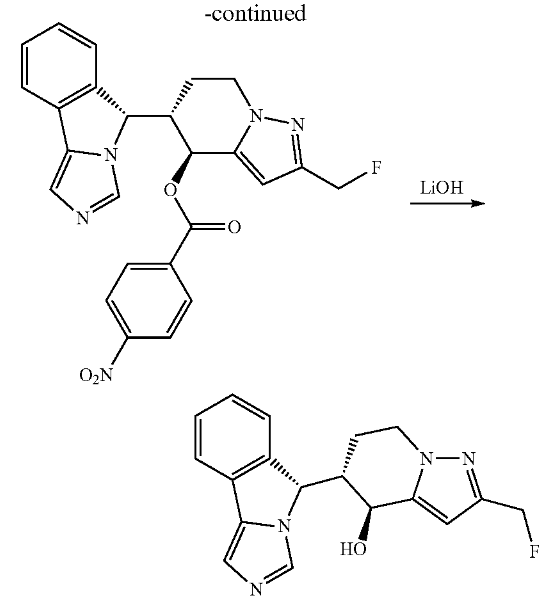

Step 1: methyl 6,7-dihydro-5H-spiro[pyrazolo[1,5-a]pyridine-4,2'-[1,3]dioxolane]-2-carboxylate

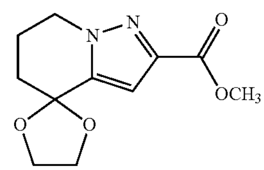 [SMILES: COC(=O)c1cc2n(n1)CCCC21OCCO1]

Methyl 4-oxo-4,5,6,7-tetrahydropyrazolo[1,5-a]pyridine-2-carboxylate (1.4 g, 7.21 mmol), trimethoxymethane (2.3 g, 22 mmol), ethane-1,2-diol (17.9 g, 288 mmol), and pTSA (124 mg, 0.72 mmol) was dissolved in anhydrous toluene (30 mL). The reaction mixture was heated up to reflux for 3 hr. TLC show that no starting material left. The mixture was cooled to room temperature, concentrated under vacuum, and extracted with DCM (50 mL×3) and $NaHCO_3$ solution. The combined organic layers was dried over $Na_2SO_4$, filtered and concentrated to give the crude product, which is purified by column (Hex/EtOAc 20-50%): LCMS (ESI, m/z): 239.3 $[M+H]^+$; $^1H$ NMR (400 MHz, Chloroform-d) δ 6.79 (t, J=1.2 Hz, 1H), 4.28-4.03 (m, 7H), 3.97-3.85 (m, 3H), 2.25 (td, J=7.6, 7.0, 3.2 Hz, 2H), 2.14-2.07 (m, 2H).

Step 2: (6,7-dihydro-5H-spiro[pyrazolo[1,5-a]pyridine-4,2'-[1,3]dioxolan]-2-yl)methanol

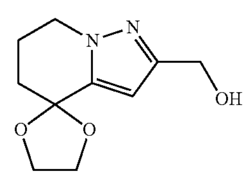 [SMILES: OCc1cc2n(n1)CCCC21OCCO1]

Methyl 6,7-dihydro-5H-spiro[pyrazolo[1,5-a]pyridine-4,2'-[1,3]dioxolane]-2-carboxylate (1.45 g, 6.1 mmol) was dissolved in dry toluene (30 mL) at 0° C. under Ar. DIBAL-H (1.2 M in toluene, 15 mL) was added slowly to the above solution in 20 min. The reaction mixture is stirred for an additional 2 hr at room temperature when TLC analysis shows the reaction to be complete. The reaction is quenched by slowly adding 1 mL of MeOH followed by 20 ml of water. The aqueous mixture is then extracted with DCM (3×50 mL). The combined organic layers are washed with brine (100 mL), dried over $Na_2SO_4$, filtered and concentrated to give the crude product, which is purified by column (EtOAc): LCMS (ESI, m/z): 211.3 $[M+H]^+$; $^1H$ NMR (400 MHz, Chloroform-d) δ 6.23 (d, J=1.7 Hz, 1H), 4.64 (d, J=1.7 Hz, 2H), 4.22-4.00 (m, 6H), 2.21 (pd, J=6.1, 1.9 Hz, 2H), 2.10-2.00 (m, 2H).

Step 3: 2-(fluoromethyl)-6,7-dihydro-5H-spiro[pyrazolo[1,5-a]pyridine-4,2'-[1,3]dioxolane]

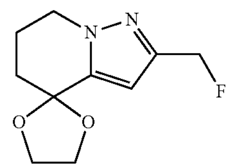 [SMILES: FCc1cc2n(n1)CCCC21OCCO1]

To a solution of (6,7-dihydro-5H-spiro[pyrazolo[1,5-a]pyridine-4,2'-[1,3]dioxolan]-2-yl)methanol (900 mg, 4.28 mmol) in dry DCM (20 mL) at 0° C. under an atmosphere of nitrogen was added (diethylamino)sulphur trifluoride (1.5 mL, 8.56 mmol). The reaction was left to warm to room temperature for 1 hr. Following addition of sodium bicarbonate (50 mL of a saturated aqueous solution), the reaction mixture was washed with DCM (3×50 mL), and the combined organic extracts was filtered and concentrated in vacuum. The residue was purified by flash chromatography (eluent hexane:EtOAc [0-100 percent] gradient) to furnish the title compound as a white solid. 0.7 g, 69% yield: LCMS (ESI, m/z): 213.3 $[M+H]^+$; $^1H$ NMR (400 MHz, Chloroform-d) δ 6.34 (d, J=1.9 Hz, 1H), 5.34 (dd, J=48.4, 1.7 Hz, 2H), 4.24-4.00 (m, 6H), 2.23 (pt, J=9.0, 4.5 Hz, 2H), 2.13-2.02 (m, 2H).

Step 4: 2-(fluoromethyl)-6,7-dihydropyrazolo[1,5-a]pyridin-4(5H)-one

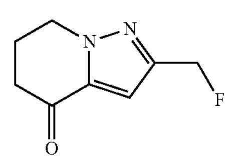 [SMILES: O=C1CCCn2nc(CF)cc21]

2-(fluoromethyl)-6,7-dihydro-5H-spiro[pyrazolo[1,5-a]pyridine-4,2'-[1,3]dioxolane] (700 mg, 3.30 mmol) was dissolved in 30 mL of THE, which was treated with HCl solution (13.2 mL, 5M). After overnight at room temperature, the reaction was basified with $NaHCO_3$ solution the reaction mixture was washed with DCM (3×50 mL), and the combined organic extracts was filtered and concentrated in vacuum. The residue was purified by flash chromatography (eluent hexane:EtOAc [0-50 percent] gradient) to furnish the title compound as a white solid. 0.52 g, 95% yield: LCMS (ESI, m/z): 169.3 $[M+H]^+$; $^1H$ NMR (400 MHz, Chloroform-d) δ 6.97-6.92 (m, 1H), 5.38 (dd, J=48.3, 0.4 Hz, 2H), 4.43-4.37 (m, 2H), 2.75-2.66 (m, 2H), 2.44-2.34 (m, 2H).

Step 4: (E)-2-(fluoromethyl)-5-(2-(1-trityl-1H-imidazol-4-yl)benzylidene)-6,7-dihydropyrazolo[1,5-a]pyridin-4(5H)-one

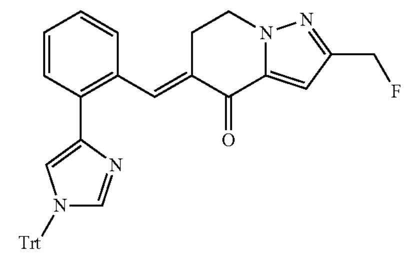

2-(fluoromethyl)-6,7-dihydropyrazolo[1,5-a]pyridin-4(5H)-one (0.45 g., 2.65 mmol) was added to a stirred mixture of 2-(1-trityl-1H-imidazol-4-yl)benzaldehyde (1.1 g., 2.65 mmol), and sodium ethoxide (2.8 mL, 2.65 mmol) in EtOH solution (25 mL). The reaction mixture was then reflux for 5 hr. TLC show the starting material is gone and a new spot formed. After cool down to room temperature, the reaction was quenched with water 100 mL and extracted by DCM (50 mL×3). Combined organic phase was dried over $Na_2SO_4$ and purified by CombiFlash using 2-4% MeOH/DCM: LCMS (ESI, m/z): 565.4 $[M+H]^+$; $^1H$ NMR (400 MHz, Chloroform-d) δ 8.13 (s, 1H), 7.77 (s, 1H), 7.55 (s, 1H), 7.33 (d, J=6.7 Hz, 13H), 7.19-7.04 (m, 9H), 5.46 (d, J=48.2 Hz, 2H), 4.26 (s, 2H), 3.09 (t, J=6.3 Hz, 2H).

Step 5: 2-(fluoromethyl)-5-(5H-imidazo[5,1-a]isoindol-5-yl)-6,7-dihydropyrazolo[1,5-a]pyridin-4(5H)-one

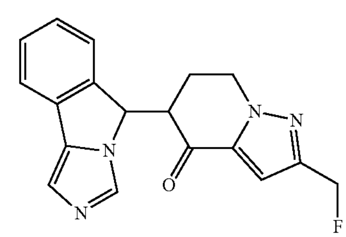 [SMILES: O=C1c2cc(CF)nn2CCC1C1c2ccccc2-c2cncn21]

(E)-2-(fluoromethyl)-5-(2-(1-trityl-1H-imidazol-4-yl)benzylidene)-6,7-dihydropyrazolo[1,5-a]pyridin-4(5H)-one was stirred in MeOH (25 mL) and AcOH (8 mL) at 80° C. for 2 hr. After cooling to room temperature, the solvent was removed under reduced pressure and sat'd $NaHCO_3$ (30 mL) was added to the residue followed by DCM (20 mL). The organic layer was collected and the aqueous layer was extracted with DCM (2×20 mL). The combined organic layers were dried over $Na_2SO_4$ and the solvent evaporated under reduced pressure to afford the crude product which was purified by Combi-flash using methanol/dcm 4%-8%: LCMS (ESI, m/z): 323.2 $[M+H]^+$; $^1H$ NMR (400 MHz, Chloroform-d) δ 7.65-7.58 (m, 1H), 7.54-7.32 (m, 3H), 7.31-7.27 (m, 1H), 7.26-7.21 (m, 1H), 7.11 (d, J=1.9 Hz, 1H), 6.36-6.20 (m, 1H), 5.41 (dd, J=48.0, 2.3 Hz, 2H), 4.44-4.32 (m, 1H), 4.31-4.17 (m, 1H), 3.39 (ddd, J=12.9, 4.7, 2.4 Hz, 1H), 1.75-1.49 (m, 2H).

Step 6: 2-(fluoromethyl)-5-(5H-imidazo[5,1-a]isoindol-5-yl)-4,5,6,7-tetrahydropyrazolo[1,5-a]pyridin-4-ol

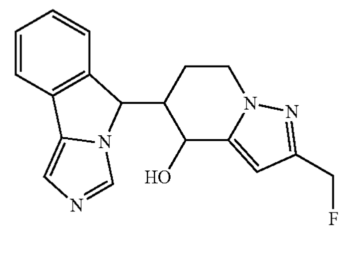 [SMILES: OC1c2cc(CF)nn2CCC1C1c2ccccc2-c2cncn21]

2-(fluoromethyl)-5-(5H-imidazo[5,1-a]isoindol-5-yl)-6,7-dihydropyrazolo[1,5-a]pyridin-4(5H)-one (400 mg, 1.24 mmol) was dissolved in dry THF (30 mL) at 0° C. LiAl(Ot-Bu)$_3$ (THF solution, 1.1M, 3.4 mL) was added slowly to the above solution, the reaction was stirred warmed up to room temperature and keep it for one hour. The reaction was quenched by water and extracted by $CF_3CH_2OH$/DCM (20%, 50 mL×3), combined organic phase was washed with brine and dried over $Na_2SO_4$. After removing solvent and the residue was purified by silica gel column chromatograph (MeOH:DCM=4:96-10:90): LCMS (ESI, m/z): 325.2 $[M+H]^+$; $^1$H NMR (400 MHz, Chloroform-d) δ 8.15 (d, J=1.8 Hz, 1H), 7.52-7.47 (m, 1H), 7.40-7.32 (m, 2H), 7.30-7.23 (m, 1H), 6.82 (d, J=1.8 Hz, 1H), 6.46 (d, J=2.1 Hz, 1H), 5.49-5.35 (m, 2H), 5.25 (d, J=1.9 Hz, 1H), 4.06 (dd, J=13.0, 5.5 Hz, 1H), 3.92-3.57 (m, 2H), 2.51 (d, J=12.6 Hz, 1H), 1.83 (qd, J=13.1, 5.7 Hz, 1H), 1.13 (d, J=13.5 Hz, 1H).

Step 7: (4S,5S)-2-(fluoromethyl)-5-((S)-5H-imidazo[5,1-a]isoindol-5-yl)-4,5,6,7-tetrahydropyrazolo[1,5-a]pyridin-4-yl 4-nitrobenzoate

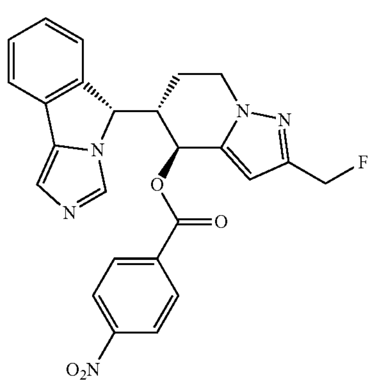 [SMILES: O=C(O[C@@H]1c2cc(CF)nn2CC[C@H]1[C@H]1c2ccccc2-c2cncn21)c1ccc([N+](=O)[O-])cc1]

Under argon, to a solution of 2-(fluoromethyl)-5-(5H-imidazo[5,1-a]isoindol-5-yl)-4,5,6,7-tetrahydropyrazolo[1,5-a]pyridin-4-ol (300 mg, 0.925 mmol, 1.000 equiv), 4-nitrobenzoic acid (232 mg, 1.39 mmol, 1.5 equiv) in THF (15.0 mL) was added n-Bu$_3$P (10 mL, 4.62 mmol, 5.000 equiv, 10% in hexane) at 0° C. This was followed by the addition of di-t-butyl azodicarboxylate (6 mL, 4.62 mol, 5.000 equiv, 20% in toluene) at 0° C. The resulting solution was stirred for 16 hr at room temperature. The resulting solution was diluted with DCM (20 mL) and then quenched by the addition of water (20 mL). The resulting solution was extracted with dichloromethane (3×15 mL) and the organic layers combined and dried over anhydrous sodium sulfate and concentrated under vacuum. The residue was applied onto a silica gel column with methanol/dichloromethane/(2-5%): LCMS (ESI, m/z): 474.2 $[M+H]^+$;

Step 8: (4R,5R)-2-(fluoromethyl)-5-((R)-5H-imidazo[5,1-a]isoindol-5-yl)-4,5,6,7-tetrahydropyrazolo[1,5-a]pyridin-4-ol (4S,5S)-2-(fluoromethyl)-5-((S)-5H-imidazo[5,1-a]isoindol-5-yl)-4,5,6,7-tetrahydropyrazolo[1,5-a]pyridin-4-ol

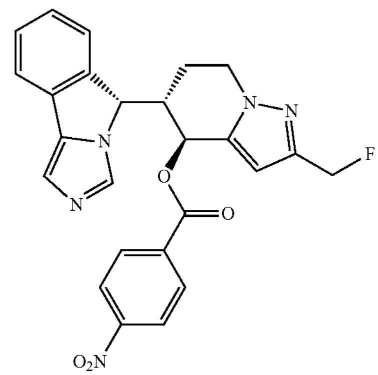

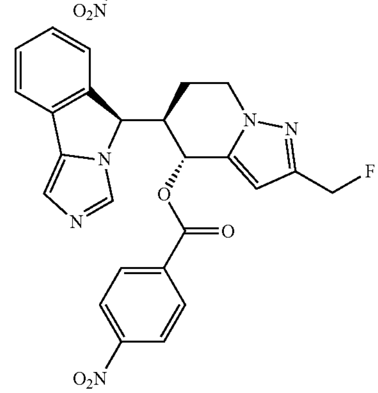

A solution of (4S,5S)-2-(fluoromethyl)-5-((S)-5H-imidazo[5,1-a]isoindol-5-yl)-4,5,6,7-tetrahydropyrazolo[1,5-a]pyridin-4-yl 4-nitrobenzoate (435 mg, 0.96 mmol, 1.000 equiv) in THF (20 mL) and water (4 mL) was added LiOH (402 mg, 9.6 mmol, 10 equiv). The resulting solution was stirred for 16 h at room temperature. The resulting solution was diluted with water (20 mL). The resulting solution was extracted with dichloromethane and the organic layers combined and dried over anhydrous sodium sulfate. The residue was applied onto a silica gel column with dichloromethane/methanol (10:1). This resulted in 270 mg (86%) of product as a white solid. The product was further isolated by chiral separation to afford 8 isomers as white solid. The stereochemistry of each isomer was arbitrarily assigned.

Example 95a: (4S,5S)-2-(fluoromethyl)-5-((S)-5H-imidazo[5,1-a]isoindol-5-yl)-4,5,6,7-tetrahydropyrazolo[1,5-a]pyridin-4-ol LCMS (ESI, m/z): 325.2 $[M+H]^+$; $^1$H NMR (400 MHz, DMSO-d6) δ 8.01 (s, 1H), 7.65 (dt, J=7.6, 0.9 Hz, 1H), 7.51 (dq, J=7.6, 1.0 Hz, 1H), 7.43 (tdd, J=7.5, 1.1, 0.6 Hz, 1H), 7.33 (td, J=7.5, 1.2 Hz, 1H), 7.20 (s, 1H), 6.46 (dd, J=2.0, 0.8 Hz, 1H), 6.32 (d, J=7.2 Hz, 1H), 5.79-5.76

(m, 1H), 5.28 (d, J=48.7 Hz, 2H), 5.05 (dd, J=10.5, 6.9 Hz, 1H), 3.97 (dd, J=12.8, 5.5 Hz, 1H), 3.86-3.75 (m, 1H), 2.56 (ddd, J=10.5, 3.2, 1.9 Hz, 1H), 1.16-0.98 (m, 2H).

Example 95b: (4R,5R)-2-(fluoromethyl)-5-((R)-5H-imidazo[5,1-a]isoindol-5-yl)-4,5,6,7-tetrahydropyrazolo[1,5-a]pyridin-4-ol LCMS (ESI, m/z): 325.2 $[M+H]^+$; $^1H$ NMR is the same as Example 3a.

Example 96a: 4-hydroxy-3-(5H-imidazo[5,1-a]isoindol-5-yl)thiochromane 1,1-dioxide

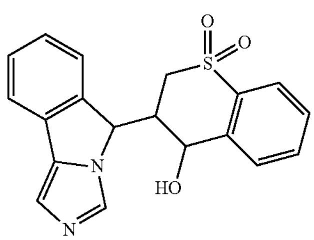 [SMILES: O=S1(=O)CC(C2c3ccccc3-c3cncn32)C(O)c2ccccc21]

Step 1: thiochroman-4-one 1,1-dioxide

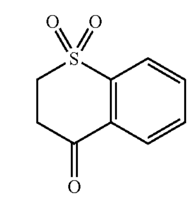 [SMILES: O=C1CCS(=O)(=O)c2ccccc21]

Into a round bottom flask containing thiochroman-4-one (1.6 g, 9.74 mmol), 12 mL of glacial acetic acid and, 4.6 mL of a 35 percent w/w solution of $H_2O_2$ (1.66 g, 48.7 mmol) were added and, the solution was heated at 100° C. for 2 hr. After the reaction mixture was cooled at room temperature, 30 mL of water were added and the product was extracted twice with DCM from the aqueous layer. The resultant organic phase was washed once with brine and dried under $Na_2SO_4$. After the solvent was removed, a solid was formed which was purified by recrystallization with EtOH (20-30 mL). After drying the solid under reduced pressure, 1.53 g (3.31 mmol) of the product was obtained in 80% yield. $^1H$ NMR (400 MHz, Chloroform-d) δ 8.15 (dd, J=7.7, 1.4 Hz, 1H), 8.04 (dd, J=7.9, 1.3 Hz, 1H), 7.85 (td, J=7.6, 1.4 Hz, 1H), 7.81-7.73 (m, 1H), 3.77-3.69 (m, 2H), 3.49-3.41 (m, 2H).

Step 2: (Z)-3-(2-(1-trityl-1H-imidazol-4-yl)benzylidene)thiochroman-4-one 1,1-dioxide

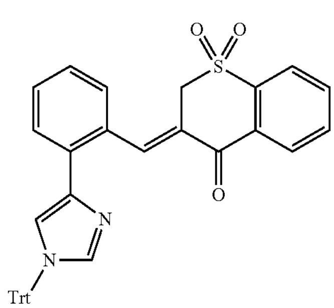

Thiochroman-4-one 1,1-dioxide (1.51 g., 7.7 mmol) was added to a stirred mixture of 2-(1-trityl-1H-imidazol-4-yl)benzaldehyde (2.9 g., 7.0 mmol), and piperidine (0.34 mL, 3.5 mmol) in methanol solution (50 mL). The reaction mixture was then reflux for 1 hr and cool to room temperature. After cooling to room temperature, the solvent was removed under reduced pressure and saturated NaCl solution (50 mL) was added to the residue followed by DCM (50 mL). The organic layer was collected and the aqueous layer was extracted with DCM (2×50 mL). The combined organic layers were dried over $Na_2SO_4$ and the solvent evaporated under reduced pressure to afford the crude product which was purified by Combi-flash using DCM: LCMS (ESI, m/z): 593.1 $[M+H]^+$ Step 3: 3-(5H-imidazo[5,1-a]isoindol-5-yl)thiochroman-4-one 1,1-dioxide

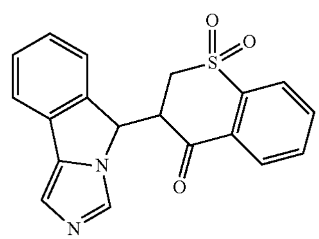 [SMILES: O=C1c2ccccc2S(=O)(=O)CC1C1c2ccccc2-c2cncn21]

(Z)-3-(2-(1-trityl-1H-imidazol-4-yl)benzylidene)thiochroman-4-one 1,1-dioxide (3.2 g., 5.4 mmol) was dissolved in dry methanol (40 mL) and acetic acid (16 mL, 270 mmol). The reaction mixture was reflux for 1 hr and cool to room temperature. The solvent was removed under reduced pressure and saturated $NaHCO_3$ (50 mL) was added to the residue followed by DCM (50 mL). The organic layer was collected and the aqueous layer was extracted with DCM (2×50 mL). The combined organic layers were dried over $Na_2SO_4$ and the solvent evaporated under reduced pressure to afford the crude product which was purified by Combi-flash using MeOH/DCM 3%: LCMS (ESI, m/z): 351.2 $[M+H]^+$ Step 3: 4-hydroxy-3-(5H-imidazo[5,1-a]isoindol-5-yl)thiochromane 1,1-dioxide

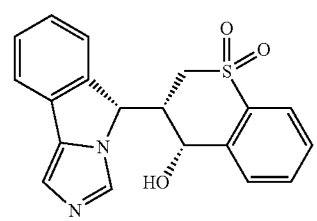 [SMILES: O=S1(=O)C[C@@H]([C@H]2c3ccccc3-c3cncn32)[C@@H](O)c2ccccc21]

Under argon, to a solution of 7-[5H-imidazo[4,3-a]isoindol-5-yl]-5,6,7,8-tetrahydroisoquinolin-8-one (30 mg, 0.086 mmol, 1.000 equiv) in THF (7 mL) at −78° C. was added L-Selectride (0.51 mL, 0.51 mmol, 6 equiv, 1.0 M in THF). The resulting solution was stirred for 3 hr at room temperature. The reaction was then quenched by the addition of ethanol (1 mL). The resulting mixture was concentrated under vacuum. The resulting solution was diluted with DCM (20 mL). The resulting mixture was washed with water and brine. The residue was applied onto combiflash separation with dichloromethane/methanol (20:1). This resulted in 26 mg (90%) of product as a light yellow solid: LCMS (ESI, m/z): 353.3 [M+H]$^+$ Step 4: 3-(5H-imidazo[5,1-a]isoindol-5-yl)-1,1-dioxidothiochroman-4-yl 4-nitrobenzoate

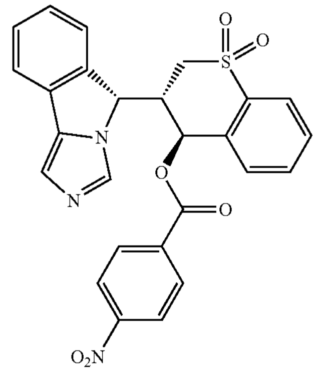 [SMILES: O=C(O[C@@H]1c2ccccc2S(=O)(=O)C[C@H]1[C@H]1c2ccccc2-c2cncn21)c1ccc([N+](=O)[O-])cc1]

Under argon, to a solution of 4-hydroxy-3-(5H-imidazo[5,1-a]isoindol-5-yl)thiochromane 1,1-dioxide (50 mg, 0.141 mmol, 1.000 equiv), 4-nitrobenzoic acid (36 mg, 0.212 mmol, 1.5 equiv) in THF (2.0 mL) was added n-$Bu_3P$ (1.5 mL, 0.71 mol, 5.000 equiv, 10% in hexane) at 0° C. This was followed by the addition of di-t-butyl azodicarboxylate (DBAD, 0.85 mL, 0.71 mmol, 5.000 equiv, 20% in toluene) at 0° C. The resulting solution was stirred for 16 hr at room temperature. The resulting solution was diluted with DCM (20 mL) and then quenched by the addition of water (20 mL). The resulting solution was extracted with dichloromethane (3×15 mL) and the organic layers combined and dried over anhydrous sodium sulfate and concentrated under vacuum. The residue was applied onto a silica gel column with methanol/dichloromethane/(2%): LCMS (ESI, m/z): 502.5 [M+H]$^+$ Step 5: 4-hydroxy-3-(5H-imidazo[5,1-a]isoindol-5-yl)thiochromane 1,1-dioxide

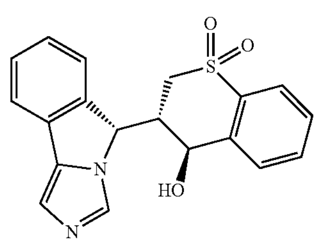 [SMILES: O=S1(=O)C[C@@H]([C@H]2c3ccccc3-c3cncn32)[C@H](O)c2ccccc21]

A solution of 3-(5H-imidazo[5,1-a]isoindol-5-yl)-1,1-dioxidothiochroman-4-yl 4-nitrobenzoate (50 mg, 0.1 mmol, 1.000 equiv) in THF (2 mL) and water (0.5 mL) was added LiOH (42 mg, 1 mmol, 10 equiv). The resulting solution was stirred for 40 min at room temperature. The resulting solution was diluted with water (10 mL). The resulting solution was extracted with dichloromethane and the organic layers combined and dried over anhydrous sodium sulfate. The residue was applied onto a silica gel column with dichloromethane/methanol (10:1). This resulted in 10 mg (30%) of product as the mixture of enantiomers: LCMS (ESI, m/z): 353.2 [M+H]$^+$. $^1$H NMR (400 MHz, DMSO-$d_6$) δ 7.99 (s, 1H), 7.92 (d, J=7.9 Hz, 1H), 7.80-7.71 (m, 2H), 7.69 (d, J=7.6 Hz, 1H), 7.58 (t, J=7.6 Hz, 1H), 7.53 (d, J=7.7 Hz, 1H), 7.47 (t, J=7.6 Hz, 1H), 7.40-7.33 (m, 1H), 7.23 (d, J=2.0 Hz, 1H), 6.82-6.70 (m, 1H), 5.97 (s, 1H), 5.25 (t, J=9.8 Hz, 1H), 3.26 (t, J=11.6 Hz, 1H), 2.89 (t, J=12.9 Hz, 1H), 2.35 (d, J=13.6 Hz, 1H).

Example 97: 5-hydroxy-6-(5H-imidazo[5,1-a]isoindol-5-yl)-N-methyl-5,6,7,8-tetrahydronaphthalene-2-carboxamide

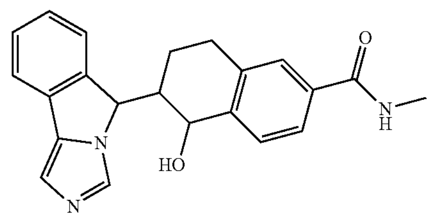

(5R,6S)-5-hydroxy-6-((S)-5H-imidazo[5,1-a]isoindol-5-yl)-N-methyl-5,6,7,8-tetrahydronaphthalene-2-carboxamide
(5S,6S)-5-hydroxy-6-((S)-5H-imidazo[5,1-a]isoindol-5-yl)-N-methyl-5,6,7,8-tetrahydronaphthalene-2-carboxamide
(5S,6R)-5-hydroxy-6-((S)-5H-imidazo[5,1-a]isoindol-5-yl)-N-methyl-5,6,7,8-tetrahydronaphthalene-2-carboxamide
(5R,6R)-5-hydroxy-6-((S)-5H-imidazo[5,1-a]isoindol-5-yl)-N-methyl-5,6,7,8-tetrahydronaphthalene-2-carboxamide
(5R,6R)-5-hydroxy-6-((R)-5H-imidazo[5,1-a]isoindol-5-yl)-N-methyl-5,6,7,8-tetrahydronaphthalene-2-carboxamide
(5R,6S)-5-hydroxy-6-((R)-5H-imidazo[5,1-a]isoindol-5-yl)-N-methyl-5,6,7,8-tetrahydronaphthalene-2-carboxamide
(5S,6S)-5-hydroxy-6-((R)-5H-imidazo[5,1-a]isoindol-5-yl)-N-methyl-5,6,7,8-tetrahydronaphthalene-2-carboxamide
(5S,6R)-5-hydroxy-6-((R)-5H-imidazo[5,1-a]isoindol-5-yl)-N-methyl-5,6,7,8-tetrahydronaphthalene-2-carboxamide Step 1: N-methyl-5-oxo-5,6,7,8-tetrahydronaphthalene-2-carboxamide

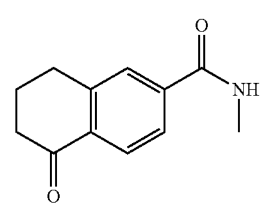

To a round-bottom flask containing 5-oxo-5,6,7,8-tetrahydronaphthalene-2-carboxylic acid (2.00 g, 10.52 mmol) in anhydrous DCM (50 mL) was added triethylamine (4.4 mL, 31.55 mmol), and HATU (4.80 g, 12.62 mmol). Methylamine solution in THF (6.31 mL, 12.62 mmol) was added to the above mixture. The reaction mixture was stirred at room temperature for 18 h and concentrated. The residue was dissolved in dichloromethane (30 mL) and poured into water (30 mL) and the aqueous layer was extracted with dichloromethane (3×30 mL). The combined organic layers were washed with water (3×10 mL), saturated $NaHCO_3$ (20 mL), dried over $Na_2SO_4$, and concentrated. The product was separated by CombiFlash and was eluted by EtOAc: Hex=75:25: LCMS (ESI, m/z): 204.4 $[M+H]^+$.

Step 2: (E)-N-methyl-5-oxo-6-(2-(1-trityl-1H-imidazol-4-yl)benzylidene)-5,6,7,8-tetrahydronaphthalene-2-carboxamide

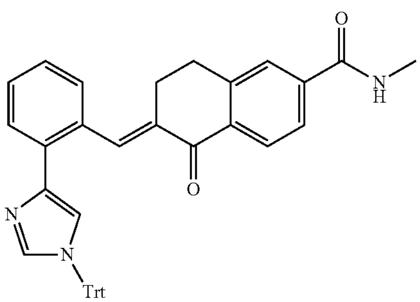

To a solution of 2-(1-trityl-1H-imidazol-4-yl)benzaldehyde (1.6 g, 3.86 mmol) and N-methyl-5-oxo-5,6,7,8-tetrahydronaphthalene-2-carboxamide (0.95 g, 4.63 mmol) in ethanol (30 mL) was added anhydrous $Ca(OH)_2$ (143 mg, 1.93 mmol). The mixture was stirred at 90° C. overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by Hex:EtOAc=20:80: LCMS (ESI, m/z): 600.4 $[M+H]^+$.

Step 3: 6-(5H-imidazo[5,1-a]isoindol-5-yl)-N-methyl-5-oxo-5,6,7,8-tetrahydronaphthalene-2-carboxamide

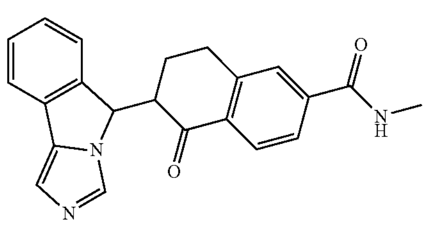 [SMILES: CNC(=O)c1ccc2c(c1)CCC(C1c3ccccc3-c3cncn31)C2=O]

(E)-N-methyl-5-oxo-6-(2-(1-trityl-1H-imidazol-4-yl)benzylidene)-5,6,7,8-tetrahydronaphthalene-2-carboxamide (1.83 g, 3.05 mmol) was stirred in 20% AcOH in MeOH (50 mL) at 90° C. for 2 h. After cooling to room temperature, the solvent was removed under reduced pressure and saturated $NaHCO_3$ (20 mL) was added to the residue followed by DCM (20 mL). The organic layer was collected and the aqueous layer was extracted with 10% trifluoroethanol in DCM (3×20 mL). The combined organic layers were dried over $Na_2SO_4$ and the solvent evaporated under reduced pressure to afford the crude product which was purified by using CombiFlash and was eluted by DCM:MeOH=95:5: LCMS (ESI, m/z): 358.2 $[M+H]^+$.

Step 4: (5R,6S)-5-hydroxy-6-((S)-5H-imidazo[5,1-a]isoindol-5-yl)-N-methyl-5,6,7,8-tetrahydronaphthalene-2-carboxamide (5S,6S)-5-hydroxy-6-((S)-5H-imidazo[5,1-a]isoindol-5-yl)-N-methyl-5,6,7,8-tetrahydronaphthalene-2-carboxamide (5S,6R)-5-hydroxy-6-((S)-5H-imidazo[5,1-a]isoindol-5-yl)-N-methyl-5,6,7,8-tetrahydronaphthalene-2-carboxamide (5R,6R)-5-hydroxy-6-((S)-5H-imidazo[5,1-a]isoindol-5-yl)-N-methyl-5,6,7,8-tetrahydronaphthalene-2-carboxamide (5R,6R)-5-hydroxy-6-((R)-5H-imidazo[5,1-a]isoindol-5-yl)-N-methyl-5,6,7,8-tetrahydronaphthalene-2-carboxamide (5R,6S)-5-hydroxy-6-((R)-5H-imidazo[5,1-a]isoindol-5-yl)-N-methyl-5,6,7,8-tetrahydronaphthalene-2-carboxamide (5S,6S)-5-hydroxy-6-((R)-5H-imidazo[5,1-a]isoindol-5-yl)-N-methyl-5,6,7,8-tetrahydronaphthalene-2-carboxamide (5S,6R)-5-hydroxy-6-((R)-5H-imidazo[5,1-a]isoindol-5-yl)-N-methyl-5,6,7,8-tetrahydronaphthalene-2-carboxamide 97a

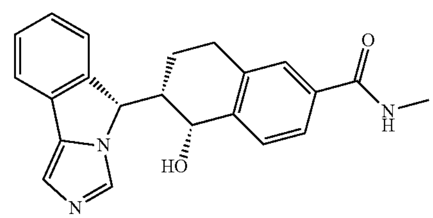

97b

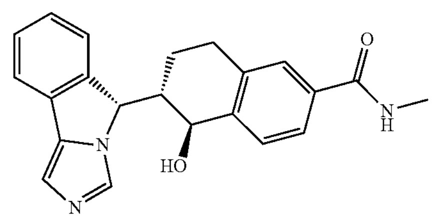

97c

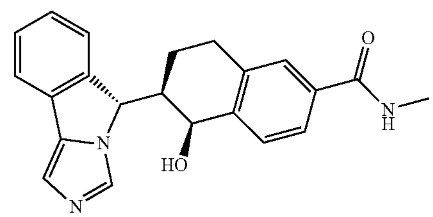

97d

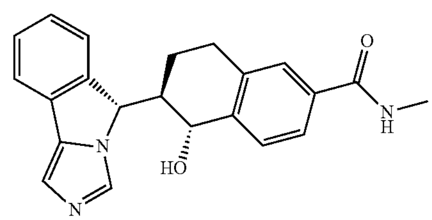

-continued

97e

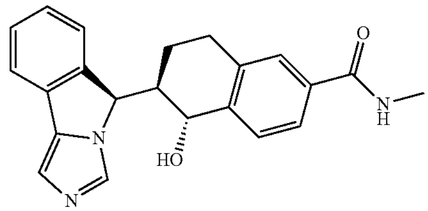

97f

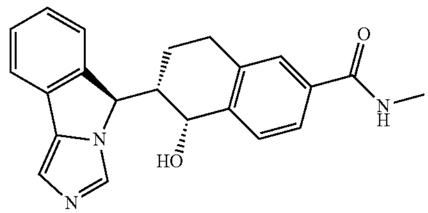

97g

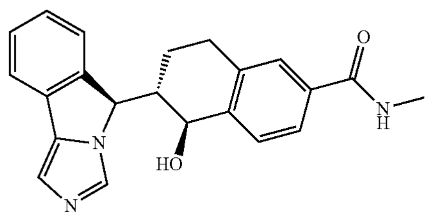

97h

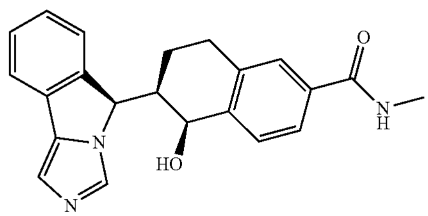

To a solution of 6-(5H-imidazo[5,1-a]isoindol-5-yl)-N-methyl-5-oxo-5,6,7,8-tetrahydronaphthalene-2-carboxamide (1.03 g, 2.88 mmol) in MeOH (20 mL) was added $NaBH_4$ (272 mg, 7.20 mmol) in portions at 0° C. and the solution was stirred at 0° C. for 2 hr. The solvent was distilled off and saturated ammonium chloride solution (20 mL) was added. The aqueous layer was extracted with 10% trifluoroethanol in DCM (3×20 mL). The combined organic extract was dried over ($Na_2SO_4$) and concentrated under reduced pressure to afford the crude product. The crude was purified by CombiFlash and the product was eluted with DCM:MeOH=90:10. The final products were further isolated by chiral separation to afford 8 isomers and the stereochemistry of each isomer was arbitrarily assigned.

Example 97a: (5R,6S)-5-hydroxy-6-((S)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.34 (q, J=4.5 Hz, 1H), 8.01 (s, 1H), 7.75 (dq, J=7.7, 0.9 Hz, 1H), 7.65-7.59 (m, 2H), 7.56 (d, J=1.7 Hz, 1H), 7.42-7.36 (m, 2H), 7.24 (td, J=7.6, 1.2 Hz, 1H), 7.13 (s, 1H), 5.61 (d, J=6.0 Hz, 1H), 5.45 (d, J=6.0 Hz, 1H), 4.82 (dd, J=6.0, 3.4 Hz, 1H), 2.85 (dd, J=17.4, 4.7 Hz, 1H), 2.75 (d, J=4.5 Hz, 3H), 2.71-2.63 (m, 1H), 2.15 (ddd, J=12.4, 6.1, 3.0 Hz, 1H), 1.95 (qd, J=12.6, 5.4 Hz, 1H), 1.71 (d, J=13.3 Hz, 1H).

Example 97b: (5S,6S)-5-hydroxy-6-((S)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.33 (q, J=4.3 Hz, 1H), 7.97 (s, 1H), 7.76-7.66 (m, 2H), 7.64 (d, J=7.6 Hz, 1H), 7.52-7.46 (m, 2H), 7.41 (t, J=7.4 Hz, 1H), 7.35-7.27 (m, 1H), 7.18 (s, 1H), 6.09 (d, J=7.7 Hz, 1H), 5.81 (s, 1H), 4.98-4.90 (m, 1H), 2.75 (d, J=4.5 Hz, 3H), 2.68-2.55 (m, 2H), 2.45-2.35 (m, 1H), 0.92 (d, J=3.4 Hz, 1H), 0.84 (dt, J=17.4, 8.3 Hz, 1H).

Example 97c: (5S,6R)-5-hydroxy-6-((S)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.35 (q, J=4.5 Hz, 1H), 7.94 (s, 1H), 7.66 (dd, J=8.0, 1.8 Hz, 1H), 7.63 (dt, J=7.7, 1.0 Hz, 1H), 7.59 (dt, J=7.5, 0.9 Hz, 1H), 7.54 (d, J=1.8 Hz, 1H), 7.46 (d, J=8.0 Hz, 1H), 7.39 (tt, J=7.6, 0.9 Hz, 1H), 7.28 (td, J=7.6, 1.2 Hz, 1H), 7.11 (s, 1H), 5.90 (d, J=6.1 Hz, 1H), 5.53 (d, J=2.3 Hz, 1H), 5.01 (dd, J=6.1, 3.8 Hz, 1H), 2.76 (d, J=4.5 Hz, 3H), 2.74-2.69 (m, 1H), 2.56 (dt, J=10.4, 5.2 Hz, 1H), 2.47 (dt, J=9.7, 3.0 Hz, 1H), 1.49 (qd, J=12.7, 5.4 Hz, 1H), 0.99 (dd, J=10.1, 3.0 Hz, 1H).

Example 97d: (5R,6R)-5-hydroxy-6-((S)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.32 (q, J=4.3 Hz, 1H), 7.91 (s, 1H), 7.68-7.59 (m, 4H), 7.48 (d, J=1.6 Hz, 1H), 7.42-7.38 (m, 1H), 7.26 (td, J=7.6, 1.2 Hz, 1H), 7.17 (s, 1H), 6.10 (d, J=7.4 Hz, 1H), 5.81 (d, J=3.3 Hz, 1H), 4.90 (dd, J=10.7, 7.5 Hz, 1H), 2.75 (d, J=4.5 Hz, 3H), 2.70-2.53 (m, 3H), 0.87 (h, J=4.9 Hz, 2H).

Example 97e: (5R,6R)-5-hydroxy-6-((R)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.33 (q, J=4.5 Hz, 1H), 7.97 (s, 1H), 7.74-7.66 (m, 2H), 7.64 (d, J=7.5 Hz, 1H), 7.51-7.46 (m, 2H), 7.44-7.39 (m, 1H), 7.31 (td, J=7.5, 1.1 Hz, 1H), 7.18 (s, 1H), 6.10 (d, J=7.7 Hz, 1H), 5.81 (d, J=1.9 Hz, 1H), 4.98-4.91 (m, 1H), 2.75 (d, J=4.5 Hz, 3H), 2.65-2.55 (m, 2H), 2.40 (t, J=11.1 Hz, 1H), 0.97-0.89 (m, 1H), 0.83 (dq, J=17.1, 6.5 Hz, 1H).

Example 97f: (5R,6S)-5-hydroxy-6-((R)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.35 (q, J=4.5 Hz, 1H), 7.94 (s, 1H), 7.66 (dd, J=8.0, 1.8 Hz, 1H), 7.63 (dq, J=7.6, 0.9 Hz, 1H), 7.59 (dt, J=7.6, 0.9 Hz, 1H), 7.54 (d, J=1.7 Hz, 1H), 7.46 (d, J=8.0 Hz, 1H), 7.39 (tt, J=7.5, 0.9 Hz, 1H), 7.28 (td, J=7.6, 1.2 Hz, 1H), 7.11 (s, 1H), 5.90 (d, J=6.1 Hz, 1H), 5.56-5.50 (m, 1H), 5.04-4.98 (m, 1H), 2.76 (d, J=4.6 Hz, 3H), 2.72 (dd, J=16.7, 4.2 Hz, 1H), 2.56 (dt, J=10.5, 5.4 Hz, 1H), 2.47 (dd, J=12.5, 3.1 Hz, 1H), 1.49 (qd, J=12.7, 5.4 Hz, 1H), 1.04-0.95 (m, 1H).

Example 97g: (5S,6S)-5-hydroxy-6-((R)-5H-imidazo[5,1-a]isoindol-5-yl)-N-methyl-5,6,7,8-tetrahydronaphthalene-2-carboxamide: LCMS (ESI, m/z): 360.3 $[M+H]^+$.

Example 97h: (5S,6R)-5-hydroxy-6-((R)-5H-imidazo[5,1-a]isoindol-5-yl)-N-methyl-5,6,7,8-tetrahydronaphthalene-2-carboxamide: LCMS (ESI, m/z): 360.3 $[M+H]^+$; $^1$HNMR (500 MHz, DMSO-$d_6$) δ 8.34 (q, J=4.4 Hz, 1H), 8.01 (s, 1H), 7.75 (dd, J=7.7, 1.0 Hz, 1H), 7.65-7.59 (m, 2H), 7.56 (d, J=1.7 Hz, 1H), 7.42-7.35 (m, 2H), 7.24 (td, J=7.6, 1.2 Hz, 1H), 7.13 (s, 1H), 5.61 (d, J=6.0 Hz, 1H), 5.45 (d, J=5.9 Hz, 1H), 4.82 (dd, J=6.1, 3.4 Hz, 1H), 2.85 (dd, J=17.3, 4.7 Hz, 1H), 2.75 (d, J=4.6 Hz, 3H), 2.72-2.61 (m, 1H), 2.15 (dq, J=9.4, 3.1 Hz, 1H), 1.95 (qd, J=12.6, 5.4 Hz, 1H), 1.71 (d, J=11.3 Hz, 1H).

Example 98: 5-hydroxy-6-(5H-imidazo[5,1-a]isoindol-5-yl)-N,N-dimethyl-5,6,7,8-tetrahydronaphthalene-2-carboxamide

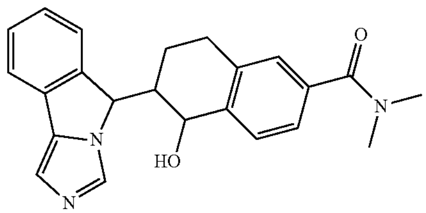 [SMILES: CN(C)C(=O)c1ccc2c(c1)CCC(C1c3ccccc3-c3cncn31)C2O]

(5S,6S)-5-hydroxy-6-((S)-5H-imidazo[5,1-a]isoindol-5-yl)-N,N-dimethyl-5,6,7,8-tetrahydronaphthalene-2-carboxamide (5S,6R)-5-hydroxy-6-((S)-5H-imidazo[5,1-a]isoindol-5-yl)-N,N-dimethyl-5,6,7,8-tetrahydronaphthalene-2-carboxamide (5R,6S)-5-hydroxy-6-((S)-5H-imidazo[5,1-a]isoindol-5-yl)-N,N-dimethyl-5,6,7,8-tetrahydronaphthalene-2-carboxamide (5S,6R)-5-hydroxy-6-((R)-5H-imidazo[5,1-a]isoindol-5-yl)-N,N-dimethyl-5,6,7,8-tetrahydronaphthalene-2-carboxamide (5R,6R)-5-hydroxy-6-((S)-5H-imidazo[5,1-a]isoindol-5-yl)-N,N-dimethyl-5,6,7,8-tetrahydronaphthalene-2-carboxamide (5S,6S)-5-hydroxy-6-((R)-5H-imidazo[5,1-a]isoindol-5-yl)-N,N-dimethyl-5,6,7,8-tetrahydronaphthalene-2-carboxamide (5R,6S)-5-hydroxy-6-((R)-5H-imidazo[5,1-a]isoindol-5-yl)-N,N-dimethyl-5,6,7,8-tetrahydronaphthalene-2-carboxamide (5R,6R)-5-hydroxy-6-((R)-5H-imidazo[5,1-a]isoindol-5-yl)-N,N-dimethyl-5,6,7,8-tetrahydronaphthalene-2-carboxamide Step 1:

N,N-dimethyl-5-oxo-5,6,7,8-tetrahydronaphthalene-2-carboxamide

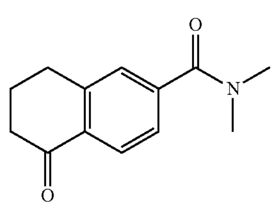 [SMILES: CN(C)C(=O)c1ccc2c(c1)CCCC2=O]

To a round-bottom flask containing 5-oxo-5,6,7,8-tetrahydronaphthalene-2-carboxylic acid (2.00 g, 10.52 mmol) in anhydrous DCM (50 mL) was added triethylamine (4.4 mL, 31.55 mmol), and HATU (4.80 g, 12.62 mmol). Dimethylamine solution in THF (6.31 mL, 12.62 mmol) was added to the above mixture. The reaction mixture was stirred at room temperature for 18 h and concentrated. The residue was dissolved in dichloromethane (30 mL) and poured into water (30 mL) and the aqueous layer was extracted with dichloromethane (3×30 mL). The combined organic layers were washed with water (3×10 mL), satd $NaHCO_3$ (20 mL), dried over $Na_2SO_4$, and concentrated. The product was separated by CombiFlash and was eluted by DCM:MeOH=97:3: LCMS (ESI, m/z): 102.2 $[M+H]^+$.

Step 2:

(E)-N,N-dimethyl-5-oxo-6-(2-(1-trityl-1H-imidazol-4-yl)benzylidene)-5,6,7,8-tetrahydronaphthalene-2-carboxamide

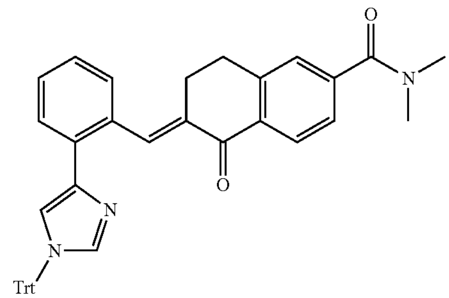

To a solution of 2-(1-trityl-1H-imidazol-4-yl)benzaldehyde (3.0 g, 7.24 mmol) and N,N-dimethyl-5-oxo-5,6,7,8-tetrahydronaphthalene-2-carboxamide (2.04 g, 9.41 mmol) in MeOH (30 mL) was added piperidine dropwise (0.36 mL, 3.62 mmol). The mixture was stirred at 80° C. overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by Hex:EtOAc=20:80: LCMS (ESI, m/z): 614.4 $[M+H]^+$.

Step 3:

6-(5H-imidazo[5,1-a]isoindol-5-yl)-N,N-dimethyl-5-oxo-5,6,7,8-tetrahydronaphthalene-2-carboxamide

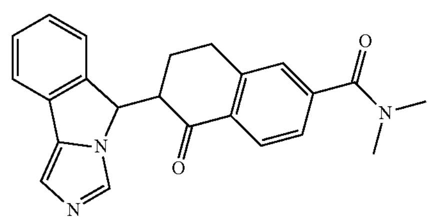 [SMILES: CN(C)C(=O)c1ccc2c(c1)CCC(C1c3ccccc3-c3cncn31)C2=O]

(E)-N,N-dimethyl-5-oxo-6-(2-(1-trityl-1H-imidazol-4-yl)benzylidene)-5,6,7,8-tetrahydronaphthalene-2-carboxamide (2.35 g, 3.83 mmol) was stirred in 20% AcOH in MeOH (20 mL) at 90° C. for 2 h. After cooling to r.t., the solvent was removed under reduced pressure and sat'd $NaHCO_3$ (20 mL) was added to the residue followed by DCM (20 mL). The organic layer was collected and the aqueous layer was extracted with DCM (3×10 mL). The combined organic layers were dried over $Na_2SO_4$ and the solvent evaporated under reduced pressure to afford the crude product which was purified by using CombiFlash and was eluted by DCM:MeOH=95:5: LCMS (ESI, m/z): 372.3 $[M+H]^+$.

Step 4:

(5S,6S)-5-hydroxy-6-((S)-5H-imidazo[5,1-a]isoindol-5-yl)-N,N-dimethyl-5,6,7,8-tetrahydronaphthalene-2-carboxamide (5S,6R)-5-hydroxy-6-((S)-5H-imidazo[5,1-a]isoindol-5-yl)-N,N-dimethyl-5,6,7,8-tetrahydronaphthalene-2-carboxamide
(5R,6S)-5-hydroxy-6-((S)-5H-imidazo[5,1-a]isoindol-5-yl)-N,N-dimethyl-5,6,7,8-tetrahydronaphthalene-2-carboxamide
(5S,6R)-5-hydroxy-6-((R)-5H-imidazo[5,1-a]isoindol-5-yl)-N,N-dimethyl-5,6,7,8-tetrahydronaphthalene-2-carboxamide
(5R,6R)-5-hydroxy-6-((S)-5H-imidazo[5,1-a]isoindol-5-yl)-N,N-dimethyl-5,6,7,8-tetrahydronaphthalene-2-carboxamide
(5S,6S)-5-hydroxy-6-((R)-5H-imidazo[5,1-a]isoindol-5-yl)-N,N-dimethyl-5,6,7,8-tetrahydronaphthalene-2-carboxamide
(5R,6S)-5-hydroxy-6-((R)-5H-imidazo[5,1-a]isoindol-5-yl)-N,N-dimethyl-5,6,7,8-tetrahydronaphthalene-2-carboxamide
(5R,6R)-5-hydroxy-6-((R)-5H-imidazo[5,1-a]isoindol-5-yl)-N,N-dimethyl-5,6,7,8-tetrahydronaphthalene-2-carboxamide 98a

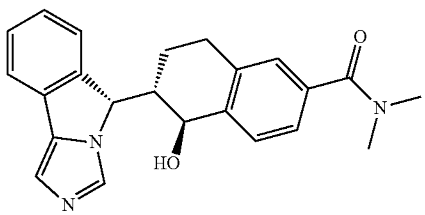

98b

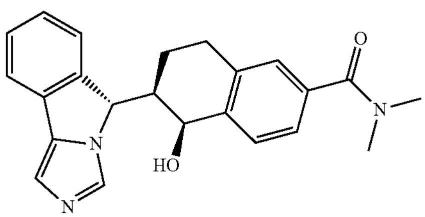

98c

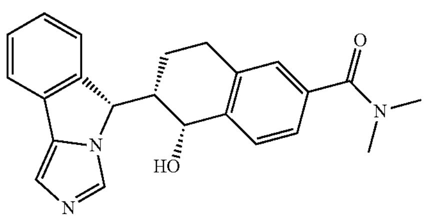

98d

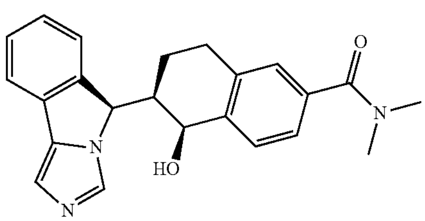

98e

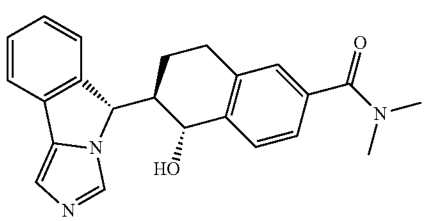

-continued

98f

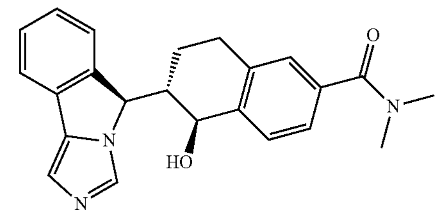

98g

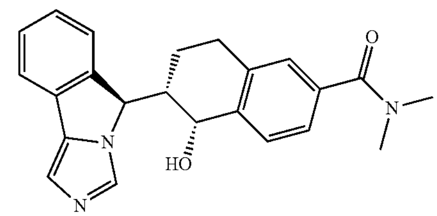

98h

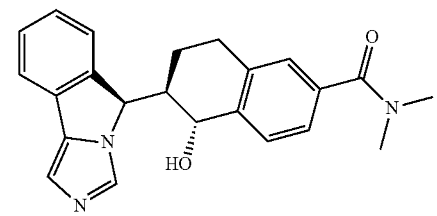

To a solution of 6-(5H-imidazo[5,1-a]isoindol-5-yl)-N,N-dimethyl-5-oxo-5,6,7,8-tetrahydronaphthalene-2-carboxamide (0.703 g, 2.33 mmol) in MeOH (20 mL) was added $NaBH_4$ (265 mg, 7.0 mmol) in portions at 0° C. and the solution was stirred at 0° C. for 2 hr. The solvent was distilled off and saturated ammonium chloride solution (10 mL) was added. The aqueous layer was extracted with DCM (3×10 mL). The combined organic extract was dried over ($Na_2SO_4$) and concentrated under reduced pressure to afford the crude product. The crude was purified by CombiFlash and the product was eluted with DCM:MeOH=92:8. The final products were further isolated by chiral separation to afford 8 isomers and the stereochemistry of each isomer was arbitrarily assigned.

Example 98a: (5S,6S)-5-hydroxy-6-((S)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.97 (s, 1H), 7.70 (d, J=8.0 Hz, 1H), 7.63 (d, J=7.6 Hz, 1H), 7.48 (dd, J=7.6, 1.0 Hz, 1H), 7.41 (s, 1H), 7.31 (d, J=1.2 Hz, 1H), 7.28-7.24 (m, 1H), 7.18 (s, 1H), 7.03 (d, J=1.7 Hz, 1H), 6.08 (d, J=7.7 Hz, 1H), 5.81 (s, 1H), 4.98-4.91 (m, 1H), 2.95 (s, 3H), 2.90 (s, 3H), 2.60 (dd, J=9.4, 5.5 Hz, 2H), 2.40 (t, J=11.3 Hz, 1H), 0.92 (dd, J=12.9, 3.8 Hz, 1H), 0.88-0.76 (m, 1H).

Example 98b: (5S,6R)-5-hydroxy-6-((S)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.91 (s, 1H), 7.64 (t, J=8.6 Hz, 3H), 7.40 (t, J=7.5 Hz, 1H), 7.25 (ddd, J=17.9, 7.8, 1.5 Hz, 2H), 7.17 (s, 1H), 7.02 (d, J=1.7 Hz, 1H), 6.09 (d, J=7.4 Hz, 1H), 5.80 (d, J=3.3 Hz, 1H), 4.89 (dd, J=10.7, 7.4 Hz, 1H), 2.95 (s, 3H), 2.89 (s, 3H), 2.60 (ddt, J=19.8, 15.9, 2.9 Hz, 3H), 0.91-0.84 (m, 2H).

Example 98c: (5R,6S)-5-hydroxy-6-((S)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.95 (s, 1H), 7.62 (dt, J=7.7, 1.0 Hz, 1H), 7.59 (dt, J=7.5, 0.9 Hz, 1H), 7.45 (d, J=7.9 Hz, 1H), 7.39 (tt, J=7.5, 0.9 Hz, 1H), 7.28 (td, J=7.6, 1.2 Hz, 1H), 7.24 (dd, J=7.8, 1.7 Hz, 1H), 7.11 (s, 1H), 7.08 (d, J=1.6 Hz, 1H), 5.90 (d, J=6.0 Hz, 1H), 5.56-5.50 (m, 1H), 5.01 (dd, J=6.1, 3.7 Hz, 1H), 2.96 (s, 3H), 2.91 (s, 3H), 2.71 (dd, J=17.3, 4.4 Hz, 1H), 2.57-2.51 (m, 1H), 2.47 (dd, J=5.7, 2.7 Hz, 1H), 1.49 (qd, J=12.7, 5.4 Hz, 1H), 0.97 (dd, J=10.0, 3.0 Hz, 1H).

Example 98d: (5S,6R)-5-hydroxy-6-((R)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.95 (s, 1H), 7.62 (dt, J=7.7, 0.9 Hz, 1H), 7.61-7.57 (m, 1H), 7.45 (d, J=7.9 Hz, 1H), 7.39 (tt, J=7.5, 0.8 Hz, 1H), 7.28 (td, J=7.5, 1.2 Hz, 1H), 7.24 (dd, J=7.9, 1.7 Hz, 1H), 7.11 (s, 1H), 7.08 (d, J=1.6 Hz, 1H), 5.90 (d, J=6.0 Hz, 1H), 5.56-5.50 (m, 1H), 5.01 (dd, J=6.0, 3.7 Hz, 1H), 2.96 (s, 3H), 2.91 (s, 3H), 2.71 (dd, J=17.3, 4.6 Hz, 1H), 2.58-2.52 (m, 1H), 2.47 (dd, J=6.4, 3.3 Hz, 1H), 1.49 (qd, J=12.7, 5.4 Hz, 1H), 0.97 (dd, J=10.1, 3.0 Hz, 1H).

Example 98e: (5R,6R)-5-hydroxy-6-((S)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 8.01 (s, 1H), 7.75 (dq, J=7.7, 0.9 Hz, 1H), 7.61 (d, J=7.5 Hz, 1H), 7.38 (dd, J=7.8, 6.4 Hz, 2H), 7.24 (td, J=7.6, 1.2 Hz, 1H), 7.20 (dd, J=7.9, 1.7 Hz, 1H), 7.13 (s, 1H), 7.11 (d, J=1.6 Hz, 1H), 5.60 (d, J=6.0 Hz, 1H), 5.46 (d, J=5.8 Hz, 1H), 4.82 (dd, J=6.0, 3.4 Hz, 1H), 2.95 (s, 3H), 2.90 (s, 3H), 2.83 (dd, J=17.4, 4.6 Hz, 1H), 2.64 (ddd, J=16.2, 12.3, 6.0 Hz, 1H), 2.17 (ddd, J=12.3, 6.0, 3.1 Hz, 1H), 1.94 (qd, J=12.6, 5.4 Hz, 1H), 1.72-1.64 (m, 1H).

Example 98f: (5S,6S)-5-hydroxy-6-((R)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 8.01 (s, 1H), 7.75 (dd, J=7.7, 1.0 Hz, 1H), 7.61 (d, J=7.5 Hz, 1H), 7.38 (dd, J=7.9, 6.5 Hz, 2H), 7.24 (td, J=7.6, 1.2 Hz, 1H), 7.20 (dd, J=7.8, 1.7 Hz, 1H), 7.13 (s, 1H), 7.11 (d, J=1.7 Hz, 1H), 5.60 (d, J=5.9 Hz, 1H), 5.46 (d, J=5.8 Hz, 1H), 4.82 (dd, J=6.2, 3.4 Hz, 1H), 2.95 (s, 3H), 2.90 (s, 3H), 2.83 (dd, J=17.4, 4.5 Hz, 1H), 2.69-2.59 (m, 1H), 2.18 (dq, J=9.3, 3.0 Hz, 1H), 1.94 (qd, J=12.6, 5.4 Hz, 1H), 1.71-1.65 (m, 1H).

Example 98g: (5R,6S)-5-hydroxy-6-((R)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.91 (s, 1H), 7.64 (t, J=8.6 Hz, 3H), 7.40 (t, J=7.5 Hz, 1H), 7.29-7.21 (m, 2H), 7.17 (s, 1H), 7.02 (d, J=1.7 Hz, 1H), 6.08 (d, J=7.4 Hz, 1H), 5.80 (d, J=3.2 Hz, 1H), 4.92-4.85 (m, 1H), 2.95 (s, 3H), 2.89 (s, 3H), 2.69-2.53 (m, 3H), 0.92-0.84 (m, 2H).

Example 98h: (5R,6R)-5-hydroxy-6-((R)-5H-imidazo[5,1-a]isoindol-5-yl)-N,N-dimethyl-5,6,7,8-tetrahydronaphthalene-2-carboxamide: LCMS (ESI, m/z): 374.3 $[M+H]^+$; $^1$HNMR (500 MHz, DMSO-$d_6$) δ 7.97 (s, 1H), 7.70 (d, J=8.0 Hz, 1H), 7.64 (d, J=7.6 Hz, 1H), 7.49 (d, J=7.6 Hz, 1H), 7.41 (t, J=7.5 Hz, 1H), 7.32 (t, J=7.5 Hz, 1H), 7.25 (dd, J=8.0, 1.7 Hz, 1H), 7.18 (s, 1H), 7.03 (d, J=1.7 Hz, 1H), 6.08 (d, J=7.6 Hz, 1H), 5.81 (s, 1H), 4.98-4.89 (m, 1H), 2.95 (s, 3H), 2.90 (s, 3H), 2.60 (q, J=6.3 Hz, 2H), 2.46-2.37 (m, 1H), 0.92 (d, J=13.2 Hz, 1H), 0.88-0.77 (m, 1H).

Example 99: 4-(9-fluoro-5H-imidazo[5,1-a]isoindol-5-yl)tetrahydro-2H-pyran-3-ol

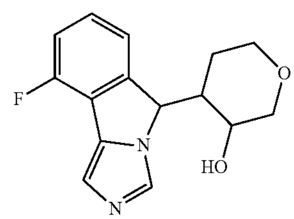

(3R,4R)-4-((R)-9-fluoro-5H-imidazo[5,1-a]isoindol-5-yl)tetrahydro-2H-pyran-3-ol (3S,4S)-4-((S)-9-fluoro-5H-imidazo[5,1-a]isoindol-5-yl)tetrahydro-2H-pyran-3-ol (3S,4S)-4-((R)-9-fluoro-5H-imidazo[5,1-a]isoindol-5-yl)tetrahydro-2H-pyran-3-ol (3R,4R)-4-((S)-9-fluoro-5H-imidazo[5,1-a]isoindol-5-yl)tetrahydro-2H-pyran-3-ol The title compound was synthesized by the same method of example 69.

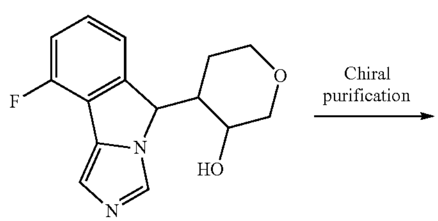

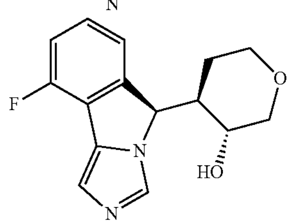

99a

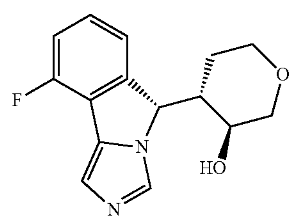

99b

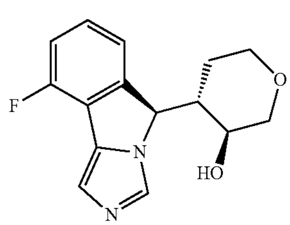

99c

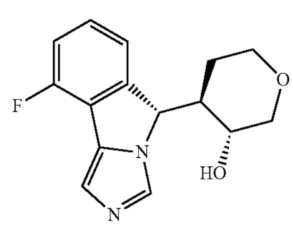

99d

The configurations of the isomers were assigned arbitrarily.

Example 99a: (3R,4R)-4-((R)-9-fluoro-5H-imidazo[5,1-a]isoindol-5-yl)tetrahydro-2H-pyran-3-ol: LCMS (ESI, m/z): 275.1 $[M+H]^+$; $^1$H NMR (500 MHz, DMSO-$d_6$) δ 8.00 (s, 1H), 7.42-7.32 (m, 2H), 7.32-7.26 (m, 1H), 7.11 (s, 1H), 5.78 (d, J=3.7 Hz, 1H), 5.47 (d, J=5.5 Hz, 1H), 3.84 (dd, J=10.5, 4.8 Hz, 1H), 3.73-3.57 (m, 2H), 3.19-3.07 (m, 1H), 2.99 (t, J=10.2 Hz, 1H), 2.40 (tt, J=10.9, 4.1 Hz, 1H), 0.65-0.50 (m, 2H). 99a and 99b are enantiomers.

Example 99b: (3S,4S)-4-((S)-9-fluoro-5H-imidazo[5,1-a]isoindol-5-yl)tetrahydro-2H-pyran-3-ol: LCMS (ESI, m/z):

275.1 [M+H]$^+$; $^1$H NMR (500 MHz, DMSO-$d_6$) δ 8.00 (s, 1H), 7.42-7.26 (m, 3H), 7.11 (s, 1H), 5.78 (d, J=3.7 Hz, 1H), 5.47 (d, J=5.4 Hz, 1H), 3.84 (dd, J=10.6, 4.9 Hz, 1H), 3.68 (tt, J=10.2, 5.1 Hz, 1H), 3.63-3.58 (m, 1H), 3.19-3.07 (m, 1H), 2.99 (t, J=10.2 Hz, 1H), 2.40 (ddd, J=14.6, 7.3, 4.0 Hz, 1H), 0.65-0.50 (m, 2H). 99a and 99b are enantiomers.

Example 99c: (3S,4S)-4-((R)-9-fluoro-5H-imidazo[5,1-a]isoindol-5-yl)tetrahydro-2H-pyran-3-ol: LCMS (ESI, m/z): 275.2 [M+H]$^+$; $^1$H NMR (500 MHz, DMSO-$d_6$) δ 7.96 (s, 1H), 7.41-7.32 (m, 2H), 7.27 (dq, J=11.7, 4.8 Hz, 1H), 7.15 (s, 1H), 5.82-5.77 (m, 1H), 5.53 (d, J=5.9 Hz, 1H), 3.91 (dd, J=10.6, 4.8 Hz, 1H), 3.74 (tt, J=10.4, 5.5 Hz, 1H), 3.59 (dd, J=11.3, 4.5 Hz, 1H), 3.19-3.08 (m, 1H), 3.04 (t, J=10.2 Hz, 1H), 2.23 (t, J=11.4 Hz, 1H), 0.72-0.65 (m, 1H), 0.47 (qd, J=12.5, 4.8 Hz, 1H). 99c and 99d are enantiomers.

Example 99d: (3R,4R)-4-((S)-9-fluoro-5H-imidazo[5,1-a]isoindol-5-yl)tetrahydro-2H-pyran-3-ol: LCMS (ESI, m/z): 275.1 [M+H]$^+$; $^1$H NMR (500 MHz, DMSO-$d_6$) δ 7.96 (s, 1H), 7.36 (td, J=3.9, 2.1 Hz, 2H), 7.29-7.24 (m, 1H), 7.14 (s, 1H), 5.80 (d, J=2.3 Hz, 1H), 5.53 (d, J=5.9 Hz, 1H), 3.91 (dd, J=10.6, 4.8 Hz, 1H), 3.74 (tt, J=10.5, 5.4 Hz, 1H), 3.58 (dd, J=11.3, 4.6 Hz, 1H), 3.11 (td, J=11.7, 2.3 Hz, 1H), 3.04 (t, J=10.3 Hz, 1H), 2.23 (ddd, J=14.3, 9.3, 3.3 Hz, 1H), 0.69 (d, J=13.3 Hz, 1H), 0.47 (qd, J=12.6, 4.8 Hz, 1H). 99c and 99d are enantiomers.

Example 100: 5-hydroxy-6-(5H-imidazo[5,1-a]isoindol-5-yl)-5,6,7,8-tetrahydronaphthalene-2-sulfonamide

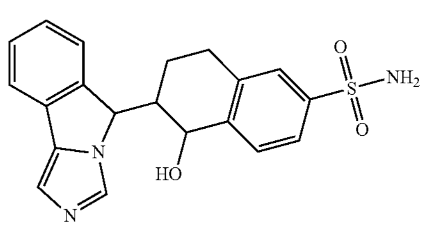 [SMILES: NS(=O)(=O)c1ccc2c(c1)CCC(C1c3ccccc3-c3cncn31)C2O]

(5R,6S)-5-hydroxy-6-((S)-5H-imidazo[5,1-a]isoindol-5-yl)-5,6,7,8-tetrahydronaphthalene-2-sulfonamide (5R,6R)-5-hydroxy-6-((S)-5H-imidazo[5,1-a]isoindol-5-yl)-5,6,7,8-tetrahydronaphthalene-2-sulfonamide (5S,6R)-5-hydroxy-6-((S)-5H-imidazo[5,1-a]isoindol-5-yl)-5,6,7,8-tetrahydronaphthalene-2-sulfonamide (5S,6S)-5-hydroxy-6-((R)-5H-imidazo[5,1-a]isoindol-5-yl)-5,6,7,8-tetrahydronaphthalene-2-sulfonamide (5S,6S)-5-hydroxy-6-((S)-5H-imidazo[5,1-a]isoindol-5-yl)-5,6,7,8-tetrahydronaphthalene-2-sulfonamide (5R,6R)-5-hydroxy-6-((R)-5H-imidazo[5,1-a]isoindol-5-yl)-5,6,7,8-tetrahydronaphthalene-2-sulfonamide (5R,6S)-5-hydroxy-6-((R)-5H-imidazo[5,1-a]isoindol-5-yl)-5,6,7,8-tetrahydronaphthalene-2-sulfonamide (5S,6R)-5-hydroxy-6-((R)-5H-imidazo[5,1-a]isoindol-5-yl)-5,6,7,8-tetrahydronaphthalene-2-sulfonamide Step 1:

6-(5H-imidazo[5,1-a]isoindol-5-yl)-5-oxo-5,6,7,8-tetrahydronaphthalene-2-sulfonamide

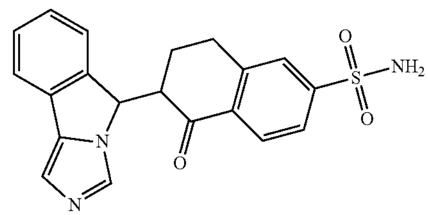 [SMILES: NS(=O)(=O)c1ccc2c(c1)CCC(C1c3ccccc3-c3cncn31)C2=O]

Lithium methoxide (10% solution, 6.94 mL, 14.47 mmol) was added drop wise to the solution of 2-(1-trityl-1H-imidazol-4-yl)benzaldehyde (1.5 g, 3.62 mmol) and 5-oxo-5,6,7,8-tetrahydronaphthalene-2-sulfonamide (815.17 mg, 3.62 mmol) in 7:3 mixture of DMF/methanol (15 mL) and stirred at room temperature. Reaction was completed after 4 hours as indicated by the TLC. Water (30 mL) was added to the reaction mixture and crude product was extracted with DCM (2×20 mL). Combined organic layers was washed with water multiple times to remove excess DMF and evaporated. Methanol (20 mL) and acetic acid (4 mL) were added to the crude product and refluxed for 3 hours. Methanol was evaporated and solid sodium carbonate was added to neutralize reaction mixture. Crude product was extracted with DCM, which was further purified over Combi-Flash. LCMS (ESI, m/z): 380.2 [M+H]$^+$ Step 2:

(5R,6S)-5-hydroxy-6-((S)-5H-imidazo[5,1-a]isoindol-5-yl)-5,6,7,8-tetrahydronaphthalene-2-sulfonamide (5R,6R)-5-hydroxy-6-((S)-5H-imidazo[5,1-a]isoindol-5-yl)-5,6,7,8-tetrahydronaphthalene-2-sulfonamide (5S,6R)-5-hydroxy-6-((S)-5H-imidazo[5,1-a]isoindol-5-yl)-5,6,7,8-tetrahydronaphthalene-2-sulfonamide (5S,6S)-5-hydroxy-6-((R)-5H-imidazo[5,1-a]isoindol-5-yl)-5,6,7,8-tetrahydronaphthalene-2-sulfonamide (5S,6S)-5-hydroxy-6-((S)-5H-imidazo[5,1-a]isoindol-5-yl)-5,6,7,8-tetrahydronaphthalene-2-sulfonamide (5R,6R)-5-hydroxy-6-((R)-5H-imidazo[5,1-a]isoindol-5-yl)-5,6,7,8-tetrahydronaphthalene-2-sulfonamide (5R,6S)-5-hydroxy-6-((R)-5H-imidazo[5,1-a]isoindol-5-yl)-5,6,7,8-tetrahydronaphthalene-2-sulfonamide (5S,6R)-5-hydroxy-6-((R)-5H-imidazo[5,1-a]isoindol-5-yl)-5,6,7,8-tetrahydronaphthalene-2-sulfonamide 100a

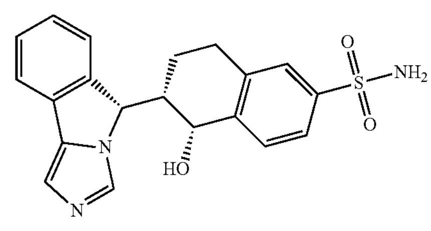

100b

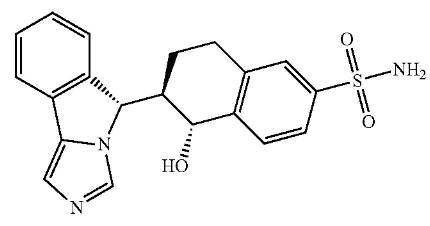

-continued

100c

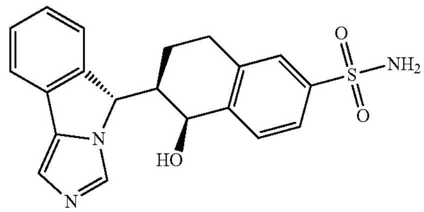

100d

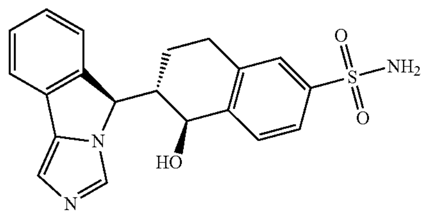

100e

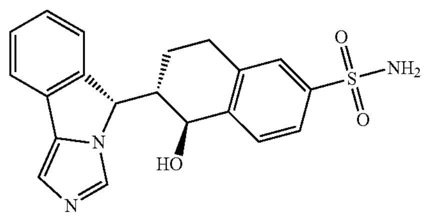

100f

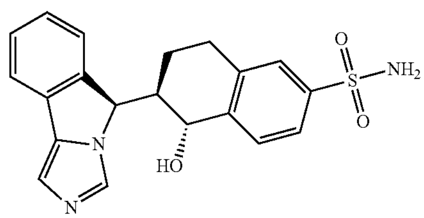

100g

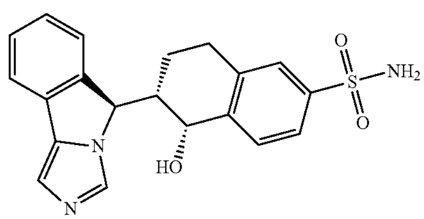

100h

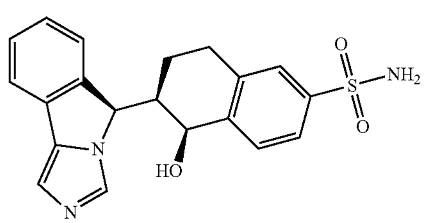

Sodium borohydride (0.358 g, 9.49 mmol) was added portion-wise to the solution of 6-(5H-imidazo[5,1-a]isoindol-5-yl)-5-oxo-5,6,7,8-tetrahydronaphthalene-2-sulfonamide (1.2 g, 3.16 mmol) in methanol (20 mL) at 0° C. Reaction flask was then removed from ice bath and reaction was stirred at room temperature for 2 hours. Saturated ammonium chloride solution (10 mL) was added to the reaction mixture and stirred at room temperature for 30 minutes. Methanol was evaporated under reduced pressure and crude product was extracted with 10% 2,2,2-trifluoroethanol in DCM (2×20 mL). Combined organic layers were evaporated to yield crude product which was further purified on Combi-Flash and further isolated by chiral separation to afford 8 isomers as white solid. The absolute configuration of all isomers was assigned arbitrarily.

Example 100a: (5R,6S)-5-hydroxy-6-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 7.95 (s, 1H), 7.65 (dd, J=8.1, 1.9 Hz, 1H), 7.62 (dd, J=7.7, 1.0 Hz, 1H), 7.60 (d, J=7.6 Hz, 1H), 7.57 (d, J=8.1 Hz, 1H), 7.52 (d, J=1.8 Hz, 1H), 7.41-7.37 (m, 1H), 7.30 (dd, J=7.6, 1.2 Hz, 1H), 7.27 (m, 2H), 7.12 (s, 1H), 6.00 (d, J=6.1 Hz, 1H), 5.54 (d, J=2.2 Hz, 1H), 5.03 (dd, J=6.1, 3.8 Hz, 1H), 2.76 (dd, J=17.2, 4.6 Hz, 1H), 2.58 (ddd, J=17.5, 12.5, 5.9 Hz, 1H), 2.47 (dd, J=6.5, 3.3 Hz, 1H), 1.50 (qd, J=12.6, 5.4 Hz, 1H), 1.25-0.98 (m, 1H).

Example 100b: (5R,6R)-5-hydroxy-6-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 7.91 (s, 1H), 7.77 (d, J=8.2 Hz, 1H), 7.68-7.60 (m, 3H), 7.46 (d, J=1.9 Hz, 1H), 7.41 (t, J=7.5 Hz, 1H), 7.27 (dd, J=7.6, 1.2 Hz, 1H), 7.25 (s, 2H), 7.17 (s, 1H), 6.21 (d, J=7.5 Hz, 1H), 5.81 (d, J=3.3 Hz, 1H), 4.90 (dd, J=10.7, 7.5 Hz, 1H), 2.70-2.54 (m, 3H), 0.89 (d, J=4.7 Hz, 2H).

Example 100c: (5S,6R)-5-hydroxy-6-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 7.97 (s, 1H), 7.82 (d, J=8.2 Hz, 1H), 7.70-7.61 (m, 2H), 7.51-7.45 (m, 2H), 7.42 (t, J=7.5 Hz, 1H), 7.32 (dd, J=7.6, 1.1 Hz, 1H), 7.25 (s, 2H), 7.18 (s, 1H), 6.21 (d, J=7.6 Hz, 1H), 5.81 (s, 1H), 4.99-4.88 (m, 1H), 2.69-2.57 (m, 2H), 2.41 (t, J=11.2 Hz, 1H), 1.00-0.72 (m, 2H).

Example 100d: (5S,6S)-5-hydroxy-6-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 8.10 (s, 1H), 7.77 (dd, J=8.3, 3.0 Hz, 1H), 7.71-7.61 (m, 3H), 7.47 (d, J=3.0 Hz, 1H), 7.43 (td, J=7.6, 2.8 Hz, 1H), 7.30 (td, J=7.6, 2.9 Hz, 2H), 7.25 (d, J=3.0 Hz, 2H), 6.24 (dd, J=7.5, 3.0 Hz, 1H), 5.85 (d, J=3.7 Hz, 1H), 4.90 (t, J=9.0 Hz, 1H), 2.74-2.54 (m, 3H), 0.96-0.85 (m, 2H).

Example 100e: (5S,6S)-5-hydroxy-6-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 8.01 (s, 1H), 7.74 (d, J=7.8 Hz, 1H), 7.64-7.59 (m, 2H), 7.55 (d, J=1.9 Hz, 1H), 7.50 (d, J=8.1 Hz, 1H), 7.39 (s, 1H), 7.26 (d, J=11.2 Hz, 3H), 7.14 (s, 1H), 5.70 (d, J=6.0 Hz, 1H), 5.46 (d, J=6.1 Hz, 1H), 4.84 (dd, J=6.1, 3.3 Hz, 1H), 2.94-2.85 (m, 1H), 2.72 (dd, J=12.1, 5.9 Hz, 1H), 2.19-2.12 (m, 1H), 1.96 (dd, J=12.5, 5.4 Hz, 1H), 1.74 (d, J=12.6 Hz, 1H).

Example 100f: (5S,6S)-5-hydroxy-6-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 8.01 (s, 1H), 7.74 (d, J=7.8 Hz, 1H), 7.64-7.59 (m, 2H), 7.55 (d, J=1.9 Hz, 1H), 7.50 (d, J=8.1 Hz, 1H), 7.39 (s, 1H), 7.26 (d, J=11.2 Hz, 3H), 7.14 (s, 1H), 5.70 (d, J=6.0 Hz, 1H), 5.46 (d, J=6.1 Hz, 1H), 4.84 (dd, J=6.1, 3.3 Hz, 1H), 2.94-2.85 (m, 1H), 2.72 (dd, J=12.1, 5.9 Hz, 1H), 2.19-2.12 (m, 1H), 1.96 (dd, J=12.5, 5.4 Hz, 1H), 1.74 (d, J=12.6 Hz, 1H).

Example 100g: ((5R,6S)-5-hydroxy-6-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1H$ NMR (500 MHz, DMSO-d6) δ 7.97 (s, 1H), 7.82 (d, J=8.2 Hz, 1H), 7.70-7.61 (m, 2H), 7.51-7.45 (m, 2H), 7.42 (t, J=7.5 Hz, 1H), 7.32 (dd, J=7.6, 1.1 Hz, 1H), 7.25 (s, 2H), 7.18 (s, 1H), 6.21 (d, J=7.6 Hz, 1H), 5.81 (s, 1H), 4.99-4.88 (m, 1H), 2.69-2.57 (m, 2H), 2.41 (t, J=11.2 Hz, 1H), 1.00-0.72 (m, 2H).

Example 100h: ((5S,6R)-5-hydroxy-6-((R)-5H-imidazo[5,1-a]isoindol-5-yl)-5,6,7,8-tetrahydronaphthalene-2-sulfonamide: LCMS (ESI, m/z): 382.2 [M+H]$^+$; $^1$H NMR (500 MHz, DMSO-d6) δ 7.95 (s, 1H), 7.65 (dd, J=8.1, 1.9 Hz, 1H), 7.62 (dd, J=7.7, 1.0 Hz, 1H), 7.60 (d, J=7.6 Hz, 1H), 7.57 (d, J=8.1 Hz, 1H), 7.52 (d, J=1.8 Hz, 1H), 7.41-7.37 (m, 1H), 7.30 (dd, J=7.6, 1.2 Hz, 1H), 7.27 (m, 2H), 7.12 (s, 1H), 6.00 (d, J=6.1 Hz, 1H), 5.54 (d, J=2.2 Hz, 1H), 5.03 (dd, J=6.1, 3.8 Hz, 1H), 2.76 (dd, J=17.2, 4.6 Hz, 1H), 2.58 (ddd, J=17.5, 12.5, 5.9 Hz, 1H), 2.47 (dd, J=6.5, 3.3 Hz, 1H), 1.50 (qd, J=12.6, 5.4 Hz, 1H), 1.25-0.98 (m, 1H).

Example 101: 4-hydroxy-5-(5H-imidazo[5,1-a]isoindol-5-yl)azepane-1-sulfonamide 101a-d

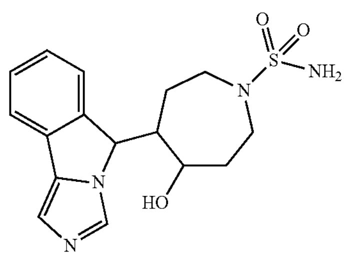

(4R,5S)-4-hydroxy-5-((S)-5H-imidazo[5,1-a]isoindol-5-yl)azepane-1-sulfonamide (4S,5R)-4-hydroxy-5-((R)-5H-imidazo[5,1-a]isoindol-5-yl)azepane-1-sulfonamide (4R,5S)-4-hydroxy-5-((R)-5H-imidazo[5,1-a]isoindol-5-yl)azepane-1-sulfonamide (4S,5R)-4-hydroxy-5-((S)-5H-imidazo[5,1-a]isoindol-5-yl)azepane-1-sulfonamide Synthetic Route

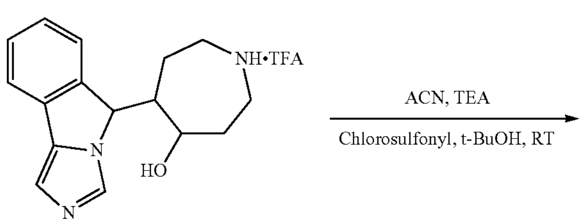

5.

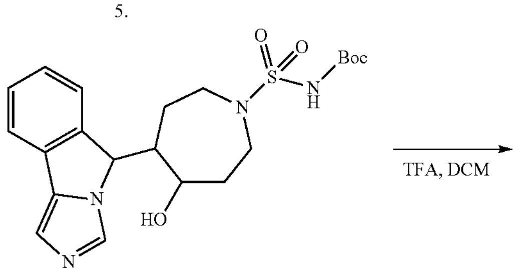

6.

-continued

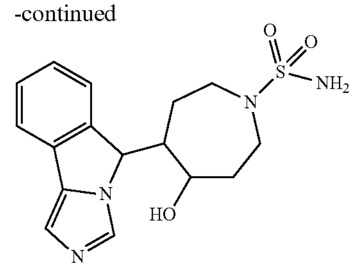

tert-butyl ((4-hydroxy-5-(5H-imidazo[5,1-a]isoindol-5-yl)azepan-1-yl)sulfonyl)carbamate

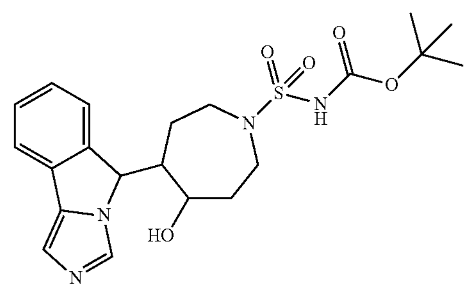 [SMILES: CC(C)(C)OC(=O)NS(=O)(=O)N1CCC(O)C(C2c3ccccc3-c3cncn32)CC1]

To a solution of 5-(5H-imidazo[1,5-b]isoindol-5-yl)azepan-4-ol; 2,2,2-trifluoroacetic acid (5, 2.01 mmol, 2.01 mmol, 100 mass) in acetonitrile (20 mL, 381 mmol, 100 mass %) was added triethylamine (4 mL, 28.7 mmol, 100 mass %). This was then stirred for 5 minutes.

To chlorosulfonyl isocyanate (1.5 equiv., 3.01 mmol, 98 mass %) in DCM was added tert-butyl alcohol (2.4 equiv., 4.82 mmol, 100 mass %). This was then added dropwise to the reaction and then stirred overnight at room temperature. Reaction quenched by adding 2-3 mL water. The reaction was then concentrated under reduced pressure and the residue purified by flash column to afford tert-butyl ((4-hydroxy-5-(5H-imidazo[5,1-a]isoindol-5-yl)azepan-1-yl)sulfonyl)carbamate as a yellow oil: LCMS (ESI, m/z): 449 [M+H]$^+$.

4-hydroxy-5-(5H-imidazo[5,1-a]isoindol-5-yl)azepane-1-sulfonamide 101a-d

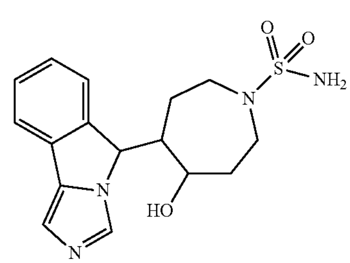

To a solution of tert-butyl N-[4-hydroxy-5-(5H-imidazo[1,5-b]isoindol-5-yl)azepan-1-yl]sulfonylcarbamate (6, 2.01 mmol, 2.01 mmol, 100 mass %) in dichloromethane (3 mL, 46.80 mmol, 100 mass %) was added trifluoroacetic acid (4.1 mL, 54 mmol, 100 mass %) and stirred at room temperature for 3 hours. The reaction was then concentrated under reduced pressure and the residue was then purified and individual isomers were separated by chiral separation (SFC, Column, PPU, 150×30 mm; mobile phase: $CO_2$:0.1% ammonium hydroxide in methanol=80:20; Isocratic, Detector, uv 270 nm; flow rate 150 mL/min, 40° C.) to afford 4 isomers.

Example 101a: LCMS (ESI, m/z): 349.1 $[M+H]^+$. $^1H$ NMR (400 MHz, DMSO-d6) δ 7.81 (s, 1H), 7.61 (d, J=7.5 Hz, 1H), 7.45 (dd, J=7.5, 1.1 Hz, 1H), 7.39 (t, J=7.4 Hz, 1H), 7.31 (td, J=7.5, 1.2 Hz, 1H), 7.15 (s, 1H), 6.58 (s, 2H), 5.74 (d, J=2.2 Hz, 1H), 5.40 (d, J=5.7 Hz, 1H), 3.88-3.81 (m, 1H), 3.38-3.33 (m, 1H), 3.01-2.93 (m, 2H), 2.79 (dt, J=12.9, 7.5 Hz, 1H), 2.34-2.29 (m, 1H), 2.13 (ddq, J=11.0, 4.7, 2.3, 1.8 Hz, 1H), 1.82 (dtd, J=14.3, 11.1, 3.4 Hz, 1H), 0.72 (h, J=4.4 Hz, 2H).

Example 101b: LCMS (ESI, m/z): 349.1 $[M+H]^+$. $^1H$ NMR (400 MHz, DMSO-d6) δ 7.89 (s, 1H), 7.62 (d, J=7.6 Hz, 1H), 7.54 (dd, J=7.7, 1.1 Hz, 1H), 7.39 (dd, J=8.0, 6.9 Hz, 1H), 7.30-7.26 (m, 1H), 7.15 (s, 1H), 6.58 (s, 2H), 5.74 (d, J=3.6 Hz, 1H), 5.35 (d, J=5.2 Hz, 1H), 3.82 (dt, J=9.9, 4.9 Hz, 1H), 3.06-3.00 (m, 1H), 2.97-2.90 (m, 1H), 2.84-2.77 (m, 1H), 2.47 (dd, J=4.0, 2.4 Hz, 1H), 2.12-2.07 (m, 1H), 1.84-1.75 (m, 1H), 0.77-0.69 (m, 1H), 0.60-0.54 (m, 1H).

Example 101c: LCMS (ESI, m/z): 349.1 $[M+H]^+$. $^1H$ NMR (400 MHz, DMSO-d6) δ 7.89 (s, 1H), 7.62 (d, J=7.5 Hz, 1H), 7.54 (d, J=7.6 Hz, 1H), 7.39 (t, J=7.3 Hz, 1H), 7.28 (td, J=7.6, 1.2 Hz, 1H), 7.15 (s, 1H), 6.58 (s, 2H), 5.74 (d, J=3.6 Hz, 1H), 5.35 (d, J=5.2 Hz, 1H), 3.82 (dt, J=10.0, 5.1 Hz, 1H), 3.03 (dt, J=12.9, 4.3 Hz, 1H), 2.97-2.90 (m, 1H), 2.84-2.77 (m, 1H), 2.47-2.43 (m, 1H), 2.13-2.07 (m, 1H), 1.84-1.75 (m, 1H), 0.78-0.68 (m, 1H), 0.61-0.54 (m, 1H).

Example 101d: LCMS (ESI, m/z): 349.1 $[M+H]^+$. $^1H$ NMR (400 MHz, DMSO-d6) δ 7.81 (s, 1H), 7.61 (d, J=7.5 Hz, 1H), 7.45 (dd, J=7.6, 1.1 Hz, 1H), 7.41-7.37 (m, 1H), 7.33-7.29 (m, 1H), 7.15 (s, 1H), 6.58 (s, 2H), 5.74 (d, J=2.3 Hz, 1H), 5.40 (d, J=5.7 Hz, 1H), 3.88-3.82 (m, 1H), 3.38-3.34 (m, 1H), 3.00-2.94 (m, 2H), 2.83-2.76 (m, 1H), 2.33-2.29 (m, 1H), 2.17-2.11 (m, 1H), 1.86-1.78 (m, 1H), 0.72 (dt, J=8.7, 4.6 Hz, 2H).

Example 102: 2-(5H-imidazo[5,1-a]isoindol-5-yl)-1,2,3,4-tetrahydronaphthalen-1-ol

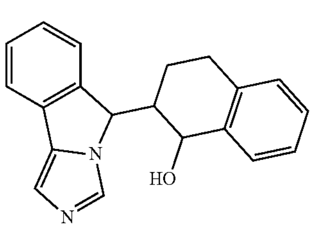 [SMILES: OC1c2ccccc2CCC1C1c2ccccc2-c2cncn21]

(1R,2S)-2-((S)-5H-imidazo[5,1-a]isoindol-5-yl)-1,2,3,4-tetrahydronaphthalen-1-ol
(1S,2R)-2-((R)-5H-imidazo[5,1-a]isoindol-5-yl)-1,2,3,4-tetrahydronaphthalen-1-ol
(1S,2R)-2-((S)-5H-imidazo[5,1-a]isoindol-5-yl)-1,2,3,4-tetrahydronaphthalen-1-ol
(1R,2S)-2-((R)-5H-imidazo[5,1-a]isoindol-5-yl)-1,2,3,4-tetrahydronaphthalen-1-ol
(1S,2S)-2-((S)-5H-imidazo[5,1-a]isoindol-5-yl)-1,2,3,4-tetrahydronaphthalen-1-ol
(1R,2R)-2-((R)-5H-imidazo[5,1-a]isoindol-5-yl)-1,2,3,4-tetrahydronaphthalen-1-ol
(1R,2R)-2-((S)-5H-imidazo[5,1-a]isoindol-5-yl)-1,2,3,4-tetrahydronaphthalen-1-ol
(1S,2S)-2-((R)-5H-imidazo[5,1-a]isoindol-5-yl)-1,2,3,4-tetrahydronaphthalen-1-ol Step 1: 2-(5H-imidazo[5,1-a]isoindol-5-yl)-3,4-dihydronaphthalen-1(2H)-one

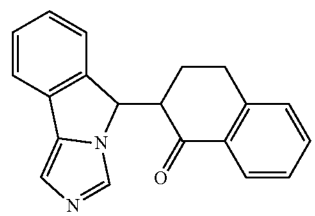 [SMILES: O=C1c2ccccc2CCC1C1c2ccccc2-c2cncn21]

3,4-dihydronaphthalen-1(2H)-one (1.27 g, 8.68 mmol) was added to a stirred mixture of 2-(1-trityl-1H-imidazol-4-yl)benzaldehyde (3 g, 7.24 mmol), and sodium ethoxide (9 mL, 8.68 mmol) in ethanol solution (50 mL). The reaction mixture was then reflux for 2 hr and cool to room temperature. Acetic acid (9 mL, 145 mmol) was then added to the reaction mixture. The reaction was heated at 80° C. for 2 hr. The solvent was removed under reduced pressure and saturated $NaHCO_3$ (30 mL) was added to the residue followed by DCM (30 mL). The organic layer was collected and the aqueous layer was extracted with DCM (2×30 mL). The combined organic layers were dried over $Na_2SO_4$ and the solvent evaporated under reduced pressure to afford the crude product which was purified by Combi-flash using methanol/DCM 2%-4%: LCMS (ESI, m/z): 301.3 $[M+H]^+$ Step 2:

(1R,2S)-2-((S)-5H-imidazo[5,1-a]isoindol-5-yl)-1,2,3,4-tetrahydronaphthalen-1-ol
(1S,2R)-2-((R)-5H-imidazo[5,1-a]isoindol-5-yl)-1,2,3,4-tetrahydronaphthalen-1-ol
(1S,2R)-2-((S)-5H-imidazo[5,1-a]isoindol-5-yl)-1,2,3,4-tetrahydronaphthalen-1-ol
(1R,2S)-2-((R)-5H-imidazo[5,1-a]isoindol-5-yl)-1,2,3,4-tetrahydronaphthalen-1-ol
(1S,2S)-2-((S)-5H-imidazo[5,1-a]isoindol-5-yl)-1,2,3,4-tetrahydronaphthalen-1-ol
(1R,2R)-2-((R)-5H-imidazo[5,1-a]isoindol-5-yl)-1,2,3,4-tetrahydronaphthalen-1-ol
(1R,2R)-2-((S)-5H-imidazo[5,1-a]isoindol-5-yl)-1,2,3,4-tetrahydronaphthalen-1-ol
(1S,2S)-2-((R)-5H-imidazo[5,1-a]isoindol-5-yl)-1,2,3,4-tetrahydronaphthalen-1-ol 102a

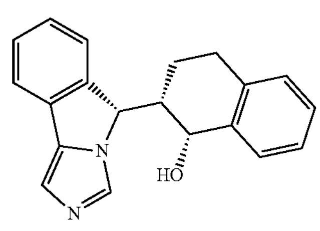

-continued

102b

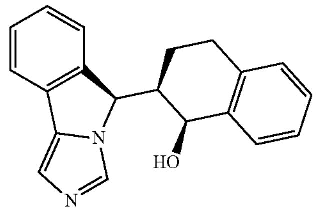

102c

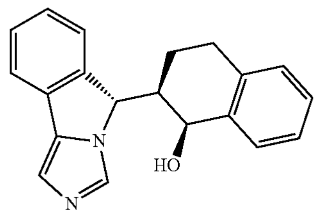

102d

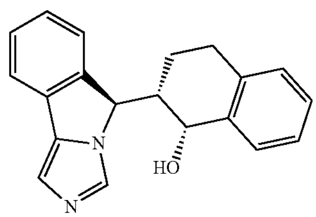

102e

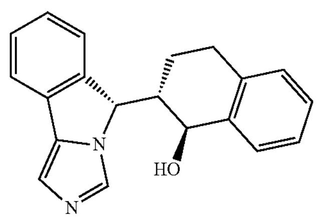

102f

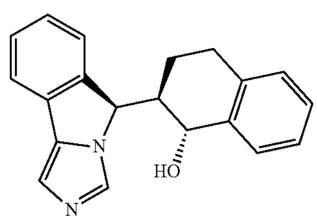

102g

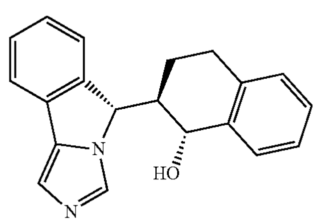

102h

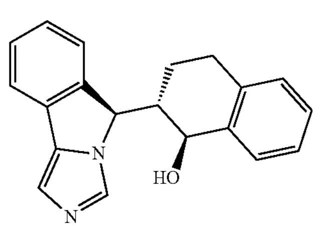

2-(5H-imidazo[5,1-a]isoindol-5-yl)-3,4-dihydronaphthalen-1(2H)-one (2.1 g, 6.99 mmol) was dissolved in dry MeOH (40 mL) at 0° C. $NaBH_4$ (1.06 mg, 28 mmol) was added in four portions. The reaction was stirred at room temperature for 0.5 hr. The reaction was quenched by water and extracted by $CF_3CH_2OH$/DCM (15%, 40 mL×3), combined organic phase was washed with brine and dried over $Na_2SO_4$. After removing solvent and the residue was purified by silica gel column chromatograph (methanol/DCM 4%-8%.). The crude product was purified by Combi-Flash and further isolated by chiral separation to afford 8 isomers as white solid. LCMS (ESI, m/z): 303.3. The absolute configuration of isomers 102e and 102f was assigned by X-ray crystallography. The absolute configuration of the rest isomers was assigned arbitrarily.

Example 102a: (1R,2S)-2-((S)-5H-imidazo[5,1-a]isoindol-5-yl)-1,2,3,4-tetrahydronaphthalen-1-ol: LCMS (ESI, m/z): 303.3 $[M+H]^+$; $^1H$ NMR (400 MHz, DMSO-d6) δ 7.96 (s, 1H), 7.62 (d, J=7.6 Hz, 1H), 7.59 (d, J=7.4 Hz, 1H), 7.42-7.35 (m, 2H), 7.28 (td, J=7.5, 1.2 Hz, 1H), 7.22-7.18 (m, 2H), 7.11 (s, 1H), 7.06 (dd, J=6.8, 2.1 Hz, 1H), 5.78 (d, J=6.1 Hz, 1H), 5.52 (d, J=2.1 Hz, 1H), 4.98 (dd, J=6.1, 3.8 Hz, 1H), 2.74-2.65 (m, 1H), 2.47-2.44 (m, 1H), 2.43 (q, J=2.9 Hz, 1H), 1.50 (qd, J=12.8, 5.6 Hz, 1H).

Example 102b: (1S,2R)-2-((R)-5H-imidazo[5,1-a]isoindol-5-yl)-1,2,3,4-tetrahydronaphthalen-1-ol: LCMS (ESI, m/z): 303.3 $[M+H]^+$; $^1H$ NMR is the same as Example 102a.

Example 102c: (1S,2R)-2-((S)-5H-imidazo[5,1-a]isoindol-5-yl)-1,2,3,4-tetrahydronaphthalen-1-ol: LCMS (ESI, m/z): 303.3 $[M+H]^+$; $^1H$ NMR (400 MHz, DMSO-$d_6$) δ 8.01 (s, 1H), 7.76 (d, J=7.7 Hz, 1H), 7.61 (d, J=7.5 Hz, 1H), 7.38 (t, J=7.4 Hz, 1H), 7.35-7.30 (m, 1H), 7.24 (td, J=7.6, 1.2 Hz, 1H), 7.20-7.16 (m, 2H), 7.13 (s, 1H), 7.10-7.06 (m, 1H), 5.49 (d, J=5.9 Hz, 1H), 5.44 (d, J=6.0 Hz, 1H), 4.79 (dd, J=6.2, 3.3 Hz, 1H), 2.81 (ddd, J=17.3, 5.6, 2.1 Hz, 1H), 2.63 (ddd, J=17.4, 12.3, 5.9 Hz, 1H), 2.12 (ddt, J=12.3, 6.1, 3.0 Hz, 1H), 1.95 (qd, J=12.5, 5.4 Hz, 1H), 1.74-1.63 (m, 1H).

Example 102d: (1R,2S)-2-((R)-5H-imidazo[5,1-a]isoindol-5-yl)-1,2,3,4-tetrahydronaphthalen-1-ol: LCMS (ESI, m/z): 303.3 $[M+H]^+$; $^1H$ NMR is the same as Example 102c.

Example 102e: (1S,2S)-2-((S)-5H-imidazo[5,1-a]isoindol-5-yl)-1,2,3,4-tetrahydronaphthalen-1-ol: LCMS (ESI, m/z): 303.3 $[M+H]^+$; $^1H$ NMR (400 MHz, DMSO-$d_6$) δ 7.96 (s, 1H), 7.66 (d, J=7.7 Hz, 1H), 7.63 (d, J=7.4 Hz, 1H), 7.50-7.46 (m, 1H), 7.41 (t, J=7.4 Hz, 1H), 7.31 (td, J=7.5, 1.2 Hz, 1H), 7.23 (td, J=7.5, 1.4 Hz, 1H), 7.18 (s, 1H), 7.14 (td, J=7.4, 1.4 Hz, 1H), 7.00 (dd, J=7.5, 1.3 Hz, 1H), 5.97 (d, J=7.7 Hz, 1H), 5.84-5.78 (m, 1H), 4.93 (dd, J=10.6, 7.8 Hz, 1H), 2.56 (s, 3H), 2.38 (tt, J=11.2, 2.9 Hz, 1H), 0.95-0.73 (m, 2H).

Example 102f: (1R,2R)-2-((R)-5H-imidazo[5,1-a]isoindol-5-yl)-1,2,3,4-tetrahydronaphthalen-1-ol: LCMS (ESI, m/z): 303.3 $[M+H]^+$; $^1H$ NMR is the same as Example 102e.

Example 102g: (1R,2R)-2-((S)-5H-imidazo[5,1-a]isoindol-5-yl)-1,2,3,4-tetrahydronaphthalen-1-ol: LCMS (ESI, m/z): 303.3 $[M+H]^+$; $^1H$ NMR (400 MHz, DMSO-$d_6$) δ 7.90 (s, 1H), 7.63 (t, J=6.8 Hz, 2H), 7.60 (d, J=4.5 Hz, 1H), 7.40 (t, J=7.4 Hz, 1H), 7.26 (td, J=7.5, 1.2 Hz, 1H), 7.21 (td, J=7.6, 1.4 Hz, 1H), 7.17 (s, 1H), 7.13 (td, J=7.4, 1.5 Hz, 1H), 6.99 (d, J=7.6 Hz, 1H), 5.98 (d, J=7.4 Hz, 1H), 5.80 (d, J=3.3 Hz, 1H), 4.89 (dd, J=10.6, 7.5 Hz, 1H), 2.68-2.53 (m, 3H), 0.85 (h, J=5.3, 4.8 Hz, 2H).

Example 102h: (1S,2S)-2-((R)-5H-imidazo[5,1-a]isoindol-5-yl)-1,2,3,4-tetrahydronaphthalen-1-ol: LCMS (ESI, m/z): 303.3 $[M+H]^+$; $^1H$ NMR is the same as Example 102g.

Example 103: (3S,4S)-4-((S)-5H-imidazo[5,1-a]isoindol-5-yl)-1-(oxetan-3-yl)piperidin-3-ol

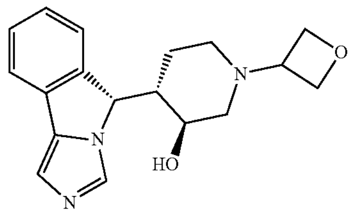

(3S,4S)-4-((S)-5H-imidazo[5,1-a]isoindol-5-yl)-1-(oxetan-3-yl)piperidin-3-ol

103

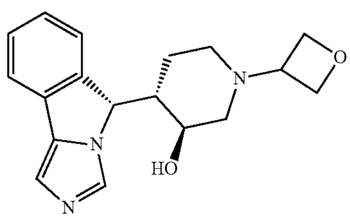 [SMILES: O[C@@H]1CN(C2COC2)CC[C@H]1[C@H]1c2ccccc2-c2cncn21]

A solution of (3S,4S)-3-hydroxy-4-((S)-5H-imidazo[5,1-a]isoindol-5-yl)piperidinium 2,2,2-trifluoroacetate (310 mg, 0.84 mmol) and oxetan-3-one (180 mg, 2.50 mmol) in DCE (5 mL) was stirred for 16 h at room temperature. After $NaBH_3CN$ (210 mg, 3.34 mmol) was added, the resulting solution was allowed to react, with stirring, for an additional 2 h at room temperature. The reaction was then quenched by the addition of Sat. sodium bicarbonate (10 mL). The resulting solution was extracted with DCM (3×20 mL) and the organic layers combined. The mixture was dried over anhydrous sodium sulfate and concentrated under vacuum. The residue was purified with Combi-flash.

Example 103: (3,4S)-4-[(5R)-5H-imidazo[4,3-a]isoindol-5-yl]-1-(oxetan-3-yl)piperidin-3-ol (66.0 mg, 25%) as a white solid: LCMS (ESI, m/z): 312.3 $[M+H]^+$. $^1H$ NMR (300 MHz, $CD_3OD$) δ 7.92 (s, 1H), 7.63 (d, J=7.5, 1H), 7.48-7.33 (m, 3H), 7.20 (s, 1H), 5.79 (d, J=3.3, 1H), 4.71-4.47 (m, 4H), 3.97-3.96 (m, 1H), 3.54-3.50 (m, 1H), 3.09-3.04 (m, 1H), 2.61-2.49 (m, 1H), 2.12-2.02 (m, 1H), 1.89-1.65 (m, 2H), 0.92-0.87 (m, 1H), 0.71-0.55 (m, 1H).

Example 104: 5-hydroxy-6-(5H-imidazo[5,1-a]isoindol-5-yl)-5,6,7,8-tetrahydroquinoline-2-carboxamide

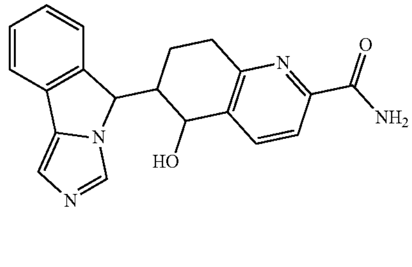 [SMILES: NC(=O)c1ccc2c(n1)CCC(C1c3ccccc3-c3cncn31)C2O]

(5R,6S)-5-hydroxy-6-((S)-5H-imidazo[5,1-a]isoindol-5-yl)-5,6,7,8-tetrahydroquinoline-2-carboxamide
(5R,6R)-5-hydroxy-6-((S)-5H-imidazo[5,1-a]isoindol-5-yl)-5,6,7,8-tetrahydroquinoline-2-carboxamide
(5S,6R)-5-hydroxy-6-((S)-5H-imidazo[5,1-a]isoindol-5-yl)-5,6,7,8-tetrahydroquinoline-2-carboxamide
(5S,6S)-5-hydroxy-6-((S)-5H-imidazo[5,1-a]isoindol-5-yl)-5,6,7,8-tetrahydroquinoline-2-carboxamide
(5R,6R)-5-hydroxy-6-((R)-5H-imidazo[5,1-a]isoindol-5-yl)-5,6,7,8-tetrahydroquinoline-2-carboxamide
(5S,6S)-5-hydroxy-6-((R)-5H-imidazo[5,1-a]isoindol-5-yl)-5,6,7,8-tetrahydroquinoline-2-carboxamide
(5R,6S)-5-hydroxy-6-((R)-5H-imidazo[5,1-a]isoindol-5-yl)-5,6,7,8-tetrahydroquinoline-2-carboxamide
(5S,6R)-5-hydroxy-6-((R)-5H-imidazo[5,1-a]isoindol-5-yl)-5,6,7,8-tetrahydroquinoline-2-carboxamide Step 1: 5-oxo-5,6,7,8-tetrahydroquinoline-2-carbonitrile

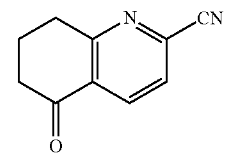 [SMILES: N#Cc1ccc2c(n1)CCCC2=O]

Under nitrogen (200 mg, 1.10 mmol) of 2-chloro-7,8-dihydroquinolin-5(6H)-one, (211 mg, 2.31 mmol) of zinc cyanide and (64 mg, 0.05 mmol) of tetrakis(triphenylphosphine)palladium were suspended in 2 mL of anhydrous N,N-dimethylacetamide (water content <0.01 percent, degassed with nitrogen beforehand), heated to 100° C. and stirred at this temperature for 2 hours. After complete conversion (monitored by TLC, mobile phase petroleum ether/ethyl acetate 2:1), the reaction mixture (grey suspension) was cooled to room temperature. The reaction mixture was diluted with EtOAc (10 mL) and was washed with water (3×2 mL). The combined organic layers was then washed with brine (2 mL) and were dried over $Na_2SO_4$ and the solvent evaporated under reduced pressure to afford the crude product which was purified by using combi flash column chromatography. LCMS (ESI, m/z): 173.2 $[M+H]^+$ Step 2: 5-oxo-5,6,7,8-tetrahydroquinoline-2-carboxamide

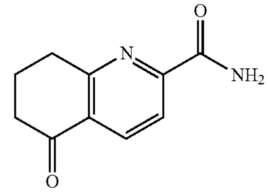 [SMILES: NC(=O)c1ccc2c(n1)CCCC2=O]

To a solution of the 5-oxo-5,6,7,8-tetrahydroquinoline-2-carbonitrile (200 mg, 1.16 mmol) in methanol (2 mL) was added NaOH solution (0.58 mL, 6 M, 3.48 mmol) followed by hydrogen peroxide (~0.28 mL) at 0° C. and the mixture was allowed to stir for 1 hour at room temperature. After an hour, TLC indicated no starting material. The reaction mixture was diluted with water and then extracted using EtOAc (3×5 mL) and the combined organic layers were dried over $Na_2SO_4$ and the solvent evaporated under reduced pressure to afford 5-oxo-5,6,7,8-tetrahydroquinoline-2-carboxamide: LCMS (ESI, m/z): 191.2 $[M+H]^+$ Step 3: (E)-5-oxo-6-(2-(1-trityl-1H-imidazol-4-yl)benzylidene)-5,6,7,8-tetrahydroquinoline-2-carboxamide

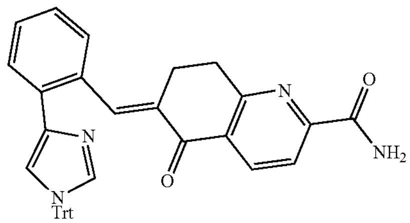

The title compounds were synthesized by General Procedure for the Synthesis of Int-2: LCMS (ESI, m/z): 587.3 $[M+H]^+$ Step 4: 6-(5H-imidazo[5,1-a]isoindol-5-yl)-5-oxo-5,6,7,8-tetrahydroquinoline-2-carboxamide

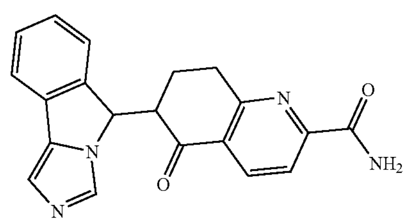 [SMILES: NC(=O)c1ccc2c(n1)CCC(C1c3ccccc3-c3cncn31)C2=O]

The title compounds were synthesized by General Procedure for the Synthesis of Int-2: LCMS (ESI, m/z): 345.2 [M+H]

Step 5: 5-hydroxy-6-(5H-imidazo[5,1-a]isoindol-5-yl)-5,6,7,8-tetrahydroquinoline-2-carboxamide

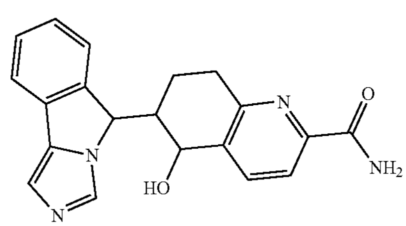 [SMILES: NC(=O)c1ccc2c(n1)CCC(C1c3ccccc3-c3cncn31)C2O]

The title compounds were synthesized by General Procedure for the Synthesis of Int-5: LCMS (ESI, m/z): 347.2 $[M+H]^+$. The mixture was isolated by Chiral separation methods and the configuration of the isomers was assigned arbitrarily. sdfgfd (5R,6S)-5-hydroxy-6-((S)-5H-imidazo[5,1-a]isoindol-5-yl)-5,6,7,8-tetrahydroquinoline-2-carboxamide (5R,6R)-5-hydroxy-6-((S)-5H-imidazo[5,1-a]isoindol-5-yl)-5,6,7,8-tetrahydroquinoline-2-carboxamide (5S,6R)-5-hydroxy-6-((S)-5H-imidazo[5,1-a]isoindol-5-yl)-5,6,7,8-tetrahydroquinoline-2-carboxamide (5S,6S)-5-hydroxy-6-((S)-5H-imidazo[5,1-a]isoindol-5-yl)-5,6,7,8-tetrahydroquinoline-2-carboxamide (5R,6R)-5-hydroxy-6-((R)-5H-imidazo[5,1-a]isoindol-5-yl)-5,6,7,8-tetrahydroquinoline-2-carboxamide (5S,6S)-5-hydroxy-6-((R)-5H-imidazo[5,1-a]isoindol-5-yl)-5,6,7,8-tetrahydroquinoline-2-carboxamide (5R,6S)-5-hydroxy-6-((R)-5H-imidazo[5,1-a]isoindol-5-yl)-5,6,7,8-tetrahydroquinoline-2-carboxamide (5S,6R)-5-hydroxy-6-((R)-5H-imidazo[5,1-a]isoindol-5-yl)-5,6,7,8-tetrahydroquinoline-2-carboxamide 104a

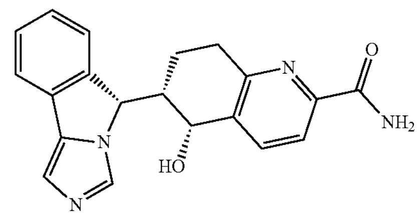

104b

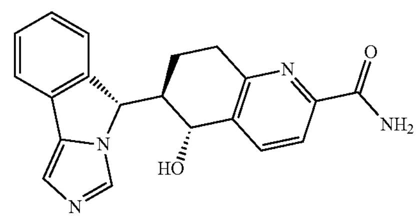

104c

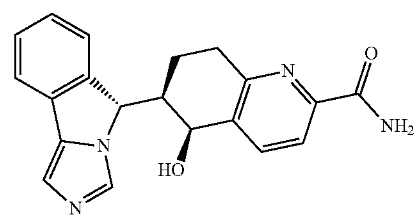

104d

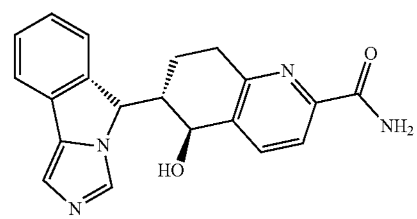

104e

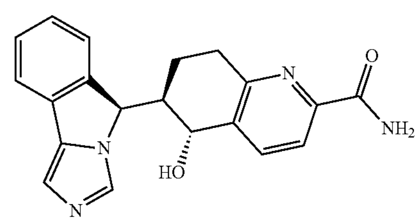

104f

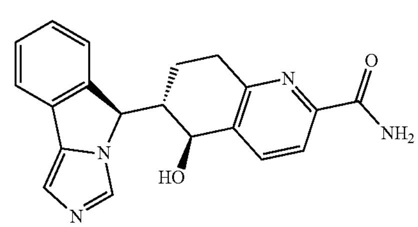

-continued

104g

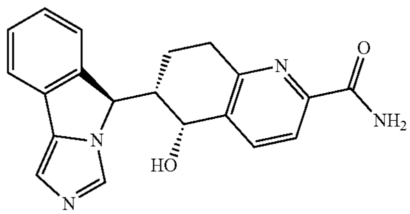

104h

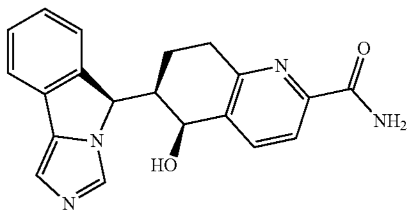

Example 104a: (5R,6S)-5-hydroxy-6-((S)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.11 (d, J=8.0 Hz, 1H), 7.97 (s, 1H), 7.90 (d, J=8.0 Hz, 1H), 7.88 (s, 1H), 7.65 (t, J=8.4 Hz, 2H), 7.52 (s, 1H), 7.41 (t, J=7.4 Hz, 1H), 7.28 (td, J=7.6, 1.1 Hz, 1H), 7.20 (s, 1H), 6.34 (d, J=7.3 Hz, 1H), 5.82 (d, J=3.1 Hz, 1H), 4.96 (dd, J=10.7, 7.4 Hz, 1H), 2.76 (dd, J=8.1, 4.7 Hz, 2H), 2.68-2.60 (m, 1H), 1.05-0.90 (m, 2H).

Example 104b: (5R,6R)-5-hydroxy-6-((S)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.16 (d, J=8.0 Hz, 1H), 7.99 (s, 1H), 7.91 (d, J=8.0 Hz, 1H), 7.87 (s, 1H), 7.64 (d, J=7.6 Hz, 1H), 7.53 (s, 1H), 7.50 (d, J=7.6 Hz, 1H), 7.42 (t, J=7.5 Hz, 1H), 7.32 (td, J=7.5, 1.0 Hz, 1H), 7.19 (s, 1H), 6.33 (d, J=7.5 Hz, 1H), 5.81 (s, 1H), 5.02 (dd, J=10.6, 7.7 Hz, 1H), 2.82-2.64 (m, 2H), 2.48-2.43 (m, 1H), 1.08-0.84 (m, 2H).

Example 104c: (5S,6R)-5-hydroxy-6-((S)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 7.97-7.93 (m, 2H), 7.90 (t, J=6.9 Hz, 2H), 7.62 (dd, J=14.9, 7.6 Hz, 2H), 7.56 (s, 1H), 7.40 (t, J=7.5 Hz, 1H), 7.30 (t, J=7.5 Hz, 1H), 7.12 (s, 1H), 6.09 (d, J=6.1 Hz, 1H), 5.57 (s, 1H), 5.15-5.06 (m, 1H), 2.85 (dd, J=17.8, 3.9 Hz, 1H), 2.68 (td, J=12.2, 6.3 Hz, 1H), 2.56 (d, J=2.7 Hz, 1H), 1.62 (qd, J=12.8, 5.5 Hz, 1H), 1.04 (d, J=6.1 Hz, 1H).

Example 104d: (5S,6S)-5-hydroxy-6-((S)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.01 (s, 1H), 7.92 (s, 1H), 7.87 (q, J=7.9 Hz, 2H), 7.74 (d, J=7.7 Hz, 1H), 7.62 (d, J=7.5 Hz, 1H), 7.56 (s, 1H), 7.39 (t, J=7.4 Hz, 1H), 7.25 (td, J=7.6, 1.1 Hz, 1H), 7.15 (s, 1H), 5.79 (d, J=6.1 Hz, 1H), 5.49 (d, J=6.0 Hz, 1H), 4.91 (dd, J=5.8, 3.2 Hz, 1H), 2.96 (dd, J=17.9, 3.7 Hz, 1H), 2.79 (ddd, J=18.1, 12.3, 6.4 Hz, 1H), 2.27 (dq, J=9.2, 3.1 Hz, 1H), 2.07 (qd, J=12.7, 5.5 Hz, 1H), 1.81 (d, J=10.0 Hz, 1H).

Example 104e: (5R,6R)-5-hydroxy-6-((R)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.01 (s, 1H), 7.93 (s, 1H), 7.87 (q, J=7.9 Hz, 2H), 7.74 (d, J=7.7 Hz, 1H), 7.63 (d, J=7.5 Hz, 1H), 7.56 (s, 1H), 7.40 (t, J=7.5 Hz, 1H), 7.25 (td, J=7.6, 1.1 Hz, 1H), 7.15 (s, 1H), 5.79 (d, J=6.1 Hz, 1H), 5.49 (d, J=5.9 Hz, 1H), 4.92 (dd, J=5.7, 3.2 Hz, 1H), 3.04-2.91 (m, 1H), 2.79 (ddd, J=18.0, 12.4, 6.3 Hz, 1H), 2.27 (dq, J=9.3, 3.0 Hz, 1H), 2.07 (qd, J=12.7, 5.5 Hz, 1H), 1.81 (d, J=7.1 Hz, 1H).

Example 104f: (5S,6S)-5-hydroxy-6-((R)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.16 (d, J=8.0 Hz, 1H), 7.98 (s, 1H), 7.91 (d, J=8.0 Hz, 1H), 7.87 (s, 1H), 7.64 (d, J=7.6 Hz, 1H), 7.53 (s, 1H), 7.50 (d, J=7.2 Hz, 1H), 7.42 (t, J=7.5 Hz, 1H), 7.32 (td, J=7.5, 1.0 Hz, 1H), 7.19 (s, 1H), 6.33 (d, J=7.5 Hz, 1H), 5.81 (s, 1H), 5.02 (dd, J=10.6, 7.7 Hz, 1H), 2.82-2.63 (m, 2H), 2.45 (d, J=11.0 Hz, 1H), 1.07-0.87 (m, 2H).

Example 104g: (5R,6S)-5-hydroxy-6-((R)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 7.97-7.93 (m, 2H), 7.91 (s, 1H), 7.89 (d, J=7.9 Hz, 1H), 7.63 (d, J=7.6 Hz, 1H), 7.60 (d, J=7.5 Hz, 1H), 7.56 (s, 1H), 7.40 (t, J=7.5 Hz, 1H), 7.30 (t, J=7.5 Hz, 1H), 7.12 (s, 1H), 6.09 (d, J=3.8 Hz, 1H), 5.57 (s, 1H), 5.10 (s, 1H), 2.85 (dd, J=17.7, 3.9 Hz, 1H), 2.67 (td, J=12.3, 6.3 Hz, 1H), 2.55 (dd, J=12.6, 2.9 Hz, 1H), 1.62 (qd, J=12.9, 5.7 Hz, 1H), 1.09 (d, J=10.0 Hz, 1H).

Example 104h: (5S,6R)-5-hydroxy-6-((R)-5H-imidazo[5,1-a]isoindol-5-yl)-5,6,7,8-tetrahydroquinoline-2-carboxamide: LCMS (ESI, m/z): 347.2 $[M+H]^+$; $^1$H NMR (500 MHz, DMSO-$d_6$) δ 8.11 (d, J=8.0 Hz, 1H), 7.92 (s, 1H), 7.90 (d, J=8.1 Hz, 1H), 7.88 (s, 1H), 7.65 (t, J=7.5 Hz, 2H), 7.52 (s, 1H), 7.41 (t, J=7.6 Hz, 1H), 7.27 (t, J=7.7 Hz, 1H), 7.18 (s, 1H), 6.33 (d, J=7.3 Hz, 1H), 5.81 (d, J=2.7 Hz, 1H), 4.96 (dd, J=10.5, 7.6 Hz, 1H), 2.76 (dd, J=8.1, 4.6 Hz, 2H), 2.64 (t, J=11.2 Hz, 1H), 0.97 (dd, J=20.0, 6.5 Hz, 2H).

Example 105: 8-hydroxy-7-(5H-imidazo[5,1-a]isoindol-5-yl)-5,6,7,8-tetrahydronaphthalene-2-sulfonamide

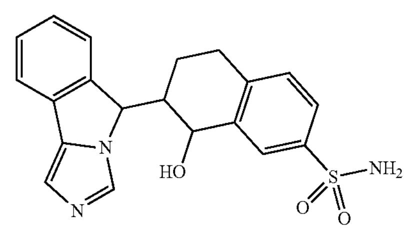 [SMILES: NS(=O)(=O)c1ccc2c(c1)C(O)C(C1c3ccccc3-c3cncn31)CC2]

(7S,8R)-8-hydroxy-7-((S)-5H-imidazo[5,1-a]isoindol-5-yl)-5,6,7,8-tetrahydronaphthalene-2-sulfonamide (7S,8S)-8-hydroxy-7-((S)-5H-imidazo[5,1-a]isoindol-5-yl)-5,6,7,8-tetrahydronaphthalene-2-sulfonamide (7R,8S)-8-hydroxy-7-((R)-5H-imidazo[5,1-a]isoindol-5-yl)-5,6,7,8-tetrahydronaphthalene-2-sulfonamide (7R,8R)-8-hydroxy-7-((S)-5H-imidazo[5,1-a]isoindol-5-yl)-5,6,7,8-tetrahydronaphthalene-2-sulfonamide (7R,8R)-8-hydroxy-7-((R)-5H-imidazo[5,1-a]isoindol-5-yl)-5,6,7,8-tetrahydronaphthalene-2-sulfonamide (7S,8R)-8-hydroxy-7-((R)-5H-imidazo[5,1-a]isoindol-5-yl)-5,6,7,8-tetrahydronaphthalene-2-sulfonamide (7S,8S)-8-hydroxy-7-((R)-5H-imidazo[5,1-a]isoindol-5-yl)-5,6,7,8-tetrahydronaphthalene-2-sulfonamide (7R,8S)-8-hydroxy-7-((S)-5H-imidazo[5,1-a]isoindol-5-yl)-5,6,7,8-tetrahydronaphthalene-2-sulfonamide Step 1:

(E)-8-oxo-7-(2-(1-trityl-1H-imidazol-4-yl)benzylidene)-5,6,7,8-tetrahydronaphthalene-2-sulfonamide

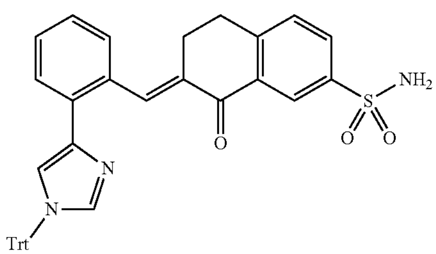

To a solution of 2-(1-trityl-1H-imidazol-4-yl)benzaldehyde (2.5 g, 6.03 mmol) and 8-oxo-5,6,7,8-tetrahydronaphthalene-2-sulfonamide (1.63 g, 7.24 mmol) in ethanol (30 mL) was added anhydrous $Ca(OH)_2$ (223 mg, 3.02 mmol). The mixture was stirred at 90° C. overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted by EtOAc: LCMS (ESI, m/z): 622.3 $[M+H]^+$.

Step 2:

7-(5H-imidazo[5,1-a]isoindol-5-yl)-8-oxo-5,6,7,8-tetrahydronaphthalene-2-sulfonamide

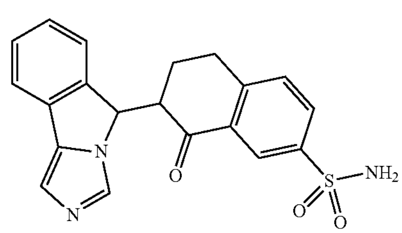 [SMILES: NS(=O)(=O)c1ccc2c(c1)C(=O)C(C1c3ccccc3-c3cncn31)CC2]

(E)-8-oxo-7-(2-(1-trityl-1H-imidazol-4-yl)benzylidene)-5,6,7,8-tetrahydronaphthalene-2-sulfonamide (3.5 g, 5.63 mmol) was stirred in 20% AcOH in MeOH (100 mL) at 90° C. for 2 h. After cooling to r.t., the solvent was removed under reduced pressure and saturated $NaHCO_3$ (50 mL) was added to the residue followed by DCM (30 mL). The organic layer was collected and the aqueous layer was extracted with 10% trifluoroethanol in DCM (3×30 mL). The combined organic layers were dried over $Na_2SO_4$ and the solvent evaporated under reduced pressure to afford the crude product which was purified by using CombiFlash and was eluted by DCM:MeOH=95:5: LCMS (ESI, m/z): 380.2 $[M+H]^+$.

Step 3:

(7S,8R)-8-hydroxy-7-((S)-5H-imidazo[5,1-a]isoindol-5-yl)-5,6,7,8-tetrahydronaphthalene-2-sulfonamide (7S,8S)-8-hydroxy-7-((S)-5H-imidazo[5,1-a]isoindol-5-yl)-5,6,7,8-tetrahydronaphthalene-2-sulfonamide (7R,8S)-8-hydroxy-7-((R)-5H-imidazo[5,1-a]isoindol-5-yl)-5,6,7,8-tetrahydronaphthalene-2-sulfonamide (7R,8R)-8-hydroxy-7-((S)-5H-imidazo[5,1-a]isoindol-5-yl)-5,6,7,8-tetrahydronaphthalene-2-sulfonamide (7R,8R)-8-hydroxy-7-((R)-5H-imidazo[5,1-a]isoindol-5-yl)-5,6,7,8-tetrahydronaphthalene-2-sulfonamide (7S,8R)-8-hydroxy-7-((R)-5H-imidazo[5,1-a]isoindol-5-yl)-5,6,7,8-tetrahydronaphthalene-2-sulfonamide (7S,8S)-8-hydroxy-7-((R)-5H-imidazo[5,1-a]isoindol-5-yl)-5,6,7,8-tetrahydronaphthalene-2-sulfonamide (7R,8S)-8-hydroxy-7-((S)-5H-imidazo[5,1-a]isoindol-5-yl)-5,6,7,8-tetrahydronaphthalene-2-sulfonamide 105a

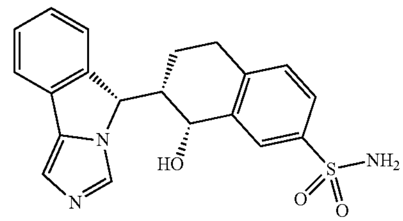

105b

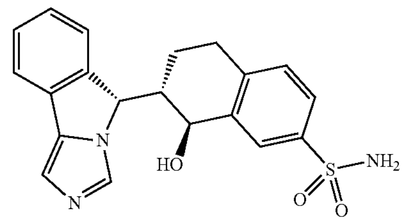

105c

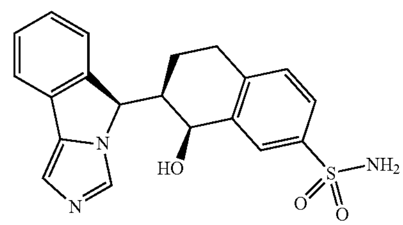

105d

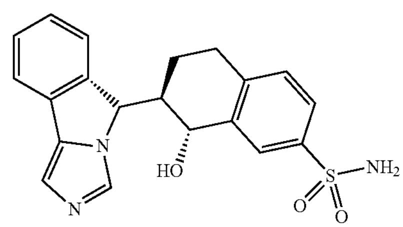

105e

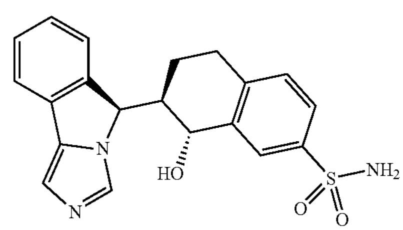

105f

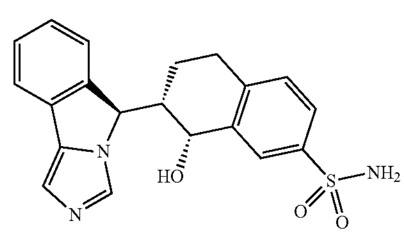

-continued

105g

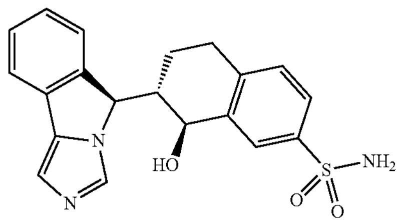

105h

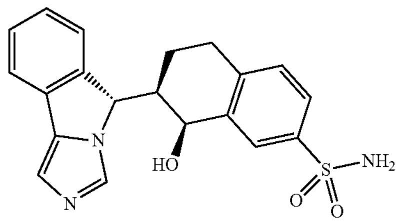

To a suspension of 7-(5H-imidazo[5,1-a]isoindol-5-yl)-8-oxo-5,6,7,8-tetrahydronaphthalene-2-sulfonamide (2.0 g, 5.27 mmol) in MeOH (50 mL) was added $NaBH_4$ (398 mg, 10.54 mmol) in portions at 0° C. and the solution was stirred at 0° C. for 2 hr. The solvent was distilled off and saturated ammonium chloride solution (50 mL) was added. The aqueous layer was extracted with DCM (3×30 mL). The combined organic extract was dried over ($Na_2SO_4$) and concentrated under reduced pressure to afford the crude product. The crude was purified by CombiFlash and the product was eluted with DCM:MeOH=90:10. The final products were further isolated by chiral separation to afford 8 isomers and the stereochemistry of each isomer was arbitrarily assigned.

Example 105a: (7S,8R)-8-hydroxy-7-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 7.94 (s, 1H), 7.88 (d, J=2.0 Hz, 1H), 7.63 (dd, J=8.0, 2.0 Hz, 2H), 7.60 (d, J=7.5 Hz, 1H), 7.42-7.36 (m, 1H), 7.33-7.27 (m, 3H), 7.25 (d, J=8.1 Hz, 1H), 7.12 (s, 1H), 6.10 (d, J=6.5 Hz, 1H), 5.54 (d, J=2.4 Hz, 1H), 5.03 (dd, J=6.5, 3.7 Hz, 1H), 2.80-2.71 (m, 1H), 2.55 (ddd, J=18.5, 12.6, 6.3 Hz, 1H), 2.48-2.43 (m, 1H), 1.49 (qd, J=12.6, 5.4 Hz, 1H), 1.06-0.96 (m, 1H).

Example 105b: (7S,8S)-8-hydroxy-7-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.11 (dd, J=2.1, 0.9 Hz, 1H), 7.91 (s, 1H), 7.64 (ddd, J=7.3, 5.7, 1.0 Hz, 2H), 7.58 (dd, J=7.9, 2.0 Hz, 1H), 7.41 (ddd, J=8.1, 7.2, 1.1 Hz, 1H), 7.32-7.23 (m, 3H), 7.21-7.13 (m, 2H), 6.29 (d, J=7.6 Hz, 1H), 5.81 (d, J=3.3 Hz, 1H), 4.95-4.87 (m, 1H), 2.70-2.53 (m, 3H), 0.86 (t, J=7.1 Hz, 2H).

Example 105c: (7R,8S)-8-hydroxy-7-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 7.93 (s, 1H), 7.88 (d, J=2.0 Hz, 1H), 7.63 (dd, J=8.0, 2.2 Hz, 2H), 7.60 (d, J=7.5 Hz, 1H), 7.39 (t, J=7.5 Hz, 1H), 7.33-7.27 (m, 3H), 7.25 (d, J=8.1 Hz, 1H), 7.12 (s, 1H), 6.10 (d, J=6.5 Hz, 1H), 5.57-5.50 (m, 1H), 5.03 (dd, J=6.5, 3.7 Hz, 1H), 2.80-2.72 (m, 1H), 2.56 (ddd, J=18.3, 12.5, 6.2 Hz, 1H), 2.46 (dd, J=12.3, 3.2 Hz, 1H), 1.49 (qd, J=12.7, 5.3 Hz, 1H), 1.05-0.98 (m, 1H).

Example 105d: (7R,8R)-8-hydroxy-7-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.16 (d, J=2.1 Hz, 1H), 7.98 (s, 1H), 7.64 (d, J=7.6 Hz, 1H), 7.60 (dd, J=8.0, 2.0 Hz, 1H), 7.48 (dd, J=7.6, 1.0 Hz, 1H), 7.42 (t, J=7.6 Hz, 1H), 7.35-7.27 (m, 3H), 7.19 (d, J=7.9 Hz, 2H), 6.26 (d, J=7.8 Hz, 1H), 5.82 (s, 1H), 4.99-4.91 (m, 1H), 2.66-2.59 (m, 2H), 2.41 (t, J=11.3 Hz, 1H), 0.96-0.88 (m, 1H), 0.88-0.77 (m, 1H).

Example 105e: (7R,8R)-8-hydroxy-7-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.11 (d, J=2.0 Hz, 1H), 7.90 (s, 1H), 7.64 (dd, J=7.6, 5.9 Hz, 2H), 7.58 (dd, J=8.0, 2.0 Hz, 1H), 7.41 (t, J=7.6 Hz, 1H), 7.32-7.23 (m, 3H), 7.21-7.13 (m, 2H), 6.29 (d, J=7.6 Hz, 1H), 5.81 (d, J=3.3 Hz, 1H), 4.95-4.87 (m, 1H), 2.67-2.54 (m, 3H), 0.85 (t, J=7.3 Hz, 2H).

Example 105f: (7S,8R)-8-hydroxy-7-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.02 (s, 1H), 7.83 (d, J=2.0 Hz, 1H), 7.73 (dq, J=7.7, 0.9 Hz, 1H), 7.65-7.59 (m, 2H), 7.42-7.35 (m, 1H), 7.31-7.20 (m, 4H), 7.14 (s, 1H), 5.82 (d, J=6.5 Hz, 1H), 5.46 (d, J=6.2 Hz, 1H), 4.85 (dd, J=6.5, 3.4 Hz, 1H), 2.88 (dd, J=17.5, 5.1 Hz, 1H), 2.72-2.62 (m, 1H), 2.14 (ddt, J=12.5, 6.3, 3.1 Hz, 1H), 1.94 (qd, J=12.7, 5.5 Hz, 1H), 1.73 (d, J=12.9 Hz, 1H).

Example 105g: (7S,8S)-8-hydroxy-7-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.16 (dd, J=2.1, 0.9 Hz, 1H), 7.98 (s, 1H), 7.64 (d, J=7.6 Hz, 1H), 7.60 (dd, J=8.0, 2.0 Hz, 1H), 7.51-7.45 (m, 1H), 7.44-7.39 (m, 1H), 7.32 (td, J=7.5, 3.2 Hz, 3H), 7.19 (d, J=7.7 Hz, 2H), 6.26 (d, J=7.8 Hz, 1H), 5.82 (d, J=1.9 Hz, 1H), 4.99-4.91 (m, 1H), 2.66-2.59 (m, 2H), 2.41 (t, J=11.1 Hz, 1H), 0.92 (dq, J=12.6, 4.3 Hz, 1H), 0.89-0.77 (m, 1H).

Example 105h: (7R,8S)-8-hydroxy-7-((S)-5H-imidazo[5,1-a]isoindol-5-yl)-5,6,7,8-tetrahydronaphthalene-2-sulfonamide: LCMS (ESI, m/z): 382.2 $[M+H]^+$; $^1$HNMR (500 MHz, DMSO-$d_6$) δ 8.02 (s, 1H), 7.83 (d, J=1.9 Hz, 1H), 7.73 (d, J=7.7 Hz, 1H), 7.65-7.59 (m, 2H), 7.39 (t, J=7.5 Hz, 1H), 7.30-7.21 (m, 4H), 7.14 (s, 1H), 5.82 (d, J=6.4 Hz, 1H), 5.46 (d, J=6.1 Hz, 1H), 4.85 (dd, J=6.6, 3.3 Hz, 1H), 2.89 (dt, J=17.8, 3.3 Hz, 1H), 2.67 (ddd, J=17.7, 12.0, 6.1 Hz, 1H), 2.14 (ddd, J=12.6, 6.3, 3.2 Hz, 1H), 1.95 (qd, J=12.6, 5.4 Hz, 1H), 1.73 (d, J=10.3 Hz, 1H).

Example 106: 2,2-difluoro-6-(5H-imidazo[5,1-a]isoindol-5-yl)cyclohexan-1-ol

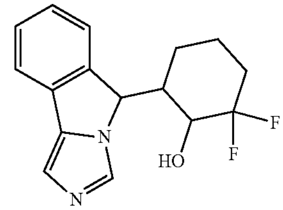 [SMILES: OC1C(C2c3ccccc3-c3cncn32)CCCC1(F)F]

(1R,6R)-2,2-difluoro-6-((R)-5H-imidazo[5,1-a]isoindol-5-yl)cyclohexan-1-ol (1S,6S)-2,2-difluoro-6-((S)-5H-imidazo[5,1-a]isoindol-5-yl)cyclohexan-1-ol (1S,6S)-2,2-difluoro-6-((R)-5H-imidazo[5,1-a]isoindol-5-yl)cyclohexan-1-ol (1R,6R)-2,2-difluoro-6-((S)-5H-imidazo[5,1-a]isoindol-5-yl)cyclohexan-1-ol Step 1:

(1R,6R)-2,2-difluoro-6-((R)-5H-imidazo[5,1-a]isoindol-5-yl)cyclohexan-1-ol (1S,6S)-2,2-difluoro-6-((S)-5H-imidazo[5,1-a]isoindol-5-yl)cyclohexan-1-ol (1S,6S)-2,2-difluoro-6-((R)-5H-imidazo[5,1-a]isoindol-5-yl)cyclohexan-1-ol (1R,6R)-2,2-difluoro-6-((S)-5H-imidazo[5,1-a]isoindol-5-yl)cyclohexan-1-ol 106a

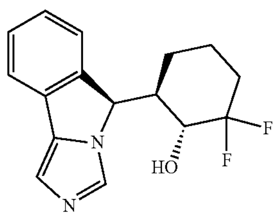

106b

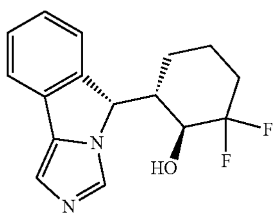

106c

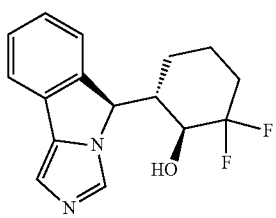

106d

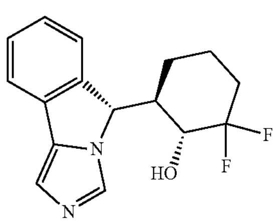

To a solution of 5H-imidazo[5,1-a]isoindole (800 mg, 5.12 mmol) in anhydrous THF (3 mL) was added n-BuLi solution (2.05 mL, 5.12 mmol) at −78° C. and stirred for 1 hr. 2,2-Difluoro-7-oxabicyclo[4.1.0]heptane (755 mg, 5.63 mmol) was dissolved in anhydrous THF (10 mL) and the solution was added into the reaction mixture drop-wise. The reaction was kept at −78° C. for another 30 min and was warmed up to room temperature. The reaction was kept for overnight and was quenched with saturated $NH_4Cl$ solution (30 mL). The mixture was extracted with 20% trifluoroethanol in DCM (3×30 mL) and the organic phase was combined, dried over $Na_2SO_4$, and concentrated. The product was purified by preparative HPLC. The final products were further isolated by chiral separation to afford 4 isomers and the stereochemistry of each isomer was arbitrarily assigned.

Example 106a: (1R,6R)-2,2-difluoro-6-((R)-5H-imidazo[5,1-a]isoindol-5-yl)cyclohexan-1-ol: LCMS (ESI, m/z): 291.2 $[M+H]^+$; $^1$HNMR (500 MHz, DMSO-$d_6$) δ 7.87 (s, 1H), 7.60 (dt, J=7.6, 0.9 Hz, 1H), 7.51-7.47 (m, 1H), 7.42-7.36 (m, 1H), 7.29 (td, J=7.5, 1.1 Hz, 1H), 7.17 (s, 1H), 6.04 (d, J=7.0 Hz, 1H), 5.65 (d, J=2.3 Hz, 1H), 3.99-3.86 (m, 1H), 2.30 (t, J=12.0 Hz, 1H), 1.98 (s, 1H), 1.71 (dt, J=32.1, 13.8 Hz, 1H), 1.46 (d, J=13.8 Hz, 1H), 1.27-1.12 (m, 1H), 0.71 (d, J=13.5 Hz, 1H), 0.36 (qd, J=13.1, 3.9 Hz, 1H).

Example 106b: (1S,6S)-2,2-difluoro-6-((S)-5H-imidazo[5,1-a]isoindol-5-yl)cyclohexan-1-ol: LCMS (ESI, m/z): 291.2 $[M+H]^+$; $^1$HNMR (500 MHz, DMSO-$d_6$) δ 7.87 (s, 1H), 7.60 (dt, J=7.6, 0.9 Hz, 1H), 7.49 (dt, J=7.6, 0.9 Hz, 1H), 7.41-7.36 (m, 1H), 7.29 (td, J=7.6, 1.2 Hz, 1H), 7.16 (s, 1H), 6.04 (d, J=7.0 Hz, 1H), 5.65 (d, J=2.4 Hz, 1H), 3.99-3.86 (m, 1H), 2.30 (t, J=12.0 Hz, 1H), 1.98 (s, 1H), 1.81-1.63 (m, 1H), 1.46 (d, J=13.8 Hz, 1H), 1.20 (q, J=14.3, 13.1 Hz, 1H), 0.71 (d, J=13.5 Hz, 1H), 0.36 (qd, J=13.1, 4.0 Hz, 1H).

Example 106c: (1S,6S)-2,2-difluoro-6-((R)-5H-imidazo[5,1-a]isoindol-5-yl)cyclohexan-1-ol: LCMS (ESI, m/z): 291.2 $[M+H]^+$; $^1$HNMR (500 MHz, DMSO-$d_6$) δ 7.93 (s, 1H), 7.62 (d, J=7.6 Hz, 1H), 7.52 (d, J=7.6 Hz, 1H), 7.41 (t, J=7.5 Hz, 1H), 7.29 (td, J=7.6, 1.1 Hz, 1H), 7.13 (s, 1H), 6.07 (d, J=6.2 Hz, 1H), 5.65 (d, J=3.8 Hz, 1H), 3.93-3.80 (m, 1H), 1.97 (s, 1H), 1.64 (dt, J=32.3, 14.0 Hz, 1H), 1.46 (d, J=13.8 Hz, 1H), 1.21 (q, J=13.7 Hz, 1H), 0.57 (d, J=13.5 Hz, 1H), 0.38 (td, J=13.1, 3.8 Hz, 1H).

Example 106d: (1R,6R)-2,2-difluoro-6-((S)-5H-imidazo[5,1-a]isoindol-5-yl)cyclohexan-1-ol: LCMS (ESI, m/z): 291.2 $[M+H]^+$; $^1$HNMR (500 MHz, DMSO-$d_6$) δ 7.93 (s, 1H), 7.62 (dt, J=7.6, 0.8 Hz, 1H), 7.52 (dd, J=7.6, 0.9 Hz, 1H), 7.41 (tt, J=7.6, 0.8 Hz, 1H), 7.30 (dd, J=7.6, 1.2 Hz, 1H), 7.13 (s, 1H), 6.07 (d, J=6.5 Hz, 1H), 5.65 (d, J=3.8 Hz, 1H), 3.86 (dddd, J=21.6, 10.9, 6.5, 3.9 Hz, 1H), 1.97 (s, 1H), 1.74-1.55 (m, 1H), 1.46 (d, J=13.7 Hz, 1H), 1.28-1.14 (m, 1H), 0.57 (d, J=13.3 Hz, 1H), 0.38 (td, J=13.1, 3.8 Hz, 1H).

Example 107: 8-hydroxy-7-(5H-imidazo[5,1-a]isoindol-5-yl)-5,6,7,8-tetrahydroquinoline-3-carbonitrile

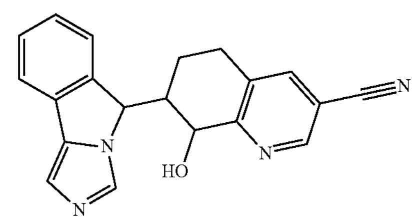 [SMILES: N#Cc1cnc2c(c1)CCC(C1c3ccccc3-c3cncn31)C2O]

(7R,8S)-8-hydroxy-7-((S)-5H-imidazo[5,1-a]isoindol-5-yl)-5,6,7,8-tetrahydroquinoline-3-carbonitrile (7S,8S)-8-hydroxy-7-((S)-5H-imidazo[5,1-a]isoindol-5-yl)-5,6,7,8-tetrahydroquinoline-3-carbonitrile (7S,8R)-8-hydroxy-7-((S)-5H-imidazo[5,1-a]isoindol-5-yl)-5,6,7,8-tetrahydroquinoline-3-carbonitrile (7R,8S)-8-hydroxy-7-((R)-5H-imidazo[5,1-a]isoindol-5-yl)-5,6,7,8-tetrahydroquinoline-3-carbonitrile (7R,8R)-8-hydroxy-7-((S)-5H-imidazo[5,1-a]isoindol-5-yl)-5,6,7,8-tetrahydroquinoline-3-carbonitrile (7S,8S)-8-hydroxy-7-((R)-5H-imidazo[5,1-a]isoindol-5-yl)-5,6,7,8-tetrahydroquinoline-3-carbonitrile (7S,8R)-8-hydroxy-7-((R)-5H-imidazo[5,1-a]isoindol-5-yl)-5,6,7,8-tetrahydroquinoline-3-carbonitrile (7R,8R)-8-hydroxy-7-((R)-5H-imidazo[5,1-a]isoindol-5-yl)-5,6,7,8-tetrahydroquinoline-3-carbonitrile Step 1: (E)-8-oxo-7-(2-(1-trityl-1H-imidazol-4-yl)benzylidene)-5,6,7,8-tetrahydroquinoline-3-carbonitrile

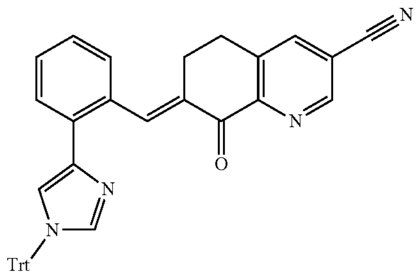

To a solution of 2-(1-trityl-1H-imidazol-4-yl)benzaldehyde (2.0 g, 4.82 mmol) and 8-oxo-5,6,7,8-tetrahydroquinoline-3-carbonitrile (914 mg, 5.31 mmol) in ethanol (50 mL) was added anhydrous $Ca(OH)_2$ (178 mg, 2.41 mmol). The mixture was stirred at 90° C. overnight. The mixture was cooled to room temperature and saturated $NH_4Cl$ solution (30 mL) was added to quench the reaction. The aqueous phase was extracted with DCM (3×20 mL) and the organic phase was combined, dried over anhydrous $Na_2SO_4$, and concentrated. The product was separated by CombiFlash and was eluted with EtOAc: LCMS (ESI, m/z): 569.1 $[M+H]^+$;

Step 2: 7-(5H-imidazo[5,1-a]isoindol-5-yl)-8-oxo-5,6,7,8-tetrahydroquinoline-3-carbonitrile

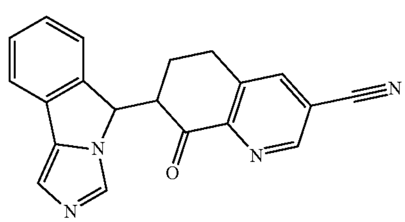 [SMILES: N#Cc1cnc2c(c1)CCC(C1c3ccccc3-c3cncn31)C2=O]

(E)-8-oxo-7-(2-(1-trityl-1H-imidazol-4-yl)benzylidene)-5,6,7,8-tetrahydroquinoline-3-carbonitrile (1.55 g, 2.73 mmol) was stirred in 20% AcOH in MeOH (200 mL) at 90° C. for 2 h. After cooling to room temperature, the solvent was removed under reduced pressure and saturated $NaHCO_3$ (60 mL) was added to the residue followed by DCM (20 mL). The organic layer was collected and the aqueous layer was extracted with 20% trifluoroethanol in DCM (3×50 mL). The combined organic layers were dried over $Na_2SO_4$ and the solvent evaporated under reduced pressure to afford the crude product which was purified by using CombiFlash and was eluted by DCM:MeOH=97:3: LCMS (ESI, m/z): 327.2 $[M+H]^+$.

Step 3:

(7R,8S)-8-hydroxy-7-((S)-5H-imidazo[5,1-a]isoindol-5-yl)-5,6,7,8-tetrahydroquinoline-3-carbonitrile (7S,8S)-8-hydroxy-7-((S)-5H-imidazo[5,1-a]isoindol-5-yl)-5,6,7,8-tetrahydroquinoline-3-carbonitrile (7S,8R)-8-hydroxy-7-((S)-5H-imidazo[5,1-a]isoindol-5-yl)-5,6,7,8-tetrahydroquinoline-3-carbonitrile (7R,8S)-8-hydroxy-7-((R)-5H-imidazo[5,1-a]isoindol-5-yl)-5,6,7,8-tetrahydroquinoline-3-carbonitrile (7R,8R)-8-hydroxy-7-((S)-5H-imidazo[5,1-a]isoindol-5-yl)-5,6,7,8-tetrahydroquinoline-3-carbonitrile (7S,8S)-8-hydroxy-7-((R)-5H-imidazo[5,1-a]isoindol-5-yl)-5,6,7,8-tetrahydroquinoline-3-carbonitrile (7S,8R)-8-hydroxy-7-((R)-5H-imidazo[5,1-a]isoindol-5-yl)-5,6,7,8-tetrahydroquinoline-3-carbonitrile (7R,8R)-8-hydroxy-7-((R)-5H-imidazo[5,1-a]isoindol-5-yl)-5,6,7,8-tetrahydroquinoline-3-carbonitrile 107a

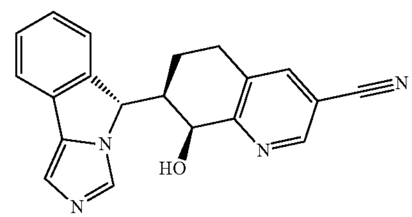

107b

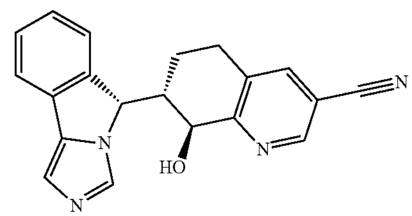

107c

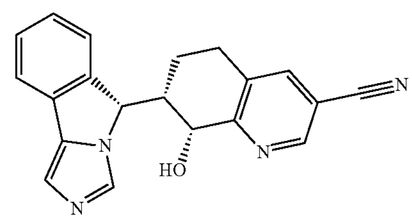

107d

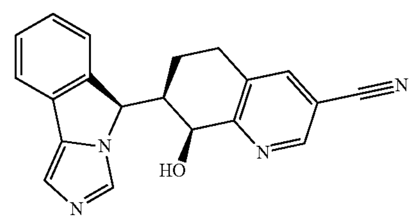

107e

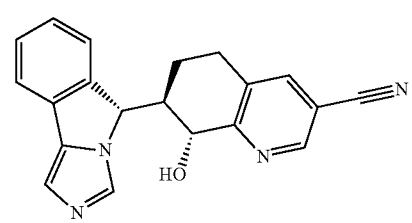

107f

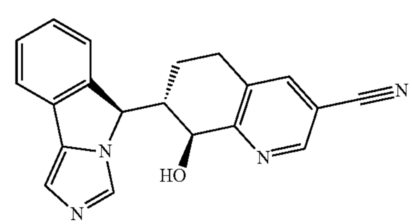

-continued

107g

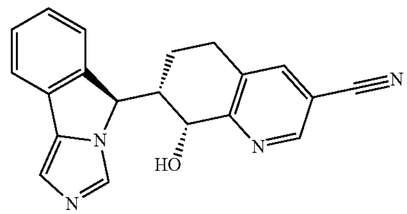

107h

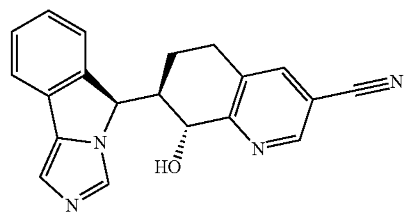

To a solution of 7-(5H-imidazo[5,1-a]isoindol-5-yl)-8-oxo-5,6,7,8-tetrahydroquinoline-3-carbonitrile (0.70 g, 2.14 mmol) in MeOH (20 mL) was added $NaBH_4$ (243 mg, 6.43 mmol) in portions at 0° C. and the solution was stirred at 0° C. for 2 hr. The solvent was distilled off and saturated ammonium chloride solution (30 mL) was added. The aqueous layer was extracted with 20% trifluoroethanol in DCM (3×30 mL). The combined organic extract was dried over ($Na_2SO_4$) and concentrated under reduced pressure to afford the crude product. The crude was purified by CombiFlash and the product was eluted with DCM:MeOH=90:10. The final products were further isolated by chiral separation to afford 8 isomers and the stereochemistry of each isomer was arbitrarily assigned.

Example 107a: (7R,8S)-8-hydroxy-7-((S)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.91 (d, J=2.0 Hz, 1H), 8.51 (s, 1H), 8.05-8.02 (m, 1H), 7.76 (d, J=7.6 Hz, 1H), 7.65 (d, J=7.7 Hz, 1H), 7.49 (s, 1H), 7.47 (d, J=7.6 Hz, 1H), 7.37 (td, J=7.5, 1.1 Hz, 1H), 6.19 (d, J=4.6 Hz, 1H), 5.94 (d, J=3.5 Hz, 1H), 4.89 (dd, J=10.7, 3.6 Hz, 1H), 2.85-2.76 (m, 1H), 2.73-2.62 (m, 2H), 0.99 (dd, J=8.6, 4.6 Hz, 2H).

Example 107b: (7S,8S)-8-hydroxy-7-((S)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.90 (d, J=2.0 Hz, 1H), 8.09 (d, J=2.0 Hz, 1H), 8.05 (s, 1H), 7.65 (dq, J=7.6, 0.9 Hz, 1H), 7.63-7.60 (m, 1H), 7.41 (tt, J=7.6, 0.8 Hz, 1H), 7.31 (td, J=7.5, 1.2 Hz, 1H), 7.18 (s, 1H), 6.34 (d, J=5.5 Hz, 1H), 5.58 (s, 1H), 5.04 (dd, J=5.3, 3.8 Hz, 1H), 2.78 (dd, J=17.5, 5.3 Hz, 1H), 2.58 (dd, J=12.2, 5.7 Hz, 2H), 1.50 (qd, J=12.8, 5.5 Hz, 1H), 1.07-0.99 (m, 1H).

Example 107c: (7S,8R)-8-hydroxy-7-((S)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.86 (d, J=2.0 Hz, 1H), 8.11 (d, J=2.0 Hz, 1H), 8.01 (s, 1H), 7.75 (dd, J=7.7, 1.0 Hz, 1H), 7.62 (d, J=7.5 Hz, 1H), 7.39 (t, J=7.5 Hz, 1H), 7.26 (dd, J=7.7, 1.2 Hz, 1H), 7.14 (s, 1H), 6.09 (d, J=5.3 Hz, 1H), 5.48 (d, J=6.0 Hz, 1H), 4.86-4.79 (m, 1H), 2.89 (dd, J=17.5, 5.3 Hz, 1H), 2.69 (ddd, J=17.8, 12.2, 6.1 Hz, 1H), 2.28 (dq, J=9.4, 3.0 Hz, 1H), 1.93 (qd, J=12.7, 5.5 Hz, 1H), 1.76-1.69 (m, 1H).

Example 107d: (7R,8S)-8-hydroxy-7-((R)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.86 (d, J=2.0 Hz, 1H), 8.11 (d, J=2.0 Hz, 1H), 8.01 (s, 1H), 7.78-7.73 (m, 1H), 7.62 (d, J=7.5 Hz, 1H), 7.39 (td, J=7.5, 0.9 Hz, 1H), 7.25 (td, J=7.6, 1.2 Hz, 1H), 7.14 (s, 1H), 6.09 (dd, J=5.5, 0.7 Hz, 1H), 5.48 (d, J=6.0 Hz, 1H), 4.82 (dd, J=5.2, 3.4 Hz, 1H), 2.89 (dd, J=17.5, 4.9 Hz, 1H), 2.69 (ddd, J=17.8, 12.3, 6.1 Hz, 1H), 2.33-2.25 (m, 1H), 1.93 (qd, J=12.8, 5.5 Hz, 1H), 1.75-1.68 (m, 1H).

Example 107e: (7R,8R)-8-hydroxy-7-((S)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.92 (d, J=2.0 Hz, 1H), 8.02 (dd, J=2.0, 1.0 Hz, 1H), 7.93 (s, 1H), 7.64 (d, J=7.5 Hz, 1H), 7.51 (dd, J=7.5, 1.0 Hz, 1H), 7.42 (t, J=7.5 Hz, 1H), 7.32 (td, J=7.5, 1.1 Hz, 1H), 7.18 (s, 1H), 6.10 (d, J=5.2 Hz, 1H), 5.80 (d, J=2.2 Hz, 1H), 4.95 (dd, J=10.7, 5.2 Hz, 1H), 2.66 (ddd, J=13.3, 10.0, 3.7 Hz, 2H), 2.57 (t, J=11.3 Hz, 1H), 1.01-0.95 (m, 1H), 0.89 (ddt, J=18.2, 12.3, 6.2 Hz, 1H).

Example 107f: (7S,8S)-8-hydroxy-7-((R)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.92 (d, J=2.0 Hz, 1H), 8.02 (dd, J=2.0, 1.0 Hz, 1H), 7.93 (s, 1H), 7.64 (dt, J=7.5, 0.9 Hz, 1H), 7.51 (dq, J=7.6, 0.9 Hz, 1H), 7.42 (tt, J=7.6, 0.8 Hz, 1H), 7.32 (td, J=7.5, 1.1 Hz, 1H), 7.18 (s, 1H), 6.10 (d, J=5.1 Hz, 1H), 5.80 (d, J=2.2 Hz, 1H), 4.95 (dd, J=10.8, 5.2 Hz, 1H), 2.71-2.61 (m, 2H), 2.60-2.53 (m, 1H), 1.01-0.94 (m, 1H), 0.94-0.84 (m, 1H).

Example 107g: (7S,8R)-8-hydroxy-7-((R)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.90 (d, J=2.0 Hz, 1H), 8.02 (dd, J=2.1, 1.0 Hz, 1H), 7.93 (s, 1H), 7.65 (d, J=7.6 Hz, 1H), 7.62-7.57 (m, 1H), 7.41 (t, J=7.5 Hz, 1H), 7.26 (td, J=7.6, 1.2 Hz, 1H), 7.17 (s, 1H), 6.13 (d, J=4.7 Hz, 1H), 5.78 (d, J=3.6 Hz, 1H), 4.87 (dd, J=10.7, 4.7 Hz, 1H), 2.77-2.64 (m, 3H), 0.92 (h, J=4.8 Hz, 2H).

Example 107h: (7R,8R)-8-hydroxy-7-((R)-5H-imidazo[5,1-a]isoindol-5-yl)-5,6,7,8-tetrahydroquinoline-3-carbonitrile: LCMS (ESI, m/z): 329.3 $[M+H]^+$; $^1$HNMR (500 MHz, DMSO-$d_6$) δ 8.90 (d, J=2.0 Hz, 1H), 8.09 (d, J=2.0 Hz, 1H), 7.97 (s, 1H), 7.64 (dq, J=7.6, 0.9 Hz, 1H), 7.60 (dt, J=7.6, 0.9 Hz, 1H), 7.39 (tt, J=7.6, 0.8 Hz, 1H), 7.29 (td, J=7.6, 1.2 Hz, 1H), 7.12 (s, 1H), 6.32 (dd, J=5.6, 0.7 Hz, 1H), 5.55 (d, J=2.5 Hz, 1H), 5.04 (dd, J=5.5, 3.8 Hz, 1H), 2.82-2.75 (m, 1H), 2.60-2.53 (m, 2H), 1.51 (qd, J=12.8, 5.5 Hz, 1H), 1.03 (d, J=13.1 Hz, 1H).

Example 108: 3-((5H-imidazo[5,1-a]isoindol-5-yl)methyl)-1-(ethylsulfonyl) azetidin-3-ol

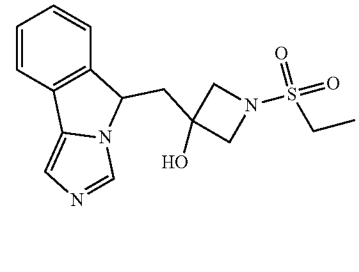 [SMILES: CCS(=O)(=O)N1CC(O)(CC2c3ccccc3-c3cncn32)C1]

Step 1: 1,1-dimethylethyl 1-oxa-5-azaspiro[2.3]hexane-5-carboxylate

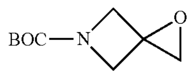 [SMILES: CC(C)(C)OC(=O)N1CC2(CO2)C1]

A solution of 1,1-dimethylethyl 3-methylideneazetidine-1-carboxylate (5 g, 29.72 mmol) in DCM (100 mL) was added MCPBA (18 g, 104.31 mmol). The resulting solution was stirred for 48 h at room temperature. The solids were filtered out. The reaction was then quenched by the addition of Sat. sodium bicarbonate (100 mL). The resulting solution was extracted with DCM (3×50 mL) and the organic layers combined. The mixture was dried over anhydrous sodium sulfate and concentrated under vacuum. The residue was purified by eluting by Combi-flash eluting with DCM/petroleum ether (1/1). This resulted in 750 mg (14%) of 1,1-dimethylethyl 1-oxa-5-azaspiro[2.3]hexane-5-carboxylate as yellow oil: LCMS (ESI, m/z): 186.0 $[M+H]^+$.

Step 2:

tert-butyl 3-((5H-imidazo[5,1-a]isoindol-5-yl)methyl)-3-hydroxyazetidine-1-carboxylate

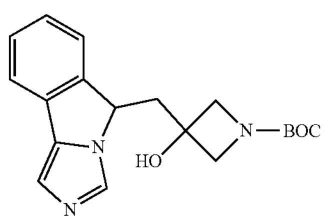 [SMILES: CC(C)(C)OC(=O)N1CC(O)(CC2c3ccccc3-c3cncn32)C1]

Under nitrogen, a solution of 5H-imidazo[4,3-a]isoindole (590 mg, 3.78 mmol) in THF (20 mL) was added n-BuLi (2.27 mL, 5.67 mmol, 2.5 mol/L in THF) at −78° C. The resulting solution was stirred for 4 h at −70° C. After tert-butyl 1-oxa-5-azaspiro[2.3]hexane-5-carboxylate (700 mg, 3.78 mmol) was added, the resulting solution was allowed to react, with stirring, for an additional 16 h at room temperature. The reaction was then quenched by the addition of 5 mL of water. The resulting mixture was concentrated under vacuum. The residue was purified by Combi-flash eluting with DCM/MeOH (5/95). This resulted in 1 g (78%) of tert-butyl 3-((5H-imidazo[5,1-a]isoindol-5-yl)methyl)-3-hydroxyazetidine-1-carboxylate as a yellow solid: LCMS (ESI, m/z): 342.1 $[M+H]^+$.

Step 3: 3-((5H-imidazo[5,1-a]isoindol-5-yl)methyl)azetidin-3-ol

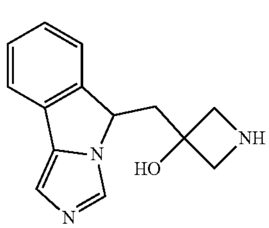 [SMILES: OC1(CC2c3ccccc3-c3cncn32)CNC1]

A solution of tert-butyl 3-hydroxy-3-[5H-imidazo[4,3-a]isoindol-5-ylmethyl]azetidine-1-carboxylate (1 g, 2.9 mmol) and trifluoroacetic acid (2 mL) in DCM (20 mL) was stirred for 2 h at room temperature. The resulting mixture was concentrated under vacuum. This resulted in 550 mg (78%) of 3-[5H-imidazo[4,3-a]isoindol-5-ylmethyl]azetidin-3-ol as yellow oil: LCMS (ESI, m/z): 242.1 $[M+H]^+$.

Step 4:

(S)-3-((5H-imidazo[5,1-a]isoindol-5-yl)methyl)-1-(ethylsulfonyl) azetidin-3-ol (R)-3-((5H-imidazo[5,1-a]isoindol-5-yl)methyl)-1-(ethylsulfonyl) azetidin-3-ol 108a

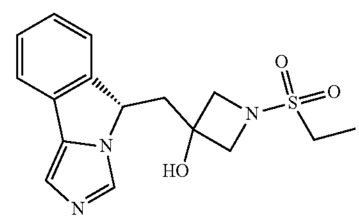

108b

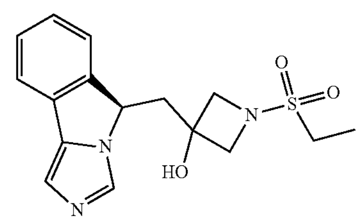

Under nitrogen, a mixture of 3-((5H-imidazo[5,1-a]isoindol-5-yl)methyl) azetidin-3-ol (300 mg, 1.24 mmol) and potassium carbonate (515 mg, 3.73 mmol) in 1,4-dioxane (20 mL) was added ethanesulfonyl chloride (240 mg, 1.87 mmol). The resulting solution was stirred for 4 h at room temperature. The solids were filtered out. The resulting mixture was concentrated under vacuum. The crude product was purified by Combi-Flash and further isolated by chiral separation. The configuration of two isomers was assigned arbitrarily.

Example 108a: (S)-3-((5H-imidazo[5,1-a]isoindol-5-yl)methyl)-1-(ethylsulfonyl) azetidin-3-ol (5.9 mg, 1%) as a white solid: LCMS (ESI, m/z): 334.0 $[M+H]^+$. $^1H$ NMR (400 MHz, $CD_3OD$) δ 8.01 (s, 1H), 7.66-7.50 (m, 2H), 7.48-7.28 (m, 2H), 7.15 (s, 1H), 5.44 (dd, J=8.5, 3.6 Hz, 1H), 4.12-3.94 (m, 3H), 3.78-3.68 (m, 1H), 3.09 (q, J=7.4 Hz, 2H), 2.67 (dd, J=14.9, 3.7 Hz, 1H), 2.27 (ddd, J=14.9, 8.6, 1.1 Hz, 1H), 1.33 (t, J=7.4 Hz, 3H). $t_R$=4.390 min (CHIRALPAK IC-3, 0.46×5 cm, Hex(0.1% DEA):EtOH=70:30, 1 ml/min). 108a and 108b are enantiomers.

Example 108b: (R)-3-((5H-imidazo[5,1-a]isoindol-5-yl)methyl)-1-(ethylsulfonyl) azetidin-3-ol (6.4 mg, 4%) as a white solid: LCMS (ESI, m/z): 334.0 $[M+H]^+$. $t_R$=5.525 min (CHIRALPAK IC-3, 0.46×5 cm, Hex(0.1% DEA):EtOH=70:30, 1 ml/min). 108a and 108b are enantiomers.

Example 109: 2-(8-fluoro-5H-imidazo[5,1-a]isoindol-5-yl)-7-oxaspiro[3.5]nonan-1-ol

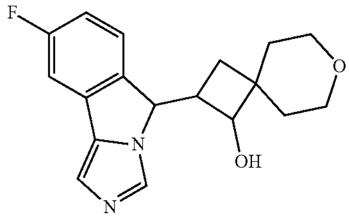 [SMILES: OC1C(C2c3ccc(F)cc3-c3cncn32)CC12CCOCC2]

(1S,2R)-2-((R)-8-fluoro-5H-imidazo[5,1-a]isoindol-5-yl)-7-oxaspiro[3.5]nonan-1-ol (1S,2S)-2-((R)-8-fluoro-5H-imidazo[5,1-a]isoindol-5-yl)-7-oxaspiro[3.5]nonan-1-ol (1R,2S)-2-((R)-8-fluoro-5H-imidazo[5,1-a]isoindol-5-yl)-7-oxaspiro[3.5]nonan-1-ol (1R,2R)-2-((R)-8-fluoro-5H-imidazo[5,1-a]isoindol-5-yl)-7-oxaspiro[3.5]nonan-1-ol (1R,2S)-2-((S)-8-fluoro-5H-imidazo[5,1-a]isoindol-5-yl)-7-oxaspiro[3.5]nonan-1-ol (1R,2R)-2-((S)-8-fluoro-5H-imidazo[5,1-a]isoindol-5-yl)-7-oxaspiro[3.5]nonan-1-ol (1S,2S)-2-((S)-8-fluoro-5H-imidazo[5,1-a]isoindol-5-yl)-7-oxaspiro[3.5]nonan-1-ol (1S,2R)-2-((S)-8-fluoro-5H-imidazo[5,1-a]isoindol-5-yl)-7-oxaspiro[3.5]nonan-1-ol Step 1: (E)-2-(4-fluoro-2-(1-trityl-1H-imidazol-4-yl)benzylidene)-7-oxaspiro[3.5]nonan-1-one

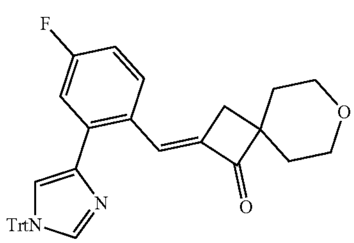

The title compound was synthesized by General Procedure for the Synthesis of Int-2. LCMS (ESI, m/z): 555.5 [M+H]+

Step 2: 2-(8-fluoro-5H-imidazo[5,1-a]isoindol-5-yl)-7-oxaspiro[3.5]nonan-1-one

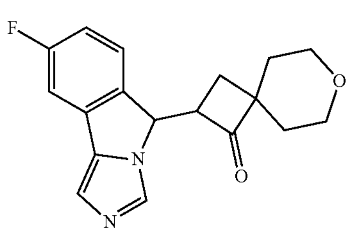 [SMILES: O=C1C(C2c3ccc(F)cc3-c3cncn32)CC12CCOCC2]

The title compound was synthesized by General Procedure for the Synthesis of Int-3. LCMS (ESI, m/z): 313.4 [M+H]+

Step 3: 2-(8-fluoro-5H-imidazo[5,1-a]isoindol-5-yl)-7-oxaspiro[3.5]nonan-1-ol

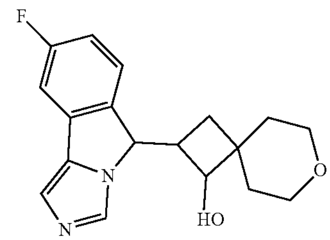 [SMILES: OC1C(C2c3ccc(F)cc3-c3cncn32)CC12CCOCC2]

The title compounds were synthesized by General Procedure for the Synthesis of Int-5: LCMS (ESI, m/z): 315.2 [M+H]+. The mixture was isolated by Chiral separation methods and the configuration of the isomers was assigned arbitrarily.

(1S,2R)-2-((R)-8-fluoro-5H-imidazo[5,1-a]isoindol-5-yl)-7-oxaspiro[3.5]nonan-1-ol (1S,2S)-2-((R)-8-fluoro-5H-imidazo[5,1-a]isoindol-5-yl)-7-oxaspiro[3.5]nonan-1-ol (1R,2S)-2-((R)-8-fluoro-5H-imidazo[5,1-a]isoindol-5-yl)-7-oxaspiro[3.5]nonan-1-ol (1R,2R)-2-((R)-8-fluoro-5H-imidazo[5,1-a]isoindol-5-yl)-7-oxaspiro[3.5]nonan-1-ol (1R,2S)-2-((S)-8-fluoro-5H-imidazo[5,1-a]isoindol-5-yl)-7-oxaspiro[3.5]nonan-1-ol (1R,2R)-2-((S)-8-fluoro-5H-imidazo[5,1-a]isoindol-5-yl)-7-oxaspiro[3.5]nonan-1-ol (1S,2S)-2-((S)-8-fluoro-5H-imidazo[5,1-a]isoindol-5-yl)-7-oxaspiro[3.5]nonan-1-ol (1S,2R)-2-((S)-8-fluoro-5H-imidazo[5,1-a]isoindol-5-yl)-7-oxaspiro[3.5]nonan-1-ol 109a

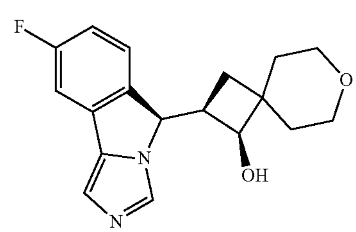

109b

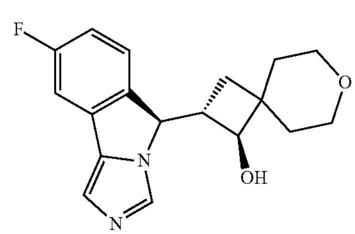

-continued

109c

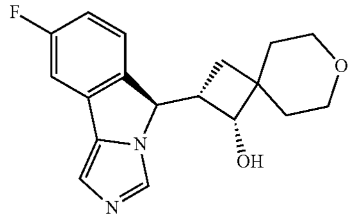

109d

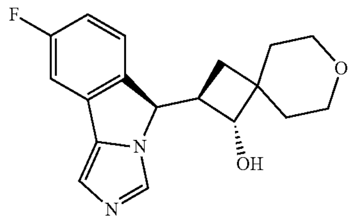

109e

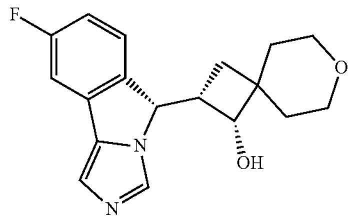

109f

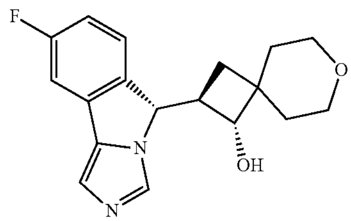

109g

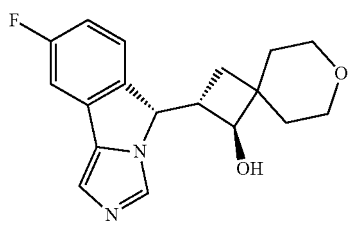

109h

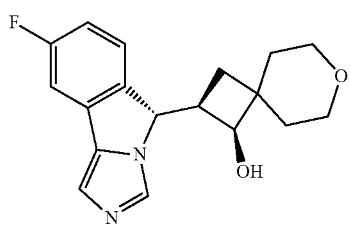

Example 109a: (1S,2R)-2-((R)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.86 (s, 1H), 7.48 (dd, J=9.0, 2.5 Hz, 1H), 7.40 (dd, J=8.4, 5.0 Hz, 1H), 7.16 (s, 1H), 7.04 (td, J=9.5, 2.5 Hz, 1H), 5.72 (d, J=5.9 Hz, 1H), 5.38 (d, J=10.9 Hz, 1H), 4.06 (td, J=5.9, 3.2 Hz, 1H), 3.61 (ddd, J=10.6, 6.7, 3.5 Hz, 1H), 3.54 (dt, J=10.3, 5.0 Hz, 1H), 3.50-3.43 (m, 2H), 2.31 (dd, J=16.4, 9.2 Hz, 1H), 2.20 (t, J=10.4 Hz, 1H), 1.91 (ddd, J=11.2, 8.4, 3.2 Hz, 1H), 1.73 (ddd, J=11.2, 7.5, 3.4 Hz, 1H), 1.50 (q, J=5.9, 4.9 Hz, 3H).

Example 109b: (1S,2S)-2-((R)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.92 (s, 1H), 7.46 (dd, J=9.0, 2.5 Hz, 1H), 7.40 (dd, J=8.4, 5.0 Hz, 1H), 7.14 (s, 1H), 7.05 (ddd, J=9.5, 8.5, 2.5 Hz, 1H), 5.36 (d, J=8.5 Hz, 1H), 5.16 (d, J=7.0 Hz, 1H), 3.84 (t, J=7.4 Hz, 1H), 3.71 (dt, J=11.2, 4.1 Hz, 1H), 3.63 (dt, J=11.2, 4.1 Hz, 1H), 3.47-3.39 (m, 1H), 3.36-3.31 (m, 1H), 2.38-2.25 (m, 1H), 1.88 (t, J=10.2 Hz, 1H), 1.71-1.56 (m, 2H), 1.50 (t, J=10.3 Hz, 1H), 1.36 (d, J=13.7 Hz, 2H), 1.06-0.99 (m, 1H).

Example 109c: (1R,2S)-2-((R)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.86 (s, 1H), 7.58 (dd, J=8.4, 5.1 Hz, 1H), 7.46 (dd, J=9.0, 2.5 Hz, 1H), 7.17 (s, 1H), 7.07 (ddd, J=9.6, 8.5, 2.5 Hz, 1H), 5.39 (d, J=7.5 Hz, 1H), 5.24 (d, J=6.7 Hz, 1H), 3.99 (t, J=7.3 Hz, 1H), 3.71 (dt, J=11.1, 4.1 Hz, 1H), 3.62 (dt, J=11.2, 4.2 Hz, 1H), 3.40 (td, J=11.1, 2.7 Hz, 1H), 3.27 (td, J=11.1, 2.7 Hz, 1H), 2.40 (ddd, J=17.2, 9.4, 7.9 Hz, 1H), 1.77-1.58 (m, 3H), 1.32 (dd, J=36.9, 13.3 Hz, 2H), 1.06 (t, J=10.3 Hz, 1H).

Example 109d: (1R,2R)-2-((R)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.88 (s, 1H), 7.63 (dd, J=8.4, 5.1 Hz, 1H), 7.46 (dd, J=9.0, 2.5 Hz, 1H), 7.17 (s, 1H), 7.08 (ddd, J=9.5, 8.5, 2.5 Hz, 1H), 5.70 (d, J=5.5 Hz, 1H), 5.43 (d, J=9.0 Hz, 1H), 4.08 (td, J=6.4, 3.1 Hz, 1H), 3.59 (ddd, J=10.5, 6.7, 3.6 Hz, 1H), 3.53 (dt, J=10.2, 4.8 Hz, 1H), 3.44 (ddt, J=16.1, 8.0, 4.4 Hz, 2H), 1.95-1.88 (m, 1H), 1.82 (ddd, J=11.2, 8.4, 3.0 Hz, 1H), 1.70 (ddd, J=11.3, 7.7, 3.5 Hz, 1H), 1.48 (d, J=4.3 Hz, 2H), 1.43 (ddd, J=13.1, 6.6, 3.3 Hz, 1H).

Example 109e: (1R,2S)-2-((S)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.85 (s, 1H), 7.48 (dd, J=9.0, 2.5 Hz, 1H), 7.40 (dd, J=8.4, 5.0 Hz, 1H), 7.15 (s, 1H), 7.03 (ddd, J=9.5, 8.5, 2.5 Hz, 1H), 5.72 (d, J=4.4 Hz, 1H), 5.38 (d, J=10.9 Hz, 1H), 4.06 (s, 2H), 3.60 (ddd, J=10.5, 6.6, 3.5 Hz, 1H), 3.54 (dt, J=10.2, 4.9 Hz, 1H), 3.46 (dq, J=11.1, 4.2, 3.0 Hz, 2H), 2.37-2.27 (m, 1H), 2.23-2.14 (m, 1H), 1.90 (ddd, J=11.2, 8.4, 3.2 Hz, 1H), 1.73 (ddd, J=11.2, 7.6, 3.5 Hz, 1H), 1.50 (q, J=5.9, 4.9 Hz, 3H).

Example 109f: (1R,2R)-2-((S)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.92 (s, 1H), 7.47 (dd, J=9.0, 2.5 Hz, 1H), 7.40 (dd, J=8.4, 5.0 Hz, 1H), 7.14 (s, 1H), 7.05 (ddd, J=9.5, 8.5, 2.5 Hz, 1H), 5.36 (d, J=8.5 Hz, 1H), 5.17 (d, J=7.0 Hz, 1H), 3.84 (t, J=7.3 Hz, 1H), 3.71 (dt, J=11.2, 4.1 Hz, 1H), 3.64 (dt, J=11.2, 4.1 Hz, 1H), 3.43 (td, J=11.2, 2.7 Hz, 1H), 3.36-3.31 (m, 1H), 2.36-2.26 (m, 1H), 1.88 (t, J=10.2 Hz, 1H), 1.72-1.58 (m, 2H), 1.50 (t, J=10.3 Hz, 1H), 1.37 (d, J=13.6 Hz, 2H).

Example 109g: (1S,2S)-2-((S)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 7.89 (s, 1H), 7.63 (dd, J=8.4, 5.1 Hz, 1H), 7.46 (dd, J=9.0, 2.5 Hz, 1H), 7.17 (s, 1H), 7.08 (ddd, J=9.6, 8.5, 2.5 Hz, 1H), 5.70 (d, J=5.5 Hz, 1H), 5.43 (d, J=9.0 Hz, 1H), 4.08 (td, J=6.4, 3.1 Hz, 1H), 3.58 (ddd, J=10.5, 6.7, 3.5 Hz, 1H), 3.53 (dt, J=10.2, 4.8 Hz, 1H), 3.43 (ddt, J=16.1, 7.9, 4.4 Hz, 2H), 1.96-1.88 (m, 1H), 1.81 (ddd, J=11.2, 8.4, 3.0 Hz, 1H), 1.70 (ddd, J=11.4, 7.7, 3.5 Hz, 1H), 1.48 (d, J=4.4 Hz, 2H), 1.43 (ddd, J=13.2, 6.7, 3.4 Hz, 1H).

Example 109h: (1S,2R)-2-((S)-8-fluoro-5H-imidazo[5,1-a]isoindol-5-yl)-7-oxaspiro[3.5]nonan-1-ol: LCMS (ESI, m/z): 315.2 $[M+H]^+$; $^1H$ NMR (500 MHz, DMSO-$d_6$) δ 8.06 (s, 1H), 7.60 (dd, J=8.4, 5.0 Hz, 1H), 7.49 (dd, J=9.0, 2.5 Hz, 1H), 7.27 (s, 1H), 7.11 (ddd, J=9.5, 8.5, 2.5 Hz, 1H), 5.44 (d, J=7.6 Hz, 1H), 5.24 (d, J=6.7 Hz, 1H), 3.98 (t, J=7.2 Hz, 1H), 3.70 (dt, J=11.2, 4.2 Hz, 1H), 3.62 (dt, J=11.2, 4.1 Hz, 1H), 3.39 (td, J=11.2, 2.7 Hz, 1H), 3.29-3.24 (m, 2H), 2.44-2.36 (m, 1H), 1.76-1.70 (m, 1H), 1.69-1.58 (m, 2H), 1.36 (d, J=13.6 Hz, 1H), 1.29 (d, J=13.2 Hz, 1H), 1.13-0.98 (m, 2H).

Example 110: 4-(7-methyl-5H-imidazo[5,1-a]isoindol-5-yl)tetrahydrofuran-3-ol

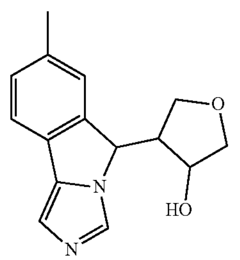 [SMILES: Cc1ccc2c(c1)C(C1COCC1O)n1cncc1-2]

(3S,4R)-4-((S)-7-methyl-5H-imidazo[5,1-a]isoindol-5-yl)tetrahydrofuran-3-ol
(3R,4S)-4-((R)-7-methyl-5H-imidazo[5,1-a]isoindol-5-yl)tetrahydrofuran-3-ol
(3S,4R)-4-((R)-7-methyl-5H-imidazo[5,1-a]isoindol-5-yl)tetrahydrofuran-3-ol
(3R,4S)-4-((S)-7-methyl-5H-imidazo[5,1-a]isoindol-5-yl)tetrahydrofuran-3-ol The title compound was synthesized by the same method of example 69.

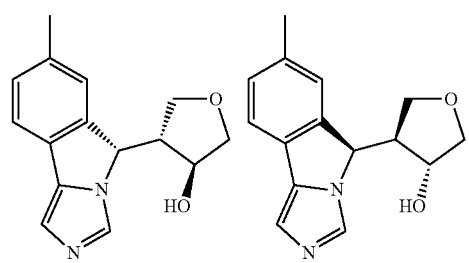

110a 110b

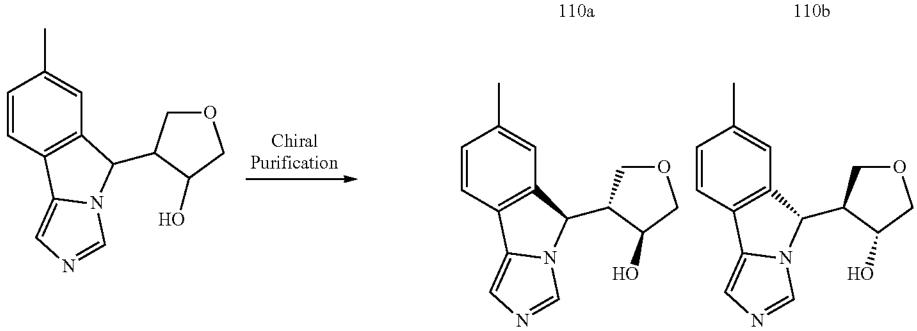

110c 110d

The configurations of the isomers were assigned arbitrarily.

Example 110a: (3S,4R)-4-((S)-7-methyl-5H-imidazo[5,1-a]isoindol-5-yl)tetrahydrofuran-3-ol: LCMS (ESI, m/z): 257.1 $[M+H]^+$; $^1$H NMR (500 MHz, DMSO-$d_6$) δ 7.96 (s, 1H), 7.48 (d, J=7.7 Hz, 1H), 7.36 (dd, J=1.7, 0.8 Hz, 1H), 7.20 (ddt, J=7.7, 1.5, 0.7 Hz, 1H), 7.11 (s, 1H), 5.54 (d, J=4.0 Hz, 1H), 5.26 (d, J=4.6 Hz, 1H), 4.33 (dq, J=5.7, 4.2 Hz, 1H), 3.69 (dd, J=9.2, 8.1 Hz, 1H), 3.61 (dd, J=9.2, 5.7 Hz, 1H), 3.46-3.36 (m, 1H), 3.10 (dd, J=9.2, 6.5 Hz, 1H), 2.80 (ddt, J=8.0, 6.4, 4.0 Hz, 1H), 2.35 (s, 3H). 110a and 110b are enantiomers.

Example 110b: (3R,4S)-4-((R)-7-methyl-5H-imidazo[5,1-a]isoindol-5-yl)tetrahydrofuran-3-ol: LCMS (ESI, m/z): 257.1 $[M+H]^+$; $^1$H NMR (500 MHz, DMSO-$d_6$) δ 7.94 (s, 1H), 7.48 (d, J=7.7 Hz, 1H), 7.38-7.33 (m, 1H), 7.20 (ddt, J=7.8, 1.6, 0.7 Hz, 1H), 7.10 (s, 1H), 5.54 (d, J=4.0 Hz, 1H), 5.26 (d, J=4.5 Hz, 1H), 4.33 (dq, J=5.7, 4.2 Hz, 1H), 3.69 (dd, J=9.2, 8.1 Hz, 1H), 3.61 (dd, J=9.2, 5.7 Hz, 1H), 3.43 (dd, J=9.2, 4.1 Hz, 1H), 3.10 (dd, J=9.2, 6.5 Hz, 1H), 2.80 (ddt, J=8.1, 6.5, 4.0 Hz, 1H), 2.35 (s, 3H). 110a and 110b are enantiomers.

Example 110c: (3S,4R)-4-((R)-7-methyl-5H-imidazo[5,1-a]isoindol-5-yl)tetrahydrofuran-3-ol: LCMS (ESI, m/z): 257.1 $[M+H]^+$; $^1$H NMR (500 MHz, DMSO-$d_6$) δ 7.97 (s, 1H), 7.51 (d, J=7.7 Hz, 1H), 7.35 (dd, J=1.6, 0.8 Hz, 1H), 7.22 (ddt, J=7.7, 1.4, 0.7 Hz, 1H), 7.12 (s, 1H), 5.48 (d, J=4.6 Hz, 1H), 5.01 (d, J=4.7 Hz, 1H), 4.03 (dd, J=9.2, 7.7 Hz, 1H), 3.87-3.79 (m, 2H), 3.42-3.34 (m, 2H), 2.76 (dtt, J=7.8, 5.3, 2.9 Hz, 1H), 2.37 (s, 3H). 110c and 110d are enantiomers.

Example 110d: (3R,4S)-4-((S)-7-methyl-5H-imidazo[5,1-a]isoindol-5-yl)tetrahydrofuran-3-ol: LCMS (ESI, m/z): 257.1 $[M+H]^+$; $^1$H NMR (500 MHz, DMSO-$d_6$) δ 7.83 (s, 1H), 7.48 (d, J=7.7 Hz, 1H), 7.33 (dq, J=1.5, 0.8 Hz, 1H), 7.21 (ddt, J=7.7, 1.5, 0.7 Hz, 1H), 7.05 (s, 1H), 5.44 (d, J=4.5 Hz, 1H), 5.00 (d, J=4.7 Hz, 1H), 4.03 (dd, J=9.2, 7.8 Hz, 1H), 3.82 (ddd, J=8.1, 5.1, 3.4 Hz, 2H), 3.42-3.32 (m, 2H), 2.79-2.71 (m, 1H), 2.36 (s, 3H). 110c and 110d are enantiomers.

Example 111: 2-amino-6-(5H-imidazo[5,1-a]isoindol-5-yl)-5,6,7,8-tetrahydroquinazolin-5-ol

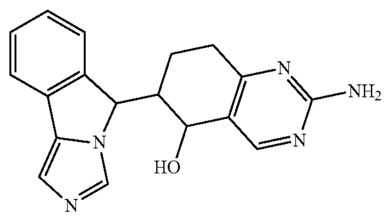 [SMILES: Nc1ncc2c(n1)CCC(C1c3ccccc3-c3cncn31)C2O]

(5R,6S)-2-amino-6-((S)-5H-imidazo[5,1-a]isoindol-5-yl)-5,6,7,8-tetrahydroquinazolin-5-ol
(5S,6S)-2-amino-6-((S)-5H-imidazo[5,1-a]isoindol-5-yl)-5,6,7,8-tetrahydroquinazolin-5-ol
(5R,6R)-2-amino-6-((S)-5H-imidazo[5,1-a]isoindol-5-yl)-5,6,7,8-tetrahydroquinazolin-5-ol
(5S,6R)-2-amino-6-((R)-5H-imidazo[5,1-a]isoindol-5-yl)-5,6,7,8-tetrahydroquinazolin-5-ol
(5R,6R)-2-amino-6-((R)-5H-imidazo[5,1-a]isoindol-5-yl)-5,6,7,8-tetrahydroquinazolin-5-ol
(5S,6R)-2-amino-6-((S)-5H-imidazo[5,1-a]isoindol-5-yl)-5,6,7,8-tetrahydroquinazolin-5-ol
(5S,6S)-2-amino-6-((R)-5H-imidazo[5,1-a]isoindol-5-yl)-5,6,7,8-tetrahydroquinazolin-5-ol Step 1: (E)-2-amino-6-(2-(1-trityl-1H-imidazol-4-yl)benzylidene)-7,8-dihydroquinazolin-5(6H)-one

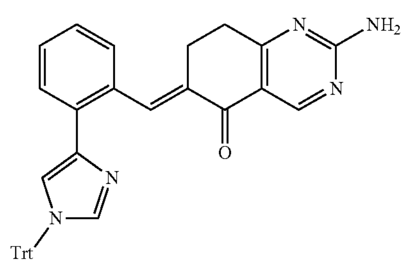

To a solution of 2-(1-trityl-1H-imidazol-4-yl)benzaldehyde (3.0 g, 7.24 mmol) and 2-amino-7,8-dihydroquinazolin-5(6H)-one (984 mg, 6.03 mmol) in ethanol (60 mL) was added anhydrous $Ca(OH)_2$ (1.12 g, 15.08 mmol). The mixture was stirred at 90° C. 40 hrs. When hot, the precipitations were filtered and re-suspended in hot MeOH (50 mL). The solid was filtered again and dried in air. The product was used directly without further purification: LCMS (ESI, m/z): 560.3 $[M+H]^+$.

Step 2: 2-amino-6-(5H-imidazo[5,1-a]isoindol-5-yl)-7,8-dihydroquinazolin-5(6H)-one

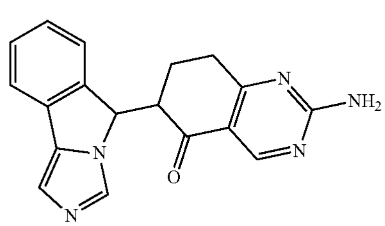 [SMILES: Nc1ncc2c(n1)CCC(C1c3ccccc3-c3cncn31)C2=O]

(E)-2-amino-6-(2-(1-trityl-1H-imidazol-4-yl)benzylidene)-7,8-dihydroquinazolin-5(6H)-one (3.38 g, 6.04 mmol) was stirred in 20% AcOH in MeOH (200 mL) at 90° C. for 3 h. After cooling to room temperature, the solvent was removed under reduced pressure and saturated $NaHCO_3$ (60 mL) was added to the residue followed by DCM (20 mL). The organic layer was collected and the aqueous layer was extracted with 20% trifluoroethanol in DCM (3×50 mL). The combined organic layers were dried over $Na_2SO_4$ and the solvent evaporated under reduced pressure to afford the crude product which was purified by using CombiFlash and was eluted by DCM:MeOH=90:10: LCMS (ESI, m/z): 318.2 $[M+H]^+$.

Step 3:

(5R,6S)-2-amino-6-((S)-5H-imidazo[5,1-a]isoindol-5-yl)-5,6,7,8-tetrahydroquinazolin-5-ol
(5S,6S)-2-amino-6-((S)-5H-imidazo[5,1-a]isoindol-5-yl)-5,6,7,8-tetrahydroquinazolin-5-ol
(5R,6R)-2-amino-6-((S)-5H-imidazo[5,1-a]isoindol-5-yl)-5,6,7,8-tetrahydroquinazolin-5-ol
(5S,6R)-2-amino-6-((R)-5H-imidazo[5,1-a]isoindol-5-yl)-5,6,7,8-tetrahydroquinazolin-5-ol
(5R,6R)-2-amino-6-((R)-5H-imidazo[5,1-a]isoindol-5-yl)-5,6,7,8-tetrahydroquinazolin-5-ol
(5S,6R)-2-amino-6-((S)-5H-imidazo[5,1-a]isoindol-5-yl)-5,6,7,8-tetrahydroquinazolin-5-ol
(5S,6S)-2-amino-6-((R)-5H-imidazo[5,1-a]isoindol-5-yl)-5,6,7,8-tetrahydroquinazolin-5-ol 111a

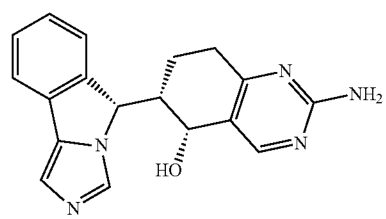

111b

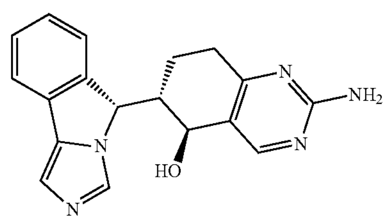

111c

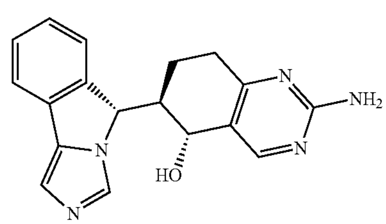

111d

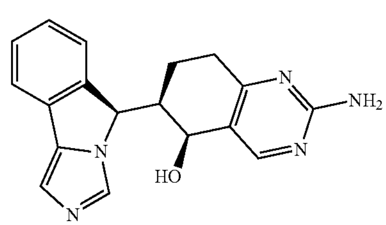

-continued

111e

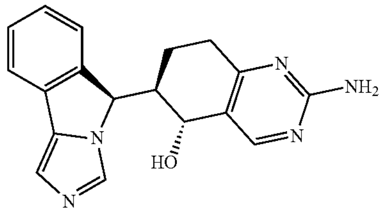

111f

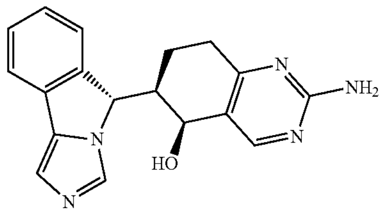

111g

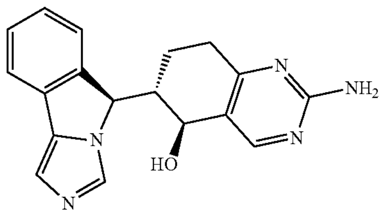

To a suspension of 2-amino-6-(5H-imidazo[5,1-a]isoindol-5-yl)-7,8-dihydroquinazolin-5(6H)-one (0.705 g, 2.22 mmol) in MeOH (50 mL) was added $NaBH_4$ (336 mg, 8.89 mmol) in portions at 0° C. and the solution was stirred at room temperature for 2 hr. The solvent was distilled off and saturated ammonium chloride solution (30 mL) was added. The aqueous layer was extracted with 20% trifluoroethanol in DCM (3×30 mL). The combined organic extract was dried over ($Na_2SO_4$) and concentrated under reduced pressure to afford the crude product. The crude was purified by CombiFlash and the product was eluted with DCM:MeOH=80:20. The final products were further isolated by chiral separation to afford 7 isomers and the stereochemistry of each isomer was arbitrarily assigned.

Example 111a: (5R,6S)-2-amino-6-((S)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.21 (s, 1H), 8.19 (s, 1H), 7.65 (d, J=1.6 Hz, 1H), 7.63 (s, 1H), 7.42 (t, J=7.5 Hz, 1H), 7.33 (td, J=7.6, 1.1 Hz, 1H), 7.27 (s, 1H), 6.47 (s, 2H), 5.69 (d, J=5.6 Hz, 1H), 5.58 (d, J=2.3 Hz, 1H), 4.92 (dd, J=5.5, 3.4 Hz, 1H), 2.49-2.44 (m, 1H), 2.43-2.34 (m, 2H), 1.55 (qd, J=12.7, 5.7 Hz, 1H), 0.96 (d, J=12.4 Hz, 1H).

Example 11b: (5S,6S)-2-amino-6-((S)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.73 (s, 1H), 8.35 (s, 1H), 7.77 (d, J=7.5 Hz, 1H), 7.61 (s, 1H), 7.57 (d, J=7.6 Hz, 1H), 7.51 (t, J=7.5 Hz, 1H), 7.48-7.40 (m, 1H), 6.41 (s, 2H), 5.94 (s, 1H), 5.81 (d, J=7.5 Hz, 1H), 4.84-4.74 (m, 1H), 2.49-2.34 (m, 3H), 1.07-0.95 (m, 2H).

Example 111c: (5R,6R)-2-amino-6-((S)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.34 (s, 1H), 7.99 (s, 1H), 7.65 (d, J=7.6 Hz, 1H), 7.61 (d, J=7.6 Hz, 1H), 7.41 (t, J=7.5 Hz, 1H), 7.28 (td, J=7.6, 1.2 Hz, 1H), 7.21 (s, 1H), 6.37 (s, 2H), 5.94 (d, J=7.1 Hz, 1H), 5.77 (d, J=3.2 Hz, 1H), 4.85 (dd, J=10.3, 7.1 Hz, 1H), 2.49-2.41 (m, 2H), 2.40-2.31 (m, 1H), 0.91-0.79 (m, 2H).

Example 111d: (5S,6R)-2-amino-6-((R)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.19 (s, 1H), 7.99 (s, 1H), 7.61 (dt, J=7.7, 0.9 Hz, 1H), 7.60-7.57 (m, 1H), 7.42-7.36 (m, 1H), 7.28 (td, J=7.5, 1.2 Hz, 1H), 7.11 (s, 1H), 6.46 (s, 2H), 5.63 (d, J=5.7 Hz, 1H), 5.51-5.46 (m, 1H), 4.90 (dd, J=5.5, 3.2 Hz, 1H), 2.48-2.44 (m, 1H), 2.43-2.31 (m, 2H), 1.58 (tt, J=12.7, 6.3 Hz, 1H), 0.98 (d, J=9.2 Hz, 1H).

Example 111e: (5R,6R)-2-amino-6-((R)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.13 (s, 1H), 7.97 (s, 1H), 7.73 (dd, J=7.7, 1.0 Hz, 1H), 7.61 (d, J=7.5 Hz, 1H), 7.41-7.36 (m, 1H), 7.25 (td, J=7.6, 1.2 Hz, 1H), 7.13 (s, 1H), 6.44 (s, 2H), 5.39 (d, J=5.2 Hz, 1H), 5.37 (d, J=5.7 Hz, 1H), 4.71 (d, J=5.9 Hz, 1H), 2.65-2.56 (m, 1H), 2.06-1.98 (m, 2H), 1.77-1.70 (m, 1H).

Example 111f: (5S,6R)-2-amino-6-((S)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.38 (s, 1H), 7.94 (s, 1H), 7.64-7.60 (m, 1H), 7.48 (dd, J=7.6, 1.0 Hz, 1H), 7.41 (t, J=7.5 Hz, 1H), 7.31 (td, J=7.5, 1.1 Hz, 1H), 7.17 (s, 1H), 6.38 (s, 2H), 5.94 (d, J=7.3 Hz, 1H), 5.76 (d, J=1.8 Hz, 1H), 4.89 (dd, J=10.3, 7.4 Hz, 1H), 2.42 (dd, J=11.8, 6.1 Hz, 1H), 2.39-2.26 (m, 2H), 0.86 (ddt, J=12.2, 9.2, 4.4 Hz, 1H), 0.79 (dt, J=12.7, 6.1 Hz, 1H).

Example 111g: (5S,6S)-2-amino-6-((R)-5H-imidazo[5,1-a]isoindol-5-yl)-5,6,7,8-tetrahydroquinazolin-5-ol: LCMS (ESI, m/z): 320.2 $[M+H]^+$; $^1$HNMR (500 MHz, DMSO-$d_6$) δ 8.34 (s, 1H), 7.90 (s, 1H), 7.63 (d, J=7.6 Hz, 1H), 7.60 (d, J=7.7 Hz, 1H), 7.40 (t, J=7.5 Hz, 1H), 7.26 (td, J=7.6, 1.1 Hz, 1H), 7.16 (s, 1H), 6.37 (s, 2H), 5.93 (d, J=7.1 Hz, 1H), 5.75 (d, J=3.2 Hz, 1H), 4.84 (dd, J=10.3, 7.1 Hz, 1H), 2.45 (q, J=9.6, 9.2 Hz, 2H), 2.36 (dt, J=17.9, 4.0 Hz, 1H), 0.83 (dd, J=9.5, 4.4 Hz, 2H).

Example 112: 6-(5H-imidazo[5,1-a]isoindol-5-yl)-5,6,7,8-tetrahydrophthalazin-5-ol

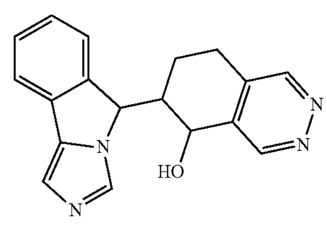 [SMILES: OC1c2cnncc2CCC1C1c2ccccc2-c2cncn21]

Step 1: 1,2,4,5-tetrazine

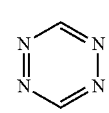

Under nitrogen, a solution of methanimidamide (50 g, 480.27 mmol) and hydrazine hydrate (50 mL, 1.03 mol) in MeOH (80 mL) and AcOH (150 mL) was added $NaNO_2$ (66 g, 956.59 mmol) at 0° C. The resulting solution was stirred for 2.5 h at 0° C. The pH value of the solution was adjusted to 7 with Sat. sodium bicarbonate. The resulting solution was extracted with DCM (4×300 mL) and the organic layers combined. The resulting mixture was washed with brine (2×800 mL). The mixture was dried over anhydrous sodium sulfate and concentrated under vacuum. This resulted in 2 g (5%) of 1,2,4,5-tetrazine as a red solid.

Step 2: 6,7,8,8a-tetrahydrophthalazin-5(4aH)-one

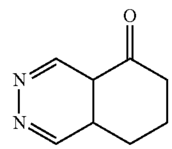 [SMILES: O=C1CCCC2C=NN=CC12]

A solution of 1,2,4,5-tetrazine (2 g, 24.37 mmol) and cyclohex-2-en-1-one (3.5 g, 36.41 mmol) in xylene (30 mL) was stirred for 4 h at 120° C. The resulting mixture was concentrated under vacuum. The residue was purified with silica gel column eluting with DCM/MeOH (1/99). This resulted in 2 g 6,7,8,8a-tetrahydrophthalazin-5(4aH)-one of as a yellow oil: LCMS (ESI, m/z): 151.1 [M+H]+.

Step 3: (E)-6-(2-(1-trityl-1H-imidazol-4-yl)benzylidene)-7,8-dihydrophthalazin-5(6H)-one

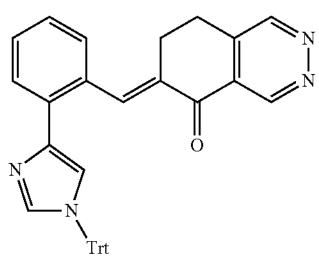

A mixture of 6,7,8,8a-tetrahydrophthalazin-5(4aH)-one (2 g, 13.32 mmol), 2-(1-trityl-1H-imidazol-4-yl)benzaldehyde (5.5 g, 13.27 mmol) and $Ca(OH)_2$ (1 g, 13.50 mmol) in ethanol (100 mL) was stirred for 48 h at 80° C. The solid was filtered out. The resulting mixture was concentrated under vacuum. The residue was purified by silica gel column eluting with DCM/MeOH (96/4). This resulted in 3 g (41%) of (E)-6-(2-(1-trityl-1H-imidazol-4-yl)benzylidene)-7,8-dihydrophthalazin-5(6H)-one as a yellow solid: LCMS (ESI, m/z): 545.1 [M+H]+.

Step 4: 6-(5H-imidazo[5,1-a]isoindol-5-yl)-7,8-dihydrophthalazin-5(6H)-one

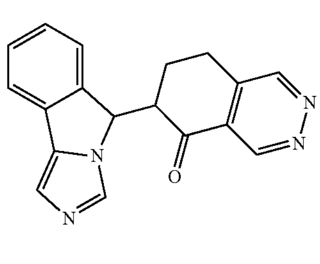 [SMILES: O=C1c2cnncc2CCC1C1c2ccccc2-c2cncn21]

The title compound was synthesized by General Procedure for the Synthesis of Int-3: LCMS (ESI, m/z): 303.0 [M+H]+.

Step 5:

(5S,6S)-6-((R)-5H-imidazo[5,1-a]isoindol-5-yl)-5,6,7,8-tetrahydrophthalazin-5-ol (5R,6R)-6-((S)-5H-imidazo[5,1-a]isoindol-5-yl)-5,6,7,8-tetrahydrophthalazin-5-ol (5S,6R)-6-((R)-5H-imidazo[5,1-a]isoindol-5-yl)-5,6,7,8-tetrahydrophthalazin-5-ol (5R,6S)-6-((S)-5H-imidazo[5,1-a]isoindol-5-yl)-5,6,7,8-tetrahydrophthalazin-5-ol (5R,6R)-6-((R)-5H-imidazo[5,1-a]isoindol-5-yl)-5,6,7,8-tetrahydrophthalazin-5-ol (5S,6S)-6-((S)-5H-imidazo[5,1-a]isoindol-5-yl)-5,6,7,8-tetrahydrophthalazin-5-ol (5R,6S)-6-((R)-5H-imidazo[5,1-a]isoindol-5-yl)-5,6,7,8-tetrahydrophthalazin-5-ol (5S,6R)-6-((S)-5H-imidazo[5,1-a]isoindol-5-yl)-5,6,7,8-tetrahydrophthalazin-5-ol 112a

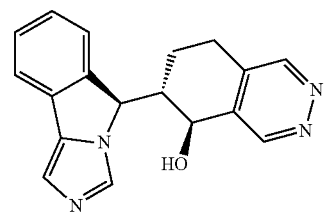

112b

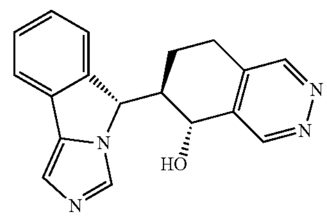

112c

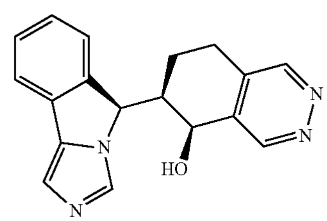

112d

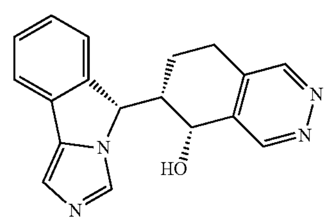

112e

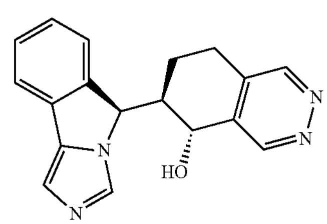

-continued

112f

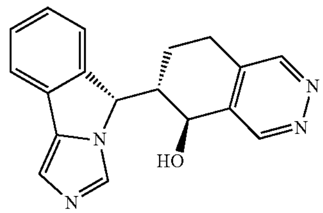

112g

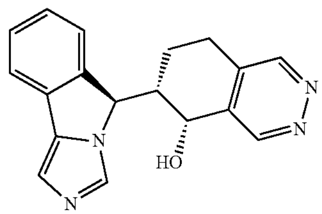

112h

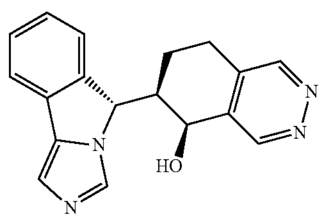

The title compounds were synthesized by General Procedure for the Synthesis of Int-6. The absolute configuration of all isomers 112a-h was assigned arbitrarily.

Example 112a: (5S,6S)-6-((R)-5H-imidazo[5,1-a]isoindol-5-yl)-5,6,7,8-tetrahydrophthalazin-5-ol (8.9 mg, 0.8%) as a white solid: LCMS (ESI, m/z): 305.3 $[M+H]^+$. $^1H$ NMR (400 MHz, $CD_3OD$) δ 9.30 (s, 1H), 8.88 (d, J=1.0 Hz, 1H), 8.30 (s, 1H), 7.78-7.69 (m, 1H), 7.60-7.34 (m, 4H), 5.97 (d, J=1.5 Hz, 1H), 5.04 (d, J=10.8 Hz, 1H), 2.75 (dd, J=8.7, 3.9 Hz, 2H), 2.66-2.50 (m, 1H), 1.36-1.08 (m, 2H). tR=1.693 min (CHIRALPAK AD-3, 0.46×5 cm, Hex(0.1% DEA): EtOH=50:50, 1 ml/min). 112a and 112b are enantiomers.

Example 112b: (5R,6R)-6-((S)-5H-imidazo[5,1-a]isoindol-5-yl)-5,6,7,8-tetrahydrophthalazin-5-ol (8.3 mg, 0.8%) as a white solid: LCMS (ESI, m/z): 305.3 $[M+H]^+$. $t_R$=2.124 min (CHIRALPAK AD-3, 0.46×5 cm, Hex(0.1% DEA): EtOH=50:50, 1 ml/min). 112a and 112b are enantiomers.

Example 112c: (5S,6R)-6-((R)-5H-imidazo[5,1-a]isoindol-5-yl)-5,6,7,8-tetrahydrophthalazin-5-ol (2.1 mg, 0.2%) as a white solid: LCMS (ESI, m/z): 305.3 $[M+H]^+$. $^1H$ NMR (400 MHz, $CD_3OD$) δ 9.29 (s, 1H), 8.86 (d, J=1.1 Hz, 1H), 7.93 (s, 1H), 7.66 (dd, J=13.1, 7.7 Hz, 2H), 7.51-7.39 (m, 1H), 7.33 (td, J=7.6, 1.2 Hz, 1H), 7.21 (s, 1H), 5.91 (d, J=3.2 Hz, 1H), 5.09 (d, J=11.0 Hz, 1H), 2.79-2.57 (m, 3H), 1.19-1.04 (m, 2H). $t_R$=4.577 min (Chiral Cellulose-SB, 0.46×5 cm, Hex(0.1% DEA):EtOH=50:50, 1 ml/min). 112c and 112d are enantiomers.

Example 112d: (5R,6S)-6-((S)-5H-imidazo[5,1-a]isoindol-5-yl)-5,6,7,8-tetrahydrophthalazin-5-ol (2.1 mg, 0.2%) as a white solid: LCMS (ESI, m/z): 305.4 $[M+H]^+$. $t_R$=3.942 min (Chiral Cellulose-SB, 0.46×5 cm, Hex(0.1% DEA): EtOH=50:50, 1 ml/min). 112c and 112d are enantiomers.

Example 112e: (5R,6R)-6-((R)-5H-imidazo[5,1-a]isoindol-5-yl)-5,6,7,8-tetrahydrophthalazin-5-ol (10.2 mg, 1%) as a white solid: LCMS (ESI, m/z): 305.3 $[M+H]^+$. $^1H$ NMR (400 MHz, $CD_3OD$) δ 9.06-8.92 (m, 2H), 8.04 (s, 1H), 7.76-7.60 (m, 2H), 7.43 (t, J=7.6 Hz, 1H), 7.29 (td, J=7.6, 1.2 Hz, 1H), 7.17 (s, 1H), 5.57 (d, J=5.8 Hz, 1H), 4.88 (d, J=3.6 Hz, 1H), 2.94 (ddd, J=18.4, 4.9, 2.6 Hz, 1H), 2.78-2.74 (m, 1H), 2.44-2.29 (m, 1H), 2.19-1.96 (m, 2H). tR=1.957 min (CHIRALPAK IA-3, 0.46×5 cm, Hex(0.1% DEA):EtOH=50:50, 1 ml/min). 112e and 112f are enantiomers.

Example 112f: (5R,6R)-6-((R)-5H-imidazo[5,1-a]isoindol-5-yl)-5,6,7,8-tetrahydrophthalazin-5-ol (13.0 mg, 1%) as a white solid: LCMS (ESI, m/z): 305.3 $[M+H]^+$. $t_R$=3.540 min (CHIRALPAK IA-3, 0.46×5 cm, Hex(0.1% DEA): EtOH=50:50, 1 ml/min). 112e and 112f are enantiomers.

Example 112g: (5R,6S)-6-((R)-5H-imidazo[5,1-a]isoindol-5-yl)-5,6,7,8-tetrahydrophthalazin-5-ol (95.5 mg, 9%) as a white solid: LCMS (ESI, m/z): 305.3 $[M+H]^+$. $^1H$ NMR (400 MHz, $CD_3OD$) δ 9.14 (d, J=1.1 Hz, 1H), 8.94 (d, J=1.1 Hz, 1H), 8.08 (s, 1H), 7.67-7.53 (m, 2H), 7.49-7.28 (m, 2H), 7.15 (s, 1H), 5.65 (s, 1H), 5.17 (d, J=3.7 Hz, 1H), 2.80 (dd, J=18.2, 4.8 Hz, 1H), 2.57-2.55 (m, 2H), 1.56-1.54 (m, 1H), 1.23-1.10 (m, 1H). $t_R$=2.863 min (Lux Cellulose-4, 0.46×5 cm, Hex(0.1% DEA):EtOH=50:50, 1 ml/min). 112g and 112h are enantiomers.

Example 112h: (5S,6R)-6-((S)-5H-imidazo[5,1-a]isoindol-5-yl)-5,6,7,8-tetrahydrophthalazin-5-ol (83.9 mg, 8%) as a white solid: LCMS (ESI, m/z): 305.2 $[M+H]^+$. $t_R$=6.421 min (Lux Cellulose-4, 0.46×5 cm, Hex(0.1% DEA): EtOH=50:50, 1 ml/min). 112g and 112h are enantiomers.

Example 113: 8-hydroxy-7-(5H-imidazo[5,1-a]isoindol-5-yl)-5,6,7,8-tetrahydronaphthalene-2-carbonitrile

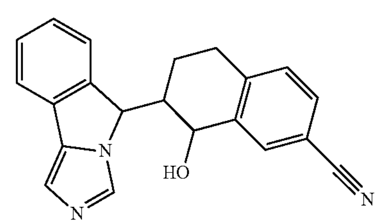 [SMILES: N#Cc1ccc2c(c1)C(O)C(C1c3ccccc3-c3cncn31)CC2]

(7R,8R)-8-hydroxy-7-((R)-5H-imidazo[5,1-a]isoindol-5-yl)-5,6,7,8-tetrahydronaphthalene-2-carbonitrile (7R,8R)-8-hydroxy-7-((S)-5H-imidazo[5,1-a]isoindol-5-yl)-5,6,7,8-tetrahydronaphthalene-2-carbonitrile (7R,8S)-8-hydroxy-7-((R)-5H-imidazo[5,1-a]isoindol-5-yl)-5,6,7,8-tetrahydronaphthalene-2-carbonitrile (7R,8S)-8-hydroxy-7-((S)-5H-imidazo[5,1-a]isoindol-5-yl)-5,6,7,8-tetrahydronaphthalene-2-carbonitrile (7S,8R)-8-hydroxy-7-((R)-5H-imidazo[5,1-a]isoindol-5-yl)-5,6,7,8-tetrahydronaphthalene-2-carbonitrile (7S,8R)-8-hydroxy-7-((S)-5H-imidazo[5,1-a]isoindol-5-yl)-5,6,7,8-tetrahydronaphthalene-2-carbonitrile (7S,8S)-8-hydroxy-7-((R)-5H-imidazo[5,1-a]isoindol-5-yl)-5,6,7,8-tetrahydronaphthalene-2-carbonitrile Step 1:

7-(5H-imidazo[5,1-a]isoindol-5-yl)-8-oxo-5,6,7,8-tetrahydronaphthalene-2-carbonitrile

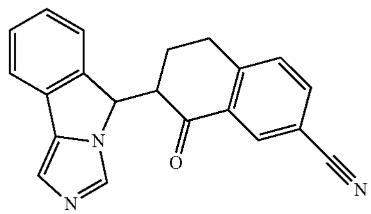 [SMILES: N#Cc1ccc2c(c1)C(=O)C(C1c3ccccc3-c3cncn31)CC2]

To a solution of the 2-(1-trityl-1H-imidazol-4-yl)benzaldehyde (2 g, 4.83 mmol) and 8-oxo-5,6,7,8-tetrahydronaphthalene-2-carbonitrile (1.03 g, 6.03 mmol) in MeOH (100 mL) was added sodium ethoxide (21% solution in ethanol, 2.7 mL, 7.24 mmol). The solution was allowed to reflux. After 5 h, reaction was complete as indicated by the TLC. Acetic acid (7 mL) was added to the reaction mixture and was refluxed for 4 hours. Methanol and acetic acid were evaporated on a rotary evaporator and crude was suspended in water, solid sodium carbonate was added portion-wise to neutralize remaining acetic acid. Crude was then extracted using DCM (2×30 mL), which was further purified over Combi-Flash. LCMS (ESI, m/z): 326.3 $[M+H]^+$ Step 2:

(7R,8R)-8-hydroxy-7-((R)-5H-imidazo[5,1-a]isoindol-5-yl)-5,6,7,8-tetrahydronaphthalene-2-carbonitrile (7R,8R)-8-hydroxy-7-((S)-5H-imidazo[5,1-a]isoindol-5-yl)-5,6,7,8-tetrahydronaphthalene-2-carbonitrile (7R,8S)-8-hydroxy-7-((R)-5H-imidazo[5,1-a]isoindol-5-yl)-5,6,7,8-tetrahydronaphthalene-2-carbonitrile (7R,8S)-8-hydroxy-7-((S)-5H-imidazo[5,1-a]isoindol-5-yl)-5,6,7,8-tetrahydronaphthalene-2-carbonitrile (7S,8R)-8-hydroxy-7-((R)-5H-imidazo[5,1-a]isoindol-5-yl)-5,6,7,8-tetrahydronaphthalene-2-carbonitrile (7S,8R)-8-hydroxy-7-((S)-5H-imidazo[5,1-a]isoindol-5-yl)-5,6,7,8-tetrahydronaphthalene-2-carbonitrile (7S,8S)-8-hydroxy-7-((R)-5H-imidazo[5,1-a]isoindol-5-yl)-5,6,7,8-tetrahydronaphthalene-2-carbonitrile 113a

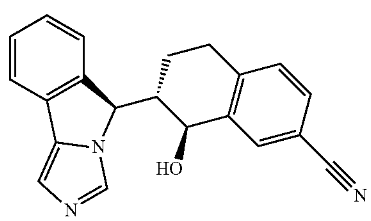

113b

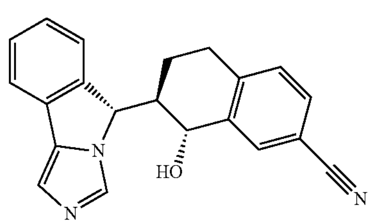

-continued

113c

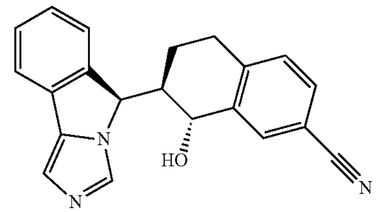

113d

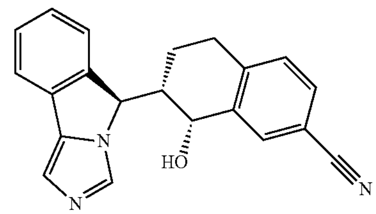

113e

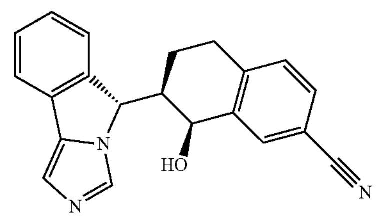

113f

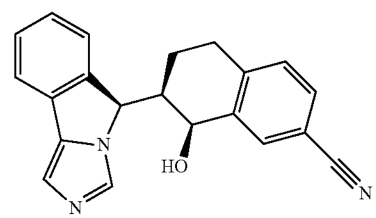

113g

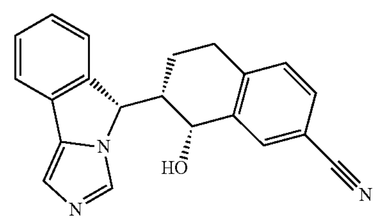

Solution of 7-(5H-imidazo[5,1-a]isoindol-5-yl)-8-oxo-5,6,7,8-tetrahydronaphthalene-2-carbonitrile (1.5 g mL, 4.61 mmol) in methanol (100 mL) was cooled to 0° C. Sodium borohydride (0.523 g, 13.83 mmol) was added portion-wise and reaction mixture was removed from ice bath. Reaction mixture was allowed to stir at room temperature for 2 hours. Reaction was quenched using sat. $NH_4Cl$ solution (15 mL). Crude was extracted using 5% solution of 2,2,2-trifluoroethanol in DCM, which was further purified on Combi-Flash and further isolated by chiral separation to afford 7 isomers as white solid. The absolute configuration of isomers 113d, 113e was determined by X-ray crystallography. The configuration of the rest isomers was assigned arbitrarily.

Example 113a: (7R,8R)-8-hydroxy-7-((R)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H), 1.47 (qd, J=12.6, 5.4 Hz, 1H), 0.99 (d, J=12.8 Hz, 1H).

Example 113b: (7R,8R)-8-hydroxy-7-((S)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H, 1.47 (qd, J=12.6, 5.4 Hz, 1H), 0.99 (d, J=12.8 Hz, 1H).

Example 113c: (7R,8S)-8-hydroxy-7-((R)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H), 1.47 (qd, J=12.6, 5.4 Hz, 1H), 0.99 (d, J=12.8 Hz, 1H).

Example 113d: (5S,6S)-5-hydroxy-6-((R)-5H-imidazo[5,1-a]isoindol-5-yl)-5,6,7,8-tetrahydronaphthalene-2-sulfonamide: LCMS (ESI, m/z): 382.2 $[M+H]^+$; $^1$H NMR (500 MHz, DMSO-d6) δ 8.10 (s, 1H), 7.77 (dd, J=8.3, 3.0 Hz, 1H), 7.71-7.61 (m, 3H), 7.47 (d, J=3.0 Hz, 1H), 7.43 (td, J=7.6, 7.6, 2.8 Hz, 1H), 7.30 (td, J=7.8, 7.7, 2.9 Hz, 2H), 7.25 (d, J=3.0 Hz, 2H), 6.24 (dd, J=7.5, 3.0 Hz, 1H), 5.85 (d, J=3.7 Hz, 1H), 4.90 (t, J=9.0 Hz, 1H), 2.74-2.54 (m, 3H), 0.96-0.85 (m, 2H).

Example 113e: (7S,8R)-8-hydroxy-7-((R)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H), 1.47 (qd, J=12.6, 5.4 Hz, 1H), 0.99 (d, J=12.8 Hz, 1H).

Example 113f: (7S,8R)-8-hydroxy-7-((S)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H), 1.47 (qd, J=12.6, 5.4 Hz, 1H), 0.99 (d, J=12.8 Hz, 1H).

Example 113g: (7S,8S)-8-hydroxy-7-((R)-5H-imidazo[5,1-a]isoindol-5-yl)-5,6,7,8-tetrahydronaphthalene-2-carbonitrile: LCMS (ESI, m/z): 328.2 $[M+H]^+$; $^1$H NMR (400 MHz, DMSO-d6) δ 7.94 (s, 1H), 7.84 (d, J=1.8 Hz, 1H), 7.68-7.56 (m, 3H), 7.44-7.35 (m, 1H), 7.32-7.23 (m, 2H), 7.11 (s, 1H), 6.03 (d, J=5.6 Hz, 1H), 5.54 (d, J=2.3 Hz, 1H), 5.08-5.00 (m, 1H), 2.78 (dd, J=17.9, 5.1 Hz, 1H), 2.68-2.52 (m, 1H), 1.47 (qd, J=12.6, 5.4 Hz, 1H), 0.99 (d, J=12.8 Hz, 1H).

Example 114: 7-(ethylsulfonyl)-2-(5H-imidazo[5,1-a]isoindol-5-yl)-7-azaspiro[3.5]nonan-1-ol

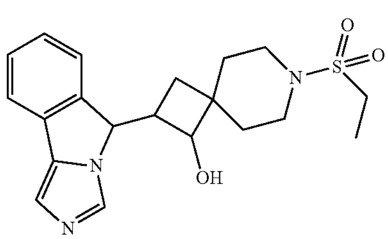 [SMILES: CCS(=O)(=O)N1CCC2(CC1)CC(C1c3ccccc3-c3cncn31)C2O]

(1S,2R)-7-(ethylsulfonyl)-2-((R)-5H-imidazo[5,1-a]isoindol-5-yl)-7-azaspiro[3.5]nonan-1-ol
(1S,2S)-7-(ethylsulfonyl)-2-((R)-5H-imidazo[5,1-a]isoindol-5-yl)-7-azaspiro[3.5]nonan-1-ol
(1R,2S)-7-(ethylsulfonyl)-2-((R)-5H-imidazo[5,1-a]isoindol-5-yl)-7-azaspiro[3.5]nonan-1-ol
(1R,2R)-7-(ethylsulfonyl)-2-((R)-5H-imidazo[5,1-a]isoindol-5-yl)-7-azaspiro[3.5]nonan-1-ol
(1S,2R)-7-(ethylsulfonyl)-2-((S)-5H-imidazo[5,1-a]isoindol-5-yl)-7-azaspiro[3.5]nonan-1-ol
(1R,2R)-7-(ethylsulfonyl)-2-((S)-5H-imidazo[5,1-a]isoindol-5-yl)-7-azaspiro[3.5]nonan-1-ol
(1S,2S)-7-(ethylsulfonyl)-2-((S)-5H-imidazo[5,1-a]isoindol-5-yl)-7-azaspiro[3.5]nonan-1-ol
(1R,2S)-7-(ethylsulfonyl)-2-((S)-5H-imidazo[5,1-a]isoindol-5-yl)-7-azaspiro[3.5]nonan-1-ol Step 1:

tert-butyl (E)-1-oxo-2-(2-(1-trityl-1H-imidazol-4-yl)benzylidene)-7-azaspiro[3.5]nonane-7-carboxylate

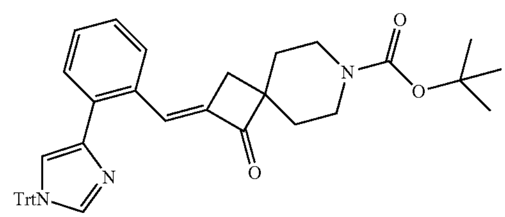

The title compound was synthesized by General Procedure for the Synthesis of Int-2. LCMS (ESI, m/z): 636.3 $[M+H]^+$ Step 2:

tert-butyl 2-(5H-imidazo[5,1-a]isoindol-5-yl)-1-oxo-7-azaspiro[3.5]nonane-7-carboxylate

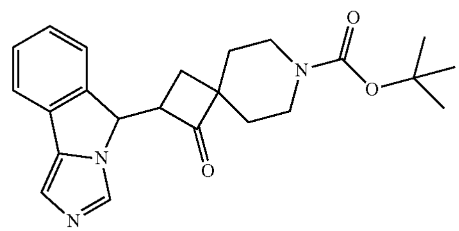 [SMILES: CC(C)(C)OC(=O)N1CCC2(CC1)CC(C1c3ccccc3-c3cncn31)C2=O]

The title compound was synthesized by General Procedure for the Synthesis of Int-3. LCMS (ESI, m/z): 394.4 $[M+H]^+$ Step 3:

tert-butyl 1-hydroxy-2-(5H-imidazo[5,1-a]isoindol-5-yl)-7-azaspiro[3.5]nonane-7-carboxylate

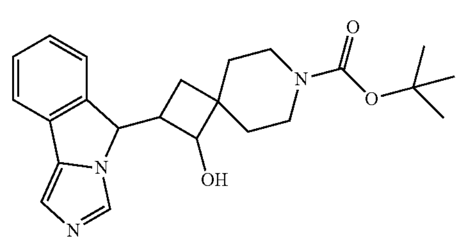 [SMILES: CC(C)(C)OC(=O)N1CCC2(CC1)CC(C1c3ccccc3-c3cncn31)C2O]

The title compounds were synthesized by General Procedure for the Synthesis of Int-5: LCMS (ESI, m/z): 396.2 $[M+H]^+$ Step 4:

7-(ethylsulfonyl)-2-(5H-imidazo[5,1-a]isoindol-5-yl)-7-azaspiro[3.5]nonan-1-ol

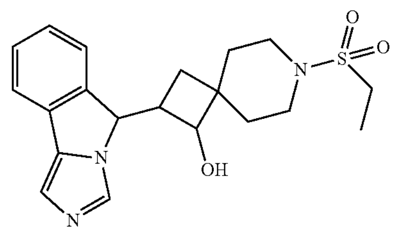 [SMILES: CCS(=O)(=O)N1CCC2(CC1)CC(C1c3ccccc3-c3cncn31)C2O]

To the diastereomeric mixture of tert-butyl 1-hydroxy-2-(5H-imidazo[5,1-a]isoindol-5-yl)-7-azaspiro[3.5]nonane-7-carboxylate (400 mg, 1.0 mmol) dissolved in dry MeOH (15 mL) at 0° C. was added sodiumborohydride (120 mg, 3.0 mmol) in four portions. The reaction was stirred at room temperature for 2 h. TLC showed no SM left. The reaction was quenched by adding saturated $NH_4Cl$ solution (5 mL) and extracted by DCM (3×25 mL), combined organic phase was washed with brine and dried over $Na_2SO_4$. After removing solvent and the residue was purified by silica gel column chromatograph. To this mixture was added 8 mL dry dichloromethane followed by trifluroacetic acid (1.5 mL, 20 mmol) at room temperature and the reaction mixture was stirred for half an hour. TLC indicated no SM and the reaction mixture was concentrated under reduced pressured and the residue was dried under high vacuum pump for few hours. This crude mixture was taken to the next step without purification. To the cruder reaction mixture in 8 mL dry dichloromethane was added triethyl amine (0.22 mL, 1.62 mmol) followed by ethyl sulfonyl chloride (0.08 mL, 0.89 mmol) at room temperature and stirred for half hour. After half hour, TLC indicated starting material. So 0.2 mL of triethylamine was added and the reaction mixture was stirred for another half hour. TLC indicated no starting material and the reaction mixture was quenched with water (2 mL) and the reaction was worked up using DCM. The combined residue was dried over $Na_2SO_4$ and concentrated under reduced pressured and purified via flash column chromatography. The title compounds was isolated and submitted for chiral separations: LCMS (ESI, m/z): 388.2 $[M+H]^+$. The pure enantiomers were isolated by chiral separation methods and the configuration of the isomers was assigned arbitrarily.

(1S,2R)-7-(ethylsulfonyl)-2-((R)-5H-imidazo[5,1-a]isoindol-5-yl)-7-azaspiro[3.5]nonan-1-ol (1S,2S)-7-(ethylsulfonyl)-2-((R)-5H-imidazo[5,1-a]isoindol-5-yl)-7-azaspiro[3.5]nonan-1-ol (1R,2S)-7-(ethylsulfonyl)-2-((R)-5H-imidazo[5,1-a]isoindol-5-yl)-7-azaspiro[3.5]nonan-1-ol (1R,2R)-7-(ethylsulfonyl)-2-((R)-5H-imidazo[5,1-a]isoindol-5-yl)-7-azaspiro[3.5]nonan-1-ol (1S,2R)-7-(ethylsulfonyl)-2-((S)-5H-imidazo[5,1-a]isoindol-5-yl)-7-azaspiro[3.5]nonan-1-ol (1R,2R)-7-(ethylsulfonyl)-2-((S)-5H-imidazo[5,1-a]isoindol-5-yl)-7-azaspiro[3.5]nonan-1-ol (1S,2S)-7-(ethylsulfonyl)-2-((S)-5H-imidazo[5,1-a]isoindol-5-yl)-7-azaspiro[3.5]nonan-1-ol (1R,2S)-7-(ethylsulfonyl)-2-((S)-5H-imidazo[5,1-a]isoindol-5-yl)-7-azaspiro[3.5]nonan-1-ol 114a

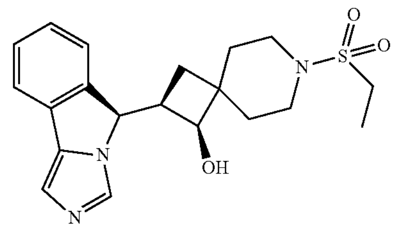

114b

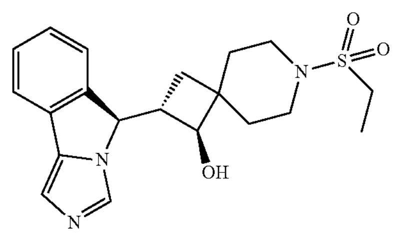

114c

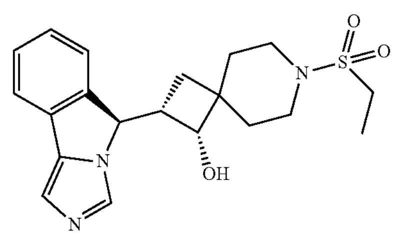

114d

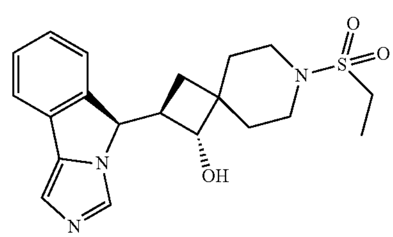

114e

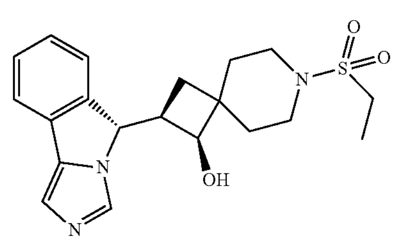

114f

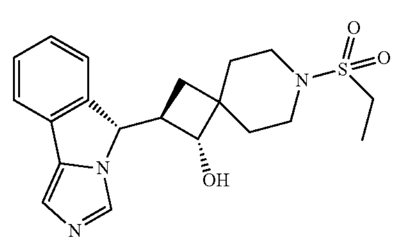

-continued

114g

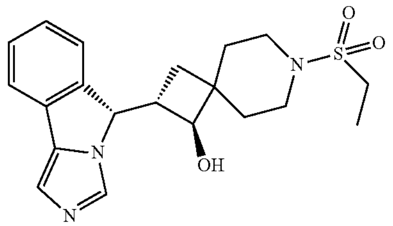

114h

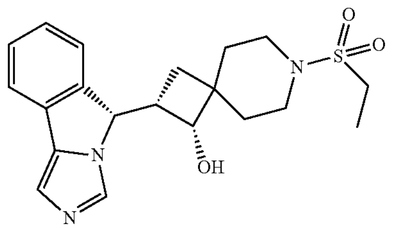

Example 114a: (1S,2R)-7-(ethylsulfonyl)-2-((R)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.84 (s, 1H), 7.57 (d, J=7.7 Hz, 2H), 7.36 (t, J=7.6 Hz, 1H), 7.26 (td, J=7.6, 1.0 Hz, 1H), 7.14 (s, 1H), 5.42 (d, J=7.1 Hz, 1H), 5.31 (d, J=6.4 Hz, 1H), 4.11-4.02 (m, 1H), 3.45-3.35 (m, 1H), 2.98 (q, J=7.4 Hz; 3H), 2.87-2.77 (m, 1H), 2.47 (d, J=7.6 Hz, 1H), 1.65 (dtd, J=27.0, 11.9, 10.1, 5.1 Hz, 3H), 1.53 (d, J=14.2 Hz, 1H), 1.46-1.34 (m, 1H), 1.17 (t, J=7.4 Hz, 3H), 0.97 (t, J=10.4 Hz, 1H).

Example 114b: (1S,2S)-7-(ethylsulfonyl)-2-((R)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.89 (s, 1H), 7.59 (d, J=7.5 Hz, 1H), 7.45-7.33 (m, 2H), 7.24 (td, J=7.6, 1.1 Hz, 1H), 7.10 (s, 1H), 5.38 (d, J=8.6 Hz, 1H), 5.24 (d, J=6.7 Hz, 1H), 3.95 (t, J=7.2 Hz, 1H), 3.43-3.37 (m, 1H), 3.37-3.33 (m, 1H), 3.00 (q, J=7.4 Hz, 3H), 2.93-2.86 (m, 1H), 2.32 (p, J=9.4 Hz, 1H), 1.86 (t, J=10.2 Hz, 1H), 1.71-1.59 (m, 2H), 1.58-1.44 (m, 3H), 1.19 (t, J=7.4 Hz, 3H).

Example 114c: (1R,2S)-7-(ethylsulfonyl)-2-((R)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.83 (s, 1H), 7.60 (d, J=7.5 Hz, 1H), 7.48-7.31 (m, 2H), 7.22 (t, J=7.2 Hz, 1H), 7.11 (s, 1H), 5.77 (d, J=6.0 Hz, 1H), 5.40 (d, J=10.9 Hz, 1H), 4.32-3.96 (m, 1H), 3.24 (td, J=7.6, 7.0, 3.4 Hz, 1H), 3.20-3.13 (m, 1H), 3.09 (dt, J=10.5, 4.7 Hz, 2H), 3.03 (q, J=7.4 Hz, 2H), 2.34 (dt, J=17.2, 9.2 Hz, 1H), 2.21 (t, J=10.4 Hz, 1H), 1.91 (td, J=9.9, 8.4, 3.1 Hz, 1H), 1.78 (ddd, J=11.9, 8.0, 3.4 Hz, 1H), 1.68-1.60 (m, 1H), 1.58 (s, 2H), 1.21 (t, J=7.4 Hz, 3H).

Example 114d: (1R,2R)-7-(ethylsulfonyl)-2-((R)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.85 (s, 1H), 7.62 (d, J=7.6 Hz, 1H), 7.58 (d, J=7.5 Hz, 1H), 7.37 (dd, J=9.3, 5.8 Hz, 1H), 7.26 (td, J=7.6, 1.1 Hz, 1H), 7.13 (s, 1H), 5.81-5.69 (m, 1H), 5.45 (d, J=8.8 Hz, 1H), 4.11 (td, J=6.5, 3.1 Hz, 1H), 3.23 (ddd, J=11.4, 7.3, 3.4 Hz, 1H), 3.20-3.13 (m, 1H), 3.07 (dt, J=13.2, 6.0 Hz, 1H), 3.04-2.98 (m, 3H), 2.60-2.53 (m, 1H), 1.89 (q, J=10.9 Hz, 1H), 1.81-1.68 (m, 2H), 1.58-1.51 (m, 3H), 1.19 (td, J=7.4, 3.1 Hz, 3H).

Example 114e: (1S,2R)-7-(ethylsulfonyl)-2-((S)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.84 (s, 1H), 7.60 (d, J=7.5 Hz, 1H), 7.46-7.32 (m, 2H), 7.22 (td, J=7.6, 1.0 Hz, 1H), 7.12 (s, 1H), 5.77 (d, J=5.9 Hz, 1H), 5.40 (d, J=10.9 Hz, 1H), 4.08 (td, J=6.1, 3.2 Hz, 1H), 3.25 (ddd, J=11.0, 6.9, 3.2 Hz, 1H), 3.17 (dt, J=11.0, 4.8 Hz, 1H), 3.09 (dt, J=10.1, 4.8 Hz, 2H), 3.03 (q, J=7.3 Hz, 2H), 2.34 (dt, J=17.4, 9.6 Hz, 1H), 2.21 (t, J=10.4 Hz, 1H), 1.91 (ddd, J=11.3, 8.4, 3.1 Hz, 1H), 1.78 (ddd, J=11.7, 8.0, 3.5 Hz, 1H), 1.66-1.60 (m, 1H), 1.58 (s, 2H), 1.21 (t, J=7.4 Hz, 3H).

Example 114f: (1R,2R)-7-(ethylsulfonyl)-2-((S)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.89 (s, 1H), 7.58 (d, J=7.5 Hz, 1H), 7.45-7.33 (m, 2H), 7.23 (td, J=7.6, 1.0 Hz, 1H), 7.10 (s, 1H), 5.38 (d, J=8.6 Hz, 1H), 5.24 (d, J=6.7 Hz, 1H), 3.95 (t, J=7.2 Hz, 1H), 3.45-3.36 (m, 1H), 3.37-3.31 (m, 1H), 3.00 (q, J=7.4 Hz, 3H), 2.94-2.84 (m, 1H), 2.36-2.28 (m, 1H), 1.85 (t, J=10.2 Hz, 1H), 1.69-1.59 (m, 2H), 1.57-1.45 (m, 3H), 1.19 (t, J=7.4 Hz, 3H).

Example 114g: (1S,2S)-7-(ethylsulfonyl)-2-((S)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.85 (s, 1H), 7.62 (d, J=7.6 Hz, 1H), 7.58 (d, J=7.5 Hz, 1H), 7.36 (t, J=7.5 Hz, 1H), 7.25 (td, J=7.6, 1.0 Hz, 1H), 7.12 (s, 1H), 5.81-5.68 (m, 1H), 5.45 (d, J=8.8 Hz, 1H), 4.11 (td, J=6.4, 3.1 Hz, 1H), 3.22 (ddd, J=11.2, 7.2, 3.8 Hz, 1H), 3.19-3.12 (m, 1H), 3.07 (q, J=6.6, 6.1 Hz, 1H), 3.04-2.96 (m, 3H), 2.60-2.52 (m, 1H), 1.93-1.85 (m, 1H), 1.82-1.71 (m, 2H), 1.55 (dt, J=11.4, 5.7 Hz, 3H), 1.19 (t, J=7.4 Hz, 3H).

Example 114h: (1R,2S)-7-(ethylsulfonyl)-2-((S)-5H-imidazo[5,1-a]isoindol-5-yl)-7-azaspiro[3.5]nonan-1-ol: LCMS (ESI, m/z): 388.2 $[M+H]^+$; $^1$H NMR (500 MHz, DMSO-$d_6$) δ 7.84 (s, 1H), 7.57 (d, J=7.9 Hz, 2H), 7.36 (t, J=7.6 Hz, 1H), 7.25 (t, J=7.9 Hz, 1H), 7.13 (s, 1H), 5.41 (d, J=7.0 Hz, 1H), 5.31 (d, J=6.4 Hz, 1H), 4.14-3.96 (m, 1H), 3.42-3.35 (m, 1H), 3.31 (s, 1H), 2.97 (q, J=7.4 Hz, 3H), 2.88-2.74 (m, 1H), 2.48-2.42 (m, 1H), 1.64 (dtd, J=27.0, 12.0, 10.1, 5.2 Hz, 3H), 1.52 (d, J=13.8 Hz, 1H), 1.40 (d, J=13.4 Hz, 1H), 1.17 (t, J=7.4 Hz, 3H), 0.96 (t, J=10.4 Hz, 1H).

Example 115: 2-(5H-imidazo[5,1-a]isoindol-5-yl)cycloheptan-1-ol 115a-d

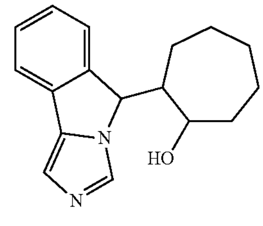

(1R,2S)-2-((S)-5H-imidazo[5,1-a]isoindol-5-yl)cycloheptan-1-ol (1S,2R)-2-((R)-5H-imidazo[5,1-a]isoindol-5-yl)cycloheptan-1-ol (1R,2S)-2-((R)-5H-imidazo[5,1-a]isoindol-5-yl)cycloheptan-1-ol (1S,2R)-2-((S)-5H-imidazo[5,1-a]isoindol-5-yl)cycloheptan-1-ol Synthetic Route:

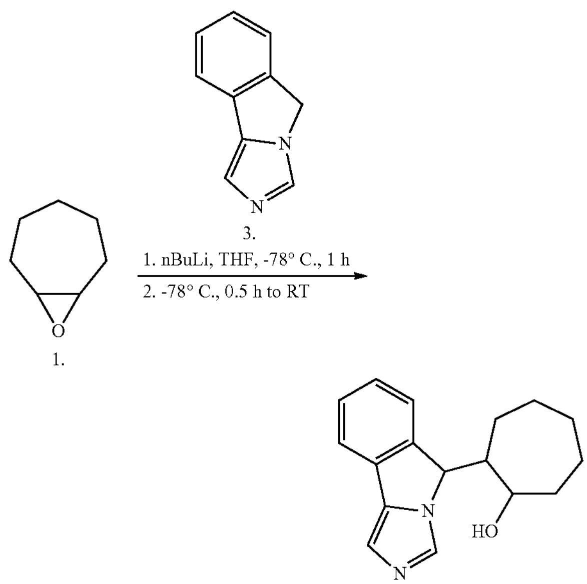

To a solution of 5H-imidazo[5,1-a]isoindole (3, 500 mg, 3.2014 mmol, 100 mass %) in tetrahydrofuran (10 mL, 123 mmol, 100 mass %) under nitrogen atmosphere at −78° C. was added dropwise n-BuLi (2.5 mol/L) in HEXANES (1.0 equiv., 3.2014 mmol, 2.5 mol/L) over 2 mins. This was then stirred at −78° C. under nitrogen for 45 minutes. To this at −78° C. under nitrogen was added dropwise over 3 minutes 8-oxabicyclo[5.1.0]octane (1, 384.9 mg, 3.260 mmol, 95 mass %) in tetrahydrofuran (2 mL, 24.6 mmol, 100 mass %). This was then stirred at −78° C. under nitrogen warming to room temperature in the process. Reaction quenched with sat. ammonium chloride (20 mL) and stirred for 5 minutes. This was then extracted with ethyl acetate (3×50 mL). The combined ethyl acetate layers were dried with magnesium sulfate, filtered. The filtrate was concentrated under reduced pressure and the residue then purified and individual isomers were separated by chiral separation (SFC, Column, Chiralpak OX, 250×21.2 mm; mobile phase: $CO_2$:0.1% ammonium hydroxide in methanol=70:30; Isocratic, Detector, uv 270 nm; flow rate 70 mL/min, 40° C.) to afford 4 isomers.

Example 115a: LCMS (ESI, m/z): 269.1 $[M+H]^+$. $^1H$ NMR (400 MHz, DMSO-d6) δ 7.84 (s, 1H), 7.59 (dt, J=7.7, 0.9 Hz, 1H), 7.45 (dt, J=7.5, 0.9 Hz, 1H), 7.39-7.35 (m, 1H), 7.29 (td, J=7.5, 1.2 Hz, 1H), 7.13 (s, 1H), 5.66-5.64 (m, 1H), 5.15 (d, J=5.4 Hz, 1H), 3.92-3.86 (m, 1H), 2.13 (ddd, J=9.6, 7.1, 2.4 Hz, 1H), 1.98-1.92 (m, 1H), 1.74-1.66 (m, 1H), 1.64-1.56 (m, 1H), 1.46-1.26 (m, 4H), 1.10-1.03 (m, 1H), 0.59-0.45 (m, 2H).

Example 115b: LCMS (ESI, m/z): 269.2 $[M+H]^+$. $^1H$ NMR (400 MHz, DMSO-d6) δ 7.89 (s, 1H), 7.60 (dd, J=7.5, 1.0 Hz, 1H), 7.53 (dd, J=7.8, 1.0 Hz, 1H), 7.39-7.35 (m, 1H), 7.27-7.23 (m, 1H), 7.12 (s, 1H), 5.65 (d, J=3.3 Hz, 1H), 5.10 (d, J=4.7 Hz, 1H), 3.90-3.85 (m, 1H), 2.29 (ddt, J=9.4, 6.2, 2:8 Hz, 1H), 1.89 (ddq, J=10.2, 6.4, 1.9 Hz, 1H), 1.68-1.57 (m, 2H), 1.50-1.44 (m, 1H), 1.35 (tdd, J=8.3, 4.4, 2.6 Hz, 2H), 1.29-1.23 (m, 1H), 1.13-1.06 (m, 1H), 0.51 (q, J=4.1, 3.0 Hz, 2H).

Example 115c: LCMS (ESI, m/z): 269.2 $[M+H]^+$. $^1H$ NMR (400 MHz, DMSO-d6) δ 7.84 (s, 1H), 7.59 (d, J=7.5 Hz, 1H), 7.45 (d, J=7.4 Hz, 1H), 7.37 (t, J=7.5 Hz, 1H), 7.31-7.27 (m, 1H), 7.13 (s, 1H), 5.66-5.65 (m, 1H), 5.15 (d, J=5.4 Hz, 1H), 3.92-3.87 (m, 1H), 2.13 (ddd, J=9.6, 7.1, 2.4 Hz, 1H), 1.98-1.92 (m, 1H), 1.74-1.67 (m, 1H), 1.61 (ddq, J=10.9, 5.6, 2.3 Hz, 1H), 1.46-1.28 (m, 4H), 1.06 (dq, J=13.9, 4.3, 3.7 Hz, 1H), 0.56 (tt, J=6.5, 3.2 Hz, 1H), 0.52-0.44 (m, 1H).

Example 115d: LCMS (ESI, m/z): 269.1 $[M+H]^+$. $^1H$ NMR (400 MHz, DMSO-d6) δ 7.89 (s, 1H), 7.60 (dd, J=7.5, 1.0 Hz, 1H), 7.53 (dd, J=7.6, 1.1 Hz, 1H), 7.39-7.35 (m, 1H), 7.12 (s, 1H), 5.65 (d, J=3.2 Hz, 1H), 5.09 (d, J=4.9 Hz, 1H), 3.87 (dt, J=6.7, 1.8 Hz, 1H), 2.29 (td, J=5.9, 5.0, 2.7 Hz, 1H), 1.89 (dtd, J=8.3, 4.5, 2.3 Hz, 1H), 1.67-1.57 (m, 2H), 1.48 (dt, J=7.7, 3.0 Hz, 1H), 1.36 (dtd, J=8.1, 4.4, 2.5 Hz, 2H), 1.26 (ddd, J=9.1, 5.1, 2.5 Hz, 1H), 1.13-1.07 (m, 1H), 0.52-0.49 (m, 2H).

Example 116: 3-(5H-imidazo[5,1-a]isoindol-5-yl)-1-(methylsulfonyl)pyrrolidin-3-ol

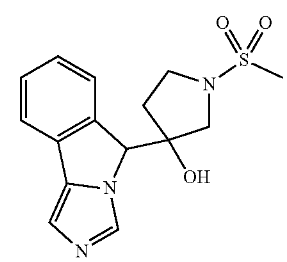 [SMILES: CS(=O)(=O)N1CCC(O)(C2c3ccccc3-c3cncn32)C1]

(R)-3-((R)-5H-imidazo[5,1-a]isoindol-5-yl)-1-(methylsulfonyl)pyrrolidin-3-ol
(S)-3-((R)-5H-imidazo[5,1-a]isoindol-5-yl)-1-(methylsulfonyl)pyrrolidin-3-ol
(R)-3-((S)-5H-imidazo[5,1-a]isoindol-5-yl)-1-(methylsulfonyl)pyrrolidin-3-ol
(S)-3-((S)-5H-imidazo[5,1-a]isoindol-5-yl)-1-(methylsulfonyl)pyrrolidin-3-ol Step 1:

tert-butyl 3-hydroxy-3-(5H-imidazo[5,1-a]isoindol-5-yl)pyrrolidine-1-carboxylate

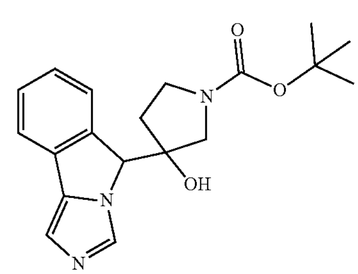 [SMILES: CC(C)(C)OC(=O)N1CCC(O)(C2c3ccccc3-c3cncn32)C1]

To a solution of 5H-imidazo[5,1-a]isoindole (3.0 g, 19.2 mmol) in anhydrous THF (30 mL) was added n-BuLi solution (9.2 mL, 23.05 mmol) at −78° C. and stirred for 1 hr. Tert-butyl 3-oxopyrrolidine-1-carboxylate (5.34 g, 28.81 mmol) was dissolved by anhydrous THF (10 mL) and the solution was added into the reaction mixture drop-wise. The reaction was kept at −78° C. for another 30 min and was warmed up to room temperature. The reaction was kept at room temperature for overnight and was quenched with saturated $NH_4Cl$ solution (20 mL). The mixture was extracted with DCM (3×20 ml) and the organic phase was combined, dried over $Na_2SO_4$, and concentrated. The product was separated by CombiFlash and was eluted with DCM:MeOH=95:5: LCMS (ESI, m/z): 342.2 [M+H]+.

Step 2:

3-(5H-imidazo[5,1-a]isoindol-5-yl)pyrrolidin-3-ol

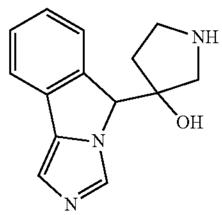 [SMILES: OC1(C2c3ccccc3-c3cncn32)CCNC1]

To a solution of tert-butyl 3-hydroxy-3-(5H-imidazo[5,1-a]isoindol-5-yl)pyrrolidine-1-carboxylate (1.0 g, 2.93 mmol) in anhydrous DCM (30 mL) was added trifluoroacetic acid (2.24 mL, 29.29 mmol) at room temperature and stirred for 2 hr. The solvent was removed under reduced pressure and the residue was left on vacuum pump overnight to get rid of trifluoroacetic acid. The product was used directly without further purification: LCMS (ESI, m/z): 242.3 [M+H]+.

Step 3:

(R)-3-((R)-5H-imidazo[5,1-a]isoindol-5-yl)-1-(methylsulfonyl)pyrrolidin-3-ol (S)-3-((R)-5H-imidazo[5,1-a]isoindol-5-yl)-1-(methylsulfonyl)pyrrolidin-3-ol (R)-3-((S)-5H-imidazo[5,1-a]isoindol-5-yl)-1-(methylsulfonyl)pyrrolidin-3-ol (S)-3-((S)-5H-imidazo[5,1-a]isoindol-5-yl)-1-(methylsulfonyl)pyrrolidin-3-ol 116a

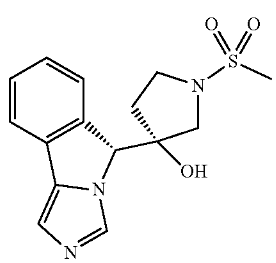

116b

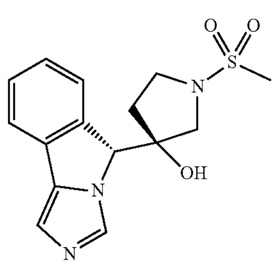

-continued

116c

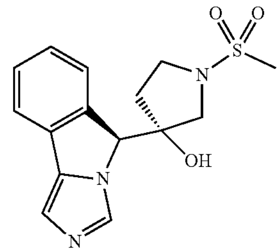

116d

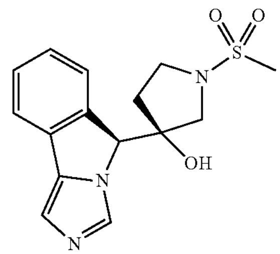

To a solution of 3-(5H-imidazo[5,1-a]isoindol-5-yl)pyrrolidin-3-ol (707 mg, 2.93 mmol) and trimethylamine (1.22 mL, 8.79 mmol) in anhydrous DCM (30 mL) was added methyl sulfonyl chloride (0.25 mL, 3.22 mmol) on ice-bath and stirred for 2 hr. The reaction was quenched by saturated ammonium chloride solution (30 mL). The mixture was extracted with 20% 2,2,2-trifluoroethanol in DCM (3×20 ml) and the organic phase was combined, dried over $Na_2SO_4$, and concentrated. The product was separated by Combi-Flash and was eluted with DCM:MeOH=92:8. The final products were further isolated by chiral separation to afford 4 isomers and the stereochemistry of each isomer was arbitrarily assigned.

Example 116a: (R)-3-((R)-5H-imidazo[5,1-a]isoindol-5-yl)-1-(methylsulfonyl)pyrrolidin-3-ol: LCMS (ESI, m/z): 320.1 [M+H]+; $^1$HNMR (400 MHz, DMSO-$d_6$) δ 7.85 (s, 1H), 7.59 (ddd, J=9.6, 7.6, 0.9 Hz, 2H), 7.44-7.37 (m, 1H), 7.26 (td, J=7.6, 1.2 Hz, 1H), 7.15 (s, 1H), 5.48 (s, 1H), 5.47 (s, 1H), 3.50 (d, J=11.1 Hz, 1H), 3.34 (d, J=4.6 Hz, 4H), 2.84 (s, 3H), 2.07 (dt, J=12.7, 9.8 Hz, 1H), 1.92-1.81 (m, 1H).

Example 116b: (S)-3-((R)-5H-imidazo[5,1-a]isoindol-5-yl)-1-(methylsulfonyl)pyrrolidin-3-ol: LCMS (ESI, m/z): 320.1 [M+H]+; $^1$HNMR (400 MHz, DMSO-$d_6$) δ 7.90 (s, 1H), 7.61 (dt, J=7.7, 1.0 Hz, 1H), 7.51 (dq, J=7.7, 0.9 Hz, 1H), 7.44-7.38 (m, 1H), 7.28 (td, J=7.6, 1.2 Hz, 1H), 7.14 (s, 1H), 5.48 (s, 1H), 5.39 (s, 1H), 3.47 (d, J=10.9 Hz, 1H), 3.41-3.34 (m, 2H), 3.19 (dd, J=11.0, 1.5 Hz, 1H), 2.83 (s, 3H), 2.20 (ddd, J=12.7, 10.8, 8.8 Hz, 1H), 2.13-2.03 (m, 1H).

Example 116c: (R)-3-((S)-5H-imidazo[5,1-a]isoindol-5-yl)-1-(methylsulfonyl)pyrrolidin-3-ol: LCMS (ESI, m/z): 320.1 [M+H]+; $^1$HNMR (400 MHz, DMSO-$d_6$) δ 7.90 (d, J=0.7 Hz, 1H), 7.61 (dt, J=7.5, 0.9 Hz, 1H), 7.51 (dq, J=7.7, 0.9 Hz, 1H), 7.41 (tdd, J=7.6, 1.1, 0.6 Hz, 1H), 7.28 (td, J=7.6, 1.2 Hz, 1H), 7.14 (s, 1H), 5.48 (s, 1H), 5.39 (s, 1H), 3.47 (d, J=10.9 Hz, 1H), 3.42-3.33 (m, 2H), 3.22-3.16 (m, 1H), 2.83 (s, 3H), 2.20 (ddd, J=12.7, 10.7, 8.7 Hz, 1H), 2.13-2.04 (m, 1H).

Example 116d: (S)-3-((S)-5H-imidazo[5,1-a]isoindol-5-yl)-1-(methylsulfonyl)pyrrolidin-3-ol: LCMS (ESI, m/z): 320.1 [M+H]+; $^1$HNMR (400 MHz, DMSO-$d_6$) δ 7.85 (s, 1H), 7.60 (ddt, J=9.5, 7.7, 0.8 Hz, 2H), 7.41 (tt, J=7.5, 0.8 Hz, 1H), 7.26 (td, J=7.6, 1.2 Hz, 1H), 7.15 (s, 1H), 5.49 (s, 1H), 5.48 (s, 1H), 3.50 (d, J=11.0 Hz, 1H), 3.34 (t, J=4.8 Hz, 3H), 2.85 (s, 3H), 2.12-2.01 (m, 1H), 1.92-1.82 (m, 1H).

Example 117: 7-(8-fluoro-5H-imidazo[5,1-a]isoindol-5-yl)-5,6,7,8-tetrahydroisoquinolin-8-ol

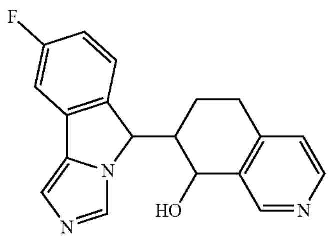 [SMILES: OC1c2cnccc2CCC1C1c2ccc(F)cc2-c2cncn21]

Step 1:

(E)-7-(4-fluoro-2-(1-trityl-1H-imidazol-4-yl)benzylidene)-6,7-dihydroisoquinolin-8(5H)-one

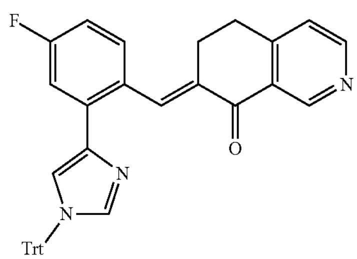

The title compound was synthesized by General Procedure for the Synthesis of Int-2: LCMS (ESI, m/z): 562.1 $[M+H]^+$.

Step 2:

7-(8-fluoro-5H-imidazo[5,1-a]isoindol-5-yl)-6,7-dihydroisoquinolin-8(5H)-one

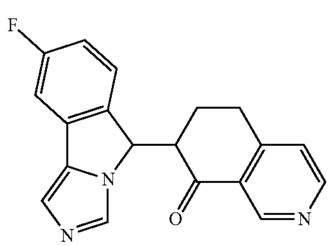 [SMILES: O=C1c2cnccc2CCC1C1c2ccc(F)cc2-c2cncn21]

The title compound was synthesized by General Procedure for the Synthesis of Int-3: LCMS (ESI, m/z): 320.1 $[M+H]^+$.

Step 3:

7-(8-fluoro-5H-imidazo[5,1-a]isoindol-5-yl)-5,6,7,8-tetrahydroisoquinolin-8-ol

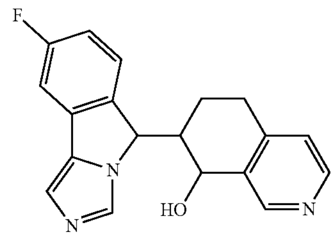 [SMILES: OC1c2cnccc2CCC1C1c2ccc(F)cc2-c2cncn21]

Under nitrogen, a solution of 7-[8-fluoro-5H-imidazo[4,3-a]isoindol-5-yl]-5,6,7,8-tetrahydroisoquinolin-8-one (1.6 g, 5.01 mmol) in THF (100 mL) was added L-selectride (15 mL, 15.0 mmol, 1 mol/L in THF) −78° C. The resulting solution was stirred for 3 h at −78° C. The resulting mixture was concentrated under vacuum. The resulting solution was diluted with water (20 mL). The solids were filtered out and washed by DCM. The resulting solution was extracted with DCM (3×100 mL) and the organic layers combined. The solution was dried over anhydrous sodium sulfate and concentrated under vacuum. The residue was purified by silica gel column eluting with DCM/MeOH (12:1). This resulted in 1.5 g (93%) of 7-[8-fluoro-5H-imidazo[4,3-a]isoindol-5-yl]-5,6,7,8-tetrahydroisoquinolin-8-ol as a yellow solid: LCMS (ESI, m/z): 322.1 $[M+H]^+$.

Step 4:

7-(8-fluoro-5H-imidazo[5,1-a]isoindol-5-yl)-5,6,7,8-tetrahydroisoquinolin-8-yl 4-nitrobenzoate

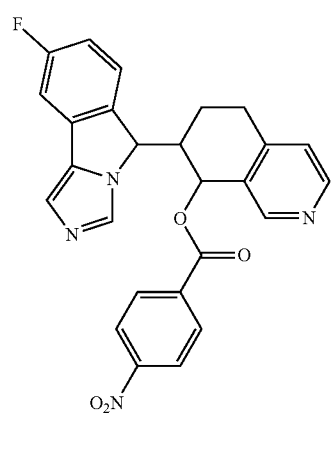 [SMILES: O=C(OC1c2cnccc2CCC1C1c2ccc(F)cc2-c2cncn21)c1ccc([N+](=O)[O-])cc1]

The title compound was synthesized by General Procedure for the Synthesis of 071aa and 071bb: LCMS (ESI, m/z): 471.1 $[M+H]^+$.

Step 5:

(7S,8S)-7-((S)-8-fluoro-5H-imidazo[5,1-a]isoindol-5-yl)-5,6,7,8-tetrahydroisoquinolin-8-ol (7R,8R)-7-((R)-8-fluoro-5H-imidazo[5,1-a]isoindol-5-yl)-5,6,7,8-tetrahydroisoquinolin-8-ol 117a

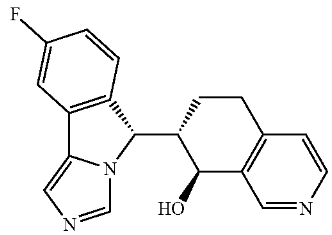

117b

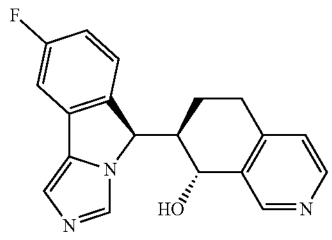

The title compounds were synthesized by General Procedure for the Synthesis of 071aa and 071bb. The absolute configuration of all isomers 117a-b was assigned arbitrarily.

Example 117a: (7S,8S)-7-((S)-8-fluoro-5H-imidazo[5,1-a]isoindol-5-yl)-5,6,7,8-tetrahydroisoquinolin-8-ol (56.2 mg, 14%) as a white solid: LCMS (ESI, m/z): 322.3 $[M+H]^+$. $^1H$ NMR (400 MHz, $CD_3OD$) δ 8.79 (s, 1H), 8.28 (dd, J=5.2, 0.8 Hz, 1H), 8.05 (s, 1H), 7.55-7.39 (m, 2H), 7.28 (s, 1H), 7.17-7.03 (m, 2H), 5.90 (d, J=1.8 Hz, 1H), 5.09 (d, J=10.7 Hz, 1H), 2.78-2.67 (m, 2H), 2.55-2.39 (m, 1H), 1.23-0.91 (m, 2H). $t_R$=2.134 min (Lux Cellulose-4, 0.46×5 cm, Hex(0.1% DEA):EtOH=65:35, 1 ml/min). 117a and 117b are enantiomers.

Example 117b: (7R,8R)-7-((R)-8-fluoro-5H-imidazo[5,1-a]isoindol-5-yl)-5,6,7,8-tetrahydroisoquinolin-8-ol (61.9 mg, 15%) as a white solid: LCMS (ESI, m/z): 322.2 $[M+H]^+$. $t_R$=2.737 min (Lux Cellulose-4, 0.46×5 cm, Hex (0.1% DEA):EtOH=65:35, 1 ml/min). 117a and 117b are enantiomers.

Example 118: 3-(8-fluoro-5H-imidazo[5,1-a]isoindol-5-yl)-1-(methylsulfonyl)piperidin-4-ol

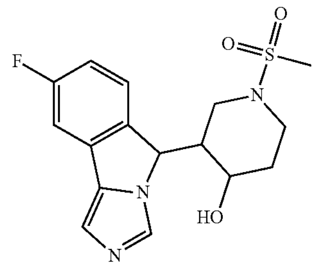 [SMILES: CS(=O)(=O)N1CCC(O)C(C2c3ccc(F)cc3-c3cncn32)C1]

(3S,4R)-3-((S)-8-fluoro-5H-imidazo[5,1-a]isoindol-5-yl)-1-(methylsulfonyl)piperidin-4-ol (3R,4S)-3-((S)-8-fluoro-5H-imidazo[5,1-a]isoindol-5-yl)-1-(methylsulfonyl)piperidin-4-ol (3S,4R)-3-((R)-8-fluoro-5H-imidazo[5,1-a]isoindol-5-yl)-1-(methylsulfonyl)piperidin-4-ol (3R,4S)-3-((R)-8-fluoro-5H-imidazo[5,1-a]isoindol-5-yl)-1-(methylsulfonyl)piperidin-4-ol The title compound was synthesized by the same method of example 92.

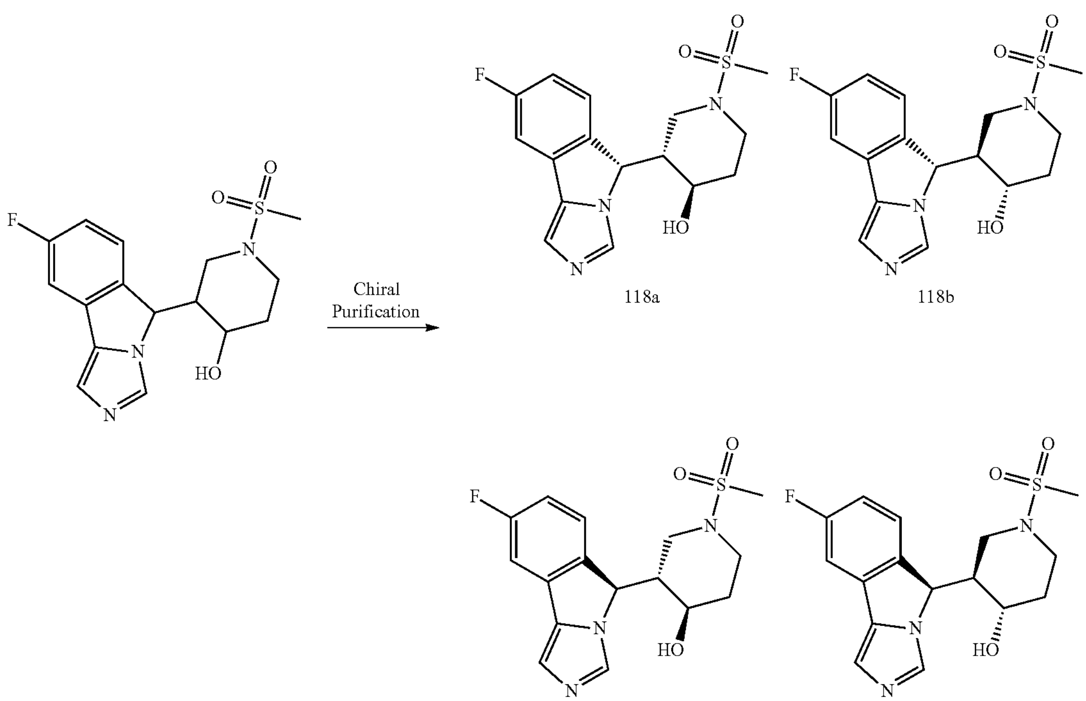

118a 118b 118c 118d

The configurations of the isomers were assigned arbitrarily.

Example 118a: (3S,4R)-3-((S)-8-fluoro-5H-imidazo[5,1-a]isoindol-5-yl)-1-(methylsulfonyl)piperidin-4-ol: LCMS (ESI, m/z): 352.3 $[M+H]^+$; $^1H$ NMR (400 MHz, DMSO-$d_6$) δ 8.04 (s, 1H), 7.59-7.47 (m, 2H), 7.19 (s, 1H), 7.11 (ddd, J=9.5, 8.5, 2.6 Hz, 1H), 5.69 (d, J=3.5 Hz, 1H), 5.43 (d, J=5.3 Hz, 1H), 3.72 (tt, J=10.2, 4.7 Hz, 1H), 3.52-3.44 (m, 1H), 2.77-2.63 (m, 5H), 2.45 (ddt, J=10.9, 7.6, 3.8 Hz, 1H), 2.03-1.94 (m, 2H), 1.62-1.47 (m, 1H). 118a and 118d are enantiomers.

Example 118b: (3R,4S)-3-((S)-8-fluoro-5H-imidazo[5,1-a]isoindol-5-yl)-1-(methylsulfonyl)piperidin-4-ol: LCMS (ESI, m/z): 352.3 $[M+H]^+$; $^1H$ NMR (400 MHz, DMSO-$d_6$) δ 7.89 (s, 1H), 7.62-7.56 (m, 1H), 7.51 (dd, J=9.0, 2.5 Hz, 1H), 7.21 (s, 1H), 7.14 (ddd, J=9.6, 8.4, 2.5 Hz, 1H), 5.76-5.70 (m, 1H), 5.56 (dd, J=5.7, 1.2 Hz, 1H), 3.91-3.78 (m, 1H), 3.53-3.47 (m, 1H), 2.83-2.64 (m, 5H), 2.31 (ddt, J=11.1, 6.5, 3.4 Hz, 1H), 2.10-2.00 (m, 1H), 1.83 (t, J=11.6 Hz, 1H), 1.66-1.51 (m, 1H). 118b and 118c are enantiomers.

Example 119: 4-(8-fluoro-5H-imidazo[5,1-a]isoindol-5-yl)-1-(methylsulfonyl)piperidin-3-ol

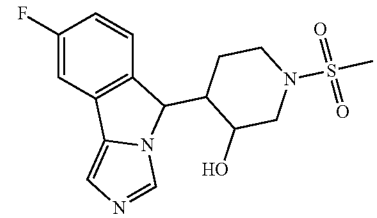 [SMILES: CS(=O)(=O)N1CCC(C2c3ccc(F)cc3-c3cncn32)C(O)C1]

(3S,4S)-4-((S)-8-fluoro-5H-imidazo[5,1-a]isoindol-5-yl)-1-(methylsulfonyl)piperidin-3-ol (3R,4R)-4-((R)-8-fluoro-5H-imidazo[5,1-a]isoindol-5-yl)-1-(methylsulfonyl)piperidin-3-ol (3R,4R)-4-((S)-8-fluoro-5H-imidazo[5,1-a]isoindol-5-yl)-1-(methylsulfonyl)piperidin-3-ol The title compound was synthesized by the same method of example 92.

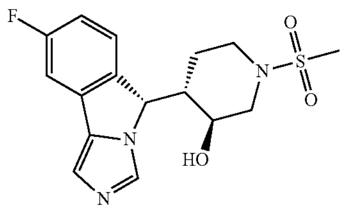

119a

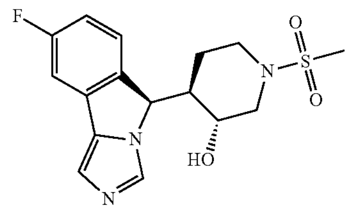

119b

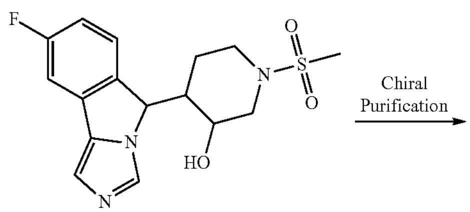

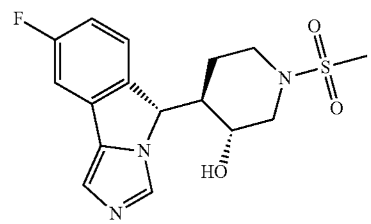

119c

Example 118c: (3S,4R)-3-((R)-8-fluoro-5H-imidazo[5,1-a]isoindol-5-yl)-1-(methylsulfonyl)piperidin-4-ol: LCMS (ESI, m/z): 352.3 $[M+H]^+$; $^1H$ NMR (400 MHz, DMSO-$d_6$) δ 7.89 (s, 1H), 7.59 (ddd, J=8.5, 5.1, 0.9 Hz, 1H), 7.51 (dd, J=9.0, 2.5 Hz, 1H), 7.21 (s, 1H), 7.14 (ddd, J=9.5, 8.4, 2.5 Hz, 1H), 5.73 (t, J=1.7 Hz, 1H), 5.56 (d, J=5.7 Hz, 1H), 3.85 (dp, J=10.3, 5.0 Hz, 1H), 3.50 (ddq, J=12.1, 4.7, 2.5 Hz, 1H), 2.80 (ddd, J=11.6, 3.7, 2.0 Hz, 1H), 2.72 (td, J=12.6, 2.8 Hz, 1H), 2.66 (s, 3H), 2.36-2.25 (m, 1H), 2.11-2.00 (m, 1H), 1.83 (t, J=11.6 Hz, 1H), 1.66-1.51 (m, 1H). 118b and 118c are enantiomers.

Example 118d: (3R,4S)-3-((R)-8-fluoro-5H-imidazo[5,1-a]isoindol-5-yl)-1-(methylsulfonyl)piperidin-4-ol: LCMS (ESI, m/z): 352.3 $[M+H]^+$; $^1H$ NMR (400 MHz, DMSO-$d_6$) δ 8.04 (s, 1H), 7.59-7.47 (m, 2H), 7.19 (s, 1H), 7.11 (ddd, J=9.5, 8.4, 2.6 Hz, 1H), 5.69 (d, J=3.7 Hz, 1H), 5.43 (d, J=5.3 Hz, 1H), 3.72 (tt, J=10.1, 4.7 Hz, 1H), 3.52-3.44 (m, 1H), 2.79-2.62 (m, 5H), 2.48-2.41 (m, 1H), 2.03-1.94 (m, 2H), 1.62-1.47 (m, 1H). 118a and 118d are enantiomers.

The configurations of the isomers were assigned arbitrarily.

Example 119a: (3S,4S)-4-((S)-8-fluoro-5H-imidazo[5,1-a]isoindol-5-yl)-1-(methylsulfonyl)piperidin-3-ol: LCMS (ESI, m/z): 352.3 $[M+H]^+$; $^1H$ NMR (400 MHz, DMSO-$d_6$) δ 7.94 (s, 1H), 7.54-7.49 (m, 2H), 7.19 (s, 1H), 7.11 (ddd, J=9.4, 8.4, 2.5 Hz, 1H), 5.76 (d, J=4.8 Hz, 1H), 5.71 (d, J=3.7 Hz, 1H), 3.73 (ddt, J=12.1, 6.6, 4.7 Hz, 2H), 3.35 (ddt, J=4.5, 3.0, 0.7 Hz, 1H), 2.84 (s, 3H), 2.56-2.53 (m, 1H), 2.28 (h, J=6.5, 5.4 Hz, 1H), 0.70 (dd, J=13.3, 3.4 Hz, 1H), 0.52 (qd, J=12.7, 4.6 Hz, 1H). 119a and 119b are enantiomers.

Example 119b: (3R,4R)-4-((R)-8-fluoro-5H-imidazo[5,1-a]isoindol-5-yl)-1-(methylsulfonyl)piperidin-3-ol: LCMS (ESI, m/z): 352.3 $[M+H]^+$; $^1H$ NMR (400 MHz, DMSO-$d_6$) δ 7.94 (s, 1H), 7.56-7.47 (m, 2H), 7.19 (s, 1H), 7.14-7.08 (m, 1H), 5.76 (d, J=4.8 Hz, 1H), 5.71 (d, J=3.6 Hz, 1H), 3.78-3.67 (m, 2H), 3.35 (dt, J=4.2, 2.3 Hz, 1H), 2.84 (s, 3H), 2.56-2.51 (m, 1H), 2.28 (tt, J=10.2, 3.7 Hz, 1H), 0.70 (dd, J=13.4, 3.3 Hz, 1H), 0.52 (qd, J=12.7, 4.5 Hz, 1H). 119a and 119b are enantiomers.

Example 119c: (3R,4R)-4-((S)-8-fluoro-5H-imidazo[5,1-a]isoindol-5-yl)-1-(methylsulfonyl)piperidin-3-ol: LCMS (ESI, m/z): 352.3 $[M+H]^+$; $^1H$ NMR (400 MHz, DMSO-$d_6$)

δ 7.91 (s, 1H), 7.50 (ddd, J=8.4, 4.6, 1.4 Hz, 2H), 7.21 (s, 1H), 7.12 (ddd, J=9.5, 8.4, 2.5 Hz, 1H), 5.79 (d, J=5.1 Hz, 1H), 5.72 (d, J=2.0 Hz, 1H), 3.86-3.73 (m, 2H), 3.35 (ddd, J=4.1, 2.4, 1.3 Hz, 1H), 2.84 (s, 3H), 2.59-2.52 (m, 2H), 2.19-2.08 (m, 1H), 0.87-0.79 (m, 1H), 0.44 (qd, J=12.7, 4.6 Hz, 1H).

Example 120: 4-(6-fluoro-5H-imidazo[5,1-a]isoindol-5-yl)tetrahydro-2H-pyran-3-ol

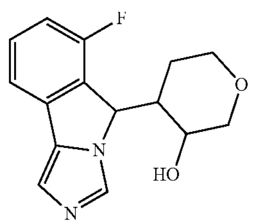 [SMILES: OC1COCCC1C1c2c(F)cccc2-c2cncn21]

(3S,4S)-4-((S)-6-fluoro-5H-imidazo[5,1-a]isoindol-5-yl)tetrahydro-2H-pyran-3-ol
(3R,4R)-4-((R)-6-fluoro-5H-imidazo[5,1-a]isoindol-5-yl)tetrahydro-2H-pyran-3-ol
(3S,4S)-4-((R)-6-fluoro-5H-imidazo[5,1-a]isoindol-5-yl)tetrahydro-2H-pyran-3-ol
(3R,4R)-4-((S)-6-fluoro-5H-imidazo[5,1-a]isoindol-5-yl)tetrahydro-2H-pyran-3-ol The title compound was synthesized by the same method of example 69.

The absolute configuration of isomers 120a and 120b was determined by X-ray crystallography. The configuration of rest of the isomers was assigned arbitrarily.

Example 120a: (3S,4S)-4-((S)-6-fluoro-5H-imidazo[5,1-a]isoindol-5-yl)tetrahydro-2H-pyran-3-ol: LCMS (ESI, m/z): 275.1 $[M+H]^+$; $^1$H NMR (500 MHz, DMSO-$d_6$) δ 7.90 (s, 1H), 7.52-7.41 (m, 2H), 7.22 (s, 1H), 7.17-7.05 (m, 1H), 5.95 (d, J=2.4 Hz, 1H), 5.57 (d, J=5.9 Hz, 1H), 3.90 (dd, J=10.6, 4.9 Hz, 1H), 3.71 (tt, J=10.4, 5.3 Hz, 1H), 3.60 (dd, J=11.4, 4.6 Hz, 1H), 3.19-3.09 (m, 1H), 3.05 (dd, J=10.7, 9.8 Hz, 1H), 2.28 (s, 1H), 0.82-0.68 (m, 1H), 0.45 (qd, J=12.7, 4.8 Hz, 1H). 120a and 120b are enantiomers.

Example 120b: (3R,4R)-4-((R)-6-fluoro-5H-imidazo[5,1-a]isoindol-5-yl)tetrahydro-2H-pyran-3-ol: LCMS (ESI, m/z): 275.1 $[M+H]^+$; $^1$H NMR (500 MHz, DMSO-$d_6$) δ 7.90 (s, 1H), 7.54-7.41 (m, 2H), 7.22 (s, 1H), 7.17-7.07 (m, 1H), 5.95 (d, J=2.3 Hz, 1H), 5.57 (d, J=5.9 Hz, 1H), 3.90 (dd, J=10.7, 4.9 Hz, 1H), 3.71 (tt, J=10.4, 5.4 Hz, 1H), 3.60 (dd, J=11.4, 4.6 Hz, 1H), 3.20-3.09 (m, 1H), 3.05 (dd, J=10.7, 9.8 Hz, 1H), 2.28 (s, 1H), 0.82-0.65 (m, 1H), 0.45 (qd, J=12.7, 4.9 Hz, 1H). 120a and 120b are enantiomers.

Example 120c: (3S,4S)-4-((R)-6-fluoro-5H-imidazo[5,1-a]isoindol-5-yl)tetrahydro-2H-pyran-3-ol: LCMS (ESI, m/z): 275.1 $[M+H]^+$; $^1$H NMR (500 MHz, DMSO-$d_6$) δ 7.95 (s, 1H), 7.56-7.39 (m, 2H), 7.19 (s, 1H), 7.16-7.06 (m, 1H), 5.87 (d, J=2.4 Hz, 1H), 5.13 (d, J=5.4 Hz, 1H), 3.80 (dd, J=10.6, 5.0 Hz, 1H), 3.65 (dd, J=11.2, 4.2 Hz, 1H), 3.56 (tt, J=10.1, 5.0 Hz, 1H), 3.22-3.08 (m, 1H), 2.93 (td, J=10.3, 1.8 Hz, 1H), 2.37-2.26 (m, 1H), 1.01-0.79 (m, 2H). 120c and 120d are enantiomers.

Example 120d: (3R,4R)-4-((S)-6-fluoro-5H-imidazo[5,1-a]isoindol-5-yl)tetrahydro-2H-pyran-3-ol: LCMS (ESI, m/z): 275.1 $[M+H]^+$; $^1$H NMR (500 MHz, DMSO-$d_6$) δ 7.95 (s, 1H), 7.54-7.39 (m, 2H), 7.19 (d, J=1.2 Hz, 1H), 7.16-7.05

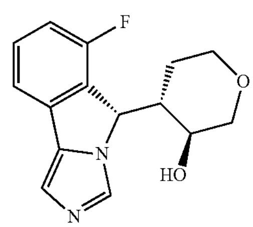

120a

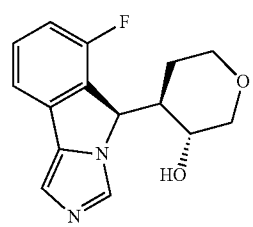

120b

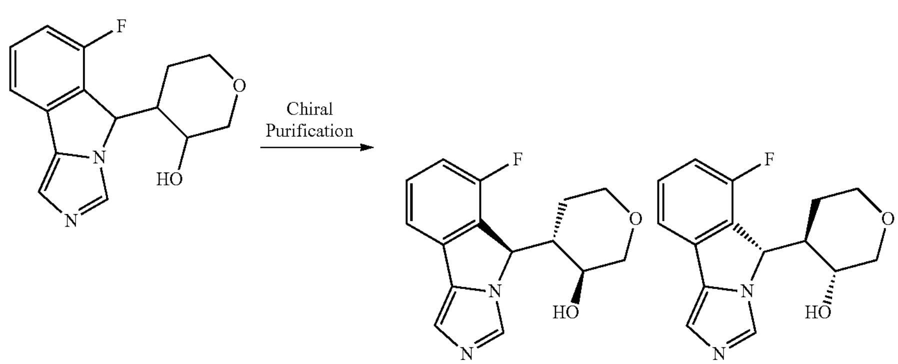

120c 120d (m, 1H), 5.87 (d, J=2.3 Hz, 1H), 5.13 (d, J=5.3 Hz, 1H), 3.80 (dd, J=10.6, 5.0 Hz, 1H), 3.65 (dd, J=11.0, 4.0 Hz, 1H), 3.56 (tt, J=10.3, 5.2 Hz, 1H), 3.13 (td, J=11.5, 2.7 Hz, 1H), 3.01-2.88 (m, 1H), 1.00-0.76 (m, 2H). 120c and 120d are enantiomers.

Example 121: 2-amino-6-(5H-imidazo[5,1-a]isoindol-5-yl)-5,6,7,8-tetrahydroquinolin-5-ol

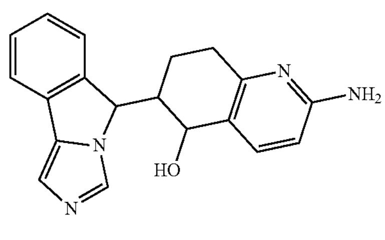 [SMILES: Nc1ccc2c(n1)CCC(C1c3ccccc3-c3cncn31)C2O]

(5S,6R)-2-amino-6-((S)-5H-imidazo[5,1-a]isoindol-5-yl)-5,6,7,8-tetrahydroquinolin-5-ol (5R,6S)-2-amino-6-((R)-5H-imidazo[5,1-a]isoindol-5-yl)-5,6,7,8-tetrahydroquinolin-5-ol (5R,6R)-2-amino-6-((S)-5H-imidazo[5,1-a]isoindol-5-yl)-5,6,7,8-tetrahydroquinolin-5-ol (5S,6S)-2-amino-6-((R)-5H-imidazo[5,1-a]isoindol-5-yl)-5,6,7,8-tetrahydroquinolin-5-ol (5S,6S)-2-amino-6-((S)-5H-imidazo[5,1-a]isoindol-5-yl)-5,6,7,8-tetrahydroquinolin-5-ol (5R,6R)-2-amino-6-((R)-5H-imidazo[5,1-a]isoindol-5-yl)-5,6,7,8-tetrahydroquinolin-5-ol (5S,6R)-2-amino-6-((R)-5H-imidazo[5,1-a]isoindol-5-yl)-5,6,7,8-tetrahydroquinolin-5-ol (5R,6S)-2-amino-6-((S)-5H-imidazo[5,1-a]isoindol-5-yl)-5,6,7,8-tetrahydroquinolin-5-ol Step 1:

(E)-2-amino-6-(2-(1-trityl-1H-imidazol-4-yl)benzylidene)-7,8-dihydroquinolin-5(6H)-one

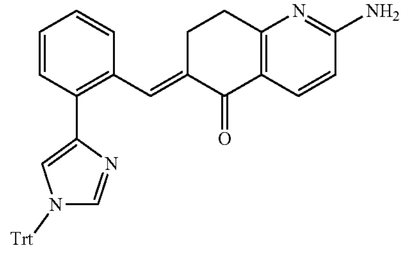

To a solution of 2-(1-trityl-1H-imidazol-4-yl)benzaldehyde (2.5 g, 6.03 mmol) and 2-amino-7,8-dihydroquinolin-5(6H)-one (1.17 g, 7.24 mmol) in ethanol (50 mL) was added anhydrous $Ca(OH)_2$ (1.12 g, 15.08 mmol). The mixture was stirred at 90° C. overnight. When hot, the precipitations were filtered and re-suspended in hot MeOH (20 mL). The solid was filtered again and dried in air. The product was used directly without further purification: LCMS (ESI, m/z): 559.2 [M+H]$^+$.

Step 2:

2-amino-6-(5H-imidazo[5,1-a]isoindol-5-yl)-7,8-dihydroquinolin-5(6H)-one

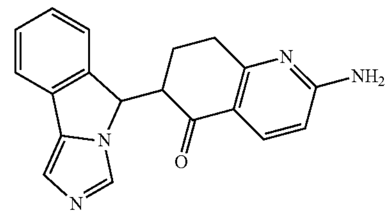 [SMILES: Nc1ccc2c(n1)CCC(C1c3ccccc3-c3cncn31)C2=O]

(E)-2-amino-6-(2-(1-trityl-1H-imidazol-4-yl)benzylidene)-7,8-dihydroquinolin-5(6H)-one (3.37 g, 6.03 mmol) was stirred in 20% AcOH in MeOH (200 mL) at 90° C. for 2 h. After cooling to room temperature, the solvent was removed under reduced pressure and saturated $NaHCO_3$ (60 mL) was added to the residue followed by DCM (20 mL). The organic layer was collected and the aqueous layer was extracted with 20% trifluoroethanol in DCM (3×50 mL). The combined organic layers were dried over $Na_2SO_4$ and the solvent evaporated under reduced pressure to afford the crude product which was purified by using CombiFlash and was eluted by DCM:MeOH=90:10: LCMS (ESI, m/z): 317.3 [M+H]$^+$.

Step 3:

(5S,6R)-2-amino-6-((S)-5H-imidazo[5,1-a]isoindol-5-yl)-5,6,7,8-tetrahydroquinolin-5-ol (5R,6S)-2-amino-6-((R)-5H-imidazo[5,1-a]isoindol-5-yl)-5,6,7,8-tetrahydroquinolin-5-ol (5R,6R)-2-amino-6-((S)-5H-imidazo[5,1-a]isoindol-5-yl)-5,6,7,8-tetrahydroquinolin-5-ol (5S,6S)-2-amino-6-((R)-5H-imidazo[5,1-a]isoindol-5-yl)-5,6,7,8-tetrahydroquinolin-5-ol (5S,6S)-2-amino-6-((S)-5H-imidazo[5,1-a]isoindol-5-yl)-5,6,7,8-tetrahydroquinolin-5-ol (5R,6R)-2-amino-6-((R)-5H-imidazo[5,1-a]isoindol-5-yl)-5,6,7,8-tetrahydroquinolin-5-ol (5S,6R)-2-amino-6-((R)-5H-imidazo[5,1-a]isoindol-5-yl)-5,6,7,8-tetrahydroquinolin-5-ol (5R,6S)-2-amino-6-((S)-5H-imidazo[5,1-a]isoindol-5-yl)-5,6,7,8-tetrahydroquinolin-5-ol 121a

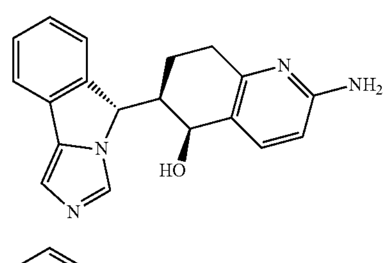

121b

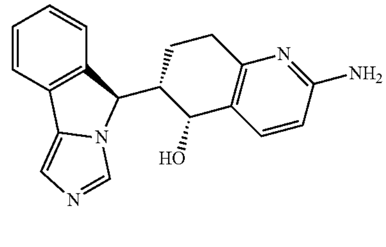

-continued

121c

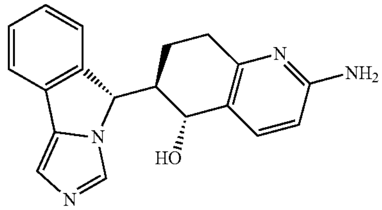

121d

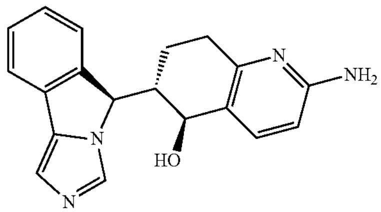

121e

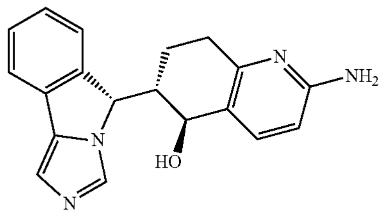

121f

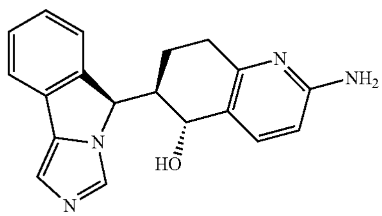

121g

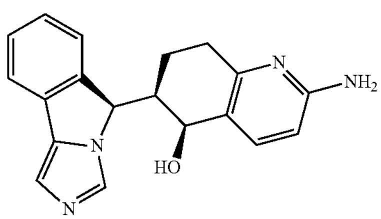

121h

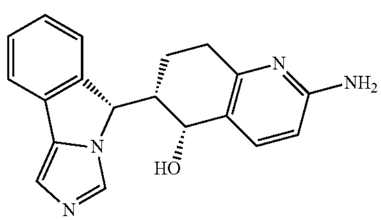

To a suspension of 2-amino-6-(5H-imidazo[5,1-a]isoindol-5-yl)-7,8-dihydroquinolin-5(6H)-one (0.724 g, 2.29 mmol) in MeOH (50 mL) was added $NaBH_4$ (346 mg, 9.15 mmol) in portions at 0° C. and the solution was stirred at room temperature for 2 hr. The solvent was distilled off and saturated ammonium chloride solution (30 mL) was added. The aqueous layer was extracted with 20% trifluoroethanol in DCM (3×30 mL). The combined organic extract was dried over ($Na_2SO_4$) and concentrated under reduced pressure to afford the crude product. The crude was purified by CombiFlash and the product was eluted with DCM:MeOH=80:20. The final products were further isolated by chiral separation to afford 8 isomers and the stereochemistry of each isomer was arbitrarily assigned.

Example 121a: (5S,6R)-2-amino-6-((S)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121b: (5R,6S)-2-amino-6-((R)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121c: (5R,6R)-2-amino-6-((S)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121d: (5S,6S)-2-amino-6-((R)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121e: (5S,6S)-2-amino-6-((S)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121f: (5R,6R)-2-amino-6-((R)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121g: (5S,6R)-2-amino-6-((R)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 121h: (5R,6S)-2-amino-6-((S)-5H-imidazo[5,1-a]isoindol-5-yl)-5,6,7,8-tetrahydroquinolin-5-ol: LCMS (ESI, m/z): 319.3 $[M+H]^+$; $^1$HNMR (400 MHz, DMSO-$d_6$) δ 7.96 (s, 1H), 7.69-7.59 (m, 2H), 7.48 (dq, J=7.6, 0.9 Hz, 1H), 7.41 (tt, J=7.6, 0.9 Hz, 1H), 7.32 (td, J=7.5, 1.1 Hz, 1H), 7.18 (s, 1H), 6.37 (d, J=8.5 Hz, 1H), 5.84 (s, 2H), 5.78-5.74 (m, 2H), 4.89-4.78 (m, 1H), 2.47-2.23 (m, 3H), 1.28-1.22 (m, 2H).

Example 122: 8-hydroxy-7-(5H-imidazo[5,1-a]isoindol-5-yl)-5,6,7,8-tetrahydronaphthalene-2-carboxamide

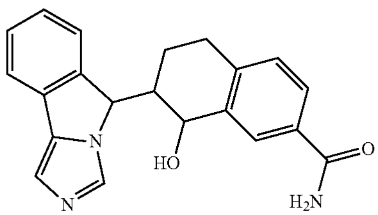 [SMILES: NC(=O)c1ccc2c(c1)C(O)C(C1c3ccccc3-c3cncn31)CC2]

(7R,8R)-8-hydroxy-7-((R)-5H-imidazo[5,1-a]isoindol-5-yl)-5,6,7,8-tetrahydronaphthalene-2-carboxamide (7R,8R)-8-hydroxy-7-((S)-5H-imidazo[5,1-a]isoindol-5-yl)-5,6,7,8-tetrahydronaphthalene-2-carboxamide (7R,8S)-8-hydroxy-7-((R)-5H-imidazo[5,1-a]isoindol-5-yl)-5,6,7,8-tetrahydronaphthalene-2-carboxamide (7R,8S)-8-hydroxy-7-((S)-5H-imidazo[5,1-a]isoindol-5-yl)-5,6,7,8-tetrahydronaphthalene-2-carboxamide (7S,8R)-8-hydroxy-7-((R)-5H-imidazo[5,1-a]isoindol-5-yl)-5,6,7,8-tetrahydronaphthalene-2-carboxamide (7S,8S)-8-hydroxy-7-((R)-5H-imidazo[5,1-a]isoindol-5-yl)-5,6,7,8-tetrahydronaphthalene-2-carboxamide Step 1:

(7R,8R)-8-hydroxy-7-((R)-5H-imidazo[5,1-a]isoindol-5-yl)-5,6,7,8-tetrahydronaphthalene-2-carboxamide (7R,8R)-8-hydroxy-7-((S)-5H-imidazo[5,1-a]isoindol-5-yl)-5,6,7,8-tetrahydronaphthalene-2-carboxamide (7R,8S)-8-hydroxy-7-((R)-5H-imidazo[5,1-a]isoindol-5-yl)-5,6,7,8-tetrahydronaphthalene-2-carboxamide (7R,8S)-8-hydroxy-7-((S)-5H-imidazo[5,1-a]isoindol-5-yl)-5,6,7,8-tetrahydronaphthalene-2-carboxamide (7S,8R)-8-hydroxy-7-((R)-5H-imidazo[5,1-a]isoindol-5-yl)-5,6,7,8-tetrahydronaphthalene-2-carboxamide (7S,8S)-8-hydroxy-7-((R)-5H-imidazo[5,1-a]isoindol-5-yl)-5,6,7,8-tetrahydronaphthalene-2-carboxamide 122a

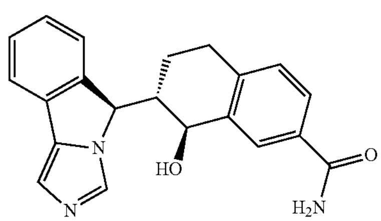

122b

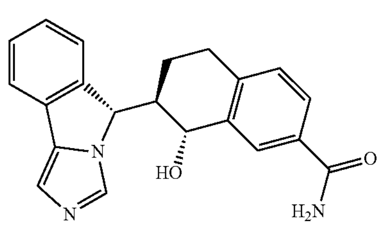

-continued

122c

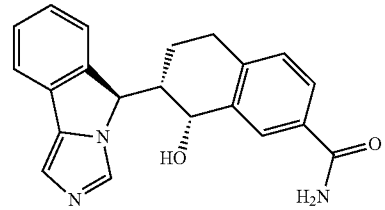

122d

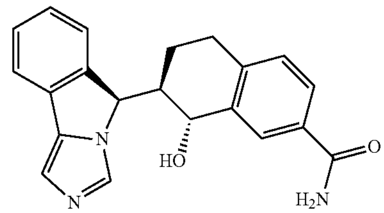

122e

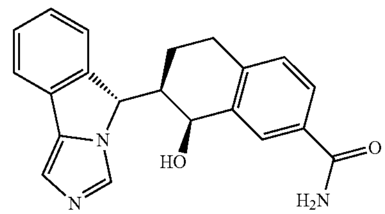

122f

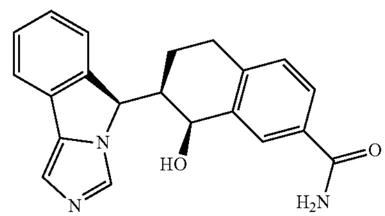

To the solution of 8-hydroxy-7-(5H-imidazo[5,1-a]isoindol-5-yl)-5,6,7,8-tetrahydronaphthalene-2-carbonitrile (1.45 g, 4.43 mmol) in methanol (100 mL), sodium hydroxide (1.77 g, 44.29 mmol) and hydrogen peroxide (30% solution in water, 1.33 mL, 13.29 mmol) were added and stirred for 2 hours at room temperature. Solvent was removed and crude product was extracted with a solution of 5% 2,2,2-trifluoroetthanol in DCM. Combined organic layers were washed with water, brine, dried over sodium sulfate and evaporated to yield crude product. Crude product was purified on Combi-Flash and further isolated by chiral separation to afford 6 isomers as white solid. The absolute configuration of all isomers was assigned arbitrarily.

Example 122a: (7R,8R)-8-hydroxy-7-((R)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 8.22 (dd, J=1.9, 0.9 Hz, 1H), 7.95 (t, J=0.6 Hz, 1H), 7.90 (s, 1H), 7.69-7.61 (m, 2H), 7.48 (dq, J=7.6, 0.9 Hz, 1H), 7.46-7.37 (m, 1H), 7.31 (td, J=7.5, 1.1 Hz, 1H), 7.24 (s, 1H), 7.18 (s, 1H), 7.06 (d, J=7.9 Hz, 1H), 6.06 (d, J=7.8 Hz, 1H), 5.83 (d, J=1.9 Hz, 1H), 5.04-4.85 (m, 1H), 3.51-3.39 (m, 1H), 2.65-2.56 (m, 2H), 2.45-2.32 (m, 1H), 1.30-1.19 (m, 1H).

Example 122b: (7R,8R)-8-hydroxy-7-((S)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 8.27-8.19 (m, 1H), 7.95 (s, 1H), 7.90 (s, 1H), 7.69-7.60 (m, 2H), 7.48 (dq, J=7.5, 0.9 Hz, 1H), 7.41 (tt, J=7.7, 0.9 Hz, 1H), 7.31 (td, J=7.5, 1.2 Hz, 1H), 7.26 (d, J=10.9 Hz, 1H), 7.06 (d, J=8.0 Hz, 1H), 6.06 (d, J=7.8 Hz, 1H), 5.83 (d, J=2.0 Hz, 1H), 4.97-4.90 (m, 1H), 4.33 (t, J=5.1 Hz, 1H), 3.44 (qd, J=7.0, 5.1 Hz, 1H), 2.61 (dd, J=8.9, 4.6 Hz, 2H), 2.06-1.90 (m, 2H).

Example 122c: (7R,8S)-8-hydroxy-7-((R)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 7.98-7.94 (m, 2H), 7.91 (s, 1H), 7.70 (dd, J=8.0, 1.9 Hz, 1H), 7.64 (dq, J=7.6, 0.9 Hz, 1H), 7.59 (dt, J=7.6, 0.9 Hz, 1H), 7.42-7.36 (m, 1H), 7.29 (td, J=7.5, 1.2 Hz, 2H), 7.16-7.08 (m, 2H), 5.85 (d, J=6.1 Hz, 1H), 5.56-5.50 (m, 1H), 5.01 (dd, J=6.1, 3.6 Hz, 1H), 2.75 (dd, J=17.5, 5.1 Hz, 1H), 2.61-2.53 (m, 1H), 2.43 (dq, J=12.6, 3.1 Hz, 1H), 1.60-1.46 (m, 1H), 1.05-0.98 (m, 1H).

Example 122d: (7R,8S)-8-hydroxy-7-((S)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 8.20-8.13 (m, 1H), 7.91 (t, J=0.6 Hz, 1H), 7.88 (s, 1H), 7.67-7.59 (m, 3H), 7.40 (tt, J=7.6, 0.8 Hz, 1H), 7.26 (td, J=7.6, 1.2 Hz, 2H), 7.17 (d, J=0.5 Hz, 1H), 7.06 (d, J=8.0 Hz, 1H), 6.08 (d, J=7.6 Hz, 1H), 5.82 (d, J=3.3 Hz, 1H), 4.95-4.85 (m, 1H), 2.66-2.54 (m, 3H), 0.91-0.80 (m, 2H).

Example 122e: (7S,8R)-8-hydroxy-7-((R)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 7.99-7.93 (m, 2H), 7.91 (d, J=2.5 Hz, 1H), 7.70 (dd, J=8.0, 1.9 Hz, 1H), 7.61 (ddt, J=16.2, 7.6, 0.9 Hz, 2H), 7.47-7.35 (m, 1H), 7.29 (td, J=7.6, 1.2 Hz, 2H), 7.15-7.09 (m, 2H), 5.85 (d, J=6.1 Hz, 1H), 5.54 (d, J=2.5 Hz, 1H), 5.01 (dd, J=6.2, 3.6 Hz, 1H), 3.44 (qd, J=7.0, 5.1 Hz, 1H), 2.75 (dd, J=17.3, 5.2 Hz, 1H), 2.56 (dt, J=11.3, 5.8 Hz, 1H), 2.44 (dt, J=12.7, 3.1 Hz, 1H), 1.53 (tt, J=12.7, 6.3 Hz, 1H).

Example 122f: ((7S,8S)-8-hydroxy-7-((R)-5H-imidazo[5,1-a]isoindol-5-yl)-5,6,7,8-tetrahydronaphthalene-2-carboxamide: LCMS (ESI, m/z): 346.2 $[M+H]^+$; $^1H$ NMR (400 MHz, DMSO-$d_6$) δ 8.01 (t, J=0.7 Hz, 1H), 7.89 (d, J=1.9 Hz, 1H), 7.87 (s, 1H), 7.75 (dq, J=7.8, 0.9 Hz, 1H), 7.69 (dd, J=7.9, 1.9 Hz, 1H), 7.62 (dt, J=7.7, 0.9 Hz, 1H), 7.39 (tt, J=7.6, 0.8 Hz, 1H), 7.25 (td, J=7.6, 1.2 Hz, 2H), 7.18-7.10 (m, 2H), 5.58 (d, J=5.9 Hz, 1H), 5.44 (d, J=6.1 Hz, 1H), 4.82 (dd, J=6.0, 3.2 Hz, 1H), 2.88 (dd, J=17.4, 5.1 Hz, 1H), 2.73-2.60 (m, 1H), 2.11 (ddt, J=12.2, 6.0, 2.9 Hz, 1H), 1.99 (qd, J=12.4, 5.4 Hz, 1H), 1.80-1.71 (m, 1H).

Example 123: 6-(5H-imidazo[5,1-a]isoindol-5-yl)-5,6,7,8-tetrahydroquinoxalin-5-ol

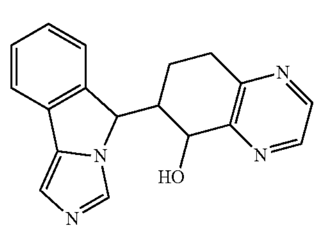 [SMILES: OC1c2nccnc2CCC1C1c2ccccc2-c2cncn21]

(5S,6S)-6-((S)-5H-imidazo[5,1-a]isoindol-5-yl)-5,6,7,8-tetrahydroquinoxalin-5-ol (5R,6R)-6-((R)-5H-imidazo[5,1-a]isoindol-5-yl)-5,6,7,8-tetrahydroquinoxalin-5-ol Step 1:

(E)-6-(2-(1-trityl-1H-imidazol-4-yl)benzylidene)-7,8-dihydroquinoxalin-5(6H)-one

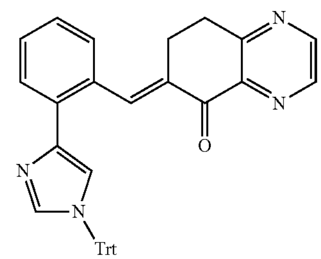

To a solution of 2-(1-trityl-1H-imidazol-4-yl)benzaldehyde (2.4 g, 5.79 mmol) and 7,8-dihydroquinoxalin-5(6H)-one (944 mg, 6.37 mmol) in ethanol (50 mL) was added calcium hydroxide (643 mg, 8.68 mmol). The mixture was stirred at 100° C. 16 hrs. The mixture was cooled to room temperature and water (50 mL) was added to quench the reaction. The aqueous phase was extracted with DCM (3×30 mL) and the organic phase was combined, dried over anhydrous $Na_2SO_4$, and concentrated. The desired product was separated by CombiFlash and was eluted with EtOAc: Hex=90:10: LCMS (ESI, m/z): 545.3 $[M+H]^+$.

Step 2:

6-(5H-imidazo[5,1-a]isoindol-5-yl)-7,8-dihydroquinoxalin-5(6H)-one

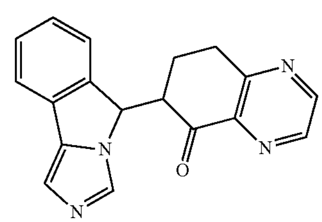 [SMILES: O=C1c2nccnc2CCC1C1c2ccccc2-c2cncn21]

(E)-6-(2-(1-trityl-1H-imidazol-4-yl)benzylidene)-7,8-dihydroquinoxalin-5(6H)-one (1.8 g, 3.30 mmol) was stirred in methanol (16 mL) and acetic acid (4 mL) at 90° C. for 2 h. After cooling to room temperature, the solvent was removed under reduced pressure and saturated $NaHCO_3$ (50 mL) was added to the residue followed by DCM (20 mL). The organic layer was collected and the aqueous layer was extracted with DCM (3×50 mL). The combined organic layers were dried over $Na_2SO_4$ and the solvent evaporated under reduced pressure to afford the crude product which was purified by using CombiFlash and was eluted by DCM: MeOH=92:8: LCMS (ESI, m/z): 303.1 $[M+H]^+$.

Step 3:

(5R)-6-(5H-imidazo[5,1-a]isoindol-5-yl)-5,6,7,8-tetrahydroquinoxalin-5-ol

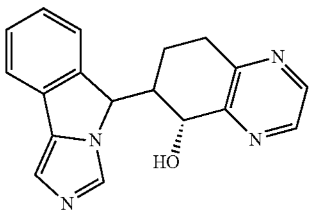 [SMILES: O[C@H]1c2nccnc2CCC1C1c2ccccc2-c2cncn21]

To a 6-(5H-imidazo[5,1-a]isoindol-5-yl)-7,8-dihydroquinoxalin-5(6H)-one (200 mg, 0.66 mmol) in anhydrous THF (10 mL) suspension was added L-selectride THE solution (1.32 mL, 1.32 mmol) dropwise at −78° C. and the reaction was warmed to −10° C. and kept at 0° C. for another 5 min. TLC indicated fully consumption of starting material. The reaction was quenched with methanol (5 mL) and the mixture was poured into saturated ammonium chloride solution (20 mL) was added. The aqueous layer was extracted with 20% 2,2,2-trifluoroethanol in DCM (3×20 mL). The combined organic extract was dried over ($Na_2SO_4$) and concentrated under reduced pressure to afford the crude product. The product was separated by CombiFlash and was eluted with DCM:MeOH=96:4: LCMS (ESI, m/z): 305.3 $[M+H]^+$.

Step 4:

(5S)-6-(5H-imidazo[5,1-a]isoindol-5-yl)-5,6,7,8-tetrahydroquinoxalin-5-yl 4-nitrobenzoate

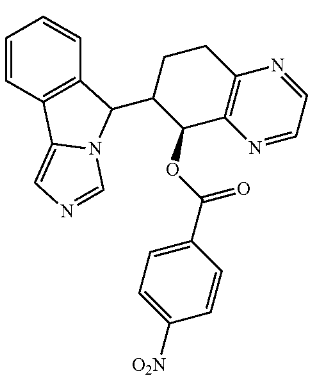 [SMILES: O=C(O[C@@H]1c2nccnc2CCC1C1c2ccccc2-c2cncn21)c1ccc([N+](=O)[O-])cc1]

Under nitrogen, a solution of (5R)-6-(5H-imidazo[5,1-a]isoindol-5-yl)-5,6,7,8-tetrahydroquinoxalin-5-ol (270 mg, 0.89 mmol), 4-nitrobenzoic acid (222 mg, 1.33 mmol) in THF (10 mL) was added n-$Bu_3P$ (12 mL, 4.44 mmol, 10% in hexane) at 0° C. This was followed by the addition of DBAD (5.8 mL, 4.44 mmol, 20% in toluene) at 0° C. The resulting solution was stirred for 2 h at room temperature. The resulting solution was diluted with DCM (20 mL) and then quenched by the addition of water (20 mL). The resulting solution was extracted with 20% 2,2,2,-trifluoroethanol in dichloromethane (3×20 mL) and the organic layers combined and dried over anhydrous sodium sulfate and concentrated under vacuum. The desired product was separated by CombiFlash and was eluted with DCM:MeOH=95:5: LCMS (ESI, m/z): 454.2 $[M+H]^+$.

Step 5:

(5S,6S)-6-((S)-5H-imidazo[5,1-a]isoindol-5-yl)-5,6,7,8-tetrahydroquinoxalin-5-ol (5R,6R)-6-((R)-5H-imidazo[5,1-a]isoindol-5-yl)-5,6,7,8-tetrahydroquinoxalin-5-ol 123a

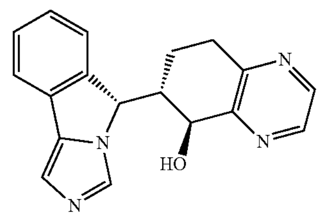

123b

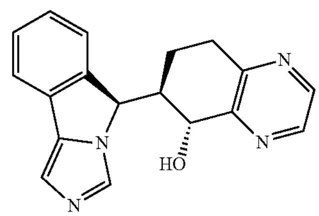

A solution of (5S,6S)-6-((S)-5H-imidazo[5,1-a]isoindol-5-yl)-5,6,7,8-tetrahydroquinoxalin-5-yl 4-nitrobenzoate (135 mg, 0.3 mmol) in THF (3 mL) and water (1 mL) was added $LiOH \cdot H_2O$ (187 mg, 4.47 mmol). The resulting solution was stirred for 2 h at room temperature. LC-MS indicated the consumption of the starting material. The resulting solution was diluted with water (20 mL). The resulting solution was extracted with 20% 2,2,2,-trifluoroethanol in dichloromethane (3×20 mL) and the organic layers combined and dried over anhydrous sodium sulfate. The desired product was separated by CombiFlash and was eluted with DCM:MeOH=95:5. The final products were further isolated by chiral separation to afford 2 isomers and the stereochemistry of each isomer was arbitrarily assigned.

Example 123a: (5S,6S)-6-((S)-5H-imidazo[5,1-a]isoindol-5-yl)-5,6,7,8-tetrahydroquinoxalin-5-ol: LCMS (ESI, m/z): 305.2 $[M+H]^+$; $^1$HNMR (400 MHz, DMSO-$d_6$) δ 8.55 (dd, J=2.5, 0.9 Hz, 1H), 8.45 (dd, J=2.5, 0.8 Hz, 1H), 7.94 (t, J=0.6 Hz, 1H), 7.65 (dt, J=7.5, 1.0 Hz, 1H), 7.55-7.49 (m, 1H), 7.46-7.39 (m, 1H), 7.32 (td, J=7.5, 1.1 Hz, 1H), 7.19 (s, 1H), 6.10 (d, J=5.5 Hz, 1H), 5.82-5.78 (m, 1H), 5.01 (dd, J=10.7, 5.4 Hz, 1H), 2.85-2.65 (m, 2H), 2.59 (tdd, J=10.7, 4.1, 2.2 Hz, 1H), 0.98 (ddd, J=13.5, 8.5, 3.3 Hz, 2H).

Example 123b: (5R,6R)-6-((R)-5H-imidazo[5,1-a]isoindol-5-yl)-5,6,7,8-tetrahydroquinoxalin-5-ol: LCMS (ESI, m/z): 305.2 $[M+H]^+$; $^1$HNMR (400 MHz, DMSO-$d_6$) δ 8.55 (dd, J=2.5, 0.9 Hz, 1H), 8.45 (dd, J=2.5, 0.8 Hz, 1H), 7.94 (d, J=0.6 Hz, 1H), 7.64 (dt, J=7.6, 0.9 Hz, 1H), 7.55-7.48 (m, 1H), 7.46-7.39 (m, 1H), 7.32 (td, J=7.5, 1.2 Hz, 1H), 7.19 (s, 1H), 6.10 (d, J=5.5 Hz, 1H), 5.82-5.77 (m, 1H), 5.00 (dd, J=10.8, 5.3 Hz, 1H), 2.85-2.65 (m, 2H), 2.64-2.54 (m, 1H), 1.04-0.94 (m, 2H).

Example 124: 6-(5H-imidazo[5,1-a]isoindol-5-yl)-2-methyl-5,6,7,8-tetrahydroquinazolin-5-ol

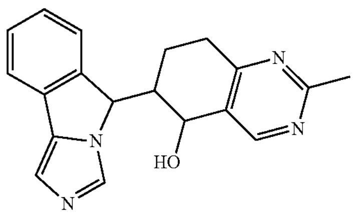 [SMILES: Cc1ncc2c(n1)CCC(C1c3ccccc3-c3cncn31)C2O]

(5S,6S)-6-((S)-5H-imidazo[5,1-a]isoindol-5-yl)-2-methyl-5,6,7,8-tetrahydroquinazolin-5-ol (5R,6R)-6-((R)-5H-imidazo[5,1-a]isoindol-5-yl)-2-methyl-5,6,7,8-tetrahydroquinazolin-5-ol 124a

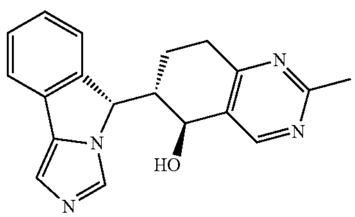

124b

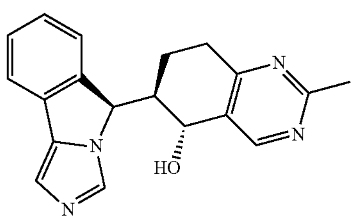

The title compound was synthesized by the same method of examples 096 and 169. The product was isolated by chiral separation to afford 2 isomers as white solid. The stereochemistry of each isomer was arbitrarily assigned.

Example 124a: (5S,6S)-6-((S)-5H-imidazo[5,1-a]isoindol-5-yl)-2-methyl-5,6,7,8-tetrahydroquinazolin-5-ol: LCMS (ESI, m/z): 319.4 $[M+H]^+$; $^1$H NMR (400 MHz, DMSO-$d_6$) δ 8.35 (ddd, J=4.7, 1.8, 0.7 Hz, 1H), 8.01 (s, 1H), 8.00-7.97 (m, 1H), 7.53 (ddd, J=9.6, 6.4, 3.7 Hz, 2H), 7.27 (dd, J=7.8, 4.7 Hz, 1H), 7.23 (s, 1H), 7.14 (ddd, J=9.6, 8.4, 2.5 Hz, 1H), 6.21 (d, J=7.5 Hz, 1H), 5.80 (s, 1H), 4.97 (dd, J=10.6, 7.6 Hz, 1H), 2.68 (dd, J=8.8, 4.0 Hz, 2H), 2.47-2.38 (m, 1H), 1.02-0.82 (m, 2H).

Example 124b: (5R,6R)-6-((R)-5H-imidazo[5,1-a]isoindol-5-yl)-2-methyl-5,6,7,8-tetrahydroquinazolin-5-ol: LCMS (ESI, m/z): 319.4 $[M+H]^+$; $^1$H NMR is the same as Example 124a.

Example 125: 5-(5H-imidazo[5,1-a]isoindol-5-yl)-4,5,6,7-tetrahydrobenzo[d]thiazol-4-ol

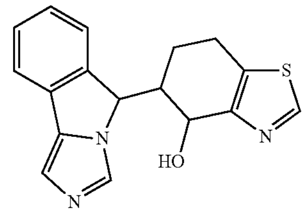 [SMILES: OC1c2ncsc2CCC1C1c2ccccc2-c2cncn21]

(4R,5R)-5-((R)-5H-imidazo[5,1-a]isoindol-5-yl)-4,5,6,7-tetrahydrobenzo[d]thiazol-4-ol (4S,5S)-5-((S)-5H-imidazo[5,1-a]isoindol-5-yl)-4,5,6,7-tetrahydrobenzo[d]thiazol-4-ol Step 1:

(E)-5-(2-(1-trityl-1H-imidazol-4-yl)benzylidene)-6,7-dihydrobenzo[d]thiazol-4(5H)-one

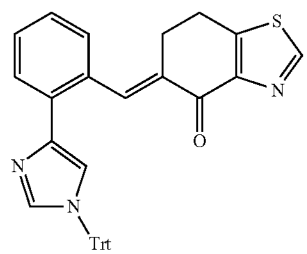

To a solution of 2-(1-trityl-1H-imidazol-4-yl)benzaldehyde (2.25 g, 5.43 mmol) and 6,7-dihydrobenzo[d]thiazol-4(5H)-one (915 mg, 5.97 mmol) in methanol (30 mL) was added pyrrolidine (0.49 mL, 5.97 mmol). The mixture was stirred at 90° C. 24 hrs. The mixture was cooled to room temperature and water (30 mL) was added to quench the reaction. The aqueous phase was extracted with DCM (3×30 mL) and the organic phase was combined, dried over anhydrous $Na_2SO_4$, and concentrated. The desired product was separated by CombiFlash and was eluted with EtOAc: Hex=60:40: LCMS (ESI, m/z): 550.4 $[M+H]^+$.

Step 2:

5-(5H-imidazo[5,1-a]isoindol-5-yl)-6,7-dihydrobenzo[d]thiazol-4(5H)-one

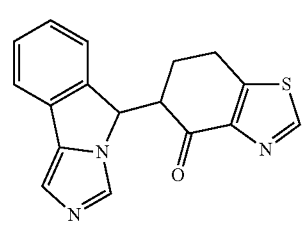 [SMILES: O=C1c2ncsc2CCC1C1c2ccccc2-c2cncn21]

(E)-5-(2-(1-trityl-1H-imidazol-4-yl)benzylidene)-6,7-dihydrobenzo[d]thiazol-4(5H)-one (2.41 g, 4.38 mmol) was stirred in methanol (40 mL) and acetic acid (10 mL) at 90° C. for 2 h. After cooling to room temperature, the solvent was removed under reduced pressure and saturated $NaHCO_3$ (50 mL) was added to the residue followed by DCM (20 mL). The organic layer was collected and the aqueous layer was extracted with DCM (3×50 mL). The combined organic layers were dried over $Na_2SO_4$ and the solvent evaporated under reduced pressure to afford the crude product which was purified by using CombiFlash and was eluted by DCM: MeOH=96:4: LCMS (ESI, m/z): 308.2 [M+H]$^+$.

Step 3:

(4R)-5-(5H-imidazo[5,1-a]isoindol-5-yl)-4,5,6,7-tetrahydrobenzo[d]thiazol-4-ol

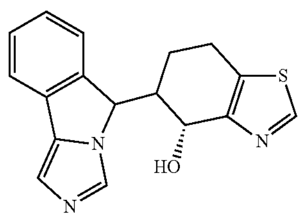 [SMILES: O[C@H]1c2ncsc2CCC1C1c2ccccc2-c2cncn21]

To a 5-(5H-imidazo[5,1-a]isoindol-5-yl)-6,7-dihydrobenzo[d]thiazol-4(5H)-one (1.08 g, 3.51 mmol) in anhydrous THF (15 mL) was added L-Selectride solution (5.3 mL, 5.27 mmol) in THE dropwise at −78° C. and the solution was stirred at −78° C. for 1 hr. The reaction was quenched with methanol (5 mL) and the mixture was poured into saturated ammonium chloride solution (20 mL). The aqueous layer was extracted with 20% 2,2,2-trifluoroethanol in DCM (3×20 mL). The combined organic extract was dried over ($Na_2SO_4$) and concentrated under reduced pressure to afford the crude product. The crude was purified by CombiFlash and the product was eluted with DCM:MeOH=94:6: LCMS (ESI, m/z): 310.2 [M+H]$^+$.

Step 4:

(4S)-5-(5H-imidazo[5,1-a]isoindol-5-yl)-4,5,6,7-tetrahydrobenzo[d]thiazol-4-yl 4-nitrobenzoate

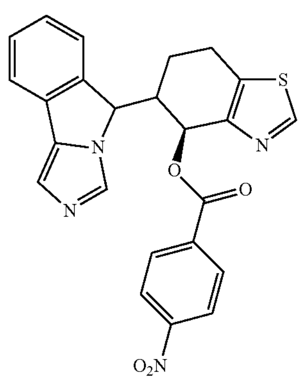 [SMILES: O=C(O[C@@H]1c2ncsc2CCC1C1c2ccccc2-c2cncn21)c1ccc([N+](=O)[O-])cc1]

Under nitrogen, to a solution of (4R)-5-(5H-imidazo[5,1-a]isoindol-5-yl)-4,5,6,7-tetrahydrobenzo[d]thiazol-4-ol (270 mg, 0.89 mmol), 4-nitrobenzoic acid (222 mg, 1.33 mmol) in THF (10 mL) was added n-$Bu_3P$ (12 mL, 4.44 mmol, 10% in hexane) at 0° C. This was followed by the addition of DBAD (5.8 mL, 4.44 mmol, 20% in toluene) at 0° C. The resulting solution was stirred for 2 h at room temperature. The reaction was quenched by the addition of water (20 mL). The resulting solution was extracted with 20% 2,2,2,-trifluoroethanol in dichloromethane (3×20 mL) and the organic layers combined and dried over anhydrous sodium sulfate and concentrated under vacuum. The desired product was separated by CombiFlash and was eluted with DCM:MeOH=95:5: LCMS (ESI, m/z): 459.4 [M+H]$^+$.

Step 5:

(4R,5R)-5-((R)-5H-imidazo[5,1-a]isoindol-5-yl)-4,5,6,7-tetrahydrobenzo[d]thiazol-4-ol (4S,5S)-5-((S)-5H-imidazo[5,1-a]isoindol-5-yl)-4,5,6,7-tetrahydrobenzo[d]thiazol-4-ol 125a

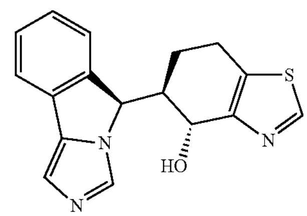

125b

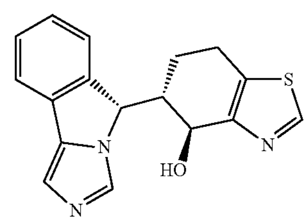

A solution of (4S)-5-(5H-imidazo[5,1-a]isoindol-5-yl)-4,5,6,7-tetrahydrobenzo[d]thiazol-4-yl 4-nitrobenzoate (1.17 g, 2.55 mmol) in THF (15 mL) and water (5 mL) was added LiOH·$H_2O$ (1.07 g, 25.52 mmol). The resulting solution was stirred for 2 h at room temperature. LC-MS indicated the consumption of the starting material. The resulting solution was diluted with water (20 mL). The resulting solution was extracted with 20% 2,2,2,-trifluoroethanol in dichloromethane (3×20 mL) and the organic layers combined and dried over anhydrous sodium sulfate. The desired product was separated by CombiFlash and was eluted with DCM: MeOH=95:5. The final products were further isolated by chiral separation to afford 2 isomers and the stereochemistry of each isomer was arbitrarily assigned.

Example 125a: (4R,5R)-5-((R)-5H-imidazo[5,1-a]isoindol-5-yl)-4,5,6,7-tetrahydrobenzo[d]thiazol-4-ol: LCMS (ESI, m/z): 310.1 [M+H]$^+$; $^1$HNMR (400 MHz, DMSO-$d_6$) δ 8.94 (d, J=0.6 Hz, 1H), 7.94 (s, 1H), 7.63 (dt, J=7.7, 1.0 Hz, 1H), 7.49 (dq, J=7.6, 1.0 Hz, 1H), 7.46-7.39 (m, 1H), 7.32 (td, J=7.5, 1.2 Hz, 1H), 7.17 (s, 1H), 5.91 (d, J=6.6 Hz, 1H), 5.77 (t, J=1.4 Hz, 1H), 5.06 (t, J=8.2 Hz, 1H), 2.69-2.55 (m, 2H), 2.48-2.42 (m, 1H), 1.03-0.86 (m, 2H).

Example 125b: (4S,5S)-5-((S)-5H-imidazo[5,1-a]isoindol-5-yl)-4,5,6,7-tetrahydrobenzo[d]thiazol-4-ol: LCMS (ESI, m/z): 310.1 [M+H]$^+$; $^1$HNMR (400 MHz, DMSO-$d_6$) δ 8.94 (d, J=0.6 Hz, 1H), 7.94 (s, 1H), 7.63 (dt, J=7.7, 1.0 Hz, 1H), 7.49 (dq, J=7.6, 1.0 Hz, 1H), 7.46-7.39 (m, 1H), 7.32 (td, J=7.5, 1.2 Hz, 1H), 7.17 (s, 1H), 5.91 (d, J=6.6 Hz, 1H), 5.77 (t, J=1.4 Hz, 1H), 5.06 (t, J=8.2 Hz, 1H), 2.69-2.55 (m, 2H), 2.48-2.42 (m, 1H), 1.03-0.86 (m, 2H).

Example 126: 7-(5H-imidazo[5,1-a]isoindol-5-yl)-5,6,7,8-tetrahydroquinolin-8-ol

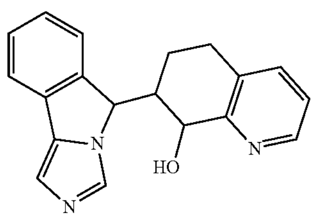 [SMILES: OC1c2ncccc2CCC1C1c2ccccc2-c2cncn21]

(7S,8S)-7-((S)-5H-imidazo[5,1-a]isoindol-5-yl)-5,6,7,8-tetrahydroquinolin-8-ol (7R,8R)-7-((R)-5H-imidazo[5,1-a]isoindol-5-yl)-5,6,7,8-tetrahydroquinolin-8-ol Step 1:

(E)-7-(2-(1-trityl-1H-imidazol-4-yl)benzylidene)-6,7-dihydroquinolin-8(5H)-one

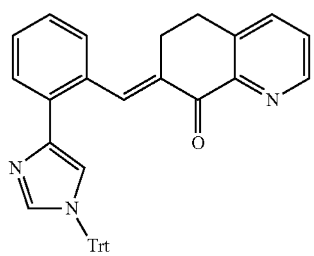

To a solution of 2-(1-trityl-1H-imidazol-4-yl)benzaldehyde (2.5 g, 6.03 mmol) and 6,7-dihydroquinolin-8(5H)-one (1.07 g, 7.24 mmol) in ethanol (20 mL) was added sodium ethoxide ethanol solution (2.7 mL, 7.24 mmol). The mixture was stirred at 90° C. for 1 hr. The mixture was cooled to room temperature and water (50 mL) was added to quench the reaction. The aqueous phase was extracted with DCM (3×30 mL) and the organic phase was combined, dried over anhydrous $Na_2SO_4$, and concentrated. The desired product was separated by CombiFlash and was eluted with EtOAc:Hex=80:20: LCMS (ESI, m/z): 544.3 $[M+H]^+$.

Step 2:

7-(5H-imidazo[5,1-a]isoindol-5-yl)-6,7-dihydroquinolin-8(5H)-one

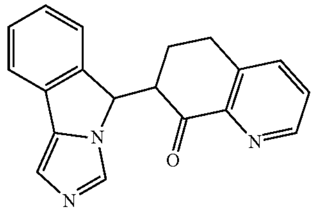 [SMILES: O=C1c2ncccc2CCC1C1c2ccccc2-c2cncn21]

(E)-7-(2-(1-trityl-1H-imidazol-4-yl)benzylidene)-6,7-dihydroquinolin-8(5H)-one (2.05 g, 3.77 mmol) was stirred in methanol (40 mL) and acetic acid (10 mL) at 90° C. for 2 h. After cooling to room temperature, the solvent was removed under reduced pressure and saturated $NaHCO_3$ (50 mL) was added to the residue followed by DCM (20 mL). The organic layer was collected and the aqueous layer was extracted with DCM (3×50 mL). The combined organic layers were dried over $Na_2SO_4$ and the solvent evaporated under reduced pressure to afford the crude product which was purified by using CombiFlash and was eluted by DCM:MeOH=95:5: LCMS (ESI, m/z): 302.2 $[M+H]^+$.

Step 3:

(8R)-7-(5H-imidazo[5,1-a]isoindol-5-yl)-5,6,7,8-tetrahydroquinolin-8-ol

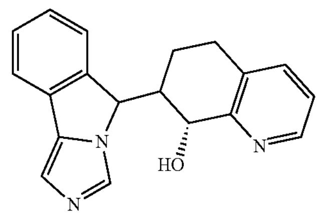 [SMILES: O[C@H]1c2ncccc2CCC1C1c2ccccc2-c2cncn21]

To a 7-(5H-imidazo[5,1-a]isoindol-5-yl)-6,7-dihydroquinolin-8(5H)-one (810 mg, 2.69 mmol) in anhydrous THF (10 mL) suspension was added L-selectride THF solution (1.32 mL, 1.32 mmol) dropwise at −78° C. and the reaction was warmed to −10° C. and kept at 0° C. for another 5 min. TLC indicated fully consumption of starting material. The reaction was quenched with methanol (5 mL) and the mixture was poured into saturated ammonium chloride solution (20 mL) was added. The aqueous layer was extracted with 20% 2,2,2-trifluoroethanol in DCM (3×20 mL). The combined organic extract was dried over ($Na_2SO_4$) and concentrated under reduced pressure to afford the crude product. The product was separated by CombiFlash and was eluted with DCM:MeOH=96:4: LCMS (ESI, m/z): 304.1 $[M+H]^+$.

Step 4:

(8S)-7-(5H-imidazo[5,1-a]isoindol-5-yl)-5,6,7,8-tetrahydroquinolin-8-yl 4-nitrobenzoate

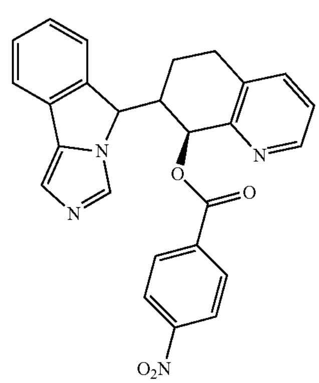 [SMILES: O=C(O[C@@H]1c2ncccc2CCC1C1c2ccccc2-c2cncn21)c1ccc([N+](=O)[O-])cc1]

Under nitrogen, to a solution of (8R)-7-(5H-imidazo[5,1-a]isoindol-5-yl)-5,6,7,8-tetrahydroquinolin-8-ol (200 mg, 0.66 mmol), 4-nitrobenzoic acid (165 mg, 0.99 mmol) in THF (10 mL) was added $n\text{-}Bu_3P$ (5.34 mL, 1.98 mmol, 10% in hexane) at 0° C. This was followed by the addition of DBAD (2.59 mL, 1.98 mmol, 20% in toluene) at 0° C. The resulting solution was stirred for 2 h at room temperature. The resulting solution was diluted with DCM (20 mL) and then quenched by the addition of water (20 mL). The resulting solution was extracted with 2 dichloromethane (3×20 mL) and the organic layers combined and dried over anhydrous sodium sulfate and concentrated under vacuum. The desired product was separated by CombiFlash and was eluted with DCM:MeOH=95:5: LCMS (ESI, m/z): 453.2 $[M+H]^+$.

Step 5:

(7S,8S)-7-((S)-5H-imidazo[5,1-a]isoindol-5-yl)-5,6,7,8-tetrahydroquinolin-8-ol (7R,8R)-7-((R)-5H-imidazo[5,1-a]isoindol-5-yl)-5,6,7,8-tetrahydroquinolin-8-ol 126a

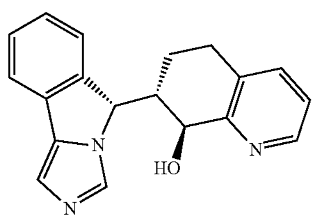

126b

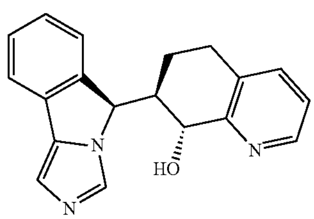

A solution of (8S)-7-(5H-imidazo[5,1-a]isoindol-5-yl)-5,6,7,8-tetrahydroquinolin-8-yl 4-nitrobenzoate (298 mg, 0.66 mmol, calculated based on step 4) in THF (3 mL) and water (1 mL) was added $LiOH{\cdot}H_2O$ (276 mg, 6.59 mmol). The resulting solution was stirred for 2 h at room temperature. LC-MS indicated the consumption of the starting material. The resulting solution was diluted with water (20 mL). The resulting solution was extracted with dichloromethane (3×20 mL) and the organic layers combined and dried over anhydrous sodium sulfate. The desired product was separated by CombiFlash and was eluted with DCM:MeOH=95:5. The final products were further isolated by chiral separation to afford 2 isomers and the stereochemistry of each isomer was arbitrarily assigned.

Example 126a: (7S,8S)-7-((S)-5H-imidazo[5,1-a]isoindol-5-yl)-5,6,7,8-tetrahydroquinolin-8-ol: LCMS (ESI, m/z): 304.1 $[M+H]^+$; $^1$HNMR (400 MHz, DMSO-$d_6$) δ 8.48 (dd, J=4.7, 1.6 Hz, 1H), 7.93 (s, 1H), 7.64 (dt, J=7.5, 0.9 Hz, 1H), 7.52 (dq, J=7.6, 1.0 Hz, 1H), 7.47 (ddd, J=7.7, 1.7, 0.9 Hz, 1H), 7.45-7.39 (m, 1H), 7.32 (td, J=7.5, 1.1 Hz, 1H), 7.23 (ddd, J=7.7, 4.7, 0.7 Hz, 1H), 7.18 (s, 1H), 5.80 (d, J=2.1 Hz, 1H), 5.72 (d, J=4.1 Hz, 1H), 4.91 (dd, J=10.6, 4.0 Hz, 1H), 2.70-2.58 (m, 2H), 2.58-2.52 (m, 1H), 0.95 (dtd, J=9.7, 6.8, 6.3, 3.5 Hz, 1H), 0.91-0.80 (m, 1H).

Example 126b: (7R,8R)-7-((R)-5H-imidazo[5,1-a]isoindol-5-yl)-5,6,7,8-tetrahydroquinolin-8-ol: LCMS (ESI, m/z): 304.1 $[M+H]^+$; $^1$HNMR (400 MHz, DMSO-$d_6$) δ 8.48 (dd, J=4.7, 1.7 Hz, 1H), 7.93 (t, J=0.6 Hz, 1H), 7.64 (dt, J=7.5, 1.0 Hz, 1H), 7.52 (dq, J=7.6, 1.0 Hz, 1H), 7.47 (ddd, J=7.7, 1.8, 0.9 Hz, 1H), 7.45-7.38 (m, 1H), 7.32 (td, J=7.5, 1.2 Hz, 1H), 7.23 (ddd, J=7.7, 4.7, 0.7 Hz, 1H), 7.18 (s, 1H), 5.85-5.77 (m, 1H), 5.71 (d, J=4.1 Hz, 1H), 4.91 (dd, J=10.5, 4.0 Hz, 1H), 2.71-2.59 (m, 2H), 2.59-2.54 (m, 1H), 1.01-0.79 (m, 2H).

Example 127: tert-Butyl 3-hydroxy-3-(5H-imidazo[5,1-a]isoindol-5-yl)piperidine-1-carboxylate

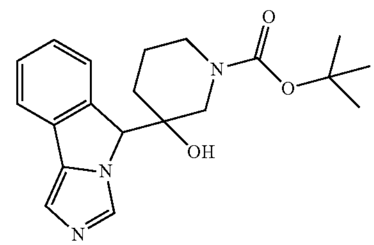 [SMILES: CC(C)(C)OC(=O)N1CCCC(O)(C2c3ccccc3-c3cncn32)C1]

tert-Butyl (R)-3-hydroxy-3-((R)-5H-imidazo[5,1-a]isoindol-5-yl)piperidine-1-carboxylate tert-Butyl (R)-3-hydroxy-3-((S)-5H-imidazo[5,1-a]isoindol-5-yl)piperidine-1-carboxylate tert-Butyl(S)-3-hydroxy-3-((R)-5H-imidazo[5,1-a]isoindol-5-yl)piperidine-1-carboxylate 127a

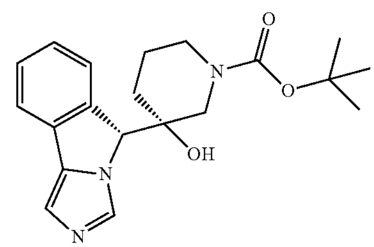

127b

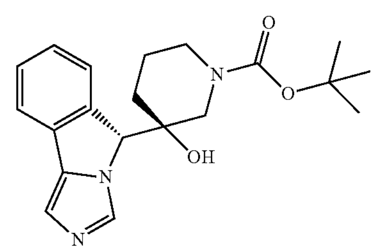

127c

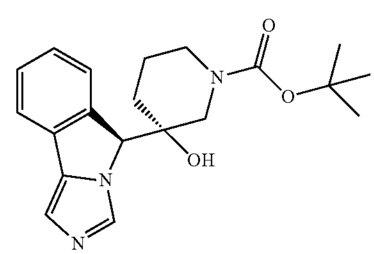

To a solution of 5H-imidazo[5,1-a]isoindole (1.00 g, 6.40 mmol) in anhydrous THF (50 mL) at −78° C. was added n-BuLi (3.20 mL, 7.04 mmol, 2.2 M solution cyclohexane). After stirring for 0.5 at −78° C., a solution of tert-butyl 3-oxopiperidine-1-carboxylate (2.55 g, 12.8 mmol) in THF (8 mL) was added and the reaction was allowed to warm to RT over a period of 2 h and continued stirring overnight (18 h). The reaction was quenched by adding satd. $NH_4Cl$ (50 mL) and the reaction was diluted with water (20 mL), the product was extracted with $CH_2Cl_2$ (3×40 mL). The combined organic extract was dried over $Na_2SO_4$ and concentrated under reduced pressure. The crude was purified by combi-flash using MeOH/DCM (5:95) as eluent. The final products were further isolated by chiral separation to afford 3 isomers and the stereochemistry of each isomer was arbitrarily assigned.

Example 127a: tert-Butyl (R)-3-hydroxy-3-((R)-5H-imidazo[5,1-a]isoindol-5-yl)piperidine-1-carboxylate: LCMS (ESI, m/z): 356.4 $[M+H]^+$; $^1$HNMR (400 MHz, DMSO-$d_6$) δ 7.87 (s, 1H), 7.60 (d, J=7.6 Hz, 2H), 7.43-7.36 (m, 1H), 7.29-7.22 (m, 1H), 7.13 (s, 1H), 5.25 (s, 1H), 5.22 (s, 1H), 3.87-3.68 (m, 2H), 3.04-2.85 (m, 1H), 1.72-1.59 (m, 1H), 1.39 (s, 9H), 1.35-1.25 (m, 1H), 1.21-1.08 (m, 2H).

Example 127b: tert-Butyl (R)-3-hydroxy-3-((S)-5H-imidazo[5,1-a]isoindol-5-yl)piperidine-1-carboxylate: LCMS (ESI, m/z): 356.4 $[M+H]^+$; $^1$HNMR (400 MHz, DMSO-$d_6$) δ 7.89 (s, 1H), 7.61 (dd, J=12.4, 7.7 Hz, 2H), 7.40 (t, J=7.6 Hz, 1H), 7.26 (t, J=7.6 Hz, 1H), 7.14 (s, 1H), 5.22 (s, 2H), 3.85-3.72 (m, 1H), 1.86-1.46 (m, 3H), 1.45-1.38 (m, 1H), 1.34 (s, 9H).

Example 127c: tert-Butyl(S)-3-hydroxy-3-((R)-5H-imidazo[5,1-a]isoindol-5-yl)piperidine-1-carboxylate: LCMS (ESI, m/z): 356.4 $[M+H]^+$; $^1$HNMR (400 MHz, DMSO-$d_6$) δ 7.87 (s, 1H), 7.60 (d, J=7.6 Hz, 2H), 7.43-7.36 (m, 1H), 7.29-7.22 (m, 1H), 7.13 (s, 1H), 5.25 (s, 1H), 5.22 (s, 1H), 3.87-3.68 (m, 2H), 3.04-2.85 (m, 1H), 1.72-1.59 (m, 1H), 1.39 (s, 9H), 1.35-1.25 (m, 1H), 1.21-1.08 (m, 2H).

Example 128: 1-(5H-imidazo[5,1-a]isoindol-5-yl)cycloheptan-1-ol

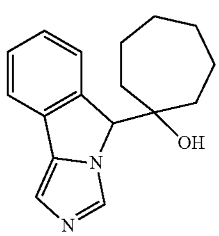 [SMILES: OC1(C2c3ccccc3-c3cncn32)CCCCCC1]

Final product (racemate) is a mixture of the following isomers:

(R)-1-(5H-imidazo[5,1-a]isoindol-5-yl)cycloheptan-1-ol (S)-1-(5H-imidazo[5,1-a]isoindol-5-yl)cycloheptan-1-ol To a solution of 5H-imidazo[5,1-a]isoindole (500 mg, 3.20 mmol) in anhydrous THF (20 mL) at −40° C. was added n-BuLi (1.28 mL, 3.20 mmol, 2.5 M solution in hexanes). After stirring for 1.0 hr at −40° C., cycloheptanone (395 mg, 3.52 mmol) was added and the reaction was allowed to warm to rt over a period of 2 hr and continued stirring overnight (18 hr). The reaction was quenched by adding satd. $NH_4Cl$ (5 mL) and water (15 mL), the product was extracted with $CH_2Cl_2$ (3×30 mL). The combined organic extract was dried over $Na_2SO_4$ and concentrated under reduced pressure, the crude was purified by Combi-Flash to afford 1-(5H-imidazo[5,1-a]isoindol-5-yl)cycloheptan-1-ol as beige solid (187 mg, 22% yield): LCMS (ESI, m/z): 269.21 $[M+H]^+$. $^1$H NMR (Chloroform-d, 400 MHz): δ (ppm) 7.96 (s, 1H), 7.53 (t, J=6.8 Hz, 2H), 7.37 (t, J=7.6 Hz, 1H), 7.22 (td, J=7.6, 1.0 Hz, 1H), 7.15 (s, 1H), 5.30 (s, 1H), 5.10 (s, 1H), 2.11-1.78 (m, 3H), 1.69-1.40 (m, 5H), 1.38-1.14 (m, 3H), 1.14-1.01 (m, 1H).

Example 129: 3-(5H-imidazo[5,1-a]isoindol-5-yl)tetrahydrofuran-3-ol

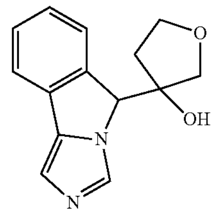 [SMILES: OC1(C2c3ccccc3-c3cncn32)CCOC1]

(S)-3-((R)-5H-imidazo[5,1-a]isoindol-5-yl)tetrahydrofuran-3-ol (R)-3-((R)-5H-imidazo[5,1-a]isoindol-5-yl)tetrahydrofuran-3-ol (S)-3-((S)-5H-imidazo[5,1-a]isoindol-5-yl)tetrahydrofuran-3-ol (R)-3-((S)-5H-imidazo[5,1-a]isoindol-5-yl)tetrahydrofuran-3-ol Step 1:

(S)-3-((R)-5H-imidazo[5,1-a]isoindol-5-yl)tetrahydrofuran-3-ol (R)-3-((R)-5H-imidazo[5,1-a]isoindol-5-yl)tetrahydrofuran-3-ol (S)-3-((S)-5H-imidazo[5,1-a]isoindol-5-yl)tetrahydrofuran-3-ol (R)-3-((S)-5H-imidazo[5,1-a]isoindol-5-yl)tetrahydrofuran-3-ol 129a

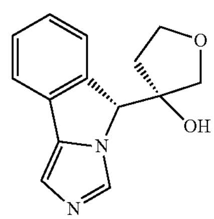

129b

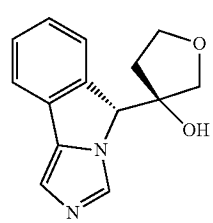

129c

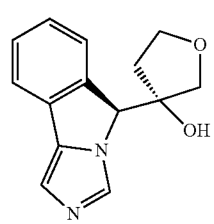

-continued

129d

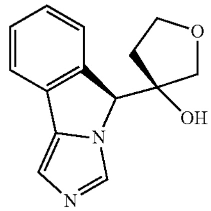

To a solution of 5H-imidazo[5,1-a]isoindole (500 mg, 3.2 mmol) in anhydrous THF (10 mL) was added n-BuLi solution (1.54 mL, 3.84 mmol) at −78° C. and stirred for 1 hr. Dihydrofuran-3(2H)-one (0.37 mL, 4.8 mmol) was added into the reaction mixture drop-wise. The reaction was kept at −78° C. for another 30 min and was warmed up to room temperature. The reaction was kept at room temperature for another 2 hrs and was quenched with saturated $NH_4Cl$ solution (20 mL). The mixture was extracted with DCM (3×20 ml) and the organic phase was combined, dried over $Na_2SO_4$, and concentrated. The product was separated by preparative HPLC. The final products were further isolated by chiral separation to afford 4 isomers and the stereochemistry of each isomer was arbitrarily assigned.

Example 129a: (S)-3-((R)-5H-imidazo[5,1-a]isoindol-5-yl)tetrahydrofuran-3-ol: LCMS (ESI, m/z): 243.1 $[M+H]^+$; $^1$HNMR (400 MHz, DMSO-$d_6$) δ 7.84 (t, J=0.6 Hz, 1H), 7.61-7.54 (m, 2H), 7.42-7.36 (m, 1H), 7.24 (d, J=1.2 Hz, 1H), 7.12 (s, 1H), 5.46 (s, 1H), 5.45 (s, 1H), 3.96 (d, J=9.3 Hz, 1H), 3.79 (ddd, J=9.1, 8.1, 6.7 Hz, 1H), 3.71-3.62 (m, 2H), 1.91 (dt, J=12.7, 8.9 Hz, 1H), 1.82-1.72 (m, 1H).

Example 129b: (R)-3-((R)-5H-imidazo[5,1-a]isoindol-5-yl)tetrahydrofuran-3-ol: LCMS (ESI, m/z): 243.1 $[M+H]^+$; $^1$HNMR (400 MHz, DMSO-$d_6$) δ 7.87 (d, J=0.7 Hz, 1H), 7.58 (s, 1H), 7.50 (d, J=0.9 Hz, 1H), 7.39 (s, 1H), 7.24 (d, J=1.2 Hz, 1H), 7.12 (s, 1H), 5.46 (s, 1H), 5.40 (s, 1H), 3.85-3.76 (m, 2H), 3.73 (td, J=8.4, 3.2 Hz, 1H), 3.56 (dd, J=9.3, 0.7 Hz, 1H), 2.09 (ddd, J=12.7, 9.4, 8.6 Hz, 1H), 1.98-1.89 (m, 1H).

Example 129c: (S)-3-((S)-5H-imidazo[5,1-a]isoindol-5-yl)tetrahydrofuran-3-ol: LCMS (ESI, m/z): 243.1 $[M+H]^+$; $^1$HNMR (400 MHz, DMSO-$d_6$) δ 7.87 (t, J=0.7 Hz, 1H), 7.59 (dt, J=7.6, 1.0 Hz, 1H), 7.51 (dq, J=7.7, 0.9 Hz, 1H), 7.39 (tdd, J=7.5, 1.1, 0.6 Hz, 1H), 7.24 (td, J=7.6, 1.2 Hz, 1H), 7.12 (s, 1H), 5.47 (s, 1H), 5.40 (s, 1H), 3.86-3.76 (m, 2H), 3.73 (td, J=8.4, 3.2 Hz, 1H), 3.56 (dd, J=9.2, 0.7 Hz, 1H), 2.09 (ddd, J=12.7, 9.4, 8.6 Hz, 1H), 1.94 (dddd, J=12.8, 6.5, 3.3, 0.8 Hz, 1H).

Example 129d: (R)-3-((S)-5H-imidazo[5,1-a]isoindol-5-yl)tetrahydrofuran-3-ol: LCMS (ESI, m/z): 243.1 $[M+H]^+$; $^1$HNMR (400 MHz, DMSO-$d_6$) δ 7.84 (t, J=0.6 Hz, 1H), 7.62-7.54 (m, 2H), 7.42-7.36 (m, 1H), 7.24 (td, J=7.6, 1.2 Hz, 1H), 7.12 (s, 1H), 5.46 (s, 1H), 5.45 (s, 1H), 3.96 (d, J=9.3 Hz, 1H), 3.79 (ddd, J=9.2, 8.1, 6.7 Hz, 1H), 3.71-3.62 (m, 2H), 1.91 (dt, J=12.7, 8.9 Hz, 1H), 1.80-1.72 (m, 1H).

Example 130: 5-(5H-imidazo[5,1-a]isoindol-5-yl)-2-methyl-4,5,6,7-tetrahydro-2H-indazol-4-ol

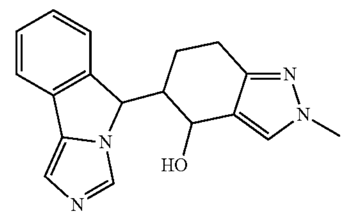 [SMILES: Cn1cc2c(n1)CCC(C1c3ccccc3-c3cncn31)C2O]

(4R,5S)-5-((S)-5H-imidazo[5,1-a]isoindol-5-yl)-2-methyl-4,5,6,7-tetrahydro-2H-indazol-4-ol
(4S,5S)-5-((S)-5H-imidazo[5,1-a]isoindol-5-yl)-2-methyl-4,5,6,7-tetrahydro-2H-indazol-4-ol
(4R,5R)-5-((S)-5H-imidazo[5,1-a]isoindol-5-yl)-2-methyl-4,5,6,7-tetrahydro-2H-indazol-4-ol
(4S,5R)-5-((S)-5H-imidazo[5,1-a]isoindol-5-yl)-2-methyl-4,5,6,7-tetrahydro-2H-indazol-4-ol
(4R,5S)-5-((R)-5H-imidazo[5,1-a]isoindol-5-yl)-2-methyl-4,5,6,7-tetrahydro-2H-indazol-4-ol
(4S,5S)-5-((R)-5H-imidazo[5,1-a]isoindol-5-yl)-2-methyl-4,5,6,7-tetrahydro-2H-indazol-4-ol
(4R,5R)-5-((R)-5H-imidazo[5,1-a]isoindol-5-yl)-2-methyl-4,5,6,7-tetrahydro-2H-indazol-4-ol
(4S,5R)-5-((R)-5H-imidazo[5,1-a]isoindol-5-yl)-2-methyl-4,5,6,7-tetrahydro-2H-indazol-4-ol The title compound was synthesized by the same method of example 88.

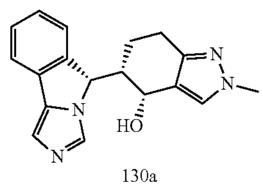
130a

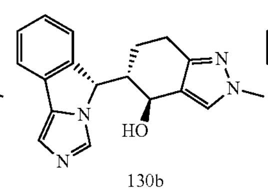
130b

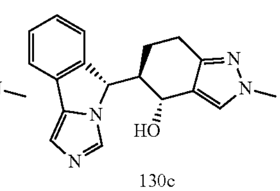
130c

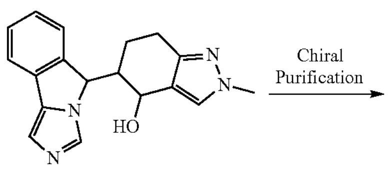

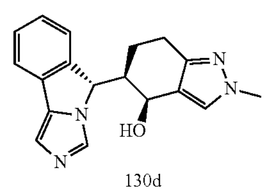
130d

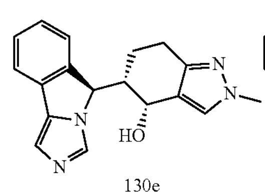
130e

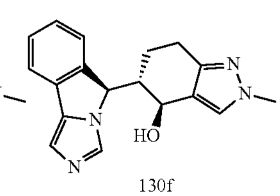
130f

-continued

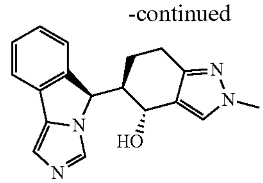

130g

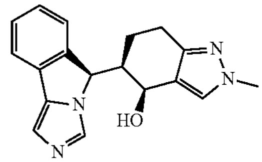

130h

The configurations of the isomers were assigned arbitrarily.

Example 130a: (4R,5S)-5-((S)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.89 (s, 1H), 7.65-7.61 (m, 1H), 7.59-7.53 (m, 2H), 7.41-7.36 (m, 1H), 7.25 (td, J=7.6, 1.2 Hz, 1H), 7.16 (s, 1H), 5.74 (d, J=2.9 Hz, 1H), 5.63 (d, J=6.6 Hz, 1H), 4.90 (dd, J=10.1, 6.6 Hz, 1H), 3.74 (s, 3H), 2.42-2.18 (m, 3H), 0.83 (m, 2H). 130a and 130h are enantiomers.

Example 130b: (4S,5S)-5-((S)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.99 (s, 1H), 7.59 (dt, J=10.7, 2.8 Hz, 3H), 7.38 (t, J=7.6 Hz, 1H), 7.28 (t, J=7.7 Hz, 1H), 7.11 (d, J=2.3 Hz, 1H), 5.46 (s, 1H), 5.41 (dd, J=5.9, 2.3 Hz, 1H), 5.02 (d, J=4.4 Hz, 1H), 3.76 (d, J=2.5 Hz, 3H), 2.34 (d, J=12.2 Hz, 1H), 2.21 (t, J=12.9 Hz, 1H), 1.48 (dd, J=12.8, 5.0 Hz, 1H), 0.89 (d, J=13.5 Hz, 1H). 130b and 130g are enantiomers.

Example 130c: (4R,5R)-5-((S)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.96 (s, 1H), 7.77 (d, J=7.7 Hz, 1H), 7.61 (d, J=7.5 Hz, 1H), 7.54 (s, 1H), 7.37 (dd, J=7.8, 6.8 Hz, 1H), 7.24 (td, J=7.7, 1.0 Hz, 2H), 5.37 (s, 1H), 5.12 (d, J=5.4 Hz, 1H), 4.83 (s, 1H), 3.74 (s, 3H), 2.63 (dd, J=16.0, 4.6 Hz, 1H), 2.39-2.24 (m, 1H), 2.05 (d, J=16.2 Hz, 1H), 1.91 (dq, J=13.6, 8.5 Hz, 1H), 1.65 (s, 1H). 130c and 130f are enantiomers.

Example 130d: (4S,5R)-5-((S)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.93 (s, 1H), 7.62 (dd, J=7.6, 0.9 Hz, 1H), 7.58 (s, 1H), 7.46 (dd, J=7.5, 1.0 Hz, 1H), 7.43-7.38 (m, 1H), 7.31 (td, J=7.5, 1.1 Hz, 1H), 7.17 (s, 1H), 5.74 (d, J=1.6 Hz, 1H), 5.62 (d, J=7.0 Hz, 1H), 4.93 (dd, J=10.1, 7.1 Hz, 1H), 3.75 (s, 3H), 2.42-2.32 (m, 1H), 2.32-2.15 (m, 2H), 0.92-0.83 (m, 1H), 0.76 (qd, J=12.5, 5.6 Hz, 1H). 130d and 130e are enantiomers.

Example 130e: (4R,5S)-5-((R)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.93 (s, 1H), 7.65-7.57 (m, 2H), 7.46 (d, J=7.6 Hz, 1H), 7.41 (t, J=7.4 Hz, 1H), 7.31 (td, J=7.6, 1.1 Hz, 1H), 7.17 (s, 1H), 5.74 (s, 1H), 5.62 (d, J=7.0 Hz, 1H), 4.93 (dd, J=10.1, 7.0 Hz, 1H), 3.75 (s, 3H), 3.29-3.23 (m, 1H), 2.37 (dd, J=16.1, 5.0 Hz, 1H), 2.32-2.15 (m, 2H), 0.92-0.68 (m, 2H). 130d and 130e are enantiomers.

Example 130f: (4S,5S)-5-((R)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.77 (d, J=7.7 Hz, 1H), 7.60 (d, J=7.6 Hz, 1H), 7.54 (s, 1H), 7.37 (td, J=7.5, 1.0 Hz, 1H), 7.24 (td, J=7.6, 1.0 Hz, 2H), 5.37 (s, 1H), 5.12 (d, J=5.5 Hz, 1H), 4.83 (s, 1H), 3.74 (s, 3H), 2.63 (dd, J=16.1, 4.5 Hz, 1H), 2.41-2.26 (m, 1H), 2.03 (s, 1H), 1.92 (tt, J=12.7, 6.3 Hz, 1H), 1.64 (d, J=10.9 Hz, 1H). 130c and 130f are enantiomers.

Example 130g: (4R,5R)-5-((R)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.98 (d, J=0.7 Hz, 1H), 7.62-7.56 (m, 3H), 7.40-7.35 (m, 1H), 7.27 (td, J=7.5, 1.2 Hz, 1H), 7.10 (s, 1H), 5.46 (d, J=1.9 Hz, 1H), 5.41 (dd, J=5.8, 0.5 Hz, 1H), 5.02 (dd, J=5.7, 3.6 Hz, 1H), 3.76 (s, 3H), 2.37-2.30 (m, 1H), 2.27-2.16 (m, 1H), 1.48 (qd, J=12.8, 5.5 Hz, 1H), 0.94-0.83 (m, 1H). 130b and 130g are enantiomers.

Example 130h: (4S,5R)-5-((R)-5H-imidazo[5,1-a]isoindol-5-yl)-2-methyl-4,5,6,7-tetrahydro-2H-indazol-4-ol: LCMS (ESI, m/z): 307.2 $[M+H]^+$; $^1H$ NMR (400 MHz, DMSO-$d_6$) δ 7.91 (s, 1H), 7.64 (d, J=7.5 Hz, 1H), 7.56 (d, J=9.2 Hz, 2H), 7.42-7.36 (m, 1H), 7.25 (td, J=7.5, 1.0 Hz, 2H), 5.72 (s, 1H), 5.63 (d, J=6.6 Hz, 1H), 4.90 (dd, J=9.9, 6.6 Hz, 1H), 3.74 (s, 3H), 2.39-2.24 (m, 3H), 0.82 (m, 2H). 130a and 130h are enantiomers.

Example 131: 1-(5H-imidazo[5,1-a]isoindol-5-yl)-1-(tetrahydro-2H-pyran-4-yl)ethan-1-ol

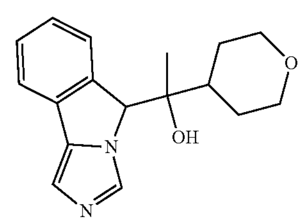 [SMILES: CC(O)(C1CCOCC1)C1c2ccccc2-c2cncn21]

To a solution of 5H-imidazo[5,1-a]isoindole (1.71 g, 10.92 mmol) in anhydrous THF (25 mL) at −40° C. was added n-BuLi (2.18 mL, 5.46 mmol, 2.5 M solution in hexanes). After stirring for 1.0 h at −40° C., 1-(tetrahydro-2H-pyran-4-yl)ethan-1-one (700 mg, 5.46 mmol) was added and the reaction was allowed to warm to −20° C. and stirred for 1 hr. The reaction was quenched by adding satd. $NH_4Cl$ (10 mL) and water (20 mL), the product was extracted with $CH_2Cl_2$ (3×35 mL). The combined organic extract was dried over $Na_2SO_4$ and concentrated under reduced pressure to afford crude mixture. The crude mixture was purified by CombiFlash to yield a pair of diastereomers (455 mg, 29% yield), the stereochemistry was assigned arbitrarily: LCMS (ESI, m/z): 285.21 $[M+H]^+$.

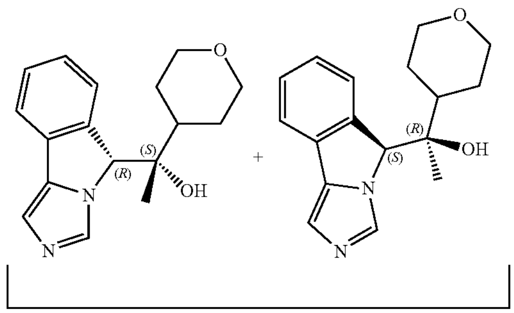

131a

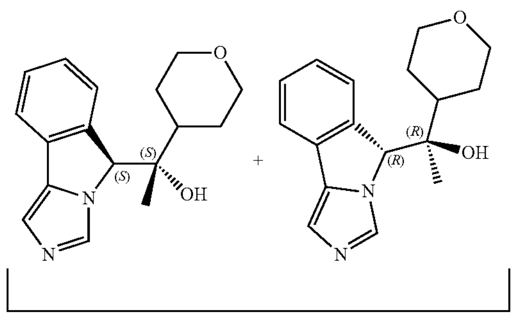

131b

Example 131a: Mixture of(S)-1-((R)-5H-imidazo[5,1-a]isoindol-5-yl)-1-(tetrahydro-2H-pyran-4-yl)ethan-1-ol and (R)-1-((S)-5H-imidazo[5,1-a]isoindol-5-yl)-1-(tetrahydro-2H-pyran-4-yl)ethan-1-ol: LCMS (ESI, m/z): 285.21 $[M+H]^+$. $^1$H NMR (Chloroform-d, 400 MHz): δ (ppm) 7.85 (s, 1H), 7.65-7.54 (m, 2H), 7.41 (t, J=7.6 Hz, 1H), 7.26 (td, J=7.8, 1.2 Hz, 1H), 7.20 (s, 1H), 5.31 (s, 1H), 4.02 (d, J=10.3 Hz, 1H), 3.91 (dd, J=11.5, 4.4 Hz, 1H), 3.40-3.30 (m, 1H), 3.25 (td, J=11.9, 2.2 Hz, 1H), 1.79-1.56 (m, 3H), 2.90 (s, 1H), 1.55-1.41 (m, 1H), 1.21 (d, J=13.2 Hz, 1H), 1.13 (s, 3H).

Example 131b: Mixture of(S)-1-((S)-5H-imidazo[5,1-a]isoindol-5-yl)-1-(tetrahydro-2H-pyran-4-yl)ethan-1-ol and (R)-1-((R)-5H-imidazo[5,1-a]isoindol-5-yl)-1-(tetrahydro-2H-pyran-4-yl)ethan-1-ol: LCMS (ESI, m/z): 285.21 $[M+H]^+$. $^1$H NMR (Chloroform-d, 400 MHz): δ (ppm) 8.01 (s, 1H), 7.58 (d, J=7.5 Hz, 1H), 7.42 (t, J=7.7 Hz, 1H), 7.35 (d, J=7.4 Hz, 1H), 7.32-7.24 (m, 1H), 7.20 (s, 1H), 5.42 (s, 1H), 4.25-4.17 (m, 1H), 4.17-4.08 (m, 1H), 3.65-3.44 (m, 3H), 2.17-2.05 (m, 2H), 1.97 (d, J=11.0 Hz, 1H), 1.87 (dq, J=19.2, 7.6, 6.1 Hz, 1H), 1.58 (d, J=13.0 Hz, 1H), 0.58 (s, 3H).

Example 132: 1-(5H-imidazo[5,1-a]isoindol-5-yl)-4,4-dimethylcyclohexan-1-ol

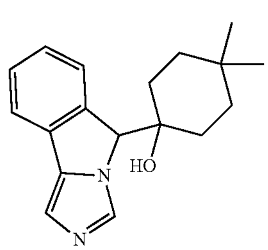 [SMILES: CC1(C)CCC(O)(C2c3ccccc3-c3cncn32)CC1]

Final product (racemate) is a mixture of the following isomers:

(R)-1-(5H-imidazo[5,1-a]isoindol-5-yl)-4,4-dimethylcyclohexan-1-ol (S)-1-(5H-imidazo[5,1-a]isoindol-5-yl)-4,4-dimethylcyclohexan-1-ol To a solution of 5H-imidazo[5,1-a]isoindole (300 mg, 1.92 mmol) in anhydrous THF (15 mL) at −78° C. was added n-BuLi (0.85 mL, 2.11 mmol, 2.5 M solution in hexanes). After stirring for 1 hr at −78° C., the above suspension mixture was treated with a solution of 4,4'-dimethylcyclohexone (363 mg, 2.88 mmol) in 3 mL of THF. After 1 hr at −78° C., the reaction was quenched with water (1 mL) and $NH_4Cl$ solution (20 mL). The separated aqueous layer was subsequently extracted with DCM (20 mL×3). Combined organic phase was dried over $Na_2SO_4$, filtrated and purified on Combi-Flash using MeOH/DCM (4%-8%): LCMS (ESI, m/z): 283.2 $[M+H]^+$; $^1$H NMR (400 MHz, DMSO-$d_6$) δ 7.86 (s, 1H), 7.60 (ddt, J=9.1, 7.4, 0.9 Hz, 2H), 7.39 (ddd, J=8.0, 7.4, 0.9 Hz, 1H), 7.26 (td, J=7.6, 1.2 Hz, 1H), 7.13 (s, 1H), 5.11 (s, 1H), 5.04 (s, 1H), 1.69-1.51 (m, 2H), 1.44 (ddd, J=13.3, 8.8, 2.7 Hz, 2H), 1.14-0.91 (m, 3H), 0.84 (s, 3H), 0.79 (d, J=2.9 Hz, 1H), 0.63 (s, 3H).

Example 133: 5-(5H-imidazo[5,1-a]isoindol-5-yl)-5,6,7,8-tetrahydro-4H-pyrazolo[1,5-a]azepin-4-ol

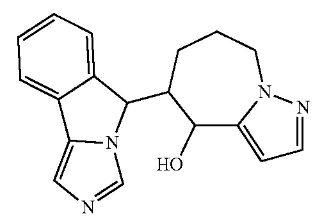 [SMILES: OC1c2ccnn2CCCC1C1c2ccccc2-c2cncn21]

Step 1: ethyl 5-(1H-pyrazol-1-yl) pentanoate

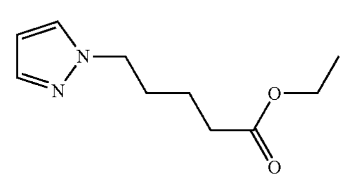

A mixture of sodium hydride (3.5 g, 87.5 mmol, 60% oil dispersion) in ethylene glycol dimethyl ether (300 mL) was added 1H-pyrazole (5.0 g, 73.45 mmol) in portions at 0° C. The resulting solution was stirred for 20 min at 0° C. Ethyl 5-bromopentanoate (20 g, 95.66 mmol) was added. The resulting solution was allowed to react, with stirring, for an additional 16 h at 60° C. The reaction was then quenched by the addition of water (100 mL). The resulting solution was extracted with ether (3×100 mL). The organic combined layer was dried over anhydrous sodium sulfate and concentrated under vacuum. The residue was applied onto a silica gel column with EtOAc/petroleum ether (1:3). This resulted in 12 g (83%) of ethyl 5-(1H-pyrazol-1-yl) pentanoate as light yellow oil: LCMS (ESI, m/z): 197.2 $[M+H]^+$ Step 2: 5-(1H-pyrazol-1-yl) pentanoic acid

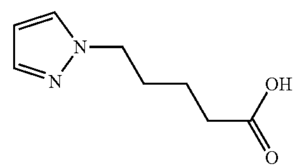 [SMILES: O=C(O)CCCCn1cccn1]

A solution of ethyl 5-(1H-pyrazol-1-yl) pentanoate (12 g, 61.15 mmol) in THF (100 mL) was added sodium hydroxide solution (200 mL, 4.0 mol, 2.0 M in water). The resulting solution was stirred for 16 h at room temperature. The pH value of the solution was adjusted to 5 with 6 M hydrogen chloride. The resulting solution was extracted with EtOAc (3×500 mL). The organic layers were combined, dried over anhydrous sodium sulfate, and concentrated under vacuum. This resulted in 10 g (97%) of 5-(1H-pyrazol-1-yl) pentanoic acid as light yellow oil: LCMS (ESI, m/z): 169.1 $[M+H]^+$.

Step 3: 5,6,7,8-tetrahydropyrazolo[1,5-a]azepin-4-one

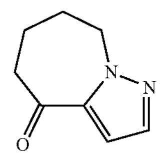 [SMILES: O=C1CCCCn2nccc21]

A solution of 5-(1H-pyrazol-1-yl) pentanoic acid (5.0 g, 29.73 mmol) in THF (200 mL) was added n-butyllithium (30 mL, 75.00 mmol, 2.5 M in THF) under nitrogen at −70° C. The resulting solution was stirred for 1 h at −45° C. The resulting solution was allowed to react, with stirring, for an additional 1 h at room temperature. The reaction was then quenched by the addition of Sat. ammonium chloride (30 mL). The mixture was concentrated under vacuum. The resulting solution was extracted with ether (3×200 mL). The organic combined layer was dried over anhydrous sodium sulfate and concentrated under vacuum. The residue was purified by a silica gel column eluting with EtOAc/petroleum ether (1:3). This resulted in 600 mg (13%) of 5,6,7,8-tetrahydropyrazolo[1,5-a]azepin-4-one as light yellow oil: LCMS (ESI, m/z): 151.1 $[M+H]^+$.

Step 4: (E)-5-(2-(1-trityl-1H-imidazol-4-yl)benzylidene)-5,6,7,8-tetrahydropyrazolo[1,5-a]azepin-4-one

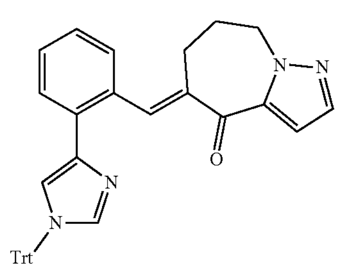

Into the mixture of 5,6,7,8-tetrahydropyrazolo[1,5-a]azepin-4-one (600 mg, 3.995 mmol) and 2-[1-(triphenylmethyl)-1H-imidazol-4-yl]benzaldehyde (1.5 g, 3.619 mmol) in MeOH (30 mL) was added sodium ethanolate (3.1 mL, 9.57 mmol, 21% in MeOH). The resulting solution was stirred for 16 h at 80° C. in an oil bath. The resulting solution was diluted with DCM (50 mL). The reaction was then quenched by the addition of water (20 mL). The resulting solution was extracted with DCM (3×100 mL). The organic combined layer was dried over sodium sulfate and concentrated under vacuum. The residue was applied onto a silica gel column with DCM/MeOH (13:1). This resulted in 1.9 g (87%) of (E)-5-(2-(1-trityl-1H-imidazol-4-yl)benzylidene)-5,6,7,8-tetrahydropyrazolo[1,5-a]azepin-4-one as a light yellow solid: LCMS (ESI, m/z): 547.3 $[M+H]^+$ Step 5: 5-(5H-imidazo[5,1-a]isoindol-5-yl)-5,6,7,8-tetrahydropyrazolo[1,5-a]azepin-4-one

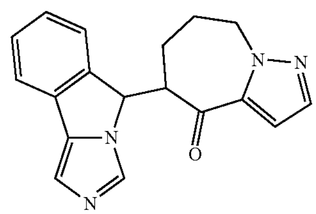 [SMILES: O=C1c2ccnn2CCCC1C1c2ccccc2-c2cncn21]

A mixture of (E)-5-(2-(1-trityl-1H-imidazol-4-yl)benzylidene)-5,6,7,8-tetrahydropyrazolo[1,5-a]azepin-4-one (1.9 g, 3.48 mmol) in MeOH (20 mL) was added acetic acid (4 mL). The resulting solution was stirred for 16 h at 80° C. in an oil bath. The resulting mixture was concentrated under vacuum. The resulting solution was diluted with EtOAc (500 mL). The resulting mixture was washed with Sat. ammonium chloride (1×50 mL) and brine (1×50 mL). The solid was dried over sodium sulfate and concentrated under vacuum. The residue was purified by silica gel column eluting with DCM/MeOH (13:1). This resulted in 800 mg (76%) of 5-(5H-imidazo[5,1-a]isoindol-5-yl)-5,6,7,8-tetrahydropyrazolo[1,5-a]azepin-4-one as a yellow solid: LCMS (ESI, m/z): 305.1 $[M+H]^+$ Step 6:

(4R,5S)-5-((R)-5H-imidazo[5,1-a]isoindol-5-yl)-5,6,7,8-tetrahydro-4H-pyrazolo[1,5-a]azepin-4-ol (4S,5R)-5-((S)-5H-imidazo[5,1-a]isoindol-5-yl)-5,6,7,8-tetrahydro-4H-pyrazolo[1,5-a]azepin-4-ol (4S,5S)-5-((R)-5H-imidazo[5,1-a]isoindol-5-yl)-5,6,7,8-tetrahydro-4H-pyrazolo[1,5-a]azepin-4-ol (4R,5R)-5-((S)-5H-imidazo[5,1-a]isoindol-5-yl)-5,6,7,8-tetrahydro-4H-pyrazolo[1,5-a]azepin-4-ol (4S,5R)-5-((R)-5H-imidazo[5,1-a]isoindol-5-yl)-5,6,7,8-tetrahydro-4H-pyrazolo[1,5-a]azepin-4-ol (4R,5R)-5-((R)-5H-imidazo[5,1-a]isoindol-5-yl)-5,6,7,8-tetrahydro-4H-pyrazolo[1,5-a]azepin-4-ol (4S,5S)-5-((S)-5H-imidazo[5,1-a]isoindol-5-yl)-5,6,7,8-tetrahydro-4H-pyrazolo[1,5-a]azepin-4-ol (4R,5S)-5-((S)-5H-imidazo[5,1-a]isoindol-5-yl)-5,6,7,8-tetrahydro-4H-pyrazolo[1,5-a]azepin-4-ol 133a

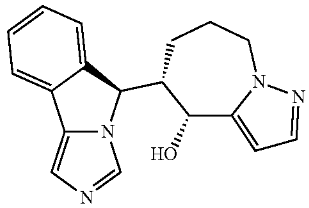

133b

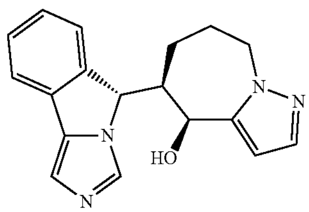

133c

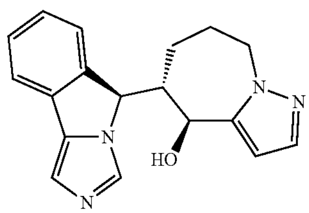

133d

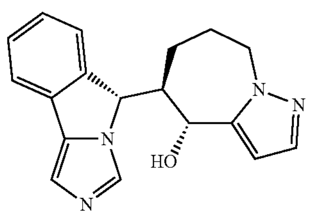

133e

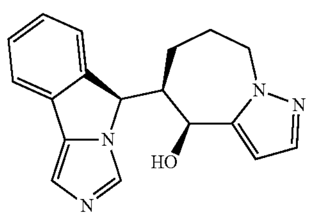

133f

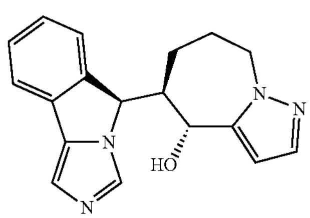

133g

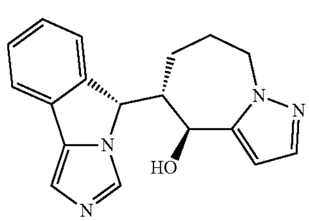

-continued

133h

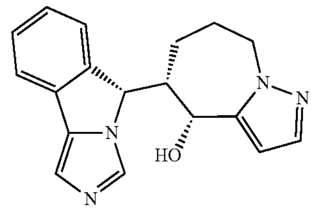

A solution of 5-(5H-imidazo[5,1-a]isoindol-5-yl)-5,6,7,8-tetrahydropyrazolo[1,5-a]azepin-4-one (1.2 g, 3.943 mmol) in MeOH (100 mL) was added sodium borohydride (1.5 g, 39.65 mmol). The resulting solution was stirred for 30 min at room temperature. The resulting mixture was concentrated under vacuum. The residue was diluted with DCM (300 mL). The solid was filtered out. The resulting mixture was concentrated under vacuum. The crude product was purified by Combi-Flash and further isolated by chiral separation. The absolute configuration of all isomers 133a-h was assigned arbitrarily.

Example 133a: (4R,5S)-5-((R)-5H-imidazo[5,1-a]isoindol-5-yl)-5,6,7,8-tetrahydro-4H-pyrazolo[1,5-a]azepin-4-ol (9.1 mg, 1%) as a white solid: LCMS $[M+H]^+$307.3; 1H NMR (300 MHz, $CD_3OD$) δ 7.92 (s, 1H), 7.68-7.59 (m, 2H), 7.46-7.37 (m, 1H), 7.34-7.26 (m, 1H), 7.20 (d, J=2.4 Hz, 1H), 7.12 (s, 1H), 5.98 (d, J=2.1 Hz, 1H), 5.44 (d, J=1.8 Hz, 1H), 4.75 (d, J=1.2 Hz, 1H), 4.39-4.00 (m, 2H), 2.50-2.39 (m, 2H), 2.18-2.06 (m, 1H), 1.81-1.60 (m, 2H): LCMS (ESI, m/z): 307.1 $[M+H]^+$. tR=1.111 min (CHIRALPAK IB-3, 0.46×5 cm, Hex(0.1% DEA):EtOH=50:50, 1 ml/min). 133a and 133b are enantiomers.

Example 133b: (4S,5R)-5-((S)-5H-imidazo[5,1-a]isoindol-5-yl)-5,6,7,8-tetrahydro-4H-pyrazolo[1,5-a]azepin-4-ol (8.0 mg, 1%) as a white solid: LCMS (ESI, m/z): 307.3 $[M+H]^+$. tR=2.647 min (CHIRALPAK IB-3, 0.46×5 cm, Hex(0.1% DEA):EtOH-50:50, 1 ml/min). 133a and 133b are enantiomers.

Example 133c: (4S,5S)-5-((R)-5H-imidazo[5,1-a]isoindol-5-yl)-5,6,7,8-tetrahydro-4H-pyrazolo[1,5-a]azepin-4-ol (7.5 mg, 1%) as a white solid: LCMS (ESI, m/z): 307.1 $[M+H]^+$. $^1H$ NMR (300 MHz, $CD_3OD$) δ 7.90 (s, 1H), 7.69-7.65 (m, 2H), 7.45-7.35 (m, 3H), 7.20 (s, 1H), 6.45 (d, J=1.5 Hz, 1H), 6.04 (d, J=3.6 Hz, 1H), 5.04 (d, J=10.3 Hz, 1H), 4.38-4.26 (m, 1H), 3.93-3.81 (m, 1H), 2.59-2.42 (m, 1H), 1.87-1.71 (m, 1H), 1.49-1.27 (m, 1H), 1.08-0.82 (m, 2H). tR=2.067 min (CHIRALPAK IA-3, 0.46×5 cm, Hex (0.1% DEA):EtOH=80:20, 1 ml/min). 133c and 133d are enantiomers.

Example 133d: (4R,5R)-5-((S)-5H-imidazo[5,1-a]isoindol-5-yl)-5,6,7,8-tetrahydro-4H-pyrazolo[1,5-a]azepin-4-ol (8.8 mg, 1%) as a white solid: LCMS (ESI, m/z): 307.2 $[M+H]^+$. tR=6.144 min (CHIRALPAK IA-3, 0.46×5 cm, Hex(0.1% DEA):EtOH=80:20, 1 ml/min). 133c and 133d are enantiomers.

Example 133e: (4S,5R)-5-((R)-5H-imidazo[5,1-a]isoindol-5-yl)-5,6,7,8-tetrahydro-4H-pyrazolo[1,5-a]azepin-4-ol (38.3 mg, 31%) as a white solid: LCMS (ESI, m/z): 307.4 $[M+H]^+$. $^1H$ NMR (300 MHz, $CD_3OD$) δ 8.18 (s, 1H), 7.61-7.59 (m, 1H), 7.48-7.33 (m, 3H), 7.31 (d, J=1.5 Hz, 1H), 7.17 (s, 1H), 6.34 (d, J=1.5 Hz, 1H), 5.58 (d, J=1.5 Hz, 1H), 5.40 (d, J=10.2 Hz, 1H), 4.32-4.28 (m, 2H), 2.49-2.41 (m, 1H), 1.92-1.68 (m, 2H), 1.57-1.36 (m, 1H), 1.05-0.92 (m, 1H). tR=2.991 min (CHIRAL Cellulose-SB, 0.46×5 cm, Hex(0.1% DEA):EtOH=50:50, 1 ml/min). 133e and 133h are enantiomers.

Example 133f: (4R,5R)-5-((R)-5H-imidazo[5,1-a]isoindol-5-yl)-5,6,7,8-tetrahydro-4H-pyrazolo[1,5-a]azepin-4-ol (41.5 mg, 31%) as a white solid: LCMS (ESI, m/z): 307.4 $[M+H]^+$. $^1H$ NMR (300 MHz, $CD_3OD$) δ 7.92 (s, 1H), 7.64-7.62 (m, 1H), 7.43-7.33 (m, 4H), 7.22 (s, 1H), 6.47 (d, J=1.5 Hz, 1H), 6.00 (d, J=1.5 Hz, 1H), 5.05 (d, J=10.2 Hz, 1H), 4.30-4.28 (m, 1H), 3.98-3.89 (m, 1H), 2.41-2.32 (m, 1H), 1.70-1.66 (m, 1H), 1.42-1.16 (m, 2H), 0.99-0.81 (m, 1H). tR=4.079 min (CHIRAL Cellulose-SB, 0.46×5 cm, Hex(0.1% DEA):EtOH=50:50, 1 ml/min). 133f and 133g are enantiomers.

Example 133g: (4S,5S)-5-((S)-5H-imidazo[5,1-a]isoindol-5-yl)-5,6,7,8-tetrahydro-4H-pyrazolo[1,5-a]azepin-4-ol (33.3 mg, 3%) as a white solid: LCMS (ESI, m/z): 307.1 $[M+H]^+$. R=3.049 min (CHIRAL Cellulose-SB, 0.46×5 cm, Hex(0.1% DEA):EtOH=50:50, 1 ml/min). 133f and 133g are enantiomers.

Example 133h: (4R,5S)-5-((S)-5H-imidazo[5,1-a]isoindol-5-yl)-5,6,7,8-tetrahydro-4H-pyrazolo[1,5-a]azepin-4-ol 40.2 mg, 3%) as a white solid: LCMS (ESI, m/z): 307.1 $[M+H]^+$. tR=5.696 min (CHIRAL Cellulose-SB, 0.46×5 cm, Hex(0.1% DEA):EtOH=50:50, 1 ml/min). 133e and 133h are enantiomers.

Example 134a: (R)-3-((S)-5H-imidazo[5,1-a]isoindol-5-yl)-1-(methylsulfonyl)piperidin-3-ol

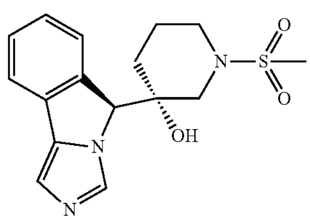 [SMILES: CS(=O)(=O)N1CCC[C@](O)([C@@H]2c3ccccc3-c3cncn32)C1]

To a solution of tert-butyl (R)-3-hydroxy-3-((S)-5H-imidazo[5,1-a]isoindol-5-yl)piperidine-1-carboxylate (Example 127c, 72.2 mg, 0.20 mmol) in anhydrous MeOH was added 4N HCl (0.51 mL, 20 mmol) at room temperature and stirred for another 4 hr. The reaction was monitored by LC-MS. After consumption of the starting material, the solvent was evaporated and the crude product was dried by vacuum. The crude product was dissolved in anhydrous DCM and was added triethylamine (72 uL, 0.51 mmol) at 0° C. Methanesulfonyl chloride (24 uL, 0.31 mmol) was then added into the mixture. The reaction was warmed to room temperature and stirred for another 2 hr. The reaction was quenched by adding saturated $NaHCO_3$ aqueous solution (10 mL). The crude product was extracted with DCM (3× mL) and the organic phase was combined, dried over anhydrous $Na_2SO_4$, and concentrated. The product was separated by CombiFlash and was eluted with DCM: MeOH=94:6: LCMS (ESI, m/z): 334.1 $[M+H]^+$; $^1H$ NMR (400 MHz, DMSO-d6) 7.88 (s, 1H), 7.66 (dd, J=7.6, 1.0 Hz, 1H), 7.63-7.59 (m, 1H), 7.44-7.38 (m, 1H), 7.30-7.24 (m, 1H), 7.15 (s, 1H), 5.50-5.48 (m, 1H), 5.34-5.31 (m, 1H), 3.53-3.47 (m, 1H), 2.93 (s, 3H), 2.71-2.60 (m, 1H), 1.86-1.75 (m, 1H), 1.53-1.41 (m, 1H), 1.18-1.10 (m, 2H).

Example 135: 1-(8-fluoro-5H-imidazo[5,1-a]isoindol-5-yl)-2-methylpropan-1-ol

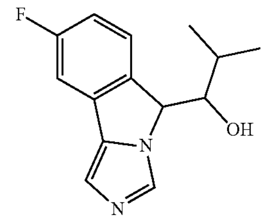 [SMILES: CC(C)C(O)C1c2ccc(F)cc2-c2cncn21]

The title compound was synthesized by the same method of example 128, the product was obtained in 30% yield. The stereoisomers were separated by chiral SFC, the stereochemistry was assigned arbitrarily: LCMS (ESI, m/z): 247.34 $[M+H]^+$ 135a

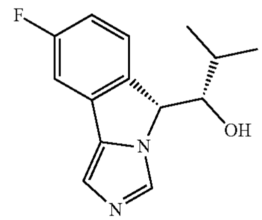

135b

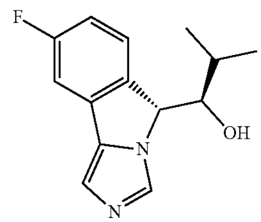

135c

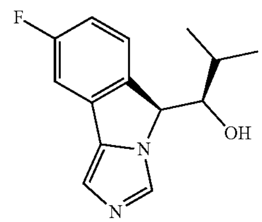

135d

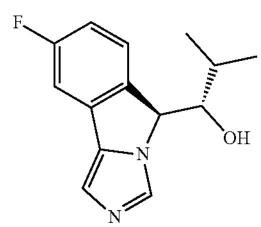

Example 135a: (S)-1-((R)-8-fluoro-5H-imidazo[5,1-a]isoindol-5-yl)-2-methylpropan-1-ol: LCMS (ESI, m/z): 247.34 $[M+H]^+$. $^1H$ NMR (DMSO-$d_6$, 400 MHz): δ (ppm) 7.85 (d, J=0.7 Hz, 1H), 7.56-7.43 (m, 2H), 7.16 (s, 1H), 7.06 (ddd, J=9.6, 8.4, 2.5 Hz, 1H), 5.38 (d, J=4.6 Hz, 1H), 5.26 (d, J=5.8 Hz, 1H), 3.80-3.71 (m, 1H), 1.63 (dq, J=13.4, 6.7 Hz, 1H), 0.84 (d, J=6.8 Hz, 3H), 0.69 (d, J=6.6 Hz, 3H).

Example 135b: (R)-1-((R)-8-fluoro-5H-imidazo[5,1-a]isoindol-5-yl)-2-methylpropan-1-ol: LCMS (ESI, m/z):

247.34 $[M+H]^+$. $^1H$ NMR (DMSO-$d_6$, 400 MHz): δ (ppm) 7.84 (s, 1H), 7.54-7.42 (m, 2H), 7.16 (s, 1H), 7.06 (ddd, J=9.6, 8.4, 2.5 Hz, 1H), 5.33 (d, J=4.8 Hz, 1H), 5.11 (d, J=6.4 Hz, 1H), 3.48 (td, J=6.5, 4.9 Hz, 1H), 1.89 (h, J=6.6 Hz, 1H), 0.98 (d, J=6.6 Hz, 3H), 0.94 (d, J=6.8 Hz, 3H).

Example 135c: (R)-1-((S)-8-fluoro-5H-imidazo[5,1-a]isoindol-5-yl)-2-methylpropan-1-ol: LCMS (ESI, m/z): 247.34 $[M+H]^+$. $^1H$ NMR (DMSO-$d_6$, 400 MHz): Same as 135a Example 135d: (S)-1-((S)-8-fluoro-5H-imidazo[5,1-a]isoindol-5-yl)-2-methylpropan-1-ol: LCMS (ESI, m/z): 247.34 $[M+H]^+$. $^1H$ NMR (DMSO-$d_6$, 400 MHz): Same as 135b.

Example 136: 7-(5H-imidazo[5,1-a]isoindol-5-yl)-5,6,7,8-tetrahydroindolizin-8-ol

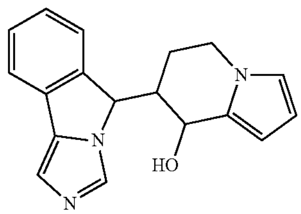 [SMILES: OC1c2cccn2CCC1C1c2ccccc2-c2cncn21]

(7S,8R)-7-((S)-5H-imidazo[5,1-a]isoindol-5-yl)-5,6,7,8-tetrahydroindolizin-8-ol
(7R,8S)-7-((R)-5H-imidazo[5,1-a]isoindol-5-yl)-5,6,7,8-tetrahydroindolizin-8-ol
(7S,8S)-7-((S)-5H-imidazo[5,1-a]isoindol-5-yl)-5,6,7,8-tetrahydroindolizin-8-ol
(7R,8S)-7-((S)-5H-imidazo[5,1-a]isoindol-5-yl)-5,6,7,8-tetrahydroindolizin-8-ol
(7R,8R)-7-((R)-5H-imidazo[5,1-a]isoindol-5-yl)-5,6,7,8-tetrahydroindolizin-8-ol
(7S,8S)-7-((R)-5H-imidazo[5,1-a]isoindol-5-yl)-5,6,7,8-tetrahydroindolizin-8-ol
(7R,8R)-7-((S)-5H-imidazo[5,1-a]isoindol-5-yl)-5,6,7,8-tetrahydroindolizin-8-ol Step 1:

(E)-7-(2-(1-trityl-1H-imidazol-4-yl)benzylidene)-6,7-dihydroindolizin-8(5H)-one

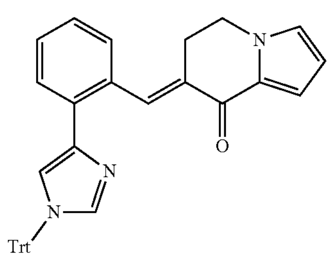

To a solution of 2-(1-trityl-1H-imidazol-4-yl)benzaldehyde (3.0 g, 7.24 mmol) and 6,7-dihydroindolizin-8(5H)-one (1.17 g, 8.68 mmol) in ethanol (50 mL) was added anhydrous $Ca(OH)_2$ (268 mg, 3.62 mmol). The mixture was stirred at 90° C. overnight. The mixture was cooled to room temperature and saturated $NH_4Cl$ solution (50 mL) was added to quench the reaction. The aqueous phase was extracted with DCM (3×50 mL) and the organic phase was combined, dried over anhydrous $Na_2SO_4$, and concentrated. The product was separated by CombiFlash and was eluted with EtOAc:Hex=50:50: LCMS (ESI, m/z): 532.3 $[M+H]^+$.

Step 2:

7-(5H-imidazo[5,1-a]isoindol-5-yl)-6,7-dihydroindolizin-8(5H)-one

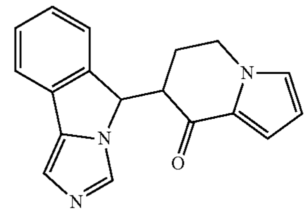 [SMILES: O=C1c2cccn2CCC1C1c2ccccc2-c2cncn21]

(E)-7-(2-(1-trityl-1H-imidazol-4-yl)benzylidene)-6,7-dihydroindolizin-8(5H)-one (3.2 g, 6.02 mmol) was stirred in 20% AcOH in MeOH (50 mL) at 90° C. for 2 h. After cooling to room temperature, the solvent was removed under reduced pressure and saturated $NaHCO_3$ (60 mL) was added to the residue followed by DCM (20 mL). The organic layer was collected and the aqueous layer was extracted with 20% trifluoroethanol in DCM (3×50 mL). The combined organic layers were dried over $Na_2SO_4$ and the solvent evaporated under reduced pressure to afford the crude product which was purified by using CombiFlash and was eluted by DCM:MeOH=97:3: LCMS (ESI, m/z): 290.4 $[M+H]^+$.

Step 3:

(7S,8R)-7-((S)-5H-imidazo[5,1-a]isoindol-5-yl)-5,6,7,8-tetrahydroindolizin-8-ol
(7R,8S)-7-((R)-5H-imidazo[5,1-a]isoindol-5-yl)-5,6,7,8-tetrahydroindolizin-8-ol
(7S,8S)-7-((S)-5H-imidazo[5,1-a]isoindol-5-yl)-5,6,7,8-tetrahydroindolizin-8-ol
(7R,8S)-7-((S)-5H-imidazo[5,1-a]isoindol-5-yl)-5,6,7,8-tetrahydroindolizin-8-ol
(7R,8R)-7-((R)-5H-imidazo[5,1-a]isoindol-5-yl)-5,6,7,8-tetrahydroindolizin-8-ol
(7S,8S)-7-((R)-5H-imidazo[5,1-a]isoindol-5-yl)-5,6,7,8-tetrahydroindolizin-8-ol
(7R,8R)-7-((S)-5H-imidazo[5,1-a]isoindol-5-yl)-5,6,7,8-tetrahydroindolizin-8-ol 136a

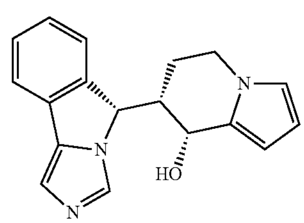

136b

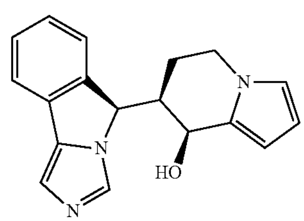

-continued

136c

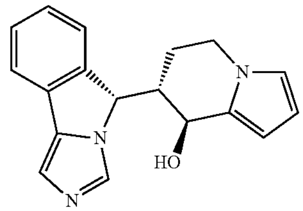

136d

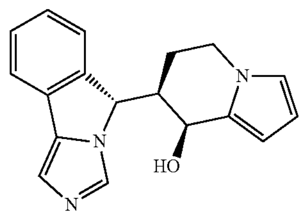

136e

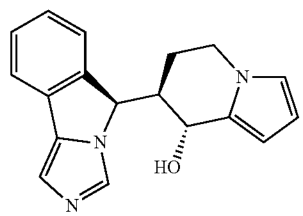

136f

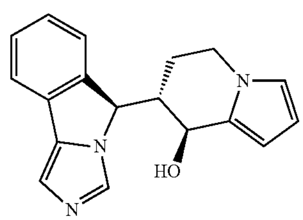

136g

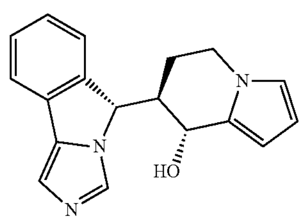

To a solution of 7-(5H-imidazo[5,1-a]isoindol-5-yl)-6,7-dihydroindolizin-8(5H)-one (1.0 g, 3.46 mmol) in MeOH (50 mL) was added sodium borohydride (261 mg, 6.91 mmol) in portion-wise at 0° C. The reaction was kept at 0° C. for 2 hrs. The reaction was quenched by saturated ammonium chloride solution (30 mL). The aqueous layer was extracted with DCM (3×30 mL). The combined organic extract was dried over ($Na_2SO_4$) and concentrated under reduced pressure to afford the crude product. The product was separated by CombiFlash and was eluted with MeOH:DCM=2:98. The final products were further isolated by chiral separation to afford 7 isomers and the stereochemistry of each isomer was arbitrarily assigned.

Example 136a: (7S,8R)-7-((S)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.93 (d, J=0.6 Hz, 1H), 7.63 (dt, J=7.5, 1.0 Hz, 1H), 7.49 (dd, J=7.5, 0.9 Hz, 1H), 7.44-7.39 (m, 1H), 7.33 (dd, J=7.5, 1.2 Hz, 1H), 7.18 (s, 1H), 6.54-6.50 (m, 1H), 6.09 (ddd, J=3.5, 1.8, 1.0 Hz, 1H), 6.02 (dd, J=3.5, 2.6 Hz, 1H), 5.79 (d, J=7.5 Hz, 1H), 5.76 (s, 1H), 4.96 (dd, J=10.3, 7.4 Hz, 1H), 3.81-3.74 (m, 1H), 3.65-3.55 (m, 1H), 2.47-2.38 (m, 1H), 0.99 (dq, J=9.0, 4.9 Hz, 2H).

Example 136b: (7R,8S)-7-((R)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.94 (d, J=0.7 Hz, 1H), 7.64 (dt, J=7.6, 1.0 Hz, 1H), 7.59 (dt, J=7.6, 1.0 Hz, 1H), 7.43-7.36 (m, 1H), 7.29 (td, J=7.5, 1.2 Hz, 1H), 7.12 (s, 1H), 6.58 (dd, J=2.6, 1.7 Hz, 1H), 6.04 (dd, J=3.6, 1.7 Hz, 1H), 6.02 (dd, J=3.5, 2.6 Hz, 1H), 5.63 (dd, J=5.2, 0.7 Hz, 1H), 5.49 (d, J=2.6 Hz, 1H), 5.10 (t, J=4.4 Hz, 1H), 3.91 (ddd, J=12.4, 5.6, 2.1 Hz, 1H), 3.59 (td, J=12.3, 4.6 Hz, 1H), 1.82 (qd, J=12.5, 5.7 Hz, 1H), 1.17-1.07 (m, 1H).

Example 136c: (7S,8S)-7-((S)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.98 (d, J=0.7 Hz, 1H), 7.74 (dq, J=7.8, 0.9 Hz, 1H), 7.62 (dt, J=7.6, 1.0 Hz, 1H), 7.41-7.36 (m, 1H), 7.25 (td, J=7.6, 1.2 Hz, 1H), 7.14 (s, 1H), 6.59 (dd, J=2.5, 1.9 Hz, 1H), 6.01-5.96 (m, 2H), 5.42 (d, J=6.1 Hz, 1H), 5.39 (dd, J=5.1, 0.7 Hz, 1H), 4.91 (ddd, J=4.8, 3.3, 0.9 Hz, 1H), 4.05 (ddd, J=12.4, 5.4, 1.8 Hz, 1H), 3.68 (td, J=12.1, 4.6 Hz, 1H), 2.30-2.12 (m, 2H), 1.79 (d, J=3.4 Hz, 1H).

Example 136d: (7R,8S)-7-((S)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.94 (s, 1H), 7.67-7.62 (m, 1H), 7.58 (dd, J=7.6, 1.0 Hz, 1H), 7.44-7.38 (m, 1H), 7.26 (td, J=7.6, 1.2 Hz, 1H), 7.19 (s, 1H), 6.51 (dd, J=2.6, 1.8 Hz, 1H), 6.06 (ddd, J=3.5, 1.8, 1.0 Hz, 1H), 6.00 (dd, J=3.5, 2.6 Hz, 1H), 5.80 (d, J=7.0 Hz, 1H), 5.76 (d, J=3.2 Hz, 1H), 4.91 (dd, J=10.4, 7.0 Hz, 1H), 3.79 (ddt, J=11.3, 5.8, 2.9 Hz, 1H), 3.63 (td, J=12.2, 4.7 Hz, 1H), 2.63-2.54 (m, 1H), 1.05 (ddt, J=17.6, 12.2, 6.1 Hz, 1H), 0.99-0.89 (m, 1H).

Example 136e: (7R,8R)-7-((S)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.98 (s, 1H), 7.76-7.70 (m, 1H), 7.61 (dt, J=7.6, 1.0 Hz, 1H), 7.42-7.35 (m, 1H), 7.24 (td, J=7.6, 1.2 Hz, 1H), 7.13 (s, 1H), 6.59 (dd, J=2.5, 1.9 Hz, 1H), 6.01-5.96 (m, 2H), 5.42 (d, J=6.1 Hz, 1H), 5.39 (dd, J=5.1, 0.7 Hz, 1H), 4.94-4.87 (m, 1H), 4.08-4.00 (m, 1H), 3.68 (td, J=12.1, 4.6 Hz, 1H), 2.30-2.11 (m, 2H), 1.81 (d, J=12.5 Hz, 1H).

Example 136f: (7S,8S)-7-((R)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.94 (d, J=0.7 Hz, 1H), 7.64 (dd, J=7.6, 0.9 Hz, 1H), 7.61-7.57 (m, 1H), 7.42-7.36 (m, 1H), 7.29 (td, J=7.6, 1.2 Hz, 1H), 7.12 (s, 1H), 6.58 (dd, J=2.6, 1.7 Hz, 1H), 6.03 (d, J=1.7 Hz, 1H), 6.02 (dd, J=3.5, 2.6 Hz, 1H), 5.63 (dd, J=5.1, 0.7 Hz, 1H), 5.49 (d, J=2.6 Hz, 1H), 5.10 (t, J=4.2 Hz, 1H), 3.91 (ddd, J=12.4, 5.6, 2.1 Hz, 1H), 3.59 (td, J=12.3, 4.7 Hz, 1H), 1.83 (qd, J=12.5, 5.7 Hz, 1H), 1.15-1.07 (m, 1H).

Example 136g: (7R,8R)-7-((S)-5H-imidazo[5,1-a]isoindol-5-yl)-5,6,7,8-tetrahydroindolizin-8-ol: LCMS (ESI, m/z): 292.2 $[M+H]^+$; $^1$HNMR (400 MHz, DMSO-$d_6$) δ 7.93 (d, J=0.6 Hz, 1H), 7.63 (dt, J=7.7, 1.0 Hz, 1H), 7.49 (dd, J=7.5, 1.0 Hz, 1H), 7.45-7.39 (m, 1H), 7.33 (dd, J=7.5, 1.2 Hz, 1H), 7.18 (s, 1H), 6.52 (dd, J=2.6, 1.8 Hz, 1H), 6.09 (dq, J=2.8, 0.9 Hz, 1H), 6.02 (dd, J=3.5, 2.6 Hz, 1H), 5.79 (d, J=7.4 Hz, 1H), 5.76 (d, J=1.8 Hz, 1H), 5.00-4.91 (m, 1H), 3.78 (dt, J=12.3, 3.9 Hz, 1H), 3.66-3.55 (m, 1H), 2.46-2.38 (m, 1H), 0.99 (dq, J=9.2, 5.0 Hz, 2H).

Example 137: 1-(5H-imidazo[5,1-a]isoindol-5-yl)propan-1-ol

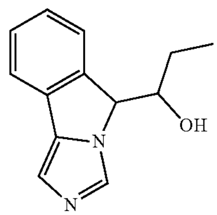 [SMILES: CCC(O)C1c2ccccc2-c2cncn21]

The title compound was synthesized by the same method of example 128, the product was obtained in 57% yield. The stereoisomers were separated by chiral SFC, the stereochemistry was assigned arbitrarily: LCMS (ESI, m/z): 215.21 $[M+H]^+$.

137a

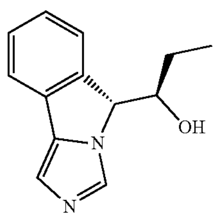

137b

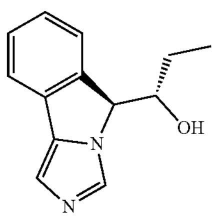

137c

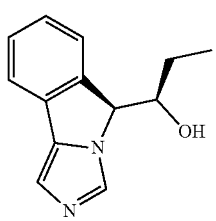

137d

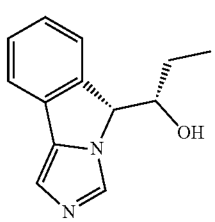

Example 137a: (R)-1-((R)-5H-imidazo[5,1-a]isoindol-5-yl)propan-1-ol: LCMS (ESI, m/z): 215.21 $[M+H]^+$. $^1H$ NMR (DMSO-$d_6$, 400 MHz): δ (ppm) 7.85 (s, 1H), 7.61-7.50 (m, 2H), 7.37 (tdd, J=7.5, 1.2, 0.6 Hz, 1H), 7.25 (td, J=7.5, 1.2 Hz, 1H), 7.11 (s, 1H), 5.27 (s, 1H), 5.24 (s, 1H), 3.90-3.79 (m, 1H), 1.27 (qd, J=7.8, 6.0 Hz, 2H), 0.88 (t, J=7.4 Hz, 3H).

Example 137b: (S)-1-((S)-5H-imidazo[5,1-a]isoindol-5-yl)propan-1-ol: LCMS (ESI, m/z): 215.21 $[M+H]^+$. $^1H$ NMR (DMSO-$d_6$, 400 MHz): Same as 137a Example 137c: (R)-1-((S)-5H-imidazo[5,1-a]isoindol-5-yl)propan-1-ol: LCMS (ESI, m/z): 215.21 $[M+H]^+$. $^1H$ NMR (DMSO-$d_6$, 400 MHz): δ (ppm) 7.79 (s, 1H), 7.59 (dt, J=7.7, 1.1 Hz, 1H), 7.50 (dq, J=7.6, 0.9 Hz, 1H), 7.38 (tdd, J=7.5, 1.1, 0.6 Hz, 1H), 7.26 (td, J=7.5, 1.1 Hz, 1H), 7.13 (s, 1H), 5.46 (d, J=4.7 Hz, 1H), 5.37 (d, J=3.7 Hz, 1H), 4.06 (ddt, J=9.5, 4.6, 3.4 Hz, 1H), 0.90-0.67 (m, 5H)

Example 137d: (S)-1-((R)-5H-imidazo[5,1-a]isoindol-5-yl)propan-1-ol: LCMS (ESI, m/z): 215.21 $[M+H]^+$. $^1H$ NMR (DMSO-$d_6$, 400 MHz): Same as 137c Example 138: (5H-imidazo[5,1-a]isoindol-5-yl)(tetrahydro-2H-pyran-4-yl)methanol

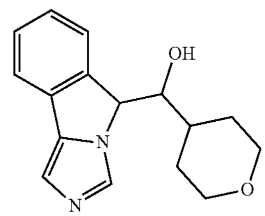 [SMILES: OC(C1CCOCC1)C1c2ccccc2-c2cncn21]

(R)—((S)-5H-imidazo[5,1-a]isoindol-5-yl)(tetrahydro-2H-pyran-4-yl)methanol (S)—((R)-5H-imidazo[5,1-a]isoindol-5-yl)(tetrahydro-2H-pyran-4-yl)methanol (R)—((R)-5H-imidazo[5,1-a]isoindol-5-yl)(tetrahydro-2H-pyran-4-yl)methanol (S)—((S)-5H-imidazo[5,1-a]isoindol-5-yl)(tetrahydro-2H-pyran-4-yl)methanol Step 1:

(R)—((S)-5H-imidazo[5,1-a]isoindol-5-yl)(tetrahydro-2H-pyran-4-yl)methanol (S)—((R)-5H-imidazo[5,1-a]isoindol-5-yl)(tetrahydro-2H-pyran-4-yl)methanol (R)—((R)-5H-imidazo[5,1-a]isoindol-5-yl)(tetrahydro-2H-pyran-4-yl)methanol (S)—((S)-5H-imidazo[5,1-a]isoindol-5-yl)(tetrahydro-2H-pyran-4-yl)methanol 138a

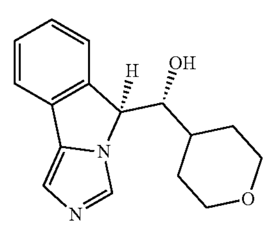

138b

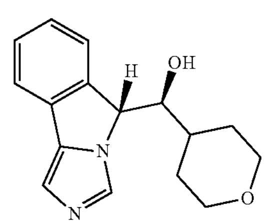

-continued

138c

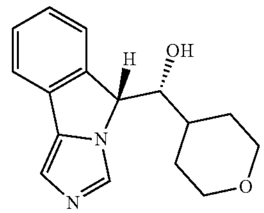

138d

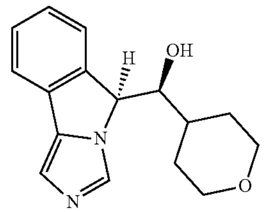

The title compound was synthesized by the same method of example 148.

Example 138a: (R)—((S)-5H-imidazo[5,1-a]isoindol-5-yl)(tetrahydro-2H-pyran-4-yl)methanol: LCMS (ESI, m/z): 271.1 [M+H]$^+$. $^1$H NMR (400 MHz, DMSO-d6) δ 7.83 (s, 1H), 7.59 (dd, J=7.6, 1.0 Hz, 1H), 7.51 (dd, J=7.5, 1.0 Hz, 1H), 7.38 (ddd, J=8.2, 7.5, 1.1 Hz, 1H), 7.26 (td, J=7.5, 1.2 Hz, 1H), 7.12 (s, 1H), 5.42 (d, J=4.0 Hz, 1H), 5.33 (d, J=5.7 Hz, 1H), 3.87 (td, J=5.8, 4.1 Hz, 1H), 3.74 (dd, J=10.9, 3.8 Hz, 2H), 3.20-3.05 (m, 2H), 1.56 (tt, J=10.2, 5.3 Hz, 1H), 1.45-1.31 (m, 1H), 1.31-1.19 (m, 3H). tR=0.956 min (Chiralpak AD, 15% $CH_3OH$ with 0.1% $NH_4OH$ co-solvent).

Example 138b: (S)—((R)-5H-imidazo[5,1-a]isoindol-5-yl)(tetrahydro-2H-pyran-4-yl)methanol: LCMS (ESI, m/z): 271.1 [M+H]$^+$. $^1$H NMR (400 MHz, DMSO-$d_6$) δ 7.83 (s, 1H), 7.59 (dd, J=7.6, 1.0 Hz, 1H), 7.51 (dd, J=7.5, 1.0 Hz, 1H), 7.38 (ddd, J=8.2, 7.5, 1.1 Hz, 1H), 7.26 (td, J=7.5, 1.2 Hz, 1H), 7.12 (s, 1H), 5.42 (d, J=4.0 Hz, 1H), 5.33 (d, J=5.7 Hz, 1H), 3.87 (td, J=5.8, 4.1 Hz, 1H), 3.74 (dd, J=10.9, 3.8 Hz, 2H), 3.20-3.05 (m, 2H), 1.56 (tt, J=10.2, 5.3 Hz, 1H), 1.45-1.31 (m, 1H), 1.31-1.19 (m, 3H). tR=1.024 min (Chiralpak AD, 15% $CH_3OH$ with 0.1% $NH_4OH$ co-solvent).

Example 138c: (R)—((R)-5H-imidazo[5,1-a]isoindol-5-yl)(tetrahydro-2H-pyran-4-yl)methanol: LCMS (ESI, m/z): 271.1 [M+H]$^+$. $^1$H NMR (400 MHz, DMSO-$d_6$) δ 7.84 (s, 1H), 7.61-7.54 (m, 1H), 7.51 (dd, J=7.5, 1.0 Hz, 1H), 7.37 (tt, J=7.7, 0.8 Hz, 1H), 7.26 (td, J=7.5, 1.2 Hz, 1H), 7.12 (s, 1H), 5.36 (d, J=4.2 Hz, 1H), 5.10 (d, J=6.5 Hz, 1H), 3.92-3.78 (m, 2H), 3.64 (td, J=6.8, 4.2 Hz, 1H), 1.93-1.79 (m, 1H), 1.78-1.69 (m, 1H), 1.51-1.30 (m, 3H). tR=1.545 min (Chiralpak AD, 15% $CH_3OH$ with 0.1% $NH_4OH$ co-solvent).

Example 138d: (S)—((S)-5H-imidazo[5,1-a]isoindol-5-yl)(tetrahydro-2H-pyran-4-yl)methanol: LCMS (ESI, m/z): 271.1 [M+H]$^+$. $^1$H NMR (400 MHz, DMSO-$d_6$) δ 7.84 (s, 1H), 7.61-7.54 (m, 1H), 7.51 (dd, J=7.5, 1.0 Hz, 1H), 7.37 (tt, J=7.7, 0.8 Hz, 1H), 7.26 (td, J=7.5, 1.2 Hz, 1H), 7.12 (s, 1H), 5.36 (d, J=4.2 Hz, 1H), 5.10 (d, J=6.5 Hz, 1H), 3.92-3.78 (m, 2H), 3.64 (td, J=6.8, 4.2 Hz, 1H), 1.93-1.79 (m, 1H), 1.78-1.69 (m, 1H), 1.51-1.30 (m, 3H). tR=1.521 min (Chiralpak AD, 15% $CH_3OH$ with 0.1% $NH_4OH$ co-solvent).

Example 139 and 139-1: 5-(5H-imidazo[5,1-a]isoindol-5-yl)-4,5,6,7-tetrahydro-[1,2,3]triazolo[1,5-a]pyridin-4-ol and 6-(5H-imidazo[5,1-a]isoindol-5-yl)-2-methyl-4,5,6,7-tetrahydro-2H-indazol-7-ol

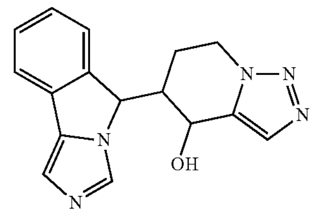

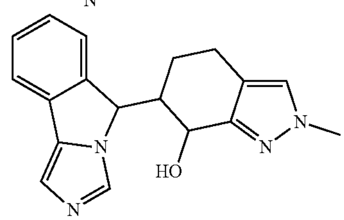

Step 1: 3-(benzyloxy)picolinaldehyde

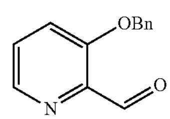 [SMILES: O=Cc1ncccc1OCc1ccccc1]

A solution of (3-(benzyloxy)pyridin-2-yl)methanol (6.9 g, 32.06 mmol) in 1,4-dioxane (150 mL) was added manganese dioxide (15.4 g, 177.14 mmol). The resulting solution was stirred for 20 h at 80° C. in an oil bath. The solids were filtered out. The resulting mixture was concentrated under vacuum. This resulted in 5.6 g (82%) of 3-(benzyloxy)picolinaldehyde as brown oil: LCMS (ESI, m/z): 214.2 [M+H]$^+$.

Step 2: 4-(benzyloxy)-[1,2,3]triazolo[1,5-a]pyridine

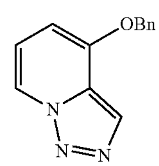 [SMILES: c1ccc(COc2cccn3nncc23)cc1]

A solution of 3-(benzyloxy)picolinaldehyde (5.6 g, 26.26 mmol) in DCM (30 mL) and MeOH (30 mL) was added 4-methylbenzene-1-sulfonohydrazide (5.6 g, 30.070 mmol). The resulting solution was stirred for 1.5 h at room temperature. The resulting mixture was concentrated under vacuum. The residue was diluted with morpholine (15 mL). The resulting solution was stirred for 2 h at 95° C. in an oil bath. The resulting mixture was concentrated under vacuum. The residue was purified by silica gel column eluting with EtOAc/petroleum ether (1:3). This resulted in 4.6 g (78%) of 4-(benzyloxy)-[1,2,3]triazolo[1,5-a]pyridine as a light yellow solid: LCMS (ESI, m/z): 226.1 [M+H]$^+$ Step 3: 6,7-dihydro-[1,2,3]triazolo[1,5-a]pyridin-4(5H)-one

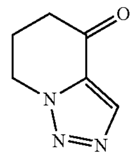

Under hydrogen, a mixture of 4-(benzyloxy)-[1,2,3]triazolo[1,5-a]pyridine (2.0 g, 8.88 mmol) in MeOH (80 mL) was added Palladium carbon (1.45 g, 13.625 mmol). The resulting solution was stirred for 20 h at room temperature. The solids were filtered out. The resulting mixture was concentrated under vacuum. The residue was diluted with EtOAc (600 mL). The solution was washed with Sat. potassium carbonate. The resulting mixture was dried over sodium sulfate and concentrated under vacuum. This resulted in 500 mg (41%) of 4H,5H,6H,7H-[1,2,3]triazolo[1,5-a]pyridin-4-one as a light yellow solid: LCMS (ESI, m/z): 138.2 $[M+H]^+$.

Step 4: (5E)-5-([2-[1-(triphenylmethyl)-1H-imidazol-4-yl]phenyl]methylidene)-4H,5H,6H,7H-[1,2,3]triazolo[1,5-a]pyridin-4-one

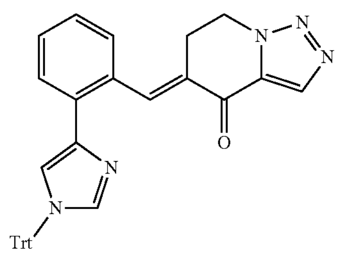

The title compounds were synthesized by General Procedure for the Synthesis of Int-2.

Step 5: 5-[5H-imidazo[4,3-a]isoindol-5-yl]-4H,5H,6H,7H-[1,2,3]triazolo[1,5-a]pyridin-4-one

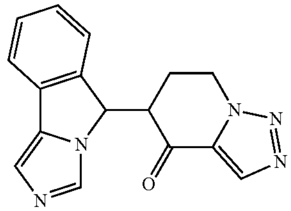 [SMILES: O=C1c2cnnn2CCC1C1c2ccccc2-c2cncn21]

The title compounds were synthesized by General Procedure for the Synthesis of Int-3.

Step 6:
(4R,5S)-5-((S)-5H-imidazo[5,1-a]isoindol-5-yl)-4,5,6,7-tetrahydro-[1,2,3]triazolo[1,5-a]pyridin-4-ol
(4S,5R)-5-((R)-5H-imidazo[5,1-a]isoindol-5-yl)-4,5,6,7-tetrahydro-[1,2,3]triazolo[1,5-a]pyridin-4-ol 139a

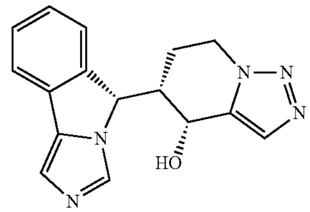

139b

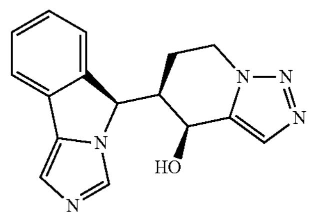

Under nitrogen, a solution of 5-[5H-imidazo[4,3-a]isoindol-5-yl]-4H,5H,6H,7H-[1,2,3]triazolo[1,5-a]pyridin-4-one (580 mg, 1.99 mmol) in THF (20 mL) was added L-Selectride (10 mL, 10 mmol, 1 mol/L in THF) at −65° C. The resulting solution was stirred for 1 h at −65° C. The reaction was then quenched by the addition of ethanol (10 mL). The resulting solution was diluted with water (50 mL). The resulting solution was extracted with DCM (3×200 mL). The organic combined layer was dried over anhydrous sodium sulfate and concentrated under vacuum. The residue was purified by silica gel column eluting with DCM/MeOH (13:1). The crude product was purified by Prep-HPLC and further isolated by chiral separation with the following conditions:

1. XBridge Prep C18 OBD Column 19×150 mm 5 um; Mobile Phase A: Water (0.05% NH3H2O), Mobile Phase B: ACN; Flow rate: 20 mL/min; Gradient: 10% B to 27% B in 11 min; 254/220 nm.
2. Column: Chiralpak IC, 2×25 cm, 5 um; Mobile Phase A:Hex-HPLC, Mobile Phase B: EtOH-HPLC; Flow rate: 16 mL/min; Gradient: 50 B to 50 B in 24 min; 220/254 nm.

The absolute configuration of all isomers 139a-b was assigned arbitrarily.

Example 139a: (4R,5S)-5-((S)-5H-imidazo[5,1-a]isoindol-5-yl)-4,5,6,7-tetrahydro-[1,2,3]triazolo[1,5-a]pyridin-4-ol (21.4 mg, 2%) as a white solid: LCMS (ESI, m/z): 294.3 $[M+H]^+$. $^1$H NMR (300 MHz, DMSO-$d_6$) δ 7.93 (s, 1H), 7.76 (s, 1H), 7.63 (d, J=7.8 Hz, 1H), 7.61 (d, J=7.8 Hz, 1H), 7.43-7.39 (m, 1H), 7.33-7.28 (m, 1H), 7.15 (s, 1H), 6.33 (d, J=5.4 Hz, 1H), 5.58 (d, J=4.8 Hz, 1H), 5.31-5.29 (m, 1H), 4.44-4.38 (m, 1H), 4.05-3.95 (m, 1H), 2.71-2.66 (m, 1H), 1.92-1.76 (m, 1H), 1.30-1.17 (m, 1H). tR=4.092 min (CHIRALPAK IC-3, 0.46×5 cm, Hex(0.1% DEA):EtOH=40:60, 1 ml/min). 139a and 139b are enantiomers.

Example 139b: (4S,5R)-5-((R)-5H-imidazo[5,1-a]isoindol-5-yl)-4,5,6,7-tetrahydro-[1,2,3]triazolo[1,5-a]pyridin-4-ol (17.4 mg, 2%) as a white solid: LCMS (ESI, m/z): 294.2 $[M+H]^+$. tR=5.055 min (CHIRALPAK IC-3, 0.46×5 cm, Hex(0.1% DEA):EtOH=40:60, 1 ml/min). 139a and 139b are enantiomers.

Step 1:

2-methyl-2H-indazol-7-amine

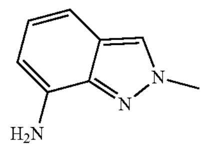

A mixture of 2-methyl-7-nitro-2H-indazole (10 g, 56.45 mmol5) and Palladium carbon (2 g, 18.80 mmol, 5%) in MeOH (100 mL) was added hydrazine (20 mL). The resulting solution was stirred for 4 h at 70° C. The solid was filtered out. The resulting mixture was concentrated under vacuum. This resulted in 7 g (84%) of 2-methyl-2H-indazol-7-amine: LCMS (ESI, m/z): 148.2 $[M+H]^+$.

Step 2:

2-methyl-2H-indazol-7-ol

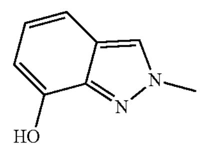

A solution of 2-methyl-2H-indazol-7-amine (3 g, 20.38 mmol) in water (40 mL) and sulfuric acid (30 mL, 562.82 mmol) was added $NaNO_2$ (1.4 g, 20.29 mmol) in water (20 mL). The resulting solution was stirred for 1.5 h at 0° C. The resulting solution was allowed to react for 3 h at 100° C. The reaction was then quenched by Sat. sodium bicarbonate (200 mL). The pH value of the solution was adjusted to 8 with sodium bicarbonate. The resulting solution was extracted with EtOAc (3×200 mL). The organic layers were combined, dried over anhydrous sodium sulfate, and concentrated under vacuum. The residue was purified by silica gel column eluting with EtOAc/petroleum ether (3/7). This resulted in 0.8 g (27%) of 2-methyl-2H-indazol-7-ol as a yellow solid: LCMS (ESI, m/z): 149.2 $[M+H]^+$.

Step 3:

2-methyl-4,5,6,7-tetrahydro-2H-indazol-7-one

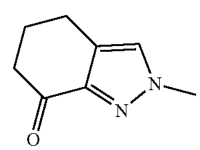

A solution of 2-methyl-2H-indazol-7-ol (1.8 g, 12.15 mmol) in MeOH (50 mL) was added Palladium carbon (300 mg, 2.82 mmol, 10%). The mixture was hydrogenated under 20 bar of hydrogen at 25° C. for 24 h. The solids were filtered out. The resulting mixture was concentrated under vacuum. This resulted in 1.5 g (82%) of 2-methyl-4,5,6,7-tetrahydro-2H-indazol-7-one as a black oil.

Step 4: (6E)-2-methyl-6-([2-[1-(triphenylmethyl)-1H-imidazol-4-yl]phenyl]methylidene)-4,5,6,7-tetrahydro-2H-indazol-7-one

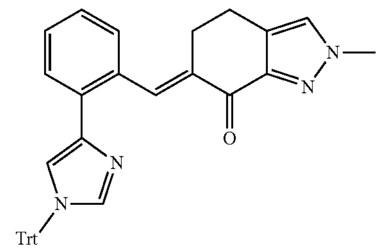

The title compound was synthesized by General Procedure for the Synthesis of int-2.

Step 5:

6-[5H-imidazo[4,3-a]isoindol-5-yl]-2-methyl-4,5,6,7-tetrahydro-2H-indazol-7-one

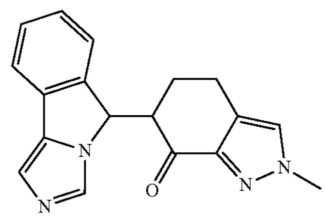 [SMILES: Cn1cc2c(n1)C(=O)C(C1c3ccccc3-c3cncn31)CC2]

The title compound was synthesized by General Procedure for the Synthesis of int-3.

Step 6:

(6S,7R)-6-((R)-5H-imidazo[5,1-a]isoindol-5-yl)-2-methyl-4,5,6,7-tetrahydro-2H-indazol-7-ol (6R,7S)-6-((S)-5H-imidazo[5,1-a]isoindol-5-yl)-2-methyl-4,5,6,7-tetrahydro-2H-indazol-7-ol (6S,7R)-6-((S)-5H-imidazo[5,1-a]isoindol-5-yl)-2-methyl-4,5,6,7-tetrahydro-2H-indazol-7-ol (6R,7S)-6-((R)-5H-imidazo[5,1-a]isoindol-5-yl)-2-methyl-4,5,6,7-tetrahydro-2H-indazol-7-ol

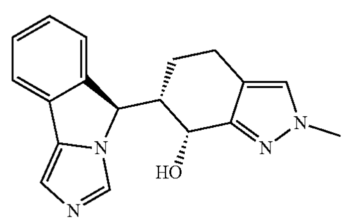

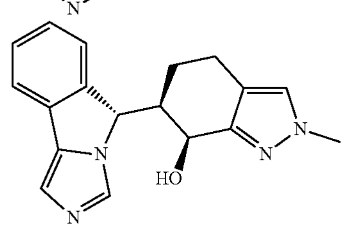

-continued

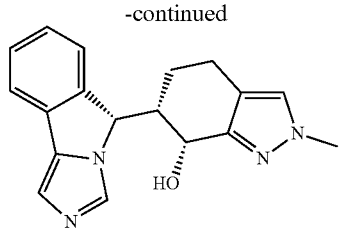

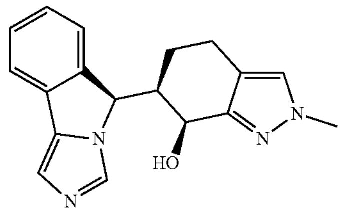

A solution of 6-[5H-imidazo[4,3-a]isoindol-5-yl]-2-methyl-4,5,6,7-tetrahydro-2H-indazol-7-one (900 mg, 2.96 mmol) in THF (30 mL) was added L-Selectride (8.42 mL, 8.42 mmol, 1 mol/L in THF). The resulting solution was stirred for 3 h at −78° C. The reaction was then quenched by water (4 mL). The resulting mixture was concentrated under vacuum. The residue was purified by silica gel column eluting with DCM/MeOH (96/4). The crude product was purified by Prep-HPLC and further isolated by chiral separation.

The absolute configuration of all isomers 139-1a-d was assigned arbitrarily.

Example 139-1a: (6S,7R)-6-((R)-5H-imidazo[5,1-a]isoindol-5-yl)-2-methyl-4,5,6,7-tetrahydro-2H-indazol-7-ol (3.7 mg, 0.4%) as a white solid: LCMS (ESI, m/z): 307.3 $[M+H]^+$. $^1$H NMR (300 MHz, $CD_3OD$) δ 7.92 (s, 1H), 7.64 (dd, J=23.2, 7.6 Hz, 2H), 7.44 (dd, J=8.1, 7.2 Hz, 1H), 7.32 (td, J=7.6, 1.1 Hz, 1H), 7.22 (d, J=15.5 Hz, 2H), 5.86 (d, J=3.0 Hz, 1H), 5.08 (d, J=10.2 Hz, 1H), 3.86 (s, 3H), 2.56 (ddd, J=14.1, 10.4, 3.5 Hz, 1H), 2.46-2.28 (m, 2H), 1.04-0.88 (m, 2H). tR=2.164 min (CHIRAL Cellulose-SB, 0.46×5 cm, Hex(0.1% DEA):EtOH=40:60, 1 ml/min). 139-1a and 139-1b are enantiomers.

Example 139-1b: (6R,7S)-6-((S)-5H-imidazo[5,1-a]isoindol-5-yl)-2-methyl-4,5,6,7-tetrahydro-2H-indazol-7-ol (3.7 mg, 0.4%) as a white solid: LCMS (ESI, m/z): 307.2 $[M+H]^+$. tR=4.219 min (CHIRAL Cellulose-SB, 0.46×5 cm, Hex(0.1% DEA):EtOH=40:60, 1 ml/min). 139-1a and 139-1b are enantiomers.

Example 139-1c: (6S,7R)-6-((S)-5H-imidazo[5,1-a]isoindol-5-yl)-2-methyl-4,5,6,7-tetrahydro-2H-indazol-7-ol (16.1 mg, 0.4%) as a white solid: LCMS (ESI, m/z): 307.3 $[M+H]^+$. $^1$H NMR (300 MHz, $CD_3OD$) δ 8.16 (s, 1H), 7.66-7.54 (m, 2H), 7.47-7.25 (m, 3H), 7.16 (s, 1H), 5.60 (s, 1H), 5.16 (d, J=3.5 Hz, 1H), 3.88 (s, 3H), 2.56 (ddd, J=16.1, 5.5, 2.3 Hz, 2H), 2.31-2.18 (m, 1H), 1.51 (qd, J=12.7, 5.5 Hz, 1H), 1.01-0.91 (m, 1H). tR=3.828 min (CHIRAL Cellulose-SB, 0.46×5 cm, Hex(0.1% DEA):EtOH=60:40, 1 ml/min). 139-1c and 139-1d are enantiomers.

Example 139-1d: (6R,7S)-6-((R)-5H-imidazo[5,1-a]isoindol-5-yl)-2-methyl-4,5,6,7-tetrahydro-2H-indazol-7-ol (14.7 mg, 2%) as a white solid: LCMS (ESI, m/z): 307.2 $[M+H]^+$. tR=4.616 min (CHIRAL Cellulose-SB, 0.46×5 cm, Hex(0.1% DEA):EtOH=60:40, 1 ml/min). 139-1c and 139-1d are enantiomers.

(6S,7S)-6-((S)-5H-imidazo[5,1-a]isoindol-5-yl)-2-methyl-4,5,6,7-tetrahydro-2H-indazol-7-ol (6R,7R)-6-((R)-5H-imidazo[5,1-a]isoindol-5-yl)-2-methyl-4,5,6,7-tetrahydro-2H-indazol-7-ol The title compound was synthesized by General Procedure for the Synthesis of 117a-b. The absolute configuration of all isomers 139-1e-f was assigned arbitrarily.

Example 139-1e: (6S,7S)-6-((S)-5H-imidazo[5,1-a]isoindol-5-yl)-2-methyl-4,5,6,7-tetrahydro-2H-indazol-7-ol (30.4 mg, 6%) as a white solid: LCMS (ESI, m/z): 307.3 $[M+H]^+$. $^1$H NMR (300 MHz, $CD_3OD$) δ 7.97 (s, 1H), 7.66 (d, J=7.5 Hz, 1H), 7.50 (d, J=7.6 Hz, 1H), 7.46 (t, J=7.4 Hz, 1H), 7.37 (td, J=7.5, 0.9 Hz, 2H), 7.25 (s, 1H), 7.21 (s, 1H), 5.86 (s, 1H), 5.06 (d, J=10.2 Hz, 1H), 2.48-2.24 (m, 3H), 1.11-1.00 (m, 1H), 0.95-0.84 (m, 1H). tR=5.758 min (CHIRALPAK AD-3, 0.46×5 cm, Hex(0.1% DEA):EtOH=80:20, 1 ml/min). 139-1e and 139-1f are enantiomers.

Example 139-1f: (6R,7R)-6-((R)-5H-imidazo[5,1-a]isoindol-5-yl)-2-methyl-4,5,6,7-tetrahydro-2H-indazol-7-ol (29.9 mg, 6%) as a white solid: LCMS (ESI, m/z): 307.2 $[M+H]^+$. tR=7.006 min (CHIRALPAK AD-3, 0.46×5 cm, Hex(0.1% DEA):EtOH=80:20, 1 ml/min). 139-1e and 139-1f are enantiomers.

Example 140: 4-hydroxy-4-(5H-imidazo[5,1-a]isoindol-5-yl)cyclohexane-1-carboxamide

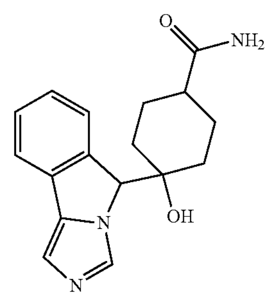 [SMILES: NC(=O)C1CCC(O)(C2c3ccccc3-c3cncn32)CC1]

(1R,4r)-4-hydroxy-4-((R)-5H-imidazo[5,1-a]isoindol-5-yl)cyclohexane-1-carboxamide (1S,4r)-4-hydroxy-4-((S)-5H-imidazo[5,1-a]isoindol-5-yl)cyclohexane-1-carboxamide (1S,4s)-4-hydroxy-4-((R)-5H-imidazo[5,1-a]isoindol-5-yl)cyclohexane-1-carboxamide (1R,4s)-4-hydroxy-4-((S)-5H-imidazo[5,1-a]isoindol-5-yl)cyclohexane-1-carboxamide 140a

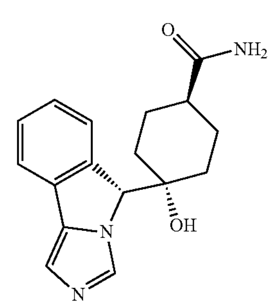

-continued

140b

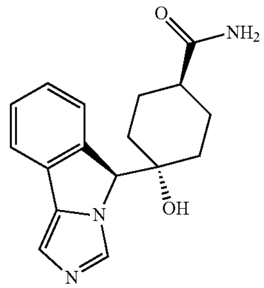

140c

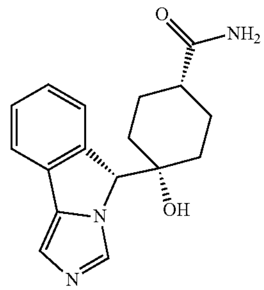

140d

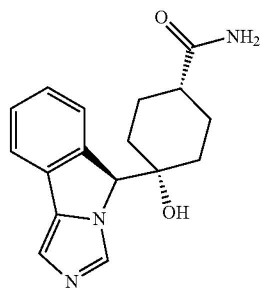

To the solution of 4-hydroxy-4-(5H-imidazo[5,1-a]isoindol-5-yl)cyclohexane-1-carbonitrile (Example 145, 540 mg, 2.1 mmol) in methanol (15 mL), sodium hydroxide (840 mg, 21 mmol) and 30% hydrogen peroxide (2.11 mL, 21 mmol) were added and stirred for overnight at room temperature. Solvent was removed and crude product was extracted with 5% 2,2,2-trifluoroethanol in DCM. Combined organic layers were washed with water, brine, dried over sodium sulfate and purified on combi-flash using MeOH/DCM (6%-10%). The product was further isolated by chiral separation to afford 4 isomers as white solid. The stereochemistry of each isomer was arbitrarily assigned.

Example 140a: (1R,4r)-4-hydroxy-4-((R)-5H-imidazo[5,1-a]isoindol-5-yl)cyclohexane-1-carboxamide: LCMS (ESI, m/z): 298.1 $[M+H]^+$; $^1H$ NMR (DMSO-d6) δ :7.79 (s, 1H), 7.56 (dt, J=7.6, 0.9 Hz, 1H), 7.51 (dd, J=7.8, 1.0 Hz, 1H), 7.42-7.32 (m, 1H), 7.22 (td, J=7.6, 1.2 Hz, 1H), 7.10 (s, 1H), 7.08-7.00 (m, 1H), 6.60 (s, 1H), 5.10 (s, 1H), 4.99 (s, 1H), 2.36-2.26 (m, 1H), 1.89-1.55 (m, 5H), 1.42 (d, J=7.0 Hz, 1H), 1.23 (td, J=12.9, 4.3 Hz, 1H), 0.82 (d, J=13.3 Hz, 1H)

Example 140b: (1S,4r)-4-hydroxy-4-((S)-5H-imidazo[5,1-a]isoindol-5-yl)cyclohexane-1-carboxamide: LCMS (ESI, m/z): 298.1 $[M+H]^+$; $^1H$ NMR is the same as Example 140a.

Example 140c: (1S,4s)-4-hydroxy-4-((R)-5H-imidazo[5,1-a]isoindol-5-yl)cyclohexane-1-arboxamide, LCMS (ESI, m/z): 298.1 $[M+H]^+$; $^1H$ NMR (400 MHz, DMSO-d6) δ 7.61-7.56 (m, 2H), 7.39 (ddt, J=8.0, 7.5, 0.6 Hz, 1H), 7.25 (td, J=7.6, 1.2 Hz, 1H), 7.12 (d, J=0.5 Hz, 1H), 7.04 (s, 1H), 6.59 (s, 1H), 5.14 (s, 1H), 5.11 (s, 1H), 1.88-1.54 (m, 4H), 1.43 (ddd, J=29.0, 26.2, 13.7 Hz, 3H), 1.04-0.95 (m, 1H), 0.86 (td, J=13.3, 4.2 Hz, 1H).

Example 140d: (1R,4s)-4-hydroxy-4-((S)-5H-imidazo[5,1-a]isoindol-5-yl)cyclohexane-1-carboxamide: LCMS (ESI, m/z): 298.1 $[M+H]^+$; $^1H$ NMR is the same as Example 140c.

Example 141: 8-(5H-imidazo[5,1-a]isoindol-5-yl)-5,6,7,8-tetrahydroisoquinolin-8-ol

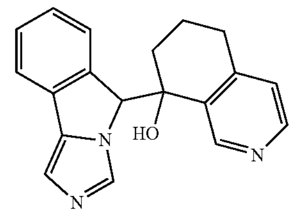 [SMILES: OC1(C2c3ccccc3-c3cncn32)CCCc2ccncc21]

(R)-8-((R)-5H-imidazo[5,1-a]isoindol-5-yl)-5,6,7,8-tetrahydroisoquinolin-8-ol
(S)-8-((R)-5H-imidazo[5,1-a]isoindol-5-yl)-5,6,7,8-tetrahydroisoquinolin-8-ol
(R)-8-((S)-5H-imidazo[5,1-a]isoindol-5-yl)-5,6,7,8-tetrahydroisoquinolin-8-ol
(S)-8-((S)-5H-imidazo[5,1-a]isoindol-5-yl)-5,6,7,8-tetrahydroisoquinolin-8-ol 141a

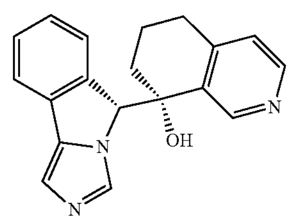

141b

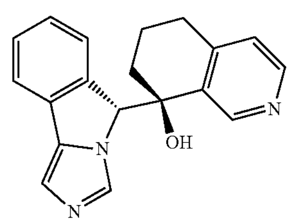

141c

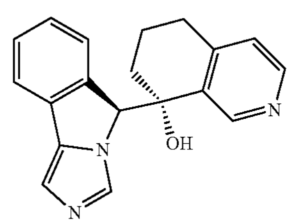

141d

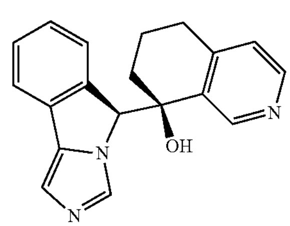

To a solution of 5H-imidazo[5,1-a]isoindole (573 mg, 3.67 mmol) in anhydrous THF (15 mL) at −70° C. was added n-BuLi (1.47 mL, 3.67 mmol, 2.5 M solution in hexanes). After stirring for 1 hr at −70° C., a mixture of 6,7-dihydroisoquinolin-8(5H)-one (180 mg, 1.22 mmol) in 5 mL THF was added. After 1 hr at −78° C., the reaction was quenched with water (1 mL) and $NH_4Cl$ solution (20 mL). The separated aqueous layer was subsequently extracted with DCM (20 mL×3). Combined organic phase was dried over $Na_2SO_4$, filtrated and purified on Combi-Flash using MeOH/DCM (4%-10%). The product was further isolated by chiral separation to afford 4 isomers as white solid. The stereochemistry of each isomer was arbitrarily assigned.

Example 141a: (R)-8-((R)-5H-imidazo[5,1-a]isoindol-5-yl)-5,6,7,8-tetrahydroisoquinolin-8-ol: LCMS (ESI, m/z): 304.2 $[M+H]^+$; $^1H$ NMR is the same as Example 141d.

Example 141b: (S)-8-((R)-5H-imidazo[5,1-a]isoindol-5-yl)-5,6,7,8-tetrahydroisoquinolin-8-ol: LCMS (ESI, m/z): 304.2 $[M+H]^+$; $^1H$ NMR (400 MHz, DMSO-$d_6$) δ 9.16 (s, 1H), 8.48 (d, J=5.0 Hz, 1H), 7.94 (s, 1H), 7.59 (dt, J=7.7, 1.0 Hz, 1H), 7.30 (tt, J=7.6, 1.0 Hz, 1H), 7.23-7.16 (m, 2H), 6.92 (td, J=7.6, 1.1 Hz, 1H), 6.31 (s, 1H), 6.04 (s, 1H), 5.74 (dq, J=7.8, 0.9 Hz, 1H), 2.60 (dt, J=17.4, 4.7 Hz, 1H), 2.23-2.10 (m, 1H), 1.59-1.43 (m, 1H), 1.28-1.10 (m, 2H), 0.85 (ddd, J=13.6, 11.2, 2.9 Hz, 1H).

Example 141c: (R)-8-((S)-5H-imidazo[5,1-a]isoindol-5-yl)-5,6,7,8-tetrahydroisoquinolin-8-ol: LCMS (ESI, m/z): 304.2 $[M+H]^+$; $^1H$ NMR is the same as Example 141b.

Example 141d: (S)-8-((S)-5H-imidazo[5,1-a]isoindol-5-yl)-5,6,7,8-tetrahydroisoquinolin-8-ol: LCMS (ESI, m/z): 304.2 $[M+H]^+$; $^1H$ NMR (400 MHz, DMSO-$d_6$) δ 9.11 (s, 1H), 8.46 (d, J=5.0 Hz, 1H), 7.81 (dq, J=7.7, 1.0 Hz, 1H), 7.61 (dt, J=7.5, 1.0 Hz, 1H), 7.42 (tdd, J=7.5, 1.2, 0.6 Hz, 1H), 7.31 (td, J=7.6, 1.2 Hz, 1H), 7.18 (dd, J=5.0, 0.8 Hz, 1H), 7.08 (s, 1H), 6.31 (s, 1H), 5.99 (s, 1H), 5.90 (s, 1H), 2.68-2.56 (m, 1H), 2.24 (ddd, J=16.6, 10.2, 5.2 Hz, 1H), 1.64-1.49 (m, 1H), 1.35 (dd, J=12.8, 6.1 Hz, 1H), 1.16 (t, J=7.0 Hz, 1H), 0.92 (ddd, J=14.3, 11.4, 3.1 Hz, 1H).

Example 142: 2-(5H-imidazo[5,1-a]isoindol-5-yl)-7-(methylsulfonyl)-1,2,3,4-tetrahydronaphthalen-1-ol

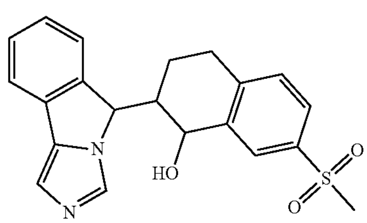 [SMILES: CS(=O)(=O)c1ccc2c(c1)C(O)C(C1c3ccccc3-c3cncn31)CC2]

(1R,2R)-2-((R)-5H-imidazo[5,1-a]isoindol-5-yl)-7-(methylsulfonyl)-1,2,3,4-tetrahydronaphthalen-1-ol (1S,2S)-2-((S)-5H-imidazo[5,1-a]isoindol-5-yl)-7-(methylsulfonyl)-1,2,3,4-tetrahydronaphthalen-1-ol Step 1:

2-(5H-imidazo[5,1-a]isoindol-5-yl)-7-(methylthio)-3,4-dihydronaphthalen-1(2H)-one

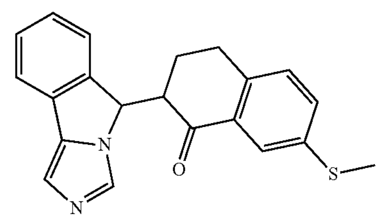 [SMILES: CSc1ccc2c(c1)C(=O)C(C1c3ccccc3-c3cncn31)CC2]

To the solution of 2-(1-trityl-1H-imidazol-4-yl)benzaldehyde (1.5 g, 3.62 mmol) and 7-(methylthio)-3,4-dihydronaphthalen-1(2H)-one (869 mg, 4.52 mmol) in Methanol (120 mL) was added sodium ethoxide (2.03 mL, 5.43 mmol, 21% in ethanol) and reaction was refluxed for 5 hours. Acetic acid (7 mL) was added to the reaction mixture and was refluxed for 2 hours. Methanol and acetic acid were evaporated on a rotary evaporator and crude was dissolved in water, solid sodium carbonate was added portion to neutralize remaining acetic acid. Crude was then extracted using DCM (2×30 mL), which was further purified on a Combi-Flash. LCMS (ESI, m/z): 347.2 $[M+H]^+$ Step 2:

(1R,2S)-2-((S)-5H-imidazo[5,1-a]isoindol-5-yl)-7-(methylthio)-1,2,3,4-tetrahydronaphthalen-1-ol

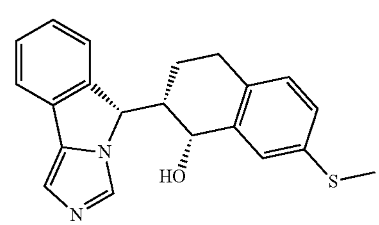 [SMILES: CSc1ccc2c(c1)[C@H](O)[C@H]([C@H]1c3ccccc3-c3cncn31)CC2]

Under argon, a solution of 2-(5H-imidazo[5,1-a]isoindol-5-yl)-7-(methylthio)-3,4-dihydronaphthalen-1(2H)-one (800 mg, 2.31 mmol, 1.000 equiv) in THF (50 mL) was added to L-Selectride (3.46 mL, 3.46 mmol, 1.0 M in THF) at −78° C. The resulting solution was stirred for 15 minutes at −78° C. The reaction was then quenched by the addition of ethanol (25 mL). The resulting mixture was concentrated under vacuum, washed with water and brine. The residue was applied onto Combi-Flash for further purification: LCMS (ESI, m/z): 349.2 $[M+H]^+$. $^1H$ NMR (400 MHz, DMSO-$d_6$) δ 7.97 (s, 1H), 7.65-7.57 (m, 2H), 7.39 (tt, J=7.6, 0.9 Hz, 1H), 7.32-7.22 (m, 3H), 7.15-7.09 (m, 3H), 7.03 (t, J=7.8 Hz, 1H), 5.86 (d, J=5.7 Hz, 1H), 5.51 (d, J=2.2 Hz, 1H), 4.99-4.93 (m, 1H), 2.48 (s, 3H), 2.45 (s, 1H), 1.47 (qd, J=12.6, 5.4 Hz, 1H), 0.95 (d, J=12.9 Hz, 1H).

Step 3:

(1R,2S)-2-((S)-5H-imidazo[5,1-a]isoindol-5-yl)-7-(methylsulfonyl)-1,2,3,4-tetrahydronaphthalen-1-ol

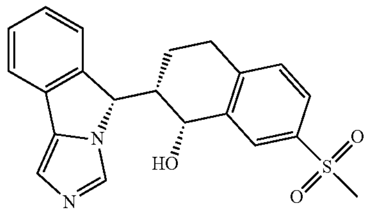 [SMILES: CS(=O)(=O)c1ccc2c(c1)[C@H](O)[C@H]([C@H]1c3ccccc3-c3cncn31)CC2]

To the solution 2-(5H-imidazo[5,1-a]isoindol-5-yl)-7-(methylthio)-1,2,3,4-tetrahydronaphthalen-1-ol (0.4 g, 1.15 mmol) in acetic acid (3 mL) was added hydrogen peroxide (30% solution in water, 0.39 g, 1.14 mL, 11.48 mmol) and the reaction was stirred at room temperature for 28 hours. Acetic acid was then removed using a rotovapor, residual acetic acid was quenched using saturated sodium carbonate solution. Crude product was extracted using 2,2,2-trifluoroethanol in DCM (2×30 mL). Combined organic layers were washed with brine, dried over sodium sulfate, evaporated on a rotovapor to yield crude product. The residue was applied onto Combi-Flash for further purification: LCMS (ESI, m/z): 381.2 $[M+H]^+$ Step 4:

(1S,2S)-2-((S)-5H-imidazo[5,1-a]isoindol-5-yl)-7-(methylsulfonyl)-1,2,3,4-tetrahydronaphthalen-1-yl 4-nitrobenzoate

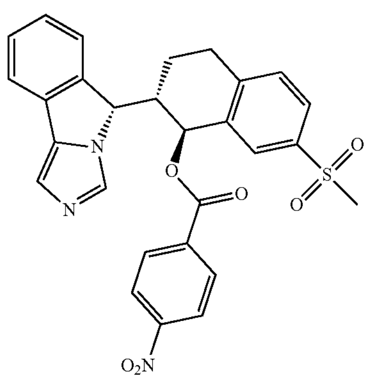 [SMILES: CS(=O)(=O)c1ccc2c(c1)[C@@H](OC(=O)c1ccc([N+](=O)[O-])cc1)[C@H]([C@H]1c3ccccc3-c3cncn31)CC2]

Under argon, To a solution of 2-(5H-imidazo[5,1-a]isoindol-5-yl)-7-(methylsulfonyl)-1,2,3,4-tetrahydronaphthalen-1-ol (420 mg, 1.1 mmol), 4-nitrobenzoic acid (276 mg, 1.66 mmol, 1.5 equiv) in THF (20 mL) was added n-$Bu_3P$ (16.92 mL, 5.52 mmol, 10% in hexane) at 0° C. This was followed by the addition of DBAD (7.39 mL, 5.52 mmol, 20% in toluene) at 0° C. The resulting solution was stirred for 16 h at room temperature. The resulting solution was diluted with DCM (30 mL) and then quenched by the addition of water (10 mL). The resulting solution was extracted with dichloromethane (3×15 mL) and the organic layers combined and dried over anhydrous sodium sulfate and concentrated under vacuum. Crude product was further purified on a Combi-Flash: LCMS (ESI, m/z): 530.1 $[M+H]^+$. $^1$H NMR (400 MHz, DMSO-$d_6$) δ 8.41-8.35 (m, 2H), 8.25 (d, J=8.8 Hz, 2H), 8.07 (s, 1H), 7.81 (dd, J=8.0, 2.0 Hz, 1H), 7.68 (s, 1H), 7.63-7.55 (m, 2H), 7.43 (dd, J=21.3, 7.8 Hz, 2H), 7.30 (d, J=1.2 Hz, 1H), 6.65 (d, J=10.1 Hz, 1H), 5.63 (s, 1H), 3.15 (s, 3H), 1.96-1.81 (m, 2H), 1.80-1.57 (m, 3H).

Step 5:

(1R,2R)-2-((R)-5H-imidazo[5,1-a]isoindol-5-yl)-7-(methylsulfonyl)-1,2,3,4-tetrahydronaphthalen-1-ol (1S,2S)-2-((S)-5H-imidazo[5,1-a]isoindol-5-yl)-7-(methylsulfonyl)-1,2,3,4-tetrahydronaphthalen-1-ol 142a

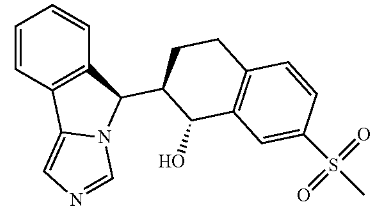

142b

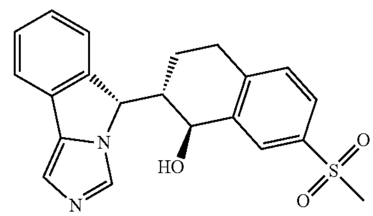

A solution of 2-(5H-imidazo[5,1-a]isoindol-5-yl)-7-(methylsulfonyl)-1,2,3,4-tetrahydronaphthalen-1-yl 4-nitrobenzoate (360 mg, 0.68 mmol) in THF (10 mL) and water (2 mL) was added LiOH (167 mg, 6.8 mmol). The resulting solution was stirred for 40 min at room temperature. The resulting solution was diluted with water (10 mL). The resulting solution was extracted with dichloromethane and the organic layers combined and dried over anhydrous sodium sulfate to obtain crude product, which was purified on a Combi-Flash and further isolated by chiral separation to afford 2 isomers as white solid. The absolute configuration of all isomers was assigned arbitrarily.

Example 142a: (1R,2R)-2-((R)-5H-imidazo[5,1-a]isoindol-5-yl)-7-(methylsulfonyl)-1,2,3,4-tetrahydronaphthalen-1-ol: LCMS (ESI, m/z): 381.2 $[M+H]^+$; $^1$H NMR (400 MHz, DMSO-$d_6$) δ 8.22-8.18 (m, 1H), 7.98 (s, 1H), 7.71 (dd, J=8.0, 2.1 Hz, 1H), 7.64 (d, J=7.5 Hz, 1H), 7.52-7.47 (m, 1H), 7.42 (t, J=7.4 Hz, 1H), 7.34-7.28 (m, 2H), 7.19 (s, 1H), 6.36 (d, J=7.6 Hz, 1H), 5.82 (s, 1H), 5.06-4.94 (m, 1H), 3.20 (s, 3H), 2.68 (dd, J=8.5, 4.5 Hz, 2H), 2.43 (s, 1H), 0.97-0.78 (m, 2H).

Example 142b: (1S,2S)-2-((S)-5H-imidazo[5,1-a]isoindol-5-yl)-7-(methylsulfonyl)-1,2,3,4-tetrahydronaphthalen-1-ol Example 143: 1-(5H-imidazo[5,1-a]isoindol-5-yl)-1-(1H-imidazol-2-yl)ethan-1-ol

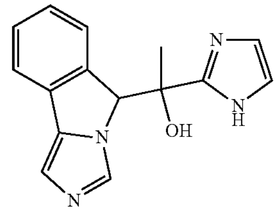 [SMILES: CC(O)(c1ncc[nH]1)C1c2ccccc2-c2cncn21]

(R)-1-((R)-5H-imidazo[5,1-a]isoindol-5-yl)-1-(1H-imidazol-2-yl)ethan-1-ol (R)-1-((S)-5H-imidazo[5,1-a]isoindol-5-yl)-1-(1H-imidazol-2-yl)ethan-1-ol (S)-1-((R)-5H-imidazo[5,1-a]isoindol-5-yl)-1-(1H-imidazol-2-yl)ethan-1-ol (S)-1-((S)-5H-imidazo[5,1-a]isoindol-5-yl)-1-(1H-imidazol-2-yl)ethan-1-ol Step 1:

1-(1-((2-(trimethylsilyl) ethoxy)methyl)-1H-imidazol-2-yl)ethan-1-one

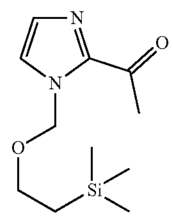 [SMILES: CC(=O)c1nccn1COCC[Si](C)(C)C]

To a solution of 1-(1H-imidazol-2-yl)ethanone (500 mg, 4.54 mmol) in DCM (20 mL) was added DIPEA (1.58 ml, 9.09 mmol) and SEM chloride (0.80 ml dissolved in 5 mL DCM, 4.54 mmol). The resulting mixture was stirred at RT for 1 hr. Saturated aqueous sodium bicarbonate (10 mL) was then added and the aqueous phase was extracted with DCM (3×10 mL extractions). The combined organic extracts were dried ($Na_2SO_4$), filtered and concentrated in vacuo to yield the title compound as a yellow oil. LCMS (ESI, m/z): 183.2 $[M+H]^+$. $^1$H NMR (400 MHz, DMSO-$d_6$) δ 7.66 (d, J=1.1 Hz, 1H), 7.16 (d, J=1.0 Hz, 1H), 5.68 (s, 2H), 3.55-3.44 (m, 2H), 2.55 (s, 3H), 0.87-0.74 (m, 2H), −0.07 (s, 9H).

Step 2: 1-(5H-imidazo[5,1-a]isoindol-5-yl)-1-(1-((2-(trimethylsilyl) ethoxy)methyl)-1H-imidazol-2-yl) ethan-1-ol

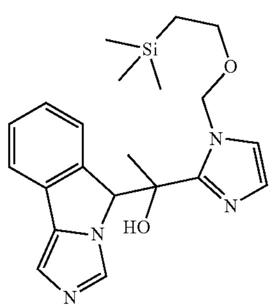 [SMILES: CC(O)(c1nccn1COCC[Si](C)(C)C)C1c2ccccc2-c2cncn21]

To a solution of 5H-imidazo[5,1-a]isoindole (870 mg, 5.57 mmol) in anhydrous THF (20 mL) at −40° C. was added n-BuLi (2.5M solution in hexanes, 0.357 g, 2.23 mL, 5.57 mmol) and stirred for 1 hr. Solution of 1-(1-((2-(trimethylsilyl) ethoxy)methyl)-1H-imidazol-2-yl)ethan-1-one (0.67 g, 2.79 mmol) in anhydrous THF (3 mL) was added dropwise and reaction was slowly warmed to 0° C. over a period of 3 hours. Reaction was again cooled to 40° C. and quenched with sat. $NH_4Cl$ solution. Crude product was extracted using DCM and further purified on a Combi-Flash. LCMS (ESI, m/z): 397.3 $[M+H]^+$.

Step 3:

(R)-1-((R)-5H-imidazo[5,1-a]isoindol-5-yl)-1-(1H-imidazol-2-yl)ethan-1-ol (R)-1-((S)-5H-imidazo[5,1-a]isoindol-5-yl)-1-(1H-imidazol-2-yl)ethan-1-ol (S)-1-((R)-5H-imidazo[5,1-a]isoindol-5-yl)-1-(1H-imidazol-2-yl)ethan-1-ol (S)-1-((S)-5H-imidazo[5,1-a]isoindol-5-yl)-1-(1H-imidazol-2-yl)ethan-1-ol 143a

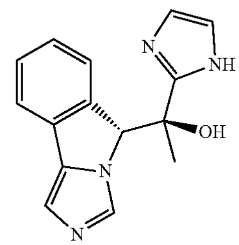

143b

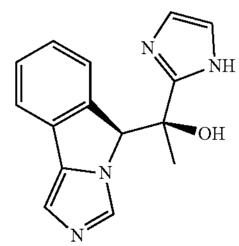

143c

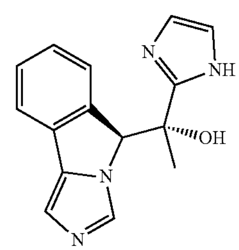

143d

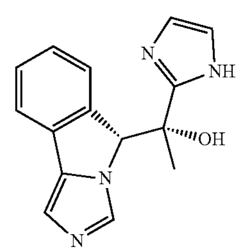

Solution of 4M HCl in dioxane (3 mL) was added to 1-(5H-imidazo[5,1-a]isoindol-5-yl)-1-(1-((2-(trimethylsilyl) ethoxy)methyl)-1H-imidazol-2-yl)ethan-1-ol (480 mg) and mixture was stirred at 50° C. for 3 hours. Reaction was quenched by sat $Na_2CO_3$ solution, and crude product was extracted using 10% TFE in DCM. Crude product was further purified on a Combi-Flash and further isolated by chiral separation to afford 4 isomers as white solid. The absolute configuration of all isomers was assigned arbitrarily.

Example 143a: (R)-1-((R)-5H-imidazo[5,1-a]isoindol-5-yl)-1-(1H-imidazol-2-yl)ethan-1-ol: LCMS (ESI, m/z): 267.2 $[M+H]^+$; $^1$H NMR (500 MHz, DMSO-$d_6$) δ 12.24 (s, 1H), 7.64 (s, 1H), 7.57 (d, J=7.6 Hz, 1H), 7.32 (dd, J=8.0, 7.1 Hz, 1H), 7.24-7.22 (m, 1H), 7.15 (s, 1H), 7.05-6.99 (m, 2H), 6.20 (s, 1H), 6.03-5.98 (m, 1H), 5.79 (s, 1H), 0.92 (s, 3H).

Example 143b: (R)-1-((S)-5H-imidazo[5,1-a]isoindol-5-yl)-1-(1H-imidazol-2-yl)ethan-1-ol: LCMS (ESI, m/z): 267.2 $[M+H]^+$; $^1$H NMR (500 MHz, DMSO-$d_6$) δ 12.13 (s, 1H), 7.59-7.55 (m, 1H), 7.38 (ddd, J=7.6, 6.8, 1.0 Hz, 1H), 7.29 (d, J=7.6 Hz, 1H), 7.21 (td, J=7.6, 1.1 Hz, 1H), 7.18 (dd, J=2.1, 1.2 Hz, 1H), 7.06 (s, 1H), 6.98 (t, J=1.3, 1.3 Hz, 1H), 6.54 (s, 1H), 6.17 (s, 1H), 5.74 (s, 1H), 1.10 (s, 3H).

Example 143c: (S)-1-((R)-5H-imidazo[5,1-a]isoindol-5-yl)-1-(1H-imidazol-2-yl)ethan-1-ol: LCMS (ESI, m/z): 267.2 $[M+H]^+$; $^1$H NMR (500 MHz, DMSO-$d_6$) δ 12.24 (s, 1H), 7.64 (s, 1H), 7.57 (dd, J=7.6, 0.9 Hz, 1H), 7.32 (t, J=0.9, 0.9 Hz, 1H), 7.23 (dd, J=2.1, 1.2 Hz, 1H), 7.15 (s, 1H), 7.06-6.98 (m, 2H), 6.20 (s, 1H), 6.01 (dd, J=7.7, 1.0 Hz, 1H), 5.79 (s, 1H), 0.92 (s, 3H).

Example 143d: (S)-1-((S)-5H-imidazo[5,1-a]isoindol-5-yl)-1-(1H-imidazol-2-yl)ethan-1-ol: LCMS (ESI, m/z): 267.2 $[M+H]^+$; $^1$H NMR (500 MHz, DMSO-$d_6$) δ 12.13 (s, 1H), 7.57 (dt, J=7.5, 0.9 Hz, 1H), 7.38 (tt, J=7.5, 0.8 Hz, 1H), 7.29 (d, J=7.6 Hz, 1H), 7.25-7.13 (m, 2H), 7.07 (s, 1H), 6.98 (s, 1H), 6.54 (s, 1H), 6.17 (s, 1H), 5.74 (s, 1H), 1.11 (s, 3H): LCMS (ESI, m/z): 381.2 $[M+H]^+$; $^1$H NMR (400 MHz, DMSO-$d_6$) δ 8.22-8.18 (m, 1H), 7.98 (s, 1H), 7.71 (dd, J=8.0, 2.1 Hz, 1H), 7.64 (d, J=7.5 Hz, 1H), 7.52-7.47 (m, 1H), 7.42 (t, J=7.4 Hz, 1H), 7.34-7.28 (m, 2H), 7.19 (s, 1H), 6.36 (d, J=7.6 Hz, 1H), 5.82 (s, 1H), 5.06-4.94 (m, 1H), 3.20 (s, 3H), 2.68 (dd, J=8.5, 4.5 Hz, 2H), 2.43 (s, 1H), 0.97-0.78 (m, 2H).

Example 144: 3-(5H-Imidazo[5,1-a]isoindol-5-yl) tetrahydro-2H-pyran-3-ol

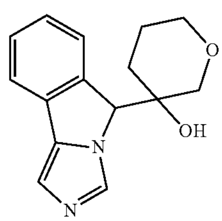 [SMILES: OC1(C2c3ccccc3-c3cncn32)CCCOC1]

(S)-3-((R)-5H-Imidazo[5,1-a]isoindol-5-yl)tetrahydro-2H-pyran-3-ol (S)-3-((S)-5H-Imidazo[5,1-a]isoindol-5-yl)tetrahydro-2H-pyran-3-ol (R)-3-((R)-5H-Imidazo[5,1-a]isoindol-5-yl)tetrahydro-2H-pyran-3-ol (R)-3-((S)-5H-Imidazo[5,1-a]isoindol-5-yl)tetrahydro-2H-pyran-3-ol Step 1:

(S)-3-((R)-5H-Imidazo[5,1-a]isoindol-5-yl)tetrahydro-2H-pyran-3-ol (S)-3-((S)-5H-Imidazo[5,1-a]isoindol-5-yl)tetrahydro-2H-pyran-3-ol (R)-3-((R)-5H-Imidazo[5,1-a]isoindol-5-yl)tetrahydro-2H-pyran-3-ol (R)-3-((S)-5H-Imidazo[5,1-a]isoindol-5-yl)tetrahydro-2H-pyran-3-ol 144a

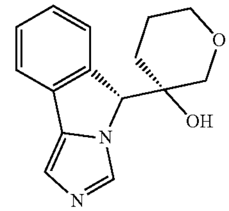

144b

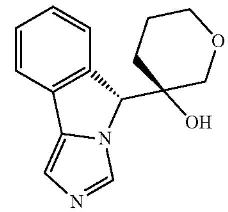

144c

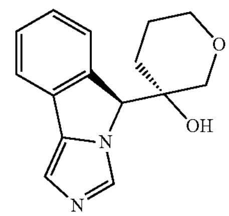

144d

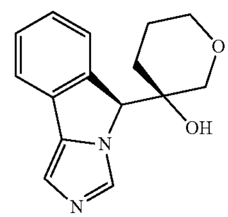

To a solution of 5H-imidazo[5,1-a]isoindole (500 mg, 3.20 mmol) in anhydrous THF (5 mL) at −78° C. was added n-BuLi (1.28 mL, 3.20 mmol, 2.5 M solution hexanes). After stirring for 0.5 at −78° C., a solution of dihydro-2H-pyran-3(4H)-one (160 mg, 1.60 mmol) in THF (2 mL) was added and the reaction was allowed to warm to RT over a period of 3 h and was quenched by adding satd. $NH_4Cl$ (5 mL) and the reaction was diluted with water (30 mL), the product was extracted with $CH_2Cl_2$ (3×40 mL). The combined organic extract was dried over $Na_2SO_4$ and concentrated under reduced pressure. The crude was purified by combi-flash using MeOH/DCM (1:9) as eluent. The final products were further isolated by chiral separation to afford 4 isomers and the stereochemistry of each isomer was arbitrarily assigned.

Example 144a: (R)-3-((S)-5H-imidazo[5,1-a]isoindol-5-yl)tetrahydro-2H-pyran-3-ol: LCMS (ESI, m/z): 257.2 $[M+H]^+$; $^1$HNMR (500 MHz, DMSO-$d_6$) δ 7.87 (s, 1H), 7.61 (dq, J=7.6, 0.9 Hz, 1H), 7.58 (dt, J=7.6, 0.9 Hz, 1H), 7.39 (tt, J=7.6, 0.8 Hz, 1H), 7.25 (td, J=7.6, 1.2 Hz, 1H), 7.12 (s, 1H), 5.36 (s, 1H), 5.19 (s, 1H), 3.69 (d, J=11.2 Hz, 1H), 3.28-3.21 (m, 2H), 3.16 (td, J=11.2, 2.6 Hz, 1H), 1.86 (ddt, J=21.4, 10.6, 5.1 Hz, 1H), 1.58-1.47 (m, 2H).

Example 144b: (R)-3-((R)-5H-imidazo[5,1-a]isoindol-5-yl)tetrahydro-2H-pyran-3-ol: LCMS (ESI, m/z): 257.2 $[M+H]^+$; $^1$HNMR (500 MHz, DMSO-$d_6$) δ 7.84 (s, 1H), 7.59 (dt, J=7.6, 0.9 Hz, 1H), 7.55 (dq, J=7.9, 1.0 Hz, 1H), 7.39 (tt, J=7.5, 0.8 Hz, 1H), 7.25 (td, J=7.6, 1.2 Hz, 1H), 7.13 (s, 1H), 5.37 (s, 1H), 5.20 (s, 1H), 3.70 (dd, J=11.5, 2.2 Hz, 2H), 3.58 (d, J=11.5 Hz, 1H), 3.14 (td, J=11.3, 2.6 Hz, 1H), 1.16-1.02 (m, 2H).

Example 144c: (S)-3-((S)-5H-imidazo[5,1-a]isoindol-5-yl)tetrahydro-2H-pyran-3-ol: LCMS (ESI, m/z): 257.2 $[M+H]^+$; $^1$HNMR (500 MHz, DMSO-$d_6$) δ 7.84 (s, 1H), 7.59 (dt, J=7.6, 0.9 Hz, 1H), 7.55 (dq, J=7.9, 1.0 Hz, 1H), 7.39 (tt, J=7.5, 0.8 Hz, 1H), 7.25 (td, J=7.6, 1.2 Hz, 1H), 7.13 (s, 1H), 5.37 (s, 1H), 5.20 (s, 1H), 3.70 (dd, J=11.5, 2.2 Hz, 2H), 3.58 (d, J=11.5 Hz, 1H), 3.14 (td, J=11.3, 2.6 Hz, 1H), 1.16-1.02 (m, 2H).

Example 144d: (S)-3-((R)-5H-imidazo[5,1-a]isoindol-5-yl)tetrahydro-2H-pyran-3-ol: LCMS (ESI, m/z): 257.2 $[M+H]^+$; $^1$HNMR (500 MHz, DMSO-$d_6$) δ 7.87 (s, 1H), 7.61 (dq, J=7.6, 0.9 Hz, 1H), 7.58 (dt, J=7.6, 0.9 Hz, 1H), 7.39 (tt, J=7.6, 0.8 Hz, 1H), 7.25 (td, J=7.6, 1.2 Hz, 1H), 7.12 (s, 1H), 5.36 (s, 1H), 5.19 (s, 1H), 3.69 (d, J=11.2 Hz, 1H), 3.28-3.21 (m, 2H), 3.16 (td, J=11.2, 2.6 Hz, 1H), 1.86 (ddt, J=21.4, 10.6, 5.1 Hz, 1H), 1.58-1.47 (m, 2H).

Example 145: 4-hydroxy-4-(5H-imidazo[5,1-a]isoindol-5-yl)cyclohexane-1-carbonitrile

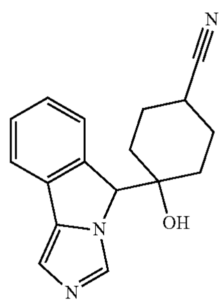 [SMILES: N#CC1CCC(O)(C2c3ccccc3-c3cncn32)CC1]

(1R,4r)-4-hydroxy-4-((R)-5H-imidazo[5,1-a]isoindol-5-yl)cyclohexane-1-carbonitrile (1R,4s)-4-hydroxy-4-((S)-5H-imidazo[5,1-a]isoindol-5-yl)cyclohexane-1-carbonitrile (1S,4s)-4-hydroxy-4-((R)-5H-imidazo[5,1-a]isoindol-5-yl)cyclohexane-1-carbonitrile (1S,4r)-4-hydroxy-4-((S)-5H-imidazo[5,1-a]isoindol-5-yl)cyclohexane-1-carbonitrile 145a

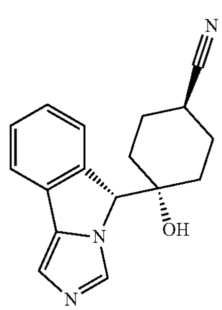

-continued

145b

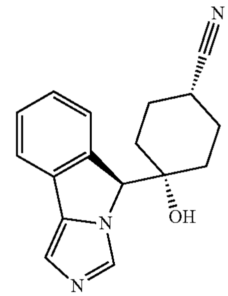

145c

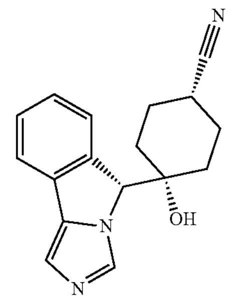

145d

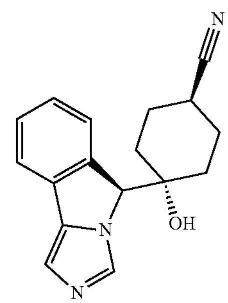

To a solution of 5H-imidazo[5,1-a]isoindole (600 mg, 3.84 mmol) in anhydrous THF (15 mL) at −78° C. was added n-BuLi (1.54 mL, 3.84 mmol, 2.5 M solution hexanes). After stirring for 1 hr at −78° C., the solution was warm up to 0° C. In the second flask containing a mixture of 4-oxocyclohexane-1-carbonitrile (473 mg, 3.84 mmol) in 10 mL THF was cooled to −78° C., which was treated with the above in-situ generated lithium reagent dropwise in 10 min. After 1 hr at −78° C., the reaction was quenched with water (1 mL) and $NH_4Cl$ solution (20 mL). The separated aqueous layer was subsequently extracted with DCM (20 mL×3). Combined organic phase was dried over $Na_2SO_4$, filtrated and purified on Combi-Flash using MeOH/DCM (4%-8%). The product was further isolated by chiral separation to afford 4 isomers as white solid. The stereochemistry of each isomer was arbitrarily assigned.

Example 145a: (1R,4r)-4-hydroxy-4-((R)-5H-imidazo[5,1-a]isoindol-5-yl)cyclohexane-1-carbonitrile: LCMS (ESI, m/z): 280.2 $[M+H]^+$; $^1$H NMR (500 MHz, DMSO-d6) δ 7.83 (s, 1H), 7.59 (dt, J=7.6, 0.9 Hz, 1H), 7.56 (dt, J=7.8, 1.0 Hz, 1H), 7.39 (tt, J=7.5, 0.8 Hz, 1H), 7.25 (td, J=7.6, 1.2 Hz, 1H), 7.13 (s, 1H), 5.35 (s, 1H), 5.14 (s, 1H), 1.90-1.78 (m, 2H), 1.78-1.66 (m, 2H), 1.62 (dd, J=13.4, 3.0 Hz, 1H), 1.47 (td, J=13.1, 6.1 Hz, 1H), 1.00 (dd, J=13.1, 3.1 Hz, 1H), 0.93 (td, J=12.8, 4.8 Hz, 1H).

Example 145b: (1R,4s)-4-hydroxy-4-((S)-5H-imidazo[5,1-a]isoindol-5-yl)cyclohexane-1-carbonitrile: LCMS (ESI, m/z): 280.2 $[M+H]^+$; $^1$H NMR (500 MHz, DMSO-d6) δ 7.85 (d, J=0.6 Hz, 1H), 7.62 (dt, J=1.7, 0.9 Hz, 1H), 7.60

(dq, J=2.0, 0.9 Hz, 1H), 7.40 (tt, J=7.6, 0.8 Hz, 1H), 7.27 (td, J=7.6, 1.2 Hz, 1H), 7.14 (s, 1H), 5.33 (s, 1H), 5.16 (s, 1H), 3.07 (s, 1H), 1.92 (ddt, J=12.8, 8.7, 4.0 Hz, 1H), 1.85-1.60 (m, 4H), 1.53 (d, J=13.6 Hz, 1H), 1.09 (td, J=13.6, 4.0 Hz, 1H), 0.96 (d, J=14.2 Hz, 1H).

Example 145c: (1S,4s)-4-hydroxy-4-((R)-5H-imidazo[5,1-a]isoindol-5-yl)cyclohexane-1-carbonitrile: LCMS (ESI, m/z): 280.2 $[M+H]^+$; $^1H$ NMR is the same as Example 145b.

Example 145d: (1S,4r)-4-hydroxy-4-((S)-5H-imidazo[5,1-a]isoindol-5-yl)cyclohexane-1-carbonitrile: LCMS (ESI, m/z): 280.2 $[M+H]^+$; $^1H$ NMR is the same as Example 145a.

Example 146 and 146-1: 5-(5H-imidazo[5,1-a]isoindol-5-yl)-4,5,6,7-tetrahydro-[1,2,3]triazolo[1,5-a]pyridin-4-ol and 7-(5H-imidazo[5,1-a]isoindol-5-yl)-5,6,7,8-tetrahydro-[1,2,4]triazolo[4,3-a]pyridin-8-ol

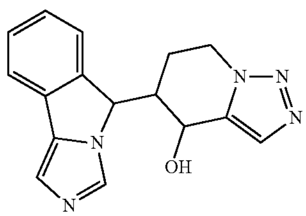

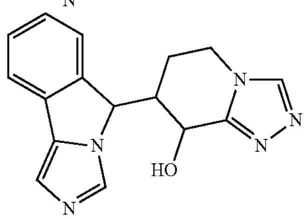

Step 1:

(4S,5S)-5-((S)-5H-imidazo[5,1-a]isoindol-5-yl)-4,5,6,7-tetrahydro-[1,2,3]triazolo[1,5-a]pyridin-4-ol (4R,5R)-5-((R)-5H-imidazo[5,1-a]isoindol-5-yl)-4,5,6,7-tetrahydro-[1,2,3]triazolo[1,5-a]pyridin-4-ol 146a

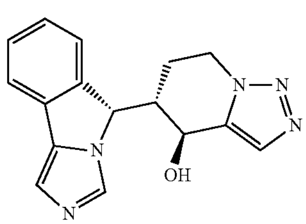

146b

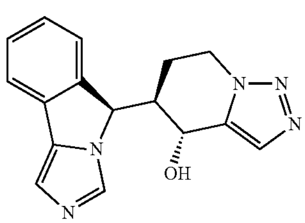

The title compound was synthesized by General Procedure for the Synthesis of 117a-b.

The crude product was purified by Prep-HPLC and further isolated by chiral separation with the following conditions:

1. Column, XBridge Prep C18 OBD Column 19×150 mm 5 um; mobile phase, water (0.05% $NH_4OH$): acetonitrile=10%-27%; Detector, uv 254/220 nm; flow rate, 20.0 mL/min.
2. Column, EnantioPak A1-5, 2.12×25 cm, 5 um; mobile phase:IPA:hexane=30:70; Detector, uv 254/220 nm; flow rate, 20 mL/min to afford 2 compounds:

The absolute configuration of all isomers 146a-b was assigned arbitrarily.

Example 146a: (4S,5S)-5-((S)-5H-imidazo[5,1-a]isoindol-5-yl)-4,5,6,7-tetrahydro-[1,2,3]triazolo[1,5-a]pyridin-4-ol (11.0 mg, 1%) as a white solid: LCMS (ESI, m/z): 294.3 $[M+H]^+$. $^1H$ NMR (300 MHz, $CD_3OD$) δ 8.04 (s, 1H), 7.76 (s, 1H), 7.66 (d, J=7.5 Hz, 1H), 7.52 (d, J=7.5 Hz, 1H), 7.46-7.42 (m, 1H), 7.36-7.31 (m, 1H), 7.21 (s, 1H), 6.46 (d, J=7.2 Hz, 1H), 5.78 (d, J=2.4 Hz, 1H), 5.18-5.12 (m, 1H), 4.32-4.26 (m, 1H), 4.08-4.00 (m, 1H), 2.64-2.51 (m, 1H), 1.26-1.07 (m, 2H). tR=3.570 min (Repaired Chiral ADH, 0.46×5 cm, Hex(0.2% IPAmine):IPA=70:30, 1 ml/min). 146a and 146b are enantiomers.

Example 146b: (4R,5R)-5-((R)-5H-imidazo[5,1-a]isoindol-5-yl)-4,5,6,7-tetrahydro-[1,2,3]triazolo[1,5-a]pyridin-4-ol (12.5 mg, 1%) as a white solid: LCMS (ESI, m/z): 294.2 $[M+H]^+$. tR=4.661 min (Repaired Chiral ADH, 0.46×5 cm, Hex(0.2% IPAmine):IPA=70:30, 1 ml/min). 146a and 146b are enantiomers.

Step 1: 3-(benzyloxy)-2-chloropyridine

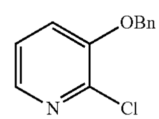 [SMILES: Clc1ncccc1OCc1ccccc1]

A mixture of 2-chloropyridin-3-ol (20 g, 154.39 mmol) and potassium carbonate (23 g, 166.42 mmol) in acetone (150 mL) was added BnBr (28.9 g, 168.97 mmol). The resulting solution was stirred for 16 h at room temperature. The solids were filtered out. The resulting solution was concentrated under vacuum. The residue was purified by silica gel column eluting with EtOAc/petroleum ether (3.5/96.5). This resulted in 27 g (80%) of 3-(benzyloxy)-2-chloropyridine as off-white oil: LCMS (ESI, m/z): 220.2 $[M+H]^+$.

Step 2:

3-(benzyloxy)-2-hydrazinylpyridine

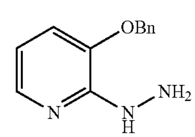 [SMILES: NNc1ncccc1OCc1ccccc1]

A solution of 3-(benzyloxy)-2-chloropyridine (7 g, 31.87 mmol), hydrazine (50 mL) in 2-methylpropan-2-ol (90 mL) was added potassium carbonate (13 g, 94.06 mmol). The resulting solution was stirred for 5 days at 100° C. The solids were filter out. The resulting solution was concentrated under vacuum. This resulted in 3.5 g (50%) of 3-(benzyloxy)-2-hydrazinylpyridine as a yellow solid: LCMS (ESI, m/z): 216.2 $[M+H]^+$.

Step 3: 8-(benzyloxy)-[1,2,4]triazolo[4,3-a]pyridine

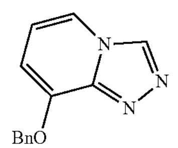 [SMILES: c1ccc(COc2cccn3cnnc23)cc1]

A solution of 3-(benzyloxy)-2-hydrazinylpyridine (22 g, 102.21 mmol) in (diethoxymethoxy)ethane (100 mL) was stirred for 3 h at 160° C. The solids were collected by filtration. This resulted in 15 g (65%) of 8-(benzyloxy)-[1,2,4]triazolo[4,3-a]pyridine as a yellow solid: LCMS (ESI, m/z): 226.2 $[M+H]^+$.

Step 4: 5H,6H,7H,8H-[1,2,4]triazolo[4,3-a]pyridin-8-ol

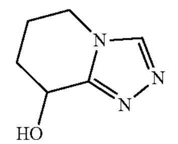

Under hydrogen, a solution of 8-(benzyloxy)-[1,2,4]triazolo[4,3-a]pyridine (6.5 g, 28.86 mmol) in MeOH (200 mL) was added Palladium carbon (2 g, 18.793 mmol). The resulting mixture was stirred for 24 h at room temperature. The solids were filtered out. The resulting solution was concentrated under vacuum. This resulted in 3.8 g (95%) of 5H,6H,7H,8H-[1,2,4]triazolo[4,3-a]pyridin-8-ol as a yellow solid: LCMS (ESI, m/z): 140.2 $[M+H]^+$.

Step 5: 6,7-dihydro-[1,2,4]triazolo[4,3-a]pyridin-8(5H)-one

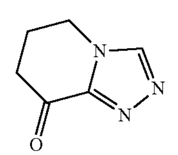

A solution of 5H,6H,7H,8H-[1,2,4]triazolo[4,3-a]pyridin-8-ol (2 g, 14.37 mmol, 1.000 equiv) in DCM (100 mL) was added DMP (12 g, 28.29 mmol). The resulting solution was stirred for 3 h at 25° C. The pH value of the solution was adjusted to 7-8 with $Ca(OH)_2$. The solids were filtered out. The residue was purified by silica gel column eluting with DCM/MeOH (95/5). This resulted in 1.6 g (81%) of 5H,6H,7H,8H-[1,2,4]triazolo[4,3-a]pyridin-8-one as a white solid.

Step 6: (E)-7-(2-(1-trityl-1H-imidazol-4-yl)benzylidene)-6,7-dihydro-[1,2,4]triazolo[4,3-a]pyridin-8(5H)-one

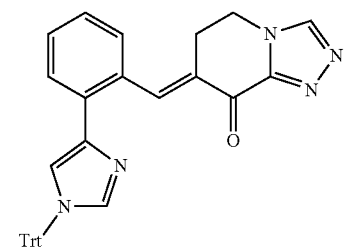

The title compound was synthesized by General Procedure for the Synthesis of int-2.

Step 7:

7-(5H-imidazo[5,1-a]isoindol-5-yl)-6,7-dihydro-[1,2,4]triazolo[4,3-a]pyridin-8(5H)-one

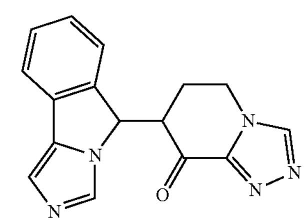 [SMILES: O=C1c2nncn2CCC1C1c2ccccc2-c2cncn21]

The title compound was synthesized by General Procedure for the Synthesis of int-3.

Step 8:

(7S,8R)-7-((S)-5H-imidazo[5,1-a]isoindol-5-yl)-5,6,7,8-tetrahydro-[1,2,4]triazolo[4,3-a]pyridin-8-ol (7R,8S)-7-((R)-5H-imidazo[5,1-a]isoindol-5-yl)-5,6,7,8-tetrahydro-[1,2,4]triazolo[4,3-a]pyridin-8-ol 146-1a

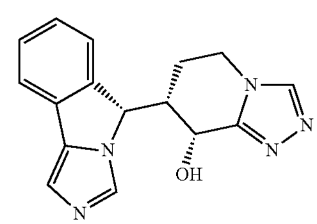

146-1b

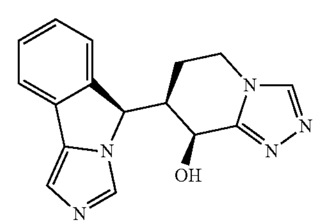

The title compound was synthesized by General Procedure for the Synthesis of 139-1a-d. The absolute configuration of all isomers 146c-d was assigned arbitrarily.

Example 146-1a: (7S,8R)-7-((S)-5H-imidazo[5,1-a]isoindol-5-yl)-5,6,7,8-tetrahydro-[1,2,4]triazolo[4,3-a]pyridin-8- ol (14.8 mg, 1%) as a white solid: LCMS (ESI, m/z): 294.3 [M+H]$^+$. $^1$H NMR (300 MHz, $CD_3OD$) δ 8.41 (s, 1H), 8.13 (s, 1H), 7.69-7.56 (m, 2H), 7.50-7.29 (m, 2H), 7.17 (s, 1H), 5.68 (s, 1H), 5.47 (d, J=3.5 Hz, 1H), 4.25-4.12 (m, 1H), 3.79-3.61 (m, 1H), 2.88-2.75 (m, 1H), 1.95-1.89 (m, 1H), 1.24 (d, J=13.9 Hz, 1H). tR=2.759 min (Repaired Chiral ADH, 0.46×5 cm, Hex(0.2% IPAmine):IPA=50:50, 1 ml/min). 146c and 146d are enantiomers.

Example 146-1b: (7R,8S)-7-((R)-5H-imidazo[5,1-a]isoindol-5-yl)-5,6,7,8-tetrahydro-[1,2,4]triazolo[4,3-a]pyridin-8-ol (11.0 mg, 1%) as a white solid: LCMS (ESI, m/z): 294.2 [M+H]$^+$. tR=3.867 min (Repaired Chiral ADH, 0.46×5 cm, Hex(0.2% IPAmine):IPA=50:50, 1 ml/min). 146c and 146d are enantiomers.

(7S,8S)-7-((S)-5H-imidazo[5,1-a]isoindol-5-yl)-5,6,7,8-tetrahydro-[1,2,4]triazolo[4,3-a]pyridin-8-ol (7R,8R)-7-((R)-5H-imidazo[5,1-a]isoindol-5-yl)-5,6,7,8-tetrahydro-[1,2,4]triazolo[4,3-a]pyridin-8-ol 146-1c

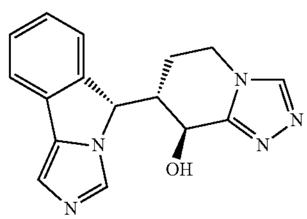

146-1d

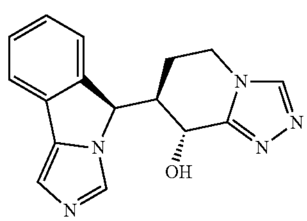

The title compound was synthesized by General Procedure for the Synthesis of 117a-b.

The absolute configuration of all isomers 146e-f was assigned arbitrarily.

Example 146-1c: (7S,8S)-7-((S)-5H-imidazo[5,1-a]isoindol-5-yl)-5,6,7,8-tetrahydro-[1,2,4]triazolo[4,3-a]pyridin-8-ol (8 mg, 6%) as a white solid: LCMS (ESI, m/z): 294.3 [M+H]$^+$. $^1$H NMR (300 MHz, $CD_3OD$) δ 8.38 (s, 1H), 8.03 (s, 1H), 7.68 (d, J=7.6 Hz, 1H), 7.59-7.33 (m, 3H), 7.27-7.20 (m, 1H), 5.90 (s, 1H), 5.21 (d, J=10.7 Hz, 1H), 4.12-4.00 (m, 1H), 3.92-3.75 (m, 1H), 2.73 (s, 1H), 1.35-1.28 (m, 3H). tR=3.994 min (Repaired Chiral ADH, 0.46×5 cm, Hex(0.2% IPAmine):IPA=50:50, 1 ml/min). 146e and 146f are enantiomers.

Example 146-1d: (7R,8R)-7-((R)-5H-imidazo[5,1-a]isoindol-5-yl)-5,6,7,8-tetrahydro-[1,2,4]triazolo[4,3-a]pyridin-8-ol (8.1 mg, 6%) as a white solid: LCMS (ESI, m/z): 294.2 [M+H]$^+$. tR=4.805 min (Repaired Chiral ADH, 0.46×5 cm, Hex(0.2% IPAmine):IPA=50:50, 1 ml/min). 146e and 146f are enantiomers.

Example 147: 1-(5H-imidazo[5,1-a]isoindol-5-yl)-3,3-dimethylcyclobutan-1-ol

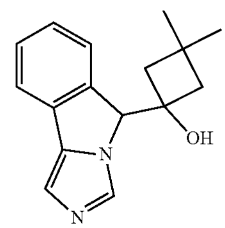

Final product (racemate) is a mixture of the following isomers:

(R)-1-(5H-imidazo[5,1-a]isoindol-5-yl)-3,3-dimethylcyclobutan-1-ol (S)-1-(5H-imidazo[5,1-a]isoindol-5-yl)-3,3-dimethylcyclobutan-1-ol Step 1:

1-(5H-imidazo[5,1-a]isoindol-5-yl)-3,3-dimethylcyclobutan-1-ol

147a

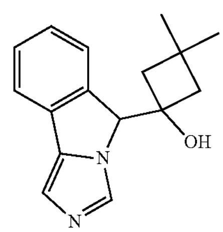 [SMILES: CC1(C)CC(O)(C2c3ccccc3-c3cncn32)C1]

To a solution of 5H-imidazo[5,1-a]isoindole (400 mg, 2.56 mmol) in anhydrous tetrahydrofuran (10 mL) was added n-BuLi solution (1.23 mL, 3.07 mmol) at −78° C. and stirred for 1 hr. 3,3-Dimethylcyclobutan-1-one (0.377 g, 3.84 mmol) was added into the reaction mixture drop-wise. The reaction was kept at −78° C. for another 30 min and was warmed up to room temperature. The reaction was kept at room temperature for another 2 hrs and was quenched with saturated $NH_4Cl$ solution (20 mL). The mixture was extracted with 20% 2,2,2-trifluoroethanol in dichloromethane (3×20 ml) and the organic phase was combined, dried over $Na_2SO_4$, and concentrated. The product was separated by CombiFlash and was eluted with DCM:MeOH=97:3. The product was obtained as mixture of enantiomers.

Example 147a: 1-(5H-imidazo[5,1-a]isoindol-5-yl)-3,3-dimethylcyclobutan-1-ol: LCMS (ESI, m/z): 255.2 [M+H]$^+$; $^1$HNMR (400 MHz, DMSO-$d_6$) δ 7.84 (s, 1H), 7.57 (d, J=7.5 Hz, 1H), 7.52 (d, J=7.6 Hz, 1H), 7.36 (t, J=7.5 Hz, 1H), 7.23 (d, J=7.7 Hz, 1H), 7.10 (s, 1H), 5.27 (s, 1H), 5.23 (s, 1H), 2.19 (dd, J=20.2, 12.4 Hz, 2H), 1.88-1.69 (m, 2H), 1.21 (s, 3H), 0.93 (s, 3H).

Example 148: cyclohexyl(5H-imidazo[5,1-a]isoindol-5-yl)methanol

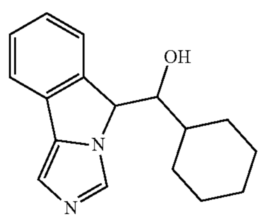 [SMILES: OC(C1CCCCC1)C1c2ccccc2-c2cncn21]

(R)-cyclohexyl((S)-5H-imidazo[5,1-a]isoindol-5-yl)methanol (S)-cyclohexyl((R)-5H-imidazo[5,1-a]isoindol-5-yl)methanol (R)-cyclohexyl((R)-5H-imidazo[5,1-a]isoindol-5-yl)methanol (S)-cyclohexyl((S)-5H-imidazo[5,1-a]isoindol-5-yl)methanol Step 1:

(R)-cyclohexyl((S)-5H-imidazo[5,1-a]isoindol-5-yl)methanol (S)-cyclohexyl((R)-5H-imidazo[5,1-a]isoindol-5-yl)methanol (R)-cyclohexyl((R)-5H-imidazo[5,1-a]isoindol-5-yl)methanol (S)-cyclohexyl((S)-5H-imidazo[5,1-a]isoindol-5-yl)methanol 148a

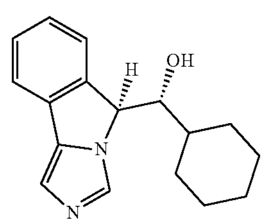

148b

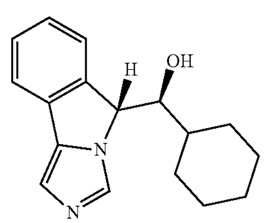

148c

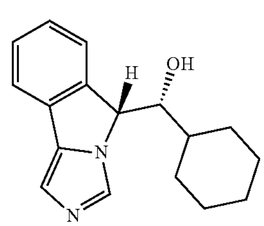

-continued

148d

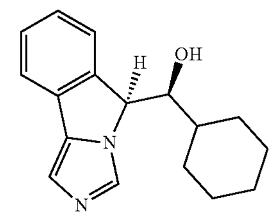

An anhydrous THF (32 mL) solution of 5H-imidazo[5,1-a]isoindole (1.00 g, 6.40 mmol, 1.0 equiv) was cooled to −78° C. in an acetone-dry ice bath under a dinitrogen atmosphere for 15 min. Sec-butyllithium in cyclohexane (1.4 mol/L, 5.0 mL, 7.04 mmol, 1.10 equiv) was added dropwise over 5 min. The solution was then stirred at −78° C. for 60 min. An anhydrous THF (6.4 mL) solution of cyclohexanecarbaldehyde (790 mg, 7.04 mmol, 1.10 equiv) was added down the side of the flask at −78° C. After 30 min, the flask was removed from the cold bath and allowed to warm to room temperature for 60 min. The reaction quenched by slow addition of saturated aqueous ammonium chloride solution (100 mL). The biphasic mixture was transferred to a separatory funnel and extracted with dichloromethane (3×50 mL). The combined organic extracts were dried ($Na_2SO_4$) and concentrated. The crude product was purified by Combi-Flash and further isolated by chiral separation to afford 4 isomers as a colorless solid. The relative configuration of isomers was assigned by $^1$H NMR. The absolute configuration was assigned arbitrarily.

Example 148a: (R)-cyclohexyl((S)-5H-imidazo[5,1-a]isoindol-5-yl)methanol: LCMS (ESI, m/z): 269.1 $[M+H]^+$. $^1$H NMR (400 MHz, DMSO-d6) δ 7.79 (s, 1H), 7.62-7.55 (m, 1H), 7.48 (dd, J=7.5, 1.0 Hz, 1H), 7.37 (td, J=7.5, 1.3 Hz, 1H), 7.25 (td, J=7.5, 1.2 Hz, 1H), 7.11 (s, 1H), 5.40 (d, J=4.3 Hz, 1H), 5.17 (d, J=5.8 Hz, 1H), 3.79 (td, J=5.9, 4.4 Hz, 1H), 1.63-1.44 (m, 4H), 1.36 (s, 1H), 1.20-0.94 (m, 3H). tR=0.945 min (Chiralcel-3, 10% EtOH with 0.1% $NH_4OH$ co-solvent).

Example 148b: (S)-cyclohexyl((R)-5H-imidazo[5,1-a]isoindol-5-yl)methanol: LCMS (ESI, m/z): 269.1 $[M+H]^+$. $^1$H NMR (400 MHz, DMSO-d6) δ 7.79 (s, 1H), 7.62-7.55 (m, 1H), 7.48 (dd, J=7.5, 1.0 Hz, 1H), 7.37 (td, J=7.5, 1.3 Hz, 1H), 7.25 (td, J=7.5, 1.2 Hz, 1H), 7.11 (s, 1H), 5.40 (d, J=4.3 Hz, 1H), 5.17 (d, J=5.8 Hz, 1H), 3.79 (td, J=5.9, 4.4 Hz, 1H), 1.63-1.44 (m, 4H), 1.36 (s, 1H), 1.20-0.94 (m, 3H). tR=0.807 min (Chiralcel-3, 10% EtOH with 0.1% $NH_4OH$ co-solvent).

Example 148c: (R)-cyclohexyl((R)-5H-imidazo[5,1-a]isoindol-5-yl)methanol: LCMS (ESI, m/z): 269.1 $[M+H]^+$. $^1$H NMR (400 MHz, DMSO-d6) δ 7.77 (s, 1H), 7.58 (dt, J=7.6, 0.9 Hz, 1H), 7.45 (dt, J=7.5, 1.0 Hz, 1H), 7.46-7.32 (m, 1H), 7.26 (td, J=7.5, 1.2 Hz, 1H), 7.12 (s, 1H), 5.35 (d, J=5.1 Hz, 1H), 5.04 (d, J=6.5 Hz, 1H), 3.50 (td, J=6.4, 4.9 Hz, 1H), 1.93 (d, J=12.7 Hz, 1H), 1.84-1.51 (m, 2H), 1.36-1.06 (m, 4H). tR=0.820 min (Chiralcel-3, 10% EtOH with 0.1% $NH_4OH$ co-solvent).

Example 148d: (S)-cyclohexyl((S)-5H-imidazo[5,1-a]isoindol-5-yl)methanol: LCMS (ESI, m/z): 269.1 $[M+H]^+$. $^1$H NMR (400 MHz, DMSO-$d_6$) δ 7.77 (s, 1H), 7.58 (dt, J=7.6, 0.9 Hz, 1H), 7.45 (dt, J=7.5, 1.0 Hz, 1H), 7.46-7.32 (m, 1H), 7.26 (td, J=7.5, 1.2 Hz, 1H), 7.12 (s, 1H), 5.35 (d, J=5.1 Hz, 1H), 5.04 (d, J=6.5 Hz, 1H), 3.50 (td, J=6.4, 4.9 Hz, 1H), 1.93 (d, J=12.7 Hz, 1H), 1.84-1.51 (m, 2H), 1.36-1.06 (m, 4H). tR=0.691 min (Chiralcel-3, 10% EtOH with 0.1% $NH_4OH$ co-solvent).

Example 149: 4-hydroxy-5-(5H-imidazo[5,1-a]isoindol-5-yl)-4,5,6,7-tetrahydrobenzo[d]thiazole-2-carboxamide

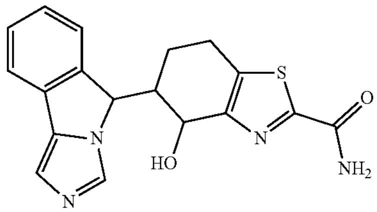 [SMILES: NC(=O)c1nc2c(s1)CCC(C1c3ccccc3-c3cncn31)C2O]

(4R,5R)-4-hydroxy-5-((R)-5H-imidazo[5,1-a]isoindol-5-yl)-4,5,6,7-tetrahydrobenzo[d]thiazole-2-carboxamide (4S,5S)-4-hydroxy-5-((R)-5H-imidazo[5,1-a]isoindol-5-yl)-4,5,6,7-tetrahydrobenzo[d]thiazole-2-carboxamide (4R,5S)-4-hydroxy-5-((R)-5H-imidazo[5,1-a]isoindol-5-yl)-4,5,6,7-tetrahydrobenzo[d]thiazole-2-carboxamide (4S,5R)-4-hydroxy-5-((R)-5H-imidazo[5,1-a]isoindol-5-yl)-4,5,6,7-tetrahydrobenzo[d]thiazole-2-carboxamide (4R,5R)-4-hydroxy-5-((S)-5H-imidazo[5,1-a]isoindol-5-yl)-4,5,6,7-tetrahydrobenzo[d]thiazole-2-carboxamide (4S,5R)-4-hydroxy-5-((S)-5H-imidazo[5,1-a]isoindol-5-yl)-4,5,6,7-tetrahydrobenzo[d]thiazole-2-carboxamide (4R,5S)-4-hydroxy-5-((S)-5H-imidazo[5,1-a]isoindol-5-yl)-4,5,6,7-tetrahydrobenzo[d]thiazole-2-carboxamide (4S,5S)-4-hydroxy-5-((S)-5H-imidazo[5,1-a]isoindol-5-yl)-4,5,6,7-tetrahydrobenzo[d]thiazole-2-carboxamide Step 1: 3-bromocyclohexane-1,2-dione

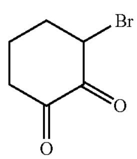

To a solution of 1,2-cyclohexanedione (5.1 g, 45.5 mmol) in diethyl ether (46 mL) at 0° C. was added $Br_2$ (2.34 mL, 45.5 mmol) dropwise over 10 min. When the addition was complete, the reaction was allowed to come to room temperature and stirred for 15 min., at which time the reaction mixture was concentrated under reduced pressure. The resulting dark oil was taken up in 2.5% $MeOH/CHCl_3$ and run through a pad of silica gel, eluting with the same solvent mixture. The solvent was then removed under reduced pressure and the resulting yellow solid was triturated with cold diethyl ether (15 mL). The product was filtered and dried. $^1$HNMR (400 MHz, Chloroform-d) δ 6.45 (s, 1H), 2.90 (td, J=6.0, 5.6, 0.6 Hz, 2H), 2.54-2.61 (m, 2H), 2.05-2.13 (m, 2H).

Step 2: ethyl 4-oxo-4,5,6,7-tetrahydrobenzo[d]thiazole-2-carboxylate

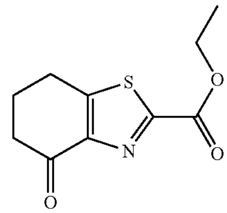

A mixture of 3-bromocyclohexane-1,2-dione 3 (10.76 g, 56.32 mmol) and ethyl 2-amino-2-thioxoacetate (5.0 g, 37.55 mmol) in ethanol (150 mL) was heated to reflux and stirred for 15 h. The mixture was cooled to room temperature. The solvent was removed under reduced pressure and the product was separated by CombiFlash. The product was eluted with EtOAc:Hexane=50:50: LCMS (ESI, m/z): 226.2 $[M+H]^+$.

Step 3: 4-oxo-4,5,6,7-tetrahydrobenzo[d]thiazole-2-carboxamide

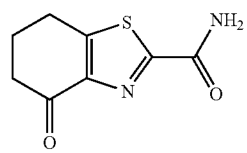 [SMILES: NC(=O)c1nc2c(s1)CCCC2=O]

To a solution of ethyl 4-oxo-4,5,6,7-tetrahydrobenzo[d]thiazole-2-carboxylate (1.6 g, 7.1 mmol) in ethanol (10 mL) was added ammonium hydroxide aqueous solution (26.88 mL, 426 mmol) solution at room temperature. The resulting mixture was stirred at 95° C. for 30 min. TLC indicated full consumption of starting material and the mixture was cooled to room temperature. The precipitation was filtered and washed with cold methanol (10 mL). The product was dried and used directly without further purification: LCMS (ESI, m/z): 197.2 $[M+H]^+$.

Step 4: (E)-4-oxo-5-(2-(1-trityl-1H-imidazol-4-yl)benzylidene)-4,5,6,7-tetrahydrobenzo[d]thiazole-2-carboxamide

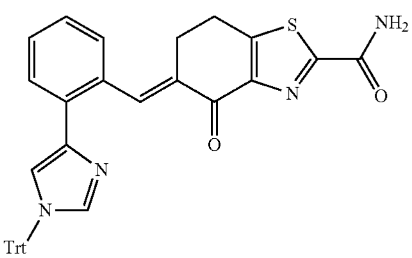

To a solution of 2-(1-trityl-1H-imidazol-4-yl)benzaldehyde (2.0 g, 4.82 mmol) and 6,7-dihydrobenzo[d]thiazol-4(5H)-one (1.14 g, 5.79 mmol) in methanol (30 mL) was added pyrrolidine (0.48 mL, 5.79 mmol). The mixture was stirred at 90° C. 6 hrs. The solid was filtered and washed with cold methanol (10 mL). The desired product was collected as light yellow solid and used directly without further purification: LCMS (ESI, m/z): 593.2 [M+H]$^+$.

Step 5: 5-(5H-imidazo[5,1-a]isoindol-5-yl)-4-oxo-4,5,6,7-tetrahydrobenzo[d]thiazole-2-carboxamide

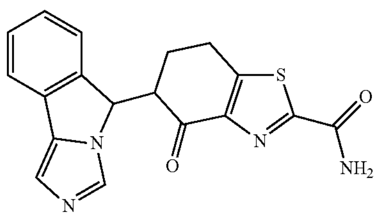 [SMILES: NC(=O)c1nc2c(s1)CCC(C1c3ccccc3-c3cncn31)C2=O]

(E)-4-oxo-5-(2-(1-trityl-1H-imidazol-4-yl)benzylidene)-4,5,6,7-tetrahydrobenzo[d]thiazole-2-carboxamide (1.37 g, 2.30 mmol) was stirred in methanol (55 mL) and acetic acid (12.5 mL) at 90° C. for 2 h. After cooling to room temperature, the solvent was removed under reduced pressure and saturated $NaHCO_3$ (20 mL) was added to quench the acetic acid. The aqueous layer was extracted with 10% 2,2,2-trifluoroethanol in DCM (3×30 mL). The combined organic layers were dried over $Na_2SO_4$ and the solvent evaporated under reduced pressure to afford the crude product which was purified by using CombiFlash and was eluted with DCM:MeOH=94:6: LCMS (ESI, m/z): 351.2 [M+H]$^+$.

Step 6:
(4R,5R)-4-hydroxy-5-((R)-5H-imidazo[5,1-a]isoindol-5-yl)-4,5,6,7-tetrahydrobenzo[d]thiazole-2-carboxamide
(4S,5S)-4-hydroxy-5-((R)-5H-imidazo[5,1-a]isoindol-5-yl)-4,5,6,7-tetrahydrobenzo[d]thiazole-2-carboxamide
(4R,5S)-4-hydroxy-5-((R)-5H-imidazo[5,1-a]isoindol-5-yl)-4,5,6,7-tetrahydrobenzo[d]thiazole-2-carboxamide
(4S,5R)-4-hydroxy-5-((R)-5H-imidazo[5,1-a]isoindol-5-yl)-4,5,6,7-tetrahydrobenzo[d]thiazole-2-carboxamide
(4R,5R)-4-hydroxy-5-((S)-5H-imidazo[5,1-a]isoindol-5-yl)-4,5,6,7-tetrahydrobenzo[d]thiazole-2-carboxamide
(4S,5R)-4-hydroxy-5-((S)-5H-imidazo[5,1-a]isoindol-5-yl)-4,5,6,7-tetrahydrobenzo[d]thiazole-2-carboxamide
(4R,5S)-4-hydroxy-5-((S)-5H-imidazo[5,1-a]isoindol-5-yl)-4,5,6,7-tetrahydrobenzo[d]thiazole-2-carboxamide
(4S,5S)-4-hydroxy-5-((S)-5H-imidazo[5,1-a]isoindol-5-yl)-4,5,6,7-tetrahydrobenzo[d]thiazole-2-carboxamide 149a

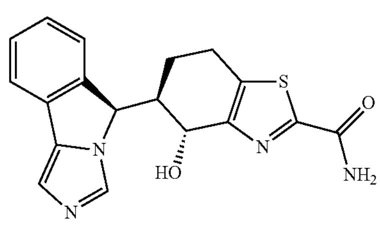

149b

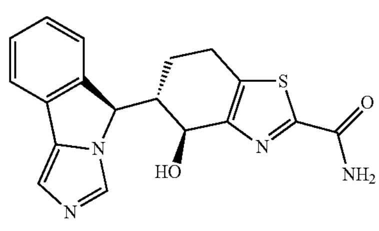

-continued

149c

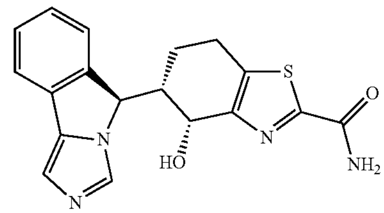

149d

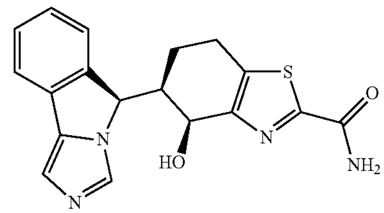

149e

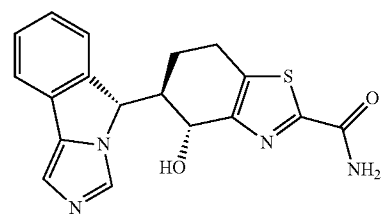

149f

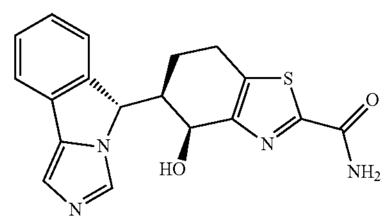

149g

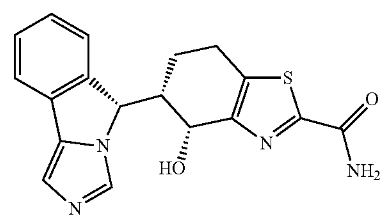

149h

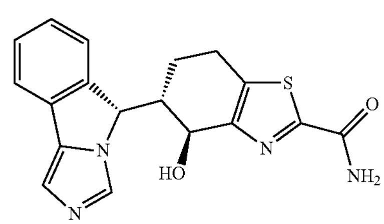

To a suspension of 5-(5H-imidazo[5,1-a]isoindol-5-yl)-4-oxo-4,5,6,7-tetrahydrobenzo[d]thiazole-2-carboxamide (755 mg, 2.15 mmol) in methanol (15 mL) was added sodium borohydride (163 mg, 4.31 mmol) at 0° C. portionwise. The mixture was allowed to warm up to room temperature and stirred for additional 1 hr. The reaction was quenched with saturated ammonium chloride solution (20 mL). The aqueous layer was extracted with 20% 2,2,2-trifluoroethanol in DCM (3×20 mL). The combined organic extract was dried over ($Na_2SO_4$) and concentrated under reduced pressure to afford the crude product. The crude was purified by CombiFlash and the product was eluted with DCM:MeOH=90:10. The final products were further isolated by chiral separation to afford 8 isomers and the stereochemistry of each isomer was arbitrarily assigned.

Example 149a: (4R,5R)-4-hydroxy-5-((R)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 7.90 (s, 1H), 7.84 (s, 1H), 7.81 (s, 1H), 7.64 (d, J=7.6 Hz, 1H), 7.56 (d, J=7.7 Hz, 1H), 7.40 (t, J=7.5 Hz, 1H), 7.25 (td, J=7.6, 1.1 Hz, 1H), 7.17 (s, 1H), 5.91 (d, J=7.0 Hz, 1H), 5.77 (d, J=3.3 Hz, 1H), 5.04-4.97 (m, 1H), 2.70-2.61 (m, 3H), 1.03-0.94 (m, 2H).

Example 149b: (4S,5S)-4-hydroxy-5-((R)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 7.94 (s, 1H), 7.87 (s, 1H), 7.81 (s, 1H), 7.64 (d, J=7.6 Hz, 1H), 7.49 (dd, J=7.6, 1.0 Hz, 1H), 7.42 (dd, J=8.0, 7.1 Hz, 1H), 7.33 (td, J=7.5, 1.1 Hz, 1H), 7.18 (s, 1H), 5.88 (d, J=7.5 Hz, 1H), 5.78 (s, 1H), 5.05 (t, J=8.7 Hz, 1H), 2.72-2.56 (m, 3H), 1.03-0.91 (m, 2H).

Example 149c: (4R,5S)-4-hydroxy-5-((R)-5H-imidazo[5,1-a]isoindol-5-yl)-4,5,6,7-tetrahydrobenzo[d]thiazole-2-carboxamide: LCMS (ESI, m/z): 353.2 $[M+H]^+$; (HNMR (500 MHz, DMSO-$d_6$) δ 8.04 (s, 1H), 7.99 (s, 1H), 7.78 (s, 1H), 7.65 (dd, J=7.6, 1.0 Hz, 1H), 7.60 (d, J=7.5 Hz, 1H), 7.39 (dd, J=7.9, 7.0 Hz, 1H), 7.29 (td, J=7.5, 1.1 Hz, 1H), 7.13 (s, 1H), 5.97 (d, J=6.9 Hz, 1H), 5.52 (s, 1H), 5.11 (dd, J=7.0, 3.5 Hz, 1H), 2.88 (dd, J=17.6, 5.2 Hz, 1H), 2.61-2.52 (m, 2H), 1.56 (qd, J=12.8, 5.6 Hz, 1H), 1.05 (d, J=13.2 Hz, 1H).

Example 149d: (4S,5R)-4-hydroxy-5-((R)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 7.99 (s, 1H), 7.97 (s, 1H), 7.78 (s, 1H), 7.77 (s, 1H), 7.62 (d, J=7.6 Hz, 1H), 7.39 (t, J=7.5 Hz, 1H), 7.28-7.23 (m, 1H), 7.14 (s, 1H), 5.75 (d, J=7.0 Hz, 1H), 5.45 (d, J=5.9 Hz, 1H), 4.91 (dd, J=7.1, 3.3 Hz, 1H), 2.98 (dd, J=17.4, 5.3 Hz, 1H), 2.68 (dt, J=11.4, 5.8 Hz, 1H), 2.23 (d, J=11.1 Hz, 1H), 1.97 (tt, J=12.9, 6.5 Hz, 1H), 1.74 (d, J=12.7 Hz, 1H).

Example 149e: (4R,5R)-4-hydroxy-5-((S)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 7.94 (s, 1H), 7.87 (s, 1H), 7.81 (s, 1H), 7.64 (d, J=7.6 Hz, 1H), 7.49 (d, J=7.6 Hz, 1H), 7.42 (t, J=7.5 Hz, 1H), 7.33 (td, J=7.6, 1.2 Hz, 1H), 7.18 (s, 1H), 5.88 (d, J=7.4 Hz, 1H), 5.78 (s, 1H), 5.05 (t, J=8.6 Hz, 1H), 2.72-2.56 (m, 2H), 1.04-0.89 (m, 2H).

Example 149f: (4S,5R)-4-hydroxy-5-((S)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 8.04 (s, 1H), 7.99 (s, 1H), 7.82-7.74 (m, 1H), 7.65 (dq, J=7.7, 1.0 Hz, 1H), 7.62-7.57 (m, 1H), 7.43-7.36 (m, 1H), 7.29 (td, J=7.6, 1.1 Hz, 1H), 7.13 (s, 1H), 5.97 (d, J=6.9 Hz, 1H), 5.54-5.49 (m, 1H), 5.11 (dd, J=7.0, 3.5 Hz, 1H), 2.88 (dd, J=17.3, 5.3 Hz, 1H), 2.57 (dd, J=11.9, 5.7 Hz, 1H), 1.56 (qd, J=12.7, 5.5 Hz, 1H), 1.05 (d, J=11.7 Hz, 1H).

Example 149g: (4R,5S)-4-hydroxy-5-((S)-5H-imidazo[5,1-a]isoindol-5-yl)-4,5,6,7-tetrahydrobenzo[d]thiazole-2-carboxamide: LCMS (ESI, m/z): 353.2 $[M+H]^+$.

Example 149h: (4S,5S)-4-hydroxy-5-((S)-5H-imidazo[5,1-a]isoindol-5-yl)-4,5,6,7-tetrahydrobenzo[d]thiazole-2-carboxamide: LCMS (ESI, m/z): 353.2 $[M+H]^+$; $^1$HNMR (500 MHz, DMSO-$d_6$) δ 7.90 (s, 1H), 7.84 (s, 1H), 7.81 (s, 1H), 7.64 (d, J=7.6 Hz, 1H), 7.56 (d, J=7.7 Hz, 1H), 7.40 (t, J=7.5 Hz, 1H), 7.25 (td, J=7.6, 1.1 Hz, 1H), 7.17 (s, 1H), 5.91 (d, J=7.0 Hz, 1H), 5.77 (d, J=3.3 Hz, 1H), 5.01 (s, 1H), 2.66 (s, 3H), 1.05-0.90 (m, 2H).

Example 150: 3,3-bis(fluoromethyl)-2-(5H-imidazo[5,1-a]isoindol-5-yl)cyclobutan-1-ol

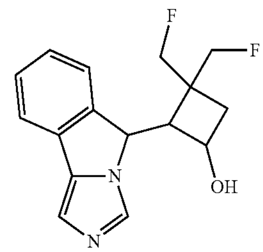 [SMILES: OC1CC(CF)(CF)C1C1c2ccccc2-c2cncn21]

(1R,2R)-3,3-bis(fluoromethyl)-2-((S)-5H-imidazo[5,1-a]isoindol-5-yl)cyclobutan-1-ol (1R,2R)-3,3-bis(fluoromethyl)-2-((R)-5H-imidazo[5,1-a]isoindol-5-yl)cyclobutan-1-ol (1S,2S)-3,3-bis(fluoromethyl)-2-((R)-5H-imidazo[5,1-a]isoindol-5-yl)cyclobutan-1-ol (1S,2R)-3,3-bis(fluoromethyl)-2-((R)-5H-imidazo[5,1-a]isoindol-5-yl)cyclobutan-1-ol (1R,2S)-3,3-bis(fluoromethyl)-2-((S)-5H-imidazo[5,1-a]isoindol-5-yl)cyclobutan-1-ol (1S,2S)-3,3-bis(fluoromethyl)-2-((S)-5H-imidazo[5,1-a]isoindol-5-yl)cyclobutan-1-ol Step 1:

(E)-3,3-bis(fluoromethyl)-2-(2-(1-trityl-1H-imidazol-4-yl)benzylidene)cyclobutan-1-one

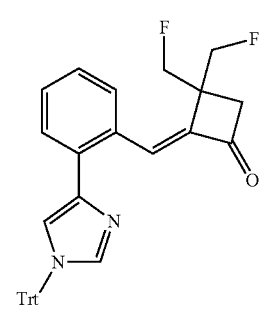

To a solution of 2-(1-trityl-1H-imidazol-4-yl)benzaldehyde (2.4 g, 5.79 mmol) and 3,3-bis(fluoromethyl)cyclobutan-1-one (932 mg, 6.95 mmol) in anhydrous ethanol (30 mL) was added calcium hydroxide (515 mg, 6.95 mmol) and the resulting mixture was stirred at 90° C. for 16 hr. The reaction was quenched by 50 mL water and the mixture was extracted with dichloromethane (3×30 mL). The organic layer was combined, washed with brine and water, and dried by anhydrous $Na_2SO_4$: LCMS (ESI, m/z): 531.4 $[M+H]^+$.

Step 2:

3,3-bis(fluoromethyl)-2-(5H-imidazo[5,1-a]isoindol-5-yl)cyclobutan-1-one

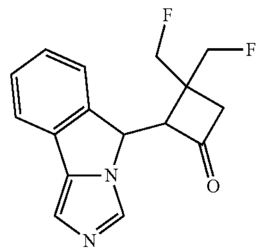 [SMILES: O=C1CC(CF)(CF)C1C1c2ccccc2-c2cncn21]

To a solution of the (E)-2-(2-(1H-imidazol-4-yl)benzylidene)-3,3-bis(fluoromethyl)cyclobutan-1-one (510 mg, 1.77 mmol) in DCM (10 mL) was added trifluoroacetic acid (2.73 mL, 35.38 mmol) and the solution was stirred at room temperature for overnight. The solvent was evaporated under reduced pressure and the reaction was quenched by 30 mL saturated $NaHCO_3$ solution and the mixture was extracted by 20% 2,2,2-trifluoroethanol in DCM (3×30 mL). The organic layer was combined, washed with brine and water, and dried by anhydrous $Na_2SO_4$. The product was separated by CombiFlash and was eluted with DCM: MeOH=94:6: LCMS (ESI, m/z): 289.2 $[M+H]^+$.

Step 3:

(1R,2R)-3,3-bis(fluoromethyl)-2-((S)-5H-imidazo[5,1-a]isoindol-5-yl)cyclobutan-1-ol (1R,2R)-3,3-bis(fluoromethyl)-2-((R)-5H-imidazo[5,1-a]isoindol-5-yl)cyclobutan-1-ol (1S,2S)-3,3-bis(fluoromethyl)-2-((R)-5H-imidazo[5,1-a]isoindol-5-yl)cyclobutan-1-ol (1S,2R)-3,3-bis(fluoromethyl)-2-((R)-5H-imidazo[5,1-a]isoindol-5-yl)cyclobutan-1-ol (1R,2S)-3,3-bis(fluoromethyl)-2-((S)-5H-imidazo[5,1-a]isoindol-5-yl)cyclobutan-1-ol (1S,2S)-3,3-bis(fluoromethyl)-2-((S)-5H-imidazo[5,1-a]isoindol-5-yl)cyclobutan-1-ol 150a

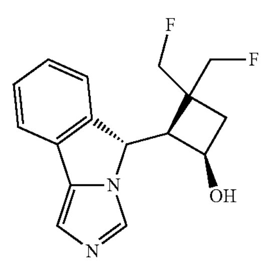

150b

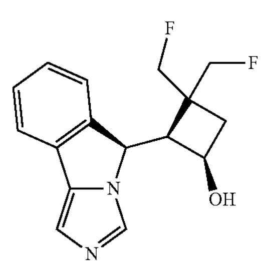

-continued

150c

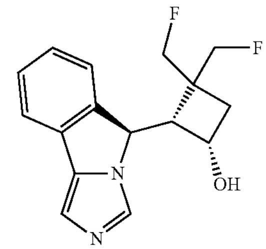

150d

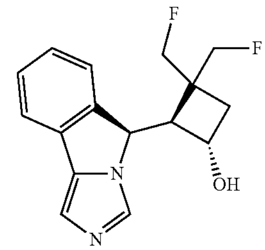

150e

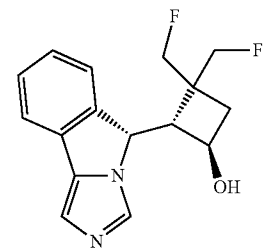

150f

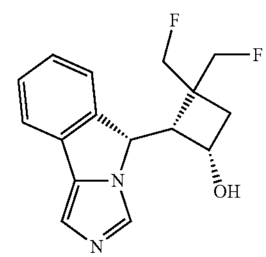

To a solution of the 3,3-bis(fluoromethyl)-2-(5H-imidazo[5,1-a]isoindol-5-yl)cyclobutan-1-one (346 mg, 1.2 mmol) in MeOH (10 mL) was added $NaBH_4$ (91 mg, 2.4 mmol) in portions at 0° C. and the solution was stirred at 0° C. for 30 min. The reaction was quenched by saturated ammonium chloride (10 mL). The aqueous layer was extracted with 20% 2,2,2-trifluoroethanol in DCM (3×10 mL). The combined organic extract was dried over ($Na_2SO_4$) and concentrated under reduced pressure to afford the crude product. The crude was purified by CombiFlash and the product was eluted with DCM:MeOH=94:6. The final products were further isolated by chiral separation to afford 6 isomers and the stereochemistry of each isomer was arbitrarily assigned.

Example 105a: (1R,2R)-3,3-bis(fluoromethyl)-2-((S)-5H-imidazo[5,1-a]isoindol-5-yl)cyclobutan-1-ol: LCMS (ESI, m/z): 291.1 $[M+H]^+$; $^1$HNMR (500 MHz, DMSO-$d_6$) δ 7.94 (s, 1H), 7.73 (dt, J=7.8, 0.9 Hz, 1H), 7.60 (dd, J=7.7, 1.0 Hz, 1H), 7.41-7.34 (m, 1H), 7.26 (td, J=7.6, 1.2 Hz, 1H), 7.15 (s, 1H), 6.01 (d, J=3.2 Hz, 1H), 5.55 (d, J=8.8 Hz, 1H), 4.89 (dd, J=47.7, 9.7 Hz, 1H), 4.65-4.45 (m, 3H), 4.42-4.36 (m, 1H), 4.30 (d, J=9.5 Hz, 1H), 2.55 (t, J=7.8 Hz, 1H), 2.12 (dt, J=12.5, 4.7 Hz, 1H), 1.64 (d, J=12.5 Hz, 1H).

Example 150b: (1R,2R)-3,3-bis(fluoromethyl)-2-((R)-5H-imidazo[5,1-a]isoindol-5-yl)cyclobutan-1-ol: LCMS (ESI, m/z): 291.1 [M+H]$^+$; $^1$HNMR (500 MHz, DMSO-$d_6$) δ 7.86 (s, 1H), 7.62-7.56 (m, 1H), 7.50 (dd, J=7.7, 0.9 Hz, 1H), 7.38 (dd, J=7.9, 7.1 Hz, 1H), 7.25 (td, J=7.6, 1.2 Hz, 1H), 7.09 (s, 1H), 5.52 (d, J=10.0 Hz, 1H), 5.33 (d, J=7.8 Hz, 1H), 4.91 (dd, J=46.8, 10.1 Hz, 1H), 4.75-4.59 (m, 2H), 4.52 (dd, J=47.5, 9.5 Hz, 1H), 4.38 (dd, J=47.5, 9.5 Hz, 1H), 2.25-2.19 (m, 1H), 2.10 (dd, J=11.4, 7.9 Hz, 1H), 1.75 (ddd, J=12.0, 8.1, 4.8 Hz, 1H)

Example 150c: (1S,2S)-3,3-bis(fluoromethyl)-2-((R)-5H-imidazo[5,1-a]isoindol-5-yl)cyclobutan-1-ol: LCMS (ESI, m/z): 291.1 [M+H]$^+$; $^1$HNMR (500 MHz, DMSO-$d_6$) δ 7.94 (s, 1H), 7.73 (dd, J=7.7, 1.0 Hz, 1H), 7.60 (d, J=7.5 Hz, 1H), 7.41-7.35 (m, 1H), 7.26 (td, J=7.6, 1.2 Hz, 1H), 7.15 (s, 1H), 6.01 (d, J=3.3 Hz, 1H), 5.55 (d, J=8.8 Hz, 1H), 4.89 (dd, J=47.8, 9.7 Hz, 1H), 4.56 (dd, J=47.4, 9.6 Hz, 1H), 4.48 (d, J=9.4 Hz, 2H), 4.41-4.37 (m, 1H), 4.30 (d, J=9.5 Hz, 1H), 2.56 (s, 1H), 2.16-2.08 (m, 1H), 1.64 (d, J=12.7 Hz, 1H).

Example 150d: (1S,2R)-3,3-bis(fluoromethyl)-2-((R)-5H-imidazo[5,1-a]isoindol-5-yl)cyclobutan-1-ol: LCMS (ESI, m/z): 291.1 [M+H]$^+$; $^1$HNMR (500 MHz, DMSO-$d_6$) δ 7.83 (s, 1H), 7.59 (ddt, J=8.3, 7.3, 0.9 Hz, 2H), 7.37 (tt, J=7.5, 0.8 Hz, 1H), 7.24 (td, J=7.6, 1.2 Hz, 1H), 7.14 (s, 1H), 5.50 (d, J=8.7 Hz, 1H), 5.33 (d, J=7.6 Hz, 1H), 4.74-4.51 (m, 3H), 4.46-4.41 (m, 1H), 4.32 (dd, J=20.2, 9.5 Hz, 1H), 4.21 (d, J=9.5 Hz, 1H), 2.36 (t, J=8.4 Hz, 1H), 2.10 (dd, J=11.5, 8.0 Hz, 1H), 1.74 (ddd, J=11.8, 8.1, 4.2 Hz, 1H).

Example 150e: (1R,2S)-3,3-bis(fluoromethyl)-2-((S)-5H-imidazo[5,1-a]isoindol-5-yl)cyclobutan-1-ol: LCMS (ESI, m/z): 291.1 [M+H]$^+$; $^1$HNMR (500 MHz, DMSO-$d_6$) δ 7.83 (s, 1H), 7.58 (tt, J=7.5, 0.9 Hz, 2H), 7.37 (tt, J=7.6, 0.8 Hz, 1H), 7.24 (td, J=7.6, 1.2 Hz, 1H), 7.14 (s, 1H), 5.50 (d, J=8.7 Hz, 1H), 5.33 (d, J=7.6 Hz, 1H), 4.74-4.56 (m, 2H), 4.55-4.40 (m, 2H), 4.32 (dd, J=20.2, 9.5 Hz, 1H), 4.21 (d, J=9.5 Hz, 1H), 2.36 (t, J=8.4 Hz, 1H), 2.10 (dd, J=11.4, 8.0 Hz, 1H), 1.74 (ddd, J=11.8, 8.1, 4.3 Hz, 1H).

Example 150f: (1S,2S)-3,3-bis(fluoromethyl)-2-((S)-5H-imidazo[5,1-a]isoindol-5-yl)cyclobutan-1-ol: LCMS (ESI, m/z): 291.1 [M+H]$^+$; $^1$HNMR (500 MHz, DMSO-$d_6$) δ 7.86 (s, 1H), 7.59 (dt, J=7.6, 0.9 Hz, 1H), 7.54-7.48 (m, 1H), 7.38 (tt, J=7.6, 0.8 Hz, 1H), 7.25 (td, J=7.6, 1.2 Hz, 1H), 7.09 (s, 1H), 5.52 (d, J=10.0 Hz, 1H), 5.33 (d, J=7.7 Hz, 1H), 4.91 (ddd, J=46.9, 10.2, 1.8 Hz, 1H), 4.75-4.59 (m, 2H), 4.52 (dd, J=47.5, 9.4 Hz, 1H), 4.38 (dd, J=47.5, 9.4 Hz, 1H), 2.22 (dd, J=9.9, 7.9 Hz, 1H), 2.10 (dd, J=11.4, 7.9 Hz, 1H), 1.75 (ddd, J=11.4, 8.1, 4.8 Hz, 1H).

Example 151: 3-fluoro-5-(5H-imidazo[5,1-a]isoindol-5-yl)-4,5,6,7-tetrahydropyrazolo[1,5-a]pyridin-4-ol

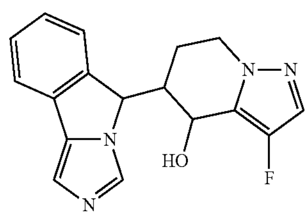 [SMILES: OC1c2c(F)cnn2CCC1C1c2ccccc2-c2cncn21]

Step 1:

O-(mesitylsulfonyl)hydroxylamine

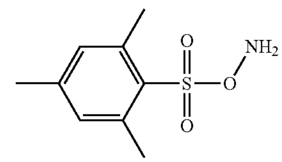

A solution of (Z)-(ethyl N-[[(2,4,6-trimethylbenzene) sulfonyl]oxy]-ethenecarboximidate) (43.5 g, 152.44 mmol) in 1,4-dioxane (100 mL) was added perchloric acid (50 mL, 70% solution) dropwise at 0° C. The resulting solution was stirred for 1 h at 0° C. The reaction was then quenched by the addition of ice water. The solids were collected by filtration. This resulted in 30 g (crude) of amino O-(mesitylsulfonyl)hydroxylamine as a white solid. The crude product was directly used for the next step reaction without characterization.

Step 2:

1-amino-3-methoxypyridin-1-ium 2,4,6-trimethylbenzen-1-olate

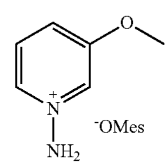

A solution of amino 3-methoxypyridine (15 g, 137.46 mmol) in DCM (100 mL) was added 2,4,6-trimethylbenzene-1-sulfonate (30 g, 139.36 mmol) in DCM (50 mL) at 0° C. The resulting solution was stirred for 1 overnight at room temperature. The resulting mixture was concentrated under vacuum. This resulted in 33 g of 1-amino-3-methoxypyridin-1-ium 2,4,6-trimethylbenzen-1-olate as colorless oil: LCMS (ESI, m/z): 226.2 [M+H]$^+$.

Step 3:

ethyl 4-methoxypyrazolo[1,5-a]pyridine-3-carboxylate

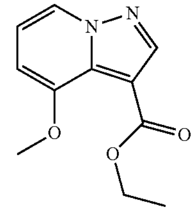 [SMILES: CCOC(=O)c1cnn2cccc(OC)c12]

A solution of 1-amino-3-methoxypyridin-1-ium 2,4,6-trimethylbenzen-1-olate (33 g, 126.76 mmol) and ethyl prop-2-ynoate (18.2 g, 185.56 mmol) in DMF (100 mL, 1.29 mol) was added potassium carbonate (25.6 g, 185.23 mmol). The resulting solution was stirred for 24 h at room temperature. The solids were filtered out. The solution was diluted with water (500 mL). The resulting solution was extracted with EtOAc (2×300 mL) and the organic layers combined. The resulting mixture was washed with brine (1×200 mL). The organic layers was concentrated under vacuum. The residue was purified by silica gel column eluting with EtOAc/petroleum ether (13:87). This resulted in 11.3 g (40%) of ethyl 4-methoxypyrazolo[1,5-a]pyridine-3-carboxylate as brown oil: LCMS (ESI, m/z): 221.3 [M+H]$^+$.

Step 4: pyrazolo[1,5-a]pyridin-4-ol

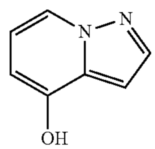

A solution of ethyl 4-methoxypyrazolo[1,5-a]pyridine-3-carboxylate (5 g, 22.70 mmol) in HBr (100 mL, 48% w/v) was stirred for 2 days at 100° C. in an oil bath. The resulting mixture was concentrated under vacuum. The pH value of the solution was adjusted to weak acid with 2 M sodium hydroxide solution. The resulting solution was extracted with EtOAc (2×200 mL). The organic layers were combined, dried over anhydrous sodium sulfate, and concentrated under vacuum. The residue was purified by silica gel column eluting with EtOAc/petroleum ether (30:70). This resulted in 1.6 g (53%) of pyrazolo[1,5-a]pyridin-4-ol as a white solid: LCMS (ESI, m/z): 135.3 [M+H]$^+$.

Step 5: 4H,5H,6H,7H-pyrazolo[1,5-a]pyridin-4-ol

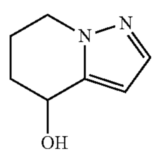

Under hydrogen, a solution of pyrazolo[1,5-a]pyridin-4-ol (1.6 g, 11.93 mmol) in MeOH (100 mL) was added Palladium carbon (1.6 g, 10%). The resulting solution was stirred for 3 days at room temperature. The solids were filtered out. The resulting mixture was concentrated under vacuum. The residue was purified by silica gel column eluting with DCM/MeOH (98:2). This resulted in 900 mg (55%) of 4H,5H,6H,7H-pyrazolo[1,5-a]pyridin-4-ol as a white solid: LCMS (ESI, m/z): 139.2 [M+H]$^+$.

Step 6: 3-fluoro-4H,5H,6H,7H-pyrazolo[1,5-a]pyridin-4-ol

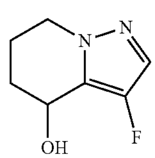 [SMILES: OC1CCCn2ncc(F)c21]

A solution of 4H,5H,6H,7H-pyrazolo[1,5-a]pyridin-4-ol (900 mg, 6.52 mmol) in acetonitrile (30 mL) was added selectfluor (4.6 g, 12.99 mmol). The resulting solution was stirred for 4 h at room temperature and then quenched with water (100 mL). The resulting solution was extracted with EtOAc (3×100 mL). The organic layers were combined, dried over anhydrous sodium sulfate, and concentrated under vacuum. The residue was purified by silica gel column eluting with EtOAc/petroleum ether (30:70). This resulted in 400 mg (39%) of 3-fluoro-4H,5H,6H,7H-pyrazolo[1,5-a]pyridin-4-ol as yellow oil: LCMS (ESI, m/z): 157.2 [M+H]$^+$.

Step 7: 3-fluoro-4H,5H,6H,7H-pyrazolo[1,5-a]pyridin-4-one

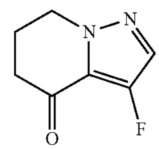 [SMILES: O=C1CCCn2ncc(F)c21]

A solution of 3-fluoro-4H,5H,6H,7H-pyrazolo[1,5-a]pyridin-4-ol (750 mg, 4.80 mmol) in DCM (30 mL) was added DMP (4.05 g, 9.55 mmol). The resulting solution was stirred for 2 h at room temperature. The reaction was then quenched by the addition of $Ca(OH)_2$ (4 g). The solids were filtered out. The residue was purified by silica gel column eluting with EtOAc/petroleum ether (30:70). This resulted in 400 mg (54%) of 3-fluoro-4H,5H,6H,7H-pyrazolo[1,5-a]pyridin-4-one as yellow oil.

Step 8: (E)-3-fluoro-5-(2-(1-trityl-1H-imidazol-4-yl)benzylidene)-6,7-dihydropyrazolo[1,5-a]pyridin-4(5H)-one

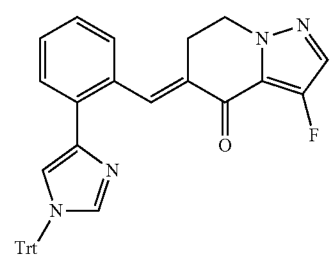

The title compound was synthesized by General Procedure for the Synthesis of 146c-d.

Step 9: 3-fluoro-5-(5H-imidazo[5,1-a]isoindol-5-yl)-6,7-dihydropyrazolo[1,5-a]pyridin-4(5H)-one

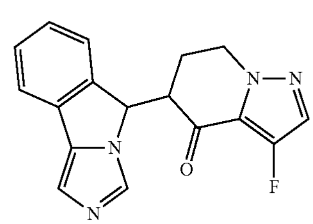 [SMILES: O=C1c2c(F)cnn2CCC1C1c2ccccc2-c2cncn21]

The title compound was synthesized by General Procedure for the Synthesis of 146c-d.

Step 10: (4S,5R)-3-fluoro-5-((R)-5H-imidazo[5,1-a]isoindol-5-yl)-4,5,6,7-tetrahydropyrazolo[1,5-a]pyridin-4-ol (4R,5S)-3-fluoro-5-((S)-5H-imidazo[5,1-a]isoindol-5-yl)-4,5,6,7-tetrahydropyrazolo[1,5-a]pyridin-4-ol 151a

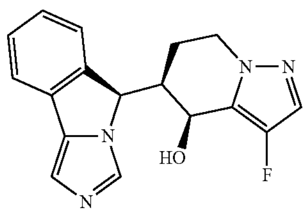

151b

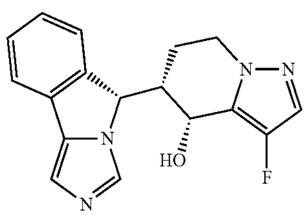

The title compound was synthesized by General Procedure for the Synthesis of 146c-d.

The crude product was purified by Prep-HPLC and further isolated by chiral separation with the following conditions:

1. Column, XBridge C18 OBD Prep Column, 100, 10 um, 19 mm×250 mm; mobile phase, Water (10 MMOL/L $NH_4HCO_3$) and ACN (15.0% ACN up to 37.0% in 10 min); Detector, UV 254/220 nm.
2. Column, Chiralpak IC, 2×25 cm, 5 um; mobile phase, Hex-HPLC and ethanol-HPLC (hold 50% ethanol-HPLC in 25 min); Detector, UV 220/254 nm. The absolute configuration of all isomers 151a-b was assigned arbitrarily.

Example 151a: (4S,5R)-3-fluoro-5-((R)-5H-imidazo[5,1-a]isoindol-5-yl)-4,5,6,7-tetrahydropyrazolo[1,5-a]pyridin-4-ol (25.8 mg, 13%) as a white solid: LCMS (ESI, m/z): 311.3 $[M+H]^+$. $^1$H NMR (300 MHz, $CD_3OD$) δ 8.15 (s, 1H), 7.63 (td, J=7.7, 1.0 Hz, 2H), 7.47-7.34 (m, 3H), 7.18 (s, 1H), 5.65 (d, J=1.7 Hz, 1H), 5.42-5.41 (m, 1H), 4.16-4.10 (m, 1H), 3.85-3.76 (m, 1H), 2.75-2.68 (m, 1H), 2.00-1.91 (m, 1H), 1.27-1.22 (m, 1H). $t_R$=1.397 min (Lux 3 u Cellulose-4, 0.46×5 cm; 3 um, Hex(0.1% DEA):EtOH=50:50, 1 ml/min). 151a and 151b are enantiomers.

Example 151b: (4R,5S)-3-fluoro-5-((S)-5H-imidazo[5,1-a]isoindol-5-yl)-4,5,6,7-tetrahydropyrazolo[1,5-a]pyridin-4-ol (30.4 mg, 15%) as a white solid: LCMS (ESI, m/z): 311.2 $[M+H]^+$. $t_R$=1.997 min (Lux 3 u Cellulose-4, 0.46×5 cm; 3 um, Hex(0.1% DEA):EtOH=50:50, 1 ml/min). 151a and 151b are enantiomers.

(4R,5R)-3-fluoro-5-((R)-5H-imidazo[5,1-a]isoindol-5-yl)-4,5,6,7-tetrahydropyrazolo[1,5-a]pyridin-4-ol (4S,5S)-3-fluoro-5-((S)-5H-imidazo[5,1-a]isoindol-5-yl)-4,5,6,7-tetrahydropyrazolo[1,5-a]pyridin-4-ol 151c

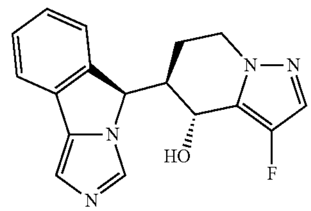

151d

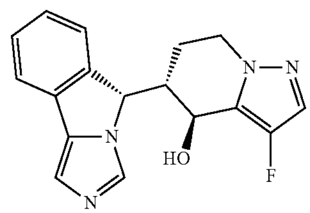

The title compound was synthesized by General Procedure for the Synthesis of 146e-f. The crude product was purified by Prep-HPLC and further isolated by chiral separation with the following conditions:

1. Column, XBridge C18 OBD Prep Column, 100, 10 um, 19 mm×250 mm; mobile phase, Water (10 MMOL/L $NH_4HCO_3$) and ACN (15.0% ACN up to 37.0% in 10 min); Detector, UV 254/220 nm.
2. Column, Chiralpak IC, 2×25 cm, 5 um; mobile phase, Hex-HPLC and ethanol-HPLC (hold 50% ethanol-HPLC in 25 min); Detector, UV 220/254 nm. The absolute configuration of all isomers 151c-d was assigned arbitrarily.

Example 151c: (4R,5R)-3-fluoro-5-((R)-5H-imidazo[5,1-a]isoindol-5-yl)-4,5,6,7-tetrahydropyrazolo[1,5-a]pyridin-4-ol (32.7 mg, 10%) as a white solid: LCMS (ESI, m/z): 311.3 $[M+H]^+$. $^1$H NMR (300 MHz, $CD_3OD$) δ 7.99 (s, 1H), 7.68 (d, J=7.5 Hz, 1H), 7.59-7.38 (m, 4H), 7.23 (s, 1H), 5.87 (d, J=1.9 Hz, 1H), 5.25 (d, J=10.3 Hz, 1H), 3.98-3.77 (m, 2H), 2.61-2.59 (m, 1H), 1.32-1.28 (m, 2H). $t_R$=1.296 min (CHIRALPAK IF-3, 0.46×5 cm; 3 um, Hex(0.1% DEA):EtOH=50:50, 1 ml/min). 151c and 151d are enantiomers.

Example 151d: (4S,5S)-3-fluoro-5-((S)-5H-imidazo[5,1-a]isoindol-5-yl)-4,5,6,7-tetrahydropyrazolo[1,5-a]pyridin-4-ol (30.8 mg, 9%) as a white solid: LCMS (ESI, m/z): 311.2 $[M+H]^+$. $t_R$=1.898 min (CHIRALPAK IF-3, 0.46×5 cm; 3 um, Hex(0.1% DEA):EtOH=50:50, 1 ml/min). 151c and 151d are enantiomers.

Example 152a: (S)—((R)-5H-imidazo[5,1-a]isoindol-5-yl) (pyridin-4-yl)methanol: LCMS (ESI, m/z): 264.1 $[M+H]^+$; $^1$HNMR (400 MHz, DMSO-$d_6$) δ 8.27-8.22 (m, 2H), 7.83 (t, J=0.7 Hz, 1H), 7.43 (dt, J=7.6, 1.0 Hz, 1H), 7.40 (dt, J=7.6, 1.0 Hz, 1H), 7.30 (tdd, J=7.5, 1.2, 0.6 Hz, 1H), 7.21 (td, J=7.5, 1.2 Hz, 1H), 6.96 (s, 1H), 6.91-6.86 (m, 2H), 6.35 (d, J=3.9 Hz, 1H), 5.71 (d, J=4.0 Hz, 1H), 5.40 (t, J=3.9 Hz, 1H).

Example 152b: (R)—((S)-5H-imidazo[5,1-a]isoindol-5-yl) (pyridin-4-yl)methanol: LCMS (ESI, m/z): 264.1 $[M+H]^+$; $^1$HNMR (400 MHz, DMSO-$d_6$) δ 8.29-8.22 (m, 2H), 7.83 (d, J=0.7 Hz, 1H), 7.44 (dd, J=7.5, 1.0 Hz, 1H), 7.40 (dt, J=7.5, 1.0 Hz, 1H), 7.32-7.27 (m, 1H), 7.21 (td, J=7.5, 1.2 Hz, 1H), 6.96 (s, 1H), 6.91-6.86 (m, 2H), 6.35 (d, J=3.9 Hz, 1H), 5.72 (d, J=4.0 Hz, 1H), 5.40 (t, J=3.9 Hz, 1H).

Example 152c: (S)—((S)-5H-imidazo[5,1-a]isoindol-5-yl) (pyridin-4-yl)methanol: LCMS (ESI, m/z): 264.1 $[M+H]^+$; $^1$HNMR (400 MHz, DMSO-$d_6$) δ 8.46-8.41 (m, 2H), 7.59 (d, J=0.6 Hz, 1H), 7.48 (dt, J=7.5, 1.0 Hz, 1H), 7.35-7.28 (m, 1H), 7.20-7.12 (m, 4H), 7.04 (s, 1H), 6.30 (d, J=4.6 Hz, 1H), 5.64 (d, J=5.5 Hz, 1H), 5.12 (t, J=5.1 Hz, 1H).

Example 152d: (R)—((R)-5H-imidazo[5,1-a]isoindol-5-yl) (pyridin-4-yl)methanol: LCMS (ESI, m/z): 264.1 $[M+H]^+$; $^1$HNMR (400 MHz, DMSO-$d_6$) δ 8.46-8.41 (m, 2H), 7.60 (t, J=0.6 Hz, 1H), 7.48 (dt, J=7.7, 1.0 Hz, 1H), 7.35-7.29 (m, 1H), 7.21-7.12 (m, 4H), 7.04 (s, 1H), 6.30 (d, J=4.6 Hz, 1H), 5.65 (d, J=5.5 Hz, 1H), 5.12 (t, J=5.1 Hz, 1H).

Example 153: 1-(hydroxy (5H-imidazo[5,1-a]isoindol-5-yl)methyl)cyclopropane-1-carbonitrile

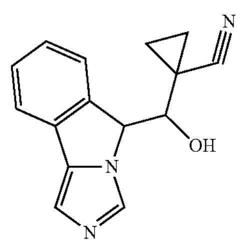 [SMILES: N#CC1(C(O)C2c3ccccc3-c3cncn32)CC1]

1-((R)-hydroxy((R)-5H-imidazo[5,1-a]isoindol-5-yl) methyl)cyclopropane-1-carbonitrile 1-((S)-hydroxy((R)-5H-imidazo[5,1-a]isoindol-5-yl) methyl)cyclopropane-1-carbonitrile Step 1:

1-((R)-hydroxy((R)-5H-imidazo[5,1-a]isoindol-5-yl) methyl)cyclopropane-1-carbonitrile 1-((S)-hydroxy((R)-5H-imidazo[5,1-a]isoindol-5-yl) methyl)cyclopropane-1-carbonitrile 153a

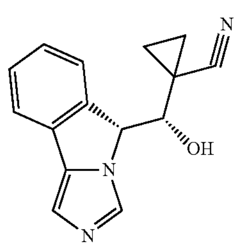

153b

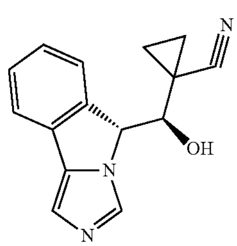

To the solution of 5H-imidazo[5,1-a]isoindole (2 g, 12.81 mmol) in anhydrous THF at −40° C. was added n-BuLi (5.12 mL, 12.81 mmol, 2.5M solution in hexanes) and stirred at −40° C. for 1 hour. Solution of ethyl 1-cyanocyclopropane-1-carboxylate (1.78 g, 12.81 mmol) in anhydrous THF (5 mL) was added slowly at −40° C. and the reaction was gradually warmed to 0° C. over the period of 4 hours. Reaction was the quenched by cooling it to −40° C. and adding methanol (10 mL). Reaction was warmed to 0° C. and $NaBH_4$ (1 g) was added. Reaction was stirred for 2 hours while slowly warming it to the room temperature. Crude product was further purified on a Combi-Flash and further isolated by preparative HPLC to afford 2 isomers as mixtures of enantiomers. The configuration of all isomers was assigned arbitrarily.

Example 153a: 1-((R)-hydroxy((R)-5H-imidazo[5,1-a]isoindol-5-yl)methyl)cyclopropane-1-carbonitrile: LCMS (ESI, m/z): 252.1 $[M+H]^+$; $^1$H NMR (400 MHz, DMSO-$d_6$) δ 7.86 (t, J=0.7 Hz, 1H), 7.67-7.58 (m, 2H), 7.46-7.37 (m, 1H), 7.30-7.22 (m, 1H), 7.14 (s, 1H), 6.46 (s, 1H), 5.48 (d, J=5.3 Hz, 1H), 3.71 (d, J=5.3 Hz, 1H), 1.08-0.86 (m, 3H), 0.73 (dd, J=3.9, 2.7 Hz, 1H).

Example 153b: 1-((S)-hydroxy((R)-5H-imidazo[5,1-a]isoindol-5-yl)methyl)cyclopropane-1-carbonitrile: LCMS (ESI, m/z): 252.2 $[M+H]^+$; $^1$H NMR (400 MHz, DMSO-$d_6$) δ 7.88 (t, J=0.7 Hz, 1H), 7.67 (dd, J=7.7, 0.9 Hz, 1H), 7.64-7.59 (m, 1H), 7.45-7.40 (m, 1H), 7.29 (d, J=1.2 Hz, 1H), 7.14 (s, 1H), 6.52 (s, 1H), 5.42 (d, J=7.2 Hz, 1H), 3.26 (d, J=7.3 Hz, 1H), 1.34-1.22 (m, 2H), 1.01 (d, J=6.8 Hz, 1H), 0.77 (s, 1H). Example 154: (1-fluorocyclopropyl) (5H-imidazo[5,1-a]isoindol-5-yl)methanol

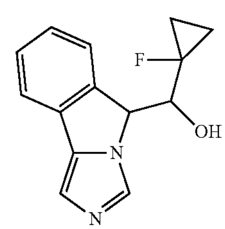 [SMILES: OC(C1c2ccccc2-c2cncn21)C1(F)CC1]

(R)-(1-fluorocyclopropyl) ((R)-5H-imidazo[5,1-a]isoindol-5-yl)methanol (S)-(1-fluorocyclopropyl) ((S)-5H-imidazo[5,1-a]isoindol-5-yl)methanol(S)

(1-fluorocyclopropyl) ((R)-5H-imidazo[5,1-a]isoindol-5-yl) methanol (R)-(1-fluorocyclopropyl) ((S)-5H-imidazo[5,1-a]isoindol-5-yl)methanol Step 1:

(R)-(1-fluorocyclopropyl) ((R)-5H-imidazo[5,1-a]isoindol-5-yl)methanol (S)-(1-fluorocyclopropyl) ((S)-5H-imidazo[5,1-a]isoindol-5-yl)methanol (S)-(1-fluorocyclopropyl) ((R)-5H-imidazo[5,1-a]isoindol-5-yl)methanol (R)-(1-fluorocyclopropyl) ((S)-5H-imidazo[5,1-a]isoindol-5-yl)methanol 154a

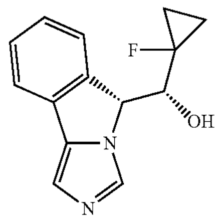

154b

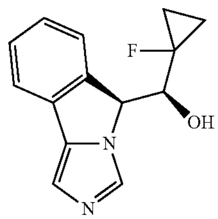

154c

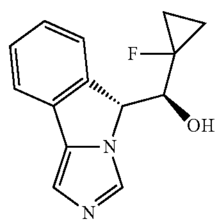

154d

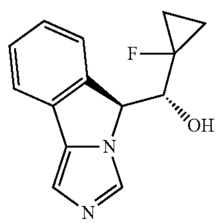

To a solution of 5H-imidazo[5,1-a]isoindole (300 mg, 1.92 mmol) in anhydrous THF (10 mL) was added n-BuLi solution (0.92 mL, 2.3 mmol) at −78° C. and stirred for 1 hr. 1-Fluorocyclopropane-1-carbaldehyde (237 mg, 2.69 mmol) in anhydrous THF (2.0 mL) was added into the reaction mixture drop-wise. The reaction was kept at −78° C. for another 30 min and was warmed up to room temperature. The reaction was kept at room temperature for another 2 hrs and was quenched with saturated $NH_4Cl$ solution (20 mL). The mixture was extracted with 20% 2,2,2-trifluoroethanol in DCM (3×20 ml) and the organic phase was combined, dried over $Na_2SO_4$, and concentrated. The product was separated by CombiFlash and was eluted with DCM: MeOH=96:4. The final products were further isolated by chiral separation to afford 4 isomers and the stereochemistry of each isomer was arbitrarily assigned.

Example 154a: (R)-(1-fluorocyclopropyl) ((R)-5H-imidazo[5,1-a]isoindol-5-yl)methanol: LCMS (ESI, m/z): 245 $[M+H]^+$; $^1$HNMR (400 MHz, DMSO-$d_6$) δ 7.83 (d, J=0.7 Hz, 1H), 7.64 (dq, J=7.7, 0.9 Hz, 1H), 7.58 (dt, J=7.5, 1.0 Hz, 1H), 7.38 (tdd, J=7.6, 1.1, 0.6 Hz, 1H), 7.24 (td, J=7.6, 1.1 Hz, 1H), 7.11 (s, 1H), 6.01 (d, J=5.4 Hz, 1H), 5.49 (d, J=5.9 Hz, 1H), 3.87 (dt, J=20.5, 5.6 Hz, 1H), 0.98-0.80 (m, 2H), 0.66-0.52 (m, 2H).

Example 154b: (S)-(1-fluorocyclopropyl) ((S)-5H-imidazo[5,1-a]isoindol-5-yl)methanol: LCMS (ESI, m/z): 245 $[M+H]^+$; $^1$HNMR (400 MHz, DMSO-$d_6$) δ 7.83 (q, J=0.6 Hz, 1H), 7.66-7.61 (m, 1H), 7.58 (dt, J=7.6, 1.0 Hz, 1H), 7.38 (tdd, J=7.5, 1.1, 0.6 Hz, 1H), 7.24 (td, J=7.6, 1.2 Hz, 1H), 7.11 (s, 1H), 6.00 (d, J=5.5 Hz, 1H), 5.49 (d, J=5.9 Hz, 1H), 3.87 (dt, J=20.6, 5.7 Hz, 1H), 0.98-0.80 (m, 2H), 0.66-0.52 (m, 2H).

Example 154c: (S)-(1-fluorocyclopropyl) ((R)-5H-imidazo[5,1-a]isoindol-5-yl)methanol: LCMS (ESI, m/z): 245 $[M+H]^+$; $^1$HNMR (400 MHz, DMSO-$d_6$) δ 7.82 (s, 1H), 7.63-7.57 (m, 2H), 7.42-7.36 (m, 1H), 7.26 (td, J=7.6, 1.2 Hz, 1H), 7.12 (s, 1H), 5.92 (d, J=5.8 Hz, 1H), 5.50 (d, J=6.3 Hz, 1H), 3.60 (dt, J=22.0, 6.0 Hz, 1H), 1.17-0.99 (m, 2H), 0.77-0.70 (m, 1H), 0.70-0.60 (m, 1H).

Example 154d: (R)-(1-fluorocyclopropyl) ((S)-5H-imidazo[5,1-a]isoindol-5-yl)methanol: LCMS (ESI, m/z): 245 $[M+H]^+$; $^1$HNMR (400 MHz, DMSO-$d_6$) δ 7.83 (d, J=0.7 Hz, 1H), 7.60 (ddt, J=6.7, 5.9, 0.8 Hz, 2H), 7.42-7.35 (m, 1H), 7.26 (td, J=7.6, 1.3 Hz, 1H), 7.12 (s, 1H), 5.92 (d, J=5.8 Hz, 1H), 5.50 (d, J=6.3 Hz, 1H), 3.61 (dt, J=21.9, 6.1 Hz, 1H), 1.18-0.99 (m, 2H), 0.81-0.71 (m, 1H), 0.71-0.61 (m, 1H).

Example 155: 3-hydroxy-3-(5H-imidazo[5,1-a]isoindol-5-yl)-2,2-dimethylpropanamide

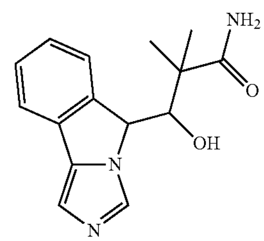 [SMILES: CC(C)(C(N)=O)C(O)C1c2ccccc2-c2cncn21]

(R)-3-hydroxy-3-((R)-5H-imidazo[5,1-a]isoindol-5-yl)-2,2-dimethylpropanamide (R)-3-hydroxy-3-((S)-5H-imidazo[5,1-a]isoindol-5-yl)-2,2-dimethylpropanamide (S)-3-hydroxy-3-((R)-5H-imidazo[5,1-a]isoindol-5-yl)-2,2-dimethylpropanamide (S)-3-hydroxy-3-((S)-5H-imidazo[5,1-a]isoindol-5-yl)-2,2-dimethylpropanamide Step 1: 3-hydroxy-3-(5H-imidazo[5,1-a]isoindol-5-yl)-2,2-dimethylpropanenitrile

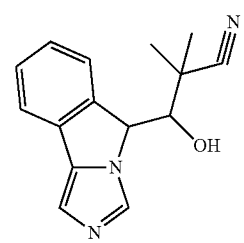 [SMILES: CC(C)(C#N)C(O)C1c2ccccc2-c2cncn21]

To the solution of 5H-imidazo[5,1-a]isoindole (0.5 g, 3.20 mmol) in anhydrous THF at −40° C. was added n-BuLi (1.28 mL, 3.2 mmol, 2.5M solution in hexanes) and stirred at −40° C. for 1 hour. Solution of ethyl 2-cyano-2-methylpropanoate (0.45 g, 3.2 mmol) in anhydrous THF (1 mL) was added slowly at −40° C. and the reaction was gradually warmed to 0° C. over the period of 4 hours. Reaction was the quenched by cooling it to −40° C. and adding sat. $NH_4Cl$ solution. Crude product was extracted using DCM which was further purified on a Combi-Flash. LCMS (ESI, m/z): 254.2 $[M+H]^+$.

Step 2:

(R)-3-hydroxy-3-((R)-5H-imidazo[5,1-a]isoindol-5-yl)-2,2-dimethylpropanamide (R)-3-hydroxy-3-((S)-5H-imidazo[5,1-a]isoindol-5-yl)-2,2-dimethylpropanamide (S)-3-hydroxy-3-((R)-5H-imidazo[5,1-a]isoindol-5-yl)-2,2-dimethylpropanamide (S)-3-hydroxy-3-((S)-5H-imidazo[5,1-a]isoindol-5-yl)-2,2-dimethylpropanamide 155a

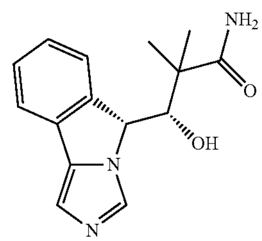

155b

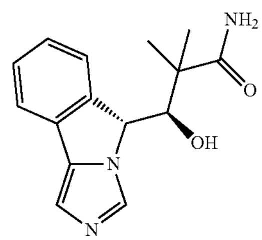

155c

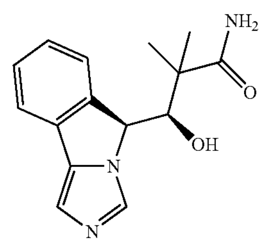

155d

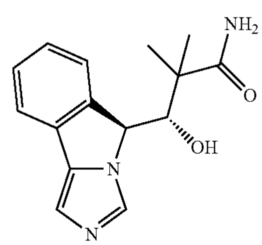

To the solution of 3-hydroxy-3-(5H-imidazo[5,1-a]isoindol-5-yl)-2,2-dimethylpropanenitrile (200 mg, 0.79 mmol) in methanol NaOH (315 mg, 7.90 mmol) and hydrogen peroxide (0.8 mL, 7.9 mmol). The reaction mixture was stirred for 3 days. Crude product was extracted using 2,2,2-trifluoroethanol. Crude product was further purified on a Combi-Flash and further isolated by chiral separation to afford 4 isomers as white solid. The absolute configuration of all isomers was assigned arbitrarily Example 155a: (R)-3-hydroxy-3-((R)-5H-imidazo[5,1-a]isoindol-5-yl)-2,2-dimethylpropanamide: LCMS (ESI, m/z): 272.2 $[M+H]^+$; $^1H$ NMR (400 MHz, DMSO-$d_6$) δ 7.83 (t, J=0.7 Hz, 1H), 7.55 (dt, J=7.6, 1.0 Hz, 1H), 7.48 (dq, J=7.7, 0.9 Hz, 1H), 7.36-7.31 (m, 1H), 7.20 (td, J=7.6, 1.2 Hz, 1H), 7.10 (d, J=8.5 Hz, 2H), 6.92 (s, 1H), 5.36 (d, J=2.9 Hz, 1H), 4.34 (d, J=3.0 Hz, 1H), 0.98 (s, 3H), 0.97 (s, 3H).

Example 155b: (R)-3-hydroxy-3-((S)-5H-imidazo[5,1-a]isoindol-5-yl)-2,2-dimethylpropanamide: LCMS (ESI, m/z): 272.2 $[M+H]^+$; $^1H$ NMR (400 MHz, DMSO-$d_6$) δ 7.83 (s, 1H), 7.55 (d, J=7.7 Hz, 1H), 7.47 (d, J=1.0 Hz, 1H), 7.34 (s, 1H), 7.20 (d, J=1.2 Hz, 1H), 7.09 (s, 2H), 6.93 (s, 1H), 5.67 (d, J=6.0 Hz, 1H), 5.36 (d, J=2.9 Hz, 1H), 4.34 (dd, J=6.0, 3.0 Hz, 1H), 0.98 (s, 3H), 0.97 (s, 3H).

Example 155c: (S)-3-hydroxy-3-((R)-5H-imidazo[5,1-a]isoindol-5-yl)-2,2-dimethylpropanamide: LCMS (ESI, m/z): 272.2 $[M+H]^+$; $^1H$ NMR (400 MHz, DMSO-$d_6$) δ 7.67 (d, J=0.7 Hz, 1H), 7.54 (s, 2H), 7.38-7.32 (m, 1H), 7.26 (d, J=1.2 Hz, 2H), 7.12 (s, 1H), 7.07 (s, 1H), 5.32-5.18 (m, 1H), 4.17 (d, J=2.1 Hz, 1H), 1.26 (s, 3H), 1.21 (s, 3H).

Example 155d: (S)-3-hydroxy-3-((S)-5H-imidazo[5,1-a]isoindol-5-yl)-2,2-dimethylpropanamide: LCMS (ESI, m/z): 272.2 $[M+H]^+$; $^1H$ NMR (400 MHz, DMSO-$d_6$) δ 7.67 (s, 1H), 7.54 (ddt, J=6.5, 5.7, 0.9 Hz, 2H), 7.38-7.32 (m, 1H), 7.29-7.23 (m, 2H), 7.12 (s, 1H), 7.07 (s, 1H), 5.44 (d, J=6.7 Hz, 1H), 5.29-5.24 (m, 1H), 4.17 (dd, J=6.7, 2.0 Hz, 1H), 1.26 (s, 3H), 1.21 (s, 3H).

Example 156: 4-hydroxy-5-(5H-imidazo[5,1-a]isoindol-5-yl)-4,5,6,7-tetrahydropyrazolo[1,5-a]pyridine-3-carbonitrile

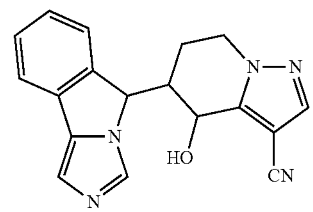 [SMILES: N#Cc1cnn2c1C(O)C(C1c3ccccc3-c3cncn31)CC2]

Step 1: 4H,5H,6H,7H-pyrazolo[1,5-a]pyridin-4-one

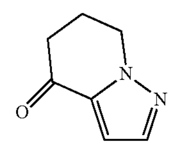

The title compound was synthesized by General Procedure for the Synthesis of 151a-b.

Step 2: 3-iodo-4H,5H,6H,7H-pyrazolo[1,5-a]pyridin-4-one

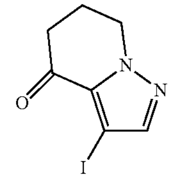 [SMILES: O=C1CCCn2ncc(I)c21]

A solution of 4H,5H,6H,7H-pyrazolo[1,5-a]pyridin-4-one (600 mg, 4.41 mmol) in acetonitrile (30 mL) was added $I_2$ (667 mg, 2.628 mmol) and CAN (2.880 g, 5.23 mmol). The resulting solution was stirred for 1 day at room temperature. The reaction was then quenched by the addition of Sat. $NaS2O_3$ solution (100 mL). The resulting solution was extracted with EtOAc (2×100 mL) and the organic layers combined. The residue waspurified by silica gel column eluting with EtOAc/petroleum ether (30:70). This resulted in 600 mg (52%) of 3-iodo-4H,5H,6H,7H-pyrazolo[1,5-a]pyridin-4-one as a yellow solid: LCMS (ESI, m/z): 263.2 $[M+H]^+$.

Step 3: 4-oxo-4,5,6,7-tetrahydropyrazolo[1,5-a]pyridine-3-carbonitrile

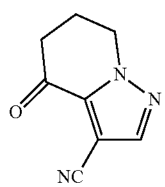 [SMILES: N#Cc1cnn2c1C(=O)CCC2]

A mixture of 3-iodo-4H,5H,6H,7H-pyrazolo[1,5-a]pyridin-4-one (900 mg, 3.43 mmol) and CuCN (900 mg, 10.05 mmol) in DMF (50 mL) was stirred for 1 h at 150° C. The solids were filtered out. The solution was diluted with water (200 mL). The resulting solution was extracted with EtOAc (2×200 mL). The organic layers were combined, dried over anhydrous sodium sulfate, and concentrated under vacuum. The residue was purified by silica gel column eluting with EtOAc/petroleum ether (42:58). This resulted in 570 mg (crude) of 4-oxo-4H,5H,6H,7H-pyrazolo[1,5-a]pyridine-3-carbonitrile as a brown solid: LCMS (ESI, m/z): 162.2 $[M+H]^+$.

Step 4: (E)-4-oxo-5-(2-(1-trityl-1H-imidazol-4-yl)benzylidene)-4,5,6,7-tetrahydropyrazolo[1,5-a]pyridine-3-carbonitrile

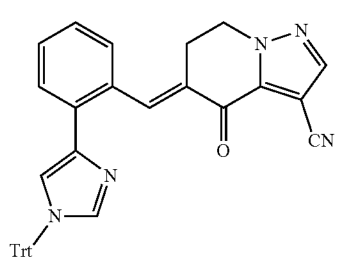

The title compound was synthesized by General Procedure for the Synthesis of 146c-d.

Step 5: 5-(5H-imidazo[5,1-a]isoindol-5-yl)-4-oxo-4,5,6,7-tetrahydropyrazolo[1,5-a]pyridine-3-carbonitrile

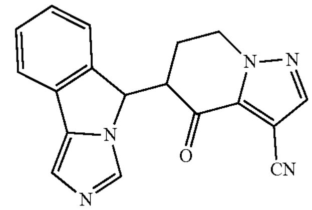 [SMILES: N#Cc1cnn2c1C(=O)C(C1c3ccccc3-c3cncn31)CC2]

The title compound was synthesized by General Procedure for the Synthesis of 146c-d.

Step 6:

(4S,5R)-4-hydroxy-5-((R)-5H-imidazo[5,1-a]isoindol-5-yl)-4,5,6,7-tetrahydropyrazolo[1,5-a]pyridine-3-carbonitrile (4R,5S)-4-hydroxy-5-((S)-5H-imidazo[5,1-a]isoindol-5-yl)-4,5,6,7-tetrahydropyrazolo[1,5-a]pyridine-3-carbonitrile (4S,5R)-4-hydroxy-5-((S)-5H-imidazo[5,1-a]isoindol-5-yl)-4,5,6,7-tetrahydropyrazolo[1,5-a]pyridine-3-carbonitrile (4R,5S)-4-hydroxy-5-((R)-5H-imidazo[5,1-a]isoindol-5-yl)-4,5,6,7-tetrahydropyrazolo[1,5-a]pyridine-3-carbonitrile 156a

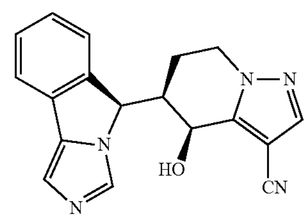

156b

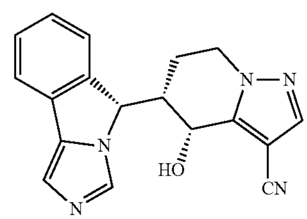

156c

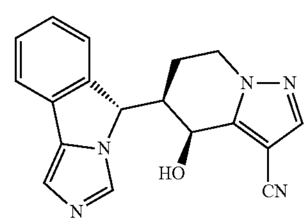

156d

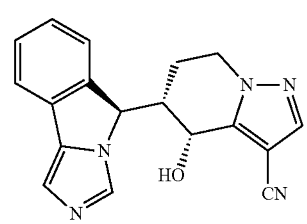

The title compound was synthesized by General Procedure for the Synthesis of 146c-d.

The crude product was purified by Prep-HPLC and further isolated by chiral separation with the following conditions:

1. Column, XBridge Shield RP18 OBD Column, 5 um, 19×150 mm; mobile phase, Water (0.05% $NH_3H_2O$) and ACN (13.0% ACN up to 40.0% in 7 min); Detector, UV 220 nm.
2. Column, Chiralpak IC, 2×25 cm, 5 um; mobile phase, Hex-HPLC and ethanol-HPLC (hold 50% ethanol-HPLC in 25 min); Detector, UV 220/254 nm.
3. Column, CHIRALPAK IA, 2.12×15 cm, 5 um; mobile phase, Hex- and ethanol-(hold 50.0% ethanol-in 10 min); Detector, UV 220/254 nm.

The absolute configuration of all isomers 156a-e was assigned arbitrarily.

Example 156a: (4S,5R)-4-hydroxy-5-((R)-5H-imidazo[5,1-a]isoindol-5-yl)-4,5,6,7-tetrahydropyrazolo[1,5-a]pyridine-3-carbonitrile (22.4 mg, 11%) as a white solid: LCMS (ESI, m/z): 318.3 $[M+H]^+$. $^1$H NMR (300 MHz, $CD_3OD$) δ 8.09 (s, 1H), 7.92 (s, 1H), 7.66-7.60 (m, 2H), 7.48-7.34 (m, 2H), 7.18 (s, 1H), 5.68 (s, 1H), 5.49 (d, J=3.6 Hz, 1H), 4.24-4.18 (m, 1H), 3.95-3.84 (m, 1H), 2.84-2.80 (m, 1H), 2.06-1.87 (m, 1H), 1.31-1.29 (m, 1H). $t_R$=2.082 min (Repaired Chiral IC, 0.46×10 cm; 5 um, MeOH (0.1% DEA): EtOH=70:30, 1 ml/min). 156a and 156b are enantiomers.

Example 156b: (4R,5S)-4-hydroxy-5-((S)-5H-imidazo[5,1-a]isoindol-5-yl)-4,5,6,7-tetrahydropyrazolo[1,5-a]pyridine-3-carbonitrile (23.0 mg, 12%) as a white solid: LCMS (ESI, m/z): 318.2 $[M+H]^+$. $t_R$=2.784 min (Repaired Chiral IC, 0.46×10 cm; 5 um, MeOH (0.1% DEA):EtOH=70:30, 1 ml/min). 156a and 156b are enantiomers.

Example 156c: (4S,5R)-4-hydroxy-5-((S)-5H-imidazo[5,1-a]isoindol-5-yl)-4,5,6,7-tetrahydropyrazolo[1,5-a]pyridine-3-carbonitrile (4.1 mg, 2%) as a white solid: LCMS (ESI, m/z): 318.3 $[M+H]^+$. $^1$H NMR (300 MHz, $CD_3OD$) δ 8.06 (s, 1H), 7.90 (s, 1H), 7.75-7.66 (m, 2H), 7.51-7.39 (m, 1H), 7.32 (td, J=7.6, 1.2 Hz, 1H), 7.20 (s, 1H), 5.63 (d, J=5.2 Hz, 1H), 5.21 (d, J=3.5 Hz, 1H), 4.21-4.15 (m, 1H), 4.03-1.00 (m, 1H), 2.60-2.58 (m, 1H), 2.42-2.39 (m, 1H), 2.08-2.05 (m, 1H). $t_R$=4.180 min (CHIRAL Cellulose-SB, 0.46×15 cm; 5 um, Hex(0.1% IPAmine):EtOH=50:50, 1 ml/min). 156c and 156d are enantiomers.

Example 156d: (4R,5S)-4-hydroxy-5-((R)-5H-imidazo[5,1-a]isoindol-5-yl)-4,5,6,7-tetrahydropyrazolo[1,5-a]pyridine-3-carbonitrile (3.8 mg, 2%) as a white solid: LCMS (ESI, m/z): 318.2 $[M+H]^+$. $t_R$=5.039 min (CHIRAL Cellulose-SB, 0.46×15 cm; 5 um, Hex(0.1% IPAmine):EtOH=50:50, 1 ml/min). 156c and 156d are enantiomers.

(4R,5R)-4-hydroxy-5-((R)-5H-imidazo[5,1-a]isoindol-5-yl)-4,5,6,7-tetrahydropyrazolo[1,5-a]pyridine-3-carbonitrile (4S,5S)-4-hydroxy-5-((S)-5H-imidazo[5,1-a]isoindol-5-yl)-4,5,6,7-tetrahydropyrazolo[1,5-a]pyridine-3-carbonitrile 156e

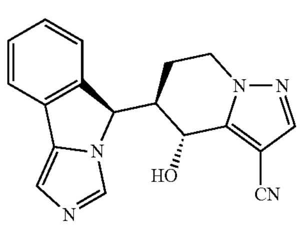

-continued

156f

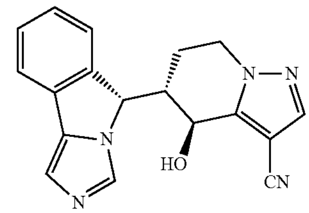

The title compound was synthesized by General Procedure for the Synthesis of 146e-f. The crude product was purified by Prep-HPLC and further isolated by chiral separation with the following conditions:

1. Column, XBridge Shield RP18 OBD Column, 5 um, 19×150 mm; mobile phase, Water (0.05% $NH_3H_2O$) and ACN (13% ACN up to 40% in 7 min); Detector, UV 220 nm.
2. Column, Chiralpak IC, 2×25 cm, 5 um; mobile phase, Hex-HPLC and ethanol-HPLC (hold 50% ethanol-HPLC in 25 min); Detector, UV 220/254 nm. The absolute configuration of all isomers 156e-f was assigned arbitrarily.

Example 156e: (4R,5R)-4-hydroxy-5-((R)-5H-imidazo[5,1-a]isoindol-5-yl)-4,5,6,7-tetrahydropyrazolo[1,5-a]pyridine-3-carbonitrile (10.9 mg, 4%) as a white solid: LCMS (ESI, m/z): 318.3 $[M+H]^+$. $^1$H NMR (300 MHz, $CD_3OD$) δ 8.07 (s, 1H), 7.90 (s, 1H), 7.71-7.68 (m, 1H), 7.56-7.37 (m, 3H), 7.25 (s, 1H), 5.87 (d, J=2.5 Hz, 1H), 5.29 (d, J=10.7 Hz, 1H), 4.15-4.08 (m, 1H), 4.00-3.90 (m, 1H), 2.71-2.61 (m, 1H), 1.39-1.30 (m, 2H). $t_R$=3.016 min (CHIRALPAK IF-3, 0.46×5 cm; 3 um, Hex(0.1% DEA):EtOH=60:40, 1 ml/min). 156e and 156f are enantiomers.

Example 156f: (4S,5S)-4-hydroxy-5-((S)-5H-imidazo[5,1-a]isoindol-5-yl)-4,5,6,7-tetrahydropyrazolo[1,5-a]pyridine-3-carbonitrile (10.0 mg, 4%) as a white solid: LCMS (ESI, m/z): 318.2 $[M+H]^+$. $t_R$=1.875 min (CHIRALPAK IF-3, 0.46×5 cm; 3 um, Hex(0.1% DEA):EtOH=60:40, 1 ml/min). 156e and 156f are enantiomers.

Example 157: 6-(5H-imidazo[5,1-a]isoindol-5-yl)-4,5,6,7-tetrahydro-1H-indazol-7-ol

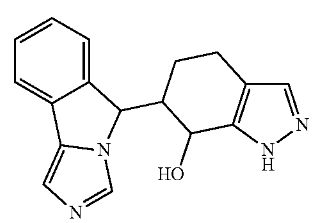 [SMILES: OC1c2[nH]ncc2CCC1C1c2ccccc2-c2cncn21]

Step 1: 5,6-dihydro-1H-indazol-7 (4H)-one

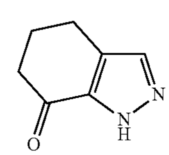

A solution of 1H-indazol-7-ol (4.0 g, 22.37 mmol) in EtOH (30 mL) was added 10% Pd/C (1.0 g). The mixture was hydrogenated under 20 bar of hydrogen at 80° C. for 16 h. The mixture was filtered, and the filtrate was evaporated. The residue was purified by flash chromatography (PE-EtOAc 7:3) to afford 1.5 g (43%) of 4,5,6,7-tetrahydro-1H-indazol-7-one as brown oil: LCMS (ESI, m/z): 137.2

Step 2: (E)-6-(2-(1-trityl-1H-imidazol-4-yl)benzylidene)-5,6-dihydro-1H-indazol-7 (4H)-one

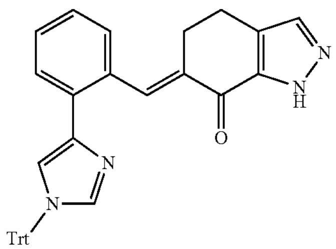

The title compound was synthesized by General Procedure for the Synthesis of 146c-d.

Step 3: 6-(5H-imidazo[5,1-a]isoindol-5-yl)-5,6-dihydro-1H-indazol-7 (4H)-one

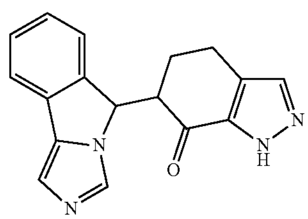 [SMILES: O=C1c2[nH]ncc2CCC1C1c2ccccc2-c2cncn21]

The title compound was synthesized by General Procedure for the Synthesis of 146c-d.

Step 4:

(6R,7R)-6-((S)-5H-imidazo[5,1-a]isoindol-5-yl)-4,5,6,7-tetrahydro-1H-indazol-7-ol (6S,7S)-6-((R)-5H-imidazo[5,1-a]isoindol-5-yl)-4,5,6,7-tetrahydro-1H-indazol-7-ol (6R,7R)-6-((R)-5H-imidazo[5,1-a]isoindol-5-yl)-4,5,6,7-tetrahydro-1H-indazol-7-ol (6S,7R)-6-((S)-5H-imidazo[5,1-a]isoindol-5-yl)-4,5,6,7-tetrahydro-1H-indazol-7-ol (6R,7S)-6-((R)-5H-imidazo[5,1-a]isoindol-5-yl)-4,5,6,7-tetrahydro-1H-indazol-7-ol (6S,7R)-6-((R)-5H-imidazo[5,1-a]isoindol-5-yl)-4,5,6,7-tetrahydro-1H-indazol-7-ol (6S,7S)-6-((S)-5H-imidazo[5,1-a]isoindol-5-yl)-4,5,6,7-tetrahydro-1H-indazol-7-ol (6R,7S)-6-((S)-5H-imidazo[5,1-a]isoindol-5-yl)-4,5,6,7-tetrahydro-1H-indazol-7-ol 157a

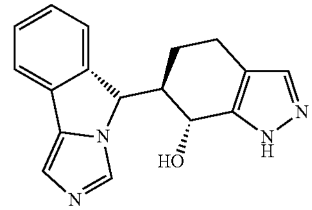

157b

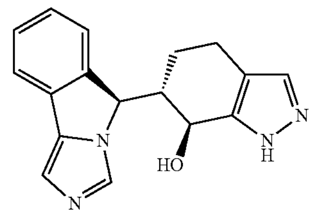

157c

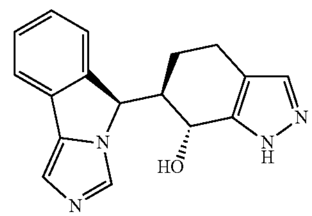

157d

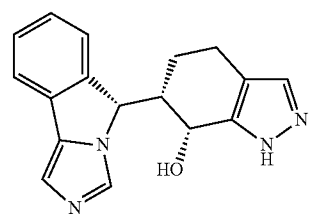

157e

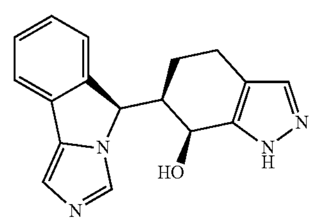

157f

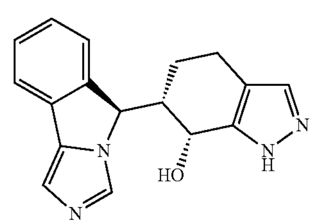

157g

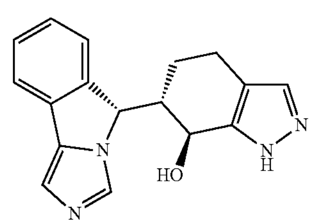

-continued

157h

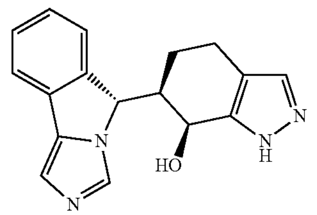

A solution of 6-[5H-imidazo[4,3-a]isoindol-5-yl]-4,5,6,7-tetrahydro-1H-indazol-7-one (800 mg, 2.77 mmol) in MeOH (20 mL) was added $NaBH_4$ (314 mg, 8.30 mmol). The resulting solution was stirred for 20 min at room temperature. The reaction was then quenched by the addition water (100 mL). The resulting solution was extracted with EtOAc (2×100 mL). The organic layers were combined, dried over anhydrous sodium sulfate, and concentrated under vacuum. the residue was purified by silica gel column eluting with DCM/MeOH (80:10). The crude product was purified by Prep-HPLC and further isolated by chiral separation. The absolute configuration of all isomers 157a-h was assigned arbitrarily.

Example 157a: (6R,7R)-6-((S)-5H-imidazo[5,1-a]isoindol-5-yl)-4,5,6,7-tetrahydro-1H-indazol-7-ol (18.1 mg, 2%) as a white solid: LCMS (ESI, m/z): 293.3 $[M+H]^+$. $^1H$ NMR (300 MHz, $CD_3OD$) δ 8.05 (s, 1H), 7.75-7.59 (m, 2H), 7.53-7.24 (m, 4H), 5.94-5.86 (m, 1H), 5.14 (d, J=10.2 Hz, 1H), 2.69-2.53 (m, 1H), 2.52-2.30 (m, 2H), 1.04 (m, 2H). $t_R$=1.872 min (CHIRALPAK IC-3, 0.46×5 cm; 3 um, Hex (0.1% DEA):EtOH=50:50, 1 ml/min). 157a and 157b are enantiomers.

Example 157b: (6S,7S)-6-((R)-5H-imidazo[5,1-a]isoindol-5-yl)-4,5,6,7-tetrahydro-1H-indazol-7-ol (20.7 mg, 3%) as a white solid: LCMS (ESI, m/z): 293.3 $[M+H]^+$. $t_R$=2.812 min (CHIRALPAK IC-3, 0.46×5 cm; 3 um, Hex(0.1% DEA):EtOH=50:50, 1 ml/min). 157a and 157b are enantiomers.

Example 157c: (6R,7R)-6-((R)-5H-imidazo[5,1-a]isoindol-5-yl)-4,5,6,7-tetrahydro-1H-indazol-7-ol (24.2 mg, 4%) as a white solid: LCMS (ESI, m/z): 293.1 $[M+H]^+$. $^1H$ NMR (300 MHz, $CD_3OD$) δ 8.00 (s, 1H), 7.73-7.63 (m, 1H), 7.56-7.26 (m, 4H), 7.23 (s, 1H), 5.87 (s, 1H), 5.18-5.08 (m, 1H), 2.55-2.31 (m, 3H), 1.15-1.03 (m, 1H), 0.96 (m, 1H). $t_R$=0.680 min (SFC, CHIRALPAK AD-3 3×100 mm, 3 um, $CO_2$:IPA (0.1% DEA) 50%, 2.0 ml/min). 157c and 157g are enantiomers.

Example 157d: (6S,7R)-6-((S)-5H-imidazo[5,1-a]isoindol-5-yl)-4,5,6,7-tetrahydro-1H-indazol-7-ol (128.4 mg, 14%) as a white solid: LCMS (ESI, m/z): 293.1 $[M+H]^+$. $^1H$ NMR (300 MHz, $CD_3OD$) δ 8.13 (s, 1H), 7.61 (m, 2H), 7.50-7.28 (m, 3H), 7.21-7.12 (m, 1H), 5.61 (s, 1H), 5.23 (d, J=3.6 Hz, 1H), 2.59 (m, 2H), 2.36-2.19 (m, 1H), 1.53 (m, 1H), 1.00 (m, 1H). tR=0.599 min (SFC, CHIRALPAK AD-3 3×100 mm, 3 um, $CO_2$:IPA (0.1% DEA) 50%, 2.0 ml/min). 157d and 157e are enantiomers.

Example 157e: (6R,7S)-6-((R)-5H-imidazo[5,1-a]isoindol-5-yl)-4,5,6,7-tetrahydro-1H-indazol-7-ol (167.1 mg, 16%) as a white solid: LCMS (ESI, m/z): 293.1 $[M+H]^+$. $t_R$=1.086 min (SFC, CHIRALPAK AD-3 3×100 mm, 3 um, $CO_2$:IPA (0.1% DEA) 50%, 2.0 ml/min). 157d and 157e are enantiomers.

Example 157f: (6S,7R)-6-((R)-5H-imidazo[5,1-a]isoindol-5-yl)-4,5,6,7-tetrahydro-1H-indazol-7-ol (35.8 mg, 4%) as a white solid: LCMS (ESI, m/z): 293.1 $[M+H]^+$. $^1H$ NMR (300 MHz, $CD_3OD$) δ 8.07 (s, 1H), 7.77 (d, J=7.7 Hz, 1H), 7.65 (d, J=7.6 Hz, 1H), 7.49-7.24 (m, 3H), 7.17 (s, 1H), 5.53 (d, J=5.7 Hz, 1H), 4.91 (s, 1H), 2.77 (d, J=16.2 Hz, 1H), 2.45 (m, 1H), 2.25 (d, J=11.0 Hz, 1H), 2.06 (m, 1H), 1.90 (m, 1H). $t_R$=1.505 min (SFC, CHIRALPAK AD-3 3×100 mm, 3 um, $CO_2$:IPA (0.1% DEA) 50%, 2.0 ml/min). 157f and 157h are enantiomers.

Example 157g: (6S,7S)-6-((S)-5H-imidazo[5,1-a]isoindol-5-yl)-4,5,6,7-tetrahydro-1H-indazol-7-ol (68.2 mg, 8%) as a white solid: LCMS (ESI, m/z): 293.1 $[M+H]^+$. tR=1.910 min (SFC, CHIRALPAK AD-3 3×100 mm, 3 um, $CO_2$:IPA (0.1% DEA) 50%, 2.0 ml/min). 157c and 157g are enantiomers.

Example 157h: (6R,7S)-6-((S)-5H-imidazo[5,1-a]isoindol-5-yl)-4,5,6,7-tetrahydro-1H-indazol-7-ol (50.5 mg, 6%) as a white solid: LCMS (ESI, m/z): 293.1 $[M+H]^+$. $t_R$=2.961 min (SFC, CHIRALPAK AD-3 3×100 mm, 3 um, $CO_2$:IPA (0.1% DEA) 50%, 2.0 ml/min). 157f and 157h are enantiomers.

Example 158a: 3-(5H-imidazo[5,1-a]isoindol-5-yl)cyclobutane-1,2-diol

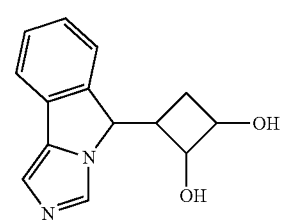 [SMILES: OC1CC(C2c3ccccc3-c3cncn32)C1O]

The stereochemistry of this product is undefined.

Step 1: 2-(benzyloxy)cyclobutanone

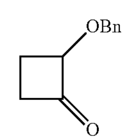

A solution of phenylmethanol (2.5 mL, 23.35 mmol) in HCl/1,4-dioxane (200 mL, 4.0 M) was added trimethyl([2-[(trimethylsilyl)oxy]cyclobut-1-en-1-yl]oxy) silane (5.0 g, 21.70 mmol). The resulting solution was stirred for 4 h at 80° C. in an oil bath. The resulting mixture was concentrated under vacuum. The resulting solution was diluted with EtOAc (500 mL). The resulting mixture was washed with Sat. sodium bicarbonate (2×100 mL) and brine (1×100 mL). The organic layer was concentrated under vacuum. The residue was purified by silica gel column eluting with EtOAc/petroleum ether (0-30%). This resulted in 2.2 g (58%) of 2-(benzyloxy)cyclobutan-1-one as colorless oil. $^1H$ NMR (300 MHz, $CDCl_3$) δ 7.41-7.34 (m, 5H), 4.81-4.72 (m, 2H), 4.68-4.62 (m, 1H), 2.83-2.74 (m, 2H), 2.40-2.27 (m, 1H), 2.05-1.92 (m, 1H).

Step 2: (E)-2-(benzyloxy)-4-(2-(1-trityl-1H-imidazol-4-yl)benzylidene)cyclobutanone

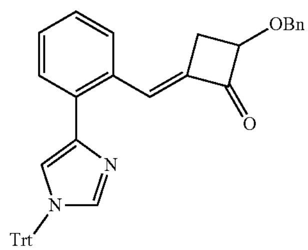

The title compound was synthesized by General Procedure for the Synthesis of 146c-d.

Step 3: 2-(benzyloxy)-4-(5H-imidazo[5,1-a]isoindol-5-yl)cyclobutanone

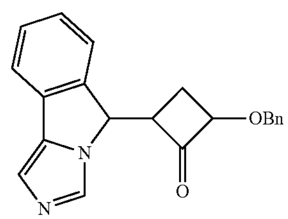 [SMILES: O=C1C(OCc2ccccc2)CC1C1c2ccccc2-c2cncn21]

A of (4E)-2-(benzyloxy)-4-([2-[1-(triphenylmethyl)-1H-imidazol-4-yl]phenyl]methylidene)cyclobutan-1-one (1.7 g, 2.97 mmol) in DCM (20 mL) was added trifluoroacetic acid (10 mL). The resulting solution was stirred for 40 min at room temperature. The resulting solution was diluted with water (50 mL). The pH value of the solution was adjusted to 10 with potassium carbonate. The resulting solution was extracted with DCM (3×100 mL). The organic layers were combined, dried over anhydrous sodium sulfate, and concentrated under vacuum. The residue was purified by silica gel column with DCM/MeOH (0-5%). This resulted in 900 mg (92%) of 2-(benzyloxy)-4-[5H-imidazo[4,3-a]isoindol-5-yl]cyclobutan-1-one as a light yellow solid: LCMS (ESI, m/z): 331.2 $[M+H]^+$.

Step 4: 3-(5H-imidazo[5,1-a]isoindol-5-yl)cyclobutane-1,2-diol

158a

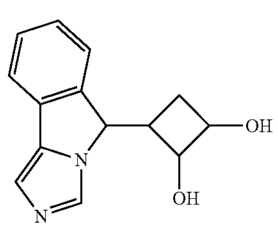

A solution of 2-(benzyloxy)-4-[5H-imidazo[4,3-a]isoindol-5-yl]cyclobutan-1-ol (1.2 g, 3.61 mmol) and ammoniumformate (3.0 g, 47.58 mmol) in MeOH (60 mL) was added Palladium carbon (1.6 g, 10%). The resulting solution was stirred for 4 h at 80° C. in an oil bath. The solid was filtered out. The filtrate was concentrated under vacuum. The residue was purified with Prep-HPLC with the following condition:

Column: XBridge BEH130 Prep C18 OBD Column 19×150 mm 5 um 13 nm; Mobile Phase A: Water (0.05% $NH_3H_2O$), Mobile Phase B: ACN; Flow rate: 20 mL/min; Gradient: 15% B to 27% B in 10 min; 254/220 nm.

Example 158a: 3-(5H-imidazo[5,1-a]isoindol-5-yl)cyclobutane-1,2-diol (21.3 mg, 2.5%) as a white solid: LCMS (ESI, m/z): 243.1 $[M+H]^+$. $^1H$ NMR (400 MHz, DMSO-$d_6$) δ 7.79 (s, 1H), 7.60 (d, J=7.2 Hz, 1H), 7.39-7.34 (m, 2H), 7.25-7.21 (m, 1H), 7.11 (s, 1H), 5.47 (d, J=5.2 Hz, 1H), 5.33 (d, J=8.1 Hz, 1H), 5.04 (d, J=8.0 Hz, 1H), 4.37-4.32 (m, 1H), 4.00-3.95 (m, 1H), 2.44-2.36 (m, 2H), 1.86-1.77 (m, 1H).

Example 159: 5-(5H-imidazo[5,1-a]isoindol-5-yl)-3-methyl-4,5,6,7-tetrahydropyrazolo[1,5-a]pyridin-4-ol

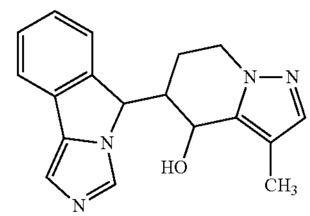

Step 1: 3-methyl-6,7-dihydropyrazolo[1,5-a]pyridin-4(5H)-one

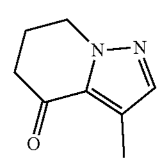

Under nitrogen, a solution of 3-iodo-4H,5H,6H,7H-pyrazolo[1,5-a]pyridin-4-one (1.3 g, 4.96 mmol) in dioxane (100 mL, 1.18 mol) was added trimethyl-1,3,5,2,4,6-trioxatriborinane (3.71 g, 14.77 mmol, 50% in THF), $Pd(PPh_3)_4$ (570 mg, 0.493 mmol) and potassium carbonate (1.35 g, 9.80 mmol). The resulting solution was stirred for 2 h at 100° C. in an oil bath. The mixture was diluted with water (100 mL). The resulting solution was extracted with EtOAc. The organic layers were combined, dried over anhydrous sodium sulfate, and concentrated under vacuum. The residue was purified by silica gel column eluting with EtOAc/petroleum ether (40:60). This resulted in 700 mg (94%) of 3-methyl-4H,5H,6H,7H-pyrazolo[1,5-a]pyridin-4-one as a brown solid: LCMS (ESI, m/z): 151.1 $[M+H]^+$.

Step 2: (E)-3-methyl-5-(2-(1-trityl-1H-imidazol-4-yl)benzylidene)-6,7-dihydropyrazolo[1,5-a]pyridin-4(5H)-one

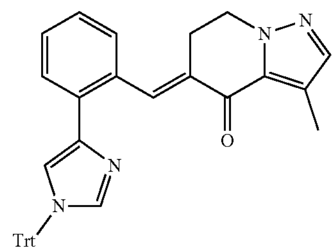

The title compound was synthesized by General Procedure for the Synthesis of 146c-d.

Step 3: 5-(5H-imidazo[5,1-a]isoindol-5-yl)-3-methyl-6,7-dihydropyrazolo[1,5-a]pyridin-4(5H)-one

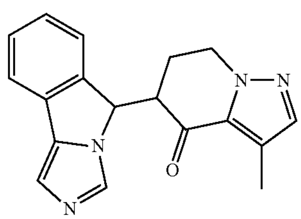 [SMILES: Cc1cnn2c1C(=O)C(C1c3ccccc3-c3cncn31)CC2]

The title compound was synthesized by General Procedure for the Synthesis of 146c-d.

Step 4:

(4S,5R)-5-((R)-5H-imidazo[5,1-a]isoindol-5-yl)-3-methyl-4,5,6,7-tetrahydropyrazolo[1,5-a]pyridin-4-ol (4R,5S)-5-((S)-5H-imidazo[5,1-a]isoindol-5-yl)-3-methyl-4,5,6,7-tetrahydropyrazolo[1,5-a]pyridin-4-ol 159a

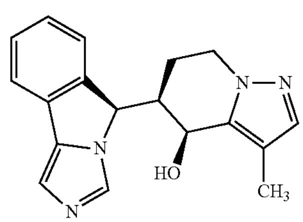

159b

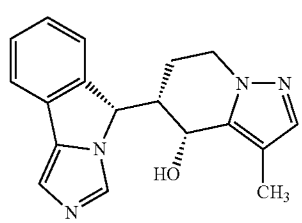

The title compound was synthesized by General Procedure for the Synthesis of 146c-d. The crude product was purified by Prep-HPLC and Chiral HPLC with the following conditions:

1. Column, XBridge BEH130 Prep C18 OBD Column, 19×150 mm 5 um 13 nm; mobile phase, Water (0.05% $NH_3H_2O$) and ACN (21.0% ACN up to 31.0% in 10 min); Detector, uv 254/220 nm.
2. Column, Lux 5 u Cellulose-4,AXIA Packed, 2.12×25 cm, 5 um; mobile phase, Hex(0.2% DEA) and ethanol (hold 50.0% ethanol-in 14 min); Detector, UV 220/254 nm. The absolute configuration of all isomers 159a-b was assigned arbitrarily.

Example 159a: (4S,5R)-5-((R)-5H-imidazo[5,1-a]isoindol-5-yl)-3-methyl-4,5,6,7-tetrahydropyrazolo[1,5-a]pyridin-4-ol (21.7 mg, 14%) as a white solid: LCMS (ESI, m/z): 307.3 $[M+H]^+$. $^1$H NMR (300 MHz, $CD_3OD$) δ 8.16 (dd, J=1.5, 0.8 Hz, 1H), 7.66-7.60 (m, 2H), 7.47-7.32 (m, 3H), 7.19 (s, 1H), 5.66 (s, 1H), 5.32 (dd, J=3.6, 1.2 Hz, 1H), 4.18-4.13 (m, 1H), 3.83-3.73 (m, 1H), 2.73-2.66 (m, 1H), 2.19 (s, 3H), 1.98-1.87 (m, 1H), 1.22 (d, J=13.7 Hz, 1H). $t_R$=1.436 min (Lux 3 u Cellulose-4, 0.46×5 cm; 3 um, Hex(0.1% DEA):EtOH=50:50, 1 ml/min). 159a and 159b are enantiomers.

Example 159b: (4R,5S)-5-((S)-5H-imidazo[5,1-a]isoindol-5-yl)-3-methyl-4,5,6,7-tetrahydropyrazolo[1,5-a]pyridin-4-ol (24.4 mg, 16%) as a white solid: LCMS (ESI, m/z): 307.2 $[M+H]^+$. $t_R$=2.115 min (Lux 3 u Cellulose-4, 0.46×5 cm; 3 um, Hex(0.1% DEA):EtOH=50:50, 1 ml/min). 159a and 159b are enantiomers.

(4R,5R)-5-((R)-5H-imidazo[5,1-a]isoindol-5-yl)-3-methyl-4,5,6,7-tetrahydropyrazolo[1,5-a]pyridin-4-ol (4S,5S)-5-((S)-5H-imidazo[5,1-a]isoindol-5-yl)-3-methyl-4,5,6,7-tetrahydropyrazolo[1,5-a]pyridin-4-ol 159c

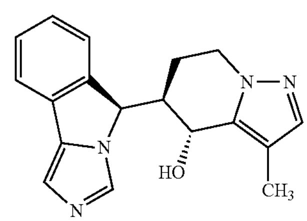

159d

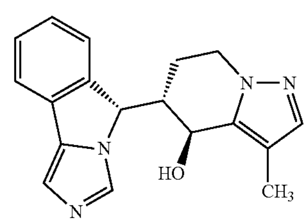

The title compound was synthesized by General Procedure for the Synthesis of 146e-f. The crude product was purified by Prep-HPLC and further isolated by chiral separation with the following conditions:

1. Column, XBridge BEH130 Prep C18 OBD Column, 19×150 mm 5 um 13 nm; mobile phase, Water (0.05% $NH_3H_2O$) and ACN (17.0% ACN up to 30.0% in 7 min); Detector, uv 254/220 nm.
2. Column, Phenomenex Lux 5 u Cellulose-4 AXIA Packed, 2.12×25 cm, 5 um; mobile phase, Hex and ethanol (hold 30.0% ethanol-in 16 min); Detector, UV 254/220 nm.

The absolute configuration of all isomers 159c-d was assigned arbitrarily.

Example 159c: (4R,5R)-5-((R)-5H-imidazo[5,1-a]isoindol-5-yl)-3-methyl-4,5,6,7-tetrahydropyrazolo[1,5-a]pyridin-4-ol (37.5 mg, 8%) as a white solid: LCMS (ESI, m/z): 307.3 [M+H]$^+$. $^1$H NMR (300 MHz, $CD_3OD$) δ 8.40 (d, J=6.3 Hz, 1H), 7.78-7.76 (m, 1H), 7.60-7.44 (m, 4H), 7.27 (s, 1H), 5.97 (d, J=1.6 Hz, 1H), 5.12 (d, J=10.1 Hz, 1H), 4.03-3.85 (m, 2H), 2.71-2.64 (m, 1H), 2.22 (s, 3H), 1.44-1.31 (m, 2H). tR=1.603 min (Lux 3 u Cellulose-4, 0.46×5 cm; 3 um, Hex(0.1% DEA):EtOH=70:30, 1 ml/min). 159c and 159d are enantiomers.

Example 159d: (4S,5S)-5-((S)-5H-imidazo[5,1-a]isoindol-5-yl)-3-methyl-4,5,6,7-tetrahydropyrazolo[1,5-a]pyridin-4-ol (38.0 mg, 8%) as a white solid: LCMS (ESI, m/z): 307.2 [M+H]$^+$. $t_R$=1.603 min (Lux 3 u Cellulose-4, 0.46×5 cm; 3 um, Hex(0.1% DEA):EtOH=70:30, 1 ml/min). 159c and 159d are enantiomers.

Example 160: 3-chloro-5-(5H-imidazo[5,1-a]isoindol-5-yl)-4,5,6,7-tetrahydropyrazolo[1,5-a]pyridin-4-ol

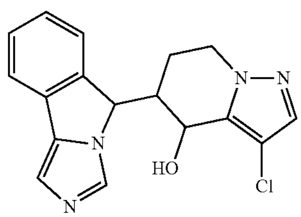

Step 1: 3-chloro-6,7-dihydropyrazolo[1,5-a]pyridin-4(5H)-one

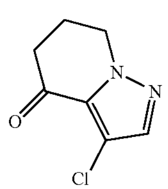 [SMILES: O=C1CCCn2ncc(Cl)c21]

A solution of 4H,5H,6H,7H-pyrazolo[1,5-a]pyridin-4-one (1.7 g, 12.49 mmol) in DMF (100 mL) was added NCS (1.7 g, 12.73 mmol). The resulting solution was stirred for 2 h at 100° C. in an oil bath. The reaction was diluted with water (200 mL). The resulting solution was extracted with EtOAc (2×200 mL). The organic layers were combined, dried over anhydrous sodium sulfate, and concentrated under vacuum. The residue was purified by silica gel column eluting with EtOAc/petroleum ether (1:1). This resulted in 2.3 g (crude) of 3-chloro-4H,5H,6H,7H-pyrazolo[1,5-a]pyridin-4-one as a yellow solid: LCMS (ESI, m/z): 171.3 [M+H]$^+$.

Step 2: (E)-3-chloro-5-(2-(1-trityl-1H-imidazol-4-yl)benzylidene)-6,7-dihydropyrazolo[1,5-a]pyridin-4(5H)-one

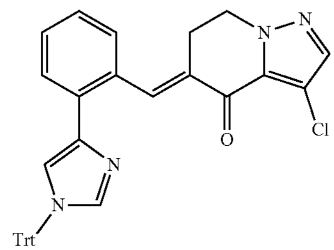

The title compound was synthesized by General Procedure for the Synthesis of 146c-d.

Step 3: 3-chloro-5-(5H-imidazo[5,1-a]isoindol-5-yl)-6,7-dihydropyrazolo[1,5-a]pyridin-4(5H)-one

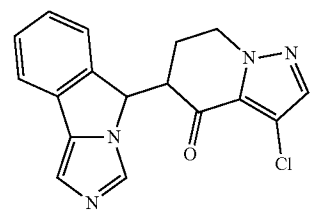 [SMILES: O=C1c2c(Cl)cnn2CCC1C1c2ccccc2-c2cncn21]

The title compound was synthesized by General Procedure for the Synthesis of 146c-d.

Step 4:

(4S,5R)-3-chloro-5-((R)-5H-imidazo[5,1-a]isoindol-5-yl)-4,5,6,7-tetrahydropyrazolo[1,5-a]pyridin-4-ol (4R,5S)-3-chloro-5-((S)-5H-imidazo[5,1-a]isoindol-5-yl)-4,5,6,7-tetrahydropyrazolo[1,5-a]pyridin-4-ol (4S,5R)-3-chloro-5-((S)-5H-imidazo[5,1-a]isoindol-5-yl)-4,5,6,7-tetrahydropyrazolo[1,5-a]pyridin-4-ol (4R,5S)-3-chloro-5-((R)-5H-imidazo[5,1-a]isoindol-5-yl)-4,5,6,7-tetrahydropyrazolo[1,5-a]pyridin-4-ol 160a

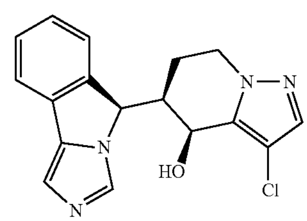

160b

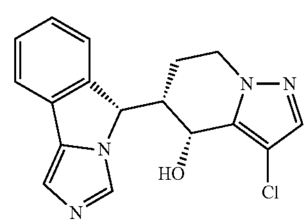

-continued

160c

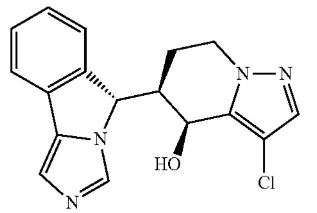

160d

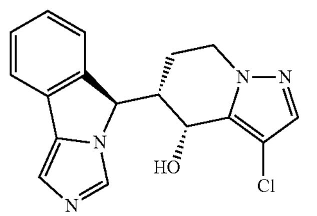

The title compound was synthesized by General Procedure for the Synthesis of 146c-d. The crude product was purified by Prep-HPLC and Chiral HPLC with the following conditions:

1. Column, XBridge BEH130 Prep C18 OBD Column, 19×150 mm 5 um 13 nm; mobile phase, Water (0.05% $NH_3H_2O$) and ACN (22% ACN up to 30% in 10 min); Detector, uv 254/220 nm.
2. Column, Chiralpak IC, 2×25 cm, 5 um; mobile phase, Hex(0.1% DEA)-HPLC and ethanol-HPLC (hold 50% ethanol-HPLC in 19 min); Detector, UV 220/254 nm.

The absolute configuration of all isomers 160a-d was assigned arbitrarily.

Example 160a: (4S,5R)-3-chloro-5-((R)-5H-imidazo[5,1-a]isoindol-5-yl)-4,5,6,7-tetrahydropyrazolo[1,5-a]pyridin-4-ol (51.4 mg, 29%) as a white solid: LCMS (ESI, m/z): 327.3 $[M+H]^+$. $^1H$ NMR (300 MHz, $CD_3OD$) δ 8.15 (d, J=0.8 Hz, 1H), 7.65-7.60 (m, 2H), 7.50-7.33 (m, 3H), 7.18 (d, J=0.6 Hz, 1H), 5.65 (d, J=1.6 Hz, 1H), 5.36 (dd, J=3.5, 1.2 Hz, 1H), 4.22-4.16 (m, 1H), 3.87-3.77 (m, 1H), 2.75-2.68 (m, 1H), 2.05-1.91 (m, 1H), 1.27-1.22 (m, 1H). $t_R$=1.340 min (CHIRALPAK IC-3, 0.46×5 cm; 3 um, Hex (0.1% DEA):EtOH=50:50, 1.0 ml/min). 160a and 160b are enantiomers.

Example 160b: (4R,5S)-3-chloro-5-((S)-5H-imidazo[5,1-a]isoindol-5-yl)-4,5,6,7-tetrahydropyrazolo[1,5-a]pyridin-4-ol (49.8 mg, 28%) as a white solid: LCMS (ESI, m/z): 327.2 $[M+H]^+$. $t_R$=1.770 min (CHIRALPAK IC-3, 0.46×5 cm; 3 um, Hex(0.1% DEA):EtOH=50:50, 1.0 ml/min). 160a and 160b are enantiomers.

Example 160c: (4S,5R)-3-chloro-5-((S)-5H-imidazo[5,1-a]isoindol-5-yl)-4,5,6,7-tetrahydropyrazolo[1,5-a]pyridin-4-ol (14.0 mg, 8%) as a white solid: LCMS (ESI, m/z): 307.3 $[M+H]^+$. $^1H$ NMR (300 MHz, $CD_3OD$) δ 8.07 (t, J=0.7 Hz, 1H), 7.79-7.77 (m, 1H), 7.68-7.66 (m, 1H), 7.47-7.31 (m, 3H), 7.19 (s, 1H), 5.59 (d, J=5.2 Hz, 1H), 5.07 (dd, J=3.0, 1.3 Hz, 1H), 4.36-4.30 (m, 1H), 4.00-3.91 (m, 1H), 2.52-2.41 (m, 2H), 2.13-2.07 (m, 1H). $t_R$=1.593 min (CHIRALPAK IC-3, 0.46×5 cm; 3 um, Hex(0.1% DEA):EtOH=50:50, 1.0 ml/min). 160c and 160d are enantiomers.

Example 160d: (4R,5S)-3-chloro-5-((R)-5H-imidazo[5,1-a]isoindol-5-yl)-4,5,6,7-tetrahydropyrazolo[1,5-a]pyridin-4-ol (12.5 mg, 7%) as a white solid: LCMS (ESI, m/z): 307.2 $[M+H]^+$. $t_R$=2.068 min (CHIRALPAK IC-3, 0.46×5 cm; 3 um, Hex(0.1% DEA):EtOH=50:50, 1.0 ml/min). 160c and 160d are enantiomers.

(4R,5R)-3-chloro-5-((R)-5H-imidazo[5,1-a]isoindol-5-yl)-4,5,6,7-tetrahydropyrazolo[1,5-a]pyridin-4-ol (4S,5S)-3-chloro-5-((S)-5H-imidazo[5,1-a]isoindol-5-yl)-4,5,6,7-tetrahydropyrazolo[1,5-a]pyridin-4-ol 160e

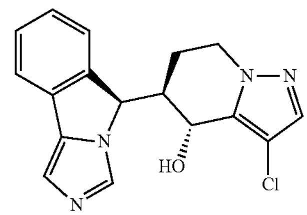

160f

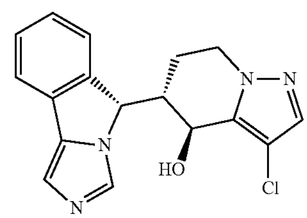

The title compound was synthesized by General Procedure for the Synthesis of 146e-f.

The crude product was purified by Prep-HPLC and further isolated by chiral separation with the following conditions:

1. Column, XBridge BEH130 Prep C18 OBD Column, 19×150 mm Sum 13 nm; mobile phase, Water (0.05% $NH_3H_2O$) and ACN (22.0% ACN up to 30.0% in 10 min); Detector, uv 254/220 nm.
2. Column, CHIRALPAK IF, 2×25 cm, 5 um; mobile phase, Hex 0.1% DEA and ethanol (hold 50.0% ethanol-in 17 min); Detector, UV 220/254 nm.

The absolute configuration of all isomers 160e-f was assigned arbitrarily.

Example 160e: (4R,5R)-3-chloro-5-((R)-5H-imidazo[5,1-a]isoindol-5-yl)-4,5,6,7-tetrahydropyrazolo[1,5-a]pyridin-4-ol (6.0 mg, 1%) as a white solid: LCMS (ESI, m/z): 327.3 $[M+H]^+$. $^1H$ NMR (300 MHz, $CD_3OD$) δ 7.96 (s, 1H), 7.70-7.67 (m, 1H), 7.56-7.37 (m, 4H), 7.23 (s, 1H), 5.86 (d, J=1.4 Hz, 1H), 5.24 (d, J=9.8 Hz, 1H), 4.00-3.86 (m, 2H), 2.70-2.61 (m, 1H), 1.38-1.17 (m, 2H). $t_R$=2.208 min (Lux 3 u Cellulose-4, 0.46×5 cm; 3 um, Hex(0.1% DEA):IPA=50:50, 1.0 ml/min). 160e and 160f are enantiomers.

Example 160f: (4S,5S)-3-chloro-5-((S)-5H-imidazo[5,1-a]isoindol-5-yl)-4,5,6,7-tetrahydropyrazolo[1,5-a]pyridin-4-ol (24.0 mg, 3%) as a white solid: LCMS (ESI, m/z): 327.2 $[M+H]^+$. $t_R$=1.515 min (Lux 3 u Cellulose-4, 0.46×5 cm; 3 um, Hex(0.1% DEA):EtOH=70:30, 1 ml/min). 160e and 160f are enantiomers.

Example 161: 2-amino-5-(5H-imidazo[5,1-a]isoindol-5-yl)-4,5,6,7-tetrahydropyrazolo[1,5-a]pyridin-4-ol

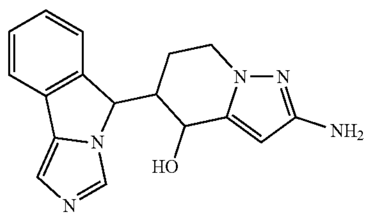 [SMILES: Nc1cc2n(n1)CCC(C1c3ccccc3-c3cncn31)C2O]

(4R,5R)-2-amino-5-((S)-5H-imidazo[5,1-a]isoindol-5-yl)-4,5,6,7-tetrahydropyrazolo[1,5-a]pyridin-4-ol
(4S,5S)-2-amino-5-((S)-5H-imidazo[5,1-a]isoindol-5-yl)-4,5,6,7-tetrahydropyrazolo[1,5-a]pyridin-4-ol
(4R,5S)-2-amino-5-((R)-5H-imidazo[5,1-a]isoindol-5-yl)-4,5,6,7-tetrahydropyrazolo[1,5-a]pyridin-4-ol
(4S,5R)-2-amino-5-((S)-5H-imidazo[5,1-a]isoindol-5-yl)-4,5,6,7-tetrahydropyrazolo[1,5-a]pyridin-4-ol
(4S,5R)-2-amino-5-((S)-5H-imidazo[5,1-a]isoindol-5-yl)-4,5,6,7-tetrahydropyrazolo[1,5-a]pyridin-4-ol
(4R,5S)-2-amino-5-((R)-5H-imidazo[5,1-a]isoindol-5-yl)-4,5,6,7-tetrahydropyrazolo[1,5-a]pyridin-4-ol
(4R,5R)-2-amino-5-((R)-5H-imidazo[5,1-a]isoindol-5-yl)-4,5,6,7-tetrahydropyrazolo[1,5-a]pyridin-4-ol
(4S,5R)-2-amino-5-((S)-5H-imidazo[5,1-a]isoindol-5-yl)-4,5,6,7-tetrahydropyrazolo[1,5-a]pyridin-4-ol Step 1: (tert-butyl (E)-(4-oxo-5-(2-(1-trityl-1H-imidazol-4-yl)benzylidene)-4,5,6,7-tetrahydropyrazolo[1,5-a]pyridin-2-yl)carbamate

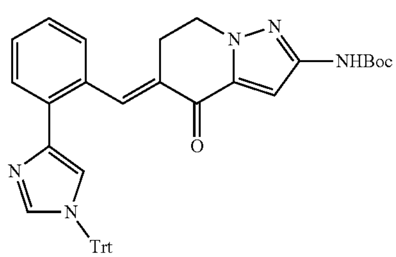

The title compound was synthesized by General Procedure for the Synthesis of Int-2. LCMS (ESI, m/z): 648.3 $[M+H]^+$ Step 2: tert-butyl(5-(5H-imidazo[5,1-a]isoindol-5-yl)-4-oxo-4,5,6,7-tetrahydropyrazolo[1,5-a]pyridin-2-yl)carbamate

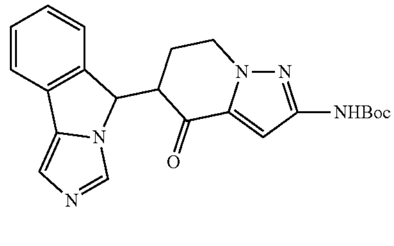 [SMILES: CC(C)(C)OC(=O)Nc1cc2n(n1)CCC(C1c3ccccc3-c3cncn31)C2=O]

The title compound was synthesized by General Procedure for the Synthesis of Int-3. LCMS (ESI, m/z): 406.3 $[M+H]^+$ Step 3: 2-amino-5-(5H-imidazo[5,1-a]isoindol-5-yl)-4,5,6,7-tetrahydropyrazolo[1,5-a]pyridin-4-ol

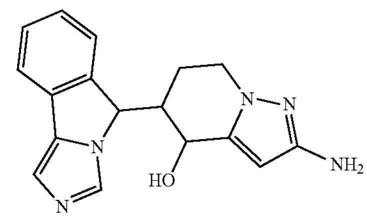 [SMILES: Nc1cc2n(n1)CCC(C1c3ccccc3-c3cncn31)C2O]

To a solution of tert-butyl(5-(5H-imidazo[5,1-a]isoindol-5-yl)-4-oxo-4,5,6,7-tetrahydropyrazolo[1,5-a]pyridin-2-yl) carbamate (1.4 g, 3.45 mmol) in MeOH (30 mL) was added $NaBH_4$ (391 mg, 10.36 mmol) in portions at −10° C. and the solution was stirred at room temperature for 1 hr. The reaction was quenched by saturated ammonium chloride (10 mL). The aqueous layer was extracted with 20% 2,2,2-trifluoroethanol in DCM (3×30 mL). The combined organic extract was dried over ($Na_2SO_4$) and concentrated under reduced pressure to afford the crude product. The crude was purified by CombiFlash and the product was eluted with DCM:MeOH=94:6. To a solution of the alcohol (1 g, 2.45 mmol) in DCM (15 mL) was added TFA (~5 mL, 61.35 mmol) at room temperature and stirred for 4 hrs. After 4 h, the solvent was removed under reduced pressure and sat'd $NaHCO_3$ (20 mL) was added to the residue slowly followed by DCM (20 mL). The organic layer was collected and the aqueous layer was extracted with DCM with trifluro ethanol (2×20 mL). The combined organic layers were dried over $Na_2SO_4$ and the solvent evaporated under reduced pressure to afford the crude product which was purified using combi flash.: LCMS (ESI, m/z): 308.2 $[M+H]^+$. The mixture was isolated by Chiral separation methods and the configuration of the isomers was assigned arbitrarily.

(4R,5R)-2-amino-5-((S)-5H-imidazo[5,1-a]isoindol-5-yl)-4,5,6,7-tetrahydropyrazolo[1,5-a]pyridin-4-ol (4S,5S)-2-amino-5-((S)-5H-imidazo[5,1-a]isoindol-5-yl)-4,5,6,7-tetrahydropyrazolo[1,5-a]pyridin-4-ol (4R,5S)-2-amino-5-((R)-5H-imidazo[5,1-a]isoindol-5-yl)-4,5,6,7-tetrahydropyrazolo[1,5-a]pyridin-4-ol (4S,5R)-2-amino-5-((S)-5H-imidazo[5,1-a]isoindol-5-yl)-4,5,6,7-tetrahydropyrazolo[1,5-a]pyridin-4-ol (4S,5R)-2-amino-5-((S)-5H-imidazo[5,1-a]isoindol-5-yl)-4,5,6,7-tetrahydropyrazolo[1,5-a]pyridin-4-ol (4R,5S)-2-amino-5-((R)-5H-imidazo[5,1-a]isoindol-5-yl)-4,5,6,7-tetrahydropyrazolo[1,5-a]pyridin-4-ol (4R,5R)-2-amino-5-((R)-5H-imidazo[5,1-a]isoindol-5-yl)-4,5,6,7-tetrahydropyrazolo[1,5-a]pyridin-4-ol (4S,5R)-2-amino-5-((S)-5H-imidazo[5,1-a]isoindol-5-yl)-4,5,6,7-tetrahydropyrazolo[1,5-a]pyridin-4-ol 161a

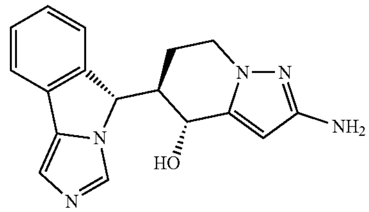

161b

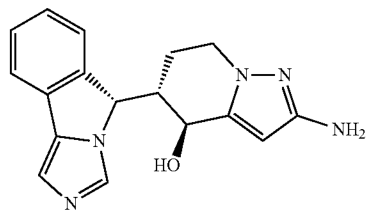

161c

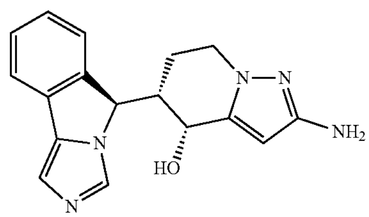

161d

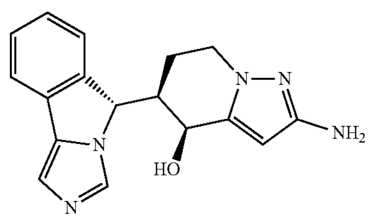

161e

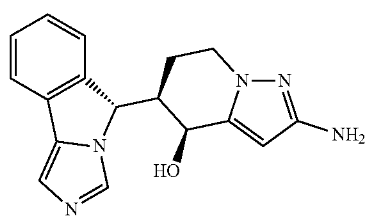

161f

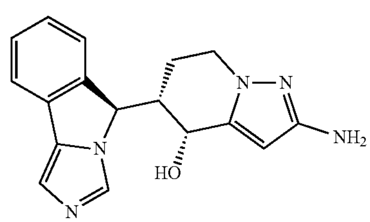

161g

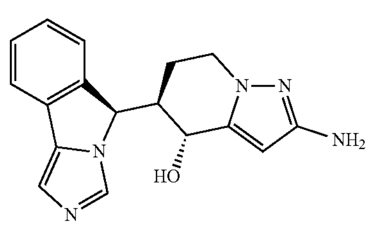

-continued

161h

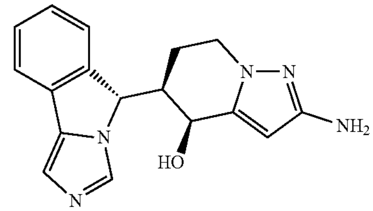

Example 161b: (4S,5S)-2-amino-5-((S)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.96 (s, 1H), 7.63 (d, J=7.5 Hz, 1H), 7.50 (d, J=6.9 Hz, 1H), 7.42 (t, J=7.4 Hz, 1H), 7.32 (td, J=7.5, 1.1 Hz, 1H), 7.18 (s, 1H), 5.98 (d, J=7.3 Hz, 1H), 5.72 (s, 1H), 5.51 (s, 1H), 4.88 (dd, J=10.4, 7.3 Hz, 1H), 4.50 (s, 2H), 3.64 (dd, J=10.9, 4.1 Hz, 1H), 3.49 (td, J=11.6, 5.8 Hz, 1H), 2.48-2.31 (m, 1H), 1.06-0.88 (m, 2H).

Example 161c: (4R,5S)-2-amino-5-((R)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.92 (s, 1H), 7.62 (d, J=7.7 Hz, 1H), 7.59 (d, J=7.5 Hz, 1H), 7.39 (t, J=7.5 Hz, 1H), 7.29 (td, J=7.6, 1.0 Hz, 1H), 7.12 (s, 1H), 5.94 (d, J=5.4 Hz, 1H), 5.49 (d, J=2.1 Hz, 1H), 5.44 (s, 1H), 5.07-4.92 (m, 1H), 4.52 (s, 2H), 3.81-3.64 (m, 1H), 3.49 (td, J=12.1, 4.8 Hz, 1H), 2.49-2.45 (m, 1H), 1.79 (tq, J=12.3, 5.7 Hz, 1H), 1.12 (d, J=13.8 Hz, 1H).

Example 161d: (4S,5R)-2-amino-5-((S)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.95 (s, 1H), 7.71 (d, J=7.7 Hz, 1H), 7.61 (d, J=7.5 Hz, 1H), 7.39 (t, J=7.5 Hz, 1H), 7.24 (td, J=7.6, 1.1 Hz, 1H), 7.13 (s, 1H), 5.68 (d, J=5.4 Hz, 1H), 5.42 (d, J=5.4 Hz, 1H), 5.38 (s, 1H), 4.81 (d, J=5.3 Hz, 1H), 4.50 (s, 2H), 3.85 (dd, J=11.3, 4.3 Hz, 1H), 3.69-3.45 (m, 1H), 2.32-2.09 (m, 2H), 1.81 (d, J=10.9 Hz, 1H).

Example 161e: (4S,5R)-2-amino-5-((S)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.92 (s, 1H), 7.62 (d, J=7.6 Hz, 1H), 7.59 (d, J=7.5 Hz, 1H), 7.39 (t, J=7.5 Hz, 1H), 7.29 (td, J=7.6, 1.0 Hz, 1H), 7.12 (s, 1H), 5.94 (d, J=5.4 Hz, 1H), 5.49 (d, J=2.1 Hz, 1H), 5.44 (s, 1H), 5.05-4.96 (m, 1H), 4.52 (s, 2H), 3.81-3.62 (m, 1H), 3.49 (td, J=12.1, 4.8 Hz, 1H), 2.47 (d, J=2.9 Hz, 1H), 1.79 (tq, J=12.3, 5.8 Hz, 1H), 1.12 (d, J=13.0 Hz, 1H).

Example 161f: (4R,5S)-2-amino-5-((R)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.96 (s, 1H), 7.71 (d, J=7.7 Hz, 1H), 7.62 (d, J=7.5 Hz, 1H), 7.39 (t, J=7.4 Hz, 1H), 7.25 (td, J=7.6, 1.1 Hz, 1H), 7.13 (s, 1H), 5.68 (d, J=5.4 Hz, 1H), 5.43 (d, J=5.4 Hz, 1H), 5.39 (s, 1H), 4.81 (d, J=5.4 Hz, 1H), 4.50 (s, 2H), 3.85 (dd, J=11.3, 4.3 Hz, 1H), 3.66-3.50 (m, 1H), 2.33-2.11 (m, 2H), 1.82 (d, J=10.7 Hz, 1H).

Example 161g: (4R,5R)-2-amino-5-((R)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1$H NMR (500 MHz, DMSO-d6) δ 7.96 (s, 1H), 7.63 (d, J=7.6 Hz, 1H), 7.50 (d, J=7.6 Hz, 1H), 7.42 (t, J=7.5 Hz, 1H), 7.32 (td, J=7.5, 1.0 Hz, 1H), 7.18 (s, 1H), 5.98 (d, J=7.3 Hz, 1H), 5.73 (s, 1H), 5.51 (s, 1H), 4.88 (dd, J=10.3, 7.4 Hz, 1H), 4.50 (s, 2H), 3.64

(dd, J=10.7, 4.0 Hz, 1H), 3.49 (td, J=11.5, 5.8 Hz, 1H), 2.49-2.28 (m, 1H), 1.05-0.85 (m, 2H).

Example 161h: (4S,5R)-2-amino-5-((S)-5H-imidazo[5,1-a]isoindol-5-yl)-4,5,6,7-tetrahydropyrazolo[1,5-a]pyridin-4-ol: LCMS (ESI, m/z): 308.2 $[M+H]^+$; $^1H$ NMR (500 MHz, DMSO-$d_6$) δ 7.92 (s, 1H), 7.64 (d, J=7.6 Hz, 1H), 7.57 (d, J=7.7 Hz, 1H), 7.41 (t, J=7.5 Hz, 1H), 7.27 (td, J=7.6, 1.1 Hz, 1H), 7.17 (s, 1H), 5.98 (d, J=6.7 Hz, 1H), 5.72 (d, J=3.1 Hz, 1H), 5.47 (s, 1H), 4.81 (dd, J=10.5, 6.4 Hz, 1H), 4.49 (s, 2H), 3.65 (dd, J=12.2, 4.2 Hz, 1H), 3.52 (td, J=12.0, 4.7 Hz, 1H), 2.65-2.54 (m, 1H), 1.06 (tq, J=12.5, 5.9 Hz, 1H), 0.93 (d, J=13.7 Hz, 1H).

Example 162: 4-hydroxy-5-(5H-imidazo[5,1-a]isoindol-5-yl)-N-methyl-4,5,6,7-tetrahydrobenzo[d]thiazole-2-carboxamide

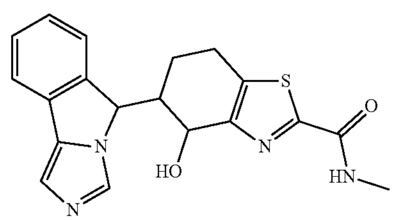 [SMILES: CNC(=O)c1nc2c(s1)CCC(C1c3ccccc3-c3cncn31)C2O]

(4R,5R)-4-hydroxy-5-((S)-5H-imidazo[5,1-a]isoindol-5-yl)-N-methyl-4,5,6,7-tetrahydrobenzo[d]thiazole-2-carboxamide (4R,5R)-4-hydroxy-5-((R)-5H-imidazo[5,1-a]isoindol-5-yl)-N-methyl-4,5,6,7-tetrahydrobenzo[d]thiazole-2-carboxamide (4S,5S)-4-hydroxy-5-((S)-5H-imidazo[5,1-a]isoindol-5-yl)-N-methyl-4,5,6,7-tetrahydrobenzo[d]thiazole-2-carboxamide (4S,5S)-4-hydroxy-5-((R)-5H-imidazo[5,1-a]isoindol-5-yl)-N-methyl-4,5,6,7-tetrahydrobenzo[d]thiazole-2-carboxamide (4R,5S)-4-hydroxy-5-((S)-5H-imidazo[5,1-a]isoindol-5-yl)-N-methyl-4,5,6,7-tetrahydrobenzo[d]thiazole-2-carboxamide (4R,5S)-4-hydroxy-5-((R)-5H-imidazo[5,1-a]isoindol-5-yl)-N-methyl-4,5,6,7-tetrahydrobenzo[d]thiazole-2-carboxamide (4S,5R)-4-hydroxy-5-((R)-5H-imidazo[5,1-a]isoindol-5-yl)-N-methyl-4,5,6,7-tetrahydrobenzo[d]thiazole-2-carboxamide (4S,5R)-4-hydroxy-5-((S)-5H-imidazo[5,1-a]isoindol-5-yl)-N-methyl-4,5,6,7-tetrahydrobenzo[d]thiazole-2-carboxamide

Step 1: 3-bromocyclohexane-1,2-dione

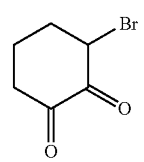

To a solution of 1,2-cyclohexanedione (5.1 g, 45.5 mmol) in diethyl ether (46 mL) at 0° C. was added $Br_2$ (2.34 mL, 45.5 mmol) dropwise over 10 min. When the addition was complete, the reaction was allowed to come to room temperature and stirred for 15 min., at which time the reaction mixture was concentrated under reduced pressure. The resulting dark oil was taken up in 2.5% MeOH/$CHCl_3$ and run through a pad of silica gel, eluting with the same solvent mixture. The solvent was then removed under reduced pressure and the resulting yellow solid was triturated with cold diethyl ether (15 mL). The product was filtered and dried. $^1$HNMR (400 MHz, Chloroform-d) δ 6.45 (s, 1H), 2.90 (td, J=6.0, 5.6, 0.6 Hz, 2H), 2.54-2.61 (m, 2H), 2.05-2.13 (m, 2H).

Step 2: ethyl 4-oxo-4,5,6,7-tetrahydrobenzo[d]thiazole-2-carboxylate

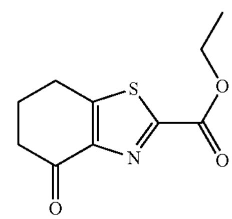

A mixture of 3-bromocyclohexane-1,2-dione 3 (10.76 g, 56.32 mmol) and ethyl 2-amino-2-thioxoacetate (5.0 g, 37.55 mmol) in ethanol (150 mL) was heated to reflux and stirred for 15 h. The mixture was cooled to room temperature. The solvent was removed under reduced pressure and the product was separated by CombiFlash. The product was eluted with EtOAc:Hexane=50:50: LCMS (ESI, m/z): 226.2 $[M+H]^+$.

Step 3: N-methyl-4-oxo-4,5,6,7-tetrahydrobenzo[d]thiazole-2-carboxamide

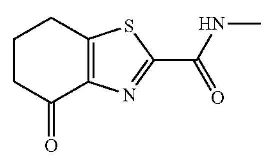

To a solution of ethyl 4-oxo-4,5,6,7-tetrahydrobenzo[d]thiazole-2-carboxylate (2.0 g, 8.88 mmol) in ethanol (13.5 mL) was added methylamine solution (2.0 M) in THF (13.3 mL, 26.64 mmol) solution at room temperature. The resulting mixture was stirred at room temperature for 3 hr. TLC indicated full consumption of starting material. The solvent was removed under reduced pressure and the product was separated by CombiFlash. The desired product was eluted with MeOH:DCM=3:97: LCMS (ESI, m/z): 211.2 $[M+H]^+$.

Step 4: (E)-N-methyl-4-oxo-5-(2-(1-trityl-1H-imidazol-4-yl)benzylidene)-4,5,6,7-tetrahydrobenzo[d]thiazole-2-carboxamide

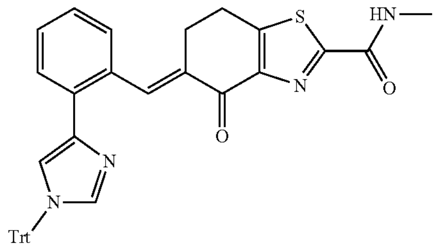

To a solution of 2-(1-trityl-1H-imidazol-4-yl)benzaldehyde (2.45 g, 5.91 mmol) and N-methyl-4-oxo-4,5,6,7-tetrahydrobenzo[d]thiazole-2-carboxamide (1.49 g, 7.09 mmol) in ethanol (40 mL) was added pyrrolidine (388 mL, 4.73 mmol). The mixture was stirred at 95° C. for 5 hrs. The solvent was removed under reduced pressure and the product was separated by CombiFlash. The desired product was eluted with EtOAc:Hex=60:40: LCMS (ESI, m/z): 607.3 $[M+H]^+$.

Step 5: 5-(5H-imidazo[5,1-a]isoindol-5-yl)-N-methyl-4-oxo-4,5,6,7-tetrahydrobenzo[d]thiazole-2-carboxamide

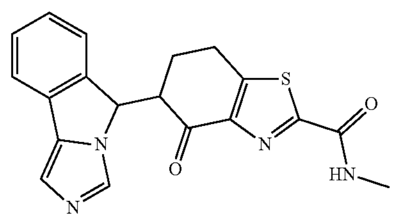 [SMILES: CNC(=O)c1nc2c(s1)CCC(C1c3ccccc3-c3cncn31)C2=O]

E)-N-methyl-4-oxo-5-(2-(1-trityl-1H-imidazol-4-yl)benzylidene)-4,5,6,7-tetrahydrobenzo[d]thiazole-2-carboxamide (2.59 g, 4.27 mmol) was stirred in methanol (20 mL) and acetic acid (5 mL) at 90° C. for 2 h. After cooling to room temperature, the solvent was removed under reduced pressure and saturated $NaHCO_3$ (20 mL) was added to quench the acetic acid. The aqueous layer was extracted with DCM (3×30 mL). The combined organic layers were dried over $Na_2SO_4$ and the solvent evaporated under reduced pressure to afford the crude product which was purified by using CombiFlash and was eluted with DCM:MeOH=95:5: LCMS (ESI, m/z): 365.2 $[M+H]^+$.

Step 6:

(4R,5R)-4-hydroxy-5-((S)-5H-imidazo[5,1-a]isoindol-5-yl)-N-methyl-4,5,6,7-tetrahydrobenzo[d]thiazole-2-carboxamide (4R,5R)-4-hydroxy-5-((R)-5H-imidazo[5,1-a]isoindol-5-yl)-N-methyl-4,5,6,7-tetrahydrobenzo[d]thiazole-2-carboxamide (4S,5S)-4-hydroxy-5-((S)-5H-imidazo[5,1-a]isoindol-5-yl)-N-methyl-4,5,6,7-tetrahydrobenzo[d]thiazole-2-carboxamide (4S,5S)-4-hydroxy-5-((R)-5H-imidazo[5,1-a]isoindol-5-yl)-N-methyl-4,5,6,7-tetrahydrobenzo[d]thiazole-2-carboxamide (4R,5S)-4-hydroxy-5-((S)-5H-imidazo[5,1-a]isoindol-5-yl)-N-methyl-4,5,6,7-tetrahydrobenzo[d]thiazole-2-carboxamide (4R,5S)-4-hydroxy-5-((R)-5H-imidazo[5,1-a]isoindol-5-yl)-N-methyl-4,5,6,7-tetrahydrobenzo[d]thiazole-2-carboxamide (4S,5R)-4-hydroxy-5-((R)-5H-imidazo[5,1-a]isoindol-5-yl)-N-methyl-4,5,6,7-tetrahydrobenzo[d]thiazole-2-carboxamide (4S,5R)-4-hydroxy-5-((S)-5H-imidazo[5,1-a]isoindol-5-yl)-N-methyl-4,5,6,7-tetrahydrobenzo[d]thiazole-2-carboxamide 162a

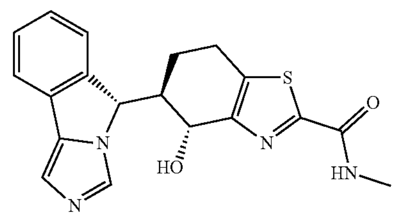

162b

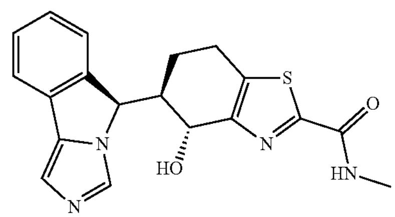

162c

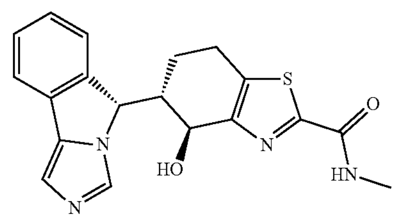

162d

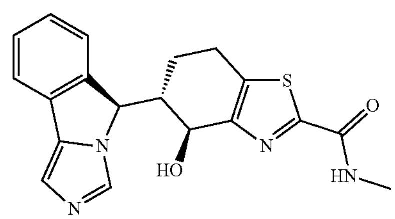

162e

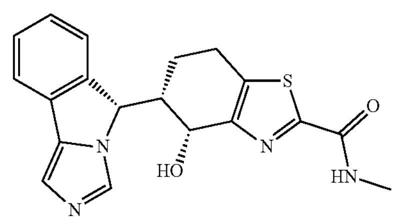

162f

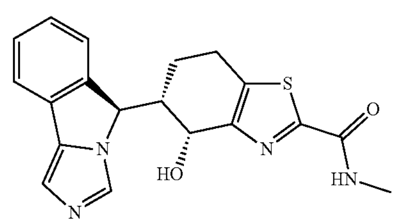

-continued

162g

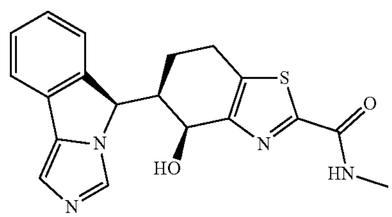

162h

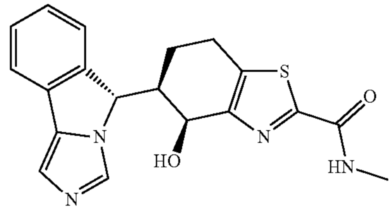

To a solution of 5-(5H-imidazo[5,1-a]isoindol-5-yl)-N-methyl-4-oxo-4,5,6,7-tetrahydrobenzo[d]thiazole-2-carboxamide (1.02 g, 2.80 mmol) in methanol (20 mL) was added sodium borohydride (212 mg, 5.60 mmol) at 0° C. portion-wise. The mixture was allowed to warm up to room temperature and stirred for additional 1 hr. The reaction was quenched with saturated ammonium chloride solution (20 mL). The aqueous layer was extracted with 20% 2,2,2-trifluoroethanol in DCM (3×20 mL). The combined organic extract was dried over ($Na_2SO_4$) and concentrated under reduced pressure to afford the crude product. The crude was purified by CombiFlash and the product was eluted with DCM:MeOH=95:5. The final products were further isolated by chiral separation to afford 8 isomers and the stereochemistry of each isomer was arbitrarily assigned.

Example 162a: (4R,5R)-4-hydroxy-5-((S)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.53 (q, J=4.8 Hz, 1H), 7.90 (s, 1H), 7.64 (dd, J=7.6, 1.0 Hz, 1H), 7.55 (dd, J=7.7, 1.0 Hz, 1H), 7.40 (t, J=7.5 Hz, 1H), 7.25 (td, J=7.6, 1.1 Hz, 1H), 7.17 (s, 1H), 5.90 (d, J=7.3 Hz, 1H), 5.77 (d, J=3.2 Hz, 1H), 5.00 (dd, J=9.4, 7.4 Hz, 1H), 2.81 (d, J=4.8 Hz, 3H), 2.70-2.60 (m, 3H), 0.99 (dt, J=9.8, 6.9 Hz, 2H).

Example 162b: (4R,5R)-4-hydroxy-5-((R)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.56 (q, J=4.7 Hz, 1H), 7.93 (s, 1H), 7.64 (dt, J=7.5, 0.9 Hz, 1H), 7.52-7.46 (m, 1H), 7.46-7.39 (m, 1H), 7.33 (td, J=7.5, 1.1 Hz, 1H), 7.18 (s, 1H), 5.87 (d, J=7.7 Hz, 1H), 5.78 (d, J=1.8 Hz, 1H), 5.04 (t, J=8.7 Hz, 1H), 2.81 (d, J=4.7 Hz, 3H), 2.73-2.56 (m, 2H), 1.03-0.88 (m, 2H).

Example 162c: (4S,5S)-4-hydroxy-5-((S)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.56 (q, J=4.7 Hz, 1H), 7.93 (s, 1H), 7.64 (dt, J=7.6, 0.9 Hz, 1H), 7.49 (dq, J=7.6, 0.9 Hz, 1H), 7.42 (tt, J=7.5, 0.8 Hz, 1H), 7.33 (td, J=7.5, 1.1 Hz, 1H), 7.18 (s, 1H), 5.87 (d, J=7.8 Hz, 1H), 5.78 (d, J=1.8 Hz, 1H), 5.04 (t, J=8.6 Hz, 1H), 2.81 (d, J=4.7 Hz, 3H), 2.73-2.56 (m, 2H), 1.03-0.88 (m, 2H).

Example 162d: (4S,5S)-4-hydroxy-5-((R)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.53 (q, J=4.5 Hz, 1H), 7.90 (s, 1H), 7.64 (d, J=7.6 Hz, 1H), 7.55 (d, J=7.7 Hz, 1H), 7.40 (t, J=7.5 Hz, 1H), 7.25 (td, J=7.6, 1.1 Hz, 1H), 7.17 (s, 1H), 5.90 (d, J=7.3 Hz, 1H), 5.77 (d, J=3.2 Hz, 1H), 5.05-4.96 (m, 1H), 2.80 (d, J=4.8 Hz, 3H), 2.70-2.61 (m, 3H), 1.03-0.93 (m, 2H).

Example 162e: (4R,5S)-4-hydroxy-5-((S)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.70 (q, J=4.7 Hz, 1H), 7.99 (s, 1H), 7.65 (dq, J=7.6, 0.9 Hz, 1H), 7.60 (dt, J=7.5, 0.9 Hz, 1H), 7.39 (tt, J=7.6, 0.9 Hz, 1H), 7.29 (td, J=7.5, 1.2 Hz, 1H), 7.13 (s, 1H), 5.95 (d, J=7.1 Hz, 1H), 5.52 (d, J=2.4 Hz, 1H), 5.11 (dd, J=7.1, 3.5 Hz, 1H), 2.92-2.84 (m, 1H), 2.80 (d, J=4.8 Hz, 3H), 2.60-2.51 (m, 2H), 1.55 (qd, J=12.7, 5.5 Hz, 1H), 1.04 (d, J=6.7 Hz, 1H).

Example 162f: (4R,5S)-4-hydroxy-5-((R)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.66 (q, J=4.7 Hz, 1H), 7.97 (s, 1H), 7.78 (dq, J=7.7, 0.9 Hz, 1H), 7.62 (dt, J=7.5, 0.9 Hz, 1H), 7.39 (tt, J=7.6, 0.8 Hz, 1H), 7.25 (td, J=7.6, 1.2 Hz, 1H), 7.14 (s, 1H), 5.74 (d, J=7.1 Hz, 1H), 5.46 (d, J=5.7 Hz, 1H), 4.92 (dd, J=7.2, 3.3 Hz, 1H), 2.98 (ddd, J=17.4, 5.5, 1.6 Hz, 1H), 2.66 (ddd, J=17.5, 11.9, 5.8 Hz, 1H), 2.28-2.19 (m, 1H), 1.96 (qd, J=12.7, 5.5 Hz, 1H), 1.76-1.66 (m, 1H).

Example 162g: (4S,5R)-4-hydroxy-5-((R)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.70 (q, J=4.7 Hz, 1H), 7.99 (s, 1H), 7.65 (dq, J=7.6, 0.9 Hz, 1H), 7.60 (dt, J=7.5, 0.9 Hz, 1H), 7.39 (tt, J=7.6, 0.8 Hz, 1H), 7.29 (td, J=7.5, 1.1 Hz, 1H), 7.13 (s, 1H), 5.95 (d, J=7.1 Hz, 1H), 5.55-5.47 (m, 1H), 5.11 (dd, J=7.1, 3.5 Hz, 1H), 2.92-2.84 (m, 1H), 2.80 (d, J=4.8 Hz, 3H), 2.60-2.51 (m, 2H), 1.55 (qd, J=12.7, 5.5 Hz, 1H), 1.04 (d, J=7.3 Hz, 1H).

Example 162h: (4R,5S)-4-hydroxy-5-((R)-5H-imidazo[5,1-a]isoindol-5-yl)-N-methyl-4,5,6,7-tetrahydrobenzo[d]thiazole-2-carboxamide: LCMS (ESI, m/z): 367.5 $[M+H]^+$; $^1$HNMR (500 MHz, DMSO-$d_6$) δ 8.66 (q, J=4.7 Hz, 1H), 7.97 (s, 1H), 7.78 (dd, J=7.7, 1.0 Hz, 1H), 7.66-7.58 (m, 1H), 7.39 (dd, J=8.0, 7.0 Hz, 1H), 7.25 (td, J=7.6, 1.2 Hz, 1H), 7.14 (s, 1H), 5.74 (d, J=7.1 Hz, 1H), 5.46 (d, J=5.7 Hz, 1H), 4.92 (dd, J=7.2, 3.3 Hz, 1H), 2.98 (ddd, J=17.4, 5.6, 1.7 Hz, 1H), 2.78 (d, J=4.8 Hz, 3H), 2.66 (ddd, J=17.5, 11.9, 5.8 Hz, 1H), 2.24 (ddt, J=12.0, 5.9, 2.9 Hz, 1H), 1.96 (qd, J=12.7, 5.5 Hz, 1H), 1.72 (d, J=7.2 Hz, 1H).

Example 163: 5-(5H-imidazo[5,1-a]isoindol-5-yl)-4,5,6,7-tetrahydrobenzo[c][1,2,5]oxadiazol-4-ol

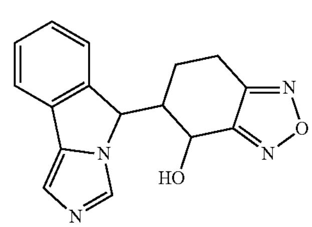 [SMILES: OC1c2nonc2CCC1C1c2ccccc2-c2cncn21]

(4R,5R)-5-((R)-5H-imidazo[5,1-a]isoindol-5-yl)-4,5,6,7-tetrahydrobenzo[c][1,2,5]oxadiazol-4-ol (4R,5R)-5-((S)-5H-imidazo[5,1-a]isoindol-5-yl)-4,5,6,7-tetrahydrobenzo[c][1,2,5]oxadiazol-4-ol (4R,5S)-5-((R)-5H-imidazo[5,1-a]isoindol-5-yl)-4,5,6,7-tetrahydrobenzo[c][1,2,5]oxadiazol-4-ol (4R,5S)-5-((S)-5H-imidazo[5,1-a]isoindol-5-yl)-4,5,6,7-tetrahydrobenzo[c][1,2,5]oxadiazol-4-ol
(4S,5R)-5-((R)-5H-imidazo[5,1-a]isoindol-5-yl)-4,5,6,7-tetrahydrobenzo[c][1,2,5]oxadiazol-4-ol
(4S,5R)-5-((S)-5H-imidazo[5,1-a]isoindol-5-yl)-4,5,6,7-tetrahydrobenzo[c][1,2,5]oxadiazol-4-ol
(4S,5S)-5-((R)-5H-imidazo[5,1-a]isoindol-5-yl)-4,5,6,7-tetrahydrobenzo[c][1,2,5]oxadiazol-4-ol
(4S,5S)-5-((S)-5H-imidazo[5,1-a]isoindol-5-yl)-4,5,6,7-tetrahydrobenzo[c][1,2,5]oxadiazol-4-ol Step 1: 5-(5H-imidazo[5,1-a]isoindol-5-yl)-6,7-dihydrobenzo[c][1,2,5]oxadiazol-4(5H)-one

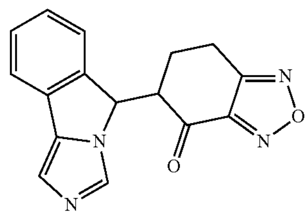 [SMILES: O=C1c2nonc2CCC1C1c2ccccc2-c2cncn21]

To the solution of 2-(1-trityl-1H-imidazol-4-yl)benzaldehyde (2 g, 4.82 mmol) and 6,7-dihydrobenzo[c][1,2,5]oxadiazol-4(5H)-one (749.76 mg, 5.43 mmol) in methanol (130 mL) was added pyrrolidine (0.98 mL, 2.41 mmol) and reaction was refluxed overnight. Acetic acid (7 mL) was added to the reaction mixture and was refluxed for 4 hours. Methanol and acetic acid were evaporated on a rotary evaporator and crude was dissolved in water, solid sodium carbonate was added portion wise to neutralize remaining acetic acid. Crude was then extracted using DCM (2×30 mL), which was further purified on Combi-Flash. LCMS (ESI, m/z): 293.2.2 $[M+H]^+$ Step 2:

(4R,5R)-5-((R)-5H-imidazo[5,1-a]isoindol-5-yl)-4,5,6,7-tetrahydrobenzo[c][1,2,5]oxadiazol-4-ol
(4R,5R)-5-((S)-5H-imidazo[5,1-a]isoindol-5-yl)-4,5,6,7-tetrahydrobenzo[c][1,2,5]oxadiazol-4-ol
(4R,5S)-5-((R)-5H-imidazo[5,1-a]isoindol-5-yl)-4,5,6,7-tetrahydrobenzo[c][1,2,5]oxadiazol-4-ol
(4R,5S)-5-((S)-5H-imidazo[5,1-a]isoindol-5-yl)-4,5,6,7-tetrahydrobenzo[c][1,2,5]oxadiazol-4-ol
(4S,5R)-5-((R)-5H-imidazo[5,1-a]isoindol-5-yl)-4,5,6,7-tetrahydrobenzo[c][1,2,5]oxadiazol-4-ol
(4S,5R)-5-((S)-5H-imidazo[5,1-a]isoindol-5-yl)-4,5,6,7-tetrahydrobenzo[c][1,2,5]oxadiazol-4-ol
(4S,5S)-5-((R)-5H-imidazo[5,1-a]isoindol-5-yl)-4,5,6,7-tetrahydrobenzo[c][1,2,5]oxadiazol-4-ol
(4S,5S)-5-((S)-5H-imidazo[5,1-a]isoindol-5-yl)-4,5,6,7-tetrahydrobenzo[c][1,2,5]oxadiazol-4-ol 163a

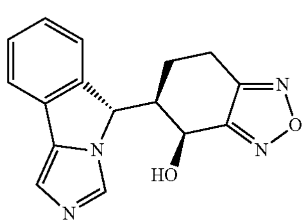

-continued

163b

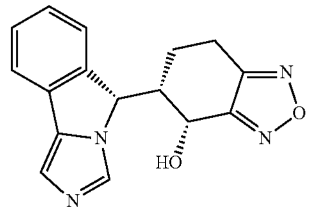

163c

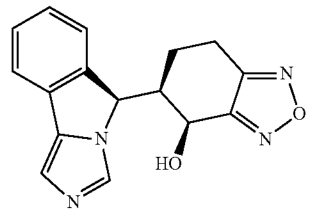

163d

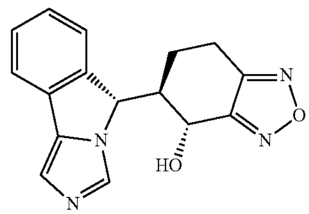

163e

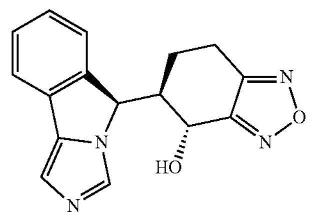

163f

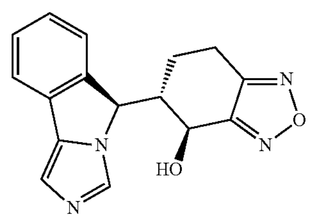

163g

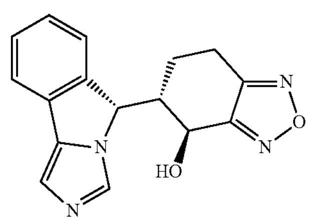

163h

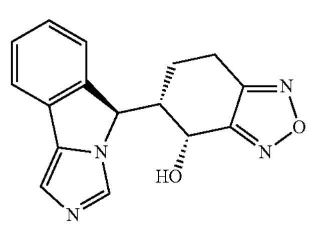

To the solution of 5-(5H-imidazo[5,1-a]isoindol-5-yl)-6,7-dihydrobenzo[c][1,2,5]oxadiazol-4(5H)-one (800 mg, 2.74 mmol) in methanol (30 mL) was added, sodium borohydride (0.31 g, 8.21 mmol) at 0° C. Reaction flask was then removed from ice bath and reaction was stirred for 2 hours. Reaction was quenched by adding sat $NH_4Cl$ slowly. The resulting mixture was concentrated under vacuum and crude product was extracted using 10% TFE in DCM. Combined organic layers were evaporated to yield crude product which was further purified on Combi-Flash and further isolated by chiral separation to afford 8 isomers as white solid. The absolute configuration of all isomers was assigned arbitrarily.

Example 163a: (4R,5R)-5-((R)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.93 (s, 1H), 7.73 (dd, J=7.8, 0.9 Hz, 1H), 7.62 (d, J=7.6 Hz, 1H), 7.42-7.35 (m, 1H), 7.29-7.22 (m, 1H), 7.14 (s, 1H), 6.36 (d, J=5.7 Hz, 1H), 5.55 (d, J=4.9 Hz, 1H), 5.22 (d, J=2.4 Hz, 1H), 3.06-2.91 (m, 1H), 2.73-2.61 (m, 1H), 1.95 (qd, J=12.8, 5.6 Hz, 1H), 1.68 (dd, J=13.4, 6.2 Hz, 1H), 0.90-0.78 (m, 1H).

Example 163b: (4R,5R)-5-((S)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.92 (s, 1H), 7.60 (ddt, J=7.7, 6.6, 0.9 Hz, 2H), 7.40 (tt, J=7.7, 0.8 Hz, 1H), 7.30 (td, J=7.5, 1.2 Hz, 1H), 7.13 (s, 1H), 6.69 (d, J=5.7 Hz, 1H), 5.62-5.55 (m, 1H), 5.46 (dd, J=5.9, 3.5 Hz, 1H), 2.91 (ddd, J=17.4, 5.6, 1.9 Hz, 1H), 2.68 (dq, J=12.6, 2.7, Hz, 1H), 2.55 (ddd, J=17.4, 12.6, 6.3 Hz, 1H), 1.56 (qd, J=12.9, 5.6 Hz, 1H), 1.06-0.95 (m, 1H).

Example 163c: (4R,5S)-5-((R)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.92 (s, 1H), 7.60 (tt, J=7.3, 0.9 Hz, 2H), 7.40 (tt, J=7.5, 0.8 Hz, 1H), 7.30 (td, J=7.5, 1.2 Hz, 1H), 7.13 (s, 1H), 6.69 (d, J=5.5 Hz, 1H), 5.62-5.55 (m, 1H), 5.46 (t, J=4.5 Hz, 1H), 2.91 (ddd, J=17.4, 5.6, 1.8 Hz, 1H), 2.68 (dq, J=12.5, 2.6 Hz, 1H), 2.55 (ddd, J=17.4, 12.6, 6.2 Hz, 1H), 1.61-1.50 (m, 1H), 1.06-0.98 (m, 1H).

Example 163d: (4R,5S)-5-((S)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.99 (s, 1H), 7.64 (dt, J=7.7, 1.0 Hz, 1H), 7.52-7.46 (m, 1H), 7.43 (tt, J=7.6, 0.9 Hz, 1H), 7.33 (td, J=7.6, 1.1 Hz, 1H), 7.19 (s, 1H), 6.69 (d, J=7.2 Hz, 1H), 5.80-5.71 (m, 1H), 5.26 (dd, J=11.0, 7.3 Hz, 1H), 2.78 (dt, J=17.3, 3.8 Hz, 1H), 2.65-2.53 (m, 2H), 0.96 (dtd, J=11.2, 6.4, 3.9 Hz, 2H).

Example 163e: (4S,5R)-5-((R)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.90 (s, 1H), 7.65 (d, J=7.5 Hz, 1H), 7.61 (dd, J=7.7, 0.9 Hz, 1H), 7.44-7.38 (m, 1H), 7.28 (td, J=7.6, 1.2 Hz, 1H), 7.18 (s, 1H), 6.71 (d, J=6.9 Hz, 1H), 5.78 (d, J=3.2 Hz, 1H), 5.17 (dd, J=11.1, 6.8 Hz, 1H), 2.80-2.68 (m, 2H), 2.66-2.56 (m, 1H), 0.89-1.04 (m, 2H).

Example 163f: (4S,5R)-5-((S)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.99 (s, 1H), 7.64 (dt, J=7.6, 0.9 Hz, 1H), 7.52-7.47 (m, 1H), 7.46-7.40 (m, 1H), 7.33 (td, J=7.6, 1.1 Hz, 1H), 7.19 (s, 1H), 6.68 (d, J=7.3 Hz, 1H), 5.80-5.76 (m, 1H), 5.25 (dd, J=11.1, 7.3 Hz, 1H), 2.78 (dt, J=17.3, 3.8 Hz, 1H), 2.65-2.53 (m, 2H), 1.01-0.91 (m, 2H).

Example 163g: (4S,5S)-5-((R)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.90 (s, 1H), 7.65 (d, J=7.5 Hz, 1H), 7.61 (dd, J=7.7, 1.0 Hz, 1H), 7.41 (d, J=0.8 Hz, 1H), 7.28 (dd, J=7.6, 1.1 Hz, 1H), 7.18 (s, 1H), 6.71 (d, J=6.7 Hz, 1H), 5.78 (d, J=3.2 Hz, 1H), 5.17 (dd, J=11.1, 6.5 Hz, 1H), 2.83-2.69 (m, 2H), 2.66-2.57 (m, 1H), 1.06-0.94 (m, 1H), 0.81-0.93 (m, 1H).

Example 163h: (4S,5S)-5-((S)-5H-imidazo[5,1-a]isoindol-5-yl)-4,5,6,7-tetrahydrobenzo[c][1,2,5]oxadiazol-4-ol: LCMS (ESI, m/z): 295.4 [M+H]$^+$; $^1$H NMR (500 MHz, DMSO-d6) δ 7.93 (s, 1H), 7.73 (dd, J=7.7, 0.9 Hz, 1H), 7.63 (d, J=7.6 Hz, 1H), 7.40 (t, J=0.8 Hz, 1H), 7.25 (d, J=1.2 Hz, 1H), 7.14 (s, 1H), 6.36 (d, J=5.8 Hz, 1H), 5.55 (d, J=4.8 Hz, 1H), 5.22 (dd, J=5.9, 3.3 Hz, 1H), 3.00 (ddd, J=17.5, 5.6, 1.9 Hz, 1H), 2.68 (ddd, J=17.4, 12.3, 6.3 Hz, 1H), 1.95 (qd, J=12.8, 5.6 Hz, 1H), 1.68 (dd, J=13.4, 6.2 Hz, 1H), 1.22-1.26 (m, 1H).

Example 164: 1-(5H-imidazo[5,1-a]isoindol-5-yl)-2,2-dimethylcyclohexan-1-ol

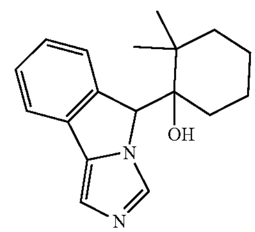 [SMILES: CC1(C)CCCCC1(O)C1c2ccccc2-c2cncn21]

To a solution of 5H-imidazo[5,1-a]isoindole (0.866 g, 5.55 mmol) in anhydrous THF (25 mL) at −40° C. was added n-BuLi (2.22 mL, 5.55 mmol, 2.5 M solution in hexanes). After stirring for 1.0 hr at −40° C., 2,2-dimethylcyclohexan-1-one (350 mg, 2.77 mmol) was added and the reaction was allowed to warm to −10° C. and stirred for 3 hr. The reaction was quenched by adding satd. $NH_4Cl$ (10 mL) and water (20 mL), the product was extracted with $CH_2Cl_2$ (3×35 mL). The combined organic extract was dried over $Na_2SO_4$ and concentrated under reduced pressure to afford crude mixture. The crude product was purified by Combi-Flash and further isolated by chiral separation to afford 2 isomers as white solid, the stereochemistry was assigned arbitrarily: LCMS (ESI, m/z): 283.23 [M+H]$^+$.

164a

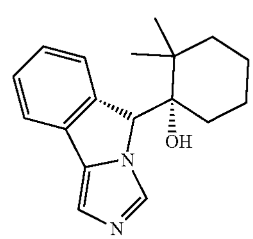

164b

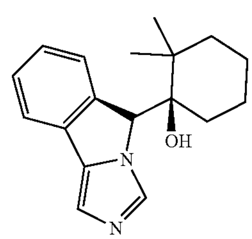

Example 164a: (S)-1-((R)-5H-imidazo[5,1-a]isoindol-5-yl)-2,2-dimethylcyclohexan-1-ol: LCMS (ESI, m/z): 283.23 $[M+H]^+$. $^1$H NMR (DMSO-$d_6$, 500 MHz): δ (ppm) 7.90 (s, 1H), 7.66-7.53 (m, 2H), 7.37 (tt, J=7.5, 0.8 Hz, 1H), 7.21 (td, J=7.6, 1.2 Hz, 1H), 7.11 (s, 1H), 5.12 (s, 1H), 5.11 (s, 1H), 2.40-2.26 (m, 1H), 1.87-1.69 (m, 3H), 1.56 (d, J=11.9 Hz, 1H), 1.43-1.20 (m, 2H), 0.65 (d, J=13.1 Hz, 1H), 0.19 (s, 3H), 0.13 (s, 3H).

Example 164b: (R)-1-((R)-5H-imidazo[5,1-a]isoindol-5-yl)-2,2-dimethylcyclohexan-1-ol: LCMS (ESI, m/z): 283.23 $[M+H]^+$. $^1$H NMR (DMSO-$d_6$, 500 MHz): Same as 164a.

Example 165: 1-(hydroxy (5H-imidazo[5,1-a]isoindol-5-yl)methyl)cyclopropane-1-carboxamide

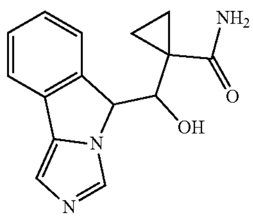 [SMILES: NC(=O)C1(C(O)C2c3ccccc3-c3cncn32)CC1]

Step 1:

1-((R)-hydroxy((R)-5H-imidazo[5,1-a]isoindol-5-yl)methyl)cyclopropane-1-carboxamide 1-((R)-hydroxy ((S)-5H-imidazo[5,1-a]isoindol-5-yl)methyl)cyclopropane-1-carboxamide 1-((S)-hydroxy((R)-5H-imidazo[5,1-a]isoindol-5-yl)methyl)cyclopropane-1-carboxamide 1-((S)-hydroxy ((S)-5H-imidazo[5,1-a]isoindol-5-yl)methyl)cyclopropane-1-carboxamide 165a

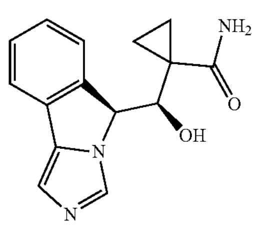

165b

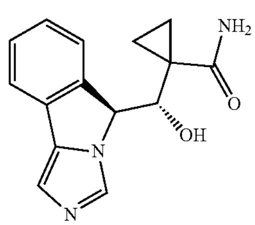

165c

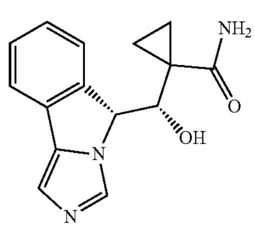

-continued

165d

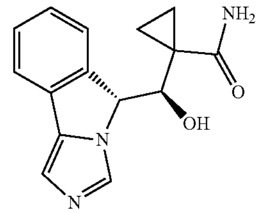

To the solution of 1-(hydroxy (5H-imidazo[5,1-a]isoindol-5-yl)methyl)cyclopropane-1-carbonitrile (800 mg, 3.18 mmol) in methanol, NaOH (1.27 g, 31.84 mmol) and hydrogen peroxide (2.49 mL, 31.84 mmol, 30% solution in water). The reaction mixture was stirred for 3 days. Crude product was extracted using the solution of 5% 2,2,2-trifluoroethanol in DCM and was purified on a Combi-Flash and further isolated by chiral separation to afford 4 isomers as white solid. The absolute configuration of all isomers was assigned arbitrarily.

Example 165a: 1-((R)-hydroxy((R)-5H-imidazo[5,1-a]isoindol-5-yl)methyl)cyclopropane-1-carboxamide: LCMS (ESI, m/z): 270.2 $[M+H]^+$; $^1$H NMR (500 MHz, DMSO-d6) δ 7.76 (s, 1H), 7.66-7.62 (m, 1H), 7.56 (dt, J=7.5, 0.9 Hz, 1H), 7.41-7.33 (m, 1H), 7.29-7.17 (m, 3H), 7.09 (s, 1H), 5.94 (d, J=5.1 Hz, 1H), 5.48 (d, J=6.9 Hz, 1H), 1.02-0.95 (m, 2H), 0.73-0.65 (m, 1H), 0.52-0.42 (m, 1H).

Example 165b: 1-((R)-hydroxy ((S)-5H-imidazo[5,1-a]isoindol-5-yl)methyl)cyclopropane-1-carboxamide: LCMS (ESI, m/z): 270.2 $[M+H]^+$; $^1$H NMR (500 MHz, DMSO-d6) δ 7.83 (s, 1H), 7.57 (dt, J=7.5, 0.9 Hz, 1H), 7.51 (dd, J=7.6, 0.9 Hz, 1H), 7.40-7.35 (m, 1H), 7.32-7.21 (m, 3H), 7.10 (s, 1H), 6.05 (s, 1H), 5.57 (d, J=7.3 Hz, 1H), 1.10 (ddd, J=9.4, 6.8, 4.2 Hz, 1H), 0.97 (ddd, J=9.4, 6.4, 4.1 Hz, 1H), 0.78 (ddd, J=9.4, 6.8, 4.2 Hz, 1H), 0.40 (ddd, J=9.4, 6.5, 4.2 Hz, 1H).

Example 165c: 1-((S)-hydroxy((R)-5H-imidazo[5,1-a]isoindol-5-yl)methyl)cyclopropane-1-carboxamide: LCMS (ESI, m/z): 270.2 $[M+H]^+$; $^1$H NMR (500 MHz, DMSO-d6) δ 7.76 (s, 1H), 7.64 (dd, J=7.7, 1.0 Hz, 1H), 7.59-7.54 (m, 1H), 7.37 (t, J=7.4 Hz, 1H), 7.23 (td, J=7.6, 1.2 Hz, 3H), 7.09 (s, 1H), 5.94 (d, J=5.8 Hz, 1H), 5.48 (d, J=6.9 Hz, 1H), 1.00-0.97 (q, 2H), 0.72-0.66 (m, 1H), 0.51-0.43 (m, 1H).

Example 165d: 1-((S)-hydroxy ((S)-5H-imidazo[5,1-a]isoindol-5-yl)methyl)cyclopropane-1-carboxamide: LCMS (ESI, m/z): 270.2 $[M+H]^+$; $^1$H NMR (500 MHz, DMSO-d6) δ 7.83 (s, 1H), 7.57 (dt, J=7.5, 0.9 Hz, 1H), 7.51 (dd, J=7.6, 0.9 Hz, 1H), 7.40-7.35 (m, 1H), 7.32-7.21 (m, 3H), 7.10 (s, 1H), 6.05 (s, 1H), 5.57 (d, J=7.3 Hz, 1H), 1.10 (ddd, J=9.4, 6.8, 4.2 Hz, 1H), 0.97 (ddd, J=9.4, 6.4, 4.1 Hz, 1H), 0.78 (ddd, J=9.4, 6.8, 4.2 Hz, 1H), 0.40 (ddd, J=9.4, 6.5, 4.2 Hz, 1H).

Example 166: 5-(5H-imidazo[5,1-a]isoindol-5-yl)-2-methyl-4,5,6,7-tetrahydropyrazolo[1,5-a]pyridin-4-ol

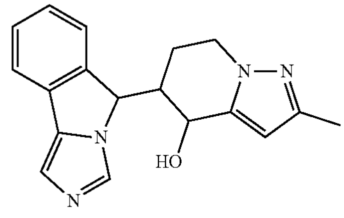 [SMILES: Cc1cc2n(n1)CCC(C1c3ccccc3-c3cncn31)C2O]

(4S,5S)-5-((S)-5H-imidazo[5,1-a]isoindol-5-yl)-2-methyl-4,5,6,7-tetrahydropyrazolo[1,5-a]pyridin-4-ol (4R,5R)-5-((R)-5H-imidazo[5,1-a]isoindol-5-yl)-2-methyl-4,5,6,7-tetrahydropyrazolo[1,5-a]pyridin-4-ol The title compound was synthesized by the same method of example 96.

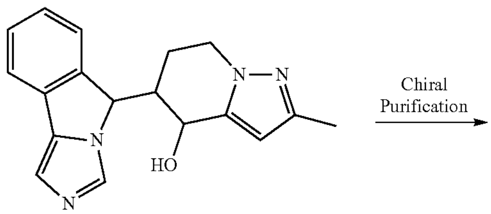

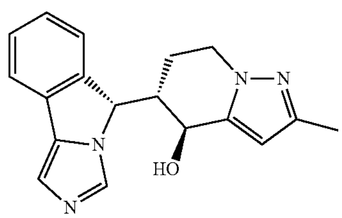

166a

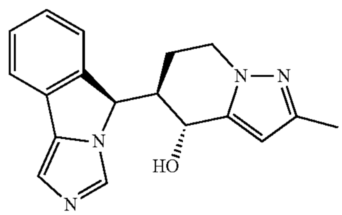

166b

The configurations of the isomers were assigned arbitrarily.

Example 166a: (4S,5S)-5-((S)-5H-imidazo[5,1-a]isoindol-5-yl)-2-methyl-4,5,6,7-tetrahydropyrazolo[1,5-a]pyridin-4-ol: LCMS (ESI, m/z): 307.2 $[M+H]^+$; $^1$H NMR (500 MHz, DMSO-$d_6$) δ 7.97 (s, 1H), 7.64 (dt, J=7.6, 0.9 Hz, 1H), 7.50 (dq, J=7.6, 1.0 Hz, 1H), 7.42 (tt, J=7.4, 0.9 Hz, 1H), 7.32 (td, J=7.5, 1.1 Hz, 1H), 7.19 (s, 1H), 6.10 (d, J=5.6 Hz, 1H), 6.08 (s, 1H), 5.75 (d, J=1.8 Hz, 1H), 4.97 (dd, J=10.5, 5.1 Hz, 1H), 3.89-3.82 (m, 1H), 3.69 (td, J=12.0, 5.4 Hz, 1H), 2.49-2.43 (m, 1H), 2.12 (s, 3H), 1.08-1.00 (m, 2H). 166a and 166b are enantiomers.

Example 166b: (4R,5R)-5-((R)-5H-imidazo[5,1-a]isoindol-5-yl)-2-methyl-4,5,6,7-tetrahydropyrazolo[1,5-a]pyridin-4-ol: LCMS (ESI, m/z): 307.2 $[M+H]^+$; $^1$H NMR (500 MHz, DMSO-$d_6$) δ 7.97 (s, 1H), 7.64 (dt, J=7.6, 0.9 Hz, 1H), 7.50 (dq, J=7.6, 1.0 Hz, 1H), 7.42 (tt, J=7.4, 0.9 Hz, 1H), 7.32 (td, J=7.5, 1.1 Hz, 1H), 7.19 (s, 1H), 6.10 (d, J=5.6 Hz, 1H), 6.08 (s, 1H), 5.75. (d, J=1.8 Hz, 1H), 4.97 (dd, J=10.5, 5.1 Hz, 1H), 3.89-3.82 (m, 1H), 3.69 (td, J=12.0, 5.4 Hz, 1H), 2.49-2.43 (m, 1H), 2.12 (s, 3H), 1.08-1.00 (m, 2H). 166a and 166b are enantiomers.

Example 167: 6-(5H-imidazo[5,1-a]isoindol-5-yl)-4,5,6,7-tetrahydrobenzo[d]thiazol-7-ol

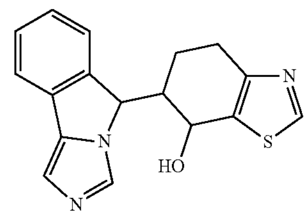 [SMILES: OC1c2scnc2CCC1C1c2ccccc2-c2cncn21]

(6R,7R)-6-((S)-5H-imidazo[5,1-a]isoindol-5-yl)-4,5,6,7-tetrahydrobenzo[d]thiazol-7-ol (6S,7S)-6-((S)-5H-imidazo[5,1-a]isoindol-5-yl)-4,5,6,7-tetrahydrobenzo[d]thiazol-7-ol (6R,7S)-6-((S)-5H-imidazo[5,1-a]isoindol-5-yl)-4,5,6,7-tetrahydrobenzo[d]thiazol-7-ol (6S,7R)-6-((R)-5H-imidazo[5,1-a]isoindol-5-yl)-4,5,6,7-tetrahydrobenzo[d]thiazol-7-ol (6S,7R)-6-((S)-5H-imidazo[5,1-a]isoindol-5-yl)-4,5,6,7-tetrahydrobenzo[d]thiazol-7-ol (6S,7S)-6-((R)-5H-imidazo[5,1-a]isoindol-5-yl)-4,5,6,7-tetrahydrobenzo[d]thiazol-7-ol (6R,7R)-6-((R)-5H-imidazo[5,1-a]isoindol-5-yl)-4,5,6,7-tetrahydrobenzo[d]thiazol-7-ol (6R,7S)-6-((R)-5H-imidazo[5,1-a]isoindol-5-yl)-4,5,6,7-tetrahydrobenzo[d]thiazol-7-ol The title compound was synthesized by the same method of example 88.

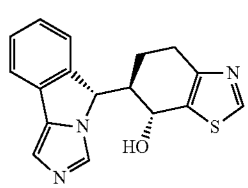

167a

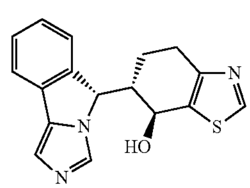

167b

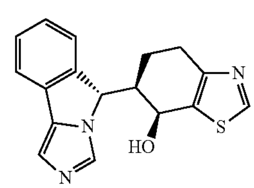

167c

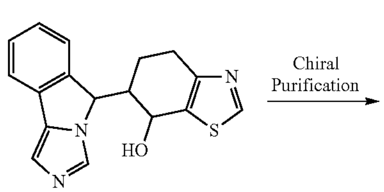

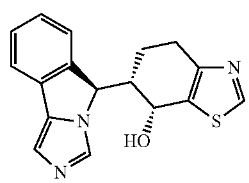

167d

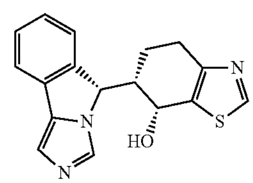

167e

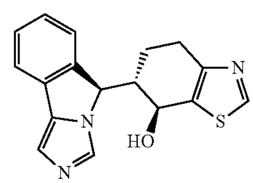

167f

-continued

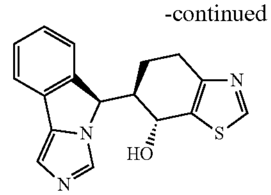

167g

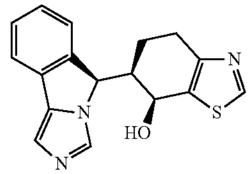

167h

The configurations of the isomers were assigned arbitrarily.

Example 167a: (6R,7R)-6-((S)-5H-imidazo[5,1-a]isoindol-5-yl)-4,5,6,7-tetrahydrobenzo[d]thiazol-7-ol: LCMS (ESI, m/z): 310.1 $[M+H]^+$; $^1$H NMR (500 MHz, DMSO-$d_6$) δ 8.97 (s, 1H), 7.97 (s, 1H), 7.75 (dd, J=7.7, 1.0 Hz, 1H), 7.61 (d, J=7.5 Hz, 1H), 7.38 (dd, J=8.0, 7.1 Hz, 1H), 7.24 (td, J=7.6, 1.1 Hz, 1H), 7.13 (s, 1H), 5.87 (d, J=6.7 Hz, 1H), 5.47 (d, J=5.5 Hz, 1H), 5.07 (dd, J=6.8, 3.6 Hz, 1H), 2.82 (dd, J=16.8, 3.9 Hz, 1H), 2.57 (ddd, J=16.9, 11.7, 5.9 Hz, 1H), 2.37-2.28 (m, 1H), 1.94 (qd, J=12.6, 5.3 Hz, 1H), 1.69 (d, J=12.6 Hz, 1H). 167a and 167f are enantiomers.

Example 167b: (6S,7S)-6-((S)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 8.94 (d, J=0.7 Hz, 1H), 7.92 (s, 1H), 7.63 (ddd, J=14.2, 7.7, 1.0 Hz, 2H), 7.41 (ddd, J=7.5, 6.9, 0.9 Hz, 1H), 7.26 (td, J=7.6, 1.2 Hz, 1H), 7.17 (s, 1H), 6.37 (d, J=6.4 Hz, 1H), 5.76 (d, J=3.0 Hz, 1H), 5.15 (s, 1H), 2.60-2.52 (m, 2H), 1.06-0.82 (m, 3H). 167b and 167g are enantiomers.

Example 167c: (6R,7S)-6-((S)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 8.96 (d, J=0.8 Hz, 1H), 8.00 (s, 1H), 7.66-7.62 (m, 1H), 7.49 (dq, J=7.7, 1.0 Hz, 1H), 7.44-7.41 (m, 1H), 7.33 (td, J=7.5, 1.1 Hz, 1H), 7.18 (s, 1H), 6.34 (d, J=7.6 Hz, 1H), 5.76 (s, 1H), 5.20 (t, J=8.6 Hz, 1H), 2.64-2.57 (m, 1H), 2.46-2.33 (m, 2H), 0.96-0.84 (m, 2H). 167c and 167d are enantiomers.

Example 167d: (6S,7R)-6-((R)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 8.96 (d, J=0.7 Hz, 1H), 8.00 (s, 1H), 7.64 (d, J=7.5 Hz, 1H), 7.52-7.47 (m, 1H), 7.42 (t, J=7.5 Hz, 1H), 7.33 (td, J=7.5, 1.1 Hz, 1H), 7.18 (s, 1H), 6.33 (d, J=7.6 Hz, 1H), 5.76 (s, 1H), 5.20 (t, J=8.7 Hz, 1H), 2.59 (s, 1H), 2.43 (t, J=10.6 Hz, 2H), 0.99-0.84 (m, 2H). 167c and 167d are enantiomers.

Example 167e: (6S,7R)-6-((S)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 9.00 (s, 1H), 7.94 (s, 1H), 7.61 (ddt, J=12.0, 7.7, 0.9 Hz, 2H), 7.39 (tt, J=7.5, 0.9 Hz, 1H), 7.29 (td, J=7.5, 1.2 Hz, 1H), 7.12 (s, 1H), 6.16 (d, J=6.6 Hz, 1H), 5.53 (d, J=1.5 Hz, 1H), 5.25 (dd, J=6.6, 3.9 Hz, 1H), 2.76-2.68 (m, 1H), 2.62-2.55 (m, 1H), 2.48-2.42 (m, 1H), 1.52 (qd, J=12.7, 5.6 Hz, 1H), 1.01-0.93 (m, 1H). 167e and 167h are enantiomers.

Example 167f: (6S,7S)-6-((R)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 8.97 (s, 1H), 7.97 (s, 1H), 7.75 (dd, J=7.7, 1.0 Hz, 1H), 7.61 (d, J=7.5 Hz, 1H), 7.41-7.36 (m, 1H), 7.24 (td, J=7.6, 1.2 Hz, 1H), 7.13 (s, 1H), 5.87 (d, J=6.7 Hz, 1H), 5.47 (d, J=5.6 Hz, 1H), 5.07 (dd, J=6.7, 3.7 Hz, 1H), 2.85-2.79 (m, 1H), 2.57 (ddd, J=17.0, 11.7, 5.8 Hz, 1H), 2.33 (ddd, J=12.9, 5.8, 3.0 Hz, 1H), 1.94 (qd, J=12.6, 5.5 Hz, 1H), 1.69 (d, J=11.3 Hz, 1H). 167a and 167f are enantiomers.

Example 167g: (6R,7R)-6-((R)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 8.94 (d, J=0.7 Hz, 1H), 7.92 (s, 1H), 7.63 (dd, J=15.0, 7.6 Hz, 2H), 7.41 (dd, J=7.9, 7.1 Hz, 1H), 7.26 (td, J=7.6, 1.2 Hz, 1H), 7.17 (s, 1H), 6.35 (d, J=7.3 Hz, 1H), 5.76 (d, J=2.9 Hz, 1H), 5.14 (t, J=8.6 Hz, 1H), 2.61-2.54 (m, 2H), 1.06-0.79 (m, 3H). 167b and 167g are enantiomers.

Example 167h: (6R,7S)-6-((R)-5H-imidazo[5,1-a]isoindol-5-yl)-4,5,6,7-tetrahydrobenzo[d]thiazol-7-ol: LCMS (ESI, m/z): 310.2 $[M+H]^+$; $^1$H NMR (500 MHz, DMSO-$d_6$) δ 9.00 (s, 1H), 7.94 (s, 1H), 7.61 (ddt, J=12.1, 7.7, 1.0 Hz, 2H), 7.39 (tt, J=7.6, 0.9 Hz, 1H), 7.29 (td, J=7.5, 1.2 Hz, 1H), 7.12 (s, 1H), 6.16 (d, J=6.6 Hz, 1H), 5.53 (d, J=1.7 Hz, 1H), 5.25 (dd, J=6.6, 3.9 Hz, 1H), 2.76-2.69 (m, 1H), 2.62-2.55 (m, 1H), 2.47-2.41 (m, 1H), 1.52 (qd, J=12.6, 5.5 Hz, 1H), 1.01-0.94 (m, 1H). 167e and 167h are enantiomers.

Example 168: 5H-imidazo[5,1-a]isoindol-5-yl)-2-methyl-4,5,6,7-tetrahydrobenzo[d]oxazol-4-ol 168a

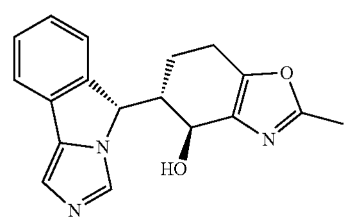

168b

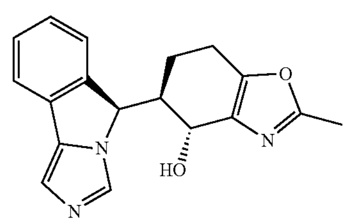

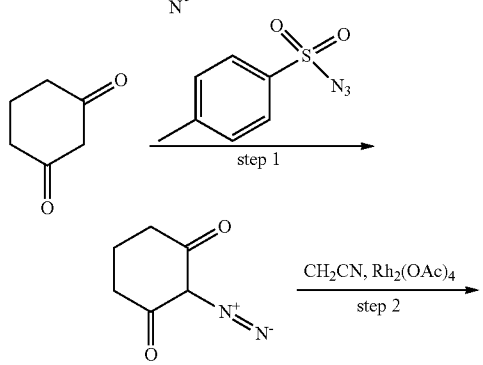

-continued

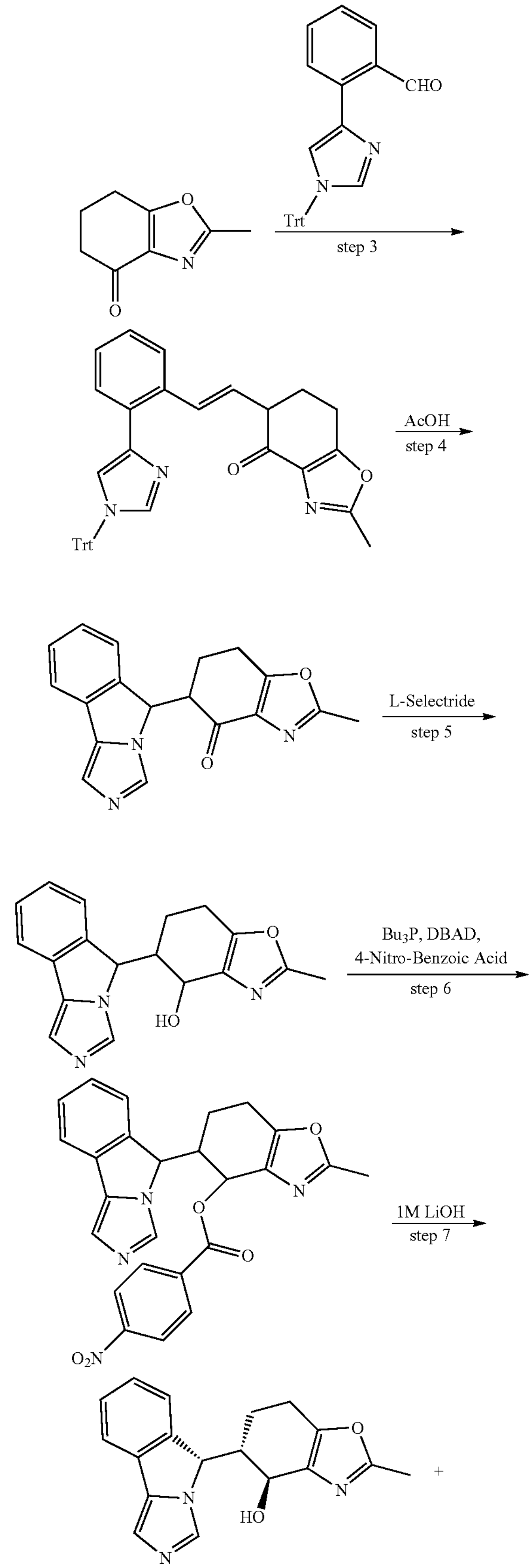

168a

-continued

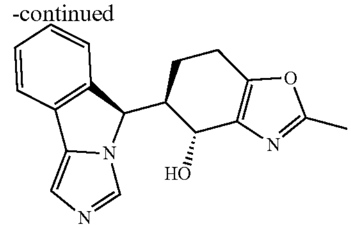

168b

Step 1: 2-diazocyclohexane-1,3-dione

Cyclohexane-1,3-dione (5.0 g, 44.6 mmol) was dissolved in 80 g of 11% p-toluene-sulfonyl azide (44.6 mmol) in toluene and charged with trimethylamine (18.6 mL, 134 mmol) with. After stirring at room temperature overnight, the solution was diluted with 500 mL of EtOAc and 500 mL of water. The aqueous was discarded and the organic was washed once with water, dried over $Na_2SO_4$, filtered, and concentrated in vacuo. The crude residue was then purified by silica-gel chromatography (15-50% Heptane in EtOAc) to afford 2-diazocyclohexane-1,3-dione (5.1 g, 83% yield) LCMS (ESI, m/z): 139.1 (M+H).

Step 2: 2-methyl-6,7-dihydrobenzo[d]oxazol-4(5H)-one 2-diazocyclohexane-1,3-dione was (300 mg, 2.2 mmol) was dissolved in 10 ml of ACN and charged with dirhodium tetraacetate (88 mg, 0.2 mmol). After heating the mixture at 60° C. overnight, the mixture was diluted with 50 mL of EtOAc and 50 ml of water. The aqueous was discarded and the organic was washed once with water, dried over $Na_2SO_4$, filtered, and concentrated in vacuo. The crude residue was then purified by silica-gel chromatography (1-15% MeOH in DCM) to afford 2-methyl-6,7-dihydrobenzo[d]oxazol-4(5H)-one (210 mg, 64% yield). LCMS (ESI, m/z): 152.1 (M+H).

Step 3: (E)-2-methyl-5-(2-(1-trityl-1H-imidazol-4-yl) styryl)-6,7-dihydrobenzo[d]oxazol-4(5H)-one Diisopropylamine (1.3 mL, 9.3 mmol) was dissolved in 5 mL of anhydrous THF, cooled to 0° C., and charged with 2.5M n-butyl lithium in hexane (3.7 mL, 9.3 mmol). The solution was then stirred at 0° C. for 15 minutes and cooled to −78° C. In a separate flask,2-methyl-6,7-dihydrobenzo [d]oxazol-4(5H)-one (1.4 g, 9.3 mmol) was dissolved in 5 ml of anhydrous THF and added dropwise to the aforementioned mixture of diisopropylamine/n-butyl lithium in THF at −78° C. In a separate flask, 2-(1-trityl-1Himidazol-4-yl) benzaldehyde (3.5 g, 8.4 mmol) was dissolved in 20 mL of anhydrous THF and then added dropwise to the aforementioned mixture at −78° C. The solution was then stirred at room temperature overnight, the solution was diluted with 500 mL of EtOAc and 500 ml of water. The aqueous was discarded and the organic was washed once with water, dried over $Na_2SO_4$, filtered, and concentrated in vacuo. The crude residue was then purified by silica-gel chromatography (15-50% Heptane in EtOAc) to afford (E)-2-methyl-5-(2-(1-trityl-1H-imidazol-4-yl) styryl)-6,7-dihydrobenzo[d]oxazol-4(5H)-one (3.3 g, 71% yield) LCMS (ESI, m/z): 562.2 (M+H).

Step 4: 5-(5H-imidazo[5,1-a]isoindol-5-yl)-2-methyl-6,7-dihydrobenzo[d]oxazol-4(5H)-one (E)-2-methyl-5-(2-(1-trityl-1H-imidazol-4-yl) styryl)-6,7-dihydrobenzo[d]oxazol-4(5H)-one (3.0 g, 5.5 mmol) was dissolved in 10 mL of AcOH and 30 mL of MeOH and heated at 80° C. for two hours. The solution was then concentrated in vacuo and purified by silica-gel chromatography (1-15% MeOH in DCM) to afford 5-(5H-imidazo[5,1-a]isoindol-5-yl)-2-methyl-6,7-dihydrobenzo[d]oxazol-4(5H)-one (1.1 g, 66% yield). LCMS (ESI, m/z): 306.1 (M+H).

Step 5: 5-(5H-imidazo[5,1-a]isoindol-5-yl)-2-methyl-4,5,6,7-tetrahydrobenzo[d]oxazol-4-ol 5-(5H-imidazo[5,1-a]isoindol-5-yl)-2-methyl-6,7-dihydrobenzo[d]oxazol-4(5H)-one (1.1 g, 3.6 mmol) was dissolved in 10 mL of THF, cooled to −78° C., and charged with L-Selectride (1.0 M in THF, 20 mL, 20 mmol). After stirring at −78° C. for 30 minutes, 2 mL of AcOH was added. The solution was then diluted with 100 mL of EtOAc and 100 ml of water. The aqueous was discarded and the organic was washed once with water, dried over $Na_2SO_4$, filtered, and concentrated in vacuo. The crude residue was then purified by silica-gel chromatography (1-15% MeOH in DCM) to afford 5-(5H-imidazo[5,1-a]isoindol-5-yl)-2-methyl-4,5,6,7-tetrahydrobenzo[d]oxazol-4-ol (800 mg, 72% yield). LCMS (ESI, m/z): 308.1 (M+H).

Step 6: 5-(5H-imidazo[5,1-a]isoindol-5-yl)-2-methyl-4,5,6,7-tetrahydrobenzo[d]oxazol-4-yl 4-nitrobenzoate 5-(5H-imidazo[5,1-a]isoindol-5-yl)-2-methyl-4,5,6,7-tetrahydrobenzo[d]oxazol-4-ol (230 mg, 0.74 mmol) was dissolved in 3 ml of THF and charged with di-tert-butylazidocarboxylate (861 mg, 3.7 mmol), 4-nitro-benzoic acid (188 mg, 1.1 mmol), and tributylphosphine (930 uL, 3.7 mmol). After stirring at room temperature overnight, the solution was concentrated in vacuo. The crude residue was then charged 10 mL of 1.0 M citric acid and 10 mL of EtOAc. The organic layer was discarded and the aqueous layer was treated with 10 mL of 1.0 M Sodium Bicarbonate. The aqueous was then extracted twice with EtOAc and the organics were combined and concentrated in vacuo. The residue was then purified by silica-gel chromatography to afford 5-(5H-imidazo[5,1-a]isoindol-5-yl)-2-methyl-4,5,6,7-tetrahydrobenzo[d]oxazol-4-yl 4-nitrobenzoate (200 mg, 59% yield). LCMS (ESI, m/z): 457.1 (M+H)

Step 7: (5H-imidazo[5,1-a]isoindol-5-yl)-2-methyl-4,5,6,7-tetrahydrobenzo[d]oxazol-4-ol 5-(5H-imidazo[5,1-a]isoindol-5-yl)-2-methyl-4,5,6,7-tetrahydrobenzo[d]oxazol-4-yl 4-nitrobenzoate (100 mg, 0.21 mmol) was dissolved in 1 mL of THF and charged with 600 µL of 1 M LiOH (aq). After stirring at room temperature for 30 minutes, the solution was then diluted with 10 mL of EtOAc and 5 mL of water. The aqueous was discarded and the organic was washed once with water, dried over $Na_2SO_4$, filtered, and concentrated in vacuo. The crude residue was then purified by silica-gel chromatography (1-15% MeOH in DCM) to afford 5-(5H-imidazo[5,1-a]isoindol-5-yl)-2-methyl-4,5,6,7-tetrahydrobenzo[d]oxazol-4-ol (40 mg, 62% yield). LCMS (ESI, m/z): 308.1 (M+H)

(5H-imidazo[5,1-a]isoindol-5-yl)-2-methyl-4,5,6,7-tetrahydrobenzo[d]oxazol-4-ol was purified by chiral SFC (Methanol w/0.1% $NH_4OH$, Isocratic @ 10% MeOH, Cellulose-3 (150×21 mm, 5 um)) to afford single stereoisomers of undetermined absolute configuration. Examples 168a and 168b are enantiomers of one another. The absolute configuration was assigned arbiturily.

Example 168a: (4S,5S)-5-((S)-5H-imidazo[5,1-a]isoindol-5-yl)-2-methyl-4,5,6,7-tetrahydrobenzo[d]oxazol-4-ol. LCMS (ESI, m/z): 308.1 (M+H). $^1H$ NMR (400 MHz, DMSO-d6) δ 7.91 (s, 1H), 7.63 (dt, J=7.5, 1.0 Hz, 1H), 7.49-7.37 (m, 2H), 7.32 (td, J=7.5, 1.2 Hz, 1H), 7.17 (s, 1H), 5.72 (m, J=6.9 Hz, 2H), 4.89 (m, 1H), 2.43-2.26 (m, 5H), 0.99-0.78 (m, 2H). tR=0.39 min (Cellulose 3, Methanol w/0.1% $NH_4OH$, 1.5 ml/min).

Example 168b: (4R,5R)-5-((R)-5H-imidazo[5,1-a]isoindol-5-yl)-2-methyl-4,5,6,7-tetrahydrobenzo[d]oxazol-4-ol. LCMS (ESI, m/z): 308.1 (M+H). $^1H$ NMR same as 168a. tR=0.59 min (Cellulose 3, Methanol w/0.1% $NH_4OH$, 1.5 ml/min).

Example 169: 8-fluoro-5H-imidazo[5,1-a]isoindol-5-yl)-5,6,7,8-tetrahydroquinolin-5-ol

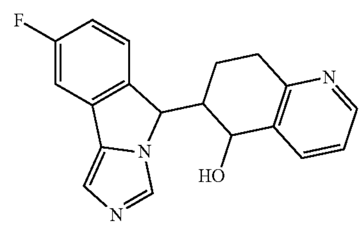 [SMILES: OC1c2cccnc2CCC1C1c2ccc(F)cc2-c2cncn21]

(5S,6S)-6-((S)-8-fluoro-5H-imidazo[5,1-a]isoindol-5-yl)-5,6,7,8-tetrahydroquinolin-5-ol
(5R,6R)-6-((R)-8-fluoro-5H-imidazo[5,1-a]isoindol-5-yl)-5,6,7,8-tetrahydroquinolin-5-ol 169a

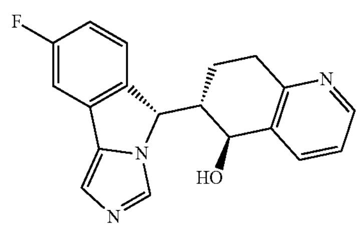

169b

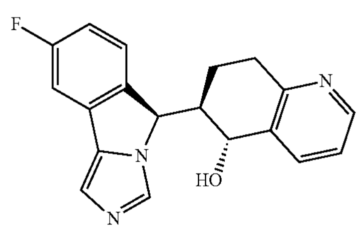

The title compound was synthesized by the same method of example 096. The product was isolated by chiral separation to afford 2 isomers as white solid. The stereochemistry of each isomer was arbitrarily assigned.

Example 169a: (5S,6S)-6-((S)-8-fluoro-5H-imidazo[5,1-a]isoindol-5-yl)-5,6,7,8-tetrahydroquinolin-5-ol: LCMS (ESI, m/z): 322.3 [M+H]$^+$; $^1$H NMR (400 MHz, DMSO-d6) δ 8.35 (ddd, J=4.7, 1.8, 0.7 Hz, 1H), 8.01 (s, 1H), 8.00-7.97 (m, 1H), 7.53 (ddd, J=9.6, 6.4, 3.7 Hz, 2H), 7.27 (dd, J=7.8, 4.7 Hz, 1H), 7.23 (s, 1H), 7.14 (ddd, J=9.6, 8.4, 2.5 Hz, 1H), 6.21 (d, J=7.5 Hz, 1H), 5.80 (s, 1H), 4.97 (dd, J=10.6, 7.6 Hz, 1H), 2.68 (dd, J=8.8, 4.0 Hz, 2H), 2.47-2.38 (m, 1H), 1.02-0.82 (m, 2H).

Example 169b: (5R,6R)-6-((R)-8-fluoro-5H-imidazo[5,1-a]isoindol-5-yl)-5,6,7,8-tetrahydroquinolin-5-ol: LCMS (ESI, m/z): 322.3 [M+H]$^+$; $^1$H NMR is the same as Example 122g.

Example 170: 3-(9-fluoro-5H-imidazo[5,1-a]isoindol-5-yl)tetrahydro-2H-pyran-4-ol

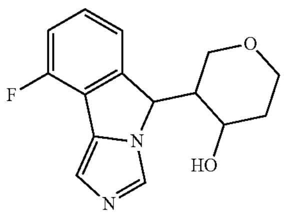 [SMILES: OC1CCOCC1C1c2cccc(F)c2-c2cncn21]

(3R,4R)-3-((S)-9-fluoro-5H-imidazo[5,1-a]isoindol-5-yl)tetrahydro-2H-pyran-4-ol (3S,4S)-3-((R)-9-fluoro-5H-imidazo[5,1-a]isoindol-5-yl)tetrahydro-2H-pyran-4-ol (3R,4R)-3-((R)-9-fluoro-5H-imidazo[5,1-a]isoindol-5-yl)tetrahydro-2H-pyran-4-ol (3S,4S)-3-((S)-9-fluoro-5H-imidazo[5,1-a]isoindol-5-yl)tetrahydro-2H-pyran-4-ol The title compound was synthesized by the same method of example 69.

The configurations of the isomers were assigned arbitrarily.

Example 170a: (3R,4R)-3-((S)-9-fluoro-5H-imidazo[5,1-a]isoindol-5-yl)tetrahydro-2H-pyran-4-ol: LCMS (ESI, m/z): 261.2 [M+H]$^+$; $^1$H NMR (500 MHz, DMSO-$d_6$) δ 7.97 (s, 1H), 7.45-7.33 (m, 2H), 7.28 (ddt, J=9.0, 8.2, 0.8 Hz, 1H), 7.13 (s, 1H), 5.81-5.77 (m, 1H), 5.48 (d, J=5.7 Hz, 1H), 3.94 (tt, J=10.4, 5.0 Hz, 1H), 3.77 (dd, J=11.6, 4.7 Hz, 1H), 3.26-3.15 (m, 1H), 3.03-2.96 (m, 1H), 2.39 (t, J=11.2 Hz, 1H), 2.25 (tt, J=10.8, 3.5 Hz, 1H), 1.96-1.88 (m, 1H), 1.62-1.50 (m, 1H). 170a and 170b are enantiomers.

Example 170b: (3S,4S)-3-((R)-9-fluoro-5H-imidazo[5,1-a]isoindol-5-yl)tetrahydro-2H-pyran-4-ol: LCMS (ESI, m/z): 261.2 [M+H]$^+$; $^1$H NMR (500 MHz, DMSO-$d_6$) δ 7:97 (s, 1H), 7.45-7.33 (m, 2H), 7.28 (t, J=8.8 Hz, 1H), 7.13 (s, 1H), 5.79 (d, J=2.5 Hz, 1H), 5.48 (d, J=5.6 Hz, 1H), 3.94 (tt, J=10.3, 4.9 Hz, 1H), 3.77 (dd, J=11.7, 4.7 Hz, 1H), 3.20 (td, J=12.2, 2.1 Hz, 1H), 2.99 (dd, J=11.5, 4.0 Hz, 1H), 2.39 (t, J=11.2 Hz, 1H), 2.25 (tt, J=10.7, 3.5 Hz, 1H), 1.92 (ddt, J=12.6, 4.2, 2.0 Hz, 1H), 1.56 (tdd, J=12.5, 10.5, 4.8 Hz, 1H). 170a and 170b are enantiomers.

Example 170c: (3R,4R)-3-((R)-9-fluoro-5H-imidazo[5,1-a]isoindol-5-yl)tetrahydro-2H-pyran-4-ol: LCMS (ESI, m/z): 261.2 [M+H]$^+$; $^1$H NMR (500 MHz, DMSO-$d_6$) δ 8.06 (s, 1H), 7.41 (dq, J=7.6, 0.9 Hz, 1H), 7.38-7.33 (m, 1H), 7.33-7.23 (m, 1H), 7.12 (s, 1H), 5.73 (d, J=3.5 Hz, 1H), 5.29 (d, J=5.2 Hz, 1H), 3.79 (qd, J=13.2, 11.7, 4.7 Hz, 2H), 3.17 (td, J=12.0, 2.3 Hz, 1H), 3.02-2.95 (m, 1H), 2.61 (t, J=11.2 Hz, 1H), 2.41 (ddt, J=10.7, 6.9, 3.8 Hz, 1H), 1.87-1.79 (m, 1H), 1.57-1.45 (m, 1H). 170c and 170d are enantiomers.

Example 170d: (3S,4S)-3-((S)-9-fluoro-5H-imidazo[5,1-a]isoindol-5-yl)tetrahydro-2H-pyran-4-ol: LCMS (ESI, m/z): 261.2 [M+H]$^+$; $^1$H NMR (500 MHz, DMSO-$d_6$) δ 8.06 (t, J=0.7 Hz, 1H), 7.41 (dd, J=7.6, 1.0 Hz, 1H), 7.38-7.33 (m, 1H), 7.33-7.24 (m, 1H), 7.11 (s, 1H), 5.73 (d, J=3.5 Hz, 1H), 5.29 (s, 1H), 3.78 (ddd, J=21.3, 10.9, 4.4 Hz, 2H), 3.17 (td, J=12.0, 2.2 Hz, 1H), 2.99 (dd, J=11.3, 3.9 Hz, 1H), 2.61 (t, J=11.2 Hz, 1H), 2.41 (tt, J=10.8, 3.8 Hz, 1H), 1.87-1.79 (m, 1H), 1.57-1.45 (m, 1H). 170c and 170d are enantiomers.

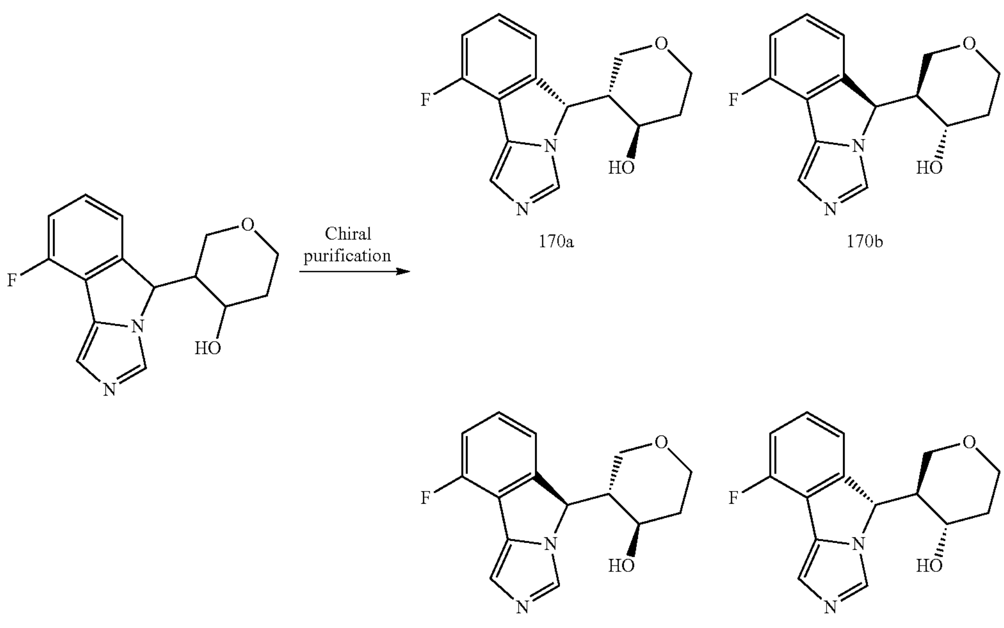

170a 170b 170c 170d

Example 171: 4-(8-methyl-5H-imidazo[5,1-a]isoindol-5-yl)tetrahydrofuran-3-ol

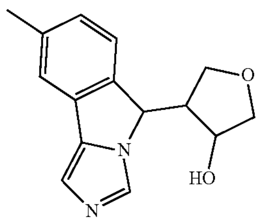 [SMILES: Cc1ccc2c(c1)-c1cncn1C2C1COCC1O]

(3S,4R)-4-((S)-8-methyl-5H-imidazo[5,1-a]isoindol-5-yl)tetrahydrofuran-3-ol (3R,4S)-4-((R)-8-methyl-5H-imidazo[5,1-a]isoindol-5-yl)tetrahydrofuran-3-ol (3S,4R)-4-((R)-8-methyl-5H-imidazo[5,1-a]isoindol-5-yl)tetrahydrofuran-3-ol (3R,4S)-4-((S)-8-methyl-5H-imidazo[5,1-a]isoindol-5-yl)tetrahydrofuran-3-ol The title compound was synthesized by the same method of example 69.

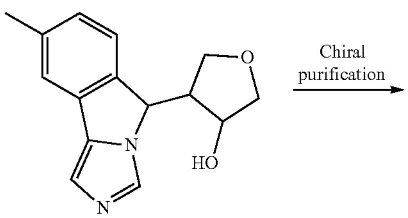

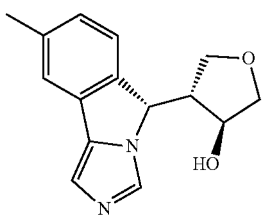

171a

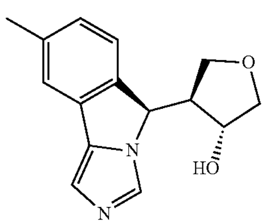

171b

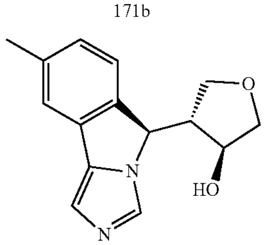

171c

-continued

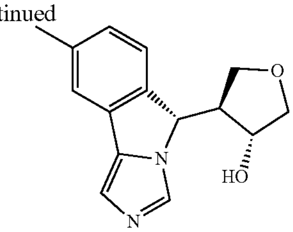

171d

The configurations of the isomers were assigned arbitrarily.

Example 171a: (3S,4R)-4-((S)-8-methyl-5H-imidazo[5,1-a]isoindol-5-yl)tetrahydrofuran-3-ol: LCMS (ESI, m/z): 257.1 $[M+H]^+$; $^1H$ NMR (500 MHz, DMSO-$d_6$) δ 8.01 (s, 1H), 7.45-7.39 (m, 2H), 7.16 (s, 1H), 7.12-7.06 (m, 1H), 5.54 (d, J=4.1 Hz, 1H), 5.22 (d, J=4.6 Hz, 1H), 4.26 (dq, J=5.7, 4.1 Hz, 1H), 3.71 (dd, J=9.2, 8.1 Hz, 1H), 3.57 (dd, J=9.2, 5.6 Hz, 1H), 3.42 (dd, J=9.2, 4.0 Hz, 1H), 3.16 (dd, J=9.2, 6.3 Hz, 1H), 2.81 (ddt, J=8.1, 6.3, 4.0 Hz, 1H), 2.36 (d, J=0.8 Hz, 3H). 171a and 171b are enantiomers.

Example 171b: (3R,4S)-4-((R)-8-methyl-5H-imidazo[5,1-a]isoindol-5-yl)tetrahydrofuran-3-ol: LCMS (ESI, m/z): 257.1 $[M+H]^+$; $^1H$ NMR (500 MHz, DMSO-$d_6$) δ 8.06 (s, 1H), 7.46-7.40 (m, 2H), 7.19 (s, 1H), 7.10 (ddd, J=7.8, 1.7, 0.8 Hz, 1H), 5.55 (d, J=4.1 Hz, 1H), 5.22 (d, J=4.6 Hz, 1H), 4.25 (dd, J=5.6, 4.0 Hz, 1H), 3.72 (dd, J=9.2, 8.1 Hz, 1H), 3.58 (dd, J=9.2, 5.7 Hz, 1H), 3.41 (dd, J=9.2, 4.1 Hz, 1H), 3.18 (dd, J=9.2, 6.3 Hz, 1H), 2.81 (ddt, J=8.0, 6.2, 4.0 Hz, 1H), 2.38-2.34 (m, 3H). 171a and 171b are enantiomers.

Example 171c: (3S,4R)-4-((R)-8-methyl-5H-imidazo[5,1-a]isoindol-5-yl)tetrahydrofuran-3-ol: LCMS (ESI, m/z): 257.1 $[M+H]^+$; $^1H$ NMR (500 MHz, DMSO-$d_6$) δ 8.19 (s, 1H), 7.50-7.46 (m, 1H), 7.43 (d, J=7.8 Hz, 1H), 7.28 (s, 1H), 7.15 (ddd, J=7.9, 1.7, 0.8 Hz, 1H), 5.54 (d, J=4.7 Hz, 1H), 5.03 (d, J=4.8 Hz, 1H), 4.00 (dd, J=9.3, 7.7 Hz, 1H), 3.87 (s, 1H), 3.80 (dd, J=9.3, 5.5 Hz, 1H), 3.44-3.37 (m, 2H), 2.75 (dtd, J=8.1, 5.3, 3.1 Hz, 1H), 2.38 (s, 3H). 171c and 171d are enantiomers.

Example 171d: (3R,4S)-4-((S)-8-methyl-5H-imidazo[5,1-a]isoindol-5-yl)tetrahydrofuran-3-ol: LCMS (ESI, m/z): 257.1 $[M+H]^+$; $^1H$ NMR (500 MHz, DMSO-$d_6$) δ 8.16 (s, 1H), 7.50-7.45 (m, 1H), 7.42 (d, J=7.8 Hz, 1H), 7.26 (s, 1H), 7.14 (ddd, J=7.8, 1.7, 0.8 Hz, 1H), 5.53 (d, J=4.7 Hz, 1H), 5.03 (d, J=4.7 Hz, 1H), 4.00 (dd, J=9.3, 7.7 Hz, 1H), 3.87 (d, J=4.7 Hz, 1H), 3.79 (dd, J=9.3, 5.5 Hz, 1H), 3.40 (qd, J=9.3, 4.5 Hz, 2H), 2.75 (dtd, J=8.0, 5.3, 3.1 Hz, 1H), 2.37 (s, 3H). 171c and 171d are enantiomers.

Example 179: 8-(methylsulfonyl)-2-(5H-imidazo[5,1-a]isoindol-5-yl)-8-azaspiro[4.5]decan-1-ol

179

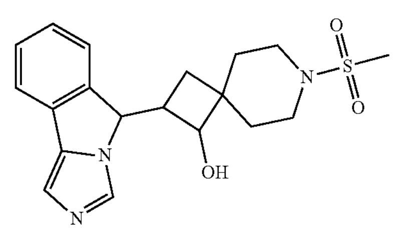

Step 1:

tert-butyl 1-hydroxy-2-(5H-imidazo[4,3-a]isoindol-5-yl)-7-azaspiro[3.5]nonane-7-carboxylate

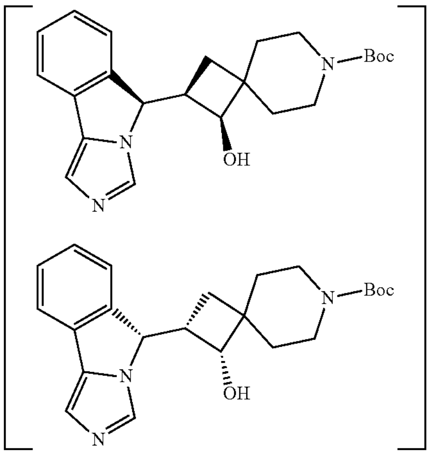

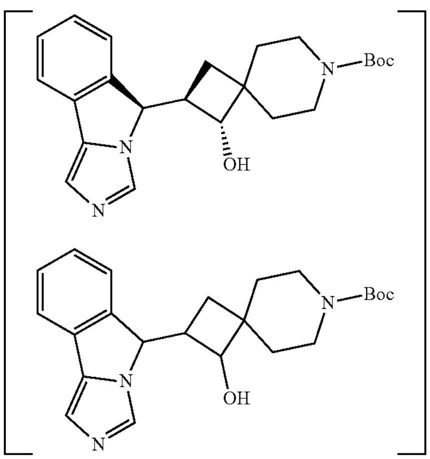

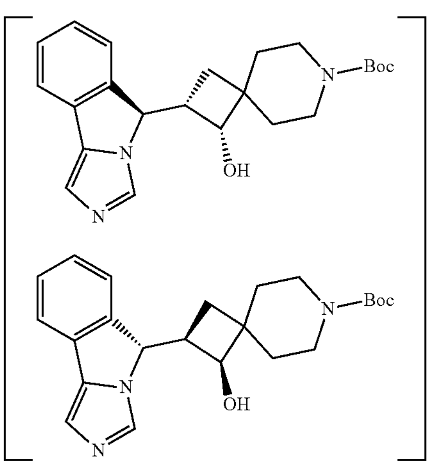

-continued

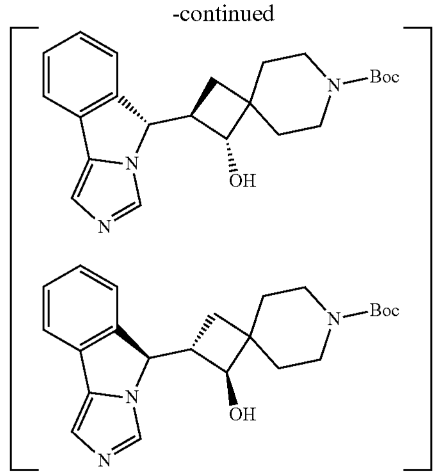

The title compounds were synthesized by General Procedure for the Synthesis of Int-5: LCMS (ESI, m/z): 396.2 $[M+H]^+$. Four pairs of racemate mixture were isolated by Prep-HPLC and each pair was taken to next step separately. The configuration of the isomers was assigned arbitrarily.

Step 2:

(1S,2R)-2-[(5R)-5H-imidazo[4,3-a]isoindol-5-yl]-7-methanesulfonyl-7-azaspiro[3.5]nonan-1-ol (1R,2S)-2-[(5S)-5H-imidazo[4,3-a]isoindol-5-yl]-7-methanesulfonyl-7-azaspiro[3.5]nonan-1-ol 179a

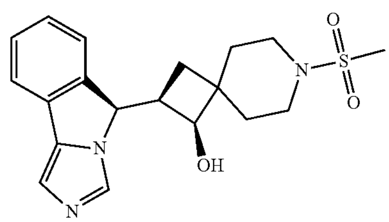

179b

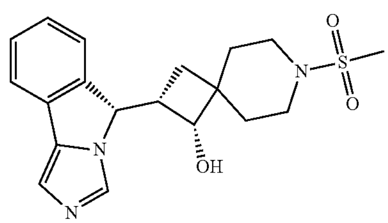

A racemate mixture of tert-butyl(1S,2R)-1-hydroxy-2-[(5R)-5H-imidazo[4,3-a]isoindol-5-yl]-7-azaspiro[3.5]nonane-7-carboxylate and tert-butyl(1R,2S)-1-hydroxy-2-[(5S)-5H-imidazo[4,3-a]isoindol-5-yl]-7-azaspiro[3.5]nonane-7-carboxylate (150 mg, 0.38 mmol) in DCM (8 mL) was added TFA (2 ml). The resulting solution was stirred for 1 h at room temperature. The solvent was then evaporated out. The resulting mixture was dissolved in DCM (10 ml). TEA (0.419 mL, 3.03 mmol) and methanesulfonyl chloride (43 mg, 0.38 mmol) was added at 0° C. The mixture was stirred for 1 h at room temperature. The solution was diluted with DCM (50 mL). The solution was washed with water (50 mL), dried over sodium sulfate and concentrated under vacuum. The residue was purified by silica gel column eluting with DCM/MeOH (97:3). The crude product was further isolated by Prep-HPLC and chiral separation. The absolute configuration of 179a and 179b was assigned arbitrarily.

Example 179a: (1S,2S)-8-(methylsulfonyl)-2-((R)-5H-imidazo[5,1-a]isoindol-5-yl)-8-azaspiro[4.5]decan-1-ol (21.7 mg, 31%) as a white solid: LCMS (ESI, m/z): 374.2 $[M+H]^+$; $^1H$ NMR (400 MHz, DMSO-$d_6$) δ 7.86 (s, 1H), 7.63-7.57 (m, 2H), 7.40-7.24 (m, 2H), 7.15 (s, 1H), 5.43 (d, J=6.9 Hz, 1H), 5.32 (d, J=6.3 Hz, 1H), 4.08 (dd, J=7.9, 6.2 Hz, 1H), 3.37-3.31 (m, 1H), 3.28-3.24 (m, 1H), 2.95-2.69 (m, 5H), 2.52-2.47 (m, 1H), 1.74-1.54 (m, 4H), 1.45-1.41 (m, 1H), 0.95 (t, J=10.4 Hz, 1H). tR=2.862 min (CHIRALPAK IF-3, 0.46×5 cm; 3 um, Hex(0.1% DEA):EtOH=50:50, 1 ml/min). 179a and 179b are enantiomers.

Example 179b: (1R,2R)-8-(methylsulfonyl)-2-((S)-5H-imidazo[5,1-a]isoindol-5-yl)-8-azaspiro[4.5]decan-1-ol (24.1 mg, 34%) as a white solid: LCMS (ESI, m/z): 374.2 $[M+H]^+$; $^1H$ NMR (400 MHz, DMSO-$d_6$) δ 7.86 (s, 1H), 7.63-7.57 (m, 2H), 7.40-7.24 (m, 2H), 7.15 (s, 1H), 5.43 (d, J=6.9 Hz, 1H), 5.32 (d, J=6.4 Hz, 1H), 4.08 (dd, J=7.9, 6.3 Hz, 1H), 3.34-3.32 (m, 1H), 3.32-3.24 (m, 1H), 2.91-2.69 (m, 5H), 1.74-1.54 (m, 4H), 1.43 (d, J=13.5 Hz, 1H), 0.95 (t, J=10.5 Hz, 1H). $t_R$=4.216 min (CHIRALPAK IF-3, 0.46×5 cm; 3 um, Hex(0.1% DEA):EtOH=50:50, 1 ml/min). 179a and 179b are enantiomers.

Step 3:

(1R,2R)-2-[(5R)-5H-imidazo[4,3-a]isoindol-5-yl]-7-methanesulfonyl-7-azaspiro[3.5]nonan-1-ol (1S,2S)-2-[(5S)-5H-imidazo[4,3-a]isoindol-5-yl]-7-methanesulfonyl-7-azaspiro[3.5]nonan-1-ol 179c

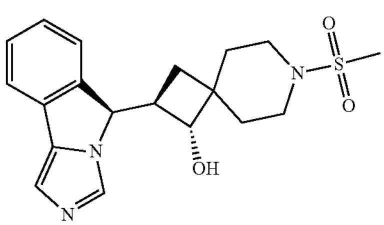

179d

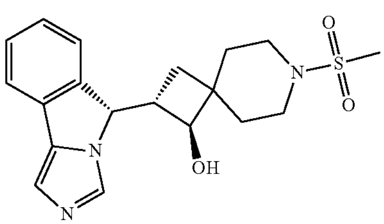

The title compounds were synthesized by General Procedure for the Synthesis of 179a and 179b. The configuration of the isomers was assigned arbitrarily.

Example 179c: (1R,2R)-2-[(5R)-5H-imidazo[4,3-a]isoindol-5-yl]-7-methanesulfonyl-7-azaspiro[3.5]nonan-1-ol (43.8 mg, 31%) as a white solid: LCMS (ESI, m/z): 374.2 $[M+H]^+$; $^1H$ NMR (400 MHz, DMSO-$d_6$) δ 7.95 (s, 1H), 7.61 (dd, J=7.2, 1.5 Hz, 1H), 7.39 (t, J=7.5 Hz, 2H), 7.28-7.23 (m, 2H), 7.14 (s, 1H), 5.41 (d, J=8.6 Hz, 1H), 5.26 (d, J=6.7 Hz, 1H), 3.98 (t, J=7.2 Hz, 1H), 3.37-3.27 (m, 2H), 2.94-2.77 (m, 5H), 2.36-2.30 (m, 1H), 1.86 (dd, J=11.0, 9.5 Hz, 1H), 1.72-1.45 (m, 5H). tR=1.119 min (CHIRALPAK IA-3, 0.46×5 cm; 3 um, (Hex:DCM=5:1):EtOH=50:50, 1.0 ml/min). 179c and 179d are enantiomers.

Example 179d: (1S,2S)-2-[(5S)-5H-imidazo[4,3-a]isoindol-5-yl]-7-methanesulfonyl-7-azaspiro[3.5]nonan-1-ol (49.5 mg, 35%) as a white solid: LCMS (ESI, m/z): 374.2 $[M+H]^+$; $^1H$ NMR (400 MHz, DMSO-$d_6$) δ 7.90 (s, 1H), 7.67 (d, J=7.5 Hz, 1H), 7.59 (d, J=7.5 Hz, 1H), 7.41-7.36 (m, 1H), 7.30-7.25 (m, 1H), 7.13 (s, 1H), 5.40 (d, J=4.0 Hz, 1H), 5.38 (d, J=5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H). tR=2.995 min (CHIRALPAK IA-3, 0.46×5 cm; 3 um, (Hex: DCM=5:1):EtOH=50:50, 1.0 ml/min). 179c and 179d are enantiomers.

Step 4:

(1R,2S)-2-[(5R)-5H-imidazo[4,3-a]isoindol-5-yl]-7-methanesulfonyl-7-azaspiro[3.5]nonan-1-ol (1S,2R)-2-[(5S)-5H-imidazo[4,3-a]isoindol-5-yl]-7-methanesulfonyl-7-azaspiro[3.5]nonan-1-ol 179e

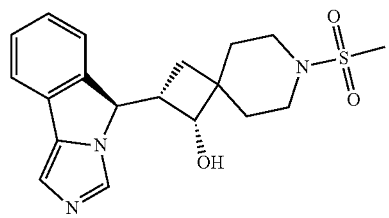

179f

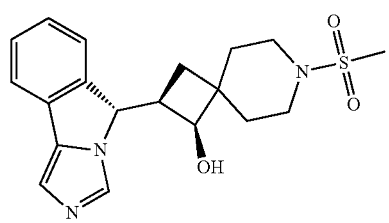

The title compounds were synthesized by General Procedure for the Synthesis of 179a and 179b.

The configuration of the isomers was assigned arbitrarily.

Example 179e: (1R,2S)-2-[(5R)-5H-imidazo[4,3-a]isoindol-5-yl]-7-methanesulfonyl-7-azaspiro[3.5]nonan-1-ol (19.1 mg, 6.2%) as a white solid: LCMS (ESI, m/z): 374.2 $[M+H]^+$; $^1H$ NMR (400 MHz, DMSO-$d_6$) δ 7.86 (s, 1H), 7.70-7.58 (m, 2H), 7.48-7.24 (m, 2H), 7.14 (d, J=2.9 Hz, 1H), 5.76 (d, J=5.5 Hz, 1H), 5.47 (d, J=8.7 Hz, 1H), 4.12 (dd, J=9.0, 4.8 Hz, 1H), 3.32-2.92 (m, 4H), 2.83 (s, 1H), 2.67-2.52 (m, 1H), 1.94-1.79 (m, 3H), 1.60 (t, J=5.8 Hz, 3H). tR=1.836 min (CHIRALPAK IC-3, 0.46×5 cm; 3 um, Hex(0.1% DEA):IPA=70:30, 1.0 ml/min). 179e and 179f are enantiomers.

Example 179f: (1S,2R)-2-[(5S)-5H-imidazo[4,3-a]isoindol-5-yl]-7-methanesulfonyl-7-azaspiro[3.5]nonan-1-ol (21.3 mg, 7%) as a white solid: LCMS (ESI, m/z): 374.2 $[M+H]^+$; $^1H$ NMR (400 MHz, DMSO-$d_6$) δ 7.86 (s, 1H), 7.65-7.58 (m, 2H), 7.40-7.24 (m 2H), 7.14 (s, 1H), 5.75 (d, J=5.5 Hz, 1H), 5.47 (d, J=8.7 Hz, 1H), 4.13 (td, J=6.3, 3.0 Hz, 1H), 3.19-2.95 (m, 4H), 2.83 (s, 3H), 2.61-2.51 (m, 1H), 1.94-1.75 (m, 3H), 1.60 (t, J=5.8 Hz, 3H). tR=2.941 min (CHIRALPAK IC-3, 0.46×5 cm; 3 um, Hex(0.1% DEA): IPA=70:30, 1.0 ml/min). 179e and 179f are enantiomers.

Step 5:

(1R,2R)-2-[(5S)-5H-imidazo[4,3-a]isoindol-5-yl]-7-methanesulfonyl-7-azaspiro[3.5]nonan-1-ol (1S,2S)-2-[(5R)-5H-imidazo[4,3-a]isoindol-5-yl]-7-methanesulfonyl-7-azaspiro[3.5]nonan-1-ol 179g

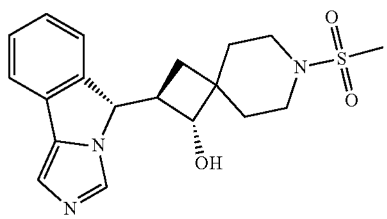

179h

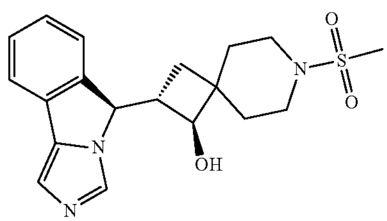

The title compounds were synthesized by General Procedure for the Synthesis of 179a and 179b.

The configuration of the isomers was assigned arbitrarily.

Example 179g: (1R,2R)-2-[(5S)-5H-imidazo[4,3-a]isoindol-5-yl]-7-methanesulfonyl-7-azaspiro[3.5]nonan-1-ol (24.4 mg, 52%) as a white solid: LCMS (ESI, m/z): 374.2 $[M+H]^+$; $^1H$ NMR (400 MHz, DMSO-$d_6$) δ 7.85 (s, 1H), 7.63-7.60 (m, 1H), 7.41-7.36 (m, 2H), 7.26-7.20 (m, 1H), 7.13 (s, 1H), 5.79 (d, J=6.0 Hz, 1H), 5.42 (d, J=10.6 Hz, 1H), 4.08 (td, J=5.9, 2.9 Hz, 1H), 3.20-2.98 (m, 4H), 2.85 (s, 3H), 2.35-2.19 (m, 2H), 1.95-1.61 (m, 5H). tR=2.279 min (Lux Cellulose-4, 0.46×5 cm; 3 um, Hex(0.1% DEA):EtOH-50:50, 1.0 ml/min). 179g and 179h are enantiomers.

Example 179h: (1S,2S)-2-[(5R)-5H-imidazo[4,3-a]isoindol-5-yl]-7-methanesulfonyl-7-azaspiro[3.5]nonan-1-ol (22.7 mg, 48%) as a white solid: LCMS (ESI, m/z): 374.2 $[M+H]^+$; $^1H$ NMR (400 MHz, DMSO-$d_6$) δ 7.86 (s, 1H), 7.63-7.60 (m, 1H), 7.42-7.36 (m, 2H), 7.26-7.20 (m, 1H), 7.14 (s, 1H), 5.79 (d, J=6.0 Hz, 1H), 5.42 (d, J=10.7 Hz, 1H), 4.08 (td, J=6.1, 3.0 Hz, 1H), 3.20-2.98 (m, 4H), 2.85 (s, 3H), 2.35-2.19 (m, 2H), 1.95-1.61 (m, 5H). tR=3.761 min (Lux Cellulose-4, 0.46×5 cm; 3 um, Hex(0.1% DEA):EtOH=50:50, 1.0 ml/min). 179g and 179h are enantiomers.

Example 180: 8-(methylsulfonyl)-2-(5H-imidazo[5,1-a]isoindol-5-yl)-8-azaspiro[4.5]decan-1-ol

180

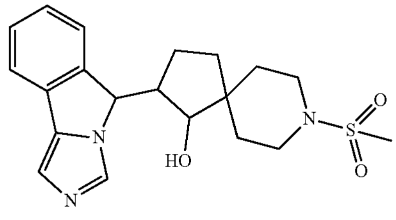

Step 1:

tert-butyl 1-hydroxy-2-(5H-imidazo[4,3-a]isoindol-5-yl)-8-azaspiro[4.5]decane-8-carboxylate

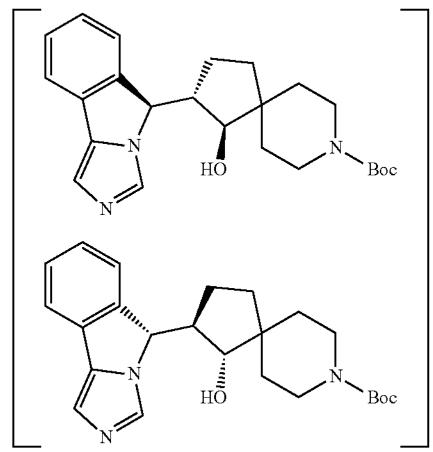

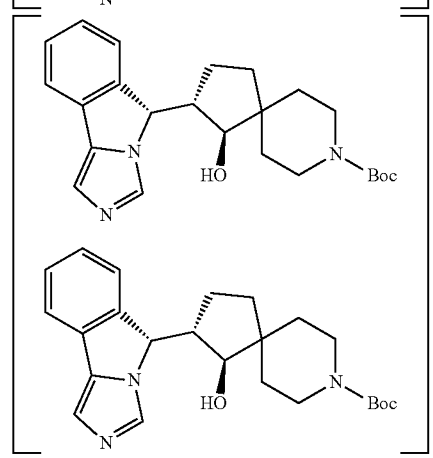

The title compounds were synthesized by General Procedure for the Synthesis of Int-5: LCMS (ESI, m/z): 410.2 $[M+H]^+$. Two pair of racemate mixture were isolated by Prep-HPLC and each pair was taken to next step separately. The configuration of the racemate isomers was assigned arbitrarily.

Step 2:

(1S,2S)-8-(methylsulfonyl)-2-((R)-5H-imidazo[5,1-a]isoindol-5-yl)-8-azaspiro[4.5]decan-1-ol (1R,2R)-8-(methylsulfonyl)-2-((S)-5H-imidazo[5,1-a]isoindol-5-yl)-8-azaspiro[4.5]decan-1-ol 180a

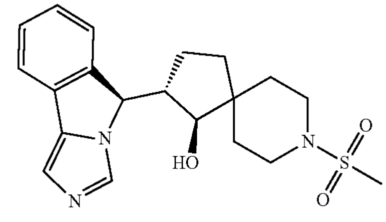

-continued

180b

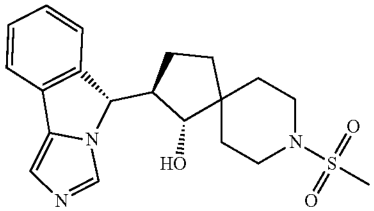

A racemate mixture of tert-butyl(1S,2S)-1-hydroxy-2-[(5R)-5H-imidazo[4,3-a]isoindol-5-yl]-8-azaspiro[4.5]decane-8-carboxylate and tert-butyl(1R,2R)-1-hydroxy-2-[(5S)-5H-imidazo[4,3-a]isoindol-5-yl]-8-azaspiro[4.5] decane-8-carboxylate (506 mg, 1.246 mmol) in DCM (20 mL) was added TFA (1 mL). The resulting solution was stirred for 2 h at rt and the solvent was removed under vacuum. The resulting residue in DCM (20 mL) was added TEA (1.2 mL, 8.72 mmol). Then methanesulfonyl chloride (185 mg, 1.62 mmol) was added at 0° C. The mixture was stirred for 1 h at rt. The solution was diluted with dichloromethane (100 mL). The solution was washed with water (50 mL), dried over sodium sulfate and concentrated under vacuum. The residue was purified by silica gel column eluting with MeOH/DCM (0%-10%). The crude product was further purified by Prep-HPLC and chiral separation.

The absolute configuration of 180a and 180b was assigned arbitrarily.

Example 180a: (1S,2S)-8-(methylsulfonyl)-2-((R)-5H-imidazo[5,1-a]isoindol-5-yl)-8-azaspiro[4.5]decan-1-ol (4.8 mg, 5%) as a white solid: LCMS (ESI, m/z): 388.2 $[M+H]^+$; $^1H$ NMR (400 MHz, DMSO-$d_6$) δ 7.93 (s, 1H), 7.60 (d, J=7.6 Hz, 1H), 7.54 (d, J=7.6 Hz, 1H), 7.41-7.37 (m, 1H), 7.29-7.25 (m, 1H), 7.11 (s, 1H), 5.45 (d, J=4.0 Hz, 1H), 5.08 (d, J=5.6 Hz, 1H), 3.60-3.57 (m, 1H), 3.44-3.35 (m, 2H), 2.82 (s, 3H), 2.81-2.64 (m, 3H), 1.73-1.58 (m, 3H), 1.35-1.04 (m, 4H), 0.88-0.85 (m, 1H). tR=4.843 min (CHIRALPAK IA-3, 0.46×5 cm; 3 um, Hex(0.1% DEA):EtOH=50:50, 1.0 ml/min). 180a and 180b are enantiomers.

Example 180b: (1R,2R)-8-(methylsulfonyl)-2-((S)-5H-imidazo[5,1-a]isoindol-5-yl)-8-azaspiro[4.5]decan-1-ol (8.3 mg, 8%) as a white solid: LCMS (ESI, m/z): 388.2 $[M+H]^+$; $^1H$ NMR (400 MHz, DMSO-$d_6$) δ 7.93 (s, 1H), 7.60 (d, J=7.6 Hz, 1H), 7.54 (d, J=7.6 Hz, 1H), 7.41-7.37 (m, 1H), 7.29-7.25 (m, 1H), 7.11 (s, 1H), 5.45 (d, J=4.0 Hz, 1H), 5.08 (d, J=5.6 Hz, 1H), 3.60-3.57 (m, 1H), 3.44-3.35 (m, 2H), 2.82 (s, 3H), 2.81-2.64 (m, 3H), 1.73-1.58 (m, 3H), 1.35-1.04 (m, 4H), 0.88-0.85 (m, 1H). tR=1.690 min (CHIRALPAK IA-3, 0.46×5 cm; 3 um, Hex(0.1% DEA):EtOH=50:50, 1.0 ml/min). 180a and 180b are enantiomers.

Step 3:
(1S,2S)-8-(methylsulfonyl)-2-((S)-5H-imidazo[5,1-a]isoindol-5-yl)-8-azaspiro[4.5]decan-1-ol
(1R,2R)-8-(methylsulfonyl)-2-((R)-5H-imidazo[5,1-a] isoindol-5-yl)-8-azaspiro[4.5]decan-1-ol 180c

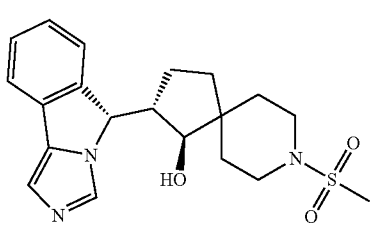

-continued

180d

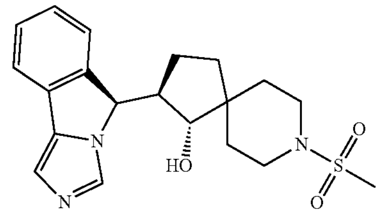

The title compounds were synthesized by General Procedure for the Synthesis of 180a and 180b. The configuration of the isomers was assigned arbitrarily.

Example 180c: (1S,2S)-8-(methylsulfonyl)-2-((S)-5H-imidazo[5,1-a]isoindol-5-yl)-8-azaspiro[4.5]decan-1-ol (56.1 mg, 24%) as a white solid: LCMS (ESI, m/z): 388.2 $[M+H]^+$; $^1H$ NMR (400 MHz, DMSO-$d_6$) δ 7.90 (s, 1H), 7.67 (d, J=7.5 Hz, 1H), 7.59 (d, J=7.5 Hz, 1H), 7.41-7.36 (m, 1H), 7.30-7.25 (m, 1H), 7.13 (s, 1H), 5.40 (d, J=4.0 Hz, 1H), 5.38 (d, J=5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H). tR=2.258 min (CHIRALPAK IA-3, 0.46×5 cm; 3 um, Hex (0.1% DEA):EtOH=50:50, 1.0 ml/min). 180c and 180d are enantiomers.

Example 180d: (1R,2R)-8-(methylsulfonyl)-2-((R)-5H-imidazo[5,1-a]isoindol-5-yl)-8-azaspiro[4.5]decan-1-ol (29.9 mg, 13%) as a white solid: LCMS (ESI, m/z): 388.2 $[M+H]^+$; $^1H$ NMR (400 MHz, DMSO-$d_6$) δ 7.90 (s, 1H), 7.67 (d, J=7.5 Hz, 1H), 7.59 (d, J=7.5 Hz, 1H), 7.41-7.36 (m, 1H), 7.30-7.25 (m, 1H), 7.13 (s, 1H), 5.40 (d, J=4.0 Hz, 1H), 5.38 (d, J=5.6 Hz, 1H), 3.92-3.89 (m, 1H), 3.39-3.35 (m, 1H), 3.22-3.17 (m, 1H), 3.93-2.86 (m, 1H), 2.80 (s, 3H), 2.35-2.28 (m, 1H), 1.75-1.52 (m, 6H), 1.35-1.24 (m, 2H). tR=3.315 min (CHIRALPAK IA-3, 0.46×5 cm; 3 um, Hex (0.1% DEA):EtOH=50:50, 1.0 ml/min). 180c and 180d are enantiomers.

Example 181: 1-hydroxy-2-(5H-imidazo[4,3-a] isoindol-5-yl)-7-azaspiro[3.5]nonane-7-sulfonamide

181

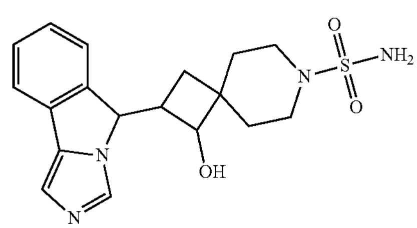

Step 1:

Racemate mixture of tert-butyl N-[(1S,2R)-1-hydroxy-2-[(5R)-5H-imidazo[4,3-a]isoindol-5-yl]-7-azaspiro[3.5]nonane-7-sulfonyl]carbamate and tert-butyl N-[(1R,2S)-1-hydroxy-2-[(5S)-5H-imidazo[4,3-a]isoindol-5-yl]-7-azaspiro[3.5]nonane-7-sulfonyl]carbamate

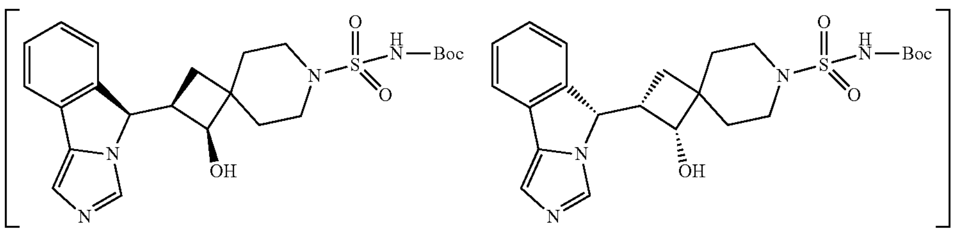

A racemate mixture of tert-butyl(1S,2R)-1-hydroxy-2-[(5R)-5H-imidazo[4,3-a]isoindol-5-yl]-7-azaspiro[3.5]nonane-7-carboxylate and tert-butyl(1R,2S)-1-hydroxy-2-[(5S)-5H-imidazo[4,3-a]isoindol-5-yl]-7-azaspiro[3.5]nonane-7-carboxylate (600 mg, 1.52 mmol) in DCM (20 mL) was added TFA (4 mL). The resulting solution was stirred for 0.5 h at room temperature. The resulting mixture was concentrated under vacuum. This resulted in 2-[5H-imidazo[4,3-a]isoindol-5-yl]-7-azaspiro[3.5]nonan-1-ol as a yellow oil. A solution of [(chlorosulfonyl)imino]methanone (214 mg, 1.51 mmol) in DCM (10 mL), was added tert-butanol (336 mg, 4.533 mmol) at 0° C. The resulting solution was stirred for 0.5 h at 0° C. The crude 2-[5H-imidazo[4,3-a]isoindol-5-yl]-7-azaspiro[3.5]nonan-1-ol and TEA (1.68 mL, 12.06 mmol) were dissolved in DCM (10 mL) and then stirred for 0.5 h. After that, the mixture of [(chlorosulfonyl)imino]methanone was added into the mixture of 2-[5H-imidazo[4,3-a]isoindol-5-yl]-7-azaspiro[3.5]nonan-1-ol at 0° C. The resulting solution was stirred for 0.5 h at room temperature. The reaction was then quenched by the addition of water. The resulting solution was extracted with EA and the organic layers combined. The residue was purified by silica gel column eluting with DCM/MeOH (96:4). This resulted in 630 mg (76%) of tert-butyl N-(1-hydroxy-2-[5H-imidazo[4,3-a]isoindol-5-yl]-7-azaspiro[3.5]nonane-7-sulfonyl)carbamate as a yellow solid: LCMS (ESI, m/z): 475.2 $[M+H]^+$ Step 2:

(1S,2R)-1-hydroxy-2-[(5R)-5H-imidazo[4,3-a]isoindol-5-yl]-7-azaspiro[3.5]nonane-7-sulfonamide (1R,2S)-1-hydroxy-2-[(5S)-5H-imidazo[4,3-a]isoindol-5-yl]-7-azaspiro[3.5]nonane-7-sulfonamide 181a

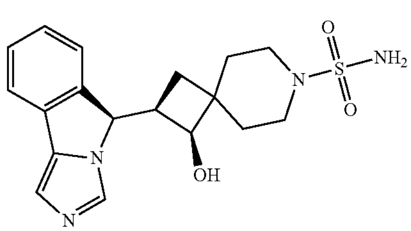

-continued

181b

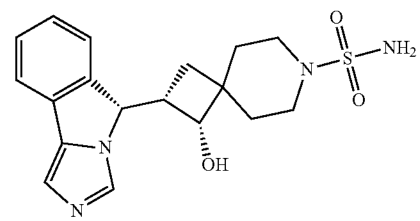

A solution of tert-butyl N-(1-hydroxy-2-{5H-imidazo[4,3-a]isoindol-5-yl}-7-azaspiro[3.5]nonane-7-sulfonyl)carbamate (510 mg, 1.074 mmol) in DCM (20 mL) was added TFA (5 mL). The mixture was stirred for 30 min at room temperature. The solution was concentrated under vacuum. The crude product was further isolated by Prep-HPLC and chiral separation. The configuration of the isomers was assigned arbitrarily.

Example 181a: (1S,2R)-1-hydroxy-2-[(5R)-5H-imidazo[4,3-a]isoindol-5-yl]-7-azaspiro[3.5]nonane-7-sulfonamide (38.0 mg, 19%) as a white solid: LCMS (ESI, m/z): 375.3 $[M+H]^+$; $^1H$ NMR (400 MHz, DMSO-$d_6$) δ 7.93 (s, 1H), 7.61-7.58 (m, 2H), 7.41-7.25 (m, 2H), 7.18 (s, 1H), 6.64 (s, 2H), 5.43 (d, J=7.3 Hz, 1H), 5.29 (d, J=6.7 Hz, 1H), 4.06 (t, J=7.2 Hz, 1H), 3.32-3.15 (m, 2H), 2.73-2.51 (m, 4H), 2.50-2.43 (m, 1H), 1.73-1.39 (m, 5H), 1.04 (t, J=10.4 Hz, 1H). tR=8.881 min (CHIRALPAK IG-3, 0.46×5 cm; 3 um, Hex(0.1% DEA):IPA=70:30, 1 ml/min). 181a and 181b are enantiomers.

Example 181b: (1R,2S)-1-hydroxy-2-[(5S)-5H-imidazo[4,3-a]isoindol-5-yl]-7-azaspiro[3.5]nonane-7-sulfonamide (33.8 mg, 17%) as a white solid: LCMS (ESI, m/z): 375.2 $[M+H]^+$; $^1H$ NMR (400 MHz, DMSO-$d_6$) δ 7.96 (s, 1H), 7.61 (d, J=7.5 Hz, 2H), 7.47-7.26 (m, 2H), 7.20 (s, 1H), 6.65 (s, 2H), 5.44 (d, J=7.4 Hz, 1H), 5.29 (d, J=6.6 Hz, 1H), 4.06 (t, J=6.8 Hz, 1H), 3.20-3.16 (m, 2H), 2.73-2.54 (m, 4H), 2.50-2.41 (m, 1H), 1.73-1.43 (m, 5H), 1.05 (t, J=10.5 Hz, 1H). tR=11.147 min (CHIRALPAK IG-3, 0.46×5 cm; 3 um, Hex(0.1% DEA):IPA=70:30, 1 ml/min). 181a and 181b are enantiomers.

Step 3:

(1R,2R)-1-hydroxy-2-[(5R)-5H-imidazo[4,3-a]isoindol-5-yl]-7-azaspiro[3.5]nonane-7-sulfonamide (1S,2S)-1-hydroxy-2-[(5S)-5H-imidazo[4,3-a]isoindol-5-yl]-7-azaspiro[3.5]nonane-7-sulfonamide 181c

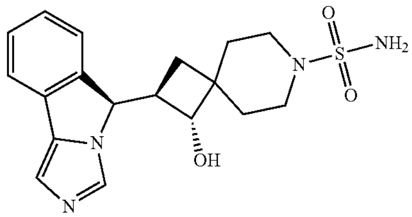

181d

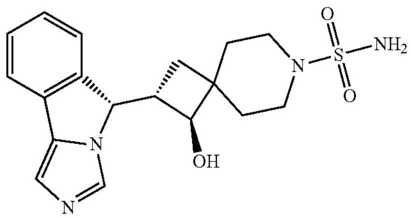

The title compounds were synthesized by General Procedure for the Synthesis of 181a-b. The configuration of the isomers was assigned arbitrarily.

Example 181c: (1R,2R)-1-hydroxy-2-[(5R)-5H-imidazo[4,3-a]isoindol-5-yl]-7-azaspiro[3.5]nonane-7-sulfonamide (74.9 mg, 34%) as a white solid: LCMS (ESI, m/z): 375.3 $[M+H]^+$; $^1H$ NMR (400 MHz, DMSO-$d_6$) δ 8.05 (s, 1H), 7.62 (d, J=7.5 Hz, 1H), 7.43-7.38 (m, 2H), 7.30-7.24 (m, 1H), 7.20 (s, 1H), 6.67 (s, 2H), 5.43 (d, J=8.7 Hz, 1H), 5.24 (d, J=6.9 Hz, 1H), 3.97 (t, J=7.1 Hz, 1H), 3.26-3.18 (m, 2H), 2.75-2.60 (m, 2H), 2.35-2.29 (m, 1H), 1.86-1.64 (m, 3H), 1.58-1.47 (m, 3H); tR=1.297 min (Lux Cellulose-4, 0.46×5 cm; 3 um, Hex(0.1% DEA):EtOH=50:50, 1.0 ml/min). 181c and 181d are enantiomers.

Example 181d: (1S,2S)-1-hydroxy-2-[(5S)-5H-imidazo[4,3-a]isoindol-5-yl]-7-azaspiro[3.5]nonane-7-sulfonamide (66.8 mg, 31%) as a white solid: LCMS (ESI, m/z): 375.2 $[M+H]^+$; $^1H$ NMR (400 MHz, DMSO-$d_6$) δ 7.99 (s, 1H), 7.61 (d, J=7.5 Hz, 1H), 7.43-7.37 (m, 2H), 7.28-7.23 (m, 1H), 7.16 (s, 1H), 6.67 (s, 2H), 5.41 (d, J=8.7 Hz, 1H), 5.24 (d, J=7.0 Hz, 1H), 3.96 (t, J=7.2 Hz, 1H), 3.26-3.19 (m, 1H), 2.75-2.60 (m, 2H), 2.38-2.26 (m, 1H), 1.86-1.64 (m, 3H), 1.58-1.47 (m, 3H). tR=3.276 min (Lux Cellulose-4, 0.46×5 cm; 3 um, Hex(0.1% DEA):EtOH=50:50, 1.0 ml/min). 181c and 181d are enantiomers.

Step 4:

(1R,2S)-1-hydroxy-2-[(5R)-5H-imidazo[4,3-a]isoindol-5-yl]-7-azaspiro[3.5]nonane-7-sulfonamide (1S,2R)-1-hydroxy-2-[(5S)-5H-imidazo[4,3-a]isoindol-5-yl]-7-azaspiro[3.5]nonane-7-sulfonamide 181e

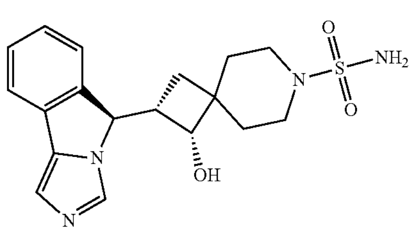

-continued

181f

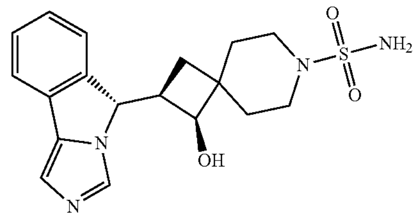

The title compounds were synthesized by General Procedure for the Synthesis of 181a-b. The configuration of the isomers was assigned arbitrarily.

Example 181e: (1R,2R)-1-hydroxy-2-[(5R)-5H-imidazo[4,3-a]isoindol-5-yl]-7-azaspiro[3.5]nonane-7-sulfonamide (76.3 mg, 31%) as a white solid: LCMS (ESI, m/z): 375.3 $[M+H]^+$; $^1H$ NMR (400 MHz, DMSO-$d_6$) δ 7.86 (s, 1H), 7.65-7.58 (m, 2H), 7.40-7.35 (m, 1H), 7.29-7.24 (m, 1H), 7.14 (s, 1H), 6.69 (s, 2H), 5.76 (d, J=5.7 Hz, 1H), 5.46 (d, J=8.9 Hz, 1H), 4.09 (td, J=6.2, 2.9 Hz, 1H), 3.08-2.98 (m, 2H), 2.88-2.76 (m, 2H), 2.63-2.50 (m, 1H), 1.93 (t, J=10.4 Hz, 1H), 1.79-1.73 (m, 2H), 1.60 (t, J=5.5 Hz, 3H). tR=3.997 min (CHIRALPAK IF-3, 0.46×5 cm; 3 um, Hex(8 mM NH3):EtOH=80:20, 1.0 ml/min). 181e and 181f are enantiomers.

Example 181f: (1S,2S)-1-hydroxy-2-[(5S)-5H-imidazo[4,3-a]isoindol-5-yl]-7-azaspiro[3.5]nonane-7-sulfonamide (72.2 mg, 29%) as a white solid: LCMS (ESI, m/z): 375.2 $[M+H]^+$; $^1H$ NMR (400 MHz, DMSO-$d_6$) δ 7.86 (s, 1H), 7.65-7.58 (m, 2H), 7.40-7.35 (m, 1H), 7.29-7.24 (m, 1H), 7.14 (s, 1H), 6.69 (s, 2H), 5.77 (d, J=5.6 Hz, 1H), 5.46 (d, J=8.9 Hz, 1H), 4.09 (td, J=6.1, 2.8 Hz, 1H), 3.08-2.98 (m, 2H), 2.88-2.76 (m, 2H), 2.63-2.50 (m, 1H), 1.93 (t, J=10.4 Hz, 1H), 1.79-1.73 (m, 2H), 1.60 (t, J=5.5 Hz, 3H). tR=5.326 min (CHIRALPAK IF-3, 0.46×5 cm; 3 um, Hex(8 mM NH3):EtOH=80:20, 1.0 ml/min). 181e and 181f are enantiomers.

Step 5:

(1R,2R)-1-hydroxy-2-[(5S)-5H-imidazo[4,3-a]isoindol-5-yl]-7-azaspiro[3.5]nonane-7-sulfonamide (1S,2S)-1-hydroxy-2-[(5R)-5H-imidazo[4,3-a]isoindol-5-yl]-7-azaspiro[3.5]nonane-7-sulfonamide 181g

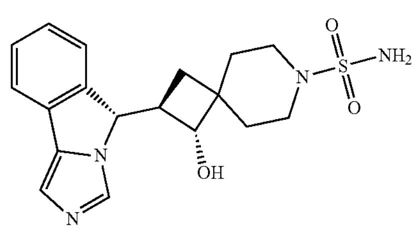

181h

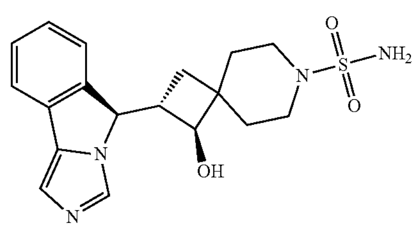

The title compounds were synthesized by General Procedure for the Synthesis of 181a-b. The configuration of the isomers was assigned arbitrarily.

Example 181g: (1R,2R)-1-hydroxy-2-[(5R)-5H-imidazo[4,3-a]isoindol-5-yl]-7-azaspiro[3.5]nonane-7-sulfonamide (17.0 mg, 29%) as a white solid: LCMS (ESI, m/z): 375.3 $[M+H]^+$; $^1H$ NMR (400 MHz, DMSO-$d_6$) δ 7.89 (s, 1H), 7.62 (d, J=7.6 Hz, 1H), 7.42-7.36 (m, 2H), 7.26-7.21 (m, 1H), 7.15 (s, 1H), 6.71 (s, 2H), 5.79 (d, J=6.1 Hz, 1H), 5.42 (d, J=10.7 Hz, 1H), 4.06 (td, J=6.4, 3.2 Hz, 1H), 3.20-2.98 (m, 2H), 2.89-2.85 (m, 2H), 2.41-2.28 (m, 1H), 2.22 (t, J=10.3 Hz, 1H), 1.92-1.76 (m, 2H), 1.68-1.61 (m, 3H). tR=2.075 min (Lux Cellulose-4, 0.46×5 cm; 3 um, Hex (0.1% DEA):EtOH=50:50, 1.0 ml/min). 181g and 181h are enantiomers.

Example 181h: (1S,2S)-1-hydroxy-2-[(5S)-5H-imidazo[4,3-a]isoindol-5-yl]-7-azaspiro[3.5]nonane-7-sulfonamide (17.4 mg, 29%) as a white solid: LCMS (ESI, m/z): 375.2 $[M+H]^+$; $^1H$ NMR (400 MHz, DMSO-$d_6$) δ 7.89 (s, 1H), 7.62 (d, J=7.5 Hz, 1H), 7.42-7.36 (m, 2H), 7.26-7.21 (m, 1H), 7.15 (s, 1H), 6.71 (s, 2H), 5.80 (d, J=6.1 Hz, 1H), 5.42 (d, J=10.6 Hz, 1H), 4.06 (td, J=6.0, 2.9 Hz, 1H), 3.20-2.98 (m, 2H), 2.89-2.85 (m, 2H), 2.54 (s, 6H), 2.44-2.29 (m, 1H), 2.22 (t, J=10.3 Hz, 1H), 1.92-1.76 (m, 2H), 1.68-1.61 (m, 3H). tR=3.203 min (Lux Cellulose-4, 0.46×5 cm; 3 um, Hex(0.1% DEA):EtOH=50:50, 1.0 ml/min). 181g and 181h are enantiomers.

Example 182: 8-(methylsulfonyl)-2-(5H-imidazo[5,1-a]isoindol-5-yl)-8-azaspiro[4.5]decan-1-ol

182

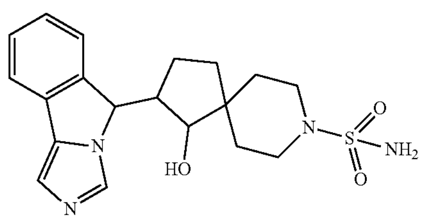

(1S,2S)-1-hydroxy-2-[(5R)-5H-imidazo[4,3-a]isoindol-5-yl]-8-azaspiro[4.5]decane-8-sulfonamide
(1R,2R)-1-hydroxy-2-[(5S)-5H-imidazo[4,3-a]isoindol-5-yl]-8-azaspiro[4.5]decane-8-sulfonamide 182a

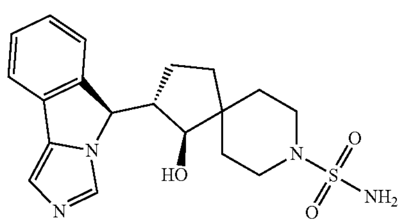

182b

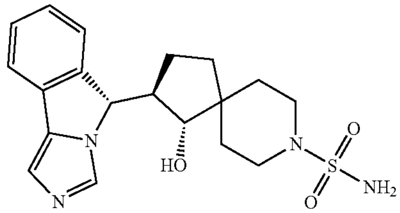

The title compounds were synthesized by General Procedure for the Synthesis of 181a-h. The configuration of the isomers was assigned arbitrarily.

Example 182a: (1S,2S)-1-hydroxy-2-[(5R)-5H-imidazo[4,3-a]isoindol-5-yl]-8-azaspiro[4.5]decane-8-sulfonamide (11.3 mg, 14%) as a white solid: LCMS (ESI, m/z): 389.3 $[M+H]^+$; $^1H$ NMR (400 MHz, DMSO-$d_6$) δ 8.03 (s, 1H), 7.62 (d, J=7.6 Hz, 1H), 7.54 (d, J=7.6 Hz, 1H), 7.42-7.30 (m, 1H), 7.29-7.25 (m, 1H), 7.16 (s, 1H), 6.63 (s, 2H), 5.47 (d, J=4.0 Hz, 1H), 5.07 (d, J=5.6 Hz, 1H), 3.60-3.55 (m, 1H), 3.28-3.25 (m, 2H), 2.68-2.51 (m, 2H), 2.49-2.45 (m, 1H), 1.74-1.68 (m, 2H), 1.55-1.54 (m, 1H), 1.33-1.01 (m, 4H), 0.86-0.85 (m, 1H). tR=1.314 min (CHIRALPAK IA-3, 0.46×5 cm; 3 um, Hex(8 mM NH3):EtOH=50:50, 1.0 ml/min). 182a and 182b are enantiomers.

Example 182b: (1R,2R)-1-hydroxy-2-[(5S)-5H-imidazo[4,3-a]isoindol-5-yl]-8-azaspiro[4.5]decane-8-sulfonamide (11.0 mg, 14%) as a white solid: LCMS (ESI, m/z): 389.2 $[M+H]^+$; $^1H$ NMR (400 MHz, DMSO-$d_6$) δ 8.03 (s, 1H), 7.62 (d, J=7.6 Hz, 1H), 7.54 (d, J=7.6 Hz, 1H), 7.42-7.30 (m, 1H), 7.29-7.25 (m, 1H), 7.16 (s, 1H), 6.63 (s, 2H), 5.47 (d, J=4.0 Hz, 1H), 5.07 (d, J=5.6 Hz, 1H), 3.60-3.55 (m, 1H), 3.28-3.25 (m, 2H), 2.68-2.51 (m, 2H), 2.49-2.45 (m, 1H), 1.74-1.68 (m, 2H), 1.55-1.54 (m, 1H), 1.33-1.01 (m, 4H), 0.86-0.85 (m, 1H). tR=2.846 min (CHIRALPAK IA-3, 0.46×5 cm; 3 um, Hex(8 mM NH3):EtOH=50:50, 1.0 ml/min). 182a and 182b are enantiomers.

(1S,2S)-1-hydroxy-2-[(5S)-5H-imidazo[4,3-a]isoindol-5-yl]-8-azaspiro[4.5]decane-8-sulfonamide
(1R,2R)-1-hydroxy-2-[(5R)-5H-imidazo[4,3-a]isoindol-5-yl]-8-azaspiro[4.5]decane-8-sulfonamide 182c

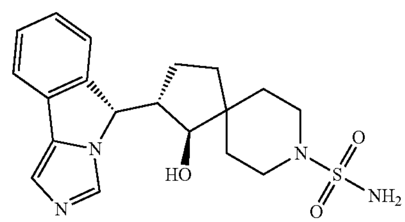

182d

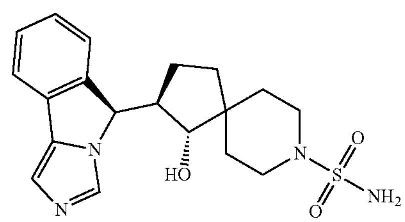

The title compounds were synthesized by General Procedure for the Synthesis of 181a-h. The configuration of the isomers was assigned arbitrarily.

Example 182c: (1S,2S)-1-hydroxy-2-[(5S)-5H-imidazo[4,3-a]isoindol-5-yl]-8-azaspiro[4.5]decane-8-sulfonamide (104.4 mg, 37%) as a white solid: LCMS (ESI, m/z): 389.3 $[M+H]^+$; $^1H$ NMR (400 MHz, DMSO-$d_6$) δ 8.03 (s, 1H), 7.69 (d, J=7.6 Hz, 1H), 7.61 (d, J=7.6 Hz, 1H), 7.42-7.38 (m, 1H), 7.31-7.28 (m, 1H), 7.18 (s, 1H), 6.68 (s, 2H), 5.40 (d, J=4.0 Hz, 1H), 5.38 (d, J=5.6 Hz, 1H), 3.90-3.88 (m, 1H), 3.23-3.20 (m, 1H), 3.08-3.05 (m, 1H), 2.76-2.67 (m, 2H), 2.32-2.29 (m, 1H), 1.78-1.34 (m, 8H). tR=3.132 min (Lux Cellulose-4, 0.46×5 cm; 3 um, Hex(8 mM NH3):EtOH=50:50, 1.0 ml/min). 182c and 182d are enantiomers.

Example 182d: (1R,2R)-1-hydroxy-2-[(5R)-5H-imidazo[4,3-a]isoindol-5-yl]-8-azaspiro[4.5]decane-8-sulfonamide (102.0 mg, 37%) as a white solid: LCMS (ESI, m/z): 389.2 $[M+H]^+$; $^1H$ NMR (400 MHz, DMSO-$d_6$) δ 8.03 (s, 1H), 7.69 (d, J=7.6 Hz, 1H), 7.61 (d, J=7.6 Hz, 1H), 7.42-7.38 (m, 1H), 7.31-7.28 (m, 1H), 7.18 (s, 1H), 6.68 (s, 2H), 5.40 (d, J=4.0 Hz, 1H), 5.38 (d, J=5.6 Hz, 1H), 3.90-3.88 (m, 1H), 3.23-3.20 (m, 1H), 3.08-3.05 (m, 1H), 2.76-2.67 (m, 2H), 2.32-2.29 (m, 1H), 1.78-1.34 (m, 8H). tR=2.128 min (Lux Cellulose-4, 0.46×5 cm; 3 um, Hex(8 mM NH3):EtOH=50:50, 1.0 ml/min). 182c and 182d are enantiomers.

The TDO2 biochemical assays measure the ability of compounds to inhibit the activity of human recombinant TDO2 which catabolizes tryptophan substrate to generate the product N-Formylkynurenine (NFK). Substrate and product concentrations are monitored by RapidFire-mass spectroscopy (RF-MS).

IDO1 and TDO2 Cell Assay

The NFK GreenScreen™ (NTRC, Netherlands) uses a specific chemical probe that binds to N-Formylkynurenine (NFK), a product of tryptophan catabolism facilitated by IDO or TDO and causes fluorescence at 510 nm when excited at 410 nm. The assay is used to assess compound inhibition of TDO and IDO leading to decreased levels of NFK in SW48 cells (high TDO expressing cells) and to determine whether compounds are selective against A172+IFNg cells (high IDO expressing cells) or are dual inhibitors in cells. The assay is multiplexed with Cell Titer-Glo® (Promega) to determine if compounds are cytotoxic. Briefly, SW48 or A172 cells are harvested in growth media, RPMI 1640 with 10% FBS, 2 mM L-glutamine, and 1× pen/strep. Cells are re-suspended in assay media, tryptophan-free RPMI 1640 supplemented with 2% dialyzed FBS, 2 mM L-glutamine, and 1× pen/strep. Cells are counted on a Vi-Cell (Beckman Coulter). SW48 cells are diluted to 1×10ˆ6 cells/ml in assay media. A172 cells are diluted to 0.24×10ˆ6 cells/ml in assay media. 25 ul of cells are dispensed with a Multi-Flo (Bio-Tek) dispenser to a 384 well greiner µclear plate (Greiner, 781091) with 14 compounds in duplicate. Compounds are dispensed into plates with an Echo® (Labcyte) starting at the highest concentration of 25 µM and are diluted approximately 3× in a 10 point titration. 5 ul of assay media containing 1.2 mM tryptophan are added to the SW48 cells for a final concentration of 200 uM tryptophan in each well. 5 ul of assay media containing 600 uM tryptophan and 600 ng/ml IFNγ are added to the A172 cells for a final concentration of 100 uM tryptophan and 100 ng/ml IFNγ in each well. The final DMSO concentration is 0.5%. Cell plates are placed at room temperature in a closed TC hood with the blower off to allow cells to settle for approximately 30 min. Plates are then moved to an incubator set at 37° C., 5% $CO_2$ for 24 hours. After the 24 hour compound incubation, 8 ul of NFK green reagent is added to each well with a Multidrop™ Combi dispenser (Thermo Scientific). Plates are sealed and incubated at 37° C., 5% $CO_2$ for 5 hours, then read on a PHERAstar® (BMG labtech). Data are analyzed by normalizing to DMSO and high inhibitor controls. After the plates have been read for NFK green, 25 ul of Cell Titer-Glo® (Promega) are added to each well, incubated for 15 minutes at room temperature, and read on the Envision (Perkin Elmer). Cell Titer-Glo data are analyzed by normalizing to the DMSO controls. Four-parameter curve fitting is used and EC50 data are reported.

TABLE 3

| Ex. # | TDO2 Cell Fluor EC50 [µM] |
|---|---|
| 01a | 14 |
| 01b | 0.15 |
| 01c | >25 |
| 01d | 0.037 |

TABLE 3-continued

| Ex. # | TDO2 Cell Fluor EC50 [µM] |
|---|---|
| 01e | 1.1 |
| 01f | >25 |
| 01g | 3.3 |
| 01h | 16 |
| 02a | 12 |
| 02b | 0.12 |
| 02c | 0.30 |
| 02d | 14 |
| 02e | 17 |
| 02f | 0.070 |
| 02g | 0.34 |
| 02h | >25 |
| 03a | 0.077 |
| 03b | 0.083 |
| 03c | >25 |
| 03d | 0.036 |
| 03e | 16 |
| 03f | 0.30 |
| 03g | 7.6 |
| 03h | 13 |
| 04a | 1.3 |
| 04b | >25 |
| 04c | 1.0 |
| 04d | 20 |
| 04e | 0.049 |
| 04f | 2.3 |
| 04g | 19 |
| 04h | 0.13 |
| 05a | 23 |
| 05b | 0.21 |
| 05c | >25 |
| 05d | 1.0 |
| 06a | >25 |
| 06b | 0.078 |
| 06c | 11 |
| 06d | 1.3 |
| 06e | >25 |
| 06f | 0.90 |
| 06g | 0.56 |
| 06h | >25 |
| 07a | 15 |
| 07b | >25 |
| 07c | 0.43 |
| 07d | >25 |
| 07e | 2.2 |
| 07f | >25 |
| 07g | >25 |
| 07h | 0.86 |
| 08a | 0.048 |
| 08b | 0.60 |
| 08c | 5.2 |
| 08d | 0.51 |
| 08e | 0.23 |
| 08f | 12 |
| 08g | 8.3 |
| 08h | 0.10 |
| 09a | >25 |
| 09b | 3.0 |
| 09c | >25 |
| 09d | >25 |
| 10a | 2.1 |
| 10b | >25 |
| 10c | 19 |
| 10d | >25 |
| 11a | 15 |
| 11b | >25 |
| 11c | >25 |
| 11d | 22 |
| 12a | 2.7 |
| 12b | >25 |
| 12c | >25 |
| 12d | >25 |
| 13a | 0.030 |

TABLE 3-continued

| Ex. # | TDO2 Cell Fluor EC50 [μM] |
|---|---|
| 13b | 1.8 |
| 13c | 1.7 |
| 13d | 0.83 |
| 13e | 0.24 |
| 13f | 4.6 |
| 13g | 17 |
| 13h | 2.1 |
| 14a | 0.36 |
| 14b | >25 |
| 14c | 20 |
| 14d | >25 |
| 15a | >25 |
| 15b | >25 |
| 15c | 7.5 |
| 15d | >25 |
| 16a | 0.11 |
| 16b | >25 |
| 16c | 5.7 |
| 16d | >25 |
| 17a | 16 |
| 17b | 1.4 |
| 17c | 0.22 |
| 17d | 0.26 |
| 17e | 0.086 |
| 18a | 0.065 |
| 18b | 0.062 |
| 18c | 0.32 |
| 18d | 8.0 |
| 18e | 7.5 |
| 18f | 15 |
| 18g | 0.11 |
| 18h | 13 |
| 19a | 7.4 |
| 19b | 0.51 |
| 19c | 0.18 |
| 19d | 0.20 |
| 19e | 2.0 |
| 19f | 4.4 |
| 20a | >25 |
| 20b | 0.43 |
| 20c | 3.6 |
| 20d | 0.099 |
| 21a | 0.053 |
| 21b | 4.5 |
| 21c | 9.0 |
| 21d | 0.043 |
| 21e | 6.7 |
| 21f | 0.40 |
| 22a | 0.060 |
| 22b | 0.016 |
| 22c | >25 |
| 22d | 6.9 |
| 22e | 3.5 |
| 22f | 1.1 |
| 22g | 0.78 |
| 22h | 0.40 |
| 23a | >25 |
| 23b | 0.085 |
| 23c | 0.081 |
| 23d | 0.11 |
| 23e | 17 |
| 23f | 2.7 |
| 24a | 0.057 |
| 24b | 8.7 |
| 24c | 5.5 |
| 24d | 1.1 |
| 24e | 0.13 |
| 24f | na |
| 24g | 0.34 |
| 24h | 12 |
| 25a | 0.51 |
| 25b | >25 |
| 25c | 20 |
| 25d | 0.048 |
| 26a | >25 |
| 26b | 0.23 |

TABLE 3-continued

| Ex. # | TDO2 Cell Fluor EC50 [μM] |
|---|---|
| 26c | 0.71 |
| 26d | >25 |
| 27a | >25 |
| 27b | 18 |
| 27c | >25 |
| 27d | 3.0 |
| 28a | >25 |
| 28b | 4.4 |
| 28c | >25 |
| 28d | >25 |
| 29a | >25 |
| 29b | 0.67 |
| 29c | 24 |
| 29d | 5.7 |
| 29e | 0.44 |
| 29f | >25 |
| 30a | 0.26 |
| 30b | 15 |
| 30c | 2.1 |
| 30d | >25 |
| 31a | >25 |
| 31b | 1.4 |
| 31c | 17 |
| 31d | >25 |
| 31e | 1.1 |
| 31f | 0.082 |
| 31g | 1.8 |
| 31h | 0.12 |
| 32a | >25 |
| 32b | 11 |
| 32c | 5.2 |
| 32d | >25 |
| 33a | >25 |
| 33b | 0.12 |
| 33c | 3.5 |
| 33d | >25 |
| 34a | 1.8 |
| 34b | >25 |
| 34c | >25 |
| 34d | 0.23 |
| 35a | >25 |
| 35b | 0.45 |
| 35c | >25 |
| 35d | 0.35 |
| 36a | 1.3 |
| 36b | 0.058 |
| 36c | 7.4 |
| 36d | 3.8 |
| 36e | 2.7 |
| 36f | 0.14 |
| 36g | 19 |
| 36h | 0.98 |
| 37a | 0.057 |
| 37b | 0.022 |
| 37c | 0.14 |
| 37d | 21 |
| 37e | 11 |
| 37f | 11 |
| 37g | 0.13 |
| 38a | 16 |
| 38b | 0.15 |
| 38c | 22 |
| 38d | 3.8 |
| 39a | >25 |
| 39b | 3.7 |
| 39c | >25 |
| 39d | 0.056 |
| 40a | 6.4 |
| 40b | 16 |
| 40c | >25 |
| 40d | >25 |
| 41a | >25 |
| 41b | 0.8 |
| 41c | 23 |
| 41d | 3.2 |
| 41e | 0.62 |

TABLE 3-continued

| Ex. # | TDO2 Cell Fluor EC50 [μM] |
|---|---|
| 41f | 17 |
| 41g | >25 |
| 41h | 0.75 |
| 42a | >25 |
| 42b | 11.8 |
| 42c | 0.25 |
| 42d | 23.7 |
| 43 | 2.86 |
| 44 | 6.84 |
| 45 | 0.28 |
| 46a | 0.15 |
| 46b | 14.1 |
| 47a | 0.35 |
| 47b | >25 |
| 48 | 7.26 |
| 49a | 18 |
| 49b | 19.6 |
| 49c | >25 |
| 49d | 1.44 |
| 50 | 2.6 |
| 51a | >25 |
| 51b | >25 |
| 51c | 0.11 |
| 51d | 14 |
| 52a | 0.24 |
| 52b | 23.7 |
| 52c | >25 |
| 52d | 2 |
| 53 | 0.17 |
| 54 | 3.4 |
| 55 | 1.6 |
| 56a | 0.15 |
| 56b | 0.37 |
| 56c | >25 |
| 56d | >25 |
| 56e | 0.76 |
| 56f | 3.8 |
| 56g | >25 |
| 57a | 11 |
| 57b | 5.0 |
| 57c | 0.40 |
| 57d | >25 |
| 57e | 0.077 |
| 57f | 0.73 |
| 57g | 0.21 |
| 57h | >25 |
| 58a | 0.36 |
| 58b | >25 |
| 58c | 20 |
| 58d | >25 |
| 59a | 0.95 |
| 59b | 0.82 |
| 59c | 1.6 |
| 59d | >25 |
| 60a | 0.48 |
| 60b | 4.1 |
| 60c | 2.4 |
| 60d | 0.74 |
| 60e | 0.035 |
| 60f | 0.057 |
| 61a | 0.57 |
| 61b | 2.6 |
| 61c | 9.1 |
| 61d | 21 |
| 62a | 10 |
| 62b | 0.31 |
| 62c | 6.6 |
| 62d | 0.082 |
| 62e | 0.52 |
| 62f | 2.5 |
| 62g | 14 |
| 63a | 0.061 |
| 63b | 19 |
| 63c | 20 |
| 63e | 0.70 |
| 64a | >25 |

TABLE 3-continued

| Ex. # | TDO2 Cell Fluor EC50 [μM] |
|---|---|
| 64b | 0.087 |
| 64c | >25 |
| 64d | 2.5 |
| 66a | >25 |
| 66b | 0.19 |
| 66c | 4.8 |
| 66d | 2.0 |
| 66e | 25 |
| 66f | 0.16 |
| 66g | 0.071 |
| 67a | 1.2 |
| 67b | >25 |
| 67c | 1.1 |
| 67d | 0.24 |
| 67e | 0.044 |
| 67f | 0.046 |
| 67g | 2.4 |
| 67h | 16 |
| 68a | 6.8 |
| 68b | 7.4 |
| 68c | >25 |
| 68d | >25 |
| 68e | 0.27 |
| 68f | 0.12 |
| 68g | >25 |
| 68h | >25 |
| 69a | >25 |
| 69b | >25 |
| 69c | 11 |
| 69d | >25 |
| 69-1a | >25 |
| 69-1b | >25 |
| 69-1c | >25 |
| 69-1d | 4.6 |
| 70a | >25 |
| 70b | 1.1 |
| 70c | >25 |
| 70d | >25 |
| 71a | 17 |
| 71aa | >25 |
| 71b | 0.63 |
| 71bb | 0.49 |
| 71c | >25 |
| 71d | 1.6 |
| 71e | 11 |
| 71f | >25 |
| 72a | 6.6 |
| 72b | 0.65 |
| 72c | 10 |
| 72d | 9.0 |
| 72e | 0.052 |
| 72f | 11 |
| 72g | 11 |
| 72h | 18 |
| 73a | 6.4 |
| 73b | 2.2 |
| 73c | 0.34 |
| 73d | >25 |
| 74a | 4.0 |
| 74b | 0.11 |
| 75a | >25 |
| 75b | 1.2 |
| 75c | 19 |
| 75d | 0.52 |
| 75-1a | 5.7 |
| 75-1b | >25 |
| 75-1c | 0.11 |
| 75-1d | >25 |
| 76a | 9.5 |
| 76b | 15 |
| 76c | 0.071 |
| 76d | 15 |
| 76e | 0.25 |
| 77a | >25 |
| 77b | 0.086 |
| 78a | 4.5 |

TABLE 3-continued

| Ex. # | TDO2 Cell Fluor EC50 [μM] |
|---|---|
| 78b | 0.16 |
| 79a | 8.1 |
| 79b | 5.2 |
| 80a | >25 |
| 80b | 0.14 |
| 80c | 15 |
| 80d | >25 |
| 81a | 5.3 |
| 81b | >25 |
| 82a | 4.4 |
| 82b | 0.33 |
| 83a | >25 |
| 83b | 1.4 |
| 84a | 14 |
| 84b | 0.067 |
| 84c | 13 |
| 84d | 3.6 |
| 84e | >25 |
| 84f | >25 |
| 85a | 24 |
| 85b | 0.13 |
| 85c | 11 |
| 85d | 0.66 |
| 85e | >25 |
| 85f | >25 |
| 85g | 0.14 |
| 85h | 0.66 |
| 86a | 14 |
| 86b | 0.52 |
| 86c | >25 |
| 86d | 0.14 |
| 86e | >25 |
| 86f | 0.15 |
| 86g | 0.84 |
| 87a | 18 |
| 87b | 0.30 |
| 87c | 6.0 |
| 87d | >25 |
| 87e | 14 |
| 87f | 17 |
| 87g | 0.24 |
| 87h | 11 |
| 88a | >25 |
| 88b | >25 |
| 88c | >25 |
| 88d | 21 |
| 88e | >25 |
| 88f | 5.8 |
| 88g | 0.73 |
| 88h | >25 |
| 89a | 14 |
| 89b | >25 |
| 90a | >25 |
| 90b | >25 |
| 90c | 0.057 |
| 90d | 9.4 |
| 90e | |
| 90f | 0.41 |
| 91a | 2.8 |
| 91b | >25 |
| 91c | >25 |
| 91d | 0.36 |
| 91e | 6.1 |
| 91f | 0.81 |
| 91g | 2.3 |
| 91h | >25 |
| 92a | 1.2 |
| 92b | 8.6 |
| 92c | 18 |
| 92d | 0.24 |
| 93a | 0.38 |
| 93b | 5.5 |
| 93c | 1.4 |
| 93d | 1.4 |
| 93e | 4.3 |
| 93f | 0.81 |

TABLE 3-continued

| Ex. # | TDO2 Cell Fluor EC50 [μM] |
|---|---|
| 93g | >25 |
| 94a | 2.3 |
| 94b | 3.1 |
| 94c | 0.11 |
| 94d | 0.13 |
| 94e | 2.0 |
| 94f | 12 |
| 94g | 14 |
| 94h | >25 |
| 95a | >25 |
| 95b | 0.24 |
| 96a | 0.89 |
| 97a | 14 |
| 97b | 0.040 |
| 97c | 0.10 |
| 97d | 0.25 |
| 97e | 3.1 |
| 97f | 8.7 |
| 97g | 5.7 |
| 97h | 1.3 |
| 98a | 0.073 |
| 98b | 8.7 |
| 98c | 0.18 |
| 98d | 9.5 |
| 98e | 22 |
| 98f | 2.5 |
| 98g | 0.86 |
| 98h | 9.8 |
| 99a | >25 |
| 99b | >25 |
| 99c | >25 |
| 99d | 0.73 |
| 100a | 0.12 |
| 100b | 1.3 |
| 100c | 7.4 |
| 100d | >25 |
| 100e | 1.3 |
| 100f | 15 |
| 100g | 0.057 |
| 100h | 4.8 |
| 101a | >25 |
| 101b | 5.1 |
| 101c | >25 |
| 101d | 0.77 |
| 102a | 0.072 |
| 102b | 19 |
| 102c | 0.32 |
| 102d | 11 |
| 102e | 0.032 |
| 102f | 5.4 |
| 102g | 0.35 |
| 102h | 8.4 |
| 103 | 12 |
| 104a | 2.2 |
| 104b | 0.20 |
| 104c | 23 |
| 104d | 14 |
| 104e | 3.4 |
| 104f | 8.6 |
| 104g | 0.33 |
| 104h | 20 |
| 105a | 12 |
| 105b | 8.6 |
| 105c | 0.077 |
| 105d | 0.044 |
| 105e | 0.46 |
| 105f | 16 |
| 105g | 9.2 |
| 105h | 0.51 |
| 106a | >25 |
| 106b | 0.17 |
| 106c | 8.1 |
| 106d | 0.93 |
| 107a | 17 |
| 107b | >25 |
| 107c | 21 |

TABLE 3-continued

| Ex. # | TDO2 Cell Fluor EC50 [μM] |
|---|---|
| 107d | 2.4 |
| 107e | 23 |
| 107f | 0.42 |
| 107g | 0.87 |
| 107h | 0.16 |
| 108a | 2.8 |
| 108b | >25 |
| 109a | 0.62 |
| 109b | 3.9 |
| 109c | 0.23 |
| 109d | 3.7 |
| 109e | 9.5 |
| 109f | >25 |
| 109g | 0.15 |
| 109h | >25 |
| 110a | 0.52 |
| 110b | >25 |
| 110c | 3.9 |
| 110d | >25 |
| 110e | 1.00 |
| 110f | >25 |
| 110g | 5.8 |
| 110h | 18 |
| 111a | 0.54 |
| 111b | 0.12 |
| 111c | 7.8 |
| 111d | >25 |
| 111e | 5.7 |
| 111f | >25 |
| 111g | >25 |
| 112a | >25 |
| 112b | 0.24 |
| 112c | >25 |
| 112d | 5.6 |
| 112e | >25 |
| 112f | 3.8 |
| 112g | 0.27 |
| 112h | >25 |
| 113a | 1.0 |
| 113b | 5.0 |
| 113c | 0.060 |
| 113d | 12 |
| 113e | 1.3 |
| 113f | 0.17 |
| 113g | 3.3 |
| 114a | 0.39 |
| 114b | >25 |
| 114c | 15 |
| 114d | 0.22 |
| 114e | 1.2 |
| 114f | 0.91 |
| 115a | 14 |
| 115b | 3.4 |
| 115c | 0.050 |
| 115d | 0.10 |
| 116a | >25 |
| 116b | 2.5 |
| 116c | >25 |
| 116d | 0.73 |
| 117a | 16 |
| 117b | 0.069 |
| 118a | >25 |
| 118b | >25 |
| 118c | 13 |
| 118d | >25 |
| 119a | >25 |
| 119b | 8.4 |
| 119c | 0.22 |
| 120a | >25 |
| 120b | >25 |
| 120c | 14 |
| 120d | >25 |
| 121a | 0.84 |
| 121b | >25 |
| 121c | 0.22 |
| 121d | 17 |

TABLE 3-continued

| Ex. # | TDO2 Cell Fluor EC50 [μM] |
|---|---|
| 121e | 16 |
| 121f | 24 |
| 121g | >25 |
| 121h | 4.8 |
| 122a | 0.035 |
| 122b | 12 |
| 122c | 23 |
| 122d | 0.37 |
| 122e | 0.090 |
| 122f | 0.91 |
| 123a | 24 |
| 123b | 0.23 |
| 124a | 16 |
| 124b | 0.29 |
| 125a | >25 |
| 125b | 0.067 |
| 126a | >25 |
| 126b | 0.083 |
| 127a | 3.7 |
| 127b | 0.89 |
| 127c | 0.76 |
| 128a | 0.31 |
| 129a | >25 |
| 129b | 17 |
| 129c | 4.5 |
| 129d | 2.6 |
| 130a | 1.5 |
| 130b | 0.65 |
| 130c | >25 |
| 130d | 0.087 |
| 130e | 3.1 |
| 130f | 1.2 |
| 130g | 4.5 |
| 130h | >25 |
| 131a | 19 |
| 131b | 3.7 |
| 132a | 0.76 |
| 133a | >25 |
| 133b | 0.94 |
| 133c | 6.0 |
| 133d | >25 |
| 133e | 0.28 |
| 133f | >25 |
| 133g | 3.0 |
| 133h | >25 |
| 134a | 1.1 |
| 135a | >25 |
| 135b | >25 |
| 135c | 3.0 |
| 135d | 0.13 |
| 136a | 25 |
| 136b | >25 |
| 136c | 6.7 |
| 136d | 15 |
| 136e | 0.64 |
| 136f | 0.36 |
| 136g | 0.20 |
| 137a | >25 |
| 137b | 7.9 |
| 137c | 0.20 |
| 138a | 9.7 |
| 138b | >25 |
| 138c | >25 |
| 138d | 10 |
| 139a | >25 |
| 139b | 1.0 |
| 139-1a | 5.3 |
| 139-1b | >25 |
| 139-1c | >25 |
| 139-1d | 0.70 |
| 139-1e | >25 |
| 139-1f | 0.21 |
| 140a | >25 |
| 140b | >25 |
| 140c | >25 |
| 140d | 3.5 |

TABLE 3-continued

| Ex. # | TDO2 Cell Fluor EC50 [μM] |
|---|---|
| 141a | 17 |
| 141b | 3.8 |
| 141c | >25 |
| 141d | >25 |
| 142a | 0.037 |
| 142b | 5.9 |
| 143a | >25 |
| 143b | >25 |
| 143c | 16 |
| 143d | >25 |
| 144a | 1.0 |
| 144b | >25 |
| 144c | 2.1 |
| 144d | >25 |
| 145a | 4.2 |
| 145b | 1.1 |
| 145c | 19 |
| 145d | >25 |
| 146a | 0.33 |
| 146b | >25 |
| 146-1a | >25 |
| 146-1b | 7.4 |
| 146-1c | >25 |
| 146-1d | 12 |
| 147a | 0.81 |
| 148a | 14 |
| 148b | 16 |
| 148c | 0.88 |
| 148d | >25 |
| 149a | 0.19 |
| 149b | 0.055 |
| 149c | 0.15 |
| 149d | 9.6 |
| 149e | 1.4 |
| 149f | >25 |
| 149g | 24.2 |
| 149h | 24 |
| 150a | 12 |
| 150b | 2.1 |
| 150c | 0.11 |
| 150d | 18 |
| 150e | 0.053 |
| 150f | 11 |
| 151a | 0.52 |
| 151b | >25 |
| 151c | >25 |
| 151d | 0.13 |
| 152a | 14 |
| 152b | >25 |
| 152c | >25 |
| 152d | >25 |
| 153a | 0.62 |
| 153b | 11 |
| 154a | 0.13 |
| 154b | >25 |
| 154c | 5.4 |
| 154d | 13 |
| 155a | 0.33 |
| 155b | >25 |
| 155c | 21 |
| 155d | >25 |
| 156a | >25 |
| 156b | 0.24 |
| 156c | 19 |
| 156d | >25 |
| 156e | 0.25 |
| 156f | >25 |
| 157a | 0.37 |
| 157b | 22 |
| 157c | 14 |
| 157d | 23 |
| 157e | 0.096 |
| 157f | >25 |
| 157g | 0.042 |
| 157h | 0.76 |
| 158a | 7.9 |

TABLE 3-continued

| Ex. # | TDO2 Cell Fluor EC50 [μM] |
|---|---|
| 159a | 0.27 |
| 159b | 14 |
| 159c | 0.25 |
| 159d | 3.7 |
| 160a | >25 |
| 160b | 0.20 |
| 160c | 23 |
| 160d | 6.0 |
| 160e | >25 |
| 160e | 0.11 |
| 161a | 18 |
| 161b | 0.70 |
| 161c | 1.0 |
| 161d | 12 |
| 161e | >25 |
| 161f | >25 |
| 161g | >25 |
| 161h | 18 |
| 162a | 18 |
| 162b | 1.7 |
| 162c | 0.059 |
| 162d | 0.13 |
| 162e | 1.9 |
| 162f | 11 |
| 162g | 0.14 |
| 162h | 0.61 |
| 163a | 0.10 |
| 163b | 0.060 |
| 163c | 15 |
| 163d | 0.054 |
| 163e | 6.1 |
| 163f | >25 |
| 163g | 0.44 |
| 163h | 0.93 |
| 164a | 0.040 |
| 164b | 7.5 |
| 165a | 16 |
| 165b | >25 |
| 165c | 11 |
| 165d | >25 |
| 166a | >25 |
| 166b | 0.27 |
| 167a | 0.28 |
| 167b | 0.36 |
| 167c | 6.3 |
| 167d | 0.043 |
| 167e | 4.7 |
| 167f | 23 |
| 167g | 2.0 |
| 167h | 0.089 |
| 168a | 0.14 |
| 169a | 0.21 |
| 169b | 16 |
| 170a | >25 |
| 170b | 2.1 |
| 170c | >25 |
| 170d | 13 |
| 171a | 0.999 |
| 171b | >25 |
| 171c | 5.8 |
| 171d | 17.7 |
| 172a | >25 |
| 172b | 1.1 |
| 173a | >25 |
| 173b | 0.43 |
| 174a | >25 |
| 174b | 0.15 |
| 175a | 0.066 |
| 175b | 11.9 |
| 176a | 0.068 |
| 176b | 12 |
| 177 | 0.98 |
| 178a | 0.12 |
| 178b | >25 |
| 179a | 0.4 |
| 179b | >25 |

TABLE 3-continued

| Ex. # | TDO2 Cell Fluor EC50 [μM] |
|---|---|
| 179c | >25 |
| 179d | 0.54 |
| 179e | 6.8 |
| 179f | 0.12 |
| 179g | 0.79 |
| 179h | 8.6 |
| 180a | 0.37 |
| 180b | >25 |
| 180c | 0.098 |
| 180d | >25 |
| 181a | 0.66 |
| 181b | >25 |
| 181c | >25 |
| 181d | 3.0 |
| 181e | 12 |
| 181f | 0.20 |
| 181g | 0.93 |
| 181h | 11 |
| 182a | >25 |
| 182b | 0.54 |
| 182c | 4.6 |
| 182d | 0.092 |
| 183 | 0.22 |

TDO Selectivity

Compounds of the invention were tested for selectivity against TDO over IDO. The cell based assay described above was used to test for TDO and IDO activity. The following results were obtained:

| Ex. # | IDO cell Fluor EC50 [μM] | TDO2 cell Fluor EC50 [μM] |
|---|---|---|
| 1d | 2.4 | 0.037 |
| 4e | 1.2 | 0.049 |
| 6b | 1.6 | 0.078 |
| 7h | >25 | 0.86 |
| 13a | 6.8 | 0.030 |
| 16a | 1.2 | 0.11 |
| 17e | 2.3 | 0.086 |
| 21d | 1.1 | 0.043 |
| 22b | 2.0 | 0.016 |
| 37g | 4.0 | 0.13 |
| 42c | 5.0 | 0.25 |
| 45 | 6.3 | 0.28 |
| 46a | 2.9 | 0.15 |
| 56a | 4.5 | 0.15 |
| 60e | 1.4 | 0.035 |
| 93a | 13 | 0.38 |
| 94c | 8.4 | 0.11 |
| 97b | 1.4 | 0.040 |
| 100g | 1.7 | 0.057 |
| 101d | 21 | 0.77 |
| 109c | >25 | 0.23 |
| 112b | 15 | 0.24 |
| 117b | 9.3 | 0.069 |
| 122a | 2.6 | 0.035 |
| 130d | 1.8 | 0.087 |
| 149b | 2.1 | 0.055 |
| 157g | 8.0 | 0.042 |
| 162c | 1.5 | 0.059 |
| 167d | 1.0 | 0.043 |
| 177 | >25 | 0.98 |

The invention claimed is:

1. A compound of the formula

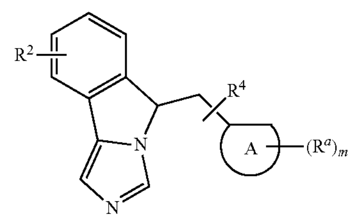

or a pharmaceutically acceptable salt thereof wherein

Ring A is $C_{3-8}$cycloalkyl, 3-7 membered heterocyclyl or heteroaryl;

m is 0, 1, 2 or 3;

$R^4$ is OH; and each $R^a$ is independently selected from halogen, $C_{1-6}$alkyl, —$S(O)_2R$, —$C(O)N(R)_2$ and $C_{1-6}$alkyl-cyano;

$R^2$ is independently hydrogen, halogen, $C_1$-$C_6$ alkyl, $C_3$cycloalkyl, $C_1$-$C_6$ haloalkyl, halogen, cyano, —OR, —$NR_2$ or —SR; and each R is independently hydrogen, $C_{1-6}$alkyl or $C_{1-6}$haloalkyl.

2. A pharmaceutical composition comprising a compound according to claim 1 and a pharmaceutically acceptable diluent, excipient, or carrier.

3. A method for treating tryptophan 2,3-dioxygenase (TDO2) mediated immunosuppression associated with a disease in a subject in need thereof, comprising administering an effective tryptophan 2,3-dioxygenase inhibiting amount of a compound according to claim 1.

4. The method of claim 3, wherein the disease is cancer.

5. The method of claim 4, wherein the cancer is colon, pancreas, breast, prostate, lung, brain, ovary, cervix, testes, renal, head, or neck cancer, or lymphoma, leukemia, or melanoma.

6. A compound that is 1-(5H-imidazo[5,1-a]isoindol-5-yl)ethan-1-ol, 2-(5H-imidazo[5,1-a]isoindol-5-yl)propan-2-ol, 1-(5H-imidazo[5,1-a]isoindol-5-yl)ethane-1,2-diol, 1-(5H-imidazo[5,1-a]isoindol-5-yl)-2-methylpropan-1-ol, cyclopropyl(5H-imidazo[5,1-a]isoindol-5-yl)methanol, 1-(5H-imidazo[5,1-a]isoindol-5-yl)-1-(tetrahydro-2H-pyran-4-yl)ethan-1-ol, 1-(8-fluoro-5H-imidazo[5,1-a]isoindol-5-yl)-2-methylpropan-1-ol, 1-(5H-imidazo[5,1-a]isoindol-5-yl)propan-1-ol, (5H-imidazo[5,1-a]isoindol-5-yl)(tetrahydro-2H-pyran-4-yl)methanol, 1-(5H-imidazo[5,1-a]isoindol-5-yl)-1-(1H-imidazol-2-yl)ethan-1-ol, cyclohexyl(5H-imidazo[5,1-a]isoindol-5-yl)methanol, (5H-imidazo[5,1-a]isoindol-5-yl) (pyridin-4-yl)methanol, (1-fluorocyclopropyl) (5H-imidazo[5,1-a]isoindol-5-yl)methanol, (R)-1-((S)-5H-imidazo[5,1-a]isoindol-5-yl)ethan-1-ol, (R)-1-((R)-5H-imidazo[5,1-a]isoindol-5-yl)ethan-1-ol, (S)-1-((R)-5H-imidazo[5,1-a]isoindol-5-yl)ethan-1-ol, (S)-1-((S)-5H-imidazo[5,1-a]isoindol-5-yl)ethan-1-ol, (R)-2-(5H-imidazo[5,1-a]isoindol-5-yl)propan-2-ol, (S)-2-(5H-imidazo[5,1-a]isoindol-5-yl)propan-2-ol, (R)-1-((R)-5H-imidazo[5,1-a]isoindol-5-yl)ethane-1,2-diol, (R)-1-((S)-5H-imidazo[5,1-a]isoindol-5-yl)ethane-1,2-diol, (S)-1-((R)-5H-imidazo[5,1-a]isoindol-5-yl)ethane-1,2-diol,
(S)-1-((S)-5H-imidazo[5,1-a]isoindol-5-yl)ethane-1,2-diol,
(S)-1-((S)-5H-imidazo[5,1-a]isoindol-5-yl)-2-methylpropan-1-ol,
(R)-1-((S)-5H-imidazo[5,1-a]isoindol-5-yl)-2-methylpropan-1-ol,
(S)-1-((R)-5H-imidazo[5,1-a]isoindol-5-yl)-2-methylpropan-1-ol,
(R)-1-((R)-5H-imidazo[5,1-a]isoindol-5-yl)-2-methylpropan-1-ol,
(S)-cyclopropyl((S)-5H-imidazo[5,1-a]isoindol-5-yl)methanol,
(S)-cyclopropyl((R)-5H-imidazo[5,1-a]isoindol-5-yl)methanol,
(R)-cyclopropyl((S)-5H-imidazo[5,1-a]isoindol-5-yl)methanol,
(R)-cyclopropyl((R)-5H-imidazo[5,1-a]isoindol-5-yl)methanol,
(S)-1-((R)-5H-imidazo[5,1-a]isoindol-5-yl)-1-(tetrahydro-2H-pyran-4-yl)ethan-1-ol,
(R)-1-((S)-5H-imidazo[5,1-a]isoindol-5-yl)-1-(tetrahydro-2H-pyran-4-yl)ethan-1-ol,
(S)-1-((R)-8-fluoro-5H-imidazo[5,1-a]isoindol-5-yl)-2-methylpropan-1-ol,
(R)-1-((R)-8-fluoro-5H-imidazo[5,1-a]isoindol-5-yl)-2-methylpropan-1-ol,
(R)-1-((S)-8-fluoro-5H-imidazo[5,1-a]isoindol-5-yl)-2-methylpropan-1-ol,
(S)-1-((S)-8-fluoro-5H-imidazo[5,1-a]isoindol-5-yl)-2-methylpropan-1-ol,
(R)-1-((R)-5H-imidazo[5,1-a]isoindol-5-yl)propan-1-ol,
(S)-1-((S)-5H-imidazo[5,1-a]isoindol-5-yl)propan-1-ol,
(R)-1-((S)-5H-imidazo[5,1-a]isoindol-5-yl)propan-1-ol,
(S)-1-((R)-5H-imidazo[5,1-a]isoindol-5-yl)propan-1-ol,
(R)—((S)-5H-imidazo[5,1-a]isoindol-5-yl)(tetrahydro-2H-pyran-4-yl)methanol,
(S)—((R)-5H-imidazo[5,1-a]isoindol-5-yl)(tetrahydro-2H-pyran-4-yl)methanol,
(R)—((R)-5H-imidazo[5,1-a]isoindol-5-yl)(tetrahydro-2H-pyran-4-yl)methanol,
(S)—((S)-5H-imidazo[5,1-a]isoindol-5-yl)(tetrahydro-2H-pyran-4-yl)methanol,
(R)-1-((R)-5H-imidazo[5,1-a]isoindol-5-yl)-1-(1H-imidazol-2-yl)ethan-1-ol,
(R)-1-((S)-5H-imidazo[5,1-a]isoindol-5-yl)-1-(1H-imidazol-2-yl)ethan-1-ol,
(S)-1-((R)-5H-imidazo[5,1-a]isoindol-5-yl)-1-(1H-imidazol-2-yl)ethan-1-ol,
(S)-1-((S)-5H-imidazo[5,1-a]isoindol-5-yl)-1-(1H-imidazol-2-yl)ethan-1-ol,
(R)-cyclohexyl((S)-5H-imidazo[5,1-a]isoindol-5-yl)methanol,
(S)-cyclohexyl((R)-5H-imidazo[5,1-a]isoindol-5-yl)methanol,
(R)-cyclohexyl((R)-5H-imidazo[5,1-a]isoindol-5-yl)methanol,
(S)-cyclohexyl((S)-5H-imidazo[5,1-a]isoindol-5-yl)methanol,
(S)—((R)-5H-imidazo[5,1-a]isoindol-5-yl) (pyridin-4-yl)methanol,
(R)—((S)-5H-imidazo[5,1-a]isoindol-5-yl) (pyridin-4-yl)methanol,
(S)—((S)-5H-imidazo[5,1-a]isoindol-5-yl) (pyridin-4-yl)methanol,
(R)—((R)-5H-imidazo[5,1-a]isoindol-5-yl) (pyridin-4-yl)methanol,
(R)-(1-fluorocyclopropyl) ((R)-5H-imidazo[5,1-a]isoindol-5-yl)methanol,
(S)-(1-fluorocyclopropyl) ((S)-5H-imidazo[5,1-a]isoindol-5-yl)methanol,
(S)-(1-fluorocyclopropyl) ((R)-5H-imidazo[5,1-a]isoindol-5-yl)methanol, or
(R)-(1-fluorocyclopropyl) ((S)-5H-imidazo[5,1-a]isoindol-5-yl)methanol.

7. A compound according to claim 6, which is
1-(5H-imidazo[5,1-a]isoindol-5-yl)ethan-1-ol,
2-(5H-imidazo[5,1-a]isoindol-5-yl)propan-2-ol,
1-(5H-imidazo[5,1-a]isoindol-5-yl)ethane-1,2-diol,
1-(5H-imidazo[5,1-a]isoindol-5-yl)-2-methylpropan-1-ol,
cyclopropyl(5H-imidazo[5,1-a]isoindol-5-yl)methanol,
1-(8-fluoro-5H-imidazo[5,1-a]isoindol-5-yl)-2-methylpropan-1-ol,
1-(5H-imidazo[5,1-a]isoindol-5-yl)propan-1-ol,
(5H-imidazo[5,1-a]isoindol-5-yl)(tetrahydro-2H-pyran-4-yl)methanol,
1-(5H-imidazo[5,1-a]isoindol-5-yl)-1-(1H-imidazol-2-yl)ethan-1-ol,
cyclohexyl(5H-imidazo[5,1-a]isoindol-5-yl)methanol,
(5H-imidazo[5,1-a]isoindol-5-yl) (pyridin-4-yl)methanol, or
(1-fluorocyclopropyl) (5H-imidazo[5,1-a]isoindol-5-yl)methanol.

8. A compound of the formula:

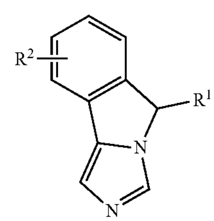

or a pharmaceutically acceptable salt thereof wherein
$R^1$ is
$C_4$-$C_6$ cycloalkyl or 5-6-membered heterocyclyl, each of which is substituted with hydroxy on the carbon atom adjacent to the carbon atom bonded to the 5H-imidazo[5,1-a]isoindolyl; or
$C_4$-$C_6$ cycloalkyl substituted with =(spiro-(4-6-membered heterocyclyl)), each of which ring systems is further substituted with hydroxy on the carbon atom adjacent to the carbon atom bonded to the 5H-imidazo[5,1-a]isoindolyl; and
wherein each $R^1$ is optionally further substituted by one, two, three, or four $R^a$ groups independently selected from, halogen, cyano, nitro, —OR, —$NR_2$, —SR, —C(O)OR, —C(O)N$(R)_2$, —C(O)R, —S(O)R, —S(O)OR, —S(O)N$(R)_2$, —$S(O)_2$R, —$S(O)_2$OR, —$S(O)_2$N$(R)_2$, —OC(O)R, —OC(O)OR, —OC(O)N$(R)_2$, —N(R)C(O)R, —N(R)C(O)OR, and —N(R)C(O)N$(R)_2$; wherein
$R^2$ is independently $C_1$-$C_6$ alkyl, $C_3$cycloalkyl, $C_1$-$C_6$ haloalkyl, halogen, cyano, —OR, —$NR_2$ or —SR; and
each R is independently hydrogen, $C_{1-6}$alkyl or $C_{1-6}$haloalkyl.

9. A compound according to claim 8, wherein $R^1$ is $C_4$-$C_6$ cycloalkyl or 5-6-membered heterocyclyl, each of which is substituted with hydroxy on the carbon atom adjacent to the carbon atom bonded to the 5H-imidazo[5,1-a]isoindolyl; and wherein each $R^1$ is optionally further substituted by one, two, three, or four $R^a$ groups independently selected from, halogen, cyano, nitro, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

wherein each $R^2$ is independently $C_1$-$C_6$ alkyl, $C_3$cycloalkyl, $C_1$-$C_6$ haloalkyl, halogen, cyano, —OR, —$NR_2$ or —SR; and each R is independently hydrogen, $C_{1-6}$alkyl or $C_{1-6}$haloalkyl.

10. A compound according to claim 8, wherein $R^1$ is $C_4$-$C_6$ cycloalkyl substituted with =(spiro-(4-6-membered heterocyclyl)), each of which ring systems is further substituted with hydroxy on the carbon atom adjacent to the carbon atom bonded to the 5H-imidazo[5,1-a]isoindolyl; and wherein each $R^1$ is optionally further substituted by one, two, three, or four $R^a$ groups independently selected from, halogen, cyano, nitro, —OR, —$NR_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$;

wherein each $R^2$ is independently $C_1$-$C_6$ alkyl, $C_3$cycloalkyl, $C_1$-$C_6$ haloalkyl, halogen, cyano, —OR, —$NR_2$ or —SR; and each R is independently hydrogen, $C_{1-6}$alkyl or $C_{1-6}$haloalkyl.

11. A pharmaceutical composition comprising a compound according to claim 8 and a pharmaceutically acceptable diluent, excipient, or carrier.

12. A method for treating tryptophan 2,3-dioxygenase (TDO2) mediated immunosuppression associated with a disease in a subject in need thereof, comprising administering an effective tryptophan 2,3-dioxygenase inhibiting amount of a compound according to claim 8.

13. A method according to claim 12, wherein the disease is cancer.

14. A method according to claim 13, wherein the cancer is colon, pancreas, breast, prostate, lung, brain, ovary, cervix, testes, renal, head, or neck cancer, or lymphoma, leukemia, or melanoma.

* * * * *